United States Patent
Amigorena et al.

(10) Patent No.: US 12,152,077 B1
(45) Date of Patent: *Nov. 26, 2024

(54) IMMUNOTHERAPY TARGETING TUMOR NEOANTIGENIC PEPTIDES

(71) Applicants: INSTITUT CURIE, Paris (FR); MNEMO THERAPEUTICS, Paris (FR); INSTITUT NATIONAL DE LA SANTE ET DE LA RECHERCHE MEDICAL (INSERM), Paris (FR)

(72) Inventors: Sebastian Amigorena, Paris (FR); Marianne Burbage, Paris (FR); Alexandre Houy, Vitry sur Seine (FR); Marc-Henri Stern, Paris (FR); Joshua Waterfall, Paris (FR); Benjamin Sadacca, Paris (FR); Antonela Merlotti Ippolito, Paris (FR); Yago Arribas De Sandoval, Paris (FR)

(73) Assignees: INSTITUT CURIE, Paris (FR); MNEMO THERAPEUTICS, Paris (FR); INSTITUT NATIONAL DE LA SANTE ET DE LA RECHERCHE MEDICALE (INSERM), Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 18/316,628

(22) Filed: May 12, 2023

Related U.S. Application Data

(63) Continuation of application No. 17/639,568, filed as application No. PCT/EP2020/074429 on Sep. 2, 2020.

(30) Foreign Application Priority Data

| Sep. 2, 2019 | (EP) | 19306064 |
| Dec. 20, 2019 | (EP) | 19218556 |
| Jul. 1, 2020 | (EP) | 20305743 |

(51) Int. Cl.
*C07K 16/28* (2006.01)
*C07K 14/74* (2006.01)
*C12N 5/078* (2010.01)

(52) U.S. Cl.
CPC .... *C07K 16/2833* (2013.01); *C07K 14/70539* (2013.01); *C12N 5/0634* (2013.01); *C07K 2317/92* (2013.01)

(58) Field of Classification Search
CPC .......... C07K 16/2833; C07K 14/70539; C07K 2317/92; C12N 5/0634
See application file for complete search history.

(56) References Cited

U.S. PATENT DOCUMENTS

| 4,235,871 A | 11/1980 | Papahadjopoulos et al. |
| 4,501,728 A | 2/1985 | Geho et al. |
| 4,722,848 A | 2/1988 | Paoletti et al. |
| 4,837,028 A | 6/1989 | Allen |
| 5,019,369 A | 5/1991 | Presant et al. |
| 5,204,253 A | 4/1993 | Sanford et al. |
| 5,279,833 A | 1/1994 | Rose |
| 5,580,859 A | 12/1996 | Felgner et al. |
| 5,589,466 A | 12/1996 | Felgner et al. |
| 6,410,319 B1 | 6/2002 | Raubitschek et al. |
| 6,451,995 B1 | 9/2002 | Cheung et al. |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |
| 8,324,353 B2 | 12/2012 | Jensen et al. |
| 8,339,645 B2 | 12/2012 | Nakawaki et al. |
| 8,398,282 B2 | 3/2013 | Kuhlman et al. |
| 8,479,118 B2 | 7/2013 | Lyndersay et al. |
| 2002/0131960 A1 | 9/2002 | Sadelain et al. |

(Continued)

FOREIGN PATENT DOCUMENTS

| EP | 2537416 A1 | 12/2012 |
| WO | WO-1991/06309 A1 | 5/1991 |

(Continued)

OTHER PUBLICATIONS

Belancio et al. (Genome Medicine, 1(97): 1-8, 2009).*
Wright et al. (Trends in Cell Biology, 32(3): 243-251, 2022).*
Bantysh et al. (Biochemistry (Moscow), 74(12): 1393-1399, 2009).*
Vorechovsky (Hum Genet, 127: 135-154, 2010).*
Shah et al. (Nature Genetics, 55: 631-639, 2023).*

(Continued)

*Primary Examiner* — Nelson B Moseley, II
(74) *Attorney, Agent, or Firm* — RinLaures LLC; Li-Hsien Rin-Laures; Kristen A. Dola

(57) ABSTRACT

The present disclosure relates to a method for selecting a tumor neoantigenic peptide wherein said method comprises:
- a step of identifying, among mRNA sequences from cancer cells of a subject, a fusion transcript sequence comprising a transposable element (TE) sequence and an exonic sequence, and including an open reading frame (ORF), and
- a step of selecting a tumor neoantigenic peptide of at least 8 amino acids, encoded by a part of said ORF of the fusion transcript sequence, wherein said ORF overlaps the junction between the TE and the exonic sequence, is pure TE and/or is non-canonical, and wherein said tumor neoantigenic peptide binds to at least one Major Histocompatibility Complex (MHC) molecule of said subject.

The present disclosure also relates to tumor neoantigenic peptide obtained according to the present method, vaccine or immunogenic composition, antibodies and immune cells derived thereof and their use in therapy of cancer.

9 Claims, 19 Drawing Sheets
Specification includes a Sequence Listing.

(56) References Cited

U.S. PATENT DOCUMENTS

| | | |
|---|---|---|
| 2013/0149337 A1 | 6/2013 | Cooper et al. |
| 2013/0287748 A1 | 10/2013 | June et al. |
| 2014/0120622 A1 | 5/2014 | Gregory et al. |
| 2019/0177383 A1 | 6/2019 | Mahr et al. |

FOREIGN PATENT DOCUMENTS

| | | |
|---|---|---|
| WO | WO-1993/24640 A2 | 12/1993 |
| WO | WO-1996/18372 A2 | 6/1996 |
| WO | WO-2000/14257 A1 | 3/2000 |
| WO | WO-2012/129514 A1 | 9/2012 |
| WO | WO-2013/071154 A1 | 5/2013 |
| WO | WO-2013/123061 A1 | 8/2013 |
| WO | WO-2013/126726 A1 | 8/2013 |
| WO | WO-2013/166321 A1 | 11/2013 |
| WO | WO-2014/031687 A1 | 2/2014 |
| WO | WO-2014/055668 A1 | 4/2014 |
| WO | WO-2016/172722 A1 | 10/2016 |

OTHER PUBLICATIONS

An et al., NCG 5.0: updates of a manually curated repository of cancer genes and associated properties from cancer mutational screenings. *Nucl. Acids Res.*, 44(D1): 992-9 (2016).

Baeuerle et al., Bispecific T-cell engaging antibodies for cancer therapy. *Cancer Res.*, 69(12): 4941-4 (2009).

Boegel et al., HLA typing from RNA-Seq sequence reads. *Genome Med.*, 4(12): 102 (2012).

Boudousquie et al., Polyfunctional response by ImmTAC (IMCgpIOO) redirected CD8+ and CD4+ T cells. *Immunology*, 152(3): 425-38 (2017).

Bulik-Sullivan et al., Deep learning using tumor HLA peptide mass spectrometry datasets improves neoantigen identification. *Nat. Biotechnol.*, 37(1): 55-63 (2018).

Chiappinelli et al., Inhibiting DNA methylation causes an interferon response in cancer via dsRNA including endogenous retroviruses. *Cell*, 162(5): 974-86 (2015).

Chong et al., Integrated proteogenomic deep sequencing and analytics accurately identify non-canonical peptides in tumor immunopeptidomes. *Nat. Commun.*, 11(1): 1293 (2020).

Chothia et al., The outline structure of the T-cell alpha beta receptor. *EMBO J.*, 7(12): 3745-55 (1988).

Cohen et al., Recognition of fresh human tumor by human peripheral blood lymphocytes transduced with a bicistronic retroviral vector encoding a murine anti-p53 TCR. *J. Immunol.*, 175(9): 5799-808 (2005).

Davila et al., CD19 CAR-targeted T cells induce long-term remission and B Cell Aplasia in an immunocompetent mouse model of B cell acute lymphoblastic leukemia. *PLoS One*, 8(4): e61338 (2013).

Dobin et al., STAR: ultrafast universal RNA-seq aligner. *Bioinformatics*, 29(1): 15-21 (2013).

Felgner et al., Lipofection: a highly efficient, lipid-mediated DNA-transfection procedure. *Proc. Natl. Acad. Sci. U.S.A*, 84(21): 7413-17 (1987).

Graham et al., Allogeneic CAR-T cells: more than ease of access? *Cells*, 7(10): 155 (2018).

Hasan et al., Artificial antigen presenting cells: an off the shelf approach for generation of desirable T-cell populations for broad application of adoptive immunotherapy. *Adv. Genet. Eng.*, 4(3): 130 (2015).

Helman et al., Somatic retrotransposition in human cancer revealed by whole- genome and exome sequencing. *Genome Res.*, 24(7): 1053-63 (2014).

Javitt et al., Pro-inflammatory cytokines alter the immunopeptidome landscape by modulation of HLA-B expression. *Front Immunol.*, 10(141): 1-16 (2019).

Jores et al., Resolution of hypervariable regions in T-cell receptor beta chains by a modified Wu-Kabat index of amino acid diversity. *Proc. Natl. Acad. Sci U.S.A.*, 87(23): 9138-42 (1990).

Kim et al., The ABCs of artificial antigen presentation. *Nat. Biotechnol.*, 22(4): 403-10 (2004).

Kim et al., TopHat2: accurate alignment of transcriptomes in the presence of insertions, deletions and gene fusions. *Genome Biol.*, 14(4): R36 (2013).

Kim et al., HISAT: a fast spliced aligner with low memory requirements. *Nat. Methods*, 12(4): 357-60 (2015).

Kiyotani et al., Immunopharmacogenomics towards personalized cancer immunotherapy targeting neoantigens. *Cancer Sci.*, 109(3): 542-9 (2018).

Kong et al., Transposable element expression in tumors is associated with immune infiltration and increased antigenicity. *Nat. Commun.*, 10(1): 5228 (2019).

Langmead et al., Ultrafast and memory-efficient alignment of short DNA sequences to the human genome. *Genome Biol.*, 10: R25 (2009).

Laumont et al., Noncoding regions are the main source of targetable tumor- specific antigens. *Sci. Transl. Med.*, 10(470): 1-11 (2018).

Lefranc et al., IMGT unique numbering for immunoglobulin and T cell receptor variable domains and Ig superfamily V-like domains. *Dev. Comp. Immunol.*, 27(1): 55-77 (2003).

Li et al., Directed evolution of human T-cell receptors with picomolar affinities by phage display. *Nat. Biotechnol.*, 23(3): 349-54 (2005).

Lundegaard et al., NetMHC-3.0: accurate web accessible predictions of human, mouse and monkey MHC class I affinities for peptides of length 8-11. *Nucl. Acids Res.*, 36(Web Server issue): W509-12 (2008).

Neal et al., The basics of artificial antigen presenting cells in T cell-based cancer immunotherapies. *J. Immunol. Res. Ther.*, 2(1): 68-79 (2017).

Nielsen et al., NetMHCpan, a method for quantitative predictions of peptide binding to any HLA-A and -B locus protein of known sequence. *PLoS One*, 2(8): e796 (2007).

Parkhurst et al., Characterization of genetically modified T-cell receptors that recognize the CEA:691-699 peptide in the context of HLA-A2.1 on human colorectal cancer cells. *Clin. Cancer Res.*, 15(1): 169-80 (2009).

Pradeepkiran et al., CGMD: An integrated database of cancer genes and markers. *Sci. Rep.*, 5: 12035 (2015).

Rathe et al., Identification of candidate neoantigens produced by fusion transcripts in human osteosarcomas. *Sci. Rep.*, 9(1): 358 (2019).

Ren et al., Multiplex genome editing to generate universal Car T cells resistant to PD1 inhibition. Clin. Cancer Res., 23(9): 2255-66 (2017).

Sadelain et al., The basic principles of chimeric antigen receptor design. *Cancer Discov.*, 3(4): 388-98 (2013).

Schiavetti et al., A human endogenous retroviral sequence encoding an antigen recognized on melanoma by cytolytic T lymphocytes. *Cancer Res.*, 62(19): 5510-6 (2002).

Shen et al., Double agents: genes with both oncogenic and tumor-suppressor functions. *Oncogenesis*, 7(3): 25 (2018).

Stover et al., New use of BCG for recombinant vaccines. *Nature*, 351(6326): 456-60 (1991).

Szoka et al., Comparative properties and methods of preparation of lipid vesicles (liposomes). *Annu. Rev. Biophys. Bioeng.*, 9: 467-508 (1980).

Takahashi et al., Regression of human kidney cancer following allogeneic stem cell transplantation is associated with recognition of an HERV-E antigen by T cells. *J. Clin. Invest.*, 118(3): 1099-109 (2008).

Torikai et al., Toward eliminating HLA class I expression to generate universal cells from allogeneic donors. *Blood*, 122(8): 1341-9 (2013).

Turtle et al., Engineered T cells for anti-cancer therapy. *Curr. Opin. Immunol.*, 24(5): 633-9 (2012).

Varela-Rohena et al., Control of HIV-1 immune escape by CD8 T cells expressing enhanced T-cell receptor. *Nat. Med.*, 14(12): 1390-5 (2008).

Verhoef et al., Des-enkephalin-γ-endorphin (DEyE): biotransformation in rat, dog and human plasma. *Eur. J. Drug. Metab. Pharmacokin*, 11(4): 291-302 (1986).

(56) References Cited

OTHER PUBLICATIONS

Walseng et al., Soluble T-cell receptors produced in human cells for targeted delivery. *PLoS One,* 10(4): e0119559 (2015).

Wang et al., Bioengineering of artificial sntigen presenting cells and lymphoid organs. *Theranostics,* 7(14): 3504-16 (2017).

Wolff et al., Direct gene transfer into mouse muscle in vivo. *Science,* 247(4949): 1465-68 (1990).

Wu et al., Adoptive T-cell therapy using autologous tumor-infiltrating lymphocytes for metastatic melanoma: current status and future outlook. *Cancer J.,* 18(2): 160-75 (2012).

Yarchoan et al., Targeting neoantigens to augment antitumour immunity. *Nat. Rev. Cancer.,* 17(4): 209-22 (2017).

Zhao et al., TSGene 2.0: an updated literature-based knowledgebase for tumor suppressor genes. *Nucl. Acids Res.,* 44(D1): D1023-31 (2016).

\* cited by examiner

TE-derived epitopes expressed in B16F10-OVA cells

TE-derived epitopes expressed in MCA101-OVA cells

TE-derived epitopes shared between B16OVA and MCAOVA cells

N25 (expected size 313 bp)

N26 (expected size 379bp)

*Lung cancer*

*Breast cancer*

*Lung cancer*

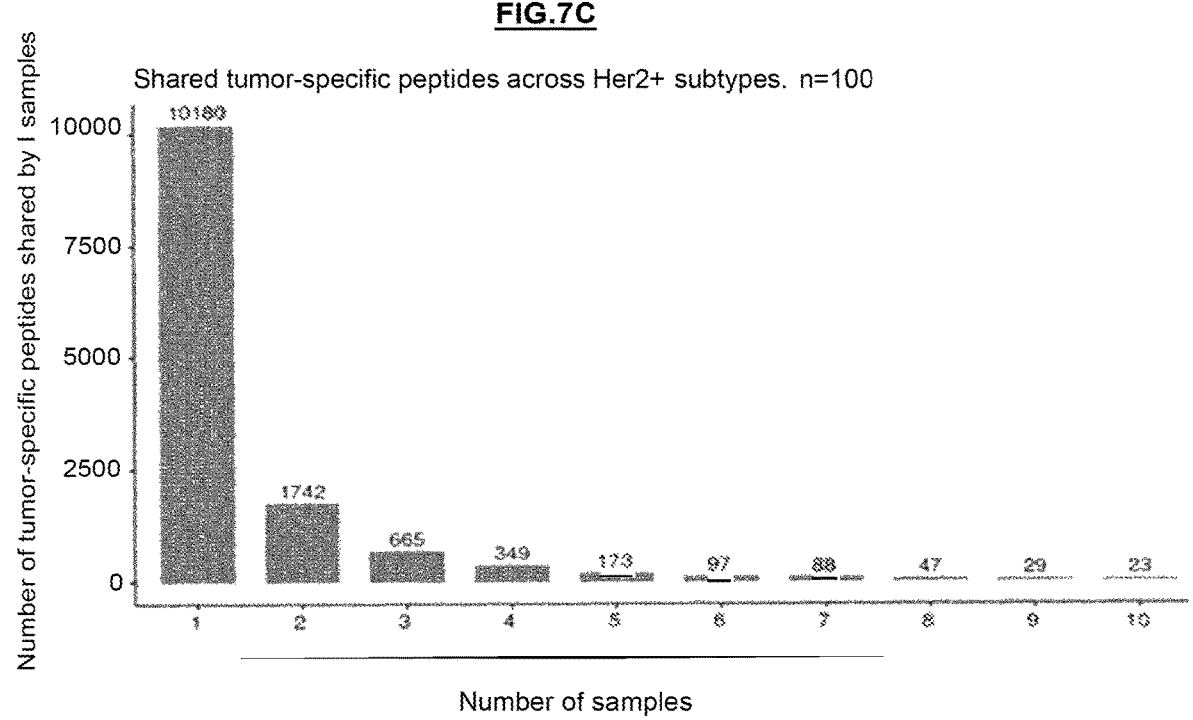
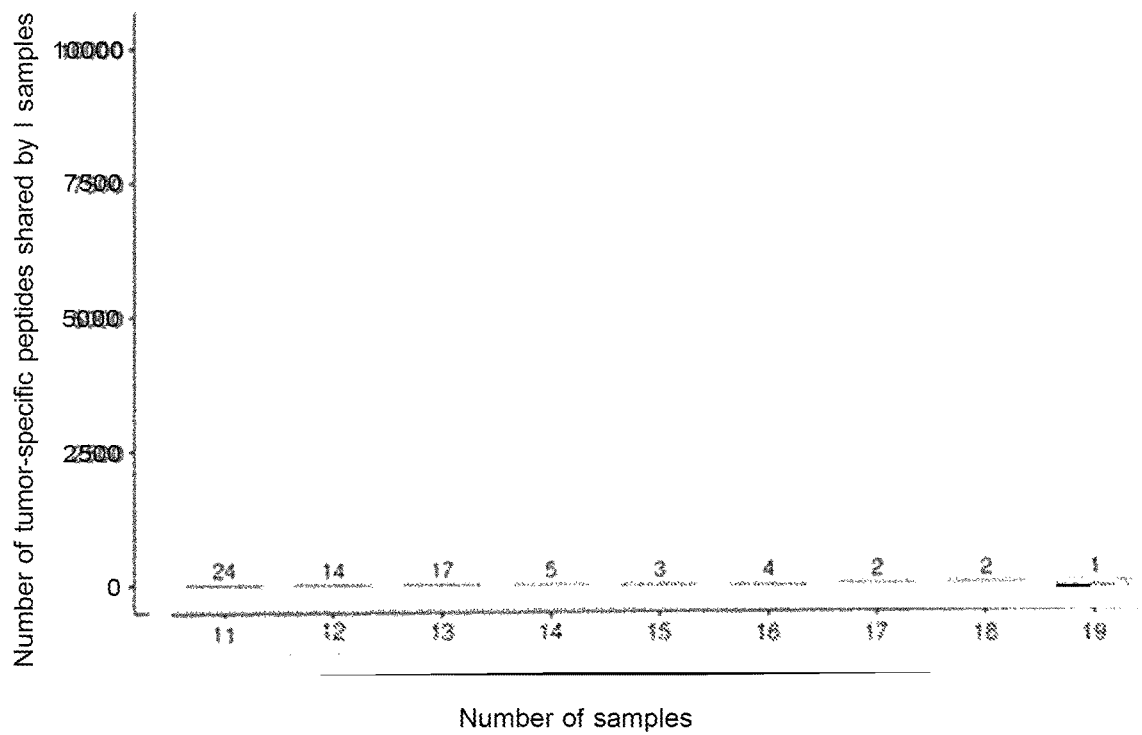
FIG.7C

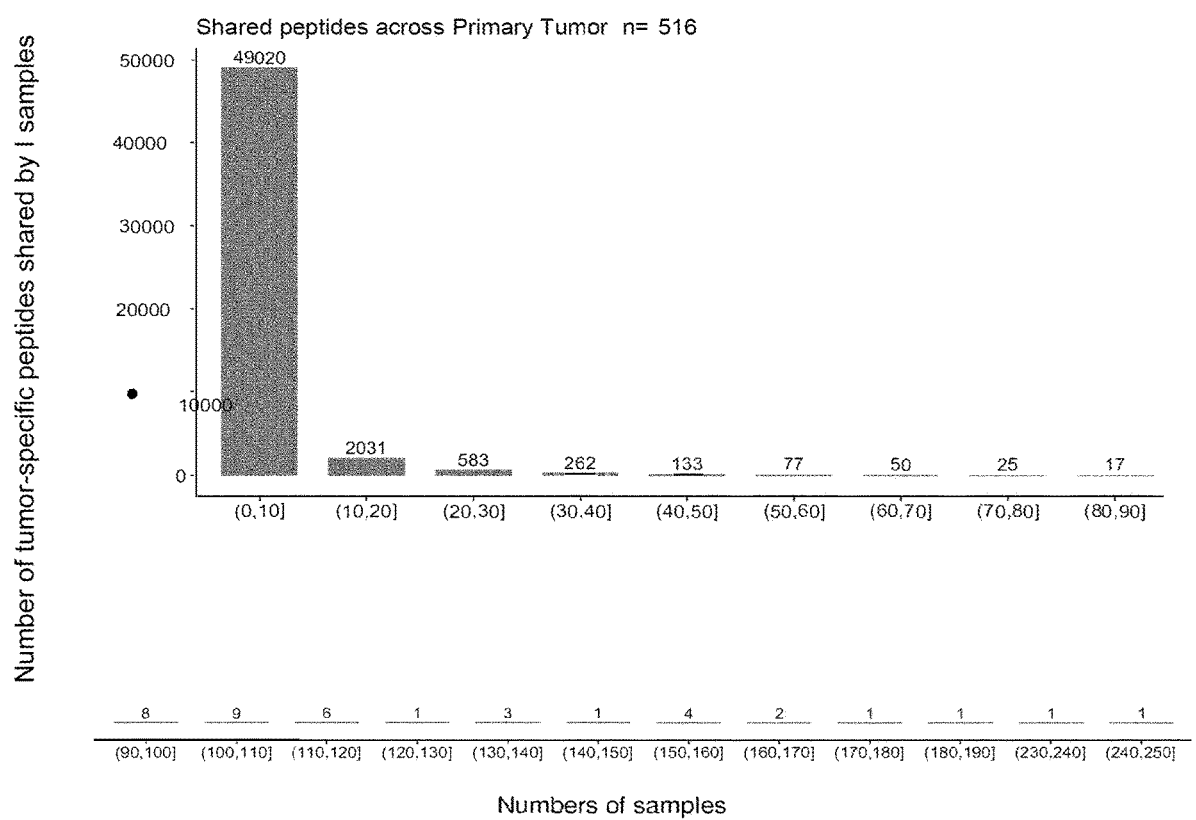

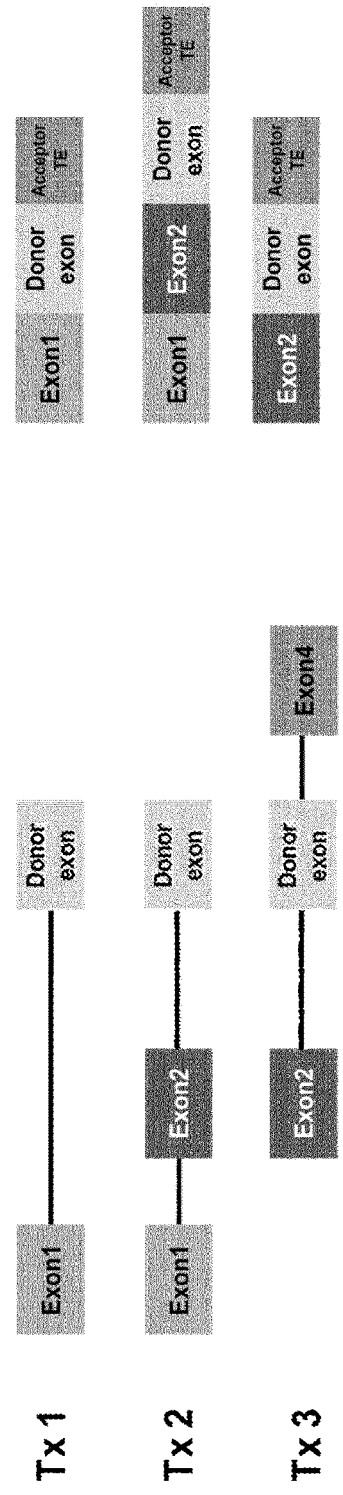

FIG. 12
Target cells: H1650
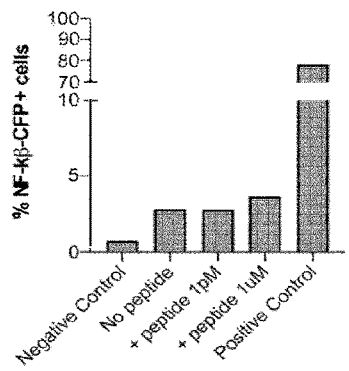
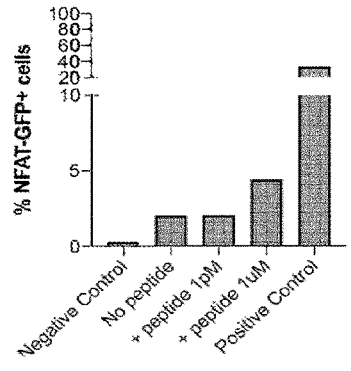
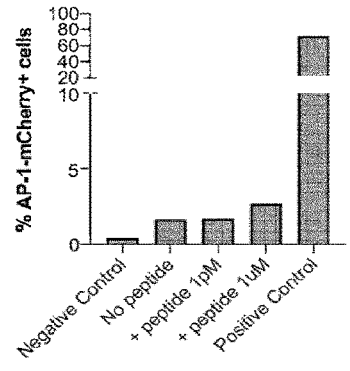
Target cells: H1395
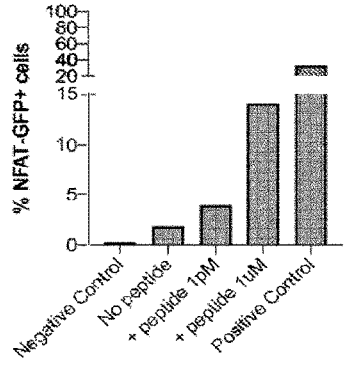
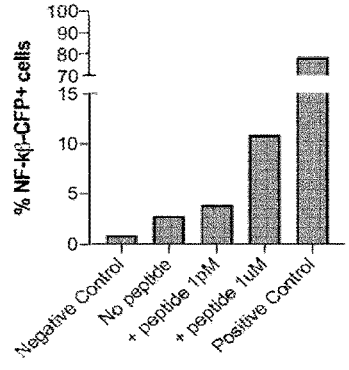
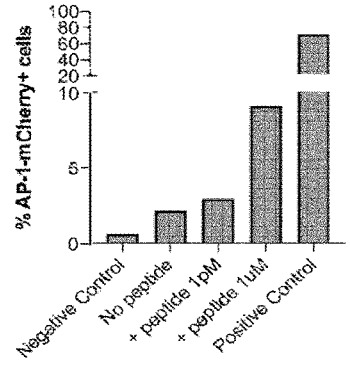

IMMUNOTHERAPY TARGETING TUMOR NEOANTIGENIC PEPTIDES

RELATED APPLICATIONS

This application is a continuation of U.S. patent application Ser. No. 17/639,568, filed Mar. 1, 2022, which is the national phase of International Patent Application No. PCT/EP2020/074429, filed Sep. 2, 2020, which claims priority to European Patent Application Nos. 19218556.9, filed Dec. 20, 2019; 19306064.7, filed Sep. 2, 2019 and 20305743.5, filed Jul. 1, 2020, all of which is hereby incorporated by reference in their entirety.

INCORPORATION BY REFERENCE OF SEQUENCE LISTING

This application includes, as a separate part of disclose, a Sequence Listing in computer-readable form (Filename: 1908CON.xml, Size: 40,972,698 bytes; Created: May 12, 2023). The contents of the Sequence Listing text file incorporated herein by reference in its entirety.

FIELD OF THE DISCLOSURE

The present disclosure provides neoantigenic peptides encoded by transposable element (TE)-exon fusion transcripts, nucleic acids, vaccines, antibodies and immune cells that can be used in cancer therapy.

BACKGROUND

Harnessing the immune system to generate effective responses against tumors is a central goal of cancer immunotherapy. Part of the effective immune response involves T lymphocytes specific for tumor antigens. T cell activation requires their interaction with antigen-presenting cells (APCs), commonly dendritic cells (DCs), expressing TCR-cognate peptides presented in the context of a major histocompatibility molecule (MHC) and co-stimulation signals. Subsequently, activated T cells can recognize peptide-MHC complexes presented by all cell types, even malignant cells. Neoplasms often contain infiltrating T lymphocytes reactive with tumor cells.

However, the efficiency of immune responses against tumors is severely dampened by various immunosuppressive strategies developed by tumors; e.g, tumor cells express receptors that provide inhibitory signals to infiltrating T cells, or they secrete inhibitory cytokines. The development of checkpoint blockade therapy has provided means to bypass some of these mechanisms, leading to more efficient killing of cancer cells. The promising results yielded by this approach have opened up new avenues for the development of T cell-based immunotherapy. Checkpoint inhibitors are, however, effective in a minority of patients and only in limited types of cancer.

A major goal in immunotherapy is to increase the proportion of responding patients and extend the cancer indications. Vaccination, administration of anti-tumor antibodies, or administration of immune cells specific for tumor antigens have all been proposed to increase the anti-tumor immune response, and can be administered alone, with other therapies such as chemotherapy or radiation, or as a combination therapy with checkpoint blockers. The selection of antigens able to trigger anti-tumor immunity without targeting healthy tissues has been a long-standing challenge.

The search for tumor neoantigens has mostly been focused on mutated sequences appearing as in cancer cells. These antigens are unique to each patient. Tumor antigens (the ones preferentially expressed in tumor cells) are, however, self-antigens that represent poor targets for vaccination (probably due to central tolerance). Identifying shared true neoantigens (absent from tissues) is a major challenge for the field.

A few prior reports regarding transposable elements (TE) in tumors include (Helman, E. et al. (2014). *Genome Res.*) (Schiavetti, F. et al. (2002). *Cancer Res.*, Takahashi, Y. et al. (2008). *J Clin. Invest.*). (Chiappinelli, K. B. et al. (2015). *Cell*, Roulois, D. et al. (2015). *Cell*). However, the relationship of TE to the antigenic landscape presented by tumor cells has not been investigated in depth.

New tumor neoantigens would be of interest and might improve or reduce the cost of cancer therapy in particular in the case of vaccination and adoptive cell therapy.

SUMMARY

The present disclosure provides a tumor neoantigenic peptide comprising at least 8 amino acids, wherein said neoantigenic peptide is encoded by a part of an open reading frame (ORF) from a fusion transcript sequence comprising a transposable element (TE) sequence and an exonic sequence.

Typically said ORF may
overlaps the junction between the TE and the exonic sequence,
be pure TE, and/or
be non-canonical.

The present disclosure also provides a method for selecting a tumor neoantigenic peptide which comprises:
a step of identifying, among mRNA sequences from cancer cells of a subject, a fusion transcript sequence comprising a transposable element (TE) sequence and exonic sequence, including an open reading frame (ORF), and
a step of selecting a tumor neoantigenic peptide of at least 8 amino acids, encoded by a part of said ORF of the fusion transcript sequence,
wherein said ORF overlaps the junction between the TE and the exonic sequence, is pure TE and/or is non-canonical, and
wherein said tumor neoantigenic peptide binds to at least one Major Histocompatibility Complex (MHC) molecule of said subject.

In one embodiment, the tumor neoantigenic peptide is 8 or 9 amino acids long, notably 8 to 11, and binds to at least one MHC class I molecule.

In another embodiment, the tumor neoantigenic peptide is from 13 to 25 amino acids long, and binds to at least one MHC class II molecule of said subject.

According to the present disclosure, "neoantigen peptide characteristics" include:
the TE sequence can be located in 5' end of the fusion transcript sequence and the exonic sequence can be located in 3' end of the fusion transcript sequence, and the part of the ORF of said fusion transcript sequence, which encodes the neoantigenic peptide, can overlap the junction;
the TE sequence can be located in 5' end of the fusion transcript sequence and the exonic sequence can be located in 3' end of the fusion transcript sequence, and the part of ORF which encodes said tumor neoantigenic peptide, can be downstream of the junction such that the open reading frame is non-canonical;

the TE sequence can be located in 3' end of the fusion transcript sequence and the exonic sequence can be located in 5' end of the fusion transcript sequence and the part of said fusion transcript sequence, which encodes the tumor neoantigenic peptide, can overlap the junction; or the TE sequence is located in 3' end of the fusion transcript sequence and the exonic sequence is located in 5' end of the chimeric transcript sequence, the part of the ORF which encodes a tumor neoantigenic peptide, is downstream of the junction between the exonic sequence and the TE sequence, optionally wherein the peptide sequence which is thus encoded by the pure TE sequence is non-canonical.

The TE sequences can be selected from the TE class I: Endogenous RetroVirus (ERVs), Long interspersed nuclear elements (LINEs) and short interspersed nuclear element (SINEs) and MaLR sequences or the DNA transposons of class II.

The present disclosure also encompasses peptides obtainable by the method as herein disclosed.

The present disclosure also provides neoantigenic peptides, comprising at least 8 amino acids and encoded by an open reading frame (ORF) of any one of the fusions transcripts of any of SEQ ID NO: 118-17492, preferably a peptide with one or more of the neoantigen peptide characteristics described above. More particularly neoantigenic peptide comprising at least 8 amino acids of any of SEQ ID NO: 1-117 are herein provided.

Said neoantigenic peptides are typically expressed at higher levels, or higher frequency, in tumor samples compared to normal, optionally said neoantigenic peptides are not expressed in normal tissue samples (i.e. normal healthy cells), or not detectably expressed in normal healthy samples.

In some embodiments said neoantigenic peptides are expressed in at least 1%, 5%, 10%, 15%, 20% 25% or even at least 30% of subjects from a population of subjects suffering from cancer and notably from a population of subjects suffering from cancer, notably from lung cancer, more particularly Non-small cell lung cancer (NSCLC), even more particularly from lung adenocarcinoma (LUAD).

Typically, the neoantigenic peptides bind MHC class I or class II with a binding affinity Kd of less than about $10^{-4}$, $10^{-5}$, $10^{-6}$, $10^{-7}$, $10^{-8}$ or $10^{-9}$ M (lower numbers indicating higher binding affinity).

Typically, the neoantigenic peptides bind MHC class I with a binding affinity of less than 2% percentile rank score predicted by NetMHCpan 4.0

Typically, the neoantigenic peptides bind MHC class II with a binding affinity of less than 10% percentile rank score predicted by NetMHCpanII 3.2.

The present disclosure also encompasses:
a population of autologous dendritic cells or antigen presenting cells that have been pulsed with one or more of the peptides as herein defined, or transfected with a polynucleotide encoding one or more of the peptides as herein described;
a vaccine or immunogenic composition, notably a sterile vaccine or immunogenic composition, capable of raising a specific T-cell response comprising
  a. one or more neoantigenic peptides as herein defined,
  b. one or more polynucleotides encoding a neoantigenic peptide as herein defined, optionally wherein the one or more polynucleotides are linked to a heterologous regulatory control nucleotide sequence; or
  c. a population of autologous dendritic cells or antigen presenting cells (notably artificial APC) that have been pulsed or loaded with one or more of the peptides as herein defined,
optionally in combination with a physiologically or pharmacologically acceptable buffer, carrier, excipient, immunostimulant and/or adjuvant.

an antibody, or an antigen-binding fragment thereof, a T cell receptor (TCR), or a chimeric antigen receptor (CAR) that has been selected for its binding affinity to a neoantigenic peptide as herein defined, or a composition comprising such antibody, antigen-binding fragment thereof, TCR or CAR.

a polynucleotide encoding a neoantigenic peptide, an antibody, a CAR or a TCR as herein defined, typically operatively linked to a heterologous regulatory control nucleotide sequence, and a vector encoding such polynucleotide, or a vaccine or immunogenic composition comprising such polynucleotide or vector;

an immune cell, or a population or immune cells that targets one or more neoantigenic peptides, as herein defined, wherein the population of immune cells preferably targets a plurality of different tumor neoantigenic peptides as herein disclosed, or a composition comprising such immune cells or population of immune cells optionally in combination with a physiologically or pharmacologically acceptable buffer, carrier, excipient, immunostimulant and/or adjuvant.

Typically, the antibody or antigen-binding fragment thereof, TCR or CAR binds a neoantigenic peptide, optionally in association with an MHC molecule, with a Kd affinity of about $10^{-6}$ M or less.

In some embodiments, the T cell receptor can be made soluble and fused to an antibody fragment directed to a T cell antigen, optionally wherein the targeted antigen is CD3 or CD16.

In some embodiments, the antibody can be a multispecific antibody that further targets at least an immune cell antigen, optionally wherein the immune cell is a T cell, a NK cell or a dendritic cell, optionally wherein the targeted antigen is CD3, CD16, CD30 or a TCR. In any of the embodiments relating to an antibody, the antibody can be chimeric, humanized, or human, and may be IgG, e.g. IgG1, IgG2, IgG3, IgG4.

The immune cell can be typically a T cell or a NK cell, a CD4+ and/or CD8+ cell, a TILs/tumor derived CD8 T cells, a central memory CD8+ T cells, a Treg, a MAIT, or a Yδ T cell. The cell can also be autologous or allogenic.

The T cell can comprises comprise a recombinant antigen receptor selected from T cell receptor and chimeric antigen receptor as herein defined, wherein the antigen is a tumor neoantigenic receptor as herein disclosed.

The present disclosure also encompasses a method of producing an antibody, TCR or CAR that specifically binds a neoantigenic peptide as herein defined and comprising the step of selecting an antibody, TCR or CAR that binds to a tumor neoantigen peptide of the present disclosure, optionally in association with an MHC or HLA molecule, optionally with a Kd binding affinity of about $10^{-6}$ M or less. Antibodies, TCRs and CARs selected by said method are also part of the present application, and thus any references to antibodies, TCRs or CARs herein also means an antibody, TCR or CAR that has been selected by said method.

A polynucleotide encoding a neoantigenic peptide as herein defined, or encoding an antibody, a CAR or a TCR as herein defined, optionally linked to a heterologous regulatory control sequence are also part of the present application.

As per the present disclosure, the neoantigenic peptide, the population of dendritic cells, the vaccine or immunogenic composition, the polynucleotide or the vector encoding the peptide can be used in cancer vaccination therapy of a subject; or for treating cancer in a subject suffering from cancer or at risk of cancer; or can be used for inhibiting proliferation of cancer cells. Typically the peptide(s) bind at least one MHC molecule of said subject.

As per the present disclosure, the antibody or the antigen-binding fragment thereof, the multispecific antibody, the TCR, the CAR, the polynucleotide, or the vector encoding such antibody, TCR or CAR, as herein defined can be used in the treatment of cancer in a subject in need thereof, the subject suffering from cancer or at risk of cancer, or can be used for inhibiting proliferation of cancer cells. Still as per the present disclosure, the population of immune cells as herein defined can be used in cell therapy of a subject suffering from cancer or at risk of cancer, or can be used for inhibiting proliferation of cancer cells.

Particularly, the neoantigenic peptide, the population of dendritic cells, the vaccine or immunogenic composition, the polynucleotide or the vector encoding the peptide, the antibody or the antigen-binding fragment thereof, the multispecific antibody, the TCR, the CAR, the polynucleotide, or the vector encoding such antibody, TCR or CAR or the population of immune cells (collectively referenced herein as the "Cancer Therapeutic Products") are used in the treatment of a subject who is suffering from NSCLC or who is at risk of suffering from NSCLC and/or in the treatment of NSCLC.

Pharmaceutical compositions comprising any of the foregoing, optionally with a sterile pharmaceutically acceptable excipient(s), carrier, and/or buffer are also contemplated as well as methods of using them.

In any of the embodiments described herein, the Cancer Therapeutic Products as above defined can be administered in combination with at least one further therapeutic agent. Such further therapeutic agent can typically be a chemotherapeutic agent, or an immunotherapeutic agent.

For example, according to the present disclosure, any of the Cancer Therapeutic Products can be administered in combination with an anti-immunosuppressive/immunostimulatory agent. For example, the subject is further administered with one or more checkpoint inhibitors typically selected from PD-1 inhibitors, PD-L1 inhibitors, Lag-3 inhibitors, Tim-3 inhibitors, TIGIT inhibitors, BTLA inhibitors, V-domain Ig suppressor of T-cell activation (VISTA) inhibitors and CTLA-4 inhibitors, or IDO inhibitors.

Various embodiments of the methods, neoantigenic peptides and Cancer Therapeutic Products are described in detailed below. Except for alternatives clearly mentioned, combinations of such embodiments are encompassed by the present application.

DETAILED DISCLOSURE

Transposable elements (TEs) expression in normal tissues is silenced by DNA methylation established early during embryonic development. An additional layer of inhibition is provided by histone modifications. TEs can be re-activated in tumor cells.

The Inventors have developed a method for selecting a tumor neoantigenic peptide encoded by a fusion transcript sequence comprising a part of a TE sequence and a part of an exonic sequence.

The neoantigenic tumor specific peptides identified by the method according to the present disclosure are highly immunogenic. Indeed, because they are derived from a fusion transcripts (composed of a transposable element, TE, and an exonic sequence) absent from normal cells, the peptides of the present disclosure are expected to exhibit very low immunological tolerance.

The present disclosure also allows selecting peptides having shared tumor neoepitopes among a population of patients. Such shared tumor peptides are of high therapeutic interest since they may be used in immunotherapy for a large population of patients.

Definitions

According to the present disclosure, the term "disease" refers to any pathological state, including cancer diseases, in particular those forms of cancer diseases described herein.

The term "normal" refers to the healthy state or the conditions in a healthy subject or tissue, i.e., non-pathological conditions, wherein "healthy" preferably means non-cancerous.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not.

Malignant tumor is essentially synonymous with cancer. Malignancy, malignant neoplasm, and malignant tumor are essentially synonymous with cancer.

As used herein, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease.

Tumors show partial or complete lack of structural organization and functional coordination with the normal tissue, and usually form a distinct mass of tissue, which may be either benign, pre-malignant or malignant.

A benign tumor is a tumor that lacks all three of the malignant properties of a cancer. Thus, by definition, a benign tumor does not grow in an unlimited, aggressive manner, does not invade surrounding tissues, and does not spread to non-adjacent tissues (metastasize).

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

"Growth of a tumor" or "tumor growth" according to the present disclosure relates to the tendency of a tumor to increase its size and/or to the tendency of tumor cells to proliferate.

For purposes of the present disclosure, the terms "cancer" and "cancer disease" are used interchangeably with the terms "tumor" and "tumor disease".

Cancers are classified by the type of cell that resembles the tumor and, therefore, the tissue presumed to be the origin of the tumor. These are the histology and the location, respectively.

According to the present application, cancer may affect any one of the following tissues or organs: breast; liver; kidney; heart, mediastinum, pleura; floor of mouth; lip; salivary glands; tongue; gums; oral cavity; palate; tonsil; larynx; trachea; bronchus, lung; pharynx, hypopharynx, oropharynx, nasopharynx; esophagus; digestive organs such as stomach, intrahepatic bile ducts, biliary tract, pancreas, small intestine, colon; rectum; urinary organs such as bladder, gallbladder, ureter; rectosigmoid junction; anus, anal canal; skin; bone; joints, articular cartilage of limbs; eye and adnexa; brain; peripheral nerves, autonomic nervous system; spinal cord, cranial nerves, meninges; and various parts of the central nervous system; connective, subcutaneous and other soft tissues; retroperitoneum, peritoneum; adrenal gland; thyroid gland; endocrine glands and related structures; female genital organs such as ovary, uterus, cervix uteri; corpus uteri, vagina, vulva; male genital organs such as penis, testis and prostate gland; hematopoietic and reticuloendothelial systems; blood; lymph nodes; thymus.

The term "cancer" according to the disclosure therefore comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the present disclosure also comprises cancer metastases and relapse of cancer.

The main types of lung cancer are small cell lung carcinoma (SCLC) and non-small cell lung carcinoma (NSCLC). There are three main sub-types of the non-small cell lung carcinomas: squamous cell lung carcinoma, lung adenocarcinoma (LUAD), and large cell lung carcinoma. Adenocarcinomas account for approximately 10% of lung cancers. This cancer usually is seen peripherally in the lungs, as opposed to small cell lung cancer and squamous cell lung cancer, which both tend to be more centrally located.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the present disclosure relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the present disclosure, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject. In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The therapeutically active agents, vaccines and compositions described herein may be administered via any conventional route, including by injection or infusion.

The agents described herein are administered in effective amounts. An "effective amount" refers to the amount which achieves a desired reaction or a desired effect alone or together with further doses or together with further therapeutic agents. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent described herein will depend on the condition to be treated, the severity of the disease, the individual parameters of the patient, including age, physiological condition, size and weight, the duration of treatment, the type of an accompanying therapy (if present), the specific route of administration and similar factors.

Accordingly, the doses administered of the agents described herein may depend on various of such parameters. In the case that a reaction in a patient is insufficient with an initial dose, higher doses (or effectively higher doses achieved by a different, more localized route of administration) may be used.

The pharmaceutical compositions as herein described are preferably sterile and contain an effective amount of the therapeutically active substance to generate the desired reaction or the desired effect.

The pharmaceutical compositions as herein described are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible.

In the present application, the terms "fusion transcript" or "chimeric transcripts" are used indifferently as synonyms. A "fusion or a chimeric" "transcript or sequence", as per the present disclosure is defined as a transcript that aligns in part with an exon sequence and in part with a transposable element (TE) sequence and has a normalized number of read greater than $2.10^{-6}$. The normalized number of reads is defined as the number of reads that cover the fusion divided by the library size of the sample.

Unless specifically stated or obvious from context, as used herein, the term "about" is to be understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

A "transposable element" is to be understood as both class I (retrotransposons, including those containing LTRs, LINEs and SINEs) and class II (DNA transposons) endogenously part of the genome (i.e.: not from infection). This includes both autonomous and non-autonomous elements from both classes. According to the present disclosure the TE sequences can be for example selected from TE of class I, such as retrotransposons including Endogenous RetroVirus (ERVs), Long interspersed nuclear elements (LINEs) and short interspersed nuclear element (SINEs) and mammalian long terminal repeat transposon (MaLR), and TE of class II, such as DNA transposons endogenously part of the genome.

A reading frame is a way of dividing the sequence of nucleotides in a nucleic acid (DNA or RNA) molecule into a set of consecutive, non-overlapping triplets.

An open reading frame (ORF) is the part of a reading frame that has the ability to be translated into a peptide. An ORF is a continuous stretch of codons that contain a start codon (for example AUG) at a transcription starting site (TSS) and a stop codon (for example UAA, UAG or UGA). An ATG codon within the ORF (not necessarily the first) may indicate where translation starts. The transcription termination site is located after the ORF, beyond the translation stop codon. In eukaryotic genes with multiple exons, ORFs span intron/exon regions, which may be spliced together after transcription of the ORF to yield the final mRNA for protein translation.

A "canonical ORF" as herein intended is a protein coding sequence with specified reading frame within a mRNA sequence which is described or annotated in databases such as for example Ensembl genome/transcriptome/proteome database collection (typically HG19). Typically, a canonical ORF is the same as one of the exons in normal healthy cells.

A "non-canonical ORF" as herein intended is a protein coding sequence with specified reading frame within a mRNA sequence which is not described (i.e. unannotated) in genome databases such as for example in Ensembl genome/transcriptome/proteome database. Typically a non-canonical ORF means thus that the reading frame is shifted compared to the usual reading frame of exons in normal healthy cells. In some embodiments however, a non-canonical can be described in genome databases (such as Ensembl database), but the mRNA sequence represents minor species in normal cells. By minor species it is typically intended less that 5%, notably less than 2%, or preferentially less than 1% species in normal cells.

An exon is any part of a gene that will encode a part of the final mature RNA produced by that gene after introns have been removed by RNA splicing. The term exon refers to both the DNA sequence within a gene and to the corresponding sequence in RNA transcripts. In RNA splicing, introns are removed and exons are covalently joined to one another as part of generating the mature messenger RNA. An exonic sequence as per the present applicant comprises at least a portion of one or more exon. Typically, the exonic sequence comprises at least a portion of one or 2 exons.

Thus, the untranslated sequences in 3'end and in 5' end (3'UTR and 5'UTR) present in mature RNA after splicing are exonic sequences, but are non-coding sequences because these sequences are located upstream of the start codon for the translation (5'UTR) or downstream of the stop codon ending the translation (3'UTR).

The term "peptide or polypeptide," is used interchangeably with "neoantigenic peptide or polypeptide" in the present specification to designate a series of residues, typically L-amino acids, connected one to the other, typically by peptide bonds between the α-amino and carboxyl groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

A "reference genome, or "representative genome" is a digital nucleic acid sequence data base, assembled by scientists as a representative example of species set of genes. As they are often assembled from the sequencing of DNA from a number of donors, reference genomes do not accurately represent the set of genes of any single individual (animal or person). Instead a reference provides a haploid mosaic of different DNA sequences from each donor.

Method for Selecting a Tumor Neoantigenic Peptide

The method for selecting a tumor neoantigenic peptide as per the present disclosure comprises
  a step of identifying, among mRNA sequences from a cancer cell sample of a subject, a fusion transcript sequence comprising a transposable element (TE) sequence and an exonic sequence, and including an open reading frame (ORF), and
  a step of selecting a tumor neoantigenic peptide of at least 8 amino acids, encoded by a part of said ORF of the fusion transcript sequence,
wherein said ORF overlaps the junction between the TE and the exonic sequence, is pure TE and/or is non-canonical, and wherein said tumor neoantigenic peptide binds to at least one Major Histocompatibility Complex (MHC) molecule of said subject.

Typically, a peptide translated from a part of non-canonical ORF of an exonic sequence is recognized as non-self by the immune system.

In some embodiments, the exonic sequence is from oncogene and/or a tumor suppressor gene and their mutated variants.

Conceptually, cancer is a result of consecutive somatic mutation accumulation. Many studies have shown that both the gain of function in oncogenes and the loss of function in tumor-suppressor genes are required for the development of cancer from a normal cell. For a diploid organism, gain-of-function mutations are often dominant or semi-dominant, whereas loss-of-function mutations are usually recessive. Two-hit hypothesis of oncogenesis proposes that the development of cancer is initiated by the loss of both alleles of a tumor-suppressor gene.

Oncogenes (also named cancer genes) are genes whose action positively promotes cell proliferation or growth. The normal nonmutant versions are known as proto-oncogenes. The mutant versions are excessively or inappropriately active leading to tumor growth. Oncogenes can be identified in the Cancer Gene Marker Database (CGMD) (Pradeepkiran, J., Sainath, S., Kramthi Kumar, K. et al. CGMD: Sci Rep 5, 12035 (2015) "*An integrated database of cancer genes and markers*"). Oncogenes (ONCs) can also be downloaded from Network of Cancer Genes database (NCG 5.0) (An O, Dall'Olio G M, Mourikis T P, Ciccarelli F D, Nucleic Acids Res. 2016 Jan. 4: 44 (D1): D992-9: "*NCG 5.0: updates of a manually curated repository of cancer genes and associated properties from cancer mutational screenings*"). Non-limitatives examples of oncogenes include: L-MYC, LYL-1, LYT-10, LYT-10/Cα1, MAS, MDM-2, MLL, MOS, MTG8 AML1, MYB, MYH11/CBFB, NEU, N-MYC, OST, PAX-5, PBX1/E2A, PIM-1, PRAD-1, RAF, RAR/PML, RAS-H, RAS-K, RAS-N, REL/NRG, RET, RHOM1, RHOM2, ROS, SKI, SIS, SET CAN, SRC, TAL1, TAL2, TAN-1, TIAM1, TSC2, and TRK.

Tumor suppressor genes (also named anti-oncogenes) represent the opposite side of cell growth control, normally acting to inhibit cell proliferation and tumor development. Thus tumor suppressor genes are genes that normally suppress cell division or growth. Loss of TSG function promotes uncontrolled cell division and tumor growth. Rb, a tumor suppressor gene that was identified by the genetic analysis of retinoblastoma an encoding a transcriptional regulatory protein, served as the prototype for the identification of additional tumor suppressor genes that contribute to the development of many different human cancers. Tumor suppressor genes are notably described in "Cooper G M. The Cell: A Molecular Approach. 2nd edition. Sunderland (MA): Sinauer Associates: 2000. Tumor Suppressor Genes". Tumor-suppressor genes (TSGs) can also be downloaded from Tumor Suppressor Gene database (TSGene 2.0) (see for reference Zhao M, Kim P, Mitra R, Zhao J, Zhao Z: Nucleic Acids Res. 2016 Jan. 4: 44 (D1): D1023-31: "*TSGene 2.0: an updated literature-based knowledgebase for tumor suppressor genes*"). In this context, non-limitative examples of tumor suppressor genes include: APC, BRCA1, BRCA2, DPC4, INK4, MADR2, NF1, NF2, p53, PTC, PTEN, Rb, RB1, VHL, WT1, BUB1, BUBR1, TGF-βRII, Axin, DPC4, p300, PPARγ, p16, DPC4, PTEN, and hSNF5.

Oncogenes, tumor suppressor genes or "double agent" genes (with both oncogenic and tumor-suppressor functions) can be systematically identified through database search and text mining. Indeed, information on oncogenes or tumor suppressor genes can typically be found in Ensembl database (but see also Shen L, Shi Q, Wang W. Double agents: genes with both oncogenic and tumor-suppressor functions. Oncogenesis. 2018: 7 (3): 25. Published 2018 Mar. 13). Double agent genes may be identified as genes overlapped between the two above mentioned databases (see also Shen et al., Oncogenesis 2018 above).

Without to be bound by any theory, the inventors believe that selection of fusion wherein the exonic sequence is from an oncogene and/or a tumor suppressor gene is of high relevance for the reason below:

TE insertion in oncogenes can alter their oncogenic activity. Insertion of TE sequences in oncogene active domains could therefore result in constitutive activity of the oncogenes, similar to driver mutations. These fusions giving chimeric oncogenes could thus represent a new family of oncogenic proteins. If this is the case, targeting the activity of these new "fusion oncogenes" with small molecule antagonists could represent a potential therapeutic approach for cancer where these chimeric oncogenes are expressed.

TE insertions in tumor suppressors could inactivate their suppressor functions, leading typically to a loss of function (for example through introduction of stop codons, changes in ORF or disruptive amino acid stretches), thereby contributing to the oncogenic process.

Fusions implicating cancer driver genes would be excellent targets for adoptive cell therapies, antibodies, ADCs, T cell engagers, etc. If they are involved in oncogenesis, fusions oncogenes are expected to be more specific for cancer cells, and thus to reduce the development of resistances (because of the oncogenic activity of the target).

In one embodiment, the TE sequence is located in 5' end of the fusion transcript sequence (it is also said that the TE sequence is the donor sequence) and the exonic sequence is located in 3' end of the fusion transcript sequence with respect to the junction (the exon sequence is thus called an acceptor sequence). The expression "is located in 5' end of the fusion transcript sequence" means that the element is located upstream of the junction in the fusion transcript sequence. The expression "is located in 3' end of the fusion transcript sequence" means that the element is located downstream of the junction in the fusion transcript sequence.

In a particular embodiment, the TE sequence is located in 5' end of the fusion transcript sequence and the exonic sequence is located in 3' end of the fusion transcript sequence, and the part of the ORF of said fusion transcript sequence, which encodes the neoantigenic peptide, overlaps the junction. In this case, the ORF can be canonical or non-canonical. It is understood that the ORF may comprise the junction but the neoantigenic peptide need not comprise the junction. In some embodiments, where the neoantigenic peptide comprises the junction, the obtained peptide is encoded by both TE sequence and exonic sequence.

The expression "the part of the ORF is overlapping or overlaps the junction between the TE sequence and the exonic sequence", means that said junction is contained in the part of the ORF of the fusion transcript sequence, which encodes said neoantigenic peptide.

In embodiments wherein (i) the part of the ORF encoding the neoantigenic peptide is overlapping the junction between the TE sequence and the exonic sequence, and (ii) the TE sequence and the exonic sequence are respectively in 5' end and 3'end of the fusion transcript sequence, said part of the ORF typically encodes a neoantigenic peptide of at least 8 amino acids, including at least between 1 to 6 amino acids, notably 2 to 6 from the TE sequence and at least between 1 and 6, notably 2 to 6 amino acids from the exonic sequence.

In another embodiment wherein the TE sequence is located in 5' end of the fusion transcript sequence and the exonic sequence is located in 3' end of the fusion transcript sequence, the part of ORF which encodes said neoantigenic peptide, is downstream of the junction and the ORF is thus non-canonical.

The expression "the part of the ORF is downstream of the junction" means that the part of the ORF encoding the neoantigenic peptide is not overlapping the junction, but it is contained in the 3'end part of said fusion transcript sequence with respect to the junction. In this embodiment, as the 3' end part with respect to the junction, is the exonic sequence, the part of the ORF encoding the neoantigenic peptide is thus contained in the exonic sequence. Thus, as the part of the ORF is only located in the exonic sequence, the obtained peptide is therefore encoded by the exonic sequence, in a non-canonical ORF. Thus, in the particular embodiment wherein the exonic sequence is located in 3' end of the fusion transcript sequence with respect to the junction, and wherein the part of the ORF which encodes the neoantigenic peptide is downstream of the junction with a non-canonical reading frame, the part of the ORF of the fusion transcript sequence encodes a neoantigenic peptide including 0 amino acid from the TE sequence, and at least 8 amino acids from the exonic sequence.

In another embodiment, the TE sequence is located in 3' end of the fusion transcript sequence and the exonic sequence is located in 5' end of the fusion transcript sequence with respect to the junction.

In some embodiments, the TE sequence is located in 3' end of the fusion transcript sequence and the exonic sequence is located in 5' end of the fusion transcript sequence and the part of the ORF of said fusion transcript sequence, which encodes a neoantigenic peptide, is overlapping the junction between the TE sequence and the exonic sequence. In this case, the ORF can also be canonical or non-canonical. The obtained peptide is encoded by both TE sequence and exonic sequence.

In the particular embodiment wherein the part of the ORF encoding the neoantigenic peptide, is overlapping the junction between the exonic sequence and the TE sequence, and wherein the exonic sequence and the TE sequence are respectively in 5' end and 3'end of the fusion transcript sequence, said part of the ORF encodes a neoantigenic peptide of at least 8 amino acids, including at least between 1 to 6, notably 2 to 6 amino acids from the TE sequence and at least between 1 and 6, notably 2 to 6 amino acids from the exonic sequence.

In still another embodiment, the TE sequence is located in 3' end of the fusion transcript sequence, the exonic sequence is located in 5' end of the fusion transcript sequence, and the part of the ORF which encodes a neoantigenic peptide, is downstream of the junction between the exonic sequence and the TE sequence. Optionally, the peptide sequence which is thus encoded by the pure TE sequence is non-canonical.

In this embodiment, as the 3' end part with respect to the junction is the TE sequence, the part of the ORF encoding the neoantigenic peptide is therefore encoded by the TE sequence. Thus, the part of the ORF encodes a neoantigenic peptide including no amino acid from the exonic sequence and at least 8 amino acids from the TE sequence. In the particular embodiment wherein the TE sequence is located in 3' end of the fusion transcript sequence with respect to the junction, and the part of the ORF which encodes the neoantigenic peptide is downstream the junction, the part of the ORF of the fusion transcript sequence encodes a neoantigenic peptide including 0 amino acid from the exonic sequence, and at least 8 amino acids from the TE sequence.

A tumor neoantigenic peptide is a peptide that arises from somatic alterations (classically mutations in the DNA sequence), is recognized as different from self, and is presented by antigen-presenting cells (APC), such as dendritic cells (DC) and tumor cells themselves. Cross-presentation plays an important role as the APC is able to translocate exogenous antigens from the phagosome into the cytosol for proteolytic cleavage into the major histocompatibility complex I (MHC I) epitopes by the proteasome.

In the present disclosure the alteration corresponds to the transcription of fusion mRNA sequences that comprise a transposable element (TE) sequence and an exonic sequence. This may arise from somatic (i.e.: specifically in the tumor clone) transposition. It may also arise not from de novo transposition but from tumor specific transcriptional de-repression such that a TE and nearby gene are co-transcribed.

A neoantigenic peptide according to the present disclosure may be completely absent from normal healthy samples (i.e., not expressed in normal healthy samples) and thus be specific to tumor samples. Alternatively, it may be expressed at low levels in normal cells and/or disproportionately expressed on tumor samples as compared to normal (healthy) samples.

It can also be selectively expressed by the cell lineage from which the cancer evolved.

Cancer or tumor samples according to the present disclosure can be isolated from any solid tumor or non-solid tumor of any of the tissues or organs as defined previously, for example, breast cancer, lung cancer and/or melanoma. In some embodiments cancer samples are from Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma or Uveal Melanoma samples. In a particular embodiment, cancer samples are from lung cancer samples, notably from LUAD samples.

Typically as per the present disclosure, the step of identifying said fusion transcript sequence is carried out by mapping mRNA sequences from cancer sample against a reference genome, and then distinguishing normal and abnormal junctions.

According to the present disclosure, normal junctions correspond to junctions donor and acceptor on the same strand and not too far apart (e.g.: not on different chromosomes).

According to the present disclosure, abnormal junctions correspond to junctions between donor and acceptor sequences on different chromosomes, or in cis but on different strands (no matter the order and the 5'-3' sense).

In one embodiment, the mRNA sequences can be mapped against a corresponding reference genome, with an adapted software, such as for example: Spliced Transcripts Alignment to a Reference (i.e.: STAR-see Dobin, Alexander et al. "STAR: ultrafast universal RNA-seq aligner." Bioinformatics (Oxford, England) vol. 29.1 (2013): 15-21), TopHat2 (Kim, Daehwan et al. "TopHat2: accurate alignment of transcriptomes in the presence of insertions, deletions and gene fusions." Genome biology vol. 14.4 R36. 25 Apr. 2013, doi: 10.1186/gb-2013-14-4-r36) or HISAT (Kim, Daehwan et al. "HISAT: a fast spliced aligner with low memory requirements." Nature methods vol. 12.4 (2015): 357-60. doi: 10.1038/nmeth.3317). STAR is a standalone software that uses sequential maximum mappable seed search followed by seed clustering and stitching to align RNA-seq reads. It is able to detect canonical junctions, non-canonical splices, and fusion/chimeric transcripts.

In a particular embodiment, the normal and abnormal junctions are determined in silico using dedicated databases, such as for example Ensembl and Repeatmasker databases, and the fusion transcripts having junctions between a TE and an exonic sequence are extracted in silico.

According to the present disclosure, the mRNA sequences can come from all types of cancer cell or tumor cell sample(s). The tumor may be a solid or a non-solid tumor. In particular, the mRNA sequences come from any tissues or organs affected by a cancer or tumor as previously defined, for example from breast cancer, lung cancer and/or melanoma. In a particular embodiment, mRNA sequences are from LUAD samples.

Typically, as per the present disclosure, the fusion transcript sequences are shared in more than 1%: notably more than 5%, more than 10%, more than 15%, more than 20% or even more than 25% of the cancer samples. In other words, a fusion transcript sequence as per the present disclosure is shared in cancer samples from more than 1%: notably more than 5%, more than 10%, more than 15%, more than 20% or even more than 25% of the subjects suffering from a cancer. The fusion transcript sequence may thus be specific for a cancer type of shared between several cancers.

According to the present disclosure, the fusion transcript sequences are expressed at higher levels in tumor cells compared to normal healthy cells. In some embodiments, the fusion transcript sequence is expressed in cancer cells and not in healthy cells, in particular not in thymus healthy cells. Such fusion transcript may be called tumor specific fusion as per the present disclosure. Fusion transcripts that are expressed at higher level(s) in tumor cells as compared to normal cell, typically that are disproportionally expressed in cancers cells as compared to normal cells as defined above may be called tumor associated fusion transcripts (TAF) as per the present disclosure. Tumor associated fusion transcripts may be selected according to the present application if they are present in more than 10% of the tumor samples and in less than 20% of the normal samples.

In some embodiments, the method further comprises a step of determining, optionally in silico or using in vitro techniques (see notably the example for illustration), the binding affinity of the tumor neoantigenic peptide with at least one MHC molecule of the said subject suffering from a cancer.

MHC class I proteins form a functional receptor on most nucleated cells of the body. There are 3 major MHC class I genes in HLA: HLA-A, HLA-B, HLA-C and three minor genes HLA-E, HLA-F and HLA-G. B2-microglobulin binds with major and minor gene subunits to produce a heterodimer. MHC molecules of class I consist of a heavy chain and a light chain and are capable of binding a peptide of about 8 to 11 amino acids, but usually 8 or 9 amino acids, if this peptide has suitable binding motifs, and presenting it to cytotoxic T-lymphocytes. The binding of the peptide is stabilized at its two ends by contacts between atoms in the main chain of the peptide and invariant sites in the peptide-binding groove of all MHC class I molecules. There are invariant sites at both ends of the groove which bind the amino and carboxy termini of the peptide. Variations in peptide length are accommodated by a kinking in the peptide backbone, often at proline or glycine residues that allow the required flexibility. The peptide bound by the MHC molecules of class I usually originates from an endogenous protein antigen. As an example, the heavy chain of the MHC molecules of class I is typically an HLA-A, HLA-B or HLA-C monomer, and the light chain is $\beta$-2-microglobulin, in humans.

There are 3 major and 2 minor MHC class II proteins encoded by the HLA. The genes of the class II combine to form heterodimeric ($\alpha\beta$) protein receptors that are typically expressed on the surface of antigen-presenting cells. The peptide bound by the MHC molecules of class II usually originates from an extracellular or exogenous protein antigen. As an example, the $\alpha$-chain and the $\beta$-chain are in particular HLA-DR, HLA-DQ and HLA-DP monomers, in humans. MHC class II molecules are capable of binding a peptide of about 8 to 20 amino acids, notably from 10 to 25 or from 13 to 25 if this peptide has suitable binding motifs and presenting it to T-helper cells. These peptides lie in an extended conformation along the MHC II peptide-binding groove which (unlike the MHC class I peptide-binding groove) is open at both ends. The peptide is held in place mainly by main-chain atom contacts with conserved residues that line the peptide-binding groove.

When the method is carried out on human samples, the method may comprise a step of determining the patient's class I or class I Major Histocompatibility Complex (MHC, aka human leukocyte antigen (HLA) alleles). It is to be noticed that as MHC alleles for laboratory mice are generally known such that this step may not be necessary in that particular context. In the present application, "MHC molecule" refers to at least one MHC class I molecule or at least one MHC Class II molecule.

A MHC allele database is carried out by analyzing known sequences of MHC I and MHC II and determining allelic variability for each domain. This can be typically determined in silico using appropriate software algorithms well-known in the field. Several tools have been developed to obtain HLA allele information from genome-wide sequencing data (whole-exome, whole-genome, and RNA sequencing data), including OptiType, Polysolver, PHLAT, HLAreporter, HLAforest, HLAminer, and seq2HLA (see Kiyotani K et al., Immunopharmacogenomics towards personalized cancer immunotherapy targeting neoantigens: Cancer Science 2018:109:542-549). For example, the seq2hla tool (see Boegel S. Lower M, Schafer M, et al. HLA typing from RNA-Seq sequence reads. Genome Med. 2012:4:102), which is well designed to perform the method as herein disclosed is an in silico method written in python and R, which takes standard RNA-Seq sequence reads in fastq format as input, uses a bowtie index (Langmead B, et al., Ultrafast and memory-efficient alignment of short DNA sequences to the human genome. Genome Biol. 2009, 10: R25-10.1186/gb-2009-10-3-r25) comprising all HLA alleles and outputs the most likely HLA class I and class II genotypes (in 4 digit resolution), a p-value for each call, and the expression of each class.

Typically, the sequences having junctions between a TE and an exonic sequence are extracted in silico. The affinity of all possible peptides encoded by each sequence for each MHC allele from the patient (or mouse) can be for example determined in silico using computational methods to predict peptide binding-affinity to HLA molecules. Indeed, accurate prediction approaches are based on artificial neural networks with predicted $IC_{50}$. For example, NetMHCpan software which has been modified from NetMHC to predict peptides binding to alleles for which no ligands have been reported, is well appropriate to implement the method as herein disclosed (Lundegaard C et al., NetMHC-3.0: accurate web accessible predictions of human, mouse and monkey MHC class I affinities for peptides of length 8-11: Nucleic Acids Res. 2008:36:W509-W512: Nielsen M et al. NetMHCpan, a method for quantitative predictions of peptide binding to any HLA-A and -B locus protein of known sequence. PLOS One. 2007:2:e796, but see also Kiyotani K et al., Immunopharmacogenomics towards personalized cancer immunotherapy targeting neoantigens: Cancer Science 2018:109: 542-549 and Yarchoan M et al., Nat rev. cancer 2017: 17 (4): 209-222). NetMHCpan software predicts binding of peptides to any MHC molecule of known sequence using artificial neural networks (ANNs). The method is trained on a combination of more than 180,000 quantitative binding data and MS derived MHC eluted ligands. The binding affinity data covers 172 MHC molecules from human (HLA-A, B, C, E), mouse (H-2), cattle (BoLA), primates (Patr, Mamu, Gogo) and swine (SLA). The MS eluted ligand data covers 55 HLA and mouse alleles.

In example embodiments, neoantigenic peptides encoded by fusion transcripts as above described and a Kd affinity of predicted peptides for MHC alleles of less than $10^{-4}$, $10^{-5}$, $10^{-6}$, $10^{-7}$ M or less than 500 nM, notably less than 50 nM are selected as tumor neoantigenic peptides.

As above mentioned, affinity of the selected peptide for MHC alleles can be determined in silico using appropriate software such as netMHCpan. Thus, in some embodiments, neoantigenic peptides bind MHC class I with a binding affinity of less than 2% percentile rank score predicted by NetMHCpan 4.0. In other embodiments, the neoantigenic peptides bind MHC class II with a binding affinity of less than 10% percentile rank score predicted by NetMHCpanII 3.2.

Affinity can also (alternatively or in addition) be estimated in vitro, for example using MHC tetramer formation assay as described in the results included therein (see example 2, point 2.1 and 2.2.2). Commercial assays for example from ImmunAware® can typically be used by the skilled person (EasYmers R; kits are from ImmunAware®; are notably used according to their training guide). Typically, binding affinity is determined as a percentage of binding to a positive control. Generally, peptides showing a percentage of binding of at least 30%, notably at least 40% or even at least 50% of the positive control are selected. Typically, the neoantigenic peptide as per the present disclosure, and typically obtainable as per the present method, binds at least one HLA/MHC molecule with an affinity sufficient for the peptide to be presented on the surface of a cell as an antigen. Generally, the neoantigenic peptide has an IC50 affinity of less than $10^{-4}$, or $10^{-5}$, or $10^{-6}$, or $10^{-7}$ or less than 500 nM, at least less than 250 nM, at least less than 200 nM, at least less than 150 nM, at least less than 100 nM, at least less than 50 nM or less for at least one HLA/MHC molecule (lower numbers indicating greater binding affinity), typically a molecule of said subject suffering from a cancer.

Further optional steps according to the present method may thus independently include:
- a step of exclusion of fusion transcripts or predicted peptides expressed at high levels or high frequency on healthy cells. An alignment of the fusion transcript sequence against the RNAseq data of healthy cells, typically allows determining the relative amount of fusion transcript sequence(s) present in healthy cells: In one embodiment, fusion transcripts or predicted peptides expressed on healthy cells are discarded.
- a step to confirm that a tumor neoantigenic peptide is not expressed in healthy cells of the subject. This step can be carried out using typically the Basic local alignment search tool (BLAST) and performing alignment of the sequence of the neoantigenic peptide against the proteome of healthy cells: Preferably, peptides that align against the proteome of normal healthy cells (for example using BLAST) are discarded.
- a step to confirm that the fusion transcript or predicted peptide is expressed in cancer cells of the subject. The presence of the selected fusion transcript sequence in cancer cells can be checked typically by RT-PCR in mRNA extracted from cancer cell sample.

Neoantigenic Peptides, Polynucleotides and Vectors

The present disclosure also relates to an isolated tumor neoantigenic peptide comprising at least 8, 9, 10, 11, or 12 amino acids, encoded by a portion of an open reading frame (ORF) from a fusion transcript that is a human mRNA sequence comprising a transposable element (TE) sequence and an exonic sequence. The peptide may be 8-9, 8-10, 8-11, 12-25, 13-25, 12-20, or 13-20 amino acids in length. Although the ORF overlaps a junction between a TE sequence and an exonic sequence, it is understood that the tumor neoantigenic peptide itself may not comprise the junction.

The present disclosure also more specifically encompasses an isolated tumor neoantigenic peptide encoded by a portion of a human fusion mRNA sequence from a cancer cell, said fusion mRNA comprising a TE sequence and an exonic sequence. In example embodiments the neoantigenic peptide comprising at least 8, 9, 10, 11 or 12 amino acids is encoded by a part of an open reading frame (ORF) of any of the fusion transcript sequences of any one of SEQ ID NO: 118-910, preferably a peptide with one or more of the neoantigen peptide characteristics described above.

The peptide may be 8-9, 8-10, 8-11, 12-25, 13-25, 12-20, or 13-20 amino acids in length and fulfills one or more of the neoantigen peptide characteristics described above. The N-terminus of the peptide of at least 8 amino acids may be encoded by the triplet codon starting at any of nucleotide positions 1, 2, 3, 4, 5, 6, 7, 8, 9, 10, 11, 12, 13, 14, 15, 16, 17, 18, and higher (it being understood that the disclosure contemplates a start position that is any of the integers between 1 and 8000 without having to list every number between 1 and 8000).

A peptide as above defined is typically obtainable according to the method of the present disclosure and thus encompasses one or more of the characteristics as previously described. In particular a neoantigenic peptide as per the present disclosure may exhibit one or a combination of the following further characteristics:
- It binds or specifically binds MHC class I of a subject and is 8 to 11 amino acids, notably 8, 9, 10, or 11 amino acids. Typically the neoantigenic peptide is 8 or 9 amino acids long, and binds to at least one MHC class I molecule of the subject: or alternatively, it binds to at least one MHC class II molecule of said subject and contains from 12 to 25 amino acids, notably is 12, 13, 14, 15, 16, 17, 18, 19, 20, 21, 22, 23, 24 or 25 amino acids long.

It binds at least one HLA/MHC molecule of said subject suffering from a cancer with an affinity sufficient for the peptide to be presented on the surface of a cell as an antigen. Typically the neoantigenic peptide has an IC50 of less than $10^{-4}$, or $10^{-5}$, or $10^{-6}$, or $10^{-7}$ or less than 500 nM, at least less than 250 nM, at least less than 200 nM, at least less than 150 nM, at least less than 100 nM, at least less than 50 nM or less (lower numbers indicating greater binding affinity).

It does not induce a significant autoimmune response and/or invoke immunological tolerance when administered to a subject.

It is expressed at higher levels in tumor samples compared to normal healthy samples. Typically, as per the present disclosure, a fusion transcript may be selected if it is present in more than 10% of the tumor samples and in less than 20% of the normal samples. In some embodiments, the neoantigenic is more specifically a tumor specific antigen (TSA), i.e.: it is only expressed in cancer sample and not in normal samples, or is expressed at relatively low levels in normal samples (e.g. the expressed mRNA sequences represent minor species in normal cells from normal samples).

It comprises the junction between the TE sequence and the exonic sequence, in other words it is encoded by a part of a TE sequence and a part of an exonic sequence, the ORF being either canonical or non-canonical or It is encoded by a non-canonical ORF of an exonic sequence or It is encoded by the TE sequence, optionally in a non-canonical ORF A tumor neoantigenic peptide may first be validated by RT transcription analysis of fusion transcripts sequence in tumors cell from a subject. Typically also, immunization with a tumor neoantigenic peptide as per the present disclosure elicits a T cell response In a particular embodiment, the present disclosure encompasses a NSCLC neoantigenic peptide comprising at least 8 amino acids of any one of SEQ ID NOS: 1-117. Typically, said neoantigenic peptides of SEQ ID NOS: 1-117 binds to HLA-A02 with an affinity sufficient for the peptide to be presented on the surface of cells as an antigen. Affinity for MHC alleles can be determined by known techniques in the field and notably in silico or in vitro as exemplified above:

In a particular embodiment, a tumor neoantigenic peptide as per the present disclosure binds to a MHC molecule present in at least 1%, 5%, 10%, 15%, 20%, 25% or more of subjects. Notably, a tumor neoantigenic peptide as herein disclosed is expressed in at least 1%, 5%, 10%, 15%, 20%, 25% of subjects from a population of subjects suffering from cancer More particularly, a tumor neoantigenic peptide of the present disclosure is capable of eliciting an immune response against a tumor present in at least 1%, 5%, 10%, 15%, 20%, or 25% of the subjects in the population of subjects suffering from cancer.

As previously defined, cancer may affect any one of the following tissues or organs: breast; liver: kidney: heart, mediastinum, pleura: floor of mouth: lip: salivary glands: tongue: gums; oral cavity: palate: tonsil: larynx: trachea: bronchus, lung: pharynx, hypopharynx, oropharynx, nasopharynx: esophagus: digestive organs such as stomach, intrahepatic bile ducts, biliary tract, pancreas, small intestine, colon: rectum: urinary organs such as bladder, gallbladder, ureter: rectosigmoid junction: anus, anal canal: skin: bone: joints, articular cartilage of limbs: eye and adnexa: brain: peripheral nerves, autonomic nervous system; spinal cord, cranial nerves, meninges; and various parts of the central nervous system; connective, subcutaneous and other soft tissues: retroperitoneum, peritoneum: adrenal gland; thyroid gland: endocrine glands and related structures: female genital organs such as ovary, uterus, cervix uteri: corpus uteri, vagina, vulva: male genital organs such as penis, testis and prostate gland: hematopoietic and reticuloendothelial systems: blood: lymph nodes: thymus. For example, the tumors or cancers as per the present application includes leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the present disclosure also comprises cancer metastases and relapse of cancer.

Typically a neoantigenic peptide as per the present disclosure does not induce a significant autoimmune response and/or invoke immunological tolerance when administered to a subject. Tolerating mechanisms involve clonal deletion, ignorance, anergy, or suppression in the host w the reduction in the number of high-affinity self-reactive T cells.

The neoantigenic peptide can also be modified by extending or decreasing the compound's amino acid sequence, e.g., by the addition or deletion of amino acids. The peptides can also be modified by altering the order or composition of certain residues, it being readily appreciated that certain amino acid residues essential for biological activity, e.g., those at critical contact sites or conserved residues, may generally not be altered without an adverse effect on biological activity. The non-critical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

Typically, a series of peptides with single amino acid substitutions are employed to determine the effect of electrostatic charge, hydrophobicity, etc. on binding. For instance, a series of positively charged (e.g., Lys or Arg) or negatively charged (e.g., Glu) amino acid substitutions are made along the length of the peptide revealing different patterns of sensitivity towards various MHC molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding.

Amino acid substitutions are typically of single residues. Substitutions, deletions, insertions or any combination thereof may be combined to arrive at a final peptide. Substitutional variants are those in which at least one residue of a peptide has been removed and a different residue inserted in its place. Such substitutions are generally made in accordance with the following Table 1 when it is desired to finely modulate the characteristics of the peptide.

TABLE 1

| Original residue | Exemplary substitution |
| --- | --- |
| Ala | Ser |
| Arg | Lys, His |
| Asn | Gln |
| Asp | Glu |
| Cys | Ser |
| Gln | Asn |
| Glu | Asp |
| Gly | Pro |
| His | Lys, Arg |
| Ile | Leu, Val |
| Leu | Ile, Val |
| Lys | Tyr, Trp |
| Met | Thr |
| Phe | Ser |
| Ser | Tyr, Phe |
| Tyr | Trp, Phe |
| Val | Ile, Leu |
| Pro | Gly |

Substantial changes in function (e.g., affinity for MHC molecules or T cell receptors) are made by selecting substitutions that are less conservative than those in above Table, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in peptide properties will be those in which (a) hydrophilic residue, e.g. seryl, is substituted for (or by) a hydrophobic residue, e.g. leucyl, isoleucyl, phenylalanyl, valyl or alanyl: (b) a residue having an electropositive side chain, e.g., lysl, arginyl, or histidyl, is substituted for (or by) an electronegative residue, e.g. glutamyl or aspartyl: or (c) a residue having a bulky side chain, e.g. phenylalanine, is substituted for (or by) one not having a side chain, e.g., glycine.

The peptides and polypeptides may also comprise isosteres of two or more residues in the neoantigenic peptide or polypeptides. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, Chemistry and Biochemistry of Amino Acids, Peptides and Proteins, Vol. VII (Weinstein ed., 1983).

In addition, the neoantigenic peptide may be conjugated to a carrier protein, a ligand, or an antibody. Half-life of the peptide may be improved by PEGylation, glycosylation, polysialylation, HESylation, recombinant PEG mimetics, Fc fusion, albumin fusion, nanoparticle attachment, nanoparticulate encapsulation, cholesterol fusion, iron fusion, or acylation.

Modifications of peptides and polypeptides with various amino acid mimetics or unnatural amino acids are particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half life of the peptides of the present disclosure is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

The peptides and polypeptides may be modified to provide desired attributes other than improved serum half-life. For instance, the ability of the peptides to induce CTL activity can be enhanced by linkage to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the peptide may be linked to the T helper peptide without a spacer.

The neoantigenic peptide may be linked to the T helper peptide either directly or via a spacer either at the amino or carboxy terminus of the peptide. The amino terminus of either the neoantigenic peptide or the T helper peptide may be acylated. Exemplary T helper peptides include tetanus toxoid 830-843, influenza 307-319, malaria circumsporozoite 382-398 and 378-389

Multiple neoantigenic peptides described herein can also be linked together, optionally by a spacer.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

In a further aspect the present disclosure provides a nucleic acid (e.g. polynucleotide) encoding a neoantigenic peptide as herein disclosed. The polynucleotide may be selected from DNA, cDNA, PNA, CNA, RNA, either single- and/or double-stranded, or native or stabilized forms of polynucleotides, such as for example polynucleotides with a phosphorothiate backbone, or combinations thereof and it may or may not contain introns so long as it codes for the peptide. Only peptides that contain naturally occurring amino acid residues joined by naturally occurring peptide bonds are encodable by a polynucleotide.

A still further aspect of the disclosure provides an expression vector capable of expressing a neoantigenic peptide as herein disclosed. Expression vectors for different cell types are well known in the art and can be selected without undue experimentation. Generally, the DNA is inserted into an expression vector, such as a plasmid, in proper orientation and correct reading frame for expression. The expression vector will comprise the appropriate heterologous transcriptional and/or translational regulatory control nucleotide sequences recognized by the desired host. The polynucleotide encoding the tumor neoantigenic peptide may be linked to such heterologous regulatory control nucleotide sequences or may be non-adjacent yet operably linked to such heterologous regulatory control nucleotide sequences. The vector is then introduced into the host through standard techniques. Guidance can be found for example in Sambrook et al. (1989) Molecular Cloning, A Laboratory Manual, Cold Spring Harbor Laboratory, Cold Spring Harbor, N.Y.

Antigen Presenting Cells (APCs)

The present disclosure also encompasses a population of antigen presenting cells that have been pulsed with one or more of the peptides as previously defined and/or obtainable in a method as previously described. Preferably, the antigen presenting cells are dendritic cell (DCs) or artificial antigen presenting cells (aAPCs) (see Neal, Lillian R et al. "The Basics of Artificial Antigen Presenting Cells in T Cell-Based Cancer Immunotherapies." Journal of immunology research and therapy vol. 2.1 (2017): 68-79). Dendritic cells (DC) are professional antigen-presenting cells (APC) that have an extraordinary capacity to stimulate naive T-cells and initiate primary immune responses to pathogens. Indeed, the main role of mature DCs are to sense antigens and produce mediators that activate other immune cells, particularly T cells. DCs are potent stimulators for lymphocyte activation as they express MHC molecules that trigger TCRs (signal 1) and co-stimulatory molecules (signal 2) on T cells. Additionally, DCs also secrete cytokines that support T cell expansion. T cells require presented antigen in the form of a processed peptide to recognize foreign pathogens or tumor. Presentation of peptide epitopes derived from pathogen/tumor proteins is achieved through MHC molecules. MHC class I (MHC-I) and MHC class II (MHC-II) molecules present processed peptides to CD8+ T cells and CD4+ T cells, respectively. Importantly, DCs home to inflammatory sites containing abundant T cell populations to foster an immune response. Thus, DCs can be a crucial component of any immunotherapeutic approach, as they are intimately involved with the activation of the adaptive immune response. In the context of vaccines, DC therapy can enhance T cell immune responses to a desired target in healthy volunteers or patients with infectious disease or cancer. In one embodiment, APCS are artificial APC, which are genetically modified to express the desired T-cell co-stimulatory molecules, human HLA alleles and/or cytokines. Such artificial antigen presenting cells (aAPC) are able to provide the requirements for adequate T-cell engagement, co-stimulation, as well as sustained release of cytokines that allow for controlled T-cell expansion. These cells are not subject to the constraints of time and limited availability and can be stored in small aliquots for subsequent use in generating T-cell lines from different donors, thus representing an off the shelf reagent for immunotherapy applications. Expression of potent co-stimulatory signals on these aAPC endows this system with higher efficiency lending to increased efficacy of adoptive immunotherapy. Furthermore, aAPC can be engineered to express genes directing release of specific cytokines to facilitate the preferential expansion of desirable T-cell subsets for adoptive transfer: such as long lived memory T-cells (see for review Hasan A H et al. Artificial Antigen Presenting Cells: An Off the Shelf Approach for Generation of Desirable T-Cell Populations for Broad Application of Adoptive Immunotherapy: Adv Genet Eng. 2015: 4 (3): 130, Kim J V, Latouche J B, Rivière I, Sadelain M. The ABCs of artificial antigen presentation. Nat Biotechnol. 2004:22:403-410 or Wang C. Sun W. Ye Y. Bomba H N, Gu Z. Bioengineering of Artificial Antigen Presenting Cells and Lymphoid Organs. Theranostics 2017: 7 (14): 3504-3516.).

Typically, the dendritic cells are autologous dendritic cells that are pulsed with a neoantigenic peptide as herein disclosed. The peptide may be any suitable peptide that gives rise to an appropriate T-cell response. The antigen-presenting cell (or stimulator cell) typically has an MHC class I or II molecule on its surface, and in one embodiment is substantially incapable of itself loading the MHC class I or II molecule with the selected antigen. The MHC class I or II molecule may readily be loaded with the selected antigen in vitro.

As an alternative the antigen presenting cell may comprise an expression construct encoding a tumor neoantigenic peptide as herein disclosed. The polynucleotide may be any suitable polynucleotide as previously defined and it is preferred that it is capable of transducing the dendritic cell, thus resulting in the presentation of a peptide and induction of immunity Thus the present disclosure encompasses a population of APCs than can be pulsed or loaded with the neoantigenic peptide as herein disclosed, genetically modified (via DNA or RNA transfer) to express at least one neoantigenic peptide as herein disclosed, or that comprise an expression construct encoding a tumor neoantigenic peptide of the present disclosure. Typically the population of APCs is pulsed or loaded, modified to express or comprises at least one, at least 5, at least 10, at least 15, or at least 20 different neoantigenic peptide or expression construct encoding it.

The present disclosure also encompasses compositions comprising APCs as herein disclosed. APCs can be suspended in any known physiologically compatible pharmaceutical carrier, such as cell culture medium, physiological saline, phosphate-buffered saline, cell culture medium, or the like, to form a physiologically acceptable, aqueous pharmaceutical composition. Parenteral vehicles include sodium chloride solution, Ringer's dextrose, dextrose and sodium chloride, lactated Ringer's. Other substances may be added as desired such as antimicrobials. As used herein, a "carrier" refers to any substance suitable as a vehicle for delivering an APC to a suitable in vitro or in vivo site of action. As such, carriers can act as an excipient for formulation of a therapeutic or experimental reagent containing an APC. Preferred carriers are capable of maintaining an APC in a form that is capable of interacting with a T cell. Examples of such carriers include, but are not limited to water, phosphate buffered saline, saline, Ringer's solution, dextrose solution, serum-containing solutions, Hank's solution and other aqueous physiologically balanced solutions or cell culture medium. Aqueous carriers can also contain suitable auxiliary substances required to approximate the physiological conditions of the recipient, for example, enhancement of chemical stability and isotonicity. Suitable auxiliary substances include, for example, sodium acetate, sodium chloride, sodium lactate, potassium chloride, calcium chloride, sorbitan monolaurate, triethanolamine oleate, and other substances used to produce phosphate buffer, Tris buffer, and bicarbonate buffer.

Vaccine Compositions

The present disclosure further encompasses a vaccine or immunogenic composition capable of raising a specific T-cell response comprising:
  one or more neoantigenic peptides as herein defined,
  one or more polynucleotides encoding a neoantigenic peptide as herein defined; and/or
  a population of antigen presenting cells (such as autologous dendritic cells or artificial APC) as described above.

Preferably, neoantigenic peptide which are encoded by tumor specific fusions as previously defined are used in vaccine compositions as per the present disclosure. Said neoantigenic peptide can be also named tumor specific peptides. Preferably also polynucleotides encoding tumor specific peptides are used as per the present disclosure.

A suitable vaccine or immunogenic composition will preferably contain between 1 and 20 neoantigenic peptides, more preferably 2, 3, 4, 5, 6, 7, 8, 9, 10, 11, 12, 13, 14, 15, 16, 17, 18, 19, 20, 21, 22, 23, 24, 25 different neoantigenic peptides, further preferred 6, 7, 8, 9, 10 11, 12, 13, or 14 different neoantigenic peptides, and most preferably 12, 13 or 14 different neoantigenic peptides.

The neoantigenic peptide(s) may be linked to a carrier protein. Where the composition contains two or more neoantigenic peptides, the two or more (e.g. 2-25) peptides may be linearly linked by a spacer molecule as described above, e.g. a spacer comprising 2-6 nonpolar or neutral amino acids.

In one embodiment of the present disclosure the different neoantigenic peptides, encoding polynucleotides, vectors, or APCs are selected so that one vaccine or immunogenic composition comprises neoantigenic peptides capable of associating with different MHC molecules, such as different MHC class I molecules. Preferably, such neoantigenic peptides are capable of associating with the most frequently occurring MHC class I molecules, e.g. different fragments capable of associating with at least 2 preferred, more preferably at least 3 preferred, even more preferably at least 4 preferred MHC class I molecules. In some embodiments, the compositions comprise peptides, encoding polynucleotides, vectors, or APCs capable of associating with one or more MHC class II molecules. The MHC is optionally HLA-A, -B, -C, -DP, -DQ, or -DR.

The vaccine or immunogenic composition is capable of raising a specific cytotoxic T-cells response and/or a specific helper T-cell response.

Thus in a particular embodiment, the present disclosure also relates to a neoantigenic peptide as described above, wherein the neoantigenic peptide has a tumor specific neoepitope and is included in a vaccine or immunogenic composition. A vaccine composition is to be understood as meaning a composition for generating immunity for the prophylaxis and/or treatment of diseases. Accordingly, vaccines are medicines which comprise or generate antigens and are intended to be used in humans or animals for generating specific defense and protective substance by vaccination. An "immunogenic composition" is to be understood as meaning a composition that comprises or generates antigen(s) and is capable of eliciting an antigen-specific humoral or cellular immune response, e.g. T-cell response.

In a preferred embodiment, the neoantigenic peptide according to the disclosure is 8 or 9 residues long, or from 13 to 25 residues long. When the peptide is less than 20 residues, in order to have a peptide better suited for in vivo immunization, said neoantigenic peptide, is optionally flanked by additional amino acids to obtain an immunization peptide of more amino acids, usually more than 20.

Pharmaceutical compositions (i.e., the vaccine or immunogenic composition) comprising a peptide as herein described may be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 μg to about 50,000 μg of peptide for a 70 kg patient, followed by boosting dosages or from about 1.0 μg to about 10,000 μg of peptide pursuant to a boosting regimen over weeks to months depending upon the patient's response and condition by measuring specific CTL activity in the patient's blood. It must be kept in mind that the peptide and compositions of the present invention may generally be employed in serious disease states, that is, life-threatening or potentially life threatening situations, especially when the cancer has metastasized. In such cases, in view of the minimization of extraneous substances and the relative nontoxic nature of the peptide, it is possible and may be felt desirable by the treating physician to administer substantial excesses of these peptide compositions.

For therapeutic use, administration should begin at the detection or surgical removal of tumors. This is followed by boosting doses until at least symptoms are substantially abated and for a period thereafter.

The vaccine or immunogenic compositions for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor.

The vaccine or immunogenic composition may be a pharmaceutical composition which additionally comprises a pharmaceutically acceptable adjuvant, immunostimulatory agent, stabilizer, carrier, diluent, excipient and/or any other materials well known to those skilled in the art. Such materials should be non-toxic and should not interfere with the efficacy of the active ingredient. The carrier is preferably an aqueous carrier but its precise nature of the carrier or other material will depend on the route of administration. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may further contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. See, for example, Butterfield, B M J. 2015 22:350 for a discussion of cancer vaccines.

Example adjuvants that increase or expand the immune response of a host to an antigenic compound include emulsifiers, muramyl dipeptides, avridine, aqueous adjuvants such as aluminum hydroxide, chitosan-based adjuvants, saponins, oils, Amphigen, LPS, bacterial cell wall extracts, bacterial DNA, CpG sequences, synthetic oligonucleotides, cytokines and combinations thereof. Emulsifier include, for example, potassium, sodium and ammonium salts of lauric and oleic acid, calcium, magnesium and aluminum salts of fatty acids, organic sulfonates such as sodium lauryl sulfate, cetyltrhethylammonlum bromide, glycerylesters, polyoxyethylene glycol esters and ethers, and sorbitan fatty acid esters and their polyoxyethylene, acacia, gelatin, lecithin and/or cholesterol. Adjuvants that comprise an oil component include mineral oil, a vegetable oil, or an animal oil. Other adjuvants include Freund's Complete Adjuvant (FCA) or Freund's Incomplete Adjuvant (FIA). Cytokines useful as additional immunostimulatory agents include interferon alpha, interleukin-2 (IL-2), and granulocyte macrophage-colony stimulating factor (GM-CSF), or combinations thereof.

The concentration of peptides as herein described in the vaccine or immunogenic formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptides as herein described may also be administered via liposomes, which target the peptides to a particular cells tissue, such as lymphoid tissue. Liposomes are also useful in increasing the half-life of the peptides. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9:467 (1980), U.S. Pat. Nos. 4,235,871, 4,501,728 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, as with, e.g., lecithin for intranasal delivery.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and antigen presenting cell (APC) is present. Correspondingly, it may enhance the immune response if not only the peptide is used for activation of CTLs, but if additionally APCs with the respective MHC molecule are added. Therefore, in some embodiments the vaccine or immunogenic composition according to the present disclosure alternatively or additionally contains at least one antigen presenting cell, preferably a population of APCs.

The vaccine or immunogenic composition may thus be delivered in the form of a cell, such as an antigen presenting cell, for example as a dendritic cell vaccine. The antigen presenting cells such as a dendritic cell may be pulsed or loaded with a neoantigenic peptide as herein disclosed, may comprise an expression construct encoding a neoantigenic peptide as herein disclosed, or may be genetically modified (via DNA or RNA transfer) to express one, two or more of the herein disclosed neoantigenic peptides, for example at least 2, 3, 4, 5, 6, 7, 8, 9, or 10 neoantigenic peptides.

Suitable vaccines or immunogenic compositions may also be in the form of DNA or RNA relating to neoantigenic peptides as described herein. For example, DNA or RNA encoding one or more neoantigenic peptides or proteins derived therefrom may be used as the vaccine, for example by direct injection to a subject. For example, DNA or RNA encoding at least 2, 3, 4, 5, 6, 7, 8, 9, 10, 11, 12, 13, 14, 15, 16, 17, 18, 19, 20, 21, 22, 23, 24 or 25 neoantigenic peptides or proteins derived therefrom.

A number of methods are conveniently used to deliver the nucleic acids to the patient. For instance, the nucleic acid can be delivered directly, as "naked DNA". This approach is described, for instance, in Wolff et al., Science 247:1465-1468 (1990) as well as USAU.S. U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles.

The nucleic acids can also be delivered complexed to cationic compounds, such as cationic lipids. Lipid-mediated gene delivery methods are described, for instance, in 9618372WOAWO 96/18372: 9324640WOAWO 93/24640: Mannino & Gould-Fogerite, BioTechniques 6 (7): 682-691 (1988): U.S. Pat. No. 5,279,833 USA Rose U.S. Pat. No. 5,279,833; 9106309WOAWO 91/06309; and Felgner et al., Proc. Natl. Acad. Sci. USA 84:7413-7414 (1987).

Delivery systems may optionally include cell-penetrating peptides, nanoparticulate encapsulation, virus like particles, liposomes, or any combination thereof. Cell penetrating peptides include TAT peptide, herpes simplex virus VP22, transportan, Antp. Liposomes may be used as a delivery system. Listeria vaccines or electroporation may also be used.

The one or more neoantigenic peptides may also be delivered via a bacterial or viral vector containing DNA or RNA sequences which encode one or more neoantigenic peptides. The DNA or RNA may be delivered as a vector itself or within attenuated bacteria virus or live attenuated virus, such as vaccinia or fowlpox. This approach involves the use of vaccinia virus as a vector to express nucleotide sequences that encode the peptide of the invention.

Upon introduction into an acutely or chronically infected host or into a noninfected host, the recombinant vaccinia virus expresses the immunogenic peptide, and thereby elicits a host CTL response. Vaccinia vectors and methods useful in immunization protocols are described in, e.g., U.S. Pat. No. 4,722,848 . . . . Another vector is BCG (Bacille Calmette Guerin). BCG vectors are described in Stover et al. (Nature 351:456-460 (1991)). A wide variety of other vectors useful for therapeutic administration or immunization of the peptides of the invention, e.g., *Salmonella* typhivectors and the like, will be apparent to those skilled in the art from the description herein.

An appropriate mean of administering nucleic acids encoding the peptides as herein described involves the use of minigene constructs encoding multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Standard regulatory sequences well known to those of skill in the art are included in the vector to ensure expression in the target cells. Thus, the DNA or RNA encoding the neoantigenic peptide(s) may typically be operably linked to one or more of:

a promoter that can be used to drive nucleic acid molecule expression. AAV ITR can serve as a promoter and is advantageous for eliminating the need for an additional promoter element. For ubiquitous expression, the following promoters can be used: CMV (notably human cytomegalovirus immediate early promoter (hCMV-IE)), CAG, CBh, PGK, SV40, RSV, Ferritin heavy or light chains, etc. For brain expression, the following promoters can be used: SynapsinI for all neurons, CaMKIIalpha for excitatory neurons, GAD67 or GAD65 or VGAT for GABAergic neurons, etc. Promoters used to drive RNA synthesis can include: Pol III promoters such as U6 or HI. The use of a Pol II promoter and intronic cassettes can be used to express guide RNA (gRNA). Typically, the promoter includes a down-stream cloning site for minigene insertion. For examples of suitable promoters sequences, see notably U.S. Pat. Nos. 5,580,859 and 5,589,466.

Transcriptional transactivators or other enhancer elements, which can also increase transcription activity, e.g. the regulatory R region from the 5' long terminal repeat (LTR) of human T-cell leukemia virus type 1 (HTLV-1) (which when combined with a CMV promoter has been shown to induce higher cellular immune response).

Translation optimizing sequences e.g. a Kozak sequence flanking the AUG initiator codon (ACCAUGG) within mRNA, and codon optimization.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences can also be considered for increasing minigene expression. It has recently been proposed that immunostimulatory sequences (ISSs or CpGs) play a role in the immunogenicity of DNA' vaccines. These sequences could be included in the vector, outside the minigene coding sequence, if found to enhance immunogenicity.

In some embodiments, a bicistronic expression vector, to allow production of the minigene-encoded epitopes and a second protein included to enhance or decrease immunogenicity can be used.

DNA vaccines or immunogenic compositions as herein described can be enhanced by co-delivering cytokines that promote cell-mediated immune responses, such as IL-2, IL-12, IL-18, GM-CSF and IFNγ. CXC chemokines such as IL-8, and CC chemokines such as macrophage inflammatory protein (MIP)-1α, MIP-3α, MIP-3β, and RANTES, may increase the potency of the immune response. DNA vaccine immunogenicity can also be enhanced by co-delivering plasmid-encoded cytokine-inducing molecules (e.g. LeIF), co-stimulatory and adhesion molecules, e.g. B7-1 (CD80) and/or B7-2 (CD86). Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-β) may be beneficial in certain diseases.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

Purified plasmid DNA can be prepared for injection using a variety of formulations. The simplest of these is reconstitution of lyophilized DNA in sterile phosphate-buffer saline (PBS). A variety of methods have been described, and new techniques may become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intra-muscular dispersion, or trafficking to specific organs or cell types.

Vaccines or immunogenic compositions comprising peptides may be administered in combination with vaccines or immunogenic compositions comprising polynucleotide encoding the peptides. For example, administration of peptide vaccine and DNA vaccine may be alternated in a prime-boost protocol. For example, priming with a peptide immunogenic composition and boosting with a DNA immunogenic composition is contemplated, as is priming with a DNA immunogenic composition and boosting with a peptide immunogenic composition.

The present disclosure also encompasses a method for producing a vaccine composition comprising the steps of:
 a) Optionally, identifying at least one neoantigenic peptide according to the method as previously described;
 b) producing said at least one neoantigenic peptide, at least one polypeptide encoding neoantigenic peptide (s), or at least a vector comprising said polypeptide(s) as described herein; and
 c) optionally adding physiologically acceptable buffer, excipient and/or adjuvant and producing a vaccine with said at least one neoantigenic peptide, polypeptide or vector.

Another aspect of the present disclosure, is a method for producing a DC vaccine, wherein said DCs present at least one neoantigenic peptide as herein disclosed.

Antibodies TCRs, CARs and Derivatives Thereof

The present disclosure also relates to an antibody or an antigen-binding fragment thereof that specifically binds a neoantigenic peptide as herein defined.

In some embodiments, the neoantigenic peptide is in association with an MHC or HLA molecule.

Typically, said antibody, or antigen-binding fragment thereof binds a neoantigenic peptide as herein defined, alone or optionally in association with an MHC or HLA molecule, with a Kd binding affinity of $10^{-7}$ M or less, $10^{-8}$ M or less, $10^{-9}$ M or less, $10^{-10}$ M or less, or $10^{-11}$ M or less.

To promote the infiltration and recognition of tumor cells by lymphocytes T (LT), another strategy consists in using antibodies capable of recognizing more than one antigenic target simultaneously and more particularly two antigenic targets simultaneously. There are many formats of bispecific antibodies. BiTE (bi-specific T-cell engager) are the first to have been developed. These are proteins of fusion consisting of two scFvs (variable domains heavy VH and light VL chains) from two antibodies linked by a binding peptide: one recognizes the LT marker (CD3+) and the other a tumor antigen. The goal is to favor recruitment and activation of LTs in contact with tumor, thus leading to cell lysis tumor (See for review Patrick A. Baeuerle and Carsten Reinhardt: Bispecific T-Cell Engaging Antibodies for Cancer Therapy; Cancer Res 2009:69: (12). Jun. 15, 2009; and Galaine et al., Innovations & Thérapeutiques en Oncologie, vol. 3-no 3-7, mai-août 2017).

In a particular embodiment, said antibody is a bi-specific T-cell engager that targets a tumor neoantigenic peptide as herein defined, optionally in association with a MHC or an HLA molecule and which further targets at least an immune cell antigen. Typically, the immune cell is a T cell, a NK cell or a dendritic cell. In this context, the targeted immune cell antigen may be for example CD3, CD16, CD30 or a TCR.

The term "antibody" herein is used in the broadest sense and includes polyclonal and monoclonal antibodies, including intact antibodies and functional (antigen-binding) antibody fragments, including fragment antigen binding (Fab) fragments, F(ab') 2 fragments, Fab' fragments, Fv fragments, recombinant IgG (rIgG) fragments, variable heavy chain (VH) regions capable of specifically binding the antigen, single chain antibody fragments, including single chain variable fragments (scFv), and single domain antibodies (e.g., VHH antibodies, sdAb, sdFv, nanobody) fragments. The term encompasses genetically engineered and/or otherwise variants modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody and fragments thereof. The term also encompasses intact or full-length antibodies, including antibodies of any class or sub-class, including IgG and sub-classes thereof, IgG1, IgG2, IgG3, IgG4, IgM, IgE, IgA, and IgD. In some embodiments, the antibody comprises a light chain variable domain and a heavy chain variable domain, e.g. in an scFv format.

Antibodies include variant polypeptide species that have one or more amino acid substitutions, insertions, or deletions in the native amino acid sequence, provided that the antibody retains or substantially retains its specific binding function. Conservative substitutions of amino acids are well known and described above.

The present disclosure further includes a method of producing an antibody, or antigen-binding fragment thereof, comprising a step of selecting antibodies that bind to a tumor neoantigen peptide as herein defined, optionally in association with an MHC or HLA molecule, with a Kd binding affinity of about $10^{-6}$ M or less, $10^{-7}$ M or less, $10^{-8}$ M or less, $10^{-9}$ M or less, $10^{-10}$ M or less, or $10^{-11}$ M or less.

In some embodiments, the antibodies are selected from a library of human antibody sequences. In some embodiments, the antibodies are generated by immunizing an animal with a polypeptide comprising the neoantigenic peptide, optionally in association with an MHC or HLA molecule, followed by the selection step.

Antibodies including chimeric, humanized or human antibodies can be further affinity matured and selected as described above. Humanized antibodies contain rodent-sequence derived CDR regions: typically the rodent CDRs are engrafted into a human framework, and some of the human framework residues may be back-mutated to the original rodent framework residue to preserve affinity, and/or one or a few of the CDR residues may be mutated to increase affinity. Fully human antibodies have no murine sequence, and are typically produced via phage display technologies of human antibody libraries, or immunization of transgenic mice whose native immunoglobin loci have been replaced with segments of human immunoglobulin loci.

Antibodies produced by said method, as well as immune cells expressing such antibodies or fragments thereof are also encompassed by the present disclosure.

The present disclosure also encompasses pharmaceutical compositions comprising one or more antibodies as herein disclosed alone or in combination with at least one other agent, such as a stabilizing compound, which may be administered in any sterile, biocompatible pharmaceutical carrier and optionally formulated with formulated with sterile pharmaceutically acceptable buffer(s), diluent(s), and/or excipient(s). Pharmaceutically acceptable carriers typically enhance or stabilize the composition, and/or can be used to facilitate preparation of the composition. Pharmaceutically acceptable carriers include solvents, dispersion media, coatings, antibacterial and antifungal agents, isotonic and absorption delaying agents, and the like that are physiologically compatible and in some embodiments pharmaceutically inert.

Administration of a pharmaceutical composition comprising antibodies as herein disclosed can be accomplished orally or parenterally. Methods of parenteral delivery include topical, intra-arterial (directly to the tumor), intramuscular, spinal, subcutaneous, intramedullary, intrathecal, intraventricular, intravenous, intraperitoneal, or intranasal administration.

Thus, in addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Ed. Maack Publishing Co, Easton, Pa.).

Depending on the route of administration, the active compound, i.e., antibody, bispecific and multispecific molecule, may be coated in a material to protect the compound from the action of acids and other natural conditions that may inactivate the compound.

The composition is typically sterile and preferably fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol: starch from corn, wheat, rice, potato, or other plants: cellulose such as methyl, cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, ie. dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Pharmaceutical compositions of the disclosure can be prepared in accordance with methods well known and routinely practiced in the art. See. e.g., Remington: The Science and Practice of Pharmacy, Mack Publishing Co., 20th ed., 2000; and Sustained and Controlled Release Drug Delivery Systems, J R. Robinson, ed., Marcel Dekker, Inc., New York, 1978. Pharmaceutical compositions are preferably manufactured under GMP conditions.

The present disclosure also encompasses a T cell receptor (TCR) that targets a neoantigenic peptide as herein defined in association with an MHC or HLA molecule.

The present disclosure further includes a method of producing a TCR, or an antigen-binding fragment thereof, comprising a step of selecting TCRs that bind to a tumor neoantigen peptide as herein defined, optionally in association with an MHC or HLA molecule, with a Kd binding affinity of about $10^{-6}$ M or less, $10^{-7}$ M or less, $10^{-8}$ M or less, $10^{-9}$ M or less, $10^{-10}$ M or less, or $10^{-11}$ M or less.

Nucleic acid encoding the TCR can be obtained from a variety of sources, such as by polymerase chain reaction (PCR) amplification of naturally occurring TCR DNA sequences, followed by expression of antibody variable regions, followed by the selecting step described above. In some embodiments, the TCR is obtained from T-cells isolated from a patient, or from cultured T-cell hybridomas. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

A "T cell receptor" or "TCR" refers to a molecule that contains a variable α and β chains (also known as TCRa and TCRb, respectively) or a variable γ and δ chains (also known as TCRg and TCRd, respectively) and that is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et ah, Immunobiology: The Immune System in Health and Disease, 3 rd Ed., Current Biology Publications, p. 4:33, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) {see, e.g., Jores et al., Pwc. Nat'l Acad. Sci. U.S.A. 87:9138, 1990: Chothia et al., EMBO J. 7:3745, 1988; see also Lefranc et al., Dev. Comp. Immunol. 27:55, 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains {e.g., α-chain, β-chain) can contain two immunoglobulin domains, a variable domain {e.g., Va or Vp: typically amino acids 1 to 116 based on Kabat numbering Kabat et al., "Sequences of Proteins of Immunological Interest, US Dept. Health and Human Services, Public Health Service National Institutes of Health, 1991, 5th ed.) at the N-terminus, and one constant domain {e.g., a-chain constant domain or Ca, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contain a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3y chain, a CD35 chain, two CD3s chains, and a homodimer of CD3ζ chains. The CD3y, CD35, and CD3s chains are highly related cell surface proteins of the immunoglobulin superfamily containing a single immunoglobulin domain. The transmembrane regions of the CD3y, CD35, and CD3s chains are negatively charged, which is a characteristic that allows these chains to associate with the positively charged T cell receptor chains. The intracellular tails of the CD3y, CD35, and CD3s chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

While T-cell receptors (TCRs) are transmembrane proteins and do not naturally exist in soluble form, antibodies can be secreted as well as membrane bound. Importantly, TCRs have the advantage over antibodies that they in principle can recognize peptides generated from all degraded cellular proteins, both intra- and extracellular, when presented in the context of MHC molecules. Thus TCRs have important therapeutic potential.

The present disclosure also relates to soluble T-cell receptors (sTCRs) that contain the antigen recognition part directed against a tumor neoantigenic peptide as herein disclosed (see notably Walseng E, Wälchli S, Fallang L-E, Yang W, Vefferstad A, Areffard A, et al. (2015) Soluble T-Cell Receptors Produced in Human Cells for Targeted Delivery. PLOS ONE 10 (4): e0119559). In a particular embodiment, the soluble TCR can be fused to an antibody fragment directed to a T cell antigen, optionally wherein the targeted antigen is CD3 or CD16 (see for example Boudousquie, Caroline et al. "Polyfunctional response by ImmTAC (IMCgp100) redirected CD8+ and CD4+ T cells." Immunology vol. 152.3 (2017): 425-438. doi: 10.1111/imm.12779).

The present disclosure also encompasses a chimeric antigen receptor (CAR) which is directed against a tumor neoantigenic peptide as herein disclosed. CARs are fusion proteins comprising an antigen-binding domain, typically derived from an antibody, linked to the signalling domain of the TCR complex. CARs can be used to direct immune cells such T-cells or NK cells against a tumor neoantigenic peptide as previously defined with a suitable antigen-binding domain selected.

The antigen-binding domain of a CAR is typically based on a scFv (single chain variable fragment) derived from an antibody. In addition to an N-terminal, extracellular antibody-binding domain, CARs typically may comprise a hinge domain, which functions as a spacer to extend the antigen-binding domain away from the plasma membrane of the immune effector cell on which it is expressed, a transmembrane (TM) domain, an intracellular signalling domain (e.g. the signalling domain from the zeta chain of the CD3 molecule (CD3ζ) of the TCR complex, or an equivalent) and optionally one or more co-stimulatory domains which may assist in signalling or functionality of the cell expressing the CAR. Signalling domains from co-stimulatory molecules including CD28, OX-40 (CD134), and 4-1BB (CD137) can be added alone (second generation) or in combination (third generation) to enhance survival and increase proliferation of CAR modified T cells. Potential co-stimulatory domains also include ICOS-1, CD27, GITR, and DAP10.

Thus, the CAR may include
(1) In its extracellular portion, one or more antigen binding molecules, such as one or more antigen-binding fragment, domain, or portion of an antibody, or one or more antibody variable domains, and/or antibody molecules.
(2) In its transmembrane portion, a transmembrane domain derived from human T cell receptor-alpha or -beta chain, a CD3 zeta chain, CD28, CD3-epsilon, CD45, CD4, CD5, CD8, CD9, CD16, CD22, CD33, CD37, CD64, CD80, CD86, CD134, CD137, ICOS, CD154, or a GITR. In some embodiments, the transmembrane domain is derived from CD28, CD8 or CD3-zeta.
(3) One or more co-stimulatory domains, such as co-stimulatory domains derived from human CD28, 4-1BB (CD137), ICOS-1, CD27, OX 40 (CD137), DAP10, and GITR (AITR). In some embodiments, the CAR comprises co-stimulating domains of both CD28 and 4-1BB.
(4) In its intracellular signalling domain, an intracellular signalling domain comprising one or more ITAMs, for example, the intracellular signalling domain is CD3-zeta, or a variant thereof lacking one or two ITAMs (e.g. ITAM3 and ITAM2), or the intracellular signalling domain is derived from FcεRIγ.

The CAR can be designed to recognize tumor neoantigenic peptide alone or in association with an HLA or MHC molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April: 3 (4): 388-398; Davila et al. (2013) PLOS ONE 8 (4): e61338; Turtle et al., Curr. Opin. Immunol., 2012 October: 24 (5): 633-39; Wu et al., Cancer, 2012 Mar. 18 (2): 160-75. In some aspects, the genetically engineered antigen receptors include a CAR as described in U.S. Pat. No. 7,446,190, and those described in International Patent Application Publication No.: WO/2014055668 A1.

The present disclosure also encompasses polynucleotides encoding antibodies, antigen-binding fragments or derivatives thereof, TCRs and CARs as previously described as well as vector comprising said polynucleotide(s).

Immune Cells

The present disclosure further encompasses immune cells which target one or more tumor neoantigenic peptides as previously described.

As used herein, the term "immune cell" includes cells that are of hematopoietic origin and that play a role in the immune response. Immune cells include lymphocytes, such as B cells and T cells, natural killer cells, myeloid cells, such as monocytes, macrophages, eosinophils, mast cells, basophils, and granulocytes.

As used herein, the term "T cell" includes cells bearing a T cell receptor (TCR), in particular TCR directed against a tumor neoantigenic peptide as herein disclosed. T-cells according to the present disclosure can be selected from the group consisting of inflammatory T-lymphocytes, cytotoxic T-lymphocytes, regulatory T-lymphocytes, Mucosal-Associated Invariant T cells (MAIT), γδ T cell, tumour infiltrating lymphocyte (TILs) or helper T-lymphocytes included both type 1 and 2 helper T cells and Th17 helper cells. In another embodiment, said cell can be derived from the group consisting of CD4+ T-lymphocytes and CD8+ T-lymphocytes. Said immune cells may originate from a healthy donor or from a subject suffering from a cancer.

Immune cells can be extracted from blood or derived from stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells.

T-cells can be obtained from a number of non-limiting sources, including peripheral blood mononuclear cells, bone marrow; lymph node tissue, cord blood, thymus tissue, tissue from a site of infection, ascites, pleural effusion, spleen tissue, and tumors. In certain embodiments, T-cells can be obtained from a unit of blood collected from a subject using any number of techniques known to the skilled person, such as FICOLL™ separation. In one embodiment, cells from the circulating blood of a subject are obtained by apheresis. In certain embodiments, T-cells are isolated from PBMCs. PBMCs may be isolated from buffy coats obtained by density gradient centrifugation of whole blood, for instance centrifugation through a LYMPHOPREP™ gradient, a PERCOLL™ gradient or a FICOLL™ gradient. T-cells may be isolated from PBMCs by depletion of the monocytes, for instance by using CD14 DYNABEADS®. In some embodiments, red blood cells may be lysed prior to the density gradient centrifugation.

In another embodiment, said cell can be derived from a healthy donor, from a subject diagnosed with cancer. The cell can be autologous or allogeneic.

In allogeneic immune cell therapy, immune cells are collected from healthy donors, rather than the patient. Typically these are HLA matched to reduce the likelihood of graft vs. host disease. Alternatively, universal "off the shelf" products that may not require HLA matching comprise modifications designed to reduce graft vs. host disease, such as disruption or removal of the TCRαβ receptor. See Graham et al., Cells. 2018 October: 7 (10): 155 for a review. Because a single gene encodes the alpha chain (TRAC) rather than the two genes encoding the beta chain, the TRAC locus is a typical target for removing or disrupting TCRαβ receptor expression. Alternatively, inhibitors of TCRαβ signalling may be expressed, e.g. truncated forms of CD3ζ can act as a TCR inhibitory molecule. Disruption or removal of HLA class I molecules has also been employed. For example, Torikai et al., Blood. 2013:122: 1341-1349 used ZFNs to knock out the HLA-A locus, while Ren et al., Clin. Cancer Res. 2017:23:2255-2266 knocked out Beta-2 microglobulin (B2M), which is required for HLA class I expression. Ren et al. simultaneously knocked out TCRαβ, B2M and the immune-checkpoint PD1. Generally, the immune cells are activated and expanded to be utilized in the adoptive cell therapy. The immune cells as herein disclosed can be expanded in vivo or ex vivo. The immune cells, in particular T-cells can be activated and expanded generally using methods known in the art. Generally the T-cells are expanded by contact with a surface having attached thereto an agent that stimulates a CD3/TCR complex associated signal and a ligand that stimulates a co-stimulatory molecule on the surface of the T cells.

In one embodiment of the present disclosure, the immune cell can be modified to be directed to tumor neoantigenic peptides as previously defined. In a particular embodiment, said immune cell may express a recombinant antigen receptor directed to said neoantigenic peptide its cell surface. By "recombinant" is meant an antigen receptor which is not encoded by the cell in its native state, i.e. it is heterologous, non-endogenous. Expression of the recombinant antigen receptor can thus be seen to introduce new antigen specificity to the immune cell, causing the cell to recognise and bind a previously described peptide. The antigen receptor may be isolated from any useful source. In some embodiments, the cells comprise one or more nucleic acids introduced via genetic engineering that encode one or more antigen receptors, wherein the antigen include at least one tumor neoantigenic peptide as per the present disclosure.

Among the antigen receptors as per the present disclosure are genetically engineered T cell receptors (TCRs) and components thereof, as well as functional non-TCR antigen receptors, such as chimeric antigen receptors (CAR) as previously described.

Methods by which immune cells can be genetically modified to express a recombinant antigen receptor are well known in the art. A nucleic acid molecule encoding the antigen receptor may be introduced into the cell in the form of e.g. a vector, or any other suitable nucleic acid construct. Vectors, and their required components, are well known in the art. Nucleic acid molecules encoding antigen receptors can be generated using any method known in the art, e.g. molecular cloning using PCR. Antigen receptor sequences can be modified using commonly-used methods, such as site-directed mutagenesis.

The present disclosure also relates to a method for providing a T cell population which targets a tumor neoantigenic peptide as herein disclosed.

The T cell population may comprise CD8+ T cells, CD4+ T cells or CD8+ and CD4+ T cells. T cell populations produced in accordance with the present disclosure may be enriched with T cells that are specific to, i.e. target, the tumor neoantigenic peptide of the present disclosure.

That is, the T cell population that is produced in accordance with the present disclosure will have an increased number of T cells that target one or more tumor neoantigenic peptide. For example, the T cell population of the disclosure will have an increased number of T cells that target a tumor neoantigenic peptide compared with the T cells in the sample isolated from the subject. That is to say, the composition of the T cell population will differ from that of a "native" T cell population (i.e. a population that has not undergone the identification and expansion steps discussed herein), in that the percentage or proportion of T cells that target a tumor neoantigenic peptide will be increased.

T cell populations produced in accordance with the present disclosure may be enriched with T cells that are specific to, i.e. target, tumor neoantigenic peptide. That is, the T cell population that is produced in accordance with the present disclosure will have an increased number of T cells that target one or more tumor neoantigenic peptide of the present disclosure. For example, the T cell population of the present disclosure will have an increased number of T cells that target a tumor neoantigenic peptide compared with the T cells in the sample isolated from the subject. That is to say, the composition of the T cell population will differ from that of a "native" T cell population (i.e. a population that has not undergone the identification and expansion steps discussed herein), in that the percentage or proportion of T cells that target a tumor neoantigenic peptide will be increased.

The T cell population according to the present disclosure may have at least about 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100% T cells that target a tumor neoantigenic peptide as herein disclosed. For example, the T cell population may have about 0.2%-5%, 5%-10%, 10-20%, 20-30%, 30-40%, 40-50%, 50-70% or 70-100% T cells that target a tumor neoantigenic peptide of the present disclosure.

An expanded population of tumor neoantigenic peptide-reactive T cells may have a higher activity than a population of T cells not expanded, for example, using a tumor neoantigenic peptide. Reference to "activity" may represent the response of the T cell population to restimulation with a tumor neoantigenic peptide, e.g. a peptide corresponding to the peptide used for expansion, or a mix of tumor neoantigenic peptide. Suitable methods for assaying the response are known in the art. For example, cytokine production may be measured (e.g. IL2 or IFNy production may be measured). The reference to a "higher activity" includes, for example, a 1-5, 5-10, 10-20, 20-50, 50-100, 100-500, 500-1000-fold increase in activity. In one aspect the activity may be more than 1000-fold higher.

In a preferred embodiment present disclosure provides a plurality or population, i.e. more than one, of T cells wherein the plurality of T cells comprises a T cell which recognizes a clonal tumor neoantigenic peptide and a T cell which recognizes a different clonal tumor neoantigenic peptide. As such, the present disclosure provides a plurality of T cells which recognize different clonal tumor neoantigenic peptide. Different T cells in the plurality or population may alternatively have different TCRs which recognize the same tumor neoantigenic peptide.

In a preferred embodiment the number of clonal tumor neoantigenic peptide recognized by the plurality of T cells is from 2 to 1000. For example, the number of clonal neoantigens recognized may be 2, 3, 4, 5, 6, 7, 8, 9, 10, 20, 50, 100, 150, 200, 250, 300, 350, 400, 450, 500, 550, 600, 650, 700, 750, 800, 850, 900, 950 or 1000, preferably 2 to 100. There may be a plurality of T cells with different TCRs but which recognize the same clonal neo-antigen.

The T cell population may be all or primarily composed of CD8+ T cells, or all or primarily composed of a mixture of CD8+ T cells and CD4+ T cells or all or primarily composed of CD4+ T cells.

In particular embodiments, the T cell population is generated from T cells isolated from a subject with a tumor. For example, the T cell population may be generated from T cells in a sample isolated from a subject with a tumor. The sample may be a tumor sample, a peripheral blood sample or a sample from other tissues of the subject.

In a particular embodiment the T cell population is generated from a sample from the tumor in which the tumor neoantigenic peptide is identified. In other words, the T cell population is isolated from a sample derived from the tumor of a patient to be treated. Such T cells are referred to herein as 'tumor infiltrating lymphocytes' (TILs).

T cells may be isolated using methods which are well known in the art. For example, T cells may be purified from single cell suspensions generated from samples on the basis of expression of CD3, CD4 or CD8. T cells may be enriched from samples by passage through a Ficoll-paque gradient.

Cancer Therapeutic Methods

In any of the embodiments, the Cancer Therapeutic Products described herein may be used in methods for inhibiting proliferation of cancer cells. The Cancer Therapeutic Products described herein may also be used in the treatment of cancer, in patients suffering from cancer, or for the prophylactic treatment of cancer, in patients at risk of cancer.

Cancers that can be treated using the therapy described herein include any solid or non-solid tumors as previously defined. Of particular interest according to the present disclosure are breast cancer, melanoma and lung cancer. In a specific embodiment of the present disclosure, the cancer is non-small cell lung cancer (NSCLC).

Cancers includes also the cancers which are refractory to treatment with other chemotherapeutics. The term "refractory, as used herein refers to a cancer (and/or metastases thereof), which shows no or only weak antiproliferative response (e.g., no or only weak inhibition of tumor growth) after treatment with another chemotherapeutic agent. These are cancers that cannot be treated satisfactorily with other chemotherapeutics. Refractory cancers encompass not only (i) cancers where one or more chemotherapeutics have already failed during treatment of a patient, but also (ii) cancers that can be shown to be refractory by other means, e.g., biopsy and culture in the presence of chemotherapeutics.

The therapy described herein is also applicable to the treatment of patients in need thereof who have not been previously treated.

A subject as per the present disclosure is typically a patient in need thereof that has been diagnosed with cancer or is at risk of developing cancer. The subject is typically a human, dog, cat, horse or any animal in which a tumor specific immune response is desired.

The present disclosure also pertains to a neoantigenic peptide, a population of APCs, a vaccine or immunogenic composition, a polynucleotide encoding a neoantigenic peptide or a vector as previously defined for use in cancer vaccination therapy of a subject or for treating cancer in a subject, wherein the peptide(s) binds at least one MHC molecule of said subject.

The present disclosure also provides a method for treating cancer in a subject comprising administering a vaccine or immunogenic composition as described herein to said subject in a therapeutically effective amount to treat the subject. The method may additionally comprise the step of identifying a subject who has cancer.

The present disclosure also relates to a method of treating cancer comprising producing an antibody or antigen-binding fragment thereof by the method as herein described and administering to a subject with cancer said antibody or antigen-binding fragment thereof, or with an immune cell expressing said antibody or antigen-binding fragment thereof, in a therapeutically effective amount to treat said subject.

The present disclosure also relates to an antibody (including variants and derivatives thereof), a T cell receptor (TCR) (including variants and derivatives thereof), or a CAR (including variants and derivatives thereof) which are directed against a tumor neoantigenic peptide as herein described, optionally in association with an MHC or HLA molecule, for use in cancer therapy of a subject, wherein the tumor neoantigenic peptide binds at least one MHC molecule of said subject.

The present disclosure also relates to an antibody (including variants and derivatives thereof), a T cell receptor (TCR) (including variants and derivatives thereof), or a CAR (including variants and derivatives thereof) which are directed against a tumor neoantigenic peptide as herein described, optionally in association with an MHC or HLA molecule, or an immune cell which targets a neoantigenic peptide, as previously defined, for use in adoptive cell or CAR-T cell therapy in a subject, wherein the tumor neoantigenic peptide binds at least one MHC molecule of said subject.

Typically, the skilled person is able to select an appropriate antigen receptor which binds and recognizes a tumor neoantigenic peptide as previously defined with which to redirect an immune cell to be used for use in cancer cell therapy. In a particular embodiment, the immune cell for use in the method of the present disclosure is a redirected T-cell, e.g. a redirected CD8+ and/or CD4+ T-cell.

In some embodiments, cancer treatment, vaccination therapy and/or adoptive cell cancer therapy as above described are administered in combination with additional cancer therapies. In particular, the T cell compositions according to the present disclosure may be administered in combination with checkpoint blockade therapy, co-stimulatory antibodies, chemotherapy and/or radiotherapy, targeted therapy or monoclonal antibody therapy.

Checkpoint inhibitors include, but are not limited to, PD-1 inhibitors, PD-L1 inhibitors, Lag-3 inhibitors, Tim-3 inhibitors, TIGIT inhibitors, BTLA inhibitors, V-domain Ig suppressor of T-cell activation (VISTA) inhibitors and CTLA-4 inhibitors, IDO inhibitors for example. Co-stimulatory antibodies deliver positive signals through immune-regulatory receptors including but not limited to ICOS, CD137, CD27 OX-40 and GITR. In a preferred embodiment the checkpoint inhibitor is a CTLA-4 inhibitor.

A chemotherapeutic entity as used herein refers to an entity which is destructive to a cell, that is the entity reduces the viability of the cell. The chemotherapeutic entity may be a cytotoxic drug. A chemotherapeutic agent contemplated includes, without limitation, alkylating agents, anthracyclines, epothilones, nitrosoureas, ethylenimines/methylmelamine, alkyl sulfonates, alkylating agents, antimetabolites, pyrimidine analogs, epipodophylotoxins, enzymes such as L-asparaginase: biological response modifiers such as IFNa, IL-2, G-CSF and GM-CSF; platinum coordination complexes such as cisplatin, oxaliplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide: hormones and antagonists including adrenocorticosteroid antagonists such as prednisone and equivalents, dexamethasone and aminoglutethimide: progestin such as hydroxyprogesterone caproate, medroxyprogesterone acetate and megestrol acetate: estrogen such as diethylstilbestrol and ethinyl estradiol equivalents: antiestrogen such as tamoxifen: androgens including testosterone propionate and fluoxymesterone/ equivalents: antiandrogens such as flutamide, gonadotropin-releasing hormone analogs and leuprolide; and non-steroidal antiandrogens such as flutamide.

'In combination' may refer to administration of the additional therapy before, at the same time as or after administration of the T cell composition according to the present disclosure.

In addition or as an alternative to the combination with checkpoint blockade, the T cell composition of the present disclosure may also be genetically modified to render them resistant to immune-checkpoints using gene-editing technologies including but not limited to TALEN and Crispr/Cas. Such methods are known in the art, see e.g. US20140120622. Gene editing technologies may be used to prevent the expression of immune checkpoints expressed by T cells including but not limited to PD-1, Lag-3, Tim-3, TIGIT, BTLA CTLA-4 and combinations of these. The T cell as discussed here may be modified by any of these methods.

The T cell according to the present disclosure may also be genetically modified to express molecules increasing homing into tumours and or to deliver inflammatory mediators into the tumour microenvironment, including but not limited to cytokines, soluble immune-regulatory receptors and/or ligands.

In a particular embodiment, said tumor neoantigenic peptide is used in cancer vaccination therapy in combination with another immunotherapy such as immune checkpoint therapy, more particularly in combination with antibodies anti-PD1, anti-PDL1, anti-CTLA-4, anti-TIM-3, anti-LAG3, anti-GITR.

BRIEF DESCRIPTION OF THE DRAWINGS

FIG. 5A: Number of fusion transcript sequence (TE-exon fusions) in different subtypes of breast cancer (HER2+, TNBC, normal breast tissue and luminal). FIG. 5B Number of fusion transcript sequence (TE-exon fusions) in different subtypes of lung cancer (primary lung adenocarcinomas, normal lung tissue).

FIG. 6A: Samples of different subtypes of breast cancer (HER2+, TNBC, normal breast tissue and luminal). FIG. 6B: Samples of different subtypes of lung cancer (non-small cell lung cancer, normal lung tissue).

FIG. 7A: Numbers of tumor-specific HLA-binding peptides per subtypes of breast cancer patient are shown. FIG. 7B: Numbers of predicted tumor neoantigenic peptides shared across luminal subtypes samples (n=784) (abscissa). FIG. 7C: Numbers of predicted tumor neoantigenic peptides shared across HER2+ subtypes samples (n=100) (abscissa). FIG. 7D: Numbers of predicted tumor neoantigenic peptides shared across TNBC subtypes samples (n=197) (abscissa).

FIG. 8B: Distribution of tumor-specific peptides per patient across lung adenocarcinomas. Numbers of predicted tumor neoantigenic peptides shared across primary tumor subtypes samples (n=516) (abscissa).

FIGS. 9A-9B: Reconstruction of the fusion nucleotide sequence when the donor is the exon (FIG. 9A) and when the donor is the TE (FIG. 9B).

FIG. 11A: Percentage of tetramer positive CD8 T cells for the indicated fusion transcript-derived peptides induced by autologous moDCs in immunogenicity assays for the 6 healthy donors analyzed. FIG. 11B: Cytokine secretion of CTL-clones after stimulation with different concentration of specific peptide. On the right is listed the CTL-clones generated and their peptide specificity. FIG. 11C: Killing assay for CTL-clone 9 in co-culture with target cells loaded with 2 different peptide concentration in combination with anti-MHC-I antibodies or Isotype control (Left panel), or with un-loaded targets cells at different ratios (Right panel). FIG. 11D: Killing assays for CTL-clone 9, 80 and 64 when co-cultured with peptide unloaded target cells in combination with anti-MHCI-I antibodies or isotype control. Effector:Target ratio is indicated in each individual plot. H1650 were used as target cells for each plot of this figure.

FIG. 12. Expression of TCR recognizing fusion-derived peptides. Transduced Jurkat-reporter cells with TCR sequence derived from CTL-clone 9 co-cultured with target cells alone, or loaded with 2 different peptide concentration. Plots show percentage of positive Jurkat cells for the 3 reporter genes evaluated by flow cytometry, using H1650 cell line as target cells (upper plots) or H1395 cell line as target cells (lower plots). Negative control: non-transduced Jurkat cells. No peptide: transduced Jurkat cells co-cultured with peptide unloaded target cells. Positive control: Transduced Jurkat cells stimulated with PMA/ionomycin.

FIG. 14B is shown the percentage of Naïve (CCR7+CD45+), Central Memory (CM, CCR7+CD45−), Effector Memory (EM, CCR7-CD45−) and Terminal Effector (TE, CCR7-CD45+) cells of tetramer positive parental cell population.

EXAMPLES

Figure 1A:
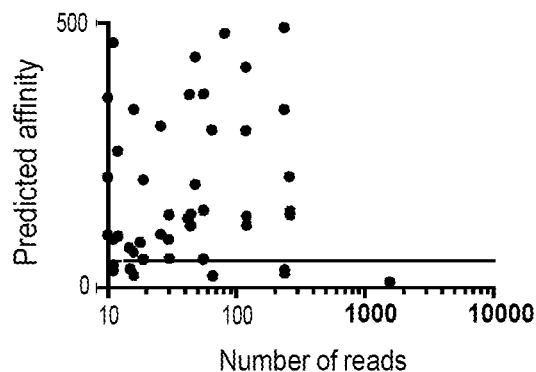
FIGS. 1A-1C: Tumor neoantigenic peptides (or TE-derived epitopes) having a predicted affinity for MHC alleles of less than 500 nM, identified by the in silico method according to the disclosure in the tumor mouse lines B16F10-OVA cells (FIG. 1A) and in MCA101-OVA cells (FIG. 1B) and identified both in the two lines (FIG. 1C).

1. Example 1: Identification of Fusion Transcript Sequence Encoded Tumor Neoantigenic Peptide 1.1 Proof of Concept in Mice To detect individual and shared tumor neoantigenic peptide issued from fusion transcripts sequences, a bioinformatics pipeline has been developed. This pipeline is designed to identify tumor-specific mRNA sequences composed in part of a TE sequence and in part of an exonic sequence. This pipeline implies determining the MHC alleles. For each human sample, the Class I and Class II MHC alleles can be determined using the seq2hla (v2.2) tool (bitbucket.org/sebastian_boegel/seq2hla). For mouse models, murine H-2 alleles are generally known. The bioinformatics method comprises the mapping of transcripts from RNA-sequencing against the reference genome. For the proof of concept analyses described here, mm10) was used for mouse and hg19 for human. Different versions of assembled genomes can be used for example hg19, hg38, mm9 or mm10. This mapping is carried out with STAR (v2.5.3a) (github.com/alexdobin/STAR), with the following setting:

For allowing multi-hits mapping the parameter outFilterMultimapNmax which sets the maximum number of loci, the read is allowed to map to, is set at 1000, and For detecting the abnormal junction (fusion), the parameter chimSegmentMin which sets the minimum length of fusion segment, is set at 10, the parameter chimJunctionOverhangMin which sets the minimum overhang for a fusion junction is set at 10.

Normal (from SJ.out.tab output file) and abnormal (from Chimeric.out.junction output file) junctions are annotated using Ensembl and repeatmasker databases. Normal junctions define all the junctions that match the parameters used for the mapping (maximum intron length <=1 000 000 bp (set by --alignIntronMax), same chromosome and well oriented) and abnormal ones are junctions that do not match with at least one of the previous criteria. This mean that a TE/Exon junction could be in both junction type but a Exon/Exon junction must be in normal file (SJ.out.tab). Transcript sequences comprising a junction between a TE sequence and an exonic sequence are extracted in silico. From the area of the transcript sequence which overlaps the junction, or downstream of the junction when out-of-frame (reading frame non-canonical), the software predicts, in all reading frames, all possible peptides of 8 or 9 mers. Then, the binding affinity of all these possible peptides for the MHC alleles previously defined for is the matched sample determined netMHCpan (v3.4) (cbs.dtu.dk/services/NetMHCpan/). There are currently more than a dozen various prediction algorithms for predicting the binding affinity of peptides, with NetMHC being the most widely used and validated algorithm for neoantigen prediction pipelines.

Peptides with either less than 500 nM or with a percentile rank less than 2% are considered as potential neo-antigens. Each splice site (donor or acceptor) is uniquely annotated as TE or as Exon. The part in the 5' end is qualified "donor", and the part in the 3' is qualified "acceptor".

Predicted HLA-binding peptides shared between cancer and normal tissues are excluded from further analyses.

This method has been applied to RNAseq data obtained from 7 well-characterized murine tumor cell lines (B16F10, B16F10-OVA, MCA101, MCA101-OVA, MC38, MC38-

GFP, MC38-GFP-OVA). The cell lines with the extension-OVA corresponding to the same model but further expressing ovalbumin. In this study, this line is considered as the similar model, that is to say for example that an assay carried out on the cell line from B16F10-OVA is considered as a repeat of an assay carried out on the cell line from B16F10.

Figure 1B:
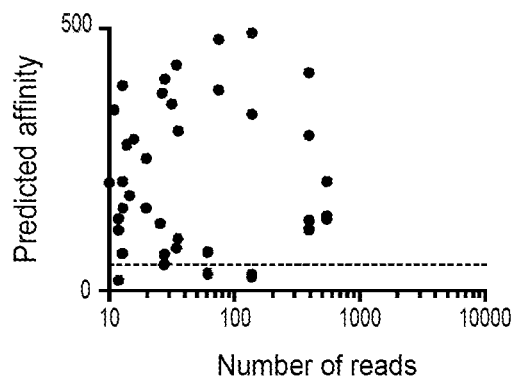
Figure 1C:
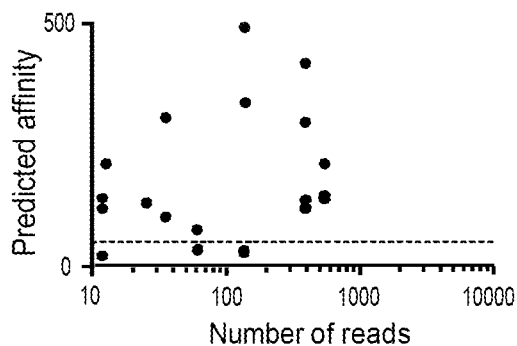

A list of candidate peptides has been obtained with these parameters (FIGS. 1A, 1B and 1C), some were specific to particular cell lines (FIGS. 1A and 1B), and some were shared between the two tumor cell lines (FIG. 1C).

For validation, we selected a range of peptides, expressed either in B16F10-OVA or MCA101-OVA, with predicted affinities less than 500 nM. Peptides were selected trying to optimize the ratio between number of reads and predicted affinity for MHC-I.

Four predicted tumor neoantigenic peptides were selected and characterized by identifying the TE and the exonic sequence (table 3).

TABLE 2

Characterization of 4 predicted tumor neoantigenic peptides selected by the method

| Peptide | Cell line | Donor | Acceptor | Predicted affinity |
| --- | --- | --- | --- | --- |
| N25 | B16/B16-OVA | ERV-MaLR (subfamily MTA) | Chmp3, exon2 | H2-Db, 51.8937 |
| N26 | MCA/MCA-OVA MC38-GFP/MC38-OVAGFP | SINE-Alu(B1F) | Angel2, exon2 | H2-Kb, 392.0384 |
| N90 | MCA/MCA-OVA | Predicted gene 45873 | ERVL-MaLR (subfamily ORR1A2-int) | H2-Kb, 403.8959 and 50.5416 |
| N94 | MCA/MCA-OVA MC38-GFP/MC38-OVAGFP | Rsrc1 | ERV1 (subfamily RLTR4 MM-int) | H2-Kb, 431.0564 |

1.2 Validation by RT-PCR of the Fusion Transcript Sequence

First, a validation by regular RT-PCR has been performed, using primer pairs with one primer in the TE sequence, and the other one in the exonic sequence.

For the RNA extraction and reverse transcription, $3-5 \cdot 10^6$ cells were lyzed in 500 µL Trizol, and 100 µL phenol-chloroform added to the lyzates prior centrifugation. Aqueous phase was collected, mixed in a 1:1 ratio with 100% EtOH and transferred to RNAeasy minikit columns. RNA was then collected following manufacturer's instructions (including on column DNAse treatment). After RNA elution, DNA contaminants were further removed by treatment with Turbo DNAse (Fisher scientific), according to manufacturer's instructions). RNA concentration was measured using a nanodrop, and 1 µg of RNA used for reverse transcription. First strand synthesis was performed with Superscript III (Life technologies) using oligodT (15) as primers, according to manufacturer's instructions. Primers were ordered from Eurogentec. PCR reactions were performed using Taq polymerase. After identification of optimal conditions for each reaction, PCR products were extracted from agarose gels, and sequencing was performed using GATC lightrun. Sequence alignment was checked with APE software.

Figure 2A:
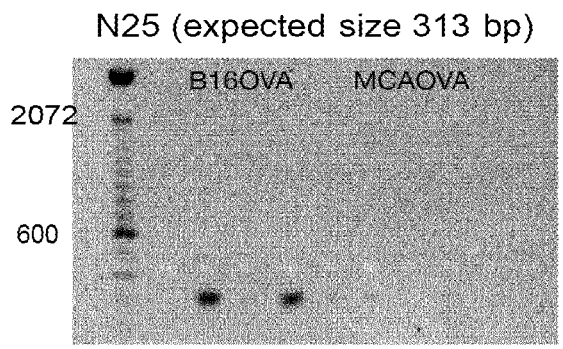
FIG. 2A: RT-PCR gels of amplification of the fusion transcript sequence encoding the neoantigenic peptide N25, in cDNA of tumor mouse lines B16F10-OVA and MCA101-OVA.
Figure 2B:
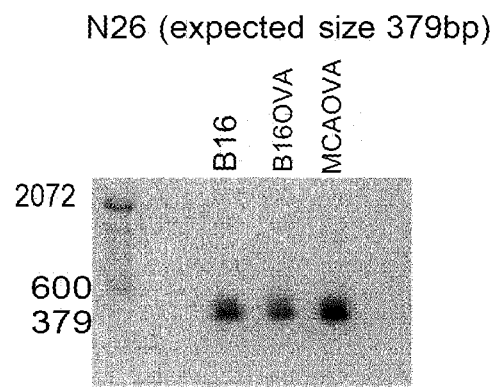
FIG. 2B: RT-PCR gels of amplification of the fusion transcript sequence encoding the neoantigenic peptide N26, in cDNA of tumor mouse lines B16F10, B16F10-OVA and MCA101-OVA.

Using this approach, bands matching predicted size for N25, N26, N90 and N94 were detected, respectively in the cell lines identified in Table 1 (See FIG. 2A for N25). Interestingly, although N26 was detected only in MCA and MC38 cells in silico by RNAseq as previously described in the pipeline, using RT-PCR we detected a band corresponding to N26 in B16F10-OVA cells (FIG. 2B), indicating that this sequence is shared between three independent tumor cell lines (MCA, MC38 and B16F10). By re-analyzing the RNAseq data, we found that the N26 junction was present in B16F10-OVA cells, but below the detection threshold of the algorithm. Moreover, sequencing of the RT-PCR product showed exact match with sequences predicted by the algorithm.

1.3 In Vivo Immunization of Mice

Figure 3A:
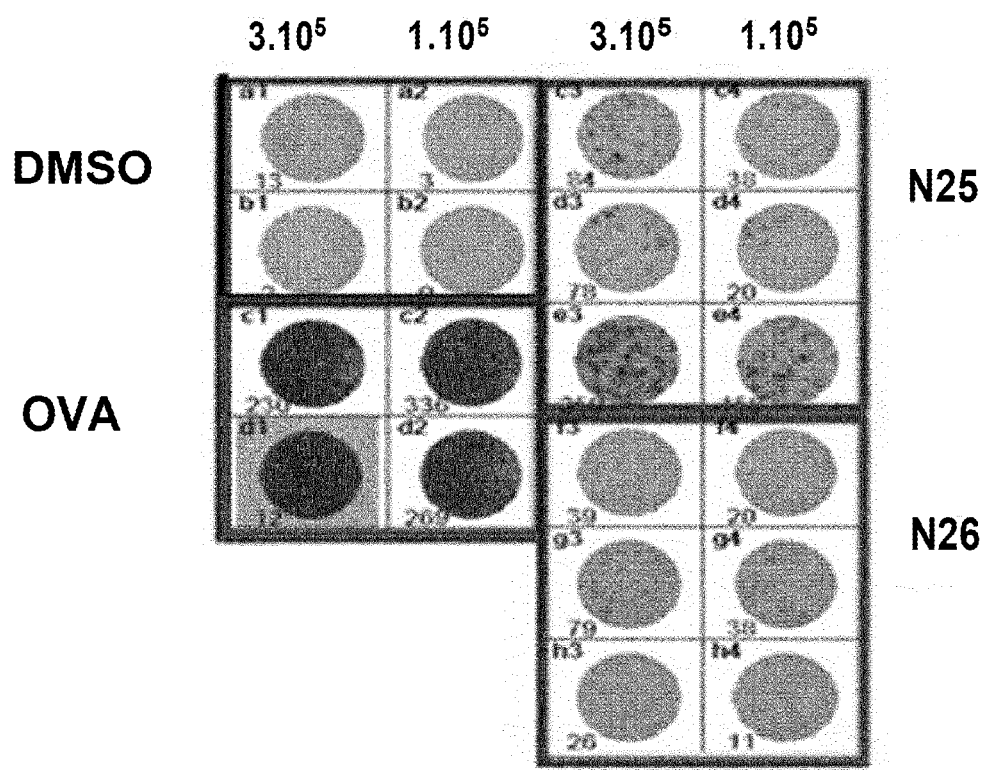
FIG. 3A: Detection of peptide-reactive IFNg-secreting cells by ELISPOT in inguinal lymph nodes from immunized animals with DMSO (negative control), OVA (ovalbumine) (positive control), peptide N25 or peptide N26.
Figure 3B:
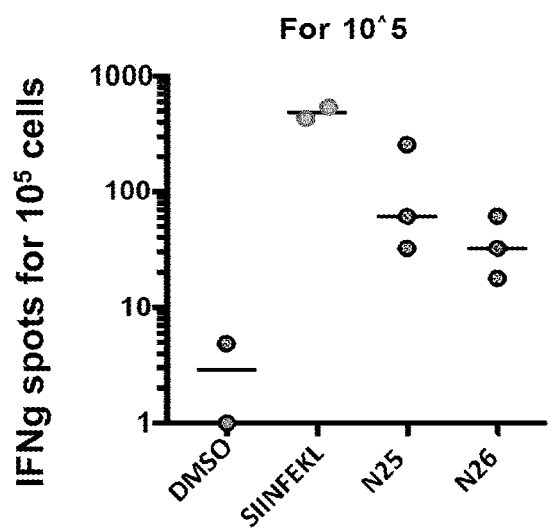
FIG. 3B: IFNg spots for 10^5 cells for immunized animals with DMSO (negative control), SIINFEKL (positive control), N25 or N26 peptide.

To validate these candidates in vivo, short (9-mers) peptides corresponding to neoantigenic peptide which binds to the MHC class I sequences, were synthetized. For the in vivo assays, long (27-mers) peptides, which include the flanking regions to the predicted MHC-binding short peptides of 9 mers, were synthetized, because this length is better suited for in vivo immunization. B16F10 OVA and MCA101-OVA were maintained in RPMI, Glutamax, 10% FCS, 1% penicillin-streptomycin and passaged using TrypLE. Cells were kept in culture for a maximum of one month, and new vials were thawed for each in vivo experiment. C57BL6J recipient mice were immunized with 100 µg long peptide (N25L or N26L), SIINFEKL peptide (short OVA peptide), OVA (Sigma) or DMSO, each with 50 µg polyI: C, by subcutaneous injection into the flank. Immunizations were repeated 7 days after primary immunization. 3 days later (10 days after primary immunization), animals were sacrificed and numbers of peptide-specific IFNg-secreting CD8 T cells in inguinal lymph nodes were detected by ELISPOT (FIG. 3A). Short peptides (N25, N26, or SIINFEKL) or DMSO at 10 µg·mL$^{-1}$ were used to restimulate T cells. Alternatively, 7 days after secondary immunization, animals were injected subcutaneously with $2.5 \cdot 10^5$ B16F10-OVA or $5 \cdot 10^5$ MCA-OVA cells in PBS. We found that N25, and to a lesser extent N26 were able to induce immune responses (FIG. 3B).

1.4 In Vivo Treatment of Mice with Tumor

To test whether these peptides were protective against tumor cells, we immunized C57BL6 mice with 100 mg peptides N25L or N26L, or OVA (control peptide) and 50 µg polyI: C in PBS at d0 and d7, and at d14, we injected $2.5 \cdot 10^5$ B16F10-OVA cells to mice immunized with OVA, N25L and N26L. B16F10 OVA and MCA101-OVA were maintained in RPMI, Glutamax, 10% FCS, 1% penicillin-streptomycin and passaged using TrypLE. Cells were kept in culture for a maximum of one month, and new vials were thawed for each in vivo experiment. C57BL6J recipient mice were immunized with 100 µg long peptide (N25L or N26L), OVA (Sigma) or DMSO, each with 50 µg polyI: C, by subcutaneous injection into the flank. Immunizations were repeated 7 days after primary immunization.

Figure 4A:
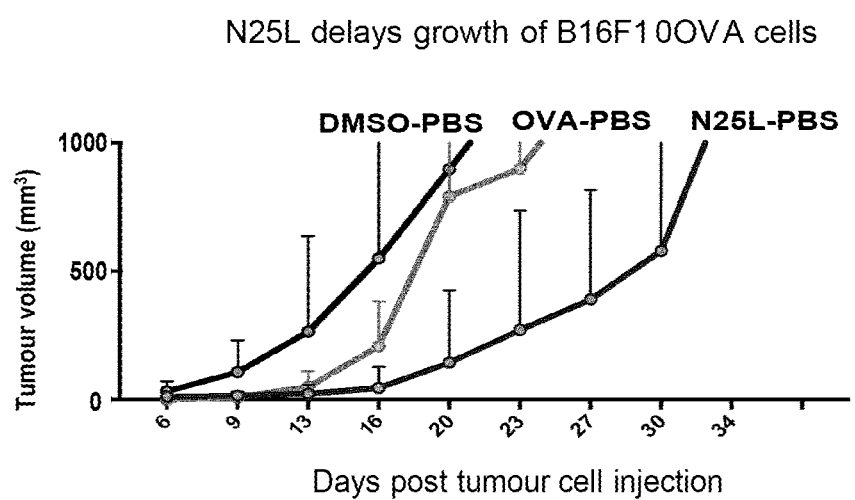
FIG. 4A: Evolution of the tumor volume (mm3) in mice beforehand immunized with DMSO, OVA or N25L peptide, following the days after the injection of tumor cells B16F10-OVA into said immunized mice.
Figure 4B:
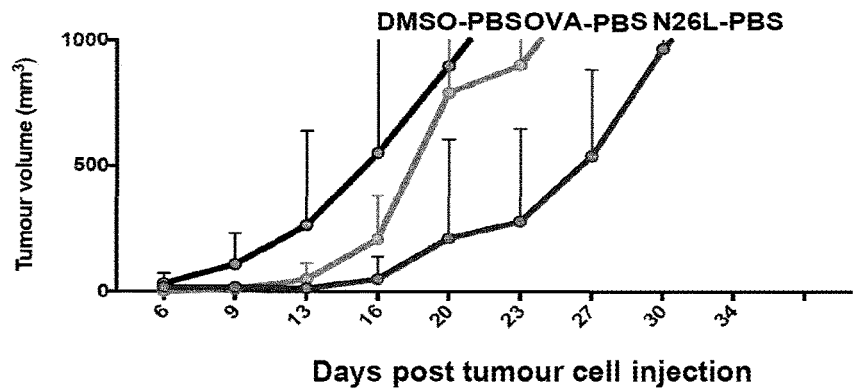
FIG. 4B: Evolution of the tumor volume (mm3) in mice beforehand immunized with DMSO, OVA or N26L peptide, following the days after the injection of tumor cells B16F10-OVA into said immunized mice.
Figure 5A:
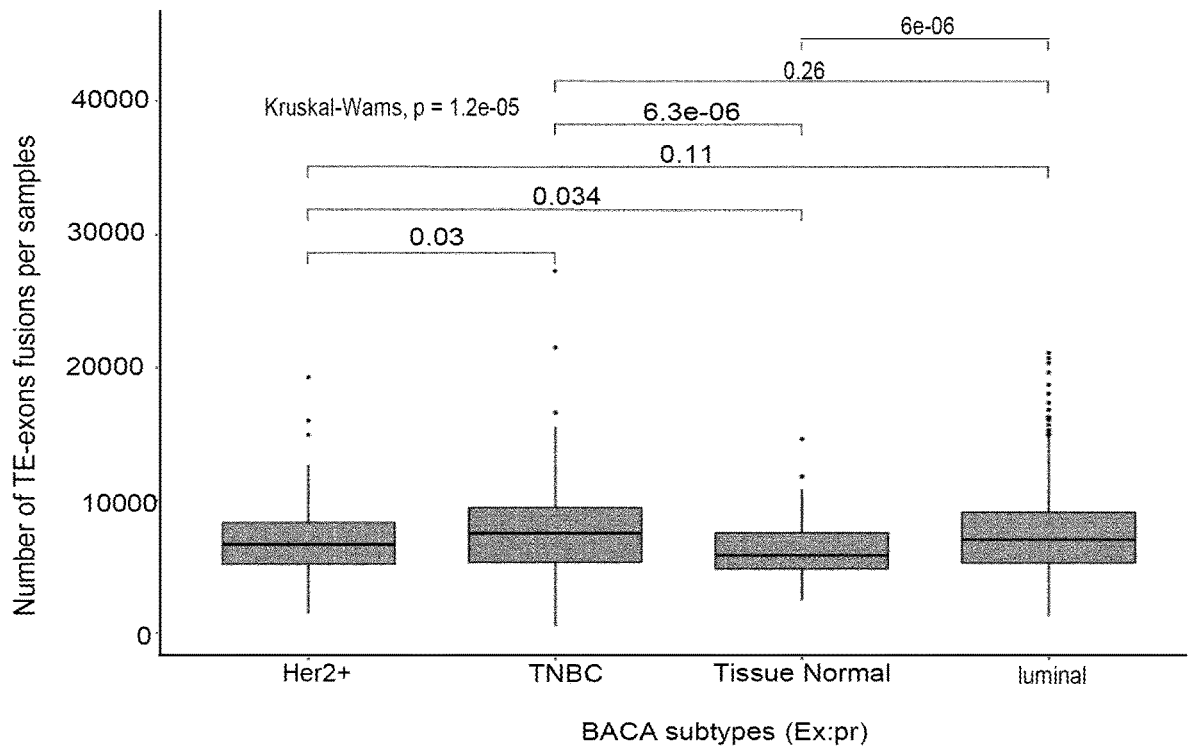
FIGS. 5A-5B: TCGA data sets for 784 luminal, 100 HER2+, 197 TNBC, 112 normal breast tissue, 516 primary lung adenocarcinomas (primary tumor) and 59 normal lung tissue (solid tissue normal), were analyzed by the method for identifying fusion transcript sequence encoded tumor neoantigenic peptide described.
Figure 5B:
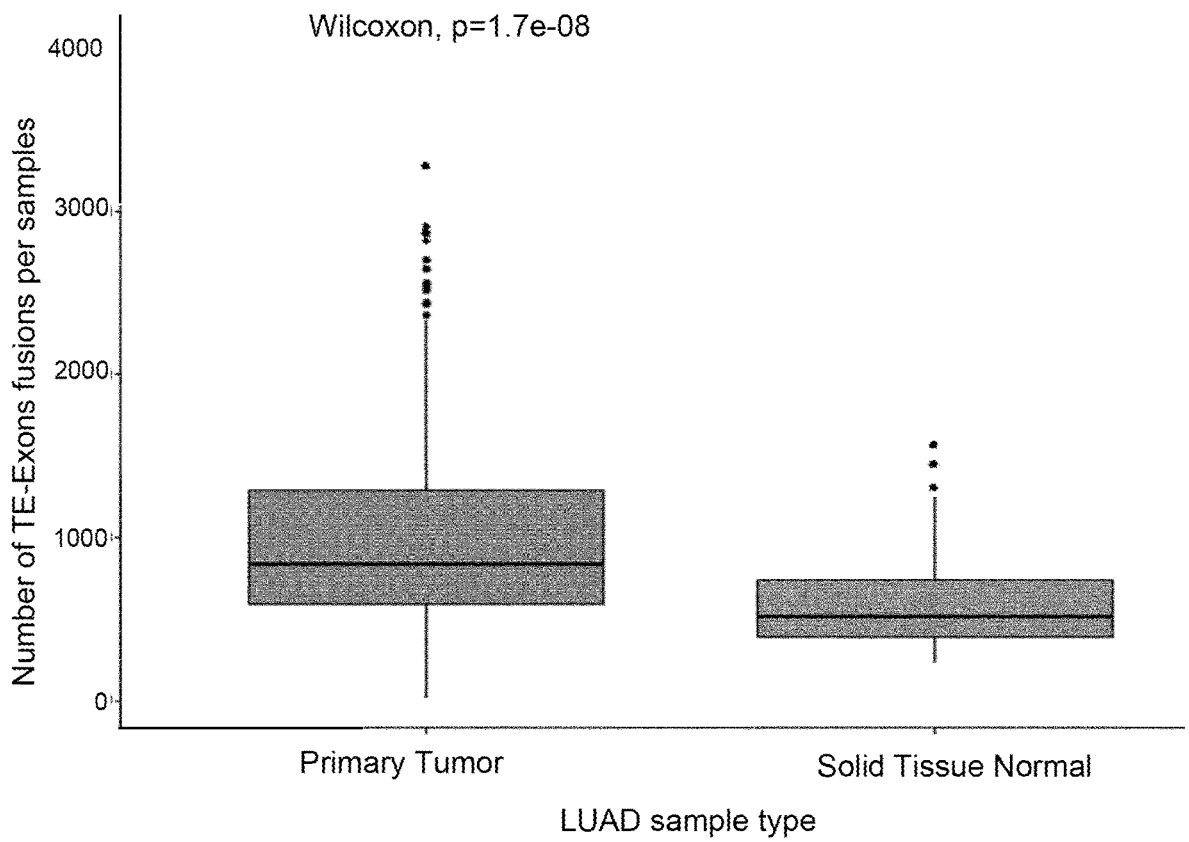
Figure 6A:
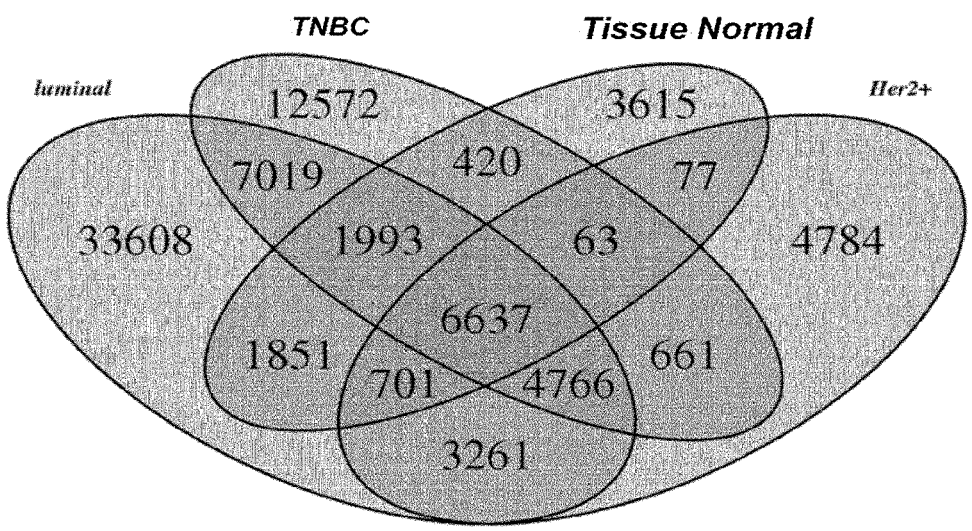
FIGS. 6A-6B: 8-9 amino acid-long peptides predicted from TE-gene fusion products from each sample were tested in silico for binding to the predicted HLA alleles expressed in the same sample. Shown are peptides with predicted affinity below 500 nM for at least one HLA-A, -B, or -C allele from each sample.
Figure 6B:
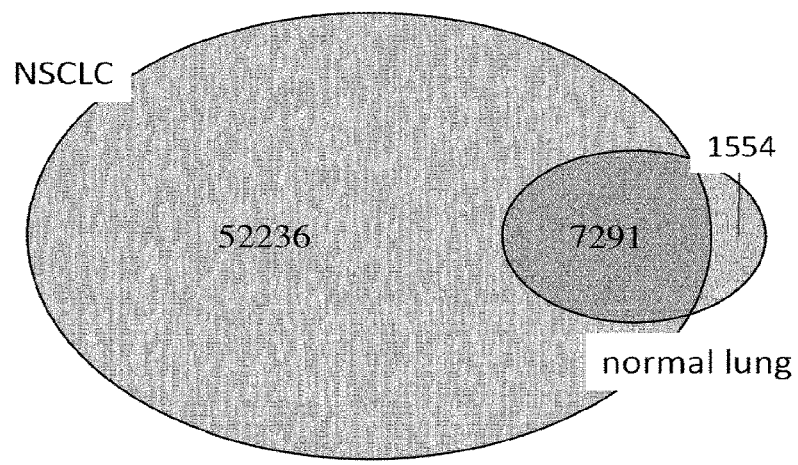
Figure 7A:
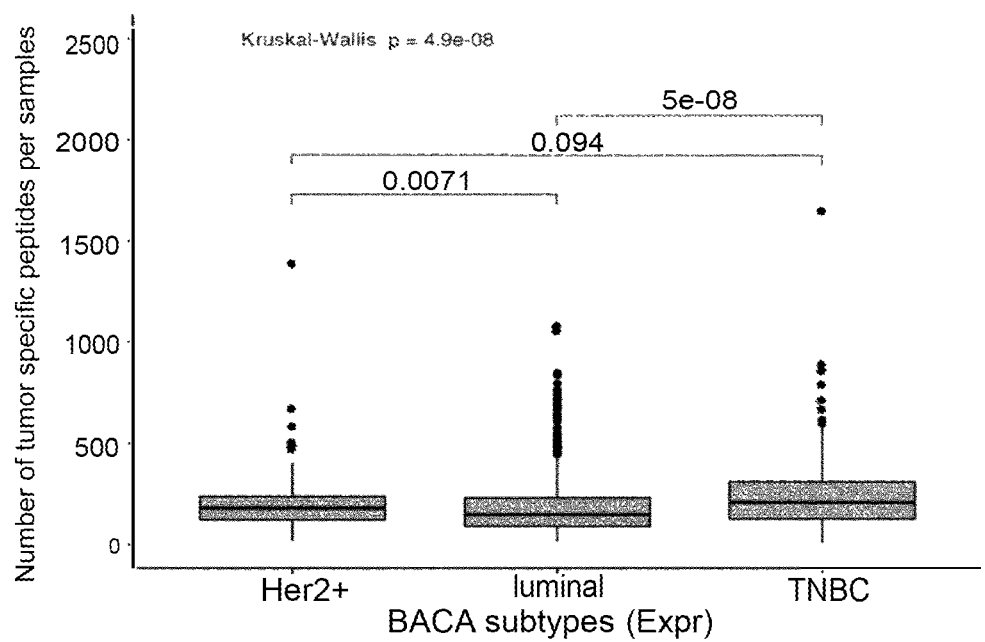
FIGS. 7A-7D: Distribution of tumor-specific peptides per patient across breast tumor subtypes.
Figure 7B:
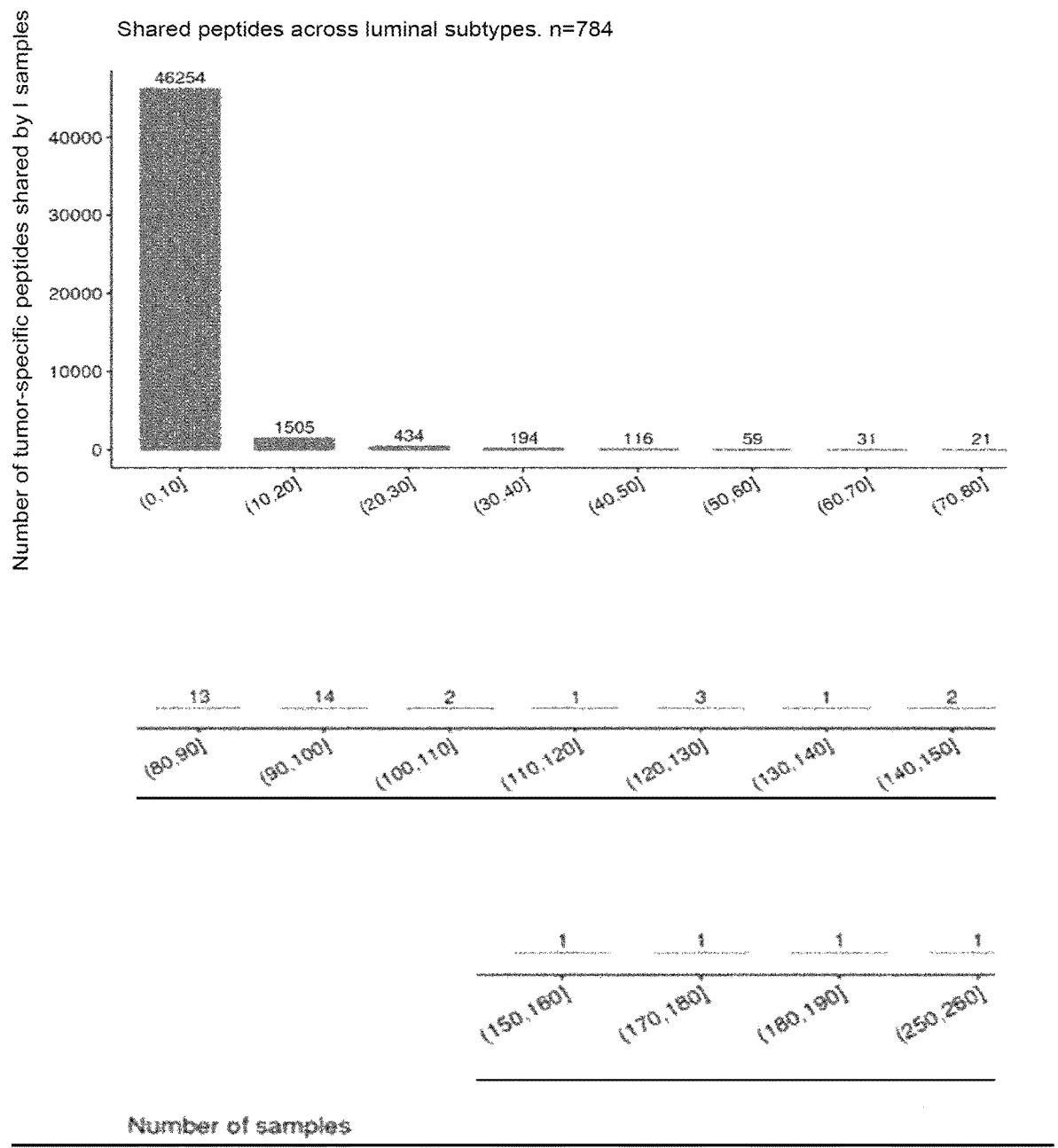
Figure 7C:
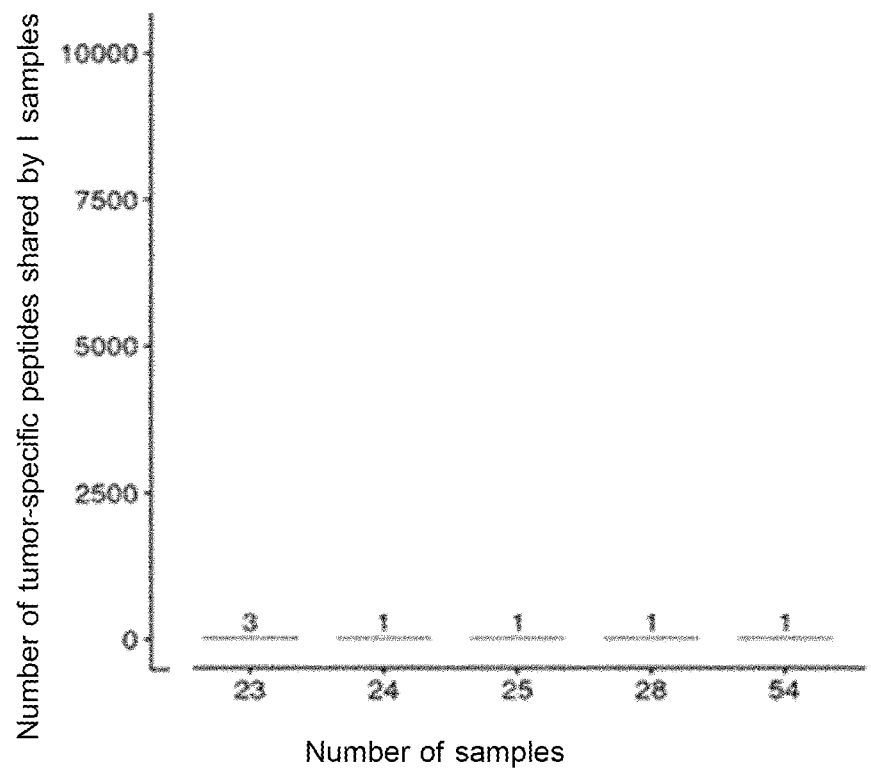
Figure 7D:
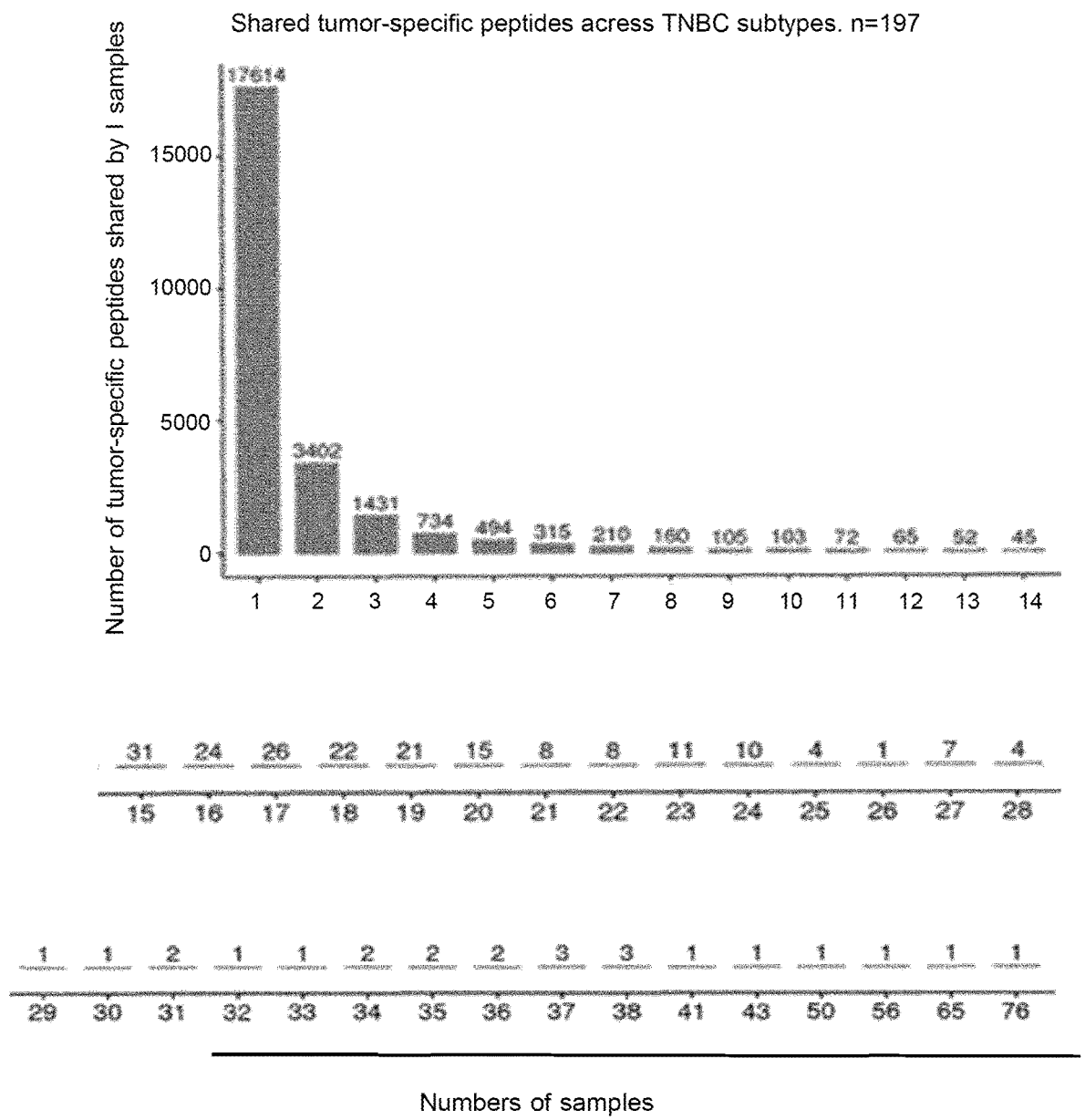
Figure 8A:
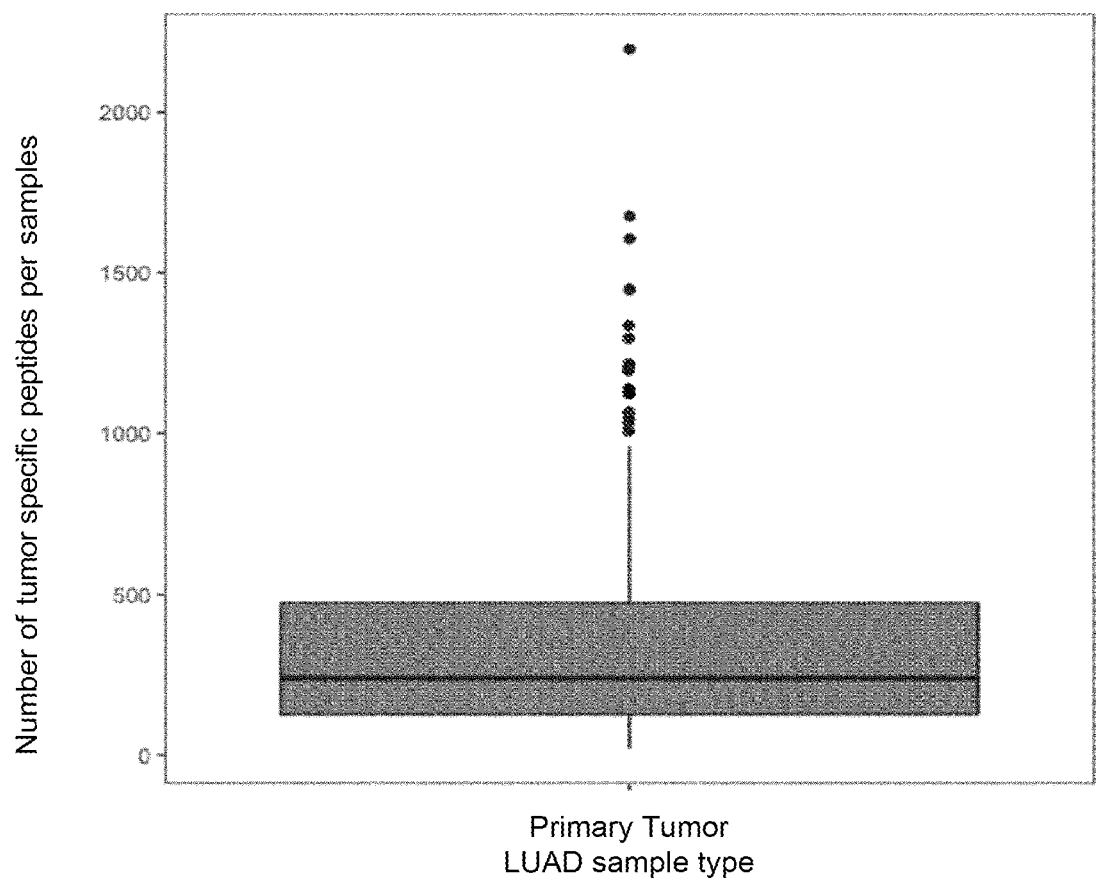
FIG. 8A: Numbers of tumor-specific HLA-binding peptides per primary lung adenocarcinomas (LUAD) sample (lung cancer).

Short peptides (N25, N26, or SIINFEKL) or DMSO at 10 µg·mL-1 were used to restimulate T cells. Alternatively, 7 days after secondary immunization, animals were injected subcutaneously with $2.5 \cdot 10^5$ B16F10-OVA or $5 \cdot 10^5$ MCA-OVA cells in PBS. Tumor size was measured twice weekly using a manual caliper, and animal health status monitored throughout the experiment timeframe (FIGS. 4A and 4B). Animals were sacrificed when tumor volume reached 1 mm3. Strikingly, we observed that N25L significantly delayed the formation of B16OVA tumors, in a more efficient way than OVA. Moreover, we obtained a similar result upon N26L immunization.

2 Example 2: Identification of Human Lung Adenocarcinoma (LUAD) Neoantigenic Peptides Derived from Fusion Transcripts Composed of a TE Element and an Exonic Sequence 2.1 Material and Methods RNA extraction. Tumour and juxtatumour samples were cut into pieces of #1 mm3 and resuspended in 700 μl RTL lysis buffer (Quiagen) supplemented with 1% β-mercaptoethanol and homogenized using Perecellys 24 Tissue Homogenizer (Bertin Technologies). Total RNA isolation was performed using RNeasy Micro Kit (Qiagen) following manufacturer instructions. Total RNA from tumour cell lines were extracted from $5 \cdot 10^6$ tumor cell lines using the same procedure.

PCR and Sequencing. Primers were designed using APE software. For each sample, 1 μg of RNA was retrotranscribed into cDNA using SuperScript III Reverse transcriptase (ThermoFisher), as indicated by the provider. PCR reaction was performed using GoTaq G2 Hot Start Polymarase (Promega). All primers were used in a concentration of 0.5 μM. Reactions were carried out in Veriti™ 96-Well Thermal Cycler (ThermoFisher). PCR products were loaded in LabChip GX (Caliper LifeSciences) and analysed by LabChip GX Software (v4.2).

PCR reactions were repeated for those samples with an amplification product on the expected size. Then, the PCR products were run in a 2% agarose gel SYBR Free Dye (1/10000) (Invitrogen). The specific bands were cut and the DNA products were purified using QIAquick Gel Extraction Kit (Qiagen) following manufacturer instructions. Finally, these products were sequenced by EuroFins Scientific. The resulting sequences were compared to the expected one using Serial Cloner software.

Tetramer formation. HLA-A2 monomers were purchased from ImmunAware® and the formation of tetramers was evaluated with synthetic ER-derived peptides following manufacturer instructions. Briefly, synthetic HLA-A2 monomers were incubated with synthetic peptides during 48 h at 18° C. Tetramerization was done by further incubation of monomers with biotinylated-sepharose. Finally, tetramer formation was measured by flow cytometry using a PE-conjugated anti-β2-microglobulin antibody. As a positive control we used a peptide derived from CMV provided by the manufacturer.

In experiments addressed to evaluate the presence of specific CD8+ T cells, the tetramerization step was performed by incubating the monomers with different combinations of fluorescent streptavidin (PE, APC, PE-Cy5, PE-CF594, BV421, BV711 and FITC).

Priming of naïve CTLs. PBMCs were obtained by Ficoll gradient separation from HLA-A2+ healthy blood donors. CD14+, CD4+ and CD8+ cells were purified by positive selection using magnetic beads (Miltenyi Biotec). While CD4+ and CD8+ T cells were cryopreserved until the experiment day, CD14+ fraction was cultured in the presence of IL-4 (50 ng/mL) and GM-CSF (10 ng/ml) at $10^6$ cells/mL during 5 days to obtain moDCs. After this period of time, the moDCs were maturated with LPS and incubated with synthetic ER-derived peptides at a final concentration of 1 μg/mL for 2 hours. Finally, peptide-loaded moDCs were co-cultured with autologous CD4+ and CD8+ T cells in culture medium supplemented with with IL-2 (10 U/ml) and IL-7 (100 ng/ml). The ER-derived peptide stimulation of specific CD8+ CTL populations was assessed by MHC-I tetramer staining by flow cytometry using a combination of two-color tetramer for each peptide.

Tetramer Staining. Cells were resuspended in PBS, stained with Live/Dead Aqua-405 nm (ThermoFisher) during 20 minutes at 4° C. and washed once. After that, cells were resuspended in PBS-1% BSA containing the mix of SA-coupled tetramers and incubated in the dark at room temperature during 20 minutes. Without further washing, surface antibodies were added in PBS-1% BSA and cells were incubated 20 minutes in the dark at 4° C. Surface antibodies were a combination of anti-CD3-BV650+ anti-CD8-PECy7 in combination with anti-CCR7-AF700+ anti-CD45RA-BUV395 when required. Finally, cells were washed twice and resuspended in FACS buffer for flow cytometry analysis.

CTL-clones generation. Tetramer positive cells were single-cell FACS sorted (ARIA-sorter, BD) in U bottom 96-well plates. Sorted cells were collected in 100 μl of RPMI 10% human serum AB (Sigma-Aldrich) containing 150.000 feeders' cells. Finally, 100 μl of AIM-medium containing IL-2 (3000 IU/ml) and anti-CD3 (100 μg/ml. OKT3 clone from Miltenyi) were added and cells were cultured during 15-20 days maximum. When evident cell growth was observed in wells, we perform a second round of expansions with new feeders' cells for an additional period of 15 days maximum. Cells were feed and split as necessary during this period with the same culture media (AIM-RPMI 50/50+5% Human Serum) but only containing IL-2 at 500 IU/ml. Finally, expanded clones were checked for their specificity by FACs-tetramer staining and only clones with >85% of tetramer positive clones were used for further analysis.

Killing assays. To perform killing assays, xCELLigence RTCA S16 Real Time Cell Analyzer was used. H1650 cell-line were plated at $0.5 \times 10^6$ cells/ml in pre-coated 16 well plates. One day after, cells were incubated or not during 1 h with different concentration of the correspondent synthetic peptides. After that, cells were washed twice with culture medium and incubated or not for additional 30 minutes with anti-MHC-I antibodies (clone W6/32, 50 μg/well) or isotype control at the same concentration. Without additional wash, CTL-clones were added at the correspondent ratio. The complete assay was done in free-serum culture medium in a final volume of 200 at 37° C. connected to the xCELLigence system. Impedance variation (cell-index) was measured in real-time during 40 h. Each condition was performed by duplicates.

Cytokine secretion and Jurkat cells activation. 50.000 H1650 cells were plated in 96-well plate in culture medium supplemented with 5% of fetal bovine serum. The day after, cells were culture during 1-2 h with synthetic peptides at different final concentrations. After that, cells were washed twice, CTL-clones were added at 1:1 ratio and co-cultured during 18 h with peptide-loaded target cells. Culture supernatants were collected and cytokine concentration analyzed by cytokine beads arrays (CBA, BD Biosciences) following manufacturer's instructions.

The same experiment was performed using transduced Jurkat cells instead of CTL-clones and two different types of target cells: H1650 and H1395 cell lines. In this assay, after co-cultured with peptide-loaded target cells, Jurkat cells were assessed by flow cytometry analyzing the expression of reporter markers. PMA/Ionomycin was used as positive control to activate Jurkat cells.

Tissues and Blood samples. Lung tumor, juxta tumor and lymph nodes samples were cut into small pieces and digested using a mix of collagenase-I (2 mg/ml), hyaluronidase (2 mg/ml) and DNasa (25 µg/ml) in a final volume of 2 ml culture medium (CO2 independent medium+5) during 40 min at 37° C. After digestion single cell suspensions were collected through a cell Strainer and washed. Tumor and Juxta tumor suspensions were enriched on lymphocyte fractions by a ficoll gradient. After that cells were staining for tetramer analysis by FACs as described before.

Blood samples were seeded on a ficoll gradient and PBMCs were isolated. After that, PBMCs were enriched for CD8+ T cells using EasyStep Human CD8+ T cell Enrichment Kit (STEMCELL Technologies). Finally, enriched cells were stained for tetramer analysis as described before.

Tumor infiltrating lymphocytes (TILs) cultures. Tumor tissue was cut into small pieces (1-3 mm3 size, 6-12 pieces maximum). Each tumor fragment was transferred into individual wells from 24-well plates and cultured in a final volume of 2 ml RPMI 10% Human Serum+IL-2 6000 IU/ml. Cells were feed/split as necessary during 15-20 days and cryopreserve or analyzed for tetramer staining.

TCR cloning. Total RNA was extracted from CTL-clones and retrotranscribed into cDNA using SuperScript III (ThermoFisher). TCRα and β were amplified by PCR as described in Li et al 2019. DNA products were run in 2% agarose gels and sequenced after gel band extraction (Qiagen). TCR V regions (α and β) were concatenated with murine TCR constant chain and cloned into a PEW-pEF1A-inactEGFP vector and amplified in transformed bacteria.

Jurkat transduction. Lentivirus particles were produced by HEK-293 FT cell line transfected with TCR-expression plasmids together with envelope (pVSVG) and packaging (psPAX2) plasmids. After 64 h, supernatant was collected and lentivirus particles were concentrated using 100 kDa centrifugal filter (Sigma-Aldrich). Lentivirus suspension was transferred by spinoculation into TCR-negative Jurkat cells expressing reporter genes (NFAT-GPF, NF-KB-CFP and AP-1-mCherry). After 5 days, transduction efficiency was evaluated by FACS using anti-murine TCR-B antibody (Clone H57-597). This Jurkat cells were described in Rosskopf S. et al. 2018.

Mass spectrometry data analysis. Public immunopeptidomics raw data derived from MHC-eluted peptides were analysed using ProteomeDiscoverer 1.4 (ThermoFisher) with the following parameters: no-enzyme, peptide length 8-15 aa, precursor mass tolerance 20 ppm and fragment mass tolerance 0.02 Da. Methionine was enabled as variable modification and a false discovery rate (FDR) of 1% was applied. MS/MS spectra were searched against the human proteome from Uniprot/SwissProt (updated 6 Mar. 2020) concatenated with the list of all fusion transcripts-derived proteins from lung TCGA projects. Finally, peptides matching with Uniprot database or with translated fusion transcripts present in lung normal samples were discarded.

2.2 Results: Identification of Fusion Transcript Sequences Encoding Tumor Neoantigenic Peptide in Human Subject 2.2.1 Characterization of Neoantigens First the TE-Exon fusion transcript landscape was characterized in normal samples from TCGA public database. A total of 8876 unique fusions were identified in 679 normal samples from 19 different tissues (bile duct, bladder, brain, breast, cervical, colon, head and neck, kidneys, liver, pancreas, PCPG, prostate, rectum, sarcoma, skin, thymus, thyroid, uterine). Specific fusions to each tissue type were found with a very small portion of pan-tissue fusion transcripts. These results suggest that a dedicated tissue specific regulatory mechanism is associated with these fusion transcripts.

Then the number of identified fusions in 514 LUAD samples from TCGA has been compared to their 59 normal associated pulmonary samples present in TCGA. On average, 235 fusions were identified in NSCLC samples, compared with 200 in healthy lung samples (Wilcoxon pvalue=$9\times10^{-10}$). 8269 total unique fusions were identified in NSCLC tumors.

A first category of fusions called TSF (tumor specific fusion) was obtained as those found in at least 1% of tumor samples and in none of the normal samples. 210 fusions were thus defined as TSF.

Some high-frequency fusion transcripts in tumors and low frequency in normal cells may also be good candidates for neo-antigens. Thus, a second category called TAF (tumor associated fusion) was notably defined as fusions present in less than 4% of normal tissues, notably less than 2%, and more than 10% of the tumors and that is over expressed in tumors compared to normal tissue samples.

Tables 3 and 4 (see below) describe the fusion according to whether the Exon or the TE is the donor. The first column indicates the frequency of the fusion in the NSCLC cohort. The columns Donor and Acceptor introduce the type of each element. All the columns starting with "Donor" (respectively "Acceptor") are information relative to the donor (resp. the acceptor). The sequence of the fusion can be retrieved as follow:

Donor sequence: on chromosome "Donor_Chromosome_X" starting from "Donor_start_X" to "Donor_Breakpoint_X" on strand "Donor_strand_X"

Acceptor sequence: on chromosome "Acceptor_Chromosome_X" starting from "Acceptor_Breakpoint_X" to "Acceptor_end_X" on strand "Donor_strand_X"

Care should be taken to take the reverse complement of the sequence if the fusion is present on the minus strand.

Fusion Sequence:

In order to reconstruct the fusion nucleotide sequence, the sequence of the donor on chromosome "Donor_Chromosome_X" from "Donor_start_X" to "Donor_Breakpoint_X" on strand "Donor_strand_X" and the acceptor sequence on the chromosome "Acceptor_Chromosome_X" starting from "Acceptor_Breakpoint_X" to "Acceptor_end_X" on the strand "Acceptor_strand_X" have been extracted from the Ensembl HG19 human assembly database. It is to be noted that the use of the Ensembl HG19 human database is not limitative and that any other adapted database may be used such as NCBI reference Sequence Database (RefSeq).

Care should be taken to take the reverse complement of the sequence if the fusion is present on the minus strand.

The "fusion sequence" consists of the donor sequence followed by the acceptor sequence.

Nucleotide Sequence of the Fusion Transcript:

On the basis of the known canonical transcripts in which the exon is involved, all the "fusion transcripts" were reconstructed.

When the donor is the exon (see FIG. 9A)

it starts with the beginning of the canonical transcript to the donor exon and replace the complete canonical exon sequence with the fusion sequence. In this case, the fusion transcript stops after the TE sequence of the acceptor.

When the donor is the TE (FIG. 9B)
The sequence begins at the canonical position of the acceptor exon in the transcript and forget all exons upstream. The canonical sequence of the acceptor exon was replaced with the fusion sequence and the transcript was reconstructed until the end.

Each nucleotide sequence of size k (i.e. from 24 to 75 nucleotides) of the fusion transcript (translation of the first k-mer starts at the first nucleotide of the fusion transcript, translation of the second k-mer starts at the second nucleotide of the fusion transcript, etc.) was then translated into a peptide sequence.

The obtained peptides are then further analyzed with NetMHCpan for MHC binding prediction. Affinity for binding to at least one of the known human alleles was thus predicted, (see also example 1 for further illustration) for each k-mer present in the sequence.

Table 3. Coordinates of the fusion sequences for which the donor is the exon. The names of the columns are the following:

1. Frequency in LUAD cohort
2. Donor Chromosome Exon
3. Donor start Exon
4. Donor Breakpoint Exon
5. Donor strand Exon
6. Donor transcript (i.e. Donor_tx_name_Exon)
7. Acceptor Chromosome TE
8. Acceptor Breakpoint TE
9. Acceptor end TE
10. Acceptor strand TE
11. Fusion type The fusion transcript sequence of table 3 correspond in the same order to SEQ ID NO: 118-431 (typically line 1 is SEQ ID NO: 118, line 2 is SEQ ID NO: 119, line 3 corresponds to SEQ ID NO: 120 and 121, because of the 2 donor transcripts (ENST00000296474 and ENST00000344206 respectively as indicated in col. 6), etc.).

| 1 | 2 | 3 | 4 | 5 | 6 | 7 | 8 | 9 | 10 | 11 |
|---|---|---|---|---|---|---|---|---|---|---|
| 31% | chr19 | 42265157 | 42265435 | + | ENST00000199764 | chr19 | 42274707 | 42275202 | + | TSA |
| 17% | chr12 | 71509630 | 71509630 | − | ENST00000549357 | chr12 | 71504233 | 71504376 | − | TSA |
| 15% | chr3 | 49927357 | 49927357 | − | ENST00000296474;ENST000003442066 | chr3 | 49927248 | 49927342 | − | TSA |
| 12% | chr5 | 82554349 | 82554496 | + | ENST00000282268;ENST000003386335;ENST00000396027;ENST00000511817 | chr5 | 82606608 | 82606935 | + | TSA |
| 10% | chr3 | 98600384 | 98600384 | − | ENST00000449482;ENST000003268400;ENST00000326857 | chr3 | 98586282 | 98586295 | − | TSF |
| 8% | chrX | 100169327 | 100169610 | − | ENST00000328526;ENST000003729566 | chrX | 100143801 | 100143850 | − | TSF |
| 7% | chrX | 100177782 | 100177782 | − | ENST00000328526;ENST000003729566 | chrX | 100143801 | 100143850 | − | TSF |
| 6% | chr1 | 225156461 | 225156576 | + | ENST00000430092;ENST00000400952;ENST00000366849;ENST00000439375 | chr1 | 225157336 | 225158402 | + | TSF |
| 6% | chr8 | 63502273 | 63502353 | + | ENST00000523211;ENST000003284722 | chr8 | 63546747 | 63547118 | + | TSF |
| 4% | chr4 | 57319769 | 57319927 | + | ENST00000514888;ENST00000264221;ENST00000505164;ENST00000399688;ENST000000512576 | chr4 | 57321183 | 57321327 | + | TSF |
| 4% | chr12 | 113623819 | 113623826 | + | ENST00000552495 | chr12 | 113623998 | 113624117 | + | TSF |
| 4% | chr3 | 32280465 | 32280611 | + | ENST00000458535;ENST000003075266 | chr3 | 32324083 | 32324625 | + | TSF |
| 4% | chr19 | 3868963 | 3868963 | − | ENST00000586578;ENST00000262961;ENST00000438164;ENST00000587212;ENST000004390866 | chr19 | 3855694 | 3856396 | − | TSF |
| 4% | chr4 | 56230241 | 56230438 | + | ENST00000264228 | chr4 | 56252510 | 56252750 | + | TSF |
| 3% | chr10 | 126205749 | 126205840 | + | ENST00000368842 | chr10 | 126251911 | 126252288 | + | TSF |
| 3% | chr1 | 241803184 | 241803184 | − | ENST00000366554;ENST000000331838 | chr1 | 241771682 | 241771840 | − | TSF |

-continued

| 1 | 2 | 3 | 4 | 5 | 6 | 7 | 8 | 9 | 10 | 11 |
|---|---|---|---|---|---|---|---|---|---|---|
| 3% | chr12 | 56742313 | 56742313 | − | ENST00000314128; ENST0000055723 5 | chr12 | 56740986 | 56741274 | − | TSF |
| 3% | chr1 | 234546191 | 234546191 | − | ENST00000040877 | chr1 | 234545319 | 234545408 | − | TSF |
| 3% | chr7 | 81964451 | 81964451 | − | ENST00000356860; ENST0000035625 3;ENST000004235 88 | chr7 | 81929467 | 81929664 | − | TSF |
| 3% | chr2 | 89160398 | 89160398 | − | ENST00000390239 | chr2 | 89129384 | 89129429 | − | TSF |
| 3% | chr5 | 54993674 | 54993674 | − | ENST00000396865; ENST0000053976 8;ENST000003186 72;ENST00000508 124;ENST0000051 1233;ENST000005 03891;ENST00000 513993;ENST0000 0505563;ENST000 00506624;ENST00 000507109 | chr5 | 54993040 | 54993109 | − | TSF |
| 3% | chrX | 119708406 | 119708406 | − | ENST00000404115 | chrX | 119705855 | 119706010 | − | TSF |
| 3% | chr2 | 135223685 | 135223685 | − | ENST00000281924 | chr2 | 135216236 | 135216307 | − | TSF |
| 3% | chr11 | 20981978 | 20982106 | + | ENST00000298925; ENST0000035713 4;ENST000003253 19;ENST00000532 434 | chr11 | 21041136 | 21041271 | + | TSF |
| 2% | chr13 | 53307354 | 53307354 | − | ENST00000431550; ENST0000044890 4;ENST000003779 62 | chr13 | 53304269 | 53304818 | − | TSF |
| 2% | chr3 | 138289160 | 138289160 | − | ENST00000264982; ENST0000054223 7;ENST000004848 88;ENST00000474 781;ENST0000048 1834;ENST000004 68900;ENST00000 462419;ENST0000 0464035 | chr3 | 138261631 | 138262493 | − | TSF |
| 2% | chr1 | 1255836 | 1255836 | − | ENST00000435064; ENST0000054043 7;ENST000004509 26;ENST00000545 578;ENST0000052 8879;ENST000004 34694;ENST00000 526797;ENST0000 0527719;ENST000 00530031;ENST00 000534345;ENST0 0000498476 | chr1 | 1255085 | 1255253 | − | TSF |
| 2% | chr2 | 135470770 | 135470770 | − | ENST00000281924 | chr2 | 135443800 | 135443808 | − | TSF |
| 2% | chr5 | 23976106 | 23976159 | + | ENST00000512559; ENST0000050793 6 | chr5 | 24177946 | 24178380 | + | TSF |
| 2% | chr9 | 125054028 | 125054119 | + | ENST00000297908; ENST0000034464 1;ENST000003737 23;ENST00000373 729;ENST0000039 4315 | chr9 | 125068067 | 125068171 | + | TSF |
| 2% | chrX | 117900807 | 117900939 | + | ENST00000371666 | chrX | 117902549 | 117902902 | + | TSF |
| 2% | chr5 | 31493314 | 31493314 | − | ENST00000511367; ENST0000034462 4;ENST000004427 43;ENST0000513 349 | chr5 | 31489188 | 31489272 | | TSF |
| 2% | chr2 | 89416833 | 89416936 | − | ENST00000490686 | chr2 | 89370042 | 89370075 | − | TSF |

-continued

| 1 | 2 | 3 | 4 | 5 | 6 | 7 | 8 | 9 | 10 | 11 |
|---|---|---|---|---|---|---|---|---|----|----|
| 2% | chr20 | 29632611 | 29632721 | + | ENST00000278882; ENST00000358464 | chr20 | 29652086 | 29652324 | + | TSF |
| 2% | chr14 | 66096210; 66096217 | 66096324 | + | ENST00000360689; ENST00000394586;ENST00000342677;ENST00000394585;ENST000003 58307;ENST00000557164 | chr14 | 66099743 | 66101298 | + | TSF |
| 2% | chr | 130678687 | 130678687 | − | ENST00000335791 | chr9 | 130678527 | 130678564 | − | TSF |
| 2% | chr1 | 180283827 | 180283827 | − | ENST00000367595 | chr1 | 180281457 | 180281879 | − | TSF |
| 2% | chr20 | 44333136 | 44333136 | − | ENST00000335769 | chr20 | 44322980 | 44322991 | − | TSF |
| 2% | chr2 | 89512908 | 89512947 | − | ENST00000498435 | chr2 | 89389297 | 89389324 | − | TSF |
| 2% | chr8 | 62546242 | 62546242 | − | ENST00000541428; ENST00000379454;ENST00000522919;ENST00000356457;ENST00000519234;ENST00000518068;ENST00000517903;ENST00000445642;ENST00000517847;ENST00000522835 | chr8 | 62544521 | 62544571 | − | TSF |
| 2% | chr4 | 1102131 | 1102131 | − | ENST00000382968; ENST00000433731;ENST00000511620;ENST00000510715;ENST00000333673 | chr4 | 1101132 | 1101138 | − | TSF |
| 2% | chr6 | 24551662 | 24551662 | − | ENST00000430948; ENST00000535378;ENST00000378214;ENST00000543707 | chr6 | 24548828 | 24548834 | − | TSF |
| 2% | chr1 | 11115838 | 11115838 | − | ENST00000490101; ENST00000376957 | chr1 | 11115464 | 11115465 | − | TSF |
| 2% | chr7 | 55270210 | 55270401 | + | ENST00000455089 | chr7 | 55272949 | 55272949 | + | TSF |
| 2% | chr8 | 42924698; 42924750 | 42924802 | + | ENST00000534420; ENST00000302279;ENST00000533998;ENST00000342116;ENST00000531266;ENST00000533336;ENST00000525699;ENST00000529687 | chr8 | 42925245 | 42925476 | + | TSF |
| 2% | chr2 | 176860281; 176860286 | 176860286 | − | ENST00000392540; ENST00000272748;ENST00000544803;ENST00000445472 | chr2 | 176859008 | 176859011 | − | TSF |
| 2% | chr1 | 63955754 | 63955754 | − | ENST00000371092; ENST00000271002;ENST00000489099;ENST00000283568 | chr1 | 63952444 | 63952998 | − | TSF |
| 2% | chr16 | 2825452 | 2825452 | − | ENST00000262306; ENST00000409906; ENST00000409477;ENST00000494946 | chr16 | 2823822 | 2823948 | − | TSF |
| 2% | chr7 | 16900083; 16900124 | 16900124 | − | ENST00000402239; ENST00000310398;ENST00000414935 | chr7 | 16894536 | 16894625 | − | TSF |
| 2% | chr17 | 79532346; 79532531 | 79532531 | − | ENST00000374747; ENST00000539314;ENST000005727 | chr17 | 79527702 | 79527706 | − | TSF |

| 1 | 2 | 3 | 4 | 5 | 6 | 7 | 8 | 9 | 10 | 11 |
|---|---|---|---|---|---|---|---|---|---|---|
|  |  |  |  |  | 60;ENST00000573876;ENST0000033 1134;ENST000005 73519;ENST00000 571714;ENST0000 0572824;ENST000 00573212 |  |  |  |  |  |
| 2% | chr19 | 55178145; 55178148 | 55178200 | + | ENST00000391733; ENST0000039173 6;ENST000002704 52;ENST00000430 952;ENST0000039 1734;ENST000004 34286 | chr19 | 55178294 | 55178458 | + | TSF |
| 2% | chr3 | 48715987; 48715997 | 48715997 | − | ENST00000413374; ENST0000034152 0;ENST000004166 49;ENST00000294 129 | chr3 | 48702393 | 48702506 | − | TSF |
| 2% | chr3 | 137906397; 137906427 | 137906441 | + | ENST00000469044; ENST0000046160 0;ENST000004618 22;ENST00000470 821;ENST0000047 1709;ENST000005 38260;ENST00000 463485;ENST0000 0393058 | chr3 | 137907243 | 137907252 | + | TSF |
| 2% | chr12 | 93873164 | 93873248 | + | ENST00000549982; ENST0000036163 0;ENST000005522 17;ENST00000393 128;ENST0000054 7098;ENST000005 49561;ENST00000 548545 | chr12 | 93876129 | 93876286 | + | TSF |
| 2% | chr1 | 53558226 | 53558226 | − | ENST00000371494 | chr1 | 53556655 | 53556736 | − | TSF |
| 2% | chr2 | 143743517 | 143743590 | + | ENST00000264170; ENST0000037577 3;ENST000004095 12 | chr2 | 143745513 | 143745682 | + | TSF |
| 1% | chr12 | 117537030 | 117537030 | − | ENST00000470612 ENST0000033520 9;ENST000005412 10;ENST00000462 502;ENST0000039 2545 | chr12 | 117513606 | 117513652 | − | TSF |
| 1% | chr11 | 63365533 | 63365533 | − | ENST00000323646; ENST0000041582 6 | chr11 | 63360665 | 63361041 | − | TSF |
| 1% | chr16 | 14782022 | 14782022 | − | ENST00000438167; ENST0000056746 2 | chr16 | 14779702 | 14779829 | − | TSF |
| 1% | chr7 | 22532184 | 22532184 | − | ENST00000406890; ENST0000040436 9;ENST000004243 63 | chr7 | 22512853 | 22512874 | − | TSF |
| 1% | chr5 | 1802435 | 1802488 | + | ENST00000274137; ENST0000046917 6 | chr5 | 1811112 | 1811428 | + | TSF |
| 1% | chr7 | 93516573 | 93516573 | − | ENST00000451238; ENST0000022254 3 | chr7 | 93492029 | 93492238 | − | TSF |
| 1% | chr14 | 106235574 | 106235574 | − | ENST00000390551 | chr14 | 106216701 | 106216951 | − | TSF |
| 1% | chr22 | 47071365 | 47071449 | + | ENST00000406902; ENST0000036103 4;ENST000004080 31 | chr22 | 47078308 | 47078350 | + | TSF |
| 1% | chr16 | 16381600 | 16381719 | + | ENST00000399336; ENST0000026301 2;ENST000005384 68 | chr16 | 16382422 | 16382605 | + | TSF |

-continued

| 1 | 2 | 3 | 4 | 5 | 6 | 7 | 8 | 9 | 10 | 11 |
|---|---|---|---|---|---|---|---|---|---|---|
| 1% | chr7 | 22532184 | 22532184 | − | ENST00000406890;ENST00000404369;ENST00000424363 | chr7 | 22531483 | 22531483 | − | TSF |
| 1% | chr18 | 56807181 | 56807267 | + | ENST00000587834;ENST00000299714;ENST00000588875 | chr18 | 56814218 | 56814267 | + | TSF |
| 1% | chr22 | 48885405 | 48885516 | + | ENST00000402357;ENST00000336769 | chr22 | 48915770 | 48916108 | + | TSF |
| 1% | chr10 | 75555297 | 75555421 | + | ENST00000604729;ENST00000603114;ENST00000604524;ENST00000398706;ENST00000605216;ENST00000433366;ENST00000492395;ENST00000603187;ENST00000412198;ENST00000604754 | chr10 | 75556079 | 75556138 | + | TSF |
| 1% | chr16 | 4401233 | 4401233 | − | ENST00000577031;ENST00000318059;ENST00000571986;ENST00000576217;ENST00000571178 | chr16 | 4398819 | 4398944 | − | TSF |
| 1% | chr1 | 220240644 | 220240644 | − | ENST00000322067;ENST00000469520;ENST00000354807;ENST00000544404;ENST00000414869;ENST00000463953;ENST00000498791;ENST00000480959 | chr1 | 220237757 | 220238024 | − | TSF |
| 1% | chr14 | 106092109 | 106092109 | − | ENST00000390543 | chr14 | 105470421 | 105470731 | − | TSF |
| 1% | chr1 | 53569018 | 53569018 | − | ENST00000371494 | chr1 | 53568657 | 53568729 | − | TSF |
| 1% | chr9 | 5163913 | 5164179 | − | ENST00000381641 | chr9 | 4992433 | 4992489 | − | TSF |
| 1% | chr7 | 8198157 | 8198157 | − | ENST00000402384;ENST00000406470;ENST00000265577;ENST00000396675;ENST00000339809;ENST00000401396;ENST00000422063;ENST00000407906;ENST00000317367 | chr7 | 8197727 | 8198053 | − | TSF |
| 1% | chr8 | 17872093 | 17872349 | + | ENST00000325083;ENST00000519253;ENST00000327578;ENST00000522275 | chr8 | 17873210 | 17873221 | + | TSF |
| 1% | chr2 | 192546672; 192546682 | 192546743 | + | ENST00000307849;ENST00000451500;ENST00000425611;ENST00000435931;ENST00000307834;ENST00000410026;ENST00000409510 | chr2 | 192548016 | 192548103 | + | TSF |
| 1% | chr11 | 67786242 | 67786362 | + | ENST00000539229 ENST00000316367;ENST00000007633;ENST00000342456 | chr11 | 67786535 | 67786588 | + | TSF |
| 1% | chr8 | 62546242 | 62546242 | − | ENST00000541428;ENST00000379454;ENST00000522919;ENST00000356457;ENST00000519234;ENST000005 | chr8 | 62544404 | 62544571 | − | TSF |

| 1 | 2 | 3 | 4 | 5 | 6 | 7 | 8 | 9 | 10 | 11 |
|---|---|---|---|---|---|---|---|---|---|---|
| 1% | chr12 | 102547647 | 102547754 | + | 18068;ENST00000517903;ENST00000445642;ENST00000517847;ENST00000522835 ENST00000327680; ENST000003781 28;ENST000005413 94;ENST00000358 383;ENST0000039 2911;ENST000004 12715;ENST00000 417507;ENST0000 0457614 | chr12 | 102548605 | 102548938 | + | TSF |
| 1% | chr19 | 18710375 | 18710375 | − | ENST00000392386 | chr19 | 18709961 | 18710215 | − | TSF |
| 1% | chr10 | 79796952 | 79797062 | + | ENST00000435275; ENST0000044069 2;ENST000003723 60;ENST00000360 830 | chr4 | 176584518 | 176584519 | + | TSF |
| 1% | chrX | 41598637 | 41598637 | − | ENST00000421587; ENST0000031858 8;ENST000003619 62;ENST00000378 163;ENST0000037 8158;ENST000003 78166;ENST00000 442742;ENST0000 0378154 | chrX | 41557348 | 41557352 | − | TSF |
| 1% | chr10 | 5037511 | 5037511 | − | ENST00000380753; ENST0000042119 6;ENST000004076 74 | chr10 | 5023140 | 5023482 | − | TSF |
| 1% | chr20 | 37384500 | 37384682 | + | ENST00000243903 | chr20 | 37390296 | 37390409 | + | TSF |
| 1% | chr4 | 169086398 | 169086477 | + | ENST00000359299 | chr4 | 169090666 | 169090754 | + | TSF |
| 1% | chr22 | 23165476 | 23165642 | + | ENST00000390317 | chr22 | 23175722 | 23175755 | + | TSF |
| 1% | chr4 | 25759156 | 25759156 | − | ENST00000399878; ENST0000026486 8;ENST000005029 49;ENST00000510 448 | chr4 | 25723603 | 25724054 | − | TSF |

Table 4. Coordinates of the fusion sequences for which the donor is the TE. The names of the columns are the following:
1. Frequency in LUAD cohort
2. Donor Chromosome TE
3. Donor start TE
4. Donor Breakpoint TE
5. Donor strand TE
6. Acceptor Chromosome exon
7. Acceptor Breakpoint exon
8. Acceptor end exon
9. Acceptor strand exon
10. Acceptor transcript
11. Fusion type The fusion transcript sequences of table 4 correspond in the same order to SEQ ID NO: 432-910 (with same reasoning as table 3 above).

| 1 | 2 | 3 | 4 | 5 | 6 | 7 | 8 | 9 | 10 | 11 |
|---|---|---|---|---|---|---|---|---|---|---|
| 51% | chr12 | 122430912 | 122431655 | + | chr12 | 122437622 | 122437850 | + | ENST00000288912 | TSA |
| 50% | chr12 | 122430912 | 122431578 | + | chr12 | 122437622 | 122437850 | + | ENST00000288912 | TSA |
| 42% | chr8 | 104389530 | 104389551 | + | chr8 | 104390255 | 104390471 | + | ENST00000330295; ENST00000520337 | TSA |
| 36% | chr12 | 122430912 | 122431615 | + | chr12 | 122437622 | 122437850 | + | ENST00000288912 | TSA |
| 36% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513; ENST00000412079 | TSA |
| 32% | chr20 | 44420870 | 44421070 | + | chr20 | 44421316 | 44421386 | + | ENST00000372622; ENST00000449078; ENST00000456939 | |

-continued

| 1 | 2 | 3 | 4 | 5 | 6 | 7 | 8 | 9 | 10 | 11 |
|---|---|---|---|---|---|---|---|---|---|---|
| 32% | chr6 | 80021194 | 80022085 | − | chr6 | 79924739 | 79924739 | − | ENST00000275036; ENST00000344726 | TSF |
| 24% | chr7 | 116364854 | 116364901 | + | chr7 | 116371722 | 116371913 | + | ENST00000397752; ENST00000318493; ENST00000436117 | TSA |
| 23% | chr17 | 70713482 | 70713885 | − | chr17 | 70645407 | 70645407 | − | ENST00000255559; ENST00000542342; ENST00000582769 | TSF |
| 22% | chr10 | 5077666 | 5077808 | + | chr10 | 5138602 | 5138769 | + | ENST00000602997; ENST00000605149; ENST00000380554 | TSA |
| 19% | chr10 | 5059958 | 5060092 | − | chr10 | 5043873 | 5043873 | − | ENST00000380753; ENST00000421196; ENST00000407674; ENST00000604507; ENST00000455190 | TSA |
| 18% | chr11 | 423924 | 423942 | − | chr11 | 421198 | 421198 | − | ENST00000332826 | TSA |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSA |
| 16% | chr4 | 100015102 | 100021056 | − | chr4 | 100006367 | 100006367 | − | ENST00000296412; ENST00000512659; ENST00000503130; ENST00000502590; ENST00000505652 | TSA |
| 16% | chr11 | 93467948 | 93468129 | − | chr11 | 93467826 | 93467826 | − | ENST00000393259; ENST00000527169 | TSA |
| 15% | chr17 | 70670228 | 70670643 | − | chr17 | 70645407 | 70645407 | − | ENST00000255559; ENST00000542342; ENST00000582769 | TSA |
| 14% | chr5 | 822923 | 823504 | − | chr5 | 822010 | 822010 | − | ENST00000424784; ENST00000283441 | TSA |
| 12% | chr20 | 31764878 | 31764929 | + | chr20 | 31765953 | 31766034 | + | ENST00000253362; ENST00000354932 | TSA |
| 10% | chr5 | 1474878 | 1475076 | − | chr5 | 1474800 | 1474800 | − | ENST00000475622; ENST00000283415 | TSF |
| 9% | chr19 | 14129234 | 14129243 | + | chr19 | 14141522 | 14141549; 14141760 | + | ENST00000585987; ENST00000431365 | TSF |
| 9% | chr7 | 48039432 | 48039725 | − | chr7 | 48035743 | 48035743 | − | ENST00000453071; ENST00000297325; ENST00000412371; ENST00000412142; ENST00000395572; ENST00000453192; ENST00000438771 | TSF |
| 8% | chr10 | 33505378 | 33505616 | − | chr10 | 33502645 | 33502645 | − | ENST00000432372; ENST00000374875; ENST00000265371; ENST00000374867; ENST00000395995; ENST00000374821; ENST00000374822; ENST00000374823; ENST00000374816 | TSF |
| 7% | chrX | 107293989 | 107294242 | + | chrX | 107301268 | 107301431 | + | ENST00000415430; ENST00000217957; ENST00000458383 | TSF |
| 5% | chr7 | 7558677 | 7558760 | − | chr7 | 7557468 | 7557468 | − | ENST00000399429; ENST00000444268 | TSF |
| 5% | chr3 | 182832430 | 182833262 | − | chr3 | 182812393 | 182812393 | − | ENST00000265594; ENST00000497830; ENST00000495767; ENST00000476176; ENST00000487634; ENST00000466650; ENST00000486226 | TSF |
| 5% | chr3 | 98584565 | 98586135 | − | chr3 | 98568442 | 98568442 | − | ENST00000449482; ENST00000326840; ENST00000326857 | TSF |

| 1 | 2 | 3 | 4 | 5 | 6 | 7 | 8 | 9 | 10 | 11 |
|---|---|---|---|---|---|---|---|---|---|---|
| 4% | chr2 | 143794737 | 143794842 | + | chr2 | 143797997 | 143798227 | + | ENST00000264170; ENST00000409512 | TSF |
| 4% | chr10 | 5056485 | 5057095 | − | chr10 | 5043873 | 5043873 | − | ENST00000380753; ENST00000421196; ENST00000407674; ENST00000604507; ENST00000455190 | TSF |
| 4% | chr12 | 122430912 | 122432103 | + | chr12 | 122437622 | 122437850 | + | ENST00000288912 | TSF |
| 4% | chr12 | 122430912 | 122431795 | + | chr12 | 122437622 | 122437850 | + | ENST00000288912 | TSF |
| 4% | chr22 | 22899861 | 22899965 | − | chr22 | 22893511 | 22893511 | − | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr12 | 117498474 | 117498567 | − | chr12 | 117494691 | 117494691 | − | ENST00000470612; ENST00000335209; ENST00000392545; ENST00000462502 | TSF |
| 4% | chr8 | 104389530 | 104389536 | + | chr8 | 104390255 | 104390471 | + | ENST00000330295; ENST00000520337 | TSF |
| 4% | chr2 | 38982396 | 38983253 | − | chr2 | 38977336 | 38977336 | − | ENST00000313117; ENST00000425778; ENST00000425941; ENST00000446327; ENST00000409276; ENST00000431066; ENST00000443213 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr20 | 45337040 | 45337192 | + | chr20 | 45353680 | 45354963 | + | ENST00000359271 | TSF |
| 4% | chr4 | 57559029 | 57559845 | − | chr4 | 57522178 | 57522178 | − | ENST00000420433; ENST00000554144; ENST00000508121; ENST00000557328 | TSF |
| 4% | chr7 | 56018506 | 56018522 | + | chr7 | 56020872 | 56021011 | + | ENST00000426595 | TSF |
| 4% | chr6 | 117763522 | 117763597 | − | chr6 | 117739669 | 117739669 | − | ENST00000368507; ENST00000368508 | TSF |
| 3% | chr19 | 1114639 | 1114676 | − | chr19 | 1114421 | 1114421 | − | ENST00000361757; ENST00000587024; ENST00000438103 | TSF |
| 3% | chr5 | 147244208 | 147245387 | + | chr5 | 147261009 | 147261211 | + | ENST00000296694 | TSF |
| 3% | chr17 | 39974832 | 39974893 | + | chr17 | 39975462 | 39975651 | + | ENST00000321562 | TSF |
| 3% | chr12 | 122430912 | 122432282 | + | chr12 | 122437622 | 122437850 | + | ENST00000288912 | TSF |
| 3% | chr4 | 57559029 | 57559885 | − | chr4 | 57522178 | 57522178 | − | ENST00000420433; ENST00000554144; ENST00000508121; ENST00000557328 | TSF |
| 3% | chr4 | 872984 | 873014 | − | chr4 | 871597 | 871597 | − | ENST00000314167; ENST00000511163 | TSF |
| 3% | chr22 | 42509838 | 42511212 | − | chr22 | 42483179 | 42483179 | − | ENST00000602404; ENST00000498737 | TSF |
| 3% | chr22 | 29117270 | 29117506 | − | chr22 | 29115473 | 29115473 | − | ENST00000348295; ENST00000382566; ENST00000382578; ENST00000404276; ENST00000328354; ENST00000405598; ENST00000382580; ENST00000433728; | TSF |

-continued

| 1 | 2 | 3 | 4 | 5 | 6 | 7 | 8 | 9 | 10 | 11 |
|---|---|---|---|---|---|---|---|---|---|---|
| | | | | | | | | | ENST00000402731; ENST00000403642; ENST00000439200; ENST00000448511 | |
| 3% | chr8 | 117816470 | 117816753 | + | chr8 | 117861127 | 117861256; 117861276 | + | ENST00000517820; ENST00000520733 | TSF |
| 3% | chr16 | 66461229 | 66461334 | + | chr16 | 66503505 | 66503768 | + | ENST00000536005 | TSF |
| 3% | chr17 | 70713482 | 70713885 | − | chr17 | 70709120 | 70709120 | − | ENST00000581581 | TSF |
| 3% | chr17 | 39976225 | 39976301 | + | chr17 | 39976521 | 39976713 | + | ENST00000321562; ENST00000455106; ENST00000544340 | TSF |
| 3% | chr1 | 223720296 | 223720355 | − | chr1 | 223718212 | 223718212 | − | ENST00000430824; ENST00000366872 | TSF |
| 3% | chrX | 151404470 | 151410406 | − | chrX | 151393317 | 151393317 | − | ENST00000370314; ENST00000535043 | TSF |
| 3% | chr16 | 74833176 | 74833256 | − | chr16 | 74774013 | 74774013 | − | ENST00000219368; ENST00000567683; ENST00000569949 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr1 | 1422590 | 1422685 | + | chr1 | 1423243 | 1423294 | + | ENST00000308647 | TSF |
| 2% | chr7 | 44158104 | 44158351 | − | chr7 | 44157663 | 44157663 | − | ENST00000406581; ENST00000223361; ENST00000452185; ENST00000433715; ENST00000456038; ENST00000418438 | TSF |
| 2% | chr10 | 5059958 | 5060092 | − | chr10 | 5043777 | 5043873 | − | ENST00000380753; ENST00000421196; ENST00000407674; ENST00000604507; ENST00000455190 | TSF |
| 2% | chr8 | 121656402 | 121662337 | − | chr8 | 121644891 | 121644891 | − | ENST00000395601; ENST00000517992 | TSF |
| 2% | chr15 | 43467899 | 43467988 | + | chr15 | 43470805 | 43470909 | + | ENST00000260403 | TSF |
| 2% | chr5 | 58596413 | 58596862 | − | chr5 | 58511794 | 58511794 | − | ENST00000340635; ENST00000360047; ENST00000507116; ENST00000503258; ENST00000405755; ENST00000502484; ENST00000546160; ENST00000309641; ENST00000502575 | TSF |
| 2% | chr14 | 106258470 | 106258725 | − | chr14 | 106209234 | 106209408 | − | ENST00000390548; ENST00000390549; ENST00000390542 | TSF |
| 2% | chrX | 149996757 | 149996779 | − | chrX | 149963959 | 149963959 | − | ENST00000370377; ENST00000466436; ENST00000418547 | TSF |
| 2% | chr14 | 106258470 | 106258725 | − | chr14 | 106237569 | 106237742 | − | ENST00000390551 | TSF |
| 2% | chrX | 123617772 | 123617816 | − | chrX | 123615814 | 123615814 | − | ENST00000371130; ENST00000422452 | TSF |
| 2% | chrX | 100654643 | 100654732 | − | chrX | 100653934 | 100653934 | − | ENST00000218516 | TSF |
| 2% | chr1 | 156716126 | 156716133 | − | chr1 | 156715165 | 156715165 | − | ENST00000357325; ENST00000537739; ENST00000368209; ENST00000368206 | TSF |
| 2% | chr18 | 70839859 | 70840073 | − | chr18 | 7082920 | 70829208 | − | ENST00000581011; ENST00000581862 | TSF |
| 2% | chr5 | 132737208 | 132737281 | − | chr5 | 132736678 | 132736678 | − | ENST00000265342; ENST00000510685 | TSF |
| 2% | chr2 | 89366766 | 89370031 | − | chr2 | 89292018 | 89292223 | − | ENST00000495489 | TSF |
| 2% | chr6 | 32745845 | 32746483 | − | chr6 | 32731247 | 32731247 | − | ENST00000411527; ENST00000435145; ENST00000437316 | TSF |
| 2% | chr1 | 236485526 | 236485567 | − | chr1 | 236433294 | 236433294 | − | ENST00000354619; ENST00000327333 | TSF |

-continued

| 1 | 2 | 3 | 4 | 5 | 6 | 7 | 8 | 9 | 10 | 11 |
|---|---|---|---|---|---|---|---|---|---|---|
| 2% | chr1 | 224527533 | 224527861 | + | chr1 | 224553581 | 224553693 | + | ENST00000465271; ENST00000366858; ENST00000366857; ENST00000366856 | TSF |
| 2% | chr16 | 74834260 | 74834274 | − | chr16 | 74774013 | 74774013 | − | ENST00000219368; ENST00000567683; ENST00000569949 | TSF |
| 2% | chr18 | 71976895 | 71977013 | − | chr18 | 71930712 | 71930712 | − | ENST00000340533; ENST00000494131; ENST00000397914 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr14 | 92119780 | 92119864 | − | chr14 | 92105594 | 92105594 | − | ENST00000256343; ENST00000557036 | TSF |
| 2% | chr4 | 57559029 | 57559962 | − | chr4 | 57522178 | 57522178 | − | ENST00000420433; ENST00000554144; ENST00000508121; ENST00000557328 | TSF |
| 2% | chr8 | 144690895 | 144690934 | − | chr8 | 144690296 | 144690296 | − | ENST00000220966; ENST00000433751 | TSF |
| 2% | chr12 | 104681506 | 104681628 | + | chr12 | 104682709 | 104682818 | + | ENST00000378070; ENST00000525566; ENST00000429002; ENST00000526691; ENST00000388854; ENST00000542918 | TSF |
| 2% | chr5; chr5 | 52897435; 52897700 | 52897704 | +  + | chr5 | 52899282 | 52899360 | + | ENST00000502423; ENST00000296684; ENST00000506974; ENST00000506765 | TSF |
| 2% | chr11 | 60694460 | 60694542 | + | chr11 | 60694676 | 60694890 | + | ENST00000453848; ENST00000005286 | TSF |
| 2% | chr1 | 23762004 | 23762216 | − | chr1 | 23761111 | 23761111 | − | ENST00000495646; ENST00000336689; ENST00000437606 | TSF |
| 2% | chr7 | 50763231 | 50763289 | − | chr7 | 50742355 | 50742355 | − | ENST00000439599; ENST00000398812; ENST00000403097; ENST00000357271; ENST00000401949; ENST00000439044 | TSF |
| 2% | chr15 | 34452835 | 34453416 | − | chr15 | 34446885 | 34446885 | − | ENST00000256544; ENST00000557877; ENST00000560108; ENST00000559515 | TSF |
| 2% | chr12 | 6458902 | 6458996 | − | chr12 | 6458387 | 6458387 | − | ENST00000360168; ENST00000358945; ENST00000540037; ENST00000228916; ENST00000543768 | TSF |
| 2% | chr7 | 95053024 | 95053104 | − | chr7 | 95045609 | 95045609 | − | ENST00000536183; ENST00000455123; ENST00000433091; ENST00000222572 | TSF |
| 2% | chr19 | 11140024 | 11140045 | + | chr19 | 11141406 | 11141569 | + | ENST00000358026; ENST00000344626; ENST00000429416; ENST00000541122; ENST00000589677; ENST00000444061; ENST00000590574; ENST00000413806; ENST00000450717 | TSF |
| 2% | chr12 | 58189709 | 58189746 | + | chr12 | 58189960 | 58189980; 58190044; 58190366 | + | ENST00000540550; ENST00000457189; ENST00000454289; ENST00000323833; ENST00000350762 | TSF |
| 2% | chr14 | 70466641 | 70466673 | + | chr14 | 70477471 | 70477663 | + | ENST00000361956; ENST00000381280 | TSF |
| 2% | chr10 | 3133726 | 3133857 | + | chr10 | 3141467 | 3141544 | + | ENST00000607886; ENST00000381125; ENST00000381075; ENST00000407806 | TSF |

-continued

| 1 | 2 | 3 | 4 | 5 | 6 | 7 | 8 | 9 | 10 | 11 |
|---|---|---|---|---|---|---|---|---|---|---|
| 2% | chr7 | 134212336 | 134212386 | + | chr7 | 134215479 | 134215562 | + | ENST00000359579 | TSF |
| 2% | chr2 | 135250006 | 135250213 | − | chr2 | 135223796 | 135223796 | − | ENST00000281924 | TSF |
| 2% | chr7 | 30468003 | 30468120 | − | chr7 | 30465326 | 30465326 | − | ENST00000222823 | TSF |
| 2% | chr17 | 90088 | 90313 | − | chr17 | 69527 | 69527 | − | ENST00000331302; ENST00000323434; ENST00000536489 | TSF |
| 1% | chr7 | 6423751 | 6423803 | + | chr7 | 6426843 | 6426914 | + | ENST00000348035; ENST00000356142 | TSF |
| 1% | chr7 | 95053024 | 95053140 | − | chr7 | 95045609 | 95045609 | − | ENST00000536183; ENST00000455123; ENST00000433091; ENST00000222572 | TSF |
| 1% | chr10 | 5049827 | 5050220 | − | chr10 | 5043873 | 5043873 | − | ENST00000380753; ENST00000421196; ENST00000407674; ENST00000604507; ENST00000455190 | TSF |
| 1% | chr15 | 43431174 | 43431330 | + | chr15 | 43440953 | 43441077 | + | ENST00000564698; ENST00000260403; ENST00000564494 | TSF |
| 1% | chr19 | 50492001 | 50492051 | − | chr19 | 50491749 | 50491749 | − | ENST00000593919; ENST00000316763; ENST00000377011; ENST00000599538; ENST00000443401; ENST00000601341; ENST00000594948; ENST00000601912; ENST00000594092; ENST00000593912 | TSF |
| 1% | chr1 | 26595323 | 26595855 | + | chr1 | 26595951 | 26596105 | + | ENST00000451429; ENST00000476272; ENST00000252992; ENST00000453146 | TSF |
| 1% | chr20 | 43561150 | 43561175 | + | chr20 | 43561713 | 43561826 | + | ENST00000255136; ENST00000217073 | TSF |
| 1% | chr10 | 5059958 | 5060092 | − | chr10 | 5043783 | 5043873 | − | ENST00000380753; ENST00000421196; ENST00000407674; ENST00000604507; ENST00000455190 | TSF |
| 1% | chr2 | 26947307 | 26947428 | + | chr2 | 26950535 | 26951436 | + | ENST00000302909 | TSF |
| 1% | chr10 | 99600727 | 99601513 | + | chr10 | 99619215 | 99619340 | + | ENST00000370602 | TSF |
| 1% | chr20 | 58402976 | 58403213 | + | chr20 | 58411560 | 58411615 | + | ENST00000359926; ENST00000371015; ENST00000395639; ENST00000541461; ENST00000355648; ENST00000361300; ENST00000395636 | TSF |
| 1% | chr14 | 105641713 | 105641815 | − | chr14 | 105639598 | 105639598 | − | ENST00000392568 | TSF |
| 1% | chr5 | 34913998 | 34914032 | − | chr5 | 34913683 | 34913683 | − | ENST00000382038; ENST00000341754 | TSF |
| 1% | chr4 | 39516293 | 39516533 | − | chr4 | 39515804 | 39515804 | − | ENST00000316423; ENST00000501493; ENST00000506179; ENST00000515021; ENST00000514106; ENST00000509391; ENST00000505698 | TSF |
| 1% | chr8 | 140818301 | 140818376 | − | chr8 | 140744445 | 140744445 | − | ENST00000389327; ENST00000389328; ENST00000520857; ENST00000438773 | TSF |
| 1% | chr20 | 44442461 | 44442685 | + | chr20 | 44443023 | 44443109 | + | ENST00000356455; ENST00000405520; ENST00000335046; ENST00000372568 | TSF |
| 1% | chr17 | 66244121 | 66244199 | + | chr17 | 66244785 | 66244846 | + | ENST00000584837 | TSF |
| 1% | chr17 | 17051276 | 17051346 | + | chr17 | 17053458 | 17053547 | + | ENST00000395811; ENST00000444976; ENST00000395804; ENST00000341712; ENST00000584067 | TSF |

-continued

| 1 | 2 | 3 | 4 | 5 | 6 | 7 | 8 | 9 | 10 | 11 |
|---|---|---|---|---|---|---|---|---|---|---|
| 1% | chr6 | 39267897 | 39268149 | − | chr6 | 39267513 | 39267513 | − | ENST00000373231 | TSF |
| 1% | chr20 | 25840234 | 25840376 | − | chr20 | 25755948 | 25755948; 25755972 | − | ENST00000376403; ENST00000584071 | TSF |
| 1% | chr2 | 90168849 | 90168893 | + | chr2 | 90193334 | 90193424 | + | ENST00000390275 | TSF |
| 1% | chr19 | 50174724 | 50174836 | + | chr19 | 50176955 | 50177005; 50177034 | + | ENST00000441864; ENST00000246785; ENST00000598306; ENST00000600947 | TSF |
| 1% | chr11 | 85339945 | 85340247 | + | chr11 | 85342731 | 85342852 | + | ENST00000358867; ENST00000534341 | TSF |
| 1% | chr19 | 17421511 | 17421655 | + | chr19 | 17424832 | 17424912 | + | ENST00000593466; ENST00000359866; ENST00000596582 | TSF |
| 1% | chr3 | 32323981 | 32324151 | + | chr3 | 32398865 | 32399038 | + | ENST00000307526 | TSF |
| 1% | chr4 | 57559029 | 57559925 | − | chr4 | 57522178 | 57522178 | − | ENST00000420433; ENST00000554144; ENST00000508121; ENST00000557328 | TSF |
| 1% | chrX | 107265928 | 107266261 | + | chrX | 107301268 | 107301431 | + | ENST00000415430; ENST00000217957; ENST00000458383 | TSF |
| 1% | chr2 | 143715736 | 143715823 | + | chr2 | 143718193 | 143718339 | + | ENST00000264170; ENST00000375773; ENST00000409512 | TSF |
| 1% | chr20 | 25841897 | 25842039 | − | chr20 | 25755948 | 25755948; 25755972 | − | ENST00000376403; ENST00000584071 | TSF |
| 1% | chr8 | 98817265 | 98817331 | + | chr8 | 98817581 | 98817692 | + | ENST00000445593; ENST00000521545; ENST00000517924 | TSF |
| 1% | chr17 | 45698288 | 45698367 | + | chr17 | 45699134 | 45699286 | + | ENST00000530173; ENST00000322157; ENST00000544660; ENST00000528565 | TSF |
| 1% | chr19 | 46194383 | 46194670 | − | chr19 | 46191824 | 46191824 | − | ENST00000342669; ENST00000588301; ENST00000590212 | TSF |
| 1% | chr21 | 38272435 | 38272892 | − | chr21 | 38269431 | 38269431 | − | ENST00000336648; ENST00000399120 | TSF |
| 1% | chr4 | 162585892 | 162585968 | − | chr4 | 162577646 | 162577646 | − | ENST00000306100; ENST00000379164; ENST00000536695; ENST00000427802 | TSF |
| 1% | chr4 | 40352026 | 40352049 | + | chr4 | 40355996 | 40356537 | + | ENST00000310169 | TSF |
| 1% | chr20 | 25843554 | 25843696 | − | chr20 | 25755948 | 25755948; 25755972 | − | ENST00000376403; ENST00000584071 | TSF |
| 1% | chrX | 138072586 | 138072670 | − | chrX | 137939841 | 137939841 | − | ENST00000370603; ENST00000436198; ENST00000455663; ENST00000448673 | TSF |
| 1% | chr2 | 97560868 | 97560977 | − | chr2 | 97559788 | 97559788 | − | ENST00000327896; ENST00000417561; ENST00000490605 | TSF |
| 1% | chr11 | 60933230 | 60933962 | − | chr11 | 60901679 | 60901679 | − | ENST00000301765; ENST00000538036 | TSF |
| 1% | chr9 | 130929707 | 130929818 | − | chr9 | 130929443 | 130929443 | − | ENST00000372954; ENST00000393608; ENST00000541172; ENST00000325721; ENST00000357558; ENST00000538431; ENST00000277465; ENST00000372948; ENST00000372938; ENST00000415526 | TSF |
| 1% | chr21 | 39513161 | 39513404 | + | chr21 | 39528398 | 39528496 | + | ENST00000357704; ENST00000400477 | TSF |
| 1% | chr8 | 63314966 | 63315263 | + | chr8 | 63492098 | 63492235 | + | ENST00000523211; ENST00000524201; ENST00000328472 | TSF |
| 1% | chr4 | 186460593 | 186460994 | − | chr22 | 23243156 | 23243475 | − | ENST00000390323 | TSF |
| 1% | chr12 | 8864869 | 8864879 | + | chr12 | 8866407 | 8866637 | + | ENST00000537189 | TSF |
| 1% | chr10 | 5059958 | 5060040 | − | chr10 | 5043873 | 5043873 | − | ENST00000380753; ENST00000421196; ENST00000407674; ENST00000604507; ENST00000455190 | TSF |

-continued

| 1 | 2 | 3 | 4 | 5 | 6 | 7 | 8 | 9 | 10 | 11 |
|---|---|---|---|---|---|---|---|---|---|---|
| 1% | chr7 | 65418154 | 65418399 | + | chr7 | 65419061 | 65419287; 65419400 | + | ENST00000360768; ENST00000434382 | TSF |
| 1% | chr1 | 156305244 | 156305264 | − | chr1 | 156304709 | 156304709 | − | ENST00000295688; ENST00000368258; ENST00000413555; ENST00000496684; ENST00000478640; ENST00000415548 | TSF |

The peptides were then further screened against a reference proteome, typically for human subject against all sequences present in Uniprot (representing all the sequences encoded in the human exome). Peptides were considered equal to those in Uniprot if they had the same amino acid sequence or if they only differed in the amino acid in the first or last position. All these equal sequences were then discarded from the candidate list. 117 peptide sequences derived from these 230 fusion transcripts where thus predicted to bind to HLA-A2: 01 (see table 5 below).

TABLE 5

Peptides LUAD

| SEQ ID | Peptide sequence |
|---|---|
| 1 | RLLHLESFL |
| 2 | TLMNLVQVL |
| 3 | ILHSLVTGV |
| 4 | FMMEQVGLA |
| 5 | AMDGKELSL |
| 6 | TLAYGKYYI |
| 7 | GLIQLIWLA |
| 8 | GMVDGGSNI |
| 9 | YLWTTFFPL |
| 10 | ALWEAKMII |
| 11 | WLSSRVTQL |
| 12 | AILPKANTV |
| 13 | VLLFEVELV |
| 14 | GLDTGLQGM |
| 15 | SLLDGTQLF |
| 16 | GLPTGYLFV |
| 17 | LLDRFGYHV |
| 18 | SLLEETQAI |
| 19 | MLLVQPAEL |
| 20 | GLLNISHTA |
| 21 | HLYEPWFPV |
| 22 | YLQGLPLPL |
| 23 | KAVEGILAV |
| 24 | MIYEENNRL |

TABLE 5-continued

Peptides LUAD

| SEQ ID | Peptide sequence |
|---|---|
| 25 | YLPYFLKSL |
| 26 | GLYSLSSVV |
| 27 | LMISRTPEV |
| 28 | LLGGPSVFL |
| 29 | ILSGYGPCV |
| 30 | FLPDLDRPL |
| 31 | AMDGKELSL |
| 32 | RMDFEDLGL |
| 33 | TLIFNPTEI |
| 34 | LLPGLLLLL |
| 35 | LLLVHQHAV |
| 36 | FLDDAPPGT |
| 37 | VLIRYVWTL |
| 38 | YLCGHLHTL |
| 39 | VLSQLTILI |
| 40 | TLGGLMPVL |
| 41 | FLQGSITFI |
| 42 | MLLLYIWQV |
| 43 | YLKIMPVHL |
| 44 | HTLGGLMPV |
| 45 | YIMARVLFV |
| 46 | FILRTDHYI |
| 47 | IMSSAIAYL |
| 48 | FIIGILQLA |
| 49 | YLLQEIYGI |
| 50 | GVFPVVIQA |
| 51 | ALVHLPSQL |
| 52 | GLHPAKPQV |
| 53 | MLVTWELAL |
| 54 | VLLTNTIWL |

TABLE 5-continued

Peptides LUAD

| SEQ ID | Peptide sequence |
|---|---|
| 55 | ALVHLPSQL |
| 56 | CLIDEMPEA |
| 57 | ALMGGFMKT |
| 58 | LLLHLPLXL |
| 59 | TLQDKNLGL |
| 60 | ILANLPPAL |
| 61 | PLWDGMAGL |
| 62 | GLDHQTHPL |
| 63 | GMFLLPPQL |
| 64 | RLADHLSFC |
| 65 | RMRDQLPAL |
| 66 | GLLHAEVAL |
| 67 | SLQNCQVSV |
| 68 | VISAFPSEV |
| 69 | ALAIAALEL |
| 70 | VLDGLDVLL |
| 71 | ELFPPLFMA |
| 72 | FLIVAEILI |
| 73 | IVAEILISL |
| 74 | KAVEGILAV |
| 75 | YLPHLPQVL |
| 76 | MLLDPMGGI |
| 77 | RLLHLESFL |
| 78 | YLAYILYFV |
| 79 | LMTSSIMSV |
| 80 | MLMKTVWQA |
| 81 | SLQPEDMAL |
| 82 | KILTYFPMV |
| 83 | FLGTRVTRV |
| 84 | SLMQSGSPV |
| 85 | VLMWTMAHL |
| 86 | LLGETKVYV |
| 87 | KILTYFPMV |
| 88 | SLLERGLEA |
| 89 | VLSSLNVPL |
| 90 | FLERKSIRV |
| 91 | FVGSSTFYL |
| 92 | FLYTGDFFL |
| 93 | SVGPFALTV |
| 94 | NLALPLPKV |
| 95 | VLESGLYQV |
| 96 | MLVAITVLI |
| 97 | FMDDAKILF |
| 98 | ALVHLPSQL |
| 99 | ILTASITSI |
| 100 | AMDGKELSL |
| 101 | SLGWNISGV |
| 102 | MISAFPNEV |
| 103 | RLTHELPGI |
| 104 | LLFSDGEKV |
| 105 | RLNESTTFV |
| 106 | KLEELKSFV |
| 107 | SINEEIQTV |
| 108 | RLHDGPLRA |
| 109 | MISAFPNEV |
| 110 | ILHTSVPFL |
| 111 | YLENMVSGV |
| 112 | QLLGRLESL |
| 113 | RLLHLESFL |
| 114 | ALLRQMEGI |
| 115 | TLNKDFQEV |
| 116 | IMEQGDLSV |
| 117 | RLLHLESFL |

2.2.2 Validation on HLA-A2 Associated Peptides

Given that HLA-A2 allele is expressed in almost 50% of the Caucasian population, together with the existence of different technical tools, validations were focused on HLA-A2-associated peptides.

In the following paragraphs TE-Exon derived-transcripts is used interchangeably with "fusion transcripts" and the term "TE-derived peptides" is used interchangeably with "fusion transcripts-derived peptides.

Expression of TE-Exon Derived-Transcripts in Lung Adenocarcinoma Samples

To experimentally validate the predicted TE-Exon transcripts, the expression by PCR in LUAD tumor samples and tumor cell lines was validated firstly. Specific primers for each chimeric fusion were thus designed, in order to have one of them binding to the TE part and the other to the Exon part of the fusion. The results were further confirmed by sequencing of the PCR products.

In particular, specific primers were designed in such a way that the forward primer was binding in the "donor" sequence and the reverse primer was binding in the "acceptor" sequence of the reconstructed fusion sequence. PCR reactions were run on RNA derived from lung tumor samples and human tumor cell lines. Amplifications products were seeded on agarose gels and bands found on the expected size were cut and sequenced. Finally, sequenced PCR products were compared with the reconstructed fusion sequence. Using this approach, it was possible to confirm the presence of predicted fusion transcripts both in LUAD tumor samples and tumor cell lines. Table 6 below summarizes the results found for 8 of the most frequent chimeric fusions with a predicted peptide associated to bind with high affinity to HLA-A2 allele.

Table 6: Most frequent fusion transcript validation. The most frequent fusions peptides were validated by PCR in 15 LUAD tumor samples and 6 LUAD tumor cell lines. The status 'Yes' or 'No' in the table below indicates the presence or absence of the PCR product on the expected size. When the PCR product was further validated by sequencing, is denoted as 'Yes'.

Figure 11A:
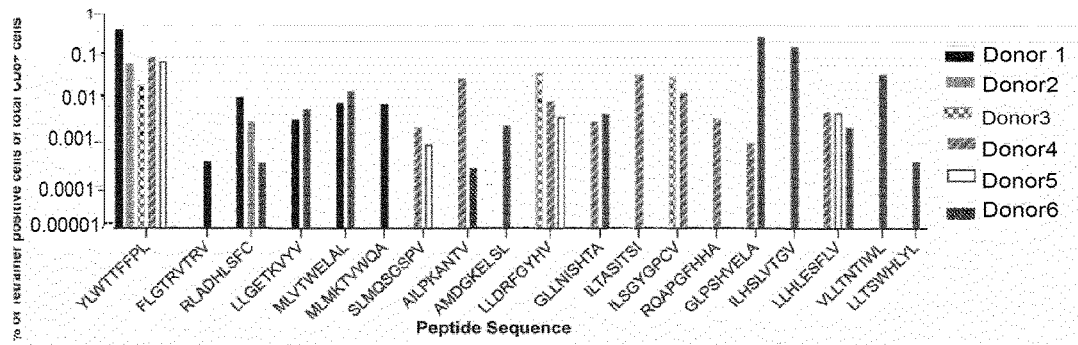
FIGS. 11A-11D: Immunogenicity of fusion transcripts-derived peptides and reactive CD8+ T cells generation.

PBMCs from HLA-A2+ healthy donors were used to generate monocyte derived-DCs (moDCs). After loading the moDCs with a mix of synthetic peptides, autologous co-culture was performed with CD4+ and CD8+ T cells. Finally, the expansion of specific CD8+ T cells was analysed by flow cytometry using two-colours tetramer staining. As a control of specific expansion, the co-culture was performed in the absence of peptides. By using this approach in one donor, it has been possible to identify and expand specific CD8+ T cells recognizing 6 of the most frequent chimeric fusion derived-peptides (RLLHLESFL, LLGETKVYV, AILPKANTV, RLADHLSFC, FLIVAEILI, YLWTTFFPL). This result is evidenced by an increase in at least one magnitude order of the percentage of tetramer positive cells compared to control test among total CD8+ T cells. The same experiment was performed in order to evaluate the response in additional 5 donors. FIG. 11A summarizes the results obtained for the total of 6 donors analyzed in which we found specific CD8+ T expansions for 21 of the most frequent fusions transcripts-derived peptides

|  |  | TE-Exon fusion derived-peptides asociated to bind HLA-A2 | | | | | | | |
|---|---|---|---|---|---|---|---|---|---|
|  | Frequency | 119 | 48 | 28 | 24 | 23 | 19 | 18 | 16 |
|  | peptide sequence | RLLHL ESFL | MLMKT VWQA | FLGTR VTRV | AILPKA NTV | YLPYF LKSL | AMDG KELSL | FLIVAEILI | RLADHLSFC |
| LUAD tumor cell lines | H1975 | Yes | Yes | No | No | Yes | No | No | No |
|  | H1650 | Yes | No | No | No | No | No | No | Yes |
|  | H1299 | Yes | No | No | No | No | No | No | Yes |
|  | A549 | Yes | Yes | No | No | Yes | No | No | No |
|  | H2052 | Yes | No | No | No | No | No | No | No |
|  | HCC827 | Yes | Yes | No | No | Yes | yes | No | No |
| LUAD tumor samples | Tumor 1 | Yes | No | No | No | Yes | Yes | No | Yes |
|  | Tumor 2 | Yes | Yes | No | No | Yes | Yes | No | No |
|  | Tumor 3 | Yes | No | No | No | Yes | No | No | Yes |
|  | Tumor 4 | Yes | No | No | No | Yes | Yes | No | No |
|  | Tumor 5 | Yes | No | No | No | No | No | No | No |
|  | Tumor 6 | Yes | No | No | Yes | Yes | Yes | Yes | Yes |
|  | Tumor 7 | Yes | No | No | No | No | Yes | No | No |
|  | Tumor 8 | Yes | No | No | No | Yes | Yes | No | No |
|  | Tumor 9 | Yes | No | No | No | No | Yes | Yes | No |
|  | Tumor 10 | Yes | Yes | Yes | Yes | Yes | Yes | Yes | No |
|  | Tumor 11 | Yes | Yes | No | No | Yes | Yes | Yes | No |
|  | Tumor 12 | Yes | Yes | Yes | Yes | Yes | Yes | No | No |
|  | Tumor 13 | Yes | Yes | No | Yes | Yes | No | No | Yes |
|  | Tumor 14 | Yes | Yes | Yes | Yes | Yes | Yes | No | Yes |
|  | Tumor 15 | No | No | No | No | No | Yes | No | No |

Binding of ER-Derived Peptides to HLA-A2 Molecule

Figure 10:
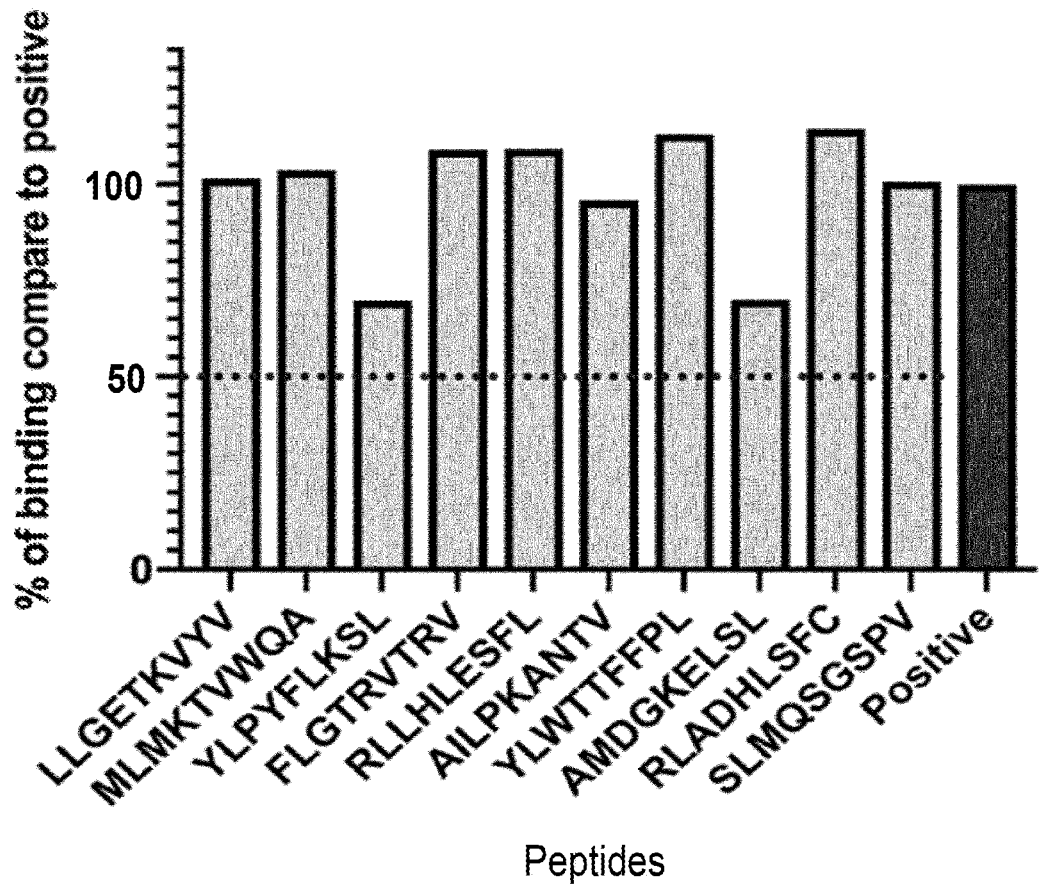
FIG. 10: Binding of chimeric transcripts-derived peptides to HLA-A2. Binding to HLA-A2 allele of predicted peptides from the most frequent chimeric fusions were validated by flow cytometry using tetramer formation assay. The results are shown as percentage of binding relative to positive control. Dotted line indicates the threshold considered to confirm the binding to this allele.

Once confirmed the expression of chimeric transcripts, the derived-peptides were synthetized and their binding to HLA-A2 was confirmed. Because monomer stabilization and tetramer formation are only possible in the presence of a high affinity binding peptide, the formation of HLA-A2 tetramers was estimated in the presence of synthetized peptides by flow cytometry. All predicted peptides were able to stabilize tetramer formation, showing a percentage of fluorescence higher than 50% relative to positive control. As positive control, a known high affinity binding peptide to HLA-A2 derived from Cytomegalovirus (CMV) was used. This result confirmed the predicted high affinity binding to HLA-A2 allele. FIG. 10 shows the result for 10 peptides derived from the most frequent fusions peptides.

Immunogenicity of ER-Derived Peptides

The following step after binding validation to HLA-A2 allele, was to test the immunogenicity of predicted peptides. Priming assays were thus performed to test the ability of identified peptides to expand specific cytotoxic T cells.

(YLWTTFFPL, FLGTRVTRV, RLADHLSFC, LLGETKVYV, MLVTWELAL, MLMKTVWQA, SLMQSGSPV, AILPKANTV, AMDGKELSL, LLDRFGYHV, GLLNISHTA, ILTASITSI, ILSGYGPCV, RQAPGFHHA, GLPSHVELA, ILHSLVTGV, LLHLESFLV, VLLTNTIWL, LLTSWHLYL). These experiments show that these peptides are able to induce an immune response and confirms the immunogenicity of ER-derived peptides.

Generation of Cytotoxic T Lymphocytes Clones Recognizing ER-Derived Peptides

Expanded CD8+ tetramer positive T-cells from immunogenicity assays (FIG. 11A) were single cell FACS-sorted in order to generate cytotoxic T lymphocytes (CTLs) clones. We generated 10 clones recognizing 5 different ER-derived peptides: YLWTTFFPL, LLGETKVYV, MLVTWELAL, MLMKTVWQA, RLADHLSF. These peptides are listed in Table 5 as peptide 9, 86, 53, 80 and 64 respectively. We will refer to these numbers to indicate the specificity of each generated CTL-clone. Example, CTL-clone 9 recognize ER-derived peptide 9.

In order to evaluate the cytotoxic capacity of generated CTL-clones, two different functional assays were conducted using the H1650 cell line as target cells. This is a LUAD-derived tumor cell line expressing HLA-A2 allele.

Figure 11B:
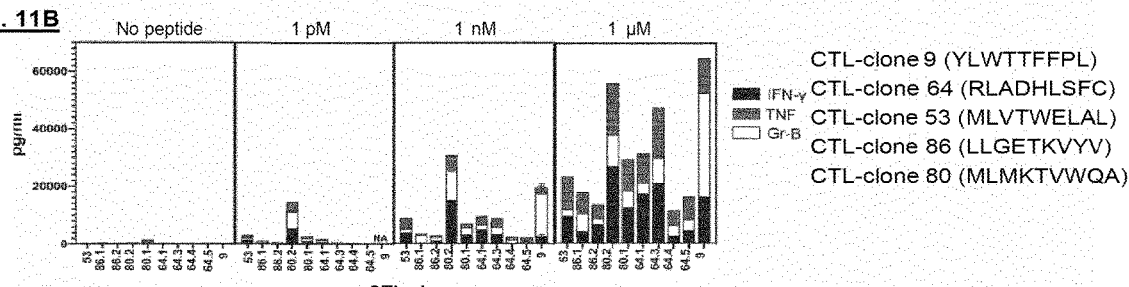

First, we measure the ability of CTL-clones to secret cytokines after exposure to ER-derived peptides. After co-cultured CTL-clones with target cells loaded with the specific ER-derived peptides during 18 h, secretion of INF-γ, TNF and Granzyme-B (Gr-B) was measured in culture supernatants. All CTL-clones were activated after exposure specific ER-derived peptides, secreting cytokines in a dose-dependent manner (FIG. 11B).

In a second set of experiments, CTL clones killing capacity was assessed. CTL-clones were co-cultured in different conditions with target cells loaded or not with ER-derived peptides. Using xCELLigence system we measure the real-time impedance variation in a target cells monolayer. In these assays, a decrease in cell-index is related with a decrease in the number of cells in the monolayer reflecting cell viability.

Figure 11C:
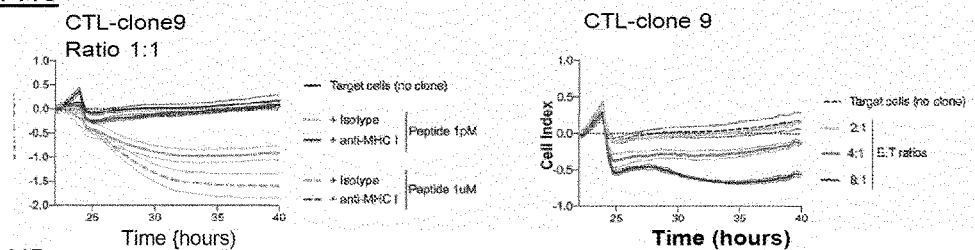

When CTL-clone 9 was co-culture in 1:1 ratio with target cells loaded with ER-derived peptide 9, we saw a decrease in cell-index over time compared to the control cells (target cells alone). This decrease in the cell index was inhibited when co-culture is performed in presence of blocking anti-MHC-I antibody (+ anti-MHC-I). Performing the co-culture using the same concentration of isotype control (+ isotype) did not inhibit the decrease in cell-index. Moreover, these decrease increases when target cells were loaded with higher concentration of peptide (1 pM compared to 1 uM) (FIG. 11C, left panel). This result show that a cytotoxic T cell that recognizes a peptide identified by the methods disclosed herein, CTL clone 9, is killing target tumor cells.

We reasoned that if ER-derived peptides are naturally expressed and presented by target cells, we should be able to kill them by co-culturing with CTL-clones without external addition of peptides. To this aim, we performed co-culture of CTL-clone 9 with H1650 target cells at different ratios to find the one in which effectors are sufficient to kill target cells. In the right panel of FIG. 11C, we saw that CTL-9 was able to kill target cells at a ratio effector-target 4:1 compared with the control cells (target cells alone). Moreover, killing is increased at bigger ratios (8:1). No killing of target cells was evidenced at lower ratios (2:1).

Figure 11D:
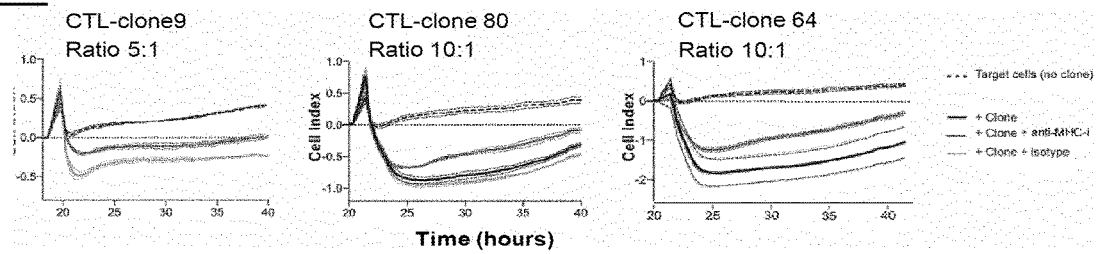

Finally, similar experiments were performed with CTL-clone 9, CTL-clone 64, and CTL-clone 80 showing a specific killing of target cells that could be also inhibited when the co-culture is performed in the presence of anti-MCH-I antibodies (FIG. 11D).

All together, these results confirm that cytotoxic T cells that recognizes several different peptides identified by the methods disclosed herein are able to recognize and kill tumor cells expressing specific fusion transcripts-derived peptides and that this effect is due to the specific recognition of peptides in the context of MHC-I molecules. Moreover, the fact that CTL-clones are able to kill target cells without addition of external peptides, indicates that fusion transcripts-derived peptides 9, 64 and 80 are naturally expressed and presented by H1650 LUAD tumor cell line.

Generation of Engineered T-Cells Recognizing Fusion-Derived Peptides

Jurkat cells transduced with lentiviral vector encoding for CTL-9 TCR sequence were co-cultured with two different target cells, H1650 and H1395. Both are LUAD-derived cell lines expressing HLA-A2 allele. TCR-mediated activation of Jurkat cells was evaluated by flow cytometry analyzing an increase in the fluorescence of reporter genes (NFAT-GPF, NF-KB-CFP and AP-1-mCherry). Preliminary results show that Jurkat cells are activated when co-cultured with both target cells compared to negative control (non-transduced Jurkat cells). Furthermore, this activation increased in a dose-dependent manner when the co-culture was performed with target cells loaded with specific peptides. PMA/ionomycin was used as positive control (FIG. 12). These results are in line with the results shown in FIGS. 11 C and D, suggesting that LUAD-derived tumor cells express TE-derived peptides. Furthermore, we demonstrated the potential use of CTL-clones TCR sequences in the development of engineered T cells.

Presence of CD8+ Cells Recognizing Fusion-Derived Peptides in LUAD Patients

We aimed to identify presence of CTL cells recognizing fusion-derived peptides in LUAD tumor samples.

Figure 13A:
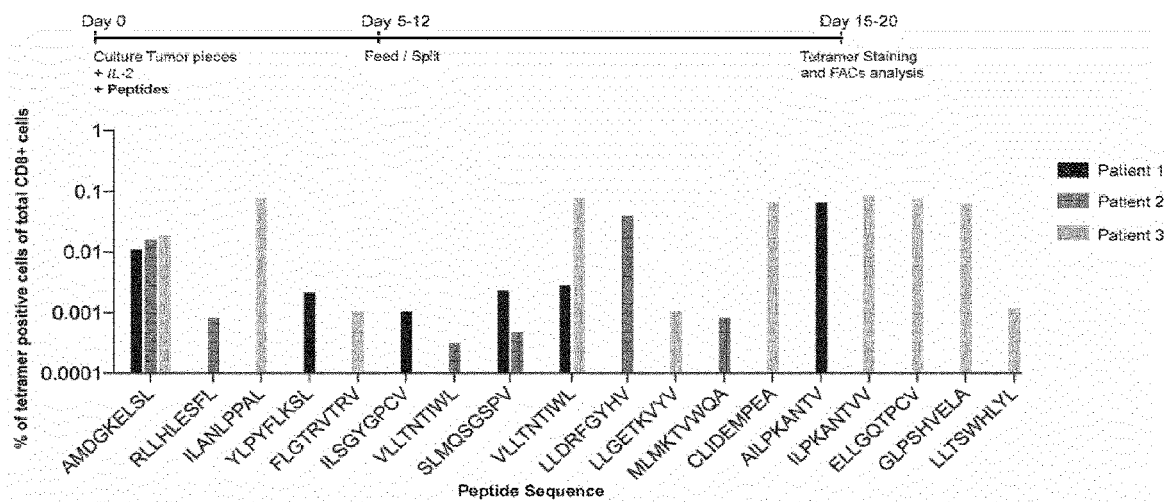
FIGS. 13A-13B: Tumor infiltrating lymphocytes recognizing fusion transcripts-derived peptides. Percentage of tetramer positive CD8 T cells for the indicated fusion transcript-derived peptides found in tumor infiltrating lymphocytes (TILs) expanded in the presence of fusion transcripts-derived peptide's mix+IL2 (FIG. 13A) or only with IL-2 (FIG. 13B).

In a first set of experiments tumor infiltrating lymphocytes (TILs) expanded with a mix of TE-derived peptides and Il-2, or only with Il-2, were analyzed by tetramer staining. As is shown in FIGS. 13A and B, we found CD8+ T-cells cells recognizing fusion-derived peptides in TILs derived from LUAD patients.

Figure 13B:
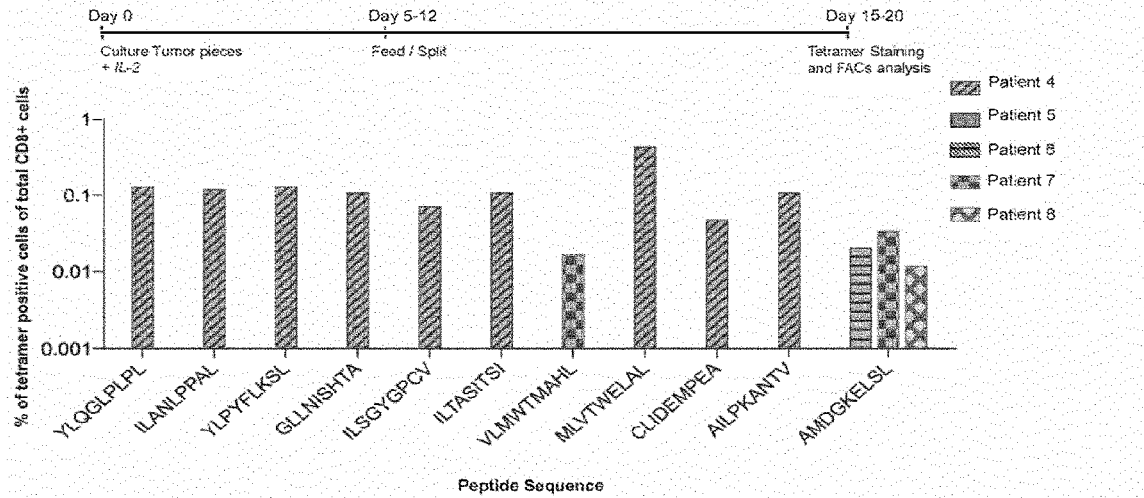
Figure 14A:
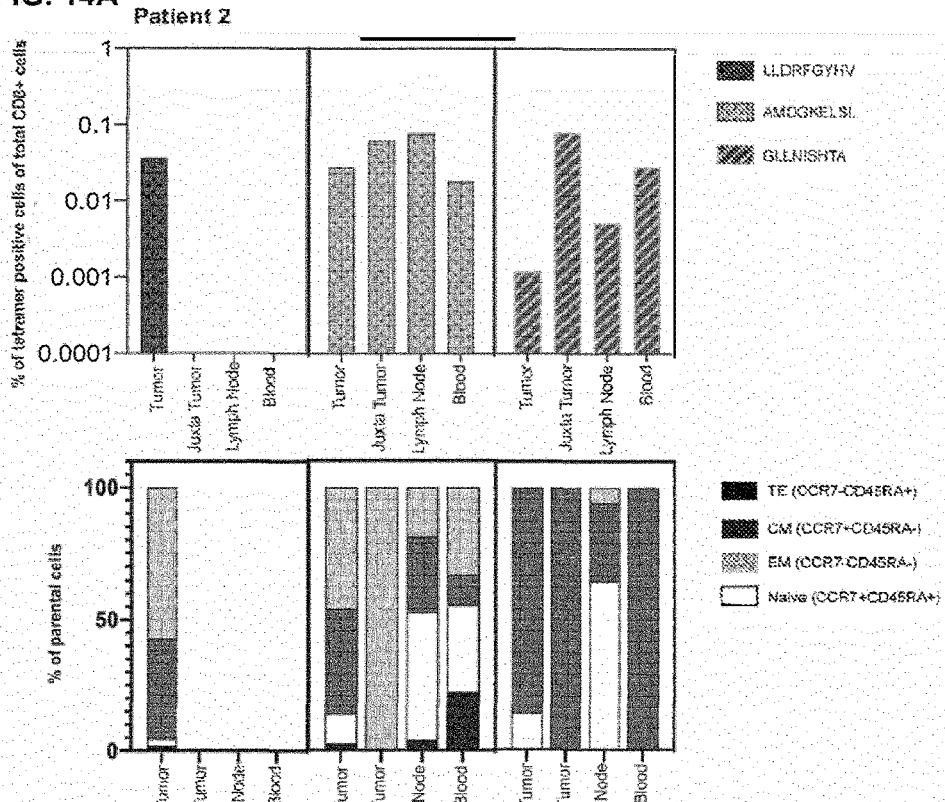
FIGS. 14A-14B: Phenotype of CD8+ T cells recognizing fusion transcripts-derived peptides in LUAD patient's derived samples. Percentage of tetramer positive CD8 T cells recognizing fusion transcripts-derived peptides present in tumor, juxta tumor, lymph nodes and blood samples derived from LUAD Patient 2 (FIG. 14A, upper panel) and Patient 3 (FIG. 14B, upper panel). In lower panel of FIG. 14A
Figure 14B:
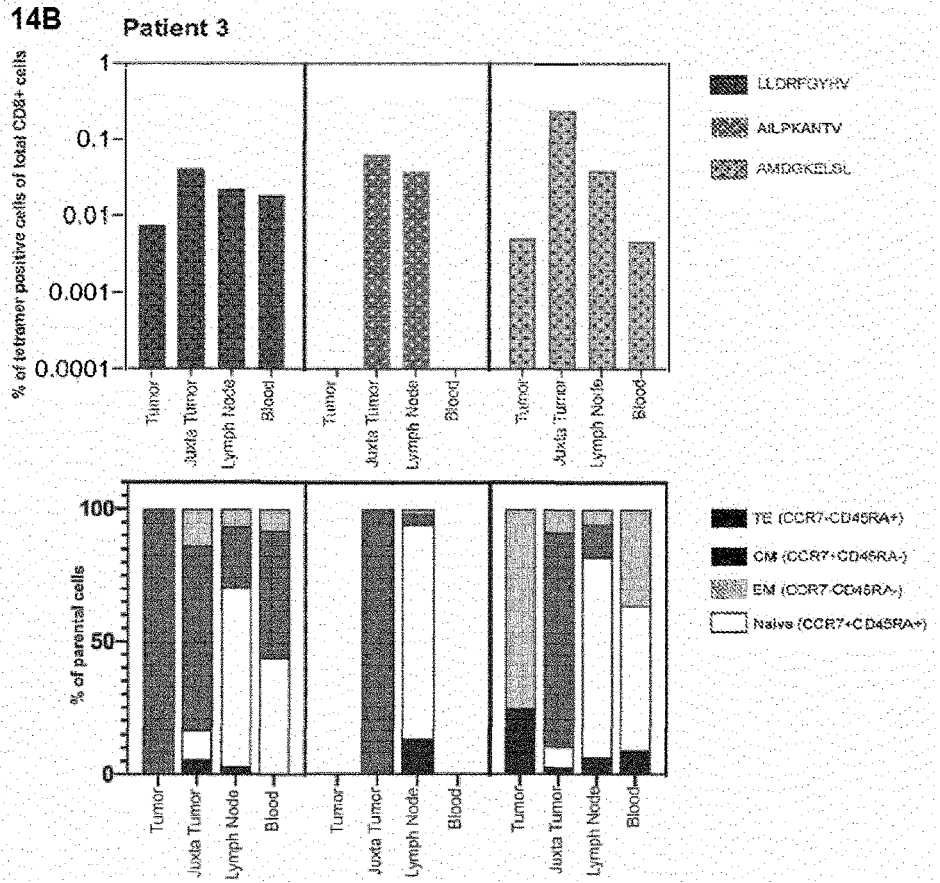

Then, we analyzed whether if we detect tetramer positive cells and their phenotype in non-expanded CD8+ T cells derived from fresh tumor samples. Using this strategy, we analyzed CD8+ T cells present in Tumor, juxta-tumor, invaded lymph-nodes and blood derived from LUAD patient samples. Phenotype was determined considering the expression of surface markers CCR7 and CD45RA as Naïve (CCR7+CD45+), Central Memory (CM, CCR7+CD45RA−) Effector Memory (EM, CCR7-CD45−) and Terminal Effectors (TE, CCR7-CD45+). Interestingly, tetramer positive cells found in tumor tissues shared preferentially a memory phenotype whereas naïve cells (CCR7+CD45+) are found mostly cells derived from lymph nodes (FIGS. 14A and B). Patient 2 and 3 are the same in FIG. 13 and FIG. 14.

All samples tested derived from HLA-A2+ patients.

Presence of tetramer positive cells with a memory phenotype in tumor tissues, together with the presence of tetramer positive cells in TILs, are consistent with an immune response generated against TE-derived peptides in these patients. Moreover, the existence of naïve tetramer positive cells in lymph nodes suggest the potential capacity to generate an immune response against these particularly TE-derived peptides.

Peptide Identification by Mass Spectrometry in LUAD Biopsies.

Presentation by MHC class I molecules on the tumour cell surface is required for ER-derived peptides in order to be recognized by cytotoxic T cells. In order to confirm that predicted peptides are express on MHC class I molecules, public data from MHC I immunopeptidome derived from 3 LUAD biopsies (Laumont C M et al., "Noncoding regions are the main source of targetable tumor-specific antigens" Sci Transl Med. 2018 10 (470)) were used. OpenMS Software was used to analyse the raw data uploaded to PRIDE database from MHC-I immunopurification of 3 LUAD tumours (PXD009752, PXD009754 and PXD009755). Having in mind that data-dependent acquisition in proteomics only allows the identification of those sequences contained in a target database (generally the whole human proteome): the peptides as per the present application had not been previously identified because they derive from non-coding sequences. The MS/MS identifications incorporating the sequences of the herein predicted peptides in the target database has been re-analyzed. Five peptides among the 3 samples biopsies (peptides ID: 3304, 269, 757, 1810, 3953)

were found. To perform this analysis, all predicted peptides derived from chimeric fusions present in at least 5 samples in the TCGA binding to any MHC I allele were considered. This result confirms the expression of chimeric fusion-derived peptides on MHC class I molecules in LUAD tumors.

Figure 15:
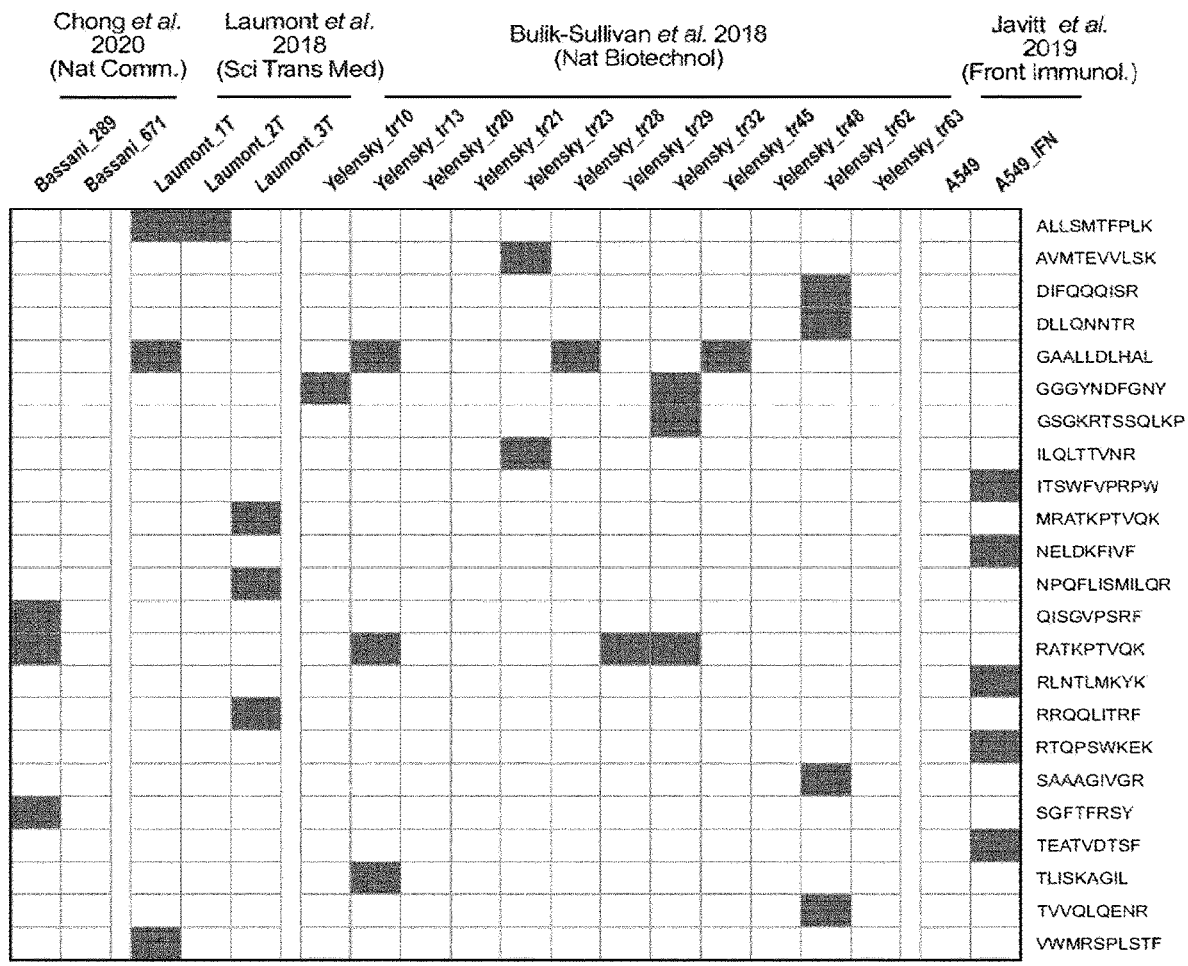
FIG. 15. Immunopeptidomics analysis of lung tumor samples. Fusion transcript-derived peptide sequences were searched in public MHC-I immunopeptidomes datasets. Each column represents a different sample. Each row represents a different peptide sequence (specify on the right). Colored squares indicate in which sample is found each fusion transcript-derived peptide. Publications describing each sample data-sets are annotated on the top.

Later, we extended our analysis to new lung immunopeptidomics datasets (Bulik-Sullivan et al. Nat. Biotec 2018, Chong et al. Nat. Comm. 2020 and Javitt et al. Front Immunol 2019). Of note, all datasets were generated with fresh lung tumor samples with the exception of Javitt et al. Front Immunol 2019 containing LUAD tumor cell line. For this second analysis, ProteomeDiscoverer 1.4 Software was used to identify the ER-derived peptides. Considering the 4 datasets, 23 unique ER-derived peptides were present in at least one of the total 19 immunopeptidomic samples. In FIG. 15, ER-derived peptides (rows) identified in each MHC sample (column) are indicated with a grey square. On the right, the peptide sequence found is indicated. Interestingly, some of them were observed in more than 1 MHC sample indicating that they are shared across samples. These results confirm that fusion transcripts-derived peptides are processed and presented by HLA-I molecules on tumor cells surface.

Peptide RLADHLSFC derived from a fusion transcript where the gene part of the fusion is a tumor suppressor gene (Fusion ID: chr22: 29117506:→chr22: 29115473:-/gene involved: CHEK2) and peptide GLPSHVELA derived from a fusion transcript where the gene part is an oncogene (Fusion ID: chr6: 117763597:→chr6: 117739669:-/gene involved: ROS1). Interestingly, both peptides were found to be immunogenic (FIG. 11A) and particularly for peptide RLADHLSFC, results show in FIG. 11 D indicate that could be express by H1650 cell line. Furthermore, we found TILs recognizing peptide GLPSHVELA (FIG. 12A), which indicates that this fusion transcript-derived peptide could be express in LUAD tumor samples.

3 Example 3: Identification Neoantigenic Peptides Derived from Fusion Transcripts Composed of a TE Element and an Exonic Sequence from Various Cancer Samples 9184 samples from 32 different cancer types (Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma and Uveal Melanoma) were analyzed according to the method as previously described.

Fusion transcripts of SEQ ID NO: 911-17492 were identified.

In the following tables, columns will be referenced as follow:

1. Frequency in the cohort
2. Donor Chromosome Exon/2' Donor Chromosome Exon
3. Donor start Exon/3' Donor start TE
4. Donor Breakpoint Exon/4'Donor Breakpoint TE
5. Donor strand Exon/5' Donor strand TE
6. Donor transcript (i.e. Donor_tx_name_Exon)/6' Acceptor chromosome exon
7. Acceptor Chromosome TE/7' acceptor breakpoint exon
8. Acceptor Breakpoint TE/8' acceptor end exon
9. Acceptor end TE/9' acceptor strand exon
10. Acceptor strand TE/10' acceptor transcript (i.e. Acceptor_tx_name_Exon)
11. Fusion type/11' fusion type

TABLE 5

Transcript fusion for Adrenocortical carcinoma Coordinates of the fusion sequences for which the donor is the exon.

| 1 | 2 | 2 | 4 | 5 | 6 | 7 | 8 | 9 | 10 | 11 |
|---|---|---|---|---|---|---|---|---|---|---|
| 59% | chr14 | 101200486 | 101200513 | + | ENST00000341267;ENST000003312 24 | chr14 | 101473144 | 101473392 | + | TAF |
| 29% | chr5 | 147649636 | 147649705 | + | ENST00000512953;ENST000003984 50 | chr5 | 147650500 | 147650640 | + | TAF |
| 27% | chr7 | 95125070 | 95125369 | + | ENST00000428113;ENST000003258 85 | chr7 | 95147506 | 95147874 | + | TAF |
| 24% | chrX | 152830379 | 152830561 | + | ENST00000349466;ENST000003701 86;ENST00000393842;ENST000003 59149;ENST00000263519;ENST000 00370181 | chrX | 152831276 | 152831321 | + | TAF |
| 24% | chrX | 152830379 | 152830561 | + | ENST00000349466;ENST000003701 86;ENST00000393842;ENST000003 59149;ENST00000263519;ENST000 00370181 | chrX | 152831276 | 152831321 | + | TAF |
| 22% | chr7 | 95165749 | 95165862 | + | ENST00000325885 | chr7 | 95168895 | 95169198 | + | TAF |
| 22% | chr5 | 147649636 | 147649705 | + | ENST00000512953;ENST000003984 50 | chr5 | 147650360 | 147650640 | + | TAF |
| 22% | chr18 | 33767503 | 33767644 | + | ENST00000261326 | chr18 | 33773430 | 33773774 | + | TAF |
| 22% | chrX | 49054298 | 49054174 | − | ENST00000263233;ENST000004798 08;ENST00000469389;ENST000004 66635 | chrX | 49053735 | 49053463 | − | TSF |

TABLE 5-continued

Transcript fusion for Adrenocortical carcinoma Coordinates of the fusion sequences for which the donor is the exon.

| 1 | 2 | 2 | 4 | 5 | 6 | 7 | 8 | 9 | 10 | 11 |
|---|---|---|---|---|---|---|---|---|---|---|
| 20% | chr3 | 48716169 | 48715997 | − | ENST00000341520;ENST00000416649;ENST00000294129;ENST00000413374 | chr3 | 48702393 | 48702198 | − | TSF |
| 20% | chr3 | 48716169 | 48715997 | − | ENST00000341520;ENST00000416649;ENST00000294129;ENST00000413374 | chr3 | 48702393 | 48702198 | − | TSF |
| 20% | chr3 | 48716169 | 48715997 | − | ENST00000341520;ENST00000416649;ENST00000294129;ENST00000413374 | chr3 | 48702393 | 48702198 | − | TSF |
| 19% | chr22 | 24323139 | 24323226 | + | ENST00000215780;ENST00000402588 | chr22 | 24324557 | 24324632 | + | TAF |
| 19% | chr5 | 74984990 | 74984837 | − | ENST00000428202;ENST00000514838;ENST00000380475;ENST00000510798;ENST00000446329 | chr5 | 74983153 | 74982863 | − | TAF |
| 19% | chr5 | 74984990 | 74984837 | − | ENST00000428202;ENST00000514838;ENST00000380475;ENST00000510798;ENST00000446329 | chr5 | 74983153 | 74982863 | − | TAF |
| 19% | chr5 | 74984990 | 74984837 | − | ENST00000428202;ENST00000514838;ENST00000380475;ENST00000510798;ENST00000446329 | chr5 | 74983153 | 74982863 | − | TAF |
| 19% | chr5 | 74984990 | 74984837 | − | ENST00000428202;ENST00000514838;ENST00000380475;ENST00000510798;ENST00000446329 | chr5 | 74983153 | 74982863 | − | TAF |
| 16% | chr6 | 10749855; 10749898 | 10749931 | + | ENST00000379542;ENST00000473166;ENST00000463448;ENST00000460341;ENST00000480294;ENST00000473807;ENST00000461342;ENST00000475942;ENST00000379530;ENST00000463100;ENST00000481240;ENST00000467317;ENST00000478732 | chr6 | 10829240 | 10829256 | + | TAF |
| 16% | chr6 | 10749855; 10749898 | 10749931 | + | ENST00000379542;ENST00000473166;ENST00000463448;ENST00000460341;ENST00000480294;ENST00000473807;ENST00000461342;ENST00000475942;ENST00000379530;ENST00000463100;ENST00000481240;ENST00000467317;ENST00000478732 | chr6 | 10829240 | 10829256 | + | TAF |
| 16% | chr19 | 50984141 | 50984234 | + | ENST00000334976;ENST00000376918;ENST00000598585 | chr19 | 51009025 | 51009080 | + | TAF |
| 16% | chr20 | 32247538; 32247356 | 32247303 | − | ENST00000246190;ENST00000375238;ENST00000480994 | chr20 | 32246861 | 32246725 | − | TAF |
| 16% | chr20 | 32247538; 32247356 | 32247303 | − | ENST00000246190;ENST00000375238;ENST00000480994 | chr20 | 32246861 | 32246725 | − | TAF |
| 16% | chr20 | 32247538; 32247356 | 32247303 | − | ENST00000246190;ENST00000375238;ENST00000480994 | chr20 | 32246861 | 32246725 | − | TAF |
| 15% | chr10 | 104650301 | 104650435 | + | ENST00000369880 | chr10 | 104654553 | 104654816 | + | TAF |
| 15% | chr17 | 19568261 | 19568360 | + | ENST00000176643;ENST00000581518;ENST00000395575;ENST00000339618;ENST00000579855;ENST00000571163 | chr17 | 19588588 | 19589107 | + | TAF |
| 15% | chr17 | 19568261 | 19568360 | + | ENST00000176643;ENST00000581518;ENST00000395575;ENST00000339618;ENST00000579855;ENST00000571163 | chr17 | 19588588 | 19589107 | + | TAF |
| 15% | chr8 | 74939024 | 74939076 | + | ENST00000284818;ENST00000518893 | chr8 | 74944554 | 74944936 | + | TAF |
| 15% | chr8 | 74939024 | 74939076 | + | ENST00000284818;ENST00000518893 | chr8 | 74944554 | 74944936 | + | TAF |
| 15% | chr17 | 72861942 | 72861841 | − | ENST00000293195;ENST00000544854;ENST00000420580;ENST00000581530;ENST00000455107;ENST00000583917;ENST00000442102;ENST00000582944;ENST00000413947;ENST00000579893 | chr17 | 72861374 | 72861251 | − | TSF |
| 15% | chr17 | 72861942 | 72861841 | − | ENST00000293195;ENST00000544854;ENST00000420580;ENST00000581530;ENST00000455107;ENST00000583917;ENST00000442102;ENST00000582944;ENST00000413947;ENST00000579893 | chr17 | 72861374 | 72861251 | − | TSF |
| 15% | chr17 | 72861942 | 72861841 | − | ENST00000293195;ENST00000544854;ENST00000420580;ENST00000581530;ENST00000455107;ENST000 | chr17 | 72861374 | 72861251 | − | TSF |

TABLE 5-continued

Transcript fusion for Adrenocortical carcinoma Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 15% | chr17 | 72861942 | 72861841 | − | 00583917;ENST00000442102;ENST00000582944;ENST00000413947;ENST00000579893 ENST00000293195;ENST000005448 54;ENST00000420580;ENST000005 81530;ENST00000455107;ENST000 00583917;ENST00000442102;ENST 00000582944;ENST00000413947;EN ST00000579893 | chr17 | 72861374 | 72861251 | − | TSF |
| 15% | chr17 | 72861942 | 72861841 | − | ENST00000293195;ENST000005448 54;ENST00000420580;ENST000005 81530;ENST00000455107;ENST000 00583917;ENST00000442102;ENST 00000582944;ENST00000413947;EN ST00000579893 | chr17 | 72861374 | 72861251 | − | TSF |
| 15% | chr17 | 72861942 | 72861841 | − | ENST00000293195;ENST000005448 54;ENST00000420580;ENST000005 81530;ENST00000455107;ENST000 00583917;ENST00000442102;ENST 00000582944;ENST00000413947;EN ST00000579893 | chr17 | 72861374 | 72861251 | − | TSF |
| 15% | chr17 | 72861942 | 72861841 | − | ENST00000293195;ENST000005448 54;ENST00000420580;ENST000005 81530;ENST00000455107;ENST000 00583917;ENST00000442102;ENST 00000582944;ENST00000413947;EN ST00000579893 | chr17 | 72861374 | 72861251 | − | TSF |
| 15% | chr17 | 72861942 | 72861841 | − | ENST00000293195;ENST000005448 54;ENST00000420580;ENST000005 81530;ENST00000455107;ENST000 00583917;ENST00000442102;ENST 00000582944;ENST00000413947;EN ST00000579893 | chr17 | 72861374 | 72861251 | − | TSF |
| 15% | chr17 | 72861942 | 72861841 | − | ENST00000293195;ENST000005448 54;ENST00000420580;ENST000005 81530;ENST00000455107;ENST000 00583917;ENST00000442102;ENST 00000582944;ENST00000413947;EN ST00000579893 | chr17 | 72861374 | 72861251 | − | TSF |
| 14% | chr20 | 35842163 | 35842268 | + | ENST00000237530;ENST000003736 22 | chr20 | 35844460 | 35844765 | + | TAF |
| 14% | chr20 | 35842163 | 35842268 | + | ENST00000237530;ENST000003736 22 | chr20 | 35844460 | 35844765 | + | TAF |
| 14% | chr7 | 75611542; 75611580; 75611597 | 75611640 | + | ENST00000461988;ENST000004198 40;ENST00000394893;ENST000004 12064;ENST00000447222;ENST000 00545601;ENST00000450476;ENST 00000439269 | chr7 | 75612546 | 75612675 | + | TAF |
| 14% | chr7 | 75611542; 75611580; 75611597 | 75611640 | + | ENST00000461988;ENST000004198 40;ENST00000394893;ENST000004 12064;ENST00000447222;ENST000 00545601;ENST00000450476;ENST 00000439269 | chr7 | 75612546 | 75612675 | + | TAF |
| 14% | chr7 | 75611542; 75611580; 75611597 | 75611640 | + | ENST00000461988;ENST000004198 40;ENST00000394893;ENST000004 12064;ENST00000447222;ENST000 00545601;ENST00000450476;ENST 00000439269 | chr7 | 75612546 | 75612675 | + | TAF |
| 14% | chr7 | 75611542; 75611580; 75611597 | 75611640 | + | ENST00000461988;ENST000004198 40;ENST00000394893;ENST000004 12064;ENST00000447222;ENST000 00545601;ENST00000450476;ENST 00000439269 | chr7 | 75612546 | 75612675 | + | TAF |
| 14% | chr7 | 75611542; 75611580; 75611597 | 75611640 | + | ENST00000461988;ENST000004198 40;ENST00000394893;ENST000004 12064;ENST00000447222;ENST000 00545601;ENST00000450476;ENST 00000439269 | chr7 | 75612546 | 75612675 | + | TAF |
| 14% | chr7 | 75611542; 75611580; 75611597 | 75611640 | + | ENST00000461988;ENST000004198 40;ENST00000394893;ENST000004 12064;ENST00000447222;ENST000 00545601;ENST00000450476;ENST 00000439269 | chr7 | 75612546 | 75612675 | + | TAF |

TABLE 5-continued

Transcript fusion for Adrenocortical carcinoma Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 14% | chr7 | 75611542; 75611580; 75611597 | 75611640 | + | ENST00000461988;ENST00000419840;ENST00000394893;ENST00000412064;ENST00000447222;ENST00000545601;ENST00000450476;ENST00000439269 | chr7 | 75612546 | 75612675 | + | TAF |
| 14% | chrX | 152602138 | 152602168 | + | ENST00000370251;ENST00000421401 | chrX | 152617375 | 152617427 | + | TSF |
| 13% | chr19 | 52671325 | 52671311 | − | ENST00000597252;ENST00000322146;ENST00000596428;ENST00000597065 | chr19 | 52666101 | 52665762 | − | TSF |
| 13% | chr15 | 74631109 | 74630912 | − | ENST00000358632;ENST00000268053;ENST00000419019 | chr15 | 74624041 | 74623995 | − | TSF |
| 13% | chr15 | 74631109 | 74630912 | − | ENST00000358632;ENST00000268053;ENST00000419019 | chr15 | 74624041 | 74623995 | − | TSF |
| 11% | chr11 | 110306558 | 110306682 | + | ENST00000260270 | chr11 | 110313385 | 110313534 | + | TAF |
| 11% | chr7 | 27582719 | 27582586 | − | ENST00000265395;ENST00000425715 | chr7 | 27581374 | 27579272 | − | TAF |
| 11% | chr7 | 27582719 | 27582586 | − | ENST00000265395;ENST00000425715 | chr7 | 27581374 | 27579272 | − | TAF |
| 11% | chr17 | 7130588 | 7130409 | − | ENST00000005340;ENST00000575458;ENST00000575086 | chr17 | 7130277 | 7130132 | − | TAF |
| 11% | chr17 | 7130588 | 7130409 | − | ENST00000005340;ENST00000575458;ENST00000575086 | chr17 | 7130277 | 7130132 | − | TAF |
| 11% | chr17 | 7130588 | 7130409 | − | ENST00000005340;ENST00000575458;ENST00000575086 | chr17 | 7130277 | 7130132 | − | TAF |
| 10% | chr8 | 63502273 | 63502353 | + | ENST00000523211;ENST00000328472 | chr8 | 63546747 | 63547118 | + | TSF |
| 9% | chr5 | 147649636 | 147649705 | + | ENST00000512953;ENST00000398450 | chr5 | 147650327 | 147650640 | + | TSF |
| 8% | chr16 | 50666192 | 50666319 | + | ENST00000268459 | chr16 | 50682755 | 50682972 | + | TSF |
| 8% | chr19 | 48382387 | 48382293 | − | ENST00000222002 | chr19 | 48379566 | 48379257 | − | TSF |
| 8% | chr1 | 173157708 | 173157660 | − | ENST00000367718;ENST00000281834 | chr1 | 173142495 | 173142335 | − | TSF |
| 8% | chr1 | 173157708 | 173157660 | − | ENST00000367718;ENST00000281834 | chr1 | 173142495 | 173142335 | − | TSF |

TABLE 6

Transcript fusion for Adrenocortical carcinoma Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 84% | chr9 | 111648536 | 111648048 | − | chr9 | 111644467 | 111644405 | − | ENST00000495759; ENST00000374647; ENST00000537196 | TAF |
| 84% | chr9 | 111648536 | 111648048 | − | chr9 | 111644467 | 111644405 | − | ENST00000495759; ENST00000374647; ENST00000537196 | TAF |
| 75% | chr2 | 132281819 | 132281839 | + | chr2 | 132287220 | 132287264 | + | ENST00000295171; ENST00000409856; ENST00000434330 | TAF |
| 75% | chr2 | 132281819 | 132281839 | + | chr2 | 132287220 | 132287264 | + | ENST00000295171; ENST00000409856; ENST00000434330 | TAF |
| 75% | chr2 | 132281819 | 132281839 | + | chr2 | 132287220 | 132287264 | + | ENST00000295171; ENST00000409856; ENST00000434330 | TAF |
| 70% | chr12 | 94167005 | 94167262 | + | chr12 | 94243746 | 94244047 | + | ENST00000332896; ENST00000542893 | TAF |
| 68% | chr7 | 150938296 | 150938250 | − | chr7 | 150937608 | 150937511 | − | ENST00000262188; ENST00000392811; ENST00000356800 | TAF |
| 59% | chr11 | 110329921 | 110329943 | + | chr11 | 110333078 | 110333192 | + | ENST00000260270 | TAF |
| 54% | chr12 | 125263794 | 125263744 | − | chr12 | 125263132 | 125263013; 125263125 | − | ENST00000339570; ENST00000415380 | TAF |
| 54% | chr12 | 125263794 | 125263744 | − | chr12 | 125263132 | 125263013; 125263125 | − | ENST00000339570; ENST00000415380 | TAF |
| 47% | chr4 | 140216524 | 140216458 | − | chr4 | 140216300 | 140216197 | − | ENST00000503997; ENST00000539002; ENST00000544855; ENST00000394228; ENST00000539387; ENST00000265500; ENST00000505036; ENST00000394223 | TAF |
| 43% | chr12 | 102411559 | 102411498 | − | chr12 | 102406970 | 102406886 | − | ENST00000240079; ENST00000545679; ENST00000542923 | TAF |
| 35% | chr9 | 114546431 | 114546079 | − | chr9 | 114543297 | 114543210 | − | ENST00000374283 | TAF |
| 35% | chr14 | 94518197 | 94518094 | − | chr14 | 94517808 | 94517537 | − | ENST00000330836; ENST00000544005; ENST00000555054 | TAF |

TABLE 6-continued

Transcript fusion for Adrenocortical carcinoma Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 33% | chr9 | 111633879 | 111632734 | − | chr9 | 111631462 | 111631395 | − | ENST00000374647; ENST00000537196 | TAF |
| 30% | chr10 | 104637349 | 104637429 | + | chr10 | 104638136 | 104638267 | + | ENST00000369880 | TAF |
| 30% | chr19 | 40330448 | 40330344 | − | chr19 | 40329845 | 40329675; 40329835; 40329714 | − | ENST00000595545; ENST00000221801; ENST00000594443; ENST00000597224; ENST00000601274; ENST00000597634; ENST00000598417; ENST00000594309; ENST00000599134 | TAF |
| 30% | chr19 | 40330448 | 40330344 | − | chr19 | 40329845 | 40329675; 40329835; 40329714 | − | ENST00000595545; ENST00000221801; ENST00000594443; ENST00000597224; ENST00000601274; ENST00000597634; ENST00000598417; ENST00000594309; ENST00000599134 | TAF |
| 30% | chr19 | 40330448 | 40330344 | − | chr19 | 40329845 | 40329675; 40329835; 40329714 | − | ENST00000595545; ENST00000221801; ENST00000594443; ENST00000597224; ENST00000601274; ENST00000597634; ENST00000598417; ENST00000594309; ENST00000599134 | TAF |
| 30% | chr19 | 40330448 | 40330344 | − | chr19 | 40329845 | 40329675; 40329835; 40329714 | − | ENST00000595545; ENST00000221801; ENST00000594443; ENST00000597224; ENST00000601274; ENST00000597634; ENST00000598417; ENST00000594309 ENST00000599134 | TAF |
| 30% | chr19 | 40330448 | 40330344 | − | chr19 | 40329845 | 40329675; 40329835; 40329714 | − | ENST00000595545; ENST00000221801; ENST00000594443; ENST00000597224; ENST00000601274; ENST00000597634; ENST00000598417; ENST00000594309 ENST00000599134 | TAF |
| 30% | chr19 | 40330448 | 40330344 | − | chr19 | 40329845 | 40329675; 40329835; 40329714 | − | ENST00000595545; ENST00000221801; ENST00000594443; ENST00000597224; ENST00000601274; ENST00000597634; ENST00000598417; ENST00000594309 ENST00000599134 | TAF |
| 30% | chr19 | 40330448 | 40330344 | − | chr19 | 40329845 | 40329675; 40329835; 40329714 | − | ENST00000595545; ENST00000221801; ENST00000594443; ENST00000597224; ENST00000601274; ENST00000597634; ENST00000598417; ENST00000594309 ENST00000599134 | TAF |
| 30% | chr19 | 40330448 | 40330344 | − | chr19 | 40329845 | 40329675; 40329835; 40329714 | − | ENST00000595545; ENST00000221801; ENST00000594443; ENST00000597224; ENST00000601274; ENST00000597634; ENST00000598417; ENST00000594309 ENST00000599134 | TAF |
| 30% | chr19 | 40330448 | 40330344 | − | chr19 | 40329845 | 40329675; 40329835; 40329714 | − | ENST00000595545; ENST00000221801; ENST00000594443; ENST00000597224; ENST00000601274; ENST00000597634; ENST00000598417; ENST00000594309 ENST00000599134 | TAF |
| 30% | chr19 | 4454954 | 4454819 | − | chr19 | 4454090 | 4453927 | − | ENST00000591919; ENST00000301281; ENST00000592515 | TSF |
| 30% | chr19 | 4454954 | 4454819 | − | chr19 | 4454090 | 4453927 | − | ENST00000591919; ENST00000301281; ENST00000592515 | TSF |
| 30% | chr19 | 4454954 | 4454819 | − | chr19 | 4454090 | 4453927 | − | ENST00000591919; ENST00000301281; ENST00000592515 | TSF |
| 28% | chr7 | 120447469 | 120447344 | − | chr7 | 120446746 | 120446603 | − | ENST00000222747; ENST00000415871 | TSF |
| 27% | chr4 | 107241932 | 107242850 | + | chr4 | 107246142 | 107246275 | + | ENST00000394701 | TAF |
| 24% | chr9 | 127173550 | 127173482 | − | chr9 | 127167711 | 127167596 | − | ENST00000259457; ENST00000441097 | TAF |
| 24% | chr9 | 127173550 | 127173482 | − | chr9 | 127167711 | 127167596 | − | ENST00000259457; ENST00000441097 | TAF |
| 23% | chr11 | 110317098 | 110317561 | + | chr11 | 110327642 | 110327771 | + | ENST00000260270 | TAF |
| 20% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 20% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |

TABLE 6-continued

Transcript fusion for Adrenocortical carcinoma Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 20% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 20% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 20% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 20% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 20% | chr19 | 48388785 | 48388506 | − | chr19 | 48387042 | 48386834 | − | ENST00000222002 | TAF |
| 19% | chr10 | 104654213 | 104654429 | + | chr10 | 104660350 | 104660457 | + | ENST00000369880 | TAF |
| 19% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 19% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 19% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 19% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 19% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 18% | chr12 | 55223983 | 55224659 | + | chr12 | 55248900 | 55248941 | + | ENST00000546809; ENST00000308796 | TAF |
| 18% | chr20 | 43919547 | 43919514 | − | chr20 | 43882374 | 43882216 | − | ENST00000338380 | TAF |
| 16% | chr17 | 79214190 | 79214239 | + | chr17 | 79214787 | 79214816; 79214953 | + | ENST00000431388; ENST00000576002 | TAF |
| 16% | chr17 | 79214190 | 79214239 | + | chr17 | 79214787 | 79214816; 79214953 | + | ENST00000431388; ENST00000576002 | TAF |
| 16% | chr13 | 76173531 | 76175706 | + | chr13 | 76178905 | 76178963 | + | ENST00000377595; ENST00000419068 | TAF |
| 16% | chr14 | 76123655 | 76123598 | − | chr14 | 76121319 | 76121229 | − | ENST00000256319 | TAF |
| 16% | chr9 | 133953597 | 133953695 | + | chr9 | 133954536 | 133954685 | + | ENST00000361069 | TSF |
| 15% | chr11 | 110301592 | 110301671 | + | chr11 | 110306558 | 110306682 | + | ENST00000260270 | TAF |
| 15% | chr7 | 1014593 | 1014543 | − | chr7 | 1012928 | 1012817 | − | ENST00000457254; ENST00000344111 | TSF |
| 15% | chr7 | 1014593 | 1014543 | − | chr7 | 1012928 | 1012817 | − | ENST00000457254; ENST00000344111 | TSF |
| 14% | chr5 | 147650185 | 147650475 | + | chr5 | 147653910 | 147653947 | + | ENST00000512953; ENST00000398450 | TAF |
| 14% | chr10 | 104634953 | 104634957 | + | chr10 | 104636711 | 104636792 | + | ENST00000369880 | TAF |
| 14% | chr19 | 54631006 | 54631115 | + | chr19 | 54631448 | 54631575 | + | ENST00000321030; ENST00000419967 | TAF |
| 14% | chr19 | 54631006 | 54631115 | + | chr19 | 54631448 | 54631575 | + | ENST00000321030; ENST00000419967 | TAF |
| 14% | chr3 | 122863450 | 122863676 | + | chr3 | 122864369 | 122864384; 122864439 | + | ENST00000489923; ENST00000316218 | TAF |
| 14% | chr3 | 122863450 | 122863676 | + | chr3 | 122864369 | 122864384; 122864439 | + | ENST00000489923; ENST00000316218 | TAF |
| 14% | chr5 | 176950300 | 176950160 | − | chr5 | 176949072 | 176948976 | − | ENST00000514747; ENST00000329540; ENST00000443375; ENST00000524677 | TAF |
| 14% | chr5 | 68663671 | 68663666 | − | chr5 | 68662422 | 68662330 | − | ENST00000380822; ENST00000380818 | TAF |
| 14% | chr3 | 13060700 | 13060650 | − | chr3 | 12983365 | 12983071 | − | ENST00000273221; ENST00000450726; ENST00000429247 | TAF |
| 14% | chr3 | 13060700 | 13060650 | − | chr3 | 12983365 | 12983071 | − | ENST00000273221; ENST00000450726; ENST00000429247 | TAF |
| 14% | chr3 | 13060700 | 13060650 | − | chr3 | 12983365 | 12983071 | − | ENST00000273221; 04ENST000050726; ENST00000429247 | TAF |
| 13% | chr10 | 104637349 | 104637429 | + | chr10 | 104638606 | 104638748 | + | ENST00000369880 | TAF |
| 13% | chr12 | 113808893 | 113809071 | + | chr12 | 113810454 | 113810612; 113810475 | + | ENST00000545182; ENST00000280800; ENST00000548997 | TAF |
| 13% | chr12 | 113808893 | 113809071 | + | chr12 | 113810454 | 113810612; 113810475 | + | ENST00000545182; ENST00000280800; ENST00000548997 | TAF |
| 13% | chr12 | 113808893 | 113809071 | + | chr12 | 113810454 | 113810612; 113810475 | + | ENST00000545182; ENST00000280800; ENST00000548997 | TAF |

TABLE 6-continued

Transcript fusion for Adrenocortical carcinoma Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 13% | chr11 | 110301592 | 110301776 | + | chr11 | 110306558 | 110306682 | + | ENST00000260270 | TAF |
| 13% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 13% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 13% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 13% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 13% | chr2 | 230409549 | 230409481 | − | chr2 | 230377652 | 230377499 | − | ENST00000341772 | TAF |
| 13% | chr12 | 6602868 | 6602840 | − | chr12 | 6602138 | 6602028 | − | ENST00000229238 | TAF |
| 13% | chrX | 150886281 | 150886376 | + | chrX | 150889867 | 150889973 | + | ENST00000370350 | TSF |
| 13% | chr7 | 100406138 | 100406138 | − | chr7 | 100405202 | 100404987 | − | ENST00000360620; ENST00000358173 | TSF |
| 13% | chr7 | 100406138 | 100406138 | − | chr7 | 100405202 | 100404987 | − | ENST00000360620; ENST00000358173 | TSF |
| 11% | chr14 | 94581487 | 94581557 | + | chr14 | 94582127 | 94582191; 94582279; 94582176 | + | ENST00000554448; ENST00000448882; ENST00000554800; ENST00000556544; ENST00000298902; ENST00000557634; ENST00000555744; ENST00000557035 | TAF |
| 11% | chr14 | 94581487 | 94581557 | + | chr14 | 94582127 | 94582191; 94582279; 94582176 | + | ENST00000554448; ENST00000448882; ENST00000554800; ENST00000556544; ENST00000298902; ENST00000557634; ENST00000555744; ENST00000557035 | TAF |
| 11% | chr14 | 94581487 | 94581557 | + | chr14 | 94582127 | 94582191; 94582279; 94582176 | + | ENST00000554448; ENST00000448882; ENST00000554800; ENST00000556544; ENST00000298902; ENST00000557634; ENST00000555744; ENST00000557035 | TAF |
| 11% | chr14 | 94581487 | 94581557 | + | chr14 | 94582127 | 94582191; 94582279; 94582176 | + | ENST00000554448; ENST00000448882; ENST00000554800; ENST00000556544; ENST00000298902; ENST00000557634; ENST00000555744; ENST00000557035 | TAF |
| 11% | chr14 | 94581487 | 94581557 | + | chr14 | 94582127 | 94582191; 94582279; 94582176 | + | ENST00000554448; ENST00000448882; ENST00000554800; ENST00000556544; ENST00000298902; ENST00000557634; ENST00000555744; ENST00000557035 | TAF |
| 11% | chr11 | 77909738 | 77909764 | + | chr11 | 77910641 | 77910770 | + | ENST00000528910; ENST00000529308 | TAF |
| 11% | chr11 | 77909738 | 77909764 | + | chr11 | 77910641 | 77910770 | + | ENST00000528910; ENST00000529308 | TAF |
| 11% | chr20 | 1453431 | 1453360 | − | chr20 | 1438919 | 1438845; 1438917 | − | ENST00000353088; ENST00000555944; ENST00000476071; ENST00000216879; ENST00000350991; ENST00000381653; ENST00000555568; ENST00000489203 | TAF |
| 11% | chr20 | 1453431 | 1453360 | − | chr20 | 1438919 | 1438845; 1438917 | − | ENST00000353088; ENST00000555944; ENST00000476071; ENST00000216879; ENST00000350991; ENST00000381653; ENST00000555568; ENST00000489203 | TAF |
| 11% | chr20 | 1453431 | 1453360 | − | chr20 | 1438919 | 1438845; 1438917 | − | ENST00000353088; ENST00000555944; ENST00000476071; ENST00000216879; ENST00000350991; ENST00000381653; ENST00000555568; ENST00000489203 | TAF |
| 11% | chr20 | 1453431 | 1453360 | − | chr20 | 1438919 | 1438845; 1438917 | − | ENST00000353088; ENST00000555944; ENST00000476071; ENST00000216879; ENST00000350991; ENST00000381653; ENST00000555568; ENST00000489203 | TAF |
| 11% | chr20 | 1453431 | 1453360 | − | chr20 | 1438919 | 1438845; 1438917 | − | ENST00000353088; ENST00000555944; ENST00000476071; ENST00000216879; ENST00000350991; ENST00000381653; ENST00000555568; ENST00000489203 | TAF |
| 11% | chr20 | 1453431 | 1453360 | − | chr20 | 1438919 | 1438845; 1438917 | − | ENST00000353088; ENST00000555944; ENST00000476071; ENST00000216879; ENST00000350991; ENST00000381653; ENST00000555568; ENST00000489203 | TAF |

TABLE 6-continued

Transcript fusion for Adrenocortical carcinoma Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 11% | chr20 | 1453431 | 1453360 | − | chr20 | 1438919 | 1438845; 1438917 | − | ENST00000353088; ENST00000555944; ENST00000476071; ENST00000216879; ENST00000350991; ENST00000381653; ENST00000555568; ENST00000489203 | TAF |
| 11% | chr12 | 94208725 | 94209257 | + | chr12 | 94243746 | 94244047 | + | ENST00000332896; ENST00000542893 | TSF |
| 10% | chr9 | 133961993 | 133962061 | + | chr9 | 133962863 | 133963009 | + | ENST00000361069; ENST00000355452 | TAF |
| 10% | chr14 | 24105943 | 24105981 | + | chr14 | 24112361 | 24112428 | + | ENST00000432832; ENST00000250383; ENST00000344777; ENST00000557535; ENST00000553600 | TAF |
| 10% | chr14 | 24105943 | 24105981 | + | chr14 | 24112361 | 24112428 | + | ENST00000432832; ENST00000250383; ENST00000344777; ENST00000557535; ENST00000553600 | TAF |
| 10% | chr14 | 24105943 | 24105981 | + | chr14 | 24112361 | 24112428 | + | ENST00000432832; ENST00000250383; ENST00000344777; ENST00000557535; ENST00000553600 | TAF |
| 10% | chr14 | 24105943 | 24105981 | + | chr14 | 24112361 | 24112428 | + | ENST00000432832; ENST00000250383; ENST00000344777; ENST00000557535; ENST00000553600 | TAF |
| 10% | chr14 | 24105943 | 24105981 | + | chr14 | 24112361 | 24112428 | + | ENST00000432832; ENST00000250383; ENST00000344777; ENST00000557535; ENST00000553600 | TAF |
| 10% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 10% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 10% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 10% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 10% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 10% | chr13 | 43628887 | 43629679 | + | chr13 | 43643066 | 43643139 | + | ENST00000379221 | TAF |
| 10% | chr11 | 87906665 | 87906580 | − | chr11 | 87883123 | 87882843 | − | ENST00000243662; ENST00000526372 | TAF |
| 10% | chr19 | 15493496 | 15493406 | − | chr19 | 15491423 | 15491328 | − | ENST00000397410; ENST00000595465 | TAF |
| 10% | chr1 | 40781678 | 40781517 | − | chr1 | 40781336 | 40781262 | − | ENST00000372748; ENST00000417105; ENST00000372736 | TAF |
| 10% | chr1 | 40781678 | 40781517 | − | chr1 | 40781336 | 40781262 | − | ENST00000372748; ENST00000417105; ENST00000372736 | TAF |
| 10% | chr1 | 40781678 | 40781517 | − | chr1 | 40781336 | 40781262 | − | ENST00000372748; ENST00000417105; ENST00000372736 | TAF |
| 10% | chr5 | 173041966 | 173041919 | − | chr5 | 173040258 | 173040134 | − | ENST00000311086; ENST00000285908 | TAF |
| 10% | chr5 | 173041966 | 173041919 | − | chr5 | 173040258 | 173040134 | − | ENST00000311086; ENST00000285908 | TAF |
| 10% | chr1 | 154925216 | 154925088 | − | chr1 | 154924397 | 154924271 | − | ENST00000368463; ENST00000368460; ENST00000490230 | TAF |
| 10% | chr1 | 154925216 | 154925088 | − | chr1 | 154924397 | 154924271 | − | ENST00000368463; ENST00000368460; ENST00000490230 | TAF |
| 10% | chr1 | 154925216 | 154925088 | − | chr1 | 154924397 | 154924271 | − | ENST00000368463; ENST00000368460; ENST00000490230 | TAF |
| 9% | chr2 | 74762302 | 74762039 | − | chr2 | 74761901 | 74761658 | − | ENST00000264094; ENST00000393937; ENST00000409549; ENST00000409986 | TSF |
| 9% | chr2 | 74762302 | 74762039 | − | chr2 | 74761901 | 74761658 | − | ENST00000264094; ENST00000393937; ENST00000409549; ENST00000409986 | TSF |
| 9% | chr10 | 99119563 | 99119361 | − | chr10 | 99118767 | 99118700 | − | ENST00000370992; ENST00000536831; ENST00000315563; ENST00000414986 | TSF |
| 8% | chr12 | 55223983 | 55224659 | + | chr12 | 55250554 | 55250676 | + | ENST00000546809; ENST00000308796 | TSF |
| 8% | chr11 | 1891186 | 1891243 | + | chr11 | 1901317 | 1901454 | + | ENST00000311604; ENST00000381775; ENST00000457279; ENST00000429923; ENST00000418975 | TSF |
| 8% | chr11 | 1891186 | 1891243 | + | chr11 | 1901317 | 1901454 | + | ENST00000311604; ENST00000381775; ENST00000457279; ENST00000429923; ENST00000418975 | TSF |
| 8% | chr11 | 1891186 | 1891243 | + | chr11 | 1901317 | 1901454 | + | ENST00000311604; ENST00000381775; ENST00000457279; ENST00000429923; ENST00000418975 | TSF |
| 8% | chr11 | 1891186 | 1891243 | + | chr11 | 1901317 | 1901454 | + | ENST00000311604; ENST00000381775; ENST00000457279; ENST00000429923; ENST00000418975 | TSF |

TABLE 7

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 44% | chr12 | 71509738 | 71509630 | − | ENST00000549357 | chr12 | 71504233 | 71503634 | − | TAF |
| 27% | chr15 | 58957396 | 58957296 | − | ENST00000260408 | chr15 | 58947615 | 58947395 | − | TAF |
| 25% | chr10 | 47747112 | 47747132 | + | ENST00000340243; ENST00000374277; ENST00000449464; ENST00000538825 | chr10 | 48278725 | 48278896 | + | TAF |
| 23% | chr20 | 35842163 | 35842268 | + | ENST00000237530; ENST00000373622 | chr20 | 35844460 | 35844765 | + | TAF |
| 23% | chr20 | 35842163 | 35842268 | + | ENST00000237530; ENST00000373622 | chr20 | 35844460 | 35844765 | + | TAF |
| 22% | chr3 | 49927493 | 49927357 | − | ENST00000296474; ENST00000344206 | chr3 | 49927248 | 49927204 | − | TAF |
| 22% | chr3 | 49927493 | 49927357 | − | ENST00000296474; ENST00000344206 | chr3 | 49927248 | 49927204 | − | TAF |
| 21% | chr1 | 60370730 | 60370543 | − | ENST00000371204 | chr1 | 60370188 | 60370144 | − | TAF |
| 20% | chr22 | 45689062 | 45689194 | + | ENST00000216211; ENST00000396082 | chr22 | 45691275 | 45691319 | + | TAF |
| 20% | chr22 | 45689062 | 45689194 | + | ENST00000216211; ENST00000396082 | chr22 | 45691275 | 45691319 | + | TAF |
| 20% | chr3 | 118943092 | 118942905 | − | ENST00000483209; ENST00000467604; ENST00000359213; ENST00000393765; ENST00000480814 | chr3 | 1189385122 | 118938188 | − | TAF |
| 17% | chr11 | 64594027 | 64593942 | − | ENST00000342711 | chr11 | 64592957 | 64592752 | − | TAF |
| 16% | chr20 | 43560983 | 43561073 | + | ENST00000255136; ENST00000217073 | chr20 | 43561176 | 43561224 | + | TAF |
| 15% | chr10 | 120905865 | 120905748 | − | ENST00000355697; ENST00000330036 | chr10 | 120901885 | 120901741 | − | TAF |
| 15% | chr10 | 120905865 | 120905748 | − | ENST00000355697; ENST00000330036 | chr10 | 120901885 | 120901741 | − | TAF |
| 15% | chr1 | 32696528 | 32696620 | + | ENST00000373586 | chr1 | 32696861 | 32697110 | + | TAF |
| 14% | chr17 | 40821639; 40821538 | 40821448 | − | ENST00000591022; ENST00000412503; ENST00000293349 | chr17 | 40820920 | 40820864 | − | TAF |
| 14% | chr17 | 40821639; 40821538 | 40821448 | − | ENST00000591022; ENST00000412503; ENST00000293349 | chr17 | 40820920 | 40820864 | − | TAF |
| 14% | chr17 | 40821639; 40821538 | 40821448 | − | ENST00000591022; ENST00000412503; ENST00000293349 | chr17 | 40820920 | 40820864 | − | TAF |
| 14% | chr8 | 54793576 | 54793644 | + | ENST00000276500 | chr8 | 54826057 | 54826421 | + | TAF |
| 14% | chr5 | 82554349 | 82554496 | + | ENST00000282268; ENST00000338635; ENST00000396027; ENST00000511817 | chr5 | 82606608 | 82606935 | + | TAF |
| 13% | chr14 | 24868453 | 24868650 | + | ENST00000382554 | chr14 | 24874817 | 24875031 | + | TAF |
| 13% | chr9 | 15506635 | 15506559 | − | ENST00000380738; ENST00000380733; ENST00000380715; ENST00000380716; ENST00000397519 | chr9 | 15492223 | 15492056 | − | TAF |
| 13% | chr1 | 11115983; 11115877 | 11115838 | − | ENST00000376957; ENST00000490101 | chr1 | 11115464 | 11115178 | − | TSF |
| 13% | chr1 | 11115983; 11115877 | 11115838 | − | ENST00000376957; ENST00000490101 | chr1 | 11115464 | 11115178 | − | TSF |
| 12% | chr5 | 147207691 | 147207585 | − | ENST00000296695; ENST00000510027 | chr5 | 147185494 | 147185375 | − | TAF |
| 12% | chr8 | 101721451 | 101721361 | − | ENST00000318607; ENST00000519004; ENST00000522387; ENST00000523636; ENST00000517403 | chr8 | 101720235 | 101719431 | − | TAF |
| 12% | chr8 | 101721451 | 101721361 | − | ENST00000318607; ENST00000519004; ENST00000522387; ENST00000523636; ENST00000517403 | chr8 | 101720235 | 101719431 | − | TAF |
| 12% | chr8 | 101721451 | 101721361 | − | ENST00000318607; ENST00000519004; ENST00000522387; ENST00000523636; ENST00000517403 | chr8 | 101720235 | 101719431 | − | TAF |
| 12% | chr8 | 101721451 | 101721361 | − | ENST00000318607; ENST00000519004; ENST00000522387; ENST00000523636; ENST00000517403 | chr8 | 101720235 | 101719431 | − | TAF |
| 12% | chr8 | 101721451 | 101721361 | − | ENST00000318607; ENST00000519004; ENST00000522387; ENST00000523636; ENST00000517403 | chr8 | 101720235 | 101719431 | − | TAF |
| 12% | chr5 | 74984990 | 74984837 | − | ENST00000428202; ENST00000514838; ENST00000380475; ENST00000510798; ENST00000446329 | chr5 | 74983153 | 74982863 | − | TAF |
| 12% | chr5 | 74984990 | 74984837 | − | ENST00000428202; ENST00000514838; ENST00000380475; ENST00000510798; ENST00000446329 | chr5 | 74983153 | 74982863 | − | TAF |
| 12% | chr5 | 74984990 | 74984837 | − | ENST00000428202; ENST00000514838; ENST00000380475; ENST00000510798; ENST00000446329 | chr5 | 74983153 | 74982863 | − | TAF |
| 12% | chr5 | 74984990 | 74984837 | − | ENST00000428202; ENST00000514838; ENST00000380475; ENST00000510798; ENST00000446329 | chr5 | 74983153 | 74982863 | − | TAF |
| 11% | chr1 | 153534067 | 153533988 | − | ENST00000368708; ENST00000487430; ENST00000497140; ENST00000368710; ENST00000368709 | chr1 | 153532853 | 153532704 | | TAF |
| 11% | chr1 | 153534067 | 153533988 | − | ENST00000368708; ENST00000487430; ENST00000497140; ENST00000368710; ENST00000368709 | chr1 | 153532853 | 153532704 | | TAF |
| 11% | chr19 | 35612126 | 35612149 | + | ENST00000454903; ENST00000406242; ENST00000604404; ENST00000435734; ENST00000603181; ENST00000604255; ENST00000344013; ENST00000346446; ENST00000603449; ENST00000406988; | chr19 | 35613565 | 35613610 | + | TAF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 11% | chr19 | 35612126 | 35612149 | + | ENST00000605550; ENST00000604804; ENST00000605552; ENST00000535103 ENST00000603524; ENST00000604621; ENST00000605677 ENST00000454903; ENST00000406242; ENST00000604404; ENST00000435734; ENST00000603181; ENST00000604255; ENST00000344013; ENST00000346446; ENST00000603449; ENST00000406988; ENST00000605550; ENST00000604804; ENST00000605552; ENST00000535103 ENST00000603524; ENST00000604621; ENST00000605677 | chr19 | 35613565 | 35613610 | + | TAF |
| 11% | chr3 | 196230044 | 196229744 | − | ENST00000318037; ENST00000437070 | chr3 | 196223342 | 196223041 | − | TAF |
| 11% | chr9 | 125054028 | 125054119 | + | ENST00000297908; ENST00000344641; ENST00000373723; ENST00000373729; ENST00000394315 | chr9 | 125068067 | 125068171 | + | TSF |
| 11% | chr9 | 125054028 | 125054119 | + | ENST00000297908; ENST00000344641; ENST00000373723; ENST00000373729; ENST00000394315 | chr9 | 125068067 | 125068171 | + | TSF |
| 11% | chr9 | 125054028 | 125054119 | + | ENST00000297908; ENST00000344641; ENST00000373723; ENST00000373729; ENST00000394315 | chr9 | 125068067 | 125068171 | + | TSF |
| 11% | chr3 | 118917904 | 118917987 | + | ENST00000497685; ENST00000264234; ENST00000460625 | chr3 | 118922347 | 118922648 | + | TSF |
| 11% | chr3 | 118917904 | 118917987 | + | ENST00000497685; ENST00000264234; ENST00000460625 | chr3 | 118922347 | 118922648 | + | TSF |
| 11% | chr3 | 118917904 | 118917987 | + | ENST00000497685; ENST00000264234; ENST00000460625 | chr3 | 118922347 | 118922648 | + | TSF |
| 10% | chr17 | 61907631; 61907746 | 61907861 | + | ENST00000579708; ENST00000310144; ENST00000581842; ENST00000582130; ENST00000584320; ENST00000585123; ENST00000580864; ENST00000584536; ENST00000375812; ENST00000581882; ENST00000584880 | chr17 | 61908085 | 61908122 | + | TAF |
| 10% | chr17 | 61907631; 61907746 | 61907861 | + | ENST00000579708; ENST00000310144; ENST00000581842; ENST00000582130; ENST00000584320; ENST00000585123; ENST00000580864; ENST00000584536; ENST00000375812; ENST00000581882; ENST00000584880 | chr17 | 61908085 | 61908122 | + | TAF |
| 10% | chr17 | 61907631; 61907746 | 61907861 | + | ENST00000579708; ENST00000310144; ENST00000581842; ENST00000582130; ENST00000584320; ENST00000585123; ENST00000580864; ENST00000584536; ENST00000375812; ENST00000581882; ENST00000584880 | chr17 | 61908085 | 61908122 | + | TAF |
| 10% | chr17 | 61907631; 61907746 | 61907861 | + | ENST00000579708; ENST00000310144; ENST00000581842; ENST00000582130; ENST00000584320; ENST00000585123; ENST00000580864; ENST00000584536; ENST00000375812; ENST00000581882; ENST00000584880 | chr17 | 61908085 | 61908122 | + | TAF |
| 10% | chr17 | 61907631; 61907746 | 61907861 | + | ENST00000579708; ENST00000310144; ENST00000581842; ENST00000582130; ENST00000584320; ENST00000585123; ENST00000580864; ENST00000584536; ENST00000375812; ENST00000581882; ENST00000584880 | chr17 | 61908085 | 61908122 | + | TAF |
| 10% | chr4 | 6695660 | 6695797 | + | ENST00000296370 | chr4 | 6698154 | 6698226 | + | TAF |
| 9% | chr1 | 225156461 | 225156576 | + | ENST00000430092; ENST00000400952; ENST00000366849; ENST00000439375 | chr1 | 225157336 | 225158402 | + | TSF |
| 9% | chr1 | 225156461 | 225156576 | + | ENST00000430092; ENST00000400952; ENST00000366849; ENST00000439375 | chr1 | 225157336 | 225158402 | + | TSF |
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 8% | chr19 | 53352466; 53352373 | 53352340 | − | ENST00000595646; ENST00000243639; ENST00000597924; ENST00000601847 | chr19 | 53339322 | 53339166 | − | TSF |
| 8% | chr19 | 53352466; 53352373 | 53352340 | − | ENST00000595646; ENST00000243639; ENST00000597924; ENST00000601847 | chr19 | 53339322 | 53339166 | − | TSF |
| 7% | chr17 | 36288631 | 36288740 | + | ENST00000327454; ENST00000378174; ENST00000505415; ENST00000539424 | chr17 | 36289142 | 36289609 | + | TSF |
| 7% | chr17 | 36288631 | 36288740 | + | ENST00000327454; ENST00000378174; ENST00000505415; ENST00000539424 | chr17 | 36289142 | 36289609 | + | TSF |
| 7% | chr3 | 48716169 | 48715997 | − | ENST00000341520; ENST00000416649; ENST00000294129; ENST00000413374 | chr3 | 48702393 | 48702198 | − | TSF |
| 7% | chr3 | 48716169 | 48715997 | − | ENST00000341520; ENST00000416649; ENST00000294129; ENST00000413374 | chr3 | 48702393 | 48702198 | − | TSF |
| 7% | chr3 | 48716169 | 48715997 | − | ENST00000341520; ENST00000416649; ENST00000294129; ENST00000413374 | chr3 | 48702393 | 48702198 | − | TSF |
| 6% | chr17 | 36343995 | 36343886 | − | ENST00000518551; ENST00000354664; ENST00000339023; ENST00000519532; ENST00000537432 | chr17 | 36343484 | 36343017 | − | TSF |
| 6% | chr17 | 36343995 | 36343886 | − | ENST00000518551; ENST00000354664; ENST00000339023; ENST00000519532; ENST00000537432 | chr17 | 36343484 | 36343017 | − | TSF |
| 5% | chr17 | 43475413 | 43475315 | − | ENST00000532038; ENST00000376922; ENST00000528384; ENST00000455881; ENST00000428638; ENST00000442348; ENST00000532891 | chr17 | 43474814 | 43474703 | − | TSF |
| 5% | chr17 | 43475413 | 43475315 | − | ENST00000532038; ENST00000376922; ENST00000528384; ENST00000455881; ENST00000428638; ENST00000442348; ENST00000532891 | chr17 | 43474814 | 43474703 | − | TSF |
| 5% | chr17 | 43475413 | 43475315 | − | ENST00000532038; ENST00000376922; ENST00000528384; ENST00000455881; ENST00000428638; ENST00000442348; ENST00000532891 | chr17 | 43474814 | 43474703 | − | TSF |
| 5% | chr17 | 43475413 | 43475315 | − | ENST00000532038; ENST00000376922; ENST00000528384; ENST00000455881; ENST00000428638; ENST00000442348; ENST00000532891 | chr17 | 43474814 | 43474703 | − | TSF |
| 5% | chr17 | 43475413 | 43475315 | − | ENST00000532038; ENST00000376922; ENST00000528384; ENST00000455881; ENST00000428638; ENST00000442348; ENST00000532891 | chr17 | 43474814 | 43474703 | − | TSF |
| 5% | chr17 | 43475413 | 43475315 | − | ENST00000532038; ENST00000376922; ENST00000528384; ENST00000455881; ENST00000428638; ENST00000442348; ENST00000532891 | chr17 | 43474814 | 43474703 | − | TSF |
| 5% | chr11 | 60701014 | 60701216 | + | ENST00000453848; ENST00000005286; ENST00000536409 | chr11 | 60701443 | 60701575 | + | TSF |
| 5% | chr11 | 60701014 | 60701216 | + | ENST00000453848; ENST00000005286; ENST00000536409 | chr11 | 60701443 | 60701575 | + | TSF |
| 5% | chr11 | 60701014 | 60701216 | + | ENST00000453848; ENST00000005286; ENST00000536409 | chr11 | 60701443 | 60701575 | + | TSF |
| 5% | chr4 | 169086398 | 169086477 | + | ENST00000359299 | chr4 | 169090666 | 169090754 | + | TSF |
| 5% | chr16 | 2825557; 2825626 | 2825452 | − | ENST00000262306; ENST00000409906; ENST00000409477; ENST00000494946 | chr16 | 2823822 | 2823809 | − | TSF |
| 5% | chr16 | 2825557; 2825626 | 2825452 | − | ENST00000262306; ENST00000409906; ENST00000409477; ENST00000494946 | chr16 | 2823822 | 2823809 | − | TSF |
| 5% | chr16 | 2825557; 2825626 | 2825452 | − | ENST00000262306; ENST00000409906; ENST00000409477; ENST00000494946 | chr16 | 2823822 | 2823809 | − | TSF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 5% | chr1 | 40313763; 40313769; 40313673; 40313734 | 40313658 | − | ENST00000441669; ENST00000462797; ENST00000316891; ENST00000372818; ENST00000537223; ENST00000537440; ENST00000545233 | chr1 | 40313419 | 40313374 | − | TSF |
| 5% | chr1 | 40313763; 40313769; 40313673; 40313734 | 40313658 | − | ENST00000441669; ENST00000462797; ENST00000316891; ENST00000372818; ENST00000537223; ENST00000537440; ENST00000545233 | chr1 | 40313419 | 40313374 | − | TSF |
| 5% | chr1 | 40313763; 40313769; 40313673; 40313734 | 40313658 | − | ENST00000441669; ENST00000462797; ENST00000316891; ENST00000372818; ENST00000537223; ENST00000537440; ENST00000545233 | chr1 | 40313419 | 40313374 | − | TSF |
| 5% | chr1 | 40313763; 40313769; 40313673; 40313734 | 40313658 | − | ENST00000441669; ENST00000462797; ENST00000316891; ENST00000372818; ENST00000537223; ENST00000537440; ENST00000545233 | chr1 | 40313419 | 40313374 | − | TSF |
| 5% | chr19 | 45895598 | 45895138 | − | ENST00000360957; ENST00000418234 | chr19 | 45889495 | 45889472 | − | TSF |
| 4% | chr19 | 3114942 | 3115070 | + | ENST00000078429; ENST00000587636 | chr19 | 3115258 | 3115402 | + | TSF |
| 4% | chr19 | 3114942 | 3115070 | + | ENST00000078429; ENST00000587636 | chr19 | 3115258 | 3115402 | + | TSF |
| 4% | chr3 | 12458203 | 12458653 | + | ENST00000397010; ENST00000309576; ENST00000397015; ENST00000397012; ENST00000397026; ENST00000287820 | chr3 | 12493109 | 12493334 | + | TSF |
| 4% | chr3 | 12458203 | 12458653 | + | ENST00000397010; ENST00000309576; ENST00000397015; ENST00000397012; ENST00000397026; ENST00000287820 | chr3 | 12493109 | 12493334 | + | TSF |
| 4% | chr3 | 12458203 | 12458653 | + | ENST00000397010; ENST00000309576; ENST00000397015; ENST00000397012; ENST00000397026; ENST00000287820 | chr3 | 12493109 | 12493334 | + | TSF |
| 4% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 4% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 4% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 4% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 4% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 4% | chr5 | 54993786 | 54993674 | − | ENST00000396865; ENST00000539768; ENST00000318672; ENST00000508124; ENST00000511233; ENST00000503891; ENST00000513993; ENST00000505563; ENST00000506624; ENST00000507109 | chr5 | 54993040 | 54992544 | − | TSF |
| 4% | chr7 | 8198282 | 8198157 | − | ENST00000402384; ENST00000406470; ENST00000265577; ENST00000396675; ENST00000339809; ENST00000401396; ENST00000422063; ENST00000407906; ENST00000317367 | chr7 | 8197727 | 8197714 | − | TSF |
| 4% | chr7 | 8198282 | 8198157 | − | ENST00000402384; ENST00000406470; ENST00000265577; ENST00000396675; ENST00000339809; ENST00000401396; ENST00000422063; ENST00000407906; ENST00000317367 | chr7 | 8197727 | 8197714 | − | TSF |
| 4% | chr7 | 8198282 | 8198157 | − | ENST00000402384; ENST00000406470; ENST00000265577; ENST00000396675; ENST00000339809; ENST00000401396; ENST00000422063; ENST00000407906; ENST00000317367 | chr7 | 8197727 | 8197714 | − | TSF |
| 4% | chr12 | 56742407 | 56742313 | − | ENST00000314128; ENST00000557235 | chr12 | 56740986 | 56740975 | − | TSF |
| 4% | chr12 | 56742407 | 56742313 | − | ENST00000314128; ENST00000557235 | chr12 | 56740986 | 56740975 | − | TSF |
| 3% | chr20 | 29632611 | 29632721 | + | ENST00000278882; ENST00000358464 | chr20 | 29652086 | 29652324 | + | TSF |
| 3% | chr8 | 101620791 | 101620722 | − | ENST00000311812; ENST00000428383 | chr8 | 101619733 | 101619704 | − | TSF |
| 3% | chr8 | 101620791 | 101620722 | − | ENST00000311812; ENST00000428383 | chr8 | 101619733 | 101619704 | − | TSF |
| 3% | chr4 | 57319766 | 57319927 | + | ENST00000514888; ENST00000264221; ENST00000505164; ENST00000399688; ENST00000512576 | chr4 | 57321183 | 57321327 | + | TSF |
| 3% | chr4 | 57319766 | 57319927 | + | ENST00000514888; ENST00000264221; ENST00000505164; ENST00000399688; ENST00000512576 | chr4 | 57321183 | 57321327 | + | TSF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr4 | 57319766 | 57319927 | + | ENST00000514888; ENST00000264221; ENST00000505164; ENST00000399688; ENST00000512576 | chr4 | 57321183 | 57321327 | + | TSF |
| 3% | chr22 | 25202408 | 25202451 | + | ENST00000400358; ENST00000400359 | chr22 | 25209976 | 25210040 | + | TSF |
| 3% | chr1 | 24700300 | 24700192 | − | ENST00000374409; ENST00000440416; ENST00000003583; ENST00000337248; ENST00000438866 | chr1 | 24696970 | 24696808 | − | TSF |
| 3% | chr1 | 24700300 | 24700192 | − | ENST00000374409; ENST00000440416; ENST00000003583; ENST00000337248; ENST00000438866 | chr1 | 24696970 | 24696808 | − | TSF |
| 3% | chr1 | 24700300 | 24700192 | − | ENST00000374409; ENST00000440416; ENST00000003583; ENST00000337248; ENST00000438866 | chr1 | 24696970 | 24696808 | − | TSF |
| 3% | chr19 | 54104626 | 54104519 | − | ENST00000600193 | chr19 | 54104407 | 54104303 | − | TSF |
| 3% | chr1 | 110233076 | 110233186 | + | ENST00000309851; ENST00000369823 | chr1 | 110235581 | 110235619 | + | TSF |
| 3% | chr1 | 110233076 | 110233186 | + | ENST00000309851; ENST00000369823 | chr1 | 110235581 | 110235619 | + | TSF |
| 3% | chr17 | 59481967 | 59482130 | + | ENST00000240328 | chr17 | 59482423 | 59482469 | + | TSF |
| 3% | chr12 | 71509738 | 71509686 | − | ENST00000549357 | chr12 | 71504233 | 71503634 | − | TSF |
| 3% | chr7 | 22532348 | 22532184 | − | ENST00000406890; ENST00000404369; ENST00000424363 | chr7 | 22512853 | 22512669 | − | TSF |
| 3% | chr7 | 22532348 | 22532184 | − | ENST00000406890; ENST00000404369; ENST00000424363 | chr7 | 22512853 | 22512669 | − | TSF |
| 3% | chr1 | 32560385 | 32560572 | + | ENST00000336294; ENST00000373634; ENST00000427288 | chr1 | 32561261 | 32561358 | + | TSF |
| 3% | chr1 | 32560385 | 32560572 | + | ENST00000336294; ENST00000373634; ENST00000427288 | chr1 | 32561261 | 32561358 | + | TSF |
| 3% | chr1 | 32560385 | 32560572 | + | ENST00000336294; ENST00000373634; ENST00000427288 | chr1 | 32561261 | 32561358 | + | TSF |
| 3% | chr8 | 71619168 | 71619388 | + | ENST00000408926; ENST00000520030 | chr8 | 71625661 | 71625673 | + | TSF |
| 3% | chr7 | 55270210 | 55270401 | + | ENST00000455089 | chr7 | 55272949 | 55272949 | + | TSF |
| 3% | chr5 | 1802435 | 1802488 | + | ENST00000274137; ENST00000469176 | chr5 | 1811082 | 1811428 | + | TSF |
| 3% | chr19 | 50165585 | 50165205 | − | ENST00000309877; ENST00000600911; ENST00000601291; ENST00000377139; ENST00000597198; ENST00000597636; ENST00000593922; ENST00000599144; ENST00000598808 | chr19 | 50164882 | 50164836 | − | TSF |
| 3% | chr19 | 50165585 | 50165205 | − | ENST00000309877; ENST00000600911; ENST00000601291; ENST00000377139; ENST00000597198; ENST00000597636; ENST00000593922; ENST00000599144; ENST00000598808 | chr19 | 50164882 | 50164836 | − | TSF |
| 2% | chr6 | 44200080 | 44200165 | + | ENST00000393844; ENST00000313248; ENST00000427851; ENST00000371740; ENST00000371755; ENST00000371731; ENST00000393841; ENST00000371713; ENST00000371724; ENST00000371708 | chr6 | 44209921 | 44210213 | + | TSF |
| 2% | chr6 | 44200080 | 44200165 | + | ENST00000393844; ENST00000313248; ENST00000427851; ENST00000371740; ENST00000371755; ENST00000371731; ENST00000393841; ENST00000371713; ENST00000371724; ENST00000371708 | chr6 | 44209921 | 44210213 | + | TSF |
| 2% | chr20 | 58581768 | 58581842 | + | ENST00000244047; ENST00000348616; ENST00000370991; ENST00000244049; ENST00000350849; ENST00000456106 | chr20 | 58600042 | 58600249 | + | TSF |
| 2% | chr20 | 58581768 | 58581842 | + | ENST00000244047; ENST00000348616; ENST00000370991; ENST00000244049; ENST00000350849; ENST00000456106 | chr20 | 58600042 | 58600249 | + | TSF |
| 2% | chr20 | 58581768 | 58581842 | + | ENST00000244047; ENST00000348616; ENST00000370991; ENST00000244049; ENST00000350849; ENST00000456106 | chr20 | 58600042 | 58600249 | + | TSF |
| 2% | chr20 | 58581768 | 58581842 | + | ENST00000244047; ENST00000348616; ENST00000370991; ENST00000244049; ENST00000350849; ENST00000456106 | chr20 | 58600042 | 58600249 | + | TSF |
| 2% | chr20 | 58581768 | 58581842 | + | ENST00000244047; ENST00000348616; ENST00000370991; ENST00000244049; ENST00000350849; ENST00000456106 | chr20 | 58600042 | 58600249 | + | TSF |
| 2% | chr20 | 58581768 | 58581842 | + | ENST00000244047; ENST00000348616; ENST00000370991; ENST00000244049; ENST00000350849; ENST00000456106 | chr20 | 58600042 | 58600249 | + | TSF |
| 2% | chr7 | 76144362 | 76144473 | + | ENST00000334348; ENST00000448265; ENST00000419923; ENST00000443097; ENST00000257632; ENST00000394849 | chr7 | 76648226 | 76648393 | + | TSF |
| 2% | chr7 | 76144362 | 76144473 | + | ENST00000334348; ENST00000448265; ENST00000419923; ENST00000443097; ENST00000257632; ENST00000394849 | chr7 | 76648226 | 76648393 | + | TSF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr7 | 76144362 | 76144473 | + | ENST00000334348; ENST00000448265; ENST00000419923; ENST00000443097; ENST00000257632; ENST00000394849 | chr7 | 76648226 | 76648393 | + | TSF |
| 2% | chr11 | 101937216; 101937273 | 101937382 | + | ENST00000434758; ENST00000526781; ENST00000529204 | chr11 | 101937956 | 101938097 | + | TSF |
| 2% | chr11 | 101937216; 101937273 | 101937382 | + | ENST00000434758; ENST00000526781; ENST00000529204 | chr11 | 101937956 | 101938097 | + | TSF |
| 2% | chr1 | 63955889 | 63955754 | − | ENST00000371092; ENST00000271002; ENST00000489099; ENST00000283568 | chr1 | 63952444 | 63951983 | − | TSF |
| 2% | chr1 | 63955889 | 63955754 | − | ENST00000371092; ENST00000271002; ENST00000489099; ENST00000283568 | chr1 | 63952444 | 63951983 | − | TSF |
| 2% | chr9 | 127622543 | 127622462 | − | ENST00000373570; ENST00000493018; ENST00000348462 | chr9 | 127621011 | 127621010 | − | TSF |
| 2% | chr6 | 65098733 | 65098583 | − | ENST00000503581; ENST00000370621; ENST00000370616 | chr6 | 65097495 | 65097442 | − | TSF |
| 2% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 2% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 2% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 2% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 2% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 2% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 2% | chr3 | 98600611; 98600498 | 98600384 | − | ENST00000326840; ENST00000326857; ENST00000449482 | chr3 | 98586282 | 98584565 | − | TSF |
| 2% | chr3 | 98600611; 98600498 | 98600384 | − | ENST00000326840; ENST00000326857; ENST00000449482 | chr3 | 98586282 | 98584565 | − | TSF |
| 2% | chr5 | 1802435 | 1802488 | + | ENST00000274137; ENST00000469176 | chr5 | 1811112 | 1811428 | + | TSF |
| 2% | chr7 | 76144362 | 76144473 | + | ENST00000334348; ENST00000448265; ENST00000419923; ENST00000443097; ENST00000257632; ENST00000394849 | chr7 | 76676146 | 76676313 | + | TSF |
| 2% | chr7 | 76144362 | 76144473 | + | ENST00000334348; ENST00000448265; ENST00000419923; ENST00000443097; ENST00000257632; ENST00000394849 | chr7 | 76676146 | 76676313 | + | TSF |
| 2% | chr7 | 76144362 | 76144473 | + | ENST00000334348; ENST00000448265; ENST00000419923; ENST00000443097; ENST00000257632; ENST00000394849 | chr7 | 76676146 | 76676313 | + | TSF |
| 2% | chr12 | 69656249 | 69656342 | + | ENST00000551516 | chr12 | 69673004 | 69673309 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; | chr12 | 53865082 | 53865327 | + | TSF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| | | | | | ENST00000546463; ENST00000552296; ENST00000552819; ENST00000455667; ENST00000439930; ENST00000548933; ENST00000562264; ENST00000553064; ENST00000547859 | | | | |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr5 | 70858101 | 70858347 | + | ENST00000358731; ENST00000525844 | chr5 | 70868141 | 70868205 | + | TSF |
| 2% | chr5 | 70858101 | 70858347 | + | ENST00000358731; ENST00000525844 | chr5 | 70868141 | 70868205 | + | TSF |
| 2% | chr18 | 43307367; 43307237 | 43307383 | + | ENST00000502059; ENST00000415427; ENST00000588179; ENST00000436407; ENST00000589891 | chr18 | 43309951 | 43309986 | + | TSF |
| 2% | chr18 | 43307367; 43307237 | 43307383 | + | ENST00000502059; ENST00000415427; ENST00000588179; ENST00000436407; ENST00000589891 | chr18 | 43309951 | 43309986 | + | TSF |
| 2% | chr16 | 4401235; 4401294 | 4401233 | − | ENST00000577031; ENST00000318059; ENST00000571986; ENST00000576217; ENST00000571178 | chr16 | 4398819 | 4398660 | − | TSF |
| 2% | chr16 | 4401235; 4401294 | 4401233 | − | ENST00000577031; ENST00000318059; ENST00000571986; ENST00000576217; ENST00000571178 | chr16 | 4398819 | 4398660 | − | TSF |
| 2% | chrX | 41598709 | 41598637 | − | ENST00000421587; ENST00000318588; ENST00000361962; ENST00000378163; ENST00000378158; ENST00000378166; ENST00000442742; ENST00000378154 | chrX | 41557348 | 41557057 | − | TSF |
| 2% | chr3 | 49928739 | 49928630 | − | ENST00000296474; ENST00000344206; ENST00000434765; ENST00000440292 | chr3 | 49928452 | 49928163 | − | TSF |
| 2% | chr3 | 49928739 | 49928630 | − | ENST00000296474; ENST00000344206; ENST00000434765; ENST00000440292 | chr3 | 49928452 | 49928163 | − | TSF |
| 2% | chr3 | 49928739 | 49928630 | − | ENST00000296474; ENST00000344206; ENST00000434765; ENST00000440292 | chr3 | 49928452 | 49928163 | − | TSF |
| 2% | chr3 | 49928739 | 49928630 | − | ENST00000296474; ENST00000344206; ENST00000434765; ENST00000440292 | chr3 | 49928452 | 49928163 | − | TSF |
| 2% | chr12 | 113440737 | 113440907 | + | ENST00000342315; ENST00000392583 | chr12 | 113442280 | 113442294 | + | TSF |
| 2% | chr4 | 91321187 | 91321280 | + | ENST00000505073; ENST00000509176; ENST00000432775; ENST00000333691 | chr4 | 91325075 | 91325176 | + | TSF |
| 2% | chr1 | 156352539 | 156352660 | + | ENST00000451864; ENST00000255013; ENST00000368246; ENST00000400992; ENST00000368249 | chr1 | 156354082 | 156354192 | + | TSF |
| 2% | chr1 | 156352539 | 156352660 | + | ENST00000451864; ENST00000255013; ENST00000368246; ENST00000400992; ENST00000368249 | chr1 | 156354082 | 156354192 | + | TSF |
| 2% | chr1 | 156352539 | 156352660 | + | ENST00000451864; ENST00000255013; ENST00000368246; ENST00000400992; ENST00000368249 | chr1 | 156354082 | 156354192 | + | TSF |
| 2% | chr1 | 156352539 | 156352660 | + | ENST00000451864; ENST00000255013; ENST00000368246; ENST00000400992; ENST00000368249 | chr1 | 156354082 | 156354192 | + | TSF |
| 2% | chr16 | 16381600 | 16381719 | + | ENST00000399336; ENST00000263012; ENST00000538468 | chr16 | 16382422 | 16382605 | + | TSF |
| 2% | chr16 | 16381600 | 16381719 | + | ENST00000399336; ENST00000263012; ENST00000538468 | chr16 | 16382422 | 16382605 | + | TSF |
| 2% | chr19 | 15289752 | 15289634 | − | ENST00000263388; ENST00000601011 | chr19 | 15289244 | 15289201 | − | TSF |
| 2% | chr19 | 15289752 | 15289634 | − | ENST00000263388; ENST00000601011 | chr19 | 15289244 | 15289201 | − | TSF |
| 2% | chr7 | 73973957 | 73973985 | + | ENST00000265755; ENST00000455841; ENST00000424337; ENST00000476977; ENST00000470715 | chr7 | 73985447 | 73985582 | + | TSF |
| 2% | chr7 | 73973957 | 73973985 | + | ENST00000265755; ENST00000455841; ENST00000424337; ENST00000476977; ENST00000470715 | chr7 | 73985447 | 73985582 | + | TSF |
| 2% | chr7 | 73973957 | 73973985 | + | ENST00000265755; ENST00000455841; ENST00000424337; ENST00000476977; ENST00000470715 | chr7 | 73985447 | 73985582 | + | TSF |
| 2% | chr7 | 73973957 | 73973985 | + | ENST00000265755; ENST00000455841; ENST00000424337; ENST00000476977; ENST00000470715 | chr7 | 73985447 | 73985582 | + | TSF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chrX | 71401561; 71401615; 71401644 | 71401678 | + | ENST00000373662; ENST00000218432; ENST00000423432; ENST00000373669; ENST00000496835; ENST00000439980; ENST00000446576 | chrX | 71405250 | 71405452 | + | TSF |
| 2% | chrX | 71401561; 71401615; 71401644 | 71401678 | + | ENST00000373662; ENST00000218432; ENST00000423432; ENST00000373669; ENST00000496835; ENST00000439980; ENST00000446576 | chrX | 71405250 | 71405452 | + | TSF |
| 2% | chrX | 71401561; 71401615; 71401644 | 71401678 | + | ENST00000373662; ENST00000218432; ENST00000423432; ENST00000373669; ENST00000496835; ENST00000439980; ENST00000446576 | chrX | 71405250 | 71405452 | + | TSF |
| 2% | chr18 | 61627392 | 61627509 | + | ENST00000408945 | chr18 | 61628870 | 61629168 | + | TSF |
| 2% | chr4 | 143003338 | 143003184 | − | ENST00000513000; ENST00000262992; ENST00000308502; ENST00000508116; ENST00000509777 | chr4 | 142977129 | 142976903 | − | TSF |
| 2% | chr19 | 53352466; 53352373 | 53352340 | − | ENST00000595646; ENST00000243639; ENST00000597924; ENST00000601847 | chr19 | 53297373 | 53297176 | − | TSF |
| 2% | chr19 | 53352466; 53352373 | 53352340 | − | ENST00000595646; ENST00000243639; ENST00000597924; ENST00000601847 | chr19 | 53297373 | 53297176 | − | TSF |
| 2% | chr19 | 53348549 | 53348432 | − | ENST00000243639 | chr19 | 53339322 | 53339166 | − | TSF |
| 2% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 2% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 2% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 2% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 2% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 2% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 2% | chr1 | 180283857 | 180283827 | − | ENST00000367595 | chr1 | 180281120 | 180281103 | − | TSF |
| 2% | chr7 | 91771800 | 91771777 | − | ENST00000435873 | chr7 | 91767155 | 91766808 | − | TSF |
| 2% | chr3 | 49456584 | 49456404 | − | ENST00000427987; ENST00000395338; ENST00000458307; ENST00000538581; ENST00000273588; ENST00000546031; ENST00000430521 | chr3 | 49455661 | 49455617 | − | TSF |
| 2% | chr3 | 49456584 | 49456404 | − | ENST00000427987; ENST00000395338; ENST00000458307; ENST00000538581; ENST00000273588; ENST00000546031; ENST00000430521 | chr3 | 49455661 | 49455617 | − | TSF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr3 | 49456584 | 49456404 | − | ENST00000427987; ENST00000395338; ENST00000458307; ENST00000538581; ENST00000273588; ENST00000546031; ENST00000430521 | chr3 | 49455661 | 49455617 | − | TSF |
| 2% | chr3 | 49456584 | 49456404 | − | ENST00000427987; ENST00000395338; ENST00000458307; ENST00000538581; ENST00000273588; ENST00000546031; ENST00000430521 | chr3 | 49455661 | 49455617 | − | TSF |
| 2% | chr3 | 49456584 | 49456404 | − | ENST00000427987; ENST00000395338; ENST00000458307; ENST00000538581; ENST00000273588; ENST00000546031; ENST00000430521 | chr3 | 49455661 | 49455617 | − | TSF |
| 2% | chr17 | 34802073 | 34802035 | − | ENST00000330458; ENST00000535805; ENST00000535592; ENST00000394453; ENST00000592614; ENST00000341264 | chr17 | 34772854 | 34772787 | − | TSF |
| 2% | chr17 | 34802073 | 34802035 | − | ENST00000330458; ENST00000535805; ENST00000535592; ENST00000394453; ENST00000592614; ENST00000341264 | chr17 | 34772854 | 34772787 | − | TSF |
| 2% | chr17 | 73887428 | 73887358 | − | ENST00000591668; ENST00000592642; ENST00000269383; ENST00000543309 | chr17 | 73885428 | 73885139 | − | TSF |
| 2% | chr17 | 73887428 | 73887358 | − | ENST00000591668; ENST00000592642; ENST00000269383; ENST00000543309 | chr17 | 73885428 | 73885139 | − | TSF |
| 2% | chr17 | 73887428 | 73887358 | − | ENST00000591668; ENST00000592642; ENST00000269383; ENST00000543309 | chr17 | 73885428 | 73885139 | − | TSF |
| 2% | chr17 | 73887428 | 73887358 | − | ENST00000591668; ENST00000592642; ENST00000269383; ENST00000543309 | chr17 | 73885428 | 73885139 | − | TSF |
| 1% | chr19 | 40711028 | 40711203 | + | ENST00000253055; ENST00000593502; ENST00000597986 | chr19 | 40711395 | 40711597 | + | TSF |
| 1% | chr19 | 40711028 | 40711203 | + | ENST00000253055; ENST00000593502; ENST00000597986 | chr19 | 40711395 | 40711597 | + | TSF |
| 1% | chr19 | 40711028 | 40711203 | + | ENST00000253055; ENST00000593502; ENST00000597986 | chr19 | 40711395 | 40711597 | + | TSF |
| 1% | chr19 | 44564902 | 44564994 | + | ENST00000591793; ENST00000434772; ENST00000585552; ENST00000593088; ENST00000591850 | chr19 | 44565998 | 44566256 | + | TSF |
| 1% | chr19 | 44564902 | 44564994 | + | ENST00000591793; ENST00000434772; ENST00000585552; ENST00000593088; ENST00000591850 | chr19 | 44565998 | 44566256 | + | TSF |
| 1% | chr19 | 44564902 | 44564994 | + | ENST00000591793; ENST00000434772; ENST00000585552; ENST00000593088; ENST00000591850 | chr19 | 44565998 | 44566256 | + | TSF |
| 1% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 1% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 1% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 1% | chr19 | 38872757 | 38872868 | + | ENST00000215071; ENST00000602911; ENST00000592561; ENST00000592035 | chr19 | 38873037 | 38873046 | + | TSF |
| 1% | chr19 | 38872757 | 38872868 | + | ENST00000215071; ENST00000602911; ENST00000592561; ENST00000592035 | chr19 | 38873037 | 38873046 | + | TSF |
| 1% | chr19 | 38872757 | 38872868 | + | ENST00000215071; ENST00000602911; ENST00000592561; ENST00000592035 | chr19 | 38873037 | 38873046 | + | TSF |
| 1% | chr19 | 38872757 | 38872868 | + | ENST00000215071; ENST00000602911; ENST00000592561; ENST00000592035 | chr19 | 38873037 | 38873046 | + | TSF |
| 1% | chr7 | 87022264 | 87022383 | + | ENST00000419147; ENST00000331536; ENST00000442291 | chr7 | 87025232 | 87025462 | + | TSF |
| 1% | chr7 | 87022264 | 87022383 | + | ENST00000419147; ENST00000331536; ENST00000442291 | chr7 | 87025232 | 87025462 | + | TSF |
| 1% | chr3 | 137906397 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 1% | chr3 | 137906397 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 1% | chr17 | 75277618 | 75277636 | + | ENST00000427177; ENST00000591833; ENST00000591198 | chr17 | 75313547 | 75313852 | + | TSF |
| 1% | chr12 | 69764668 | 69764755 | + | ENST00000247843; ENST00000548020; ENST00000549685 | chr12 | 69791470 | 69791492 | + | TSF |

TABLE 7-continued

Transcript fusion for Bladder Carcinoma (BLCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 1% | chr12 | 69764668 | 69764755 | + | ENST00000247843; ENST00000548020; ENST00000549685 | chr12 | 69791470 | 69791492 | + | TSF |
| 1% | chr12 | 69764668 | 69764755 | + | ENST00000247843; ENST00000548020; ENST00000549685 | chr12 | 69791470 | 69791492 | + | TSF |
| 1% | chr13 | 114157811 | 114157903 | + | ENST00000434316; ENST00000375391 | chr13 | 114159741 | 114159770 | + | TSF |
| 1% | chr9 | 5689959 | 5690038 | + | ENST00000251879; ENST00000414202; ENST00000381532; ENST00000418622; ENST00000449720; ENST00000545641 | chr9 | 5710416 | 5711239 | + | TSF |
| 1% | chr9 | 5689959 | 5690038 | + | ENST00000251879; ENST00000414202; ENST00000381532; ENST00000418622; ENST00000449720; ENST00000545641 | chr9 | 5710416 | 5711239 | + | TSF |
| 1% | chr9 | 5689959 | 5690038 | + | ENST00000251879; ENST00000414202; ENST00000381532; ENST00000418622; ENST00000449720; ENST00000545641 | chr9 | 5710416 | 5711239 | + | TSF |
| 1% | chr12 | 113623819 | 113623826 | + | ENST00000552495 | chr12 | 113623998 | 113624117 | + | TSF |
| 1% | chr7 | 91509397 | 91509369 | − | ENST00000351870; ENST00000442961 | chr7 | 91430582 | 91429696 | − | TSF |
| 1% | chr7 | 81964567 | 81964451 | − | ENST00000356860; ENST00000356253; ENST00000423588 | chr7 | 81929467 | 81929190 | − | TSF |
| 1% | chr11 | 64599981 | 64599900 | − | ENST00000342711 | chr11 | 64599599 | 64599309 | − | TSF |
| 1% | chr7 | 619014 | 618893 | − | ENST00000544935; ENST00000537384; ENST00000406797; ENST00000403562; ENST00000360274; ENST00000400758; ENST00000430040 | chr7 | 618449 | 618307 | − | TSF |
| 1% | chr7 | 619014 | 618893 | − | ENST00000544935; ENST00000537384; ENST00000406797; ENST00000403562; ENST00000360274; ENST00000400758; ENST00000430040 | chr7 | 618449 | 618307 | − | TSF |
| 1% | chr1 | 156236171 | 156235572 | − | ENST00000361813 | chr1 | 156234234 | 156234174 | − | TSF |
| 1% | chr22 | 22280035 | 22279942 | − | ENST00000263212; ENST00000407142; ENST00000538191; ENST00000397495 | chr22 | 22279401 | 22279262 | − | TSF |
| 1% | chr22 | 22280035 | 22279942 | − | ENST00000263212; ENST00000407142; ENST00000538191; ENST00000397495 | chr22 | 22279401 | 22279262 | − | TSF |
| 1% | chr22 | 22280035 | 22279942 | − | ENST00000263212; ENST00000407142; ENST00000538191; ENST00000397495 | chr22 | 22279401 | 22279262 | − | TSF |
| 1% | chr6 | 33271766 | 33271732 | − | ENST00000434618; ENST00000475304; ENST00000489157; ENST00000426633; ENST00000456592 | chr6 | 33267676 | 33267587 | − | TSF |
| 1% | chr6 | 33271766 | 33271732 | − | ENST00000434618; ENST00000475304; ENST00000489157; ENST00000426633; ENST00000456592 | chr6 | 33267676 | 33267587 | − | TSF |
| 1% | chr6 | 33271766 | 33271732 | − | ENST00000434618; ENST00000475304; ENST00000489157; ENST00000426633; ENST00000456592 | chr6 | 33267676 | 33267587 | − | TSF |

TABLE 8

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 51% | chr14 | 24105943 | 24105981 | + | chr14 | 24112361 | 24112428 | + | ENST00000432832; ENST00000250383; ENST00000344777; ENST00000557535; ENST00000553600 | TAF |
| 51% | chr14 | 24105943 | 24105981 | + | chr14 | 24112361 | 24112428 | + | ENST00000432832; ENST00000250383; ENST00000344777; ENST00000557535; ENST00000553600 | TAF |
| 51% | chr14 | 24105943 | 24105981 | + | chr14 | 24112361 | 24112428 | + | ENST00000432832; ENST00000250383; ENST00000344777; ENST00000557535; ENST00000553600 | TAF |
| 51% | chr14 | 24105943 | 24105981 | + | chr14 | 24112361 | 24112428 | + | ENST00000432832; ENST00000250383; ENST00000344777; ENST00000557535; ENST00000553600 | TAF |
| 51% | chr14 | 24105943 | 24105981 | + | chr14 | 24112361 | 24112428 | + | ENST00000432832; ENST00000250383; ENST00000344777; ENST00000557535; ENST00000553600 | TAF |
| 45% | chr17 | 79214190 | 79214239 | + | chr17 | 79214787 | 79214816; 79214953 | + | ENST00000431388; ENST00000576002 | TAF |
| 45% | chr17 | 79214190 | 79214239 | + | chr17 | 79214787 | 79214816; 79214953 | + | ENST00000431388; ENST00000576002 | TAF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 40% | chr14 | 24113093 | 24113155 | + | chr14 | 24113320 | 24113371 | + | ENST00000432832; ENST00000250383; ENST00000344777; ENST00000557535; ENST00000553600 | TAF |
| 40% | chr14 | 24113093 | 24113155 | + | chr14 | 24113320 | 24113371 | + | ENST00000432832; ENST00000250383; ENST00000344777; ENST00000557535; ENST00000553600 | TAF |
| 40% | chr14 | 24113093 | 24113155 | + | chr14 | 24113320 | 24113371 | + | ENST00000432832; ENST00000250383; ENST00000344777; ENST00000557535; ENST00000553600 | TAF |
| 40% | chr14 | 24113093 | 24113155 | + | chr14 | 24113320 | 24113371 | + | ENST00000432832; ENST00000250383; ENST00000344777; ENST00000557535; ENST00000553600 | TAF |
| 40% | chr14 | 24113093 | 24113155 | + | chr14 | 24113320 | 24113371 | + | ENST00000432832; ENST00000250383; ENST00000344777; ENST00000557535; ENST00000553600 | TAF |
| 33% | chr6 | 34966613 | 34966878 | + | chr6 | 34985250 | 34985836 | + | ENST00000360359 | TAF |
| 33% | chr8 | 104389530 | 1043869551 | + | chr8 | 104390255 | 104390471 | + | ENST00000330295; ENST00000520337 | TAF |
| 29% | chr14 | 24105943 | 24105981 | + | chr14 | 24109003 | 24109104 | + | ENST00000432832; ENST00000250383; ENST00000344777; ENST00000557535; ENST00000553600 | TAF |
| 29% | chr14 | 24105943 | 24105981 | + | chr14 | 24109003 | 24109104 | + | ENST00000432832; ENST00000250383; ENST00000344777; ENST00000557535; ENST00000553600 | TAF |
| 29% | chr14 | 24105943 | 24105981 | + | chr14 | 24109003 | 24109104 | + | ENST00000432832; ENST00000250383; ENST00000344777; ENST00000557535; ENST00000553600 | TAF |
| 29% | chr14 | 24105943 | 24105981 | + | chr14 | 24109003 | 24109104 | + | ENST00000432832; ENST00000250383; ENST00000344777; ENST00000557535; ENST00000553600 | TAF |
| 29% | chr14 | 24105943 | 24105981 | + | chr14 | 24109003 | 24109104 | + | ENST00000432832; ENST00000250383; ENST00000344777; ENST00000557535; ENST00000553600 | TAF |
| 29% | chr11 | 93468219 | 93468129 | − | chr11 | 93467826 | 93467791; 93467814 | − | ENST00000393259; ENST00000527169 | TAF |
| 29% | chr11 | 93468219 | 93468129 | − | chr11 | 93467826 | 93467791; 93467814 | − | ENST00000393259; ENST00000527169 | TAF |
| 26% | chr5 | 147210961 | 147210946 | − | chr5 | 147209193 | 147209162 | − | ENST00000296695; ENST00000510027 | TAF |
| 26% | chr5 | 147210961 | 147210946 | − | chr5 | 147209193 | 147209162 | − | ENST00000296695; ENST00000510027 | TAF |
| 24% | chr10 | 124091515 | 124091773 | + | chr10 | 124091951 | 124092028 | + | ENST00000368994; ENST00000260723 | TAF |
| 23% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 23% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 23% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 23% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 22% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 22% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 22% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 22% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 22% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 20% | chr19 | 54631006 | 5463115 | + | chr19 | 54631448 | 54631575 | + | ENST00000321030; ENST00000419967 | TAF |
| 20% | chr19 | 54631006 | 5463115 | + | chr19 | 54631448 | 54631575 | + | ENST00000321030; ENST00000419967 | TAF |
| 19% | chr19 | 55558521 | 55558473 | − | chr19 | 55556677 | 55556442 | − | ENST00000415061; ENST00000396247 | TAF |
| 18% | chr7 | 116364854 | 116364901 | + | chr7 | 116371722 | 116371913 | + | ENST00000397752; ENST00000318493; ENST00000436117 | TAF |
| 18% | chr7 | 116364854 | 116364901 | + | chr7 | 116371722 | 116371913 | + | ENST00000397752; ENST00000318493; ENST00000436117 | TAF |
| 18% | chr7 | 116364854 | 116364901 | + | chr7 | 116371722 | 116371913 | + | ENST00000397752; ENST00000318493; ENST00000436117 | TAF |
| 18% | chr17 | 74261446 | 74261484 | + | chr17 | 74261988 | 74262050 | + | ENST00000327490 | TAF |
| 17% | chr10 | 100147690 | 100147622 | − | chr10 | 100147064 | 100146958 | − | ENST00000370575 | TAF |
| 17% | chr12 | 6602868 | 6602840 | − | chr12 | 6602138 | 6602028 | − | ENST00000229238 | TAF |
| 16% | chr8 | 143751981 | 143751986 | + | chr8 | 143762745 | 143762852; 143762884 | + | ENST00000301258; ENST00000513264 | TAF |
| 16% | chr8 | 143751981 | 143751986 | + | chr8 | 143762745 | 143762852; 143762884 | + | ENST00000301258; ENST00000513264 | TAF |
| 15% | chr5 | 54528691 | 54528595 | − | chr5 | 54528374 | 54528189 | − | ENST00000282572 | TAF |
| 15% | chr12 | 122430912 | 122431615 | + | chr12 | 122437622 | 122437850 | + | ENST00000288912 | TAF |
| 14% | chr11 | 124618894 | 124618862 | − | chr11 | 124618659 | 124618540 | − | ENST00000326621; ENST00000403470 | TAF |
| 14% | chr11 | 124618894 | 124618540 | − | chr11 | 124618659 | 124618540 | − | ENST00000326621; ENST00000403470 | TAF |
| 14% | chr10 | 120902016 | 120901765 | − | chr10 | 120900831 | 120900754 | − | ENST00000355697; ENST00000330036 | TAF |
| 14% | chr13 | 76173531 | 76175706 | + | chr13 | 76178905 | 76178963 | + | ENST00000377595; ENST00000419068 | TAF |
| 14% | chr1 | 169819657 | 169819707 | + | chr1 | 169820958 | 169821077 | + | ENST00000359326; ENST00000286031 | TSF |
| 14% | chr19 | 54104302 | 54104248 | − | chr19 | 54103688 | 54103573 | − | ENST00000600193 | TSF |
| 13% | chr17 | 40820773 | 40820708 | − | chr17 | 40820321 | 40820145 | − | ENST00000591022; ENST00000412503; ENST00000293349 | TAF |
| 13% | chr4 | 48013268 | 48012811 | | chr4 | 47954720 | 47954600 | − | ENST00000402813 | TAF |
| 12% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr3 | 12440939 | 12440989 | + | chr3 | 12447381 | 12447580 | + | ENST00000397010; ENST00000309576; ENST00000397015; ENST00000397012; ENST00000397026; ENST00000397000; ENST00000539812; ENST00000287820 | TAF |
| 12% | chr3 | 12440939 | 12440989 | + | chr3 | 12447381 | 12447580 | + | ENST00000397010; ENST00000309576; ENST00000397015; ENST00000397012; ENST00000397026; ENST00000397000; ENST00000539812; ENST00000287820 | TAF |
| 12% | chr4 | 107241932 | 107241850 | + | chr4 | 107246142 | 107246275 | + | ENST00000394701 | TAF |
| 12% | chr5 | 1811001 | 1811176 | + | chr5 | 1814453 | 1814575; 1814785 | + | ENST00000274137; ENST00000469176 | TAF |
| 12% | chr5 | 1811001 | 1811176 | + | chr5 | 1814453 | 1814575; 1814785 | + | ENST00000274137; ENST00000469176 | TAF |
| 11% | chr9 | 130569975 | 13050054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 11% | chr9 | 130569975 | 13050054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 11% | chr9 | 130569975 | 13050054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 11% | chr9 | 130569975 | 13050054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 11% | chr17 | 48164136 | 48164357 | + | chr17 | 48165108 | 48165233 | + | ENST00000320031; ENST00000007722 | TAF |
| 11% | chr17 | 48164136 | 48164357 | + | chr17 | 48165108 | 48165233 | + | ENST00000320031; ENST00000007722 | TAF |
| 11% | chr1 | 31887686 | 31887779 | + | chr1 | 31896540 | 31896701 | + | ENST00000373710; ENST00000536859; ENST00000373709; ENST00000536384 | TAF |
| 11% | chr1 | 86821476 | 86821330 | − | chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 11% | chr1 | 86821476 | 86821330 | − | chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 11% | chr1 | 86821476 | 86821330 | − | chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 11% | chr1 | 86821476 | 86821330 | − | chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 11% | chr11 | 19190423 | 19190515 | + | chr11 | 19191958 | 19192115 | + | ENST00000446113; ENST00000399351 | TAF |
| 11% | chr19 | 1114930 | 1114676 | − | chr19 | 1114421 | 1114230 | − | ENST00000361757; ENST00000587024; ENST00000438103 | TSF |
| 9% | chr7 | 56018506 | 56018522 | + | chr7 | 56020872 | 56021011 | + | ENST00000426595 | TSF |
| 9% | chr17 | 70713894 | 70713885 | − | chr17 | 70645407 | 70645309 | − | ENST00000255559; ENST00000542342; ENST00000582769 | TSF |
| 9% | chr17 | 70713894 | 70713885 | − | chr17 | 70645407 | 70645309 | − | ENST00000255559; ENST00000542342; ENST00000582769 | TSF |
| 8% | chr20 | 110606 | 110697 | + | chr20 | 126056 | 126333 | + | ENST00000382398 | TSF |
| 7% | chr1 | 1422590 | 1422685 | + | chr1 | 1423243 | 1423294 | + | ENST00000308647 | TSF |
| 7% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 7% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 7% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 7% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 7% | chr2 | 38983894 | 38983253 | − | chr2 | 38977336 | 38977156 | − | ENST00000313117; ENST00000425778; ENST00000425941; ENST00000446327; ENST00000409276; ENST00000431066; | TSF |
| 7% | chr19 | 54105034 | 54105030 | − | chr19 | 54104626 | 54104519 | − | ENST00000600193 | TSF |
| 7% | chr7 | 136953098 | 136953071 | − | chr7 | 136939714 | 136939606 | − | ENST00000348225; ENST00000393083 | TSF |
| 7% | chr7 | 136953098 | 136953071 | − | chr7 | 136939714 | 136939606 | − | ENST00000348225; ENST00000393083 | TSF |
| 6% | chr18 | 43415105 | 43415246 | + | chr18 | 43416994 | 43417053 | + | ENST00000389474 | TSF |
| 6% | chr2 | 143794737 | 143794842 | + | chr2 | 143797997 | 143798227 | + | ENST00000264170; ENST00000409512 | TSF |
| 6% | chr1 | 41465686 | 41465756 | + | chr1 | 41466701 | 41466789 | + | ENST00000372621; ENST00000541520; ENST00000372616 | TSF |
| 5% | chr10 | 124066312 | 124066425 | + | chr10 | 124066704 | 124066823 | + | ENST00000368994; ENST00000260723 | TSF |
| 5% | chr7 | 1477059 | 1476990 | − | chr7 | 1476492 | 1476378 | − | ENST00000405088; ENST00000297508 | TSF |
| 5% | chr19 | 20737134 | 20737096 | − | chr19 | 20736641 | 20736515; 20736611 | − | ENST00000427401; ENST00000597940; ENST00000596797 | TSF |
| 5% | chr19 | 20737134 | 20737096 | − | chr19 | 20736641 | 20736515; 20736611 | − | ENST00000427401; ENST00000597940; ENST00000596797 | TSF |
| 5% | chr19 | 20737134 | 20737096 | − | chr19 | 20736641 | 20736515; 20736611 | − | ENST00000427401; ENST00000597940; ENST00000596797 | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr1 | 15562769 | 15563257 | + | chr1 | 15578267 | 15578373 | + | ENST00000433640 | TSF |
| 5% | chr1 | 167832811 | 167833076 | + | chr1 | 167921038 | 167921099 | + | ENST00000367843; ENST00000470721; ENST00000432587; ENST00000312263; ENST00000367840 | TSF |
| 5% | chr1 | 167832811 | 167833076 | + | chr1 | 167921038 | 167921099 | + | ENST00000367843; ENST00000470721; ENST00000432587; ENST00000312263; ENST00000367840 | TSF |
| 5% | chr1 | 167832811 | 167833076 | + | chr1 | 167921038 | 167921099 | + | ENST00000367843; ENST00000470721; ENST00000432587; ENST00000312263; ENST00000367840 | TSF |
| 5% | chr1 | 167832811 | 167833076 | + | chr1 | 167921038 | 167921099 | + | ENST00000367843; ENST00000470721; ENST00000432587; ENST00000312263; ENST00000367840 | TSF |
| 5% | chr1 | 167832811 | 167833076 | + | chr1 | 167921038 | 167921099 | + | ENST00000367843; ENST00000470721; ENST00000432587; ENST00000312263; ENST00000367840 | TSF |
| 5% | chr17 | 40820773 | 40820676 | − | chr17 | 40820321 | 40820145 | − | ENST00000591022; ENST00000412503; ENST00000293349 | TSF |
| 4% | chr8 | 101647768 | 101647627 | − | chr8 | 101642619 | 101642555 | − | ENST00000311812; ENST00000520352; ENST00000520661 | TSF |
| 4% | chr8 | 101647768 | 101647627 | − | chr8 | 101642619 | 101642555 | − | ENST00000311812; ENST00000520352; ENST00000520661 | TSF |
| 4% | chr8 | 101647768 | 101647627 | − | chr8 | 101642619 | 101642555 | − | ENST00000311812; ENST00000520352; ENST00000520661 | TSF |
| 4% | chr12 | 6602868 | 6602754 | − | chr12 | 6602138 | 6602028 | − | ENST00000229238 | TSF |
| 4% | chr12 | 48058419 | 48058373 | − | chr12 | 48057373 | 48057288 | − | ENST00000005386; ENST00000432584; ENST00000380650 | TSF |
| 4% | chr1 | 84740629 | 84740758 | + | chr1 | 84791320 | 84791431 | + | ENST00000370673; ENST00000370671; ENST00000394834; ENST00000370669; ENST00000370668; ENST00000370670 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr11 | 60694460 | 60694542 | + | chr11 | 60694676 | 60694890 | + | ENST00000453848; ENST00000005286 | TSF |
| 4% | chr11 | 60694460 | 60694542 | + | chr11 | 60694676 | 60694890 | + | ENST00000453848; ENST00000005286 | TSF |
| 4% | chr14 | 24104836 | 24105801 | + | chr14 | 24112361 | 24112428 | + | ENST00000432832; ENST00000250383; ENST00000344777; ENST00000557535; ENST00000553600 | TSF |
| 4% | chr14 | 24104836 | 24105801 | + | chr14 | 24112361 | 24112428 | + | ENST00000432832; ENST00000250383; ENST00000344777; ENST00000557535; ENST00000553600 | TSF |
| 4% | chr14 | 24104836 | 24105801 | + | chr14 | 24112361 | 24112428 | + | ENST00000432832; ENST00000250383; ENST00000344777; ENST00000557535; ENST00000553600 | TSF |
| 4% | chr14 | 24104836 | 24105801 | + | chr14 | 24112361 | 24112428 | + | ENST00000432832; ENST00000250383; ENST00000344777; ENST00000557535; ENST00000553600 | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr14 | 24104836 | 24105801 | + | chr14 | 24112361 | 24112428 | + | ENST00000432832; ENST00000250383; ENST00000344777; ENST00000557535; ENST00000553600 | |
| 4% | chr20 | 43561150 | 43561175 | + | chr20 | 43561713 | 43561826 | + | ENST00000255136; ENST00000217073 | TSF |
| 4% | chr6 | 161637963 | 161637691 | − | chr6 | 161587449 | 161587280; 161587148 | − | ENST00000320285; ENST00000366908; ENST00000436279; ENST00000366905 | TSF |
| 4% | chr6 | 161637963 | 161637691 | − | chr6 | 161587449 | 161587280; 161587148 | − | ENST00000320285; ENST00000366908; ENST00000436279; ENST00000366905 | TSF |
| 4% | chr6 | 161637963 | 161637691 | − | chr6 | 161587449 | 161587280; 161587148 | − | ENST00000320285; ENST00000366908; ENST00000436279; ENST00000366905 | TSF |
| 3% | chr14 | 24105862 | 24105898 | + | chr14 | 24112361 | 24112428 | + | ENST00000432832; ENST00000250383; ENST00000344777; ENST00000557535; ENST00000553600 | TSF |
| 3% | chr14 | 24105862 | 24105898 | + | chr14 | 24112361 | 24112428 | + | ENST00000432832; ENST00000250383; ENST00000344777; ENST00000557535; ENST00000553600 | TSF |
| 3% | chr14 | 24105862 | 24105898 | + | chr14 | 24112361 | 24112428 | + | ENST00000432832; ENST00000250383; ENST00000344777; ENST00000557535; ENST00000553600 | TSF |
| 3% | chr14 | 24105862 | 24105898 | + | chr14 | 24112361 | 24112428 | + | ENST00000432832; ENST00000250383; ENST00000344777; ENST00000557535; ENST00000553600 | TSF |
| 3% | chr14 | 24105862 | 24105898 | + | chr14 | 24112361 | 24112428 | + | ENST00000432832; ENST00000250383; ENST00000344777; ENST00000557535; ENST00000553600 | TSF |
| 3% | chr12 | 58189709 | 58189746 | + | chr12 | 58189960 | 58190366; 58189980; 58190044 | + | ENST00000454289; ENST00000540550; ENST00000323833; ENST00000350762; ENST00000457189 | TSF |
| 3% | chr12 | 58189709 | 58189746 | + | chr12 | 58189960 | 58190366; 58189980; 58190044 | + | ENST00000454289; ENST00000540550; ENST00000323833; ENST00000350762; ENST00000457189 | TSF |
| 3% | chr12 | 58189709 | 58189746 | + | chr12 | 58189960 | 58190366; 58189980; 58190044 | + | ENST00000454289; ENST00000540550; ENST00000323833; ENST00000350762; ENST00000457189 | TSF |
| 3% | chr8 | 74036014 | 74035742 | − | chr8 | 73993448 | 73993254 | − | ENST00000297354 | TSF |
| 3% | chr2 | 242559097 | 242559034 | − | chr2 | 242545888 | 242545729 | − | ENST00000402136; ENST00000407315; ENST00000402545 | TSF |
| 3% | chr2 | 242559097 | 242559034 | − | chr2 | 242545888 | 242545729 | − | ENST00000402136; ENST00000407315; ENST00000402545 | TSF |
| 3% | chr20 | 45337040 | 45337192 | + | chr20 | 45353680 | 45354963 | + | ENST00000359271 | TSF |
| 3% | chr19 | 45289567 | 45289633 | + | chr19 | 45293261 | 45293348 | + | ENST00000270279; ENST00000341505 | TSF |
| 3% | chr3 | 195593372 | 195593261 | − | chr3 | 195591058 | 195591052 | − | ENST00000416152; ENST00000381916; ENST00000333602; ENST00000428187; ENST00000392400 | TSF |
| 3% | chr7 | 100850556 | 100850506 | − | chr7 | 100850185 | 100850060 | − | ENST00000454310; ENST00000223127 | TSF |
| 3% | chr20 | 410407 | 410425 | + | chr20 | 410994 | 411074 | + | ENST00000356286; ENST00000353660; ENST00000382181 | TSF |
| 3% | chr14 | 24105943 | 24105981 | + | chr14 | 24113618 | 24113752; 24113763; 24113704 | + | ENST00000432832; ENST00000250383; ENST00000344777; ENST00000557535; ENST00000553600 | TSF |
| 3% | chr14 | 24105943 | 24105981 | + | chr14 | 24113618 | 24113752; 24113763; 24113704 | + | ENST00000432832; ENST00000250383; ENST00000344777; ENST00000557535; ENST00000553600 | TSF |
| 3% | chr14 | 24105943 | 24105981 | + | chr14 | 24113618 | 24113752; 24113763; 24113704 | + | ENST00000432832; ENST00000250383; ENST00000344777; ENST00000557535; ENST00000553600 | TSF |
| 3% | chr14 | 24105943 | 24105981 | + | chr14 | 24113618 | 24113752; 24113763; 24113704 | + | ENST00000432832; ENST00000250383; ENST00000344777; ENST00000557535; ENST00000553600 | TSF |
| 3% | chr14 | 24105943 | 24105981 | + | chr14 | 24113618 | 24113752; 24113763; 24113704 | + | ENST00000432832; ENST00000250383; ENST00000344777; ENST00000557535; ENST00000553600 | TSF |
| 3% | chr6 | 5498702 | 5498789 | + | chr6 | 5545413 | 5545573 | + | ENST00000324331; ENST00000274680 | TSF |
| 3% | chr4 | 1745002 | 1745264 | + | chr4 | 1746245 | 1746351 | + | ENST00000313288 | TSF |
| 3% | chr10 | 12277215 | 12277329 | + | chr10 | 12279143 | 12279265; 12279223 | + | ENST00000281141; ENST00000442050; ENST00000440613 | TSF |
| 3% | chr10 | 12277215 | 12277329 | + | chr10 | 12279143 | 12279265; 12279223 | + | ENST00000281141; ENST00000442050; ENST00000440613 | TSF |
| 3% | chr10 | 12277215 | 12277329 | + | chr10 | 12279143 | 12279265; 12279223 | + | ENST00000281141; ENST00000442050; ENST00000440613 | TSF |
| 3% | chr14 | 24105943 | 24105955 | + | chr14 | 24112361 | 24112428 | + | ENST00000432832; ENST00000250383; ENST00000344777; ENST00000557535; ENST00000553600 | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr14 | 24105943 | 24105955 | + | chr14 | 24112361 | 24112428 | + | ENST00000432832; ENST00000250383; ENST00000344777; ENST00000557535; ENST00000553600 | TSF |
| 3% | chr14 | 24105943 | 24105955 | + | chr14 | 24112361 | 24112428 | + | ENST00000432832; ENST00000250383; ENST00000344777; ENST00000557535; ENST00000553600 | TSF |
| 3% | chr14 | 24105943 | 24105955 | + | chr14 | 24112361 | 24112428 | + | ENST00000432832; ENST00000250383; ENST00000344777; ENST00000557535; ENST00000553600 | TSF |
| 3% | chr14 | 24105943 | 24105955 | + | chr14 | 24112361 | 24112428 | + | ENST00000432832; ENST00000250383; ENST00000344777; ENST00000557535; ENST00000553600 | TSF |
| 3% | chr1 | 23762222 | 23762216 | − | chr1 | 23761111 | 23761026 | − | ENST00000495646; ENST00000336689; ENST00000437606 | TSF |
| 3% | chr18 | 33076776 | 33076739 | − | chr18 | 33060527 | 33060417 | − | ENST00000592173; ENST00000334598; ENST00000441607; ENST00000591139 | TSF |
| 3% | chr18 | 33076776 | 33076739 | − | chr18 | 33060527 | 33060417 | − | ENST00000592173; ENST00000334598; ENST00000441607; ENST00000591139 | TSF |
| 3% | chr18 | 33076776 | 33076739 | − | chr18 | 33060527 | 33060417 | − | ENST00000592173; ENST00000334598; ENST00000441607; ENST00000591139 | TSF |
| 3% | chr1 | 100177044 | 100176911 | − | chr1 | 100176505 | 100176390; 100176362 | − | ENST00000287474; ENST00000414213 | TSF |
| 3% | chr1 | 100177044 | 100176911 | − | chr1 | 100176505 | 100176390; 100176362 | − | ENST00000287474; ENST00000414213 | TSF |
| 3% | chr11 | 67073292 | 67073338 | + | chr11 | 67074309 | 67074433 | + | ENST00000308127; ENST00000308298; ENST00000376757 | TSF |
| 3% | chr11 | 67073292 | 67073338 | + | chr11 | 67074309 | 67074433 | + | ENST00000308127; ENST00000308298; ENST00000376757 | TSF |
| 3% | chr11 | 67073292 | 67073338 | + | chr11 | 67074309 | 67074433 | + | ENST00000308127; ENST00000308298; ENST00000376757 | TSF |
| 3% | chr14 | 24105943 | 24105981 | + | chr14 | 24108127 | 24108213 | + | ENST00000432832; ENST00000250383; ENST00000344777 | TSF |
| 3% | chr14 | 24105943 | 24105981 | + | chr14 | 24108127 | 24108213 | + | ENST00000432832; ENST00000250383; ENST00000344777 | TSF |
| 3% | chr14 | 24105943 | 24105981 | + | chr14 | 24108127 | 24108213 | + | ENST00000432832; ENST00000250383; ENST00000344777 | TSF |
| 3% | chr1 | 246886599 | 246886803 | + | chr1 | 246890194 | 246890306 | + | ENST00000366510 | TSF |
| 3% | chr5 | 76107394 | 76108135 | + | chr5 | 76128515 | 76129626 | + | ENST00000296677 | TSF |
| 3% | chr19 | 55501071 | 55501120 | + | chr19 | 55501390 | 55501560; 55501464 | + | ENST00000543010; ENST00000391721; ENST00000339757; ENST00000448584; ENST00000537859; ENST00000427260; ENST00000538819; ENST00000263437; ENST00000543277 | TSF |
| 3% | chr19 | 55501071 | 55501120 | + | chr19 | 55501390 | 55501560; 55501464 | + | ENST00000543010; ENST00000391721; ENST00000339757; ENST00000448584; ENST00000537859; ENST00000427260; ENST00000538819; ENST00000263437; ENST00000543277 | TSF |
| 3% | chr17 | 39976225 | 39976301 | + | chr17 | 39976521 | 39976713 | + | ENST00000321562; ENST00000455106; ENST00000544340 | TSF |
| 3% | chr17 | 39974832 | 39974893 | + | chr17 | 39975462 | 39975651 | + | ENST00000321562 | TSF |
| 3% | chr19 | 39347374 | 39346430 | − | chr19 | 39338074 | 39337956 | − | ENST00000221419; ENST00000601449; ENST00000600233; ENST00000601813 | TSF |
| 3% | chr19 | 39347374 | 39346430 | − | chr19 | 39338074 | 39337956 | − | ENST00000221419; ENST00000601449; ENST00000600233; ENST00000601813 | TSF |
| 3% | chr19 | 39347374 | 39346430 | − | chr19 | 39338074 | 39337956 | − | ENST00000221419; ENST00000601449; ENST00000600233; ENST00000601813 | TSF |
| 3% | chr19 | 39347374 | 39346206 | − | chr19 | 39338074 | 39337956 | − | ENST00000221419; ENST00000601449; ENST00000600233; ENST00000601813 | TSF |
| 3% | chr19 | 39347374 | 39346206 | − | chr19 | 39338074 | 39337956 | − | ENST00000221419; ENST00000601449; ENST00000600233; ENST00000601813 | TSF |
| 3% | chr19 | 39347374 | 39346206 | − | chr19 | 39338074 | 39337956 | − | ENST00000221419; ENST00000601449; ENST00000600233; ENST00000601813 | TSF |
| 3% | chr9 | 130929922 | 1309298918 | − | chr9 | 130929443 | 130929374 | − | ENST00000372954; ENST00000393608; ENST00000541172; ENST00000325721; ENST00000357558; ENST00000538431; ENST00000277465; ENST00000372948; ENST00000372938; ENST00000415526 | TSF |
| 3% | chr4 | 142977397 | 142977072 | − | chr4 | 142950067 | 142949935 | − | ENST00000513000; ENST00000262992; ENST00000308502; ENST00000508116 | TSF |
| 3% | chrX | 154534914 | 154534773 | − | chrX | 154528458 | 154528349 | − | ENST00000369449; ENST00000321926 | TSF |
| 3% | chrX | 154534914 | 154534773 | − | chrX | 154528458 | 154528349 | − | ENST00000369449; ENST00000321926 | TSF |
| 2% | chr19 | 56811235 | 56811344 | + | chr19 | 56813337 | 56813464 | + | ENST00000588026 | TSF |
| 2% | chr10 | 72621217 | 72622628 | + | chr10 | 72628102 | 72628190 | + | ENST00000373202 | TSF |
| 2% | chr13 | 43670805 | 43671144 | + | chr13 | 43681314 | 43681384 | + | ENST00000379221 | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr1 | 111960622 | 111960373 | − | chr1 | 111959080 | 111958945; 111959068 | − | ENST00000369732; ENST00000540696 | TSF |
| 2% | chr1 | 111960622 | 111960373 | − | chr1 | 111959080 | 111958945; 111959068 59068 | − | ENST00000369732; ENST00000540696 | TSF |
| 2% | chr2 | 230769 | 230547 | − | chr2 | 230044 | 229966; 229922 | − | ENST00000403712; ENST00000415006; ENST00000403657; ENST00000405430; ENST00000356150; ENST00000403658; ENST00000451005; ENST00000431160 | TSF |
| 2% | chr2 | 230769 | 230547 | − | chr2 | 230044 | 229966; 229922 | − | ENST00000403712; ENST00000415006; ENST00000403657; ENST00000405430; ENST00000356150; ENST00000403658; ENST00000451005; ENST00000431160 | TSF |
| 2% | chr2 | 230769 | 230547 | − | chr2 | 230044 | 229966; 229922 | − | ENST00000403712; ENST00000415006; ENST00000403657; ENST00000405430; ENST00000356150; ENST00000403658; ENST00000451005; ENST00000431160 | TSF |
| 2% | chr19 | 46194689 | 46194670 | − | chr19 | 46198241 | 46191645 | − | ENST00000342669; ENST00000588301; ENST00000590212 | TSF |
| 2% | chr19 | 46194689 | 46194670 | − | chr19 | 46198241 | 46191645 | − | ENST00000342669; ENST00000588301; ENST00000590212 | TSF |
| 2% | chr6 | 80022917 | 80022085 | − | chr6 | 79924739 | 79924689 | − | ENST00000275036; ENST00000344726 | TSF |
| 2% | chr6 | 80022917 | 80022085 | − | chr6 | 79924739 | 79924689 | − | ENST00000275036; ENST00000344726 | TSF |
| 2% | chr17 | 34221697 | 34221113 | − | chr17 | 34205643 | 34205532 | − | ENST00000293272; ENST00000366113; ENST00000463941 | TSF |
| 2% | chr17 | 34221697 | 34221113 | − | chr17 | 34205643 | 34205532 | − | ENST00000293272; ENST00000366113; ENST00000463941 | TSF |
| 2% | chrX | 154534914 | 154534817 | − | chrX | 154528458 | 154528349 | − | ENST00000369449; ENST00000321926 | TSF |
| 2% | chrX | 154534914 | 154534817 | − | chrX | 154528458 | 154528349 | − | ENST00000369449; ENST00000321926 | TSF |
| 2% | chr11 | 64599672 | 64599483 | − | chr11 | 64599193 | 64598977 | − | ENST00000342711 | TSF |
| 2% | chr19 | 35613389 | 35613502 | + | chr19 | 35613669 | 35613862; 35613743; 35613858 | + | ENST00000406242; ENST00000604404; ENST00000435734; ENST00000603181; ENST00000604255; ENST00000344013; ENST00000346446; ENST00000406988; ENST00000605550; ENST00000604804; ENST00000535103; ENST00000603524; ENST00000604621; ENST00000605677 | TSF |
| 2% | chr19 | 35613389 | 35613502 | + | chr19 | 35613669 | 35613862; 35613743; 35613858 | + | ENST00000406242; ENST00000604404; ENST00000435734; ENST00000603181; ENST00000604255; ENST00000344013; ENST00000346446; ENST00000406988; ENST00000605550; ENST00000604804; ENST00000535103; ENST00000603524; ENST00000604621; ENST00000605677 | TSF |
| 2% | chr19 | 35613389 | 35613502 | + | chr19 | 35613669 | 35613862; 35613743; 35613858 | + | ENST00000406242; ENST00000604404; ENST00000435734; ENST00000603181; ENST00000604255; ENST00000344013; ENST00000346446; ENST00000406988; ENST00000605550; ENST00000604804; ENST00000535103; ENST00000603524; ENST00000604621; ENST00000605677 | TSF |
| 2% | chr19 | 35613389 | 35613502 | + | chr19 | 35613669 | 35613862; 35613743; 35613858 | + | ENST00000406242; ENST00000604404; ENST00000435734; ENST00000603181; ENST00000604255; ENST00000344013; ENST00000346446; ENST00000406988; ENST00000605550; ENST00000604804; ENST00000535103; ENST00000603524; ENST00000604621; ENST00000605677 | TSF |
| 2% | chr11 | 66048968 | 66049045 | + | chr11 | 66049730 | 66049798 66049824 | + | ENST00000528852; ENST00000311445; ENST00000528063 | TSF |
| 2% | chr11 | 66048968 | 66049045 | + | chr11 | 66049730 | 66049798 66049824 | + | ENST00000528852; ENST00000311445; ENST00000528063 | TSF |
| 2% | chr11 | 66048968 | 66049045 | + | chr11 | 66049730 | 66049798 66049824 | + | ENST00000528852; ENST00000311445; ENST00000528063 | TSF |
| 2% | chr4 | 107241932 | 107242046 | + | chr4 | 107246142 | 107246275 | + | ENST00000394701 | TSF |
| 2% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 2% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 2% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 2% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 2% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr9 | 19419482 | 19419707 | + | chr9 | 19423860 | 19423974 | + | ENST00000340967 | TSF |
| 2% | chr1 | 17603989 | 17604315 | + | chr1 | 17606845 | 17606924 | + | ENST00000375460 | TSF |
| 2% | chr20 | 43561150 | 43561175 | + | chr20 | 43564032 | 43564138 | + | ENST00000255136; ENST00000217073; ENST00000372824; ENST00000372819; ENST00000217075; ENST00000479873; ENST00000372826 | TSF |
| 2% | chr20 | 43561150 | 43561175 | + | chr20 | 43564032 | 43564138 | + | ENST00000255136; ENST00000217073; ENST00000372824; ENST00000372819; ENST00000217075; ENST00000479873; ENST00000372826 | TSF |
| 2% | chr20 | 43561150 | 43561175 | + | chr20 | 43564032 | 43564138 | + | ENST00000255136; ENST00000217073; ENST00000372824; ENST00000372819; ENST00000217075; ENST00000479873; ENST00000372826 | TSF |
| 2% | chr20 | 43561150 | 43561175 | + | chr20 | 43564032 | 43564138 | + | ENST00000255136; ENST00000217073; ENST00000372824; ENST00000372819; ENST00000217075; ENST00000479873; ENST00000372826 | TSF |
| 2% | chr20 | 43561150 | 43561175 | + | chr20 | 43564032 | 43564138 | + | ENST00000255136; ENST00000217073; ENST00000372824; ENST00000372819; ENST00000217075; ENST00000479873; ENST00000372826 | TSF |
| 2% | chr19 | 43980514 | 43980487 | − | chr19 | 43979696 | 43979562 | − | ENST00000292140 | TSF |
| 2% | chr21 | 38273278 | 38272892 | − | chr21 | 38269431 | 38269160 | − | ENST00000336648; ENST00000399120 | TSF |
| 2% | chr10 | 5057417 | 5057095 | − | chr10 | 5043873 | 5043706 | − | ENST00000380753; ENST00000421196; ENST00000407674; ENST00000604507; ENST00000455190 | TSF |
| 2% | chr10 | 5057417 | 5057095 | − | chr10 | 5043873 | 5043706 | − | ENST00000380753; ENST00000421196; ENST00000407674; ENST00000604507; ENST00000455190 | TSF |
| 2% | chr10 | 5057417 | 5057095 | − | chr10 | 5043873 | 5043706 | − | ENST00000380753; ENST00000421196; ENST00000407674; ENST00000604507; ENST00000455190 | TSF |
| 2% | chr10 | 5057417 | 5057095 | − | chr10 | 5043873 | 5043706 | − | ENST00000380753; ENST00000421196; ENST00000407674; ENST00000604507; ENST00000455190 | TSF |
| 2% | chr19 | 48654965 | 48654725 | − | chr19 | 48654596 | 48654489 | − | ENST00000263274; ENST00000601091; ENST00000542460 | TSF |
| 2% | chr19 | 48654965 | 48654725 | − | chr19 | 48654596 | 48654489 | − | ENST00000263274; ENST00000601091; ENST00000542460 | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr19 | 48654965 | 48654725 | − | chr19 | 48654596 | 48654489 | − | ENST00000263274; ENST00000601091; ENST00000542460 | TSF |
| 2% | chr1 | 246581335 | 246580598 | − | chr1 | 246518396 | 246518333 | − | ENST00000388985; ENST00000403792 | TSF |
| 2% | chr1 | 246581335 | 246580598 | − | chr1 | 246518396 | 246518333 | − | ENST00000388985; ENST00000403792 | TSF |
| 2% | chr7 | 136953098 | 136952826 | − | chr7 | 136939714 | 136939606 | − | ENST00000348225; ENST00000393083 | TSF |
| 2% | chr7 | 136953098 | 136952826 | − | chr7 | 136939714 | 136939606 | − | ENST00000348225; ENST00000393083 | TSF |
| 2% | chr11 | 60663653 | 60661987 | − | chr11 | 60658735 | 60658638 | − | ENST00000227524; ENST00000535326 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 00000418438 | TSF |
| 2% | chr1 | 44446234 | 44446286 | + | chr1 | 44446781 | 44447145 | + | ENST00000309519 | TSF |
| 2% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 2% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 2% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 2% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 2% | chr14 | 56129674 | 56129713 | + | chr14 | 56130673 | 56130759 | + | ENST00000395309; ENST00000413890; ENST00000395314; ENST00000459737; ENST00000395308; ENST00000395311; ENST00000416613; ENST00000555573 | TSF |
| 2% | chr14 | 56129674 | 56129713 | + | chr14 | 56130673 | 56130759 | + | ENST00000395309; ENST00000413890; ENST00000395314; ENST00000459737; ENST00000395308; ENST00000395311; ENST00000416613; ENST00000555573 | TSF |
| 2% | chr1 | 151017459 | 151017509 | + | chr1 | 151018273 | 151018359 | + | ENST00000368931; ENST00000295294; ENST00000361277 | TSF |
| 2% | chr15 | 83092312 | 83092387 | + | chr15 | 83100556 | 83100675 | + | ENST00000561062; ENST00000358583 | TSF |
| 2% | chr15 | 83092312 | 83092387 | + | chr15 | 83100556 | 83100675 | + | ENST00000561062; ENST00000358583 | TSF |
| 2% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 2% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 2% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 2% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 2% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 2% | chr1 | 29648112 | 29648148 | + | chr1 | 29649883 | 29650008 | + | ENST00000345512; ENST00000373779; ENST00000323874; ENST00000356870; ENST00000428026; ENST00000460170 | TSF |
| 2% | chr1 | 29648112 | 29648148 | + | chr1 | 29649883 | 29650008 | + | ENST00000345512; ENST00000373779; ENST00000323874; ENST00000356870; ENST00000428026; ENST00000460170 | TSF |
| 2% | chr15 | 82715787 | 82715862 | + | chr15 | 82724031 | 82724150 | + | ENST00000300515 | TSF |
| 2% | chr1 | 150951160 | 150951226 | + | chr1 | 151018273 | 151018359 | + | ENST00000368931; ENST00000295294; ENST00000361277 | TSF |
| 2% | chr16 | 23360523 | 23360640 | + | chr16 | 23364122 | 23364395 | + | ENST00000343070; ENST00000307331; ENST00000564275; ENST00000568085; ENST00000568923 | TSF |
| 2% | chr16 | 23360523 | 23360640 | + | chr16 | 23364122 | 23364395 | + | ENST00000343070; ENST00000307331; ENST00000564275; ENST00000568085; ENST00000568923 | TSF |
| 2% | chr16 | 23360523 | 23360640 | + | chr16 | 23364122 | 23364395 | + | ENST00000343070; ENST00000307331; ENST00000564275; ENST00000568085; ENST00000568923 | TSF |
| 2% | chr16 | 23360523 | 23360640 | + | chr16 | 23364122 | 23364395 | + | ENST00000343070; ENST00000307331; ENST00000564275; ENST00000568085; ENST00000568923 | TSF |
| 2% | chr7 | 96339660 | 96339504 | − | chr7 | 96324203 | 96324110 | − | ENST00000417009; ENST00000444799; ENST00000449279; ENST00000413065; ENST00000248566 | TSF |
| 2% | chr7 | 96339660 | 96339504 | − | chr7 | 96324203 | 96324110 | − | ENST00000417009; ENST00000444799; ENST00000449279; ENST00000413065; ENST00000248566 | TSF |
| 2% | chr7 | 96339660 | 96339504 | − | chr7 | 96324203 | 96324110 | − | ENST00000417009; ENST00000444799; ENST00000449279; ENST00000413065; ENST00000248566 | TSF |
| 2% | chr7 | 96339660 | 96339504 | − | chr7 | 96324203 | 96324110 | − | ENST00000417009; ENST00000444799; ENST00000449279; ENST00000413065; ENST00000248566 | TSF |
| 2% | chr10 | 5060345 | 5060092 | − | chr10 | 5043777 | 5043706 | − | ENST00000380753; ENST00000421196; ENST00000407674; ENST00000604507; ENST00000455190 | TSF |
| 2% | chr10 | 5060345 | 5060092 | − | chr10 | 5043777 | 5043706 | − | ENST00000380753; ENST00000421196; ENST00000407674; ENST00000604507; ENST00000455190 | TSF |
| 2% | chr10 | 5060345 | 5060092 | − | chr10 | 5043777 | 5043706 | − | ENST00000380753; ENST00000421196; ENST00000407674; ENST00000604507; ENST00000455190 | TSF |
| 2% | chr10 | 5060345 | 5060092 | − | chr10 | 5043777 | 5043706 | − | ENST00000380753; ENST00000421196; ENST00000407674; ENST00000604507; ENST00000455190 | TSF |
| 2% | chr12 | 14670381 | 14670239 | − | chr12 | 14664645 | 14664445 | − | ENST00000240617 | TSF |
| 2% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 2% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 2% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 2% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 2% | chr18 | 51273 | 49727 | − | chr18 | 49237 | 49129 | − | ENST00000308911 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr1 | 150914336 | 150914402 | + | chr1 | 151018273 | 151018359 | + | ENST00000368931; ENST00000295294; ENST00000361277 | TSF |
| 2% | chr13 | 43628887 | 43629679 | + | chr13 | 43681314 | 43681384 | + | ENST00000379221 | TSF |
| 2% | chr1 | 110235391 | 110235454 | + | chr1 | 110235828 | 110235917 | + | ENST00000309851; ENST00000369823; ENST00000349334; ENST00000369819 | TSF |
| 2% | chr19 | 50174724 | 50174836 | + | chr19 | 50176955 | 50177005; 50177034 | + | ENST00000441864; ENST00000246785; ENST00000600947; ENST00000598306 | TSF |
| 2% | chr19 | 50174724 | 50174836 | + | chr19 | 50176955 | 50177005; 50177034 | + | ENST00000441864; ENST00000246785; ENST00000600947; ENST00000598306 | TSF |
| 2% | chr12 | 122387836 | 122388242 | + | chr12 | 122389386 | 122389436 | + | ENST00000288912; ENST00000397454 | TSF |
| 2% | chr12 | 122387836 | 122388242 | + | chr12 | 122389386 | 122389436 | + | ENST00000288912; ENST00000397454 | TSF |
| 2% | chr17 | 59480183 | 59480242 | + | chr17 | 59480422 | 59480568 | + | ENST00000240328 | TSF |
| 2% | chr7 | 26677781 | 26678069 | + | chr7 | 26678815 | 26678963 | + | ENST00000409974 | TSF |
| 2% | chr1 | 168348640 | 168349020 | + | chr1 | 168549301 | 168549415 | + | ENST00000367818 | TSF |
| 2% | chr5 | 1475119 | 1475076 | − | chr5 | 1474800 | 1474675 | − | ENST00000475622; ENST00000283415 | TSF |
| 2% | chr19 | 40327657 | 40327534 | − | chr19 | 40327308 | 40327196 | − | ENST00000595545; ENST00000221801; ENST00000597224; ENST00000601274; ENST00000597634 | TSF |
| 2% | chr19 | 40327657 | 40327534 | − | chr19 | 40327308 | 40327196 | − | ENST00000595545; ENST00000221801; ENST00000597224; ENST00000601274; ENST00000597634 | TSF |
| 2% | chr19 | 40327657 | 40327534 | − | chr19 | 40327308 | 40327196 | − | ENST00000595545; ENST00000221801; ENST00000597224; ENST00000601274; ENST00000597634 | TSF |
| 2% | chr19 | 40327657 | 40327534 | − | chr19 | 40327308 | 40327196 | − | ENST00000595545; ENST00000221801; ENST00000597224; ENST00000601274; ENST00000597634 | TSF |
| 2% | chr19 | 40327657 | 40327534 | − | chr19 | 40327308 | 40327196 | − | ENST00000595545; ENST00000221801; ENST00000597224; ENST00000601274; ENST00000597634 | TSF |
| 2% | chr15 | 40187476 | 40186733 | − | chr15 | 40099459 | 40099207 | − | ENST00000561100; ENST00000543580 | TSF |
| 2% | chr8 | 91107662 | 91105645 | − | chr8 | 91094330 | 91094254 | − | ENST00000265431 | TSF |
| 2% | chr19 | 54106196 | 54106162 | − | chr19 | 54105417 | 54105251 | − | ENST00000600193 | TSF |
| 2% | chr6 | 31114486 | 31114237 | − | chr6 | 31113585 | 31113473 | − | ENST00000396268; ENST00000376266; ENST00000451521 | TSF |
| 2% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 2% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 2% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 1% | chr20 | 110606 | 110697 | + | chr20 | 126220 | 126333 | + | ENST00000382398 | TSF |
| 1% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 1% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 1% | chr12 | 122430912 | 122432103 | + | chr12 | 122437622 | 122437850 | + | ENST00000288912 | TSF |
| 1% | chr1 | 27158561 | 27158563 | + | chr1 | 27158938 | 27159098 | + | ENST00000374142 | TSF |
| 1% | chr10 | 124064536 | 124064644 | + | chr10 | 124066704 | 124066823 | + | ENST00000368994; ENST00000260723 | TSF |
| 1% | chr14 | 24105943 | 24105981 | + | chr14 | 24113320 | 24113371 | + | ENST00000432832; ENST00000250383; ENST00000344777; ENST00000557535; ENST00000553600 | TSF |
| 1% | chr14 | 24105943 | 24105981 | + | chr14 | 24113320 | 24113371 | + | ENST00000432832; ENST00000250383; ENST00000344777; ENST00000557535; ENST00000553600 | TSF |
| 1% | chr14 | 24105943 | 24105981 | + | chr14 | 24113320 | 24113371 | + | ENST00000432832; ENST00000250383; ENST00000344777; ENST00000557535; ENST00000553600 | TSF |
| 1% | chr14 | 24105943 | 24105981 | + | chr14 | 24113320 | 24113371 | + | ENST00000432832; ENST00000250383; ENST00000344777; ENST00000557535; ENST00000553600 | TSF |
| 1% | chr14 | 24105943 | 24105981 | + | chr14 | 24113320 | 24113371 | + | ENST00000432832; ENST00000250383; ENST00000344777; ENST00000557535; ENST00000553600 | TSF |
| 1% | chr12 | 122430912 | 122431795 | + | chr12 | 122437622 | 122437850 | + | ENST00000288912 | TSF |
| 1% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 1% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 1% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 1% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 1% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 1% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 1% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 1% | chr5 | 66178759 | 66179020 | + | chr5 | 66195779 | 66195810 | + | ENST00000404260; ENST00000403625; ENST00000406374; ENST00000406039; | TSF |

TABLE 8-continued

Transcript fusion for Bladder Carcinoma (BLCA) Coordinates of the fusion sequences for which the donor is the TE.

| 1 | 2' | 3' | 4' | 5' | 6' | 7' | 8' | 9' | 10' | 11' |
|---|----|-----|-----|---|----|-----|-----|---|-----|-----|
| 1% | chr5 | 66178759 | 66179020 | + | chr5 | 66195779 | 66195810 | + | ENST00000452953; ENST00000432817; ENST00000434115; ENST00000411628; ENST00000490016; ENST00000403666; ENST00000450827 ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 1% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 1% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 1% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 1% | chr9 | 90301842 | 90301883 | + | chr9 | 90311922 | 90312119 | + | ENST00000358077; ENST00000472284; ENST00000469640; ENST00000408954 | TSF |
| 1% | chr9 | 90301842 | 90301883 | + | chr9 | 90311922 | 90312119 | + | ENST00000358077; ENST00000472284; ENST00000469640; ENST00000408954 0408954 | TSF |
| 1% | chr2 | 150044073 | 150044093 | + | chr2 | 150061767 | 150061918 | + | ENST00000409642; ENST00000409876; ENST00000409029; ENST00000442722; ENST00000280115 | TSF |
| 1% | chr2 | 150044073 | 150044093 | + | chr2 | 150061767 | 150061918 | + | ENST00000409642; ENST00000409876; ENST00000409029; ENST00000442722; ENST00000280115 | TSF |
| 1% | chr8 | 104389530 | 104389536 | + | chr8 | 104390255 | 104390471 | + | ENST00000330295; ENST00000520337 | TSF |
| 1% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 1% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 1% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 1% | chr17 | 49346367 | 49346514 | + | chr17 | 49350723 | 49350811 | + | ENST00000225298 | TSF |
| 1% | chr21 | 45165597 | 45165696 | + | chr21 | 45165960 | 45166006 | + | ENST00000468090; ENST00000291565; ENST00000467908 | TSF |
| 1% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 1% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 1% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 1% | chr20 | 45138455 | 45138244 | − | chr20 | 45133379 | 45133253 | − | ENST00000593880; ENST00000347606 | TSF |
| 1% | chr20 | 45138455 | 45138244 | − | chr20 | 45133379 | 45133253 | − | ENST00000593880; ENST00000347606 | TSF |
| 1% | chr8 | 63949410 | 63948932 | − | chr8 | 63948329 | 63948215 | − | ENST00000260118 | TSF |
| 1% | chr3 | 9823188 | 9823088 | − | chr3 | 9822233 | 9822041 | − | ENST00000301964; ENST00000440161 | TSF |
| 1% | chr12 | 120566093 | 120566088 | − | chr12 | 120565778 | 120565653 | − | ENST00000300648 | TSF |
| 1% | chr12 | 54862718 | 54862609 | − | chr12 | 54858951 | 54858851 | − | ENST00000546931; ENST00000552397; ENST00000305879 | TSF |
| 1% | chr12 | 54862718 | 54862609 | − | chr12 | 54858951 | 54858851 | − | ENST00000546931; ENST00000552397; ENST00000305879 | TSF |
| 1% | chr4 | 873272 | 873014 | − | chr4 | 871597 | 871403 | − | ENST00000314167; ENST00000511163 | TSF |
| 1% | chr2 | 43616365 | 43616285 | − | chr2 | 43571376 | 43571261 | − | ENST00000405975; ENST00000415080; ENST00000407351; ENST00000405006 | TSF |

TABLE 8-continued

Transcript fusion for Bladder Carcinoma (BLCA) Coordinates of the fusion sequences for which the donor is the TE.

| 1  | 2'   | 3'        | 4'        | 5' | 6'   | 7'        | 8'        | 9' | 10'                              | 11' |
|----|------|-----------|-----------|----|------|-----------|-----------|----|----------------------------------|-----|
| 1% | chr9 | 132512208 | 132512163 | –  | chr9 | 132511016 | 132510934 | –  | ENST00000340607                  | TSF |
| 1% | chr1 | 8924664   | 8924519   | –  | chr1 | 8924151   | 8923950   | –  | ENST00000234590                  | TSF |
| 1% | chrX | 76851229  | 76851182  | –  | chrX | 76849319  | 76849166  | –  | ENST00000373344; ENST00000395603 | TSF |

TABLE 9

Transcript fusion for Breast Invasive Carcinoma (BRCA) Coordinates of the fusion sequences for which the donor is the Exon.

| 1   | 2     | 3                    | 4         | 5 | 6                                                                                                       | 7     | 8         | 9         | 10 | 11  |
|-----|-------|----------------------|-----------|---|---------------------------------------------------------------------------------------------------------|-------|-----------|-----------|----|-----|
| 39% | chr10 | 22171368             | 22171211  | – | ENST00000376980                                                                                         | chr10 | 22168812  | 22168560  | –  | TAF |
| 38% | chr6  | 152382126            | 152382259 | + | ENST00000440973; ENST00000338799; ENST00000456483; ENST00000443427; ENST00000206249; ENST00000406599; ENST00000427531 | chr6  | 152399927 | 152404932 | +  | TAF |
| 38% | chr6  | 152382126            | 152382259 | + | ENST00000440973; ENST00000338799; ENST00000456483; ENST00000443427; ENST00000206249; ENST00000406599; ENST00000427531 | chr6  | 152399927 | 152404932 | +  | TAF |
| 38% | chr6  | 152382126            | 152382259 | + | ENST00000440973; ENST00000338799; ENST00000456483; ENST00000443427; ENST00000206249; ENST00000406599; ENST00000427531 | chr6  | 152399927 | 152404932 | +  | TAF |
| 38% | chr6  | 152382126            | 152382259 | + | ENST00000440973; ENST00000338799; ENST00000456483; ENST00000443427; ENST00000206249; ENST00000406599; ENST00000427531 | chr6  | 152399927 | 152404932 | +  | TAF |
| 18% | chr3  | 4927450              | 4927407   | – | ENST00000449914; ENST00000441894                                                                        | chr3  | 4898429   | 4898242   | –  | TSF |
| 16% | chr10 | 37490163             | 37490253  | + | ENST00000361713; ENST00000374660; ENST00000602533                                                       | chr10 | 37494228  | 37494539  | +  | TAF |
| 16% | chr10 | 37490163             | 37490253  | + | ENST00000361713; ENST00000374660; ENST00000602533                                                       | chr10 | 37494228  | 37494539  | +  | TAF |
| 15% | chr10 | 17432619             | 17432530  | – | ENST00000377602                                                                                         | chr10 | 17428932  | 17428606  | –  | TAF |
| 15% | chr17 | 40821538; 40821639   | 40821448  | – | ENST00000412503; ENST00000591022; ENST00000293349                                                       | chr17 | 40820920  | 40820864  | –  | TAF |
| 15% | chr17 | 40821538; 40821639   | 40821448  | – | ENST00000412503; ENST00000591022; ENST00000293349                                                       | chr17 | 40820920  | 40820864  | –  | TAF |
| 15% | chr17 | 40821538; 40821639   | 40821448  | – | ENST00000412503; ENST00000591022; ENST00000293349                                                       | chr17 | 40820920  | 40820864  | –  | TAF |
| 13% | chr1  | 47571800             | 47571933  | + | ENST00000334194                                                                                         | chr1  | 47579327  | 47581130  | +  | TAF |
| 13% | chrX  | 117900807            | 117900939 | + | ENST00000371666                                                                                         | chrX  | 117938895 | 117939267 | +  | TAF |
| 13% | chr1  | 180366740            | 180366651 | – | ENST00000367595                                                                                         | chr1  | 180295697 | 180293314 | –  | TAF |
| 13% | chr2  | 220239744            | 220239577 | – | ENST00000273075; ENST00000373972; ENST00000523282                                                       | chr2  | 220227530 | 220227195 | –  | TAF |
| 13% | chr2  | 220239744            | 220239577 | – | ENST00000273075; ENST00000373972; ENST00000523282                                                       | chr2  | 220227530 | 220227195 | –  | TAF |
| 13% | chr2  | 220239744            | 220239577 | – | ENST00000273075; ENST00000373972; ENST00000523282                                                       | chr2  | 220227530 | 220227195 | –  | TAF |
| 11% | chr14 | 51355542             | 51355621  | + | ENST00000337334; ENST00000353130; ENST00000395752                                                       | chr14 | 51359931  | 51360328  | +  | TAF |
| 11% | chr14 | 51355542             | 51355621  | + | ENST00000337334; ENST00000353130; ENST00000395752                                                       | chr14 | 51359931  | 51360328  | +  | TAF |
| 11% | chr14 | 51355542             | 51355621  | + | ENST00000337334; ENST00000353130; ENST00000395752                                                       | chr14 | 51359931  | 51360328  | +  | TAF |
| 11% | chr6  | 151742456            | 151742380 | – | ENST00000336451; ENST00000367303; ENST00000444024                                                       | chr6  | 151739714 | 151739579 | –  | TSF |
| 11% | chr6  | 151742456            | 151742380 | – | ENST00000336451; ENST00000367303; ENST00000444024                                                       | chr6  | 151739714 | 151739579 | –  | TSF |
| 11% | chr6  | 151742456            | 151742380 | – | ENST00000336451; ENST00000367303; ENST00000444024                                                       | chr6  | 151739714 | 151739579 | –  | TSF |
| 9%  | chr3  | 4872702              | 4872631   | – | ENST00000449914; ENST00000441894                                                                        | chr3  | 4871958   | 4871639   | –  | TSF |
| 7%  | chr1  | 225156461            | 225156576 | + | ENST00000430092; ENST00000400952; ENST00000366849; ENST00000439375                                      | chr1  | 225157336 | 225158402 | +  | TSF |
| 7%  | chr1  | 225156461            | 225156576 | + | ENST00000430092; ENST00000400952; ENST00000366849; ENST00000439375                                      | chr1  | 225157336 | 225158402 | +  | TSF |
| 7%  | chr4  | 57319769             | 57319927  | + | ENST00000514888; ENST00000264221; ENST00000505164; ENST00000399688; ENST00000512576                     | chr4  | 57321183  | 57321327  | +  | TSF |
| 7%  | chr4  | 57319769             | 57319927  | + | ENST00000514888; ENST00000264221; ENST00000505164; ENST00000399688; ENST00000512576                     | chr4  | 57321183  | 57321327  | +  | TSF |

TABLE 9-continued

Transcript fusion for Breast Invasive Carcinoma (BRCA) Coordinates of the fusion sequences for which the donor is the Exon.

| 1 | 2 | 3 | 4 | 5 | 6 | 7 | 8 | 9 | 10 | 11 |
|---|---|---|---|---|---|---|---|---|---|---|
| 7% | chr4 | 57319769 | 57319927 | + | ENST00000514888; ENST00000264221; ENST00000505164; ENST00000399688; ENST00000512576 | chr4 | 57321183 | 57321327 | + | TSF |
| 6% | chr1 | 227842037 | 227843464 | + | ENST00000397097; ENST00000343776 | chr1 | 227864880 | 227866572 | + | TSF |
| 6% | chr1 | 227842037 | 227843464 | + | ENST00000397097; ENST00000343776 | chr1 | 227864880 | 227866572 | + | TSF |
| 6% | chr19 | 58320471 | 58320401 | − | ENST00000391701 | chr19 | 58315432 | 58315298 | − | TSF |
| 5% | chr1 | 180283857 | 180283827 | − | ENST00000367595 | chr1 | 180281457 | 180281103 | − | TSF |
| 5% | chr20 | 41306799 | 41306506 | − | ENST00000356100; ENST00000373184; ENST00000373187; ENST00000373190; ENST00000373193; ENST00000373198; ENST00000373201 | chr20 | 41225908 | 41225560 | − | TSF |
| 5% | chr12 | 113403549; 113403702 | 113403834 | + | ENST00000228928; ENST00000546973 | chr12 | 113404028 | 113404051 | + | TSF |
| 5% | chr12 | 113403549; 113403702 | 113403834 | + | ENST00000228928; ENST00000546973 | chr12 | 113404028 | 113404051 | + | TSF |
| 5% | chr8 | 117950483 | 117950806 | + | ENST00000378279 | chr8 | 117960753 | 117961020 | + | TSF |
| 4% | chr11 | 60701014 | 60701216 | + | ENST00000453848; ENST00000005286; ENST00000536409 | chr11 | 60701443 | 60701575 | + | TSF |
| 4% | chr11 | 60701014 | 60701216 | + | ENST00000453848; ENST00000005286; ENST00000536409 | chr11 | 60701443 | 60701575 | + | TSF |
| 4% | chr11 | 60701014 | 60701216 | + | ENST00000453848; ENST00000005286; ENST00000536409 | chr11 | 60701443 | 60701575 | + | TSF |
| 4% | chr2 | 142238102 | 142237965 | − | ENST00000389484 | chr2 | 142187372 | 142187047 | − | TSF |
| 3% | chr20 | 49458303 | 49458437 | + | ENST00000358791; ENST00000371608; ENST00000609336 | chr20 | 49468479 | 49468517 | + | TSF |
| 3% | chr20 | 49458303 | 49458437 | + | ENST00000358791; ENST00000371608; ENST00000609336 | chr20 | 49468479 | 49468517 | + | TSF |
| 3% | chr7 | 16900207 | 16900124 | − | ENST00000402239; ENST00000310398; ENST00000414935 | chr7 | 16894536 | 16894260 | − | TSF |
| 3% | chr7 | 16900207 | 16900124 | − | ENST00000402239; ENST00000310398; ENST00000414935 | chr7 | 16894536 | 16894260 | − | TSF |
| 3% | chr13 | 111315865 | 111315798 | − | ENST00000257347; ENST00000487253; ENST00000537743 | chr13 | 111312615 | 111311877 | − | TSF |
| 3% | chr13 | 111315865 | 111315798 | − | ENST00000257347; ENST00000487253; ENST00000537743 | chr13 | 111312615 | 111311877 | − | TSF |
| 3% | chr13 | 111315865 | 111315798 | − | ENST00000257347; ENST00000487253; ENST00000537743 | chr13 | 111312615 | 111311877 | − | TSF |
| 3% | chr5 | 70858101 | 70858347 | + | ENST00000358731; ENST00000525844 | chr5 | 70868141 | 70868205 | + | TSF |
| 3% | chr5 | 70858101 | 70858347 | + | ENST00000358731; ENST00000525844 | chr5 | 70868141 | 70868205 | + | TSF |
| 3% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 3% | chr6 | 152201790; 152201792 | 152201906 | + | ENST00000440973; ENST00000338799; ENST00000456483; ENST00000443427; ENST00000206249; ENST00000427531; ENST00000415488 | chr6 | 152261821 | 152262024 | + | TSF |

TABLE 9-continued

Transcript fusion for Breast Invasive Carcinoma (BRCA) Coordinates of the fusion sequences for which the donor is the Exon.

| 1 | 2 | 3 | 4 | 5 | 6 | 7 | 8 | 9 | 10 | 11 |
|---|---|---|---|---|---|---|---|---|---|---|
| 3% | chr6 | 152201790; 152201792 | 152201906 | + | ENST00000440973; ENST00000338799; ENST00000456483; ENST00000443427; ENST00000206249; ENST00000427531; ENST00000415488 | chr6 | 152261821 | 152262024 | + | TSF |
| 3% | chr6 | 152201790; 152201792 | 152201906 | + | ENST00000440973; ENST00000338799; ENST00000456483; ENST00000443427; ENST00000206249; ENST00000427531; ENST00000415488 | chr6 | 152261821 | 152262024 | + | TSF |
| 3% | chr10 | 116020945 | 116021054 | + | ENST00000603594; ENST00000392982 | chr10 | 116030863 | 116030985 | + | TSF |
| 3% | chr16 | 16381600 | 16381719 | + | ENST00000399336; ENST00000263012; ENST00000538468 | chr16 | 16382422 | 16382605 | + | TSF |
| 3% | chr16 | 16381600 | 16381719 | + | ENST00000399336; ENST00000263012; ENST00000538468 | chr16 | 16382422 | 16382605 | + | TSF |
| 3% | chr3 | 148563211 | 148563413 | + | ENST00000491148; ENST00000282957 | chr3 | 148570090 | 148570266 | + | TSF |
| 3% | chr1 | 117712793 | 117712729 | − | ENST00000359008; ENST00000328189; ENST00000369458 | chr1 | 117699971 | 117699928 | − | TSF |
| 3% | chr1 | 117712793 | 117712729 | − | ENST00000359008; ENST00000328189; ENST00000369458 | chr1 | 117699971 | 117699928 | − | TSF |
| 3% | chr8 | 126194345 | 126194498 | + | ENST00000523741; ENST00000517532; ENST00000287437; ENST00000522563; ENST00000517315 | chr8 | 126207297 | 126207395 | + | TSF |
| 3% | chr8 | 126194345 | 126194498 | + | ENST00000523741; ENST00000517532; ENST00000287437; ENST00000522563; ENST00000517315 | chr8 | 126207297 | 126207395 | + | TSF |
| 2% | chr20 | 29632611 | 29632721 | + | ENST00000278882; ENST00000358464 | chr20 | 29652086 | 29652324 | + | TSF |
| 2% | chr10 | 19571948 | 19572110 | + | ENST00000377266; ENST00000454679 | chr10 | 19575490 | 19575970 | + | TSF |
| 2% | chr10 | 19571948 | 19572110 | + | ENST00000377266; ENST00000454679 | chr10 | 19575490 | 19575970 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr8 | 52287291 | 52287157 | − | ENST00000522628; ENST00000356297; ENST00000543296 | chr8 | 52286772 | 52286772 | − | TSF |
| 2% | chr8 | 52287291 | 52287157 | − | ENST00000522628; ENST00000356297; ENST00000543296 | chr8 | 52286772 | 52286772 | − | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |

TABLE 9-continued

Transcript fusion for Breast Invasive Carcinoma (BRCA) Coordinates of the fusion sequences for which the donor is the Exon.

| 1 | 2 | 3 | 4 | 5 | 6 | 7 | 8 | 9 | 10 | 11 |
|---|---|---|---|---|---|---|---|---|---|---|
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr7 | 142829210 | 142829304 | + | ENST00000291009 | chr7 | 142856912 | 142857269 | + | TSF |
| 2% | chr9 | 37842086 | 37842283 | + | ENST00000377724; ENST00000242323 | chr9 | 37853047 | 37853165 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr8 | 42932359 | 42932507 | + | ENST00000302279; ENST00000342116; ENST00000529687; ENST00000533336 | chr8 | 42934165 | 42935743 | + | TSF |
| 2% | chr8 | 42932359 | 42932507 | + | ENST00000302279; ENST00000342116; ENST00000529687; ENST00000533336 | chr8 | 42934165 | 42935743 | + | TSF |
| 2% | chr8 | 42932359 | 42932507 | + | ENST00000302279; ENST00000342116; ENST00000529687; ENST00000533336 | chr8 | 42934165 | 42935743 | + | TSF |
| 2% | chr8 | 42932359 | 42932507 | + | ENST00000302279; ENST00000342116; ENST00000529687; ENST00000533336 | chr8 | 42934165 | 42935743 | + | TSF |
| 2% | chr1 | 180283857 | 180283827 | − | ENST00000367595 | chr1 | 180281120 | 180281103 | − | TSF |
| 2% | chrX | 41598709 | 41598637 | − | ENST00000421587; ENST00000318588; ENST00000361962; ENST00000378163; ENST00000378158; ENST00000378166; ENST00000442742; ENST00000378154 | chrX | 41557348 | 41557057 | − | TSF |
| 2% | chr17 | 70732858 | 70732789 | − | ENST00000255559; ENST00000542342; ENST00000582769; ENST00000581581 | chr17 | 70670711 | 70670228 | − | TSF |
| 2% | chr17 | 70732858 | 70732789 | − | ENST00000255559; ENST00000542342; ENST00000582769; ENST00000581581 | chr17 | 70670711 | 70670228 | − | TSF |
| 2% | chr17 | 70732858 | 70732789 | − | ENST00000255559; ENST00000542342; ENST00000582769; ENST00000581581 | chr17 | 70670711 | 70670228 | − | TSF |
| 2% | chr17 | 70732858 | 70732789 | − | ENST00000255559; ENST00000542342; ENST00000582769; ENST00000581581 | chr17 | 70670711 | 70670228 | − | TSF |
| 2% | chr10 | 43601824 | 43602019 | + | ENST00000355710; ENST00000340058 | chr10 | 43602522 | 43602638 | + | TSF |
| 2% | chr12 | 113623819 | 113623826 | + | ENST00000552495 | chr12 | 113623998 | 113624117 | + | TSF |
| 2% | chrX | 148628285 | 148628463 | + | ENST00000434353; ENST00000514208; ENST00000422892; ENST00000450602; ENST00000441248; ENST00000393985; ENST00000423421; ENST00000423540; ENST00000428236; ENST00000359293 | chrX | 148638635 | 148638790 | + | TSF |

TABLE 9-continued

Transcript fusion for Breast Invasive Carcinoma (BRCA) Coordinates of the fusion sequences for which the donor is the Exon.

| 1 | 2 | 3 | 4 | 5 | 6 | 7 | 8 | 9 | 10 | 11 |
|---|---|---|---|---|---|---|---|---|---|---|
| 2% | chrX | 148628285 | 148628463 | + | ENST00000434353; ENST00000514208; ENST00000422892; ENST00000450602; ENST00000441248; ENST00000393985; ENST00000423421; ENST00000423540; ENST00000428236; ENST00000359293 | chrX | 148638635 | 148638790 | + | TSF |
| 2% | chr22 | 47882528 | 47882479 | − | ENST00000405369 | chr22 | 47880391 | 47879942 | − | TSF |
| 2% | chr2 | 214228800 | 214228869 | + | ENST00000331683; ENST00000272898; ENST00000447990; ENST00000374309; ENST00000413312 | chr2 | 214233538 | 214233723 | + | TSF |
| 2% | chr2 | 214228800 | 214228869 | + | ENST00000331683; ENST00000272898; ENST00000447990; ENST00000374309; ENST00000413312 | chr2 | 214233538 | 214233723 | + | TSF |
| 2% | chr2 | 214228800 | 214228869 | + | ENST00000331683; ENST00000272898; ENST00000447990; ENST00000374309; ENST00000413312 | chr2 | 214233538 | 214233723 | + | TSF |
| 2% | chr9 | 125054028 | 125054119 | + | ENST00000297908; ENST00000344641; ENST00000373723; ENST00000373729; ENST00000394315 | chr9 | 125068067 | 125068171 | + | TSF |
| 2% | chr9 | 125054028 | 125054119 | + | ENST00000297908; ENST00000344641; ENST00000373723; ENST00000373729; ENST00000394315 | chr9 | 125068067 | 125068171 | + | TSF |
| 2% | chr9 | 125054028 | 125054119 | + | ENST00000297908; ENST00000344641; ENST00000373723; ENST00000373729; ENST00000394315 | chr9 | 125068067 | 125068171 | + | TSF |
| 2% | chrX | 149100985 | 149100807 | − | ENST00000370406; ENST00000355203; ENST00000370404; ENST00000370409; ENST00000462691 | chrX | 149090624 | 149090469 | − | TSF |
| 2% | chr3 | 4867546 | 4867430 | − | ENST00000449914 | chr3 | 4841712 | 4841679 | − | TSF |
| 2% | chr11 | 9069109 | 9068903 | − | ENST00000457346; ENST00000309263; ENST00000450649; ENST00000520467 | chr11 | 9062448 | 9062264 | − | TSF |
| 2% | chr11 | 9069109 | 9068903 | − | ENST00000457346; ENST00000309263; ENST00000450649; ENST00000520467 | chr11 | 9062448 | 9062264 | − | TSF |
| 2% | chr11 | 9069109 | 9068903 | − | ENST00000457346; ENST00000309263; ENST00000450649; ENST00000520467 | chr11 | 9062448 | 9062264 | − | TSF |
| 2% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 2% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 2% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 2% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 2% | chr8 | 145001050 | 1450010952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 2% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 2% | chr8 | 145001050 | 145000952 | − | ENST00000345136; ENST00000357649; ENST00000354589; ENST00000398774; ENST00000322810; ENST00000354958; ENST00000356346; ENST00000436759; | chr8 | 144977746 | 144977671 | − | TSF |

TABLE 9-continued

Transcript fusion for Breast Invasive Carcinoma (BRCA) Coordinates of the fusion sequences for which the donor is the Exon.

| 1 | 2 | 3 | 4 | 5 | 6 | 7 | 8 | 9 | 10 | 11 |
|---|---|---|---|---|---|---|---|---|---|---|
| 2% | chr8 | 145001050 | 145000952 | − | ENST00000527096; ENST00000527303 ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 2% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 2% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 2% | chr8 | 104778455 | 104778765 | + | ENST00000504942; ENST00000406091 | chr8 | 104821508 | 104821527 | + | TSF |
| 2% | chr12 | 40940937 | 40940984 | + | ENST00000380816 | chr12 | 40941279 | 40941378 | + | TSF |
| 2% | chr1 | 155036300 | 155036412 | + | ENST00000368409; ENST00000359751; ENST00000556931; ENST00000505139; ENST00000427683 | chr1 | 155036918 | 155037085 | + | TSF |
| 2% | chr8 | 109468102 | 109468159 | + | ENST00000220853; ENST00000519642 | chr8 | 109468381 | 109468590 | + | TSF |
| 2% | chr8 | 109468102 | 109468159 | + | ENST00000220853; ENST00000519642 | chr8 | 109468381 | 109468590 | + | TSF |
| 2% | chr10 | 37490163 | 37490253 | + | ENST00000361713; ENST00000374660; ENST00000602533 | chr10 | 37491222 | 37494539 | + | TSF |
| 2% | chr10 | 37490163 | 37490253 | + | ENST00000361713; ENST00000374660; ENST00000602533 | chr10 | 37491222 | 37494539 | + | TSF |
| 2% | chr6 | 610178 | 610098 | − | ENST00000230449 | chr6 | 607066 | 606461 | − | TSF |
| 2% | chr10 | 127483547 | 127483449 | − | ENST00000368797; ENST00000368786 | chr10 | 127473829 | 127473633 | − | TSF |
| 1% | chr7 | 142832287 | 142832392 | + | ENST00000291009 | chr7 | 142856912 | 142857269 | + | TSF |
| 1% | chr5 | 54993786 | 54993674 | − | ENST00000396865; ENST00000539768; ENST00000318672; ENST00000508124; ENST00000511233; ENST00000503891; ENST00000513993; ENST00000505563; ENST00000506624; ENST00000507109 | chr5 | 54993040 | 54992544 | − | TSF |
| 1% | chr1 | 11115877; 11115983 | 11115838 | − | ENST00000490101; ENST00000376957 | chr1 | 11115464 | 11115178 | − | TSF |
| 1% | chr1 | 11115877; 11115983 | 11115838 | − | ENST00000490101; ENST00000376957 | chr1 | 11115464 | 11115178 | − | TSF |
| 1% | chr8 | 71619168 | 71619388 | + | ENST00000408926; ENST00000520030 | chr8 | 71625661 | 71625673 | + | TSF |
| 1% | chr15 | 74219125 | 74220226 | + | ENST00000566011; ENST00000261921 | chr15 | 74234853 | 74234966 | + | TSF |
| 1% | chrX | 117900807 | 117900939 | + | ENST00000371666 | chrX | 117902549 | 117902902 | + | TSF |
| 1% | chr11 | 9069109 | 9068903 | − | ENST00000457346; ENST00000309263; ENST00000450649; ENST00000520467 | chr11 | 9068729 | 9068631 | − | TSF |
| 1% | chr11 | 9069109 | 9068903 | − | ENST00000457346; ENST00000309263; ENST00000450649; ENST00000520467 | chr11 | 9068729 | 9068631 | − | TSF |
| 1% | chr11 | 9069109 | 9068903 | − | ENST00000457346; ENST00000309263; ENST00000450649; ENST00000520467 | chr11 | 9068729 | 9068631 | − | TSF |
| 1% | chr17 | 60107012 | 60106902 | − | ENST00000397786; ENST00000583958 | chr17 | 60101011 | 60100641 | − | TSF |
| 1% | chr17 | 60107012 | 60106902 | − | ENST00000397786; ENST00000583958 | chr17 | 60101011 | 60100641 | − | TSF |
| 1% | chr6 | 151738534 | 151738414 | − | ENST00000336451; ENST00000367303 | chr6 | 151732046 | 151731858 | − | TSF |
| 1% | chr6 | 151738534 | 151738414 | − | ENST00000336451; ENST00000367303 | chr6 | 151732046 | 151731858 | − | TSF |
| 1% | chr20 | 41306799 | 41306506 | − | ENST00000356100; ENST00000373184; ENST00000373187; ENST00000373190; ENST00000373193; ENST00000373198; ENST00000373201 | chr20 | 41171740 | 41171524 | − | TSF |
| 1% | chr14 | 24845500; 24845580 | 24846084 | + | ENST00000555590; ENST00000556279; ENST00000250373; ENST00000553879; ENST00000554344; ENST00000555453; ENST00000556759; ENST00000413692; ENST00000424781; ENST00000539237; ENST00000553708; ENST00000422617; ENST00000557451; ENST00000555167; ENST00000555802; ENST00000555393 | chr14 | 24854777 | 24855120 | + | TSF |
| 1% | chr14 | 24845500; 24845580 | 24846084 | + | ENST00000555590; ENST00000556279; ENST00000250373; ENST00000553879; ENST00000554344; ENST00000555453; ENST00000556759; ENST00000413692; ENST00000424781; ENST00000539237; ENST00000553708; ENST00000422617; | chr14 | 24854777 | 24855120 | + | TSF |

TABLE 9-continued

Transcript fusion for Breast Invasive Carcinoma (BRCA) Coordinates of the fusion sequences for which the donor is the Exon.

| 1 | 2 | 3 | 4 | 5 | 6 | 7 | 8 | 9 | 10 | 11 |
|---|---|---|---|---|---|---|---|---|---|---|
| 1% | chr14 | 24845500; 24845580 | 24846084 | + | ENST00000557451; ENST00000555167; ENST00000555802; ENST00000555393 ENST00000555590; ENST00000556279; ENST00000250373; ENST00000553879; ENST00000554344; ENST00000555453; ENST00000556759; ENST00000413692; ENST00000424781; ENST00000539237; ENST00000553708; ENST00000422617; | chr14 | 24854777 | 24855120 | + | TSF |
| 1% | chr14 | 24845500; 24845580 | 24846084 | + | ENST00000557451; ENST00000555167; ENST00000555802; ENST00000555393 ENST00000555590; ENST00000556279; ENST00000250373; ENST00000553879; ENST00000554344; ENST00000555453; ENST00000556759; ENST00000413692; ENST00000424781; ENST00000539237; ENST00000553708; ENST00000422617; | chr14 | 24854777 | 24855120 | + | TSF |
| 1% | chr14 | 24845500; 24845580 | 24846084 | + | ENST00000557451; ENST00000555167; ENST00000555802; ENST00000555393 ENST00000555590; ENST00000556279; ENST00000250373; ENST00000553879; ENST00000554344; ENST00000555453; ENST00000556759; ENST00000413692; ENST00000424781; ENST00000539237; ENST00000553708; ENST00000422617; | chr14 | 24854777 | 24855120 | + | TSF |
| 1% | chr14 | 24845500; 24845580 | 24846084 | + | ENST00000557451; ENST00000555167; ENST00000555802; ENST00000555393 ENST00000555590; ENST00000556279; ENST00000250373; ENST00000553879; ENST00000554344; ENST00000555453; ENST00000556759; ENST00000413692; ENST00000424781; ENST00000539237; ENST00000553708; ENST00000422617; | chr14 | 24854777 | 24855120 | + | TSF |
| 1% | chr14 | 24845500; 24845580 | 24846084 | + | ENST00000557451; ENST00000555167; ENST00000555802; ENST00000555393 ENST00000555590; ENST00000556279; ENST00000250373; ENST00000553879; ENST00000554344; ENST00000555453; ENST00000556759; ENST00000413692; ENST00000424781; ENST00000539237; ENST00000553708; ENST00000422617; | chr14 | 24854777 | 24855120 | + | TSF |
| 1% | chr14 | 24845500; 24845580 | 24846084 | + | ENST00000557451; ENST00000555167; ENST00000555802; ENST00000555393 ENST00000555590; ENST00000556279; ENST00000250373; ENST00000553879; ENST00000554344; ENST00000555453; ENST00000556759; ENST00000413692; ENST00000424781; ENST00000539237; ENST00000553708; ENST00000422617; | chr14 | 24854777 | 24855120 | + | TSF |
| 1% | chr10 | 37490163 | 37490253 | + | ENST00000361713; ENST00000374660; ENST00000602533 | chr10 | 37501432 | 37501641 | + | TSF |
| 1% | chr10 | 37490163 | 37490253 | + | ENST00000361713; ENST00000374660; ENST00000602533 | chr10 | 37501432 | 37501641 | + | TSF |
| 1% | chr4 | 146617711 | 146617784 | + | ENST00000438731; ENST00000511965 | chr4 | 146620339 | 146620424 | + | TSF |
| 1% | chr4 | 146617711 | 146617784 | + | ENST00000438731; ENST00000511965 | chr4 | 146620339 | 146620424 | + | TSF |
| 1% | chr8 | 17872093 | 17872349 | + | ENST00000325083; ENST00000519253; ENST00000327578; ENST00000522275 | chr8 | 17873210 | 17873221 | + | TSF |
| 1% | chr8 | 17872093 | 17872349 | + | ENST00000325083; ENST00000519253; ENST00000327578; ENST00000522275 | chr8 | 17873210 | 17873221 | + | TSF |
| 1% | chr8 | 17872093 | 17872349 | + | ENST00000325083; ENST00000519253; ENST00000327578; ENST00000522275 | chr8 | 17873210 | 17873221 | + | TSF |
| 1% | chr8 | 17872093 | 17872349 | + | ENST00000325083; ENST00000519253; ENST00000327578; ENST00000522275 | chr8 | 17873210 | 17873221 | + | TSF |
| 1% | chr6 | 152201790; 152201792 | 152201906 | + | ENST00000440973; ENST00000338799; ENST00000456483; ENST00000443427; ENST00000206249; ENST00000427531; ENST00000415488 | chr6 | 152233905 | 152234264 | + | TSF |
| 1% | chr6 | 152201790; 152201792 | 152201906 | + | ENST00000440973; ENST00000338799; ENST00000456483; ENST00000443427; ENST00000206249; ENST00000427531; ENST00000415488 | chr6 | 152233905 | 152234264 | + | TSF |

TABLE 9-continued

Transcript fusion for Breast Invasive Carcinoma (BRCA) Coordinates of the fusion sequences for which the donor is the Exon.

| 1 | 2 | 3 | 4 | 5 | 6 | 7 | 8 | 9 | 10 | 11 |
|---|---|---|---|---|---|---|---|---|---|---|
| 1% | chr6 | 152201790; 152201792 | 152201906 | + | ENST00000440973; ENST00000338799; ENST00000456483; ENST00000443427; ENST00000206249; ENST00000427531; ENST00000415488 | chr6 | 152233905 | 152234264 | + | TSF |
| 1% | chr20 | 41101202 | 41100906 | − | ENST00000356100; ENST00000373184; ENST00000373187; ENST00000373190; ENST00000373193; ENST00000373198; ENST00000373201 | hr20 | 41094843 | 41094411 | − | TSF |
| 1% | chr3 | 188956522 | 188956698 | + | ENST00000433971; ENST00000345063; ENST00000425670 | chr3 | 188963972 | 188964159 | + | TSF |
| 1% | chr3 | 188956522 | 188956698 | + | ENST00000433971; ENST00000345063; ENST00000425670 | chr3 | 188963972 | 188964159 | + | TSF |
| 1% | chr5 | 23976106 | 23976159 | + | ENST00000512559; ENST00000507936 | chr5 | 24177946 | 24178380 | + | TSF |
| 1% | chr7 | 16901071 | 16901008 | − | ENST00000310398; ENST00000402239; ENST00000414935 | chr7 | 16894536 | 16894260 | − | TSF |
| 1% | chr7 | 16901071 | 16901008 | − | ENST00000310398; ENST00000402239; ENST00000414935 | chr7 | 16894536 | 16894260 | − | TSF |
| 1% | chr11 | 100912833 | 100912676 | − | ENST00000325455; ENST00000534013; ENST00000263463 | chr11 | 100911331 | 100910821 | − | TSF |
| 1% | chr11 | 100912833 | 100912676 | − | ENST00000325455; ENST00000534013; ENST00000263463 | chr11 | 100911331 | 100910821 | − | TSF |
| 1% | chr11 | 10092833 | 100912676 | − | ENST00000325455; ENST00000534013; ENST00000263463 | chr11 | 100911331 | 100910821 | − | TSF |
| 1% | chr17 | 34802073 | 34802035 | − | ENST00000330458; ENST00000535805; ENST00000535592; ENST00000394453; ENST00000592614; ENST00000341264 | chr17 | 34772854 | 34772787 | − | TSF |
| 1% | chr17 | 34802073 | 34802035 | − | ENST00000330458; ENST00000535805; ENST00000535592; ENST00000394453; ENST00000592614; ENST00000341264 | chr17 | 34772854 | 34772787 | − | TSF |
| 1% | chr19 | 23556639 | 23556544 | − | ENST00000599743; ENST00000300619 | chr19 | 23491899 | 23491588 | − | TSF |
| 1% | chr17 | 1928159 | 1928147 | − | ENST00000331238 | chr17 | 1917588 | 1917538 | − | TSF |
| 1% | chr13 | 114157811 | 114157903 | + | ENST00000434316; ENST00000375391 | chr13 | 114159741 | 114159770 | + | TSF |
| 1% | chr13 | 98642687; 98642769 | 98642791 | + | ENST00000261574; ENST00000357602; ENST00000490680; ENST00000469360; ENST00000539640 | chr13 | 98643835 | 98643958 | + | TSF |
| 1% | chr13 | 98642687; 98642769 | 98642791 | + | ENST00000261574; ENST00000357602; ENST00000490680; ENST00000469360; ENST00000539640 | chr13 | 98643835 | 98643958 | + | TSF |
| 1% | chr13 | 98642687; 98642769 | 98642791 | + | ENST00000261574; ENST00000357602; ENST00000490680; ENST00000469360; ENST00000539640 | chr13 | 98643835 | 98643958 | + | TSF |
| 1% | chr13 | 98642687; 98642769 | 98642791 | + | ENST00000261574; ENST00000357602; ENST00000490680; ENST00000469360; ENST00000539640 | chr13 | 98643835 | 98643958 | + | TSF |
| 1% | chr4 | 56230241 | 56230438 | + | ENST00000264228 | chr4 | 56252510 | 56252750 | + | TSF |
| 1% | chr1 | 33138392 | 33138502 | + | ENST00000414241; ENST00000373493; ENST00000544435; ENST00000373485; ENST00000458695; ENST00000475321; ENST00000463378; ENST00000460669; ENST00000482190 | chr1 | 33145073 | 33145159 | + | TSF |
| 1% | chr1 | 33138392 | 33138502 | + | ENST00000414241; ENST00000373493; ENST00000544435; ENST00000373485; ENST00000458695; ENST00000475321; ENST00000463378; ENST00000460669; ENST00000482190 | chr1 | 33145073 | 33145159 | + | TSF |
| 1% | chr1 | 33138392 | 33138502 | + | ENST00000414241; ENST00000373493; ENST00000544435; ENST00000373485; ENST00000458695; ENST00000475321; ENST00000463378; ENST00000460669; ENST00000482190 | chr1 | 33145073 | 33145159 | + | TSF |
| 1% | chr1 | 33138392 | 33138502 | + | ENST00000414241; ENST00000373493; ENST00000544435; ENST00000373485; ENST00000458695; ENST00000475321; ENST00000463378; ENST00000460669; ENST00000482190 | chr1 | 33145073 | 33145159 | + | TSF |
| 1% | chr1 | 33138392 | 33138502 | + | ENST00000414241; ENST00000373493; ENST00000544435; ENST00000373485; ENST00000458695; ENST00000475321; ENST00000463378; ENST00000460669; ENST00000482190 | chr1 | 33145073 | 33145159 | + | TSF |

TABLE 9-continued

Transcript fusion for Breast Invasive Carcinoma (BRCA) Coordinates of the fusion sequences for which the donor is the Exon.

| 1 | 2 | 3 | 4 | 5 | 6 | 7 | 8 | 9 | 10 | 11 |
|---|---|---|---|---|---|---|---|---|----|----|
| 1% | chr1 | 33138392 | 33138502 | + | ENST00000414241; ENST00000373493; ENST00000544435; ENST00000373485; ENST00000458695; ENST00000475321; ENST00000463378; ENST00000460669; ENST00000482190 | chr1 | 33145073 | 33145159 | + | TSF |
| 1% | chr1 | 33138392 | 33138502 | + | ENST00000414241; ENST00000373493; ENST00000544435; ENST00000373485; ENST00000458695; ENST00000475321; ENST00000463378; ENST00000460669; ENST00000482190 | chr1 | 33145073 | 33145159 | + | TSF |
| 1% | chr1 | 33138392 | 33138502 | + | ENST00000414241; ENST00000373493; ENST00000544435; ENST00000373485; ENST00000458695; ENST00000475321; ENST00000463378; ENST00000460669; ENST00000482190 | chr1 | 33145073 | 33145159 | + | TSF |
| 1% | chr2 | 143743517 | 143743590 | + | ENST00000264170; ENST00000375773; ENST00000409512 | chr2 | 143745513 | 143745682 | + | TSF |
| 1% | chr1 | 63955889 | 63955754 | − | ENST00000371092; ENST00000271002; ENST00000489099; ENST00000283568 | chr1 | 63952444 | 63951983 | − | TSF |
| 1% | chr1 | 63955889 | 63955754 | − | ENST00000371092; ENST00000271002; ENST00000489099; ENST00000283568 | chr1 | 63952444 | 63951983 | − | TSF |
| 1% | chr8 | 141711121 | 141710990 | − | ENST00000522684; ENST00000519654; ENST00000535192; ENST00000519465; ENST00000517887; ENST00000521059; ENST00000395218; ENST00000523539; ENST00000538769; ENST00000340930; ENST00000519419; ENST00000430260; ENST00000521986 | chr8 | 141701376 | 141701371 | − | TSF |
| 1% | chr8 | 141711121 | 141710990 | − | ENST00000522684; ENST00000519654; ENST00000535192; ENST00000519465; ENST00000517887; ENST00000521059; ENST00000395218; ENST00000523539; ENST00000538769; ENST00000340930; ENST00000519419; ENST00000430260; ENST00000521986 | chr8 | 141701376 | 141701371 | − | TSF |
| 1% | chr8 | 141711121 | 141710990 | − | ENST00000522684; ENST00000519654; ENST00000535192; ENST00000519465; ENST00000517887; ENST00000521059; ENST00000395218; ENST00000523539; ENST00000538769; ENST00000340930; ENST00000519419; ENST00000430260; ENST00000521986 | chr8 | 141701376 | 141701371 | − | TSF |
| 1% | chr8 | 141711121 | 141710990 | − | ENST00000522684; ENST00000519654; ENST00000535192; ENST00000519465; ENST00000517887; ENST00000521059; ENST00000395218; ENST00000523539; ENST00000538769; ENST00000340930; ENST00000519419; ENST00000430260; ENST00000521986 | chr8 | 141701376 | 141701371 | − | TSF |
| 1% | chr8 | 141711121 | 141710990 | − | ENST00000522684; ENST00000519654; ENST00000535192; ENST00000519465; ENST00000517887; ENST00000521059; ENST00000395218; ENST00000523539; ENST00000538769; ENST00000340930; ENST00000519419; ENST00000430260; ENST00000521986 | chr8 | 141701376 | 141701371 | − | TSF |
| 1% | chr8 | 141711121 | 141710990 | − | ENST00000522684; ENST00000519654; ENST00000535192; ENST00000519465; ENST00000517887; ENST00000521059; ENST00000395218; ENST00000523539; ENST00000538769; ENST00000340930; ENST00000519419; ENST00000430260; ENST00000521986 | chr8 | 141701376 | 141701371 | − | TSF |
| 1% | chr8 | 141711121 | 141710990 | − | ENST00000522684; ENST00000519654; ENST00000535192; ENST00000519465; ENST00000517887; ENST00000521059; ENST00000395218; ENST00000523539; ENST00000538769; ENST00000340930; ENST00000519419; ENST00000430260; ENST00000521986 | chr8 | 141701376 | 141701371 | − | TSF |

TABLE 9-continued

Transcript fusion for Breast Invasive Carcinoma (BRCA) Coordinates of the fusion sequences for which the donor is the Exon.

| 1 | 2 | 3 | 4 | 5 | 6 | 7 | 8 | 9 | 10 | 11 |
|---|---|---|---|---|---|---|---|---|---|---|
| 1% | chr8 | 141711121 | 141710990 | − | ENST00000522684; ENST00000519654; ENST00000535192; ENST00000519465; ENST00000517887; ENST00000521059; ENST00000395218; ENST00000523539; ENST00000538769; ENST00000340930; ENST00000519419; ENST00000430260; ENST00000521986 | chr8 | 141701376 | 141701371 | − | TSF |
| 1% | chr8 | 141711121 | 141710990 | − | ENST00000522684; ENST00000519654; ENST00000535192; ENST00000519465; ENST00000517887; ENST00000521059; ENST00000395218; ENST00000523539; ENST00000538769; ENST00000340930; ENST00000519419; ENST00000430260; ENST00000521986 | chr8 | 141701376 | 141701371 | − | TSF |
| 1% | chr12 | 56742407 | 56742313 | − | ENST00000314128; ENST00000557235 | chr12 | 56740986 | 56740975 | − | TSF |
| 1% | chr12 | 56742407 | 56742313 | − | ENST00000314128; ENST00000557235 | chr12 | 56740986 | 56740975 | − | TSF |
| 1% | chr19 | 3869013; 3869015 | 3868963 | − | ENST00000586578; ENST00000262961; ENST00000438164; ENST00000587212; ENST00000439086 | chr19 | 3855694 | 3855445 | − | TSF |
| 1% | chr19 | 3869013; 3869015 | 3868963 | − | ENST00000586578; ENST00000262961; ENST00000438164; ENST00000587212; ENST00000439086 | chr19 | 3855694 | 3855445 | − | TSF |
| 1% | chr3 | 4872702 | 4872631 | − | ENST00000449914; ENST00000441894 | chr3 | 4871474 | 4871202 | − | TSF |
| 1% | chr11 | 86534430 | 86534635 | + | ENST00000532234; ENST00000533902 | chr11 | 86589356 | 86590488 | + | TSF |
| 1% | chr11 | 82698812 | 82698629 | − | ENST00000525117; ENST00000532548; ENST00000524635; ENST00000533486; ENST00000260056; ENST00000533014; ENST00000527633; ENST00000531021; ENST00000534301 | chr11 | 82695638 | 82695143 | − | TSF |
| 1% | chr11 | 82698812 | 82698629 | − | ENST00000525117; ENST00000532548; ENST00000524635; ENST00000533486; ENST00000260056; ENST00000533014; ENST00000527633; ENST00000531021; ENST00000534301 | chr11 | 82695638 | 82695143 | − | TSF |
| 1% | chr11 | 82698812 | 82698629 | − | ENST00000525117; ENST00000532548; ENST00000524635; ENST00000533486; ENST00000260056; ENST00000533014; ENST00000527633; ENST00000531021; ENST00000534301 | chr11 | 82695638 | 82695143 | − | TSF |
| 1% | chr11 | 82698812 | 82698629 | − | ENST00000525117; ENST00000532548; ENST00000524635; ENST00000533486; ENST00000260056; ENST00000533014; ENST00000527633; ENST00000531021; ENST00000534301 | chr11 | 82695638 | 82695143 | − | TSF |
| 1% | chr3 | 48716169 | 48715997 | − | ENST00000413374; ENST00000341520; ENST00000416649; ENST00000294129 | chr3 | 48702393 | 48702198 | − | TSF |
| 1% | chr3 | 48716169 | 48715997 | − | ENST00000413374; ENST00000341520; ENST00000416649; ENST00000294129 | chr3 | 48702393 | 48702198 | − | TSF |
| 1% | chr3 | 48716169 | 48715997 | − | ENST00000413374; ENST00000341520; ENST00000416649; ENST00000294129 | chr3 | 48702393 | 48702198 | − | TSF |
| 1% | chr11 | 9047401 | 9047249 | − | ENST00000519202; ENST00000457346; ENST00000309263; ENST00000450649; ENST00000520467; ENST00000528651 | chr11 | 9045506 | 9045449 | − | TSF |
| 1% | chr11 | 9047401 | 9047249 | − | ENST00000519202; ENST00000457346; ENST00000309263; ENST00000450649; ENST00000520467; ENST00000528651 | chr11 | 9045506 | 9045449 | − | TSF |
| 1% | chr11 | 9047401 | 9047249 | − | ENST00000519202; ENST00000457346; ENST00000309263; ENST00000450649; ENST00000520467; ENST00000528651 | chr11 | 9045506 | 9045449 | − | TSF |
| 1% | chr11 | 9047401 | 9047249 | − | ENST00000519202; ENST00000457346; ENST00000309263; ENST00000450649; ENST00000520467; ENST00000528651 | chr11 | 9045506 | 9045449 | − | TSF |
| 1% | chr11 | 9047401 | 9047249 | − | ENST00000519202; ENST00000457346; ENST00000309263; ENST00000450649; ENST00000520467; ENST00000528651 | chr11 | 9045506 | 9045449 | − | TSF |
| 1% | chr11 | 9047401 | 9047249 | − | ENST00000519202; ENST00000457346; ENST00000309263; ENST00000450649; ENST00000520467; ENST00000528651 | chr11 | 9045506 | 9045449 | − | TSF |

TABLE 10

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 39% | chr8 | 104389530 | 104389551 | + | chr8 | 104390255 | 104390471 | + | ENST00000330295; ENST00000520337 | TAF |
| 31% | chr4 | 95982945 | 95983246 | + | chr4 | 96025559 | 96025718 | + | ENST00000440890 | TAF |
| 25% | chr17 | 75318693 | 75318752 | + | chr17 | 75398141 | 75398484; 75398497; 75398565; 75398785 | + | ENST00000589070; ENST00000591934; ENST00000589140; ENST00000427177; ENST00000591198; ENST00000329047; ENST00000590294; ENST00000423034 | TAF |
| 25% | chr17 | 75318693 | 75318752 | + | chr17 | 75398141 | 75398484; 75398497; 75398565; 75398785 | + | ENST00000589070; ENST00000591934; ENST00000589140; ENST00000427177; ENST00000591198; ENST00000329047; ENST00000590294; ENST00000423034 | TAF |
| 25% | chr17 | 75318693 | 75318752 | + | chr17 | 75398141 | 75398484; 75398497; 75398565; 75398785 | + | ENST00000589070; ENST00000591934; ENST00000589140; ENST00000427177; ENST00000591198; ENST00000329047; ENST00000590294; ENST00000423034 | TAF |
| 25% | chr17 | 75318693 | 75318752 | + | chr17 | 75398141 | 75398484; 75398497; 75398565; 75398785 | + | ENST00000589070; ENST00000591934; ENST00000589140; ENST00000427177; ENST00000591198; ENST00000329047; ENST00000590294; ENST00000423034 | TAF |
| 24% | chr16 | 78085262 | 78085350 | + | chr16 | 78085855 | 78085865 | + | ENST00000567430 | TAF |
| 21% | chr5 | 54528691 | 54528595 | − | chr5 | 54528374 | 54528189 | − | ENST00000282572 | TAF |
| 20% | chr17 | 30771499 | 30771536 | + | chr17 | 30773963 | 30774064 | + | ENST00000261712; ENST00000457654; ENST00000579451 | TAF |
| 20% | chr17 | 30771499 | 30771536 | + | chr17 | 30773963 | 30774064 | + | ENST00000261712; ENST00000457654; ENST00000579451 | TAF |
| 20% | chr10 | 22170801 | 22168673 | − | chr10 | 22095028 | 22094909 | − | ENST00000376980 | TSF |
| 19% | chr16 | 1631056 | 1630957 | − | chr16 | 1630851 | 1630760; 1630836 | − | ENST00000426508; ENST00000397417 | TAF |
| 19% | chr16 | 1631056 | 1630957 | − | chr16 | 1630851 | 1630760; 1630836 | − | ENST00000426508; ENST00000397417 | TAF |
| 18% | chr4 | 141581072 | 141581072 | − | chr4 | 141580859 | 141580742 | − | ENST00000442267 | TAF |
| 18% | chr5 | 70927667 | 70927725 | + | chr5 | 70927948 | 70928012 | + | ENST00000512218; ENST00000340941; ENST00000509358; ENST00000323375; ENST00000509539 | TAF |
| 18% | chr5 | 70927667 | 70927725 | + | chr5 | 70927948 | 70928012 | + | ENST00000512218; ENST00000340941; ENST00000509358; ENST00000323375; ENST00000509539 | TAF |
| 18% | chr5 | 70927667 | 70927725 | + | chr5 | 70927948 | 70928012 | + | ENST00000512218; ENST00000340941; ENST00000509358; ENST00000323375; ENST00000509539 | TAF |
| 18% | chr5 | 70927667 | 70927725 | + | chr5 | 70927948 | 70928012 | + | ENST00000512218; ENST00000340941; ENST00000509358; ENST00000323375; ENST00000509539 | TAF |
| 18% | chr19 | 49121994 | 49121817 | − | chr19 | 49121134 | 49121048 | − | ENST00000549920; ENST00000547897; ENST00000550645; ENST00000549370; ENST00000549273; ENST00000084795 | TAF |
| 18% | chr19 | 49121994 | 49121817 | − | chr19 | 49121134 | 49121048 | − | ENST00000549920; ENST00000547897; ENST00000550645; ENST00000549370; ENST00000549273; ENST00000084795 | TAF |
| 18% | chr19 | 49121994 | 49121817 | − | chr19 | 49121134 | 49121048 | − | ENST00000549920; ENST00000547897; ENST00000550645; ENST00000549370; ENST00000549273; ENST00000084795 | TAF |
| 18% | chr19 | 49121994 | 49121817 | − | chr19 | 49121134 | 49121048 | − | ENST00000549920; ENST00000547897; ENST00000550645; ENST00000549370; ENST00000549273; ENST00000084795 | TAF |
| 18% | chr19 | 49121994 | 49121817 | − | chr19 | 49121134 | 49121048 | − | ENST00000549920; ENST00000547897; ENST00000550645; ENST00000549370; ENST00000549273; ENST00000084795 | TAF |
| 18% | chr10 | 37457109 | 37457331 | + | chr10 | 37458458 | 37458486 | + | ENST00000361713; ENST00000374660 | TAF |
| 18% | chr10 | 37457109 | 37457331 | + | chr10 | 37458458 | 37458486 | + | ENST00000361713; ENST00000374660 | TAF |
| 18% | chr3 | 4858133 | 4857857 | − | chr3 | 4856115 | 4856088 | − | ENST00000449914; ENST00000441894 | TSF |
| 17% | chr10 | 37468901 | 37469123 | + | chr10 | 37470250 | 37470278 | + | ENST00000374660; ENST00000602533 | TAF |
| 17% | chr10 | 37457109 | 37457331 | + | chr10 | 37470250 | 37470278 | + | ENST00000374660; ENST00000602533 | TAF |
| 17% | chr3 | 4859338 | 4859117 | − | chr3 | 4856115 | 4856088 | − | ENST00000449914; ENST00000441894 | TSF |
| 16% | chr14 | 24105943 | 24105981 | + | chr14 | 24112361 | 24112428 | + | ENST00000432832; ENST00000250383; ENST00000344777; ENST00000557535; ENST00000553600 | TAF |
| 16% | chr14 | 24105943 | 24105981 | + | chr14 | 24112361 | 24112428 | + | ENST00000432832; ENST00000250383; ENST00000344777; ENST00000557535; ENST00000553600 | TAF |
| 16% | chr14 | 24105943 | 24105981 | + | chr14 | 24112361 | 24112428 | + | ENST00000432832; ENST00000250383; ENST00000344777; ENST00000557535; ENST00000553600 | TAF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 16% | chr14 | 24105943 | 24105981 | + | chr14 | 24112361 | 24112428 | + | ENST00000432832; ENST00000250383; ENST00000344777; ENST00000557535; ENST00000553600 | TAF |
| 16% | chr14 | 24105943 | 24105981 | + | chr14 | 24112361 | 24112428 | + | ENST00000432832; ENST00000250383; ENST00000344777; ENST00000557535; ENST00000553600 | TAF |
| 15% | chr3 | 4898685 | 4898320 | − | chr3 | 4872702 | 4872631 | − | ENST00000449914; ENST00000441894 | TAF |
| 15% | chr3 | 4898685 | 4898320 | − | chr3 | 4872702 | 4872631 | − | ENST00000449914; ENST00000441894 | TAF |
| 14% | chr7 | 16914458 | 16914438 | − | chr7 | 16913467 | 16913404 | − | ENST00000310398; ENST00000402239; ENST00000414935 | TAF |
| 14% | chr7 | 16914458 | 16914438 | − | chr7 | 16913467 | 16913404 | − | ENST00000310398; ENST00000402239; ENST00000414935 | TAF |
| 14% | chr7 | 16914458 | 16914438 | − | chr7 | 16913467 | 16913404 | − | ENST00000310398; ENST00000402239; ENST00000414935 | TAF |
| 14% | chr6 | 151739722 | 151739668 | − | chr6 | 151738534 | 151738414; 151738471 | − | ENST00000336451; ENST00000367303; ENST00000444024 | TAF |
| 14% | chr6 | 151739722 | 151739668 | − | chr6 | 151738534 | 151738414; 151738471 | − | ENST00000336451; ENST00000367303; ENST00000444024 | TAF |
| 14% | chr1 | 246581335 | 246580598 | − | chr1 | 246518396 | 246518333 | − | ENST00000388985; ENST00000403792 | TSF |
| 14% | chr1 | 246581335 | 246580598 | − | chr1 | 246518396 | 246518333 | − | ENST00000388985; ENST00000403792 | TSF |
| 13% | chr3 | 124560577 | 124560517 | − | chr3 | 124560398 | 124560230; 124560268 | − | ENST00000296181; ENST00000488466; ENST00000496703; ENST00000608657 | TAF |
| 13% | chr3 | 124560577 | 124560517 | − | chr3 | 124560398 | 124560230; 124560268 | − | ENST00000296181; ENST00000488466; ENST00000496703; ENST00000608657 | TAF |
| 13% | chr3 | 124560577 | 124560517 | − | chr3 | 124560398 | 124560230; 124560268 | − | ENST00000296181; ENST00000488466; ENST00000496703; ENST00000608657 | TAF |
| 13% | chr3 | 124560577 | 124560517 | − | chr3 | 124560398 | 124560230; 124560268 | − | ENST00000296181; ENST00000488466; ENST00000496703; ENST00000608657 | TAF |
| 13% | chr7 | 16840326 | 16840006 | − | chr7 | 16839441 | 16839368 | − | ENST00000419304; ENST00000450569; ENST00000419572; ENST00000401412; ENST00000412973 | TAF |
| 13% | chr7 | 16840326 | 16840006 | − | chr7 | 16839441 | 16839368 | − | ENST00000419304; ENST00000450569; ENST00000419572; ENST00000401412; ENST00000412973 | TAF |
| 13% | chr7 | 16840326 | 16840006 | − | chr7 | 16839441 | 16839368 | − | ENST00000419304; ENST00000450569; ENST00000419572; ENST00000401412; ENST00000412973 | TAF |
| 13% | chr7 | 16840326 | 16840006 | − | chr7 | 16839441 | 16839368 | − | ENST00000419304; ENST00000450569; ENST00000419572; ENST00000401412; ENST00000412973 | TAF |
| 12% | chr14 | 24631729 | 24631779 | + | chr14 | 24632175 | 24632191; 24632358 | + | ENST00000561342; ENST00000560852; ENST00000396864; ENST00000559284; ENST00000560275 | TAF |
| 12% | chr14 | 24631729 | 24631779 | + | chr14 | 24632175 | 24632191; 24632358 | + | ENST00000561342; ENST00000560852; ENST00000396864; ENST00000559284; ENST00000560275 | TAF |
| 12% | chr14 | 24631729 | 24631779 | + | chr14 | 24632175 | 24632191; 24632358 | + | ENST00000561342; ENST00000560852; ENST00000396864; ENST00000559284; ENST00000560275 | TAF |
| 12% | chr14 | 24631729 | 24631779 | + | chr14 | 24632175 | 24632191; 24632358 | + | ENST00000561342; ENST00000560852; ENST00000396864; ENST00000559284; ENST00000560275 | TAF |
| 12% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513; ENST00000412079 | TAF |
| 12% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513; ENST00000412079 | TAF |
| 12% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513; ENST00000412079 | TAF |
| 12% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513; ENST00000412079 | TAF |
| 12% | chr8 | 126168241 | 126168340 | + | chr8 | 126194345 | 126194498 | + | ENST00000523741; ENST00000517532; ENST00000287437; ENST00000522563; ENST00000517315 | TAF |
| 12% | chr8 | 126168241 | 126168340 | + | chr8 | 126194345 | 126194498 | + | ENST00000523741; ENST00000517532; ENST00000287437; ENST00000522563; ENST00000517315 | TAF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 12% | chr8 | 126168241 | 126168340 | + | chr8 | 126194345 | 126194498 | + | ENST00000523741; ENST00000517532; ENST00000287437; ENST00000522563; ENST00000517315 | TAF |
| 12% | chr19 | 16267516 | 16267566 | + | chr19 | 16268020 | 16268139; 16268205; 16268208; 16268448 | + | ENST00000593031; ENST00000397372; ENST00000253680; ENST00000593154; ENST00000588246 | TAF |
| 12% | chr19 | 16267516 | 16267566 | + | chr19 | 16268020 | 16268139; 16268205; 16268208; 16268448 | + | ENST00000593031; ENST00000397372; ENST00000253680; ENST00000593154; ENST00000588246 | TAF |
| 12% | chr19 | 16267516 | 16267566 | + | chr19 | 16268020 | 16268139; 16268205; 16268208; 16268448 | + | ENST00000593031; ENST00000397372; ENST00000253680; ENST00000593154; ENST00000588246 | TAF |
| 12% | chr19 | 16267516 | 16267566 | + | chr19 | 16268020 | 16268139; 16268205; 16268208; 16268448 | + | ENST00000593031; ENST00000397372; ENST00000253680; ENST00000593154; ENST00000588246 | TAF |
| 11% | chr11 | 93468219 | 93468129 | − | chr11 | 93467826 | 93467791; 93467814 | − | ENST00000393259; ENST00000527169 | TAF |
| 11% | chr11 | 93468219 | 93468129 | − | chr11 | 93467826 | 93467791; 93467814 | − | ENST00000393259; ENST00000527169 | TAF |
| 11% | chr6 | 33673107 | 33673041 | − | chr6 | 33669197 | 33669123 | − | ENST00000374231; ENST00000607484 | TAF |
| 11% | chr18 | 43686699 | 43686799 | + | chr18 | 43698147 | 43698282 | + | ENST00000282058; ENST00000592471 | TAF |
| 11% | chr18 | 43686699 | 43686799 | + | chr18 | 43698147 | 43698282 | + | ENST00000282058; ENST00000592471 | TAF |
| 10% | chr1 | 33142637 | 33142971 | + | chr1 | 33145241 | 33145299; 33145306; 33145415 | + | ENST00000482190; ENST00000414241; ENST00000373493; ENST00000544435; ENST00000458695; ENST00000460669; ENST00000463378 | TAF |
| 10% | chr1 | 33142637 | 33142971 | + | chr1 | 33145241 | 33145299; 33145306; 33145415 | + | ENST00000482190; ENST00000414241; ENST00000373493; ENST00000544435; ENST00000458695; ENST00000460669; ENST00000463378 | TAF |
| 10% | chr1 | 33142637 | 33142971 | + | chr1 | 33145241 | 33145299; 33145306; 33145415 | + | ENST00000482190; ENST00000414241; ENST00000373493; ENST00000544435; ENST00000458695; ENST00000460669; ENST00000463378 | TAF |
| 10% | chr4 | 107241932 | 107242850 | + | chr4 | 107246142 | 107246275 | + | ENST00000394701 | TAF |
| 10% | chrX | 80548900 | 80548905 | + | chrX | 80552694 | 80552726 | + | ENST00000373212 | TAF |
| 9% | chr18 | 33711482 | 33711615 | + | chr18 | 33713201 | 33713279 | + | ENST00000358232; ENST00000351393; ENST00000442325; ENST00000423854; ENST00000539560; ENST00000542430; ENST00000350494; ENST00000542824; ENST00000540799 | TSF |
| 9% | chr18 | 33711482 | 33711615 | + | chr18 | 33713201 | 33713279 | + | ENST00000358232; ENST00000351393; ENST00000442325; ENST00000423854; ENST00000539560; ENST00000542430; ENST00000350494; ENST00000542824; ENST00000540799 | TSF |
| 9% | chr18 | 33711482 | 33711615 | + | chr18 | 33713201 | 33713279 | + | ENST00000358232; ENST00000351393; ENST00000442325; ENST00000423854; ENST00000539560; ENST00000542430; ENST00000350494; ENST00000542824; ENST00000540799 | TSF |
| 9% | chr18 | 33711482 | 33711615 | + | chr18 | 33713201 | 33713279 | + | ENST00000358232; ENST00000351393; ENST00000442325; ENST00000423854; ENST00000539560; ENST00000542430; ENST00000350494; ENST00000542824; ENST00000540799 | TSF |
| 9% | chr18 | 33711482 | 33711615 | + | chr18 | 33713201 | 33713279 | + | ENST00000358232; ENST00000351393; ENST00000442325; ENST00000423854; ENST00000539560; ENST00000542430; ENST00000350494; ENST00000542824; ENST00000540799 | TSF |
| 9% | chr18 | 33711482 | 33711615 | + | chr18 | 33713201 | 33713279 | + | ENST00000358232; ENST00000351393; ENST00000442325; ENST00000423854; ENST00000539560; ENST00000542430; ENST00000350494; ENST00000542824; ENST00000540799 | TSF |
| 9% | chr18 | 33711482 | 33711615 | + | chr18 | 33713201 | 33713279 | + | ENST00000358232; ENST00000351393; ENST00000442325; ENST00000423854; ENST00000539560; ENST00000542430; ENST00000350494; ENST00000542824; ENST00000540799 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 9% | chr18 | 33711482 | 33711615 | + | chr18 | 33713201 | 33713279 | + | ENST00000358232; ENST00000351393; ENST00000442325; ENST00000423854; ENST00000539560; ENST00000542430; ENST00000350494; ENST00000542824; ENST00000540799 | TSF |
| 9% | chr18 | 33711482 | 33711615 | + | chr18 | 33713201 | 33713279 | + | ENST00000358232; ENST00000351393; ENST00000442325; ENST00000423854; ENST00000539560; ENST00000542430; ENST00000350494; ENST00000542824; ENST00000540799 | TSF |
| 9% | chr7 | 56018506 | 56018522 | + | chr7 | 56020872 | 56021011 | + | ENST00000426595 | TSF |
| 8% | chr1 | 162768504 | 162768725 | + | chr1 | 162769533 | 162769727 | + | ENST00000367917; ENST00000254521 | TSF |
| 8% | chr1 | 162768504 | 162768725 | + | chr1 | 162769533 | 162769727 | + | ENST00000367917; ENST00000254521 | TSF |
| 8% | chr15 | 39896167 | 39896087 | − | chr15 | 39893127 | 39893081 | − | ENST00000350221; ENST00000559547 | TSF |
| 6% | chr11 | 60694460 | 60694542 | + | chr11 | 60694676 | 60694890 | + | ENST00000453848; ENST00000005286 | TSF |
| 6% | chr11 | 60694460 | 60694542 | + | chr11 | 60694676 | 60694890 | + | ENST00000453848; ENST00000005286 | TSF |
| 6% | chr21 | 39513161 | 39513404 | + | chr21 | 39528398 | 39528496 | + | ENST00000357704; ENST00000400477 | TSF |
| 6% | chr8 | 100905650 | 100905547 | − | chr8 | 100899846 | 100899733 | − | ENST00000522934; ENST00000520517; ENST00000520468; ENST00000297564; ENST00000520271; ENST00000517682; ENST00000524245; ENST00000522940; ENST00000518171; ENST00000523016 | TSF |
| 6% | chr8 | 144691011 | 144690934 | − | chr8 | 144690296 | 144690232 | − | ENST00000220966; ENST00000433751 | TSF |
| 6% | chr8 | 144691011 | 144690934 | − | chr8 | 144690296 | 144690232 | − | ENST00000220966; ENST00000433751 | TSF |
| 6% | chr8 | 130855946 | 130855855 | − | chr8 | 130854451 | 130854388 | − | ENST00000519824; ENST00000522746; ENST00000523509; ENST00000401979; ENST00000519110; ENST00000522250; ENST00000517654; ENST00000519540; ENST00000522941 | TSF |
| 5% | chrX | 16671913 | 16671984 | + | chrX | 16672528 | 16672632 | + | ENST00000380200 | TSF |
| 5% | chr10 | 8110441 | 8110501 | + | chr10 | 8111436 | 8111561 | + | ENST00000379328; ENST00000346208 | TSF |
| 5% | chr9 | 95843657 | 95843805 | + | chr9 | 95846819 | 95846949; 95847029 | + | ENST00000465709; ENST00000375472; ENST00000375469; ENST00000471462 | TSF |
| 5% | chr9 | 95843657 | 95843805 | + | chr9 | 95846819 | 95846949; 95847029 | + | ENST00000465709; ENST00000375472; ENST00000375469; ENST00000471462 | TSF |
| 5% | chr12 | 51785233 | 51785272 | + | chr12 | 51834492 | 51834573 | + | ENST00000358657; ENST00000453097 | TSF |
| 5% | chr12 | 51785233 | 51785272 | + | chr12 | 51834492 | 51834573 | + | ENST00000358657; ENST00000453097 | TSF |
| 4% | chr21 | 38273278 | 38272892 | − | chr21 | 38269431 | 38269160 | − | ENST00000336648; ENST00000399120 | TSF |
| 4% | chr19 | 41514770 | 41514950 | + | chr19 | 41515124 | 41515300 | + | ENST00000324071 | TSF |
| 4% | chr15 | 39898214 | 39898131 | − | chr15 | 39893127 | 39893081 | − | ENST00000350221; ENST00000559547 | TSF |
| 4% | chr11 | 66048968 | 66049045 | + | chr11 | 66049730 | 66049798; 66049824 | + | ENST00000528852; ENST00000311445; ENST00000528063 | TSF |
| 4% | chr11 | 66048968 | 66049045 | + | chr11 | 66049730 | 66049798; 66049824 | + | ENST00000528852; ENST00000311445; ENST00000528063 | TSF |
| 4% | chr11 | 66048968 | 66049045 | + | chr11 | 66049730 | 66049798; 66049824 | + | ENST00000528852; ENST00000311445; ENST00000528063 | TSF |
| 4% | chr21 | 39513161 | 39513404 | + | chr21 | 39526527 | 39526623 | + | ENST00000357704; ENST00000400477 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr6 | 152261756 | 152261988 | + | chr6 | 152265308 | 152265643 | + | ENST00000440973; ENST00000338799; ENST00000443427; ENST00000206249; ENST00000427531 | TSF |
| 4% | chr6 | 152261756 | 152261988 | + | chr6 | 152265308 | 152265643 | + | ENST00000440973; ENST00000338799; ENST00000443427; ENST00000206249; ENST00000427531 | TSF |
| 4% | chr20 | 45337040 | 45337192 | + | chr20 | 45353680 | 45354963 | + | ENST00000359271 | TSF |
| 4% | chr6 | 151755279 | 151755140 | − | chr6 | 151754365 | 151754290 | − | ENST00000367303; ENST00000444024 | TSF |
| 4% | chr6 | 151755279 | 151755140 | − | chr6 | 151754365 | 151754290 | − | ENST00000367303; ENST00000444024 | TSF |
| 4% | chr6 | 151784315 | 151784765 | + | chr6 | 151785588 | 151785753 | + | ENST00000367294; ENST00000545879 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000423100; ENST00000436883; ENST00000414510; ENST00000432124; ENST00000419582; ENST00000432651; ENST00000435132; ENST00000434095; ENST00000411917; ENST00000524946; ENST00000435305 | TSF |
| 4% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000423100; ENST00000436883; ENST00000414510; ENST00000432124; ENST00000419582; ENST00000432651; ENST00000435132; ENST00000434095; ENST00000411917; ENST00000524946; ENST00000435305 | TSF |
| 4% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000423100; ENST00000436883; ENST00000414510; ENST00000432124; ENST00000419582; ENST00000432651; ENST00000435132; ENST00000434095; ENST00000411917; ENST00000524946; ENST00000435305 | TSF |
| 4% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000423100; ENST00000436883; ENST00000414510; ENST00000432124; ENST00000419582; ENST00000432651; ENST00000435132; ENST00000434095; ENST00000411917; ENST00000524946; ENST00000435305 | TSF |
| 4% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000423100; ENST00000436883; ENST00000414510; ENST00000432124; ENST00000419582; ENST00000432651; ENST00000435132; ENST00000434095; ENST00000411917; ENST00000524946; ENST00000435305 | TSF |
| 4% | chr17 | 40820773 | 40820676 | − | chr17 | 40820321 | 40820145 | − | ENST00000591022; ENST00000412503; ENST00000293349 | TSF |
| 4% | chr22 | 22899971 | 22899965 | − | chr22 | 22893511 | 22893185; 22893189; 22893274; 22893481 | − | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | − | chr22 | 22893511 | 22893185; 22893189; 22893274; 22893481 | − | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | − | chr22 | 22893511 | 22893185; 22893189; 22893274; 22893481 | − | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr22 | 22899971 | 22899965 | − | chr22 | 22893511 | 22893185; 22893189; 22893274; 22893481 | − | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | − | chr22 | 22893511 | 22893185; 22893189; 22893274; 22893481 | − | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | − | chr22 | 22893511 | 22893185; 22893189; 22893274; 22893481 | − | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | − | chr22 | 22893511 | 22893185; 22893189; 22893274; 22893481 | − | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 3% | chr9 | 95777456 | 95777506 | + | chr9 | 95778019 | 95778111 | + | ENST00000375482; ENST00000416701; ENST00000337352; ENST00000467786 | TSF |
| 3% | chr9 | 95777456 | 95777506 | + | chr9 | 95778019 | 95778111 | + | ENST00000375482; ENST00000416701; ENST00000337352; ENST00000467786 | TSF |
| 3% | chr9 | 95777456 | 95777506 | + | chr9 | 95778019 | 95778111 | + | ENST00000375482; ENST00000416701; ENST00000337352; ENST00000467786 | TSF |
| 3% | chrX | 16718539 | 16718441 | − | chrX | 16717216 | 16717046 | − | ENST00000443824; ENST00000359276; ENST00000380241 | TSF |
| 3% | chr1 | 116205952 | 116206078 | + | chr1 | 116206282 | 116206889 | + | ENST00000355485; ENST00000369510; ENST00000310260; ENST00000369509 | TSF |
| 3% | chr17 | 64988088 | 64988129 | + | chr17 | 65014305 | 65014388 | + | ENST00000262138 | TSF |
| 3% | chr19 | 41311935 | 41312059 | + | chr19 | 41312460 | 41312579 | + | ENST00000303961; ENST00000406058; ENST00000593726 | TSF |
| 3% | chr16 | 78060352 | 78060356 | + | chr16 | 78062004 | 78062087 | + | ENST00000299642; ENST00000575655 | TSF |
| 3% | chr6 | 80022917 | 80022085 | − | chr6 | 79924739 | 79924689 | − | ENST00000275036; ENST00000344726 | TSF |
| 3% | chr6 | 80022917 | 80022085 | − | chr6 | 79924739 | 79924689 | − | ENST00000275036; ENST00000344726 | TSF |
| 3% | chr8 | 75580849 | 75580998 | + | chr8 | 75614614 | 75614691 | + | ENST00000523442; ENST00000523118 | TSF |
| 3% | chr2 | 171222296 | 171222632 | + | chr2 | 171225732 | 171225887 | + | ENST00000317935; ENST00000408978; ENST00000409044; ENST00000484338; ENST00000334231; ENST00000442690 | TSF |
| 3% | chr2 | 171222296 | 171222632 | + | chr2 | 171225732 | 171225887 | + | ENST00000317935; ENST00000408978; ENST00000409044; ENST00000484338; ENST00000334231; ENST00000442690 | TSF |
| 3% | chr2 | 171222296 | 171222632 | + | chr2 | 171225732 | 171225887 | + | ENST00000317935; ENST00000408978; ENST00000409044; ENST00000484338; ENST00000334231; ENST00000442690 | TSF |
| 3% | chr2 | 171222296 | 171222632 | + | chr2 | 171225732 | 171225887 | + | ENST00000317935; ENST00000408978; ENST00000409044; ENST00000484338; ENST00000334231; ENST00000442690 | TSF |
| 3% | chr2 | 171222296 | 171222632 | + | chr2 | 171225732 | 171225887 | + | ENST00000317935; ENST00000408978; ENST00000409044; ENST00000484338; ENST00000334231; ENST00000442690 | TSF |
| 3% | chr1 | 180281096 | 180280936 | − | chr1 | 180257652 | 180257498 | − | ENST00000367595 | TSF |
| 3% | chr7 | 16920082 | 16920016 | − | chr7 | 16913467 | 16913404 | − | ENST00000310398; ENST00000402239; ENST00000414935 | TSF |
| 3% | chr7 | 16920082 | 16920016 | − | chr7 | 16913467 | 16913404 | − | ENST00000310398; ENST00000402239; ENST00000414935 | TSF |
| 3% | chr7 | 16920082 | 16920016 | − | chr7 | 16913467 | 16913404 | − | ENST00000310398; ENST00000402239; ENST00000414935 | TSF |
| 3% | chr17 | 39976225 | 39976301 | + | chr17 | 39976521 | 39976713 | + | ENST00000321562; ENST00000455106; ENST00000544340 | TSF |
| 3% | chr2 | 132286104 | 132286168 | + | chr2 | 132287220 | 132287264 | + | ENST00000434330; ENST00000295171; ENST00000409856 | TSF |
| 3% | chr2 | 132286104 | 132286168 | + | chr2 | 132287220 | 132287264 | + | ENST00000434330; ENST00000295171; ENST00000409856 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr2 | 132286104 | 132286168 | + | chr2 | 132287220 | 132287264 | + | ENST00000434330; ENST00000295171; ENST00000409856 | TSF |
| 3% | chr20 | 14676179 | 14676510 | + | chr20 | 15210586 | 15210707 | + | ENST00000217246; ENST00000310348 | TSF |
| 3% | chr20 | 14676179 | 14676510 | + | chr20 | 15210586 | 15210707 | + | ENST00000217246; ENST00000310348 | TSF |
| 3% | chr17 | 37886362 | 37886333 | − | chr17 | 37886014 | 37885851; 37885938 | − | ENST00000577810; ENST00000394231 | TSF |
| 3% | chr17 | 37886362 | 37886333 | − | chr17 | 37886014 | 37885851; 37885938 | − | ENST00000577810; ENST00000394231 | TSF |
| 3% | chr10 | 117194803 | 117194993 | + | chr10 | 117221451 | 117221526; 117221545 | + | ENST00000526373; ENST00000355044; ENST00000423111 | TSF |
| 3% | chr10 | 117194803 | 117194993 | + | chr10 | 117221451 | 117221526; 117221545 | + | ENST00000526373; ENST00000355044; ENST00000423111 | TSF |
| 3% | chr1 | 165854440 | 165854616 | + | chr1 | 165859441 | 165859600 | + | ENST00000367879; ENST00000372212 | TSF |
| 3% | chr1 | 165854440 | 165854616 | + | chr1 | 165859441 | 165859600 | + | ENST00000367879; ENST00000372212 | TSF |
| 3% | chr10 | 37480642 | 37480864 | + | chr10 | 37481992 | 37482020 | + | ENST00000361713; ENST00000374660; ENST00000602533 | TSF |
| 3% | chr12 | 116400299 | 116400244 | − | chr12 | 116399203 | 116399071 | − | ENST00000281928 | TSF |
| 3% | chrX | 100655477 | 100654732 | − | chrX | 100653934 | 100653773 | − | ENST00000218516 | TSF |
| 3% | chr8 | 100901915 | 100901910 | − | chr8 | 100899846 | 100899733 | − | ENST00000522934; ENST00000520517; ENST00000520468; ENST00000297564; ENST00000520271; ENST00000517682; ENST00000524245; ENST00000522940; ENST00000518171; ENST00000523016 | TSF |
| 2% | chr1 | 47441646 | 47446228 | + | chr1 | 47581201 | 47581265 | + | ENST00000334194 | TSF |
| 2% | chr22 | 46768579 | 46768553 | − | chr22 | 46765701 | 46765589 | − | ENST00000262738 | TSF |
| 2% | chr11 | 77909738 | 77909743 | + | chr11 | 77910641 | 77910770 | + | ENST00000528910; ENST00000529308 | TSF |
| 2% | chr11 | 77909738 | 77909743 | + | chr11 | 77910641 | 77910770 | + | ENST00000528910; ENST00000529308 | TSF |
| 2% | chr2 | 182766065 | 182766115 | + | chr2 | 182766493 | 182767193 | + | ENST00000431877; ENST00000320370; ENST00000409001; ENST00000428267 | TSF |
| 2% | chr2 | 182766065 | 182766115 | + | chr2 | 182766493 | 182767193 | + | ENST00000431877; ENST00000320370; ENST00000409001; ENST00000428267 | TSF |
| 2% | chr2 | 182766065 | 182766115 | + | chr2 | 182766493 | 182767193 | + | ENST00000431877; ENST00000320370; ENST00000409001; ENST00000428267 | TSF |
| 2% | chr1 | 159928050 | 159927784 | − | chr1 | 182766493 | 159923099 | − | ENST00000368092; ENST00000368093 | TSF |
| 2% | chr1 | 159928050 | 159927784 | − | chr1 | 182766493 | 159923099 | − | ENST00000368092; ENST00000368093 | TSF |
| 2% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 2% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 2% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 2% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 2% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 2% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 2% | chr10 | 117875752 | 117875720 | − | chr10 | 117856275 | 117856166 | − | ENST00000439649; ENST00000369236; ENST00000355422; ENST00000544592; ENST00000369234 | TSF |
| 2% | chr10 | 117875752 | 117875720 | − | chr10 | 117856275 | 117856166 | − | ENST00000439649; ENST00000369236; ENST00000355422; ENST00000544592; ENST00000369234 | TSF |
| 2% | chr19 | 16267516 | 16267584 | + | chr19 | 16268020 | 16268139; 16268205; 16268208; 16268448 | + | ENST00000593031; ENST00000397372; ENST00000253680; ENST00000593154; ENST00000588246 | TSF |
| 2% | chr19 | 16267516 | 16267584 | + | chr19 | 16268020 | 16268139; 16268205; 16268208; 16268448 | + | ENST00000593031; ENST00000397372; ENST00000253680; ENST00000593154; ENST00000588246 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr19 | 16267516 | 16267584 | + | chr19 | 16268020 | 16268139; 16268205; 16268208; 16268448 | + | ENST00000593031; ENST00000397372; ENST00000253680; ENST00000593154; ENST00000588246 | TSF |
| 2% | chr19 | 16267516 | 16267584 | + | chr19 | 16268020 | 16268139; 16268205; 16268208; 16268448 | + | ENST00000593031; ENST00000397372; ENST00000253680; ENST00000593154; ENST00000588246 | TSF |
| 2% | chr19 | 1114930 | 1114676 | − | chr19 | 1114421 | 1114230 | − | ENST00000361757; ENST00000587024; ENST00000438103 | TSF |
| 2% | chr8 | 69544201 | 69545202 | + | chr8 | 69552611 | 69552746 | + | ENST00000539993; ENST00000518698; ENST00000337103; ENST00000325233 | TSF |
| 2% | chr8 | 69544201 | 69545202 | + | chr8 | 69552611 | 69552746 | + | ENST00000539993; ENST00000518698; ENST00000337103; ENST00000325233 | TSF |
| 2% | chr19 | 45571855 | 45571862 | + | chr19 | 45572324 | 45572336; 45572382 | + | ENST00000391952; ENST00000221455; ENST00000391953; ENST00000544944; ENST00000591904 | TSF |
| 2% | chr19 | 45571855 | 45571862 | + | chr19 | 45572324 | 45572336; 45572382 | + | ENST00000391952; ENST00000221455; ENST00000391953; ENST00000544944; ENST00000591904 | TSF |
| 2% | chr19 | 45571855 | 45571862 | + | chr19 | 45572324 | 45572336; 45572382 | + | ENST00000391952; ENST00000221455; ENST00000391953; ENST00000544944; ENST00000591904 | TSF |
| 2% | chr5 | 15934695 | 15934710 | + | chr5 | 15936559 | 15937295 | + | ENST00000504595; ENST00000510662; ENST00000329673 | TSF |
| 2% | chrX | 80474528 | 80474722 | + | chrX | 80532483 | 80532668 | + | ENST00000373212 | TSF |
| 2% | chr15 | 74004214 | 74004264 | + | chr15 | 74005275 | 74005297 | + | ENST00000318443; ENST00000537340; ENST00000318424; ENST00000564751; ENST00000561176; ENST00000559073 | TSF |
| 2% | chr1 | 12002791 | 12002835 | + | chr1 | 12008033 | 12008124 | + | ENST00000449038; ENST00000376369; ENST00000429000; ENST00000196061 | TSF |
| 2% | chr1 | 12002791 | 12002835 | + | chr1 | 12008033 | 12008124 | + | ENST00000449038; ENST00000376369; ENST00000429000; ENST00000196061 | TSF |
| 2% | chr1 | 12002791 | 12002835 | + | chr1 | 12008033 | 12008124 | + | ENST00000449038; ENST00000376369; ENST00000429000; ENST00000196061 | TSF |
| 2% | chr1 | 246547998 | 246547930 | − | chr1 | 246518396 | 246518333 | − | ENST00000388985; ENST00000403792 | TSF |
| 2% | chr1 | 246547998 | 246547930 | − | chr1 | 246518396 | 246518333 | − | ENST00000388985; ENST00000403792 | TSF |
| 2% | chr7 | 94018505 | 94018589 | + | chr7 | 94057748 | 94057789 | + | ENST00000297268 | TSF |
| 2% | chr12 | 58189709 | 58189746 | + | chr12 | 58189960 | 58189980; 58190044; 58190366 | + | ENST00000540550; ENST00000457189; ENST00000454289; ENST00000323833; ENST00000350762 | TSF |
| 2% | chr12 | 58189709 | 58189746 | + | chr12 | 58189960 | 58189980; 58190044; 58190366 | + | ENST00000540550; ENST00000457189; ENST00000454289; ENST00000323833; ENST00000350762 | TSF |
| 2% | chr12 | 58189709 | 58189746 | + | chr12 | 58189960 | 58189980; 58190044; 58190366 | + | ENST00000540550; ENST00000457189; ENST00000454289; ENST00000323833; ENST00000350762 | TSF |
| 2% | chr14 | 100581223 | 100581300 | + | chr14 | 100589876 | 100589907; 100589939 | + | ENST00000555706; ENST00000402714; ENST00000544450; ENST00000392920; ENST00000557153; ENST00000557384 | TSF |
| 2% | chr14 | 100581223 | 100581300 | + | chr14 | 100589876 | 100589907; 100589939 | + | ENST00000555706; ENST00000402714; ENST00000544450; ENST00000392920; ENST00000557153; ENST00000557384 | TSF |
| 2% | chr14 | 100581223 | 100581300 | + | chr14 | 100589876 | 100589907; 100589939 | + | ENST00000555706; ENST00000402714; ENST00000544450; ENST00000392920; ENST00000557153; ENST00000557384 | TSF |
| 2% | chr14 | 100581223 | 100581300 | + | chr14 | 100589876 | 100589907; 100589939 | + | ENST00000555706; ENST00000402714; ENST00000544450; ENST00000392920; ENST00000557153; ENST00000557384 | TSF |
| 2% | chr14 | 100581223 | 100581300 | + | chr14 | 100589876 | 100589907; 100589939 | + | ENST00000555706; ENST00000402714; ENST00000544450; ENST00000392920; ENST00000557153; ENST00000557384 | TSF |
| 2% | chr19 | 50174724 | 50174836 | + | chr19 | 50176955 | 50177005; 50177034 | + | ENST00000441864; ENST00000246785; ENST00000598306; ENST00000600947 | TSF |
| 2% | chr19 | 50174724 | 50174836 | + | chr19 | 50176955 | 50177005; 50177034 | + | ENST00000441864; ENST00000246785; ENST00000598306; ENST00000600947 | TSF |
| 2% | chr1 | 169819657 | 169819707 | + | chr1 | 169820958 | 169821077 | + | ENST00000359326; ENST00000286031 | TSF |
| 2% | chrX | 80467099 | 80467350 | + | chrX | 80532483 | 80532668 | + | ENST00000373212 | TSF |
| 2% | chr11 | 60694460 | 60694539 | + | chr11 | 60694676 | 60694890 | + | ENST00000453848; ENST00000005286 | TSF |
| 2% | chr11 | 60694460 | 60694539 | + | chr11 | 60694676 | 60694890 | + | ENST00000453848; ENST00000005286 | TSF |
| 2% | chr1 | 23762222 | 23762216 | − | chr1 | 23761111 | 23761026 | − | ENST00000495646; ENST00000336689; ENST00000437606 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr1 | 156716197 | 156716133 | − | chr1 | 156715165 | 156715089 | − | ENST00000357325; ENST00000537739; ENST00000368209; ENST00000368206 | TSF |
| 2% | chr17 | 45698288 | 45698367 | + | chr17 | 45699134 | 45699286 | + | ENST00000530173; ENST00000322157; ENST00000544660; ENST00000528565 | TSF |
| 2% | chr4 | 77020173 | 77020223 | + | chr4 | 77021444 | 77021473 | + | ENST00000341029; ENST00000349321; ENST00000355810; ENST00000511188 | TSF |
| 2% | chr4 | 77020173 | 77020223 | + | chr4 | 77021444 | 77021473 | + | ENST00000341029; ENST00000349321; ENST00000355810; ENST00000511188 | TSF |
| 2% | chr4 | 77020173 | 77020223 | + | chr4 | 77021444 | 77021473 | + | ENST00000341029; ENST00000349321; ENST00000355810; ENST00000511188 | TSF |
| 2% | chr4 | 77020173 | 77020223 | + | chr4 | 77021444 | 77021473 | + | ENST00000341029; ENST00000349321; ENST00000355810; ENST00000511188 | TSF |
| 2% | chr17 | 39974832 | 39974893 | + | chr17 | 39975462 | 39975651 | + | ENST00000321562 | TSF |
| 2% | chr8 | 117662244 | 117662067 | − | chr8 | 117661165 | 117661045 | − | ENST00000521861; ENST00000276682; ENST00000518949 | TSF |
| 2% | chr8 | 117662244 | 117662067 | − | chr8 | 117661165 | 117661045 | − | ENST00000521861; ENST00000276682; ENST00000518949 | TSF |
| 2% | chr18 | 20590293 | 20590383 | + | chr18 | 20596791 | 20596887 | + | ENST00000327155; ENST00000399722; ENST00000360790; ENST00000583057 | TSF |
| 2% | chr18 | 20590293 | 20590383 | + | chr18 | 20596791 | 20596887 | + | ENST00000327155; ENST00000399722; ENST00000360790; ENST00000583057 | TSF |
| 2% | chr1 | 155031050 | 155031103 | + | chr1 | 155031186 | 155031263 | + | ENST00000355956; ENST00000356955; ENST00000359280; ENST00000360674; ENST00000368412; ENST00000449910; ENST00000526491; ENST00000529473; ENST00000368410; ENST00000271836; ENST00000368413; ENST00000531455 | TSF |
| 2% | chr1 | 155031050 | 155031103 | + | chr1 | 155031186 | 155031263 | + | ENST00000355956; ENST00000356955; ENST00000359280; ENST00000360674; ENST00000368412; ENST00000449910; ENST00000526491; ENST00000529473; ENST00000368410; ENST00000271836; ENST00000368413; ENST00000531455 | TSF |
| 2% | chr1 | 155031050 | 155031103 | + | chr1 | 155031186 | 155031263 | + | ENST00000355956; ENST00000356955; ENST00000359280; ENST00000360674; ENST00000368412; ENST00000449910; ENST00000526491; ENST00000529473; ENST00000368410; ENST00000271836; ENST00000368413; ENST00000531455 | TSF |
| 2% | chr1 | 155031050 | 155031103 | + | chr1 | 155031186 | 155031263 | + | ENST00000355956; ENST00000356955; ENST00000359280; ENST00000360674; ENST00000368412; ENST00000449910; ENST00000526491; ENST00000529473; ENST00000368410; ENST00000271836; ENST00000368413; ENST00000531455 | TSF |
| 2% | chr1 | 155031050 | 155031103 | + | chr1 | 155031186 | 155031263 | + | ENST00000355956; ENST00000356955; ENST00000359280; ENST00000360674; ENST00000368412; ENST00000449910; ENST00000526491; ENST00000529473; ENST00000368410; ENST00000271836; ENST00000368413; ENST00000531455 | TSF |
| 2% | chr1 | 155031050 | 155031103 | + | chr1 | 155031186 | 155031263 | + | ENST00000355956; ENST00000356955; ENST00000359280; ENST00000360674; ENST00000368412; ENST00000449910; ENST00000526491; ENST00000529473; ENST00000368410; ENST00000271836; ENST00000368413; ENST00000531455 | TSF |
| 2% | chr1 | 155031050 | 155031103 | + | chr1 | 155031186 | 155031263 | + | ENST00000355956; ENST00000356955; ENST00000359280; ENST00000360674; ENST00000368412; ENST00000449910; ENST00000526491; ENST00000529473; ENST00000368410; ENST00000271836; ENST00000368413; ENST00000531455 | TSF |
| 2% | chr1 | 155031050 | 155031103 | + | chr1 | 155031186 | 155031263 | + | ENST00000355956; ENST00000356955; ENST00000359280; ENST00000360674; ENST00000368412; ENST00000449910; ENST00000526491; ENST00000529473; ENST00000368410; ENST00000271836; ENST00000368413; ENST00000531455 | TSF |
| 2% | chr1 | 155031050 | 155031103 | + | chr1 | 155031186 | 155031263 | + | ENST00000355956; ENST00000356955; ENST00000359280; ENST00000360674; ENST00000368412; ENST00000449910; ENST00000526491; ENST00000529473; ENST00000368410; ENST00000271836; ENST00000368413; ENST00000531455 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr8 | 104389530 | 104389536 | + | chr8 | 104390255 | 104390471 | + | ENST00000330295; ENST00000520337 | TSF |
| 2% | chr2 | 171222296 | 171222628 | + | chr2 | 171225732 | 171225887 | + | ENST00000317935; ENST00000408978; ENST00000409044; ENST00000484338; ENST00000334231; ENST00000442690 | TSF |
| 2% | chr2 | 171222296 | 171222628 | + | chr2 | 171225732 | 171225887 | + | ENST00000317935; ENST00000408978; ENST00000409044; ENST00000484338; ENST00000334231; ENST00000442690 | TSF |
| 2% | chr2 | 171222296 | 171222628 | + | chr2 | 171225732 | 171225887 | + | ENST00000317935; ENST00000408978; ENST00000409044; ENST00000484338; ENST00000334231; ENST00000442690 | TSF |
| 2% | chr2 | 171222296 | 171222628 | + | chr2 | 171225732 | 171225887 | + | ENST00000317935; ENST00000408978; ENST00000409044; ENST00000484338; TENST00000334231; ENS00000442690 | TSF |
| 2% | chr2 | 171222296 | 171222628 | + | chr2 | 171225732 | 171225887 | + | ENST00000317935; ENST00000408978; ENST00000409044; ENST00000484338; ENST00000334231; ENST00000442690 | TSF |
| 2% | chr1 | 23397020 | 23397118 | + | chr1 | 23397718 | 23397852 | + | ENST00000356634; ENST00000400181; ENST00000542151 | TSF |
| 2% | chr6 | 123101055 | 123101091 | + | chr6 | 123101436 | 123101608 | + | ENST00000368444; ENST00000356535 | TSF |
| 2% | chr6 | 123101055 | 123101091 | + | chr6 | 123101436 | 123101608 | + | ENST00000368444; ENST00000356535 | TSF |
| 2% | chr12 | 6602868 | 6602754 | − | chr12 | 6602138 | 6602028 | − | ENST00000229238 | TSF |
| 2% | chr8 | 117816470 | 117816753 | + | chr8 | 117861127 | 117861256; 117861276 | + | ENST00000517820; ENST00000520733 | TSF |
| 2% | chr8 | 117816470 | 117816753 | + | chr8 | 117861127 | 117861256; 117861276 | + | ENST00000517820; ENST00000520733 | TSF |
| 2% | chr1 | 47345017 | 47346314 | + | chr1 | 47581201 | 47581265 | + | ENST00000334194 | TSF |
| 2% | chr1 | 31218846 | 31218765 | − | chr1 | 31215396 | 31215303 | − | ENST00000294507 | TSF |
| 2% | chr12 | 15296492 | 15296463 | − | chr12 | 15274053 | 15273997; 15273999 | − | ENST00000256953; ENST00000538313; ENST00000536465; ENST00000545567; TENST00000537647; ENS00000393736 | TSF |
| 2% | chr12 | 15296492 | 15296463 | − | chr12 | 15274053 | 15273997; 15273999 | − | ENST00000256953; ENST00000538313; ENST00000536465; ENST00000545567; ENST00000537647; ENST00000393736 | TSF |
| 2% | chr12 | 15296492 | 15296463 | − | chr12 | 15274053 | 15273997; 15273999 | − | ENST00000256953; ENST00000538313; ENST00000536465; ENST00000545567; ENST00000537647; ENST00000393736 | TSF |
| 2% | chr12 | 15296492 | 15296463 | − | chr12 | 15274053 | 15273997; 15273999 | − | ENST00000256953; ENST00000538313; ENST00000536465; ENST00000545567; ENST00000537647; ENST00000393736 | TSF |
| 2% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 2% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 2% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 2% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 2% | chr3 | 148570083 | 148570155 | + | chr3 | 148575244 | 148575328 | + | ENST00000491148; ENST00000282957 | TSF |
| 2% | chr20 | 18509077 | 18509137 | + | chr20 | 18511324 | 18511447 | + | ENST00000262544; ENST00000336714; ENST00000377475; ENST00000377465 | TSF |
| 2% | chr1 | 59843828 | 59844080 | + | chr1 | 59844421 | 59844509 | + | ENST00000413489; ENST00000371218; ENST00000303721; ENST00000430447; ENST00000371212 | TSF |
| 2% | chr1 | 59843828 | 59844080 | + | chr1 | 59844421 | 59844509 | + | ENST00000413489; ENST00000371218; ENST00000303721; ENST00000430447; ENST00000371212 | TSF |
| 2% | chr1 | 59843828 | 59844080 | + | chr1 | 59844421 | 59844509 | + | ENST00000413489; ENST00000371218; ENST00000303721; ENST00000430447; ENST00000371212 | TSF |
| 2% | chr1 | 59843828 | 59844080 | + | chr1 | 59844421 | 59844509 | + | ENST00000413489; ENST00000371218; ENST00000303721; ENST00000430447; ENST00000371212 | TSF |
| 2% | chr7 | 55464873 | 55464924 | + | chr7 | 55466116 | 55466323 | + | ENST00000254770 | TSF |
| 2% | chr4 | 95982945 | 95983291 | + | chr4 | 96025559 | 96025718 | + | ENST00000440890 | TSF |
| 2% | chr7 | 55985644 | 55985990 | + | chr7 | 55990855 | 55990981 | + | ENST00000426595; ENST00000429591 | TSF |
| 2% | chr7 | 55985644 | 55985990 | + | chr7 | 55990855 | 55990981 | + | ENST00000426595; ENST00000429591 | TSF |
| 2% | chr12 | 50389576 | 50389433 | − | chr12 | 50388292 | 50388197 | − | ENST00000427314; ENST00000312377; ENST00000434422; ENST00000454520; ENST00000551016; ENST00000547905; ENST00000549342 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr12 | 50389576 | 50389433 | − | chr12 | 50388292 | 50388197 | − | ENST00000427314; ENST00000312377; ENST00000434422; ENST00000454520; ENST00000551016; ENST00000547905; ENST00000549342 | TSF |
| 2% | chr8 | 100902036 | 100901972 | − | chr8 | 100899846 | 100899733 | − | ENST00000522934; ENST00000520517; ENST00000520468; ENST00000297564; ENST00000520271; ENST00000517682; ENST00000524245; ENST00000522940; ENST00000518171; ENST00000523016 | TSF |
| 2% | chr1 | 224493544 | 224493476 | − | chr1 | 224492868 | 224492736 | − | ENST00000469968; ENST00000391875; ENST00000281701; ENST00000469075; ENST00000361463; ENST00000467882; ENST00000488718; ENST00000492281; ENST00000436927 | TSF |
| 2% | chr1 | 224493544 | 224493476 | − | chr1 | 224492868 | 224492736 | − | ENST00000469968; ENST00000391875; ENST00000281701; ENST00000469075; ENST00000361463; ENST00000467882; ENST00000488718; ENST00000492281; ENST00000436927 | TSF |
| 2% | chr1 | 224493544 | 224493476 | − | chr1 | 224492868 | 224492736 | − | ENST00000469968; ENST00000391875; ENST00000281701; ENST00000469075; ENST00000361463; ENST00000467882; ENST00000488718; ENST00000492281; ENST00000436927 | TSF |
| 2% | chr1 | 224493544 | 224493476 | − | chr1 | 224492868 | 224492736 | − | ENST00000469968; ENST00000391875; ENST00000281701; ENST00000469075; ENST00000361463; ENST00000467882; ENST00000488718; ENST00000492281; ENST00000436927 | TSF |
| 2% | chr1 | 224493544 | 224493476 | − | chr1 | 224492868 | 224492736 | − | ENST00000469968; ENST00000391875; ENST00000281701; ENST00000469075; ENST00000361463; ENST00000467882; ENST00000488718; ENST00000492281; ENST00000436927 | TSF |
| 2% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 2% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 2% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 2% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 2% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 2% | chr8 | 133672763 | 133672739 | − | chr8 | 133669153 | 133669076 | − | ENST00000519595; ENST00000518642; ENST00000250173; ENST00000522584 | TSF |
| 2% | chr8 | 133672763 | 133672739 | − | chr8 | 133669153 | 133669076 | − | ENST00000519595; ENST00000518642; ENST00000250173; ENST00000522584 | TSF |
| 2% | chr8 | 133672763 | 133672739 | − | chr8 | 133669153 | 133669076 | − | ENST00000519595; ENST00000518642; ENST00000250173; ENST00000522584 | TSF |
| 1% | chr10 | 27470588 | 27470654 | + | chr10 | 27475308 | 27475465 | + | ENST00000375946; ENST00000375940; ENST00000342386 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr7 | 56018506 | 56018522 | + | chr7 | 56022602 | 56022865; 56022871 | + | ENST00000443449; ENST00000426595; ENST00000285298 | TSF |
| 1% | chr7 | 56018506 | 56018522 | + | chr7 | 56022602 | 56022865; 56022871 | + | ENST00000443449; ENST00000426595; ENST00000285298 | TSF |
| 1% | chr3 | 187087097 | 187087144 | + | chr3 | 187088576 | 187089161 | + | ENST00000259030 | TSF |
| 1% | chr20 | 32404108 | 32404149 | + | chr20 | 32436273 | 32436450 | + | ENST00000217402 | TSF |
| 1% | chr14 | 100606667 | 100606856 | + | chr14 | 100607517 | 100607583 | + | ENST00000402714; ENST00000392920; ENST00000554695 | TSF |
| 1% | chr17 | 72951257 | 72951178 | − | chr17 | 72950460 | 72950233 | − | ENST00000425042 | TSF |
| 1% | chr17 | 39737300 | 39737191 | − | chr17 | 39726472 | 39726390 | − | ENST00000246662 | TSF |
| 1% | chr2 | 163040340 | 163040253 | − | chr2 | 163039978 | 163039924 | − | ENST00000188790; ENST00000443424 | TSF |
| 1% | chr3 | 197640178 | 197640160 | − | chr3 | 197639620 | 197639546 | − | ENST00000265239; ENST00000455191 | TSF |
| 1% | chr19 | 20737134 | 20737096 | − | chr19 | 20736641 | 20736515; 20736611 | − | ENST00000427401; ENST00000596797; ENST00000597940 | TSF |
| 1% | chr19 | 20737134 | 20737096 | − | chr19 | 20736641 | 20736515; 20736611 | − | ENST00000427401; ENST00000596797; ENST00000597940 | TSF |
| 1% | chr19 | 20737134 | 20737096 | − | chr19 | 20736641 | 20736515; 20736611 | − | ENST00000427401; ENST00000596797; ENST00000597940 | TSF |
| 1% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 1% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 1% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 1% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 1% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 1% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 1% | chr2 | 99315948 | 99315517 | − | chr2 | 99294934 | 99294767 | − | ENST00000264968; ENST00000393487; ENST00000409391 | TSF |
| 1% | chr22 | 24967426 | 24967475 | + | chr22 | 24967884 | 24967945 | + | ENST00000215829; ENST00000404603 | TSF |
| 1% | chr10 | 37468901 | 37469123 | + | chr10 | 37481992 | 37482020 | + | ENST00000361713; ENST00000374660; ENST00000602533 | TSF |
| 1% | chr19 | 55501071 | 55501120 | + | chr19 | 55501390 | 55501464; 55501560 | + | ENST00000543277; ENST00000543010; ENST00000391721; ENST00000339757; ENST00000448584; ENST00000537859; ENST00000427260; ENST00000538819; ENST00000263437 | TSF |
| 1% | chr19 | 55501071 | 55501120 | + | chr19 | 55501390 | 55501464; 55501560 | + | ENST00000543277; ENST00000543010; ENST00000391721; ENST00000339757; ENST00000448584; ENST00000537859; ENST00000427260; ENST00000538819; ENST00000263437 | TSF |
| 1% | chr4 | 40352026 | 40352049 | + | chr4 | 40355996 | 40356537 | + | ENST00000310169 | TSF |
| 1% | chr10 | 37457109 | 37457331 | + | chr10 | 37481992 | 37482020 | + | ENST00000361713; ENST00000374660; ENST00000602533 | TSF |
| 1% | chr19 | 58366263 | 58366313 | + | chr19 | 58367475 | 58367491; 58367601 | + | ENST00000316462; ENST00000604231; ENST00000598031; ENST00000339656; ENST00000603271; ENST00000423137 | TSF |
| 1% | chr19 | 58366263 | 58366313 | + | chr19 | 58367475 | 58367491; 58367601 | + | ENST00000316462; ENST00000604231; ENST00000598031; ENST00000339656; ENST00000603271; ENST00000423137 | TSF |
| 1% | chr19 | 58366263 | 58366313 | + | chr19 | 58367475 | 58367491; 58367601 | + | ENST00000316462; ENST00000604231; ENST00000598031; ENST00000339656; ENST00000603271; ENST00000423137 | TSF |
| 1% | chr19 | 58366263 | 58366313 | + | chr19 | 58367475 | 58367491; 58367601 | + | ENST00000316462; ENST00000604231; ENST00000598031; ENST00000339656; ENST00000603271; ENST00000423137 | TSF |
| 1% | chr16 | 89649823 | 89649851 | + | chr16 | 89650105 | 89650179 | + | ENST00000268720; ENST00000319518 | TSF |
| 1% | chr1 | 154581117 | 154581067 | − | chr1 | 154575102 | 154573517 | − | ENST00000292205; ENST00000368474; ENST00000529168 | TSF |
| 1% | chr1 | 154581117 | 154581067 | − | chr1 | 154575102 | 154573517 | − | ENST00000292205; ENST00000368474; ENST00000529168 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr2 | 101024262 | 101024202 | − | chr2 | 101023169 | 101023038 | − | ENST00000542617; ENST00000448989 | TSF |
| 1% | chr2 | 101024262 | 101024202 | − | chr2 | 101023169 | 101023038 | − | ENST00000542617; ENST00000448989 | TSF |
| 1% | chr1 | 17371820 | 17371636 | − | chr1 | 17371383 | 17371256 | − | ENST00000375499 | TSF |
| 1% | chr1 | 84740629 | 84740758 | + | chr1 | 84791320 | 84791431 | + | ENST00000370673; ENST00000370671; ENST00000394834; ENST00000370669; ENST00000370668; ENST00000370670 | TSF |
| 1% | chr1 | 26595323 | 26595855 | + | chr1 | 26595951 | 26596105 | + | ENST00000451429; ENST00000476272; ENST00000252992; ENST00000453146 | TSF |
| 1% | chr1 | 26595323 | 26595855 | + | chr1 | 26595951 | 26596105 | + | ENST00000451429; ENST00000476272; ENST00000252992; ENST00000453146 | TSF |
| 1% | chr2 | 189864980 | 189865248 | + | chr2 | 189866123 | 189866176 | + | ENST00000304636; ENST00000317840 | TSF |
| 1% | chr2 | 189864980 | 189865248 | + | chr2 | 189866123 | 189866176 | + | ENST00000304636; ENST00000317840 | TSF |
| 1% | chr4 | 95985713 | 95986245 | + | chr4 | 96025559 | 96025718 | + | ENST00000440890 | TSF |
| 1% | chr8 | 69544201 | 69545202 | + | chr8 | 69621229 | 69621314 | + | ENST00000539993; ENST00000518698; ENST00000337103; ENST00000325233 | TSF |
| 1% | chr8 | 69544201 | 69545202 | + | chr8 | 69621229 | 69621314 | + | ENST00000539993; ENST00000518698; ENST00000337103; ENST00000325233 | TSF |
| 1% | chr18 | 77906423 | 77906530 | + | chr18 | 77933763 | 77933818 | + | ENST00000589574 | TSF |
| 1% | chr14 | 24105943 | 24105981 | + | chr14 | 24108127 | 24108213 | + | ENST00000432832; ENST00000250383; ENST00000344777 | TSF |
| 1% | chr14 | 24105943 | 24105981 | + | chr14 | 24108127 | 24108213 | + | ENST00000432832; ENST00000250383; 3ENST0000044777 | TSF |
| 1% | chr14 | 24105943 | 24105981 | + | chr14 | 24108127 | 24108213 | + | ENST00000432832; ENST00000250383; ENST00000344777 | TSF |
| 1% | chr8 | 67752911 | 67753611 | + | chr8 | 67753259 | 67753345 | + | ENST00000519289; ENST00000521198; ENST00000522398; ENST00000520976; ENST00000396596; ENST00000345714 | TSF |
| 1% | chr8 | 67752911 | 67753611 | + | chr8 | 67753259 | 67753345 | + | ENST00000519289; ENST00000521198; ENST00000522398; ENST00000520976; ENST00000396596; ENST00000345714 | TSF |
| 1% | chr4 | 76893390 | 76893322 | − | chr4 | 76892611 | 76892510 | − | ENST00000356260; ENST00000395711 | TSF |
| 1% | chr17 | 39696711 | 39696603 | − | chr17 | 39681525 | 39681443 | − | ENST00000361566; ENST00000455635 | TSF |
| 1% | chr17 | 39696711 | 39696603 | − | chr17 | 39681525 | 39681443 | − | ENST00000361566; ENST00000455635 | TSF |
| 1% | chr3 | 195593372 | 195593261 | − | chr3 | 195591058 | 195591052 | − | ENST00000416152; ENST00000381916; ENST00000333602; ENST00000428187; ENST00000392400 | TSF |
| 1% | chr3 | 123694808 | 123694754 | − | chr3 | 123694387 | 123694226; 123694233; 123694273 | − | ENST00000184183; ENST00000405845; ENST00000467907; ENST00000460743 | TSF |
| 1% | chr3 | 123694808 | 123694754 | − | chr3 | 123694387 | 123694226; 123694233; 912364273 | − | ENST00000184183; ENST00000405845; ENST00000467907; ENST00000460743 | TSF |
| 1% | chr3 | 123694808 | 123694754 | − | chr3 | 123694387 | 123694226; 123694233; 123694273 | − | ENST00000184183; ENST00000405845; ENST00000467907; ENST00000460743 | TSF |
| 1% | chr16 | 103424 | 103121 | − | chr16 | 101645 | 101558 | − | ENST00000293860 | TSF |
| 1% | chr3 | 72830506 | 72830456 | − | chr3 | 72799987 | 72799435 | − | ENST00000325599; ENST00000463369 | TSF |
| 1% | chr4 | 56223594 | 56223631 | + | chr4 | 56225513 | 56225655 | + | ENST00000264228; ENST00000505210 | TSF |
| 1% | chr4 | 56223594 | 56223631 | + | chr4 | 56225513 | 56225655 | + | ENST00000264228; ENST00000505210 | TSF |
| 1% | chr17 | 66244121 | 66244199 | + | chr17 | 66244785 | 66244846 | + | ENST00000584837 | TSF |
| 1% | chr8 | 42014292 | 42014390 | + | chr8 | 42015459 | 42015603; 42015630 | + | ENST00000522288; ENST00000518421; ENST00000174653; ENST00000396926; ENST00000530375; ENST00000517922; ENST00000517499 | TSF |
| 1% | chr8 | 42014292 | 42014390 | + | chr8 | 42015459 | 42015603; 42015630 | + | ENST00000522288; ENST00000518421; ENST00000174653; ENST00000396926; ENST00000530375; ENST00000517922; ENST00000517499 | TSF |
| 1% | chr8 | 42014292 | 42014390 | + | chr8 | 42015459 | 42015603; 42015630 | + | ENST00000522288; ENST00000518421; ENST00000174653; ENST00000396926; ENST00000530375; ENST00000517922; ENST00000517499 | TSF |
| 1% | chr8 | 42014292 | 42014390 | + | chr8 | 42015459 | 42015603; 42015630 | + | ENST00000522288; ENST00000518421; ENST00000174653; ENST00000396926; ENST00000530375; ENST00000517922; ENST00000517499 | TSF |
| 1% | chr8 | 42014292 | 42014390 | + | chr8 | 42015459 | 42015603; 42015630 | + | ENST00000522288; ENST00000518421; ENST00000174653; ENST00000396926; ENST00000530375; ENST00000517922; ENST00000517499 | TSF |
| 1% | chr15 | 80450039 | 80450042 | + | chr15 | 80450402 | 80450512 | + | ENST00000558022; ENST00000407106; ENST00000261755; ENST00000561421 | TSF |
| 1% | chr15 | 80450039 | 80450042 | + | chr15 | 80450402 | 80450512 | + | ENST00000558022; ENST00000407106; ENST00000261755; ENST00000561421 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 1% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 1% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 1% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 1% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 1% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 1% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 1% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 1% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 1% | chr17 | 57720819 | 57720900 | + | chr17 | 57721637 | 57721844; 57721856 | + | ENST00000393043; ENST00000269122; ENST00000579456; ENST00000584313; ENST00000580081 | TSF |
| 1% | chr17 | 57720819 | 57720900 | + | chr17 | 57721637 | 57721844; 57721856 | + | ENST00000393043; ENST00000269122; ENST00000579456; ENST00000584313; ENST00000580081 | TSF |
| 1% | chr17 | 57720819 | 57720900 | + | chr17 | 57721637 | 57721844; 57721856 | + | ENST00000393043; ENST00000269122; ENST00000579456; ENST00000584313; ENST00000580081 | TSF |
| 1% | chr17 | 57720819 | 57720900 | + | chr17 | 57721637 | 57721844; 57721856 | + | ENST00000393043; ENST00000269122; ENST00000579456; ENST00000584313; ENST00000580081 | TSF |
| 1% | chr17 | 57720819 | 57720900 | + | chr17 | 57721637 | 57721844; 57721856 | + | ENST00000393043; ENST00000269122; ENST00000579456; ENST00000584313; ENST00000580081 | TSF |
| 1% | chr7 | 156960055 | 156960055 | + | chr7 | 156961742 | 156961816 | + | ENST00000348165 | TSF |
| 1% | chr4 | 158141838 | 158141877 | + | chr4 | 158142819 | 158142875; 158142959 | + | ENST00000512774; ENST00000509417; ENST00000296526; ENST00000264426 | TSF |
| 1% | chr4 | 158141838 | 158141877 | + | chr4 | 158142819 | 158142875; 158142959 | + | ENST00000512774; ENST00000509417; ENST00000296526; ENST00000264426 | TSF |
| 1% | chr4 | 158141838 | 158141877 | + | chr4 | 158142819 | 158142875; 158142959 | + | ENST00000512774; ENST00000509417; ENST00000296526; ENST00000264426 | TSF |
| 1% | chr4 | 158141838 | 158141877 | + | chr4 | 158142819 | 158142875; 158142959 | + | ENST00000512774; ENST00000509417; ENST00000296526; ENST00000264426 | TSF |
| 1% | chr2 | 132237131 | 132237231 | + | chr2 | 132237642 | 132238322 | + | ENST00000321253 | TSF |
| 1% | chr17 | 75313396 | 75313709 | + | chr17 | 75398141 | 75398484; 75398497; 75398565; 75398785 | + | ENST00000589070; ENST00000591934; ENST00000589140; ENST00000427177; ENST00000591198; ENST00000329047; ENST00000590294; ENST00000423034 | TSF |
| 1% | chr17 | 75313396 | 75313709 | + | chr17 | 75398141 | 75398484; 75398497; 75398565; 75398785 | + | ENST00000589070; ENST00000591934; ENST00000589140; ENST00000427177; ENST00000591198; ENST00000329047; ENST00000590294; ENST00000423034 | TSF |
| 1% | chr17 | 75313396 | 75313709 | + | chr17 | 75398141 | 75398484; 75398497; 75398565; 75398785 | + | ENST00000589070; ENST00000591934; ENST00000589140; ENST00000427177; ENST00000591198; ENST00000329047; ENST00000590294; ENST00000423034 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr17 | 75313396 | 75313709 | + | chr17 | 75398141 | 75398484; 75398497; 75398565; 75398785 | + | ENST00000589070; ENST00000591934; ENST00000589140; ENST00000427177; ENST00000591198; ENST00000329047; ENST00000590294; ENST00000423034 | TSF |
| 1% | chr8 | 74036014 | 74035742 | − | chr8 | 73993448 | 73993254 | − | ENST00000297354 | TSF |
| 1% | chr9 | 117824597 | 117824593 | − | chr9 | 117822281 | 117822009 | − | ENST00000350763; ENST00000341037; ENST00000423613 | TSF |
| 1% | chr9 | 117824597 | 117824593 | − | chr9 | 117822281 | 117822009 | − | ENST00000350763; ENST00000341037; 4ENST0000023613 | TSF |
| 1% | chr9 | 117824597 | 117824593 | − | chr9 | 117822281 | 117822009 | − | ENST00000350763; ENST00000341037; | TSF |
| 1% | chr4 | 185620772 | 185620691 | − | chr4 | 185618957 | 185618801; 185618919 | − | ENST00000281453; ENST00000510146 | TSF |
| 1% | chr4 | 185620772 | 185620691 | − | chr4 | 185618957 | 185618801; 185618919 | − | ENST00000281453; ENST00000510146 | TSF |
| 1% | chrX | 76851229 | 76851182 | − | chrX | 76849319 | 76849166 | − | ENST00000373344; ENST00000395603 | TSF |
| 1% | chr2 | 97561135 | 97560977 | − | chr2 | 97559788 | 97559663 | − | ENST00000327896; ENST00000417561; ENST00000490605 | TSF |
| 1% | chr1 | 32376196 | 32376104 | − | chr1 | 32375713 | 32375639; 32375681 | − | ENST00000602725; ENST00000344035; ENST00000457805; ENST00000470404 | TSF |
| 1% | chr1 | 32376196 | 32376104 | − | chr1 | 32375713 | 32375639; 32375681 | − | ENST00000602725; ENST00000344035; ENST00000457805; ENST00000470404 | TSF |
| 1% | chr16 | 10722002 | 10721934 | − | chr16 | 10721656 | 10721440 | − | ENST0000283025 | TSF |
| 1% | chr4 | 107241932 | 107242046 | + | chr4 | 107246142 | 107246275 | + | ENST00000394701 | TSF |
| 1% | chr8 | 144102603 | 144102637 | + | chr8 | 144102731 | 144102839; 144102850; 144102900 | + | ENST00000517503; ENST00000292494; ENST00000429120; ENST00000521699; ENST00000520466; ENST00000521003; ENST00000522971; ENST00000519611; ENST00000519546; ENST00000523847; ENST00000522024; ENST00000520531 | TSF |
| 1% | chr8 | 144102603 | 144102637 | + | chr8 | 144102731 | 144102839; 144102850; 144102900 | + | ENST00000517503; ENST00000292494; ENST00000429120; ENST00000521699; ENST00000520466; ENST00000521003; ENST00000522971; ENST00000519611; ENST00000519546; ENST00000523847; ENST00000522024; ENST00000520531 | TSF |
| 1% | chr8 | 144102603 | 144102637 | + | chr8 | 144102731 | 144102839; 144102850; 144102900 | + | ENST00000517503; ENST00000292494; ENST00000429120; ENST00000521699; ENST00000520466; ENST00000521003; ENST00000522971; ENST00000519611; ENST00000519546; ENST00000523847; ENST00000522024; ENST00000520531 | TSF |
| 1% | chr8 | 144102603 | 144102637 | + | chr8 | 144102731 | 144102839; 144102850; 144102900 | + | ENST00000517503; ENST00000292494; ENST00000429120; ENST00000521699; ENST00000520466; ENST00000521003; ENST00000522971; ENST00000519611; ENST00000519546; ENST00000523847; ENST00000522024; ENST00000520531 | TSF |
| 1% | chr8 | 144102603 | 144102637 | + | chr8 | 144102731 | 144102839; 144102850; 144102900 | + | ENST00000517503; ENST00000292494; ENST00000429120; ENST00000521699; ENST00000520466; ENST00000521003; ENST00000522971; ENST00000519611; ENST00000519546; ENST00000523847; ENST00000522024; ENST00000520531 | TSF |
| 1% | chr4 | 77000253 | 77000294 | + | chr4 | 77002977 | 77003229; 77003296; 77003431; 77003512; 77003688 | + | ENST00000513353; ENST00000504914; ENST00000510423; ENST00000513122; ENST00000341029; ENST00000349321; ENST00000355810 | TSF |
| 1% | chr4 | 77000253 | 77000294 | + | chr4 | 77002977 | 77003229; 77003296; 77003431; 77003512; 77003688 | + | ENST00000513353; ENST00000504914; ENST00000510423; ENST00000513122; ENST00000341029; ENST00000349321; ENST00000355810 | TSF |
| 1% | chr4 | 77000253 | 77000294 | + | chr4 | 77002977 | 77003229; 77003296; 77003431; 77003512; 77003688 | + | ENST00000513353; ENST00000504914; ENST00000510423; ENST00000513122; ENST00000341029; ENST00000349321; ENST00000355810 | TSF |
| 1% | chr4 | 77000253 | 77000294 | + | chr4 | 77002977 | 77003229; 77003296; 77003431; 77003512; 77003688 | + | ENST00000513353; ENST00000504914; ENST00000510423; ENST00000513122; ENST00000341029; ENST00000349321; ENST00000355810 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr4 | 77000253 | 77000294 | + | chr4 | 77002977 | 77003229; 77003296; 77003431; 77003512; 77003688 | + | ENST00000513353; ENST00000504914; ENST00000510423; ENST00000513122; ENST00000341029; ENST00000349321; ENST00000355810 | TSF |
| 1% | chr4 | 77000253 | 77000294 | + | chr4 | 77002977 | 77003229; 77003296; 77003431; 77003512; 77003688 | + | ENST00000513353; ENST00000504914; ENST00000510423; ENST00000513122; ENST00000341029; ENST00000349321; ENST00000355810 | TSF |
| 1% | chr4 | 77000253 | 77000294 | + | chr4 | 77002977 | 77003229; 77003296; 77003431; 77003512; 77003688 | + | ENST00000513353; ENST00000504914; ENST00000510423; ENST00000513122; ENST00000341029; ENST00000349321; ENST00000355810 | TSF |
| 1% | chr4 | 56227367 | 56227417 | + | chr4 | 56230241 | 56230438 | + | ENST00000264228 | TSF |
| 1% | chr14 | 70466641 | 70466673 | + | chr14 | 70477471 | 70477663 | + | ENST00000361956; ENST00000381280 | TSF |
| 1% | chr14 | 70466641 | 70466673 | + | chr14 | 70477471 | 70477663 | + | ENST00000361956; ENST00000381280 | TSF |
| 1% | chr4 | 125071 | 125178 | + | chr4 | 337571 | 337697 | + | ENST00000512994; ENST00000505939; ENST00000240499 | TSF |
| 1% | chr4 | 125071 | 125178 | + | chr4 | 337571 | 337697 | + | ENST00000512994; ENST00000505939; ENST00000240499 | TSF |
| 1% | chr4 | 125071 | 125178 | + | chr4 | 337571 | 337697 | + | ENST00000512994; ENST00000505939; ENST00000240499 | TSF |
| 1% | chr9 | 70847151 | 70847411 | + | chr9 | 70860129 | 70860215 | + | ENST00000360171; ENST00000377342; ENST00000377344; ENST00000478048 | TSF |
| 1% | chr9 | 70847151 | 70847411 | + | chr9 | 70860129 | 70860215 | + | ENST00000360171; ENST00000377342; ENST00000377344; ENST00000478048 | TSF |
| 1% | chr9 | 70847151 | 70847411 | + | chr9 | 70860129 | 70860215 | + | ENST00000360171; ENST00000377342; ENST00000377344; ENST00000478048 | TSF |
| 1% | chr9 | 70847151 | 70847411 | + | chr9 | 70860129 | 70860215 | + | ENST00000360171; ENST00000377342; ENST00000377344; ENST00000478048 | TSF |
| 1% | chr18 | 33693361 | 33693356 | − | chr18 | 33692544 | 33692464 | − | ENST00000269187; ENST00000590986; ENST00000440549; ENST00000586829 | TSF |
| 1% | chr18 | 33693361 | 33693356 | − | chr18 | 33692544 | 33692464 | − | ENST00000269187; ENST00000590986; ENST00000440549; ENST00000586829 | TSF |
| 1% | chr18 | 33693361 | 33693356 | − | chr18 | 33692544 | 33692464 | − | ENST00000269187; ENST00000590986; ENST00000440549; ENST00000586829 | TSF |
| 1% | chr20 | 16294930 | 16294353 | − | chr20 | 16293063 | 16292980 | − | ENST00000354981; ENST00000355755; ENST00000378003 | TSF |
| 1% | chr7 | 94270259 | 94270209 | − | chr7 | 94268760 | 94268653 | − | ENST00000415788 | TSF |
| 1% | chr7 | 100850556 | 100850506 | − | chr7 | 100850185 | 100850060 | − | ENST00000454310; ENST00000223127 | TSF |
| 1% | chr7 | 94270259 | 94270209 | − | chr7 | 94259153 | 94259031 | − | ENST00000265735; ENST00000445866; ENST00000447873; ENST00000428696; ENST00000415788 | TSF |
| 1% | chr7 | 94270259 | 94270209 | − | chr7 | 94259153 | 94259031 | − | ENST00000265735; ENST00000445866; ENST00000447873; ENST00000428696; ENST00000415788 | TSF |
| 1% | chr7 | 94270259 | 94270209 | − | chr7 | 94259153 | 94259031 | − | ENST00000265735; ENST00000445866; ENST00000447873; ENST00000428696; ENST00000415788 | TSF |
| 1% | chr7 | 94270259 | 94270209 | − | chr7 | 94259153 | 94259031 | − | ENST00000265735; ENST00000445866; ENST00000447873; ENST00000428696; ENST00000415788 | TSF |
| 1% | chr7 | 94270259 | 94270209 | − | chr7 | 94259153 | 94259031 | − | ENST00000265735; ENST00000445866; ENST00000447873; ENST00000428696; ENST00000415788 | TSF |
| 1% | chr6 | 37326936 | 37327118 | + | chr6 | 37328222 | 37328350 | + | ENST00000373479; ENST00000229866; ENST00000394443; ENST00000469316; ENST00000469731 | TSF |
| 1% | chr6 | 37326936 | 37327118 | + | chr6 | 37328222 | 37328350 | + | ENST00000373479; ENST00000229866; ENST00000394443; ENST00000469316; ENST00000469731 | TSF |
| 1% | chr6 | 37326936 | 37327118 | + | chr6 | 37328222 | 37328350 | + | ENST00000373479; ENST00000229866; ENST00000394443; ENST00000469316; ENST00000469731 | TSF |
| 1% | chr6 | 37326936 | 37327118 | + | chr6 | 37328222 | 37328350 | + | ENST00000373479; ENST00000229866; ENST00000394443; ENST00000469316; ENST00000469731 | TSF |
| 1% | chr9 | 127110792 | 127110909 | + | chr9 | 127113116 | 127113226 | + | ENST00000540326; ENST00000373603; ENST00000373600; ENST00000320246; ENST00000545174; ENST00000394199; ENST00000546191; ENST00000539416 | TSF |

TABLE 10-continued

Transcript fusion for Breast Invasive Carcinoma (BRCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr4 | 74314427 | 74314578 | + | chr4 | 74315052 | 74315184 | + | ENST00000395792; ENST00000226359 | TSF |
| 1% | chr4 | 74314427 | 74314578 | + | chr4 | 74315052 | 74315184 | + | ENST00000395792; ENST00000226359 | TSF |
| 1% | chr8 | 95765825 | 95765986 | + | chr8 | 95768264 | 95768387 | + | ENST00000414645; ENST00000523020 | TSF |
| 1% | chr8 | 95765825 | 95765986 | + | chr8 | 95768264 | 95768387 | + | ENST00000414645; ENST00000523020 | TSF |
| 1% | chr10 | 37430220 | 37430401 | + | chr10 | 37430646 | 37431218 | + | ENST00000361713; ENST00000374660; ENST00000602533 | TSF |
| 1% | chr10 | 37430220 | 37430401 | + | chr10 | 37430646 | 37431218 | + | ENST00000361713; ENST00000374660; ENST00000602533 | TSF |
| 1% | chr4 | 146620427 | 146622789 | + | chr4 | 146648063 | 146648121 | + | ENST00000438731; ENST00000511965 | TSF |
| 1% | chr9 | 37801617 | 37801713 | + | chr9 | 37819285 | 37819398 | + | ENST00000377724; ENST00000242323 | TSF |
| 1% | chr9 | 37801617 | 37801713 | + | chr9 | 37819285 | 37819398 | + | ENST00000377724; ENST00000242323 | TSF |
| 1% | chrX | 80517692 | 80518225 | + | chrX | 80532483 | 80532668 | + | ENST00000373212 | TSF |
| 1% | chr14 | 100572435 | 100572471 | + | chr14 | 100589876 | 100589907; 100589939 | + | ENST00000555706; ENST00000402714; ENST00000544450; ENST00000392920; ENST00000557153; ENST00000557384 | TSF |
| 1% | chr14 | 100572435 | 100572471 | + | chr14 | 100589876 | 100589907; 100589939 | + | ENST00000555706; ENST00000402714; ENST00000544450; ENST00000392920; ENST00000557153; ENST00000557384 | TSF |
| 1% | chr14 | 100572435 | 100572471 | + | chr14 | 100589876 | 100589907; 100589939 | + | ENST00000555706; ENST00000402714; ENST00000544450; ENST00000392920; ENST00000557153; ENST00000557384 | TSF |
| 1% | chr14 | 100572435 | 100572471 | + | chr14 | 100589876 | 100589907; 100589939 | + | ENST00000555706; ENST00000402714; ENST00000544450; ENST00000392920; ENST00000557153; ENST00000557384 | TSF |
| 1% | chr14 | 100572435 | 100572471 | + | chr14 | 100589876 | 100589907; 100589939 | + | ENST00000555706; ENST00000402714; ENST00000544450; ENST00000392920; ENST00000557153; ENST00000557384 | TSF |
| 1% | chr17 | 42149044 | 42149179 | + | chr17 | 42151528 | 42151597; 42151634 | + | ENST00000591696; ENST00000269097 | TSF |
| 1% | chr17 | 42149044 | 42149179 | + | chr17 | 42151528 | 42151597; 42151634 | + | ENST00000591696; ENST00000269097 | TSF |
| 1% | chr1 | 45988716 | 45988450 | − | chr1 | 45981479 | 45981326 | − | ENST00000262746; ENST00000319248; ENST00000447184; ENST00000424390 | TSF |
| 1% | chr1 | 45988716 | 45988450 | − | chr1 | 45981479 | 45981326 | − | ENST00000262746; ENST00000319248; ENST00000447184; ENST00000424390 | TSF |
| 1% | chr4 | 873272 | 873014 | − | chr4 | 871597 | 871403 | − | ENST00000314167; ENST00000511163 | TSF |
| 1% | chr13 | 71011242 | 71010948 | − | chr13 | 70549934 | 70549752 | − | ENST00000377844 | TSF |
| 1% | chr2 | 214079365 | 214079242 | − | chr2 | 214013368 | 214013320 | − | ENST00000342002; ENST00000433134; ENST00000442445 | TSF |
| 1% | chr2 | 214079365 | 214079242 | − | chr2 | 214013368 | 214013320 | − | ENST00000342002; ENST00000433134; ENST00000442445 | TSF |
| 1% | chr2 | 214079365 | 214079242 | − | chr2 | 214013368 | 214013320 | − | ENST00000342002; ENST00000433134; ENST00000442445 | TSF |
| 1% | chr10 | 5473735 | 5473380 | − | chr10 | 5443050 | 5442807 | − | ENST00000380419 | TSF |
| 1% | chr8 | 125535738 | 125535448 | − | chr8 | 125535243 | 125535178 | − | ENST00000276692; ENST00000523214; ENST00000522810; ENST00000519776; ENST00000605953; ENST00000522310; ENST00000519232 | TSF |
| 1% | chr8 | 125535738 | 125535448 | − | chr8 | 125535243 | 125535178 | − | ENST00000276692; ENST00000523214; ENST00000522810; ENST00000519776; ENST00000605953; ENST00000522310; ENST00000519232 | TSF |
| 1% | chr8 | 125535738 | 125535448 | − | chr8 | 125535243 | 125535178 | − | ENST00000276692; ENST00000523214; ENST00000522810; ENST00000519776; ENST00000605953; ENST00000522310; ENST00000519232 | TSF |
| 1% | chr8 | 125535738 | 125535448 | − | chr8 | 125535243 | 125535178 | − | ENST00000276692; ENST00000523214; ENST00000522810; ENST00000519776; ENST00000605953; ENST00000522310; ENST00000519232 | TSF |
| 1% | chr8 | 125535738 | 125535448 | − | chr8 | 125535243 | 125535178 | − | ENST00000276692; ENST00000523214; ENST00000522810; ENST00000519776; ENST00000605953; ENST00000522310; ENST00000519232 | TSF |
| 1% | chr8 | 125535738 | 125535448 | − | chr8 | 125535243 | 125535178 | − | ENST00000276692; ENST00000523214; ENST00000522810; ENST00000519776; ENST00000605953; ENST00000522310; ENST00000519232 | TSF |
| 1% | chr7 | 154755921 | 154755838 | − | chr7 | 154755476 | 154755381 | − | ENST00000404141; ENST00000397192 | TSF |
| 1% | chr21 | 30382014 | 30381948 | − | chr21 | 30380942 | 30380716 | − | ENST00000493196 | TSF |

TABLE 11

Transcript fusion for Cervical squamous cell carcinoma (CESC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 38% | chr19 | 39077165 | 39077216 | + | ENST00000355481; ENST00000360985; ENST00000359596 | chr19 | 39085644 | 39085967 | + | TAF |
| 38% | chr19 | 39077165 | 39077216 | + | ENST00000355481; ENST00000360985; ENST00000359596 | chr19 | 39085644 | 39085967 | + | TAF |
| 38% | chr19 | 39077165 | 39077216 | + | ENST00000355481; ENST00000360985; ENST00000359596 | chr19 | 39085644 | 39085967 | + | TAF |
| 34% | chr10 | 47747112 | 47747132 | + | ENST00000340243; ENST00000374277; ENST00000449464; ENST00000538825 | chr10 | 48278725 | 48278896 | + | TAF |
| 31% | chr5 | 82554349 | 82554496 | + | ENST00000282268; ENST00000338635; ENST00000396027; ENST00000511817 | chr5 | 82606608 | 82606935 | + | TAF |
| 31% | chr19 | 3869015; 3869013 | 3868963 | − | ENST00000262961; ENST00000438164; ENST00000587212; ENST00000586578; ENST00000439086 | chr19 | 38556948 | 3855445 | − | TSF |
| 31% | chr19 | 3869015; 1386903 | 3868963 | − | ENST00000262961; ENST00000438164; ENST00000587212; ENST00000586578; ENST00000439086 | chr19 | 3855694 | 3855445 | − | TSF |
| 24% | chr3 | 49927493 | 49927357 | − | ENST00000296474; ENST00000344206 | chr3 | 49927248 | 49927204 | − | TAF |
| 24% | chr3 | 49927493 | 49927357 | − | ENST00000296474; ENST00000344206 | chr3 | 49927248 | 49927204 | − | TAF |
| 23% | chr1 | 153534067 | 153533988 | − | ENST00000368708; ENST00000487430; ENST00000497140; ENST00000368710; ENST00000368709 | chr1 | 153532853 | 153532704 | − | TAF |
| 23% | chr1 | 153534067 | 153533988 | − | ENST00000368708; ENST00000487430; ENST00000497140; ENST00000368710; ENST00000368709 | chr1 | 153532853 | 153532704 | − | TAF |
| 19% | chr3 | 118943092 | 118942905 | − | ENST00000483209; ENST00000467604; ENST00000359213; ENST00000393765; ENST00000480814 | chr3 | 118938512 | 118938188 | − | TAF |
| 18% | chr9 | 15506635 | 15506559 | − | ENST00000380738; ENST00000380733; ENST00000380715; ENST00000380716; ENST00000397519 | chr9 | 15492223 | 15492056 | − | TAF |
| 18% | chr18 | 61627392 | 61627509 | + | ENST00000408945 | chr18 | 61628870 | 61629168 | + | TSF |
| 15% | chr4 | 1742553 | 1742713 | + | ENST00000313288 | chr4 | 1745122 | 1745307 | + | TAF |
| 15% | chr3 | 196230044 | 196229744 | − | ENST00000318037; ENST00000437070 | chr3 | 196223342 | 196223041 | − | TAF |
| 15% | chr1 | 225156461 | 225156576 | + | ENST00000430092; ENST00000400952; ENST00000366849; ENST00000439375 | chr1 | 225157336 | 225158402 | + | TSF |
| 15% | chr1 | 225156461 | 225156576 | + | ENST00000430092; ENST00000400952; ENST00000366849; ENST00000439375 | chr1 | 225157336 | 225158402 | + | TSF |
| 14% | chr5 | 54993786 | 54993674 | − | ENST00000396865; ENST00000539768; ENST00000318672; ENST00000508124; ENST00000511233; ENST00000503891; ENST00000513993; ENST00000505563; ENST00000506624; ENST00000507109 | chr5 | 54993040 | 54992544 | − | TSF |
| 13% | chr10 | 4884613 | 4884696 | + | ENST00000474119; ENST00000463345; ENST00000298375; ENST00000532248; ENST00000334019; ENST00000345253 | chr10 | 4915406 | 4915583 | + | TAF |
| 13% | chr10 | 4884613 | 4884696 | + | ENST00000474119; ENST00000463345; ENST00000298375; ENST00000532248; ENST00000334019; ENST00000345253 | chr10 | 4915406 | 4915583 | + | TAF |
| 13% | chr10 | 4884613 | 4884696 | + | ENST00000474119; ENST00000463345; ENST00000298375; ENST00000532248; ENST00000334019; ENST00000345253 | chr10 | 4915406 | 4915583 | + | TAF |
| 13% | chr10 | 4884613 | 4884696 | + | ENST00000474119; ENST00000463345; ENST00000298375; ENST00000532248; ENST00000334019; ENST00000345253 | chr10 | 4915406 | 4915583 | + | TAF |
| 13% | chr20 | 35842163 | 35842268 | + | ENST00000237530; ENST00000373622 | chr20 | 35844460 | 35844765 | + | TAF |
| 13% | chr20 | 35842163 | 35842268 | + | ENST00000237530; ENST00000373622 | chr20 | 35844460 | 35844765 | + | TAF |
| 12% | chr18 | 33767503 | 33767644 | + | ENST00000261326 | chr18 | 33773430 | 33773774 | − | TAF |
| 12% | chr1 | 152006276 | 152006124 | − | ENST00000271638 | chr1 | 152005323 | 152005310 | − | TAF |
| 11% | chr16 | 2818998 | 2819285 | + | ENST00000301740 | chr16 | 2819873 | 2820194 | + | TAF |
| 11% | chr8 | 54793576 | 54793644 | + | ENST00000276500 | chr8 | 54826057 | 54826421 | + | TAF |
| 11% | chr12 | 71509738 | 71509630 | − | ENST00000549357 | chr12 | 71504233 | 71503634 | − | TAF |
| 11% | chr17 | 40821639; 40821538 | 40821448 | − | ENST00000591022; ENST00000412503; ENST00000293349 | chr17 | 40820920 | 40820864 | − | TAF |
| 11% | chr17 | 40821639; 40821538 | 40821448 | − | ENST00000591022; ENST00000412503; ENST00000293349 | chr17 | 40820920 | 40820864 | − | TAF |
| 11% | chr17 | 40821639; 40821538 | 40821448 | − | ENST00000591022; ENST00000412503; ENST00000293349 | chr17 | 40820920 | 40820864 | − | TAF |
| 10% | chr6 | 41606488 | 41606563 | + | ENST00000432027; ENST00000419164; ENST00000373051; ENST00000441667; ENST00000230321; ENST00000373050; ENST00000446650; ENST00000435476 | chr6 | 41607515 | 41607595 | + | TAF |
| 10% | chr1 | 32696528 | 32696620 | + | ENST00000373586 | chr1 | 3269686 | 32697110 | + | TAF |
| 10% | chr22 | 35819207 | 35819334 | + | ENST00000216122; ENST00000382011 | chr22 | 35846150 | 35846200 | + | |
| 10% | chr22 | 35819207 | 35819334 | + | ENST00000216122; ENST00000382011 | chr22 | 35846150 | 35846200 | + | TSF |
| 9% | chr1 | 6531697 | 6531548 | − | ENST00000400913; ENST00000340850 | chr1 | 6531300 | 6531188 | − | TSF |

TABLE 11-continued

Transcript fusion for Cervical squamous cell carcinoma (CESC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 9% | chr1 | 6531697 | 6531548 | − | ENST00000377748; ENST00000377725; ENST00000377728; ENST00000377732; ENST00000400915; ENST00000377740; ENST00000535355; ENST00000377737; ENST00000537245; ENST00000544978 ENST00000400913; ENST00000340850; | chr1 | 6531300 | 6531188 | − | TSF |
| 9% | chr1 | 6531697 | 6531548 | − | ENST00000377748; ENST00000377725; ENST00000377728; ENST00000377732; ENST00000400915; ENST00000377740; ENST00000535355; ENST00000377737; ENST00000537245; ENST00000544978 ENST00000400913; ENST00000340850; | chr1 | 6531300 | 6531188 | − | TSF |
| 9% | chr1 | 6531697 | 6531548 | − | ENST00000377748; ENST00000377725; ENST00000377728; ENST00000377732; ENST00000400915; ENST00000377740; ENST00000535355; ENST00000377737; ENST00000537245; ENST00000544978 ENST00000400913; ENST00000340850; | chr1 | 6531300 | 6531188 | − | TSF |
| 9% | chr1 | 6531697 | 6531548 | − | ENST00000377748; ENST00000377725; ENST00000377728; ENST00000377732; ENST00000400915; ENST00000377740; ENST00000535355; ENST00000377737; ENST00000537245; ENST00000544978 ENST00000400913; ENST00000340850; | chr1 | 6531300 | 6531188 | − | TSF |
| 9% | chr1 | 6531697 | 6531548 | − | ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 8% | chr1 | 63955889 | 63955754 | − | ENST00000371092; ENST00000271002; ENST00000489099; ENST00000283568 | chr1 | 63952444 | 63951983 | − | TSF |
| 8% | chr1 | 63955889 | 63955754 | − | ENST00000371092; ENST00000271002; ENST00000489099; ENST00000283568 | chr1 | 63952441 | 63951983 | − | TSF |
| 7% | chr19 | 3114942 | 3115070 | + | ENST00000078429; ENST00000587636 | chr19 | 3115258 | 3115402 | + | TSF |
| 7% | chr19 | 3114942 | 3115070 | + | ENST00000078429; ENST00000587636 | chr19 | 3115258 | 3115402 | + | TSF |
| 7% | chrX | 41598709 | 41598637− | − | ENST00000421587; ENST00000318588; ENST00000361962; ENST00000378163; ENST00000378158; ENST00000378166; ENST00000442742; ENST00000378154 | chrX | 41557348 | 41557057 | − | TSF |
| 6% | chr1 | 11115983; 11115877 | 11115838 | − | ENST00000376957; ENST00000490101 | chr1 | 11115464 | 11115178 | − | TSF |
| 6% | chr1 | 11115983; 11115877 | 11115838 | − | ENST00000376957; ENST00000490101 | chr1 | 11115464 | 11115178 | − | TSF |
| 6% | chr7 | 22532348 | 22532184 | − | ENST00000406890; ENST00000404369; ENST00000424363 | chr7 | 22512853 | 22512669 | − | TSF |
| 6% | chr7 | 22532348 | 22532184 | − | ENST00000406890; ENST00000404369; ENST00000424363 | chr7 | 22512853 | 22512669 | − | TSF |
| 6% | chr8 | 143867103 | 143867005 | − | ENST00000301263 | chr8 | 143859806 | 143859781 | − | TSF |
| 6% | chr19 | 45895598 | 45895138 | − | ENST00000360957; ENST00000418234 | chr19 | 45889495 | 45889472 | − | TSF |
| 5% | chr9 | 125054028 | 125054119 | + | ENST00000297908; ENST00000344641; ENST00000373723; ENST00000373729; ENST00000394315 | chr9 | 125068067 | 125068171 | + | TSF |
| 5% | chr9 | 125054028 | 125054119 | + | ENST00000373723; ENST00000373729; ENST00000297908; ENST00000344641; ENST00000394315 | chr9 | 125068067 | 125068171 | + | TSF |
| 5% | chr9 | 125054028 | 125054119 | + | ENST00000297908; ENST00000344641; ENST00000373723; ENST00000373729; ENST00000394315 | chr9 | 125068067 | 125068171 | + | TSF |
| 5% | chr22 | 35819207 | 35819334 | + | ENST00000216122; ENST00000382011 | chr22 | 35822985 | 35823438 | + | TSF |
| 5% | chr22 | 35819207 | 35819334 | + | ENST00000216122; ENST00000382011 | chr22 | 35822985 | 35823438 | + | TSF |
| 5% | chr17 | 36288631 | 36288740 | + | ENST00000327454; ENST00000378174; ENST00000505415; ENST00000539424 | chr17 | 36289142 | 36289609 | + | TSF |
| 5% | chr17 | 36288631 | 36288740 | + | ENST00000327454; ENST00000378174; ENST00000505415; ENST00000539424 | chr17 | 36289142 | 36289609 | + | TSF |

TABLE 11-continued

Transcript fusion for Cervical squamous cell carcinoma (CESC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 5% | chr22 | 35819207 | 35819334 | + | ENST00000216122; ENST00000382011 | chr22 | 35844184 | 35844261 | + | TSF |
| 5% | chr22 | 35819207 | 35819334 | + | ENST00000216122; ENST00000382011 | chr22 | 35844184 | 35844261 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr16 | 88873689 | 88873890 | + | ENST00000301019 | chr16 | 88875475 | 88875490 | + | TSF |
| 4% | chr4 | 57319769 | 57319927 | + | ENST00000514888; ENST00000264221; ENST00000505164; ENST00000399688; ENST00000512576 | chr4 | 57321183 | 57321327 | + | TSF |
| 4% | chr4 | 57319769 | 57319927 | + | ENST00000514888; ENST00000264221; ENST00000505164; ENST00000399688; ENST00000512576 | chr4 | 57321183 | 57321327 | + | TSF |
| 4% | chr4 | 57319769 | 57319927 | + | ENST00000514888; ENST00000264221; ENST00000505164; ENST00000399688; ENST00000512576 | chr4 | 57321183 | 57321327 | + | TSF |
| 4% | chr10 | 126205749 | 126205840 | + | ENST00000368842 | chr10 | 126251911 | 12625228 | + | TSF |
| 4% | chr16 | 68729680; 68729728 | 68729826 | + | ENST00000264012; ENST00000429102; ENST00000581171; ENST00000568292; ENST00000569080 | chr16 | 68761056 | 68761347 | + | TSF |
| 4% | chr16 | 68729680; 68729728 | 68729826 | + | ENST00000264012; ENST00000429102; ENST00000581171; ENST00000568292; ENST00000569080 | chr16 | 68761056 | 68761347 | + | TSF |
| 4% | chr16 | 68729680; 68729728 | 68729826 | + | ENST00000264012; ENST00000429102; ENST00000581171; ENST00000568292; ENST00000569080 | chr16 | 68761056 | 68761347 | + | TSF |
| 4% | chr16 | 68729680; 68729728 | 68729826 | + | ENST00000264012; ENST00000429102; ENST00000581171; ENST00000568292; ENST00000569080 | chr16 | 68761056 | 68761347 | + | TSF |
| 4% | chr16 | 57115439 | 57115522 | + | ENST00000262510; ENST00000308149; ENST00000539144 | chr16 | 57116257 | 57116272 | + | TSF |
| 4% | chr16 | 57115439 | 57115522 | + | ENST00000262510; ENST00000308149; ENST00000539144 | chr16 | 57116257 | 57116272 | + | TSF |
| 4% | chr7 | 73973957 | 73973985 | + | ENST00000265755; ENST00000455841; ENST00000424337; ENST00000476977; ENST00000470715 | chr7 | 73985447 | 73985582 | + | TSF |
| 4% | chr7 | 73973957 | 73973985 | + | ENST00000265755; ENST00000455841; ENST00000424337; ENST00000476977; ENST00000470715 | chr7 | 73985447 | 73985582 | + | TSF |
| 4% | chr7 | 73973957 | 73973985 | + | ENST00000265755; ENST00000455841; ENST00000424337; ENST00000476977; ENST00000470715 | chr7 | 73985447 | 73985582 | + | TSF |
| 4% | chr7 | 73973957 | 73973985 | + | ENST00000265755; ENST00000455841; ENST00000424337; ENST00000476977; ENST00000470715 | chr7 | 73985447 | 73985582 | + | TSF |
| 4% | chr3 | 48716169 | 48715997 | − | ENST00000341520; ENST00000416649; ENST00000294129; ENST00000413374 | chr3 | 48702393 | 48702198 | − | TSF |
| 4% | chr3 | 48716169 | 48715997 | − | ENST00000341520; ENST00000416649; ENST00000294129; ENST00000413374 | chr3 | 48702393 | 48702198 | − | TSF |
| 4% | chr3 | 48716169 | 48715997 | − | ENST00000341520; ENST00000416649; ENST00000294129; ENST00000413374 | chr3 | 48702393 | 48702198 | − | TSF |
| 4% | chr12 | 56742407 | 56742313 | − | ENST00000314128; ENST00000557235 | chr12 | 56740986 | 56740975 | − | TSF |
| 4% | chr12 | 56742407 | 56742313 | − | ENST00000314128; ENST00000557235 | chr12 | 56740986 | 56740975 | | TSF |
| 4% | chr11 | 60701014 | 60701216 | + | ENST00000453848; ENST00000005286; ENST00000536409 | chr11 | 60701443 | 60701575 | + | TSF |

TABLE 11-continued

Transcript fusion for Cervical squamous cell carcinoma (CESC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 4% | chr11 | 60701014 | 60701216 | + | ENST00000453848; ENST00000005286; ENST00000536409 | chr11 | 60701443 | 60701575 | + | TSF |
| 4% | chr11 | 60701014 | 60701216 | + | ENST00000453848; ENST00000005286; ENST00000536409 | chr11 | 60701443 | 60701575 | + | TSF |
| 4% | chrX | 119708472 | 119708406 | − | ENST00000404115 | chrX | 119705855 | 119705820 | − | TSF |
| 4% | chr19 | 15289752 | 15289634 | − | ENST00000263388; ENST00000601011 | chr19 | 15289244 | 15289201 | − | TSF |
| 4% | chr19 | 15289752 | 15289634 | − | ENST00000263388; ENST00000601011 | chr19 | 15289244 | 15289201 | − | TSF |
| 3% | chr11 | 101937216; 101937273 | 101937382 | + | ENST00000434758; ENST00000526781; ENST00000529204 | chr11 | 101937956 | 101938097 | + | TSF |
| 3% | chr11 | 101937216; 101937273 | 101937382 | + | ENST00000434758; ENST00000526781; ENST00000529204 | chr11 | 101937956 | 101938097 | + | TSF |
| 3% | chr5 | 1802435 | 1802488 | + | ENST00000274137; ENST00000469176 | chr5 | 1811082 | 1811428 | + | TSF |
| 3% | chr7 | 81964567 | 81964451 | − | ENST00000356860; ENST00000356253; ENST00000423588 | chr7 | 81929467 | 81929190 | − | TSF |
| 3% | chr6 | 29693224; 29693311 | 29693340 | + | ENST00000376861; ENST00000334668; ENST00000259951; ENST00000440587; ENST00000434407; ENST00000429294; ENST00000444621 | chr6 | 29700968 | 29700992 | + | TSF |
| 3% | chr6 | 29693224; 29693311 | 29693340 | + | ENST00000376861; ENST00000334668; ENST00000259951; ENST00000440587; ENST00000434407; ENST00000429294; ENST00000444621 | chr6 | 29700968 | 29700992 | + | TSF |
| 3% | chr6 | 29693224; 29693311 | 29693340 | + | ENST00000376861; ENST00000334668; ENST00000259951; ENST00000440587; ENST00000434407; ENST00000429294; ENST00000444621 | chr6 | 29700968 | 29700992 | + | TSF |
| 3% | chr6 | 29693224; 29693311 | 29693340 | + | ENST00000376861; ENST00000334668; ENST00000259951; ENST00000440587; ENST00000434407; ENST00000429294; ENST00000444621 | chr6 | 29700968 | 29700992 | + | TSF |
| 3% | chr6 | 29693224; 29693311 | 29693340 | + | ENST00000376861; ENST00000334668; ENST00000259951; ENST00000440587; ENST00000434407; ENST00000429294; ENST00000444621 | chr6 | 29700968 | 29700992 | + | TSF |
| 3% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |
| 3% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |
| 3% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |
| 3% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |
| 3% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |
| 3% | chr17 | 36343995 | 36343886 | − | ENST00000518551; ENST00000354664; ENST00000339023; ENST00000519532; ENST00000537432 | chr17 | 36343484 | 36343017 | − | TSF |
| 3% | chr17 | 36343995 | 36343886 | − | ENST00000518551; ENST00000354664; ENST00000339023; ENST00000519532; ENST00000537432 | chr17 | 36343484 | 36343017 | − | TSF |

TABLE 11-continued

Transcript fusion for Cervical squamous cell carcinoma (CESC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr16 | 2825557; 2825626 | 2825452 | − | ENST00000262306; ENST00000409906; ENST00000409477; ENST00000494946 | chr16 | 2823822 | 2823809 | − | TSF |
| 3% | chr16 | 2825557; 2825626 | 2825452 | − | ENST00000262306; ENST00000409906; ENST00000409477; ENST00000494946 | chr16 | 2823822 | 2823809 | − | TSF |
| 3% | chr16 | 2825557; 2825626 | 2825452 | − | ENST00000262306; ENST00000409906; ENST00000409477; ENST00000494946 | chr16 | 2823822 | 2823809 | − | TSF |
| 3% | chr19 | 3855446 | 3855400 | − | ENST00000592398; ENST00000591712 | chr19 | 3852385 | 3852258 | − | TSF |
| 3% | chr1 | 180283857 | 180283827 | − | ENST00000367595 | chr1 | 180281457 | 180281103 | − | TSF |
| 3% | chr17 | 73887428 | 73887358 | − | ENST00000591668; ENST00000592642; ENST00000269383; ENST00000543309 | chr17 | 73885428 | 73885139 | − | TSF |
| 3% | chr17 | 73887428 | 73887358 | − | ENST00000591668; ENST00000592642; ENST00000269383; ENST00000543309 | chr17 | 73885428 | 73885139 | − | TSF |
| 3% | chr17 | 73887428 | 73887358 | − | ENST00000591668; ENST00000592642; ENST00000269383; ENST00000543309 | chr17 | 73885428 | 73885139 | − | TSF |
| 3% | chr17 | 73887428 | 73887358 | − | ENST00000591668; ENST00000592642; ENST00000269383; ENST00000543309 | chr17 | 73885428 | 73885139 | − | TSF |
| 3% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 3% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 3% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 3% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 3% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 3% | chr22 | 38321668; 38321854 | 38322050 | + | ENST00000215957; ENST00000454685 | chr22 | 38322963 | 38322967 | + | TSF |
| 3% | chr22 | 38321668; 38321854 | 38322050 | + | ENST00000215957; ENST00000454685 | chr22 | 38322963 | 38322967 | + | TSF |
| 3% | chr22 | 42154369; 42154464 | 42154537 | + | ENST00000401548; ENST00000540833; ENST00000400107; ENST00000540880 | chr22 | 42155353 | 42155683 | + | TSF |
| 3% | chr22 | 42154369; 42154464 | 42154537 | + | ENST00000401548; ENST00000540833; ENST00000400107; ENST00000540880 | chr22 | 42155353 | 42155683 | + | TSF |
| 3% | chr22 | 42154369; 42154464 | 42154537 | + | ENST00000401548; ENST00000540833; ENST00000400107; ENST00000540880 | chr22 | 42155353 | 42155683 | + | TSF |
| 3% | chr22 | 42154369; 42154464 | 42154537 | + | ENST00000401548; ENST00000540833; ENST00000400107; ENST00000540880 | chr22 | 42155353 | 42155683 | + | TSF |
| 3% | chr3 | 129020793 | 129020985 | + | ENST00000509042; ENST00000383463; ENST00000417226; ENST00000502878; ENST00000389735 | chr3 | 129029005 | 129029042 | + | TSF |
| 3% | chr3 | 129020793 | 129020985 | + | ENST00000509042; ENST00000383463; ENST00000417226; ENST00000502878; ENST00000389735 | chr3 | 129029005 | 129029042 | + | TSF |
| 3% | chr3 | 129020793 | 129020985 | + | ENST00000509042; ENST00000383463; ENST00000417226; ENST00000502878; ENST00000389735 | chr3 | 129029005 | 129029042 | + | TSF |
| 3% | chr22 | 45813490; 45813481 | 45813826 | + | ENST00000342894; ENST00000538017 | chr22 | 45815177 | 45815331 | + | TSF |
| 3% | chr22 | 45813490; 45813481 | 45813826 | + | ENST00000342894; ENST00000538017 | chr22 | 45815177 | 45815331 | + | TSF |
| 3% | chr1 | 180283857 | 180283827 | − | ENST00000367595 | chr1 | 180281120 | 180281103 | − | TSF |
| 2% | chr16 | 3118181 | 3118240 | + | ENST00000325568; ENST00000534507; ENST00000531965; ENST00000396887; ENST00000526464; ENST00000440815; ENST00000529550; ENST00000551122; ENST00000525643; ENST00000548807; ENST00000528163; ENST00000530890; ENST00000444393; ENST00000533097; ENST00000008180; ENST00000396890; ENST00000525228; ENST00000548652; ENST00000525377; ENST00000530538; ENST00000549213; ENST00000552936; | chr16 | 3135449 | 3135770 | + | TSF |

TABLE 11-continued

Transcript fusion for Cervical squamous cell carcinoma (CESC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
|   |   |   |   |   | ENST00000548476; ENST00000552664; ENST00000552356; ENST00000551513; ENST00000382213 |   |   |   |    |    |
| 2% | chr16 | 3118181 | 3118240 | + | ENST00000325568; ENST00000534507; ENST00000531965; ENST00000396887; ENST00000526464; ENST00000440815; ENST00000529550; ENST00000551122; ENST00000525643; ENST00000548807; ENST00000528163; ENST00000530890; ENST00000444393; ENST00000533097; ENST00000008180; ENST00000396890; ENST00000525228; ENST00000548652; ENST00000525377; ENST00000530538; ENST00000549213; ENST00000552936; ENST00000548476; ENST00000552664; ENST00000552356; ENST00000551513; ENST00000382213 | chr16 | 3135449 | 3135770 | + | TSF |
| 2% | chr16 | 3118181 | 3118240 | + | ENST00000325568; ENST00000534507; ENST00000531965; ENST00000396887; ENST00000526464; ENST00000440815; ENST00000529550; ENST00000551122; ENST00000525643; ENST00000548807; ENST00000528163; ENST00000530890; ENST00000444393; ENST00000533097; ENST00000008180; ENST00000396890; ENST00000525228; ENST00000548652; ENST00000525377; ENST00000530538; ENST00000549213; ENST00000552936; ENST00000548476; ENST00000552664; ENST00000552356; ENST00000551513; ENST00000382213 | chr16 | 3135449 | 3135770 | + | TSF |
| 2% | chr16 | 3118181 | 3118240 | + | ENST00000325568; ENST00000534507; ENST00000531965; ENST00000396887; ENST00000526464; ENST00000440815; ENST00000529550; ENST00000551122; ENST00000525643; ENST00000548807; ENST00000528163; ENST00000530890; ENST00000444393; ENST00000533097; ENST00000008180; ENST00000396890; ENST00000525228; ENST00000548652; ENST00000525377; ENST00000530538; ENST00000549213; ENST00000552936; ENST00000548476; ENST00000552664; ENST00000552356; ENST00000551513; ENST00000382213 | chr16 | 3135449 | 3135770 | + | TSF |
| 2% | chr16 | 3118181 | 3118240 | + | ENST00000325568; ENST00000534507; ENST00000531965; ENST00000396887; ENST00000526464; ENST00000440815; ENST00000529550; ENST00000551122; ENST00000525643; ENST00000548807; ENST00000528163; ENST00000530890; ENST00000444393; ENST00000533097; ENST00000008180; ENST00000396890; ENST00000525228; ENST00000548652; ENST00000525377; ENST00000530538; ENST00000549213; ENST00000552936; ENST00000548476; ENST00000552664; ENST00000552356; ENST00000551513; ENST00000382213 | chr16 | 3135449 | 3135770 | + | TSF |
| 2% | chr16 | 3118181 | 3118240 | + | ENST00000325568; ENST00000534507; ENST00000531965; ENST00000396887; ENST00000526464; ENST00000440815; ENST00000529550; ENST00000551122; ENST00000525643; ENST00000548807; ENST00000528163; ENST00000530890; ENST00000444393; ENST00000533097; ENST00000008180; ENST00000396890; ENST00000525228; ENST00000548652; ENST00000525377; ENST00000530538; ENST00000549213; ENST00000552936; ENST00000548476; ENST00000552664; ENST00000552356; ENST00000551513; ENST00000382213 | chr16 | 3135449 | 3135770 | + | TSF |

TABLE 11-continued

Transcript fusion for Cervical squamous cell carcinoma (CESC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr16 | 3118181 | 3118240 | + | ENST00000325568; ENST00000534507; ENST00000531965; ENST00000396887; ENST00000526464; ENST00000440815; ENST00000529550; ENST00000551122; ENST00000525643; ENST00000548807; ENST00000528163; ENST00000530890; ENST00000444393; ENST00000533097; ENST00000008180; ENST00000396890; ENST00000525228; ENST00000548652; ENST00000525377; ENST00000530538; ENST00000549213; ENST00000552936; ENST00000548476; ENST00000552664; ENST00000552356; ENST00000551513; ENST00000382213 | chr16 | 3135449 | 3135770 | + | TSF |
| 2% | chr16 | 3118181 | 3118240 | + | ENST00000325568; ENST00000534507; ENST00000531965; ENST00000396887; ENST00000526464; ENST00000440815; ENST00000529550; ENST00000551122; ENST00000525643; ENST00000548807; ENST00000528163; ENST00000530890; ENST00000444393; ENST00000533097; ENST00000008180; ENST00000396890; ENST00000525228; ENST00000548652; ENST00000525377; ENST00000530538; ENST00000549213; ENST00000552936; ENST00000548476; ENST00000552664; ENST00000552356; ENST00000551513; ENST00000382213 | chr16 | 3135449 | 3135770 | + | TSF |
| 2% | chr14 | 76662221 | 76662315 | + | ENST00000312858; ENST00000261530; ENST00000554799; ENST00000553588 | chr14 | 76666223 | 76666696 | + | TSF |
| 2% | chr14 | 76662221 | 76662315 | + | ENST00000312858; ENST00000261530; ENST00000554799; ENST00000553588 | chr14 | 76666223 | 76666696 | + | TSF |
| 2% | chr14 | 76662221 | 76662315 | + | ENST00000312858; ENST00000261530; ENST00000554799; ENST00000553588 | chr14 | 76666223 | 76666696 | + | TSF |
| 2% | chr19 | 46627413 | 46627143 | − | ENST00000341415 | chr19 | 46623577 | 46622963 | − | TSF |
| 2% | chr11 | 64599981 | 64599900 | − | ENST00000342711 | chr11 | 64599599 | 64599309 | − | TSF |
| 2% | chr19 | 46627413 | 46627143 | − | ENST00000341415 | chr19 | 46623564 | 46622963 | − | TSF |
| 2% | chr4 | 1102192 | 1102131 | − | ENST00000382968; ENST00000433731; ENST00000511620; ENST00000510715; ENST00000333673 | chr4 | 1101132 | 1100845 | − | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr6 | 84772612 | 84772711 | + | ENST00000257776 | chr6 | 84849189 | 84849246 | + | TSF |
| 2% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 2% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 2% | chr21 | 45222155 | 45222268 | + | ENST00000497547 | chr21 | 45240407 | 45240709 | + | TSF |
| 2% | chr1 | 63944504 | 63944435 | − | ENST00000371092; ENST00000271002; ENST00000489099; ENST00000283568 | chr1 | 63927687 | 63926951 | − | TSF |
| 2% | chr1 | 63944504 | 63944435 | − | ENST00000371092; ENST00000271002; ENST00000489099; ENST00000283568 | chr1 | 63927687 | 63926951 | − | TSF |
| 2% | chr3 | 49928739 | 49928630 | − | ENST00000296474; ENST00000344206; ENST00000434765; ENST00000440292 | chr3 | 49928452 | 49928163 | − | TSF |
| 2% | chr3 | 49928739 | 49928630 | − | ENST00000296474; ENST00000344206; ENST00000434765; ENST00000440292 | chr3 | 49928452 | 49928163 | − | TSF |
| 2% | chr3 | 49928739 | 49928630 | − | ENST00000296474; ENST00000344206; ENST00000434765; ENST00000440292 | chr3 | 49928452 | 49928163 |  | TSF |
| 2% | chr3 | 49928739 | 49928630 | − | ENST00000296474; ENST00000344206; ENST00000434765; ENST00000440292 | chr3 | 49928452 | 49928163 | − | TSF |

TABLE 12

Transcript fusion for Cervical squamous cell carcinoma (CESC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 61% | chr12 | 122430912 | 122431615 | + | chr12 | 122437622 | 122437850 | + | ENST00000288912 | TAF |
| 30% | chr22 | 45814683 | 45815239 | + | chr22 | 45818170 | 45818288 | + | ENST00000342894; ENST00000538017 | TAF |
| 28% | chr11 | 93468219 | 93468129 |  | chr11 | 93467826 | 93467791; 93467814 |  | ENST00000393259; ENST00000527169 | TAF |
| 28% | chr11 | 93468219 | 93468129 | − | chr11 | 93467826 | 93467791; 93467814 | − | ENST00000393259; ENST00000527169 | TAF |
| 26% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 26% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 26% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 26% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 26% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 24% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 24% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 24% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 24% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 24% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 23% | chr19 | 54631006 | 54631115 | + | chr19 | 54631448 | 54631575 | + | ENST00000321030; ENST00000419967 | TAF |
| 23% | chr19 | 54631006 | 54631115 | + | chr19 | 54631448 | 54631575 | + | ENST00000321030; ENST00000419967 | TAF |
| 23% | chr1 | 79214190 | 79214239 | + | chr17 | 79214787 | 79214816; 79214953 | + | ENST00000431388; ENST00000576002 | TAF |
| 23% | chr1 | 79214190 | 79214239 | + | chr17 | 79214787 | 79214816; 79214953 | + | ENST00000431388; ENST00000576002 | TAF |
| 23% | chr13 | 76173531 | 76175706 | + | chr13 | 76178905 | 76178963 | + | ENST00000377595; ENST00000419068 | TAF |
| 20% | chr8 | 104389530 | 104389551 | + | chr8 | 104390255 | 104390471 | + | ENST00000330295; ENST00000520337 | TAF |
| 20% | chr6 | 138423138 | 138423021 | − | chr6 | 138417631 | 138417491 | − | ENST00000421351 | TAF |
| 19% | chr8 | 82194688 | 82194727 | + | chr8 | 82195601 | 82195773 | + | ENST00000297258 | TAF |
| 18% | chr12 | 6602868 | 6602840 | − | chr12 | 6602138 | 6602028 | − | ENST00000229238 | TAF |
| 18% | chr1 | 169819657 | 169819707 | + | chr1 | 169820958 | 169821077 | + | ENST00000359326; ENST00000286031 | TSF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 17% | chr1 | 86821476 | 86821330 | − | chr1 | 86820542 | 86820457; 86820538 | − | ENST00000359242; ENST00000460698; ENST00000317336; ENST00000370567; | TAF |

TABLE 12-continued

Transcript fusion for Cervical squamous cell carcinoma (CESC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 17% | chr1 | 86821476 | 86821330 | − | chr1 | 86820542 | 86820457; 86820538 | − | ENST00000394731; ENST00000370566; ENST00000462648; ENST00000294678; ENST00000531412 ENST00000359242; ENST00000460698; ENST00000317336; ENST00000370567; | TAF |
| 17% | chr1 | 86821476 | 86821330 | − | chr1 | 86820542 | 86820457; 86820538 | − | ENST00000394731; ENST00000370566; ENST00000462648; ENST00000294678; ENST00000531412 ENST00000359242; ENST00000460698; ENST00000317336; ENST00000370567; | TAF |
| 17% | chr1 | 86821476 | 86821330 | − | chr1 | 86820542 | 86820457; 86820538 | − | ENST00000394731; ENST00000370566; ENST00000462648; ENST00000294678; ENST00000531412 ENST00000359242; ENST00000460698; ENST00000317336; ENST00000370567; | TAF |
| 15% | chr12 | 86274449 | 86274547 | + | chr12 | 86276001 | 86276153 | + | ENST00000551529; ENST00000256010 | TAF |
| 15% | chr4 | 107241932 | 107242850 | + | chr4 | 107246142 | 107246275 | + | ENST00000394701 | TAF |
| 14% | chr19 | 55558521 | 55558473 | − | chr19 | 55556677 | 55556442 | − | ENST00000415061; ENST00000396247 | TAF |
| 14% | chr17 | 74261446 | 74261484 | + | chr17 | 74261988 | 74262050 | + | ENST00000327490 | TAF |
| 14% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 14% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 14% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 14% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 14% | chr19 | 39347374 | 39346430 | − | chr19 | 39338074 | 39337956 | − | ENST00000221419; ENST00000601449; ENST00000600233; ENST00000601813 | TSF |
| 14% | chr19 | 39347374 | 39346430 | − | chr19 | 39338074 | 39337956 | − | ENST00000221419; ENST00000601449; ENST00000600233; ENST00000601813 | TSF |
| 14% | chr19 | 39347374 | 39346430 | − | chr19 | 39338074 | 39337956 | − | ENST00000221419; ENST00000601449; ENST00000600233; ENST00000601813 | TSF |
| 14% | chr19 | 39347374 | 39346430 | − | chr19 | 39338074 | 39337956 | − | ENST00000221419; ENST00000601449; ENST00000600233; ENST00000601813 | TSF |
| 14% | chr19 | 39347374 | 39346430 | − | chr19 | 39338074 | 39337956 | − | ENST00000221419; ENST00000601449; ENST00000600233; ENST00000601813 | TSF |
| 13% | chr15 | 43889497 | 43889601 | + | chr15 | 43890391 | 43890525 | + | ENST00000300283; ENST00000441322 | TAF |
| 12% | chr7 | 116364854 | 116364901 | + | chr7 | 116371722 | 116371913 | + | ENST00000397752; ENST00000318493; ENST00000436117 | TAF |
| 12% | chr7 | 116364854 | 116364901 | + | chr7 | 116371722 | 116371913 | + | ENST00000397752; ENST00000318493; ENST00000436117 | TAF |
| 12% | chr7 | 116364854 | 116364901 | + | chr7 | 116371722 | 116371913 | + | ENST00000397752; ENST00000318493; ENST00000436117 | TAF |
| 12% | chr5 | 54528691 | 54528595 | − | chr5 | 54528374 | 54528189 | − | ENST00000282572 | TAF |
| 11% | chr5 | 1811001 | 1811176 | + | chr5 | 1814453 | 1814575; 1814785 | + | ENST00000274137; ENST00000469176 | TAF |
| 11% | chr5 | 1811001 | 1811176 | + | chr5 | 1814453 | 1814575; 1814785 | + | ENST00000274137; ENST00000469176 | TAF |
| 11% | chr15 | 43989318 | 43989422 | + | chr15 | 43990212 | 43990346 | + | ENST00000434505; ENST00000413453 | TAF |
| 11% | chr17 | 40820773 | 40820708 | − | chr17 | 40820321 | 40820145 | − | ENST00000591022; ENST00000412503; ENST00000293349 | TAF |
| 11% | chr9 | 131002678 | 131002811 | + | chr9 | 131004511 | 131004624 | + | ENST00000475805; ENST00000341179; ENST00000372923; ENST00000393594; ENST00000486160 | TAF |
| 11% | chr9 | 131002678 | 131002811 | + | chr9 | 131004511 | 131004624 | + | ENST00000475805; ENST00000341179; ENST00000372923; ENST00000393594; ENST00000486160 | TAF |
| 11% | chr11 | 19190423 | 19190515 | + | chr11 | 19191958 | 19192115 | + | ENST00000446113; ENST00000399351 | TAF |
| 11% | chr5 | 823586 | 823504 | − | chr5 | 822010 | 821976 | − | ENST00000424784; ENST00000283441 | TAF |
| 11% | chr1 | 165863702 | 165863816 | + | chr1 | 165865427 | 165865569 | + | ENST00000367879 | TAF |
| 11% | chr1 | 6380703 | 6380649 | − | chr1 | 6378638 | 6378552 | − | ENST00000608083; ENST00000377842; | TAF |

TABLE 12-continued

Transcript fusion for Cervical squamous cell carcinoma (CESC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 11% | chr1 | 6380703 | 6380649 | − | chr1 | 6378638 | 6378552 | − | ENST00000377845; ENST00000377855; ENST00000377860; ENST00000418124; ENST00000545482; ENST00000361521; ENST00000473466; ENST00000541130 ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr19 | 1114930 | 1114676 | − | chr19 | 1114421 | 1114230 | − | ENST00000361757; ENST00000587024; ENST00000438103 | TSF |
| 10% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 10% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 10% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 10% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 10% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 9% | chr12 | 122387836 | 122388242 | + | chr12 | 122389386 | 122389436 | + | ENST00000288912; ENST00000397454 | TSF |
| 9% | chr12 | 122387836 | 122388242 | + | chr12 | 122389386 | 122389436 | + | ENST00000288912; ENST00000397454 | TSF |
| 9% | chr19 | 48654965 | 48654725 | − | chr19 | 48654596 | 48654489 | − | ENST00000263274; ENST00000601091; ENST00000542460 | TSF |
| 9% | chr19 | 48654965 | 48654725 | − | chr19 | 48654596 | 48654489 | − | ENST00000263274; ENST00000601091; ENST00000542460 | TSF |
| 9% | chr19 | 48654965 | 48654725 | − | chr19 | 48654596 | 48654489 | − | ENST00000263274; ENST00000601091; ENST00000542460 | TSF |
| 8% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 8% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 8% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 8% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 7% | chr12 | 122387836 | 122388242 | + | chr12 | 122392026 | 122392240 | + | ENST00000288912; ENST00000397454 | TSF |
| 7% | chr12 | 122387836 | 122388242 | + | chr12 | 122392026 | 122392240 | + | ENST00000288912; ENST00000397454 | TSF |
| 7% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; | TSF |

TABLE 12-continued

Transcript fusion for Cervical squamous cell carcinoma (CESC) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 7% | chr22 | 29117574 | 29117506 | − | chr22 | 29115473 | 29115383; 29115458 | − | ENST00000382580; ENST00000433728; ENST00000448511; ENST00000402731; ENST00000403642; ENST00000439200 ENST00000348295; ENST00000382566; ENST00000382578; ENST00000404276; ENST00000328354; ENST00000405598 | TSF |
| 7% | chr22 | 29117574 | 29117506 | − | chr22 | 29115473 | 29115383; 29115458 | − | ENST00000382580; ENST00000433728; ENST00000448511; ENST00000402731; ENST00000403642; ENST00000439200 ENST00000348295; ENST00000382566; ENST00000382578; ENST00000404276; ENST00000328354; ENST00000405598 | TSF |
| 7% | chr22 | 29117574 | 29117506 | − | chr22 | 29115473 | 29115383; 29115458 | − | ENST00000382580; ENST00000433728; ENST00000448511; ENST00000402731; ENST00000403642; ENST00000439200 ENST00000348295; ENST00000382566; ENST00000382578; ENST00000404276; ENST00000328354; ENST00000405598 | TSF |
| 7% | chr22 | 29117574 | 29117506 | − | chr22 | 29115473 | 29115383; 29115458 | − | ENST00000382580; ENST00000433728; ENST00000448511; ENST00000402731; ENST00000403642; ENST00000439200 ENST00000348295; ENST00000382566; ENST00000382578; ENST00000404276; ENST00000328354; ENST00000405598 | TSF |
| 7% | chr8 | 82194688 | 82194723 | + | chr8 | 82195601 | 82195773 | + | ENST00000297258 | TSF |
| 7% | chr5 | 76107394 | 76108135 | + | chr5 | 76128515 | 76129626 | + | ENST00000296677 | TSF |
| 7% | chr12 | 6602868 | 6602754 | − | chr12 | 6602138 | 6602028 | − | ENST00000229238 | TSF |
| 6% | chr12 | 122430912 | 122432103 | + | chr12 | 122437622 | 122437850 | + | ENST00000288912 | TSF |
| 6% | chr12 | 122430912 | 122431795 | + | chr12 | 122437622 | 122437850 | + | ENST00000288912 | TSF |
| 6% | chr19 | 4412258 | 4412399 | + | chr19 | 4418017 | 4418073 | + | ENST00000301280 | TSF |
| 6% | chr7 | 99801794 | 99801819 | + | chr7 | 99802250 | 99802398 | + | ENST00000426455; ENST00000394018; ENST00000317296 | TSF |
| 6% | chr7 | 56018506 | 56018522 | + | chr7 | 56020872 | 56021011 | + | ENST00000426595 | TSF |
| 6% | chr12 | 58189709 | 58189746 | + | chr12 | 58189960 | 58190366; 58189980; 58190044 | + | ENST00000454289; ENST00000540550; ENST00000323833; ENST00000350762; ENST00000457189 | TSF |
| 6% | chr12 | 58189709 | 58189746 | + | chr12 | 58189960 | 58190366; 58189980; 58190044 | + | ENST00000454289; ENST00000540550; ENST00000323833; ENST00000350762; ENST00000457189 | TSF |
| 6% | chr12 | 58189709 | 58189746 | + | chr12 | 58189960 | 58190366; 58189980; 58190044 | + | ENST00000454289; ENST00000540550; ENST00000323833; ENST00000350762; ENST00000457189 | TSF |
| 6% | chr15 | 83667946 | 83667078 | | chr15 | 83657580 | 83657392 | | ENST00000514272 | TSF |
| 5% | chr2 | 143794737 | 143794842 | + | chr2 | 143797997 | 143798227 | + | ENST00000264170; ENST00000409512 | TSF |
| 5% | chr2 | 17876171 | 17876059 | − | chr2 | 17865030 | 17864905 | − | ENST00000448223; ENST00000351948; ENST00000381272; ENST00000402989 | TSF |
| 5% | chr11 | 64599672 | 64599483 | − | chr11 | 64599193 | 64598977 | − | ENST00000342711 | TSF |
| 5% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 5% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 5% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 5% | chr10 | 27470588 | 27470654 | + | chr10 | 27475308 | 27475465 | + | ENST00000375946; ENST00000375940; ENST00000342386 | TSF |
| 5% | chr1 | 1562829 | 1562875 | + | chr1 | 1563053 | 1563209 | + | ENST00000520777; ENST00000357210; ENST00000360522; ENST00000378710; ENST00000355826; ENST00000518681; | TSF |

TABLE 12-continued

Transcript fusion for Cervical squamous cell carcinoma (CESC) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 5% | chr1 | 1562829 | 1562875 | + | chr1 | 1563053 | 1563209 | + | ENST00000505820; ENST00000487053; ENST00000378712; ENST00000504599; ENST00000378708; ENST00000514234; ENST00000520777; ENST00000357210; ENST00000360522; ENST00000378710; ENST00000355826; ENST00000518681; | TSF |
| 5% | chr1 | 1562829 | 1562875 | + | chr1 | 1563053 | 1563209 | + | ENST00000505820; ENST00000487053; ENST00000378712; ENST00000504599; ENST00000378708; ENST00000514234; ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 5% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 5% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 5% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 5% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 5% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 5% | chr6 | 161637963 | 161637691 | − | chr6 | 161587449 | 161587280; 161587148 | − | ENST00000320285; ENST00000366908; ENST00000436279; ENST00000366905 | TSF |
| 5% | chr6 | 161637963 | 161637691 | − | chr6 | 161587449 | 161587280; 161587148 | − | ENST00000320285; ENST00000366908; ENST00000436279; ENST00000366905 | TSF |
| 5% | chr6 | 161637963 | 161637691 | − | chr6 | 161587449 | 161587280; 161587148 | − | ENST00000320285; ENST00000366908; ENST00000436279; ENST00000366905 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr19 | 48627094 | 48627044 | − | chr19 | 48626575 | 48626431 | − | ENST00000263274; ENST00000536218; ENST00000594759; ENST00000427526; ENST00000601091 | TSF |
| 5% | chr19 | 48627094 | 48627044 | − | chr19 | 48626575 | 48626431 | − | ENST00000263274; ENST00000536218; ENST00000594759; ENST00000427526; ENST00000601091 | TSF |
| 4% | chr19 | 56811235 | 56811344 | + | chr19 | 56813337 | 56813464 | + | ENST00000588026 | TSF |
| 4% | chr19 | 50174724 | 50174836 | + | chr19 | 50176955 | 50177005; 50177034 | + | ENST00000441864; ENST00000246785; ENST00000600947; ENST00000598306 | TSF |
| 4% | chr19 | 50174724 | 50174836 | + | chr19 | 50176955 | 50177005; 50177034 | + | ENST00000441864; ENST00000246785; ENST00000600947; ENST00000598306 | TSF |

TABLE 12-continued

Transcript fusion for Cervical squamous cell carcinoma (CESC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr22 | 45814683 | 45815239 | + | chr22 | 45821828 | 45822055 | + | ENST00000342894; ENST00000538017 | TSF |
| 4% | chr6 | 80022917 | 80022085 | − | chr6 | 79924739 | 79924689 | − | ENST00000275036; ENST00000344726 | TSF |
| 4% | chr6 | 80022917 | 80022085 | − | chr6 | 79924739 | 79924689 | − | ENST00000275036; ENST00000344726 | TSF |
| 4% | chr10 | 79700435 | 79700428 | − | chr10 | 79628955 | 79628887 | − | ENST00000372391; ENST00000372388; ENST00000468332 | TSF |
| 4% | chr10 | 79700435 | 79700428 | − | chr10 | 79628955 | 79628887 | − | ENST00000372391; ENST00000372388; ENST00000468332 | TSF |
| 4% | chr10 | 79700435 | 79700428 | − | chr10 | 79628955 | 79628887 | − | ENST00000372391; ENST00000372388; ENST00000468332 | TSF |
| 4% | chr14 | 70466641 | 70466673 | + | chr14 | 70477471 | 70477663 | + | ENST00000361956; ENST00000381280 | TSF |
| 4% | chr14 | 70466641 | 70466673 | + | chr14 | 70477471 | 70477663 | + | ENST00000361956; ENST00000381280 | TSF |
| 4% | chr1 | 1562829 | 1562973 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562973 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562973 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1422590 | 1422685 | + | chr1 | 1423243 | 1423294 | + | ENST00000308647 | TSF |
| 4% | chr15 | 40187476 | 40186733 | − | chr15 | 40099459 | 40099207 | − | ENST00000561100; ENST00000543580 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr1 | 41465686 | 41465756 | + | chr1 | 41466701 | 41466789 | + | ENST00000372621; ENST00000541520; ENST00000372616 | TSF |
| 4% | chr1 | 15562769 | 15563257 | + | chr1 | 15578267 | 15578373 | + | ENST00000433640 | TSF |
| 4% | chr8 | 91107662 | 91105645 | − | chr8 | 91094330 | 91094254 | − | ENST00000265431 | TSF |
| 4% | chr18 | 51273 | 49727 | − | chr18 | 49237 | 49129 | − | ENST00000308911 | TSF |
| 3% | chr12 | 96340433 | 96341255 | + | chr12 | 96346495 | 96346601 | + | ENST00000266736; ENST00000548310 | TSF |
| 3% | chr12 | 96340433 | 96341255 | + | chr12 | 96346495 | 96346601 | + | ENST00000266736; ENST00000548310 | TSF |
| 3% | chr11 | 60694460 | 60694542 | + | chr11 | 60694676 | 60694890 | + | ENST00000453848; ENST00000005286 | TSF |
| 3% | chr11 | 60694460 | 60694542 | + | chr11 | 60694676 | 60694890 | + | ENST00000453848; ENST00000005286 | TSF |
| 3% | chr11 | 102074849 | 102074853 | + | chr11 | 102076624 | 102076805; 210076817 | + | ENST00000526343; ENST00000282441; ENST00000345877; ENST00000537274; ENST00000531439; ENST00000524575; ENST00000529029 | TSF |
| 3% | chr11 | 102074849 | 102074853 | + | chr11 | 102076624 | 102076805; 210076817 | + | ENST00000526343; ENST00000282441; ENST00000345877; ENST00000537274; ENST00000531439; ENST00000524575; ENST00000529029 | TSF |
| 3% | chr11 | 102074849 | 102074853 | + | chr11 | 102076624 | 102076805; 210076817 | + | ENST00000526343; ENST00000282441; ENST00000345877; ENST00000537274; ENST00000531439; ENST00000524575; ENST00000529029 | TSF |
| 3% | chr11 | 102074849 | 102074853 | + | chr11 | 102076624 | 102076805; 210076817 | + | ENST00000526343; ENST00000282441; ENST00000345877; ENST00000537274; ENST00000531439; ENST00000524575; ENST00000529029 | TSF |

TABLE 12-continued

Transcript fusion for Cervical squamous cell carcinoma (CESC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr12 | 122430912 | 122432282 | + | chr12 | 122437622 | 122437850 | + | ENST00000288912 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr7 | 158431231 | 158431181 | − | chr7 | 158424409 | 158424358 | − | ENST00000541468; ENST00000356309; ENST00000409423; ENST00000441982; ENST00000275830 | TSF |
| 3% | chr7 | 56020443 | 56020541 | + | chr7 | 56020872 | 56021011 | + | ENST00000426595 | TSF |
| 3% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 3% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 3% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 3% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 3% | chr22 | 36652278 | 36652346 | + | chr22 | 36653129 | 36653182 | + | ENST00000397278; ENST00000422706; ENST00000319136; ENST00000422471; ENST00000438034; ENST00000427990; ENST00000397279; ENST00000433768; ENST00000440669; ENST00000431184 | TSF |
| 3% | chr22 | 36652278 | 36652346 | + | chr22 | 36653129 | 36653182 | + | ENST00000397278; ENST00000422706; ENST00000319136; ENST00000422471; ENST00000438034; ENST00000427990; | TSF |

TABLE 12-continued

Transcript fusion for Cervical squamous cell carcinoma (CESC) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| | | | | | | | | | ENST00000397279; ENST00000433768; ENST00000440669; ENST00000431184 | |
| 3% | chr4 | 185620772 | 185620691 | − | chr4 | 185618957 | 185618801; 185618919 | − | ENST00000281453; ENST00000510146 | TSF |
| 3% | chr4 | 185620772 | 185620691 | − | chr4 | 185618957 | 185618801; 185618919 | − | ENST00000281453; ENST00000510146 | TSF |
| 3% | chr1 | 156716197 | 156716133 | − | chr1 | 156715165 | 156715089 | − | ENST00000357325; ENST00000537739; ENST00000368209; ENST00000368206 | TSF |
| 3% | chr14 | 51360331 | 51362440 | + | chr14 | 51368547 | 51368629 | + | ENST00000337334; ENST00000353130; ENST00000395752 | TSF |
| 3% | chr3 | 129019458 | 129019508 | + | chr3 | 129020793 | 129020985; 129020977; 129020857; 129020848 | + | ENST00000509042; ENST00000383463; ENST00000417226; ENST00000510314; ENST00000502878; ENST00000389735; ENST00000509551; ENST00000511665 | TSF |
| 3% | chr3 | 129019458 | 129019508 | + | chr3 | 129020793 | 129020985; 129020977; 129020857; 129020848 | + | ENST00000509042; ENST00000383463; ENST00000417226; ENST00000510314; ENST00000502878; ENST00000389735; ENST00000509551; ENST00000511665 | TSF |
| 3% | chr3 | 129019458 | 129019508 | + | chr3 | 129020793 | 129020985; 129020977; 129020857; 129020848 | + | ENST00000509042; ENST00000383463; ENST00000417226; ENST00000510314; ENST00000502878; ENST00000389735; ENST00000509551; ENST00000511665 | TSF |
| 3% | chr3 | 129019458 | 129019508 | + | chr3 | 129020793 | 129020985; 129020977; 129020857; 129020848 | + | ENST00000509042; ENST00000383463; ENST00000417226; ENST00000510314; ENST00000502878; ENST00000389735; ENST00000509551; ENST00000511665 | TSF |
| 3% | chr3 | 129019458 | 129019508 | + | chr3 | 129020793 | 129020985; 129020977; 129020857; 129020848 | + | ENST00000509042; ENST00000383463; ENST00000417226; ENST00000510314; ENST00000502878; ENST00000389735; ENST00000509551; ENST00000511665 | TSF |
| 3% | chr11 | 66354487 | 66355279 | + | chr11 | 66361113 | 66361185 | + | ENST00000533244; ENST00000530961 | TSF |
| 3% | chr11 | 66354487 | 66355279 | + | chr11 | 66361113 | 66361185 | + | ENST00000533244; ENST00000530961 | TSF |
| 3% | chr7 | 1477059 | 1476990 | − | chr7 | 1476492 | 1476378 | − | ENST00000405088; ENST00000297508 | TSF |
| 3% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 3% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 3% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 3% | chr12 | 14670381 | 14670239 | | chr12 | 14664645 | 14664445 | − | ENST00000240617 | TSF |
| 3% | chr19 | 48654965 | 48654725 | − | chr19 | 48654593 | 48654489 | − | ENST00000263274; ENST00000594759; ENST00000427526; ENST00000601091; ENST00000542460 | TSF |
| 3% | chr19 | 48654965 | 48654725 | − | chr19 | 48654593 | 48654489 | − | ENST00000263274; ENST00000594759; ENST00000427526; ENST00000601091; ENST00000542460 | TSF |
| 3% | chr19 | 48654965 | 48654725 | − | chr19 | 48654593 | 48654489 | − | ENST00000263274; ENST00000594759; ENST00000427526; ENST00000601091; ENST00000542460 | TSF |
| 3% | chr20 | 32693720 | 32693709 | − | chr20 | 32693351 | 32693174 | − | ENST00000374980 | TSF |
| 2% | chr22 | 24967426 | 24967475 | + | chr22 | 24967884 | 24967945 | + | ENST00000215829; ENST00000404603 | TSF |
| 2% | chr19 | 36105129 | 36105133 | + | chr19 | 36105944 | 36106049 | + | ENST00000587439; ENST00000203166; ENST00000379045 | TSF |
| 2% | chr19 | 36105129 | 36105133 | + | chr19 | 36105944 | 36106049 | + | ENST00000587439; ENST00000203166; ENST00000379045 | TSF |
| 2% | chr3 | 126601624 | 126602182 | + | chr3 | 126633523 | 126633593 | + | ENST00000290913; ENST00000508789; ENST00000513253 | TSF |
| 2% | chr3 | 126601624 | 126602182 | + | chr3 | 126633523 | 126633593 | + | ENST00000290913; ENST00000508789; ENST00000513253 | TSF |
| 2% | chr3 | 126601624 | 126602182 | + | chr3 | 126633523 | 126633593 | + | ENST00000290913; ENST00000508789; ENST00000513253 | TSF |
| 2% | chr4 | 1745002 | 1745264 | + | chr4 | 1746245 | 1746351 | + | ENST00000313288 | TSF |
| 2% | chr7 | 134212336 | 134212386 | + | chr7 | 134215479 | 134215562 | | ENST00000359579 | TSF |
| 2% | chr7 | 23290404 | 23290481 | + | chr7 | 23292926 | 23293078 | + | ENST00000258733; ENST00000381990; ENST00000409458; ENST00000453162 | TSF |
| 2% | chr7 | 23290404 | 23290481 | + | chr7 | 23292926 | 23293078 | + | ENST00000258733; ENST00000381990; ENST00000409458; ENST00000453162 | TSF |
| 2% | chr7 | 23290404 | 23290481 | + | chr7 | 23292926 | 23293078 | + | ENST00000258733; ENST00000381990; ENST00000409458; ENST00000453162 | TSF |
| 2% | chr7 | 23290404 | 23290481 | + | chr7 | 23292926 | 23293078 | + | ENST00000258733; ENST00000381990; ENST00000409458; ENST00000453162 | TSF |

TABLE 12-continued

Transcript fusion for Cervical squamous cell carcinoma (CESC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr11 | 85967969 | 85968062 | + | chr11 | 85968557 | 85968638 | + | ENST00000263360; ENST00000528180; ENST00000327320; ENST00000351625 | TSF |
| 2% | chr11 | 85967969 | 85968062 | + | chr11 | 85968557 | 85968638 | + | ENST00000263360; ENST00000528180; ENST00000327320; ENST00000351625 | TSF |
| 2% | chr11 | 85967969 | 85968062 | + | chr11 | 85968557 | 85968638 | + | ENST00000263360; ENST00000528180; ENST00000327320; ENST00000351625 | TSF |
| 2% | chr11 | 85967969 | 85968062 | + | chr11 | 85968557 | 85968638 | + | ENST00000263360; ENST00000528180; ENST00000327320; ENST00000351625 | TSF |
| 2% | chr16 | 48451457 | 48450727 | − | chr16 | 48396341 | 48395491 | − | ENST00000356721 | TSF |
| 2% | chr15 | 83667946 | 83667078 | − | chr15 | 83660798 | 83660684 | − | ENST00000451195 | TSF |
| 2% | chr3 | 139245547 | 139245400 | − | chr3 | 139237364 | 139237263 | − | ENST00000232219 | TSF |
| 2% | chr5 | 76107394 | 76108212 | + | chr5 | 76128515 | 76129626 | + | ENST00000296677 | TSF |
| 2% | chr17 | 45698288 | 45698367 | + | chr17 | 45699134 | 45699286 | + | ENST00000530173; ENST00000322157; ENST00000544660; ENST00000528565 | TSF |
| 2% | chr12 | 122387836 | 122388242 | + | chr12 | 122394980 | 122395174 | + | ENST00000288912; ENST00000397454 | TSF |
| 2% | chr12 | 122387836 | 122388242 | + | chr12 | 122394980 | 122395174 | + | ENST00000288912; ENST00000397454 | TSF |
| 2% | chr3 | 100461913 | 100462018 | + | chr3 | 100463677 | 100463775 | + | ENST00000418917; ENST00000490574; ENST00000240851; ENST00000476228 | TSF |
| 2% | chr10 | 3133726 | 3133857 | + | chr10 | 3141467 | 3141544 | + | ENST00000607886; ENST00000381125; ENST00000381075; ENST00000407806 | TSF |
| 2% | chr10 | 3133726 | 3133857 | + | chr10 | 3141467 | 3141544 | + | ENST00000607886; ENST00000381125; ENST00000381075; ENST00000407806 | TSF |
| 2% | chr10 | 3133726 | 3133857 | + | chr10 | 3141467 | 3141544 | + | ENST00000607886; ENST00000381125; ENST00000381075; ENST00000407806 | TSF |
| 2% | chr10 | 3133726 | 3133857 | + | chr10 | 3141467 | 3141544 | + | ENST00000607886; ENST00000381125; ENST00000381075; ENST00000407806 | TSF |
| 2% | chr3 | 48252382 | 48252880 | + | chr3 | 48265844 | 48265951 | + | ENST00000296435; ENST00000576243 | TSF |
| 2% | chr19 | 4412258 | 4412517 | + | chr19 | 4418017 | 4418073 | + | ENST00000301280 | TSF |
| 2% | chr3 | 184749371 | 184749503 | + | chr3 | 184766267 | 184766347 | + | ENST00000287546; ENST00000437079; ENST00000436792; ENST00000446204 | TSF |
| 2% | chr22 | 45814683 | 45814802 | + | chr22 | 45818170 | 45818288 | + | ENST00000342894; ENST00000538017 | TSF |
| 2% | chr19 | 50391349 | 50391391 | + | chr19 | 50391488 | 50391574 | + | ENST00000221543; ENST00000535102 | TSF |
| 2% | chr2 | 170668914 | 170668783 | − | chr2 | 170668368 | 170668330 | − | ENST00000442181; ENST00000409340; ENST00000260953; ENST00000409965; ENST00000392640; ENST00000308099 | TSF |
| 2% | chr9 | 21974190 | 21974089 | − | chr9 | 21971207 | 21971002; 21970901; 21970975 | − | ENST00000361570; ENST00000304494; ENST00000579755; ENST00000579122; ENST00000530628; ENST00000498124; ENST00000446177 | TSF |
| 2% | chr9 | 21974190 | 21974089 | − | chr9 | 21971207 | 21971002; 21970901; 21970975 | − | ENST00000361570; ENST00000304494; ENST00000579755; ENST00000579122; ENST00000530628; ENST00000498124; ENST00000446177 | TSF |
| 2% | chr9 | 21974190 | 21974089 | − | chr9 | 21971207 | 21971002; 21970901; 21970975 | − | ENST00000361570; ENST00000304494; ENST00000579755; ENST00000579122; ENST00000530628; ENST00000498124; ENST00000446177 | TSF |
| 2% | chr9 | 21974190 | 21974089 | − | chr9 | 21971207 | 21971002; 21970901; 21970975 | − | ENST00000361570; ENST00000304494; ENST00000579755; ENST00000579122; ENST00000530628; ENST00000498124; ENST00000446177 | TSF |
| 2% | chr19 | 47343471 | 47343373 | − | chr19 | 47342835 | 47342722 | − | ENST00000352203; ENST00000601498; ENST00000599990; ENST00000593442; ENST00000263270; ENST00000597020 | TSF |
| 2% | chr3 | 195593372 | 195593261 | − | chr3 | 195591058 | 195591052 | − | ENST00000416152; ENST00000381916; ENST00000333602; ENST00000428187; ENST00000392400 | TSF |
| 2% | chr17 | 39737300 | 39737191 | − | chr17 | 39726472 | 39726390 | − | ENST00000246662 | TSF |
| 2% | chr5 | 58596952 | 58596862 | − | chr5 | 58511794 | 58511603 | − | ENST00000340635; ENST00000360047; ENST00000507116; ENST00000503258; ENST00000405755; ENST00000502484; ENST00000546160; ENST00000309641; ENST00000502575 | TSF |
| 2% | chr5 | 58596952 | 58596862 | − | chr5 | 58511794 | 58511603 | − | ENST00000340635; ENST00000360047; ENST00000507116; ENST00000503258; ENST00000405755; ENST00000502484; ENST00000546160; ENST00000309641; ENST00000502575 | TSF |
| 2% | chr5 | 58596952 | 58596862 | − | chr5 | 58511794 | 58511603 | − | ENST00000340635; ENST00000360047; ENST00000507116; ENST00000503258; ENST00000405755; ENST00000502484; ENST00000546160; ENST00000309641; ENST00000502575 | TSF |

TABLE 13

Transcript fusion for Cholangiocarcinoma (CHOL) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 44% | chr3 | 149205406 | 149205542 | + | ENST00000305354 | chr3 | 149210784 | 149210892 | + | TAF |
| 33% | chr1 | 21926110 | 21925987 | − | ENST00000374761; ENST00000290101; ENST00000374763; ENST00000471600; ENST00000374765; ENST00000542643 | chr1 | 21925313 | 21925206 | − | TAF |
| 33% | chr1 | 21926110 | 21925987 | − | ENST00000374761; ENST00000290101; ENST00000374763; ENST00000471600; ENST00000374765; ENST00000542643 | chr1 | 21925313 | 21925206 | − | TAF |
| 33% | chr1 | 21926110 | 21925987 | − | ENST00000374761; ENST00000290101; ENST00000374763; ENST00000471600; ENST00000374765; ENST00000542643 | chr1 | 21925313 | 21925206 | − | TAF |
| 33% | chr1 | 21926110 | 21925987 | − | ENST00000374761; ENST00000290101; ENST00000374763; ENST00000471600; ENST00000374765; ENST00000542643 | chr1 | 21925313 | 21925206 | − | TAF |
| 33% | chr1 | 21926110 | 21925987 | − | ENST00000374761; ENST00000290101; ENST00000374763; ENST00000471600; ENST00000374765; ENST00000542643 | chr1 | 21925313 | 21925206 | − | TAF |
| 31% | chr20 | 43560983 | 43561073 | + | ENST00000255136; ENST00000217073 | chr20 | 43561176 | 43561224 | + | TAF |
| 28% | chr4 | 88293967 | 88293861 | − | ENST00000358290; ENST00000507286 | chr4 | 88287307 | 88287019 | − | TAF |
| 28% | chr4 | 88293967 | 88293861 | − | ENST00000358290; ENST00000507286 | chr4 | 88287307 | 88287019 | − | TAF |
| 25% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 25% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 25% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 25% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 22% | chr5 | 176761404; 176761337 | 176761285 | − | ENST00000303127; ENST00000515209; ENST00000514458 | chr5 | 176744789 | 176744095 | − | TAF |
| 22% | chr5 | 176761404; 176761337 | 176761285 | − | ENST00000303127; ENST00000515209; ENST00000514458 | chr5 | 176744789 | 176744095 | − | TAF |
| 22% | chr1 | 159683928 | 159683793 | − | ENST00000255030; ENST00000368112 | chr1 | 159682370 | 159682050 | − | TAF |
| 22% | chr3 | 49927493 | 49927357 | − | ENST00000296474; ENST00000344206 | chr3 | 49927248 | 49927204 | − | TAF |
| 22% | chr3 | 49927493 | 49927357 | − | ENST00000296474; ENST00000344206 | chr3 | 49927248 | 49927204 | − | TAF |
| 19% | chr9 | 125054028 | 125054119 | + | ENST00000297908; ENST00000344641; ENST00000373723; ENST00000373729; ENST00000394315 | chr9 | 125068067 | 125068171 | + | TSF |
| 19% | chr9 | 125054028 | 125054119 | + | ENST00000297908; ENST00000344641; ENST00000373723; ENST00000373729; ENST00000394315 | chr9 | 125068067 | 125068171 | + | TSF |
| 19% | chr9 | 125054028 | 125054119 | + | ENST00000297908; ENST00000344641; ENST00000373723; ENST00000373729; ENST00000394315 | chr9 | 125068067 | 125068171 | + | TSF |
| 17% | chr20 | 33439171 | 33439034 | − | ENST00000336431 | chr20 | 33438000 | 33437979 | − | TAF |
| 17% | chr10 | 120905865 | 120905748 | − | ENST00000355697; ENST00000330036 | chr10 | 120901885 | 120901741 | − | TAF |
| 17% | chr10 | 120905865 | 120905748 | − | ENST00000355697; ENST00000330036 | chr10 | 120901885 | 120901741 | − | TAF |
| 17% | chr16 | 29913136; 29912293 | 29913241 | + | ENST00000563177; ENST00000483405; ENST00000308748; ENST00000414952; ENST00000566693 | chr16 | 29915825 | 29915953 | + | TSF |
| 17% | chr16 | 29913136; 29912293 | 29913241 | + | ENST00000563177; ENST00000483405; ENST00000308748; ENST00000414952; ENST00000566693 | chr16 | 29915825 | 29915953 | + | TSF |
| 14% | chr10 | 60272904 | 60273093 | + | ENST00000373886 | chr10 | 60299081 | 60299303 | + | TAF |
| 14% | chr9 | 131002264 | 131002275 | + | ENST00000475805; ENST00000341179; ENST00000372923; ENST00000393594; ENST00000486160 | chr9 | 131002706 | 131002973 | + | TAF |
| 14% | chr9 | 131002264 | 131002275 | + | ENST00000475805; ENST00000341179; ENST00000372923; ENST00000393594; ENST00000486160 | chr9 | 131002706 | 131002973 | + | TAF |
| 14% | chr11 | 2940537 | 2940637 | + | ENST00000347936; ENST00000312221; ENST00000449793; ENST00000380574 | chr11 | 2940947 | 2941017 | + | TAF |
| 14% | chr11 | 2940537 | 2940637 | + | ENST00000347936; ENST00000312221; ENST00000449793; ENST00000380574 | chr11 | 2940947 | 2941017 | + | TAF |
| 14% | chr19 | 35514331 | 35514451 | + | ENST00000599564; ENST00000317991; ENST00000504615; ENST00000411896 | chr19 | 35514601 | 35514631 | + | TAF |
| 14% | chr19 | 35514331 | 35514451 | + | ENST00000599564; ENST00000317991; ENST00000504615; ENST00000411896 | chr19 | 35514601 | 35514631 | + | TAF |
| 14% | chr19 | 35514331 | 35514451 | + | ENST00000599564; ENST00000317991; ENST00000504615; ENST00000411896 | chr19 | 35514601 | 35514631 | + | TAF |
| 14% | chr19 | 35514331 | 35514451 | + | ENST00000599564; ENST00000317991; ENST00000504615; ENST00000411896 | chr19 | 35514601 | 35514631 | + | TAF |

TABLE 13-continued

Transcript fusion for Cholangiocarcinoma (CHOL) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 14% | chr5 | 82554349 | 82554496 | + | ENST00000282268; ENST00000338635; ENST00000396027; ENST00000511817 | chr5 | 82606608 | 82606935 | + | TAF |
| 14% | chr10 | 47747112 | 47747132 | + | ENST00000340243; ENST00000374277; ENST00000449464; ENST00000538825 | chr10 | 48278725 | 48278896 | + | TAF |
| 14% | chr16 | 16251666 | 16251520 | − | ENST00000205557 | chr16 | 1624711 | 16249633 | − | TAF |
| 14% | chr19 | 5680497 | 5680469 | − | ENST00000309324; ENST00000587589 | chr19 | 5680194 | 5680187 | − | TAF |
| 14% | chr2 | 132249597 | 132249449 | − | ENST00000427024; ENST00000309451 | chr2 | 132245283 | 132245193 | − | TAF |
| 14% | chr2 | 132249597 | 132249449 | − | ENST00000427024; ENST00000309451 | chr2 | 132245283 | 132245193 | − | TAF |
| 14% | chr1 | 159683928 | 159683797 | − | ENST00000255030; ENST00000368112; ENST00000368111; ENST00000368110; ENST00000343919 | chr1 | 159682370 | 159682050 | − | TAF |
| 11% | chr16 | 2818998 | 2819285 | + | ENST00000301740 | chr16 | 2819676 | 2820194 | + | TAF |
| 11% | chr19 | 50984141 | 50984234 | + | ENST00000334976; ENST00000376918; 8585ENST0000059 | chr19 | 51009025 | 51009080 | + | TAF |
| 11% | chr10 | 15151838 | 15151701 | − | ENST00000378165; ENST00000378150; ENST00000540259; ENST00000535341 | chr10 | 15148697 | 15148684 | − | TAF |
| 11% | chr10 | 15151838 | 15151701 | − | ENST00000378165; ENST00000378150; ENST00000540259; ENST00000535341 | chr10 | 15148697 | 15148684 | − | TAF |
| 11% | chr10 | 15151838 | 15151701 | − | ENST00000378165; ENST00000378150; ENST00000540259; ENST00000535341 | chr10 | 15148697 | 15148684 | − | TAF |
| 11% | chr10 | 15151838 | 15151701 | − | ENST00000378165; ENST00000378150; ENST00000540259; ENST00000535341 | chr10 | 15148697 | 15148684 | − | TAF |
| 11% | chr5 | 147207691 | 147207585 | − | ENST00000296695; ENST00000510027 | chr5 | 147185494 | 147185375 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr19 | 6678034; 6677969 | 6677917 | − | ENST00000245907; ENST00000601008 | chr19 | 6670525 | 6670384 | − | TAF |
| 11% | chr19 | 6678034; 6677969 | 6677917 | − | ENST00000245907; ENST00000601008 | chr19 | 6670525 | 6670384 | − | TAF |
| 11% | chr3 | 124839669; 124839530; 124839525 | 124839443 | − | ENST00000430155; ENST00000393469; ENST00000423114; ENST00000469902; ENST00000314584; ENST00000479826 | chr3 | 124838735 | 124838686 | − | TAF |
| 11% | chr3 | 124839669; 124839530; 124839525 | 124839443 | − | ENST00000430155; ENST00000393469; ENST00000423114; ENST00000469902; ENST00000314584; ENST00000479826 | chr3 | 124838735 | 124838686 | − | TAF |
| 11% | chr3 | 124839669; 124839530; 124839525 | 124839443 | − | ENST00000430155; ENST00000393469; ENST00000423114; ENST00000469902; ENST00000314584; ENST00000479826 | chr3 | 124838735 | 124838686 | − | TAF |
| 11% | chr3 | 124839669; 124839530; 124839525 | 124839443 | − | ENST00000430155; ENST00000393469; ENST00000423114; ENST00000469902; ENST00000314584; ENST00000479826 | chr3 | 124838735 | 124838686 | − | TAF |
| 11% | chr3 | 124839669; 124839530; 124839525 | 124839443 | − | ENST00000430155; ENST00000393469; ENST00000423114; ENST00000469902; ENST00000314584; ENST00000479826 | chr3 | 124838735 | 124838686 | − | TAF |
| 11% | chr17 | 40821639; 40821538 | 40821448 | − | ENST00000591022; ENST00000412503; ENST00000293349 | chr17 | 40820920 | 40820864 | − | TAF |
| 11% | chr17 | 40821639; 40821538 | 40821448 | − | ENST00000591022; ENST00000412503; ENST00000293349 | chr17 | 40820920 | 40820864 | − | TAF |
| 11% | chr17 | 40821639; 40821538 | 40821448 | − | ENST00000591022; ENST00000412503; ENST00000293349 | chr17 | 40820920 | 40820864 | − | TAF |

TABLE 14

Transcript fusion for Cholangiocarcinoma (CHOL) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 64% | chr3 | 182757105 | 182757101 | − | chr3 | 182756923 | 182756814 | − | ENST00000265594; ENST00000492597; ENST00000497959; ENST00000539926; ENST00000476176 | TSF |
| 64% | chr3 | 182757105 | 182757101 | − | chr3 | 182756923 | 182756814 | − | ENST00000265594; ENST00000492597; ENST00000497959; ENST00000539926; ENST00000476176 | TSF |
| 64% | chr3 | 182757105 | 182757101 | − | chr3 | 182756923 | 182756814 | − | ENST00000265594; ENST00000492597; ENST00000497959; ENST00000539926; ENST00000476176 | TSF |
| 64% | chr3 | 182757105 | 182757101 | − | chr3 | 182756923 | 182756814 | − | ENST00000265594; ENST00000492597; ENST00000497959; ENST00000539926; ENST00000476176 | TSF |
| 47% | chr16 | 29915789 | 29915910 | + | chr16 | 29916173 | 29916286 | + | ENST00000563177; ENST00000483405; ENST00000308748; ENST00000414952; ENST00000566693 | TAF |
| 47% | chr16 | 29915789 | 29915910 | + | chr16 | 29916173 | 29916286 | + | ENST00000563177; ENST00000483405; ENST00000308748; ENST00000414952; ENST00000566693 | TAF |
| 44% | chrX | 2178048 | 2177670 | − | chrX | 2161271 | 2161064; 2161103 | − | ENST00000334651; ENST00000412516 | TAF |
| 44% | chrX | 2178048 | 2177670 | − | chrX | 2161271 | 2161064; 2161103 | − | ENST00000334651; ENST00000412516 | TAF |
| 42% | chr10 | 60376682 | 60376727 | + | chr10 | 60380615 | 60380661 | + | ENST00000373886 | TAF |
| 36% | chr7 | 150938296 | 150938250 | − | chr7 | 150937608 | 150937511 | − | ENST00000262188; ENST00000392811; ENST00000356800 | TAF |
| 33% | chr1 | 21925339 | 21925216 | − | chr1 | 21924995 | 21924893 | − | ENST00000374761; ENST00000290101; ENST00000374763; ENST00000374765; ENST00000542643 | TAF |
| 33% | chr1 | 21925339 | 21925216 | − | chr1 | 21924995 | 21924893 | − | ENST00000374761; ENST00000290101; ENST00000374763; ENST00000374765; ENST00000542643 | TAF |
| 33% | chr20 | 10400592 | 10400319 | − | chr20 | 10389451 | 10389276 | − | ENST00000347364; ENST00000399054 | TSF |
| 31% | chr19 | 54631006 | 54631115 | + | chr19 | 54631448 | 54631575 | + | ENST00000321030; ENST00000419967 | TAF |
| 31% | chr19 | 54631006 | 54631115 | + | chr19 | 54631448 | 54631575 | + | ENST00000321030; ENST00000419967 | TAF |
| 28% | chr6 | 24783176 | 24783543 | + | chr6 | 24784315 | 24784397; 24784347 | + | ENST00000356509; ENST00000230056; ENST00000378054; ENST00000378059 | TAF |
| 28% | chr6 | 24783176 | 24783543 | + | chr6 | 24784315 | 24784397; 24784347 | + | ENST00000356509; ENST00000230056; ENST00000378054; ENST00000378059 | TAF |
| 28% | chr6 | 24783176 | 24783543 | + | chr6 | 24784315 | 24784397; 24784347 | + | ENST00000356509; ENST00000230056; ENST00000378054; ENST00000378059 | TAF |
| 28% | chr8 | 104389530 | 104389551 | + | chr8 | 104390255 | 104390471 | + | ENST00000330295; ENST00000520337 | TAF |
| 28% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 28% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 28% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 28% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 28% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 28% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 25% | chr9 | 131002678 | 131002811 | + | chr9 | 131004511 | 131004624 | + | ENST00000475805; ENST00000341179; ENST00000372923; ENST00000393594; ENST00000486160 | TAF |
| 25% | chr9 | 131002678 | 131002811 | + | chr9 | 131004511 | 131004624 | + | ENST00000475805; ENST00000341179; ENST00000372923; ENST00000393594; ENST00000486160 | TAF |
| 25% | chr17 | 79214190 | 79214239 | + | chr17 | 79214787 | 79214816; 79214953 | + | ENST00000431388; ENST00000576002 | TAF |
| 25% | chr17 | 79214190 | 79214239 | + | chr17 | 79214787 | 79214816; 79214953 | + | ENST00000431388; ENST00000576002 | TAF |
| 25% | chr10 | 99548701 | 99548695 | − | chr10 | 99529502 | 99529425 | − | ENST00000266066 | TAF |
| 25% | chr12 | 79992039 | 79991596 | − | chr12 | 79990438 | 79990291 | − | ENST00000328827 | TAF |
| 25% | chr2 | 150044073 | 150044093 | + | chr2 | 150061767 | 150061918 | + | ENST00000409642; ENST00000409876; ENST00000409029; ENST00000442722; ENST00000280115 | TSF |

TABLE 14-continued

Transcript fusion for Cholangiocarcinoma (CHOL) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 25% | chr2 | 150044073 | 150044093 | + | chr2 | 150061767 | 150061918 | + | ENST00000409642; ENST00000409876; ENST00000409029; ENST00000442722; ENST00000280115 | TSF |
| 25% | chr5 | 59983652 | 59983552 | − | chr5 | 59983054 | 59982789 | − | ENST00000265036; ENST00000453022 | TSF |
| 25% | chr5 | 59983652 | 59983552 | − | chr5 | 59983054 | 59982789 | − | ENST00000265036; ENST00000453022 | TSF |
| 25% | chr16 | 57795289 | 57795262 | − | chr16 | 57795083 | 57794954 | − | ENST00000465878; ENST00000379655; ENST00000445690; ENST00000421376; ENST00000541240; ENST00000540079; ENST00000543930; ENST00000562903; ENST00000539578; ENST00000565270 | TSF |
| 25% | chr16 | 57795289 | 57795262 | − | chr16 | 57795083 | 57794954 | − | ENST00000465878; ENST00000379655; ENST00000445690; ENST00000421376; ENST00000541240; ENST00000540079; ENST00000543930; ENST00000562903; ENST00000539578; ENST00000565270 | TSF |
| 25% | chr16 | 57795289 | 57795262 | − | chr16 | 57795083 | 57794954 | − | ENST00000465878; ENST00000379655; ENST00000445690; ENST00000421376; ENST00000541240; ENST00000540079; ENST00000543930; ENST00000562903; ENST00000539578; ENST00000565270 | TSF |
| 22% | chr20 | 30269169 | 30269014 | − | chr20 | 30253889 | 30253752; 30253838 | − | ENST00000376062; ENST00000376055; ENST00000307677; ENST00000420653; ENST00000450273 | TAF |
| 22% | chr20 | 30269169 | 30269014 | − | chr20 | 30253889 | 30253752; 30253838 | − | ENST00000376062; ENST00000376055; ENST00000307677; ENST00000420653; ENST00000450273 | TAF |
| 22% | chr6 | 24306949 | 24306866 | − | chr6 | 24302272 | 24302196 | − | ENST00000378454 | TAF |
| 22% | chr6 | 80022917 | 80022085 | − | chr6 | 79924739 | 79924689 | − | ENST00000275036; ENST00000344726 | TSF |
| 22% | chr6 | 80022917 | 80022085 | − | chr6 | 79924739 | 79924689 | − | ENST00000275036; ENST00000344726 | TSF |
| 19% | chr17 | 48749939 | 48750209 | + | chr17 | 48750332 | 48750499 | + | ENST00000285238; ENST00000505699 | TAF |
| 19% | chr17 | 48749939 | 48750209 | + | chr17 | 48750332 | 48750499 | + | ENST00000285238; ENST00000505699 | TAF |
| 19% | chr19 | 10819783 | 10819829 | + | chr19 | 10822837 | 10822975; 10822931 | + | ENST00000250237; ENST00000591643 | TAF |
| 19% | chr19 | 10819783 | 10819829 | + | chr19 | 10822837 | 10822975; 10822931 | + | ENST00000250237; ENST00000591643 | TAF |
| 19% | chr10 | 98363669 | 98363643 | − | chr10 | 98362155 | 98362037 | − | ENST00000339364; ENST00000371110; ENST00000371109 | TAF |
| 19% | chr10 | 98363669 | 98363666 | − | chr10 | 98362155 | 98362037 | − | ENST00000339364; ENST00000371110; ENST00000371109 | TAF |
| 19% | chr2 | 101649818 | 101649808 | − | chr2 | 101648847 | 101648730 | − | ENST00000376840; ENST00000409318 | TAF |
| 19% | chr16 | 89649823 | 89649851 | + | chr16 | 89650105 | 89650179 | + | ENST00000268720; ENST00000319518 | TSF |
| 19% | chr12 | 117498589 | 117498567 | − | chr12 | 117494691 | 117494611 | − | ENST00000470612; ENST00000335209; ENST00000392545; ENST00000462502 | TSF |
| 19% | chr12 | 117498589 | 117498567 | − | chr12 | 117494691 | 117494611 | − | ENST00000470612; ENST00000335209; ENST00000392545; ENST00000462502 | TSF |
| 19% | chr12 | 117498589 | 117498567 | − | chr12 | 117494691 | 117494611 | − | ENST00000470612; ENST00000335209; ENST00000392545; ENST00000462502 | TSF |
| 17% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 17% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 17% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 17% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 17% | chr4 | 107241932 | 107242850 | + | chr4 | 107246142 | 107246275 | + | ENST00000394701 | TAF |
| 17% | chr10 | 71235761 | 71236002 | + | chr10 | 71243447 | 71243632 | + | ENST00000373290 | TAF |
| 17% | chrX | 48793481 | 48793462 | − | chrX | 48792291 | 48792227 | − | ENST00000396743; ENST00000455452; ENST00000156084; ENST00000376488; ENST00000428668 | TAF |
| 17% | chrX | 48793481 | 48793462 | − | chrX | 48792291 | 48792227 | − | ENST00000396743; ENST00000455452; ENST00000156084; ENST00000376488; ENST00000428668 | TAF |
| 17% | chr10 | 34694893 | 34694588 | − | chr10 | 34690845 | 34690754 | − | ENST00000545260; ENST00000545693; ENST00000346874; ENST00000350537; ENST00000374788; ENST00000374789; | TAF |

TABLE 14-continued

Transcript fusion for Cholangiocarcinoma (CHOL) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 17% | chr10 | 34694893 | 34694588 | − | chr10 | 34690845 | 34690754 | − | ENST00000374790; ENST00000374794; ENST00000374776; ENST00000340077; ENST00000374773 ENST00000545260; ENST00000545693; ENST00000346874; ENST00000350537; ENST00000374788; ENST00000374789; ENST00000374790; ENST00000374794; ENST00000374776; ENST00000340077; ENST00000374773 | TAF |
| 17% | chr10 | 34694893 | 34694588 | − | chr10 | 34690845 | 34690754 | − | ENST00000545260; ENST00000545693; ENST00000346874; ENST00000350537; ENST00000374788; ENST00000374789; ENST00000374790; ENST00000374794; ENST00000374776; ENST00000340077; ENST00000374773 | TAF |
| 17% | chr10 | 34694893 | 34694588 | − | chr10 | 34690845 | 34690754 | − | ENST00000545260; ENST00000545693; ENST00000346874; ENST00000350537; ENST00000374788; ENST00000374789; ENST00000374790; ENST00000374794; ENST00000374776; ENST00000340077; ENST00000374773 | TAF |
| 17% | chr10 | 34694893 | 34694588 | − | chr10 | 34690845 | 34690754 | − | ENST00000545260; ENST00000545693; ENST00000346874; ENST00000350537; ENST00000374788; ENST00000374789; ENST00000374790; ENST00000374794; ENST00000374776; ENST00000340077; ENST00000374773 | TAF |
| 17% | chr10 | 34694893 | 34694588 | − | chr10 | 34690845 | 34690754 | − | ENST00000545260; ENST00000545693; ENST00000346874; ENST00000350537; ENST00000374788; ENST00000374789; ENST00000374790; ENST00000374794; ENST00000374776; ENST00000340077; ENST00000374773 | TAF |
| 17% | chr10 | 34694893 | 34694588 | − | chr10 | 34690845 | 34690754 | − | ENST00000545260; ENST00000545693; ENST00000346874; ENST00000350537; ENST00000374788; ENST00000374789; ENST00000374790; ENST00000374794; ENST00000374776; ENST00000340077; ENST00000374773 | TAF |
| 17% | chr10 | 34694893 | 34694588 | − | chr10 | 34690845 | 34690754 | − | ENST00000545260; ENST00000545693; ENST00000346874; ENST00000350537; ENST00000374788; ENST00000374789; ENST00000374790; ENST00000374794; ENST00000374776; ENST00000340077; ENST00000374773 | TAF |
| 17% | chr10 | 34694893 | 34694588 | − | chr10 | 34690845 | 34690754 | − | ENST00000545260; ENST00000545693; ENST00000346874; ENST00000350537; ENST00000374788; ENST00000374789; ENST00000374790; ENST00000374794; ENST00000374776; ENST00000340077; ENST00000374773 | TAF |
| 17% | chr11 | 424193 | 423942 | − | chr11 | 421198 | 421141 | − | ENST00000332826 | TAF |
| 17% | chr19 | 55558521 | 55558473 | − | chr19 | 55556677 | 55556442 | − | ENST00000415061; ENST00000396247 | TAF |
| 17% | chr5 | 176950300 | 176950160 | − | chr5 | 176949072 | 176948976 | − | ENST00000514747; ENST00000329540; ENST00000443375; ENST00000524677 | TAF |
| 17% | chr5 | 823586 | 823504 | − | chr5 | 822010 | 821976 | − | ENST00000424784; ENST00000283441 | TAF |
| 17% | chr19 | 1114930 | 1114676 | − | chr19 | 1114421 | 1114230 | − | ENST00000361757; ENST00000587024; ENST00000438103 | TSF |
| 17 | chr10 | 7735189 | 7733712 | − | chr10 | 7697638 | 7697594 | − | ENST00000256861; ENST00000397146; ENST00000397145 | TSF |
| 17% | chr10 | 7735189 | 7733712 | − | chr10 | 7697638 | 7697594 | − | ENST00000256861; ENST00000397146; ENST00000397145 | TSF |
| 17% | chr10 | 7735189 | 7733712 | − | chr10 | 7697638 | 7697594 | − | ENST00000256861; ENST00000397146; ENST00000397145 | TSF |
| 17% | chr10 | 7735546 | 7735278 | − | chr10 | 7697638 | 7697594 | − | ENST00000256861; ENST00000397146; ENST00000397145 | TSF |
| 17% | chr10 | 7735546 | 7735278 | − | chr10 | 7697638 | 7697594 | − | ENST00000256861; ENST00000397146; ENST00000397145 | TSF |
| 17% | chr10 | 7735546 | 7735278 | − | chr10 | 7697638 | 7697594 | − | ENST00000256861; ENST00000397146; ENST00000397145 | TSF |
| 14% | chr20 | 43581305 | 43581345 | + | chr20 | 43586978 | 43587052 | + | ENST00000372826 | TAF |
| 14% | chr10 | 71851150 | 71851334 | + | chr10 | 71851513 | 71851710 | + | ENST00000373255 | TAF |
| 14% | chr2 | 70052223 | 70052362 | + | chr2 | 70052588 | 70052647 | + | ENST00000409920; ENST00000394295; ENST00000536030 | TAF |

TABLE 14-continued

Transcript fusion for Cholangiocarcinoma (CHOL) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 14% | chr3 | 149210772 | 149210837 | + | chr3 | 149216509 | 149216698 | + | ENST00000305354 | TAF |
| 14% | chr5 | 176950016 | 176949956 | − | chr5 | 176949072 | 176948976 | − | ENST00000514747; ENST00000329540; ENST00000443375; ENST00000524677 | TAF |
| 14% | chr11 | 11334682 | 11334475 | − | chr11 | 11314740 | 11314576 | − | ENST00000227756 | TAF |
| 14% | chr6 | 24710791 | 24710723 | − | chr6 | 24709139 | 24709005 | − | ENST00000378119; ENST00000540769; ENST00000378102 | TAF |
| 14% | chr2 | 26433512 | 26433446 | − | chr2 | 26432758 | 26432649 | − | ENST00000380649 | TAF |
| 14% | chr19 | 6761121 | 6761101 | − | chr19 | 6760998 | 6760649 | − | ENST00000245908; ENST00000597687 | TAF |
| 14% | chr19 | 6761121 | 6761101 | − | chr19 | 6760998 | 6760649 | − | ENST00000245908; ENST00000597687 | TAF |
| 11% | chr10 | 3122429 | 3122494 | + | chr10 | 3124580 | 3124653 | + | ENST00000381125; ENST00000381075 | TAF |
| 11% | chr10 | 3122429 | 3122494 | + | chr10 | 3124580 | 3124653 | + | ENST00000381125; ENST00000381075 | TAF |
| 11% | chr11 | 725232 | 725414 | + | chr11 | 725728 | 725847 | + | ENST00000318562; ENST00000533256; ENST00000530636; ENST00000526198 | TAF |
| 11% | chr1 | 44018824 | 44019043 | + | chr1 | 44019163 | 44019308 | + | ENST00000359947; ENST00000438120; ENST00000372413; ENST00000372414; ENST00000437607 | TAF |
| 11% | chr1 | 44018824 | 44019043 | + | chr1 | 44019163 | 44019308 | + | ENST00000359947; ENST00000438120; ENST00000372413; ENST00000372414; ENST00000437607 | TAF |
| 11% | chr1 | 44018824 | 44019043 | + | chr1 | 44019163 | 44019308 | + | ENST00000359947; ENST00000438120; ENST00000372413; ENST00000372414; ENST00000437607 | TAF |
| 11% | chr1 | 31887686 | 31887779 | + | chr1 | 31896540 | 31896701 | + | ENST00000373710; ENST00000536859; ENST00000373709; ENST00000536384 | TAF |
| 11% | chr8 | 144638103 | 144638200 | + | chr8 | 144640548 | 144640621 | + | ENST00000533063 | TAF |
| 11% | chr22 | 37422073 | 37422119 | + | chr22 | 37425257 | 37425555 | + | ENST00000401419; ENST00000397129; ENST00000404802; ENST00000341116; ENST00000429360; ENST00000397225 | TAF |
| 11% | chr16 | 29845718 | 29845758 | + | chr16 | 29848043 | 29848279; 29848124 | + | ENST00000357402; ENST00000566859; ENST00000452209; ENST00000395353 | TAF |
| 11% | chr16 | 29845718 | 29845758 | + | chr16 | 29848043 | 29848279; 29848124 | + | ENST00000357402; ENST00000566859; ENST00000452209; ENST00000395353 | TAF |
| 11% | chr16 | 29845718 | 29845758 | + | chr16 | 29848043 | 29848279; 29848124 | + | ENST00000357402; ENST00000566859; ENST00000452209; ENST00000395353 | TAF |
| 11% | chr20 | 36998164 | 36998324 | + | chr20 | 36999382 | 36999449 | + | ENST00000217407 | TAF |
| 11% | chr14 | 102691697 | 102691432 | − | chr14 | 102691131 | 102691116 | − | ENST00000559838 | TAF |
| 11% | chr9 | 100872455 | 100872351 | − | chr9 | 100872266 | 100872171 | − | ENST00000375098; ENST00000341469; ENST00000342043 | TAF |
| 11% | chr5 | 54722535 | 54722306 | − | chr5 | 54721867 | 54721691 | − | ENST00000264775; ENST00000307259 | TAF |
| 11% | chr10 | 7612883 | 7612834 | − | chr10 | 7611747 | 7611631 | − | ENST00000256861; ENST00000298441; ENST00000446830 | TAF |
| 11% | chr10 | 7612883 | 7612834 | − | chr10 | 7611747 | 7611631 | − | ENST00000256861; ENST00000298441; ENST00000446830 | TAF |
| 11% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 11% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 11% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 11% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 11% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 11% | chr16 | 57816467 | 57816371 | − | chr16 | 57806200 | 57806135 | − | ENST00000379655; ENST00000445690; ENST00000541240; ENST00000540079; ENST00000539578; ENST00000562503; ENST00000569222; ENST00000566648; ENST00000561524; ENST00000565684 | TAF |
| 11% | chr16 | 57816467 | 57816371 | − | chr16 | 57806200 | 57806135 | − | ENST00000379655; ENST00000445690; ENST00000541240; ENST00000540079; ENST00000539578; ENST00000562503; ENST00000569222; ENST00000566648; ENST00000561524; ENST00000565684 | TAF |
| 11% | chr16 | 57816467 | 57816371 | − | chr16 | 57806200 | 57806135 | − | ENST00000379655; ENST00000445690; ENST00000541240; ENST00000540079; ENST00000539578; ENST00000562503; ENST00000569222; ENST00000566648; ENST00000561524; ENST00000565684 | TAF |
| 11% | chr16 | 57816467 | 57816371 | − | chr16 | 57806200 | 57806135 | − | ENST00000379655; ENST00000445690; ENST00000541240; ENST00000540079; ENST00000539578; ENST00000562503; | TAF |

TABLE 14-continued

Transcript fusion for Cholangiocarcinoma (CHOL) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 11% | chr16 | 57816467 | 57816371 | – | chr16 | 57806200 | 57806135 | – | ENST00000569222; ENST00000566648; ENST00000561524; ENST00000565684 ENST00000379655; ENST00000445690; ENST00000541240; ENST00000540079; ENST00000539578; ENST00000562503; | TAF |
| 11% | chr16 | 57816467 | 57816371 | – | chr16 | 57806200 | 57806135 | – | ENST00000569222; ENST00000566648; ENST00000561524; ENST00000565684 ENST00000379655; ENST00000445690; ENST00000541240; ENST00000540079; ENST00000539578; ENST00000562503; | TAF |
| 11% | chr16 | 57816467 | 57816371 | – | chr16 | 57806200 | 57806135 | – | ENST00000569222; ENST00000566648; ENST00000561524; ENST00000565684 ENST00000379655; ENST00000445690; ENST00000541240; ENST00000540079; ENST00000539578; ENST00000562503; | TAF |
| 11% | chr19 | 1600051 | 1599987 | – | chr19 | 1599559 | 1599439 | – | ENST00000569222; ENST00000566648; ENST00000561524; ENST00000565684 ENST00000585937; ENST00000591899; ENST00000589880; ENST00000585671 | TAF |

TABLE 15

Transcript fusion for Cholangiocarcinoma (CHOL) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 44% | chr3 | 149205406 | 149205542 | + | ENST00000305354 | chr3 | 149210784 | 149210892 | + | TAF |
| 33% | chr1 | 21926110 | 21925987 | – | ENST00000374761; ENST00000290101; ENST00000374763; ENST00000471600; ENST00000374765; ENST00000542643 | chr1 | 21925313 | 21925206 | – | TAF |
| 33% | chr1 | 21926110 | 21925987 | – | ENST00000374761; ENST00000290101; ENST00000374763; ENST00000471600; ENST00000374765; ENST00000542643 | chr1 | 21925313 | 21925206 | – | TAF |
| 33% | chr1 | 21926110 | 21925987 | – | ENST00000374761; ENST00000290101; ENST00000374763; ENST00000471600; ENST00000374765; ENST00000542643 | chr1 | 21925313 | 21925206 | – | TAF |
| 33% | chr1 | 21926110 | 21925987 | – | ENST00000374761; ENST00000290101; ENST00000374763; ENST00000471600; ENST00000374765; ENST00000542643 | chr1 | 21925313 | 21925206 | – | TAF |
| 33% | chr1 | 21926110 | 21925987 | – | ENST00000374761; ENST00000290101; ENST00000374763; ENST00000471600; ENST00000374765; ENST00000542643 | chr1 | 21925313 | 21925206 | – | TAF |
| 31% | chr20 | 43560983 | 43561073 | + | ENST00000255136; ENST00000217073 | chr20 | 43561176 | 43561224 | + | TAF |
| 28% | chr4 | 88293967 | 88293861 | – | ENST00000358290; ENST00000507286 | chr4 | 88287307 | 88287019 | – | TAF |
| 28% | chr4 | 88293967 | 88293861 | – | ENST00000358290; ENST00000507286 | chr4 | 88287307 | 88287019 | – | TAF |
| 25% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 25% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 25% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 25% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 22% | chr5 | 176761404; 176761337 | 176761285 | – | ENST00000303127; ENST00000515209; ENST00000514458 | chr5 | 176744789 | 176744095 | – | TAF |
| 22% | chr5 | 176761404; 176761337 | 176761285 | – | ENST00000303127; ENST00000515209; ENST00000514458 | chr5 | 176744789 | 176744095 | – | TAF |
| 22% | chr1 | 159683928 | 159683793 | – | ENST00000255030; ENST00000368112 | chr1 | 159682370 | 159682050 | – | TAF |
| 22% | chr3 | 49927493 | 49927357 | – | ENST00000296474; ENST00000344206 | chr3 | 49927248 | 49927204 | – | TAF |
| 22% | chr3 | 49927493 | 49927357 | – | ENST00000296474; ENST00000344206 | chr3 | 49927248 | 49927204 | – | TAF |
| 19% | chr9 | 125054028 | 125054119 | + | ENST00000297908; ENST00000344641; ENST00000373723; ENST00000373729; ENST00000394315 | chr9 | 125068067 | 125068171 | + | TSF |
| 19% | chr9 | 125054028 | 125054119 | + | ENST00000297908; ENST00000344641; ENST00000373723; ENST00000373729; ENST00000394315 | chr9 | 125068067 | 125068171 | + | TSF |
| 19% | chr9 | 125054028 | 125054119 | + | ENST00000297908; ENST00000344641; ENST00000373723; ENST00000373729; ENST00000394315 | chr9 | 125068067 | 125068171 | + | TSF |

TABLE 15-continued

Transcript fusion for Cholangiocarcinoma (CHOL) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 17% | chr20 | 33439171 | 33439034 | − | ENST00000336431 | chr20 | 33438000 | 33437979 | − | TAF |
| 17% | chr10 | 120905865 | 120905748 | − | ENST00000355697; ENST00000330036 | chr10 | 120901885 | 120901741 | − | TAF |
| 17% | chr10 | 120905865 | 120905748 | − | ENST00000355697; ENST00000330036 | chr10 | 120901885 | 120901741 | − | TAF |
| 17% | chr16 | 29913136; 29912293 | 29913241 | + | ENST00000563177; ENST00000483405; ENST00000308748; ENST00000414952; ENST00000566693 | chr16 | 29915825 | 29915953 | + | TSF |
| 17% | chr16 | 29913136; 29912293 | 29913241 | + | ENST00000563177; ENST00000483405; ENST00000308748; ENST00000414952; ENST00000566693 | chr16 | 29915825 | 29915953 | + | TSF |
| 14% | chr10 | 60272904 | 60273093 | + | ENST00000373886 | chr10 | 60299081 | 60299303 | + | TAF |
| 14% | chr9 | 131002264 | 131002275 | + | ENST00000475805; ENST00000341179; ENST00000372923; ENST00000393594; ENST00000486160 | chr9 | 131002706 | 131002973 | + | TAF |
| 14% | chr9 | 131002264 | 131002275 | + | ENST00000475805; ENST00000341179; ENST00000372923; ENST00000393594; ENST00000486160 | chr9 | 131002706 | 131002973 | + | TAF |
| 14% | chr11 | 2940537 | 2940637 | + | ENST00000347936; ENST00000312221; ENST00000449793; ENST00000380574 | chr11 | 2940947 | 2941017 | + | TAF |
| 14% | chr11 | 2940537 | 2940637 | + | ENST00000347936; ENST00000312221; ENST00000449793; ENST00000380574 | chr11 | 2940947 | 2941017 | + | TAF |
| 14% | chr19 | 35514331 | 35514451 | + | ENST00000599564; ENST00000317991; ENST00000504615; ENST00000411896 | chr19 | 35514601 | 35514631 | + | TAF |
| 14% | chr19 | 35514331 | 35514451 | + | ENST00000599564; ENST00000317991; ENST00000504615; ENST00000411896 | chr19 | 35514601 | 35514631 | + | TAF |
| 14% | chr19 | 35514331 | 35514451 | + | ENST00000599564; ENST00000317991; ENST00000504615; ENST00000411896 | chr19 | 35514601 | 35514631 | + | TAF |
| 14% | chr19 | 35514331 | 35514451 | + | ENST00000599564; ENST00000317991; ENST00000504615; ENST00000411896 | chr19 | 35514601 | 35514631 | + | TAF |
| 14% | chr5 | 82554349 | 82554496 | + | ENST00000282268; ENST00000338635; ENST00000396027; ENST00000511817 | chr5 | 82606608 | 82606935 | + | TAF |
| 14% | chr10 | 47747112 | 47747132 | + | ENST00000340243; ENST00000374277; ENST00000449464; ENST00000538825 | chr10 | 48278725 | 48278896 | + | TAF |
| 14% | chr16 | 16251666 | 16251520 | − | ENST00000205557 | chr16 | 16249711 | 16249633 | − | TAF |
| 14% | chr19 | 5680497 | 5680469 | − | ENST00000309324; ENST00000587589 | chr19 | 5680194 | 5680187 | − | TAF |
| 14% | chr2 | 132249597 | 132249449 | − | ENST00000427024; ENST00000309451 | chr2 | 132245283 | 132245193 | − | TAF |
| 14% | chr2 | 132249597 | 132249449 | − | ENST00000427024; ENST00000309451 | chr2 | 132245283 | 132245193 | − | TAF |
| 14% | chr1 | 159683928 | 159683797 | − | ENST00000255030; ENST00000368112; ENST00000368111; ENST00000368110; ENST00000343919 | chr1 | 159682370 | 159682050 | − | TAF |
| 11% | chr16 | 2818998 | 2819285 | + | ENST00000301740 | chr16 | 2819676 | 2820194 | + | TAF |
| 11% | chr19 | 50984141 | 50984234 | + | ENST00000334976; ENST00000376918; ENST00000598585 | chr19 | 51009025 | 51009080 | + | TAF |
| 11% | chr10 | 15151838 | 15151701 | − | ENST00000378165; ENST00000378150; ENST00000540259; ENST00000535341 | chr10 | 15148697 | 15148684 | − | TAF |
| 11% | chr10 | 15151838 | 15151701 | − | ENST00000378165; ENST00000378150; ENST00000540259; ENST00000535341 | chr10 | 15148697 | 15148684 | − | TAF |
| 11% | chr10 | 15151838 | 15151701 | − | ENST00000378165; ENST00000378150; ENST00000540259; ENST00000535341 | chr10 | 15148697 | 15148684 | − | TAF |
| 11% | chr10 | 15151838 | 15151701 | − | ENST00000378165; ENST00000378150; ENST00000540259; ENST00000535341 | chr10 | 15148697 | 15148684 | − | TAF |
| 11% | chr5 | 147207691 | 147207585 | − | ENST00000296695; ENST00000510027 | chr5 | 147185494 | 147185375 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr19 | 6678034; 6677969 | 6677917 | − | ENST00000245907; ENST00000601008 | chr19 | 6670525 | 6670384 | − | TAF |
| 11% | chr19 | 6678034; 6677969 | 6677917 | − | ENST00000245907; ENST00000601008 | chr19 | 6670525 | 6670384 | − | TAF |
| 11% | chr3 | 124839669; 124839530; 124839525 | 124839443 | − | ENST00000430155; ENST00000393469; ENST00000423114; ENST00000469902; ENST00000314584; ENST00000479826 | chr3 | 124838735 | 124838686 | − | TAF |
| 11% | chr3 | 124839669; 124839530; 124839525 | 124839443 | − | ENST00000430155; ENST00000393469; ENST00000423114; ENST00000469902; ENST00000314584; ENST00000479826 | chr3 | 124838735 | 124838686 | − | TAF |

TABLE 15-continued

Transcript fusion for Cholangiocarcinoma (CHOL) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 11% | chr3 | 124839669; 124839530; 124839525 | 124839443 | − | ENST00000430155; ENST00000393469; ENST00000423114; ENST00000469902; ENST00000314584; ENST0000479826 | chr3 | 124838735 | 124838686 | − | TAF |
| 11% | chr3 | 124839669; 124839530; 124839525 | 124839443 | − | ENST00000430155; ENST00000393469; ENST00000423114; ENST00000469902; ENST00000314584; ENST0000479826 | chr3 | 124838735 | 124838686 | − | TAF |
| 11% | chr3 | 124839669; 124839530; 124839525 | 124839443 | − | ENST00000430155; ENST00000393469; ENST00000423114; ENST00000469902; ENST00000314584; ENST0000479826 | chr3 | 124838735 | 124838686 | − | TAF |
| 11% | chr17 | 40821639; 40821538 | 40821448 | − | ENST00000591022; ENST00000412503; ENST00000293349 | chr17 | 40820920 | 40820864 | − | TAF |
| 11% | chr17 | 40821639; 40821538 | 40821448 | − | ENST00000591022; ENST00000412503; ENST00000293349 | chr17 | 40820920 | 40820864 | − | TAF |
| 11% | chr17 | 40821639; 40821538 | 40821448 | − | ENST00000591022; ENST00000412503; ENST00000293349 | chr17 | 40820920 | 40820864 | − | TAF |

TABLE 16

Transcript fusion for Colon adenocarcinoma (COAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 31% | chr3 | 49927493 | 49927357 | − | ENST00000296474; ENST00000344206 | chr3 | 49927248 | 49927204 | − | TAF |
| 31% | chr3 | 49927493 | 49927357 | − | ENST00000296474; ENST00000344206 | chr3 | 49927248 | 49927204 | − | TAF |
| 27% | chr11 | 428199 | 428088 | − | ENST00000332826 | chr11 | 424187 | 423924 | − | TAF |
| 26% | chr13 | 43659904 | 43659974 | + | ENST00000379221 | chr13 | 43670953 | 43671210 | + | TAF |
| 24% | chr12 | 71928895 | 71928966 | + | ENST00000266674; ENST00000536515; ENST00000540815 | chr12 | 71938771 | 71938901 | + | TSF |
| 23% | chr7 | 75442741 | 75442624 | − | ENST00000222902; ENST00000416943 | chr7 | 75441450 | 75441417 | − | TAF |
| 17% | chr13 | 44433033 | 44432917 | − | ENST00000444614; ENST00000281508 | chr13 | 44413224 | 44412729 | − | TAF |
| 16% | chr1 | 24463799 | 24463621 | − | ENST00000270800 | chr1 | 24461426 | 24461370 | − | TAF |
| 13% | chr6 | 1960205 | 1960101 | − | ENST00000530927; ENST00000380815 | chr6 | 1955184 | 1955013 | − | TAF |
| 13% | chr6 | 1960205 | 1960101 | − | ENST00000530927; ENST00000380815 | chr6 | 1955184 | 1955013 | − | TAF |
| 13% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 13% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 13% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 13% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 13% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 13% | chr20 | 9453926 | 9454012 | + | ENST00000334005; ENST00000378473; ENST00000278655; ENST00000414679; ENST00000378493; ENST00000378501 | chr20 | 9484605 | 9485169 | + | TAF |
| 13% | chr20 | 9453926 | 9454012 | + | ENST00000334005; ENST00000378473; ENST00000278655; ENST00000414679; ENST00000378493; ENST00000378501 | chr20 | 9484605 | 9485169 | + | TAF |
| 12% | chr5 | 147207691 | 147207585 | − | ENST00000296695; ENST00000510027 | chr5 | 147185494 | 147185375 | − | TAF |
| 12% | chr4 | 57319769 | 57319927 | + | ENST00000514888; ENST00000264221; ENST00000505164; ENST00000399688; ENST00000512576 | chr4 | 57321183 | 57321327 | + | TSF |
| 12% | chr4 | 57319769 | 57319927 | + | ENST00000514888; ENST00000264221; ENST00000505164; ENST00000399688; ENST00000512576 | chr4 | 57321183 | 57321327 | + | TSF |
| 12% | chr4 | 57319769 | 57319927 | + | ENST00000514888; ENST00000264221; ENST00000505164; ENST00000399688; ENST00000512576 | chr4 | 57321183 | 57321327 | + | TSF |
| 11% | chr10 | 120905865 | 120905748 | − | ENST00000355697; ENST00000330036 | chr10 | 120901885 | 120901741 | − | TAF |
| 11% | chr10 | 120905865 | 120905748 | − | ENST00000355697; ENST00000330036 | chr10 | 120901885 | 120901741 | − | TAF |
| 11% | chr9 | 125054028 | 125054119 | + | ENST00000297908; ENST00000344641; ENST00000373723; ENST00000373729; ENST00000394315 | chr9 | 125068067 | 125068171 | + | TSF |
| 11% | chr9 | 125054028 | 125054119 | + | ENST00000297908; ENST00000344641; ENST00000373723; ENST00000373729; ENST00000394315 | chr9 | 125068067 | 125068171 | + | TSF |

TABLE 16-continued

Transcript fusion for Colon adenocarcinoma (COAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 11% | chr9 | 125054028 | 125054119 | + | ENST00000297908; ENST00000344641; ENST00000373723; ENST00000373729; ENST00000394315 | chr9 | 125068067 | 125068171 | + | TSF |
| 11% | chr20 | 33137782 | 33137833 | + | ENST00000374837 | chr20 | 33138384 | 33138773 | + | TSF |
| 10% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 10% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 10% | chr20 | 9382137 | 9382237 | + | ENST00000334005; ENST00000378473; ENST00000278655; ENST00000414679; ENST00000378493; ENST00000378501 | chr20 | 9383648 | 9383757 | + | TSF |
| 9% | chr16 | 50659396 | 50659491 | + | ENST00000268459 | chr16 | 50663933 | 50663990 | + | TSF |
| 8% | chr16 | 50583333 | 50583466 | + | ENST00000268459 | chr16 | 50614862 | 50614981 | + | TSF |
| 8% | chr2 | 241555805 | 241555928 | + | ENST00000270364 | chr2 | 241556208 | 241556489 | + | TSF |
| 7% | chr7 | 34888095 | 34888275 | + | ENST00000360581; ENST00000381542; ENST00000359791; ENST00000531252; ENST00000381539 | chr7 | 34935732 | 34935887 | + | TSF |
| 7% | chr7 | 34888095 | 34888275 | + | ENST00000360581; ENST00000381542; ENST00000359791; ENST00000531252; ENST00000381539 | chr7 | 34935732 | 34935887 | + | TSF |
| 7% | chr7 | 34888095 | 34888275 | + | ENST00000360581; ENST00000381542; ENST00000359791; ENST00000531252; ENST00000381539 | chr7 | 34935732 | 34935887 | + | TSF |
| 7% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 7% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 7% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 7% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 7% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 7% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr13 | 98642687; 98642769 | 98642791 | + | ENST00000261574; ENST00000357602; ENST00000490680; ENST00000539640; ENST00000469360 | chr13 | 98643835 | 98643958 | + | TSF |
| 5% | chr13 | 98642687; 98642769 | 98642791 | + | ENST00000261574; ENST00000357602; ENST00000490680; ENST00000539640; ENST00000469360 | chr13 | 98643835 | 98643958 | + | TSF |
| 5% | chr13 | 98642687; 98642769 | 98642791 | + | ENST00000261574; ENST00000357602; ENST00000490680; ENST00000539640; ENST00000469360 | chr13 | 98643835 | 98643958 | + | TSF |
| 5% | chr13 | 98642687; 98642769 | 98642791 | + | ENST00000261574; ENST00000357602; ENST00000490680; ENST00000539640; ENST00000469360 | chr13 | 98643835 | 98643958 | + | TSF |
| 5% | chr16 | 72153988; 72154048 | 72153750 | − | ENST00000537465; ENST00000237353; ENST00000355636 | chr16 | 72150929 | 72150229 | − | TSF |
| 5% | chr16 | 72153988; 72154048 | 72153750 | − | ENST00000537465; ENST00000237353; ENST00000355636 | chr16 | 72150929 | 72150229 | − | TSF |
| 5% | chr16 | 72153988; 72154048 | 72153750 | − | ENST00000537465; ENST00000237353; ENST00000355636 | chr16 | 72150929 | 72150229 | − | TSF |

TABLE 16-continued

Transcript fusion for Colon adenocarcinoma (COAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 5% | chr1 | 11115983; 11115877 | 11115838 | − | ENST00000376957; ENST00000490101 | chr1 | 11115464 | 11115178 | − | TSF |
| 5% | chr1 | 11115983; 11115877 | 11115838 | − | ENST00000376957; ENST00000490101 | chr1 | 11115464 | 11115178 | − | TSF |
| 4% | chr8 | 71619168 | 71619388 | + | ENST00000408926; ENST00000520030 | chr8 | 71625661 | 71625673 | + | TSF |
| 4% | chr3 | 49928739 | 49928630 | − | ENST00000296474; ENST00000344206; ENST00000434765; ENST00000440292 | chr3 | 49928452 | 49928163 | − | TSF |
| 4% | chr3 | 49928739 | 49928630 | − | ENST00000296474; ENST00000344206; ENST00000434765; ENST00000440292 | chr3 | 49928452 | 49928163 | − | TSF |
| 4% | chr3 | 49928739 | 49928630 | − | ENST00000296474; ENST00000344206; ENST00000434765; ENST00000440292 | chr3 | 49928452 | 49928163 | − | TSF |
| 4% | chr3 | 49928739 | 49928630 | − | ENST00000296474; ENST00000344206; ENST00000434765; ENST00000440292 | chr3 | 49928452 | 49928163 | − | TSF |
| 4% | chr8 | 109468102 | 109468159 | + | ENST00000220853; ENST00000519642 | chr8 | 109468381 | 109468590 | + | TSF |
| 4% | chr8 | 109468102 | 109468159 | + | ENST00000220853; ENST00000519642 | chr8 | 109468381 | 109468590 | − | TSF |
| 4% | chr12 | 113623819 | 113623826 | + | ENST00000552495 | chr12 | 113623998 | 113624117 | − | TSF |
| 3% | chr17 | 79912179 | 79912132 | − | ENST00000409678 | chr17 | 79911834 | 79911647 | − | TSF |
| 3% | chr7 | 73973957 | 73973985 | + | ENST00000265755; ENST00000455841; ENST00000424337; ENST00000476977; ENST00000470715 | chr7 | 73985447 | 73985582 | + | TSF |
| 3% | chr7 | 73973957 | 73973985 | + | ENST00000265755; ENST00000455841; ENST00000424337; ENST00000476977; ENST00000470715 | chr7 | 73985447 | 73985582 | + | TSF |
| 3% | chr7 | 73973957 | 73973985 | + | ENST00000265755; ENST00000455841; ENST00000424337; ENST00000476977; ENST00000470715 | chr7 | 73985447 | 73985582 | + | TSF |
| 3% | chr7 | 73973957 | 73973985 | + | ENST00000265755; ENST00000455841; ENST00000424337; ENST00000476977; ENST00000470715 | chr7 | 73985447 | 73985582 | + | TSF |
| 3% | chr19 | 42221377; 42221374 | 42221652 | + | ENST00000398599; ENST00000221992; ENST00000405816 | chr19 | 42274707 | 42275202 | + | TSF |
| 3% | chr19 | 42221377; 42221374 | 42221652 | + | ENST00000398599; ENST00000221992; ENST00000405816 | chr19 | 42274707 | 42275202 | + | TSF |
| 3% | chr1 | 225156461 | 225156576 | + | ENST00000430092; ENST00000400952; NEST00000366849; ENST00000439375 | chr1 | 225157336 | 225158402 | + | TSF |
| 3% | chr1 | 225156461 | 225156576 | + | ENST00000430092; ENST00000400952; ENST00000366849; ENST00000439375 | chr1 | 225157336 | 225158402 | + | TSF |
| 3% | chr7 | 150065992 | 150066030 | + | ENST00000466559; ENST00000475514; ENST00000488943; ENST00000467980; ENST00000518514; ENST00000522266 | chr7 | 150067849 | 150067901 | + | TSF |
| 3% | chr20 | 60578330 | 60578216 | − | ENST00000252996; ENST00000488539 | chr20 | 60576919 | 60576839 | − | TSF |
| 3% | chr20 | 60578330 | 60578216 | − | ENST00000252996; ENST00000488539 | chr20 | 60576919 | 60576839 | − | TSF |
| 3% | chr2 | 217366064 | 217366082 | + | ENST00000491306; ENST00000456586 | chr2 | 217393993 | 217394327 | + | TSF |
| 3% | chr2 | 217366064 | 217366082 | + | ENST00000491306; ENST00000456586 | chr2 | 217393993 | 217394327 | + | TSF |
| 3% | chr1 | 23208852 | 23208976 | + | ENST00000544305; ENST00000374630; ENST00000400191; ENST00000374632; ENST00000374627 | chr1 | 23211233 | 23211522 | + | TSF |
| 3% | chr1 | 23208852 | 23208976 | + | ENST00000544305; ENST00000374630; ENST00000400191; ENST00000374632; ENST00000374627 | chr1 | 23211233 | 23211522 | + | TSF |
| 3% | chr16 | 50642205 | 50642271 | + | ENST00000268459 | chr16 | 50651664 | 50651770 | + | TSF |
| 3% | chr16 | 57115439 | 57115522 | + | ENST00000262510; ENST00000308149; ENST00000539144 | chr16 | 57116257 | 57116272 | + | TSF |
| 3% | chr16 | 57115439 | 57115522 | + | ENST00000262510; ENST00000308149; ENST00000539144 | chr16 | 57116257 | 57116272 | + | TSF |
| 3% | chr12 | 4874545 | 4874712 | + | ENST00000252318; ENST00000542998; ENST00000535354 | chr12 | 4884414 | 4884790 | + | TSF |
| 3% | chr12 | 4874545 | 4874712 | + | ENST00000252318; ENST00000542998; ENST00000535354 | chr12 | 4884414 | 4884790 | + | TSF |
| 3% | chr12 | 4874545 | 4874712 | + | ENST00000252318; ENST00000542998; ENST00000535354 | chr12 | 4884414 | 4884790 | + | TSF |
| 3% | chr9 | 130213596 | 130213560 | − | ENST00000361436; ENST00000536368 | chr9 | 130213398 | 130213359 | − | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |

TABLE 16-continued

Transcript fusion for Colon adenocarcinoma (COAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 2% | chr13 | 114157811 | 114157903 | + | ENST00000434316; ENST00000375391 | chr13 | 114159741 | 114159770 | + | TSF |
| 2% | chr19 | 42218890 | 42219168 | + | ENST00000398599; ENST00000221992; ENST00000405816; ENST00000595113 | chr19 | 42274707 | 42275202 | + | TSF |
| 2% | chr19 | 42218890 | 42219168 | + | ENST00000398599; ENST00000221992; ENST00000405816; ENST00000595113 | chr19 | 42274707 | 42275202 | + | TSF |
| 2% | chr19 | 42221377; 42221374 | 42221417 | + | ENST00000398599; ENST00000221992; ENST00000405816; ENST00000595113 | chr19 | 42729297 | 42729312 | + | TSF |
| 2% | chr19 | 42221377; 42221374 | 42221417 | + | ENST00000398599; ENST00000221992; ENST00000405816; ENST00000595113 | chr19 | 42729297 | 42729312 | + | TSF |
| 2% | chr19 | 42221377; 42221374 | 42221417 | + | ENST00000398599; ENST00000221992; ENST00000405816; ENST00000595113 | chr19 | 42729297 | 42729312 | + | TSF |
| 2% | chr8 | 624047; 623326; 623657 | 623289 | − | ENST00000522706; ENST00000523415; ENST00000262109; ENST00000522893 | chr8 | 622204 | 621954 | − | TSF |
| 2% | chr8 | 624047; 623326; 623657 | 623289 | − | ENST00000522706; ENST00000523415; ENST00000262109; ENST00000522893 | chr8 | 622204 | 621954 | − | TSF |
| 2% | chr8 | 624047; 623326; 623657 | 623289 | − | ENST00000522706; ENST00000523415; ENST00000262109; ENST00000522893 | chr8 | 622204 | 621954 | − | TSF |
| 2% | chr8 | 624047; 623326; 623657 | 623289 | − | ENST00000522706; ENST00000523415; ENST00000262109; ENST00000522893 | chr8 | 622204 | 621954 | − | TSF |
| 2% | chr6 | 105771643 | 105771540 | − | ENST00000369110; ENST00000448705 | chr6 | 105764464 | 105763345 | − | TSF |
| 2% | chr6 | 105771643 | 105771540 | − | ENST00000369110; ENST00000448705 | chr6 | 105764464 | 105763345 | − | TSF |
| 2% | chr10 | 79796952 | 79797062 | + | ENST00000435275; ENST00000440692; ENST00000372360; ENST00000360830 | chr4 | 176584518 | 176584519 | + | TSF |
| 2% | chr2 | 241555805 | 241555928 | + | ENST00000270364 | chr2 | 241556476 | 241556489 | + | TSF |
| 2% | chr2 | 241555805 | 241555928 | + | ENST00000270364 | chr2 | 241556590 | 241556603 | + | TSF |
| 2% | chr6 | 1930464 | 1930337 | − | ENST00000530927; ENST00000380815 | chr6 | 1888004 | 1887962 | − | TSF |
| 2% | chr6 | 1930464 | 1930337 | − | ENST00000530927; ENST00000380815 | chr6 | 1888004 | 1887962 | − | TSF |
| 2% | chr3 | 108475435 | 108475355 | − | ENST00000295755 | chr3 | 108466866 | 108466812 | − | TSF |

TABLE 17

Transcript fusion for Colon adenocarcinoma (COAD) Coordinates of the fusion sequences for which the donor is the TE.

| 1 | 2 | 3' | 4' | 5' | 6' | 7' | 8' | 9' | 10' | 11' |
|---|---|---|---|---|---|---|---|---|---|---|
| 54% | chr11 | 93468219 | 93468129 | − | chr11 | 93467826 | 93467791; 93467814 | − | ENST00000393259; ENST00000527169 | TAF |
| 54% | chr11 | 93468219 | 93468129 | − | chr11 | 93467826 | 93467791; 93467814 | − | ENST00000393259; ENST00000527169 | TAF |
| 51% | chr9 | 6248332 | 6248555 | + | chr9 | 6250474 | 6250599 | + | ENST00000456383; ENST00000381434 | TAF |
| 51% | chr9 | 6248332 | 6248555 | + | chr9 | 6250474 | 6250599 | + | ENST00000456383; ENST00000381434 | TAF |
| 35% | chr11 | 424193 | 423942 | − | chr11 | 421198 | 421141 | − | ENST00000332826 | TAF |
| 28% | chr8 | 104389530 | 104389551 | + | chr8 | 104390255 | 104390471 | + | ENST00000330295; ENST00000520337 | TAF |
| 26% | chr13 | 43628887 | 43629679 | + | chr13 | 43643066 | 43643139 | + | ENST00000379221 | TAF |
| 23% | chr14 | 51360331 | 51362440 | + | chr14 | 51368547 | 51368629 | + | ENST00000337334; ENST00000353130; ENST00000395752 | TSF |
| 20% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 20% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 20% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 20% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 20% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |

TABLE 17-continued

Transcript fusion for Colon adenocarcinoma (COAD) Coordinates of the fusion sequences for which the donor is the TE.

| 1 | 2 | 3' | 4' | 5' | 6' | 7' | 8' | 9' | 10' | 11' |
|---|---|---|---|---|---|---|---|---|---|---|
| 20% | chr20 | 44420870 | 44421070 | + | chr20 | 44421316 | 44421386 | + | ENST00000372622; ENST00000449078; ENST00000456939 | TAF |
| 20% | chr20 | 44420870 | 44421070 | + | chr20 | 44421316 | 44421386 | + | ENST00000372622; ENST00000449078; ENST00000456939 | TAF |
| 20% | chr20 | 44420870 | 44421070 | + | chr20 | 44421316 | 44421386 | + | ENST00000372622; ENST00000449078; ENST00000456939 | TAF |
| 20% | chr13 | 43628887 | 43629679 | + | chr13 | 43639822 | 43639873 | + | ENST00000379221 | TAF |
| 18% | chr7 | 116364854 | 116364901 | + | chr7 | 116371722 | 116371913 | + | ENST00000397752; ENST00000318493; ENST00000436117 | TAF |
| 18% | chr7 | 116364854 | 116364901 | + | chr7 | 116371722 | 116371913 | + | ENST00000397752; ENST00000318493; ENST00000436117 | TAF |
| 18% | chr7 | 116364854 | 116364901 | + | chr7 | 116371722 | 116371913 | + | ENST00000397752; ENST00000318493; ENST00000436117 | TAF |
| 18% | chr13 | 101090702 | 101090970 | + | chr13 | 101101506 | 101101559 | + | ENST00000376279; ENST00000376286; ENST00000376285; ENST00000458283; ENST00000413170 | TSF |
| 18% | chr13 | 101090702 | 101090970 | + | chr13 | 101101506 | 101101559 | + | ENST00000376279; ENST00000376286; ENST00000376285; ENST00000458283; ENST00000413170 | TSF |
| 18% | chr13 | 101090702 | 101090970 | + | chr13 | 101101506 | 101101559 | + | ENST00000376279; ENST00000376286; ENST00000376285; ENST00000458283; ENST00000413170 | TSF |
| 17% | chr13 | 76173531 | 76175706 | + | chr13 | 76178905 | 76178963 | + | ENST00000377595; ENST00000419068 | TAF |
| 17% | chr14 | 65406849 | 65406835 | − | chr14 | 65406556 | 65406206 | − | ENST00000389614; ENST00000557049 | TAF |
| 17% | chr13 | 28224759 | 28225489 | + | chr13 | 28239823 | 28240090 | + | ENST00000399697 | TAF |
| 17% | chr17 | 79911953 | 79911734 | − | chr17 | 79911143 | 79910837 | − | ENST00000409678 | TAF |
| 17% | chr2 | 85053636 | 85053622 | − | chr2 | 85051328 | 85051077 | − | ENST00000335459; ENST00000409520 | TSF |
| 15% | chr5 | 54528691 | 54528595 | − | chr5 | 54528374 | 54528189 | − | ENST00000282572 | TAF |
| 15% | chr5 | 135398466 | 135398602 | + | chr5 | 135398875 | 135398915; 135398898 | + | ENST00000442011; ENST00000305126; ENST00000514554; ENST00000508076; ENST00000503087 | TAF |
| 15% | chr5 | 135398466 | 135398602 | + | chr5 | 135398875 | 135398915; 135398898 | + | ENST00000442011; ENST00000305126; ENST00000514554; ENST00000508076; ENST00000503087 | TAF |
| 15% | chr1 | 59980221 | 59980497 | + | chr1 | 60019796 | 60019899 | + | ENST00000371218; ENST00000303721; ENST00000430447; ENST00000371212 | TSF |
| 15% | chr1 | 59980221 | 59980497 | + | chr1 | 60019796 | 60019899 | + | ENST00000371218; ENST00000303721; ENST00000430447; ENST00000371212 | TSF |
| 15% | chr1 | 59980221 | 59980497 | + | chr1 | 60019796 | 60019899 | + | ENST00000371218; ENST00000303721; ENST00000430447; ENST00000371212 | TSF |
| 14% | chr20 | 61301271 | 61301405 | + | chr20 | 61303102 | 61303245 | + | ENST00000217159; ENST00000370507; ENST00000451793 | TAF |
| 13% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 13% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 13% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | lTAF |
| 13% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 13% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 12% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |

TABLE 17-continued

Transcript fusion for Colon adenocarcinoma (COAD) Coordinates of the fusion sequences for which the donor is the TE.

| 1 | 2 | 3' | 4' | 5' | 6' | 7' | 8' | 9' | 10' | 11' |
|---|---|---|---|---|---|---|---|---|---|---|
| 12% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 12% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 12% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 12% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 12% | chr12 | 20780314 | 20780410 | + | chr12 | 20782842 | 20783061 | + | ENST00000359062 | TAF |
| 12% | chr21 | 42597177 | 42597622 | + | chr21 | 42598193 | 42598281 | + | ENST00000328735; ENST00000330333; ENST00000347667 | TAF |
| 12% | chr21 | 42597177 | 42597622 | + | chr21 | 42598193 | 42598281 | + | ENST00000328735; ENST00000330333; ENST00000347667 | TAF |
| 12% | chr21 | 42597177 | 42597622 | + | chr21 | 42598193 | 42598281 | + | ENST00000328735; ENST00000330333; ENST00000347667 | TAF |
| 12% | chr2 | 85059551 | 85059512 | − | chr2 | 85059269 | 85059179 | − | ENST00000335459; ENST00000409520 | TAF |
| 12% | chrX | 100125243 | 100124234 | − | chrX | 100118584 | 100118474 | − | ENST00000372966; ENST00000372964; ENST00000217885 | TAF |
| 12% | chrX | 100125243 | 100124234 | − | chrX | 100118584 | 100118474 | − | ENST00000372966; ENST00000372964; ENST00000217885 | TAF |
| 12% | chrX | 100125243 | 100124234 | − | chrX | 100118584 | 100118474 | − | ENST00000372966; ENST00000372964; ENST00000217885 | TAF |
| 11% | chr16 | 603045 | 603077 | + | chr16 | 603343 | 603516 | + | ENST00000219611 | TAF |
| 11% | chr16 | 603045 | 603138 | + | chr16 | 603343 | 603516 | + | ENST00000219611 | TAF |
| 11% | chr10 | 120901765 | 120900831 | − | chr10 | 120900754 | − | | ENST00000355697; ENST00000330036 | TAF |
| 11% | chr13 | 41835911 | 41835827 | − | chr13 | 41835051 | 41834629 | − | ENST00000430347 | TAF |
| 11% | chr17 | 79214190 | 79214239 | + | chr17 | 79214787 | 79214816; 79214953 | + | ENST00000431388; ENST00000576002 | TAF |
| 11% | chr17 | 79214190 | 79214239 | + | chr17 | 79214787 | 79214816; 79214953 | + | ENST00000431388; ENST00000576002 | TAF |
| 11% | chr17 | 79914312 | 79914232 | − | chr17 | 79913420 | 79913273; 79913391 | − | ENST00000409678; ENST00000477214 | TAF |
| 11% | chr17 | 79914312 | 79914232 | − | chr17 | 79913420 | 79913273; 79913391 | − | ENST00000409678; ENST00000477214 | TAF |
| 10% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 10% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 10% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 10% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 10% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 10% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; | TAF |

TABLE 17-continued

Transcript fusion for Colon adenocarcinoma (COAD) Coordinates of the fusion sequences for which the donor is the TE.

| 1 | 2 | 3' | 4' | 5' | 6' | 7' | 8' | 9' | 10' | 11' |
|---|---|---|---|---|---|---|---|---|---|---|
| 10% | chr13 | 98628730 | 98628756 | + | chr13 | 98628947 | 98629040; 98629046 | + | ENST00000480611; ENST00000485433; ENST00000496368; ENST00000421861 ENST00000460070; ENST00000481455; ENST00000261574; ENST00000493281; ENST00000490369; ENST00000463157; ENST00000489058; ENST00000481689; | TAF |
| 10% | chr13 | 98628730 | 98628756 | + | chr13 | 98628947 | 98629040; 98629046 | + | ENST00000480611; ENST00000485433; ENST00000496368; ENST00000421861 ENST00000460070; ENST00000481455; ENST00000261574; ENST00000493281; ENST00000490369; ENST00000463157; ENST00000489058; ENST00000481689; | TAF |
| 10% | chr13 | 98628730 | 98628756 | + | chr13 | 98628947 | 98629040; 98629046 | + | ENST00000480611; ENST00000485433; ENST00000496368; ENST00000421861 ENST00000460070; ENST00000481455; ENST00000261574; ENST00000493281; ENST00000490369; ENST00000463157; ENST00000489058; ENST00000481689; | TAF |
| 10% | chr13 | 98628730 | 98628756 | + | chr13 | 98628947 | 98629040; 98629046 | + | ENST00000480611; ENST00000485433; ENST00000496368; ENST00000421861 ENST00000460070; ENST00000481455; ENST00000261574; ENST00000493281; ENST00000490369; ENST00000463157; ENST00000489058; ENST00000481689; | TAF |
| 10% | chr13 | 98628730 | 98628756 | + | chr13 | 98628947 | 98629040; 98629046 | + | ENST00000480611; ENST00000485433; ENST00000496368; ENST00000421861 ENST00000460070; ENST00000481455; ENST00000261574; ENST00000493281; ENST00000490369; ENST00000463157; ENST00000489058; ENST00000481689; | TAF |
| 10% | chr13 | 98628730 | 98628756 | + | chr13 | 98628947 | 98629040; 98629046 | + | ENST00000480611; ENST00000485433; ENST00000496368; ENST00000421861 ENST00000460070; ENST00000481455; ENST00000261574; ENST00000493281; ENST00000490369; ENST00000463157; ENST00000489058; ENST00000481689; | TAF |
| 9% | chr7 | 100850556 | 100850506 | − | chr7 | 100850185 | 100850060 | − | ENST00000454310; ENST00000223127 | TSF |
| 9% | chr1 | 59843828 | 59844080 | + | chr1 | 59844421 | 59844509 | + | ENST00000413489; ENST00000371218; ENST00000303721; ENST00000430447; ENST00000371212 | TSF |
| 9% | chr1 | 59843828 | 59844080 | + | chr1 | 59844421 | 59844509 | + | ENST00000413489; ENST00000371218; ENST00000303721; ENST00000430447; ENST00000371212 | TSF |
| 9% | chr1 | 59843828 | 59844080 | + | chr1 | 59844421 | 59844509 | + | ENST00000413489; ENST00000371218; ENST00000303721; ENST00000430447; ENST00000371212 | TSF |
| 9% | chr1 | 59843828 | 59844080 | + | chr1 | 59844421 | 59844509 | + | ENST00000413489; ENST00000371218; ENST00000303721; ENST00000430447; ENST00000371212 | TSF |
| 8% | chr20 | 45337040 | 45337192 | + | chr20 | 45353680 | 45354963 | + | ENST00000359271 | TSF |
| 6% | chr19 | 48627094 | 48627044 | − | chr19 | 48626575 | 48626431 | − | ENST00000263274; ENST00000536218; ENST00000594759; ENST00000427526; ENST00000601091 | TSF |
| 6% | chr19 | 48627094 | 48627044 | − | chr19 | 48626575 | 48626431 | − | ENST00000263274; ENST00000536218; ENST00000594759; ENST00000427526; ENST00000601091 | TSF |
| 6% | chr12 | 15701006 | 15701267 | + | chr12 | 15702028 | 15702160 | + | ENST00000281171; ENST00000348962; ENST00000535311 | TSF |
| 6% | chr12 | 15701006 | 15701267 | + | chr12 | 15702028 | 15702160 | + | ENST00000281171; ENST00000348962; ENST00000535311 | TSF |
| 6% | chr12 | 15701006 | 15701267 | + | chr12 | 15702028 | 15702160 | + | ENST00000281171; ENST00000348962; ENST00000535311 | TSF |
| 6% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 6% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |

TABLE 17-continued

Transcript fusion for Colon adenocarcinoma (COAD) Coordinates of the fusion sequences for which the donor is the TE.

| 1 | 2 | 3' | 4' | 5' | 6' | 7' | 8' | 9' | 10' | 11' |
|---|---|---|---|---|---|---|---|---|---|---|
| 6% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 6% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 6% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 5% | chr21 | 40180090 | 40180187 | + | chr21 | 40181959 | 40182030 | + | ENST00000360214; ENST00000360938; ENST00000432278; ENST00000456966 | TSF |
| 5% | chr21 | 40180090 | 40180187 | + | chr2 1 | 40181959 | 40182030 | + | ENST00000360214; ENST00000360938; ENST00000432278; ENST00000456966 | ITSF |
| 5% | chr21 | 40180090 | 40180187 | + | chr21 | 40181959 | 40182030 | + | ENST00000360214; ENST00000360938; ENST00000432278; ENST00000456966 | TSF |
| 5% | chr12 | 4757939 | 4757967 | + | chr12 | 4763458 | 4763628 | + | ENST00000266544; ENST00000535050 | TSF |
| 5% | chr12 | 4757939 | 4757967 | + | chr12 | 4763458 | 4763628 | + | ENST00000266544; ENST00000535050 | TSF |
| 5% | chr14 | 51360331 | 51360476 | + | chr14 | 51368547 | 51368629 | + | ENST00000337334; ENST00000353130; ENST00000395752 | TSF |
| 5% | chr17 | 1005272 | 1005142 | − | chr17 | 1003975 | 1003877 | − | ENST00000302538; ENST00000544583; ENST00000574437; ENST00000291107; ENST00000574139; ENST00000570525; ENST00000574266 | TSF |
| 5% | chr17 | 1005272 | 1005142 | − | chr17 | 1003975 | 1003877 | − | ENST00000302538; ENST00000544583; ENST00000574437; ENST00000291107; ENST00000574139; ENST00000570525; ENST00000574266 | TSF |
| 5% | chr17 | 1005272 | 1005142 | − | chr17 | 1003975 | 1003877 | − | ENST00000302538; ENST00000544583; ENST00000574437; ENST00000291107; ENST00000574139; ENST00000570525; ENST00000574266 | TSF |
| 5% | chr17 | 1005272 | 1005142 | − | chr17 | 1003975 | 1003877 | − | ENST00000302538; ENST00000544583; ENST00000574437; ENST00000291107; ENST00000574139; ENST00000570525; ENST00000574266 | ITSF |
| 5% | chr7 | 102793255 | 102793520 | + | chr7 | 102939015 | 102939155 | + | ENST00000249269; ENST00000428154; ENST00000456433; ENST00000443722; ENST00000453466 | TSF |
| 5% | chr7 | 102793255 | 102793520 | + | chr7 | 102939015 | 102939155 | + | ENST00000249269; ENST00000428154; ENST00000456433; ENST00000443722; ENST00000453466 | TSF |
| 5% | chr7 | 102793255 | 102793520 | + | chr7 | 102939015 | 102939155 | + | ENST00000249269; ENST00000428154; ENST00000456433; ENST00000443722; ENST00000453466 | TSF |
| 5% | chr7 | 102793255 | 102793520 | + | chr7 | 102939015 | 102939155 | + | ENST00000249269; ENST00000428154; ENST00000456433; ENST00000443722; ENST00000453466 | ITSF |
| 5% | chr7 | 102793255 | 102793520 | + | chr7 | 102939015 | 102939155 | + | ENST00000249269; ENST00000428154; ENST00000456433; ENST00000443722; ENST00000453466 | TSF |
| 5% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 5% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 5% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |

TABLE 17-continued

Transcript fusion for Colon adenocarcinoma (COAD) Coordinates of the fusion sequences for which the donor is the TE.

| 1 | 2 | 3' | 4' | 5' | 6' | 7' | 8' | 9' | 10' | 11' |
|---|---|---|---|---|---|---|---|---|---|---|
| 5% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 5% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 5% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 5% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 4% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr7 | 117315827 | 117316035 | + | chr7 | 117355812 | 117355913 | + | ENST00000600166 | TSF |
| 4% | chr8 | 128749913 | 128749923 | + | chr8 | 128750494 | 128751265 | + | ENST00000377970 | TSF |
| 4% | chr19 | 42246888 | 42246564 | − | chr19 | 42187994 | 42187716 | − | ENST00000006724; ENST00000401731 | TSF |
| 4% | chr1 | 59980221 | 59980497 | + | chr1 | 60073475 | 60073582 | + | ENST00000371218; ENST00000303721; ENST00000430447; ENST00000371212; ENST00000371210 | TSF |
| 4% | chr1 | 59980221 | 59980497 | + | chr1 | 60073475 | 60073582 | + | ENST00000371218; ENST00000303721; ENST00000430447; ENST00000371212; ENST00000371210 | TSF |
| 4% | chr1 | 59980221 | 59980497 | + | chr1 | 60073475 | 60073582 | + | ENST00000371218; ENST00000303721; ENST00000430447; ENST00000371212; ENST00000371210 | TSF |
| 4% | chr20 | 410407 | 410425 | + | chr20 | 410994 | 411074 | + | ENST00000356286; ENST00000353660; ENST00000382181 | TSF |
| 4% | chr19 | 42246888 | 42246564 | − | chr19 | 42181431 | 42181340 | − | ENST00000006724; ENST00000338196; ENST00000401731; ENST00000602225 | TSF |
| 4% | chr19 | 42246888 | 42246564 | − | chr19 | 42191152 | 42190790 | − | ENST00000006724; ENST00000338196; ENST00000401731; ENST00000602225 | TSF |
| 4% | chr19 | 42246888 | 42246564 | − | chr19 | 42191152 | 42190790 | − | ENST00000006724; ENST00000338196; ENST00000401731; ENST00000602225 | TSF |

TABLE 17-continued

Transcript fusion for Colon adenocarcinoma (COAD) Coordinates of the fusion sequences for which the donor is the TE.

| 1 | 2 | 3' | 4' | 5' | 6' | 7' | 8' | 9' | 10' | 11' |
|---|---|---|---|---|---|---|---|---|---|---|
| 4% | chr19 | 50174724 | 50174836 | + | chr19 | 50176955 | 50177005; 50177034 | + | ENST00000441864; ENST00000246785; ENST00000600947; ENST00000598306 | TSF |
| 4% | chr19 | 50174724 | 50174836 | + | chr19 | 50176955 | 50177005; 50177034 | + | ENST00000441864; ENST00000246785; ENST00000600947; ENST00000598306 | TSF |
| 4% | chr7 | 100854761 | 100854711 | − | chr7 | 100853923 | 100853813; 100853876 | − | ENST00000454310; ENST00000223127; ENST00000421736 | ITSF |
| 4% | chr7 | 100854761 | 100854711 | − | chr7 | 100853923 | 100853813; 100853876 | − | ENST00000454310; ENST00000223127; ENST00000421736 | TSF |
| 4% | chr7 | 100854761 | 100854711 | − | chr7 | 100853923 | 100853813; 100853876 | − | ENST00000454310; ENST00000223127; ENST00000421736 | TSF |
| 4% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 4% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 4% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 4% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 4% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 4% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 3% | chr13 | 34394352 | 34394605 | + | chr13 | 34395269 | 34395406 | + | ENST00000380071; ENST00000434425 | TSF |
| 3% | chr13 | 34394352 | 34394605 | + | chr13 | 34395269 | 34395406 | + | ENST00000380071; ENST00000434425 | TSF |
| 3% | chr1 | 1422590 | 1422685 | + | chr1 | 1423243 | 1423294 | + | ENST00000308647 | TSF |
| 3% | chr4 | 873272 | 873014 | − | chr4 | 871597 | 871403 | − | ENST00000314167; ENST00000511163 | TSF |
| 3% | chr8 | 66628514 | 66628604 | + | chr8 | 66631615 | 66631668 | + | ENST00000521247 | TSF |
| 3% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 3% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 3% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 3% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 3% | chr13 | 101090702 | 101090974 | + | chr13 | 101167681 | 101167821 | + | ENST00000376286; ENST00000376285; ENST00000428969 | TSF |
| 3% | chr13 | 101090702 | 101090974 | + | chr13 | 101167681 | 101167821 | + | ENST00000376286; ENST00000376285; ENST00000428969 | TSF |
| 3% | chr8 | 71625721 | 71625811 | + | chr8 | 71646031 | 71646659 | + | ENST00000408926; ENST00000520030 | TSF |
| 3% | chr1 | 1562829 | 1562973 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 3% | chr1 | 1562829 | 1562973 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |

TABLE 17-continued

Transcript fusion for Colon adenocarcinoma (COAD) Coordinates of the fusion sequences for which the donor is the TE.

| 1 | 2 | 3' | 4' | 5' | 6' | 7' | 8' | 9' | 10' | 11' |
|---|---|---|---|---|---|---|---|---|---|---|
| 3% | chr1 | 1562829 | 1562973 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 3% | chr16 | 89649823 | 89649851 | + | chr16 | 89650105 | 89650179 | + | ENST00000268720; ENST00000319518 | TSF |
| 3% | chr13 | 95233957 | 95233815 | − | chr13 | 95233443 | 95233345 | − | ENST00000261296 | TSF |
| 2% | chr13 | 43670805 | 43671144 | + | chr13 | 43681314 | 43681384 | + | ENST00000379221 | TSF |
| 2% | chr20 | 60878087 | 60878105 | + | chr20 | 60878775 | 60878837 | + | ENST00000253003 | TSF |
| 2% | chr7 | 56018506 | 56018522 | + | chr7 | 56020872 | 56021011 | + | ENST00000426595 | TSF |
| 2% | chr8 | 63949410 | 63948932 | − | chr8 | 63948329 | 63948215 | − | ENST00000260118 | TSF |
| 2% | chr8 | 144691011 | 144690934 | − | chr8 | 144690296 | 144690232 | − | ENST00000220966; ENST00000433751 | TSF |
| 2% | chr8 | 144691011 | 144690934 | − | chr8 | 144690296 | 144690232 | − | ENST00000220966; ENST00000433751 | TSF |
| 2% | chr17 | 56486405 | 56486202 | − | chr17 | 56448394 | 56448272 | − | ENST00000407977; ENST00000584437; ENST00000577716 | TSF |
| 2% | chr1 | 44446234 | 44446286 | + | chr1 | 44446781 | 44447145 | + | ENST00000309519 | TSF |
| 2% | chr1 | 41465686 | 41465756 | + | chr1 | 41466701 | 41466789 | + | ENST00000372621; ENST00000541520; ENST00000372616 | TSF |
| 2% | chr7 | 139714768 | 139714786 | + | chr7 | 139715523 | 139715660 | + | ENST00000425687; ENST00000263552; ENST00000336425; ENST00000414508; ENST00000416849; ENST00000436047; ENST00000448866; ENST00000458722; ENST00000411653 | TSF |
| 2% | chr7 | 139714768 | 139714786 | + | chr7 | 139715523 | 139715660 | + | ENST00000425687; ENST00000263552; ENST00000336425; ENST00000414508; ENST00000416849; ENST00000436047; ENST00000448866; ENST00000458722; ENST00000411653 | TSF |
| 2% | chrX | 69366031 | 69366077 | + | chrX | 69366483 | 69366678 | + | ENST00000342206; ENST00000356413 | TSF |
| 2% | chr7 | 117326507 | 117326829 | + | chr7 | 117355812 | 117355913 | + | ENST00000600166 | TSF |
| 2% | chr16 | 50663697 | 50663964 | + | chr16 | 50664097 | 50664244 | + | ENST00000268459 | TSF |
| 2% | chr11 | 67035528 | 67035570 | + | chr11 | 67044743 | 67044819 | + | ENST00000308595; ENST00000526285 | TSF |
| 2% | chr11 | 67035528 | 67035570 | + | chr11 | 67044743 | 67044819 | + | ENST00000308595; ENST00000526285 | TSF |
| 2% | chr17 | 39974832 | 39974893 | + | chr17 | 39975462 | 39975651 | + | ENST00000321562 | TSF |
| 2% | chr8 | 91107662 | 91105645 | − | chr8 | 91094330 | 91094254 | − | ENST00000265431 | TSF |
| 2% | chr11 | 65629362 | 65629337 | − | chr11 | 65623713 | 65623406; 65623445 | − | ENST00000525451; ENST00000308162; ENST00000534769; ENST00000532134; ENST00000526975 | TSF |
| 2% | chr11 | 65629362 | 65629337 | − | chr11 | 65623713 | 65623406; 65623445 | − | ENST00000525451; ENST00000308162; ENST00000534769; ENST00000532134; ENST00000526975 | TSF |
| 2% | chr11 | 65629362 | 65629337 | − | chr11 | 65623713 | 65623406; 65623445 | − | ENST00000525451; ENST00000308162; ENST00000534769; ENST00000532134; ENST00000526975 | TSF |
| 2% | chr1 | 156716197 | 156716133 | − | chr1 | 156715165 | 156715089 | − | ENST00000357325; ENST00000537739; ENST00000368209; ENST00000368206 | TSF |
| 2% | chr12 | 14670381 | 14670239 | − | chr12 | 14664645 | 14664445 | − | ENST00000240617 | TSF |

TABLE 19

Transcript fusion for Lymphoid Neoplasm Diffuse Large B-cell Lymphoma (DLBC)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 67% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 67% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 67% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 67% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 67% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 62% | chr12 | 9875257; 9875409 | 9875240 | − | ENST00000540988; ENST00000542530; ENST00000327839 | chr12 | 9855036 | 9854406 | − | TAF |

TABLE 19-continued

Transcript fusion for Lymphoid Neoplasm Diffuse Large B-cell Lymphoma (DLBC)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 62% | chr12 | 9875257; 9875409 | 9875240 | − | ENST00000540988; ENST00000542530; ENST00000327839 | chr12 | 9855036 | 9854406 | − | TAF |
| 62% | chr12 | 9875257; 9875409 | 9875240 | − | ENST00000540988; ENST00000542530; ENST00000327839 | chr12 | 9855036 | 9854406 | − | TAF |
| 60% | chr5 | 82554349 | 82554496 | + | ENST00000282268; ENST00000338635; ENST00000396027; ENST00000511817 | chr5 | 82606608 | 82606935 | + | TAF |
| 48% | chr5 | 74984990 | 74984837 | − | ENST00000428202; ENST00000514838; ENST00000380475; ENST00000510798; ENST00000446329 | chr5 | 74983153 | 74982863 | − | TAF |
| 48% | chr5 | 74984990 | 74984837 | − | ENST00000428202; ENST00000514838; ENST00000380475; ENST00000510798; ENST00000446329 | chr5 | 74983153 | 74982863 | − | TAF |
| 48% | chr5 | 74984990 | 74984837 | − | ENST00000428202; ENST00000514838; ENST00000380475; ENST00000510798; ENST00000446329 | chr5 | 74983153 | 74982863 | − | TAF |
| 48% | chr5 | 74984990 | 74984837 | − | ENST00000428202; ENST00000514838; ENST00000380475; ENST00000510798; ENST00000446329 | chr5 | 74983153 | 74982863 | − | TAF |
| 46% | chr9 | 101984828 | 101984925 | + | ENST00000223641 | chr9 | 101986374 | 101986588 | + | TAF |
| 44% | chr20 | 49458303 | 49458437 | + | ENST00000358791; ENST00000371608; ENST00000609336 | chr20 | 49468479 | 49468517 | + | TSF |
| 44% | chr20 | 49458303 | 49458437 | + | ENST00000358791; ENST00000371608; ENST00000609336 | chr20 | 49468479 | 49468517 | + | TSF |
| 44% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 44% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 44% | chr19 | 55178148; 55178145 | 55178200 | + | ENST00000391736; ENST00000270452; ENST00000430952; ENST00000391734; ENST00000391733; ENST00000434286 | chr19 | 55178291 | 55178458 | + | TSF |
| 42% | chr1 | 32696528 | 32696620 | + | ENST00000373586 | chr1 | 32696861 | 32697110 | + | TAF |
| 42% | chr22 | 37868566 | 37868481 | − | ENST00000416983; ENST00000356998 | chr22 | 37865350 | 37865175 | − | TAF |
| 42% | chr22 | 37868566 | 37868481 | − | ENST00000416983; ENST00000356998 | chr22 | 37865350 | 37865175 | − | TAF |
| 40% | chr9 | 15506635 | 15506559 | − | ENST00000380738; ENST00000380733; ENST00000380715; ENST00000380716; ENST00000397519 | chr9 | 15492223 | 15492056 | − | TAF |
| 38% | chr7 | 98991652 | 98991742 | + | ENST00000252725; ENST00000451682 | chr7 | 98994840 | 98994900 | + | TAF |
| 35% | chr9 | 37432005 | 37432135 | + | ENST00000318158; ENST00000607784 | chr9 | 37432530 | 37432695 | + | TAF |
| 35% | chr4 | 1742553 | 1742713 | + | ENST00000313288 | chr4 | 1745122 | 1745307 | + | TAF |
| 35% | chr16 | 28947474 | 28947522 | + | ENST00000538922; ENST00000324662; ENST00000567541 | chr16 | 28947601 | 28947688 | + | TAF |
| 33% | chr19 | 14698426 | 14698503 | + | ENST00000397439; ENST00000547437; ENST00000339847; ENST00000417570; ENST00000551730 | chr19 | 14700687 | 14700982 | + | TAF |
| 33% | chr2 | 99786073 | 99786013 | − | ENST00000422537; ENST00000289359; ENST00000409107 | chr2 | 99784175 | 99783867 | − | TAF |
| 33% | chr2 | 99786073 | 99786013 | − | ENST00000422537; ENST00000289359; ENST00000409107 | chr2 | 99784175 | 99783867 | − | TAF |
| 33% | chr2 | 99786073 | 99786013 | − | ENST00000422537; ENST00000289359; ENST00000409107 | chr2 | 99784175 | 99783867 | − | TAF |
| 33% | chr19 | 14694169 | 14694246 | + | ENST00000397439; ENST00000547437; ENST00000339847; ENST00000417570; ENST00000551730 | chr19 | 14700687 | 14700982 | + | TSF |
| 33% | chr19 | 14694169 | 14694246 | + | ENST00000397439; ENST00000547437; ENST00000339847; ENST00000417570; ENST00000551730 | chr19 | 14696424 | 14696719 | + | TSF |
| 29% | chr14 | 75991427 | 75991531 | + | ENST00000286639 | chr14 | 76001192 | 76001455 | + | TAF |
| 29% | chr19 | 10450290 | 10450215 | − | ENST00000160262; ENST00000585439 | chr19 | 10449921 | 10449718 |  | TAF |
| 27% | chr17 | 28003903 | 28003838 | − | ENST00000269033; ENST00000540801 | chr17 | 28001177 | 28000609 |  | TAF |
| 27% | chr17 | 28003903 | 28003838 | − | ENST00000269033; ENST00000540801 | chr17 | 28001177 | 28000609 |  | TAF |
| 25% | chr3 | 196230044 | 196229744 | − | ENST00000318037; ENST00000437070 | chr3 | 196223342 | 196223041 | − | TAF |
| 25% | chr5 | 150411944 | 150411848 | − | ENST00000520931; ENST00000389378; ENST00000315050; ENST00000523338; ENST00000522226; ENST00000518977; ENST00000521591; ENST00000523200 | chr5 | 150410874 | 150410734 | − | TAF |
| 25% | chr5 | 150411944 | 150411848 | − | ENST00000520931; ENST00000389378; ENST00000315050; ENST00000523338; ENST00000522226; ENST00000518977; ENST00000521591; ENST00000523200 | chr5 | 150410874 | 150410734 | − | TAF |
| 25% | chr5 | 150411944 | 150411848 | − | ENST00000520931; ENST00000389378; ENST00000315050; ENST00000523338; ENST00000522226; ENST00000518977; ENST00000521591; ENST00000523200 | chr5 | 150410874 | 150410734 | − | TAF |

TABLE 19-continued

Transcript fusion for Lymphoid Neoplasm Diffuse Large B-cell Lymphoma (DLBC)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 25% | chr22 | 35819207 | 35819334 | + | ENST00000216122; ENST00000382011 | chr22 | 35822985 | 35823438 | + | TSF |
| 25% | chr22 | 35819207 | 35819334 | + | ENST00000216122; ENST00000382011 | chr22 | 35822985 | 35823438 | + | TSF |
| 23% | chr17 | 63173850 | 63173921 | + | ENST00000584234; ENST00000262406 | chr17 | 63176114 | 63176128 | + | TAF |
| 23% | chr6 | 32826141 | 32826282 | + | ENST00000395330; ENST00000453265; ENST00000374859 | chr6 | 32828985 | 32829263 | + | TAF |
| 23% | chr6 | 32826141 | 32826282 | + | ENST00000395330; ENST00000453265; ENST00000374859 | chr6 | 32828985 | 32829263 | + | TAF |
| 23% | chr6 | 32826141 | 32826282 | + | ENST00000395330; ENST00000453265; ENST00000374859 | chr6 | 32828985 | 32829263 | + | TAF |
| 23% | chr1 | 151239649 | 151239815 | + | ENST00000368884; ENST00000368881; ENST00000445776; ENST00000453615 | chr1 | 151251832 | 151251905 | + | TAF |
| 23% | chr1 | 151239649 | 151239815 | + | ENST00000368884; ENST00000368881; ENST00000445776; ENST00000453615 | chr1 | 151251832 | 151251905 | + | TAF |
| 23% | chr1 | 151239649 | 151239815 | + | ENST00000368884; ENST00000368881; ENST00000445776; ENST00000453615 | chr1 | 151251832 | 151251905 | + | TAF |
| 23% | chr1 | 151239649 | 151239815 | + | ENST00000368884; ENST00000368881; ENST00000445776; ENST00000453615 | chr1 | 151251832 | 151251905 | + | TAF |
| 23% | chr10 | 120905865 | 120905748 | − | ENST00000355697; ENST00000330036 | chr10 | 120901885 | 120901741 | − | TAF |
| 23% | chr10 | 120905865 | 120905748 | − | ENST00000355697; ENST00000330036 | chr10 | 120901885 | 120901741 | − | TAF |
| 23% | chr8 | 68536486 | 68536411 | − | ENST00000479862; ENST00000297770; ENST00000518549 | chr8 | 68520294 | 68520139 | − | TAF |
| 23% | chr19 | 50926862 | 50927012 | + | ENST00000599632; ENST00000595883; ENST00000439922 | chr19 | 50927187 | 50927315 | + | TSF |
| 23% | chr19 | 50926862 | 50927012 | + | ENST00000599632; ENST00000595883; ENST00000439922 | chr19 | 50927187 | 50927315 | + | TSF |
| 23% | chr19 | 50926862 | 50927012 | + | ENST00000599632; ENST00000595883; ENST00000439922 | chr19 | 50927187 | 50927315 | + | TSF |
| 21% | chr1 | 209946293 | 209946364 | + | ENST00000400959; ENST00000367025; ENST00000478359; ENST00000367026; ENST00000367024; ENST00000010338 | chr1 | 209948635 | 209948677 | + | TAF |
| 21% | chr1 | 209946293 | 209946364 | + | ENST00000400959; ENST00000367025; ENST00000478359; ENST00000367026; ENST00000367024; ENST00000010338 | chr1 | 209948635 | 209948677 | + | TAF |
| 21% | chr8 | 74939024 | 74939076 | + | ENST00000284818; ENST00000518893 | chr8 | 74944554 | 74944936 | + | TAF |
| 21% | chr8 | 74939024 | 74939076 | + | ENST00000284818; ENST00000518893 | chr8 | 74944554 | 74944936 | + | TAF |
| 21% | chr6 | 139363856 | 139363999 | + | ENST00000367660 | chr6 | 139372258 | 139372516 | + | TAF |
| 21% | chr4 | 57319769 | 57319927 | + | ENST00000514888; ENST00000264221; ENST00000505164; ENST00000399688; ENST00000512576 | chr4 | 57321183 | 57321327 | + | TSF |
| 21% | chr4 | 57319769 | 57319927 | + | ENST00000514888; ENST00000264221; ENST00000505164; ENST00000399688; ENST00000512576 | chr4 | 57321183 | 57321327 | + | TSF |
| 21% | chr4 | 57319769 | 57319927 | + | ENST00000514888; ENST00000264221; ENST00000505164; ENST00000399688; ENST00000512576 | chr4 | 57321183 | 57321327 | + | TSF |
| 17% | chr7 | 86848819 | 86848742 | − | ENST00000257637; ENST00000433078; ENST00000423734 | chr7 | 86836058 | 86835850 | − | TAF |
| 17% | chr5 | 88100618 | 88100415 | − | ENST00000340208; ENST00000424173; ENST00000504921; ENST00000514028; ENST00000437473; ENST00000510942; ENST00000506554; ENST00000508569; ENST00000514015; ENST00000539796; ENST00000513252; ENST00000506716; ENST00000507984; ENST00000502983; ENST00000508610; ENST00000502831; ENST00000503075 | chr5 | 88086672 | 88086593 | − | TAF |
| 15% | chr9 | 130540906 | 130540870 | − | ENST00000314830 | chr9 | 130540563 | 130540257 | − | TAF |
| 15% | chr9 | 132719743 | 132719639 | − | ENST00000446176; ENST00000420781; ENST00000449089; ENST00000355681 | chr9 | 132718439 | 132718336 | − | TAF |
| 15% | chr9 | 132719743 | 132719639 | − | ENST00000446176; ENST00000420781; ENST00000449089; ENST00000355681 | chr9 | 132718439 | 132718336 | − | TAF |
| 15% | chr2 | 87072081 | 87072045 | − | ENST00000393759; ENST00000349455; ENST00000331469; ENST00000390655; ENST00000431506 | chr2 | 87069500 | 87069472 | − | TAF |
| 15% | chr2 | 87072081 | 87072045 | − | ENST00000393759; ENST00000349455; ENST00000331469; ENST00000390655; ENST00000431506 | chr2 | 87069500 | 87069472 | − | TAF |
| 15% | chr2 | 87072081 | 87072045 | − | ENST00000393759; ENST00000349455; ENST00000331469; ENST00000390655; ENST00000431506 | chr2 | 87069500 | 87069472 | − | TAF |
| 15% | chr7 | 102079404 | 102079628 | + | ENST00000495936; ENST00000356387; ENST00000478730; ENST00000468241; ENST00000403646; ENST00000498661; ENST00000473939 | chr7 | 102080251 | 102080534 | + | TSF |

TABLE 19-continued

Transcript fusion for Lymphoid Neoplasm Diffuse Large B-cell Lymphoma (DLBC)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 15% | chr3 | 129020793 | 129020985 | + | ENST00000509042; ENST00000383463; ENST00000417226; ENST00000502878; ENST00000389735 | chr3 | 129029005 | 129029042 | + | TSF |
| 15% | chr3 | 129020793 | 129020985 | + | ENST00000509042; ENST00000383463; ENST00000417226; ENST00000502878; ENST00000389735 | chr3 | 129029005 | 129029042 | + | TSF |
| 15% | chr3 | 129020793 | 129020985 | + | ENST00000509042; ENST00000383463; ENST00000417226; ENST00000502878; ENST00000389735 | chr3 | 129029005 | 129029042 | + | TSF |
| 15% | chr9 | 101984828 | 101984925 | + | ENST00000223641 | chr9 | 101986271 | 101986319 | + | TSF |
| 15% | chr11 | 65222908 | 65223052 | + | ENST00000309775 | chr11 | 65224109 | 65224450 | + | TSF |
| 15% | chr19 | 10450290 | 10450215 | − | ENST00000160262; ENST00000585439 | chr19 | 10449848 | 10449718 | − | TSF |
| 15% | chr1 | 154794660; 154794654 | 154794565 | − | ENST00000271915; ENST00000361147; ENST00000358505 | chr1 | 154761737 | 154761457 | − | TSF |
| 15% | chr1 | 154794660; 154794654 | 154794565 | − | ENST00000271915; ENST00000361147; ENST00000358505 | chr1 | 154761737 | 154761457 | − | TSF |
| 15% | chr1 | 154794660; 154794654 | 154794565 | − | ENST00000271915; ENST00000361147; ENST00000358505 | chr1 | 154761737 | 154761457 | − | TSF |
| 15% | chr1 | 157519370 | 157519350 | − | ENST00000361835; ENST00000368190; ENST00000368191; ENST00000368189; ENST00000368188 | chr1 | 157517485 | 157517377 | − | TSF |
| 12% | chr9 | 139872031 | 139872144 | + | ENST00000224167; ENST00000457950; ENST00000371625; ENST00000371623; ENST00000471521 | chr9 | 139873283 | 139873345 | + | TAF |
| 12% | chr10 | 100174892 | 100174766 | − | ENST00000370575 | chr10 | 100174591 | 100174461 | − | TAF |
| 12% | chr7 | 5781275; 5781446 | 5780604 | − | ENST00000425013; ENST00000389902; ENST00000389900 | chr7 | 5779256 | 5779224 | − | TAF |
| 12% | chr7 | 5781275; 5781446 | 5780604 | − | ENST00000425013; ENST00000389902; ENST00000389900 | chr7 | 5779256 | 5779224 | − | TAF |
| 12% | chr1 | 78421014 | 78420940 | − | ENST00000294623; ENST00000370768; ENST00000370767; ENST00000436586 | chr1 | 78417269 | 78417238 | − | TAF |
| 12% | chr1 | 78421014 | 78420940 | − | ENST00000294623; ENST00000370768; ENST00000370767; ENST00000436586 | chr1 | 78417269 | 78417238 | − | TAF |
| 12% | chr1 | 78421014 | 78420940 | − | ENST00000294623; ENST00000370768; ENST00000370767; ENST00000436586 | chr1 | 78417269 | 78417238 | − | TAF |
| 12% | chr12 | 121775196; 121775195 | 121775094 | − | ENST00000539079; ENST00000441917; ENST00000541887; ENST00000261819; ENST00000344395; ENST00000536366; ENST00000544442 | chr12 | 121766988 | 121766947 | − | TAF |
| 12% | chr12 | 121775196; 121775195 | 121775094 | − | ENST00000539079; ENST00000441917; ENST00000541887; ENST00000261819; ENST00000344395; ENST00000536366; ENST00000544442 | chr12 | 121766988 | 121766947 | − | TAF |
| 12% | chr12 | 121775196; 121775195 | 121775094 | − | ENST00000539079; ENST00000441917; ENST00000541887; ENST00000261819; ENST00000344395; ENST00000536366; ENST00000544442 | chr12 | 121766988 | 121766947 | − | TAF |
| 12% | chr12 | 121775196; 121775195 | 121775094 | − | ENST00000539079; ENST00000441917; ENST00000541887; ENST00000261819; ENST00000344395; ENST00000536366; ENST00000544442 | chr12 | 121766988 | 121766947 | − | TAF |
| 12% | chr6 | 110679475 | 110679358 | − | ENST00000338882 | chr2 | 115695277 | 115695018 | − | TAF |
| 12% | chr9 | 126219714 | 126219627 | − | ENST00000373624; ENST00000542603; ENST00000394219; ENST00000373620; ENST00000394215; ENST00000373618 | chr9 | 126219210 | 126219167 | − | TAF |
| 12% | chr9 | 126219714 | 126219627 | − | ENST00000373624; ENST00000542603; ENST00000394219; ENST00000373620; ENST00000394215; ENST00000373618 | chr9 | 126219210 | 126219167 | − | TAF |
| 12% | chr9 | 126219714 | 126219627 | − | ENST00000373624; ENST00000542603; ENST00000394219; ENST00000373620; ENST00000394215; ENST00000373618 | chr9 | 126219210 | 126219167 | − | TAF |
| 12% | chr9 | 126219714 | 126219627 | − | ENST00000373624; ENST00000542603; ENST00000394219; ENST00000373620; ENST00000394215; ENST00000373618 | chr9 | 126219210 | 126219167 | − | TAF |
| 12% | chr9 | 126219714 | 126219627 | − | ENST00000373624; ENST00000542603; ENST00000394219; ENST00000373620; ENST00000394215; ENST00000373618 | chr9 | 126219210 | 126219167 | − | TAF |
| 12% | chr14 | 32020101 | 32020133 | + | ENST00000550005 | chr14 | 32027031 | 32027274 | + | TSF |
| 12% | chr11 | 113857547; 113857240 | 113857768 | + | ENST00000504030; ENST00000355556; ENST00000375498; ENST00000506841; ENST00000535865; ENST00000299961 | chr11 | 113858309 | 113858477 | + | TSF |
| 12% | chr11 | 113857547; 113857240 | 113857768 | + | ENST00000504030; ENST00000355556; ENST00000375498; ENST00000506841; ENST00000535865; ENST00000299961 | chr11 | 113858309 | 113858477 | + | TSF |

TABLE 19-continued

Transcript fusion for Lymphoid Neoplasm Diffuse Large B-cell Lymphoma (DLBC)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 12% | chr11 | 113857547; 113857240 | 113857768 | + | ENST00000504030; ENST00000355556; ENST00000375498; ENST00000506841; ENST00000535865; ENST00000299961 | chr11 | 113858309 | 113858477 | + | TSF |
| 12% | chr11 | 113857547; 113857240 | 113857768 | + | ENST00000504030; ENST00000355556; ENST00000375498; ENST00000506841; ENST00000535865; ENST00000299961 | chr11 | 113858309 | 113858477 | + | TSF |
| 12% | chr11 | 113857547; 113857240 | 113857768 | + | ENST00000504030; ENST00000355556; ENST00000375498; ENST00000506841; ENST00000535865; ENST00000299961 | chr11 | 113858309 | 113858477 | + | TSF |
| 12% | chr11 | 113857547; 113857240 | 113857768 | + | ENST00000504030; ENST00000355556; ENST00000375498; ENST00000506841; ENST00000535865; ENST00000299961 | chr11 | 113858309 | 113858477 | + | TSF |
| 12% | chr1 | 11115983; 11115877 | 11115838 | − | ENST00000376957; ENST00000490101 | chr1 | 11115464 | 11115178 | − | TSF |
| 12% | chr1 | 11115983; 11115877 | 11115838 | − | ENST00000376957; ENST00000490101 | chr1 | 11115464 | 11115178 | − | TSF |
| 12% | chr4 | 25759228 | 25759156 | − | ENST00000399878; ENST00000264868; ENST00000502949; ENST00000510448 | chr4 | 25723603 | 25723555 | − | TSF |
| 12% | chr4 | 25759228 | 25759156 | − | ENST00000399878; ENST00000264868; ENST00000502949; ENST00000510448 | chr4 | 25723603 | 25723555 | − | TSF |
| 12% | chr4 | 25759228 | 25759156 | − | ENST00000399878; ENST00000264868; ENST00000502949; ENST00000510448 | chr4 | 25723603 | 25723555 | − | TSF |
| 12% | chr4 | 25759228 | 25759156 | − | ENST00000399878; ENST00000264868; ENST00000502949; ENST00000510448 | chr4 | 25723603 | 25723555 | − | TSF |
| 10% | chr21 | 45379563 | 45379740 | + | ENST00000291572; ENST00000448287; ENST00000398061; ENST00000327505; ENST00000445582; ENST00000398063; ENST00000398058; ENST00000457068; ENST00000422850; ENST00000546158 | chr21 | 45380513 | 45380695 | + | TAF |
| 10% | chr7 | 64254947 | 64254949 | + | ENST00000307355; ENST00000494380; ENST00000440155; ENST00000440598 | chr7 | 64257358 | 64257449 | + | TAF |
| 10% | chr2 | 220239744 | 220239577 | − | ENST00000273075; ENST00000373972; ENST00000523282 | chr2 | 220227530 | 220227195 | − | TAF |
| 10% | chr2 | 220239744 | 220239577 | − | ENST00000273075; ENST00000373972; ENST00000523282 | chr2 | 220227530 | 220227195 | − | TAF |
| 10% | chr2 | 220239744 | 220239577 | − | ENST00000273075; ENST00000373972; ENST00000523282 | chr2 | 220227530 | 220227195 | − | TAF |
| 10% | chr2 | 231065681 | 231065601 | − | ENST00000258381; ENST00000358662; ENST00000392048; ENST00000258382; ENST00000540870; ENST00000338556 | chr2 | 231054571 | 231054311 | − | TAF |
| 10% | chr2 | 231065681 | 231065601 | − | ENST00000258381; ENST00000358662; ENST00000392048; ENST00000258382; ENST00000540870; ENST00000338556 | chr2 | 231054571 | 231054311 | − | TAF |
| 10% | chr2 | 231065681 | 231065601 | − | ENST00000258381; ENST00000358662; ENST00000392048; ENST00000258382; ENST00000540870; ENST00000338556 | chr2 | 231054571 | 231054311 | − | TAF |
| 10% | chr2 | 231065681 | 231065601 | − | ENST00000258381; ENST00000358662; ENST00000392048; ENST00000258382; ENST00000540870; ENST00000338556 | chr2 | 231054571 | 231054311 | − | TAF |

TABLE 20

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 71% | chr17 | 79214190 | 79214239 | + | chr17 | 79214787 | 79214816; 79214953 | + | ENST00000431388; ENST00000576002 | TAF |
| 71% | chr17 | 79214190 | 79214239 | + | chr17 | 79214787 | 79214816; 79214953 | + | ENST00000431388; ENST00000576002 | TAF |
| 71% | chr11 | 44625878 | 44626051 | + | chr11 | 44626608 | 44626732; 44626675 | + | ENST00000526958; ENST00000227155; ENST00000342935; ENST00000532544; ENST00000527737; ENST00000524704; ENST00000525813; ENST00000530601 | TAF |
| 71% | chr11 | 44625878 | 44626051 | + | chr11 | 44626608 | 44626732; 44626675 | + | ENST00000526958; ENST00000227155; ENST00000342935; ENST00000532544; ENST00000527737; ENST00000524704; ENST00000525813; ENST00000530601 | TAF |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 71% | chr11 | 44625878 | 44626051 | + | chr11 | 44626608 | 44626732; 44626675 | + | ENST00000526958; ENST00000342935; ENST00000527737; ENST00000525813; ENST00000227155; ENST00000532544; ENST00000524704; ENST00000530601 | TAF |
| 71% | chr11 | 44625878 | 44626051 | + | chr11 | 44626608 | 44626732; 44626675 | + | ENST00000526958; ENST00000342935; ENST00000527737; ENST00000525813; ENST00000227155; ENST00000532544; ENST00000524704; ENST00000530601 | TAF |
| 71% | chr11 | 44625878 | 44626051 | + | chr11 | 44626608 | 44626732; 44626675 | + | ENST00000526958; ENST00000342935; ENST00000527737; ENST00000525813; ENST00000227155; ENST00000532544; ENST00000524704; ENST00000530601 | TAF |
| 71% | chr11 | 44625878 | 44626051 | + | chr11 | 44626608 | 44626732; 44626675 | + | ENST00000526958; ENST00000342935; ENST00000527737; ENST00000525813; ENST00000227155; ENST00000532544; ENST00000524704; ENST00000530601 | TAF |
| 71% | chr11 | 44625878 | 44626051 | + | chr11 | 44626608 | 44626732; 44626675 | + | ENST00000526958; ENST00000342935; ENST00000527737; ENST00000525813; ENST00000227155; ENST00000532544; ENST00000524704; ENST00000530601 | TAF |
| 71% | chr11 | 44625878 | 44626051 | + | chr11 | 44626608 | 44626732; 44626675 | + | ENST00000526958; ENST00000342935; ENST00000527737; ENST00000525813; ENST00000227155; ENST00000532544; ENST00000524704; ENST00000530601 | TAF |
| 65% | chr19 | 16267516 | 16267566 | + | chr19 | 16268020 | 16268208; 16268205; 16268448; 16268139 | + | ENST00000253680; ENST00000593154; ENST00000593031 | ENST00000397372; ENST00000588246; | TAF |
| 65% | chr19 | 16267516 | 16267566 | + | chr19 | 16268020 | 16268208; 16268205; 16268448; 16268139 | + | ENST00000253680; ENST00000593154; ENST00000593031 | ENST00000397372; ENST00000588246; | TAF |
| 65% | chr19 | 16267516 | 16267566 | + | chr19 | 16268020 | 16268208; 16268205; 16268448; 16268139 | + | ENST00000253680; ENST00000593154; ENST00000593031 | ENST00000397372; ENST00000588246; | TAF |
| 65% | chr19 | 16267516 | 16267566 | + | chr19 | 16268020 | 16268208; 16268205; 16268448; 16268139 | + | ENST00000253680; ENST00000593154; ENST00000593031 | ENST00000397372; ENST00000588246; | TAF |
| 60% | chr1 | 111670629 | 111670605 | − | chr1 | 111668916 | 111668849 | − | ENST00000286692; ENST00000496430 | ENST00000539140; | TAF |
| 60% | chr1 | 111670629 | 111670605 | − | chr1 | 111668916 | 111668849 | − | ENST00000286692; ENST00000496430 | ENST00000539140; | TAF |
| 58% | chr20 | 49434330 | 49434474 | + | chr20 | 49434748 | 49434819 | + | ENST00000358791; ENST00000371608; ENST00000445038; ENST00000262591; ENST00000609336; ENST00000463943 | TAF |
| 58% | chr20 | 49434330 | 49434474 | + | chr20 | 49434748 | 49434819 | + | ENST00000358791; ENST00000371608; ENST00000445038; ENST00000262591; ENST00000609336; ENST00000463943 | TAF |
| 58% | chr20 | 49434330 | 49434474 | + | chr20 | 49434748 | 49434819 | + | ENST00000358791; ENST00000371608; ENST00000445038; ENST00000262591; ENST00000609336; ENST00000463943 | TAF |
| 58% | chr20 | 49434330 | 49434474 | + | chr20 | 49434748 | 49434819 | + | ENST00000358791; ENST00000371608; ENST00000445038; ENST00000262591; ENST00000609336; ENST00000463943 | TAF |
| 58% | chr20 | 49434330 | 49434474 | + | chr20 | 49434748 | 49434819 | + | ENST00000358791; ENST00000371608; ENST00000445038; ENST00000262591; ENST00000609336; ENST00000463943 | TAF |
| 48% | chr12 | 6602868 | 6602840 | − | chr12 | 6602138 | 6602028 | − | ENST00000229238 | | TAF |
| 48% | chr9 | 135665394 | 135665131 | − | chr9 | 135602921 | 135602841 | − | ENST00000298545 | | TAF |
| 46% | chr17 | 74261446 | 74261484 | + | chr17 | 74261988 | 74262050 | + | ENST00000327490 | | TAF |
| 44% | chr12 | 55350849 | 55350538 | − | chr12 | 55344174 | 55343992; 55344114 | − | ENST00000528240; ENST00000532757 | | TAF |
| 44% | chr12 | 55350849 | 55350538 | − | chr12 | 55344174 | 55343992; 55344114 | − | ENST00000528240; ENST00000532757 | | TAF |
| 42% | chr19 | 17950014 | 17949989 | − | chr19 | 17949199 | 17949072 | − | ENST00000458235; ENST00000534444 | ENST00000527670; | TAF |
| 42% | chr19 | 17950014 | 17949989 | − | chr19 | 17949199 | 17949072 | − | ENST00000458235; ENST00000534444 | ENST00000527670; | TAF |
| 40% | chr14 | 75983600 | 75983948 | + | chr14 | 75991427 | 75991531; 75991513 | + | ENST00000286639; ENST00000555504 | | TSF |
| 40% | chr14 | 75983600 | 75983948 | + | chr14 | 75991427 | 75991531; 75991513 | + | ENST00000286639; ENST00000555504 | | TSF |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 40% | chr9 | 94504684 | 94504366 | − | chr9 | 94499800 | 94499673 | − | ENST00000375715; ENST00000375708 | TSF |
| 40% | chr9 | 94504684 | 94504366 | − | chr9 | 94499800 | 94499673 | − | ENST00000375715; ENST00000375708 | TSF |
| 38% | chr11 | 93468219 | 93468129 | − | chr11 | 93467826 | 93467791; 93467814 | − | ENST00000393259; ENST00000527169 | TAF |
| 38% | chr11 | 93468219 | 93468129 | − | chr11 | 93467826 | 93467791; 93467814 | − | ENST00000393259; ENST00000527169 | TAF |
| 38% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 38% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 38% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 38% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 38% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 38% | chr11 | 64508144 | 64507840 | − | chr11 | 64507635 | 64507485 | − | ENST00000377494; ENST00000394432; ENST00000377497; ENST00000354024; ENST00000431822 | TAF |
| 38% | chr11 | 64508144 | 64507840 | − | chr11 | 64507635 | 64507485 | − | ENST00000377494; ENST00000394432; ENST00000377497; ENST00000354024; ENST00000431822 | TAF |
| 38% | chr11 | 64508144 | 64507840 | − | chr11 | 64507635 | 64507485 | − | ENST00000377494; ENST00000394432; ENST00000377497; ENST00000354024; ENST00000431822 | TAF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TSF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TSF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TSF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TSF |
| 35% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TSF |
| 33% | chr12 | 122430912 | 122431615 | + | chr12 | 122437622 | 122437850 | + | ENST00000288912 | TAF |
| 33% | chr2 | 25110247 | 25109962 | − | chr2 | 25095588 | 25095439 | − | ENST00000260600; ENST00000433852 | TAF |
| 33% | chr2 | 25110247 | 25109962 | − | chr2 | 25095588 | 25095439 | − | ENST00000260600; ENST00000433852 | TAF |
| 31% | chr19 | 54631006 | 54631115 | + | chr19 | 54631448 | 54631575 | + | ENST00000321030; ENST00000419967 | TAF |
| 31% | chr19 | 54631006 | 54631115 | + | chr19 | 54631448 | 54631575 | + | ENST00000321030; ENST00000419967 | TAF |
| 31% | chr19 | 1600051 | 1599987 | − | chr19 | 1599559 | 1599439 | − | ENST00000585937; ENST00000591899; ENST00000589880; ENST00000585671 | TAF |
| 29% | chr6 | 26474324 | 26474624 | + | chr6 | 26476389 | 26476396 | + | ENST00000480218 | TAF |
| 29% | chr7 | 98974090 | 98974197 | + | chr7 | 98983325 | 98983401 | + | ENST00000432884 | TAF |
| 27% | chr10 | 120902016 | 120901765 | − | chr10 | 120900831 | 120900754 | − | ENST00000355697; ENST00000330036 | TAF |
| 25% | chr9 | 93647278 | 93648256 | + | chr9 | 93650031 | 93650171 | + | ENST00000375751; ENST00000375754; ENST00000375747; ENST00000375746 | TAF |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 23% | chr20 | 30669845 | 30669925 | + | chr20 | 30671697 | 30671846 | + | ENST00000534862; ENST00000538448; ENST00000375862; ENST00000520553; ENST00000518730; ENST00000375852 | TAF |
| 23% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 23% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 23% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 23% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 23% | chr4 | 69441933 | 69441669 | − | chr4 | 69431438 | 69431290 | − | ENST00000317746 | TAF |
| 23% | chr12 | 6602868 | 6602754 | − | chr12 | 6602138 | 6602028 | − | ENST00000229238 | TSF |
| 21% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 21% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 21% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 21% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 21% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 21% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 21% | chr2 | 97206254 | 97206414 | + | chr2 | 97213139 | 97213254 | + | ENST00000357485; ENST00000412735 | TAF |
| 21% | chr2 | 97206254 | 97206414 | + | chr2 | 97213139 | 97213254 | + | ENST00000357485; ENST00000412735 | TAF |
| 21% | chr3 | 197680391 | 197680531 | + | chr3 | 197680874 | 197681018; 197680991 | + | ENST00000464167; ENST00000448864; ENST00000442341 | TAF |
| 21% | chr3 | 197680391 | 197680531 | + | chr3 | 197680874 | 197681018; 197680991 | + | ENST00000464167; ENST00000448864; ENST00000442341 | TAF |
| 21% | chr1 | 26442407 | 26442478 | + | chr1 | 26646662 | 26646793 | + | ENST00000374213 | TAF |
| 21% | chrX | 48793481 | 48793462 | − | chrX | 48792291 | 48792227 | − | ENST00000396743; ENST00000455452; ENST00000156084; ENST00000376488; ENST00000428668 | TAF |
| 21% | chrX | 48793481 | 48793462 | − | chrX | 48792291 | 48792227 | − | ENST00000396743; ENST00000455452; ENST00000156084; ENST00000376488; ENST00000428668 | TAF |
| 21% | chr5 | 149925856 | 149925791 | − | chr5 | 149792270 | 149792188 | − | ENST00000377795; ENST00000353334; ENST00000518797; ENST00000524315; ENST00000009530; ENST00000523208; ENST00000522246; ENST00000523813 | TAF |
| 21% | chr5 | 149925856 | 149925791 | − | chr5 | 149792270 | 149792188 | − | ENST00000377795; ENST00000353334; ENST00000518797; ENST00000524315; ENST00000009530; ENST00000523208; ENST00000522246; ENST00000523813 | TAF |
| 21% | chr5 | 149925856 | 149925791 | − | chr5 | 149792270 | 149792188 | − | ENST00000377795; ENST00000353334; ENST00000518797; ENST00000524315; ENST00000009530; ENST00000523208; ENST00000522246; ENST00000523813 | TAF |
| 21% | chr5 | 149925856 | 149925791 | − | chr5 | 149792270 | 149792188 | − | ENST00000377795; ENST00000353334; ENST00000518797; ENST00000524315; ENST00000009530; ENST00000523208; ENST00000522246; ENST00000523813 | TAF |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 21% | chr5 | 149925856 | 149925791 | − | chr5 | 149792270 | 149792188 | − | ENST00000377795; ENST00000353334; ENST00000518797; ENST00000524315; ENST00000009530; ENST00000523208; ENST00000522246; ENST00000523813 | TAF |
| 21% | chr5 | 149925856 | 149925791 | − | chr5 | 149792270 | 149792188 | − | ENST00000377795; ENST00000353334; ENST00000518797; ENST00000524315; ENST00000009530; ENST00000523208; ENST00000522246; ENST00000523813 | TAF |
| 21% | chr5 | 149925856 | 149925791 | − | chr5 | 149792270 | 149792188 | − | ENST00000377795; ENST00000353334; ENST00000518797; ENST00000524315; ENST00000009530; ENST00000523208; ENST00000522246; ENST00000523813 | TAF |
| 21% | chr5 | 149925856 | 149925791 | − | chr5 | 149792270 | 149792188 | − | ENST00000377795; ENST00000353334; ENST00000518797; ENST00000524315; ENST00000009530; ENST00000523208; ENST00000522246; ENST00000523813 | TAF |
| 21% | chr1 | 212862111 | 212861469 | − | chr1 | 212860321 | 212860133 | − | ENST00000243440 | TAF |
| 21% | chr8 | 66969394 | 66970244 | + | chr8 | 66988895 | 66989108; 66989064 | + | ENST00000276570; ENST00000522619 | TSF |
| 21% | chr8 | 66969394 | 66970244 | + | chr8 | 66988895 | 66989108; 66989064 | + | ENST00000276570; ENST00000522619 | TSF |
| 19% | chr4 | 107241932 | 107242850 | + | chr4 | 107246142 | 107246275 | + | ENST00000394701 | TAF |
| 19% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 19% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 19% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 19% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 19% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 19% | chr21 | 30806412 | 30806689 | + | chr21 | 30969890 | 30970014; 30969979 | + | ENST00000422809; ENST00000468059 | TAF |
| 19% | chr21 | 30806412 | 30806689 | + | chr21 | 30969890 | 30970014; 30969979 | + | ENST00000422809; ENST00000468059 | TAF |
| 19% | chr5 | 171488028 | 171487971 | − | chr5 | 171484477 | 171484353 | − | ENST00000176763; ENST00000520476 | TAF |
| 19% | chr5 | 171488028 | 171487971 | − | chr5 | 171484477 | 171484353 | − | ENST00000176763; ENST00000520476 | TAF |
| 19% | chr3 | 47554781 | 47554681 | − | chr3 | 47552716 | 47552638 | − | ENST00000296149; ENST00000442215 | TAF |
| 19% | chr3 | 47554781 | 47554681 | − | chr3 | 47552716 | 47552638 | − | ENST00000296149; ENST00000442215 | TAF |
| 19% | chr1 | 169819657 | 169819707 | + | chr1 | 169820958 | 169821077 | + | ENST00000359326; ENST00000286031 | TSF |
| 19% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 19% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 19% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 19% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 19% | chr2 | 68983124 | 68984862 | + | chr2 | 69002353 | 69002552; 69002488 | + | ENST00000295381; ENST00000409202; ENST00000467265; ENST00000488795; ENST00000409030; ENST00000409220; ENST00000473986; ENST00000497079 | TSF |
| 19% | chr2 | 68983124 | 68984862 | + | chr2 | 69002353 | 69002552; 69002488 | + | ENST00000295381; ENST00000409202; ENST00000467265; ENST00000488795; ENST00000409030; ENST00000409220; ENST00000473986; ENST00000497079 | TSF |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 19% | chr2 | 68983124 | 68984862 | + | chr2 | 69002353 | 69002552; 69002488 | + | ENST00000295381; ENST00000409202; ENST00000467265; ENST00000488795; ENST00000409030; ENST00000409220; ENST00000473986; ENST00000497079 | TSF |
| 19% | chr2 | 68983124 | 68984862 | + | chr2 | 69002353 | 69002552; 69002488 | + | ENST00000295381; ENST00000409202; ENST00000467265; ENST00000488795; ENST00000409030; ENST00000409220; ENST00000473986; ENST00000497079 | TSF |
| 19% | chr2 | 68983124 | 68984862 | + | chr2 | 69002353 | 69002552; 69002488 | + | ENST00000295381; ENST00000409202; ENST00000467265; ENST00000488795; ENST00000409030; ENST00000409220; ENST00000473986; ENST00000497079 | TSF |
| 19% | chr2 | 68983124 | 68984862 | + | chr2 | 69002353 | 69002552; 69002488 | + | ENST00000295381; ENST00000409202; ENST00000467265; ENST00000488795; ENST00000409030; ENST00000409220; ENST00000473986; ENST00000497079 | TSF |
| 19% | chr19 | 39347374 | 39346206 | − | chr19 | 39338074 | 39337956 | − | ENST00000221419; ENST00000601449; ENST00000600233; ENST00000601813 | TSF |
| 19% | chr19 | 39347374 | 39346206 | − | chr19 | 39338074 | 39337956 | − | ENST00000221419; ENST00000601449; ENST00000600233; ENST00000601813 | TSF |
| 19% | chr19 | 39347374 | 39346206 | − | chr19 | 39338074 | 39337956 | − | ENST00000221419; ENST00000601449; ENST00000600233; ENST00000601813 | TSF |
| 19% | chr19 | 39347374 | 39346206 | − | chr19 | 39338074 | 39337956 | − | ENST00000221419; ENST00000601449; ENST00000600233; ENST00000601813 | TSF |
| 19% | chr19 | 39347374 | 39346206 | − | chr19 | 39338074 | 39337956 | − | ENST00000221419; ENST00000601449; ENST00000600233; ENST00000601813 | TSF |
| 19% | chr19 | 39347374 | 39346206 | − | chr19 | 39338074 | 39337956 | − | ENST00000221419; ENST00000601449; ENST00000600233; ENST00000601813 | TSF |
| 17% | chr4 | 154533967 | 154534548 | + | chr4 | 154541908 | 154542032 | + | ENST00000440693; ENST00000409663; ENST00000409959; ENST00000240487 | TAF |
| 17% | chr8 | 104389530 | 104389551 | + | chr8 | 104390255 | 104390471 | + | ENST00000330295; ENST00000520337 | TAF |
| 17% | chr2 | 62362210 | 62362285 | + | chr2 | 62362966 | 62363076 | + | ENST00000311832; ENST00000458337; ENST00000427417 | TAF |
| 17% | chr2 | 99797199 | 99797170 | − | chr2 | 99790479 | 99790378 | + | ENST00000422537; ENST00000289359; ENST00000409107 | TAF |
| 17% | chr2 | 99797199 | 99797170 | − | chr2 | 99790479 | 99790378 | + | ENST00000422537; ENST00000289359; ENST00000409107 | TAF |
| 17% | chr11 | 61129218 | 61129205 | − | chr11 | 61121464 | 61121256; 61121303 | − | ENST00000294072; ENST00000426130; ENST00000447532; ENST00000536915; ENST00000542361; ENST00000537364; ENST00000539128 | TAF |
| 17% | chr11 | 61129218 | 61129205 | − | chr11 | 61121464 | 61121256; 61121303 | − | ENST00000294072; ENST00000426130; ENST00000447532; ENST00000536915; ENST00000542361; ENST00000537364; ENST00000539128 | TAF |
| 17% | chr11 | 61129218 | 61129205 | − | chr11 | 61121464 | 61121256; 61121303 | − | ENST00000294072; ENST00000426130; ENST00000447532; ENST00000536915; ENST00000542361; ENST00000537364; ENST00000539128 | TAF |
| 17% | chr11 | 61129218 | 61129205 | − | chr11 | 61121464 | 61121256; 61121303 | − | ENST00000294072; ENST00000426130; ENST00000447532; ENST00000536915; ENST00000542361; ENST00000537364; ENST00000539128 | TAF |
| 17% | chr11 | 61129218 | 61129205 | − | chr11 | 61121464 | 61121256; 61121303 | − | ENST00000294072; ENST00000426130; ENST00000447532; ENST00000536915; ENST00000542361; ENST00000537364; ENST00000539128 | TAF |
| 17% | chr10 | 102260069 | 102259867 | − | chr10 | 102259355 | 102259281 | − | ENST00000370345 | TAF |
| 17% | chr2 | 3624644 | 3624710 | + | chr2 | 3625300 | 3625364 | + | ENST00000304921; ENST00000407445; ENST00000403564; ENST00000406376 | TSF |
| 17% | chr2 | 3624644 | 3624710 | + | chr2 | 3625300 | 3625364 | + | ENST00000304921; ENST00000407445; ENST00000403564; ENST00000406376 | TSF |
| 17% | chr2 | 3624644 | 3624710 | + | chr2 | 3625300 | 3625364 | + | ENST00000304921; ENST00000407445; ENST00000403564; ENST00000406376 | TSF |
| 17% | chr2 | 3624644 | 3624710 | + | chr2 | 3625300 | 3625364 | + | ENST00000304921; ENST00000407445; ENST00000403564; ENST00000406376 | TSF |
| 17% | chr1 | 17371820 | 17371636 | | chr1 | 17371383 | 17371256 | | ENST00000375499 | TSF |
| 15% | chr7 | 21979898 | 21979880 | − | chr7 | 21956512 | 21956372 | − | ENST00000406877; ENST00000373934 | TAF |
| 15% | chr7 | 21979898 | 21979880 | − | chr7 | 21956512 | 21956372 | − | ENST00000406877; ENST00000373934 | TAF |
| 15% | chr12 | 9809754 | 9809756 | + | chr12 | 9833519 | 9833629; 9833560 | + | ENST00000261340; ENST00000290855; ENST00000325960; ENST00000492359; ENST00000444971; ENST00000479877; ENST00000543300 | TSF |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 15% | chr12 | 9809754 | 9809756 | + | chr12 | 9833519 | 9833629; 9833560 | + | ENST00000261340; ENST00000290855; ENST00000325960; ENST00000492359; ENST00000444971; ENST00000479877; ENST00000543300 | TSF |
| 15% | chr12 | 9809754 | 9809756 | + | chr12 | 9833519 | 9833629; 9833560 | + | ENST00000261340; ENST00000290855; ENST00000325960; ENST00000492359; ENST00000444971; ENST00000479877; ENST00000543300 | TSF |
| 15% | chr12 | 9809754 | 9809756 | + | chr12 | 9833519 | 9833629; 9833560 | + | ENST00000261340; ENST00000290855; ENST00000325960; ENST00000492359; ENST00000444971; ENST00000479877; ENST00000543300 | TSF |
| 15% | chr12 | 9809754 | 9809756 | + | chr12 | 9833519 | 9833629; 9833560 | + | ENST00000261340; ENST00000290855; ENST00000325960; ENST00000492359; ENST00000444971; ENST00000479877; ENST00000543300 | TSF |
| 15% | chr12 | 9809754 | 9809756 | + | chr12 | 9833519 | 9833629; 9833560 | + | ENST00000261340; ENST00000290855; ENST00000325960; ENST00000492359; ENST00000444971; ENST00000479877; ENST00000543300 | TSF |
| 15% | chr19 | 49831887 | 49832338 | + | chr19 | 49838971 | 49839043; 49839039 | + | ENST00000391859; ENST00000595725; ENST00000323906; ENST00000535669; ENST00000595660 | TSF |
| 15% | chr19 | 49831887 | 49832338 | + | chr19 | 49838971 | 49839043; 49839039 | + | ENST00000391859; ENST00000595725; ENST00000323906; ENST00000535669; ENST00000595660 | TSF |
| 15% | chr19 | 49831887 | 49832338 | + | chr19 | 49838971 | 49839043; 49839039 | + | ENST00000391859; ENST00000595725; ENST00000323906; ENST00000535669; ENST00000595660 | TSF |
| 15% | chr19 | 49831887 | 49832338 | + | chr19 | 49838971 | 49839043; 49839039 | + | ENST00000391859; ENST00000595725; ENST00000323906; ENST00000535669; ENST00000595660 | TSF |
| 15% | chr19 | 49831887 | 49832338 | + | chr19 | 49838971 | 49839043; 49839039 | + | ENST00000391859; ENST00000595725; ENST00000323906; ENST00000535669; ENST00000595660 | TSF |
| 15% | chr16 | 14699964 | 14699912 | − | chr16 | 14698083 | 14698003; 14698068 | − | ENST00000437198; ENST00000420015; ENST00000341484; ENST00000539279; ENST00000538472 | TSF |
| 15% | chr16 | 14699964 | 14699912 | − | chr16 | 14698083 | 14698003; 14698068 | − | ENST00000437198; ENST00000420015; ENST00000341484; ENST00000539279; ENST00000538472 | TSF |
| 15% | chr8 | 620733 | 620243 | − | chr8 | 618782 | 618598; 618491 | − | ENST00000522706; ENST00000523415; ENST00000262109; ENST00000522893 | TSF |
| 15% | chr8 | 620733 | 620243 | − | chr8 | 618782 | 618598; 618491 | − | ENST00000522706; ENST00000523415; ENST00000262109; ENST00000522893 | TSF |
| 15% | chr8 | 620733 | 620243 | − | chr8 | 618782 | 618598; 618491 | − | ENST00000522706; ENST00000523415; ENST00000262109; ENST00000522893 | TSF |
| 15% | chr8 | 620733 | 620243 | − | chr8 | 618782 | 618598; 618491 | − | ENST00000522706; ENST00000523415; ENST00000262109; ENST00000522893 | TSF |
| 15% | chr2 | 25310179 | 25309890 | − | chr2 | 25095588 | 25095439 | − | ENST00000260600; ENST00000433852 | TSF |
| 15% | chr2 | 25310179 | 25309890 | − | chr2 | 25095588 | 25095439 | − | ENST00000260600; ENST00000433852 | TSF |
| 12% | chr5 | 149532994 | 149533002 | + | chr5 | 149562331 | 149562476 | + | ENST00000231656 | TAF |
| 12% | chr8 | 126168241 | 126168340 | + | chr8 | 126194345 | 126194498 | + | ENST00000523741; ENST00000517532; ENST00000287437; ENST00000522563; ENST00000517315 | TAF |
| 12% | chr8 | 126168241 | 126168340 | + | chr8 | 126194345 | 126194498 | + | ENST00000523741; ENST00000517532; ENST00000287437; ENST00000522563; ENST00000517315 | TAF |
| 12% | chr8 | 126168241 | 126168340 | + | chr8 | 126194345 | 126194498 | + | ENST00000523741; ENST00000517532; ENST00000287437; ENST00000522563; ENST00000517315 | TAF |
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; | TAF |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 12% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 12% | chr7 | 99747312 | 99747315 | + | chr7 | 99751023 | 99751140; 99751352 | + | ENST00000341942; ENST00000441173 | TAF |
| 12% | chr7 | 99747312 | 99747315 | + | chr7 | 99751023 | 99751140; 99751352 | + | ENST00000341942; ENST00000441173 | TAF |
| 12% | chr6 | 43026913 | 43026822 | − | chr6 | 43025971 | 43025803; 43025889; 43025777 | − | ENST00000388752; ENST00000230413; ENST00000489623; ENST00000487429; ENST00000468957 | TAF |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 12% | chr6 | 43026913 | 43026822 | – | chr6 | 43025971 | 43025803; 43025889; 43025777 | – | ENST00000388752; ENST00000489623; ENST00000468957 | ENST00000230413; ENST00000487429; TAF |
| 12% | chr6 | 43026913 | 43026822 | – | chr6 | 43025971 | 43025803; 43025889; 43025777 | – | ENST00000388752; ENST00000489623; ENST00000468957 | ENST00000230413; ENST00000487429; TAF |
| 12% | chr6 | 43026913 | 43026822 | – | chr6 | 43025971 | 43025803; 43025889; 43025777 | – | ENST00000388752; ENST00000489623; ENST00000468957 | ENST00000230413; ENST00000487429; TAF |
| 12% | chr6 | 43026913 | 43026822 | – | chr6 | 43025971 | 43025803; 43025889; 43025777 | – | ENST00000388752; ENST00000489623; ENST00000468957 | ENST00000230413; ENST00000487429; TAF |
| 12% | chr9 | 69229480 | 69229475 | – | chr9 | 69218561 | 69218510 | – | ENST00000416428; ENST00000377449; ENST00000382399 | ENST00000377457; TAF |
| 12% | chr9 | 69229480 | 69229475 | – | chr9 | 69218561 | 69218510 | – | ENST00000416428; ENST00000377449; ENST00000382399 | ENST00000377457; TAF |
| 12% | chr6 | 24710791 | 24710723 | | chr6 | 24709139 | 24709005 | – | ENST00000378119; ENST00000378102 | ENST00000540769; TAF |
| 12% | chr10 | 98363669 | 98363666 | – | chr10 | 98362155 | 98362037 | – | ENST00000339364; ENST00000371109 | ENST00000371110; TAF |
| 12% | chr1 | 6380703 | 6380649 | – | chr1 | 6378638 | 6378552 | – | ENST00000608083; ENST00000377845; ENST00000377860; ENST00000545482; ENST00000473466; ENST00000541130 | ENST00000377842; TAF ENST00000377855; ENST00000418124; ENST00000361521; |
| 12% | chr1 | 6380703 | 6380649 | – | chr1 | 6378638 | 6378552 | – | ENST00000608083; ENST00000377845; ENST00000377860; ENST00000545482; ENST00000473466; ENST00000541130 | ENST00000377842; TAF ENST00000377855; ENST00000418124; ENST00000361521; |
| 12% | chr1 | 6380703 | 6380649 | – | chr1 | 6378638 | 6378552 | – | ENST00000608083; ENST00000377845; ENST00000377860; ENST00000545482; ENST00000473466; ENST00000541130 | ENST00000377842; TAF ENST00000377855; ENST00000418124; ENST00000361521; |
| 12% | chr1 | 6380703 | 6380649 | – | chr1 | 6378638 | 6378552 | – | ENST00000608083; ENST00000377845; ENST00000377860; ENST00000545482; ENST00000473466; ENST00000541130 | ENST00000377842; TAF ENST00000377855; ENST00000418124; ENST00000361521; |
| 12% | chr1 | 6380703 | 6380649 | – | chr1 | 6378638 | 6378552 | – | ENST00000608083; ENST00000377845; ENST00000377860; ENST00000545482; ENST00000473466; ENST00000541130 | ENST00000377842; TAF ENST00000377855; ENST00000418124; ENST00000361521; |
| 12% | chr12 | 102411559 | 102411498 | – | chr12 | 102406970 | 102406886 | – | ENST00000240079; ENST00000542923 | ENST00000545679; TAF |
| 12% | chr15 | 101833626 | 101833498 | – | chr15 | 101833377 | 101833230 | – | ENST00000254193; ENST00000559309 TAF | |
| 12% | chr15 | 101833626 | 101833498 | – | chr15 | 101833377 | 101833230 | – | ENST00000254193; ENST00000559309;TAF | |
| 12% | chr1 | 9128508 | 9128439 | – | chr1 | 9118309 | 9118211 | – | ENST00000377424; ENST00000484798; ENST00000479813; ENST00000487835; ENST00000473209 | ENST00000377414;TAF ENST00000474145; ENST00000486632; ENST00000464985; |
| 12% | chr1 | 9128508 | 9128439 | – | chr1 | 9118309 | 9118211 | – | ENST00000377424; ENST00000484798; ENST00000479813; ENST00000487835; ENST00000473209 | ENST00000377414;TAF ENST00000474145; ENST00000486632; ENST00000464985; |
| 12% | chr1 | 9128508 | 9128439 | – | chr1 | 9118309 | 9118211 | – | ENST00000377424; ENST00000484798; ENST00000479813; ENST00000487835; ENST00000473209 | ENST00000377414;TAF ENST00000474145; ENST00000486632; ENST00000464985; |
| 12% | chr1 | 9128508 | 9128439 | – | chr1 | 9118309 | 9118211 | – | ENST00000377424; ENST00000484798; ENST00000479813; ENST00000487835; ENST00000473209 | ENST00000377414;TAF ENST00000474145; ENST00000486632; ENST00000464985; |
| 12% | chr1 | 9128508 | 9128439 | – | chr1 | 9118309 | 9118211 | – | ENST00000377424; ENST00000484798; ENST00000479813; ENST00000487835; ENST00000473209 | ENST00000377414;TAF ENST00000474145; ENST00000486632; ENST00000464985; |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 12% | chr1 | 9128508 | 9128439 | − | chr1 | 9118309 | 9118211 | − | ENST00000377424; ENST00000377414; ENST00000484798; ENST00000474145; ENST00000479813; ENST00000486632; ENST00000487835; ENST00000464985; ENST0000473209 | TAF |
| 12% | chr1 | 53107333 | 53107382 | + | chr1 | 53108535 | 53108674 | + | ENST00000517870 | TSF |
| 12% | chr16 | 57073351 | 57073401 | + | chr16 | 57073693 | 57073761 | + | ENST00000262510; ENST00000308149; ENST00000436936; ENST00000539144; ENST00000538805; ENST00000545081; ENST00000538110; ENST00000543030; ENST00000538453 | TSF |
| 12% | chr16 | 57073351 | 57073401 | + | chr16 | 57073693 | 57073761 | + | ENST00000262510; ENST00000308149; ENST00000436936; ENST00000539144; ENST00000538805; ENST00000545081; ENST00000538110; ENST00000543030; ENST00000538453 | TSF |
| 12% | chr16 | 57073351 | 57073401 | + | chr16 | 57073693 | 57073761 | + | ENST00000262510; ENST00000308149; ENST00000436936; ENST00000539144; ENST00000538805; ENST00000545081; ENST00000538110; ENST00000543030; ENST00000538453 | TSF |
| 12% | chr16 | 57073351 | 57073401 | + | chr16 | 57073693 | 57073761 | + | ENST00000262510; ENST00000308149; ENST00000436936; ENST00000539144; ENST00000538805; ENST00000545081; ENST00000538110; ENST00000543030; ENST00000538453 | TSF |
| 12% | chr16 | 57073351 | 57073401 | + | chr16 | 57073693 | 57073761 | + | ENST00000262510; ENST00000308149; ENST00000436936; ENST00000539144; ENST00000538805; ENST00000545081; ENST00000538110; ENST00000543030; ENST00000538453 | TSF |
| 12% | chr16 | 57073351 | 57073401 | + | chr16 | 57073693 | 57073761 | + | ENST00000262510; ENST00000308149; ENST00000436936; ENST00000539144; ENST00000538805; ENST00000545081; ENST00000538110; ENST00000543030; ENST00000538453 | TSF |
| 12% | chr16 | 57073351 | 57073401 | + | chr16 | 57073693 | 57073761 | + | ENST00000262510; ENST00000308149; ENST00000436936; ENST00000539144; ENST00000538805; ENST00000545081; ENST00000538110; ENST00000543030; ENST00000538453 | TSF |
| 12% | chr4 | 154546282 | 154546350 | + | chr4 | 154547299 | 154547377 | + | ENST00000440693; ENST00000409663; ENST00000409959; ENST00000240487 | TSF |
| 12% | chr9 | 140632674 | 140633231 | + | chr9 | 140637823 | 140637980 | + | ENST00000462484; ENST00000334856; ENST00000460843 | TSF |
| 12% | chr9 | 140632674 | 140633231 | + | chr9 | 140637823 | 140637980 | + | ENST00000462484; ENST00000334856; ENST00000460843 | TSF |
| 12% | chr9 | 140632674 | 140633231 | + | chr9 | 140637823 | 140637980 | + | ENST00000462484; ENST00000334856; ENST00000460843 | TSF |
| 12% | chr19 | 49831887 | 49832338 | + | chr19 | 49840166 | 49840290 | + | ENST00000391859; ENST00000595725; ENST00000323906; ENST00000535669; ENST00000595660 | TSF |
| 12% | chr19 | 49831887 | 49832338 | + | chr19 | 49840166 | 49840290 | + | ENST00000391859; ENST00000595725; ENST00000323906; ENST00000535669; ENST00000595660 | TSF |
| 12% | chr19 | 49831887 | 49832338 | + | chr19 | 49840166 | 49840290 | + | ENST00000391859; ENST00000595725; ENST00000323906; ENST00000535669; ENST00000595660 | TSF |
| 12% | chr19 | 49831887 | 49832338 | + | chr19 | 49840166 | 49840290 | + | ENST00000391859; ENST00000595725; ENST00000323906; ENST00000535669; ENST00000595660 | TSF |
| 12% | chr19 | 49831887 | 49832338 | + | chr19 | 49840166 | 49840290 | + | ENST00000391859; ENST00000595725; ENST00000323906; ENST00000535669; ENST00000595660 | TSF |
| 12% | chr3 | 15096823 | 15096427 | − | chr3 | 15094974 | 15094887; 15094883 | − | ENST00000253686; ENST00000449354; ENST00000420267; ENST00000447299 | TSF |
| 12% | chr3 | 15096823 | 15096427 | − | chr3 | 15094974 | 15094887; 15094883 | − | ENST00000253686; ENST00000449354; ENST00000420267; ENST00000447299 | TSF |
| 12% | chr3 | 15096823 | 15096427 | − | chr3 | 15094974 | 15094887; 15094883 | − | ENST00000253686; ENST00000449354; ENST00000420267; ENST00000447299 | TSF |
| 12% | chr14 | 94936503 | 94936425 | − | chr14 | 94935803 | 94935550; 94935708 | − | ENST00000448305; ENST00000337425; ENST00000380365; ENST00000538527; ENST00000546329 | TSF |

TABLE 20-continued

Transcript fusion for Lymphoid Neoplasm Diffuse Large B-cell Lymphoma (DLBC)
Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 12% | chr14 | 94936503 | 94936425 | − | chr14 | 94935803 | 94935550; 94935708 | − | ENST00000448305; ENST00000337425; ENST00000380365; ENST00000538527; ENST00000546329 | TSF |
| 12% | chr14 | 94936503 | 94936425 | − | chr14 | 94935803 | 94935550; 94935708 | − | ENST00000448305; ENST00000337425; ENST00000380365; ENST00000538527; ENST00000546329 | TSF |
| 10% | chr7 | 2289080 | 2289115 | + | chr7 | 2289492 | 2289637 | + | ENST00000356714; ENST00000397049; ENST00000397046; ENST00000397048; ENST00000339737; ENST00000343985 | TAF |
| 10% | chr8 | 144638103 | 144638200 | + | chr8 | 144640548 | 144640621 | + | ENST00000533063 | TAF |
| 10% | chr7 | 2289080 | 2289194 | + | chr7 | 2289492 | 2289637 | + | ENST00000356714; ENST00000397049; ENST00000397046; ENST00000397048; ENST0000033937; ENST00000343985 | TAF |
| 10% | chr1 | 33097909 | 33097809 | − | chr1 | 33097480 | 33097428 | − | ENST00000468695 | TAF |
| 10% | chr16 | 18795209 | 18795124 | − | chr16 | 18794424 | 18794331; 18794411 | − | ENST00000322989; ENST00000572008; ENST00000563390; ENST00000565420; ENST00000563579 | TAF |
| 10% | chr16 | 18795209 | 18795124 | − | chr16 | 18794424 | 18794331; 18794411 | − | ENST00000322989; ENST00000572008; ENST00000563390; ENST00000565420; ENST00000563579 | TAF |
| 10% | chr11 | 424193 | 423942 | − | chr11 | 421198 | 421141 | − | ENST00000332826 | TAF |
| 10% | chr11 | 58330466 | 58330321 | − | chr11 | 58322413 | 58322314 | − | ENST00000530561; ENST00000395074; ENST00000528954; ENST00000528489 | TAF |
| 10% | chr11 | 58330466 | 58330321 | − | chr11 | 58322413 | 58322314 | − | ENST00000530561; ENST00000395074; ENST00000528954; ENST00000528489 | TAF |
| 10% | chr19 | 39347374 | 39346635 | − | chr19 | 39338074 | 39337956 | − | ENST00000221419; ENST00000601449; ENST00000600233; ENST00000601813 | TAF |
| 10% | chr19 | 39347374 | 39346635 | − | chr19 | 39338074 | 39337956 | − | ENST00000221419; ENST00000601449; ENST00000600233; ENST00000601813 | TAF |
| 10% | chr19 | 39347374 | 39346635 | − | chr19 | 39338074 | 39337956 | − | ENST00000221419; ENST00000601449; ENST00000600233; ENST00000601813 | TAF |
| 10% | chr6 | 33039547 | 33039397 | − | chr6 | 33037663 | 33037418 | − | ENST00000419277; ENST00000428995; ENST00000453337 | TAF |
| 10% | chr6 | 33039547 | 33039397 | − | chr6 | 33037663 | 33037418 | − | ENST00000419277; ENST00000428995; ENST00000453337 | TAF |
| 10% | chr10 | 5826921 | 5825287 | − | chr10 | 5815904 | 5815805 | − | ENST00000380191; ENST00000447751; ENST00000380132; ENST00000380181; ENST00000456041 | TAF |
| 10% | chr10 | 5826921 | 5825287 | − | chr10 | 5815904 | 5815805 | − | ENST00000380191; ENST00000447751; ENST00000380132; ENST00000380181; ENST00000456041 | TAF |
| 10% | chr10 | 5826921 | 5825287 | − | chr10 | 5815904 | 5815805 | − | ENST00000380191; ENST00000447751; ENST00000380132; ENST00000380181; ENST00000456041 | TAF |

TABLE 21

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 69% | chr1 | 32696528 | 32696620 | + | ENST00000373586 | chr1 | 32696861 | 32697110 | + | TAF |
| 64% | chr20 | 47768284 | 47768119 | − | ENST00000371828; ENST00000340954; ENST00000347458; ENST00000360426; ENST00000371792; ENST00000371802; ENST00000371856; ENST00000437404; ENST00000456866 | chr20 | 47761186 | 47760181 | − | TAF |
| 64% | chr20 | 47768284 | 47768119 | − | ENST00000371828; ENST00000340954; ENST00000347458; ENST00000360426; ENST00000371792; ENST00000371802; ENST00000371856; ENST00000437404; ENST00000456866 | chr20 | 47761186 | 47760181 | − | TAF |
| 64% | chr20 | 47768284 | 47768119 | − | ENST00000371828; ENST00000340954; ENST00000347458; ENST00000360426; ENST00000371792; ENST00000371802; ENST00000371856; ENST00000437404; ENST00000456866 | chr20 | 47761186 | 47760181 | − | TAF |
| 54% | chr10 | 47747112 | 47747132 | + | ENST00000340243; ENST00000374277; ENST00000449464; ENST00000538825 | chr10 | 48278725 | 48278896 | + | TAF |
| 42% | chr12 | 71509738 | 71509630 | − | ENST00000549357 | chr12 | 71504233 | 71503634 | − | TAF |
| 41% | chr12 | 52909024 | 52908899 | − | ENST00000252242 | chr12 | 52908920 | 52908992 | + | TSF |
| 32% | chr19 | 15289752 | 15289634 | − | ENST00000263388; ENST00000601011 | chr19 | 15289244 | 15289201 | − | TSF |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 32% | chr19 | 15289752 | 15289634 | − | ENST00000263388; ENST00000601011 | chr19 | 15289244 | 15289201 | − | TSF |
| 28% | chr5 | 54993786 | 54993674 | − | ENST00000396865; ENST00000539768; ENST00000318672; ENST00000508124; ENST00000511233; ENST00000503891; ENST00000513993; ENST00000505563; ENST00000506624; ENST00000507109 | chr5 | 54993040 | 54992544 | − | TSF |
| 27% | chr1 | 24463799 | 24463621 | − | ENST00000270800 | chr1 | 24461426 | 24461370 | − | TAF |
| 27% | chr15 | 83102759 | 83103078 | + | ENST00000561062; ENST00000358583 | chr15 | 83193141 | 83193227 | + | TSF |
| 27% | chr11 | 118888255 | 118888078 | − | ENST00000527673 | chr11 | 118861152 | 118861045 | − | TSF |
| 26% | chr15 | 82726234 | 82726553 | + | ENST00000300515 | chr15 | 82808796 | 82808882 | + | TAF |
| 26% | chr18 | 33767503 | 33767644 | + | ENST00000261326 | chr18 | 33773430 | 33773774 | + | TAF |
| 26% | chr19 | 16204346; 16204382 | 16204408 | − | ENST00000344824; ENST00000538887; ENST00000300933; ENST00000588032; ENST00000592822 | chr19 | 16213047 | 16213167 | + | TSF |
| 26% | chr19 | 16204346; 16204382 | 16204408 | + | ENST00000344824; ENST00000538887; ENST00000300933; ENST00000588032; ENST00000592822 | chr19 | 16213047 | 16213167 | + | TSF |
| 26% | chr19 | 16204346; 16204382 | 16204408 | + | ENST00000344824; ENST00000538887; ENST00000300933; ENST00000588032; ENST00000592822 | chr19 | 16213047 | 16213167 | + | TSF |
| 26% | chr19 | 16204346; 16204382 | 16204408 | + | ENST00000344824; ENST00000538887; ENST00000300933; ENST00000588032; ENST00000592822 | chr19 | 16213047 | 16213167 | + | TSF |
| 24% | chr17 | 73733619 | 73733725 | + | ENST00000579662; ENST00000339591; ENST00000200181; ENST00000450894; ENST00000449880 | chr17 | 73735417 | 73735563 | + | TAF |
| 24% | chr12 | 57060050 | 57059988 | − | ENST00000262033; ENST00000414274; ENST00000436399; ENST00000456859 | chr12 | 57059571 | 57059432 | − | TAF |
| 24% | chr12 | 57060050 | 57059988 | − | ENST00000262033; ENST00000414274; ENST00000436399; ENST00000456859 | chr12 | 57059571 | 57059432 | − | TAF |
| 24% | chr12 | 57060050 | 57059988 | − | ENST00000262033; ENST00000414274; ENST00000436399; ENST00000456859 | chr12 | 57059571 | 57059432 | − | TAF |
| 24% | chr12 | 57060050 | 57059988 | − | ENST00000262033; ENST00000414274; ENST00000436399; ENST00000456859 | chr12 | 57059571 | 57059432 | − | TAF |
| 24% | chr19 | 42222047 | 42222099 | + | ENST00000398599; ENST00000221992; ENST00000405816 | chr19 | 42234250 | 42234353 | + | TSF |
| 24% | chr19 | 42222047 | 42222099 | + | ENST00000398599; ENST00000221992; ENST00000405816 | chr19 | 42234250 | 42234353 | + | TSF |
| 24% | chr12 | 52909024 | 52908918 | − | ENST00000252242 | chr12 | 52908901 | 52908992 | + | TSF |
| 23% | chr20 | 35842163 | 35842268 | + | ENST00000237530; ENST00000373622 | chr20 | 35844460 | 35844765 | + | TAF |
| 23% | chr20 | 35842163 | 35842268 | + | ENST00000237530; ENST00000373622 | chr20 | 35844460 | 35844765 | + | TAF |
| 23% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 23% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 23% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 23% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 23% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 23% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 21% | chr16 | 68849418 | 68849662 | + | ENST00000261769; ENST00000566612; ENST00000422392 | chr16 | 68851395 | 68851859 | + | TAF |
| 21% | chr16 | 68849418 | 68849662 | + | ENST00000261769; ENST00000566612; ENST00000422392 | chr16 | 68851395 | 68851859 | + | TAF |
| 19% | chr19 | 42222047 | 42222099 | + | ENST00000398599; ENST00000221992; ENST00000405816 | chr19 | 42234246 | 42234353 | + | TSF |
| 19% | chr19 | 42222047 | 42222099 | + | ENST00000398599; ENST00000221992; ENST00000405816 | chr19 | 42234246 | 42234353 | + | TSF |
| 18% | chr6 | 41606488 | 41606563 | + | ENST00000432027; ENST00000419164; ENST00000373051; ENST00000441667; ENST00000230321; ENST00000373050; ENST00000446650; ENST00000435476 | chr6 | 41607515 | 41607595 | + | TAF |
| 18% | chr6 | 74228333 | 74228077 | − | ENST00000316292; ENST00000309268; ENST00000331523 | chr6 | 74195910 | 74195882 | | TSF |
| 18% | chr3 | 185414451 | 185414400 | − | ENST00000382199; ENST00000421047; ENST00000457616; ENST00000346192 | chr3 | 185411016 | 185410789 | − | TSF |
| 18% | chr3 | 185414451 | 185414400 | − | ENST00000382199; ENST00000421047; ENST00000457616; ENST00000346192 | chr3 | 185411016 | 185410789 | − | TSF |
| 17% | chr8 | 134274410; 134274372 | 134274290 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738; ENST00000523892 | chr8 | 134272213 | 134272102 | − | TAF |
| 17% | chr8 | 134274410; 134274372 | 134274290 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738; ENST00000523892 | chr8 | 134272213 | 134272102 | − | TAF |
| 17% | chr8 | 134274410; 134274372 | 134274290 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738; ENST00000523892 | chr8 | 134272213 | 134272102 | − | TAF |
| 17% | chr8 | 134274410; 134274372 | 134274290 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738; ENST00000523892 | chr8 | 134272213 | 134272102 | − | TAF |
| 17% | chr8 | 134274410; 134274372 | 134274290 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738; ENST00000523892 | chr8 | 134272213 | 134272102 | − | TAF |
| 17% | chr8 | 134274410; 134274372 | 134274290 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738; ENST00000523892 | chr8 | 134272213 | 134272102 | − | TAF |
| 17% | chr8 | 134274410; 134274372 | 134274290 | − | ENST00000323851; ENST00000517599; ENST00000537882; ENST00000414097; ENST00000522476; ENST00000522377; ENST00000520230; ENST00000518480; | | | | | |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 17% | chr8 | 134274410; 134274372 | 134274290 | − | ENST00000519228; ENST00000519580; ENST00000522890; ENST00000520943; ENST00000521544; ENST00000522738; ENST00000523892 ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738; ENST00000523892 | chr8 | 134272213 | 134272102 | − | TAF |
| 17% | chr1 | 153534067 | 153533988 | − | ENST00000368708; ENST00000487430; ENST00000497140; ENST00000368710; ENST00000368709 | chr1 | 153532853 | 153532704 | − | TAF |
| 17% | chr1 | 153534067 | 153533988 | − | ENST00000368708; ENST00000487430; ENST00000497140; ENST00000368710; ENST00000368709 | chr1 | 153532853 | 153532704 | − | TAF |
| 17% | chr3 | 49927493 | 49927357 | − | ENST00000296474; ENST00000344206 | chr3 | 49927248 | 49927204 | − | TAF |
| 17% | chr3 | 49927493 | 49927357 | − | ENST00000296474; ENST00000344206 | chr3 | 49927248 | 49927204 | − | TAF |
| 16% | chr11 | 11394176 | 11394062 | − | ENST00000227756 | chr11 | 11386990 | 11386568 | − | TAF |
| 16% | chr7 | 55270210 | 55270401 | + | ENST00000455089 | chr7 | 55272949 | 55272949 | + | TSF |
| 15% | chr7 | 27582719 | 27582586 | − | ENST00000265395; ENST00000425715 | chr7 | 27581374 | 27579272 | − | TAF |
| 15% | chr7 | 27582719 | 27582586 | − | ENST00000265395; ENST00000425715 | chr7 | 27581374 | 27579272 | − | TAF |
| 14% | chr3 | 141640819 | 141640905 | + | ENST00000286371 | chr3 | 141642262 | 141642420 | + | TAF |
| 14% | chr8 | 144102731 | 144102850 | + | ENST00000292494; ENST00000429120; ENST00000521699; ENST00000520531; ENST00000520466; ENST00000521003; ENST00000522971; ENST00000519611; ENST00000519546; ENST00000523847; ENST00000522024 | chr8 | 144113283 | 144113885 | + | TAF |
| 14% | chr5 | 1802435 | 1802488 | + | ENST00000274137; ENST00000469176 | chr5 | 1811023 | 1811428 | + | TAF |
| 14% | chr20 | 3844903 | 3845435 | + | ENST00000416600; ENST00000428216 | chr20 | 3854441 | 3854475 | + | TAF |
| 14% | chr20 | 3844903 | 3845435 | + | ENST00000416600; ENST00000428216 | chr20 | 3854441 | 3854475 | + | TAF |
| 14% | chr1 | 33272212 | 33272083 | − | ENST00000373477 | chr1 | 33270534 | 33269340 | − | TAF |
| 14% | chr1 | 147438786 | 147438895 | + | ENST00000314163 | chr1 | 147440564 | 147440653 | + | TAF |
| 14% | chr10 | 22171368 | 22171211 | − | ENST00000376980 | chr10 | 22168812 | 22168560 | − | TAF |
| 14% | chr10 | 48255429 | 48255449 | + | ENST00000357718; ENST00000344416; ENST00000535874; ENST00000456111 | chr10 | 48278725 | 48278896 | + | TSF |
| 13% | chr3 | 57678745 | 57678509 | − | ENST00000311128 | chr3 | 57665452 | 57665436 | − | TAF |
| 12% | chr11 | 102033187 | 102033302 | + | ENST00000526343; ENST00000282441; ENST00000345877; ENST00000537274; ENST00000531439; ENST00000524575 | chr11 | 102045049 | 102045326 | + | TAF |
| 12% | chr11 | 102033187 | 102033302 | + | ENST00000526343; ENST00000282441; ENST00000345877; ENST00000537274; ENST00000531439; ENST00000524575 | chr11 | 102045049 | 102045326 | + | TAF |
| 12% | chr1 | 224544627 | 224544695 | + | ENST00000465271; ENST00000366858; ENST00000366857; ENST00000366856 | chr1 | 224551811 | 224551931 | + | TAF |
| 12% | chr21 | 45379563 | 45379740 | + | ENST00000291572; ENST00000448287; ENST00000398061; ENST00000327505; ENST00000445582; ENST00000398063; ENST00000398058; ENST00000457068; ENST00000422850; ENST00000546158 | chr21 | 45380513 | 45380695 | + | TAF |
| 12% | chr7 | 4026818 | 4026954 | + | ENST00000404826; ENST00000389531 | chr7 | 4027977 | 4028157 | + | TAF |
| 12% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 12% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 12% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 12% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 12% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 12% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 12% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 12% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 11% | chr13 | 44433033 | 44432917 | − | ENST00000444614; ENST00000281508 | chr13 | 44413224 | 44412729 | − | TAF |
| 11% | chr14 | 31922550 | 31922481 | − | ENST00000549185; ENST00000547378; ENST00000310850; ENST00000356180 | chr14 | 31907346 | 31905965 | − | TSF |
| 10% | chr7 | 5781275; 5781446 | 5780604 | − | ENST00000425013; ENST00000389902; ENST00000389900 | chr7 | 5779256 | 5779224 | − | TAF |
| 10% | chr7 | 5781275; 5781446 | 5780604 | − | ENST00000425013; ENST00000389902; ENST00000389900 | chr7 | 5779256 | 5779224 | − | TAF |
| 10% | chr6 | 27114577 | 27114201 | − | ENST00000396891; ENST00000356950 | chr6 | 27106460 | 27106003 | − | TAF |
| 10% | chr1 | 987108 | 987195 | + | ENST00000379370; ENST00000419249 | chr1 | 992542 | 992691 | + | TSF |
| 10% | chr1 | 987108 | 987195 | + | ENST00000379370; ENST00000419249 | chr1 | 992542 | 992691 | + | TSF |
| 10% | chr1 | 183441756 | 183441784 | + | ENST00000440812; ENST00000444547; ENST00000347615; ENST00000507469; ENST00000515829 | chr1 | 183470266 | 183470283 | + | TSF |
| 10% | chr12 | 52912944; 52912901 | 52912801 | − | ENST00000252242; ENST00000551188; ENST00000549420 | chr12 | 52901143 | 52899664 | − | TSF |
| 10% | chr12 | 52912944; 52912901 | 52912801 | − | ENST00000252242; ENST00000551188; ENST00000549420 | chr12 | 52901143 | 52899664 | − | TSF |
| 10% | chr12 | 52912944; 52912901 | 52912801 | − | ENST00000252242; ENST00000551188; ENST00000549420 | chr12 | 52901143 | 52899664 | − | TSF |
| 10% | chr12 | 113403549; 113403702 | 113403834 | + | ENST00000228928; ENST00000546973 | chr12 | 113404028 | 113404051 | + | TSF |
| 10% | chr12 | 113403549; 113403702 | 113403834 | + | ENST00000228928; ENST00000546973 | chr12 | 113404028 | 113404051 | + | TSF |
| 10% | chr7 | 81964567 | 81964451 | − | ENST00000356860; ENST00000356253; ENST00000423588 | chr7 | 81929467 | 81929190 | − | TSF |
| 9% | chr6 | 34210489 | 34210572 | + | ENST00000447654; ENST00000311487; ENST00000347617; ENST00000401473; ENST00000374116 | chr6 | 34212756 | 34212817 | + | TSF |
| 9% | chr6 | 34210489 | 34210572 | + | ENST00000447654; ENST00000311487; ENST00000347617; ENST00000401473; ENST00000374116 | chr6 | 34212756 | 34212817 | + | TSF |
| 9% | chr1 | 209792 | 20979114 | − | ENST00000602624; ENST00000375048; ENST00000415136 | chr1 | 20978611 | 20978295 | − | TSF |
| 9% | chr1 | 20979220 | 20979114 | − | ENST00000602624; ENST00000375048; ENST00000415136 | chr1 | 20978611 | 20978295 | − | TSF |
| 9% | chr1 | 20979220 | 20979114 | − | ENST00000602624; ENST00000375048; ENST00000415136 | chr1 | 20978611 | 20978295 | − | TSF |
| 9% | chr4 | 25759228 | 25759156 | − | ENST00000399878; ENST00000264868; ENST00000502949; ENST00000510448 | chr4 | 25723603 | 25723555 | − | TSF |
| 9% | chr4 | 25759228 | 25759156 | − | ENST00000399878; ENST00000264868; ENST00000502949; ENST00000510448 | chr4 | 25723603 | 25723555 | − | TSF |
| 9% | chr4 | 25759228 | 25759156 | − | ENST00000399878; ENST00000264868; ENST00000502949; ENST00000510448 | chr4 | 25723603 | 25723555 | − | TSF |
| 9% | chr4 | 25759228 | 25759156 | − | ENST00000399878; ENST00000264868; ENST00000502949; ENST00000510448 | chr4 | 25723603 | 25723555 | − | TSF |
| 9% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 9% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 9% | chr10 | 47173918 | 47173898 | − | ENST00000358140; ENST00000359178; ENST00000545298; ENST00000414655 | chr10 | 47139994 | 47138925 | − | TSF |
| 8% | chr4 | 146617711 | 146617784 | + | ENST00000438731; ENST00000511965 | chr4 | 146620339 | 146620424 | + | TSF |
| 8% | chr4 | 146617711 | 146617784 | + | ENST00000438731; ENST00000511965 | chr4 | 146620339 | 146620424 | + | TSF |
| 8% | chr19 | 15289752 | 15289634 | − | ENST00000263388; ENST00000601011 | chr19 | 15289358 | 15289201 | − | TSF |
| 8% | chr19 | 15289752 | 15289634 | − | ENST00000263388; ENST00000601011 | chr19 | 15289358 | 15289201 | − | TSF |
| 8% | chr8 | 71619168 | 71619388 | + | ENST00000408926; ENST00000520030 | chr8 | 71625661 | 71625673 | + | TSF |
| 8% | chrX | 24091208 | 24091333 | + | ENST00000253039 | chrX | 24091714 | 24091817 | + | TSF |
| 8% | chr2 | 176860312; 176860292 | 176860286 | − | ENST00000272748; ENST00000544803; ENST00000392540; ENST00000445472 | chr2 | 176859008 | 176858934 | − | TSF |
| 8% | chr2 | 176860312; 176860292 | 176860286 | − | ENST00000272748; ENST00000544803; ENST00000392540; ENST00000445472 | chr2 | 176859008 | 176858934 | | TSF |
| 8% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | | TSF |
| 8% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 8% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 8% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 8% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 8% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 8% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 8% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 8% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 7% | chr10 | 5788142 | 5788607 | + | ENST00000328090 | chr10 | 5845506 | 5845586 | + | TSF |
| 7% | chr8 | 104778455 | 104778765 | + | ENST00000504942; ENST00000406091 | chr8 | 104821508 | 104821527 | + | TSF |
| 7% | chr4 | 169086398 | 169086477 | + | ENST00000359299 | chr4 | 169090666 | 169090754 | + | TSF |
| 7% | chr8 | 25240190 | 25240294 | 1 | ENST00000276440 | chr8 | 25246325 | 25246384 | + | TSF |
| 7% | chr16 | 16149949 | 16150152 | + | ENST00000399410; ENST00000345148; ENST00000346370; ENST00000349029; ENST00000351154; ENST00000399408; ENST00000572882 | chr16 | 16151288 | 16151380 | + | TSF |
| 7% | chr16 | 16149949 | 16150152 | + | ENST00000399410; ENST00000345148; ENST00000346370; ENST00000349029; ENST00000351154; ENST00000399408; ENST00000572882 | chr16 | 16151288 | 16151380 | + | TSF |
| 7% | chr22 | 38321668; 38321854 | 38322050 | + | ENST00000215957; ENST00000454685 | chr22 | 38322963 | 38322967 | + | TSF |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 7% | chr22 | 38321668; 38321854 | 38322050 | + | ENST00000215957; ENST00000454685 | chr22 | 38322963 | 38322967 | + | TSF |
| 7% | chr22 | 25202408 | 25202451 | + | ENST00000400358; ENST00000400359 | chr22 | 25209976 | 25210040 | + | TSF |
| 7% | chr2 | 241555805 | 241555928 | + | ENST00000270634 | chr2 | 241556208 | 241556489 | + | TSF |
| 7% | chr1 | 234546277 | 234546191 | − | ENST00000040877 | chr1 | 234545319 | 234545287 | − | TSF |
| 7% | chr17 | 39777343 | 39777323 | − | ENST00000311208; ENST00000540235; ENST00000463128 | chr17 | 39757580 | 39757497 | − | TSF |
| 7% | chr17 | 39777343 | 39777323 | − | ENST00000311208; ENST00000540235; ENST00000463128 | chr17 | 39757580 | 39757497 | − | TSF |
| 7% | chr17 | 39777343 | 39777323 | − | ENST00000311208; ENST00000540235; ENST00000463128 | chr17 | 39757580 | 39757497 | − | TSF |
| 6% | chr12 | 86272123 | 86272347 | + | ENST00000256010 | chr12 | 86274455 | 86274746 | + | TSF |
| 6% | chr5 | 175723254 | 175723323 | + | ENST00000341199; ENST00000430704; ENST00000443967; ENST00000429602 | chr5 | 175731557 | 175732243 | + | TSF |
| 6% | chr5 | 175723254 | 175723323 | + | ENST00000341199; ENST00000430704; ENST00000443967; ENST00000429602 | chr5 | 175731557 | 175732243 | + | TSF |
| 6% | chr5 | 175723254 | 175723323 | + | ENST00000341199; ENST00000430704; ENST00000443967; ENST00000429602 | chr5 | 175731557 | 175732243 | + | TSF |
| 6% | chr20 | 3614958 | 3615036 | + | ENST00000262919 | chr20 | 3615708 | 3616042 | + | TSF |
| 6% | chr17 | 38634585 | 38634559 | − | ENST00000254051; ENST00000582747 | chr17 | 38633675 | 38633602 | − | TSF |
| 6% | chr17 | 38634585 | 38634559 | − | ENST00000254051; ENST00000582747 | chr17 | 38633675 | 38633602 | − | TSF |
| 6% | chr7 | 5434226; 5434191 | 5434071 | − | ENST00000399537; ENST00000430969; ENST00000434361; ENST00000399434 | chr7 | 5433863 | 5433797 | − | TSF |
| 6% | chr7 | 5434226; 5434191 | 5434071 | − | ENST00000399537; ENST00000430969; ENST00000434361; ENST00000399434 | chr7 | 5433863 | 5433797 | − | TSF |
| 6% | chr14 | 67878776 | 67878735 | − | ENST00000216446; ENST00000553387 | chr14 | 67864772 | 67864768 | − | TSF |
| 6% | chr17 | 39768940 | 39768493 | − | ENST00000301653 | chr17 | 39733779 | 39733579 | − | TSF |
| 5% | chr14 | 66096210; 66096217 | 66096324 | + | ENST00000360689; ENST00000394586; ENST00000342677; ENST00000557164; ENST00000394585; ENST00000358307 | chr14 | 66099743 | 66101298 | + | TSF |
| 5% | chr14 | 66096210; 66096217 | 66096324 | + | ENST00000360689; ENST00000394586; ENST00000342677; ENST00000557164; ENST00000394585; ENST00000358307 | chr14 | 66099743 | 66101298 | + | TSF |
| 5% | chr14 | 66096210; 66096217 | 66096324 | + | ENST00000360689; ENST00000394586; ENST00000342677; ENST00000557164; ENST00000394585; ENST00000358307 | chr14 | 66099743 | 66101298 | + | TSF |
| 5% | chr3 | 183454506 | 183454617 | + | ENST00000305135 | chr3 | 183456939 | 183458206 | + | TSF |
| 5% | chr3 | 189590648 | 189590784 | + | ENST00000264731; ENST00000382063; ENST00000418709; ENST00000320472; ENST00000392460; ENST00000440651; ENST00003546000; ENST00000437221; ENST00000392463; ENST00003924610; ENST00000449992; ENST00000456148 | chr3 | 189602358 | 189602438 | + | TSF |
| 5% | chr3 | 189590648 | 189590784 | + | ENST00000264731; ENST00000382063; ENST00000418709; ENST00000320472; ENST00000392460; ENST00000440651; ENST00003546000; ENST00000437221; ENST00000392463; ENST00003924610; ENST00000449992; ENST00000456148 | chr3 | 189602358 | 189602438 | + | TSF |
| 5% | chr3 | 189590648 | 189590784 | + | ENST00000264731; ENST00000382063; ENST00000418709; ENST00000320472; ENST00000392460; ENST00000440651; ENST00003546000; ENST00000437221; ENST00000392463; ENST00003924610; ENST00000449992; ENST00000456148 | chr3 | 189602358 | 189602438 | + | TSF |
| 5% | chr3 | 189590648 | 189590784 | + | ENST00000264731; ENST00000382063; ENST00000418709; ENST00000320472; ENST00000392460; ENST00000440651; ENST00003546000; ENST00000437221; ENST00000392463; ENST00003924610; ENST00000449992; ENST00000456148 | chr3 | 189602358 | 189602438 | + | TSF |
| 5% | chr3 | 189590648 | 189590784 | + | ENST00000264731; ENST00000382063; ENST00000418709; ENST00000320472; ENST00000392460; ENST00000440651; ENST00003546000; ENST00000437221; ENST00000392463; ENST00003924610; ENST00000449992; ENST00000456148 | chr3 | 189602358 | 189602438 | + | TSF |
| 5% | chr3 | 189590648 | 189590784 | + | ENST00000264731; ENST00000382063; ENST00000418709; ENST00000320472; ENST00000392460; ENST00000440651; ENST00003546000; ENST00000437221; ENST00000392463; ENST00003924610; ENST00000449992; ENST00000456148 | chr3 | 189602358 | 189602438 | + | TSF |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 5% | chr11 | 60701014 | 60701216 | + | ENST00000453848; ENST00000005286; ENST00000536409 | chr11 | 60701443 | 60701575 | + | TSF |
| 5% | chr11 | 60701014 | 60701216 | + | ENST00000453848; ENST00000005286; ENST00000536409 | chr11 | 60701443 | 60701575 | + | TSF |
| 5% | chr11 | 60701014 | 60701216 | + | ENST00000453848; ENST00000005286; ENST00000536409 | chr11 | 60701443 | 60701575 | + | TSF |
| 5% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 5% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 5% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 5% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 5% | chr11 | 71209398; 71209448 | 71209574 | + | ENST00000319023; ENST00000539574; ENST00000530055; ENST00000525593; ENST00000527963 | chr11 | 71216557 | 71216960 | + | TSF |
| 5% | chr17 | 39914770 | 39914657 | − | ENST00000393930; ENST00000310706; ENST00000393931 | chr17 | 39864294 | 39864007 | − | TSF |
| 5% | chr3 | 50153339 | 50153413 | + | ENST00000347869 | chr3 | 50155909 | 50155909 | + | TSF |
| 5% | chr7 | 23313140 | 23313233 | + | ENST00000258733; ENST00000381990; ENST00000539136; ENST00000453162 | chr7 | 23322924 | 23323223 | + | TSF |
| 5% | chr7 | 23313140 | 23313233 | + | ENST00000258733; ENST00000381990; ENST00000539136; ENST00000453162 | chr7 | 23322924 | 23323223 | + | TSF |
| 5% | chr7 | 23313140 | 23313233 | + | ENST00000258733; ENST00000381990; ENST00000539136; ENST00000453162 | chr7 | 23322924 | 23323223 | + | TSF |
| 5% | chr7 | 23313140 | 23313233 | + | ENST00000258733; ENST00000381990; ENST00000539136; ENST00000453162 | chr7 | 23322924 | 23323223 | + | TSF |
| 5% | chr1 | 32573732 | 32573735 | + | ENST00000373625; ENST00000471599 | chr1 | 32605356 | 32605563 | + | TSF |
| 5% | chr22 | 50639466 | 50640019 | + | ENST00000380903 | chr22 | 50643348 | 50643731 | + | TSF |
| 5% | chr17 | 39780761; 39780716 | 39780413 | − | ENST00000311208; ENST00000577817 | chr17 | 39733779 | 39733579 | − | TSF |
| 5% | chr17 | 39780761; 39780716 | 39780413 | − | ENST00000311208; ENST00000577817 | chr17 | 39733779 | 39733579 | − | TSF |
| 5% | chr8 | 624047; 623326; 623657 | 1623289 | | ENST00000522706; ENST00000523415; ENST00000262109; ENST00000522893 | chr8 | 622204 | 621954 | − | TSF |
| 5% | chr8 | 624047; 623326; 623657 | 1623289 | | ENST00000522706; ENST00000523415; ENST00000262109; ENST00000522893 | chr8 | 622204 | 621954 | − | TSF |
| 5% | chr8 | 624047; 623326; 623657 | 1623289 | | ENST00000522706; ENST00000523415; ENST00000262109; ENST00000522893 | chr8 | 622204 | 621954 | − | TSF |
| 5% | chr8 | 624047; 623326; 623657 | 1623289 | | ENST00000522706; ENST00000523415; ENST00000262109; ENST00000522893 | chr8 | 622204 | 621954 | − | TSF |
| 5% | chr12 | 56742407 | 56742313 | − | ENST00000314128; ENST00000557235 | chr12 | 56740986 | 56740975 | − | TSF |
| 5% | chr12 | 56742407 | 56742313 | − | ENST00000314128; ENST00000557235 | chr12 | 56740986 | 56740975 | − | TSF |
| 5% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 5% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 5% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 5% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 5% | chr8 | 11704677 | 11704561 | − | ENST00000434271; ENST00000353047; ENST00000530640; ENST00000531089; ENST00000453527; ENST00000345125; ENST00000533455; ENST00000534510 | chr8 | 11700371 | 11700139 | − | TSF |
| 5% | chrX | 41598709 | 41598637 | − | ENST00000421587; ENST00000318588; ENST00000361962; ENST00000378163; ENST00000378158; ENST00000378166; ENST00000442742; ENST00000378154 | chrX | 41557348 | 41557057 | − | TSF |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 5% | chr17 | 39741309 | 39741227 | − | ENST00000167586 | chr17 | 39741017 | 39740999 | − | TSF |
| 5% | chr16 | 72153988; 72154048 | 72153750 | − | ENST00000537465; ENST00000237353; ENST00000355636 | chr16 | 72150929 | 72150229 | − | TSF |
| 5% | chr16 | 72153988; 72154048 | 72153750 | − | ENST00000537465; ENST00000237353; ENST00000355636 | chr16 | 72150929 | 72150229 | − | TSF |
| 5% | chr16 | 72153988; 72154048 | 72153750 | − | ENST00000537465; ENST00000237353; ENST00000355636 | chr16 | 72150929 | 72150229 | − | TSF |
| 4% | chr6 | 29910534 | 29910757 | + | ENST00000396634; ENST00000376806; ENST00000376809; ENST00000376802 | chr6 | 30349606 | 30349643 | + | TSF |
| 4% | chr10 | 48264358 | 48264417 | + | ENST00000357718; ENST00000344416; ENST00000456111 | chr10 | 48270861 | 48270943 | + | TSF |
| 4% | chr10 | 48264358 | 48264417 | + | ENST00000357718; ENST00000344416; ENST00000456111 | chr10 | 48270861 | 48270943 | + | TSF |
| 4% | chr10 | 48264358 | 48264417 | + | ENST00000357718; ENST00000344416; ENST00000456111 | chr10 | 48270861 | 48270943 | + | TSF |
| 4% | chr11 | 61505607 | 61505679 | + | ENST00000257215 | chr11 | 61506649 | 61506706 | + | TSF |
| 4% | chr5 | 172110422 | 172110543 | + | ENST00000522853; ENST00000369800 | chr5 | 172114291 | 172114319 | + | TSF |
| 4% | chr5 | 172110422 | 172110543 | + | ENST00000522853; ENST00000369800 | chr5 | 172114291 | 172114319 | + | TSF |
| 4% | chr16 | 30783410 | 30783511 | + | ENST00000324685; ENST00000402121; ENST00000563683; ENST00000357890 | chr16 | 30785136 | 30785155 | + | TSF |
| 4% | chr16 | 30783410 | 30783511 | + | ENST00000324685; ENST00000402121; ENST00000563683; ENST00000357890 | chr16 | 30785136 | 30785155 | + | TSF |
| 4% | chr16 | 30783410 | 30783511 | + | ENST00000324685; ENST00000402121; ENST00000563683; ENST00000357890 | chr16 | 30785136 | 30785155 | + | TSF |
| 4% | chr16 | 30783410 | 30783511 | + | ENST00000324685; ENST00000402121; ENST00000563683; ENST00000357890 | chr16 | 30785136 | 30785155 | + | TSF |
| 4% | chr7 | 98961166 | 98961256 | + | ENST00000432884; ENST00000262942 | chr7 | 98963096 | 98963255 | + | TSF |
| 4% | chr7 | 98961166 | 98961256 | + | ENST00000432884; ENST00000262942 | chr7 | 98963096 | 98963255 | + | TSF |
| 4% | chr16 | 2825557; 2825626 | 2825452 | − | ENST00000262306; ENST00000409906; ENST00000409477; ENST00000494946 | chr16 | 2823822 | 2823809 | − | TSF |
| 4% | chr16 | 2825557; 2825626 | 2825452 | − | ENST00000262306; ENST00000409906; ENST00000409477; ENST00000494946 | chr16 | 2823822 | 2823809 | − | TSF |
| 4% | chr16 | 2825557; 2825626 | 2825452 | − | ENST00000262306; ENST00000409906; ENST00000409477; ENST00000494946 | chr16 | 2823822 | 2823809 | − | TSF |
| 4% | chr17 | 38640861 | 38640736 | − | ENST00000254051 | chr17 | 38639746 | 38639457 | − | TSF |
| 4% | chr6 | 34386201 | 34386146 | − | ENST00000605528; ENST00000344700 | chr6 | 34385704 | 34385695 | − | TSF |
| 4% | chr17 | 38066177 | 38066009 | − | ENST00000360317; ENST00000394175; ENST00000309481; ENST00000520542; ENST00000394179; ENST00000418519; ENST00000523371; ENST00000524039; ENST00000468820 | chr17 | 38065588 | 38065521 | − | TSF |
| 4% | chr17 | 38066177 | 38066009 | − | ENST00000360317; ENST00000394175; ENST00000309481; ENST00000520542; ENST00000394179; ENST00000418519; ENST00000523371; ENST00000524039; ENST00000468820 | chr17 | 38065588 | 38065521 | − | TSF |
| 4% | chr1 | 43392912 | 43392716 | − | ENST00000426263 | chr1 | 43372275 | 43371386 | − | TSF |
| 4% | chr3 | 195780429 | 195780393 | − | ENST00000426789; ENST00000420415; ENST00000360110; ENST00000392396; ENST00000535031 | chr3 | 195779399 | 195779315 | − | TSF |
| 4% | chr3 | 195780429 | 195780393 | − | ENST00000426789; ENST00000420415; ENST00000360110; ENST00000392396; ENST00000535031 | chr3 | 195779399 | 195779315 | − | TSF |
| 4% | chr3 | 195780429 | 195780393 | − | ENST00000426789; ENST00000420415; ENST00000360110; ENST00000392396; ENST00000535031 | chr3 | 195779399 | 195779315 | − | TSF |
| 4% | chr3 | 195780429 | 195780393 | − | ENST00000426789; ENST00000420415; ENST00000360110; ENST00000392396; ENST00000535031 | chr3 | 195779399 | 195779315 | − | TSF |
| 4% | chr19 | 45895598 | 45895138 | − | ENST00000360957; ENST00000418234 | chr19 | 45889495 | 45889472 | − | TSF |
| 4% | chr19 | 42222047 | 42222099 | + | ENST00000398599; ENST00000221992; ENST00000405816 | chr19 | 42233309 | 42233421 | + | TSF |
| 4% | chr19 | 42222047 | 42222099 | + | ENST00000398599; ENST00000221992; ENST00000405816 | chr19 | 42233309 | 42233421 | + | TSF |
| 4% | chr19 | 14676014 | 14676102 | + | ENST00000215567; ENST00000596073; ENST00000600083; ENST00000436007; ENST00000601187 | chr19 | 14677944 | 14677945 | + | TSF |
| 4% | chr19 | 14676014 | 14676102 | + | ENST00000215567; ENST00000596073; ENST00000600083; ENST00000436007; ENST00000601187 | chr19 | 14677944 | 14677945 | + | TSF |
| 4% | chr19 | 14676014 | 14676102 | + | ENST00000215567; ENST00000596073; ENST00000600083; ENST00000436007; ENST00000601187 | chr19 | 14677944 | 14677945 | + | TSF |
| 4% | chr19 | 14676014 | 14676102 | + | ENST00000215567; ENST00000596073; ENST00000600083; ENST00000436007; ENST00000601187 | chr19 | 14677944 | 14677945 | + | TSF |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 4% | chr19 | 45323962 | 45324032 | + | ENST00000270233 | chr19 | 45324388 | 45324391 | + | TSF |
| 4% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 4% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 4% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 4% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 4% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 4% | chr17 | 75303223 | 75303279 | + | ENST00000427177 | chr17 | 75307415 | 75307459 | + | TSF |
| 4% | chr1 | 32696528 | 32696620 | + | ENST00000373586 | chr1 | 32696865 | 32697110 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36662881 | 36662970 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36662881 | 36662970 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36662881 | 36662970 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36662881 | 36662970 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36663327 | 36663652 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36663327 | 36663652 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36663327 | 36663652 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36663327 | 36663652 | + | TSF |
| 4% | chr14 | 54903155 | 54903087 | − | ENST00000395573; ENST00000216416; ENST00000557659; ENST00000557690; ENST00000556113 | chr14 | 54854962 | 54854914 | − | TSF |
| 4% | chr10 | 47164993 | 47164934 | − | ENST00000358140; ENST00000359178; ENST00000414655 | chr10 | 47158491 | 47158409 | − | TSF |
| 4% | chr10 | 47164993 | 47164934 | − | ENST00000358140; ENST00000359178; ENST00000414655 | chr10 | 47158491 | 47158409 | − | TSF |
| 4% | chr10 | 47164993 | 47164934 | − | ENST00000358140; ENST00000359178; ENST00000414655 | chr10 | 47158491 | 47158409 | − | TSF |
| 4% | chr1 | 152006276 | 152006124 | − | ENST00000271638 | chr1 | 152005339 | 152005310 | − | TSF |
| 4% | chr6 | 74228333 | 74228077 | − | ENST00000316292; ENST00000309268; ENST00000331523 | chr6 | 74202961 | 74202718 | − | TSF |
| 4% | chr17 | 27493958 | 27492960 | − | ENST00000354329; ENST00000533112; ENST00000531253; ENST00000527372 | chr17 | 27464102 | 27464011 | − | TSF |
| 4% | chr3 | 190030825 | 190030661 | − | ENST00000295522 | chr3 | 190030018 | 190029730 | − | TSF |
| 3% | chr16 | 89795643 | 89795726 | + | ENST00000446326; ENST00000289816; ENST00000568064; ENST00000443381 | chr16 | 89796339 | 89796374 | + | TSF |
| 3% | chr16 | 89795643 | 89795726 | + | ENST00000446326; ENST00000289816; ENST00000568064; ENST00000443381 | chr16 | 89796339 | 89796374 | + | TSF |
| 3% | chr16 | 89795643 | 89795726 | + | ENST00000446326; ENST00000289816; ENST00000568064; ENST00000443381 | chr16 | 89796339 | 89796374 | + | TSF |
| 3% | chr16 | 89795643 | 89795726 | + | ENST00000446326; ENST00000289816; ENST00000568064; ENST00000443381 | chr16 | 89796339 | 89796374 | + | TSF |
| 3% | chr16 | 68729680; 68729728 | 68729826 | + | ENST00000264012; ENST00000429102; ENST00000581171; ENST00000568292; ENST00000569080 | chr16 | 68761056 | 68761347 | + | TSF |
| 3% | chr16 | 68729680; 68729728 | 68729826 | + | ENST00000264012; ENST00000429102; ENST00000581171; ENST00000568292; ENST00000569080 | chr16 | 68761056 | 68761347 | + | TSF |

TABLE 21-continued

Transcript fusion for Esophageal Carcinoma (ESCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr16 | 68729680; 68729728 | 68729826 | + | ENST00000264012; ENST00000429102; ENST00000581171; ENST00000568292; ENST00000569080 | chr16 | 68761056 | 68761347 | + | TSF |
| 3% | chr16 | 98642687; 98642769 | 68729826 | + | ENST00000264012; ENST00000429102; ENST00000581171; ENST00000568292; ENST00000569080 | chr16 | 68761056 | 68761347 | + | TSF |
| 3% | chr13 | 68729680; 68729728 | 98642791 | + | ENST00000261574; ENST00000357602; ENST00000490680; ENST00000539640; ENST00000469360 | chr13 | 98643835 | 98643958 | + | TSF |
| 3% | chr13 | 68729680; 68729728 | 98642791 | + | ENST00000261574; ENST00000357602; ENST00000490680; ENST00000539640; ENST00000469360 | chr13 | 98643835 | 98643958 | + | TSF |
| 3% | chr13 | 68729680; 68729728 | 98642791 | + | ENST00000261574; ENST00000357602; ENST00000490680; ENST00000539640; ENST00000469360 | chr13 | 98643835 | 98643958 | + | TSF |
| 3% | chr13 | 68729680; 68729728 | 98642791 | + | ENST00000261574; ENST00000357602; ENST00000490680; ENST00000539640; ENST00000469360 | chr13 | 98643835 | 98643958 | + | TSF |
| 3% | chr17 | 66040437 | 66040619 | + | ENST00000330459; ENST00000537025 | chr17 | 66040935 | 66041225 | + | TSF |
| 3% | chr10 | 47756033 | 47756092 | + | ENST00000340243; ENST00000374277; ENST00000538825 | chr10 | 47762533 | 47762615 | + | TSF |
| 3% | chr10 | 47756033 | 47756092 | + | ENST00000340243; ENST00000374277; ENST00000538825 | chr10 | 47762533 | 47762615 | + | TSF |
| 3% | chr10 | 47756033 | 47756092 | + | ENST00000340243; ENST00000374277; ENST00000538825 | chr10 | 47762533 | 47762615 | + | TSF |
| 3% | chr4 | 57319769 | 57319927 | + | ENST00000514888; ENST00000264221; ENST00000505164; ENST00000399688; ENST00000512576 | chr4 | 57321183 | 57321327 | + | TSF |
| 3% | chr4 | 57319769 | 57319927 | + | ENST00000514888; ENST00000264221; ENST00000505164; ENST00000399688; ENST00000512576 | chr4 | 57321183 | 57321327 | + | TSF |
| 3% | chr4 | 57319769 | 57319927 | + | ENST00000514888; ENST00000264221; ENST00000505164; ENST00000399688; ENST00000512576 | chr4 | 57321183 | 57321327 | + | TSF |
| 3% | chr20 | 62328681 | 62328875 | + | ENST00000369996 | chr20 | 62334477 | 62334522 | + | TSF |
| 3% | chr17 | 16012226 | 16012100 | − | ENST00000268712; ENST00000395851; ENST00000395848 | chr17 | 16009741 | 16009580 | − | TSF |
| 3% | chr17 | 16012226 | 16012100 | − | ENST00000268712; ENST00000395851; ENST00000395848 | chr17 | 16009741 | 16009580 | − | TSF |
| 3% | chr1 | 63955889 | 63955754 | − | ENST00000371092; ENST00000271002; SENST00000489099; ENT00000283568 | chr1 | 63952444 | 63951983 | − | TSF |
| 3% | chr1 | 63955889 | 63955754 | − | ENST00000371092; ENST00000271002; SENST00000489099; ENT00000283568 | chr1 | 63952444 | 63951983 | − | TSF |
| 3% | chr17 | 79912179 | 79912132 | − | ENST00000409678 | chr17 | 79911834 | 79911647 | − | TSF |
| 3% | chr14 | 106208132 | 106207921 | − | ENST00000390548; ENST00000390549; ENST00000390542 | chr14 | 106043673 | 106043390 | − | TSF |
| 3% | chr14 | 106208132 | 106207921 | − | ENST00000390548; ENST00000390549; ENST00000390542 | chr14 | 106043673 | 106043390 | − | TSF |
| 3% | chr12 | 111803370 | 111803368 | − | ENST00000361483 | chr12 | 111803267 | 111803247 | − | TSF |
| 3% | chr19 | 46627413 | 46627143 | − | ENST00000341415 | chr19 | 46623577 | 46622963 | − | TSF |
| 3% | chr7 | 98741403 | 98741349 | − | ENST00000361368; ENST00000361125 | chr7 | 98680363 | 98679576 | − | TSF |

TABLE 22

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 62% | chr7 | 116364854 | 116364901 | + | chr7 | 116371722 | 116371913 | + | ENST00000397752; ENST00000318493; ENST00000436117 | TAF |
| 62% | chr7 | 116364854 | 116364901 | + | chr7 | 116371722 | 116371913 | + | ENST00000397752; ENST00000318493; ENST00000436117 | TAF |
| 62% | chr7 | 116364854 | 116364901 | + | chr7 | 116371722 | 116371913 | + | ENST00000397752; ENST00000318493; ENST00000436117 | TAF |
| 52% | chr7 | 56018506 | 56018522 | + | chr7 | 56020872 | 56021011 | + | ENST00000426595 | TSF |
| 48% | chr11 | 93468219 | 93468129 | − | chr11 | 93467826 | 93467791; 93467814 | − | ENST00000393259; ENST00000527169 | TAF |
| 48% | chr11 | 93468219 | 93468129 | − | chr11 | 93467826 | 93467791; 93467814 | − | ENST00000393259; ENST00000527169 | TAF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 47% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 47% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 47% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 47% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 41% | chr4 | 39699858 | 39699922 | + | chr4 | 39739040 | 39739133 | + | ENST00000261427; ENST00000510934; ENST00000295963; ENST00000445950 | TAF |
| 41% | chr4 | 39699858 | 39699922 | + | chr4 | 39739040 | 39739133 | + | ENST00000261427; ENST00000510934; ENST00000295963; ENST00000445950 | TAF |
| 41% | chr4 | 39699858 | 39699922 | + | chr4 | 39739040 | 39739133 | + | ENST00000261427; ENST00000510934; ENST00000295963; ENST00000445950 | TAF |
| 41% | chr4 | 39699858 | 39699922 | + | chr4 | 39739040 | 39739133 | + | ENST00000261427; ENST00000510934; ENST00000295963; ENST00000445950 | TAF |
| 41% | chr3 | 185411133 | 185410965 | − | chr3 | 185410550 | 185410487 | − | ENST00000382199; ENST00000421047; ENST00000457616; ENST00000346192 | TAF |
| 41% | chr3 | 185411133 | 185410965 | − | chr3 | 185410550 | 185410487 | − | ENST00000382199; ENST00000421047; ENST00000457616; ENST00000346192 | TAF |
| 40% | chr9 | 100872455 | 100872351 | − | chr9 | 100872266 | 100872171 | − | ENST00000375098; ENST0000034 ENST000003420431469; | TAF |
| 39% | chr3 | 128359904 | 128359849 | − | chr3 | 128356948 | 128356642 | − | ENST0000296255 | TAF |
| 38% | chr12 | 64687157 | 64687061 | − | chr12 | 64679840 | 64679734 | − | ENST00000543942; ENST00000333722 | TAF |
| 37% | chr10 | 5826921 | 5825287 | − | chr10 | 5815904 | 5815805 | − | ENST00000380191; ENST00000447751; ENST00000380132; ENST00000380181; ENST00000456041 | TAF |
| 37% | chr10 | 5826921 | 5825287 | − | chr10 | 5815904 | 5815805 | − | ENST00000380191; ENST00000447751; ENST00000380132; ENST00000380181; ENST00000456041 | TAF |
| 37% | chr10 | 5826921 | 5825287 | − | chr10 | 5815904 | 5815805 | − | ENST00000380191; ENST00000447751; ENST00000380132; ENST00000380181; ENST00000456041 | TAF |
| 36% | chr3 | 47700203 | 47700048 | − | chr3 | 47680270 | 47680215 | − | ENST00000254480 | TAF |
| 35% | chr4 | 39585332 | 39585284 | − | chr4 | 39459881 | 39459814 | − | ENST00000295955; ENST00000449470; ENST00000508595; ENST00000503040; ENST00000504470 | TSF |
| 35% | chr4 | 39585332 | 39585284 | − | chr4 | 39459881 | 39459814 | − | ENST00000295955; ENST00000449470; ENST00000508595; ENST00000503040; ENST00000504470 | TSF |
| 35% | chr4 | 39585332 | 39585284 | − | chr4 | 39459881 | 39459814 | − | ENST00000295955; ENST00000449470; ENST00000508595; ENST00000503040; ENST00000504470 | TSF |
| 35% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 35% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 35% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 35% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 35% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 32% | chr17 | 30771499 | 30771536 | + | chr17 | 30773963 | 30774064 | + | ENST00000261712; ENST00000457654; ENST00000579451 | TAF |
| 32% | chr17 | 30771499 | 30771536 | + | chr17 | 30773963 | 30774064 | + | ENST00000261712; ENST00000457654; ENST00000579451 | TAF |

TABLE 22-continued

Transcript fusion for Esophageal Carcinoma (ESCA) Coordinates of the fusion sequences for which the donor is the TE.

| 1 | 2' | 3 | 4 | 5' | 6' | 7 | 8' | 9' | 10' | 11' |
|---|---|---|---|---|---|---|---|---|---|---|
| 30% | chr19 | 56187371 | 56187420 | 1 | chr19 | 56189893 | 56190221 | + | ENST00000411543 | TAF |
| 29% | chr5 | 76107394 | 76108135 | + | chr5 | 76128515 | 76129626 | + | ENST00000296677 | TSF |
| 28% | chr21 | 42597177 | 42597622 | + | chr21 | 42598193 | 42598281 | + | ENST00000328735; ENST00000330333; ENST00000347667 | TAF |
| 28% | chr21 | 42597177 | 42597622 | + | chr21 | 42598193 | 42598281 | + | ENST00000328735; ENST00000330333; ENST00000347667 | TAF |
| 28% | chr21 | 42597177 | 42597622 | + | chr21 | 42598193 | 42598281 | + | ENST00000328735; ENST00000330333; ENST00000347667 | TAF |
| 28% | chr17 | 74261446 | 74261484 | + | chr17 | 74261988 | 74262050 | + | ENST00000327490 | TAF |
| 28% | chr12 | 122430912 | 122431615 | + | chr12 | 122437622 | 122437850 | + | ENST00000288912 | TAF |
| 28% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 28% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 28% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 28% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 28% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 28% | chr12 | 123873690 | 123873729 | + | chr12 | 123873980 | 123874101 | + | ENST00000330479; ENST00000402868 | TSF |
| 27% | chr5 | 823586 | 823504 | − | chr5 | 822010 | 821976 | − | ENST00000424784; ENST00000283441 | TAF |
| 27% | chr11 | 70006969 | 70007088 | + | chr11 | 70007267 | 70007468 | + | ENST00000355303; ENST00000398543; ENST00000538023; ENST00000316296; ENST00000530676; ENST00000531349; ENST00000531300 | TSF |
| 27% | chr11 | 70006969 | 70007088 | + | chr11 | 70007267 | 70007468 | + | ENST00000355303; ENST00000398543; ENST00000538023; ENST00000316296; ENST00000530676; ENST00000531349; ENST00000531300 | TSF |
| 27% | chr11 | 70006969 | 70007088 | + | chr11 | 70007267 | 70007468 | + | ENST00000355303; ENST00000398543; ENST00000538023; ENST00000316296; ENST00000530676; ENST00000531349; ENST00000531300 | TSF |
| 25% | chr12 | 122387836 | 122388242 | + | chr12 | 122389386 | 122389436 | + | ENST00000288912; ENST00000397454 | TSF |
| 25% | chr12 | 122387836 | 122388242 | + | chr12 | 122389386 | 122389436 | + | ENST00000288912; ENST00000397454 | TSF |
| 24% | chr2 | 9737072 | 9736908 | − | chr2 | 9731644 | 9731521 | − | ENST00000381844; ENST00000238081; ENST00000446619 | TAF |
| 24% | chr2 | 9737072 | 9736908 | − | chr2 | 9731644 | 9731521 | − | ENST00000381844; ENST00000238081; ENST00000446619 | TAF |
| 24% | chr16 | 23118718 | 23118652 | − | chr16 | 23117808 | 23117720 | − | ENST00000219689 | TAF |
| 23% | chr22 | 37419605 | 37419606 | + | chr22 | 37420233 | 37420851 | + | ENST00000397129 | TAF |
| 23% | chr16 | 603045 | 603077 | + | chr16 | 603343 | 603516 | + | ENST00000219611 | TAF |
| 23% | chr16 | 603045 | 603138 | + | chr16 | 603343 | 603516 | + | ENST00000219611 | TAF |
| 23% | chr5 | 76107394 | 76108212 | + | chr5 | 76128515 | 76129626 | + | ENST00000296677 | TSF |
| 23% | chr10 | 89682344 | 89682384 | + | chr10 | 89685270 | 89685314 | + | ENST00000371953 | TSF |
| 22% | chr15 | 43889497 | 43889601 | + | chr15 | 43890391 | 43890525 | + | ENST00000300283; ENST00000441322 | TAF |
| 22% | chr5 | 10732874 | 10732658 | − | chr5 | 10683683 | 10683641 | − | ENST00000230895 | TAF |
| 22% | chr17 | 78344149 | 78344187 | + | chr17 | 78345674 | 78345785 | + | ENST00000508628; ENST00000582970; ENST00000336301 | TSF |
| 22% | chr1 | 44446234 | 44446286 | + | chr1 | 44446781 | 44447145 | + | ENST00000309519 | TSF |
| 21% | chr20 | 35844460 | 35844528 | + | chr20 | 35852281 | 35852372 | + | ENST00000237530; ENST00000373622 | TSF |
| 21% | chr20 | 35844460 | 35844528 | + | chr20 | 35852281 | 35852372 | + | ENST00000237530; ENST00000373622 | TAF |
| 21% | chr12 | 122387836 | 122388242 | + | chr12 | 122392026 | 122392240 | + | ENST00000288912; ENST00000397454 | TSF |
| 21% | chr12 | 122387836 | 122388242 | + | chr12 | 122392026 | 122392240 | + | ENST00000288912; ENST00000397454 | TSF |
| 20% | chr12 | 6602868 | 6602840 | − | chr12 | 6602138 | 6602028 | | ENST00000229238 | TAF |
| 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; | TAF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| | 20% | chr13 | 98628730 | 98628756 | + | chr13 | 98628947 | 98629040; 98629046 | + | ENST00000489058; ENST00000481689; ENST00000480611; ENST00000485433; ENST00000496368; ENST00000421861 ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 20% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| | 20% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| | 20% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 20% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 20% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 19% | chr15 | 41968651 | 41968463 | − | chr15 | 41815513 | 41815443 | − | ENST00000561603; ENST00000304330; ENST00000562303 | TAF |
| 19% | chr15 | 41968651 | 41968463 | − | chr15 | 41815513 | 41815443 | − | ENST00000561603; ENST00000304330; ENST00000562303 | TAF |
| 19% | chr15 | 41968651 | 41968463 | − | chr15 | 41815513 | 41815443 | − | ENST00000561603; ENST00000304330; ENST00000562303 | TAF |
| 18% | chr5 | 135398466 | 135398602 | + | chr5 | 135398875 | 135398915; 135398898 | + | ENST00000442011; ENST00000305126; ENST00000514554; ENST00000508076; ENST00000503087 | TAF |
| 18% | chr5 | 135398466 | 135398602 | + | chr5 | 135398875 | 135398915; 135398898 | + | ENST00000442011; ENST00000305126; ENST00000514554; ENST00000508076; ENST00000503087 | TAF |
| 18% | chr19 | 48240207 | 48240273 | + | chr19 | 48244138 | 48244689 | + | ENST00000263277; ENST00000538399 | TAF |
| 18% | chr11 | 87906665 | 87906580 | − | chr11 | 87883123 | 87882843 | − | ENST00000243662; ENST00000526372 | TAF |
| 18% | chr19 | 55562151 | 55562068 | − | chr19 | 55560131 | 55560027 | − | ENST00000415061; ENST00000291892; ENST00000396247; ENST00000592573 | TAF |
| 18% | chr19 | 55562151 | 55562068 | − | chr19 | 55560131 | 55560027 | − | ENST00000415061; ENST00000291892; ENST00000396247; ENST00000592573 | TAF |
| 18% | chr6 | 138423138 | 138423021 | − | chr6 | 138417631 | 138417491 | − | ENST00000421351 | TAF |
| 18% | chr9 | 119603649 | 119602892 | − | chr9 | 119583062 | 119582896 | − | ENST00000373996; ENST00000313400; ENST00000373986; ENST00000361209 | TAF |
| 18% | chr22 | 21972574 | 21972670 | + | chr22 | 21975804 | 21975958 | + | ENST00000458578; ENST00000342192; ENST00000545681 | TSF |
| 17% | chr10 | 5077666 | 5077808 | + | chr10 | 5138602 | 5138769 | + | ENST00000602997; ENST00000605149; ENST00000380554 | TAF |
| 17% | chr10 | 5077666 | 5077808 | + | chr10 | 5138602 | 5138769 | + | ENST00000602997; ENST00000605149; ENST00000380554 | TAF |
| 17% | chr5 | 175826144 | 175825958 | − | chr5 | 175825048 | 175824931; 175824945 | − | ENST00000310418; ENST00000345807; ENST00000508425 | TAF |
| 17% | chr5 | 175826144 | 175825958 | − | chr5 | 175825048 | 175824931; 175824945 | − | ENST00000310418; ENST00000345807; ENST00000508425 | TAF |
| 17% | chr5 | 175826144 | 175825958 | − | chr5 | 175825048 | 175824931; 175824945 | − | ENST00000310418; ENST00000345807; ENST00000508425 | TAF |
| 17% | chr1 | 159014388 | 159014421 | + | chr1 | 159015087 | 159015254 | + | ENST00000368131; ENST00000295809; ENST00000359709; ENST00000430894 | TAF |
| 17% | chr1 | 159014388 | 159014421 | + | chr1 | 159015087 | 159015254 | + | ENST00000368131; ENST00000295809; ENST00000359709; ENST00000430894 | TAF |
| 17% | chr8 | 82194688 | 82194727 | + | chr8 | 82195601 | 82195773 | + | ENST00000297258 | TAF |
| 17% | chr2 | 24544896 | 24544683 | − | chr2 | 24538093 | 24538001 | − | ENST00000361999; ENST00000355123; ENST00000406921; ENST00000412011 | TAF |
| 17% | chr2 | 24544896 | 24544683 | − | chr2 | 24538093 | 24538001 | − | ENST00000361999; ENST00000355123; ENST00000406921; ENST00000412011 | TAF |
| 17% | chr2 | 24544896 | 24544683 | − | chr2 | 24538093 | 24538001 | − | ENST00000361999; ENST00000355123; ENST00000406921; ENST00000412011 | TAF |
| 17% | chr2 | 24544896 | 24544683 | − | chr2 | 24538093 | 24538001 | − | ENST00000361999; ENST00000355123; ENST00000406921; ENST00000412011 | TAF |
| 17% | chr15 | 66170740 | 66170790 | + | chr15 | 66172009 | 66172089; 66172017 | + | ENST00000564910; ENST00000261890; ENST00000569896; ENST000 00567671 | TSF |
| 17% | chr15 | 66170740 | 66170790 | + | chr15 | 66172009 | 66172089; 66172017 | + | ENST00000564910; ENST00000261890; ENST00000569896; ENST00000567671 | TSF |
| 17% | chr15 | 66170740 | 66170790 | + | chr15 | 66172009 | 66172089; 66172017 | + | ENST00000564910; ENST00000261890; ENST00000569896; ENST00000567671 | TSF |
| 17% | chr14 | 105172936 | 105173038 | + | chr14 | 105173247 | 105173388 | + | ENST00000330634; ENST00000392634 | TSF |
| 17% | chr14 | 105172936 | 105173038 | + | chr14 | 105173247 | 105173388 | + | ENST00000330634; ENST00000392634 | TSF |
| 17% | chr19 | 2141057 | 2140989 | − | chr19 | 2138713 | 2138618 | − | ENST00000355272; ENST00000356926; ENST00000350812; ENST00000345016 | TSF |
| 17% | chr19 | 2141057 | 2140989 | − | chr19 | 2138713 | 2138618 | − | ENST00000355272; ENST00000356926; ENST00000350812; ENST00000345016 | TSF |
| 17% | chr19 | 2141057 | 2140989 | − | chr19 | 2138713 | 2138618 | − | ENST00000355272; ENST00000356926; ENST00000350812; ENST000 00345016 | TSF |
| 17% | chr19 | 2141057 | 2140989 | − | chr19 | 2138713 | 2138618 | − | ENST00000355272; ENST00000356926; ENST00000350812; ENST00000345016 | TSF |
| 16% | chr1 | 159014388 | 159014421 | + | chr1 | 159019222 | 159019389 | + | ENST00000368132; ENST00000295809; ENST00000359709; ENST00000430894 | TAF |
| 16% | chr4 | 15791827 | 15792541 | + | chr4 | 15818134 | 15818263 | + | ENST00000502843; ENST00000226279 | TAF |
| 16% | chr4 | 15791827 | 15792541 | + | chr4 | 15818134 | 15818263 | + | ENST00000502843; ENST00000226279 | TAF |
| 16% | chr15 | 43989318 | 43989422 | + | chr15 | 43990212 | 43990346 | + | ENST00000434505; ENST00000413453 | TAF |

TABLE 22-continued

Transcript fusion for Esophageal Carcinoma (ESCA) Coordinates of the fusion sequences for which the donor is the TE.

| 1 | 2' | 3 | 4 | 5' | 6' | 7 | 8' | 9' | 10' | 11' |
|---|---|---|---|---|---|---|---|---|---|---|
| 16% | chr2 | 242174499 | 242174421 | − | chr2 | 242173378 | 242173235; 242173268 | − | ENST00000391975; ENST00000391976; ENST00000310931; ENST00000427183; ENST00000373292 | TAF |
| 16% | chr2 | 242174499 | 242174421 | − | chr2 | 242173378 | 242173235; 242173268 | − | ENST00000391975; ENST00000391976; ENST00000310931; ENST00000427183; ENST00000373292 | TAF |
| 16% | chr3 | 141642131 | 141642345 | + | chr3 | 141644373 | 141644543 | + | ENST00000286371; ENST00000462082 | TAF |
| 16% | chr12 | 21011867 | 21011909 | + | chr12 | 21013951 | 21014072 | + | ENST00000540853; ENST00000261196; ENST00000381545; ENST00000540229; ENST00000553473 | TAF |
| 16% | chr12 | 21011867 | 21011909 | + | chr12 | 21013951 | 21014072 | + | ENST00000540853; ENST00000261196; ENST00000381545; ENST00000540229; ENST00000553473 | TAF |
| 16% | chr12 | 21011867 | 21011909 | + | chr12 | 21013951 | 21014072 | + | ENST00000540853; ENST00000261196; ENST00000381545; ENST00000540229; ENST00000553473 | TAF |
| 16% | chr19 | 35995931 | 35995843 | − | chr19 | 35994349 | 35994323; 35994334 | − | ENST00000474928; ENST00000488892; ENST00000461300; ENST00000447113; ENST00000392206; ENST00000440396; ENST00000458071; ENST00000418261; ENST00000424570; ENST00000451297; ENST00000450261 | TAF |
| 16% | chr19 | 35995931 | 35995843 | − | chr19 | 35994349 | 35994323; 35994334 | − | ENST00000474928; ENST00000488892; ENST00000461300; ENST00000447113; ENST00000392206; ENST00000440396; ENST00000458071; ENST00000418261; ENST00000424570; ENST00000451297; ENST00000450261 | TAF |
| 16% | chr13 | 99121170 | 99121063 | − | chr13 | 99118815 | 99118630 | − | ENST00000376554; ENST00000397517; ENST00000376547; ENST00000539966; ENST00000444574 | TAF |
| 16% | chr13 | 99121170 | 99121063 | − | chr13 | 99118815 | 99118630 | − | ENST00000376554; ENST00000397517; ENST00000376547; ENST00000539966; ENST00000444574 | TAF |
| 16% | chr13 | 99121170 | 99121063 | − | chr13 | 99118815 | 99118630 | − | ENST00000376554; ENST00000397517; ENST00000376547; ENST00000539966; ENST00000444574 | TAF |
| 16% | chr9 | 117824597 | 117824593 | − | chr9 | 117822281 | 117822009 | − | ENST00000350763; ENST00000341037; ENST00000423613 | TSF |
| 16% | chr9 | 117824597 | 117824593 | − | chr9 | 117822281 | 117822009 | − | ENST00000350763; ENST00000341037; ENST00000423613 | TSF |
| 16% | chr9 | 117824597 | 117824593 | − | chr9 | 117822281 | 117822009 | − | ENST00000350763; ENST00000341037; ENST00000423613 | TSF |
| 15% | chr19 | 55559415 | 55559414 | − | chr19 | 55558856 | 55558755 | − | ENST00000415061; ENST00000396247 | TAF |
| 15% | chr11 | 752380 | 752481 | + | chr11 | 755879 | 756002 | + | ENST00000319006; ENST00000528097; ENST00000530440 | TAF |
| 15% | chr11 | 752380 | 752481 | + | chr11 | 755879 | 756002 | + | ENST00000319006; ENST00000528097; ENST00000530440 | TAF |
| 15% | chr11 | 752380 | 752481 | + | chr11 | 755879 | 756002 | + | ENST00000319006; ENST00000528097; ENST00000530440 | TAF |
| 15% | chr19 | 1600051 | 1599987 | − | chr19 | 1599559 | 1599439 | − | ENST00000585937; ENST00000591899; ENST00000589880; ENST00000585671 | TAF |
| 15% | chr14 | 65406849 | 65406835 | − | chr14 | 65406556 | 65406206 | − | ENST00000389614; ENST00000557049 | TAF |
| 15% | chr10 | 105819324 | 105819196 | − | chr10 | 105817948 | 105817904 | − | ENST00000353479; ENST00000369733 | TSF |
| 15% | chr10 | 105819324 | 105819196 | − | chr10 | 105817948 | 105817904 | − | ENST00000353479; ENST00000369733 | TSF |
| 15% | chr17 | 65894489 | 65894534 | + | chr17 | 65899905 | 65900034 | + | ENST00000544778; ENST00000321892; ENST00000335221; ENST00000306378; ENST00000424123 | TSF |
| 15% | chr17 | 65894489 | 65894534 | + | chr17 | 65899905 | 65900034 | + | ENST00000544778; ENST00000321892; ENST00000335221; ENST00000306378; ENST00000424123 | TSF |
| 15% | chr17 | 65894489 | 65894534 | + | chr17 | 65899905 | 65900034 | + | ENST00000544778; ENST00000321892; ENST00000335221; ENST00000306378; ENST00000424123 | TSF |
| 14% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 14% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 14% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 14% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 14% | chr13 | 43628887 | 43629679 | + | chr13 | 43639822 | 43639873 | + | ENST00000379221 | TAF |
| 14% | chr1 | 27430428 | 27430228 | − | chr1 | 27429803 | 27429714 | − | ENST00000263980; ENST00000545949 | TAF |
| 14% | chr5 | 148909179 | 148909167 | − | chr5 | 148904734 | 148904608 | − | ENST00000261798; ENST00000377843; ENST00000515768 | TAF |
| 14% | chr5 | 148909179 | 148909167 | − | chr5 | 148904734 | 148904608 | − | ENST00000261798; ENST00000377843; ENST00000515768 | TAF |
| 14% | chr5 | 148909179 | 148909167 | − | chr5 | 148904734 | 148904608 | − | ENST00000261798; ENST00000377843; ENST00000515768 | TAF |
| 14% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 14% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 14% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 14% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 14% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 14% | chr10 | 126455800 | 126455793 | − | chr10 | 126454177 | 126453961 | − | ENST00000494792; ENST00000368836 | TAF |
| 14% | chr10 | 126455800 | 126455793 | − | chr10 | 126454177 | 126453961 | − | ENST00000494792; ENST00000368836 | TAF |
| 14% | chr12 | 86274449 | 86274547 | + | chr12 | 86276001 | 86276153 | + | ENST00000551529; ENST00000256010 | TAF |
| 14% | chr1 | 201354798 | 201354740 | | chr1 | 201353963 | 201353920 | − | ENST00000503578; ENST00000391967; ENST00000367313 | TSF |
| 14% | chr1 | 201354798 | 201354740 | | chr1 | 201353963 | 201353920 | − | ENST00000503578; ENST00000391967; ENST00000367313 | TSF |
| 14% | chr10 | 79700435 | 79700428 | − | chr10 | 79628955 | 79628887 | − | ENST00000372391; ENST00000372388; ENST00000468332 | TSF |
| 14% | chr10 | 79700435 | 79700428 | − | chr10 | 79628955 | 79628887 | − | ENST00000372391; ENST00000372388; ENST00000468332 | TSF |
| 14% | chr10 | 79700435 | 79700428 | − | chr10 | 79628955 | 79628887 | − | ENST00000372391; ENST00000372388; ENST00000468332 | TSF |
| 13% | chr19 | 42217251 | 42217314 | + | chr19 | 42218890 | 42219168 | + | ENST00000398599; ENST00000221992; ENST00000405816; ENST00000595113 | TAF |
| 13% | chr19 | 42217251 | 42217314 | + | chr19 | 42218890 | 42219168 | + | ENST00000398599; ENST00000221992; ENST00000405816; ENST00000595113 | TAF |
| 13% | chr19 | 42217251 | 42217314 | + | chr19 | 42218890 | 42219168 | + | ENST00000398599; ENST00000221992; ENST00000405816; ENST00000595113 | TAF |
| 13% | chr4 | 38696010 | 38696173 | + | chr4 | 38696367 | 38696527 | + | ENST00000261438 | TAF |
| 13% | chr9 | 131002678 | 131002811 | + | chr9 | 131004511 | 131004624 | + | ENST00000475805; ENST00000341179; ENST00000372923; ENST00000393594; ENST00000486160 | TAF |
| 13% | chr9 | 131002678 | 131002811 | + | chr9 | 131004511 | 131004624 | + | ENST00000475805; ENST00000341179; ENST00000372923; ENST00000393594; ENST00000486160 | TAF |
| 13% | chr21 | 19289273 | 19289717 | + | chr21 | 19628826 | 19629135 | + | ENST00000299295; ENST00000543733 | TAF |
| 13% | chr19 | 39347374 | 39346206 | − | chr19 | 39338074 | 39337956 | − | ENST00000221419; ENST00000601449; ENST00000600233; ENST00000601813 | TSF |
| 13% | chr19 | 39347374 | 39346206 | − | chr19 | 39338074 | 39337956 | − | ENST00000221419; ENST00000601449; ENST00000600233; ENST00000601813 | TSF |
| 13% | chr19 | 39347374 | 39346206 | − | chr19 | 39338074 | 39337956 | − | ENST00000221419; ENST00000601449; ENST00000600233; ENST00000601813 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 13% | chr6 | 80022917 | 80022085 | − | chr6 | 79924739 | 79924689 | | ENST00000275036; ENST00000344726 | TSF |
| 13% | chr6 | 80022917 | 80022085 | − | chr6 | 79924739 | 79924689 | | ENST00000275036; ENST00000344726 | TSF |
| 13% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 13% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 13% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 13% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 13% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 13% | chr17 | 17816540 | 17815566 | − | chr17 | 17810845 | 17810761 | − | ENST00000581396; ENST00000379504; ENST00000318094; ENST00000395739; ENST00000535933; ENST00000540946; ENST00000542206 | TSF |
| 12% | chr9 | 130900342 | 130900452 | + | chr9 | 130913917 | 130913996 | + | ENST00000373017; ENST00000540948; ENST00000277480; ENST00000373013 | TAF |
| 12% | chr9 | 130900342 | 130900452 | + | chr9 | 130913917 | 130913996 | + | ENST00000373017; ENST00000540948; ENST00000277480; ENST00000373013 | TAF |
| 12% | chr1 | 201356770 | 201356732 | − | chr1 | 201356306 | 201355463 | | ENST00000391967; ENST00000367313 | TAF |
| 12% | chr12 | 123873690 | 123873729 | + | chr12 | 123875258 | 123875333 | + | ENST00000330479; ENST00000402868; ENST00000437519; ENST00000437502 | TAF |
| 12% | chr12 | 123873690 | 123873729 | + | chr12 | 123875258 | 123875333 | + | ENST00000330479; ENST00000402868; ENST00000437519; ENST00000437502 | TAF |
| 12% | chr12 | 123873690 | 123873729 | + | chr12 | 123875258 | 123875333 | + | ENST00000330479; ENST00000402868; ENST00000437519; ENST00000437502 | TAF |
| 12% | chr7 | 139048120 | 139048198 | + | chr7 | 139060808 | 139060902 | + | ENST00000541170; ENST00000541515; ENST00000354926; ENST00000456182; ENST00000263545 | TAF |
| 12% | chr7 | 139048120 | 139048198 | + | chr7 | 139060808 | 139060902 | + | ENST00000541170; ENST00000541515; ENST00000354926; ENST00000456182; ENST00000263545 | TAF |
| 12% | chr7 | 139048120 | 139048198 | + | chr7 | 139060808 | 139060902 | + | ENST00000541170; ENST00000541515; ENST00000354926; ENST00000456182; ENST00000263545 | TAF |
| 12% | chr21 | 47410358 | 47410419 | + | chr21 | 47410687 | 47410740 | + | ENST00000361866 | TAF |
| 12% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 12% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 12% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 12% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 12% | chr2 | 29015237 | 29015290 | + | chr2 | 29016729 | 29016863 | + | ENST00000358506; ENST00000296122; ENST00000395366 | TAF |
| 12% | chr6 | 128380624 | 128380622 | − | chr6 | 128330413 | 128330275 | − | ENST00000368226; ENST00000368227; ENST00000532331; ENST00000368213; ENST00000368210; ENST00000368207; ENST00000415046 | TAF |
| 12% | chr6 | 128380624 | 128380622 | − | chr6 | 128330413 | 128330275 | − | ENST00000368226; ENST00000368227; ENST00000532331; ENST00000368213; ENST00000368210; ENST00000368207; ENST00000415046 | TAF |
| 12% | chr6 | 128380624 | 128380622 | − | chr6 | 128330413 | 128330275 | − | ENST00000368226; ENST00000368227; ENST00000532331; ENST00000368213; | TAF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 12% | chr6 | 128380624 | 128380622 | − | chr6 | 128330413 | 128330275 | − | ENST00000368210; ENST00000368207; ENST00000415046 ENST00000368226; ENST00000368227; ENST00000532331; ENST00000368213 | TAF |
| 12% | chr6 | 128380624 | 128380622 | − | chr6 | 128330413 | 128330275 | − | ENST00000368210; ENST00000368207; ENST00000415046 ENST00000368226; ENST00000368227; ENST00000532331; ENST00000368213 | TAF |
| 12% | chr6 | 128380624 | 128380622 | − | chr6 | 128330413 | 128330275 | − | ENST00000368210; ENST00000368207; ENST00000415046 ENST00000368226; ENST00000368227; ENST00000532331; ENST00000368213 | TAF |
| 12% | chr6 | 128380624 | 128380622 | − | chr6 | 128330413 | 128330275 | − | ENST00000368210; ENST00000368207; ENST00000415046 ENST00000368226; ENST00000368227; ENST00000532331; ENST00000368213 | TAF |
| 12% | chr17 | 38639751 | 38639593 | − | chr17 | 38638668 | 38638576 | − | ENST00000254051 | TSF |
| 12% | chr7 | 56020443 | 56020541 | + | chr7 | 56020872 | 56021011 | + | ENST00000426595 | TSF |
| 12% | chr15 | 40187476 | 40186733 | − | chr15 | 40099459 | 40099207 | − | ENST00000561100; ENST00000543580 | TSF |
| 11% | chr13 | 43659219 | 43659268 | + | chr13 | 43659904 | 43659974 | + | ENST00000379221 | TAF |
| 11% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 11% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 11% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 11% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |
| 11% | chr8 | 134272238 | 134272103 | − | chr8 | 134271473 | 134271411; 134271461 | − | ENST00000323851; ENST00000517599; ENST00000537882; ENST00000414097; ENST00000522476; ENST00000522377; ENST00000520230; ENST00000518480; ENST00000519228; ENST00000519580; ENST00000522890; ENST00000520943; ENST00000521544; ENST00000522738 | TAF |
| 11% | chr17 | 18390031 | 18390254 | + | chr17 | 18390961 | 18391071 | + | ENST00000581545; ENST00000582333; ENST00000328114; ENST00000412421; ENST00000583322; ENST00000584941 | TAF |
| 11% | chr17 | 18390031 | 18390254 | + | chr17 | 18390961 | 18391071 | + | ENST00000581545; ENST00000582333; ENST00000328114; ENST00000412421; ENST00000583322; ENST00000584941 | TAF |
| 11% | chr17 | 18390031 | 18390254 | + | chr17 | 18390961 | 18391071 | + | ENST00000581545; ENST00000582333; ENST00000328114; ENST00000412421; ENST00000583322; ENST00000584941 | TAF |
| 11% | chr17 | 18390031 | 18390254 | + | chr17 | 18390961 | 18391071 | + | ENST00000581545; ENST00000582333; ENST00000328114; ENST00000412421; ENST00000583322; ENST00000584941 | TAF |
| 11% | chr17 | 18390031 | 18390254 | + | chr17 | 18390961 | 18391071 | + | ENST00000581545; ENST00000582333; ENST00000328114; ENST00000412421; ENST00000583322; ENST00000584941 | TAF |
| 11% | chr2 | 201253013 | 201253278 | + | chr2 | 201253946 | 201254006 | + | ENST00000409755; ENST00000409151 | TAF |
| 11% | chr16 | 19487389 | 19487488 | + | chr16 | 19488762 | 19488840 | + | ENST00000541464; ENST00000381414; ENST00000396229; ENST00000542583; ENST00000219821; ENST00000561503; ENST00000564959 | TAF |
| 11% | chr16 | 19487389 | 19487488 | + | chr16 | 19488762 | 19488840 | + | ENST00000541464; ENST00000381414; ENST00000396229; ENST00000542583; ENST00000219821; ENST00000561503; ENST00000564959 | TAF |
| 11% | chr17 | 79214190 | 79214239 | + | chr17 | 79214787 | 79214816; 79214953 | + | ENST00000431388; ENST00000576002 | TAF |
| 11% | chr17 | 79214190 | 79214239 | + | chr17 | 79214787 | 79214816; 79214953 | + | ENST00000431388; ENST00000576002 | TAF |
| 11% | chr10 | 120902016 | 120901765 | − | chr10 | 120900831 | 120900754 | − | ENST00000355697; ENST00000330036 | TAF |
| 11% | chr14 | 65408081 | 65408080 | − | chr14 | 65406556 | 65406206 | − | ENST00000389614; ENST00000557049 | ITAF |
| 11% | chr12 | 27557551 | 27557646 | + | chr12 | 27568802 | 27568880 | + | ENST00000544915; ENST00000395901; ENST00000546179; ENST00000311001; ENST00000261178; ENST00000266503; ENST00000457040; ENST00000542388 | TSF |
| 11% | chr12 | 27557551 | 27557646 | + | chr12 | 27568802 | 27568880 | + | ENST00000544915; ENST00000395901; ENST00000546179; ENST00000311001; ENST00000261178; ENST00000266503; ENST00000457040; ENST00000542388 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 11% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 11% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 11% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 11% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 11% | chr19 | 39347374 | 39346430 | − | chr19 | 39338074 | 39337956 | − | ENST00000221419; ENST00000601449; ENST00000600233; ENST00000601813 | TSF |
| 11% | chr19 | 39347374 | 39346430 | − | chr19 | 39338074 | 39337956 | − | ENST00000221419; ENST00000601449; ENST00000600233; ENST00000601813 | TSF |
| 11% | chr19 | 39347374 | 39346430 | − | chr19 | 39338074 | 39337956 | − | ENST00000221419; ENST00000601449; ENST00000600233; ENST00000601813 | TSF |
| 11% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 11% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 11% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 11% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 11% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 11% | chr9 | 130732697 | 130732597 | − | chr9 | 130716204 | 130716084 | − | ENST00000373095 | TSF |
| 11% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 11% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 11% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 11% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 11% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 11% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 11% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 11% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |

TABLE 22-continued

Transcript fusion for Esophageal Carcinoma (ESCA) Coordinates of the fusion sequences for which the donor is the TE.

| 1 | 2' | 3 | 4 | 5' | 6' | 7 | 8' | 9' | 10' | 11' |
|---|---|---|---|---|---|---|---|---|---|---|
| 11% | chrX | 76851229 | 76851182 | − | chrX | 76849319 | 76849166 | − | ENST00000373344; ENST00000395603 | TSF |
| 11% | chr22 | 38620420 | 38620354 | − | chr22 | 38617717 | 38617476 | − | ENST00000361906; ENST00000361684 | TSF |
| 10% | chr19 | 42217251 | 42217314 | + | chr19 | 42223849 | 42224127; 42223947 | + | ENST00000398599; ENST00000221992; ENST00000405816; ENST00000595403 | TAF |
| 10% | chr19 | 42217251 | 42217314 | + | chr19 | 42223849 | 42224127; 42223947 | + | ENST00000398599; ENST00000221992; ENST00000405816; ENST00000595403 | TAF |
| 10% | chr5 | 179238653 | 179238682 | + | chr5 | 179249989 | 179250053 | + | ENST00000389805; ENST00000504627; ENST00000510187 | TAF |
| 10% | chr5 | 179238653 | 179238682 | + | chr5 | 179249989 | 179250053 | + | ENST00000389805; ENST00000504627; ENST00000510187 | TAF |
| 10% | chr5 | 179238653 | 179238682 | + | chr5 | 179249989 | 179250053 | + | ENST00000389805; ENST00000504627; ENST00000510187 | TAF |
| 10% | chr16 | 29915789 | 29915910 | + | chr16 | 29916173 | 29916286 | + | ENST00000563177; ENST00000483405; ENST00000308748; ENST00000414952; ENST00000566693 | TAF |
| 10% | chr16 | 29915789 | 29915910 | + | chr16 | 29916173 | 29916286 | + | ENST00000563177; ENST00000483405; ENST00000308748; ENST00000414952; ENST00000566693 | TAF |
| 10% | chr2 | 220407466 | 220407420 | − | chr2 | 220406911 | 220406338; 220406329 | − | ENST00000243776; ENST00000373891 | TAF |
| 10% | chr2 | 220407466 | 220407420 | − | chr2 | 220406911 | 220406338; 220406329 | − | ENST00000243776; ENST00000373891 | TAF |
| 10% | chr5 | 147206892 | 147206839 | − | chr5 | 147204269 | 147204224 | − | ENST00000296695 | TAF |
| 10% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 10% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 10% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 10% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 10% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 10% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 10% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 10% | chr19 | 5902574 | 5902426 | − | chr19 | 5897008 | 5896916 | − | ENST00000592091; ENST00000585661; ENST00000586349; ENST00000418389 | TAF |
| 10% | chr4 | 39933437 | 39933081 | − | chr4 | 39929784 | 39929581 | − | ENST00000303538; ENST00000503396 | TSF |
| 10% | chr4 | 39933437 | 39933081 | − | chr4 | 39929784 | 39929581 | − | ENST00000303538; ENST00000503396 | TSF |
| 10% | chr5 | 64050585 | 64050405 | − | chr5 | 64050189 | 64050142 | − | ENST00000513458 | TSF |
| 10% | chr5 | 167685522 | 167685690 | + | chr5 | 167687288 | 167687418 | + | ENST00000518659; ENST00000545108; ENST00000519204; ENST00000520394; ENST00000403607 | TSF |
| 10% | chr15 | 74004214 | 74004264 | + | chr15 | 74005275 | 74005297 | + | ENST00000318443; ENST00000537340; ENST00000318424; ENST00000564751; ENST00000561176; ENST00000559073 | TSF |
| 10% | chrX | 151410500 | 151410406 | − | chrX | 151393317 | 151393235 | − | ENST00000370314; ENST00000535043 | TSF |
| 9% | chr3 | 100461913 | 100462018 | + | chr3 | 100463677 | 100463775 | + | ENST00000418917; ENST00000490574; ENST00000240851; ENST00000476228 | TSF |
| 9% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 9% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 9% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 9% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 9% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 9% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 9% | chr17 | 38649720 | 38649640 | − | chr17 | 38645221 | 38644798 | − | ENST00000254051 | TSF |
| 9% | chr16 | 16227557 | 16227839 | + | chr16 | 16228207 | 16228365 | + | ENST00000399410; ENST00000345148; ENST00000346370; ENST00000349029; ENST00000351154; ENST00000399408; ENST00000572882 | TSF |
| 9% | chr16 | 16227557 | 16227839 | + | chr16 | 16228207 | 16228365 | + | ENST00000399410; ENST00000345148; ENST00000346370; ENST00000349029; ENST00000351154; ENST00000399408; ENST00000572882 | TSF |
| 9% | chr7 | 134212336 | 134212386 | + | chr7 | 134215479 | 134215562 | + | ENST00000359579 | TSF |
| 9% | chr4 | 6592594 | 6592648 | + | chr4 | 6594900 | 6595077; 6595011 | + | ENST00000285599; ENST00000504248; ENST00000505907 | TSF |
| 9% | chr4 | 6592594 | 6592648 | + | chr4 | 6594900 | 6595077; 6595011 | + | ENST00000285599; ENST00000504248; ENST00000505907 | TSF |
| 9% | chr4 | 6592594 | 6592648 | + | chr4 | 6594900 | 6595077; 6595011 | + | ENST00000285599; ENST00000504248; ENST00000505907 | TSF |
| 9% | chr3 | 183680609 | 183680541 | − | chr3 | 183679442 | 183679299 | − | ENST00000334444; ENST00000265586 | TSF |
| 9% | chr3 | 183680609 | 183680541 | − | chr3 | 183679442 | 183679299 | − | ENST00000334444; ENST00000265586 | TSF |
| 9% | chr11 | 14589824 | 14589773 | | chr11 | 14540587 | 14540543 | − | ENST00000419365; ENST00000555531; ENST00000396394; ENST00000396393; ENST00000418988 | TSF |
| 9% | chr11 | 14589824 | 14589773 | | chr11 | 14540587 | 14540543 | − | ENST00000419365; ENST00000555531; ENST00000396394; ENST00000396393; ENST00000418988 | TSF |
| 9% | chr7 | 7559044 | 7558760 | − | chr7 | 7557468 | 7557427 | − | ENST00000399429; ENST00000444268 | TSF |
| 9% | chr7 | 7559044 | 7558760 | − | chr7 | 7557468 | 7557427 | − | ENST00000399429; ENST00000444268 | TSF |
| 9% | chr11 | 60934781 | 60933962 | − | chr11 | 60901679 | 60901508 | − | ENST00000301765; ENST00000538036 | TSF |
| 9% | chr11 | 60934781 | 60933962 | − | chr11 | 60901679 | 60901508 | − | ENST00000301765; ENST00000538036 | TSF |
| 8% | chr19 | 1114930 | 1114676 | − | chr19 | 1114421 | 1114230 | − | ENST00000361757; ENST00000587024; ENST00000438103 | TSF |
| 8% | chr3 | 150463581 | 150463483 | − | chr3 | 150460485 | 150459928; 150460275 | − | ENST00000312960; ENST00000482706 | TSF |
| 8% | chr3 | 150463581 | 150463483 | − | chr3 | 150460485 | 150459928; 150460275 | − | ENST00000312960; ENST00000482706 | TSF |
| 8% | chr10 | 101420120 | 101420239 | + | chr10 | 101421203 | 101421385 | + | ENST00000370489 | TSF |
| 8% | chr6 | 124669760 | 124669850 | + | chr6 | 124676413 | 124676493 | + | ENST00000368416; ENST00000368417; ENST00000546092; ENST00000545433 | TSF |
| 8% | chr6 | 124669760 | 124669850 | + | chr6 | 124676413 | 124676493 | + | ENST00000368416; ENST00000368417; ENST00000546092; ENST00000545433 | TSF |
| 8% | chr6 | 124669760 | 124669850 | + | chr6 | 124676413 | 124676493 | + | ENST00000368416; ENST00000368417; ENST00000546092; ENST00000545433 | TSF |
| 8% | chr6 | 124669760 | 124669850 | + | chr6 | 124676413 | 124676493 | + | ENST00000368416; ENST00000368417; ENST00000546092; ENST00000545433 | TSF |
| 8% | chr7 | 56018506 | 56018522 | + | chr7 | 56022602 | 56022871; 56022865 | + | ENST00000426595; ENST00000285298; ENST00000443449 | TSF |
| 8% | chr7 | 56018506 | 56018522 | + | chr7 | 56022602 | 56022871; 56022865 | + | ENST00000426595; ENST00000285298; ENST00000443449 | TSF |
| 8% | chr9 | 137248112 | 137248203 | + | chr9 | 137293478 | 137293728 | + | ENST00000481739 | TSF |
| 8% | chr12 | 14506971 | 14507749 | + | chr12 | 14576843 | 14578407 | ++ | ENST00000544627 | TSF |
| 8% | chr16 | 48451457 | 48450727 | − | chr16 | 48396341 | 48395491 | − | ENST00000356721 | TSF |
| 8% | chr1 | 153431306 | 153431207 | − | chr1 | 153430446 | 153430282 | − | ENST00000368722; ENST00000368723 | TSF |
| 8% | chr7 | 100850556 | 100850506 | − | chr7 | 100850185 | 100850060 | − | ENST00000454310; ENST00000223127 | TSF |
| 7% | chr19 | 56811235 | 56811344 | + | chr19 | 56813337 | 56813464 | + | ENST00000588026 | TSF |
| 7% | chr20 | 8624404 | 8625147 | + | chr20 | 8626749 | 8626828 | + | ENST00000378641; ENST00000338037; ENST00000378637; ENST00000404098 | TSF |
| 7% | chr20 | 8624404 | 8625147 | + | chr20 | 8626749 | 8626828 | + | ENST00000378641; ENST00000338037; ENST00000378637; ENST00000404098 | TSF |
| 7% | chr20 | 8624404 | 8625147 | + | chr20 | 8626749 | 8626828 | + | ENST00000378641; ENST00000338037; ENST00000378637; ENST00000404098 | TSF |
| 7% | chr20 | 110606 | 110697 | + | chr20 | 126056 | 126333 | + | ENST00000382398 | TSF |
| 7% | chr20 | 10628319 | 10628254 | − | chr20 | 10627751 | 10627587 | − | ENST00000254958; ENST00000423891 | TSF |
| 7% | chr17 | 39976225 | 39976301 | + | chr17 | 39976521 | 39976713 | + | ENST00000321562; ENST00000455106; ENST00000544340 | TSF |
| 7% | chr17 | 39974832 | 39974893 | + | chr17 | 39975462 | 39975651 | + | ENST00000321562 | TSF |
| 7% | chr1 | 200882539 | 200882562 | + | chr1 | 200882665 | 200882757 | + | ENST00000367342; ENST00000413687 | TSF |
| 7% | chr4 | 873272 | 873014 | − | chr4 | 871597 | 871403 | − | ENST00000314167; ENST00000511163 | TSF |
| 7% | chr12 | 52849815 | 52849601 | − | chr12 | 52845683 | 52845323 | − | ENST00000252252 | TSF |
| 7% | chr12 | 6602868 | 6602754 | − | chr12 | 6602138 | 6602028 | − | ENST00000229238 | TSF |
| 7% | chrX | 53579130 | 53578958 | − | chrX | 53578441 | 53578227 | − | ENST00000427052; ENST00000342160; ENST00000262854 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 7% | chr1 | 33270876 | 33270146 | – | chr1 | 33263444 | 33263364 | – | ENST00000373477 | TSF |
| 7% | chr1 | 6366296 | 6365480 | – | chr1 | 6355040 | 6354924 | – | ENST00000608083; ENST00000377842; ENST00000377845; ENST00000377855; ENST00000377860; ENST00000418124; ENST00000545482; ENST00000361521; ENST00000473466 | TSF |
| 7% | chr1 | 6366296 | 6365480 | – | chr1 | 6355040 | 6354924 | – | ENST00000608083; ENST00000377842; ENST00000377845; ENST00000377855; ENST00000377860; ENST00000418124; ENST00000545482; ENST00000361521; ENST00000473466 | TSF |
| 7% | chr1 | 6366296 | 6365480 | – | chr1 | 6355040 | 6354924 | – | ENST00000608083; ENST00000377842; ENST00000377845; ENST00000377855; ENST00000377860; ENST00000418124; ENST00000545482; ENST00000361521; ENST00000473466 | TSF |
| 7% | chr1 | 6366296 | 6365480 | – | chr1 | 6355040 | 6354924 | – | ENST00000608083; ENST00000377842; ENST00000377845; ENST00000377855; ENST00000377860; ENST00000418124; ENST00000545482; ENST00000361521; ENST00000473466 | TSF |
| 7% | chrX | 154534914 | 154534817 | – | chrX | 154528458 | 154528349 | – | ENST00000369449; ENST00000321926 | TSF |
| 7% | chrX | 154534914 | 154534817 | – | chrX | 154528458 | 154528349 | – | ENST00000369449; ENST00000321926 | TSF |
| 7% | chr17 | 43485811 | 43485601 | | chr17 | 43483449 | 43483042; 43483213 | – | ENST00000532038; ENST00000428638; ENST00000442348; ENST00000532891; ENST00000528677 | TSF |
| 7% | chr17 | 43485811 | 43485601 | | chr17 | 43483449 | 43483042; 43483213 | – | ENST00000532038; ENST00000428638; ENST00000442348; ENST00000532891; ENST00000528677 | TSF |
| 7% | chr17 | 43485811 | 43485601 | | chr17 | 43483449 | 43483042; 43483213 | – | ENST00000532038; ENST00000428638; ENST00000442348; ENST00000532891; ENST00000528677 | TSF |
| 7% | chr17 | 43485811 | 43485601 | | chr17 | 43483449 | 43483042; 43483213 | – | ENST00000532038; ENST00000428638; ENST00000442348; ENST00000532891; ENST00000528677 | TSF |
| 6% | chr3 | 184639788 | 184640271 | + | chr3 | 184642650 | 184642769 | + | ENST00000287546; ENST00000437079; ENST00000436792; ENST00000446204 | TSF |
| 6% | chr12 | 53835137 | 53835233 | + | chr12 | 53836479 | 53836517 | + | ENST00000547368 | TSF |
| 6% | chr17 | 37902588 | 37902638 | + | chr17 | 37903004 | 37903150 | + | ENST00000309156; ENST00000394211; ENST00000445327; ENST00000394209 | TSF |
| 6% | chr2 | 101567739 | 101568117 | + | chr2 | 101580520 | 101580638 | + | ENST00000335681; ENST00000542504 | TSF |
| 6% | chr16 | 28838911 | 28839140 | + | chr16 | 28840722 | 28840813 | + | ENST00000340394; ENST00000325215; ENST00000336783; ENST00000382686; ENST00000395547; ENST00000564304; ENST00000570200; ENST00000568266 | TSF |
| 6% | chr16 | 28838911 | 28839140 | + | chr16 | 28840722 | 28840813 | + | ENST00000340394; ENST00000325215; ENST00000336783; ENST00000382686; ENST00000395547; ENST00000564304; ENST00000570200; ENST00000568266 | TSF |
| 6% | chr16 | 28838911 | 28839140 | + | chr16 | 28840722 | 28840813 | + | ENST00000340394; ENST00000325215; ENST00000336783; ENST00000382686; ENST00000395547; ENST00000564304; ENST00000570200; ENST00000568266 | TSF |
| 6% | chr16 | 28838911 | 28839140 | + | chr16 | 28840722 | 28840813 | + | ENST00000340394; ENST00000325215; ENST00000336783; ENST00000382686; ENST00000395547; ENST00000564304; ENST00000570200; ENST00000568266 | TSF |
| 6% | chr16 | 28838911 | 28839140 | + | chr16 | 28840722 | 28840813 | + | ENST00000340394; ENST00000325215; ENST00000336783; ENST00000382686; ENST00000395547; ENST00000564304; ENST00000570200; ENST00000568266 | TSF |
| 6% | chr16 | 28838911 | 28839140 | + | chr16 | 28840722 | 28840813 | + | ENST00000340394; ENST00000325215; ENST00000336783; ENST00000382686; ENST00000395547; ENST00000564304; ENST00000570200; ENST00000568266 | TSF |
| 6% | chr16 | 28838911 | 28839140 | + | chr16 | 28840722 | 28840813 | + | ENST00000340394; ENST00000325215; ENST00000336783; ENST00000382686; ENST00000395547; ENST00000564304; ENST00000570200; ENST00000568266 | TSF |
| 6% | chr7 | 134215952 | 134215973 | + | chr7 | 134216660 | 134216776 | + | ENST00000359579 | TSF |
| 6% | chr3 | 183693430 | 183693330 | – | chr3 | 183689707 | 183689351 | – | ENST00000334444; ENST00000265586 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 6% | chr3 | 183693430 | 183693330 | − | chr3 | 183689707 | 183689351 | − | ENST00000334444; ENST00000265586 | TSF |
| 6% | chr20 | 48264330 | 48264298 | − | chr20 | 48263615 | 48263502 | − | ENST00000371711 | TSF |
| 6% | chr20 | 48763148 | 48763055 | − | chr20 | 48760158 | 48760039 | − | ENST00000341698; ENST00000557021; ENST00000371650; ENST00000371652; ENST00000371658 | TSF |
| 6% | chr20 | 48763148 | 48763055 | − | chr20 | 48760158 | 48760039 | − | ENST00000341698; ENST00000557021; ENST00000371650; ENST00000371652; ENST00000371658 | TSF |
| 6% | chr20 | 48763148 | 48763055 | − | chr20 | 48760158 | 48760039 | − | ENST00000341698; ENST00000557021; ENST00000371650; ENST00000371652; ENST00000371658 | TSF |
| 6% | chr20 | 48763148 | 48763055 | − | chr20 | 48760158 | 48760039 | − | ENST00000341698; ENST00000557021; ENST00000371650; ENST00000371652; ENST00000371658 | TSF |
| 5% | chr14 | 51360331 | 51362440 | + | chr14 | 51368547 | 51368629 | + | ENST00000337334; ENST00000353130; ENST00000395752 | TSF |
| 5% | chr20 | 35778650 | 35779434 | + | chr20 | 35812583 | 35812776 | + | ENST00000237530; ENST00000373622; ENST00000373632 | TSF |
| 5% | chr20 | 35778650 | 35779434 | + | chr20 | 35812583 | 35812776 | + | ENST00000237530; ENST00000373622; ENST00000373632 | TSF |
| 5% | chr20 | 35778650 | 35779434 | + | chr20 | 35812583 | 35812776 | + | ENST00000237530; ENST00000373622; ENST00000373632 | TSF |
| 5% | chr3 | 132014279 | 132014543 | + | chr3 | 132047111 | 132047206 | + | ENST00000336375; ENST00000495911; ENST00000475741; ENST00000351273 | TSF |
| 5% | chr3 | 132014279 | 132014543 | + | chr3 | 132047111 | 132047206 | + | ENST00000336375; ENST00000495911; ENST00000475741; ENST00000351273 | TSF |
| 5% | chr3 | 132014279 | 132014543 | + | chr3 | 132047111 | 132047206 | + | ENST00000336375; ENST00000495911; ENST00000475741; ENST00000351273 | TSF |
| 5% | chr3 | 132014279 | 132014543 | + | chr3 | 132047111 | 132047206 | + | ENST00000336375; ENST00000495911; ENST00000475741; ENST00000351273 | TSF |
| 5% | chr11 | 66953459 | 66954052 | + | chr11 | 66974981 | 66975159 | + | ENST00000398645; ENST00000529006 | TSF |
| 5% | chr11 | 66953459 | 66954052 | + | chr11 | 66974981 | 66975159 | + | ENST00000398645; ENST00000529006 | TSF |
| 5% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 5% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 5% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 5% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 5% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 5% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 5% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |

TABLE 22-continued

Transcript fusion for Esophageal Carcinoma (ESCA) Coordinates of the fusion sequences for which the donor is the TE.

| 1 | 2' | 3 | 4 | 5' | 6' | 7 | 8' | 9' | 10' | 11' |
|---|---|---|---|---|---|---|---|---|---|---|
| 5% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 5% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 5% | chr2 | 3431377 | 3431530 | + | chr2 | 3624182 | 3624220 | + | ENST00000304921; ENST00000407445; ENST00000403564; ENST00000406376 | TSF |
| 5% | chr2 | 3431377 | 3431530 | + | chr2 | 3624182 | 3624220 | + | ENST00000304921; ENST00000407445; ENST00000403564; ENST00000406376 | TSF |
| 5% | chr10 | 5120335 | 5120493 | + | chr10 | 5138602 | 5138769 | + | ENST00000602997; ENST00000605149; ENST00000380554 | TSF |
| 5% | chr10 | 5120335 | 5120493 | + | chr10 | 5138602 | 5138769 | + | ENST00000602997; ENST00000605149; ENST00000380554 | TSF |
| 5% | chr10 | 74501505 | 74501603 | + | chr10 | 74594117 | 74594186; 74594190 | + | ENST00000373053; ENST00000357157; ENST00000536019; ENST00000604152 | TSF |
| 5% | chr10 | 74501505 | 74501603 | + | chr10 | 74594117 | 74594186; 74594190 | + | ENST00000373053; ENST00000357157; ENST00000536019; ENST00000604152 | TSF |
| 5% | chr10 | 74501505 | 74501603 | + | chr10 | 74594117 | 74594186; 74594190 | + | ENST00000373053; ENST00000357157; ENST00000536019; ENST00000604152 | TSF |
| 5% | chr12 | 14506971 | 14507672 | + | chr12 | 14576843 | 14578407 | + | ENST00000544627 | TSF |
| 5% | chr20 | 634541 | 634468 | − | chr20 | 629561 | 629358; 629500 | − | ENST00000381962; ENST00000488788 | TSF |
| 5% | chr20 | 634541 | 634468 | − | chr20 | 629561 | 629358; 629500 | − | ENST00000381962; ENST00000488788 | TSF |
| 5% | chr11 | 61087201 | 61087135 | − | chr11 | 61084039 | 61083964 | − | ENST00000301764; ENST00000540166; ENST00000535967; ENST00000539739; ENST00000535174 | TSF |
| 5% | chr11 | 61087201 | 61087135 | − | chr11 | 61084039 | 61083964 | − | ENST00000301764; ENST00000540166; ENST00000535967; ENST00000539739; ENST00000535174 | TSF |
| 5% | chr11 | 61087201 | 61087135 | − | chr11 | 61084039 | 61083964 | − | ENST00000301764; ENST00000540166; ENST00000535967; ENST00000539739; ENST00000535174 | TSF |
| 5% | chr11 | 61087201 | 61087135 | − | chr11 | 61084039 | 61083964 | − | ENST00000301764; ENST00000540166; ENST00000535967; ENST00000539739; ENST00000535174 | TSF |
| 5% | chr11 | 61087201 | 61087135 | − | chr11 | 61084039 | 61083964 | − | ENST00000301764; ENST00000540166; ENST00000535967; ENST00000539739; ENST00000535174 | TSF |
| 5% | chr15 | 83667946 | 83667078 | − | chr15 | 83660798 | 83660684 | − | ENST00000451195 | TSF |
| 5% | chr22 | 46778472 | 46778374 | − | chr22 | 46777947 | 46777743 | − | ENST00000262738 | TSF |
| 5% | chr10 | 5057417 | 5057095 | − | chr10 | 5043873 | 5043706 | − | ENST00000380753; ENST00000421196; ENST00000407674; ENST00000604507; ENST00000455190 | TSF |
| 5% | chr10 | 5057417 | 5057095 | − | chr10 | 5043873 | 5043706 | − | ENST00000380753; ENST00000421196; ENST00000407674; ENST00000604507; ENST00000455190 | TSF |
| 5% | chr10 | 5057417 | 5057095 | − | chr10 | 5043873 | 5043706 | − | ENST00000380753; ENST00000421196; ENST00000407674; ENST00000604507; ENST00000455190 | TSF |
| 5% | chr10 | 5057417 | 5057095 | − | chr10 | 5043873 | 5043706 | − | ENST00000380753; ENST00000421196; ENST00000407674; ENST00000604507; ENST00000455190 | TSF |
| 5% | chr1 | 45988716 | 45988450 | − | chr1 | 45980667 | 45980545 | − | ENST00000262746; ENST00000319248; ENST00000447184; ENST00000424390 | TSF |
| 5% | chr1 | 45988716 | 45988450 | − | chr1 | 45980667 | 45980545 | − | ENST00000262746; ENST00000319248; ENST00000447184; ENST00000424390 | TSF |
| 5% | chr6 | 117763870 | 117763597 | − | chr6 | 117739669 | 117739625 | − | ENST00000368507; ENST00000368508 | TSF |
| 5% | chr6 | 117763870 | 117763597 | − | chr6 | 117739669 | 117739625 | − | ENST00000368507; ENST00000368508 | TSF |
| 5% | chr10 | 90437871 | 90437988 | + | chr10 | 90438202 | 90438438 | + | ENST00000394375; ENST00000608620; ENST00000238983; ENST00000355843 | TSF |
| 5% | chr1 | 172134550 | 172134843 | + | chr1 | 172222713 | 172222822; 172222718 | + | ENST00000358155; ENST00000355305; ENST00000367731; ENST00000520906; ENST00000523513 | TSF |
| 5% | chr1 | 172134550 | 172134843 | + | chr1 | 172222713 | 172222822; 172222718 | + | ENST00000358155; ENST00000355305; ENST00000367731; ENST00000520906; ENST00000523513 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 5% | chr1 | 172134550 | 172134843 | + | chr1 | 172222713 | 172222822; 172222718 | + | ENST00000358155; ENST00000355305; ENST00000367731; ENST00000520906; ENST00000523513 | TSF |
| 5% | chr1 | 172134550 | 172134843 | + | chr1 | 172222713 | 172222822; 172222718 | + | ENST00000358155; ENST00000355305; ENST00000367731; ENST00000520906; ENST00000523513 | TSF |
| 5% | chr5 | 175697409 | 175697523 | + | chr5 | 175716657 | 175717958 | + | ENST00000443967; ENST00000429602 | TSF |
| 5% | chr5 | 175697409 | 175697523 | + | chr5 | 175716657 | 175717958 | + | ENST00000443967; ENST00000429602 | TSF |
| 5% | chr1 | 117473681 | 117473836 | + | chr1 | 117484337 | 117484705 | + | ENST00000393203 | TSF |
| 5% | chr4 | 15791827 | 15792504 | + | chr4 | 15818134 | 15818263 | + | ENST00000502843; ENST00000226279 | TSF |
| 5% | chr4 | 15791827 | 15792504 | + | chr4 | 15818134 | 15818263 | + | ENST00000502843; ENST00000226279 | TSF |
| 5% | chr17 | 75313396 | 75313709 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 5% | chr17 | 75313396 | 75313709 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 5% | chr17 | 75313396 | 75313709 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 5% | chr17 | 75313396 | 75313709 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 5% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 5% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 5% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 5% | chr5 | 76107394 | 76108438 | + | chr5 | 76128515 | 76129626 | + | ENST00000296677 | TSF |
| 5% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 5% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 5% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 5% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 5% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 5% | chr11 | 46390474 | 46390524 | + | chr11 | 46391044 | 46391100; 46391047 | + | ENST00000343674; ENST00000532868; ENST00000395574; ENST00000527911; | TSF |
| 5% | chr12 | 53353926 | 53353678 | − | chr12 | 52913570 | 52913526; 52913535 | − | ENST00000252242; ENST00000549420; ENST00000551275 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 5% | chr12 | 53353926 | 53353678 | − | chr12 | 52913570 | 52913526; 52913535 | − | ENST00000252242; ENST00000549420; ENST00000551275 | TSF |
| 5% | chr12 | 53353926 | 53353678 | − | chr12 | 52913570 | 52913526; 52913535 | − | ENST00000252242; ENST00000549420; ENST00000551275 | TSF |
| 5% | chr19 | 35979015 | 35978880 | − | chr19 | 35978661 | 35978614 | − | ENST00000484218; ENST00000338897 | TSF |
| 5% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 5% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 5% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 5% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 5% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 5% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 5% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 5% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|----|----|---|----|----|---|----|----|-----|-----|
| 5% | chr4 | 83774285 | 83774211 | − | chr4 | 83772757 | 83772584; 83772667 | − | ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 5% | chr1 | 156716197 | 156716133 | − | chr1 | 156715165 | 156715089 | − | ENST00000357325; ENST00000537739; ENST00000368209; ENST00000368206 | TSF |
| 5% | chrX | 134954053 | 134953756 | − | chrX | 134950187 | 134950078 | − | ENST00000420087; ENST00000463085; ENST00000370724; ENST00000491480 | TSF |
| 5% | chrX | 134954053 | 134953756 | − | chrX | 134950187 | 134950078 | − | ENST00000420087; ENST00000463085; ENST00000370724; ENST00000491480 | TSF |
| 5% | chr7 | 5433736 | 5433673 | − | chr7 | 5430259 | 5430116; 5429988 | − | ENST00000399537; ENST00000430969; ENST00000434361; ENST00000399434 | TSF |
| 5% | chr7 | 5433736 | 5433673 | − | chr7 | 5430259 | 5430116; 5429988 | − | ENST00000399537; ENST00000430969; ENST00000434361; ENST00000399434 | TSF |
| 5% | chr7 | 5433736 | 5433673 | − | chr7 | 5430259 | 5430116; 5429988 | − | ENST00000399537; ENST00000430969; ENST00000434361; ENST00000399434 | TSF |
| 5% | chr7 | 5433736 | 5433673 | − | chr7 | 5430259 | 5430116; 5429988 | − | ENST00000399537; ENST00000430969; ENST00000434361; ENST00000399434 | TSF |
| 5% | chr17 | 1005272 | 1005174 | − | chr17 | 1003975 | 1003877 | − | ENST00000302538; ENST00000544583; ENST00000574437; ENST00000291107; ENST00000574139; ENST00000570525; ENST00000574266 | TSF |
| 5% | chr17 | 1005272 | 1005174 | − | chr17 | 1003975 | 1003877 | − | ENST00000302538; ENST00000544583; ENST00000574437; ENST00000291107; ENST00000574139; ENST00000570525; ENST00000574266 | TSF |
| 5% | chr17 | 1005272 | 1005174 | − | chr17 | 1003975 | 1003877 | − | ENST00000302538; ENST00000544583; ENST00000574437; ENST00000291107; ENST00000574139; ENST00000570525; ENST00000574266 | TSF |
| 5% | chr17 | 1005272 | 1005174 | − | chr17 | 1003975 | 1003877 | − | ENST00000302538; ENST00000544583; ENST00000574437; ENST00000291107; ENST00000574139; ENST00000570525; ENST00000574266 | TSF |
| 4% | chr12 | 96340433 | 96341255 | + | chr12 | 96346495 | 96346601 | + | ENST00000266736; ENST00000548310 | TSF |
| 4% | chr12 | 96340433 | 96341255 | + | chr12 | 96346495 | 96346601 | + | ENST00000266736; ENST00000548310 | TSF |
| 4% | chr7 | 2403615 | 2403665 | + | chr7 | 2404007 | 2404164; 2404031 | + | ENST00000431643; ENST00000360876; ENST00000413917; ENST000 00397011 | TSF |
| 4% | chr7 | 2403615 | 2403665 | + | chr7 | 2404007 | 2404164; 2404031 | + | ENST00000431643; ENST00000360876; ENST00000413917; ENST000 00397011 | TSF |
| 4% | chr7 | 2403615 | 2403665 | + | chr7 | 2404007 | 2404164; 2404031 | + | ENST00000431643; ENST00000360876; ENST00000413917; ENST000 00397011 | TSF |
| 4% | chrX | 107293989 | 107294242 | + | chrX | 107301268 | 107301431 | + | ENST00000415430; ENST00000217957; ENST00000458383 | TSF |
| 4% | chrX | 107293989 | 107294242 | + | chrX | 107301268 | 107301431 | + | ENST00000415430; ENST00000217957; ENST00000458383 | TSF |
| 4% | chrX | 107293989 | 107294242 | + | chrX | 107301268 | 107301431 | + | ENST00000415430; ENST00000217957; ENST00000458383 | TSF |
| 4% | chr17 | 37898260 | 37898291 | + | chr17 | 37898505 | 37898709 | + | ENST00000445327 | TSF |
| 4% | chr3 | 126729058 | 126729222 | + | chr3 | 126730801 | 126731001 | + | ENST00000251772; ENST00000393409 | TSF |
| 4% | chr7 | 66386440 | 66386448 | + | chr7 | 66409963 | 66410248; 66410147; 66410019; 66410221; 66410248; | + | ENST00000341567; ENST00000607045; ENST00000433271; ENST00000413593; ENST00000424964; ENST00000418375 | TSF |
| 4% | chr7 | 66386440 | 66386448 | + | chr7 | 66409963 | 66410147; 66410019; 66410221; 66410248; 66410147; | + | ENST00000341567; ENST00000607045; ENST00000433271; ENST00000413593; ENST00000424964; ENST00000418375 | TSF |
| 4% | chr7 | 66386440 | 66386448 | + | chr7 | 66409963 | 66410019; 66410221; 66410248; 66410147; 66410019; | + | ENST00000341567; ENST00000607045; ENST00000433271; ENST00000413593; ENST00000424964; ENST00000418375 | TSF |
| 4% | chr7 | 66386440 | 66386448 | + | chr7 | 66409963 | 66410221; 66410248; | + | ENST00000341567; ENST00000607045; ENST00000433271; ENST00000413593; | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 4% | chr7 | 66386440 | 66386448 | + | chr7 | 66409963 | 66410147; 66410019; 66410221; 66410248; 66410147; 66410019; 66410221; 66410248; | + | ENST00000424964; ENST00000418375 ENST00000341567; ENST00000607045; ENST00000433271; ENST00000413593; ENST00000424964; ENST00000418375 | TSF |
| 4% | chr7 | 66386440 | 66386448 | + | chr7 | 66409963 | 66410147; 66410019; 66410221; 66410248; 66410147; | + | ENST00000341567; ENST00000607045; ENST00000433271; ENST00000413593; ENST00000424964; ENST00000418375 | TSF |
| 4% | chr14 | 97013173 | 97013272 | + | chr14 | 97014134 | 97014255 | + | ENST00000216277; ENST00000392990; ENST00000555626 | TSF |
| 4% | chr14 | 97013173 | 97013272 | + | chr14 | 97014134 | 97014255 | + | ENST00000216277; ENST00000392990; ENST00000555626 | TSF |
| 4% | chr14 | 97013173 | 97013272 | + | chr14 | 97014134 | 97014255 | + | ENST00000216277; ENST00000392990; ENST00000555626 | TSF |
| 4% | chr11 | 71508077 | 71508126 | + | chr11 | 71510607 | 71510693 | + | ENST00000346333; ENST00000359244; ENST00000426628 | TSF |
| 4% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr7 | 56020443 | 56020509 | + | chr7 | 56020872 | 56021011 | + | ENST00000426595 | TSF |
| 4% | chr2 | 202073108 | 202073190 | + | chr2 | 202073793 | 202074285 | + | ENST00000286186; ENST00000272879; ENST00000346817; ENST00000313728; ENST00000448480 | TSF |
| 4% | chr2 | 202073108 | 202073190 | + | chr2 | 202073793 | 202074285 | + | ENST00000286186; ENST00000272879; ENST00000346817; ENST00000313728; ENST00000448480 | TSF |
| 4% | chr15 | 74330065 | 74330296 | + | chr15 | 74335330 | 74335521; 74335480 | + | ENST00000395135; ENST00000268058; ENST00000565898; ENST00000564428 | TSF |
| 4% | chr15 | 74330065 | 74330296 | + | chr15 | 74335330 | 74335521; 74335480 | + | ENST00000395135; ENST00000268058; ENST00000565898; ENST00000564428 | TSF |
| 4% | chr7 | 33006587 | 33006627 | + | chr7 | 33014229 | 33014374 | + | ENST00000242209; ENST00000538336 | TSF |
| 4% | chr10 | 12277215 | 12277329 | + | chr10 | 12279143 | 12279265; 12279223 | + | ENST00000281141; ENST00000442050; ENST00000440613 | TSF |
| 4% | chr10 | 12277215 | 12277329 | + | chr10 | 12279143 | 12279265; 12279223 | + | ENST00000281141; ENST00000442050; ENST00000440613 | TSF |
| 4% | chr10 | 12277215 | 12277329 | + | chr10 | 12279143 | 12279265; 12279223 | + | ENST00000281141; ENST00000442050; ENST00000440613 | TSF |
| 4% | chr7 | 100877200 | 100877154 | − | chr7 | 100876195 | 100876114 | − | ENST00000308344; ENST00000401528; ENST00000414035; ENST00000412417 | TSF |
| 4% | chr7 | 100877200 | 100877154 | − | chr7 | 100876195 | 100876114 | − | ENST00000308344; ENST00000401528; ENST00000414035; ENST00000412417 | TSF |
| 4% | chr7 | 100877200 | 100877154 | − | chr7 | 100876195 | 100876114 | − | ENST00000308344; ENST00000401528; ENST00000414035; ENST00000412417 | TSF |
| 4% | chr9 | 132580720 | 132580632 | − | chr9 | 132576501 | 132576251 | − | ENST00000351698 | TSF |
| 4% | chr16 | 21060024 | 21059927 | − | chr16 | 21053525 | 21053349 | − | ENST00000261383; ENST00000415178 | TSF |
| 4% | chr16 | 21060024 | 21059927 | − | chr16 | 21053525 | 21053349 | − | ENST00000261383; ENST00000415178 | TSF |
| 4% | chr1 | 8924664 | 8924519 | − | chr1 | 8924151 | 8923950 | − | ENST00000234590 | TSF |
| 4% | chr9 | 130717031 | 130716974 | − | chr9 | 130716204 | 130716084 | − | ENST00000373095 | TSF |
| 4% | chr16 | 23606905 | 23606750 | − | chr16 | 23598640 | 23598518 | − | ENST00000007516; ENST00000570319 | TSF |
| 4% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 4% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 4% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 4% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 4% | chr1 | 116594535 | 116594632 | + | chr1 | 116605383 | 116605503 | + | ENST00000369503 | TSF |
| 4% | chr10 | 48230850 | 48230877 | + | chr10 | 48231779 | 48231814 | + | ENST00000453919; ENST00000456984 | TSF |
| 4% | chr10 | 48230850 | 48230877 | + | chr10 | 48231779 | 48231814 | + | ENST00000453919; ENST00000456984 | TSF |
| 4% | chr12 | 51048448 | 51048823 | + | chr12 | 51053977 | 51054102 | + | ENST00000301180 | TSF |
| 4% | chr20 | 60878087 | 60878105 | + | chr20 | 60878775 | 60878837 | + | ENST00000253003 | TSF |
| 4% | chr12 | 122387836 | 122388242 | + | chr12 | 122394980 | 122395174 | + | ENST00000288912; ENST00000397454 | TSF |
| 4% | chr12 | 122387836 | 122388242 | + | chr12 | 122394980 | 122395174 | + | ENST00000288912; ENST00000397454 | TSF |
| 4% | chr1 | 1562829 | 1562973 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562973 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr1 | 1562829 | 1562973 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 4% | chr20 | 45337040 | 45337192 | + | chr20 | 45353680 | 45354963 | + | ENST00000359271 | TSF |
| 4% | chr14 | 20973494 | 20974255 | + | chr14 | 20978626 | 20979281 | + | ENST00000430083 | TSF |
| 4% | chr12 | 49659927 | 49660025 | + | chr12 | 49663248 | 49663470; 49663252 | + | ENST00000541364; ENST00000552125; ENST00000301072; ENST00000549183 | TSF |
| 4% | chr12 | 49659927 | 49660025 | + | chr12 | 49663248 | 49663470; 49663252 | + | ENST00000541364; ENST00000552125; ENST00000301072; ENST00000549183 | TSF |
| 4% | chr12 | 49659927 | 49660025 | + | chr12 | 49663248 | 49663470; 49663252 | + | ENST00000541364; ENST00000552125; ENST00000301072; ENST00000549183 | TSF |
| 4% | chr14 | 106174427 | 106174466 | + | chr14 | 106173770 | 106173505 | − | ENST00000390547 | TSF |
| 4% | chr1 | 45988716 | 45988450 | − | chr1 | 45981479 | 45981326 | − | ENST00000262746; ENST00000319248; ENST00000447184; ENST00000424390 | TSF |
| 4% | chr1 | 45988716 | 45988450 | − | chr1 | 45981479 | 45981326 | − | ENST00000262746; ENST00000319248; ENST00000447184; ENST00000424390 | TSF |
| 4% | chr10 | 5060345 | 5060092 | − | chr10 | 5040939 | 5040817 | − | ENST00000380753; ENST00000421196; ENST00000407674; ENST00000604507 | TSF |
| 4% | chr10 | 5060345 | 5060092 | − | chr10 | 5040939 | 5040817 | − | ENST00000380753; ENST00000421196; ENST00000407674; ENST00000604507 | TSF |
| 4% | chr20 | 33351314 | 33350530 | − | chr20 | 33346736 | 33346608 | − | ENST00000374796; ENST00000359003 | TSF |
| 4% | chrX | 53664297 | 53664254 | − | chrX | 53661250 | 53661188 | − | ENST00000342160; ENST00000262854; ENST00000218328 | TSF |
| 4% | chrX | 53664297 | 53664254 | − | chrX | 53661250 | 53661188 | − | ENST00000342160; ENST00000262854; ENST00000218328 | TSF |
| 4% | chr12 | 58023123 | 58023062 | − | chr12 | 58022929 | 58022831; 58022905 | − | ENST00000341156; ENST00000418555; ENST00000552798; ENST00000549391 | TSF |
| 4% | chr12 | 58023123 | 58023062 | − | chr12 | 58022929 | 58022831; 58022905 | − | ENST00000341156; ENST00000418555; ENST00000552798; ENST00000549391 | TSF |
| 4% | chr5 | 145541009 | 145540727 | − | chr5 | 145540049 | 145539937 | − | ENST00000394434; ENST00000545646; ENST00000274562; ENST00000510191 | TSF |
| 4% | chrX | 134971303 | 134971006 | − | chrX | 134950187 | 134950078 | − | ENST00000420087; ENST00000463085; ENST00000370724; ENST00000491480 | TSF |
| 4% | chrX | 134971303 | 134971006 | − | chrX | 134950187 | 134950078 | − | ENST00000420087; ENST00000463085; ENST00000370724; ENST00000491480 | TSF |
| 4% | chr17 | 17816540 | 17815655 | − | chr17 | 17810845 | 17810761 | − | ENST00000581396; ENST00000379504; ENST00000318094; ENST00000395739; ENST00000535933; ENST00000540946; ENST00000542206 | TSF |
| 4% | chr17 | 17816540 | 17815655 | − | chr17 | 17810845 | 17810761 | − | ENST00000581396; ENST00000379504; ENST00000318094; ENST00000395739; | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 4% | chr17 | 17816540 | 17815655 | − | chr17 | 17810845 | 17810761 | − | ENST00000535933; ENST00000540946; ENST00000542206 ENST00000581396; ENST00000379504; ENST00000318094; ENST00000395739; | TSF |
| 4% | chr17 | 17816540 | 17815655 | − | chr17 | 17810845 | 17810761 | − | ENST00000535933; ENST00000540946; ENST00000542206 ENST00000581396; ENST00000379504; ENST00000318094; ENST00000395739; | TSF |
| 4% | chr17 | 17816540 | 17815655 | − | chr17 | 17810845 | 17810761 | − | ENST00000535933; ENST00000540946; ENST00000542206 ENST00000581396; ENST00000379504; ENST00000318094; ENST00000395739; | TSF |
| 4% | chr17 | 17816540 | 17815655 | − | chr17 | 17810845 | 17810761 | − | ENST00000535933; ENST00000540946; ENST00000542206 ENST00000581396; ENST00000379504; ENST00000318094; ENST00000395739; | TSF |
| 4% | chr1 | 32152700 | 32152171 | − | chr1 | 32151880 | 32151845 | − | ENST00000271069; ENST00000373672; ENST00000373668 | TSF |
| 4% | chr1 | 32152700 | 32152171 | − | chr1 | 32151880 | 32151845 | − | ENST00000271069; ENST00000373672; ENST00000373668 | TSF |
| 4% | chr1 | 32152700 | 32152171 | − | chr1 | 32151880 | 32151845 | − | ENST00000271069; ENST00000373672; ENST00000373668 | TSF |
| 4% | chr17 | 39741127 | 39741014 | − | chr17 | 39659564 | 39659539 | − | ENST00000246635; ENST00000336861; ENST00000587544; ENST00000590425; ENST00000587435 | TSF |
| 4% | chr17 | 39741127 | 39741014 | − | chr17 | 39659564 | 39659539 | − | ENST00000246635; ENST00000336861; ENST00000587544; ENST00000590425; ENST00000587435 | TSF |
| 4% | chr17 | 39741127 | 39741014 | − | chr17 | 39659564 | 39659539 | − | ENST00000246635; ENST00000336861; ENST00000587544; ENST00000590425; ENST00000587435 | TSF |
| 4% | chr17 | 39741127 | 39741014 | − | chr17 | 39659564 | 39659539 | − | ENST00000246635; ENST00000336861; ENST00000587544; ENST00000590425; ENST00000587435 | TSF |
| 4% | chr17 | 39741127 | 39741014 | − | chr17 | 39659564 | 39659539 | − | ENST00000246635; ENST00000336861; ENST00000587544; ENST00000590425; ENST00000587435 | TSF |
| 4% | chr1 | 217698243 | 217697476 | − | chr1 | 217688231 | 217688164 | − | ENST00000366935 | TSF |
| 4% | chr19 | 5714928 | 5714878 | − | chr19 | 5714282 | 5714194 | − | ENST00000360614; ENST00000590558; ENST00000585374; ENST00000593119; ENST00000590729 | TSF |
| 4% | chr19 | 5714928 | 5714878 | − | chr19 | 5714282 | 5714194 | − | ENST00000360614; ENST00000590558; ENST00000585374; ENST00000593119; ENST00000590729 | TSF |
| 4% | chr19 | 5714928 | 5714878 | − | chr19 | 5714282 | 5714194 | − | ENST00000360614; ENST00000590558; ENST00000585374; ENST00000593119; ENST00000590729 | TSF |
| 4% | chr12 | 14670381 | 14670239 | − | chr12 | 14664645 | 14664445 | − | ENST00000240617 | TSF |
| 4% | chr10 | 47198502 | 47198475 | − | chr10 | 47197573 | 47197538 | − | ENST00000452145; ENST00000413193; ENST00000355232 | TSF |
| 4% | chr10 | 47198502 | 47198475 | − | chr10 | 47197573 | 47197538 | − | ENST00000452145; ENST00000413193; ENST00000355232 | TSF |
| 4% | chr10 | 47198502 | 47198475 | − | chr10 | 47197573 | 47197538 | − | ENST00000452145; ENST00000413193; ENST00000355232 | TSF |
| 4% | chr17 | 27441253 | 27441216 | − | chr17 | 27441115 | 27441029 | − | ENST00000354329; ENST00000533112; ENST00000531253; ENST00000527372 | TSF |
| 4% | chr17 | 27441253 | 27441216 | − | chr17 | 27441115 | 27441029 | − | ENST00000354329; ENST00000533112; ENST00000531253; ENST00000527372 | TSF |
| 4% | chr17 | 27441253 | 27441216 | − | chr17 | 27441115 | 27441029 | − | ENST00000354329; ENST00000533112; ENST00000531253; ENST00000527372 | TSF |
| 4% | chrX | 134971303 | 134971006 | − | chrX | 134967437 | 134967328 | − | ENST00000491002; ENST00000448053; ENST00000472834 | TSF |
| 4% | chrX | 134975955 | 134975496 | − | chrX | 134950187 | 134950078 | − | ENST00000420087; ENST00000463085; ENST00000370724; ENST00000491480 | TSF |
| 4% | chrX | 134975955 | 134975496 | − | chrX | 134950187 | 134950078 | − | ENST00000420087; ENST00000463085; ENST00000370724; ENST00000491480 | TSF |
| 4% | chr7 | 97938760 | 97938714 | − | chr7 | 97937208 | 97937001 | − | ENST00000005260 | TSF |
| 4% | chrX | 134975955 | 134975496 | − | chrX | 134967437 | 134967328 | − | ENST00000491002; ENST00000448053; ENST00000472834 | TSF |
| 3% | chr19 | 45365391 | 45365456 | + | chr19 | 45368528 | 45368917 | + | ENST00000252485; ENST00000252483 | TSF |
| 3% | chr19 | 45365391 | 45365456 | + | chr19 | 45368528 | 45368917 | + | ENST00000252485; ENST00000252483 | TSF |
| 3% | chr2 | 28630786 | 28630878 | + | chr2 | 28631626 | 28631733 | + | ENST00000379619; ENST00000264716; ENST00000436647; ENST00000545753 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 3% | chr2 | 28630786 | 28630878 | + | chr2 | 28631626 | 28631733 | + | ENST00000379619; ENST00000264716; ENST00000436647; ENST00000545753 | TSF |
| 3% | chr2 | 28630786 | 28630878 | + | chr2 | 28631626 | 28631733 | + | ENST00000379619; ENST00000264716; ENST00000436647; ENST00000545753 | TSF |
| 3% | chr17 | 48820020 | 48820202 | + | chr17 | 48821067 | 48821171 | + | ENST00000505658; ENST00000393227; ENST00000240304; ENST00000544170 | TSF |
| 3% | chr17 | 48820020 | 48820202 | + | chr17 | 48821067 | 48821171 | + | ENST00000505658; ENST00000393227; ENST00000240304; ENST00000544170 | TSF |
| 3% | chr17 | 48820020 | 48820202 | + | chr17 | 48821067 | 48821171 | + | ENST00000505658; ENST00000393227; ENST00000240304; ENST00000544170 | TSF |
| 3% | chr7 | 134213194 | 134213199 | + | chr7 | 134215395 | 134215562 | + | ENST00000359579 | TSF |
| 3% | chr22 | 37963762 | 37963951 | + | chr22 | 37964115 | 37964827 | + | ENST00000249014 | TSF |
| 3% | chr11 | 61544394 | 61544423 | + | chr11 | 61544736 | 61544936 | + | ENST00000278836; ENST00000265460; ENST00000327797 | TSF |
| 3% | chr11 | 61544394 | 61544423 | + | chr11 | 61544736 | 61544936 | + | ENST00000278836; ENST00000265460; ENST00000327797 | TSF |
| 3% | chr11 | 61544394 | 61544423 | + | chr11 | 61544736 | 61544936 | + | ENST00000278836; ENST00000265460; ENST00000327797 | TSF |
| 3% | chr3 | 155605105 | 155605320 | + | chr3 | 155611307 | 155611488 | + | ENST00000496455 | TSF |
| 3% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 3% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 3% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 3% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 3% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 3% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 3% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 3% | chr16 | 53866877 | 53867152 | + | chr16 | 53878067 | 53878210; 53878156 | + | ENST00000471389; ENST00000464071 | TSF |
| 3% | chr16 | 53866877 | 53867152 | + | chr16 | 53878067 | 53878210; 53878156 | + | ENST00000471389; ENST00000464071 | TSF |
| 3% | chr4 | 57321042 | 57321258 | + | chr4 | 57325538 | 57325704; 57325665 | + | ENST00000514888; ENST00000264221; ENST00000505164; ENST00000399688; ENST00000512576 | TSF |
| 3% | chr4 | 57321042 | 57321258 | + | chr4 | 57325538 | 57325704; 57325665 | + | ENST00000514888; ENST00000264221; ENST00000505164; ENST00000399688; ENST00000512576 | TSF |
| 3% | chrX | 134883429 | 134883726 | + | chrX | 134887292 | 134887401 | + | ENST00000370734; ENST00000485366; ENST00000443882 | TSF |
| 3% | chr3 | 189566580 | 189567255 | + | chr3 | 189582021 | 189582207; 189582057 | + | ENST00000264731; ENST00000382063; ENST00000418709; ENST00000320472; ENST00000392460; ENST00000440651; ENST00000354600; ENST00000434928; ENST00000437221; ENST00000392463; ENST00000392461; ENST00000449992; ENST00000456148 | TSF |
| 3% | chr3 | 189566580 | 189567255 | + | chr3 | 189582021 | 189582207; 189582057 | + | ENST00000264731; ENST00000382063; ENST00000418709; ENST00000320472; | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|----|----|---|----|----|---|----|----|-----|-----|
| | | | | | | | | | ENST00000392460; ENST00000440651; ENST00000354600; ENST00000434928; ENST00000437221; ENST00000392463; ENST00000392461; ENST00000449992; ENST00000456148 | |
| | 3% | chr3 | 189566580 | 189567255 | + | chr3 | 189582021 | 189582207; 189582057 | + | ENST00000264731; ENST00000382063; ENST00000418709; ENST00000320472; ENST00000392460; ENST00000440651; ENST00000354600; ENST00000434928; ENST00000437221; ENST00000392463; ENST00000392461; ENST00000449992; ENST00000456148 | TSF |
| | 3% | chr3 | 189566580 | 189567255 | + | chr3 | 189582021 | 189582207; 189582057 | + | ENST00000264731; ENST00000382063; ENST00000418709; ENST00000320472; ENST00000392460; ENST00000440651; ENST00000354600; ENST00000434928; ENST00000437221; ENST00000392463; ENST00000392461; ENST00000449992; ENST00000456148 | TSF |
| | 3% | chr3 | 189566580 | 189567255 | + | chr3 | 189582021 | 189582207; 189582057 | + | ENST00000264731; ENST00000382063; ENST00000418709; ENST00000320472; ENST00000392460; ENST00000440651; ENST00000354600; ENST00000434928; ENST00000437221; ENST00000392463; ENST00000392461; ENST00000449992; ENST00000456148 | TSF |
| | 3% | chr3 | 189566580 | 189567255 | + | chr3 | 189582021 | 189582207; 189582057 | + | ENST00000264731; ENST00000382063; ENST00000418709; ENST00000320472; ENST00000392460; ENST00000440651; ENST00000354600; ENST00000434928; ENST00000437221; ENST00000392463; ENST00000392461; ENST00000449992; ENST00000456148 | TSF |
| | 3% | chr1 | 233789624 | 233790730 | + | chr1 | 233802341 | 233802736 | + | ENST00000366621; ENST00000366620; ENST00000446915 | TSF |
| | 3% | chr1 | 233789624 | 233790730 | + | chr1 | 233802341 | 233802736 | + | ENST00000366621; ENST00000366620; ENST00000446915 | TSF |
| | 3% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| | 3% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| | 3% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| | 3% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| | 3% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 3% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 3% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 3% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |

TABLE 22-continued

Transcript fusion for Esophageal Carcinoma (ESCA) Coordinates of the fusion sequences for which the donor is the TE.

| 1 | 2' | 3' | 4 | 5' | 6' | 7 | 8' | 9' | 10' | 11' |
|---|---|---|---|---|---|---|---|---|---|---|
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 3% | chr11 | 102045048 | 102045146 | + | chr11 | 102056749 | 102056862 | + | ENST00000282441; ENST00000537274; ENST00000531439; ENST00000524575 | TSF |
| 3% | chr11 | 102045048 | 102045146 | + | chr11 | 102056749 | 102056862 | + | ENST00000282441; ENST00000537274; ENST00000531439; ENST00000524575 | TSF |
| 3% | chr11 | 102045048 | 102045146 | + | chr11 | 102056749 | 102056862 | + | ENST00000282441; ENST00000537274; ENST00000531439; ENST00000524575 | TSF |
| 3% | chr15 | 44051756 | 44051953 | + | chr15 | 44053622 | 44053729 | + | ENST00000300289; ENST00000538521 | TSF |
| 3% | chr15 | 89717587 | 89717675 | + | chr15 | 89719043 | 89719226 | + | ENST00000352732; ENST00000565973; ENST00000355100 | TSF |
| 3% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 3% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 3% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 3% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 3% | chr7 | 55464873 | 55464924 | + | chr7 | 55466116 | 55466323 | + | ENST00000254770 | TSF |
| 3% | chr4 | 124087242 | 124087575 | + | chr4 | 124177171 | 124177335 | + | ENST00000274008 | TSF |
| 3% | chr6 | 74413627 | 74413676 | + | chr6 | 74432974 | 74433002 | + | ENST00000422508; ENST00000437994; ENST00000287097 | TSF |
| 3% | chr6 | 74413627 | 74413676 | + | chr6 | 74432974 | 74433002 | + | ENST00000422508; ENST00000437994; ENST00000287097 | TSF |
| 3% | chr6 | 74413627 | 74413676 | + | chr6 | 74432974 | 74433002 | + | ENST00000422508; ENST00000437994; ENST00000287097 | TSF |
| 3% | chr9 | 131541764 | 131542578 | + | chr9 | 131550613 | 131550686 | + | ENST00000372648; ENST00000223865 | TSF |
| 3% | chr9 | 131541764 | 131542578 | + | chr9 | 131550613 | 131550686 | + | ENST00000372648; ENST00000223865 | TSF |
| 3% | chr7 | 23290404 | 23290481 | + | chr7 | 23292926 | 23293078 | + | ENST00000258733; ENST00000381990; ENST00000409458; ENST00000453162 | TSF |
| 3% | chr7 | 23290404 | 23290481 | + | chr7 | 23292926 | 23293078 | + | ENST00000258733; ENST00000381990; ENST00000409458; ENST00000453162 | TSF |
| 3% | chr7 | 23290404 | 23290481 | + | chr7 | 23292926 | 23293078 | + | ENST00000258733; ENST00000381990; ENST00000409458; ENST00000453162 | TSF |
| 3% | chr7 | 23290404 | 23290481 | + | chr7 | 23292926 | 23293078 | + | ENST00000258733; ENST00000381990; ENST00000409458; ENST00000453162 | TSF |
| 3% | chr12 | 122430912 | 122431655 | + | chr12 | 122439403 | 122439504 | + | ENST00000288912 | TSF |
| 3% | chr22 | 38166164 | 38166230 | + | chr22 | 38167657 | 38167743 | + | ENST00000406386; ENST00000403663 | TSF |
| 3% | chr16 | 58758969 | 58758792 | − | chr16 | 58757806 | 58757650 | − | ENST00000245206; ENST00000434819 | TSF |
| 3% | chr16 | 58758969 | 58758792 | − | chr16 | 58757806 | 58757650 | − | ENST00000245206; ENST00000434819 | TSF |
| 3% | chr12 | 54862718 | 54862609 | − | chr12 | 54858951 | 54858851 | − | ENST00000546931; ENST00000552397; ENST00000305879 | TSF |
| 3% | chr12 | 54862718 | 54862609 | − | chr12 | 54858951 | 54858851 | − | ENST00000546931; ENST00000552397; ENST00000305879 | TSF |
| 3% | chr11 | 93468219 | 93468129 | − | chr11 | 93466563 | 93466528 | − | ENST00000393259 | TSF |
| 3% | chr22 | 40898710 | 40898220 | − | chr22 | 40859290 | 40859225 | − | ENST00000422851 | TSF |
| 3% | chrX | 134954053 | 134953756 | − | chrX | 134932924 | 134932815 | − | ENST00000487941; ENST00000434966; ENST00000494421 | TSF |
| 3% | chr1 | 43634418 | 43634409 | − | chr1 | 43632906 | 43632831 | − | ENST00000431635; ENST00000236051 | TSF |
| 3% | chrX | 134936794 | 134936497 | − | chrX | 134932924 | 134932815 | − | ENST00000487941; ENST00000434966; ENST00000494421 | TSF |
| 3% | chr13 | 95233957 | 95233815 | − | chr13 | 95233443 | 95233345 | − | ENST00000261296 | TSF |
| 3% | chr11 | 64599672 | 64599483 | − | chr11 | 64599193 | 64598977 | − | ENST00000342711 | TSF |

TABLE 23

Transcript fusion for Glioblastoma Multiforme (GBM)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 93% | chr17 | 40812657 | 40812725 | + | ENST00000251412 | chr17 | 40813219 | 40813265 | + | TAF |
| 82% | chr5 | 146460699; 146460671 | 146460622 | − | ENST00000504198; ENST00000394409 | chr5 | 146414803 | 146414648 | − | TAF |
| 82% | chr5 | 146460699; 146460671 | 146460622 | − | ENST00000504198; ENST00000394409 | chr5 | 146414803 | 146414648 | − | TAF |
| 76% | chr11 | 73589824 | 73589864 | + | ENST00000310571 | chr11 | 73598085 | 73598225 | + | TAF |
| 75% | chr6 | 36762426 | 36762367 | − | ENST00000244751 | chr6 | 36760223 | 36760189 | − | TAF |
| 75% | chr14 | 31922550 | 31922481 | − | ENST00000549185; ENST00000547378; ENST00000310850; ENST00000356180 | chr14 | 31907346 | 31905965 | − | TSF |
| 66% | chrX | 64743587; 64743497 | 64743440 | − | ENST00000374807; ENST00000374811; ENST00000374804; ENST00000469091 | chrX | 64742373 | 64741630 | − | TAF |
| 66% | chrX | 64743587; 64743497 | 64743440 | − | ENST00000374807; ENST00000374811; ENST00000374804; ENST00000469091 | chrX | 64742373 | 64741630 | − | TAF |
| 66% | chrX | 64743587; 64743497 | 64743440 | − | ENST00000374807; ENST00000374811; ENST00000374804; ENST00000469091 | chrX | 64742373 | 64741630 | − | TAF |
| 66% | chrX | 64743587; 64743497 | 64743440 | − | ENST00000374807; ENST00000374811; ENST00000374804; ENST00000469091 | chrX | 64742373 | 64741630 | − | TAF |
| 60% | chr4 | 134084132 | 134084437 | + | ENST00000264360 | chr4 | 134129231 | 134129518 | + | TAF |
| 50% | chr9 | 131002264 | 131002275 | + | ENST00000475805; ENST00000341179; ENST00000372923; ENST00000393594; ENST00000486160 | chr9 | 131002706 | 131002973 | + | TAF |
| 50% | chr9 | 131002264 | 131002275 | + | ENST00000475805; ENST00000341179; ENST00000372923; ENST00000393594; ENST00000486160 | chr9 | 131002706 | 131002973 | + | TAF |
| 45% | chr19 | 1235564 | 1235500 | − | ENST00000590083; ENST00000382477; ENST00000215376; ENST00000589260 | chr19 | 1235389 | 1235290 | − | TAF |
| 45% | chr19 | 1235564 | 1235500 | − | ENST00000590083; ENST00000382477; ENST00000215376; ENST00000589260 | chr19 | 1235389 | 1235290 | − | TAF |
| 44% | chr19 | 44129402 | 44129230 | − | ENST00000222374 | chr19 | 44129055 | 44128921 | − | TAF |
| 41% | chr2 | 175809671 | 175809616 | − | ENST00000409900; ENST00000409156 | chr2 | 175805622 | 175805109 | − | TAF |
| 39% | chr1 | 224544627 | 224544695 | + | ENST00000465271; ENST00000366858; ENST00000366857; ENST00000366856 | chr1 | 224551811 | 224551931 | + | TAF |
| 36% | chr1 | 48771550 | 48771459 | − | ENST00000371847; ENST00000371843; ENST00000396199 | chr1 | 48730486 | 48730045 | − | TSF |
| 36% | chr1 | 48771550 | 48771459 | − | ENST00000371847; ENST00000371843; ENST00000396199 | chr1 | 48730486 | 48730045 | − | TSF |
| 36% | chr1 | 48771550 | 48771459 | − | ENST00000371847; ENST00000371843; ENST00000396199 | chr1 | 48730486 | 48730045 | − | TSF |
| 30% | chr20 | 53092486 | 53092551 | + | ENST00000262593 | chr20 | 53111339 | 53111426 | + | TAF |
| 28% | chr11 | 61197619 | 61197654 | + | ENST00000542794; ENST00000541135; ENST00000301761; ENST00000542074; ENST00000534878; ENST00000359614; ENST00000537782; ENST00000538594; ENST00000544801; ENST00000536250; ENST00000543265 | chr11 | 61240217 | 61240660 | + | TAF |
| 28% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 28% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 28% | chr18 | 54318306 | 54318248 | − | ENST00000587613 | chr18 | 54314766 | 54314664 | − | TSF |
| 26% | chr1 | 31347435 | 31347144 | − | ENST00000336798; ENST00000339394 | chr1 | 31340352 | 31340311 | − | TSF |
| 26% | chr1 | 31347435 | 31347144 | − | ENST00000336798; ENST00000339394 | chr1 | 31340352 | 31340311 | − | TSF |
| 25% | chr11 | 73589824 | 73589864 | + | ENST00000310571 | chr11 | 73598076 | 73598225 | + | TAF |
| 25% | chrX | 152730513 | 152730446 | − | ENST00000370211; ENST00000370212; ENST00000370210 | chrX | 152728559 | 152728505 | − | TAF |
| 25% | chrX | 152730513 | 152730446 | − | ENST00000370211; ENST00000370212; ENST00000370210 | chrX | 152728559 | 152728505 | − | TAF |
| 25% | chr2 | 230411808 | 230411663 | − | ENST00000341772 | chr2 | 230409543 | 230409247 | − | TSF |
| 22% | chr4 | 47583977 | 47584081 | + | ENST00000273859 | chr4 | 47584886 | 47585171 | + | TAF |
| 22% | chr7 | 136936138 | 136935977 | − | ENST00000348225; ENST00000393083 | chr7 | 136925784 | 136925658 | − | TAF |
| 21% | chr22 | 24323139 | 24323226 | + | ENST00000215780; ENST00000402588 | chr22 | 24324557 | 24324632 | + | TAF |
| 21% | chr7 | 27582719 | 27582586 | − | ENST00000265395; ENST00000425715 | chr7 | 27581374 | 27579272 | − | TAF |
| 21% | chr7 | 27582719 | 27582586 | − | ENST00000265395; ENST00000425715 | chr7 | 27581374 | 27579272 | − | TAF |
| 21% | chr17 | 63173850 | 63173921 | + | ENST00000584234; ENST00000262406 | chr17 | 63176114 | 63176128 | + | TAF |
| 21% | chr1 | 99380476 | 99380342 | − | ENST00000263177 | chr1 | 99378537 | 99378478 | − | TSF |

TABLE 23-continued

Transcript fusion for Glioblastoma Multiforme (GBM)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 20% | chr8 | 63502273 | 63502353 | + | ENST00000523211; ENST00000328472 | chr8 | 63546747 | 63547118 | + | TSF |
| 19% | chr6 | 11000397 | 11000320 | − | ENST00000354666 | chr6 | 11000151 | 11000002 | − | TAF |
| 19% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 19% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 19% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 19% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 19% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 19% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 19% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 19% | chr12 | 102074121 | 102074307 | + | ENST00000547405; ENST00000045255; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 19% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 19% | chr12 | 102074121 | 102074307 | + | ENST00000547405; ENST00000452455 | chr12 | 102089430 | 102089665 | + | TAF |

TABLE 23-continued

Transcript fusion for Glioblastoma Multiforme (GBM)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
|   |   |   |   |   | ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 |   |   |   |   |   |
| 19% | chr4 | 151124947 | 151125041 | + | ENST00000296550; ENST00000411937; ENST00000506325; ENST00000302176 | chr4 | 151135817 | 151135831 | + | TSF |
| 19% | chr4 | 151124947 | 151125041 | + | ENST00000296550; ENST00000411937; ENST00000506325; ENST00000302176 | chr4 | 151135817 | 151135831 | + | TSF |
| 19% | chr1 | 70820635 | 70820794 | + | ENST00000359875; ENST00000370940; ENST00000531950; ENST00000432224 | chr1 | 70831829 | 70831848 | + | TSF |
| 18% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 18% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 18% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 18% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 18% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 17% | chr7 | 135635430 | 135635347 | − | ENST00000393085 | chr7 | 135585557 | 135585512 | − | TSF |
| 16% | chr7 | 102307711 | 102307537 | − | ENST00000591000; ENST00000476151; ENST00000358438 | chr7 | 102207490 | 102207365 | − | TAF |
| 16% | chr1 | 99380476 | 99380357 | − | ENST00000370188; ENST00000263177 | chr1 | 99378537 | 99378478 | − | TSF |
| 16% | chr11 | 117710545 | 117710496 | − | ENST00000532984; ENST00000584394; ENST00000529335 | chr11 | 117703821 | 117703741 | − | TSF |
| 16% | chr11 | 117710545 | 117710496 | − | ENST00000532984; ENST00000584394; ENST00000529335 | chr11 | 117703821 | 117703741 | − | TSF |
| 16% | chr11 | 117710545 | 117710496 | − | ENST00000532984; ENST00000584394; ENST00000529335 | chr11 | 117703821 | 117703741 | − | TSF |
| 15% | chr3 | 28357824 | 28357914 | + | ENST00000466830; ENST00000423894; ENST00000418849 | chr3 | 28360223 | 28360364 | + | TAF |
| 15% | chr3 | 28357824 | 28357914 | + | ENST00000466830; ENST00000423894; ENST00000418849 | chr3 | 28360223 | 28360364 | + | TAF |
| 15% | chr3 | 28357824 | 28357914 | + | ENST00000466830; ENST00000423894; ENST00000418849 | chr3 | 28360223 | 28360364 | + | TAF |
| 15% | chr2 | 153591508 | 153591640 | + | ENST00000326446 | chr2 | 153613426 | 153613893 | + | TAF |
| 15% | chr18 | 72250797 | 72250944 | + | ENST00000358821; ENST00000582365 | chr18 | 72256555 | 72256578 | + | TAF |
| 15% | chr18 | 72250797 | 72250944 | + | ENST00000358821; ENST00000582365 | chr18 | 72256555 | 72256578 | + | TAF |
| 15% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 15% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 15% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 15% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 15% | chr7 | 91509397 | 91509369 | − | ENST00000351870; ENST00000442961 | chr7 | 91430582 | 91429696 | − | TSF |
| 15% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 15% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 15% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 14% | chr19 | 3544937 | 3544807 | − | ENST00000389395; ENST00000398558 | chr19 | 3538708 | 3538306 | − | TAF |

TABLE 23-continued

Transcript fusion for Glioblastoma Multiforme (GBM)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 14% | chr19 | 3544937 | 3544807 | − | ENST00000389395; ENST00000398558; ENST00000588918; ENST00000355415; ENST00000589063 | chr19 | 3538708 | 3538306 | − | TAF |
| 14% | chr19 | 3544937 | 3544807 | − | ENST00000389395; ENST00000398558; ENST00000588918; ENST00000355415; ENST00000589063 | chr19 | 3538708 | 3538306 | − | TAF |
| 14% | chr5 | 146435301; 146435306 | 146435228 | − | ENST00000394414; ENST00000336640; ENST00000522831; ENST00000515880; ENST00000512011 | chr5 | 146414803 | 146414648 | − | TAF |
| 14% | chr5 | 146435301; 146435306 | 146435228 | − | ENST00000394414; ENST00000336640; ENST00000522831; ENST00000515880; ENST00000512011 | chr5 | 146414803 | 146414648 | − | TAF |
| 14% | chr19 | 12146354 | 12146352 | − | ENST00000344980; ENST00000550507; ENST00000548669 | chr19 | 12100261 | 12100168 | − | TAF |
| 14% | chr6 | 29913011 | 29913058 | + | ENST00000396634; ENST00000376806; ENST00000376809 | chr6 | 29915459 | 29916523 | + | TAF |
| 14% | chr6 | 29913011 | 29913058 | + | ENST00000396634; ENST00000376806; ENST00000376809 | chr6 | 29915459 | 29916523 | + | TAF |
| 14% | chr1 | 1237426 | 1237368 | − | ENST00000354700; ENST00000353662 | chr1 | 1236310 | 1236145 | − | TAF |
| 14% | chr1 | 1237426 | 1237368 | − | ENST00000354700; ENST00000353662 | chr1 | 1236310 | 1236145 | − | TAF |
| 13% | chr7 | 99821698 | 99821505 | − | ENST00000436886 | chr7 | 99810756 | 99810604 | − | TAF |
| 12% | chr6 | 35314915 | 35314927 | + | ENST00000448077 | chr6 | 35351354 | 35351915 | + | TAF |
| 12% | chr15 | 89011139 | 89011255 | + | ENST00000560708; ENST00000325844; ENST00000353598 | chr15 | 89011993 | 89012264 | + | TAF |
| 12% | chr6 | 36762426 | 36762367 | − | ENST00000244751 | chr6 | 36760220 | 36760189 | − | TAF |
| 12% | chr15 | 32976758; 32976761 | 32976870 | + | ENST00000300175; ENST00000413748; ENST00000494364; ENST00000497208; ENST00000471027 | chr15 | 32977789 | 32977906 | + | TAF |
| 12% | chr15 | 32976758; 32976761 | 32976870 | + | ENST00000300175; ENST00000413748; ENST00000494364; ENST00000497208; ENST00000471027 | chr15 | 32977789 | 32977906 | + | TAF |
| 12% | chr15 | 32976758; 32976761 | 32976870 | + | ENST00000300175; ENST00000413748; ENST00000494364; ENST00000497208; ENST00000471027 | chr15 | 32977789 | 32977906 | + | TAF |
| 12% | chr3 | 58553091 | 58552935 | − | ENST00000360997; ENST00000394481; ENST00000464064; ENST00000474531; ENST00000447756 | chr3 | 58550140 | 58549790 | − | TAF |
| 12% | chr3 | 58553091 | 58552935 | − | ENST00000360997; ENST00000394481; ENST00000464064; ENST00000474531; ENST00000447756 | chr3 | 58550140 | 58549790 | − | TAF |
| 12% | chr3 | 58553091 | 58552935 | − | ENST00000360997; ENST00000394481; ENST00000464064; ENST00000474531; ENST00000447756 | chr3 | 58550140 | 58549790 | − | TAF |
| 11% | chr2 | 26624858 | 26625012 | + | ENST00000288710; ENST00000421869 | chr2 | 26630464 | 26631004 | + | TAF |
| 11% | chr5 | 173040258; 173040180 | 173040134 | − | ENST00000311086; ENST00000285908; ENST00000462674 | chr5 | 173012591 | 173012432 | − | TAF |
| 11% | chr5 | 173040258; 173040180 | 173040134 | − | ENST00000311086; ENST00000285908; ENST00000462674 | chr5 | 173012591 | 173012432 | − | TAF |
| 11% | chrX | 103219096 | 103219195 | + | ENST00000419165; ENST00000563257; ENST00000540220; ENST00000436583; ENST00000567181; ENST00000569577 | chrX | 103231301 | 103231354 | + | TSF |
| 11% | chr5 | 146460699; 146460671 | 146460622 | − | ENST00000504198; ENST00000394409 | chr5 | 146321615 | 146321345 | − | TSF |
| 11% | chr5 | 146460699; 146460671 | 146460622 | − | ENST00000504198; ENST00000394409 | chr5 | 146321615 | 146321345 | − | TSF |
| 10% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 10% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 10% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 10% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 10% | chr5 | 149629872 | 149629789 | − | ENST00000348628; ENST00000398376 | chr5 | 149628210 | 149627911 | − | TSF |
| 10% | chr7 | 92083816 | 92083999 | + | ENST00000287957 | chr7 | 92090633 | 92090800 | + | TSF |
| 10% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; | chr3 | 98228614 | 98228468 | − | TSF |

TABLE 23-continued

Transcript fusion for Glioblastoma Multiforme (GBM)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| | | | | | ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | | | | | |
| 10% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 10% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 10% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 10% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 10% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 10% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 9% | chr7 | 65751498 | 65751696 | + | ENST00000304842 | chr7 | 65781807 | 65782076 | + | TSF |
| 9% | chr15 | 83102759 | 83103078 | + | ENST00000561062; ENST00000358583 | chr15 | 83193141 | 83193227 | + | TSF |

TABLE 23-continued

Transcript fusion for Glioblastoma Multiforme (GBM)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 9% | chr15 | 65687596 | 65687432 | − | ENST00000352385 | chr15 | 65687004 | 65686908 | − | TSF |
| 8% | chr7 | 55270210 | 55270401 | + | ENST00000455089 | chr7 | 55272949 | 55272949 | + | TSF |
| 8% | chr13 | 31531010 | 31531166 | + | ENST00000380473 | chr13 | 31534099 | 31534280 | + | TSF |
| 8% | chr4 | 159620139 | 159620282 | + | ENST00000511912; ENST00000307738 | chr4 | 159622027 | 159622060 | + | TSF |
| 8% | chr4 | 159620139 | 159620282 | + | ENST00000511912; ENST00000307738 | chr4 | 159622027 | 159622060 | + | TSF |
| 6% | chr22 | 48885405 | 48885516 | + | ENST00000402357; ENST00000336769 | chr22 | 48915770 | 48916108 | + | TSF |
| 6% | chr2 | 217366064 | 217366082 | + | ENST00000491306; ENST00000456586 | chr2 | 217393993 | 217394327 | + | TSF |
| 6% | chr2 | 217366064 | 217366082 | + | ENST00000491306; ENST00000456586 | chr2 | 217393993 | 217394327 | + | TSF |
| 6% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 6% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 6% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 6% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 6% | chrX | 74725682 | 74725656 | − | ENST00000373367; ENST00000373361 | chrX | 74722103 | 74721880 | − | TSF |
| 6% | chr20 | 62070073 | 62069978 | − | ENST00000357249; ENST00000359125; ENST00000354587; ENST00000359689; ENST00000360480; ENST00000370224; ENST00000344462; ENST00000344425 | chr20 | 62066140 | 62065806 | − | TSF |
| 6% | chr7 | 55468867 | 55469013 | + | ENST00000254770 | chr7 | 55477218 | 55477724 | + | TSF |
| 6% | chr15 | 23810930 | 23811234 | + | ENST00000314520; ENST00000568252; ENST00000564592 | chr15 | 23872913 | 23873108 | + | TSF |
| 6% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 6% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 6% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 6% | chr8 | 109468102 | 109468159 | + | ENST00000220853; ENST00000519642 | chr8 | 109468381 | 109468590 | + | TSF |
| 6% | chr8 | 109468102 | 109468159 | + | ENST00000220853; ENST00000519642 | chr8 | 109468381 | 109468590 | + | TSF |
| 6% | chr12 | 113623819 | 113623826 | + | ENST00000552495 | chr12 | 113623998 | 113624117 | + | TSF |
| 6% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023225 | 58023117 | − | TSF |
| 6% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023225 | 58023117 | − | TSF |
| 6% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023225 | 58023117 | − | TSF |
| 6% | chr19 | 11567963 | 11567925 | − | ENST00000359227; ENST00000438662 | chr19 | 11567647 | 11567483 | − | TSF |
| 6% | chr13 | 53307494; 53307473 | 53307354 | − | ENST00000448904; ENST00000377962; ENST00000431550 | chr13 | 53304269 | 53303967 | − | TSF |
| 6% | chr13 | 53307494; 53307473 | 53307354 | − | ENST00000448904; ENST00000377962; ENST00000431550 | chr13 | 53304269 | 53303967 | − | TSF |
| 6% | chr2 | 133426110; 133426006 | 133425973 | − | ENST00000397463; ENST00000345008 | chr2 | 133381838 | 133381614 | − | TSF |
| 6% | chr2 | 133426110; 133426006 | 133425973 | − | ENST00000397463; ENST00000345008 | chr2 | 133381838 | 133381614 | − | TSF |
| 6% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 6% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 6% | chr12 | 58024115 | 58023935 | − | ENST00000341156; ENST00000418555; ENST00000552798; ENST00000549391; | chr12 | 58023079 | 58022983 | − | TSF |

TABLE 23-continued

Transcript fusion for Glioblastoma Multiforme (GBM)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 6% | chr12 | 58024115 | 58023935 | − | ENST00000449184; ENST00000550764; ENST00000552350; ENST00000548888 ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 5% | chr4 | 57319769 | 57319927 | + | ENST00000514888; ENST00000264221; ENST00000505164; ENST00000399688; ENST00000512576 | chr4 | 57321183 | 57321327 | + | TSF |
| 5% | chr4 | 57319769 | 57319927 | + | ENST00000514888; ENST00000264221; ENST00000505164; ENST00000399688; ENST00000512576 | chr4 | 57321183 | 57321327 | + | TSF |
| 5% | chr4 | 57319769 | 57319927 | + | ENST00000514888; ENST00000264221; ENST00000505164; ENST00000399688; ENST00000512576 | chr4 | 57321183 | 57321327 | + | TSF |
| 5% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 5% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 5% | chr10 | 127483547 | 127483449 | − | ENST00000368797; ENST00000368786 | chr10 | 127473829 | 127473633 | − | TSF |
| 5% | chr16 | 30783410 | 30783511 | + | ENST00000324685; ENST00000402121; ENST00000563683; ENST00000357890 | chr16 | 30785136 | 30785155 | + | TSF |
| 5% | chr16 | 30783410 | 30783511 | + | ENST00000324685; ENST00000402121; ENST00000563683; ENST00000357890 | chr16 | 30785136 | 30785155 | + | TSF |
| 5% | chr16 | 30783410 | 30783511 | + | ENST00000324685; ENST00000402121; ENST00000563683; ENST00000357890 | chr16 | 30785136 | 30785155 | + | TSF |
| 5% | chr16 | 30783410 | 30783511 | + | ENST00000324685; ENST00000402121; ENST00000563683; ENST00000357890 | chr16 | 30785136 | 30785155 | + | TSF |
| 5% | chr7 | 39610105 | 39610226 | + | ENST00000223273; ENST00000448268; ENST00000432096 | chr7 | 39618101 | 39618410 | + | TSF |
| 5% | chr1 | 11115983; 11115877 | 11115838 | − | ENST00000376957; ENST00000490101 | chr1 | 11115464 | 11115178 | − | TSF |
| 5% | chr1 | 11115983; 11115877 | 11115838 | − | ENST00000376957; ENST00000490101 | chr1 | 11115464 | 11115178 | − | TSF |
| 5% | chr1 | 144852443 | 144852394 | − | ENST00000369356 | chr1 | 144836558 | 144836419 | − | TSF |
| 4% | chr2 | 112933291 | 112933416 | + | ENST00000331203; ENST00000409903; ENST00000409450; ENST00000441565 | chr2 | 112935633 | 112935771 | + | TSF |
| 4% | chr2 | 112933291 | 112933416 | + | ENST00000331203; ENST00000409903; ENST00000409450; ENST00000441565 | chr2 | 112935633 | 112935771 | + | TSF |
| 4% | chr7 | 74168178 | 74168361 | + | ENST00000324896; ENST00000346152; ENST00000353920; ENST00000416070 | chr7 | 74168612 | 74168748 | + | TSF |
| 4% | chr7 | 74168178 | 74168361 | + | ENST00000324896; ENST00000346152; ENST00000353920; ENST00000416070 | chr7 | 74168612 | 74168748 | + | TSF |
| 4% | chr7 | 74168178 | 74168361 | + | ENST00000324896; ENST00000346152; ENST00000353920; ENST00000416070 | chr7 | 74168612 | 74168748 | + | TSF |
| 4% | chr7 | 74168178 | 74168361 | + | ENST00000324896; ENST00000346152; ENST00000353920; ENST00000416070 | chr7 | 74168612 | 74168748 | + | TSF |
| 4% | chr20 | 24565492 | 24565629 | + | ENST00000376862 | chr20 | 24627217 | 24627262 | + | TSF |
| 4% | chr19 | 19349062; 19349068 | 19349220 | + | ENST00000252575; ENST00000538881; ENST00000588231 | chr19 | 19350543 | 19350866 | + | TSF |
| 4% | chr19 | 19349062; 19349068 | 19349220 | + | ENST00000252575; ENST00000538881; ENST00000588231 | chr19 | 19350543 | 19350866 | + | TSF |
| 4% | chr19 | 19349062; 19349068 | 19349220 | + | ENST00000252575; ENST00000538881; ENST00000588231 | chr19 | 19350543 | 19350866 | + | TSF |
| 4% | chr1 | 44804994; 44804988 | 44804717 | − | ENST00000372257; ENST00000457571 | chr1 | 44801643 | 44801548 | − | TSF |
| 4% | chr1 | 44804994; 44804988 | 44804717 | − | ENST00000372257; ENST00000457571 | chr1 | 44801643 | 44801548 | − | TSF |
| 4% | chr1 | 1255909 | 1255836 | − | ENST00000435064; ENST00000540437; ENST00000450926; ENST00000545578; ENST00000528879; ENST00000434694; ENST00000526797; ENST00000527719; ENST00000530031; ENST00000534345; ENST00000498476 | chr1 | 1255223 | 1254988 | − | TSF |
| 4% | chr1 | 1255909 | 1255836 | − | ENST00000435064; ENST00000540437; ENST00000450926; ENST00000545578; ENST00000528879; ENST00000434694; ENST00000526797; ENST00000527719; ENST00000530031; ENST00000534345; ENST00000498476 | chr1 | 1255223 | 1254988 | − | TSF |
| 4% | chr1 | 1255909 | 1255836 | − | ENST00000435064; ENST00000540437; ENST00000450926; ENST00000545578; ENST00000528879; ENST00000434694; | chr1 | 1255223 | 1254988 | − | TSF |

TABLE 23-continued

Transcript fusion for Glioblastoma Multiforme (GBM)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 4% | chr1 | 1255909 | 1255836 | − | ENST00000526797; ENST00000527719; ENST00000530031; ENST00000534345; ENST00000498476 ENST00000435064; ENST00000540437; ENST00000450926; ENST00000545578; ENST00000528879; ENST00000434694; | chr1 | 1255223 | 1254988 | − | TSF |
| 4% | chr1 | 1255909 | 1255836 | − | ENST00000526797; ENST00000527719; ENST00000530031; ENST00000534345; ENST00000498476 ENST00000435064; ENST00000540437; ENST00000450926; ENST00000545578; ENST00000528879; ENST00000434694; | chr1 | 1255223 | 1254988 | − | TSF |
| 4% | chr1 | 1255909 | 1255836 | − | ENST00000526797; ENST00000527719; ENST00000530031; ENST00000534345; ENST00000498476 ENST00000435064; ENST00000540437; ENST00000450926; ENST00000545578; ENST00000528879; ENST00000434694; ENST00000526797; ENST00000527719; ENST00000530031; ENST00000534345; ENST00000498476 | chr1 | 1255223 | 1254988 | − | TSF |
| 4% | chr19 | 23556639 | 23556544 | − | ENST00000599743; ENST00000300619 | chr19 | 23491899 | 23491588 | − | TSF |

TABLE 24

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 92% | chr4 | 174310858 | 174310746 | − | chr4 | 174309546 | 174309492 | − | ENST00000296506 | TAF |
| 91% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 91% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 91% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 91% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 91% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 91% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 82% | chr1 | 156374721 | 156374537 | − | chr1 | 156374393 | 156374318; 156374346 | − | ENST00000400991; ENST00000368242; ENST00000310027; ENST00000368243; ENST00000357975 | TAF |
| 82% | chr1 | 156374721 | 156374537 | − | chr1 | 156374393 | 156374318; 156374346 | − | ENST00000400991; ENST00000368242; ENST00000310027; ENST00000368243; | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 73% | chr7 | 150938296 | 150938250 | − | chr7 | 150937608 | 150937511 | − | ENST00000357975; ENST00000262188; ENST00000392811; ENST00000356800 | TAF |
| 71% | chr3 | 115350112 | 115350159 | + | chr3 | 115394860 | 115395457 | + | ENST00000305124; ENST00000393780 | TSF |
| 60% | chr9 | 131002678 | 131002811 | + | chr9 | 131004511 | 131004624 | + | ENST00000475805; ENST00000341179; ENST00000372923; ENST00000393594; ENST00000486160 | TAF |
| 60% | chr9 | 131002678 | 131002811 | + | chr9 | 131004511 | 131004624 | + | ENST00000475805; ENST00000341179; ENST00000372923; ENST00000393594; ENST00000486160 | TAF |
| 52% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 52% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 52% | chr17 | 80440912 | 80441180 | + | chr17 | 80441592 | 80441655; 804416159 | + | ENST00000390006; ENST00000309794; ENST00000345415; ENST00000457415; ENST00000412079; ENST00000577432; ENST00000584513 | TAF |
| 52% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 52% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 52% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 52% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 52% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 47% | chr8 | 82194688 | 94782127 | + | chr8 | 82195601 | 82195773 | + | ENST00000297258 | TAF |
| 45% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 45% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 45% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 45% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 45% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 44% | chr2 | 230409549 | 230409481 | − | chr2 | 230377652 | 230377499 | − | ENST00000341772 | TAF |
| 42% | chr19 | 41816860 | 41816920 | + | chr19 | 41822289 | 41822744 | + | ENST00000269967 | TAF |
| 42% | chr3 | 98482258 | 98482283 | + | chr3 | 98487274 | 98487373 | + | ENST00000492254 | TAF |
| 41% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 41% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 41% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 41% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 41% | chr19 | 49121994 | 49121817 | − | chr19 | 49121134 | 149121048 | − | ENST00000549920; ENST00000547897; ENST00000084795; ENST00000550645; | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 40% | chr6 | 3247564 | 7553243 | – | chr6 | 3226903 | 3226795 | – | ENST00000549370; ENST00000549273 ENST00000259818 | TAF |
| 38% | chr12 | 102411559 | 102411498 | – | chr12 | 102406970 | 102406886 | – | ENST00000240079; ENST00000545679; ENST00000542923 | TAF |
| 38% | chr2 | 175806110 | 175805544 | – | chr2 | 175783293 | 175783262 | – | ENST00000409900; ENST00000409156 | TAF |
| 38% | chr2 | 175806110 | 175805544 | – | chr2 | 175783293 | 175783262 | – | ENST00000409900; ENST00000409156 | TAF |
| 37% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 37% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 37% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 37% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 37% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 37% | chr8 | 51556816 | 51557016 | + | chr8 | 51569469 | 51569585 | + | ENST00000518864; ENST00000522124; ENST00000517473; ENST00000520825; ENST00000276467; ENST00000524004 | TSF |
| 37% | chr8 | 51556816 | 51557016 | + | chr8 | 51569469 | 51569585 | + | ENST00000518864; ENST00000522124; ENST00000517473; ENST00000520825; ENST00000276467; ENST00000524004 | TSF |
| 37% | chr8 | 51556816 | 51557016 | + | chr8 | 51569469 | 51569585 | + | ENST00000518864; ENST00000522124; ENST00000517473; ENST00000520825; ENST00000276467; ENST00000524004 | TSF |
| 37% | chr8 | 51556816 | 51557016 | + | chr8 | 51569469 | 51569585 | + | ENST00000518864; ENST00000522124; ENST00000517473; ENST00000520825; ENST00000276467; ENST00000524004 | TSF |
| 35% | chr15 | 75891737 | 175891599 | – | chr15 | 75891022 | 75890699 | – | ENST00000567134; ENST00000308588; ENST00000371091; ENST00000564644; ENST00000564675 | TSF |
| 34% | chr7 | 99747312 | 99747315 | + | chr7 | 99751023 | 99751140; 99751352 | + | ENST00000341942; ENST00000441173 | TAF |
| 34% | chr7 | 99747312 | 99747315 | + | chr7 | 99751023 | 99751140; 99751352 | + | ENST00000341942; ENST00000441173 | TAF |
| 34% | chr11 | 93468219 | 93468129 | – | chr11 | 93467826 | 93467791; 93467814 | – | ENST00000393259; ENST00000527169 | TAF |
| 34% | chr11 | 93468219 | 93468129 | – | chr11 | 93467826 | 93467791; 93467814 | – | ENST00000393259; ENST00000527169 | TAF |
| 32% | chr20 | 43919547 | 43919514 | – | chr20 | 43882374 | 43882216 | – | ENST00000338380 | TAF |
| 32% | chr5 | 176950300 | 176950160 | – | chr5 | 176949072 | 176948976 | – | ENST00000514747; ENST00000329540; ENST00000443375; ENST00000524677 | TAF |
| 30% | chr5 | 176950016 | 176949956 | – | chr5 | 176949072 | 176948976 | – | ENST00000514747; ENST00000329540; ENST00000443375; ENST00000524677 | TAF |
| 29% | chr3 | 39544232 | 39544405 | + | chr3 | 39554874 | 39554913; 39554874 | + | ENST00000428261; ENST00000415443; ENST00000447324; ENST00000383754; ENST00000311042; ENST00000452959; ENST00000396228; ENST00000442631 | TAF |
| 29% | chr3 | 39544232 | 39544405 | + | chr3 | 39554874 | 39554913; 39554874 | + | ENST00000428261; ENST00000415443; ENST00000447324; ENST00000383754; ENST00000311042; ENST00000452959; ENST00000396228; ENST00000442631 | TAF |
| 28% | chr1 | 79124611 | 79124650 | + | chr1 | 79124997 | 79125168; 79125113 | + | ENST00000370747; ENST00000438486 | TAF |
| 28% | chr1 | 79124611 | 79124650 | + | chr1 | 79124997 | 79125168; 79125113 | + | ENST00000370747; ENST00000438486 | TAF |
| 28% | chr4 | 151135833 | 151135882 | + | chr4 | 151141858 | 151141930 | + | ENST00000296550; ENST00000411937; ENST00000506325; ENST00000302176 | TSF |
| 28% | chr4 | 151135833 | 151135882 | + | chr4 | 151141858 | 151141930 | + | ENST00000296550; ENST00000411937; ENST00000506325; ENST00000302176 | TSF |
| 26% | chr19 | 58515808 | 58516068 | + | chr19 | 58517275 | 58517367; 58517363 | + | ENST00000550135; ENST00000553254 | TAF |
| 26% | chr19 | 58515808 | 58516068 | + | chr19 | 58517275 | 58517367; 58517363 | + | ENST00000550135; ENST00000553254 | TAF |
| 26% | chr16 | 29915789 | 29915910 | + | chr16 | 29916173 | 29916286 | + | ENST00000563177; ENST00000483405; ENST00000308748; ENST00000414952; ENST00000566693 | TAF |
| 26% | chr16 | 29915789 | 29915910 | + | chr16 | 29916173 | 29916286 | + | ENST00000563177; ENST00000483405; ENST00000308748; ENST00000414952; ENST00000566693 | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 26% | chr7 | 29899867 | 29900179 | + | chr7 | 29915446 | 29915578 | + | ENST00000409123; ENST00000242140; ENST00000409290 | TSF |
| 26% | chr7 | 29899867 | 29900179 | + | chr7 | 29915446 | 29915578 | + | ENST00000409123; ENST00000242140; ENST00000409290 | TSF |
| 26% | chr4 | 151135833 | 151135882 | + | chr4 | 151141855 | 151141930 | + | ENST00000296550; ENST00000302176 | TSF |
| 25% | chr12 | 6602868 | 6602840 | − | chr12 | 6602138 | 6602028 | − | ENST00000229238 | TAF |
| 24% | chr20 | 43581305 | 43581345 | + | chr20 | 43586978 | 43587052 | + | ENST00000372826 | TAF |
| 24% | chr11 | 66048968 | 66049045 | + | chr11 | 66049730 | 66049798; 66049824 | + | ENST00000528852; ENST00000311445; ENST00000528063 | TSF |
| 24% | chr11 | 66048968 | 66049045 | + | chr11 | 66049730 | 66049798; 66049824 | + | ENST00000528852; ENST00000311445; ENST00000528063 | TSF |
| 24% | chr11 | 66048968 | 66049045 | + | chr11 | 66049730 | 66049798; 66049824 | + | ENST00000528852; ENST00000311445; ENST00000528063 | TSF |
| 24% | chr1 | 246581335 | 246580598 | − | chr1 | 246518396 | 246518333 | − | ENST00000388985; ENST00000403792 | TSF |
| 24% | chr1 | 246581335 | 246580598 | − | chr1 | 246518396 | 246518333 | − | ENST00000388985; ENST00000403792 | TSF |
| 23% | chr13 | 111287310 | 111287482 | + | chr13 | 111287815 | 111287935 | + | ENST00000458711; ENST00000424185; ENST00000309957 | TAF |
| 23% | chr13 | 111287310 | 111287482 | + | chr13 | 111287815 | 111287935 | + | ENST00000458711; ENST00000424185; ENST00000309957 | TAF |
| 22% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 22% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 22% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 22% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 22% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 22% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 22% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 22% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 22% | chr15 | 93592614 | 93592599 | − | chr15 | 93588935 | 93588228; 93588877 | − | ENST00000425933; ENST00000543599; ENST00000329082; ENST00000542321; ENST00000538818; ENST00000557301; ENST00000557420; ENST00000556658 | TSF |
| 22% | chr15 | 93592614 | 93592599 | − | chr15 | 93588935 | 93588228; 93588877 |   | ENST00000425933; ENST00000543599; ENST00000329082; ENST00000542321; ENST00000538818; ENST00000557301; ENST00000557420; ENST00000556658 | TSF |
| 21% | chr17 | 40813377 | 40813974 | + | chr17 | 40815395 | 40815521 | + | ENST00000251412 | TAF |
| 20% | chr1 | 31346734 | 31346686 | − | chr1 | 31346224 | 31346058 | − | ENST00000336798; ENST00000339394 | TAF |
| 19% | chr22 | 45064651 | 45064685 | + | chr22 | 45098372 | 45098488 | + | ENST00000403581; ENST00000336985; ENST00000403696; ENST00000431834; ENST00000361473; ENST00000352766; ENST00000517296 | TAF |
| 19% | chr22 | 45064651 | 45064685 | + | chr22 | 45098372 | 45098488 | + | ENST00000403581; ENST00000336985; ENST00000403696; ENST00000431834; ENST00000361473; ENST00000352766; ENST00000517296 | TAF |
| 19% | chr22 | 45064651 | 45064685 | + | chr22 | 45098372 | 45098488 | + | ENST00000403581; ENST00000336985; ENST00000403696; ENST00000431834; ENST00000361473; ENST00000352766; ENST00000517296 | TAF |
| 19% | chr22 | 45064651 | 45064685 | + | chr22 | 45098372 | 45098488 | + | ENST00000403581; ENST00000336985; ENST00000403696; ENST00000431834; | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 19% | chr22 | 45064651 | 64645085 | + | chr22 | 45098372 | 45098488 | + | ENST00000361473; ENST00000352766; ENST00000517296 ENST00000403581; ENST00000336985; ENST00000403696; ENST00000431834; ENST00000361473; ENST00000352766; ENST00000517296 | TAF |
| 19% | chr5 | 92920103 | 92920128 | + | chr5 | 92921107 | 92921192 | + | ENST00000327111 | TAF |
| 19% | chr7 | 55464873 | 55464924 | + | chr7 | 55466116 | 55466323 | + | ENST00000254770 | TSF |
| 18% | chr9 | 69269543 | 69269396 | − | chr9 | 69259308 | 69259222; 69259214 | − | ENST00000377457; ENST00000377449; ENST00000382399; ENST00000377441; ENST00000377439 | TAF |
| 18% | chr9 | 69269543 | 69269396 | − | chr9 | 69259308 | 69259222; 69259214 | − | ENST00000377457; ENST00000377449; ENST00000382399; ENST00000377441; ENST00000377439 | TAF |
| 18% | chr9 | 69269543 | 69269396 | − | chr9 | 69259308 | 69259222; 69259214 | − | ENST00000377457; ENST00000377449; ENST00000382399; ENST00000377441; ENST00000377439 | TAF |
| 18% | chr9 | 69269543 | 69269396 | − | chr9 | 69259308 | 69259222; 69259214 | − | ENST00000377457; ENST00000377449; ENST00000382399; ENST00000377441; ENST00000377439 | TAF |
| 18% | chr7 | 55477082 | 55477474 | + | chr7 | 55479600 | 55479782 | + | ENST00000254770 | TSF |
| 18% | chr2 | 101024262 | 101024202 | − | chr2 | 101023169 | 101023038 | − | ENST00000542617; ENST00000448989 | TSF |
| 18% | chr2 | 101024262 | 101024202 | − | chr2 | 101023169 | 101023038 | − | ENST00000542617; ENST00000448989 | TSF |
| 18% | chr9 | 117824597 | 117824593 | − | chr9 | 117822281 | 117822009 | − | ENST00000350763; ENST00000341037; ENST00000423613 | TSF |
| 18% | chr9 | 117824597 | 117824593 | − | chr9 | 117822281 | 117822009 | − | ENST00000350763; ENST00000341037; ENST00000423613 | TSF |
| 18% | chr9 | 117824597 | 117824593 | − | chr9 | 117822281 | 117822009 | − | ENST00000350763; ENST00000341037; ENST00000423613 | TSF |
| 17% | chr9 | 131189761 | 131190058 | + | chr9 | 131190581 | 131190700; 131190702 | + | ENST00000372842; ENST00000420512; ENST00000372838 | TAF |
| 17% | chr9 | 131189761 | 190131058 | + | chr9 | 131190581 | 131190700; 131190702 | + | ENST00000372842; ENST00000420512; ENST00000372838 | TAF |
| 17% | chr18 | 48249804 | 48249890 | + | chr18 | 48252332 | 48252545 | + | ENST00000400384; ENST00000540640 | TAF |
| 17% | chr1 | 151683281 | 151683172 | − | chr1 | 151682267 | 151682219 | − | ENST00000290585; ENST00000290583; ENST00000420342 | TAF |
| 17% | chr1 | 151683281 | 151683172 | − | chr1 | 151682267 | 151682219 | − | ENST00000290585; ENST00000290583; ENST00000420342 | TAF |
| 17% | chr1 | 151683281 | 151683172 | − | chr1 | 151682267 | 151682219 | − | ENST00000290585; ENST00000290583; ENST00000420342 | TAF |
| 17% | chr9 | 100309652 | 100309653 | + | chr9 | 100315563 | 100315682 | + | ENST00000395211; ENST00000259365 | TAF |
| 17% | chr5 | 79293955 | 79294198 | + | chr5 | 79335900 | 79336103 | + | ENST00000350881 | TSF |
| 16% | chr14 | 72944225 | 44272989 | + | chr14 | 72944976 | 72945037 | + | ENST00000553525; ENST00000555571; ENST00000553530; ENST00000554474; ENST00000556437; ENST00000355512; ENST00000404301; ENST00000406236; ENST00000407322; ENST00000343854; ENST00000402788; ENST00000434263; ENST00000554782 | TAF |
| 16% | chr14 | 72944225 | 72944289 | + | chr14 | 72944976 | 72945037 | + | ENST00000553525; ENST00000555571; ENST00000553530; ENST00000554474; ENST00000556437; ENST00000355512; ENST00000404301; ENST00000406236; ENST00000407322; ENST00000343854; ENST00000402788; ENST00000434263; ENST00000554782 | TAF |
| 16% | chr14 | 72944225 | 44272989 | + | chr14 | 72944976 | 72945037 | + | ENST00000553525; ENST00000555571; ENST00000553530; ENST00000554474; ENST00000556437; ENST00000355512; ENST00000404301; ENST00000406236; ENST00000407322; ENST00000343854; ENST00000402788; ENST00000434263; ENST00000554782 | TAF |
| 16% | chr14 | 72944225 | 44272989 | + | chr14 | 72944976 | 72945037 | + | ENST00000553525; ENST00000555571; ENST00000553530; ENST00000554474; ENST00000556437; ENST00000355512; ENST00000404301; ENST00000406236; ENST00000407322; ENST00000343854; ENST00000402788; ENST00000434263; ENST00000554782 | TAF |
| 16% | chr14 | 72944225 | 72944289 | + | chr14 | 72944976 | 72945037 | + | ENST00000553525; ENST00000555571; ENST00000553530; ENST00000554474; ENST00000556437; ENST00000355512; ENST00000404301; ENST00000406236; ENST00000407322; ENST00000343854; | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 16% | chr14 | 72944225 | 72944289 | + | chr14 | 72944976 | 72945037 | + | ENST00000402788; ENST00000434263; ENST00000554782 ENST00000553525; ENST00000555571; ENST00000553530; ENST00000554474; ENST00000556437; ENST00000355512; ENST00000404301; ENST00000406236; ENST00000407322; ENST00000343854; ENST00000402788; ENST00000434263; ENST00000554782 | TAF |
| 16% | chr14 | 72944225 | 72944289 | + | chr14 | 72944976 | 72945037 | + | ENST00000553525; ENST00000555571; ENST00000553530; ENST00000554474; ENST00000556437; ENST00000355512; ENST00000404301; ENST00000406236; ENST00000407322; ENST00000343854; ENST00000402788; ENST00000434263; ENST00000554782 | TAF |
| 16% | chr14 | 72944225 | 72944289 | + | chr14 | 72944976 | 72945037 | + | ENST00000553525; ENST00000555571; ENST00000553530; ENST00000554474; ENST00000556437; ENST00000355512; ENST00000404301; ENST00000406236; ENST00000407322; ENST00000343854; ENST00000402788; ENST00000434263; ENST00000554782 | TAF |
| 16% | chr14 | 72944225 | 72944289 | + | chr14 | 72944976 | 72945037 | + | ENST00000553525; ENST00000555571; ENST00000553530; ENST00000554474; ENST00000556437; ENST00000355512; ENST00000404301; ENST00000406236; ENST00000407322; ENST00000343854; ENST00000402788; ENST00000434263; ENST00000554782 | TAF |
| 16% | chr14 | 72944225 | 72944289 | + | chr14 | 72944976 | 72945037 | + | ENST00000553525; ENST00000555571; ENST00000553530; ENST00000554474; ENST00000556437; ENST00000355512; ENST00000404301; ENST00000406236; ENST00000407322; ENST00000343854; ENST00000402788; ENST00000434263; ENST00000554782 | TAF |
| 16% | chr16 | 75685621 | 75685636 | + | chr16 | 75688171 | 75688295; 75688183 | + | ENST00000300086; ENST00000569234 | TAF |
| 16% | chr16 | 75685621 | 75685636 | + | chr16 | 75688171 | 75688295; 75688183 | + | ENST00000300086; ENST00000569234 | TAF |
| 16% | chr11 | 125351332 | 125351294 | − | chr11 | 125333466 | 125333380 | − | ENST00000278919; ENST00000577924 | TAF |
| 16% | chr11 | 125351332 | 125435194 | − | chr11 | 12533466 | 125333380 | − | ENST00000278919; ENST00000577924 | TAF |
| 16% | chr7 | 55435136 | 55435321 | + | chr7 | 55459486 | 55459603 | + | ENST00000254770 | TSF |
| 15% | chr7 | 65819313 | 65819316 | + | chr7 | 65821812 | 65821829 | + | ENST00000304842 | TAF |
| 15% | chr12 | 21478885 | 21477528 | − | chr12 | 21471857 | 21471716; 21471765 | − | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |
| 15% | chr12 | 21478885 | 21477528 | − | chr12 | 21471857 | 21471716; 21471765 | − | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |
| 15% | chr12 | 21478885 | 21477528 | − | chr12 | 21471857 | 21471716; 21471765 | − | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |
| 15% | chr12 | 21478885 | 21477528 | − | chr12 | 21471857 | 21471716; 21471765 | − | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |
| 15% | chr12 | 21478885 | 21477528 | − | chr12 | 21471857 | 21471716; 21471765 | − | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 15% | chr12 | 21478885 | 21477528 | – | chr12 | 21471857 | 21471716; 21471765 | – | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |
| 15% | chr12 | 21478885 | 21477528 | – | chr12 | 21471857 | 21471716; 21471765 | – | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |
| 15% | chr12 | 21478885 | 21477528 | – | chr12 | 21471857 | 21471716; 21471765 | – | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |
| 15% | chr12 | 21478885 | 77521428 | – | chr12 | 21471857 | 21471716; 21471765 | – | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |
| 15% | chr12 | 21478885 | 21477528 | – | chr12 | 21471857 | 21471716; 21471765 | – | ENST00000307378; ENST00000452078; ENST00000544020; ENST00000544290; ENST00000390670; ENST00000422327; ENST00000453443; ENST00000421294; ENST00000450590; ENST00000435179; ENST00000445053; ENST00000421287 | TAF |
| 15% | chr5 | 68663671 | 63668666 | – | chr5 | 68662422 | 68662330 | – | ENST00000380822; ENST00000380818 | TAF |
| 15% | chr7 | 149571552 | 149571710 | + | chr7 | 149572687 | 149572734 | + | ENST00000421974; ENST00000456496; ENST00000464683; ENST00000479613; ENST00000606024; ENST00000471877; ENST00000464662; ENST00000425642 | TAF |
| 15% | chr7 | 149571552 | 149571710 | + | chr7 | 149572687 | 149572734 | + | ENST00000421974; ENST00000456496; ENST00000464683; ENST00000479613; ENST00000606024; ENST00000471877; ENST00000464662; ENST00000425642 | TAF |
| 15% | chr7 | 149571552 | 149571710 | + | chr7 | 149572687 | 149572734 | + | ENST00000421974; ENST00000456496; ENST00000464683; ENST00000479613; ENST00000606024; ENST00000471877; ENST00000464662; ENST00000425642 | TAF |
| 15% | chr7 | 149571552 | 149571710 | + | chr7 | 149572687 | 149572734 | + | ENST00000421974; ENST00000456496; ENST00000464683; ENST00000479613; ENST00000606024; ENST00000471877; ENST00000464662; ENST00000425642 | TAF |
| 15% | chr4 | 491211 | 490916 | – | chr4 | 466490 | 466364 | – | ENST00000515578; ENST00000506646; ENST00000505900 | TAF |
| 15% | chr4 | 491211 | 490916 | – | chr4 | 466490 | 466364 | – | ENST00000515578; ENST00000506646; ENST00000505900 | TAF |
| 15% | chr4 | 491211 | 490916 | – | chr4 | 466490 | 466364 | – | ENST00000515578; ENST00000506646; ENST00000505900 | TAF |
| 15% | chr14 | 23040829 | 23040779 | – | chr14 | 23034037 | 23034012 | – | ENST00000538631 | TAF |
| 15% | chr2 | 25110247 | 25109962 | – | chr2 | 25095588 | 25095439 | – | ENST00000260600; ENST00000433852 | TAF |
| 15% | chr2 | 25110247 | 25109962 | – | chr2 | 25095588 | 25095439 | – | ENST00000260600; ENST00000433852 | TAF |
| 15% | chr12 | 49602693 | 49602732 | + | chr12 | 49621874 | 49621949 | + | ENST00000541364; ENST00000549818; ENST00000552448; ENST00000552125 | TSF |
| 15% | chr12 | 49602693 | 49602732 | + | chr12 | 49621874 | 49621949 | + | ENST00000541364; ENST00000549818; ENST00000552448; ENST00000552125 | TSF |
| 15% | chr12 | 49602693 | 49602732 | + | chr12 | 49621874 | 49621949 | + | ENST00000541364; ENST00000549818; ENST00000552448; ENST00000552125 | TSF |
| 14% | chr11 | 113094670 | 113094176 | + | chr11 | 113102367 | 113102517 | + | ENST00000533760; ENST00000524665; ENST00000534015; ENST00000401611; ENST00000316851 | TAF |
| 14% | chr11 | 113094670 | 113094766 | + | chr11 | 113102367 | 113102517 | + | ENST00000533760; ENST00000524665; ENST00000534015; ENST00000401611; ENST00000316851 | TAF |
| 14% | chr11 | 113094670 | 113094766 | + | chr11 | 113102367 | 113102517 | + | ENST00000533760; ENST00000524665; ENST00000534015; ENST00000401611; ENST00000316851 | TAF |
| 14% | chr11 | 113094670 | 113094766 | + | chr11 | 113102367 | 113102517 | + | ENST00000533760; ENST00000524665; ENST00000534015; ENST00000401611; ENST00000316851 | TAF |
| 14% | chr11 | 113094670 | 113094766 | + | chr11 | 113102367 | 113102517 | + | ENST00000533760; ENST00000524665; | TAF |

TABLE 24-continued

Transcript fusion for Glioblastoma Multiforme (GBM)
Coordinates of the fusion sequences for which the donor is the TE.

| 1 | 2' | 3' | 4' | 5' 6' | 7' | 8' | 9' 10' | 11' |
|---|---|---|---|---|---|---|---|---|
| | | | | | | | ENST00000534015; ENST00000401611; ENST00000316851 | |
| 14% | chr17 | 74261446 | 74261484 | + chr17 | 74261988 | 74262050 | + ENST00000327490 | TAF |
| 14% | chr11 | 60615047 | 60615096 | + chr11 | 60615397 | 60615526 | + ENST00000227520 | TAF |
| 14% | chr4 | 89454580 | 89454120 | − chr4 | 89443180 | 89443039 | − ENST00000273968 | TAF |
| 14% | chrX | 13907696 | 13907571 | − chrX | 13803927 | 13803741 | − ENST00000316715; ENST00000454189; ENST00000493677; ENST00000355135; ENST00000356942; ENST00000475307 | TAF |
| 14% | chrX | 13907696 | 13907571 | − chrX | 13803927 | 13803741 | − ENST00000316715; ENST00000454189; ENST00000493677; ENST00000355135; ENST00000356942; ENST00000475307 | TAF |
| 14% | chrX | 13907696 | 139107571 | − chrX | 13803927 | 13803741 | − ENST00000316715; ENST00000454189; ENST00000493677; ENST00000355135; ENST00000356942; ENST00000475307 | TAF |
| 14% | chr1 | 99718539 | 99718543 | + chr1 | 99753521 | 99753706 | + ENST00000370185; ENST00000457765 | TSF |
| 14% | chr1 | 99718539 | 99718543 | + chr1 | 99753521 | 99753706 | + ENST00000370185; ENST00000457765 | TSF |
| 14% | chr7 | 55985644 | 55985990 | + chr7 | 55990855 | 55990981 | + ENST00000426595; ENST00000429591 | TSF |
| 14% | chr7 | 55985644 | 55985990 | + chr7 | 55990855 | 55990981 | + ENST00000426595; ENST00000429591 | TSF |
| 14% | chr8 | 82356115 | 82355982 | − chr8 | 82355683 | 82355633; 82355676 | − ENST00000256103; ENST00000519260 | TSF |
| 14% | chr8 | 82356115 | 82355982 | − chr8 | 82355683 | 82355633; 82355676 | ENST00000256103; ENST00000519260 | TSF |
| 13% | chr11 | 73367079 | 73367447 | + chr11 | 73371798 | 73371897; 73371801; 73371811; 73371815; 73371918; 73371840 | + ENST00000354190; ENST00000398492; ENST00000227214; ENST00000398494; ENST00000543085; ENST00000539157; ENST00000546251; ENST00000535582; ENST00000538227; ENST00000543524; ENST00000541597; ENST00000535129; ENST00000542389; ENST00000540431 | TAF |
| 13% | chr11 | 73367079 | 73367447 | + chr11 | 73371798 | 73371897; 73371801; 73371811; 73371815; 73371918; 73371840 | + ENST00000354190; ENST00000398492; ENST00000227214; ENST00000398494; ENST00000543085; ENST00000539157; ENST00000546251; ENST00000535582; ENST00000538227; ENST00000543524; ENST00000541597; ENST00000535129; ENST00000542389; ENST00000540431 | TAF |
| 13% | chr11 | 73367079 | 73367447 | + chr11 | 73371798 | 73371897; 73371801; 73371811; 73371815; 73371918; 73371840 | + ENST00000354190; ENST00000398492; ENST00000227214; ENST00000398494; ENST00000543085; ENST00000539157; ENST00000546251; ENST00000535582; ENST00000538227; ENST00000543524; ENST00000541597; ENST00000535129; ENST00000542389; ENST00000540431 | TAF |
| 13% | chr11 | 73367079 | 73367447 | + chr11 | 73371798 | 73371897; 73371801; 73371811; 73371815; 73371918; 73371840 | + ENST00000354190; ENST00000398492; ENST00000227214; ENST00000398494; ENST00000543085; ENST00000539157; ENST00000546251; ENST00000535582; ENST00000538227; ENST00000543524; ENST00000541597; ENST00000535129; ENST00000542389; ENST00000540431 | TAF |
| 13% | chr11 | 73367079 | 73367447 | + chr11 | 73371798 | 73371897; 73371801; 73371811; 73371815; 73371918; 73371840 | + ENST00000354190; ENST00000398492; ENST00000227214; ENST00000398494; ENST00000543085; ENST00000539157; ENST00000546251; ENST00000535582; ENST00000538227; ENST00000543524; ENST00000541597; ENST00000535129; ENST00000542389; ENST00000540431 | TAF |
| 13% | chr11 | 73367079 | 73367447 | + chr11 | 73371798 | 73371897; 73371801; 73371811; 73371815; 73371918; 73371840 | + ENST00000354190; ENST00000398492; ENST00000227214; ENST00000398494; ENST00000543085; ENST00000539157; ENST00000546251; ENST00000535582; ENST00000538227; ENST00000543524; ENST00000541597; ENST00000535129; ENST00000542389; ENST00000540431 | TAF |
| 13% | chr11 | 73367079 | 73367447 | + chr11 | 73371798 | 73371897; 73371801; 73371811; 73371815; 73371918; 73371840 | + ENST00000354190; ENST00000398492; ENST00000227214; ENST00000398494; ENST00000543085; ENST00000539157; ENST00000546251; ENST00000535582; ENST00000538227; ENST00000543524; ENST00000541597; ENST00000535129; ENST00000542389; ENST00000540431 | TAF |
| 13% | chr11 | 73367079 | 73367447 | + chr11 | 73371798 | 73371897; 73371801; 73371811; 73371815; | + ENST00000354190; ENST00000398492; ENST00000227214; ENST00000398494; ENST00000543085; ENST00000539157; ENST00000546251; ENST00000535582; | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 13% | chr11 | 73367079 | 73367447 | + | chr11 | 73371798 | 73371918; 73371840 73371897; 73371801; 73371811; 73371815; 73371918; 73371840 | + | ENST00000538227; ENST00000543524; ENST00000541597; ENST00000535129; ENST00000542389; ENST00000540431 ENST00000354190; ENST00000398492; ENST00000227214; ENST00000398494; ENST00000543085; ENST00000539157; ENST00000546251; ENST00000535582; ENST00000538227; ENST00000543524; ENST00000541597; ENST00000535129; ENST00000542389; ENST00000540431 | TAF |
| 13% | chr2 | 79731998 | 79732308 | + | chr2 | 79878678 | 79878784 | + | ENST00000361291 | TAF |
| 13% | chr19 | 13127972 | 13127986 | + | chr19 | 13135835 | 13136366; 13135976; 13136309 | + | ENST00000397661; ENST00000592199; ENST00000587760; ENST00000585575; ENST00000360105; ENST00000586797; ENST00000591028; ENST00000587260; ENST00000358552 | TAF |
| 13% | chr19 | 13127972 | 13127986 | + | chr19 | 13135835 | 13136366; 13135976; 13136309 | + | ENST00000397661; ENST00000592199; ENST00000587760; ENST00000585575; ENST00000360105; ENST00000586797; ENST00000591028; ENST00000587260; ENST00000358552 | TAF |
| 13% | chr19 | 13127972 | 13127986 | + | chr19 | 13135835 | 13136366; 13135976; 13136309 | + | ENST00000397661; ENST00000592199; ENST00000587760; ENST00000585575; ENST00000360105; ENST00000586797; ENST00000591028; ENST00000587260; ENST00000358552 | TAF |
| 13% | chr19 | 13127972 | 13127986 | + | chr19 | 13135835 | 13136366; 13135976; 13136309 | + | ENST00000397661; ENST00000592199; ENST00000587760; ENST00000585575; ENST00000360105; ENST00000586797; ENST00000591028; ENST00000587260; ENST00000358552 | TAF |
| 13% | chr19 | 13127972 | 13127986 | + | chr19 | 13135835 | 13136366; 13135976; 13136309 | + | ENST00000397661; ENST00000592199; ENST00000587760; ENST00000585575; ENST00000360105; ENST00000586797; ENST00000591028; ENST00000587260; ENST00000358552 | TAF |
| 13% | chr19 | 13127972 | 13127986 | + | chr19 | 13135835 | 13136366; 13135976; 13136309 | + | ENST00000397661; ENST00000592199; ENST00000587760; ENST00000585575; ENST00000360105; ENST00000586797; ENST00000591028; ENST00000587260; ENST00000358552 | TAF |
| 13% | chr17 | 39974832 | 39974854 | + | chr17 | 39975462 | 39975651 | + | ENST00000321562 | TAF |
| 13% | chr19 | 44244036 | 44243825 | − | chr19 | 44242369 | 44242274 | − | ENST00000270066; ENST00000601170 | TAF |
| 13% | chr19 | 44244036 | 44243825 | − | chr19 | 44242369 | 44242274 | − | ENST00000270066; ENST00000601170 | TAF |
| 13% | chr13 | 51289548 | 51289014 | − | chr13 | 51287376 | 51287353 | − | ENST00000400393 | TSF |
| 13% | chr17 | 42991959 | 42991849 | − | chr17 | 42991456 | 42991396 | − | ENST00000253408; ENST00000435360; ENST00000586793; ENST00000592320; ENST00000588316; ENST00000588037 | TSF |
| 13% | chr17 | 42991959 | 42991849 | − | chr17 | 42991456 | 42991396 | − | ENST00000253408; ENST00000435360; ENST00000586793; ENST00000592320; ENST00000588316; ENST00000588037 | TSF |
| 13% | chr17 | 42991959 | 42991849 | − | chr17 | 42991456 | 42991396 | − | ENST00000253408; ENST00000435360; ENST00000586793; ENST00000592320; ENST00000588316; ENST00000588037 | TSF |
| 13% | chr17 | 42991959 | 42991849 | − | chr17 | 42991456 | 42991396 | − | ENST00000253408; ENST00000435360; ENST00000586793; ENST00000592320; ENST00000588316; ENST00000588037 | TSF |
| 13% | chr17 | 42991959 | 42991849 | − | chr17 | 42991456 | 42991396 | − | ENST00000253408; ENST00000435360; ENST00000586793; ENST00000592320; ENST00000588316; ENST00000588037 | TSF |
| 13% | chr17 | 42991959 | 42991849 | − | chr17 | 42991456 | 42991396 | − | ENST00000253408; ENST00000435360; ENST00000586793; ENST00000592320; ENST00000588316; ENST00000588037 | TSF |
| 13% | chr6 | 3229888 | 3229779 | − | chr6 | 3226903 | 3226795 | − | ENST00000259818 | TSF |
| 13% | chr6 | 34338198 | 34338038 | − | chr6 | 34309749 | 34309639 | − | ENST00000607016; ENST00000605528 | TSF |
| 13% | chr6 | 34338198 | 34338038 | − | chr6 | 34309749 | 34309639 | − | ENST00000607016; ENST00000605528 | TSF |
| 12% | chr13 | 115049833 | 115049833 | + | chr13 | 115051777 | 115051875 | + | ENST00000375299 | TAF |
| 12% | chr4 | 166400036 | 166400127 | + | chr4 | 166403394 | 166403474; 166403511; 166403499 | + | ENST00000513982; ENST00000402744; ENST00000431967; ENST00000511992 | TAF |
| 12% | chr4 | 166400036 | 166400127 | + | chr4 | 166403394 | 166403474; 166403511; 166403499 | + | ENST00000513982; ENST00000402744; ENST00000431967; ENST00000511992 | TAF |
| 12% | chr4 | 166400036 | 166400127 | + | chr4 | 166403394 | 166403474; 166403511; | + | ENST00000513982; ENST00000402744; ENST00000431967; ENST00000511992 | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 12% | chr4 | 166400036 | 166400127 | + | chr4 | 166403394 | 166403499 166403474; 166403511; 166403499 | + | ENST00000513982; ENST00000402744; ENST00000431967; ENST00000511992 | TAF |
| 12% | chr11 | 85339945 | 85340247 | + | chr11 | 85342189 | 85342230 | + | ENST00000531718; ENST00000528361; ENST00000529197 | TAF |
| 12% | chr6 | 24710791 | 24710723 | − | chr6 | 24709139 | 24709005 | − | ENST00000378119; ENST00000540769; ENST00000378102 | TAF |
| 12% | chr1 | 183600359 | 183599874 | − | chr1 | 183599772 | 183599596 | − | ENST00000367534; ENST00000359856; ENST00000294742 | TAF |
| 12% | chr1 | 183600359 | 183599874 | − | chr1 | 183599772 | 183599596 | − | ENST00000367534; ENST00000359856; ENST00000294742 | TAF |
| 12% | chr7 | 130127044 | 130127065 | + | chr7 | 130135209 | 130135363 | + | ENST00000223215; ENST00000437945 | TAF |
| 12% | chr7 | 130127044 | 130127065 | + | chr7 | 130135209 | 130135363 | + | ENST00000223215; ENST00000437945 | TAF |
| 12% | chr7 | 2289080 | 2289115 | + | chr7 | 2289492 | 2289637 | + | ENST00000356714; ENST00000397049; ENST00000397046; ENST00000397048; ENST00000339737; ENST00000343985 | TAF |
| 12% | chr17 | 79214190 | 79214239 | + | chr17 | 79214787 | 79214816; 79214953 | + | ENST00000431388; ENST00000576002 | TAF |
| 12% | chr17 | 79214190 | 79214239 | + | chr17 | 79214787 | 79214816; 79214953 | + | ENST00000431388; ENST00000576002 | TAF |
| 12% | chr2 | 133363747 | 133363763 | + | chr2 | 133402674 | 133403179 | + | ENST00000329321 | TAF |
| 12% | chrX | 13804185 | 13804092 | − | chrX | 13803927 | 13803741 | − | ENST00000316715; ENST00000454189; ENST00000493677; ENST00000355135; ENST00000356942; ENST00000475307 | TAF |
| 12% | chrX | 13804185 | 13804092 | − | chrX | 13803927 | 13803741 | − | ENST00000316715; ENST00000454189; ENST00000493677; ENST00000355135; ENST00000356942; ENST00000475307 | TAF |
| 12% | chrX | 13804185 | 13804092 | − | chrX | 13803927 | 13803741 | − | ENST00000316715; ENST00000454189; ENST00000493677; ENST00000355135; ENST00000356942; ENST00000475307 | TAF |
| 12% | chr7 | 99761456 | 99761407 | − | chr7 | 99758582 | 99757551; 99758045 | − | ENST00000413800; ENST00000360039; ENST00000423751; ENST00000411994; ENST00000426974 | TAF |
| 12% | chr7 | 99761456 | 61499707 | − | chr7 | 99758582 | 99757551; 99758045 | − | ENST00000413800; ENST00000360039; ENST00000423751; ENST00000411994; ENST00000426974 | TAF |
| 12% | chr17 | 39976225 | 76339901 | + | chr17 | 39976521 | 39976713 | + | ENST00000321562; ENST00000455106; ENST00000544340 | TSF |
| 12% | chr17 | 39974832 | 39974893 | + | chr17 | 39975462 | 39975651 | + | ENST00000321562 | TSF |
| 12% | chr1 | 32262195 | 32262170 | − | chr1 | 32259836 | 32259725 | − | ENST00000257100; ENST00000360482; ENST00000452755; ENST00000533231; ENST00000528579 | TSF |
| 12% | chr1 | 32262195 | 32262170 | − | chr1 | 32259836 | 32259725 | − | ENST00000257100; ENST00000360482; ENST00000452755; ENST00000533231; ENST00000528579 | TSF |
| 12% | chr1 | 32262195 | 32262170 | − | chr1 | 32259836 | 32259725 | − | ENST00000257100; ENST00000360482; ENST00000452755; ENST00000533231; ENST00000528579 | TSF |
| 12% | chr20 | 25843181 | 25842039 | − | chr20 | 25755948 | 25755497; 25755659 | − | ENST00000376403; ENST00000584071 | TSF |
| 12% | chr20 | 25843181 | 25842039 | − | chr20 | 25755948 | 25755497; 25755659 | − | ENST00000376403; ENST00000584071 | TSF |
| 11% | chr6 | 21201067 | 21201123 | + | chr6 | 21201341 | 21201505 | + | ENST00000274695; ENST00000378624; ENST00000378610 | TAF |
| 11% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 11% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 11% | chr7 | 150019730 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 11% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 11% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 11% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 11% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 11% | chr5 | 179238653 | 179238682 | + | chr5 | 179260032 | 179260246; 179260227 | + | ENST00000376929; ENST00000389805; ENST00000402874; ENST00000510187; ENST00000360718 | TAF |
| 11% | chr5 | 179238653 | 179238682 | + | chr5 | 179260032 | 179260246; 179260227 | + | ENST00000376929; ENST00000389805; ENST00000402874; ENST00000510187; ENST00000360718 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr17 | 21476521 | 21476490 | − | chr17 | 21438799 | 21438561; 21438772 | − | ENST00000391411; ENST00000412778 | TAF |
| 11% | chr17 | 21476521 | 21476490 | − | chr17 | 21438799 | 21438561; 21438772 | − | ENST00000391411; ENST00000412778 | TAF |
| 11% | chr19 | 5976359 | 6275973 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 6275973 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 5976273 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 5976273 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 6275973 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 5976273 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 5976273 | − | chr19 | 5957984 | 5957929; | − | ENST00000439268; ENST00000340578; | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 5957918 | | ENST00000592771; ENST00000591092; ENST00000034275; ENST00000587159; ENST00000589353; ENST00000587463; ENST00000588010; ENST00000592133; ENST00000587263; ENST00000591333 | |
| 11% | chr19 | 5976359 | 5976273 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 5976273 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 5976273 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 5976273 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr19 | 5976359 | 5976273 | − | chr19 | 5957984 | 5957929; 5957918 | − | ENST00000439268; ENST00000340578; ENST00000592771; ENST00000591092; ENST00000034275; ENST00000587159; ENST00000589353; ENST00000587463; ENST00000588010; ENST00000592133; ENST00000587263; ENST00000591333 | TAF |
| 11% | chr22 | 21972574 | 21972670 | + | chr22 | 21975804 | 21975958 | + | ENST00000458578; ENST00000342192; ENST00000545681 | TSF |
| 11% | chr11 | 62651471 | 62651559 | + | chr11 | 62651929 | 62651997 | + | ENST00000377892; ENST00000377890; ENST00000377891; ENST00000377889; ENST00000535296; ENST00000338663 | TSF |
| 11% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 11% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 11% | chr11 | 47013185 | 13147098 | + | chr11 | 47073939 | 47074069 | + | ENST00000528488; ENST00000278460; ENST00000378618; ENST00000395460; ENST00000378615; ENST00000525895 | TSF |
| 11% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 11% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 11% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 11% | chr20 | 25844836 | 25843696 | − | chr20 | 25755948 | 25755497; 25755659 | − | ENST00000376403; ENST00000584071 | TSF |
| 11% | chr20 | 25844836 | 25843696 | − | chr20 | 25755948 | 25755497; 25755659 | − | ENST00000376403; ENST00000584071 | TSF |
| 11% | chr2 | 99224680 | 99224660 | − | chr2 | 99220654 | 99220571 | − | ENST00000328709; ENST00000409997 | TSF |
| 11% | chr2 | 99224680 | 99224660 | − | chr2 | 99220654 | 99220571 | − | ENST00000328709; ENST00000409997 | TSF |
| 10% | chr7 | 73776149 | 73776406 | + | chr7 | 73778585 | 73778645 | + | ENST00000361545; ENST00000223398; ENST00000395060 | TAF |
| 10% | chr7 | 73776149 | 73776406 | + | chr7 | 73778585 | 73778645 | + | ENST00000361545; ENST00000223398; ENST00000395060 | TAF |
| 10% | chr4 | 47584885 | 47584978 | + | chr4 | 47589036 | 47589223 | + | ENST00000273859 | TAF |
| 10% | chr4 | 106355281 | 106355184 | − | chr4 | 106345479 | 106345353; 106345406 | − | ENST00000341695; ENST00000348706; ENST00000432483; ENST00000357415; ENST00000380004; ENST00000510015; ENST00000508518; ENST00000310267; ENST00000504028 | TAF |
| 10% | chr4 | 106355281 | 106355184 | − | chr4 | 106345479 | 106345353; | − | ENST00000341695; ENST00000348706; | TAF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 106345406 | | ENST00000432483; ENST00000357415; ENST00000380004; ENST00000510015; ENST00000508518; ENST00000310267; ENST00000504028 | |
| 10% | chr4 | 106355281 | 106355184 | − | chr4 | 106345479 | 106345353; 106345406 | − | ENST00000341695; ENST00000348706; ENST00000432483; ENST00000357415; ENST00000380004; ENST00000510015; ENST00000508518; ENST00000310267; ENST00000504028 | TAF |
| 10% | chr4 | 106355281 | 106355184 | − | chr1 | 106345479 | 106345353; 106345406 | − | ENST00000341695; ENST00000348706; ENST00000432483; ENST00000357415; ENST00000380004; ENST00000510015; ENST00000508518; ENST00000310267; ENST00000504028 | TAF |
| 10% | chr4 | 106355281 | 106355184 | − | chr4 | 106345479 | 106345353; 106345406 | − | ENST00000341695; ENST00000348706; ENST00000432483; ENST00000357415; ENST00000380004; ENST00000510015; ENST00000508518; ENST00000310267; ENST00000504028 | TAF |
| 10% | chr1 | 40781678 | 40781517 | − | chr1 | 40781336 | 40781262 | − | ENST00000372748; ENST00000417105; ENST00000372736 | TAF |
| 10% | chr1 | 40781678 | 40781517 | − | chr1 | 40781336 | 40781262 | − | ENST00000372748; ENST00000417105; ENST00000372736 | TAF |
| 10% | chr1 | 40781678 | 40781517 | − | chr1 | 40781336 | 40781262 | − | ENST00000372748; ENST00000417105; ENST00000372736 | TAF |
| 10% | chr14 | 35035301 | 35035230 | − | chr14 | 35032381 | 35032328 | − | ENST00000396526; ENST00000396534; ENST00000362031; ENST00000355110 | TAF |
| 10% | chr14 | 69847661 | 69847502 | − | chr14 | 69847357 | 69847255 | − | ENST00000557016 | TAF |
| 10% | chr22 | 42083838 | 42083757 | − | chr22 | 42076368 | 42076248 | − | ENST00000355257; ENST00000215956; ENST00000401959; ENST00000402458 | TAF |
| 10% | chr14 | 52338594 | 52338741 | + | chr14 | 52344335 | 52344375 | + | ENST00000556522 | TSF |
| 10% | chr4 | 54932915 | 54932834 | − | chr4 | 54915472 | 54915418 | − | ENST00000263921; ENST00000512964; ENST00000510894 | TSF |
| 10% | chr4 | 54932915 | 54932834 | − | chr4 | 54915472 | 54915418 | − | ENST00000263921; ENST00000512964; ENST00000510894 | TSF |
| 10% | chr4 | 54932915 | 54932834 | − | chr4 | 154915472 | 54915418 | − | ENST00000263921; ENST00000512964; ENST00000510894 | TSF |
| 10% | chr20 | 25841506 | 25840376 | − | chr20 | 25755948 | 25755497; 25755659 | − | ENST00000376403; ENST00000584071 | TSF |
| 10% | chr20 | 25841506 | 258140376 | − | chr20 | 25755948 | 25755497; 25755659 | − | ENST00000376403; ENST00000584071 | TSF |
| 10% | chr11 | 15114123 | 15112973 | − | chr6 | 32497961 | 32497902 | − | ENST00000374975 | TSF |
| 9% | chr6 | 31941780 | 31941829 | + | chr6 | 31946680 | 87; 31946759 31946775; 319467 | + | ENST00000375331; ENST00000375333; ENST00000483801; ENST00000519179 | TSF |
| 9% | chr6 | 31941780 | 31941829 | + | chr6 | 31946680 | 31946775; 31946787; 31946759 | + | ENST00000375331; ENST00000375333; ENST00000483801; ENST00000519179 | TSF |
| 9% | chr6 | 31941780 | 31941829 | + | chr6 | 31946680 | 31946775; 31946787; 31946759 | + | ENST00000375331; ENST00000375333; ENST00000483801; ENST00000519179 | TSF |
| 9% | chr7 | 65819313 | 65819361 | + | chr7 | 65821812 | 65821829 | + | ENST00000304842 | TSF |
| 9% | chr7 | 56018506 | 56018522 | + | chr7 | 56020872 | 56021011 | + | ENST00000426595 | TSF |
| 9% | chr15 | 74004214 | 74004264 | + | chr15 | 74005275 | 74005297 | + | ENST00000318443; ENST00000537340; ENST00000318424; ENST00000564751; ENST00000561176; ENST00000559073 | TSF |
| 9% | chr12 | 58023123 | 58023062 | − | chr12 | 58022929 | 58022831; 58022905 | − | ENST00000341156; ENST00000418555; ENST00000552798; ENST00000549391 | TSF |
| 9% | chr12 | 58023123 | 58023062 | − | chr12 | 58022929 | 58022831; 58022905 | − | ENST00000341156; ENST00000418555; ENST00000552798; ENST00000549391 | TSF |
| 8% | chr19 | 54944914 | 54945078 | + | chr19 | 54946722 | 54946864 | + | ENST00000301194; ENST00000376530; ENST00000391739; ENST00000376531 | TSF |
| 8% | chr19 | 54944914 | 54945078 | + | chr19 | 54946722 | 54946864 | + | ENST00000301194; ENST00000376530; ENST00000391739; ENST00000376531 | TSF |
| 8% | chr19 | 54944914 | 54945078 | + | chr19 | 54946722 | 54946864 | + | ENST00000301194; ENST00000376530; ENST00000391739; ENST00000376531 | TSF |
| 8% | chr19 | 54944914 | 54945078 | + | chr19 | 54946722 | 54946864 | + | ENST00000301194; ENST00000376530; ENST00000391739; ENST00000376531 | TSF |
| 8% | chr17 | 40813111 | 13240845 | + | chr17 | 40815395 | 40815521 | + | ENST00000251412 | TSF |
| 8% | chr6 | 123101055 | 101123091 | + | chr6 | 123101436 | 123101608 | + | ENST00000368444; ENST00000356535 | TSF |
| 8% | chr6 | 123101055 | 123101091 | + | chr6 | 123101436 | 123101608 | + | ENST00000368444; ENST00000356535 | TSF |
| 8% | chr16 | 70714570 | 70714506 | − | chr16 | 70713958 | 70713874 | − | ENST00000338779 | TSF |
| 8% | chr8 | 82194688 | 82194723 | + | chr8 | 82195601 | 82195773 | + | ENST00000297258 | TSF |
| 8% | chr17 | 73847069 | 73847024 | − | chr17 | 73845820 | 73845685 | − | ENST00000254806; ENST00000585462; ENST00000591399; ENST00000591831; ENST00000590221; ENST00000344296; | TSF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | 8% | chr17 | 73847069 | 73847024 | − | chr17 | 73845820 | 73845685 | − | ENST00000433525; ENST00000593002 ENST00000254806; ENST00000585462; ENST00000591399; ENST00000591831; ENST00000590221; ENST00000344296; | TSF |
| | 8% | chr17 | 73847069 | 173847024 | − | chr17 | 73845820 | 73845685 | − | ENST00000433525; ENST00000593002 ENST00000254806; ENST00000585462; ENST00000591399; ENST00000591831; ENST00000590221; ENST00000344296; | TSF |
| | 8% | chr17 | 73847069 | 73847024 | − | chr17 | 73845820 | 73845685 | − | ENST00000433525; ENST00000593002 ENST00000254806; ENST00000585462; ENST00000591399; ENST00000591831; ENST00000590221; ENST00000344296; | TSF |
| | 8% | chr17 | 73847069 | 73847024 | − | chr17 | 73845820 | 73845685 | − | ENST00000433525; ENST00000593002 ENST00000254806; ENST00000585462; ENST00000591399; ENST00000591831; ENST00000590221; ENST00000344296; | TSF |
| | 8% | chr17 | 42991959 | 91942941 | − | chr17 | 42991456 | 42991396 | − | ENST00000253408; ENST00000435360; ENST00000586793; ENST00000592320; ENST00000588316; ENST00000588037 | TSF |
| | 8% | chr17 | 42991959 | 91942941 | − | chr17 | 42991456 | 42991396 | − | ENST00000253408; ENST00000435360; ENST00000586793; ENST00000592320; ENST00000588316; ENST00000588037 | TSF |
| | 8% | chr17 | 42991959 | 91942941 | − | chr17 | 42991456 | 42991396 | − | ENST00000253408; ENST00000435360; ENST00000586793; ENST00000592320; ENST00000588316; ENST00000588037 | TSF |
| | 8% | chr17 | 42991959 | 91942941 | − | chr17 | 42991456 | 42991396 | − | ENST00000253408; ENST00000435360; ENST00000586793; ENST00000592320; ENST00000588316; ENST00000588037 | TSF |
| | 8% | chr17 | 42991959 | 42991941 | − | chr17 | 42991456 | 42991396 | − | ENST00000253408; ENST00000435360; ENST00000586793; ENST00000592320; ENST00000588316; ENST00000588037 | TSF |
| | 8% | chr17 | 42991959 | 42991941 | − | chr17 | 42991456 | 42991396 | − | ENST00000253408; ENST00000435360; ENST00000586793; ENST00000592320; ENST00000588316; ENST00000588037 | TSF |
| | 8% | chr5 | 150155913 | 150155583 | − | chr5 | 150136049 | 150135979 | − | ENST00000447998; ENST00000446090; ENST00000521448; ENST00000517421 | TSF |
| | 8% | chr5 | 150155913 | 150155583 | − | chr5 | 150136049 | 150135979 | − | ENST00000447998; ENST00000446090; ENST00000521448; ENST00000517421 | TSF |
| | 8% | chr5 | 150155913 | 150155583 | − | chr5 | 150136049 | 150135979 | − | ENST00000447998; ENST00000446090; ENST00000521448; ENST00000517421 | TSF |
| | 7% | chr11 | 60694460 | 94560642 | + | chr11 | 60694676 | 60694890 | + | ENST00000453848; ENST00000005286 | TSF |
| | 7% | chr11 | 60694460 | 94560642 | + | chr11 | 60694676 | 60694890 | + | ENST00000453848; ENST00000005286 | TSF |
| | 7% | chr19 | 19353662 | 19353712 | + | chr19 | 19356122 | 19356266 | + | ENST00000252575; ENST00000538881; ENST00000588231 | TSF |
| | 7% | chr19 | 19353662 | 53719312 | + | chr19 | 19356122 | 19356266 | + | ENST00000252575; ENST00000538881; ENST00000588231 | TSF |
| | 7% | chr20 | 45138455 | 38245144 | − | chr20 | 45133379 | 45133253 | − | ENST00000593880; ENST00000347606 | TSF |
| | 7% | chr20 | 45138455 | 38245144 | − | chr20 | 45133379 | 45133253 | − | ENST00000593880; ENST00000347606 | TSF |
| | 7% | chr4 | 5830600 | 5830583 | − | chr4 | 5830395 | 5830216 | − | ENST00000324989; ENST00000397890; ENST00000512574 | TSF |
| | 6% | chr7 | 149537664 | 537696149 | + | chr7 | 149541714 | 149541825 | + | ENST00000223210 | TSF |
| | 6% | chr7 | 121663316 | 121441663 | + | chr7 | 121668606 | 121668697 | + | ENST00000393386; ENST00000449182 | TSF |
| | 6% | chr7 | 121663316 | 121441663 | + | chr7 | 121668606 | 121668697 | + | ENST00000393386; ENST00000449182 | TSF |
| | 6% | chr4 | 5869106 | 5868912 | − | chr4 | 5868483 | 5868395 | − | ENST00000324989; ENST00000397890; ENST00000512574 | TSF |
| | 6% | chr5 | 150159175 | 150159192 | + | chr5 | 150174992 | 150174996 | + | ENST00000600109 | TSF |
| | 6% | chr7 | 56037040 | 56037358 | + | chr7 | 56045819 | 56045958 | + | ENST00000322090; ENST00000446778; ENST00000456204 | TSF |
| | 6% | chr7 | 56037040 | 56037358 | + | chr7 | 56045819 | 56045958 | + | ENST00000322090; ENST00000446778; ENST00000456204 | TSF |
| | 6% | chr7 | 56037040 | 56037358 | + | chr7 | 56045819 | 56045958 | + | ENST00000322090; ENST00000446778; ENST00000456204 | TSF |
| | 6% | chr8 | 6585268 | 6585281 | + | chr8 | 6588232 | 6588347; 6588279 | + | ENST00000285518; ENST00000523234 | TSF |
| | 6% | chr8 | 6585268 | 6585281 | + | chr8 | 6588232 | 6588347; 6588279 | + | ENST00000285518; ENST00000523234 | TSF |
| | 6% | chr19 | 18991807 | 18991757 | − | chr19 | 18991244 | 18991083 | − | ENST00000427170; ENST00000429504; ENST00000542296; ENST00000596048 | TSF |
| | 6% | chr19 | 18991807 | 18991757 | − | chr19 | 18991244 | 18991083 | − | ENST00000427170; ENST00000429504; ENST00000542296; ENST00000596048 | TSF |
| | 6% | chr19 | 18991807 | 18991757 | − | chr19 | 18991244 | 18991083 | − | ENST00000427170; ENST00000429504; ENST00000542296; ENST00000596048 | TSF |
| | 6% | chr3 | 139244518 | 139244462 | − | chr3 | 139237364 | 139237263 | − | ENST00000232219 | TSF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 6% | chr12 | 58023123 | 58023062 | − | chr12 | 58022686 | 58022496; 58022484 | − | ENST00000341156; ENST00000418555; ENST00000449184 | TSF |
| 6% | chr12 | 58023123 | 58023062 | − | chr12 | 58022686 | 58022496; 58022484 | − | ENST00000341156; ENST00000418555; ENST00000449184 | TSF |
| 6% | chr8 | 82357757 | 82357691 | − | chr8 | 82357224 | 82357052 | − | ENST00000256103 | TSF |
| 6% | chr14 | 92586341 | 86292520 | − | chr14 | 92583986 | 92583842 | − | ENST00000329559 | TSF |
| 6% | chr7 | 102208027 | 102207972 | − | chr7 | 102207530 | 102207498; 102207444; 102207440 | − | ENST00000379340; ENST00000486319; ENST00000508848; ENST00000513506; ENST00000514917; ENST00000507355; ENST00000608621; ENST00000511313 | TSF |
| 6% | chr7 | 102208027 | 102207972 | − | chr7 | 102207530 | 102207498; 102207444; 102207440 | − | ENST00000379340; ENST00000486319; ENST00000508848; ENST00000513506; ENST00000514917; ENST00000507355; ENST00000608621; ENST00000511313 | TSF |
| 6% | chr7 | 102208027 | 102207972 | − | chr7 | 102207530 | 102207444; 102207498; 102207440 | − | ENST00000379340; ENST00000486319; ENST00000508848; ENST00000513506; ENST00000514917; ENST00000507355; ENST00000608621; ENST00000511313 | TSF |
| 6% | chr7 | 102208027 | 102207972 | − | chr7 | 102207530 | 102207498; 102207444; 102207440 | − | ENST00000379340; ENST00000486319; ENST00000508848; ENST00000513506; ENST00000514917; ENST00000507355; ENST00000608621; ENST00000511313 | TSF |
| 6% | chr7 | 102208027 | 102207972 | − | chr7 | 102207530 | 102207498; 102207444; 102207440 | − | ENST00000379340; ENST00000486319; ENST00000508848; ENST00000513506; ENST00000514917; ENST00000507355; ENST00000608621; ENST00000511313 | TSF |
| 6% | chr7 | 102208027 | 102207972 | − | chr7 | 102207530 | 102207498; 102207444; 102207440 | − | ENST00000379340; ENST00000486319; ENST00000508848; ENST00000513506; ENST00000514917; ENST00000507355; ENST00000608621; ENST00000511313 | TSF |
| 5% | chr7 | 73816114 | 73816214 | + | chr7 | 73818167 | 173818178 | + | ENST00000361545; ENST00000223398; ENST00000395060; ENST00000487447 | TSF |
| 5% | chr19 | 11469032 | 11469050 | + | chr19 | 11470208 | 11470396; 11470395 | + | ENST00000251473; ENST00000591329 | TSF |
| 5% | chr19 | 11469032 | 11469050 | + | chr19 | 11470208 | 11470396; 11470395 | + | ENST00000251473; ENST00000591329 | TSF |
| 5% | chr3 | 134857832 | 134857845 | + | chr3 | 134872994 | 134873118 | + | ENST00000398015 | TSF |
| 5% | chr2 | 216976986 | 216977153 | + | chr2 | 216977739 | 216977852 | + | ENST00000392133; ENST00000392132 | TSF |
| 5% | chr8 | 9629642 | 9939623 | + | chr8 | 9634160 | 9634246 | + | ENST00000310430; ENST00000518281 | TSF |
| 5% | chr2 | 138746163 | 138746213 | + | chr2 | 138758488 | 138758595 | + | ENST00000410115; ENST00000280097 | TSF |
| 5% | chr19 | 10471727 | 10471638 | − | chr19 | 10469978 | 10469851 | − | ENST00000264818; ENST00000524462; ENST00000525621; ENST00000529370 | TSF |
| 5% | chr19 | 10471727 | 10471638 | − | chr19 | 10469978 | 10469851 | − | ENST00000264818; ENST00000524462; ENST00000525621; ENST00000529370 | TSF |
| 5% | chr21 | 34624467 | 34624553 | + | chr21 | 34624967 | 34625135 | + | ENST00000382264; ENST00000382241; ENST00000404220; ENST00000342136; ENST00000342101; ENST00000413881; ENST00000443073; ENST00000433395; ENST00000432231 | TSF |
| 5% | chr21 | 34624467 | 34624553 | + | chr21 | 34624967 | 34625135 | + | ENST00000382264; ENST00000382241; ENST00000404220; ENST00000342136; ENST00000342101; ENST00000413881; ENST00000443073; ENST00000433395; ENST00000432231 | TSF |
| 5% | chr21 | 34624467 | 34624553 | + | chr21 | 34624967 | 34625135 | + | ENST00000382264; ENST00000382241; ENST00000404220; ENST00000342136; ENST00000342101; ENST00000413881; ENST00000443073; ENST00000433395; ENST00000432231 | TSF |
| 5% | chr21 | 34624467 | 34624553 | + | chr21 | 34624967 | 34625135 | + | ENST00000382264; ENST00000382241; ENST00000404220; ENST00000342136; ENST00000342101; ENST00000413881; ENST00000443073; ENST00000433395; ENST00000432231 | TSF |
| 5% | chr21 | 34624467 | 34624553 | + | chr21 | 34624967 | 34625135 | + | ENST00000382264; ENST00000382241; ENST00000404220; ENST00000342136; ENST00000342101; ENST00000413881; ENST00000443073; ENST00000433395; ENST00000432231 | TSF |
| 5% | chr21 | 34624467 | 24534653 | + | chr21 | 34624967 | 34625135 | + | ENST00000382264; ENST00000382241; ENST00000404220; ENST00000342136; ENST00000342101; ENST00000413881; ENST00000443073; ENST00000433395; ENST00000432231 | TSF |
| 5% | chr18 | 9805890 | 9805956 | + | chr18 | 9814017 | 9814088 | + | ENST00000578921 | TSF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| | 5% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; | TSF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
|   |    |    |    |    |    |    |    |    | ENST00000601938; ENST00000602066; ENST00000598567 |   |
| 5% | chr9 | 35846065 | 35846070 | + | chr9 | 35846255 | 35846378 | + | ENST00000377996; ENST00000439587; ENST00000377991; ENST00000377988 | TSF |
| 5% | chr9 | 35846065 | 35846070 | + | chr9 | 35846255 | 35846378 | + | ENST00000377996; ENST00000439587; ENST00000377991; ENST00000377988 | TSF |
| 5% | chr17 | 42149044 | 42149179 | + | chr17 | 42151528 | 42151634; 42151597 | + | ENST00000269097; ENST00000591696 | TSF |
| 5% | chr17 | 42149044 | 42149179 | + | chr17 | 42151528 | 42151634; 42151597 | + | ENST00000269097; ENST00000591696 | TSF |
| 5% | chrX | 43703705 | 43703702 | − | chrX | 43703010 | 43702916 | − | ENST00000378069 | TSF |
| 5% | chr7 | 14309025 | 14308524 | − | chr7 | 14217776 | 14217656 | − | ENST00000258767; ENST00000399322; ENST00000403951; ENST00000402815; ENST00000407950; ENST00000444700; ENST00000406247 | TSF |
| 5% | chr7 | 14309025 | 14308524 | − | chr7 | 14217776 | 14217656 | − | ENST00000258767; ENST00000399322; ENST00000403951; ENST00000402815; ENST00000407950; ENST00000444700; ENST00000406247 | TSF |
| 5% | chr7 | 102307107 | 102307052 | − | chr7 | 102306610 | 102306578; 102306524 | − | ENST00000591000; ENST00000476151; ENST00000333432 | TSF |
| 5% | chr7 | 102307107 | 102307052 | − | chr7 | 102306610 | 102306578; 102306524 | − | ENST00000591000; ENST00000476151; ENST00000333432 | TSF |
| 5% | chr12 | 6602868 | 6602754 | − | chr12 | 6602138 | 6602028 | − | ENST00000229238 | TSF |
| 5% | chr9 | 132580720 | 132580632 | − | chr9 | 132576501 | 132576251 | − | ENST00000351698 | TSF |
| 5% | chr2 | 101024262 | 101024223 |   | chr2 | 101023169 | 101023038 | − | ENST00000542617; ENST00000448989 | TSF |
| 5% | chr2 | 101024262 | 101024223 | − | chr2 | 101023169 | 101023038 | − | ENST00000542617; ENST00000448989 | TSF |
| 5% | chr8 | 130855946 | 130855855 | − | chr8 | 130854451 | 130854388 | − | ENST00000519824; ENST00000522746; ENST00000523509; ENST00000401979; ENST00000519110; ENST00000522250; ENST00000517654; ENST00000519540; ENST00000522941 | TSF |
| 5% | chr1 | 212862111 | 212861639 | − | chr1 | 212860321 | 212860133 | − | ENST00000243440 | TSF |
| 5% | chr1 | 32264516 | 32264490 | − | chr1 | 32264202 | 32264043; 32264174 | − | ENST00000257100; ENST00000373648; ENST00000360482; ENST00000452755; ENST00000533231; ENST00000528579 | TSF |
| 5% | chr1 | 32264516 | 32264490 |   | chr1 | 32264202 | 32264043; 32264174 | − | ENST00000257100; ENST00000373648; ENST00000360482; ENST00000452755; ENST00000533231; ENST00000528579 | TSF |
| 5% | chr1 | 32264516 | 32264490 | − | chr1 | 32264202 | 32264043; 32264174 | − | ENST00000257100; ENST00000373648; ENST00000360482; ENST00000452755; ENST00000533231; ENST00000528579 | TSF |
| 5% | chr1 | 32264516 | 32264490 | − | chr1 | 32264202 | 32264043; 32264174 | − | ENST00000257100; ENST00000373648; ENST00000360482; ENST00000452755; ENST00000533231; ENST00000528579 | TSF |
| 5% | chr1 | 32264516 | 32264490 | − | chr1 | 32264202 | 32264043; 32264174 | − | ENST00000257100; ENST00000373648; ENST00000360482; ENST00000452755; ENST00000533231; ENST00000528579 | TSF |
| 5% | chr14 | 67862610 | 67862594 | − | chr14 | 67862300 | 67862119 | − | ENST00000216446; ENST00000555803; ENST00000554395 | TSF |
| 5% | chr14 | 67862610 | 67862594 | − | chr14 | 67862300 | 67862119 | − | ENST00000216446; ENST00000555803; ENST00000554395 | TSF |
| 5% | chr14 | 67862610 | 67862594 | − | chr14 | 678162300 | 67862119 | − | ENST00000216446; ENST00000555803; ENST00000554395 | TSF |
| 5% | chr7 | 76957485 | 76957483 | − | chr7 | 76955590 | 76955529 | − | ENST00000257626; ENST00000415112 | TSF |
| 5% | chr7 | 76957485 | 76957483 | − | chr7 | 76955590 | 76955529 | − | ENST00000257626; ENST00000415112 | TSF |
| 4% | chr6 | 13616316 | 13616338 | + | chr6 | 13616695 | 13616753 | + | ENST00000451315; ENST00000420088 | TSF |
| 4% | chr6 | 13616316 | 13616338 | + | chr6 | 13616695 | 13616753 | + | ENST00000451315; ENST00000420088 | TSF |
| 4% | chr8 | 136621237 | 136621239 | + | chr8 | 136657302 | 136657360; 136657310 | + | ENST00000355849; ENST00000520981; ENST00000517859; ENST00000521461 | TSF |
| 4% | chr8 | 136621237 | 136621239 | + | chr8 | 136657302 | 136657360; 136657310 | + | ENST00000355849; ENST00000520981; ENST00000517859; ENST00000521461 | TSF |
| 4% | chr19 | 13183453 | 13183471 | + | chr19 | 13183861 | 13183923 | + | ENST00000397661; ENST00000592199; ENST00000585382; ENST00000587F760; ENST00000585575; ENST00000360105; ENST00000588228; ENST00000587260; ENST00000358552 | TSF |
| 4% | chr19 | 13183453 | 13183471 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 4% | chr19 | 13183453 | 83413171 | + | chr19 | 13183861 | 13183923 | + | ENST00000397661; ENST00000592199; ENST00000585382; ENST00000587760; ENST00000585575; ENST00000360105; | TSF |

TABLE 24-continued

Transcript fusion for Glioblastoma Multiforme (GBM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr19 | 13183453 | 13183471 | + | chr19 | 13183861 | 13183923 | + | ENST00000588228; ENST00000587260; ENST00000358552 ENST00000397661; ENST00000592199; ENST00000585382; ENST00000587760; ENST00000585575; ENST00000360105; | TSF |
| 4% | chr19 | 13183453 | 13183471 | + | chr19 | 13183861 | 13183923 | + | ENST00000588228; ENST00000587260; ENST00000358552 ENST00000397661; ENST00000592199; ENST00000585382; ENST00000587760; ENST00000585575; ENST00000360105; | TSF |
| 4% | chr2 | 65243329 | 65243368 | + | chr2 | 65243574 | 65243807 | + | ENST00000234256 | |
| 4% | chr8 | 23131391 | 31523113 | + | chr8 | 231460 | 23146146 | | ENST00000411463 | TSF |
| 4% | chr7 | 56020443 | 56020509 | + | chr7 | 56020872 | 56021011 | + | ENST00000426595 | TSF |
| 4% | chr3 | 38538147 | 38538420 | + | chr3 | 38539120 | 38539175; 38539269 | + | ENST00000436414; ENST00000287675; ENST00000431472; ENST00000454803; ENST00000457367; ENST00000453767; ENST00000450732 | TSF |
| 4% | chr3 | 38538147 | 38438520 | + | chr3 | 38539120 | 38539175; 38539269 | + | ENST00000436414; ENST00000287675; ENST00000431472; ENST00000454803; ENST00000457367; ENST00000453767; ENST00000450732 | TSF |
| 4% | chr3 | 38538147 | 38438520 | + | chr3 | 38539120 | 38539175; 38539269 | + | ENST00000436414; ENST00000287675; ENST00000431472; ENST00000454803; ENST00000457367; ENST00000453767; ENST00000450732 | TSF |
| 4% | chr3 | 38538147 | 38438520 | + | chr3 | 38539120 | 38539175; 38539269 | + | ENST00000436414; ENST00000287675; ENST00000431472; ENST00000454803; ENST00000457367; ENST00000453767; ENST00000450732 | TSF |
| 4% | chr3 | 38538147 | 38438520 | + | chr3 | 38539120 | 38539175; 38539269 | + | ENST00000436414; ENST00000287675; ENST00000431472; ENST00000454803; ENST00000457367; ENST00000453767; ENST00000450732 | TSF |
| 4% | chr3 | 38538147 | 38438520 | + | chr3 | 38539120 | 38539175; 38539269 | + | ENST00000436414; ENST00000287675; ENST00000431472; ENST00000454803; ENST00000457367; ENST00000453767; ENST00000450732 | TSF |
| 4% | chr3 | 150344095 | 150344146 | + | chr3 | 150344797 | 150344921 | + | ENST00000480740; ENST00000471696; ENST00000477889; ENST00000485923 | TSF |
| 4% | chr12 | 58344612 | 58344667 | + | chr12 | 58345541 | 58345678; 58345560 | + | ENST00000300145; ENST00000549257 | TSF |
| 4% | chr12 | 58344612 | 58344667 | + | chr12 | 58345541 | 58345678; 58345560 | + | ENST00000300145; ENST00000549257 | TSF |
| 4% | chr16 | 66461229 | 66461334 | + | chr16 | 66503505 | 66503768 | + | ENST00000536005 | TSF |
| 4% | chr12 | 69217149 | 69217294 | + | chr12 | 69218143 | 69218210; 69218173; 69218169 | + | ENST00000462284; ENST00000311420; ENST00000539479; ENST00000393415; ENST00000393416; ENST00000350057; ENST00000481186; ENST00000496959; ENST00000536089; ENST00000537182; ENST00000540352; ENST00000546048 | TSF |
| 4% | chr12 | 69217149 | 69217294 | + | chr12 | 69218143 | 69218210; 69218173; 69218169 | + | ENST00000462284; ENST00000311420; ENST00000539479; ENST00000393415; ENST00000393416; ENST00000350057; ENST00000481186; ENST00000496959; ENST00000536089; ENST00000537182; ENST00000540352; ENST00000546048 | TSF |
| 4% | chr12 | 69217149 | 69217294 | + | chr12 | 69218143 | 69218210; 69218173; 69218169 | + | ENST00000462284; ENST00000311420; ENST00000539479; ENST00000393415; ENST00000393416; ENST00000350057; ENST00000481186; ENST00000496959; ENST00000536089; ENST00000537182; ENST00000540352; ENST00000546048 | TSF |
| 4% | chr12 | 69217149 | 69217294 | + | chr12 | 69218143 | 69218210; 69218173; 69218169 | + | ENST00000462284; ENST00000311420; ENST00000539479; ENST00000393415; ENST00000393416; ENST00000350057; ENST00000481186; ENST00000496959; ENST00000536089; ENST00000537182; ENST00000540352; ENST00000546048 | TSF |
| 4% | chr12 | 69217149 | 69217294 | + | chr12 | 69218143 | 69218169 69218210; 69218173; | + | ENST00000462284; ENST00000311420; ENST00000539479; ENST00000393415; ENST00000393416; ENST00000350057; ENST00000481186; ENST00000496959; ENST00000536089; ENST00000537182; | TSF |

TABLE 24-continued

Transcript fusion for Glioblastoma Multiforme (GBM)
Coordinates of the fusion sequences for which the donor is the TE.

| 1 | 2' | 3' | 4' | 5' 6' | 7' | 8' | 9' | 10' | 11' |
|---|----|----|----|-------|----|----|----|-----|-----|
| | 4% | chr12 | 69217149 | 69217294 | + chr12 | 69218143 | 69218210; 69218173; 69218169 | + | ENST00000540352; ENST00000546048 ENST00000462284; ENST00000311420; ENST00000539479; ENST00000393415; ENST00000393416; ENST00000350057; ENST00000481186; ENST00000496959; ENST00000536089; ENST00000537182; | TSF |
| | 4% | chr12 | 69217149 | 69217294 | + chr12 | 69218143 | 69218210; 69218173; 69218169 | + | ENST00000540352; ENST00000546048 ENST00000462284; ENST00000311420; ENST00000539479; ENST00000393415; ENST00000393416; ENST00000350057; ENST00000481186; ENST00000496959; ENST00000536089; ENST00000537182; | TSF |
| | 4% | chr17 | 40985441 | 40985522 | + chr17 | 40986361 | 40986393 | + | ENST00000540352; ENST00000546048 ENST00000590720; ENST00000441946; ENST00000589469; ENST00000543428; ENST00000293362; ENST00000592169 | TSF |
| | 4% | chr17 | 40985441 | 85540922 | + chr17 | 40986361 | 40986393 | + | ENST00000590720; ENST00000441946; ENST00000589469; ENST00000543428; ENST00000293362; ENST00000592169 | TSF |
| | 4% | chr17 | 40985441 | 40985522 | + chr17 | 40986361 | 40986393 | + | ENST00000590720; ENST00000441946; ENST00000589469; ENST00000543428; ENST00000293362; ENST00000592169 | TSF |
| | 4% | chr17 | 40985441 | 40985522 | + chr17 | 40986361 | 40986393 | + | ENST00000590720; ENST00000441946; ENST00000589469; ENST00000543428; ENST00000293362; ENST00000592169 | TSF |
| | 4% | chr17 | 40985441 | 40985522 | + chr17 | 40986361 | 40986393 | + | ENST00000590720; ENST00000441946; ENST00000589469; ENST00000543428; ENST00000293362; ENST00000592169 | TSF |
| | 4% | chr16 | 47350611 | 47350483 | − chr16 | 47347734 | 47347640 | − | ENST00000320640; ENST00000544001 | TSF |
| | 4% | chr16 | 47350611 | 47350483 | − chr16 | 47347734 | 47347640 | − | ENST00000320640; ENST00000544001 | TSF |
| | 4% | chr3 | 59852391 | 59851867 | chr3 | 59738047 | 59737952 | − | ENST00000476844; ENST00000492590; ENST00000468189; ENST00000341848 | TSF |
| | 4% | chr19 | 18982032 | 18981924 | − chr19 | 18981428 | 18981386 | − | ENST00000427170 | TSF |
| | 4% | chr2 | 223509679 | 223509604 | − chr2 | 223507724 | 223507570 | − | ENST00000281828 | TSF |
| | 4% | chr7 | 95055853 | 95055720 | − chr7 | 95053897 | 95053827 | − | ENST00000536183; ENST00000455123; ENST00000433091; ENST00000222572; ENST00000446142 | TSF |
| | 4% | chr7 | 95055853 | 95055720 | − chr7 | 95053897 | 95053827 | − | ENST00000536183; ENST00000455123; ENST00000433091; ENST00000222572; −ENST00000446142 | TSF |
| | 4% | chr7 | 95055853 | 95055720 | − chr7 | 95053897 | 95053827 | | ENST00000536183; ENST00000455123; ENST00000433091; ENST00000222572; ENST00000446142 | TSF |
| | 4% | chr7 | 95055853 | 95055720 | − chr7 | 95053897 | 95053827 | − | ENST00000536183; ENST00000455123; ENST00000433091; ENST00000222572; ENST00000446142 | TSF |
| | 4% | chr1 | 156305455 | 156305264 | − chr1 | 156304709 | 156304659 | − | ENST00000295688; ENST00000368258; ENST00000413555; ENST00000496684; ENST00000478640; ENST00000415548 | TSF |
| | 4% | chr1 | 156305455 | 156305264 | − chr1 | 156304709 | 156304659 | − | ENST00000295688; ENST00000368258; ENST00000413555; ENST00000496684; ENST00000478640; ENST00000415548 | TSF |
| | 4% | chr1 | 156305455 | 156305264 | − chr1 | 156304709 | 156304659 | − | ENST00000295688; ENST00000368258; ENST00000413555; ENST00000496684; ENST00000478640; ENST00000415548 | TSF |
| | 4% | chr1 | 156305455 | 156305264 | − chr1 | 156304709 | 156304659 | − | ENST00000295688; ENST00000368258; ENST00000413555; ENST00000496684; ENST00000478640; ENST00000415548 | TSF |
| | 4% | chr1 | 156305455 | 156305264 | − chr1 | 156304709 | 156304659 | − | ENST00000295688; ENST00000368258; ENST00000413555; ENST00000496684; ENST00000478640; ENST00000415548 | TSF |
| | 4% | chr1 | 156305455 | 156305264 | − chr1 | 156304709 | 156304659 | − | ENST00000295688; ENST00000368258; ENST00000413555; ENST00000496684; ENST00000478640; ENST00000415548 | TSF |
| | 4% | chr3 | 139245547 | 139245400 | − chr3 | 139237364 | 139237263 | − | ENST00000232219 | TSF |

TABLE 25

Transcript fusion for Head-Neck Squamous Cell Carcinoma HNSC) Coordinates of the fusion sequences for which the donor is the exon.

| 1 | 2 | 3 | 4 | 5 | 6 |
|---|---|---|---|---|---|
| 42% | chr5 | 54993786 | 54993674 | − | ENST00000396865;ENST00000539768;ENST00000318672;ENST00000508124;ENST00000511233;ENST00000503891;ENST00000513993;ENST00000505563;ENST00000506624;ENST00000507109 |
| 40% | chr10 | 47747112 | 47747132 | + | ENST00000340243;ENST00000374277;ENST00000449464;ENST00000538825 |
| 34% | chr12 | 71509738 | 71509630 | − | ENST00000549357 |
| 29% | chr8 | 54793576 | 54793644 | + | ENST00000276500 |
| 23% | chr1 | 153534067 | 153533988 | − | ENST00000368708;ENST00000487430;ENST00000497140;ENST00000368710;ENST00000368709 |
| 23% | chr1 | 153534067 | 153533988 | − | ENST00000368708;ENST00000487430;ENST00000497140;ENST00000368710;ENST00000368709 |
| 21% | chr6 | 41606488 | 41606563 | + | ENST00000432027;ENST00000419164;ENST00000373051;ENST00000441667;ENST00000230321;ENST00000373050;ENST00000446650;ENST00000435476 |
| 18% | chr19 | 14063948 | 14063931 | − | ENST00000538517;ENST00000538371;ENST00000585607 |
| 18% | chr19 | 51452029 | 51451896 | − | ENST00000391809;ENST00000336334;ENST00000593428 |
| 17% | chr3 | 10960014 | 10960138 | + | ENST00000254488 |
| 15% | chr1 | 32696528 | 32696620 | + | ENST00000373586 |
| 14% | chr5 | 82554349 | 82554496 | + | ENST00000282268;ENST00000338635;ENST00000396027;ENST00000511817 |
| 14% | chr3 | 182566264 | 182566345 | + | ENST00000323116;ENST00000498086 |
| 14% | chr3 | 182566264 | 182566345 | + | ENST00000323116;ENST00000498086 |
| 14% | chr4 | 47583977 | 47584081 | + | ENST00000273859 |
| 13% | chr19 | 39077165 | 39077216 | + | ENST00000355481;ENST00000360985;ENST00000359596 |
| 13% | chr19 | 39077165 | 39077216 | + | ENST00000355481;ENST00000360985;ENST00000359596 |
| 13% | chr19 | 39077165 | 39077216 | + | ENST00000355481;ENST00000360985;ENST00000359596 |
| 13% | chr10 | 5040939 | 5040817 | − | ENST00000380753;ENST00000421196;ENST00000407674;ENST00000604507 |
| 13% | chr10 | 5040939 | 5040817 | − | ENST00000380753;ENST00000421196;ENST00000407674;ENST00000604507 |
| 13% | chr3 | 196230044 | 196229744 | − | ENST00000318037;ENST00000437070 |
| 12% | chr19 | 35996667 | 35996620 | − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 | − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 | − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 | − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 | − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 | − | ENST00000434389;ENST00000402589;ENST00000339686;ENST00000436012;ENST00000414866;ENST00000480502;ENST00000467637;ENST00000429837;ENST00000419602;ENST0000044 |

TABLE 25-continued

Transcript fusion for Head-Neck Squamous Cell Carcinoma HNSC) Coordinates of the fusion sequences for which the donor is the exon.

| | | | | |
|---|---|---|---|---|
| | | | | 3640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341; ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |

TABLE 25-continued

Transcript fusion for Head-Neck Squamous Cell Carcinoma HNSC) Coordinates of the fusion sequences for which the donor is the exon.

| | | | | |
|---|---|---|---|---|
| 12% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 12% | chr18 | 21511026 | 21511165 + | ENST00000313654;ENST00000399516;ENST00000269217;ENST00000587184;ENST00000586751;ENST00000588164 |
| 12% | chr18 | 21511026 | 21511165 + | ENST00000313654;ENST00000399516;ENST00000269217;ENST00000587184;ENST00000586751;ENST00000588164 |
| 12% | chr18 | 21511026 | 21511165 + | ENST00000313654;ENST00000399516;ENST00000269217;ENST00000587184;ENST00000586751;ENST00000588164 |
| 12% | chr18 | 21511026 | 21511165 + | ENST00000313654;ENST00000399516;ENST00000269217;ENST00000587184;ENST00000586751;ENST00000588164 |
| 12% | chr18 | 21511026 | 21511165 + | ENST00000313654;ENST00000399516;ENST00000269217;ENST00000587184;ENST00000586751;ENST00000588164 |
| 12% | chr18 | 21511026 | 21511165 + | ENST00000313654;ENST00000399516;ENST00000269217;ENST00000587184;ENST00000586751;ENST00000588164 |
| 12% | chr7 | 22532348 | 22532184 − | ENST00000406890;ENST00000404369;ENST00000424363 |
| 12% | chr7 | 22532348 | 22532184 − | ENST00000406890;ENST00000404369;ENST00000424363 |
| 11% | chr20 | 35842163 | 35842268 + | ENST00000237530;ENST00000373622 |
| 11% | chr20 | 35842163 | 35842268 + | ENST00000237530;ENST00000373622 |
| 11% | chr9 | 101984828 | 101984925 + | ENST00000223641 |
| 11% | chr11 | 11394176 | 11394062 − | ENST00000227756 |
| 10% | chr19 | 35612126 | 35612149 + | ENST00000454903;ENST00000406242;ENST00000604404;ENST00000435734;ENST00000603181;ENST00000604255;ENST00000344013;ENST00000346446;ENST00000603449;ENST00000406988;ENST00000605550;ENST00000604804;ENST00000605552;ENST00000535103;ENST00000603524;ENST00000604621;ENST00000605677 |
| 10% | chr19 | 35612126 | 35612149 + | ENST00000454903;ENST00000406242;ENST00000604404;ENST00000435734;ENST00000603181;ENST00000604255;ENST00000344013;ENST00000346446;ENST00000603449;ENST00000406988;ENST00000605550;ENST00000604804;ENST00000605552;ENST00000535103;ENST00000603524;ENST00000604621;ENST00000605677 |
| 10% | chr7 | 55270210 | 55270401 + | ENST00000455089 |
| 8% | chr19 | 46627413 | 46627143 − | ENST00000341415 |
| 7% | chr16 | 68729680; 68729728 | 68729826 + | ENST00000264012;ENST00000429102;ENST00000581171;ENST00000568292;ENST00000569080 |
| 7% | chr16 | 68729680; 68729728 | 68729826 + | ENST00000264012;ENST00000429102;ENST00000581171;ENST00000568292;ENST00000569080 |
| 7% | chr16 | 68729680; 68729728 | 68729826 + | ENST00000264012;ENST00000429102;ENST00000581171;ENST00000568292;ENST00000569080 |
| 7% | chr16 | 68729680; 68729728 | 68729826 + | ENST00000264012;ENST00000429102;ENST00000581171;ENST00000568292;ENST00000569080 |
| 7% | chr12 | 113403549; 113403702 | 113403834 + | ENST00000228928;ENST00000546973 |
| 7% | chr12 | 113403549; 113403702 | 113403834 + | ENST00000228928;ENST00000546973 |
| 7% | chr19 | 3869015; 3869013 | 3868963 − | ENST00000262961;ENST00000438164;ENST00000587212;ENST00000586578;ENST00000439086 |
| 7% | chr19 | 3869015; 3869013 | 3868963 − | ENST00000262961;ENST00000438164;ENST00000587212;ENST00000586578;ENST00000439086 |
| 6% | chrX | 119708472 | 119708406 − | ENST00000404115 |
| 6% | chr19 | 46627413 | 46627143 − | ENST00000341415 |
| 5% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 5% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 5% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 5% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 5% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST0000037 |

TABLE 25-continued

Transcript fusion for Head-Neck Squamous Cell Carcinoma HNSC) Coordinates of the fusion sequences for which the donor is the exon.

| | | | | |
|---|---|---|---|---|
| 5% | chr1 | 6531697 | 6531548 − | 7737;ENST00000537245;ENST00000544978 ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 5% | chr22 | 38321668; 38321854 | 38322050 + | ENST00000215957;ENST00000454685 |
| 5% | chr22 | 38321668; 38321854 | 38322050 + | ENST00000215957;ENST00000454685 |
| 5% | chr4 | 57319769 | 57319927 + | ENST00000514888;ENST00000264221;ENST00000505164;ENST00000399688;ENST00000512576 |
| 5% | chr4 | 57319769 | 57319927 + | ENST00000514888;ENST00000264221;ENST00000505164;ENST00000399688;ENST00000512576 |
| 5% | chr4 | 57319769 | 57319927 + | ENST00000514888;ENST00000264221;ENST00000505164;ENST00000399688;ENST00000512576 |
| 4% | chr1 | 11115983; 11115877 | 11115838 − | ENST00000376957;ENST00000490101 |
| 4% | chr1 | 11115983; 11115877 | 11115838 − | ENST00000376957;ENST00000490101 |
| 4% | chr18 | 61627392 | 61627509 + | ENST00000408945 |
| 4% | chr12 | 46760728 | 46760647 − | ENST00000256689 |
| 4% | chr17 | 39768940 | 39768493 − | ENST00000301653 |
| 3% | chr9 | 125054028 | 125054119 + | ENST00000297908;ENST00000344641;ENST00000373723;ENST00000373729;ENST00000394315 |
| 3% | chr9 | 125054028 | 125054119 + | ENST00000297908;ENST00000344641;ENST00000373723;ENST00000373729;ENST00000394315 |
| 3% | chr9 | 125054028 | 125054119 + | ENST00000297908;ENST00000344641;ENST00000373723;ENST00000373729;ENST00000394315 |
| 3% | chr2 | 153003822 | 153003676 − | ENST00000263904 |
| 3% | chrX | 41598709 | 41598637 − | ENST00000421587;ENST00000318588;ENST00000361962;ENST00000378163;ENST00000378158;ENST00000378166;ENST00000442742; ENST00000378154 |
| 3% | chr9 | 94991408 | 94991283 − | ENST00000375643;ENST00000443024;ENST00000447699 |
| 3% | chr9 | 94991408 | 94991283 − | ENST00000375643;ENST00000443024;ENST00000447699 |
| 3% | chr2 | 172725333; 172725194 | 172725191 − | ENST00000422440; ENST00000263812; ENST00000392592; ENST00000426896;ENST00000475360 |
| 3% | chr2 | 172725333; 172725194 | 172725191 − | ENST00000422440;ENST00000263812;ENST00000392592;ENST00000426896;ENST00000475360 |
| 3% | chr2 | 172725333; 172725194 | 172725191 − | ENST00000422440;ENST00000263812;ENST00000392592;ENST00000426896;ENST00000475360 |
| 3% | chr14 | 67878776 | 67878735 − | JENST00000216446;ENST00000553387 |
| 3% | chr7 | 81964567 | 81964451 − | ENST00000356860;ENST00000356253;ENST00000423588 |
| 3% | chr19 | 15289752 | 15289634 − | ENST00000263388;ENST00000601011 |
| 3% | chr19 | 15289752 | 15289634 − | ENST00000263388;ENST00000601011 |
| 3% | chr12 | 56742407 | 56742313 − | ENST00000314128;ENST00000557235 |
| 3% | chr12 | 56742407 | 56742313 − | ENST00000314128;ENST00000557235 |
| 3% | chr5 | 150632778 | 150632858 + | ENST00000357164 |
| 3% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 3% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 3% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 3% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 3% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 3% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 3% | chr19 | 3114942 | 3115070 + | ENST00000078429;ENST00000587636 |
| 3% | chr19 | 3114942 | 3115070 + | ENST00000078429;ENST00000587636 |
| 3% | chr12 | 52882332 | 52882112 − | ENST00000330722 |
| 3% | chr3 | 98600611; 98600498 | 98600384 − | ENST00000326840;ENST00000326857;ENST00000449482 |
| 3% | chr3 | 98600611; 98600498 | 98600384 − | ENST00000326840;ENST00000326857;ENST00000449482 |
| 3% | chr1 | 225156461 | 225156576 + | ENST00000430092;ENST00000400952;ENST00000366849;ENST00000439375 |
| 3% | chr1 | 225156461 | 225156576 + | ENST00000430092;ENST00000400952;ENST00000366849;ENST00000439375 |
| 2% | chr22 | 35819207 | 35819334 + | ENST00000216122;ENST00000382011 |

TABLE 25-continued

Transcript fusion for Head-Neck Squamous Cell Carcinoma HNSC) Coordinates of the fusion sequences for which the donor is the exon.

| | | | | |
|---|---|---|---|---|
| 2% | chr22 | 35819207 | 35819334 + | ENST00000216122;ENST00000382011 |
| 2% | chr2 | 176860312; 176860292 | 176860286 − | ENST00000272748;ENST00000544803;ENST00000392540;ENST00000445472 |
| 2% | chr2 | 176860312; 176860292 | 176860286 − | ENST00000272748;ENST00000544803;ENST00000392540;ENST00000445472 |
| 2% | chr9 | 5689959 | 5690038 + | ENST00000251879;ENST00000414202;ENST00000381532;ENST00000418622;ENST00000449720;ENST00000545641 |
| 2% | chr9 | 5689959 | 5690038 + | ENST00000251879;ENST00000414202;ENST00000381532;ENST00000418622;ENST00000449720;ENST00000545641 |
| 2% | chr9 | 5689959 | 5690038 + | ENST00000251879;ENST00000414202;ENST00000381532;ENST00000418622;ENST00000449720;ENST00000545641 |
| 2% | chr10 | 47173918 | 47173898 − | ENST00000358140;ENST00000359178;ENST00000545298;ENST00000414655 |
| 2% | chr1 | 6378638 | 6378552 − | ENST00000608083;ENST00000377842;ENST00000377845;ENST00000377855;ENST00000377860;ENST00000418124;ENST00000545482;ENST00000361521;ENST00000473466;ENST00000541130 |
| 2% | chr1 | 6378638 | 6378552 − | ENST00000608083;ENST00000377842;ENST00000377845;ENST00000377855;ENST00000377860;ENST00000418124;ENST00000545482;ENST00000361521;ENST00000473466;ENST00000541130 |
| 2% | chr1 | 6378638 | 6378552 − | ENST00000608083;ENST00000377842;ENST00000377845;ENST00000377855;ENST00000377860;ENST00000418124;ENST00000545482;ENST00000361521;ENST00000473466;ENST00000541130 |
| 2% | chr1 | 6378638 | 6378552 − | ENST00000608083;ENST00000377842;ENST00000377845;ENST00000377855;ENST00000377860;ENST00000418124;ENST00000545482;ENST00000361521;ENST00000473466;ENST00000541130 |
| 2% | chr1 | 6378638 | 6378552 − | ENST00000608083;ENST00000377842;ENST00000377845;ENST00000377855;ENST00000377860;ENST00000418124;ENST00000545482;ENST00000361521;ENST00000473466;ENST00000541130 |
| 2% | chr1 | 6378638 | 6378552 − | ENST00000608083;ENST00000377842;ENST00000377845;ENST00000377855;ENST00000377860;ENST00000418124;ENST00000545482;ENST00000361521;ENST00000473466;ENST00000541130 |
| 2% | chr1 | 6378638 | 6378552 − | ENST00000608083;ENST00000377842;ENST00000377845;ENST00000377855;ENST00000377860;ENST00000418124;ENST00000545482;ENST00000361521;ENST00000473466;ENST00000541130 |
| 2% | chr5 | 176830398 | 176830255 − | ENST00000253496 |
| 2% | chr16 | 83520082 | 83520260 + | ENST00000566620;ENST00000268613;ENST00000428848 |
| 2% | chr16 | 83520082 | 83520260 + | ENST00000566620;ENST00000268613;ENST00000428848 |
| 2% | chr16 | 83520082 | 83520260 + | ENST00000566620;ENST00000268613;ENST00000428848 |
| 2% | chr10 | 126205749 | 126205840 + | ENST00000368842 |
| 2% | chr16 | 57115439 | 57115522 + | ENST00000262510;ENST00000308149;ENST00000539144 |
| 2% | chr16 | 57115439 | 57115522 + | ENST00000262510;ENST00000308149;ENST00000539144 |
| 2% | chr14 | 24768312 | 24768163 − | ENST00000288111;ENST00000396813;ENST00000558340 |
| 2% | chr15 | 77057413 | 77057302 − | ENST00000538941;ENST00000563290;ENST00000324767;ENST00000564590;ENST00000565970 |
| 2% | chr15 | 77057413 | 77057302 − | ENST00000538941;ENST00000563290;ENST00000324767;ENST00000564590;ENST00000565970 |
| 2% | chr15 | 77057413 | 77057302 − | ENST00000538941;ENST00000563290;ENST00000324767;ENST00000564590;ENST00000565970 |
| 2% | chr8 | 143867103 | 143867005 − | ENST00000301263 |
| 2% | chr3 | 137906397; 137906427 | 137906441 + | ENST00000469044;ENST00000461600;ENST00000461822;ENST00000470821;ENST00000471709;ENST00000393058;ENST00000538260;ENST00000463485 |
| 2% | chr3 | 137906397; 137906427 | 137906441 + | ENST00000469044;ENST00000461600;ENST00000461822;ENST00000470821;ENST00000471709;ENST00000393058;ENST00000538260;ENST00000463485 |
| 2% | chr21 | 45222155 | 45222268 + | ENST00000497547 |
| 2% | chr5 | 1802435 | 1802488 + | ENST00000274137;ENST00000469176 |
| 2% | chr1 | 63955889 | 63955754 − | ENST00000371092;ENST00000271002;ENST00000489099;ENST00000283568 |
| 2% | chr1 | 63955889 | 63955754 − | ENST00000371092;ENST00000271002;ENST00000489099;ENST00000283568 |
| 2% | chr5 | 121405863 | 121405748 − | ENST00000231004 |
| 2% | chr19 | 45895598 | 45895138 − | ENST00000360957;ENST00000418234 |
| 2% | chr8 | 120220779 | 120220844 + | ENST00000276681 |
| 2% | chr3 | 129020793 | 129020985 + | ENST00000509042;ENST00000383463;ENST00000417226;ENST00000502878;ENST00000389735 |
| 2% | chr3 | 129020793 | 129020985 + | ENST00000509042;ENST00000383463;ENST00000417226;ENST00000502878;ENST00000389735 |
| 2% | chr3 | 129020793 | 129020985 + | ENST00000509042;ENST00000383463;ENST00000417226;ENST00000502878;ENST00000389735 |

TABLE 25-continued

Transcript fusion for Head-Neck Squamous Cell Carcinoma HNSC) Coordinates of the fusion sequences for which the donor is the exon.

| | | | | |
|---|---|---|---|---|
| 2% | chr2 | 28352138 | 28352247 + | ENST00000344773;ENST00000379624;ENST00000342045;ENST00000361704;ENST00000379632;ENST00000379629 |
| 2% | chr12 | 46760728 | 46760647 − | ENST00000256689 |
| 2% | chr8 | 42932359 | 42932507 + | ENST00000302279;ENST00000342116;ENST00000529687;ENST00000533336 |
| 2% | chr8 | 42932359 | 42932507 + | ENST00000302279;ENST00000342116;ENST00000529687;ENST00000533336 |
| 2% | chr8 | 42932359 | 42932507 + | ENST00000302279;ENST00000342116;ENST00000529687;ENST00000533336 |
| 2% | chr8 | 42932359 | 42932507 + | ENST00000302279;ENST00000342116;ENST00000529687;ENST00000533336 |
| 2% | chr22 | 47071365 | 47071449 + | ENST00000406902;ENST00000361034;ENST00000408031 |
| 2% | chr22 | 47071365 | 47071449 + | ENST00000406902;ENST00000361034;ENST00000408031 |
| 2% | chr13 | 114157811 | 114157903 + | ENST00000434316;ENST00000375391 |
| 2% | chr16 | 78143675 | 78143732 + | ENST00000566780;ENST00000402655;ENST00000406884;ENST00000539474;ENST00000355860;ENST00000408984 |
| 2% | chr7 | 23300075 | 23300392 + | ENST00000258733;ENST00000381990;ENST00000539136;ENST00000453162 |
| 2% | chr7 | 23300075 | 23300392 + | ENST00000258733;ENST00000381990;ENST00000539136;ENST00000453162 |
| 2% | chr7 | 23300075 | 23300392 + | ENST00000258733;ENST00000381990;ENST00000539136;ENST00000453162 |
| 2% | chr6 | 65098733 | 65098583 − | ENST00000503581;ENST00000370621;ENST00000370616 |
| 2% | chr3 | 190030825 | 190030661 − | ENST00000295522 |
| 2% | chr9 | 130213596 | 130213560 − | ENST00000361436;ENST00000536368 |
| 2% | chr19 | 53352466;53352373 | 53352340 − | ENST00000595646;ENST00000243639;ENST00000597924;ENST00000601847 |
| 2% | chr19 | 53352466;53352373 | 53352340 − | ENST00000595646;ENST00000243639;ENST00000597924;ENST00000601847 |
| 1% | chr4 | 87869686 | 87869723 + | ENST00000395146;ENST00000507468;ENST00000503477 |
| 1% | chr2 | 131704082 | 131704208 + | ENST00000409359;ENST00000326016;ENST00000392953;ENST00000428230;ENST00000438985;ENST00000525839;ENST00000409303 |
| 1% | chr2 | 131704082 | 131704208 + | ENST00000409359;ENST00000326016;ENST00000392953;ENST00000428230;ENST00000438985;ENST00000525839;ENST00000409303 |
| 1% | chr2 | 131704082 | 131704208 + | ENST00000409359;ENST00000326016;ENST00000392953;ENST00000428230;ENST00000438985;ENST00000525839;ENST00000409303 |
| 1% | chr20 | 3614958 | 3615036 + | ENST00000262919 |
| 1% | chr9 | 5689959 | 5690038 + | ENST00000251879;ENST00000414202;ENST00000381532;ENST00000418622;ENST00000449720;ENST00000545641 |
| 1% | chr9 | 5689959 | 5690038 + | ENST00000251879;ENST00000414202;ENST00000381532;ENST00000418622;ENST00000449720;ENST00000545641 |
| 1% | chr9 | 5689959 | 5690038 + | ENST00000251879;ENST00000414202;ENST00000381532;ENST00000418622;ENST00000449720;ENST00000545641 |
| 1% | chr11 | 101937216;101937273 | 101937382 + | ENST00000434758;ENST00000526781;ENST00000529204 |
| 1% | chr11 | 101937216;101937273 | 101937382 + | ENST00000434758;ENST00000526781;ENST00000529204 |
| 1% | chr11 | 60701014 | 60701216 + | ENST00000453848;ENST00000005286;ENST00000536409 |
| 1% | chr11 | 60701014 | 60701216 + | ENST00000453848;ENST00000005286;ENST00000536409 |
| 1% | chr11 | 60701014 | 60701216 + | ENST00000453848;ENST00000005286;ENST00000536409 |
| 1% | chr11 | 71209398;71209448 | 71209574 + | ENST00000319023;ENST00000539574;ENST00000530055;ENST00000525593;ENST00000527963 |
| 1% | chr11 | 71209398;71209448 | 71209574 + | ENST00000319023;ENST00000539574;ENST00000530055;ENST00000525593;ENST00000527963 |
| 1% | chr11 | 71209398;71209448 | 71209574 + | ENST00000319023;ENST00000539574;ENST00000530055;ENST00000525593;ENST00000527963 |
| 1% | chr11 | 71209398;71209448 | 71209574 + | ENST00000319023;ENST00000539574;ENST00000530055;ENST00000525593;ENST00000527963 |
| 1% | chr11 | 71209398;71209448 | 71209574 + | ENST00000319023;ENST00000539574;ENST00000530055;ENST00000525593;ENST00000527963 |
| 1% | chr12 | 71509738 | 71509630 − | ENST00000549357 |
| 1% | chr11 | 10050104 | 10049999 − | ENST00000256190 |
| 1% | chr2 | 27610025 | 27609956 − | ENST00000344034;ENST00000350803 |
| 1% | chr19 | 15289752 | 15289634 − | ENST00000263388;ENST00000601011 |
| 1% | chr19 | 15289752 | 15289634 − | ENST00000263388;ENST00000601011 |
| 1% | chr8 | 71619168 | 71619388 + | ENST00000408926;ENST00000520030 |
| 1% | chr2 | 192546682;192546672 | 192546743 + | ENST00000307834;ENST00000307849;ENST00000410026;ENST00000451500;ENST00000409510;ENST00000425611;ENST00000435931 |
| 1% | chr2 | 192546682;192546672 | 192546743 + | ENST00000307834;ENST00000307849;ENST00000410026;ENST00000451500;ENST00000409510;ENST00000425611;ENST00000435931 |
| 1% | chr2 | 192546682;192546672 | 192546743 + | ENST00000307834;ENST00000307849;ENST00000410026;ENST00000451500;ENST00000409510;ENST00000425611;ENST000 |

TABLE 25-continued

Transcript fusion for Head-Neck Squamous Cell Carcinoma HNSC) Coordinates of the fusion sequences for which the donor is the exon.

| | | | | |
|---|---|---|---|---|
| 1% | chr8 | 104778455 | 104778765 + | 00435931<br>ENST00000504942;ENST00000406091 |
| 1% | chr19 | 14676014 | 14676102 + | ENST00000215567;ENST00000596073;ENST00000600083;ENST00000436007;ENST00000601187 |
| 1% | chr19 | 14676014 | 14676102 + | ENST00000215567;ENST00000596073;ENST00000600083;ENST00000436007;ENST00000601187 |
| 1% | chr19 | 14676014 | 14676102 + | ENST00000215567;ENST00000596073;ENST00000600083;ENST00000436007;ENST00000601187 |
| 1% | chr19 | 14676014 | 14676102 + | ENST00000215567;ENST00000596073;ENST00000600083;ENST00000436007;ENST00000601187 |
| 1% | chr12 | 28605411;<br>28605475 | 28605587 + | ENST00000536154;ENST00000539107;ENST00000545336;ENST00000381256;ENST00000381259;ENST00000306172;ENST00000535212;ENST00000542801 |
| 1% | chr12 | 28605411;<br>28605475 | 28605587 + | ENST00000536154;ENST00000539107;ENST00000545336;ENST00000381256;ENST00000381259;ENST00000306172;ENST00000535212;ENST00000542801 |
| 1% | chr12 | 28605411;<br>28605475 | 28605587 + | ENST00000536154;ENST00000539107;ENST00000545336;ENST00000381256;ENST00000381259;ENST00000306172;ENST00000535212;ENST00000542801 |
| 1% | chr12 | 28605411;<br>28605475 | 28605587 + | ENST00000536154;ENST00000539107;ENST00000545336;ENST00000381256;ENST00000381259;ENST00000306172;ENST00000535212;ENST00000542801 |
| 1% | chr12 | 28605411;<br>28605475 | 28605587 + | ENST00000536154;ENST00000539107;ENST00000545336;ENST00000381256;ENST00000381259;ENST00000306172;ENST00000535212;ENST00000542801 |
| 1% | chr12 | 28605411;<br>28605475 | 28605587 + | ENST00000536154;ENST00000539107;ENST00000545336;ENST00000381256;ENST00000381259;ENST00000306172;ENST00000535212;ENST00000542801 |
| 1% | chr13 | 42457627 | 42457523 − | ENST00000379310;ENST00000281496 |
| 1% | chr8 | 124033739 | 124033687 − | ENST00000259512;ENST00000405944;ENST00000419562;ENST00000519018;ENST00000523036 |
| 1% | chr8 | 124033739 | 124033687 − | ENST00000259512;ENST00000405944;ENST00000419562;ENST00000519018;ENST00000523036 |
| 1% | chr8 | 124033739 | 124033687 − | ENST00000259512;ENST00000405944;ENST00000419562;ENST00000519018;ENST00000523036 |
| 1% | chr19 | 49122400 | 49122398 − | ENST00000549920;ENST00000547897;ENST00000550645;ENST00000552588;ENST00000549370;ENST00000549273 |
| 1% | chr18 | 47794033 | 47793977 − | ENST00000585672;ENST00000592060 |
| 1% | chr18 | 47794033 | 47793977 − | ENST00000585672;ENST00000592060 |
| 1% | chr1 | 33272212 | 33272083 − | ENST00000373477 |
| 1% | chr16 | 72153988;<br>72154048 | 72153750 − | ENST00000537465;ENST00000237353;ENST00000355636 |
| 1% | chr16 | 72153988;<br>72154048 | 72153750 − | ENST00000537465;ENST00000237353;ENST00000355636 |
| 1% | chr16 | 72153988;<br>72154048 | 72153750 − | ENST00000537465;ENST00000237353;ENST00000355636 |

| 7 | 8 | 9 | 10 | 11 |
|---|---|---|---|---|
| chr5 | 54993040 | 54992544 | − | TSF |
| chr10 | 48278725 | 48278896 | + | TAF |
| chr12 | 71504233 | 71503634 | − | TAF |
| chr8 | 54826057 | 54826421 | + | TAF |
| chr1 | 153532853 | 153532704 | − | TAF |
| chr1 | 153532853 | 153532704 | − | TAF |
| chr6 | 41607515 | 41607595 | + | TAF |
| chr19 | 14060442 | 14060422 | − | TAF |
| chr19 | 51445160 | 51445047 | − | TAF |
| chr3 | 10965604 | 10965907 | + | TAF |
| chr1 | 32696861 | 32697110 | + | TAF |
| chr5 | 82606608 | 82606935 | + | TAF |
| chr3 | 182566968 | 182567869 | + | TAF |
| chr3 | 182566968 | 182567869 | + | TAF |
| chr4 | 47584886 | 47585171 | + | TAF |
| chr19 | 39085644 | 39085967 | + | TAF |
| chr19 | 39085644 | 39085967 | + | TAF |
| chr19 | 39085644 | 39085967 | + | TAF |
| chr10 | 5002427 | 5002117 | − | TAF |
| chr10 | 5002427 | 5002117 | − | TAF |
| chr3 | 196223342 | 196223041 | − | TAF |
| chr19 | 35995923 | 35995655 | − | TAF |
| chr19 | 35995923 | 35995655 | − | TAF |
| chr19 | 35995923 | 35995655 | − | TAF |
| chr19 | 35995923 | 35995655 | − | TAF |
| chr19 | 35995923 | 35995655 | − | TAF |
| chr19 | 35995923 | 35995655 | − | TAF |

TABLE 25-continued

Transcript fusion for Head-Neck Squamous Cell Carcinoma HNSC) Coordinates of the fusion sequences for which the donor is the exon.

| | | | |
|---|---|---|---|
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr18 | 21511381 | 21511478 + | TAF |
| chr18 | 21511381 | 21511478 + | TAF |
| chr18 | 21511381 | 21511478 + | TAF |
| chr18 | 21511381 | 21511478 + | TAF |
| chr18 | 21511381 | 21511478 + | TAF |
| chr18 | 21511381 | 21511478 + | TAF |
| chr7 | 22512853 | 22512669 − | TSF |
| chr7 | 22512853 | 22512669 − | TSF |
| chr20 | 35844460 | 35844765 + | TAF |
| chr20 | 35844460 | 35844765 + | TAF |
| chr9 | 101986374 | 101986588 + | TAF |
| chr11 | 11386990 | 11386568 − | TAF |
| chr19 | 35613565 | 35613610 + | TAF |
| chr19 | 35613565 | 35613610 + | TAF |
| chr7 | 55272949 | 55272949 + | TSF |
| chr19 | 46623577 | 46622963 − | TSF |
| chr16 | 68761056 | 68761347 + | TSF |
| chr16 | 68761056 | 68761347 + | TSF |
| chr16 | 68761056 | 68761347 + | TSF |
| chr16 | 68761056 | 68761347 + | TSF |
| chr12 | 113404028 | 113404051 + | TSF |
| chr12 | 113404028 | 113404051 + | TSF |
| chr19 | 3855694 | 3855445 − | TSF |
| chr19 | 3855694 | 3855445 − | TSF |
| chrX | 119705855 | 119705820 − | TSF |
| chr19 | 46623564 | 46622963 − | TSF |
| chr1 | 6531300 | 6531188 − | TSF |
| chr1 | 6531300 | 6531188 − | TSF |
| chr1 | 6531300 | 6531188 − | TSF |
| chr1 | 6531300 | 6531188 − | TSF |
| chr1 | 6531300 | 6531188 − | TSF |
| chr1 | 6531300 | 6531188 − | TSF |
| chr22 | 38322963 | 38322967 + | TSF |
| chr22 | 38322963 | 38322967 + | TSF |
| chr4 | 57321183 | 57321327 + | TSF |
| chr4 | 57321183 | 57321327 + | TSF |
| chr4 | 57321183 | 57321327 + | TSF |
| chr1 | 11115464 | 11115178 − | TSF |
| chr1 | 11115464 | 11115178 − | TSF |
| chr18 | 61628870 | 61629168 + | TSF |
| chr12 | 46760066 | 46759964 − | TSF |
| chr17 | 39733779 | 39733579 − | TSF |
| chr9 | 125068067 | 125068171 + | TSF |
| chr9 | 125068067 | 125068171 + | TSF |
| chr9 | 125068067 | 125068171 + | TSF |
| chr2 | 153001350 | 153001066 − | TSF |
| chrX | 41557348 | 41557057 − | TSF |
| chr9 | 94990268 | 94989087 − | TSF |
| chr9 | 94990268 | 94989087 − | TSF |
| chr2 | 172723793 | 172722363 − | TSF |
| chr2 | 172723793 | 172722363 − | TSF |
| chr2 | 172723793 | 172722363 − | TSF |
| chr14 | 67864772 | 67864768 − | TSF |
| chr7 | 81929467 | 81929190 − | TSF |
| chr19 | 15289244 | 15289201 − | TSF |
| chr19 | 15289244 | 15289201 − | TSF |
| chr12 | 56740986 | 56740975 − | TSF |
| chr12 | 56740986 | 56740975 − | TSF |
| chr5 | 150637286 | 150637636 + | TSF |
| chr8 | 42925245 | 42925476 + | TSF |
| chr8 | 42925245 | 42925476 + | TSF |
| chr8 | 42925245 | 42925476 + | TSF |
| chr8 | 42925245 | 42925476 + | TSF |
| chr8 | 42925245 | 42925476 + | TSF |
| chr8 | 42925245 | 42925476 + | TSF |
| chr19 | 3115258 | 3115402 + | TSF |
| chr19 | 3115258 | 3115402 + | TSF |
| chr12 | 52462184 | 52462137 − | TSF |

TABLE 25-continued

Transcript fusion for Head-Neck Squamous Cell Carcinoma HNSC) Coordinates of the fusion sequences for which the donor is the exon.

| | | | |
|---|---|---|---|
| chr3 | 98586282 | 98584565 − | TSF |
| chr3 | 98586282 | 98584565 − | TSF |
| chr1 | 225157336 | 225158402 + | TSF |
| chr1 | 225157336 | 225158402 + | TSF |
| chr22 | 35846150 | 35846200 + | TSF |
| chr22 | 35846150 | 35846200 + | TSF |
| chr2 | 176859008 | 176858934 − | TSF |
| chr2 | 176859008 | 176858934 − | TSF |
| chr9 | 5712361 | 5712559 + | TSF |
| chr9 | 5712361 | 5712559 + | TSF |
| chr9 | 5712361 | 5712559 + | TSF |
| chr10 | 47139994 | 47138925 − | TSF |
| chr1 | 6367453 | 6367413 − | TSF |
| chr1 | 6367453 | 6367413 − | TSF |
| chr1 | 6367453 | 6367413 − | TSF |
| chr1 | 6367453 | 6367413 − | TSF |
| chr1 | 6367453 | 6367413 − | TSF |
| chr1 | 6367453 | 6367413 − | TSF |
| chr1 | 6367453 | 6367413 − | TSF |
| chr5 | 176829864 | 176829767 − | TSF |
| chr16 | 83588547 | 83588577 + | TSF |
| chr16 | 83588547 | 83588577 + | TSF |
| chr16 | 83588547 | 83588577 + | TSF |
| chr10 | 126251911 | 126252288 + | TSF |
| chr16 | 57116257 | 57116272 + | TSF |
| chr16 | 57116257 | 57116272 + | TSF |
| chr14 | 24767944 | 24767783 − | TSF |
| chr15 | 77051709 | 77051558 − | TSF |
| chr15 | 77051709 | 77051558 − | TSF |
| chr15 | 77051709 | 77051558 − | TSF |
| chr8 | 143859806 | 143859781 − | TSF |
| chr3 | 137907243 | 137907252 + | TSF |
| chr3 | 137907243 | 137907252 + | TSF |
| chr21 | 45240407 | 45240709 + | TSF |
| chr5 | 1811082 | 1811428 + | TSF |
| chr1 | 63952444 | 63951983 − | TSF |
| chr1 | 63952444 | 63951983 − | TSF |
| chr5 | 121403052 | 121403016 − | TSF |
| chr19 | 45889495 | 45889472 − | TSF |
| chr8 | 120233190 | 120233225 + | TSF |
| chr3 | 129029005 | 129029042 + | TSF |
| chr3 | 129029005 | 129029042 + | TSF |
| chr3 | 129029005 | 129029042 + | TSF |
| chr2 | 28362015 | 28362218 + | TSF |
| chr12 | 46760023 | 46759964 − | TSF |
| chr8 | 42934165 | 42935743 + | TSF |
| chr8 | 42934165 | 42935743 + | TSF |
| chr8 | 42934165 | 42935743 + | TSF |
| chr8 | 42934165 | 42935743 + | TSF |
| chr22 | 47078308 | 47078350 + | TSF |
| chr22 | 47078308 | 47078350 + | TSF |
| chr13 | 114159741 | 114159770 + | TSF |
| chr16 | 78145717 | 78146057 + | TSF |
| chr7 | 23301185 | 23301414 + | TSF |
| chr7 | 23301185 | 23301414 + | TSF |
| chr7 | 23301185 | 23301414 + | TSF |
| chr6 | 65097495 | 65097442 − | TSF |
| chr3 | 190030018 | 190029730 − | TSF |
| chr9 | 130213398 | 130213359 − | TSF |
| chr19 | 53339322 | 53339166 − | TSF |
| chr19 | 53339322 | 53339166 − | TSF |
| chr4 | 87916831 | 87917873 + | TSF |
| chr2 | 131710021 | 131712132 + | TSF |
| chr2 | 131710021 | 131712132 + | TSF |
| chr2 | 131710021 | 131712132 + | TSF |
| chr20 | 3615708 | 3616042 + | TSF |
| chr9 | 5710416 | 5711239 + | TSF |
| chr9 | 5710416 | 5711239 + | TSF |
| chr9 | 5710416 | 5711239 + | TSF |
| chr11 | 101937956 | 101938097 + | TSF |
| chr11 | 101937956 | 101938097 + | TSF |
| chr11 | 60701443 | 60701575 + | TSF |
| chr11 | 60701443 | 60701575 + | TSF |
| chr11 | 60701443 | 60701575 + | TSF |
| chr11 | 71216557 | 71216960 + | TSF |
| chr11 | 71216557 | 71216960 + | TSF |
| chr11 | 71216557 | 71216960 + | TSF |

TABLE 25-continued

Transcript fusion for Head-Neck Squamous Cell Carcinoma HNSC) Coordinates of the fusion sequences for which the donor is the exon.

| | | | | |
|---|---|---|---|---|
| chr11 | 71216557 | 71216960 | + | TSF |
| chr11 | 71216557 | 71216960 | + | TSF |
| chr11 | 71507025 | 71506982 | − | TSF |
| chr11 | 10038326 | 10038049 | − | TSF |
| chr2 | 27609703 | 27609426 | − | TSF |
| chr19 | 15289358 | 15289201 | − | TSF |
| chr19 | 15289358 | 15289201 | − | TSF |
| chr8 | 71625661 | 71625673 | + | TSF |
| chr2 | 192548016 | 192548103 | + | TSF |
| chr2 | 192548016 | 192548103 | + | TSF |
| chr2 | 192548016 | 192548103 | + | TSF |
| chr8 | 104821508 | 104821527 | + | TSF |
| chr19 | 14677944 | 14677945 | + | TSF |
| chr19 | 14677944 | 14677945 | + | TSF |
| chr19 | 14677944 | 14677945 | + | TSF |
| chr19 | 14677944 | 14677945 | + | TSF |
| chr12 | 28624332 | 28624630 | + | TSF |
| chr12 | 28624332 | 28624630 | + | TSF |
| chr12 | 28624332 | 28624630 | + | TSF |
| chr12 | 28624332 | 28624630 | + | TSF |
| chr12 | 28624332 | 28624630 | + | TSF |
| chr12 | 28624332 | 28624630 | + | TSF |
| chr13 | 42456370 | 42455523 | − | TSF |
| chr8 | 123989465 | 123989244 | − | TSF |
| chr8 | 123989465 | 123989244 | − | TSF |
| chr8 | 123989465 | 123989244 | − | TSF |
| chr19 | 49121979 | 49121790 | − | TSF |
| chr18 | 47793455 | 47793319 | − | TSF |
| chr18 | 47793455 | 47793319 | − | TSF |
| chr1 | 33270484 | 33269340 | − | TSF |
| chr16 | 72150929 | 72150229 | − | TSF |
| chr16 | 72150929 | 72150229 | − | TSF |
| chr16 | 72150929 | 72150229 | − | TSF |

TABLE 26

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 85% | chr12 | 122430912 | 122431615 | + | chr12 | 122437622 | 122437850 | + | ENST00000288912 | TAF |
| 40% | chr11 | 93468219 | 93468129 | − | chr11 | 93467826 | 93467791; 93467814 | − | ENST00000393259;ENST00000527169 | TAF |
| 40% | chr11 | 93468219 | 93468129 | − | chr11 | 93467826 | 93467791; 93467814 | − | ENST00000393259;ENST00000527169 | TAF |
| 40% | chr5 | 76107394 | 76108135 | + | chr5 | 76128515 | 76129626 | + | ENST00000296677 | TSF |
| 39% | chr12 | 122387836 | 122388242 | + | chr12 | 122389386 | 122389436 | + | ENST00000288912;ENST00000397454 | TSF |
| 39% | chr12 | 122387836 | 122388242 | + | chr12 | 122389386 | 122389436 | + | ENST00000288912;ENST00000397454 | TSF |
| 37% | chr8 | 104389530 | 104389551 | + | chr8 | 104390255 | 104390471 | + | ENST00000330295;ENST00000520337 | TAF |
| 36% | chr4 | 15791827 | 15792541 | + | chr4 | 15818134 | 15818263 | + | ENST00000502843;ENST00000226279 | TAF |
| 36% | chr4 | 15791827 | 15792541 | + | chr4 | 15818134 | 15818263 | + | ENST00000502843;ENST00000226279 | TAF |
| 35% | chr9 | 119603649 | 119602892 | − | chr9 | 119583062 | 119582896 | − | ENST00000373996;ENST00000313400;ENST00000373986;ENST00000361209 | TAF |
| 35% | chr2 | 38983894 | 38983253 | − | chr2 | 38977336 | 38977156 | − | ENST00000313117;ENST000000425778;ENST00000425941;ENST00000446327;ENST00000409276;ENST00000431066;ENST00000443213 | TSF |
| 35% | chr2 | 38983894 | 38983253 | − | chr2 | 38977336 | 38977156 | | ENST00000313117;ENST000000425778;ENST00000425941;ENST00000446327;ENST00000409276;ENST00000431066;ENST00000443213 | TSF |
| 35% | chr2 | 38983894 | 38983253 | − | chr2 | 38977336 | 38977156 | − | ENST00000313117;ENST000000425778;ENST00000425941;ENST00000446327;ENST00000409276;ENST00000431066;ENST00000443213 | TSF |
| 35% | chr2 | 38983894 | 38983253 | − | chr2 | 38977336 | 38977156 | − | ENST00000313117;ENST000000425778;ENST00000425941;ENST000 | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 35% | chr2 | 38983894 | 38983253 | − | chr2 | 38977336 | 38977156 | − | 00446327;ENST00000409276;ENST00000431066;ENST00000443213 ENST00000313117;ENST0000042 5778;ENST00000425941;ENST00000446327;ENST00000409276;ENST00000431066;ENST00000443213 | TSF |
| 32% | chr11 | 87906665 | 87906580 | − | chr11 | 87883123 | 87882843 | − | ENST00000243662;ENST00000526372 | TAF |
| 32% | chr12 | 122387836 | 122388242 | + | chr12 | 122392026 | 122392240 | + | ENST00000288912;ENST00000397454 | TSF |
| 32% | chr12 | 122387836 | 122388242 | 1 | chr12 | 122392026 | 122392240 | + | ENST00000288912;ENST00000397454 | TSF |
| 29% | chr7 | 116364854 | 116364901 | + | chr7 | 116371722 | 116371913 | + | ENST00000397752;ENST000003 18493;ENST00000436117 | TAF |
| 29% | chr7 | 116364854 | 116364901 | + | chr7 | 116371722 | 116371913 | + | ENST00000397752;ENST000003 18493;ENST00000436117 | TAF |
| 29% | chr7 | 116364854 | 116364901 | + | chr7 | 116371722 | 116371913 | + | ENST00000397752;ENST000003 18493;ENST00000436117 | TAF |
| 28% | chr3 | 185411133 | 185410965 | − | chr3 | 185410550 | 185410487 | − | ENST00000382199;ENST0000042 1047;ENST00000457616;ENST00000346192 | TAF |
| 28% | chr3 | 185411133 | 185410965 | − | chr3 | 185410550 | 185410487 | − | ENST00000382199;ENST0000042 1047;ENST00000457616;ENST00000346192 | TAF |
| 27% | chr19 | 39347374 | 39346430 | − | chr19 | 39338074 | 39337956 | − | ENST00000221419;ENST00000601449;ENST00000600233;ENST00000601813 | TSF |
| 27% | chr19 | 39347374 | 39346430 | − | chr19 | 39338074 | 39337956 | − | ENST00000221419;ENST00000601449;ENST00000600233;ENST00000601813 | TSF |
| 27% | chr19 | 39347374 | 39346430 | − | chr19 | 39338074 | 39337956 | − | ENST00000221419;ENST00000601449;ENST00000600233;ENST00000601813 | TSF |
| 27% | chr19 | 39347374 | 39346206 | − | chr19 | 39338074 | 39337956 | − | ENST00000221419;ENST00000601449;ENST00000600233;ENST00000601813 | TSF |
| 27% | chr19 | 39347374 | 39346206 | − | chr19 | 39338074 | 39337956 | − | ENST00000221419;ENST00000601449;ENST00000600233;ENST00000601813 | TSF |
| 27% | chr19 | 39347374 | 39346206 | − | chr19 | 39338074 | 39337956 | − | ENST00000221419;ENST00000601449;ENST00000600233;ENST00000601813 | TSF |
| 22% | chr5 | 76107394 | 76108212 | + | chr5 | 76128515 | 76129626 | + | ENST00000296677 | TSF |
| 21% | chr5 | 135398466 | 135398602 | + | chr5 | 135398875 | 135398915; 135398898 | + | ENST00000442011;ENST00000305126;ENST00000514554;ENST00000508076;ENST00000503087 | TAF |
| 21% | chr5 | 135398466 | 135398602 | + | chr5 | 135398875 | 135398915; 135398898 | + | ENST00000442011;ENST00000305126;ENST00000514554;ENST00000508076;ENST00000503087 | TAF |
| 21% | chr6 | 138423138 | 138423021 | − | chr6 | 138417631 | 138417491 | − | ENST00000421351 | TAF |
| 19% | chr19 | 49121994 | 49121817 | − | chr19 | 49121134 | 49121048 | − | ENST00000549920;ENST00000547897;ENST00000084795;ENST00000550645;ENST00000549370;ENST00000549273 | TAF |
| 19% | chr19 | 49121994 | 49121817 | − | chr19 | 49121134 | 49121048 | − | ENST00000549920;ENST00000547897;ENST00000084795;ENST00000550645;ENST00000549370;ENST00000549273 | TAF |
| 19% | chr19 | 49121994 | 49121817 | − | chr19 | 49121134 | 49121048 | − | ENST00000549920;ENST00000547897;ENST00000084795;ENST00000550645;ENST00000549370;ENST00000549273 | TAF |
| 19% | chr19 | 49121994 | 49121817 | − | chr19 | 49121134 | 49121048 | − | ENST00000549920;ENST00000547897;ENST00000084795;ENST00000550645;ENST00000549370;ENST00000549273 | TAF |
| 19% | chr19 | 49121994 | 49121817 | − | chr19 | 49121134 | 49121048 | − | ENST00000549920;ENST00000547897;ENST00000084795;ENST00000550645;ENST00000549370;ENST00000549273 | TAF |
| 19% | chr2 | 38983894 | 38983132 | − | chr2 | 38977336 | 38977156 | − | ENST00000313117;ENST0000042 5778;ENST00000425941;ENST00000446327;ENST00000409276;ENST00000431066;ENST00000443213 | TAF |
| 19% | chr2 | 38983894 | 38983132 | − | chr2 | 38977336 | 38977156 | − | ENST00000313117;ENST0000042 | TAF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | 19% | chr2 | 38983894 | 38983132 | − | chr2 | 38977336 | 38977156 | − | 5778;ENST00000425941;ENST000 00446327;ENST00000409276;ENS T00000431066;ENST00000443213 ENST00000313117;ENST0000042 5778;ENST00000425941;ENST000 00446327;ENST00000409276;ENS T00000431066;ENST00000443213 | TAF |
| | 19% | chr2 | 38983894 | 38983132 | − | chr2 | 38977336 | 38977156 | − | ENST00000313117;ENST0000042 5778;ENST00000425941;ENST000 00446327;ENST00000409276;ENS T00000431066;ENST00000443213 | TAF |
| | 19% | chr2 | 38983894 | 38983132 | − | chr2 | 38977336 | 38977156 | − | ENST00000313117;ENST0000042 5778;ENST00000425941;ENST000 00446327;ENST00000409276;ENS T00000431066;ENST00000443213 | TAF |
| | 18% | chr7 | 56018506 | 56018522 | + | chr7 | 56020872 | 56021011 | + | ENST00000426595 | TSF |
| | 16% | chr11 | 70006969 | 70007088 | + | chr11 | 70007267 | 70007468 | + | ENST00000355303;ENST0000039 8543;ENST00000538023;ENST000 00316296;ENST00000530676;ENS T00000531349;ENST00000531300 | TSF |
| | 16% | chr11 | 70006969 | 70007088 | + | chr11 | 70007267 | 70007468 | + | ENST00000355303;ENST0000039 8543;ENST00000538023;ENST000 00316296;ENST00000530676;ENS T00000531349;ENST00000531300 | TSF |
| | 16% | chr11 | 70006969 | 70007088 | + | chr11 | 70007267 | 70007468 | + | ENST00000355303;ENST0000039 8543;ENST00000538023;ENST000 00316296;ENST00000530676;ENS T00000531349;ENST00000531300 | TSF |
| | 16% | chr15 | 40187476 | 40186733 | − | chr15 | 40099459 | 40099207 | − | ENST00000561100;ENST0000054 3580 | TSF |
| | 15% | chr7 | 134233804 | 134234001 | + | chr7 | 134252910 | 134253077 | + | ENST00000457545;ENST0000042 3958 | TAF |
| | 15% | chr17 | 18390031 | 18390254 | + | chr17 | 18390961 | 18391071 | + | ENST00000581545;ENST0000058 2333;ENST00000328114;ENST000 00412421;ENST00000583322;ENS T00000584941 | TAF |
| | 15% | chr17 | 18390031 | 18390254 | + | chr17 | 18390961 | 18391071 | + | ENST00000581545;ENST0000058 2333;ENST00000328114;ENST000 00412421;ENST00000583322;ENS T00000584941 | TAF |
| | 15% | chr17 | 18390031 | 18390254 | + | chr17 | 18390961 | 18391071 | + | ENST00000581545;ENST0000058 2333;ENST00000328114;ENST000 00412421;ENST00000583322;ENS T00000584941 | TAF |
| | 15% | chr17 | 18390031 | 18390254 | + | chr17 | 18390961 | 18391071 | + | ENST00000581545;ENST0000058 2333;ENST00000328114;ENST000 00412421;ENST00000583322;ENS T00000584941 | TAF |
| | 15% | chr17 | 18390031 | 18390254 | + | chr17 | 18390961 | 18391071 | + | ENST00000581545;ENST0000058 2333;ENST00000328114;ENST000 00412421;ENST00000583322;ENS T00000584941 | TAF |
| | 15% | chr17 | 20360914 | 20360691 | − | chr17 | 20359984 | 20359874 | − | ENST00000423676;ENST0000032 4290 | TAF |
| | 15% | chr17 | 20360914 | 20360691 | − | chr17 | 20359984 | 20359874 | − | ENST00000423676;ENST0000032 4290 | TAF |
| | 15% | chr1 | 6380703 | 6380649 | − | chr1 | 6378638 | 6378552 | − | ENST00000608083;ENST0000037 7842;ENST00000377845;ENST000 00377855;ENST00000377860;ENS T00000418124;ENST00000545482; ENST00000361521;ENST0000047 3466;ENST00000541130 | TAF |
| | 15% | chr1 | 6380703 | 6380649 | − | chr1 | 6378638 | 6378552 | − | ENST00000608083;ENST0000037 7842;ENST00000377845;ENST000 00377855;ENST00000377860;ENS T00000418124;ENST00000545482; ENST00000361521;ENST0000047 3466;ENST00000541130 | TAF |
| | 15% | chr1 | 6380703 | 6380649 | − | chr1 | 6378638 | 6378552 | − | ENST00000608083;ENST0000037 7842;ENST00000377845;ENST000 00377855;ENST00000377860;ENS T00000418124;ENST00000545482 ;ENST00000361521;ENST0000047 3466;ENST00000541130 | TAF |
| | 15% | chr1 | 6380703 | 6380649 | − | chr1 | 6378638 | 6378552 | − | ENST00000608083;ENST0000037 | TAF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 15% | chr1 | 6380703 | 6380649 | − | chr1 | 6378638 | 6378552 | − | ENST00000608083;ENST0000037 7842;ENST00000377845;ENST000 00377855;ENST00000377860;ENS T00000418124;ENST00000545482; ENST00000361521;ENST0000047 3466;ENST00000541130 | TAF |
| 15% | chr1 | 6380703 | 6380649 | − | chr1 | 6378638 | 6378552 | − | ENST00000608083;ENST0000037 7842;ENST00000377845;ENST000 00377855;ENST00000377860;ENS T00000418124;ENST00000545482; ENST00000361521;ENST0000047 3466;ENST00000541130 | TAF |
| 14% | chr17 | 79214190 | 79214239 | + | chr17 | 79214787 | 79214816; 79214953 | + | ENST00000431388;ENST0000057 6002 | |
| 14% | chr17 | 79214190 | 79214239 | + | chr17 | 79214787 | 79214816; 79214953 | + | ENST00000431388;ENST0000057 6002 | TAF |
| 14% | chr17 | 30771499 | 30771536 | + | chr17 | 30773963 | 30774064 | + | ENST00000261712;ENST0000045 7654;ENST00000579451 | TAF |
| 14% | chr17 | 30771499 | 30771536 | + | chr17 | 30773963 | 30774064 | + | ENST00000261712;ENST0000045 7654;ENST00000579451 | TAF |
| 14% | chr9 | 128362212 | 128362114 | − | chr9 | 128348006 | 128347834 | − | ENST00000373511;ENST0000037 3498;ENST00000350766;ENST000 00265960;ENST00000394060;ENS T00000468896 | TAF |
| 14% | chr9 | 128362212 | 128362114 | − | chr9 | 128348006 | 128347834 | − | ENST00000373511;ENST0000037 3498;ENST00000350766;ENST000 00265960;ENST00000394060;ENS T00000468896 | TAF |
| 14% | chr9 | 128362212 | 128362114 | − | chr9 | 128348006 | 128347834 | − | ENST00000373511;ENST0000037 3498;ENST00000350766;ENST000 00265960;ENST00000394060;ENS T00000468896 | TAF |
| 14% | chr9 | 128362212 | 128362114 | − | chr9 | 128348006 | 128347834 | − | ENST00000373511;ENST0000037 3498;ENST00000350766;ENST000 00265960;ENST00000394060;ENS T00000468896 | TAF |
| 14% | chr9 | 128362212 | 128362114 | − | chr9 | 128348006 | 128347834 | − | ENST00000373511;ENST0000037 3498;ENST00000350766;ENST000 00265960;ENST00000394060;ENS T00000468896 | TAF |
| 14% | chr12 | 6602868 | 6602840 | − | chr12 | 6602138 | 6602028 | − | ENST00000229238 | TAF |
| 14% | chr4 | 89454580 | 89454120 | − | chr4 | 89443180 | 89443039 | − | ENST00000273968 | TAF |
| 13% | chr8 | 82194688 | 82194727 | 1 | chr8 | 82195601 | 82195773 | + | ENST00000297258 | TAF |
| 13% | chr16 | 48451457 | 48450727 | | chr16 | 48396341 | 48395491 | − | ENST00000356721 | TSF |
| 13% | chr2 | 173999600 | 173999766 | + | chr2 | 174034533 | 174034620 | + | ENST00000539448; ENST0000040 9176;ENST00000338983;ENST000 00375213;ENST00000422149 | TSF |
| 13% | chr2 | 173999600 | 173999766 | + | chr2 | 174034533 | 174034620 | + | ENST00000539448;ENST0000040 9176;ENST00000338983;ENST000 00375213;ENST00000422149 | TSF |
| 13% | chr2 | 173999600 | 173999766 | + | chr2 | 174034533 | 174034620 | + | ENST00000539448;ENST0000040 9176;ENST00000338983;ENST000 00375213;ENST00000422149 | TSF |
| 12% | chr12 | 86274449 | 86274547 | + | chr12 | 86276001 | 86276153 | + | ENST00000551529;ENST0000025 6010 | TAF |
| 12% | chr12 | 64687157 | 64687061 | − | chr12 | 64679840 | 64679734 | − | ENST00000543942;ENST0000033 3722 | TAF |
| 12% | chr9 | 119603649 | 119602932 | − | chr9 | 119583062 | 119582896 | − | ENST00000373996; ENST0000031 3400;ENST00000373986;ENST000 00361209 | TAF |
| 12% | chr18 | 9594227 | 9594127 | − | chr18 | 9593872 | 9593766; 9593838 | − | ENST00000400556;ENST0000040 0555;ENST00000584074;ENST000 00581250;ENST00000580745;ENS T00000580182;ENST00000582240; ENST00000581835 | TAF |
| 12% | chr18 | 9594227 | 9594127 | − | chr18 | 9593872 | 9593766; 9593838 | − | ENST00000400556;ENST0000040 0555;ENST00000584074;ENST000 00581250;ENST00000580745;ENS T00000580182;ENST00000582240; ENST00000581835 | TAF |
| 12% | chr18 | 9594227 | 9594127 | − | chr18 | 9593872 | 9593766; 9593838 | − | ENST00000400556;ENST0000040 0555;ENST00000584074;ENST000 00581250;ENST00000580745;ENS T00000580182;ENST00000582240; ENST00000581835 | TAF |
| 12% | chr18 | 9594227 | 9594127 | − | chr18 | 9593872 | 9593766; | − | ENST00000400556;ENST0000040 | TAF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
|  |  |  |  |  |  |  | 9593838 |  | 0555;ENST00000584074;ENST000 00581250;ENST00000580745;ENS T00000580182;ENST00000582240; ENST00000581835 |  |
| 12% | chr18 | 9594227 | 9594127 | − | chr18 | 9593872 | 9593766; 9593838 | − | ENST00000400556;ENST0000040 0555;ENST00000584074;ENST000 00581250;ENST00000580745;ENS T00000580182;ENST00000582240; ENST00000581835 | TAF |
| 12% | chr18 | 9594227 | 9594127 | − | chr18 | 9593872 | 9593766; 9593838 | − | ENST00000400556;ENST0000040 0555;ENST00000584074;ENST000 00581250;ENST00000580745;ENS T00000580182;ENST00000582240; ENST00000581835 | TAF |
| 12% | chr18 | 9594227 | 9594127 | − | chr18 | 9593872 | 9593766; 9593838 | − | ENST00000400556;ENST0000040 0555;ENST00000584074;ENST000 00581250;ENST00000580745;ENS T00000580182;ENST00000582240; ENST00000581835 | TAF |
| 11% | chr6 | 138424848 | 138424827 | − | chr6 | 138417631 | 138417491 | − | ENST00000421351 | TAF |
| 11% | chr17 | 39740464 | 39740452 | − | chr17 | 39740173 | 39740012 | − | ENST00000167586 | TAF |
| 11% | chr12 | 14506971 | 14507749 | + | chr12 | 14576843 | 14578407 | + | ENST00000544627 | TSF |
| 10% | chr19 | 39347374 | 39346635 | − | chr19 | 39338074 | 39337956 | − | ENST00000221419;ENST0000060 1449;ENST00000600233;ENST000 00601813 | TAF |
| 10% | chr19 | 39347374 | 39346635 | − | chr19 | 39338074 | 39337956 | − | ENST00000221419;ENST0000060 1449;ENST00000600233;ENST000 00601813 | TAF |
| 10% | chr19 | 39347374 | 39346635 | − | chr19 | 39338074 | 39337956 | − | ENST00000221419;ENST0000060 1449;ENST00000600233;ENST000 00601813 | TAF |
| 10% | chr9 | 119603649 | 119602972 | − | chr9 | 119583062 | 119582896 | − | ENST00000373996;ENST0000031 3400;ENST00000373986;ENST000 00361209 | TSF |
| 10% | chr11 | 60694460 | 60694542 | + | chr11 | 60694676 | 60694890 | + | ENST00000453848; ENST0000000 5286 | TSF |
| 10% | chr11 | 60694460 | 60694542 | + | chr11 | 60694676 | 60694890 | + | ENST00000453848;ENST0000000 5286 | TSF |
| 10% | chr2 | 65243329 | 65243368 | + | chr2 | 65243574 | 65243807 | + | ENST00000234256 | TSF |
| 10% | chr9 | 117824597 | 117824593 | − | chr9 | 117822281 | 117822009 | − | ENST00000350763;ENST0000034 1037;ENST00000423613 | TSF |
| 10% | chr9 | 117824597 | 117824593 | − | chr9 | 117822281 | 117822009 | − | ENST00000350763;ENST0000034 1037;ENST00000423613 | TSF |
| 10% | chr9 | 117824597 | 117824593 | − | chr9 | 117822281 | 117822009 | − | ENST00000350763;ENST0000034 1037;ENST00000423613 | TSF |
| 9% | chr19 | 56811235 | 56811344 | + | chr19 | 56813337 | 56813464 | + | ENST00000588026 | TSF |
| 9% | chr12 | 122430912 | 122432103 | + | chr12 | 122437622 | 122437850 | + | ENST00000288912 | TSF |
| 9% | chr12 | 122430912 | 122431795 | + | chr12 | 122437622 | 122437850 | + | ENST00000288912 | TSF |
| 9% | chr6 | 80022917 | 80022085 | − | chr6 | 79924739 | 79924689 | − | ENST00000275036;ENST0000034 4726 | TSF |
| 9% | chr6 | 80022917 | 80022085 | − | chr6 | 79924739 | 79924689 | − | ENST00000275036;ENST0000034 4726 | TSF |
| 8% | chr17 | 17816540 | 17815566 | − | chr17 | 17810845 | 17810761 | − | ENST00000581396;ENST0000037 9504;ENST00000318094;ENST000 00395739;ENST00000535933;ENS T00000540946;ENST00000542206 | TSF |
| 8% | chr17 | 17816540 | 17815566 | − | chr17 | 17810845 | 17810761 | − | ENST00000581396;ENST0000037 9504;ENST00000318094;ENST000 00395739;ENST00000535933;ENS T00000540946;ENST00000542206 | TSF |
| 8% | chr17 | 17816540 | 17815566 | − | chr17 | 17810845 | 17810761 | − | ENST00000581396;ENST0000037 9504;ENST00000318094;ENST000 00395739;ENST00000535933;ENS T00000540946;ENST00000542206 | TSF |
| 8% | chr17 | 17816540 | 17815566 | − | chr17 | 17810845 | 17810761 | − | ENST00000581396;ENST0000037 9504;ENST00000318094;ENST000 00395739;ENST00000535933;ENS T00000540946;ENST00000542206 | TSF |
| 8% | chr17 | 17816540 | 17815566 | − | chr17 | 17810845 | 17810761 | − | ENST00000581396;ENST0000037 9504;ENST00000318094;ENST000 00395739;ENST00000535933;ENS T00000540946;ENST00000542206 | TSF |
| 8% | chr17 | 17816540 | 17815566 | − | chr17 | 17810845 | 17810761 | − | ENST00000581396;ENST0000037 9504;ENST00000318094;ENST000 00395739;ENS | TSF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 8% | chr20 | 8624404 | 8625147 | + | chr20 | 8626749 | 8626828 | + | T00000540946;ENST00000542206 ENST00000378641;ENST0000033 8037;ENST00000378637;ENST000 00404098 | ITSF |
| 8% | chr20 | 8624404 | 8625147 | + | chr20 | 8626749 | 8626828 | + | ENST00000378641;ENST0000033 8037;ENST00000378637;ENST000 00404098 | TSF |
| 8% | chr20 | 8624404 | 8625147 | + | chr20 | 8626749 | 8626828 | + | ENST00000378641;ENST0000033 8037;ENST00000378637;ENST000 00404098 | TSF |
| 8% | chr10 | 79700435 | 79700428 | − | chr10 | 79628955 | 79628887 | − | ENST00000372391;ENST0000037 2388;ENST00000468332 | TSF |
| 8% | chr10 | 79700435 | 79700428 | − | chr10 | 79628955 | 79628887 | − | ENST00000372391;ENST0000037 2388;ENST00000468332 | TSF |
| 8% | chr10 | 79700435 | 79700428 | − | chr10 | 79628955 | 79628887 | − | ENST00000372391;ENST0000037 2388;ENST00000468332 | TSF |
| 8% | chr7 | 48039730 | 48039725 | − | chr7 | 48035743 | 48035628 | − | ENST00000453071;ENST0000029 7325;ENST00000412371;ENST000 00412142;ENST00000395572;ENS T00000453192;ENST00000438771 | TSF |
| 8% | chr7 | 48039730 | 48039725 | − | chr7 | 48035743 | 48035628 | − | ENST00000453071;ENST0000029 7325;ENST00000412371;ENST000 00412142;ENST00000395572;ENS T00000453192;ENST00000438771 | TSF |
| 8% | chr7 | 48039730 | 48039725 | − | chr7 | 48035743 | 48035628 | − | ENST00000453071;ENST0000029 7325;ENST00000412371;ENST000 00412142;ENST00000395572;ENS T00000453192;ENST00000438771 | TSF |
| 7% | chr11 | 60934781 | 60933962 | − | chr11 | 60901679 | 60901508 | − | ENST00000301765;ENST0000053 8036 | TSF |
| 7% | chr11 | 60934781 | 60933962 | − | chr11 | 60901679 | 60901508 | − | ENST00000301765;ENST0000053 8036 | TSF |
| 7% | chr12 | 58189709 | 58189746 | + | chr12 | 58189960 | 58190366; 58189980; 58190044 | + | ENST00000454289;ENST0000054 0550;ENST00000323833;ENST000 00350762;ENST00000457189 | TSF |
| 7% | chr12 | 58189709 | 58189746 | + | chr12 | 58189960 | 58190366; 58189980; 58190044 | + | ENST00000454289;ENST0000054 0550;ENST00000323833;ENST000 00350762;ENST00000457189 | TSF |
| 7% | chr12 | 58189709 | 58189746 | + | chr12 | 58189960 | 58190366; 58189980; 58190044 | + | ENST00000454289;ENST0000054 0550;ENST00000323833;ENST000 00350762;ENST00000457189 | TSF |
| 6% | chr3 | 130586141 | 130586877 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644;ENST00000422190 | TSF |
| 6% | chr3 | 130586141 | 130586877 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644;ENST00000422190 | TSF |
| 6% | chr3 | 130586141 | 130586877 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644;ENST00000422190 | TSF |
| 6% | chr3 | 130586141 | 130586877 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644;ENST00000422190 | TSF |
| 6% | chr3 | 130586141 | 130586877 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644;ENST00000422190 | TSF |
| 6% | chr3 | 130586141 | 130586877 | + | chr3 | 130649260 | 130649370 | + | ENST00000393221;ENST0000053 3801;ENST00000510168;ENST000 00508532;ENST00000505072;ENS T00000509662;ENST00000328560; | TSF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 6% | chr3 | 130586141 | 130586877 | + | chr3 | 130649260 | 130649370 | + | ENST00000428331;ENST00000359644;ENST00000422190 ENST00000393221;ENST00000533801;ENST00000510168;ENST00000508532;ENST00000505072;ENST00000509662;ENST00000328560; ENST00000428331;ENST00000359644;ENST00000422190 | TSF |
| 6% | chr12 | 122430912 | 122432282 | + | chr12 | 122437622 | 122437850 | + | ENST00000288912 | TSF |
| 6% | chr3 | 197640178 | 197640160 | – | chr3 | 197639620 | 197639546 | – | ENST00000265239;ENST00000455191 | TSF |
| 6% | chr5 | 52897435; 52897700 | 52897704 | + | chr5 | 52899282 | 52899360 | + | ENST00000502423;ENST00000296684;ENST00000506974;ENST00000506765 | TSF |
| 6% | chr5 | 52897435; 52897700 | 52897704 | + | chr5 | 52899282 | 52899360 | + | ENST00000502423;ENST00000296684;ENST00000506974;ENST00000506765 | TSF |
| 6% | chr5 | 52897435; 52897700 | 52897704 | + | chr5 | 52899282 | 52899360 | + | ENST00000502423; ENST00000296684;ENST00000506974;ENST00000506765 | TSF |
| 6% | chr5 | 52897435; 52897700 | 52897704 | + | chr5 | 52899282 | 52899360 | + | ENST00000502423;ENST00000296684;ENST00000506974;ENST00000506765 | TSF |
| 6% | chr5 | 52897435; 52897700 | 52897704 | + | chr5 | 52899282 | 52899360 | + | ENST00000502423;ENST00000296684;ENST00000506974;ENST00000506765 | TSF |
| 6% | chr5 | 52897435; 52897700 | 52897704 | + | chr5 | 52899282 | 52899360 | + | ENST00000502423;ENST00000296684;ENST00000506974;ENST00000506765 | TSF |
| 6% | chr5 | 52897435; 52897700 | 52897704 | + | chr5 | 52899282 | 52899360 | + | ENST00000502423;ENST00000296684;ENST00000506974;ENST00000506765 | TSF |
| 6% | chr5 | 52897435; 52897700 | 52897704 | + | chr5 | 52899282 | 52899360 | + | ENST00000502423;ENST00000296684;ENST00000506974;ENST00000506765 | TSF |
| 5% | chr12 | 96340433 | 96341255 | + | chr12 | 96346495 | 96346601 | + | ENST00000266736;ENST00000548310 | TSF |
| 5% | chr12 | 96340433 | 96341255 | + | chr12 | 96346495 | 96346601 | + | ENST00000266736;ENST00000548310 | TSF |
| 5% | chr1 | 1562829 | 1562973 | + | chr1 | 1563053 | 1563209 | + | ENST00000520777;ENST00000357210;ENST00000360522;ENST00000378710;ENST00000355826;ENST00000518681;ENST00000505820;ENST00000487053;ENST00000378712;ENST00000504599;ENST00000378708;ENST00000514234 | TSF |
| 5% | chr1 | 1562829 | 1562973 | + | chr1 | 1563053 | 1563209 | + | ENST00000520777;ENST00000357210;ENST00000360522;ENST00000378710;ENST00000355826;ENST00000518681;ENST00000505820;ENST00000487053;ENST00000378712;ENST00000504599;ENST00000378708;ENST00000514234 | TSF |
| 5% | chr1 | 1562829 | 1562973 | + | chr1 | 1563053 | 1563209 | + | ENST00000520777;ENST00000357210;ENST00000360522;ENST00000378710;ENST00000355826;ENST00000518681;ENST00000505820;ENST00000487053;ENST00000378712;ENST00000504599;ENST00000378708;ENST00000514234 | TSF |
| 5% | chr1 | 1562829 | 1562926 | + | chr1 | 1563053 | 1563209 | + | ENST00000520777;ENST00000357210;ENST00000360522;ENST00000378710;ENST00000355826;ENST00000518681;ENST00000505820;ENST00000487053;ENST00000378712;ENST00000504599;ENST00000378708;ENST00000514234 | TSF |
| 5% | chr1 | 1562829 | 1562926 | + | chr1 | 1563053 | 1563209 | + | ENST00000520777;ENST00000357210;ENST00000360522;ENST00000378710;ENST00000355826;ENST00000518681;ENST00000505820;ENST00000487053;ENST00000378712;ENST00000504599;ENST00000378708;ENST00000514234 | TSF |
| 5% | chr1 | 1562829 | 1562926 | + | chr1 | 1563053 | 1563209 | + | ENST00000520777;ENST0000035 | TSF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
|  |  |  |  |  |  |  |  |  | 7210;ENST00000360522;ENST000 00378710;ENST00000355826;ENS T00000518681;ENST00000505820; ENST00000487053;ENST0000037 8712;ENST00000504599;ENST000 00378708;ENST00000514234 |  |
| 5% | chr1 | 1562829 | 1562875 | + | chr1 | 1563053 | 1563209 | + | ENST00000520777;ENST0000035 7210;ENST00000360522;ENST000 00378710;ENST00000355826;ENS T00000518681;ENST00000505820; ENST00000487053;ENST0000037 8712;ENST00000504599;ENST000 00378708;ENST00000514234 | TSF |
| 5% | chr1 | 1562829 | 1562875 | + | chr1 | 1563053 | 1563209 | + | ENST00000520777;ENST0000035 7210;ENST00000360522;ENST000 00378710;ENST00000355826;ENS T00000518681;ENST00000505820; ENST00000487053;ENST0000037 8712;ENST00000504599;ENST000 00378708;ENST00000514234 | TSF |
| 5% | chr1 | 1562829 | 1562875 | + | chr1 | 1563053 | 1563209 | + | ENST00000520777;ENST0000035 7210;ENST00000360522;ENST000 00378710;ENST00000355826;ENS T00000518681;ENST00000505820; ENST00000487053;ENST0000037 8712;ENST00000504599;ENST000 00378708;ENST00000514234 | TSF |
| 5% | chr3 | 130586141 | 130586917 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644; ENST00000422190 | TSF |
| 5% | chr3 | 130586141 | 130586917 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644; ENST00000422190 | TSF |
| 5% | chr3 | 130586141 | 130586917 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644; ENST00000422190 | TSF |
| 5% | chr3 | 130586141 | 130586917 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644; ENST00000422190 | TSF |
| 5% | chr3 | 130586141 | 130586917 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644; ENST00000422190 | TSF |
| 5% | chr3 | 130586141 | 130586917 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644; ENST00000422190 | TSF |
| 5% | chr3 | 130586141 | 130586917 | + | chr3 | 130649260 | 130649370 | + | ENST00000393221;ENST0000053 3801;ENST00000510168;ENST000 00508532;ENST00000505072;ENS T00000509662;ENST00000328560; ENST00000428331;ENST0000035 9644; ENST00000422190 | TSF |
| 5% | chr2 | 38983894 | 38983086 | − | chr2 | 38977336 | 38977156 | − | ENST00000313117;ENST0000042 5778;ENST00000425941;ENST000 00446327;ENST00000409276;ENS T00000431066;ENST00000443213 | TSF |
| 5% | chr2 | 38983894 | 38983086 | − | chr2 | 38977336 | 38977156 | − | ENST00000313117;ENST0000042 5778;ENST00000425941;ENST000 | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr2 | 38983894 | 38983086 | − | chr2 | 38977336 | 38977156 | − | 00446327;ENST00000409276;ENST00000431066;ENST00000443213 ENST00000313117;ENST00000425778;ENST00000425941;ENST00000446327;ENST00000409276;ENST00000431066;ENST00000443213 | TSF |
| 5% | chr2 | 38983894 | 38983086 | − | chr2 | 38977336 | 38977156 | − | ENST00000313117;ENST00000425778;ENST00000425941;ENST00000446327;ENST00000409276;ENST00000431066;ENST00000443213 | TSF |
| 5% | chr2 | 38983894 | 38983086 | − | chr2 | 38977336 | 38977156 | − | ENST00000313117;ENST00000425778;ENST00000425941;ENST00000446327;ENST00000409276;ENST00000431066;ENST00000443213 | TSF |
| 5% | chr7 | 44158417 | 44158351 | − | chr7 | 44157663 | 44157542 | − | ENST00000406581;ENST000002233361;ENST00000452185;ENST00000433715;ENST00000456038;ENST00000418438 | TSF |
| 5% | chr7 | 44158417 | 44158351 | − | chr7 | 44157663 | 44157542 | − | ENST00000406581;ENST000002233361;ENST00000452185;ENST00000433715;ENST00000456038;ENST00000418438 | TSF |
| 5% | chr7 | 44158417 | 44158351 | − | chr7 | 44157663 | 44157542 | − | ENST00000406581;ENST000002233361;ENST00000452185;ENST00000433715;ENST00000456038;ENST00000418438 | TSF |
| 5% | chr7 | 44158417 | 44158351 | − | chr7 | 44157663 | 44157542 | − | ENST00000406581;ENST000002233361;ENST00000452185;ENST00000433715;ENST00000456038;ENST00000418438 | TSF |
| 5% | chr7 | 44158417 | 44158351 | − | chr7 | 44157663 | 44157542 | − | ENST00000406581;ENST000002233361;ENST00000452185;ENST00000433715;ENST00000456038;ENST00000418438 | TSF |
| 5% | chr10 | 99600727 | 99601473 | + | chr10 | 99619215 | 99619340 | + | ENST00000370602 | TSF |
| 5% | chr19 | 35979015 | 35978880 | − | chr19 | 35978661 | 35978614 | − | ENST00000484218;ENST000000338897 | TSF |
| 5% | chr8 | 91107662 | 91105645 | − | chr8 | 91094330 | 91094254 | − | ENST00000265431 | TSF |
| 5% | chr8 | 82194688 | 82194723 | 1 | chr8 | 82195601 | 82195773 | + | ENST00000297258 | TSF |
| 5% | chr14 | 20973494 | 20974255 | + | chr14 | 20978626 | 20979281 | + | ENST00000430083 | TSF |
| 5% | chr16 | 53866877 | 53867152 | + | chr16 | 53878067 | 53878210; 53878156 | + | ENST00000471389;ENST000000464071 | TSF |
| 5% | chr16 | 53866877 | 53867152 | + | chr16 | 53878067 | 53878210; 53878156 | + | ENST00000471389;ENST000000464071 | TSF |
| 5% | chr11 | 66354487 | 66355279 | + | chr11 | 66361113 | 66361185 | + | ENST00000533244;ENST000000530961 | TSF |
| 5% | chr11 | 66354487 | 66355279 | + | chr11 | 66361113 | 66361185 | + | ENST00000533244;ENST000000530961 | TSF |
| 5% | chrX | 138072952 | 138072670 | − | chrX | 137939841 | 137939674 | − | ENST00000370603;ENST000000436198;ENST00000455663;ENST00000448673 | TSF |
| 5% | chrX | 138072952 | 138072670 | − | chrX | 137939841 | 137939674 | − | ENST00000370603;ENST000000436198;ENST00000455663;ENST00000448673 | TSF |
| 5% | chrX | 138072952 | 138072670 | − | chrX | 137939841 | 137939674 | − | ENST00000370603;ENST000000436198;ENST00000455663;ENST00000448673 | TSF |
| 5% | chrX | 138072952 | 138072670 | − | chrX | 137939841 | 137939674 | − | ENST00000370603;ENST000000436198;ENST00000455663;ENST00000448673 | TSF |
| 5% | chr6 | 161637963 | 161637691 | − | chr6 | 161587449 | 161587280; 161587148 | − | ENST00000320285;ENST000003666908;ENST00000436279;ENST00000366905 | TSF |
| 5% | chr6 | 161637963 | 161637691 | − | chr6 | 161587449 | 161587280; 161587148 | − | ENST00000320285;ENST000003666908;ENST00000436279;ENST00000366905 | TSF |
| 5% | chr6 | 161637963 | 161637691 | − | chr6 | 161587449 | 161587280; 161587148 | − | ENST00000320285;ENST000003666908;ENST00000436279;ENST00000366905 | TSF |
| 4% | chr12 | 14506971 | 14507672 | + | chr12 | 14576843 | 14578407 | + | ENST00000544627 | TSF |
| 4% | chr12 | 122387836 | 122388242 | + | chr12 | 122394980 | 122395174 | + | ENST00000288912;ENST000000397454 | TSF |
| 4% | chr12 | 122387836 | 122388242 | + | chr12 | 122394980 | 122395174 | + | ENST00000288912;ENST000000397454 | TSF |
| 4% | chr3 | 48252382 | 48252880 | + | chr3 | 48265844 | 48265951 | + | ENST00000296435;ENST0000057 | TSF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | 6243 | |
| 4% | chr1 | 1422590 | 1422685 | + | chr1 | 1423243 | 1423294 | + | ENST00000308647 | TSF |
| 4% | chr12 | 122430912 | 122431578 | + | chr12 | 122439403 | 122439504 | + | ENST00000288912 | TSF |
| 4% | chr19 | 48627094 | 48627044 | − | chr19 | 48626575 | 48626431 | − | ENST00000263274;ENST0000053 6218;ENST00000594759;ENST000 00427526;ENST00000601091 | TSF |
| 4% | chr19 | 48627094 | 48627044 | − | chr19 | 48626575 | 48626431 | − | ENST00000263274;ENST0000053 6218;ENST00000594759;ENST000 00427526;ENST00000601091 | TSF |
| 4% | chr5 | 167685522 | 167685690 | + | chr5 | 167687288 | 167687418 | + | ENST00000518659;ENST0000054 5108;ENST00000519204;ENST000 00520394; ENST00000403607 | TSF |
| 4% | chr1 | 6366296 | 6365480 | − | chr1 | 6355040 | 6354924 | − | ENST00000608083;ENST0000037 7842;ENST00000377845;ENST000 00377855;ENST00000377860;ENS T00000418124;ENST00000545482; ENST00000361521;ENST0000047 3466 | TSF |
| 4% | chr1 | 6366296 | 6365480 | − | chr1 | 6355040 | 6354924 | − | ENST00000608083;ENST0000037 7842;ENST00000377845;ENST000 00377855;ENST00000377860;ENS T00000418124;ENST00000545482; ENST00000361521;ENST0000047 3466 | TSF |
| 4% | chr1 | 6366296 | 6365480 | − | chr1 | 6355040 | 6354924 | − | ENST00000608083;ENST0000037 7842;ENST00000377845;ENST000 00377855;ENST00000377860;ENS T00000418124;ENST00000545482; ENST00000361521;ENST0000047 3466 | TSF |
| 4% | chr1 | 6366296 | 6365480 | − | chr1 | 6355040 | 6354924 | − | ENST00000608083;ENST0000037 7842;ENST00000377845;ENST000 00377855;ENST00000377860;ENS T00000418124;ENST00000545482; ENST00000361521;ENST0000047 3466 | TSF |
| 4% | chr1 | 27143965 | 27144423 | + | chr1 | 27158938 | 27159098 | + | ENST00000374142 | TSF |
| 4% | chr12 | 122430912 | 122431655 | + | chr12 | 122439403 | 122439504 | + | ENST00000288912 | TSF |
| 4% | chr10 | 105819324 | 105819196 | − | chr10 | 105817948 | 105817904 | − | ENST00000353479;ENST0000036 9733 | TSF |
| 4% | chr10 | 105819324 | 105819196 | − | chr10 | 105817948 | 105817904 | − | ENST00000353479;ENST0000036 9733 | TSF |
| 3% | chr17 | 45698288 | 45698367 | + | chr17 | 45699134 | 45699286 | + | ENST00000530173;ENST0000032 2157;ENST00000544660;ENST000 00528565 | TSF |
| 3% | chr14 | 51360331 | 51362440 | + | chr14 | 51368547 | 51368629 | + | ENST00000337334;ENST0000035 3130;ENST00000395752 | TSF |
| 3% | chr22 | 36652278 | 36652346 | + | chr22 | 36653129 | 36653182 | + | ENST00000397278;ENST0000042 2706;ENST00000319136;ENST000 00422471;ENST00000438034;ENS T00000427990;ENST00000397279; ENST00000433768;ENST0000044 0669;ENST00000431184 | TSF |
| 3% | chr22 | 36652278 | 36652346 | + | chr22 | 36653129 | 36653182 | + | ENST00000397278;ENST0000042 2706;ENST00000319136;ENST000 00422471;ENST00000438034;ENS T00000427990;ENST00000397279; ENST00000433768;ENST0000044 0669;ENST00000431184 | TSF |
| 3% | chr22 | 36652278 | 36652346 | + | chr22 | 36653129 | 36653182 | + | ENST00000397278;ENST0000042 2706;ENST00000319136;ENST000 00422471;ENST00000438034;ENS T00000427990;ENST00000397279; ENST00000433768;ENST0000044 0669;ENST00000431184 | TSF |
| 3% | chr22 | 36652278 | 36652346 | + | chr22 | 36653129 | 36653182 | + | ENST00000397278;ENST0000042 2706;ENST00000319136;ENST000 00422471;ENST00000438034;ENS T00000427990;ENST00000397279; ENST00000433768;ENST0000044 0669;ENST00000431184 | TSF |
| 3% | chr22 | 36652278 | 36652346 | + | chr22 | 36653129 | 36653182 | + | ENST00000397278;ENST0000042 2706;ENST00000319136;ENST000 00422471;ENST00000438034;ENS T00000427990;ENST00000397279; | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr22 | 36652278 | 36652346 | + | chr22 | 36653129 | 36653182 | + | ENST00000433768;ENST0000044 0669;ENST00000431184 ENST00000397278;ENST0000042 2706;ENST00000319136;ENST000 00422471;ENST00000438034;ENS T00000427990;ENST00000397279; ENST00000433768;ENST0000044 0669;ENST00000431184 | TSF |
| 3% | chr7 | 56018506 | 56018522 | + | chr7 | 56022602 | 56022871; 56022865 | + | ENST00000426595;ENST0000028 5298;ENST00000443449 | TSF |
| 3% | chr7 | 56018506 | 56018522 | + | chr7 | 56022602 | 56022871; 56022865 | + | ENST00000426595;ENST0000028 5298;ENST00000443449 | TSF |
| 3% | chr15 | 74004214 | 74004264 | + | chr15 | 74005275 | 74005297 | + | ENST00000318443;ENST0000053 7340;ENST00000318424;ENST000 00564751;ENST00000561176;ENS T00000559073 | TSF |
| 3% | chr1 | 44446234 | 44446286 | + | chr1 | 44446781 | 44447145 | + | ENST00000309519 | TSF |
| 3% | chr1 | 41465686 | 41465756 | + | chr1 | 41466701 | 41466789 | + | ENST00000372621;ENST0000054 1520;ENST00000372616 | TSF |
| 3% | chr15 | 73976790 | 73976801 | + | chr15 | 73994596 | 73994914; 73994934; 73994926; 73994838; 73994671 | + | ENST00000567189;ENST0000031 8443;ENST00000318424;ENST000 00558689;ENST00000560786;ENS T00000561213;ENST00000563584; ENST00000561416;ENST0000056 0995;ENST00000561260;ENST000 00564751 | TSF |
| 3% | chr15 | 73976790 | 73976801 | + | chr15 | 73994596 | 73994914; 73994934; 73994926; 73994838; 73994671 | + | ENST00000567189;ENST0000031 8443;ENST00000318424;ENST000 00558689;ENST00000560786;ENS T00000561213;ENST00000563584; ENST00000561416;ENST0000056 0995;ENST00000561260;ENST000 00564751 | TSF |
| 3% | chr15 | 73976790 | 73976801 | + | chr15 | 73994596 | 73994914; 73994934; 73994926; 73994838; 73994671 | + | ENST00000567189;ENST0000031 8443;ENST00000318424;ENST000 00558689;ENST00000560786;ENS T00000561213;ENST00000563584; ENST00000561416;ENST0000056 0995;ENST00000561260;ENST000 00564751 | TSF |
| 3% | chr15 | 73976790 | 73976801 | + | chr15 | 73994596 | 73994914; 73994934; 73994926; 73994838; 73994671 | + | ENST00000567189;ENST0000031 8443;ENST00000318424;ENST000 00558689;ENST00000560786;ENS T00000561213;ENST00000563584; ENST00000561416;ENST0000056 0995;ENST00000561260;ENST000 00564751 | TSF |
| 3% | chr15 | 73976790 | 73976801 | + | chr15 | 73994596 | 73994914; 73994934; 73994926; 73994838; 73994671 | + | ENST00000567189;ENST0000031 8443;ENST00000318424;ENST000 00558689;ENST00000560786;ENS T00000561213;ENST00000563584; ENST00000561416;ENST0000056 0995;ENST00000561260;ENST000 00564751 | TSF |
| 3% | chr15 | 73976790 | 73976801 | + | chr15 | 73994596 | 73994914; 73994934; 73994926; 73994838; 73994671 | + | ENST00000567189;ENST0000031 8443;ENST00000318424;ENST000 00558689;ENST00000560786;ENS T00000561213; ENST00000563584; ENST00000561416;ENST0000056 0995;ENST00000561260;ENST000 00564751 | TSF |
| 3% | chr15 | 73976790 | 73976801 | + | chr15 | 73994596 | 73994914; 73994934; 73994926; 73994838; 73994671 | + | ENST00000567189;ENST0000031 8443;ENST00000318424;ENST000 00558689;ENST00000560786;ENS T00000561213; ENST00000563584; ENST00000561416;ENST0000056 0995;ENST00000561260;ENST000 00564751 | TSF |
| 3% | chr15 | 73976790 | 73976801 | + | chr15 | 73994596 | 73994914; 73994934; 73994926; 73994838; 73994671 | + | ENST00000567189;ENST0000031 8443;ENST00000318424;ENST000 00558689;ENST00000560786;ENS T00000561213; ENST00000563584; ENST00000561416;ENST0000056 0995;ENST00000561260;ENST000 00564751 | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr15 | 73976790 | 73976801 | + | chr15 | 73994596 | 73994914; 73994934; 73994926; 73994838; 73994671 | + | ENST00000567189;ENST0000031 8443;ENST00000318424;ENST000 00558689;ENST00000560786;ENS T00000561213; ENST00000563584; ENST00000561416;ENST0000056 0995;ENST00000561260;ENST000 00564751 | TSF |
| 3% | chr22 | 29117574 | 29117506 | − | chr22 | 29115473 | 29115383; 29115458 | − | ENST00000348295;ENST0000038 2566;ENST00000382578;ENST000 00404276;ENST00000328354;ENS T00000405598;ENST00000382580; ENST00000433728;ENST0000044 8511;ENST00000402731;ENST000 00403642;ENST00000439200 | TSF |
| 3% | chr22 | 29117574 | 29117506 | − | chr22 | 29115473 | 29115383; 29115458 | − | ENST00000348295;ENST0000038 2566;ENST00000382578;ENST000 00404276;ENST00000328354;ENS T00000405598;ENST00000382580; ENST00000433728;ENST0000044 8511;ENST00000402731;ENST000 00403642;ENST00000439200 | TSF |
| 3% | chr22 | 29117574 | 29117506 | − | chr22 | 29115473 | 29115383; 29115458 | − | ENST00000348295;ENST0000038 2566;ENST00000382578;ENST000 00404276;ENST00000328354;ENS T00000405598;ENST00000382580; ENST00000433728;ENST0000044 8511;ENST00000402731;ENST000 00403642;ENST00000439200 | TSF |
| 3% | chr22 | 29117574 | 29117506 | − | chr22 | 29115473 | 29115383; 29115458 | − | ENST00000348295;ENST0000038 2566;ENST00000382578;ENST000 00404276;ENST00000328354;ENS T00000405598;ENST00000382580; ENST00000433728;ENST0000044 8511;ENST00000402731;ENST000 00403642;ENST00000439200 | TSF |
| 3% | chr22 | 29117574 | 29117506 | − | chr22 | 29115473 | 29115383; 29115458 | − | ENST00000348295;ENST0000038 2566;ENST00000382578;ENST000 00404276;ENST00000328354;ENS T00000405598;ENST00000382580; ENST00000433728;ENST0000044 8511;ENST00000402731;ENST000 00403642;ENST00000439200 | TSF |
| 3% | chr15 | 83667946 | 83667078 | − | chr15 | 83657580 | 83657392 | − | ENST00000514272 | TSF |
| 3% | chr1 | 156716197 | 156716133 | − | chr1 | 156715165 | 156715089 | − | ENST00000357325;ENST0000053 7739;ENST00000368209;ENST000 00368206 | TSF |
| 3% | chr12 | 6602868 | 6602754 | − | chr12 | 6602138 | 6602028 | − | ENST00000229238 | TSF |
| 3% | chr17 | 39737300 | 39737191 | − | chr17 | 39726472 | 39726390 | − | ENST00000246662 | TSF |
| 3% | chr11 | 66354487 | 66355279 | + | chr11 | 66366587 | 66366724 | + | ENST00000533244;ENST0000053 0961;ENST00000310190 | TSF |
| 3% | chr11 | 66354487 | 66355279 | + | chr11 | 66366587 | 66366724 | + | ENST00000533244;ENST0000053 0961;ENST00000310190 | TSF |
| 3% | chr20 | 10400592 | 10400319 | − | chr20 | 10389451 | 10389276 | − | ENST00000347364; ENST0000039 9054 | TSF |
| 3% | chr22 | 38182207 | 38182899 | + | chr22 | 38206034 | 38206164 | + | ENST00000323205;ENST0000024 8924;ENST00000445195;ENST000 00451984 | TSF |
| 3% | chr22 | 38182207 | 38182899 | + | chr22 | 38206034 | 38206164 | + | ENST00000323205;ENST0000024 8924;ENST00000445195;ENST000 00451984 | TSF |
| 3% | chr22 | 38182207 | 38182899 | + | chr22 | 38206034 | 38206164 | + | ENST00000323205; ENST0000024 8924;ENST00000445195;ENST000 00451984 | TSF |
| 3% | chr17 | 17816540 | 17815655 | − | chr17 | 17810845 | 17810761 | − | ENST00000581396;ENST0000037 9504;ENST00000318094;ENST000 00395739;ENST00000535933;ENS T00000540946;ENST00000542206 | TSF |
| 3% | chr17 | 17816540 | 17815655 | − | chr17 | 17810845 | 17810761 | − | ENST00000581396;ENST0000037 9504;ENST00000318094;ENST000 00395739;ENST00000535933;ENS T00000540946;ENST00000542206 | TSF |
| 3% | chr17 | 17816540 | 17815655 | − | chr17 | 17810845 | 17810761 | − | ENST00000581396;ENST0000037 9504;ENST00000318094;ENST000 00395739;ENST00000535933;ENS T00000540946;ENST00000542206 | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr17 | 17816540 | 17815655 | – | chr17 | 17810845 | 17810761 | – | ENST00000581396;ENST00000379504;ENST00000318094;ENST00000395739;ENST00000535933;ENST00000540946;ENST00000542206 | TSF |
| 3% | chr17 | 17816540 | 17815655 | – | chr17 | 17810845 | 17810761 | – | ENST00000581396;ENST00000379504;ENST00000318094;ENST00000395739;ENST00000535933;ENST00000540946;ENST00000542206 | TSF |
| 3% | chr17 | 17816540 | 17815655 | – | chr17 | 17810845 | 17810761 | – | ENST00000581396;ENST00000379504;ENST00000318094;ENST00000395739;ENST00000535933;ENST00000540946;ENST00000542206 | TSF |
| 3% | chr14 | 20974370 | 20974386 | + | chr14 | 20978626 | 20979281 | + | ENST00000430083 | TSF |
| 3% | chr17 | 15873243 | 15873282 | + | chr17 | 15877993 | 15878656 | + | ENST00000304222 | TSF |
| 3% | chr20 | 8624404 | 8625224 | + | chr20 | 8626749 | 8626828 | + | ENST00000378641;ENST00000338037;ENST00000378637;ENST00000404098 | TSF |
| 3% | chr20 | 8624404 | 8625224 | + | chr20 | 8626749 | 8626828 | + | ENST00000378641;ENST00000338037;ENST00000378637;ENST00000404098 | TSF |
| 3% | chr20 | 8624404 | 8625224 | + | chr20 | 8626749 | 8626828 | + | ENST00000378641;ENST00000338037;ENST00000378637;ENST00000404098 | TSF |
| 3% | chr1 | 15562769 | 15563257 | + | chr1 | 15578267 | 15578373 | + | ENST00000433640 | TSF |
| 3% | chr15 | 83667946 | 83667078 | – | chr15 | 83660798 | 83660684 | – | ENST00000451195 | TSF |
| 3% | chr17 | 38639751 | 38639593 | – | chr17 | 38638668 | 38638576 | – | ENST00000254051 | TSF |
| 3% | chr1 | 6366296 | 6365322 | – | chr1 | 6355040 | 6354924 | – | ENST00000608083;ENST00000377842;ENST00000377845;ENST00000377855;ENST00000377860;ENST00000418124; ENST00000545482;ENST00000361521;ENST00000473466 | TSF |
| 3% | chr1 | 6366296 | 6365322 | – | chr1 | 6355040 | 6354924 | – | ENST00000608083;ENST00000377842;ENST00000377845;ENST00000377855;ENST00000377860;ENST00000418124;ENST00000545482;ENST00000361521;ENST00000473466 | TSF |
| 3% | chr1 | 6366296 | 6365322 | – | chr1 | 6355040 | 6354924 | – | ENST00000608083;ENST00000377842;ENST00000377845;ENST00000377855;ENST00000377860;ENST00000418124;ENST00000545482;ENST00000361521;ENST00000473466 | TSF |
| 3% | chr1 | 6366296 | 6365322 | – | chr1 | 6355040 | 6354924 | – | ENST00000608083;ENST00000377842;ENST00000377845;ENST00000377855;ENST00000377860;ENST00000418124;ENST00000545482;ENST00000361521;ENST00000473466 | TSF |
| 3% | chrX | 134954053 | 134953756 | – | chrX | 134950187 | 134950078 | – | ENST00000420087;ENST00000463085;ENST00000370724;ENST00000491480 | TSF |
| 3% | chrX | 134954053 | 134953756 | – | chrX | 134950187 | 134950078 | – | ENST00000420087;ENST00000463085;ENST00000370724;ENST00000491480 | TSF |
| 2% | chr10 | 101420120 | 101420239 | + | chr10 | 101421203 | 101421385 | + | ENST00000370489 | TSF |
| 2% | chr14 | 20973494 | 20974295 | + | chr14 | 20978626 | 20979281 | + | ENST00000430083 | TSF |
| 2% | chr3 | 48252382 | 48252840 | + | chr3 | 48265844 | 48265951 | + | ENST00000296435;ENST00000576243 | TSF |
| 2% | chr4 | 15791827 | 15792504 | 1 | chr4 | 15818134 | 15818263 | + | ENST00000502843;ENST00000226279 | TSF |
| 2% | chr4 | 15791827 | 15792504 | + | chr4 | 15818134 | 15818263 | + | ENST00000502843;ENST00000226279 | TSF |
| 2% | chr17 | 39974832 | 39974893 | + | chr17 | 39975462 | 39975651 | + | ENST00000321562 | TSF |
| 2% | chr11 | 66953459 | 66954052 | + | chr11 | 66974981 | 66975159 | + | ENST00000398645;ENST00000529006 | TSF |
| 2% | chr11 | 66953459 | 66954052 | + | chr11 | 66974981 | 66975159 | + | ENST00000398645;ENST00000529006 | TSF |
| 2% | chr19 | 1114930 | 1114676 | – | chr19 | 1114421 | 1114230 | – | ENST00000361757;ENST00000587024;ENST00000438103 | TSF |
| 2% | chr2 | 163165782 | 163165417 | – | chr2 | 163163365 | 163163219 | – | ENST00000263642 | TSF |
| 2% | chr8 | 134314977 | 134314886 | – | chr8 | 134296572 | 134296492 | – | ENST00000520230;ENST00000520943;ENST00000522738 | TSF |
| 2% | chr8 | 134314977 | 134314886 | – | chr8 | 134296572 | 134296492 | – | ENST00000520230;ENST00000520943;ENST00000522738 | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr8 | 134314977 | 134314886 | − | chr8 | 134296572 | 134296492 | − | ENST00000520230;ENST00000520943;ENST00000522738 | TSF |
| 2% | chrX | 134971303 | 134971006 | − | chrX | 134950187 | 134950078 | − | ENST00000420087;ENST00000463085;ENST00000370724;ENST00000491480 | TSF |
| 2% | chrX | 134971303 | 134971006 | − | chrX | 134950187 | 134950078 | − | ENST00000420087;ENST00000463085;ENST00000370724;ENST00000491480 | TSF |
| 2% | chrX | 134971303 | 134971006 | − | chrX | 134967437 | 134967328 | − | ENST00000491002; ENST00000448053;ENST00000472834 | TSF |
| 2% | chr6 | 117763870 | 117763597 | − | chr6 | 117739669 | 117739625 | − | ENST00000368507;ENST00000368508 | TSF |
| 2% | chr6 | 117763870 | 117763597 | − | chr6 | 117739669 | 117739625 | − | ENST00000368507;ENST00000368508 | TSF |
| 2% | chr19 | 45184732 | 45184798 | + | chr19 | 45185839 | 45185892 | + | ENST00000358777;ENST00000403660 | TSF |
| 2% | chr19 | 45184732 | 45184798 | + | chr19 | 45185839 | 45185892 | + | ENST00000358777;ENST00000403660 | TSF |
| 2% | chr7 | 55477082 | 55477474 | + | chr7 | 55479600 | 55479782 | + | ENST00000254770 | TSF |
| 2% | chrX | 134866155 | 134866452 | + | chrX | 134870023 | 134870132 | + | ENST00000370736;ENST00000471213;ENST00000495729 | TSF |
| 2% | chr7 | 134212336 | 134212386 | + | chr7 | 134215479 | 134215562 | + | ENST00000359579 | TSF |
| 2% | chr17 | 7479605 | 7479718 | + | chr17 | 7479842 | 7480008; 7480010; 7479924 | + | ENST00000582169;ENST00000293831;ENST00000585024;ENST00000583802;ENST00000581544;ENST00000577269;ENST00000584784;ENST00000582746;ENST00000584860;ENST00000581384 | TSF |
| 2% | chr17 | 7479605 | 7479718 | + | chr17 | 7479842 | 7480008; 7480010; 7479924 | + | ENST00000582169;ENST00000293831;ENST00000585024;ENST00000583802;ENST00000581544;ENST00000577269;ENST00000584784;ENST00000582746;ENST00000584860;ENST00000581384 | TSF |
| 2% | chr17 | 7479605 | 7479718 | + | chr17 | 7479842 | 7480008; 7480010; 7479924 | + | ENST00000582169;ENST00000293831;ENST00000585024;ENST00000583802;ENST00000581544;ENST00000577269;ENST00000584784;ENST00000582746;ENST00000584860;ENST00000581384 | TSF |
| 2% | chr17 | 7479605 | 7479718 | + | chr17 | 7479842 | 7480008; 7480010; 7479924 | + | ENST00000582169;ENST00000293831;ENST00000585024;ENST00000583802;ENST00000581544;ENST00000577269;ENST00000584784;ENST00000582746;ENST00000584860;ENST00000581384 | TSF |
| 2% | chr17 | 7479605 | 7479718 | + | chr17 | 7479842 | 7480008; 7480010; 7479924 | + | ENST00000582169;ENST00000293831;ENST00000585024;ENST00000583802;ENST00000581544;ENST00000577269;ENST00000584784;ENST00000582746;ENST00000584860;ENST00000581384 | TSF |
| 2% | chr17 | 7479605 | 7479718 | + | chr17 | 7479842 | 7480008; 7480010; 7479924 | + | ENST00000582169;ENST00000293831;ENST00000585024;ENST00000583802;ENST00000581544;ENST00000577269;ENST00000584784;ENST00000582746;ENST00000584860;ENST00000581384 | TSF |
| 2% | chr17 | 7479605 | 7479718 | + | chr17 | 7479842 | 7480008; 7480010; 7479924 | + | ENST00000582169;ENST00000293831;ENST00000585024;ENST00000583802;ENST00000581544;ENST00000577269;ENST00000584784;ENST00000582746;ENST00000584860;ENST00000581384 | TSF |
| 2% | chr17 | 7479605 | 7479718 | + | chr17 | 7479842 | 7480008; 7480010; 7479924 | + | ENST00000582169;ENST00000293831;ENST00000585024;ENST00000583802;ENST00000581544;ENST00000577269;ENST00000584784;ENST00000582746;ENST00000584860;ENST00000581384 | TSF |
| 2% | chr17 | 7479605 | 7479718 | + | chr17 | 7479842 | 7480008; 7480010; 7479924 | + | ENST00000582169;ENST00000293831;ENST00000585024;ENST00000583802;ENST00000581544;ENST00000577269;ENST00000584784;ENST00000582746;ENST0000058 | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr17 | 7479605 | 7479718 | + | chr17 | 7479842 | 7480008; 7480010; 7479924 | + | 4860;ENST00000581384 ENST00000582169;ENST00000293831;ENST00000585024;ENST00000583802;ENST00000581544;ENST00000577269;ENST00000584784; ENST00000582746;ENST00000584860;ENST00000581384 | TSF |
| 2% | chr7 | 74480763 | 74480881 | + | chr7 | 74528191 | 74528329 | + | ENST00000356115;ENST00000430511;ENST00000312575;ENST00000423666 | TSF |
| 2% | chr7 | 74480763 | 74480881 | + | chr7 | 74528191 | 74528329 | + | ENST00000356115;ENST00000430511;ENST00000312575;ENST00000423666 | TSF |
| 2% | chr7 | 74480763 | 74480881 | + | chr7 | 74528191 | 74528329 | + | ENST00000356115;ENST00000430511;ENST00000312575;ENST00000423666 | TSF |
| 2% | chrX | 134883429 | 134883726 | + | chrX | 134887292 | 134887401 | + | ENST00000370734;ENST00000485366;ENST00000443882 | TSF |
| 2% | chr7 | 22512874 | 22512791 | − | chr7 | 22459455 | 22459423 | − | ENST00000406890 | TSF |
| 2% | chrX | 134954053 | 134953756 | − | chrX | 134932924 | 134932815 | − | ENST00000487941;ENST000004 4966;ENST00000494421 | TSF |
| 2% | chr11 | 93468219 | 93468129 | − | chr11 | 93466563 | 93466528 | − | ENST00000393259 | TSF |
| 2% | chr7 | 100850556 | 100850506 | − | chr7 | 100850185 | 100850060 | − | ENST00000454310;ENST00000223127 | TSF |
| 2% | chrX | 134936794 | 134936497 | − | chrX | 134932924 | 134932815 | − | ENST00000487941;ENST000004 4966;ENST00000494421 | TSF |
| 2% | chr2 | 143794737 | 143794842 | + | chr2 | 143797997 | 143798227 | + | ENST00000264170;ENST000004 09512 | TSF |
| 2% | chr20 | 60878087 | 60878105 | + | chr20 | 60878775 | 60878837 | + | ENST00000253003 | TSF |
| 2% | chr2 | 28630786 | 28630878 | + | chr2 | 28631626 | 28631733 | + | ENST00000379619;ENST00000264716,ENST00000436647;.ENST00000545753 | TSF |
| 2% | chr2 | 28630786 | 28630878 | + | chr2 | 28631626 | 28631733 | + | ENST00000379619;ENST00000264716,ENST00000436647;.ENST00000545753 | TSF |
| 2% | chr2 | 28630786 | 28630878 | + | chr2 | 28631626 | 28631733 | + | ENST00000379619;ENST00000264716,ENST00000436647;.ENST00000545753 | TSF |
| 2% | chr22 | 24967426 | 24967475 | + | chr22 | 24967884 | 24967945 | + | ENST00000215829;ENST00000404603 | TSF |
| 2% | chr7 | 56020443 | 56020541 | + | chr7 | 56020872 | 56021011 | + | ENST00000426595 | TSF |
| 2% | chr9 | 131902050 | 131902148 | + | chr9 | 131904724 | 131904831; 131905179 | + | ENST00000358994;ENST00000393370;ENST00000337738;ENST00000348141;ENST00000452489;ENST00000357197;ENST00000347048; ENST00000355007;ENST00000417728;ENST00000411917;ENST00000423100;ENST00000524946;ENST000000436883;ENST000004 14510; ENST00000432124;ENST00000435305;ENST00000419582;ENST00000432651;ENST00000435132;ENST000000434095 | TSF |
| 2% | chr9 | 131902050 | 131902148 | + | chr9 | 131904724 | 131904831; 131905179 | + | ENST00000358994;ENST00000393370;ENST00000337738;ENST00000348141;ENST00000452489;ENST00000357197;ENST00000347048; ENST00000355007;ENST00000417728;ENST00000411917;ENST00000423100;ENST00000524946;ENST000000436883;ENST000004 14510; ENST00000432124;ENST00000435305;ENST00000419582;ENST00000432651;ENST00000435132;ENST000000434095 | TSF |
| 2% | chr9 | 131902050 | 131902148 | + | chr9 | 131904724 | 131904831; 131905179 | + | ENST00000358994;ENST00000393370;ENST00000337738;ENST00000348141;ENST00000452489;ENST00000357197;ENST00000347048; ENST00000355007;ENST00000417728;ENST00000411917;ENST00000423100;ENST00000524946;ENST000000436883;ENST000004 14510; ENST00000432124;ENST00000435305;ENST00000419582;ENST0000 | TSF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr9 | 131902050 | 131902148 | + | chr9 | 131904724 | 131904831; 131905179 | + | 00432651;ENST00000435132;ENST000000434095 ENST00000358994;ENST00000393370;ENST00000337738;ENST00000348141;ENST00000452489;ENST00000357197;ENST00000347048; ENST00000355007;ENST00000417728;ENST00000411917;ENST00000423100;ENST00000524946;ENST000000436883;ENST000004 14510; ENST00000432124;ENST00000435305;ENST00000419582;ENST00000432651;ENST00000435132;ENST000000434095 | TSF |
| 2% | chr9 | 131902050 | 131902148 | + | chr9 | 131904724 | 131904831; 131905179 | + | ENST00000358994;ENST00000393370;ENST00000337738;ENST00000348141;ENST00000452489;ENST00000357197;ENST00000347048; ENST00000355007;ENST00000417728;ENST00000411917;ENST00000423100;ENST00000524946;ENST000000436883;ENST000004 14510; ENST00000432124;ENST00000435305;ENST00000419582;ENST00000432651;ENST00000435132;ENST000000434095 | TSF |
| 2% | chr1 | 117473681 | 117473836 | + | chr1 | 117484337 | 117484705 | + | ENST00000393203 | TSF |
| 2% | chrX | 134866155 | 1134866452 | + | chrX | 134887292 | 134887401 | + | ENST00000370734;ENST000000485366,ENST00000443882 | TSF |
| 2% | chr8 | 128749913 | 128749923 | + | chr8 | 128750494 | 128751265 | + | ENST00000377970 | TSF |
| 2% | chr1 | 169819657 | 1169819707 | + | chr1 | 169820958 | 1169821077 | | ENST00000359326;ENST00000286031 | TSF |
| 2% | chr1 | 55517012 | 155517126 | + | chr1 | 55517951 | 55518084 | + | ENST00000302118 | TSF |
| 2% | chr12 | 10104813 | 10105636 | + | chr12 | 10124176 | 10124286 | + | ENST00000355690 | TSF |
| 2% | chrX | 134971303 | 134971006 | − | chrX | 134932924 | 134932815 | − | ENST00000487941;ENST000000434966;ENST00000494421 | TSF |
| 2% | chr20 | 634541 | 634468 | − | chr20 | 1629561 | 629358; 629500 | − | ENST00000381962;ENST000000488788 | TSF |
| 2% | chr20 | 634541 | 634468 | − | chr20 | 1629561 | 629358; 629500 | − | ENST00000381962;ENST000000488788 | TSF |
| 2% | chr8 | 63949410 | 63948932 | − | chr8 | 163948329 | 63948215 | − | ENST00000260118 TSF | |
| 2% | chr15 | 40186558 | 40186430 | − | chr15 | 140099459 | 140099207 | − | ENST00000561100;ENST000000543580 | TSF |
| 2% | chrX | 151410500 | 151410406 | − | chrX | 151393317 | 151393235 | − | ENST00000370314;ENST000000535043 | TSF |
| 2% | chr20 | 10628319 | 10628254 | − | chr20 | 10627751 | 10627587 | − | ENST00000254958;ENST000000423891 | TSF |
| 2% | chr12 | 96302230 | 196301326 | − | chr12 | 96300229 | 96300165 | − | ENST00000344280 | TSF |
| 2% | chr1 | 17371820 | 17371636 | − | chr1 | 17371383 | 17371256 | − | ENST00000375499 | TSF |
| 2% | chr12 | 110306235 | 110306193 | − | chr12 | 110296546 | 110296488 | − | ENST00000318348;ENST000000544393;ENST00000540772;ENST0000000536390;ENST0000053 7066 | TSF |
| 2% | chr12 | 110306235 | 110306193 | − | chr12 | 110296546 | 110296488 | − | ENST00000318348;ENST000000544393;ENST00000540772;ENST0000000536390;ENST0000053 7066 | TSF |
| 2% | chr12 | 110306235 | 110306193 | − | chr12 | 110296546 | 110296488 | − | ENST00000318348;ENST000000544393;ENST00000540772;ENST0000000536390;ENST00000537066 | TSF |
| 2% | chr12 | 110306235 | 110306193 | − | chr12 | 110296546 | 110296488 | − | ENST00000318348;ENST000000544393;ENST00000540772;ENST0000000536390;ENST0000053 7066 | TSF |
| 2% | chr15 | 40186285 | 40186077 | − | chr15 | 140099459 | 140099207 | − | ENST00000561100;ENST000000543580 | TSF |
| 2% | chr2 | 220120254 | 220120037 | − | chr2 | 220116952 | 220116730 | − | ENST00000248437;ENST000000456818;ENST00000425551 | TSF |
| 2% | chr2 | 220120254 | 220120037 | − | chr2 | 220116952 | 220116730 | − | ENST00000248437;ENST000000456818;ENST00000425551 | TSF |
| 2% | chr2 | 220120254 | 220120037 | − | chr2 | 220116952 | 220116730 | − | ENST00000248437;ENST000000456818;ENST00000425551 | TSF |
| 2% | chr22 | 28326858 | 28326682 | − | chr22 | 28310335 | 28310305 | − | ENST00000335272;ENST000000320996;ENST00000455418;ENST00000436663 | TSF |
| 2% | chr22 | 28326858 | 28326682 | − | chr22 | 28310335 | 28310305 | − | ENST00000335272;ENST000000320996;ENST00000455418;ENST00000436663 | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr22 | 28326858 | 28326682 | − | chr22 | 28310335 | 28310305 | | ENST00000335272;ENST00000320996;ENST00000455418;ENST00000436663 | TSF |
| 2% | chr7 | 99801794 | 199801819 | + | chr | 99802250 | 99802398 | + | ENST00000426455;ENST00000394018;ENST00000317296 | TSF |
| 2% | chr1 | 36637256 | 136637320 | + | chr1 | 36638065 | 36638228; 36638141 | + | ENST00000429533;ENST00000316156,ENST00000373150;ENST00000373151;ENST00000530729 | TSF |
| 2% | chr1 | 36637256 | 136637320 | + | chr1 | 36638065 | 36638228; 36638141 | + | ENST00000429533;ENST00000316156,ENST00000373150;ENST00000373151;ENST00000530729 | TSF |
| 2% | chr1 | 36637256 | 136637320 | + | chr1 | 36638065 | 36638228; 36638141 | + | ENST00000429533;ENST00000316156,ENST00000373150;ENST00000373151;ENST00000530729 | TSF |
| 2% | chr1 | 36637256 | 136637320 | + | chr1 | 36638065 | 36638228; 36638141 | + | ENST00000429533;ENST00000316156,ENST00000373150;ENST00000373151;ENST00000530729 | TSF |
| 2% | chr1 | 36637256 | 136637320 | + | chr1 | 36638065 | 36638228; 36638141 | + | ENST00000429533;ENST00000316156,ENST00000373150;ENST00000373151;ENST00000530729 | TSF |
| 2% | chr19 | 4412258 | 4412399 | + | chr19 | 4418017 | 4418073 | + | ENST00000301280 | TSF |
| 2% | chr9 | 137326382 | 1137326400 | + | chr9 | 137328313 | 137328460 | + | ENST00000481739;ENST00000540193 | TSF |
| 2% | chr9 | 134363954 | 134364268 | + | chr9 | 134366812 | 134366967 | + | ENST00000405995;ENST000003577304;ENST00000458550;ENST00000372249;ENST00000320547 | TSF |
| 2% | chr9 | 134363954 | 134364268 | + | chr9 | 134366812 | 134366967 | + | ENST00000405995;ENST000003577304;ENST00000458550;ENST00000372249;ENST00000320547 | TSF |
| 2% | chr1 | 168348640 | 168349020 | + | chr1 | 168549301 | 168549415 | + | ENST00000367818 | TSF |
| 2% | chr12 | 49659927 | 49660025 | + | chr12 | 49663248 | 49663470; 49663252 | + | ENST00000541364;ENST00000552125;ENST00000301072;ENST00000549183 | TSF |
| 2% | chr12 | 49659927 | 49660025 | + | chr12 | 49663248 | 49663470; 49663252 | + | ENST00000541364;ENST00000552125;ENST00000301072;ENST00000549183 | TSF |
| 2% | chr12 | 49659927 | 49660025 | + | chr12 | 49663248 | 49663470; 49663252 | + | ENST00000541364;ENST00000552125;ENST00000301072;ENST00000549183 | TSF |
| 2% | chr20 | 19966479 | 119966639 | + | chr20 | 119970650 | 119970955 | + | ENST00000255006;ENST00000440354 | TSF |
| 2% | chr1 | 31218846 | 31218765 | − | chr1 | 3121539%6 | 31215303 | − | ENST00000294507 | TSF |
| 2% | chr8 | 91102885 | 191102521 | − | chrs | 91094330 | 91094254 | − | ENST00000265431 | TSF |
| 2% | chr1 | 8924664 | 8924519 | − | chr1 | 8924151 | 8923950 | − | ENST00000234590 | TSF |
| 2% | chr116 | 74833301 | 74833256 | − | chr16 | 74774013 | 74773921 | − | ENST00000219368;ENST000000567683;ENST00000569949 | TSF |
| 2% | chr116 | 74833301 | 74833256 | − | chr16 | 74774013 | 74773921 | − | ENST00000219368;ENST000000567683;ENST00000569949 | TSF |
| 2% | chr116 | 74833301 | 74833256 | − | chr16 | 74774013 | 74773921 | − | ENST00000219368;ENST000000567683;ENST00000569949 | TSF |
| 2% | chr1 | 217698243 | 217697476 | − | chr1 | 217688231 | 217688164 | − | ENST00000366935 | TSF |
| 2% | chr8 | 91108096 | 191107732 | − | chr§ | 91094330 | 91094254 | − | ENST00000265431 | TSF |
| 2% | chr12 | 96302230 | 196301454 | − | chr12 | 96300229 | 96300165 | − | ENST00000344280 | TSF |
| 2% | chr3 | 99883880 | 199884005 | + | chr3 | 99885179 | 99885238 | + | ENST00000421999;ENST000000489081;ENST00000478909;ENST00000497345 | TSF |
| 2% | chr3 | 99883880 | 199884005 | + | chr3 | 99885179 | 99885238 | + | ENST00000421999;ENST000000489081;ENST00000478909;ENST00000497345 | TSF |
| 2% | chr3 | 99883880 | 199884005 | + | chr3 | 99885179 | 99885238 | + | ENST00000421999;ENST000000489081;ENST00000478909;ENST00000497345 | TSF |
| 2% | chr10 | 99600727 | 199601513 | + | chr10 | 199619215 | 99619340 | + | ENST00000370602 | TSF |
| 2% | chr3 | 136680342 | 136680413 | + | chr3 | 136699308 | 1136699434 | + | ENST00000329582 | TSF |
| 2% | chr22 | 43552142 | 43552306 | + | chr22 | 143557058 | 43557196 | + | ENST00000337554;ENST000000428336,ENST00000329563 | TSF |
| 2% | chr22 | 43552142 | 43552306 | + | chr22 | 143557058 | 43557196 | + | ENST00000337554;ENST000000428336,ENST00000329563 | TSF |
| 2% | chr5 | 167653877 | 167654073 | + | chrs | 167654900 | 1167655135 | + | ENST00000518659;ENST00000545108;ENST00000519204;ENST00000520394;ENST00000403607 | TSF |
| 2% | chr11 | 60694460 | 160694539 | + | chr11 | 160694676 | 60694890 | + | ENST00000453848;ENST000000005286 | TSF |
| 2% | chr11 | 60694460 | 160694539 | + | chr11 | 160694676 | 60694890 | + | ENST00000453848;ENST000000005286 | TSF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr19 | 45289567 | 45289633 | + | chr19 | 45293261 | 45293348 | + | ENST00000270279;ENST0000034 1505 | TSF |
| 2% | chr12 | 52908876 | 152908919 | + | chr12 | 52908758 | 52908726 | − | ENST00000252242 | TSF |
| 2% | chr10 | 5057417 | 5057095 | − | chr10 | 5043873 | 5043706 | − | ENST00000380753;ENST0000042 1196;ENST00000407674;ENST0000 00604507;ENST00000455190 | TSF |
| 2% | chr10 | 5057417 | 5057095 | − | chr10 | 5043873 | 5043706 | − | ENST00000380753;ENST0000042 1196;ENST00000407674;ENST0000 00604507;ENST00000455190 | TSF |
| 2% | chr10 | 5057417 | 5057095 | − | chr10 | 5043873 | 5043706 | − | ENST00000380753;ENST0000042 1196;ENST00000407674;ENST0000 00604507;ENST00000455190 | TSF |
| 2% | chr10 | 5057417 | 5057095 | − | chr10 | 5043873 | 5043706 | − | ENST00000380753;ENST0000042 1196;ENST00000407674;ENST0000 00604507;ENST00000455190 | TSF |
| 2% | chr12 | 14670381 | 14670239 | − | chr12 | 14664645 | 14664445 | − | ENST00000240617 | TSF |
| 2% | chr1 | 153431306 | 153431207 | − | chr1 | 153430446 | 153430282 | − | ENST00000368722;ENST0000036 8723 | TSF |
| 2% | chr15 | 101823470 | 101823443 | − | chr15 | 101821987 | 101821929; 101821950 | − | ENST00000254193;ENST0000056 0496 | TSF |
| 2% | chr15 | 101823470 | 101823443 | − | chr15 | 101821987 | 101821929; 101821950 | − | ENST00000254193;ENST0000056 0496 | TSF |
| 2% | chr15 | 40186285 | 40186255 | − | chr15 | 140099459 | 140099207 | − | ENST00000561100;ENST0000054 3580 | TSF |
| 2% | chr22 | 40898710 | 40898220 | − | chr22 | 40859290 | 40859225 | − | ENST00000422851 | TSF |
| 2% | chr15 | 40187476 | 40186657 | − | chr15 | 140099459 | 140099207 | − | ENST00000561100;ENST0000054 3580 | TSF |
| 2% | chr17 | 43537130 | 43536749 | − | chr17 | 43531638 | 43530721 | − | ENST00000430334;ENST0000042 1073 | TSF |
| 2% | chrX | 154534914 | 154534773 | − | chrX | 154528458 | 154528349 | − | ENST00000369449;ENST0000032 1926 | TSF |
| 2% | chrX | 154534914 | 154534773 | − | chrX | 154528458 | 154528349 | − | ENST00000369449;ENST0000032 1926 | TSF |
| 1% | chr3 | 183460031 | 183460733 | + | chr3 | 183465460 | 183465504 | + | ENST00000305135 | TSF |
| 1% | chr20 | 36393263 | 36393294 | + | chr20 | 36393599 | 36393692; 36393614 | + | ENST00000361383;ENST0000044 7935;ENST00000405275;ENST0000 00373473 | TSF |
| 1% | chr20 | 36393263 | 36393294 | + | chr20 | 36393599 | 36393692; 36393614 | + | ENST00000361383;ENST0000044 7935;ENST00000405275;ENST0000 00373473 | TSF |
| 1% | chr1 | 20940040 | 20940086 | + | chr1 | 20940335 | 20940392 | + | ENST00000375071 | TSF |
| 1% | chr19 | 35613389 | 35613502 | + | ch919 | 35613669 | 35613862; 35613743; 35613858 | + | ENST00000406242;ENST0000060 4404;ENST00000435734;ENST0000 00603181;ENST00000604255;ENS T00000344013;ENST00000346446; ENST00000406988;ENST0000060 5550;ENST00000604804;ENST0000 00535103;ENST00000603524;ENS T00000604621;ENST00000605677 | TSF |
| 1% | chr19 | 35613389 | 35613502 | + | chr19 | 35613669 | 35613862; 35613743; 35613858 | + | ENST00000406242;ENST0000060 4404;ENST00000435734;ENST0000 00603181;ENST00000604255;ENS T00000344013;ENST00000346446; ENST00000406988;ENST0000060 5550;ENST00000604804;ENST0000 00535103;ENST00000603524;ENS T00000604621;ENST00000605677 | TSF |
| 1% | chr19 | 35613389 | 35613502 | + | chr19 | 35613669 | 35613862; 35613743; 35613858 | + | ENST00000406242;ENST0000060 4404;ENST00000435734;ENST0000 00603181;ENST00000604255;ENS T00000344013;ENST00000346446; ENST00000406988;ENST0000060 5550;ENST00000604804;ENST0000 00535103;ENST00000603524;ENS T00000604621;ENST00000605677 | TSF |
| 1% | chr19 | 35613389 | 35613502 | + | chr19 | 35613669 | 35613862; 35613743; 35613858 | + | ENST00000406242;ENST0000060 4404;ENST00000435734;ENST0000 00603181;ENST00000604255;ENS T00000344013;ENST00000346446; ENST00000406988;ENST0000060 5550;ENST00000604804;ENST0000 00535103;ENST00000603524;ENS T00000604621;ENST00000605677 | TSF |
| 1% | chr21 | 42801857 | 42802535 | + | chr21 | 42811621 | 42811775 | + | ENST00000398600;ENST0000039 8598;ENST00000455164;ENST0000 | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr21 | 42801857 | 42802535 | + | chr21 | 42811621 | 42811775 | + | 00424365;ENST00000417963;ENST000000288383<br>ENST00000398600;ENST00000398598;ENST00000455164;ENST0000000424365;ENST00000417963;ENST000000288383 | TSF |
| 1% | chr21 | 42801857 | 42802535 | + | chr21 | 42811621 | 42811775 | + | ENST00000398600;ENST00000398598;ENST00000455164;ENST0000000424365;ENST00000417963;ENST00000288383 | TSF |
| 1% | chr3 | 100461913 | 100462018 | + | chr3 | 100463677 | 100463775 | + | ENST00000418917;ENST000000490574;ENST00000240851;ENST00000476228 | TSF |
| 1% | chr19 | 50174724 | 50174836 | + | chr19 | 50176955 | 50177005; 501770 | + | ENST00000441864;ENST00000024 346785;ENST00000600947;ENST00000598306 | TSF |
| 1% | chr19 | 50174724 | 50174836 | + | chr19 | 50176955 | 50177005; 501770 | + | ENST00000441864;ENST00000024 346785;ENST00000600947;ENST00000598306 | TSF |
| 1% | chr7 | 55464873 | 55464924 | + | chr7 | 55466116 | 55466323 | + | ENST00000254770 | TSF |
| 1% | chr2 | 143763612 | 143763709 | + | chr2 | 143787196 | 143787248 | + | ENST00000264170;ENST00000409512 | TSF |
| 1% | chr8 | 39759879 | 39759967 | + | chr8 | 39775394 | 39775489; 39775448 | + | ENST00000518804;ENST00000519154;ENST00000522495;ENST00000522840;ENST00000518237;ENST00000253513 | TSF |
| 1% | chr8 | 39759879 | 39759967 | + | chr8 | 39775394 | 39775489; 39775448 | + | ENST00000518804;ENST00000519154;ENST00000522495;ENST00000522840;ENST00000518237;ENST00000253513 | TSF |
| 1% | chr8 | 39759879 | 39759967 | + | chr8 | 39775394 | 39775489; 39775448 | + | ENST00000518804;ENST00000519154;ENST00000522495;ENST00000522840;ENST00000518237;ENST00000253513 | TSF |
| 1% | chr8 | 39759879 | 39759967 | + | chr8 | 39775394 | 39775489; 39775448 | + | ENST00000518804;ENST00000519154;ENST00000522495;ENST00000522840;ENST00000518237;ENST00000253513 | TSF |
| 1% | chr8 | 39759879 | 39759967 | + | chr8 | 39775394 | 39775489; 39775448 | + | ENST00000518804;ENST00000519154;ENST00000522495;ENST00000522840;ENST00000518237;ENST00000253513 | TSF |
| 1% | chr17 | 15872860 | 15873143 | + | chr17 | 15877993 | 15878656 | + | ENST00000304222 | TSF |
| 1% | chr9 | 139809866 | 139809928 | + | chr9 | 139810993 | 139811067 | + | ENST00000536468;ENST00000247668;ENST00000359662 | TSF |
| 1% | chr1 | 13922411 | 13922564 | + | chr1 | 13933668 | 13933801 | + | ENST00000294489;ENST00000376057,ENST00000510906;ENST00000509009 | TSF |
| 1% | chr1 | 13922411 | 13922564 | + | chr1 | 13933668 | 13933801 | + | ENST00000294489;ENST00000376057,ENST00000510906;ENST00000509009 | TSF |
| 1% | chr1 | 13922411 | 13922564 | + | chr1 | 13933668 | 13933801 | + | ENST00000294489;ENST00000376057,ENST00000510906;ENST00000509009 | TSF |
| 1% | chr19 | 46194689 | 146194670 | − | chr19 | 46191824 | 46191645 | − | ENST00000342669;ENST000005888301;ENST00000590212 | TSF |
| 1% | chr19 | 46194689 | 146194670 | − | chr19 | 46191824 | 46191645 | − | ENST00000342669;ENST000005888301;ENST00000590212 | TSF |
| 1% | chr12 | 49310439 | 149309695 | − | chr12 | 149297691 | 49297443 | − | ENST00000398092 | TSF |
| 1% | chr22 | 40897378 | 140896995 | − | chr22 | 140859290 | 40859225 | − | ENST00000422851 | TSF |
| 1% | chr2 | 17876171 | 17876059 | − | chr2 | 17865030 | 117864905 | − | ENST00000448223;ENST00000351948;ENST00000381272;ENST00000402989 | TSF |
| 1% | chr16 | 74834658 | 74834274 | − | chr16 | 174774013 | 74773921 | − | ENST00000219368;ENST00000567683;ENST00000569949 | TSF |
| 1% | chr16 | 74834658 | 74834274 | − | chr16 | 174774013 | 74773921 | − | ENST00000219368;ENST00000567683;ENST00000569949 | TSF |
| 1% | chr16 | 74834658 | 74834274 | − | chr16 | 174774013 | 74773921 | − | ENST00000219368;ENST00000567683;ENST00000569949 | TSF |
| 1% | chr22 | 22899971 | 22899965 | − | chr22 | 22893511 | 22893189; 22893185; 22893481; 22893274 | − | ENST00000398743;ENST00000398741;ENST00000543184;ENST00000405655;ENST00000402697;ENST00000439106;ENST00000438888;ENST00000420709;ENST00000406503;ENST00000442481;ENST000 | TSF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr22 | 22899971 | 22899965 | – | chr22 | 22893511 | 22893189; 22893185; 22893481; 22893274 | – | ENST00000398743;ENST00000398741;ENST00000543184;ENST00000405655;ENST00000402697;ENST000000439106;ENST00000438888;ENST00000420709;ENST00000406503;ENST00000442481;ENST00000403441 | |
| 1% | chr22 | 22899971 | 22899965 | – | chr22 | 22893511 | 22893189; 22893185; 22893481; 22893274 | – | ENST00000398743;ENST00000398741;ENST00000543184;ENST00000405655;ENST00000402697;ENST000000439106;ENST00000438888;ENST00000420709;ENST00000406503;ENST00000442481;ENST00000403441 | |
| 1% | chr22 | 22899971 | 22899965 | – | chr22 | 22893511 | 22893189; 22893185; 22893481; 22893274 | – | ENST00000398743;ENST00000398741;ENST00000543184;ENST00000405655;ENST00000402697;ENST000000439106;ENST00000438888;ENST00000420709;ENST00000406503;ENST00000442481;ENST00000403441 | |
| 1% | chr22 | 22899971 | 22899965 | – | chr22 | 22893511 | 22893189; 22893185; 22893481; 22893274 | – | ENST00000398743;ENST00000398741;ENST00000543184;ENST00000405655;ENST00000402697;ENST000000439106;ENST00000438888;ENST00000420709;ENST00000406503;ENST00000442481;ENST00000403441 | TSF |
| 1% | chr22 | 22899971 | 22899965 | – | chr22 | 22893511 | 22893189; 22893185; 22893481; 22893274 | – | ENST00000398743;ENST00000398741;ENST00000543184;ENST00000405655;ENST00000402697;ENST000000439106;ENST00000438888;ENST00000420709;ENST00000406503;ENST00000442481;ENST00000403441 | TSF |
| 1% | chr22 | 22899971 | 22899965 | – | chr22 | 22893511 | 22893189; 22893185; 22893481; 22893274 | – | ENST00000398743;ENST00000398741;ENST00000543184;ENST00000405655;ENST00000402697;ENST000000439106;ENST00000438888;ENST00000420709;ENST00000406503;ENST00000442481;ENST00000403441 | TSF |
| 1% | chr4 | 57560508 | 57559845 | – | chr4 | 57522178 | 57522023; 57522025 | – | ENST00000420433;ENST00000554144;ENST00000508121;ENST00000557328 | TSF |
| 1% | chr4 | 57560508 | 57559845 | – | chr4 | 57522178 | 57522023; 57522025 | – | ENST00000420433;ENST00000554144;ENST00000508121;ENST00000557328 | TSF |
| 1% | chr4 | 57560508 | 57559845 | – | chr4 | 57522178 | 57522023; 57522025 | – | ENST00000420433;ENST00000554144;ENST00000508121;ENST00000557328 | TSF |
| 1% | chr20 | 30060256 | 30059441 | – | chr20 | 30053466 | 30053309 | – | ENST00000317676 | TSF |
| 1% | chr8 | 134271825 | 134271646 | – | chr8 | 134271473 | 134271411; 134271461 | – | ENST00000323851;ENST000005 17599;ENST00000537882;ENST00000414097;ENST00000522476;ENST00000522377;ENST00000520230;ENST00000518480;ENST000005 19228;ENST00000519580;ENST00000522890;ENST00000520943;ENST00000000521544;ENST00000522738 | TSF |
| 1% | chr8 | 134271825 | 134271646 | – | chr8 | 134271473 | 134271411; 134271461 | – | ENST00000323851;ENST000005 17599;ENST00000537882;ENST00000414097;ENST00000522476;ENST00000522377;ENST00000520230;ENST00000518480;ENST000005 19228;ENST00000519580;ENST00000522890;ENST00000520943;ENST00000000521544;ENST00000522738 | TSF |
| 1% | chr8 | 134271825 | 134271646 | – | chr8 | 134271473 | 134271411; 134271461 | – | ENST00000323851;ENST000005 17599;ENST00000537882;ENST00000414097;ENST00000522476;ENST00000522377;ENST00000520230;ENST00000518480;ENST000005 9228;ENST00000519580;ENST0000 | TSF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr8 | 134271825 | 134271646 | − | chr8 | 134271473 | 134271411; 134271461 | − | 00522890;ENST00000520943;ENST00000000521544;ENST00000522738 ENST00000323851;ENST00000517599;ENST00000537882;ENST0000000414097;ENST00000522476;ENST000000522377;ENST00000520230; ENST00000518480;ENST00000519228;ENST00000519580;ENST0000000522890;ENST00000520943;ENST00000000521544;ENST00000522738 | TSF |
| 1% | chr8 | 134271825 | 134271646 | − | chr8 | 134271473 | 134271411; 134271461 | − | ENST00000323851;ENST00000517599;ENST00000537882;ENST0000000414097;ENST00000522476;ENST000000522377;ENST00000520230; ENST00000518480;ENST00000519228;ENST00000519580;ENST0000000522890;ENST00000520943;ENST00000000521544;ENST00000522738 | TSF |
| 1% | chr8 | 134271825 | 134271646 | − | chr8 | 134271473 | 134271411; 134271461 | − | ENST00000323851;ENST00000517599;ENST00000537882;ENST0000000414097;ENST00000522476;ENST000000522377;ENST00000520230; ENST00000518480;ENST00000519228;ENST00000519580;ENST0000000522890;ENST00000520943;ENST00000000521544;ENST00000522738 | TSF |
| 1% | chr8 | 134271825 | 134271646 | − | chr8 | 134271473 | 134271411; 134271461 | − | ENST00000323851;ENST00000517599;ENST00000537882;ENST0000000414097;ENST00000522476;ENST000000522377;ENST00000520230; ENST00000518480;ENST00000519228;ENST00000519580;ENST0000000522890;ENST00000520943;ENST00000000521544;ENST00000522738 | TSF |
| 1% | chr8 | 134271825 | 134271646 | − | chr8 | 134271473 | 134271411; 134271461 | − | ENST00000323851;ENST00000517599;ENST00000537882;ENST0000000414097;ENST00000522476;ENST000000522377;ENST00000520230; ENST00000518480;ENST00000519228;ENST00000519580;ENST0000000522890;ENST00000520943;ENST00000000521544;ENST00000522738 | TSF |
| 1% | chr8 | 134271825 | 134271646 | − | chr8 | 134271473 | 134271411; 134271461 | − | ENST00000323851;ENST00000517599;ENST00000537882;ENST0000000414097;ENST00000522476;ENST000000522377;ENST00000520230; ENST00000518480;ENST00000519228;ENST00000519580;ENST0000000522890;ENST00000520943;ENST00000000521544;ENST00000522738 | TSF |
| 1% | chr8 | 134271825 | 134271646 | − | chr8 | 134271473 | 134271411; 134271461 | − | ENST00000323851;ENST00000517599;ENST00000537882;ENST0000000414097;ENST00000522476;ENST000000522377;ENST00000520230; ENST00000518480;ENST00000519228;ENST00000519580;ENST0000000522890;ENST00000520943;ENST00000000521544;ENST00000522738 | TSF |
| 1% | chr22 | 40898710 | 40898130 | − | chr22 | 40859290 | 40859225 | − | ENST00000422851 | TSF |
| 1% | chr20 | 8624404 | 8625264 | + | chr20 | 8626749 | 8626828 | + | ENST00000378641;ENST00000338037;ENST00000378637;ENST00000404098 | TSF |
| 1% | chr20 | 8624404 | 8625264 | + | chr20 | 8626749 | 8626828 | + | ENST00000378641;ENST00000338037;ENST00000378637;ENST00000404098 | TSF |
| 1% | chr20 | 8624404 | 8625264 | + | chr20 | 8626749 | 8626828 | + | ENST00000378641;ENST00000338037;ENST00000378637;ENST00000404098 | TSF |
| 1% | chr20 | 110606 | 110697 | + | chr20 | 126056 | 126333 | + | ENST00000382398 | TSF |
| 1% | chr5 | 79371074 | 79371193 | + | chr5 | 79372678 | 79372871 | + | ENST00000350881;ENST000000511733 | TSF |
| 1% | chr20 | 8624404 | 8625184 | + | chr20 | 8626749 | 8626828 | + | ENST00000378641;ENST00000338037;ENST00000378637;ENST00000404098 | TSF |
| 1% | chr20 | 8624404 | 8625184 | + | chr20 | 8626749 | 8626828 | + | ENST00000378641;ENST0000033 | TSF |

TABLE 26-continued

Transcript fusion for Head-Neck Squamous Cell Carcinoma HNSC) Coordinates of
the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr20 | 8624404 | 8625184 | + | chr20 | 8626749 | 8626828 | + | 8037;ENST00000378637;ENST0000 00404098 ENST00000378641;ENST0000033 8037;ENST00000378637;ENST0000 00404098 | TSF |
| 1% | chr9 | 137248112 | 137248203 | + | chr9 | 137293478 | 137293728 | + | ENST00000481739 | TSF |
| 1% | chr8 | 71625721 | 71625811 | + | chr8 | 71646031 | 71646659 | + | ENST00000408926;ENST0000052 0030 | TSF |
| 1% | chr3 | 48252382 | 48252800 | + | chr3 | 48265844 | 48265951 | + | ENST00000296435;ENST0000057 6243 | TSF |
| 1% | chr19 | 17421511 | 17421655 | + | chr19 | 17424832 | 17424912 | + | ENST00000593466;ENST0000035 9866,ENST00000596582 | TSF |
| 1% | chr3 | 126729058 | 126729222 | + | chr3 | 126730801 | 126731001 | + | ENST00000251772;ENST0000039 3409 | TSF |
| 1% | chr1 | 165854440 | 165854616 | + | chr1 | 165859441 | 165859600 | + | ENST00000367879;ENST0000037 2212 | TSF |
| 1% | chr1 | 165854440 | 165854616 | + | chr1 | 165859441 | 165859600 | + | ENST00000367879;ENST0000037 2212 | TSF |
| 1% | chr8 0337 | 104389530 | 104389536 | + | chr8 | 104390255 | 104390471 | + | ENST00000330295;ENST0000052 | TSF |
| 1% | chr3 | 48096672 | 48097516 | + | chr3 | 48265844 | 48265951 | + | ENST00000296435;ENST0000057 6243 | TSF |
| 1% | chr12 | 97286062 | 97286334 | + | chr12 | 97303530 | 97303673 | + | ENST00000554226;ENST0000055 7644 | TSF |
| 1% | chr12 | 97286062 | 97286334 | + | chr12 | 97303530 | 97303673 | + | ENST00000554226;ENST0000055 7644 | TSF |
| 1% | chr1 | 45988716 | 45988450 | − | chr1 | 45981479 | 45981326 | − | ENST00000262746;ENST0000031 9248;ENST00000447184;ENST0000 00424390 | TSF |
| 1% | chr1 | 45988716 | 45988450 | − | chr1 | 45981479 | 45981326 | − | ENST00000262746;ENST0000031 9248;ENST00000447184;ENST0000 00424390 | TSF |
| 1% | chr9 | 123165858 | 123165617 | − | chr9 | 123165349 | 123165084 | − | ENST00000359309;ENST0000036 0822;ENST00000349780;ENST000 00360190;ENST00000416449;ENS T000000425647 | TSF |
| 1% | chr1 | 209819885 | 209819875 | − | chr1 | 209811993 | 209811879 | − | ENST00000356082;ENST0000039 1911;ENST00000367030;ENST0000 00415782 | TSF |
| 1% | chr1 | 209819885 | 209819875 | − | chr1 | 209811993 | 209811879 | − | ENST00000356082;ENST0000039 1911;ENST00000367030;ENST0000 00415782 | TSF |
| 1% | chr3 | 115829645 | 115827368 | − | chr3 | 115805403 | 115805171 | − | ENST00000490035;ENST0000033 3617;ENST00000539563;ENST0000 00474851 | TSF |
| 1% | chr3 | 115829645 | 115827368 | − | chr3 | 115805403 | 115805171 | − | ENST00000490035;ENST0000033 3617;ENST00000539563;ENST0000 00474851 | TSF |
| 1% | chr3 | 115829645 | 115827368 | − | chr3 | 115805403 | 115805171 | − | ENST00000490035;ENST0000033 3617;ENST00000539563;ENST0000 00474851 | TSF |
| 1% | chr12 | 58023123 | 58023062 | − | chr12 | 58022929 | 58022831; 58022905 | − | ENST00000341156;ENST0000041 8555;ENST00000552798;ENST0000 00549391 | TSF |
| 1% | chr12 | 58023123 | 58023062 | − | chr12 | 58022929 | 58022831; 58022905 | − | ENST00000341156;ENST0000041 8555;ENST00000552798;ENST0000 00549391 | TSF |
| 1% | chr2 | 163164568 | 163164512 | − | chr2 | 163163365 | 163163219 | − | ENST00000263642 | TSF |
| 1% | chr3 | 113450271 | 113449590 | − | chr3 | 113442939 | 113442806; 113442828 | − | ENST00000240922;ENST0000047 7813;ENST00000497255;ENST000 00481432;ENST00000493900;ENS T000000478020 | TSF |
| 1% | chr3 | 113450271 | 113449590 | − | chr3 | 113442939 | 113442806; 113442828 | − | ENST00000240922;ENST0000047 7813;ENST00000497255;ENST000 00481432;ENST00000493900;ENS T000000478020 | TSF |
| 1% | chr3 | 113450271 | 113449590 | − | chr3 | 113442939 | 113442806; 113442828 | − | ENST00000240922;ENST0000047 7813;ENST00000497255;ENST000 00481432;ENST00000493900;ENS T000000478020 | TSF |
| 1% | chr3 | 113450271 | 113449590 | − | chr3 | 113442939 | 113442806; 113442828 | − | ENST00000240922;ENST0000047 7813;ENST00000497255;ENST000 00481432;ENST00000493900;ENS T000000478020 | TSF |
| 1% | chr3 | 113450271 | 113449590 | − | chr3 | 113442939 | 113442806; − | | ENST00000240922;ENST0000047 | TSF |

TABLE 26-continued

Transcript fusion for Head-Neck Squamous Cell Carcinoma HNSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | 113442828 | | 7813;ENST00000497255;ENST0000 00481432;ENST00000493900;ENS T000000478020 | |
| 1% | chrX | 154534914 | 154534817 | − | chrX | 154528458 | 154528349 | − | ENST00000369449;ENST0000032 1926 | TSF |
| 1% | chrX | 154534914 | 154534817 | − | chrX | 154528458 | 154528349 | − | ENST00000369449;ENST0000032 1926 | TSF |
| 1% | chr2 | 211161174 | 211161144 | − | chr2 | 211159142 | 211158969 | − | ENST00000341685;ENST0000035 2451 | TSF |
| 1% | chr2 | 163040340 | 163040253 | − | chr2 | 163039978 | 163039924 | − | ENST00000188790;ENST0000044 3424 | TSF |
| 1% | chr10 | 27051731 | 27051669 | − | chr10 | 27048164 | 27047991 | − | ENST00000376170;ENST0000035 9188:ENST00000376142:ENST0000 00376139;ENST00000376160;ENS T00000376166:ENST00000376138; ENST00000346832:ENST0000035 5394;ENST00000376134:ENST0000 00376140 | TSF |
| 1% | chr10 | 27051731 | 27051669 | − | chr10 | 27048164 | 27047991 | − | ENST00000376170;ENST0000035 9188:ENST00000376142:ENST0000 00376139;ENST00000376160;ENS T00000376166:ENST00000376138; ENST00000346832:ENST0000035 5394;ENST00000376134:ENST0000 00376140 | TSF |
| 1% | chr17 | 39815837 | 39815667 | − | chr17 | 39776996 | 39776911 | − | ENST00000311208;ENST0000054 0235 | TSF |
| 1% | chr20 | 30058231 | 30057772 | − | chr20 | 30053466 | 30053309 | − | ENST00000317676 | TSF |
| 1% | chr11 | 118146787 | 118146719 | − | chr11 | 118133812 | 118133646 | − | ENST00000278937:ENST0000043 8295 | TSF |

TABLE 27

Transcript fusion for Kidney Chromophobe (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 91% | chr5 | 169532962 | 169533535 | + | ENST00000306268;ENST00000449804 | chr5 | 169533921 | 169533956 | + | TAF |
| 59% | chr19 | 50984141 | 50984234 | + | ENST00000334976;ENST00000376918;ENST00000598 585 | chr19 | 51009025 | 51009080 | + | TAF |
| 53% | chr20 | 30451784 | 30451710 | − | ENST00000278979;ENST00000375966;ENST00000339 738;ENST00000428829 | chr20 | 30450876 | 30450767 | − | TSF |
| 53% | chr20 | 30451784 | 30451710 | − | ENST00000278979;ENST00000375966;ENST00000339 738;ENST00000428829 | chr20 | 30450876 | 30450767 | − | TSF |
| 53% | chr20 | 30451784 | 30451710 | − | ENST00000278979;ENST00000375966;ENST00000339 738;ENST00000428829 | chr20 | 30450876 | 30450767 | − | TSF |
| 47% | chr1 | 156352539 | 156352660 | + | ENST00000451864;ENST00000255013;ENST00000368 246;ENST00000400992;ENST00000368249 | chr1 | 156354102 | 156354192 | + | TAF |
| 47% | chr1 | 156352539 | 156352660 | + | ENST00000451864;ENST00000255013;ENST00000368 246;ENST00000400992;ENST00000368249 | chr1 | 156354102 | 156354192 | + | TAF |
| 47% | chr1 | 156352539 | 156352660 | + | ENST00000451864;ENST00000255013;ENST00000368 246;ENST00000400992;ENST00000368249 | chr1 | 156354102 | 156354192 | + | TAF |
| 47% | chr1 | 156352539 | 156352660 | + | ENST00000451864;ENST00000255013;ENST00000368 246;ENST00000400992;ENST00000368249 | chr1 | 156354102 | 156354192 | + | TAF |
| 42% | chr3 | 195456519 | 195456610 | + | ENST00000447234;ENST00000320736;ENST00000436 408;ENST00000445522;ENST00000423938 | chr3 | 195462062 | 195462761 | + | TAF |
| 42% | chr3 | 195456519 | 195456610 | + | ENST00000447234;ENST00000320736;ENST00000436 408;ENST00000445522;ENST00000423938 | chr3 | 195462062 | 195462761 | + | TAF |
| 42% | chr3 | 195456519 | 195456610 | + | ENST00000447234;ENST00000320736;ENST00000436 408;ENST00000445522;ENST00000423938 | chr3 | 195462062 | 195462761 | + | TAF |
| 42% | chr3 | 195456519 | 195456610 | + | ENST00000447234;ENST00000320736;ENST00000436 408;ENST00000445522;ENST00000423938 | chr3 | 195462062 | 195462761 | + | TAF |
| 41% | chr17 | 80656472 | 80656331 | − | ENST00000571995;ENST00000538809 | chr17 | 80634662 | 80634498 | − | TSF |
| 36% | chr5 | 59481425 | 59481384 | − | ENST00000502484;ENST00000546160;ENST00000509 368;ENST00000505507;ENST00000514552;ENST0000 0515835 | chr5 | 59300173 | 59300093 | − | TAF |
| 35% | chr8 | 6735379 | 6735319 | − | ENST00000297439 | chr8 | 6734600 | 6734532 | − | TAF |
| 32% | chr7 | 71142196 | 71142291 | + | ENST00000333538 | chr7 | 71169493 | 71170639 | + | TSF |
| 30% | chr20 | 30451784 | 30451710 | − | ENST00000278979;ENST00000375966;ENST00000339 738;ENST00000428829 | chr20 | 30450952 | 30450767 | − | TSF |
| 30% | chr20 | 30451784 | 30451710 | − | ENST00000278979;ENST00000375966;ENST00000339 | chr20 | 30450952 | 30450767 | − | TSF |

TABLE 27-continued

Transcript fusion for Kidney Chromophobe (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 30% | chr20 | 30451784 | 30451710 | − | 738;ENST00000428829 ENST00000278979;ENST00000375966;ENST00000339 738;ENST00000428829 | chr20 | 30450952 | 30450767 | − | TSF |
| 29% | chr5 | 41794180; 41794161 | 41794105 | − | ENST00000196371;ENST00000512084;ENST00000510 634;ENST00000509987 | chr5 | 41764599 | 41764486 | − | TAF |
| 29% | chr5 | 41794180; 41794161 | 41794105 | − | ENST00000196371;ENST00000512084;ENST00000510 634;ENST00000509987 | chr5 | 41764599 | 41764486 | − | TAF |
| 29% | chr5 | 41794180; 41794161 | 41794105 | − | ENST00000196371;ENST00000512084;ENST00000510 634;ENST00000509987 | chr5 | 41764599 | 41764486 | − | TAF |
| 29% | chr3 | 58355158 | 58355205 | + | ENST00000356151;ENST00000302779;ENST00000383 715;ENST00000484288;ENST00000479241;ENST0000 0477308;ENST00000491164 | chr3 | 58363636 | 58364153 | + | TSF |
| 29% | chr3 | 58355158 | 58355205 | + | ENST00000356151;ENST00000302779;ENST00000383 715;ENST00000484288;ENST00000479241;ENST0000 0477308;ENST00000491164 | chr3 | 58363636 | 58364153 | + | TSF |
| 29% | chr3 | 58355158 | 58355205 | + | ENST00000356151;ENST00000302779;ENST00000383 715;ENST00000484288;ENST00000479241;ENST0000 0477308;ENST00000491164 | chr3 | 58363636 | 58364153 | + | TSF |
| 29% | chr6 | 163735859 | 163735979 | + | ENST00000337019;ENST00000366889;ENST00000366 888 | chr6 | 163742647 | 163743208 | + | TSF |
| 29% | chr6 | 163735859 | 163735979 | + | ENST00000337019;ENST00000366889;ENST00000366 888 | chr6 | 163742647 | 163743208 | + | TSF |
| 26% | chr16 | 4409386 | 4409297 | − | ENST00000572467;ENST00000251166;ENST00000539 968;ENST00000537233;ENST00000574025;ENST0000 0576637 | chr16 | 4409070 | 4408945 | − | TAF |
| 26% | chr16 | 4409386 | 4409297 | − | ENST00000572467;ENST00000251166;ENST00000539 968;ENST00000537233;ENST00000574025;ENST0000 0576637 | chr16 | 4409070 | 4408945 | − | TAF |
| 26% | chr16 | 4409386 | 4409297 | − | ENST00000572467;ENST00000251166;ENST00000539 968;ENST00000537233;ENST00000574025;ENST0000 0576637 | chr16 | 4409070 | 4408945 | − | TAF |
| 26% | chr16 | 4409386 | 4409297 | − | ENST00000572467;ENST00000251166;ENST00000539 968;ENST00000537233;ENST00000574025;ENST0000 0576637 | chr16 | 4409070 | 4408945 | − | TAF |
| 26% | chr16 | 4409386 | 4409297 | − | ENST00000572467;ENST00000251166;ENST00000539 968;ENST00000537233;ENST00000574025;ENST0000 0576637 | chr16 | 4409070 | 4408945 | − | TAF |
| 26% | chr10 | 84718705 | 84718831 | + | ENST00000372141;ENST00000404547;ENST00000372 142;ENST00000404576;ENST00000556918;ENST0000 0537893;ENST00000545131 | chr10 | 84720295 | 84720298 | + | TSF |
| 26% | chr10 | 84718705 | 84718831 | + | ENST00000372141;ENST00000404547;ENST00000372 142;ENST00000404576;ENST00000556918;ENST0000 0537893;ENST00000545131 | chr10 | 84720295 | 84720298 | + | TSF |
| 26% | chr10 | 84718705 | 84718831 | + | ENST00000372141;ENST00000404547;ENST00000372 142;ENST00000404576;ENST00000556918;ENST0000 0537893;ENST00000545131 | chr10 | 84720295 | 84720298 | + | TSF |
| 26% | chr10 | 84718705 | 84718831 | + | ENST00000372141;ENST00000404547;ENST00000372 142;ENST00000404576;ENST00000556918;ENST0000 0537893;ENST00000545131 | chr10 | 84720295 | 84720298 | + | TSF |
| 26% | chr10 | 84718705 | 84718831 | + | ENST00000372141;ENST00000404547;ENST00000372 142;ENST00000404576;ENST00000556918;ENST0000 0537893;ENST00000545131 | chr10 | 84720295 | 84720298 | + | TSF |
| 24% | chr19 | 3114942 | 3115070 | + | ENST00000078429;ENST00000587636 | chr19 | 3115258 | 3115402 | + | TSF |
| 24% | chr19 | 3114942 | 3115070 | + | ENST00000078429;ENST00000587636 | chr19 | 3115258 | 3115402 | + | TSF |
| 24% | chr12 | 15087927 | 15087790 | − | ENST00000266397 | chr12 | 15086263 | 15086233 | − | TSF |
| 21% | chr16 | 21987488 | 21987564 | + | ENST00000268379;ENST00000561553 | chr16 | 21987742 | 21987854 | + | TAF |
| 21% | chr3 | 42610538 | 42610357 | − | ENST00000423701;ENST00000273156;ENST00000417 572;ENST00000449617;ENST00000264454;ENST0000 0456515;ENST00000383750;ENST00000450981;ENST 00000445388;ENST00000454141;ENST00000416880;E NST00000420163 | chr3 | 42605472 | 42605463 | − | TAF |
| 21% | chr19 | 23556639 | 23556544 | − | ENST00000599743;ENST00000300619 | chr19 | 23491899 | 23491588 | − | TSF |
| 20% | chrX | 119575749 | 119575585 | − | ENST00000434600;ENST00000538785;ENST00000200 639;ENST00000486593;ENST00000371335;ENST0000 0540603 | chrX | 119567897 | 119567790 | − | TAF |
| 20% | chrX | 119575749 | 119575585 | − | ENST00000434600;ENST00000538785;ENST00000200 639;ENST00000486593;ENST00000371335;ENST0000 0540603 | chrX | 119567897 | 119567790 | − | TAF |
| 20% | chrX | 119575749 | 119575585 | − | ENST00000434600;ENST00000538785;ENST00000200 639;ENST00000486593;ENST00000371335;ENST0000 0540603 | chrX | 119567897 | 119567790 | − | TAF |
| 20% | chrX | 119575749 | 119575585 | − | ENST00000434600;ENST00000538785;ENST00000200 639;ENST00000486593;ENST00000371335;ENST0000 0540603 | chrX | 119567897 | 119567790 | − | TAF |
| 20% | chr1 | 156352539 | 156352660 | + | ENST00000451864;ENST00000255013;ENST00000368 | chr1 | 156354082 | 156354192 | + | TSF |

TABLE 27-continued

Transcript fusion for Kidney Chromophobe (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 20% | chr1 | 156352539 | 156352660 | + | 246;ENST00000400992;ENST00000368249 ENST00000451864;ENST00000255013;ENST00000368 246;ENST00000400992;ENST00000368249 | chr1 | 156354082 | 156354192 | + | TSF |
| 20% | chr1 | 156352539 | 156352660 | + | ENST00000451864;ENST00000255013;ENST00000368 246;ENST00000400992;ENST00000368249 | chr1 | 156354082 | 156354192 | + | TSF |
| 20% | chr1 | 156352539 | 156352660 | + | ENST00000451864;ENST00000255013;ENST00000368 246;ENST00000400992;ENST00000368249 | chr1 | 156354082 | 156354192 | + | TSF |
| 17% | chr14 | 96703445 | 96703518 | + | ENST00000554311;ENST00000306005;ENST00000553 811 | chr14 | 96712418 | 96712440 | + | TAF |
| 17% | chr5 | 169532962 | 169533535 | + | ENST00000306268; ENST00000449804 | chr5 | 169560172 | 169560283 | + | TSF |
| 17% | chr2 | 71163085 | 71163202 | + | ENST00000234396;ENST00000432367;ENST00000412 314 | chr2 | 71168794 | 71168842 | + | TSF |
| 15% | chr22 | 37209799 | 37209690 | − | ENST00000417718;ENST00000216200;ENST00000406 910;ENST00000404171;ENST00000443735 | chr22 | 37186448 | 37186392 | − | TSF |
| 15% | chr22 | 37209799 | 37209690 | − | ENST00000417718;ENST00000216200;ENST00000406 910;ENST00000404171;ENST00000443735 | chr22 | 37186448 | 37186392 | − | TSF |
| 15% | chr22 | 37209799 | 37209690 | − | ENST00000417718;ENST00000216200;ENST00000406 910;ENST00000404171;ENST00000443735 | chr22 | 37186448 | 37186392 | − | TSF |
| 14% | chr3 | 122103113 | 122103146 | + | ENST00000477892;ENST00000469967 | chr3 | 122112280 | 122112741 | + | TAF |
| 14% | chr21 | 42622679 | 42622828 | + | ENST00000328735;ENST00000330333 | chr21 | 42628809 | 42628810 | + | TAF |
| 14% | chr12 | 56120579 | 56120484 | − | ENST00000548898;ENST00000552067;ENST00000420 846;ENST00000548160;ENST00000546939;ENST0000 0552692;ENST00000549117;ENST00000257857;ENST 00000552754;ENST00000550776;ENST00000552164;E NST00000551173 | chr12 | 56120394 | 56120116 | − | TAF |
| 14% | chr12 | 56120579 | 56120484 | − | ENST00000548898;ENST00000552067;ENST00000420 846;ENST00000548160;ENST00000546939;ENST0000 0552692;ENST00000549117;ENST00000257857;ENST 00000552754;ENST00000550776;ENST00000552164;E NST00000551173 | chr12 | 56120394 | 56120116 | − | TAF |
| 14% | chr12 | 56120579 | 56120484 | − | ENST00000548898;ENST00000552067;ENST00000420 846;ENST00000548160;ENST00000546939;ENST0000 0552692;ENST00000549117;ENST00000257857;ENST 00000552754;ENST00000550776;ENST00000552164;E NST00000551173 | chr12 | 56120394 | 56120116 | − | TAF |
| 14% | chr12 | 56120579 | 56120484 | − | ENST00000548898;ENST00000552067;ENST00000420 846;ENST00000548160;ENST00000546939;ENST0000 0552692;ENST00000549117;ENST00000257857;ENST 00000552754;ENST00000550776;ENST00000552164;E NST00000551173 | chr12 | 56120394 | 56120116 | − | TAF |
| 14% | chr9 | 114538255 | 114538071 | − | ENST00000374287;ENST00000318737;ENST00000374 283 | chr9 | 114535173 | 114532046 | − | TSF |
| 14% | chr9 | 114538255 | 114538071 | − | ENST00000374287;ENST00000318737;ENST00000374 283 | chr9 | 114535173 | 114532046 | − | TSF |
| 12% | chr3 | 49715006 | 49715066 | + | ENST00000296456;ENST00000442186;ENST00000438 011 | chr3 | 49715773 | 49715877 | + | TAF |
| 12% | chr3 | 49715006 | 49715066 | + | ENST00000296456;ENST00000442186;ENST00000438 011 | chr3 | 49715773 | 49715877 | + | TAF |
| 12% | chr4 | 38104620 | 38104778 | + | ENST00000508802;ENST00000261439 | chr4 | 38107699 | 38107796 | + | TAF |
| 12% | chr4 | 38104620 | 38104778 | + | ENST00000508802;ENST00000261439 | chr4 | 38107699 | 38107796 | + | TAF |
| 12% | chr5 | 147207691 | 147207585 | − | ENST00000296695;ENST00000510027 | chr5 | 147185494 | 147185375 | − | TAF |
| 12% | chr6 | 46867820 | 46867766 | − | ENST00000283296;ENST00000362015;ENST00000456 426;ENST00000265417 | chr6 | 46856509 | 46856439 | − | TAF |
| 12% | chr20 | 32247538; 32247356 | 32247303 | − | ENST00000246190;ENST00000375238;ENST00000480 994 | chr20 | 32246861 | 32246725 | − | TAF |
| 12% | chr20 | 32247538; 32247356 | 32247303 | − | ENST00000246190;ENST00000375238;ENST00000480 994 | chr20 | 32246861 | 32246725 | − | TAF |
| 12% | chr20 | 32247538; 32247356 | 32247303 | − | ENST00000246190;ENST00000375238;ENST00000480 994 | chr20 | 32246861 | 32246725 | − | TAF |
| 12% | chr13 | 52351257 | 52351196 | − | ENST00000444610;ENST00000218981;ENST00000280 056 | chr13 | 52350661 | 52350338 | − | TAF |
| 12% | chr13 | 52351257 | 52351196 | − | ENST00000444610;ENST00000218981;ENST00000280 056 | chr13 | 52350661 | 52350338 | − | TAF |
| 12% | chr7 | 117254667 | 117254767 | + | ENST00000003084;ENST00000454343;ENST00000426 809;ENST00000468795 | chr7 | 117258279 | 117258298 | + | TSF |
| 12% | chr7 | 117254667 | 117254767 | + | ENST00000003084;ENST00000454343;ENST00000426 809;ENST00000468795 | chr7 | 117258279 | 117258298 | + | TSF |
| 12% | chr7 | 117254667 | 117254767 | + | ENST00000003084;ENST00000454343;ENST00000426 809;ENST00000468795 | chr7 | 117258279 | 117258298 | + | TSF |
| 12% | chr7 | 117254667 | 117254767 | + | ENST00000003084;ENST00000454343;ENST00000426 809;ENST00000468795 | chr7 | 117258279 | 117258298 | + | TSF |
| 12% | chr20 | 49458303 | 49458437 | + | ENST00000358791;ENST00000371608;ENST00000609 336 | chr20 | 49468479 | 49468517 | + | TSF |
| 12% | chr20 | 49458303 | 49458437 | + | ENST00000358791;ENST00000371608;ENST00000609 336 | chr20 | 49468479 | 49468517 | + | TSF |

TABLE 27-continued

Transcript fusion for Kidney Chromophobe (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 11% | chr21 | 42629085 | 42629253 | + | ENST00000330333;ENST00000347667 | chr21 | 42635352 | 42635428 | + | TAF |
| 11% | chr21 | 42629085 | 42629253 | + | ENST00000330333;ENST00000347667 | chr21 | 42635352 | 42635428 | + | TAF |
| 11% | chr8 | 87111208 | 87111337 | + | ENST00000523635;ENST00000285393 | chr8 | 87144159 | 87144425 | + | TAF |
| 11% | chr8 | 87125938 | 87126109 | + | ENST00000285393 | chr8 | 87144167 | 87144425 | + | TAF |
| 11% | chr1 | 11718793 | 11718928 | + | ENST00000251546;ENST00000376770;ENST00000376768;ENST00000251547;ENST00000376760;ENST00000376762;ENST00000475435;ENST00000471895 | chr1 | 11719303 | 11719464 | + | TAF |
| 11% | chr1 | 11718793 | 11718928 | + | ENST00000251546;ENST00000376770;ENST00000376768;ENST00000251547;ENST00000376760;ENST00000376762;ENST00000475435;ENST00000471895 | chr1 | 11719303 | 11719464 | + | TAF |
| 11% | chr1 | 11718793 | 11718928 | + | ENST00000251546;ENST00000376770;ENST00000376768;ENST00000251547;ENST00000376760;ENST00000376762;ENST00000475435;ENST00000471895 | chr1 | 11719303 | 11719464 | + | TAF |
| 11% | chr1 | 11718793 | 11718928 | + | ENST00000251546;ENST00000376770;ENST00000376768;ENST00000251547;ENST00000376760;ENST00000376762;ENST00000475435;ENST00000471895 | chr1 | 11719303 | 11719464 | + | TAF |
| 11% | chr1 | 11718793 | 11718928 | + | ENST00000251546;ENST00000376770;ENST00000376768;ENST00000251547;ENST00000376760;ENST00000376762;ENST00000475435;ENST00000471895 | chr1 | 11719303 | 11719464 | + | TAF |
| 11% | chr19 | 5680497 | 5680469 | − | ENST00000309324;ENST00000587589 | chr19 | 5680194 | 5680187 | − | TAF |
| 11% | chr5 | 74984990 | 74984837 | − | ENST00000428202;ENST00000514838;ENST00000380475;ENST00000510798;ENST00000446329 | chr5 | 74983153 | 74982863 | − | TAF |
| 11% | chr5 | 74984990 | 74984837 | − | ENST00000428202;ENST00000514838;ENST00000380475;ENST00000510798;ENST00000446329 | chr5 | 74983153 | 74982863 | − | TAF |
| 11% | chr5 | 74984990 | 74984837 | − | ENST00000428202;ENST00000514838;ENST00000380475;ENST00000510798;ENST00000446329 | chr5 | 74983153 | 74982863 | − | TAF |
| 11% | chr5 | 74984990 | 74984837 | − | ENST00000428202;ENST00000514838;ENST00000380475;ENST00000510798;ENST00000446329 | chr5 | 74983153 | 74982863 | − | TAF |
| 9% | chr9 | 98766802 | 98766983 | + | ENST00000407474;ENST00000320486 | chr9 | 98801158 | 98801481 | + | TSF |
| 9% | chr9 | 98766802 | 98766983 | + | ENST00000407474;ENST00000320486 | chr9 | 98801158 | 98801481 | + | TSF |
| 9% | chr16 | 81990300 | 81990484 | + | ENST00000359376 | chr16 | 81995581 | 81995772 | + | TSF |
| 9% | chr8 | 42924698; 42924750 | 42924802 | + | ENST00000534420;ENST00000302279;ENST00000533998;ENST00000342116;ENST00000531266;ENST00000525699;ENST00000529687;ENST00000533336 | chr8 | 42925245 | 42925476 | + | TSF |
| 9% | chr8 | 42924698; 42924750 | 42924802 | + | ENST00000534420;ENST00000302279;ENST00000533998;ENST00000342116;ENST00000531266;ENST00000525699;ENST00000529687;ENST00000533336 | chr8 | 42925245 | 42925476 | + | TSF |
| 9% | chr8 | 42924698; 42924750 | 42924802 | + | ENST00000534420;ENST00000302279;ENST00000533998;ENST00000342116;ENST00000531266;ENST00000525699;ENST00000529687;ENST00000533336 | chr8 | 42925245 | 42925476 | + | TSF |
| 9% | chr8 | 42924698; 42924750 | 42924802 | + | ENST00000534420;ENST00000302279;ENST00000533998;ENST00000342116;ENST00000531266;ENST00000525699;ENST00000529687;ENST00000533336 | chr8 | 42925245 | 42925476 | + | TSF |
| 9% | chr8 | 42924698; 42924750 | 42924802 | + | ENST00000534420;ENST00000302279;ENST00000533998;ENST00000342116;ENST00000531266;ENST00000525699;ENST00000529687;ENST00000533336 | chr8 | 42925245 | 42925476 | + | TSF |
| 9% | chr8 | 42924698; 42924750 | 42924802 | + | ENST00000534420;ENST00000302279;ENST00000533998;ENST00000342116;ENST00000531266;ENST00000525699;ENST00000529687;ENST00000533336 | chr8 | 42925245 | 42925476 | + | TSF |
| 9% | chr11 | 72416935 | 72416850 | − | ENST00000359373; ENST00000455638; ENST00000393605;ENST00000334211;ENST00000393609;ENST00000426523;ENST00000429686 | chr11 | 72415938 | 72415877 | − | TSF |
| 9% | chr11 | 72416935 | 72416850 | − | ENST00000359373;ENST00000455638;ENST00000393605;ENST00000334211;ENST00000393609;ENST00000426523;ENST00000429686 | chr11 | 72415938 | 72415877 | − | TSF |
| 9% | chr1 | 72416935 | 72416850 | − | ENST00000359373;ENST00000455638;ENST00000393605;ENST00000334211;ENST00000393609;ENST00000426523;ENST00000429686 | chr11 | 72415938 | 72415877 | − | TSF |
| 9% | chr7 | 137080443 | 137080344 | − | ENST00000453654;ENST00000288490;ENST00000424189;ENST00000446122 | chr7 | 137053199 | 137053024 | − | TSF |
| 9% | chr7 | 137080443 | 137080344 | − | ENST00000453654; ENST00000288490;ENST00000424189;ENST00000446122 | chr7 | 137053199 | 137053024 | − | TSF |
| 9% | chr7 | 137080443 | 137080344 | − | ENST00000453654;ENST00000288490;ENST00000424189;ENST00000446122 | chr7 | 137053199 | 137053024 | − | TSF |
| 9% | chr7 | 137080443 | 137080344 | − | ENST00000453654; ENST00000288490;ENST00000424189;ENST00000446122 | chr7 | 137053199 | 137053024 | − | TSF |

TABLE 28

Transcript fusion for Kidney Chromophobe (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 88% | chr20 | 30454037 | 30453945 | – | chr20 | 30452805 | 30452756 | – | ENST00000278979;ENST00000375966;ENST00000339738;ENST00000428829 | TAF |
| 88% | chr20 | 30454037 | 30453945 | – | chr20 | 30452805 | 30452756 | – | ENST00000278979;ENST00000375966;ENST00000339738;ENST00000428829 | TAF |
| 88% | chr20 | 30454037 | 30453945 | | chr20 | 30452805 | 30452756 | – | ENST00000278979;ENST00000375966;ENST00000339738;ENST00000428829 | TAF |
| 85% | chr5 | 156399385 | 156399254 | – | chr5 | 156381767 | 156381426 | – | ENST00000274532;ENST00000407087 | TAF |
| 85% | chr5 | 156399385 | 156399254 | – | chr5 | 156381767 | 156381426 | – | ENST00000274532;ENST00000407087 | TAF |
| 71% | chr4 | 10533364 | 10533137 | – | chr4 | 10527546 | 10527465 | | ENST00000226951 | TSF |
| 68% | chr21 | 42609094 | 42609191 | + | chr21 | 42609440 | 42609656 | + | ENST00000328735;ENST00000330333;ENST00000347667 | TSF |
| 68% | chr21 | 42609094 | 42609191 | + | chr21 | 42609440 | 42609656 | + | ENST00000328735;ENST00000330333;ENST00000347667 | TSF |
| 68% | chr21 | 42609094 | 42609191 | + | chr21 | 42609440 | 42609656 | + | ENST00000328735;ENST00000330333;ENST00000347667 | TSF |
| 68% | chr1 | 156337404 | 156337862 | + | chr1 | 156339110 | 156339227 | + | ENST00000537040;ENST00000544720;ENST00000368246;ENST00000368247;ENST00000368249;ENST00000446171;ENST00000368245 | TSF |
| 68% | chr1 | 156337404 | 156337862 | + | chr1 | 156339110 | 156339227 | + | ENST00000537040;ENST00000544720;ENST00000368246;ENST00000368247;ENST00000368249;ENST00000446171;ENST00000368245 | TSF |
| 68% | chr1 | 156337404 | 156337862 | + | chr1 | 156339110 | 156339227 | + | ENST00000537040;ENST00000544720;ENST00000368246;ENST00000368247;ENST00000368249;ENST00000446171;ENST00000368245 | TSF |
| 68% | chr1 | 156337404 | 156337862 | + | chr1 | 156339110 | 156339227 | + | ENST00000537040;ENST00000544720;ENST00000368246;ENST00000368247;ENST00000368249;ENST00000446171;ENST00000368245 | TSF |
| 68% | chr1 | 156337404 | 156337862 | + | chr1 | 156339110 | 156339227 | + | ENST00000537040;ENST00000544720;ENST00000368246;ENST00000368247;ENST00000368249;ENST00000446171;ENST00000368245 | TSF |
| 61% | chr4 | 95982945 | 95983246 | + | chr4 | 96025559 | 96025718 | + | ENST00000440890 | TAF |
| 61% | chr3 | 195444683 | 195445067 | + | chr3 | 195451551 | 195453443; 195452030 | + | ENST00000447234;ENST00000320736;ENST00000436408 | TAF |
| 61% | chr3 | 195444683 | 195445067 | + | chr3 | 195451551 | 195453443; 195452030 | + | ENST00000447234;ENST00000320736;ENST00000436408 | TAF |
| 61% | chr3 | 195444683 | 195445067 | + | chr3 | 195451551 | 195453443; 195452030 | + | ENST00000447234;ENST00000320736;ENST00000436408 | TAF |
| 61% | chr8 | 39710096 | 39709866 | – | chr8 | 39694731 | 39694655 | – | ENST00000347580;ENST00000379853;ENST00000265708;ENST00000521880 | TAF |
| 61% | chr8 | 39710096 | 39709866 | – | chr8 | 39694731 | 39694655 | – | ENST00000347580;ENST00000379853;ENST00000265708;ENST00000521880 | TAF |
| 61% | chr8 | 39710096 | 39709866 | – | chr8 | 39694731 | 39694655 | – | ENST00000347580;ENST00000379853;ENST00000265708;ENST00000521880 | TAF |
| 61% | chr8 | 39710096 | 39709866 | – | chr8 | 39694731 | 39694655 | – | ENST00000347580;ENST00000379853;ENST00000265708;ENST00000521880 | TAF |
| 58% | chr19 | 3726315 | 3726414 | + | chr19 | 3728422 | 3728478 | + | ENST00000589378;ENST00000262968;ENST00000587686 | TAF |
| 58% | chr19 | 3726315 | 3726414 | + | chr19 | 3728422 | 3728478 | + | ENST00000589378;ENST00000262968;ENST00000587686 | TAF |
| 52% | chr9 | 130732697 | 130732597 | – | chr9 | 130716204 | 130716084 | – | ENST00000373095 | TSF |
| 52% | chr17 | 30185561 | 30185499 | – | chr17 | 30183884 | 30183818 | – | ENST00000302362;ENST00000378634;ENST00000496655 | TSF |
| 52% | chr17 | 30185561 | 30185499 | – | chr17 | 30183884 | 30183818 | | ENST00000302362;ENST00000378634;ENST00000496655 | TSF |
| 50% | chr12 | 15812051 | 15811892 | – | chr12 | 15811519 | 15811431 | | ENST00000543523;ENST00000281172;ENST00000543612;ENST00000540613;ENST00000542903 | TSF |
| 47% | chr3 | 58363388 | 58363791 | + | chr3 | 58368241 | 58368427; 58368405 | + | ENST00000356151;ENST00000302779;ENST00000383716;ENST00000463280;ENST00000383715;ENST00000484288;ENST00000479241;ENST00000477308;ENST00000491164 | TAF |
| 47% | chr3 | 58363388 | 58363791 | + | chr3 | 58368241 | 58368427; 58368405 | + | ENST00000356151;ENST00000302779;ENST00000383716;ENST00000463280;ENST00000383715;ENST00000484288;ENST00000479241;ENST00000477308;ENST00000491164 | TAF |
| 47% | chr3 | 58363388 | 58363791 | + | chr3 | 58368241 | 58368427; 58368405 | + | ENST00000356151;ENST00000302779;ENST00000383716;ENST00000463280;ENST00000383715;ENST00000484288;ENST00000 | TAF |

TABLE 28-continued

Transcript fusion for Kidney Chromophobe (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 47% | chr3 | 58363388 | 58363791 | + | chr3 | 58368241 | 58368427; 58368405 | + | 479241;ENST00000477308;ENST00000491164<br>ENST00000356151;ENST00000302779;ENST00000383716;ENST00000463280;ENST00000383715;ENST00000484288;ENST00000479241;ENST00000477308;ENST00000491164 | TAF |
| 47% | chr3 | 58363388 | 58363791 | + | chr3 | 58368241 | 58368427; 58368405 | + | ENST00000356151;ENST00000302779;ENST00000383716;ENST00000463280;ENST00000383715;ENST00000484288;ENST00000479241;ENST00000477308;ENST00000491164 | TAF |
| 45% | chr7 | 137617767 | 137617650 | − | chr7 | 137613112 | 137612896 | − | ENST00000330387;ENST00000456390;ENST00000452463 | TAF |
| 45% | chr7 | 137617767 | 137617650 | − | chr7 | 137613112 | 137612896 | − | ENST00000330387;ENST00000456390;ENST00000452463 | TAF |
| 45% | chr7 | 137617767 | 137617650 | − | chr7 | 137613112 | 137612896 | − | ENST00000330387;ENST00000456390;ENST00000452463 | TAF |
| 45% | chrX | 119449588 | 119449552 | − | chrX | 119438346 | 119438204 | − | ENST00000309720;ENST00000371369;ENST00000440464;ENST00000519908 | TSF |
| 45% | chrX | 119449588 | 119449552 | − | chrX | 119438346 | 119438204 | − | ENST00000309720;ENST00000371369;ENST00000440464; ENST00000519908 | TSF |
| 45% | chrX | 119449588 | 119449552 | − | chrX | 119438346 | 119438204 | − | ENST00000309720;ENST00000371369;ENST00000440464;ENST00000519908 | TSF |
| 45% | chrX | 119449588 | 119449552 | − | chrX | 119438346 | 119438204 | − | ENST00000309720;ENST00000371369;ENST00000440464;ENST00000519908 | TSF |
| 42% | chr21 | 42597177 | 42597622 | + | chr21 | 42598193 | 42598281 | + | ENST00000328735;ENST00000330333;ENST00000347667 | TAF |
| 42% | chr21 | 42597177 | 42597622 | + | chr21 | 42598193 | 42598281 | + | ENST00000328735;ENST00000330333;ENST00000347667 | TAF |
| 42% | chr21 | 42597177 | 42597622 | + | chr21 | 42598193 | 42598281 | + | ENST00000328735;ENST00000330333;ENST00000347667 | TAF |
| 42% | chr4 | 6959398 | 6959457 | + | chr4 | 6969031 | 6969151 | + | ENST00000448507;ENST00000409757;ENST00000410031 | TSF |
| 41% | chrX | 119449588 | 119449548 | − | chrX | 119438346 | 119438204 | − | ENST00000309720;ENST00000371369;ENST00000440464;ENST00000519908 | TSF |
| 41% | chrX | 119449588 | 119449548 | − | chrX | 119438346 | 119438204 | − | ENST00000309720;ENST00000371369;ENST00000440464;ENST00000519908 | TSF |
| 41% | chrX | 119449588 | 119449548 | − | chrX | 119438346 | 119438204 | − | ENST00000309720;ENST00000371369;ENST00000440464;ENST00000519908 | TSF |
| 41% | chrX | 119449588 | 119449548 | − | chrX | 119438346 | 119438204 | − | ENST00000309720;ENST00000371369;ENST00000440464;ENST00000519908 | TSF |
| 39% | chr20 | 33850895 | 33851310 | + | chr20 | 33851594 | 33851755 | + | ENST00000246186 | TAF |
| 38% | chr21 | 42609094 | 42609159 | + | chr21 | 42609440 | 42609656 | + | ENST00000328735;ENST00000330333;ENST00000347667 | TAF |
| 38% | chr21 | 42609094 | 42609159 | + | chr21 | 42609440 | 42609656 | + | ENST00000328735;ENST00000330333;ENST00000347667 | TAF |
| 38% | chr21 | 42609094 | 42609159 | + | chr21 | 42609440 | 42609656 | + | ENST00000328735;ENST00000330333;ENST00000347667 | TAF |
| 36% | chr12 | 55223983 | 55224840 | + | chr12 | 55248900 | 55248941 | + | ENST00000546809;ENST00000308796 | TAF |
| 35% | chr8 | 27947459 | 27947920 | + | chr8 | 27954736 | 27954835 | + | ENST00000256398;ENST00000523687;ENST00000518112 | TAF |
| 35% | chr8 | 27947459 | 27947920 | + | chr8 | 27954736 | 27954835 | + | ENST00000256398;ENST00000523687;ENST00000518112 | TAF |
| 35% | chr4 | 146643833 | 146644154 | + | chr4 | 146648063 | 146648121 | + | ENST00000438731;ENST00000511965 | TSF |
| 33% | chr14 | 24105943 | 24105981 | + | chr14 | 24112361 | 24112428 | + | ENST00000432832;ENST00000250383;ENST00000344777;ENST00000557535;ENST00000553600 | TAF |
| 33% | chr14 | 24105943 | 24105981 | + | chr14 | 24112361 | 24112428 | + | ENST00000432832;ENST00000250383;ENST00000344777;ENST00000557535;ENST00000553600 | TAF |
| 33% | chr14 | 24105943 | 24105981 | + | chr14 | 24112361 | 24112428 | + | ENST00000432832;ENST00000250383;ENST00000344777;ENST00000557535;ENST00000553600 | TAF |
| 33% | chr14 | 24105943 | 24105981 | + | chr14 | 24112361 | 24112428 | + | ENST00000432832;ENST00000250383;ENST00000344777;ENST00000557535;ENST00000553600 | TAF |
| 30% | chr8 | 27947459 | 27947849 | + | chr8 | 27954736 | 27954835 | + | ENST00000256398;ENST00000523687;ENST00000518112 | TAF |
| 30% | chr8 | 27947459 | 27947849 | + | chr8 | 27954736 | 27954835 | + | ENST00000256398;ENST00000523687;ENST00000518112 | TAF |
| 30% | chr4 | 71846253 | 71846787 | + | chr4 | 71847697 | 71847774 | + | ENST00000309395;ENST00000396051 | TAF |

TABLE 28-continued

Transcript fusion for Kidney Chromophobe (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 30% | chr19 | 51340308 | 51340387 | + | chr19 | 51359496 | 51359655 | + | ENST00000326003;ENST00000422986;ENST00000597483;ENST00000593997;ENST00000595392;ENST00000595952;ENST00000360617;ENST00000598145 | TAF |
| 30% | chr19 | 51340308 | 51340387 | + | chr19 | 51359496 | 51359655 | + | ENST00000326003;ENST00000422986;ENST00000597483;ENST00000593997;ENST00000595392;ENST00000595952;ENST00000360617;ENST00000598145 | TAF |
| 30% | chr19 | 51340308 | 51340387 | + | chr19 | 51359496 | 51359655 | + | ENST00000326003;ENST00000422986;ENST00000597483;ENST00000593997;ENST00000595392;ENST00000595952;ENST00000360617;ENST00000598145 | TAF |
| 30% | chr19 | 51340308 | 51340387 | + | chr19 | 51359496 | 51359655 | + | ENST00000326003;ENST00000422986;ENST00000597483;ENST00000593997;ENST00000595392;ENST00000595952;ENST00000360617;ENST00000598145 | TAF |
| 30% | chr19 | 51340308 | 51340387 | + | chr19 | 51359496 | 51359655 | + | ENST00000326003;ENST00000422986;ENST00000597483;ENST00000593997;ENST00000595392;ENST00000595952;ENST00000360617;ENST00000598145 | TAF |
| 30% | chr19 | 51340308 | 51340387 | + | chr19 | 51359496 | 51359655 | + | ENST00000326003;ENST00000422986;ENST00000597483;ENST00000593997;ENST00000595392;ENST00000595952;ENST00000360617;ENST00000598145 | TAF |
| 30% | chr19 | 51340308 | 51340387 | + | chr19 | 51359496 | 51359655 | + | ENST00000326003;ENST00000422986;ENST00000597483;ENST00000593997;ENST00000595392;ENST00000595952;ENST00000360617;ENST00000598145 | TAF |
| 30% | chr19 | 51340308 | 51340387 | + | chr19 | 51359496 | 51359655 | + | ENST00000326003;ENST00000422986;ENST00000597483;ENST00000593997;ENST00000595392;ENST00000595952;ENST00000360617;ENST00000598145 | TAF |
| 30% | chr3 | 195447345 | 195447395 | + | chr3 | 195451551 | 195453443; 195452030 | + | ENST00000447234;ENST00000320736;ENST00000436408 | TSF |
| 30% | chr3 | 195447345 | 195447395 | + | chr3 | 195451551 | 195453443; 195452030 | + | ENST00000447234;ENST00000320736;ENST00000436408 | TSF |
| 30% | chr3 | 195447345 | 195447395 | + | chr3 | 195451551 | 195453443; 195452030 | + | ENST00000447234;ENST00000320736;ENST00000436408 | TSF |
| 29% | chr15 | 80469525 | 80469529 | + | chr15 | 80469879 | 80469925 | + | ENST00000407106;ENST00000261755;ENST00000561421;ENST00000539156;ENST00000561353 | TAF |
| 29% | chr15 | 80469525 | 80469529 | + | chr15 | 80469879 | 80469925 | + | ENST00000407106;ENST00000261755;ENST00000561421;ENST00000539156;ENST00000561353 | TAF |
| 26% | chr10 | 4986182 | 4986466 | + | chr10 | 5008202 | 5008273 | + | ENST00000434459;ENST00000380872;ENST00000442997;ENST00000380859 | TAF |
| 26% | chr10 | 4986182 | 4986466 | + | chr10 | 5008202 | 5008273 | + | ENST00000434459;ENST00000380872;ENST00000442997;ENST00000380859 | TAF |
| 26% | chr10 | 4986182 | 4986466 | + | chr10 | 5008202 | 5008273 | + | ENST00000434459;ENST00000380872;ENST00000442997;ENST00000380859 | TAF |
| 26% | chr22 | 37211553 | 37211547 | − | chr22 | 37211279 | 37211147 | − | ENST00000417718;ENST00000216200;ENST00000406910;ENST00000443735 | TSF |
| 26% | chr22 | 37211553 | 37211547 | − | chr22 | 37211279 | 37211147 | − | ENST00000417718;ENST00000216200;ENST00000406910;ENST00000443735 | TSF |
| 26% | chr22 | 37211553 | 37211547 | − | chr22 | 37211279 | 37211147 | − | ENST00000417718;ENST00000216200;ENST00000406910;ENST00000443735 | TSF |
| 24% | chr14 | 24105943 | 24105981 | + | chr14 | 24109003 | 24109104 | + | ENST00000432832;ENST00000250383;ENST00000344777;ENST00000557535;ENST00000553600 | TAF |
| 24% | chr14 | 24105943 | 24105981 | + | chr14 | 24109003 | 24109104 | + | ENST00000432832;ENST00000250383;ENST00000344777;ENST00000557535;ENST00000553600 | TAF |
| 24% | chr14 | 24105943 | 24105981 | + | chr14 | 24109003 | 24109104 | + | ENST00000432832;ENST00000250383;ENST00000344777;ENST00000557535;ENST00000553600 | TAF |
| 24% | chr14 | 24105943 | 24105981 | + | chr14 | 24109003 | 24109104 | + | ENST00000432832;ENST00000250383;ENST00000344777;ENST00000557535;ENST00000553600 | TAF |
| 24% | chr14 | 24105943 | 24105981 | + | chr14 | 24109003 | 24109104 | + | ENST00000432832;ENST00000250383;ENST00000344777;ENST00000557535;ENST00000553600 | TAF |
| 24% | chr1 | 71328082 | 71327988 | − | chr1 | 71318542 | 71318522 | − | ENST00000370932;ENST00000460330 | TAF |
| 24% | chr15 | 63638414 | 63638317 | − | chr15 | 63637818 | 63637676 | − | ENST00000178638;ENST00000344366;ENST00000422263 | TAF |
| 24% | chr15 | 63638414 | 63638317 | − | chr15 | 63637818 | 63637676 | − | ENST00000178638;ENST00000344366;ENST | TAF |

TABLE 28-continued

Transcript fusion for Kidney Chromophobe (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 23% | chr15 | 78443636 | 78443886 | + | chr15 | 78447555 | 78447617 | + | T00000422263 ENST00000299518;ENST00000558933;ENST00000558554;ENST00000560667;ENST00000561279;ENST00000560396;ENST00000559865;ENST00000558509;ENST00000559803;ENST00000559106 | TAF |
| 23% | chr15 | 78443636 | 78443886 | + | chr15 | 78447555 | 78447617 | + | ENST00000299518;ENST00000558933;ENST00000558554;ENST00000560667;ENST00000561279;ENST00000560396;ENST00000559865;ENST00000558509;ENST00000559803;ENST00000559106 | TAF |
| 23% | chr15 | 78443636 | 78443886 | + | chr15 | 78447555 | 78447617 | + | ENST00000299518;ENST00000558933;ENST00000558554;ENST00000560667;ENST00000561279;ENST00000560396;ENST00000559865;ENST00000558509;ENST00000559803;ENST00000559106 | TAF |
| 23% | chr15 | 78443636 | 78443886 | + | chr15 | 78447555 | 78447617 | + | ENST00000299518;ENST00000558933;ENST00000558554;ENST00000560667;ENST00000561279;ENST00000560396;ENST00000559865;ENST00000558509;ENST00000559803;ENST00000559106 | TAF |
| 23% | chr15 | 78443636 | 78443886 | + | chr15 | 78447555 | 78447617 | + | ENST00000299518;ENST00000558933;ENST00000558554;ENST00000560667;ENST00000561279;ENST00000560396;ENST00000559865;ENST00000558509;ENST00000559803;ENST00000559106 | TAF |
| 23% | chr15 | 78443636 | 78443886 | + | chr15 | 78447555 | 78447617 | + | ENST00000299518;ENST00000558933;ENST00000558554;ENST00000560667;ENST00000561279;ENST00000560396;ENST00000559865;ENST00000558509;ENST00000559803;ENST00000559106 | TAF |
| 23% | chr2 | 71190941 | 71191014 | + | chr2 | 71191568 | 71191672 | + | ENST00000234396;ENST00000412314 | TAF |
| 23% | chr9 | 114575337 | 114575283 | − | chr9 | 114548315 | 114548192 | − | ENST00000374283 | TSF |
| 23% | chr14 | 67820507 | 67820416 | − | chr14 | 67819757 | 67819640 | − | ENST00000554087;ENST00000555474;ENST00000216442;ENST00000554236;ENST00000556058;ENST00000555012 | TSF |
| 23% | chr14 | 67820507 | 67820416 | − | chr14 | 67819757 | 67819640 | − | ENST00000554087;ENST00000555474;ENST00000216442;ENST00000554236;ENST00000556058;ENST00000555012 | TSF |
| 23% | chr14 | 67820507 | 67820416 | − | chr14 | 67819757 | 67819640 | − | ENST00000554087;ENST00000555474;ENST00000216442;ENST00000554236;ENST00000556058;ENST00000555012 | TSF |
| 23% | chr14 | 67820507 | 67820416 | − | chr14 | 67819757 | 67819640 | − | ENST00000554087;ENST00000555474;ENST00000216442;ENST00000554236;ENST00000556058;ENST00000555012 | TSF |
| 23% | chr14 | 67820507 | 67820416 | − | chr14 | 67819757 | 67819640 | − | ENST00000554087;ENST00000555474;ENST00000216442;ENST00000554236;ENST00000556058;ENST00000555012 | TSF |
| 21% | chr2 | 191111350 | 191111301 | − | chr2 | 191110938 | 191110880 | + | ENST00000392332;ENST00000359678;ENST00000410045;ENST00000416732;ENST00000409820 | TAF |
| 21% | chr2 | 191111350 | 191111301 | − | chr2 | 191110938 | 191110880 | − | ENST00000392332;ENST00000359678;ENST00000410045;ENST00000416732;ENST00000409820 | TAF |
| 21% | chr2 | 191111350 | 191111301 | − | chr2 | 191110938 | 191110880 | − | ENST00000392332;ENST00000359678;ENST00000410045;ENST00000416732;ENST00000409820 | TAF |
| 21% | chr2 | 191111350 | 191111301 | − | chr2 | 191110938 | 191110880 | − | ENST00000392332;ENST00000359678;ENST00000410045;ENST00000416732;ENST00000409820 | TAF |
| 21% | chr12 | 123070929 | 123070983 | + | chr12 | 123071248 | 123071304 | + | ENST00000333479 | TSF |
| 21% | chr10 | 4990318 | 4992053 | + | chr10 | 5008202 | 5008273 | + | ENST00000434459;ENST00000380872;ENST00000442997;ENST00000380859 | TSF |
| 21% | chr10 | 4990318 | 4992053 | + | chr10 | 5008202 | 5008273 | + | ENST00000434459;ENST00000380872;ENST00000442997;ENST00000380859 | TSF |
| 21% | chr10 | 4990318 | 4992053 | + | chr10 | 5008202 | 5008273 | + | ENST00000434459;ENST00000380872;ENST00000442997;ENST00000380859 | TSF |
| 20% | chr11 | 126273341 | 126273381 | + | chr11 | 126275991 | 126276045 | + | ENST00000534733 | TAF |
| 20% | chr8 | 87144142 | 87144238 | + | chr8 | 87151686 | 87151864 | + | ENST00000285393 | TAF |
| 20% | chr10 | 4986182 | 4986466 | + | chr10 | 5008196 | 5008273 | + | ENST00000434459;ENST00000380872;ENST00000380859 | TAF |
| 20% | chr10 | 4986182 | 4986466 | + | chr10 | 5008196 | 5008273 | − | ENST00000434459;ENST00000380872;ENST00000380859 | TAF |
| 20% | chr5 | 59300404 | 59300101 | − | chr5 | 59284544 | 59284315; 59284344; | − | ENST00000502484;ENST00000546160;ENST00000505507;ENST00000514552 | TAF |

TABLE 28-continued

Transcript fusion for Kidney Chromophobe (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 20% | chr5 | 59300404 | 59300101 | − | chr5 | 59284544 | 59284363 59284315; 59284344; 59284363 | − | ENST00000502484;ENST00000546160;ENST00000505507;ENST00000514552 | TAF |
| 20% | chr5 | 59300404 | 59300101 | − | chr5 | 59284544 | 59284363 59284315; 59284344; 59284363 | − | ENST00000502484;ENST00000546160;ENST00000505507;ENST00000514552 | TAF |
| 20% | chr3 | 43499158 | 43498855 | − | chr3 | 43474219 | 43474103 | − | ENST00000292246;ENST00000350459;ENST00000396091;ENST00000451430;ENST00000448045 | TSF |
| 18% | chr4 | 91640179 | 91640523 | + | chr4 | 91645065 | 91645142 | + | ENST00000509176;ENST00000432775;ENST00000333691;ENST00000513522 | TAF |
| 18% | chr4 | 91640179 | 91640523 | + | chr4 | 91645065 | 91645142 | + | ENST00000509176;ENST00000432775;ENST00000333691;ENST00000513522 | TAF |
| 18% | chr4 | 91640179 | 91640523 | + | chr4 | 91645065 | 91645142 | + | ENST00000509176;ENST00000432775;ENST00000333691;ENST00000513522 | TAF |
| 18% | chr3 | 98482258 | 98482283 | + | chr3 | 98487274 | 98487373 | + | ENST00000492254 | TAF |
| 18% | chr3 | 45018144 | 45018242 | + | chr3 | 45030632 | 45030733 | + | ENST00000265564 | TAF |
| 18% | chrX | 107370259 | 107370324 | + | chrX | 107372011 | 107372082 | + | ENST00000345734;ENST00000372232;ENST00000343524 | TAF |
| 18% | chrX | 107370259 | 107370324 | + | chrX | 107372011 | 107372082 | + | ENST00000345734;ENST00000372232;ENST00000343524 | TAF |
| 18% | chrX | 107370259 | 107370324 | + | chrX | 107372011 | 107372082 | + | ENST00000345734;ENST00000372232;ENST00000343524 | TAF |
| 18% | chr13 | 22253799 | 22254080 | + | chr13 | 22255181 | 22255284 | + | ENST00000382353 | TAF |
| 18% | chr20 | 30451567 | 30451427 | − | chr20 | 30450545 | 30450374 | − | ENST00000278979;ENST00000375966;ENST00000339738 | TSF |
| 18% | chr20 | 30451567 | 30451427 | − | chr20 | 30450545 | 30450374 | − | ENST00000278979;ENST00000375966;ENST00000339738 | TSF |
| 17% | chr5 | 80552027 | 80552252 | + | chr5 | 80553552 | 80553675 | + | ENST00000254035;ENST00000437669;ENST00000424301 | TAF |
| 17% | chr9 | 139611399 | 139611665 | + | chr9 | 139612029 | 139612163 | + | ENST00000371692 | TAF |
| 17% | chr10 | 99667221 | 99666955 | − | chr10 | 99664571 | 99664426 | − | ENST00000413387;ENST00000370597;ENST00000298819;ENST00000309155;ENST00000370591 | TAF |
| 17% | chr10 | 99667221 | 99666955 | − | chr10 | 99664571 | 99664426 | − | ENST00000413387;ENST00000370597;ENST00000298819;ENST00000309155;ENST00000370591 | TAF |
| 17% | chr10 | 99667221 | 99666955 | − | chr10 | 99664571 | 99664426 | − | ENST00000413387;ENST00000370597;ENST00000298819;ENST00000309155;ENST00000370591 | TAF |
| 17% | chr19 | 7895176 | 7895267 | + | chr19 | 7911468 | 7911565 | + | ENST00000270530;ENST00000538904 | TSF |
| 17% | chr19 | 7895176 | 7895267 | + | chr19 | 7911468 | 7911565 | + | ENST00000270530;ENST00000538904 | TSF |
| 15% | chr16 | 21966083 | 21966183 | + | chr16 | 21968556 | 21968639 | + | ENST00000268379;ENST00000565464;ENST00000561553;ENST00000563898;ENST00000564095 | TAF |
| 15% | chr16 | 21966083 | 21966183 | + | chr16 | 21968556 | 21968639 | + | ENST00000268379;ENST00000565464;ENST00000561553;ENST00000563898;ENST00000564095 | TAF |
| 15% | chr16 | 21966083 | 21966183 | + | chr16 | 21968556 | 21968639 | + | ENST00000268379;ENST00000565464;ENST00000561553;ENST00000563898;ENST00000564095 | TAF |
| 15% | chr16 | 21966083 | 21966183 | + | chr16 | 21968556 | 21968639 | + | ENST00000268379;ENST00000565464;ENST00000561553;ENST00000563898;ENST00000564095 | TAF |
| 15% | chr16 | 21966083 | 21966183 | + | chr16 | 21968556 | 21968639 | + | ENST00000268379;ENST00000565464;ENST00000561553;ENST00000563898;ENST00000564095 | TAF |
| 15% | chr12 | 52444147 | 52444325 | + | chr12 | 52448111 | 52448430; 52448988; 52448981 | + | ENST00000548977;ENST00000360284;ENST00000546842;ENST00000545748;ENST00000550082 | TAF |
| 15% | chr12 | 52444147 | 52444325 | + | chr12 | 52448111 | 52448430; 52448988; 52448981 | + | ENST00000548977;ENST00000360284;ENST00000546842;ENST00000545748;ENST00000550082 | TAF |
| 15% | chr12 | 52444147 | 52444325 | + | chr12 | 52448111 | 52448430; 52448988; 52448981 | + | ENST00000548977;ENST00000360284;ENST00000546842;ENST00000545748;ENST00000550082 | TAF |
| 15% | chr11 | 107998616 | 107998706 | + | chr11 | 108004547 | 108004664 | + | ENST00000265838;ENST00000299355;ENST00000531813 | TAF |
| 15% | chr11 | 107998616 | 107998706 | + | chr11 | 108004547 | 108004664 | + | ENST00000265838;ENST00000299355;ENST00000531813 | TAF |
| 15% | chr11 | 107998616 | 107998706 | + | chr11 | 108004547 | 108004664 | + | ENST00000265838;ENST00000299355;ENST00000531813 | TAF |
| 15% | chr11 | 117694170 | 117694041 | − | chr11 | 117693432 | 117693394 | − | ENST00000532119;ENST00000528014;ENST00000292079;ENST00000260287;ENST00 | TAF |

TABLE 28-continued

Transcript fusion for Kidney Chromophobe (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 15% | chr11 | 117694170 | 117694041 | − | chr11 | 117693432 | 117693394 | − | 000532984 ENST00000532119;ENST00000528014;ENST00000292079;ENST00000260287;ENST00000532984 | TAF |
| 15% | chr7 | 8267515 | 8267268 | − | chr7 | 8261028 | 8260905 | − | ENST00000402384; ENST00000406470;ENST00000265577;ENST00000396675;ENST00000339809;ENST00000401396;ENST00000422063;ENST00000407906;ENST00000317367;ENST00000447326;ENST00000430867 | TAF |
| 15% | chr7 | 8267515 | 8267268 | − | chr7 | 8261028 | 8260905 | − | ENST00000402384;ENST00000406470;ENST00000265577;ENST00000396675;ENST00000339809;ENST00000401396;ENST00000422063;ENST00000407906;ENST00000317367;ENST00000447326;ENST00000430867 | TAF |
| 15% | chr7 | 8267515 | 8267268 | − | chr7 | 8261028 | 8260905 | − | ENST00000402384;ENST00000406470;ENST00000265577;ENST00000396675;ENST00000339809;ENST00000401396;ENST00000422063;ENST00000407906;ENST00000317367;ENST00000447326;ENST00000430867 | TAF |
| 15% | chr7 | 8267515 | 8267268 | − | chr7 | 8261028 | 8260905 | − | ENST00000402384;ENST00000406470;ENST00000265577;ENST00000396675;ENST00000339809;ENST00000401396;ENST00000422063;ENST00000407906;ENST00000317367;ENST00000447326;ENST00000430867 | TAF |
| 15% | chr7 | 8267515 | 8267268 | − | chr7 | 8261028 | 8260905 | − | ENST00000402384;ENST00000406470;ENST00000265577;ENST00000396675;ENST00000339809;ENST00000401396;ENST00000422063;ENST00000407906;ENST00000317367;ENST00000447326;ENST00000430867 | TAF |
| 15% | chr7 | 8267515 | 8267268 | − | chr7 | 8261028 | 8260905 | − | ENST00000402384;ENST00000406470;ENST00000265577;ENST00000396675;ENST00000339809;ENST00000401396;ENST00000422063;ENST00000407906;ENST00000317367;ENST00000447326;ENST00000430867 | TAF |
| 15% | chr7 | 8267515 | 8267268 | − | chr7 | 8261028 | 8260905 | − | ENST00000402384;ENST00000406470;ENST00000265577;ENST00000396675;ENST00000339809;ENST00000401396;ENST00000422063;ENST00000407906;ENST00000317367;ENST00000447326;ENST00000430867 | TAF |
| 15% | chr11 | 77673812 | 77673716 | − | chr11 | 77672184 | 77672150; 77671999 | − | ENST00000433818;ENST00000534064;ENST00000529807 | TSF |
| 15% | chr11 | 77673812 | 77673716 | − | chr11 | 77672184 | 77672150; 77671999 | − | ENST00000433818;ENST00000534064;ENST00000529807 | TSF |
| 15% | chr11 | 77673812 | 77673716 | − | chr11 | 77672184 | 77672150; 77671999 | − | ENST00000433818;ENST00000534064;ENST00000529807 | TSF |
| 15% | chr15 | 63650282 | 63650004 | − | chr15 | 63638908 | 63638729 | − | ENST00000178638;ENST00000344366 | TSF |
| 15% | chr15 | 63650282 | 63650004 | − | chr15 | 63638908 | 63638729 | − | ENST00000178638;ENST00000344366 | TSF |
| 15% | chr22 | 37211553 | 37211536 | − | chr22 | 37211279 | 37211147 | − | ENST00000417718;ENST00000216200;ENST00000406910;ENST00000443735 | TSF |
| 15% | chr22 | 37211553 | 37211536 | − | chr22 | 37211279 | 37211147 | − | ENST00000417718;ENST00000216200;ENST00000406910;ENST00000443735 | TSF |
| 15% | chr22 | 37211553 | 37211536 | − | chr22 | 37211279 | 37211147 | − | ENST00000417718;ENST00000216200;ENST00000406910;ENST00000443735 | TSF |
| 14% | chr3 | 58365254 | 58365321 | + | chr3 | 58368241 | 58368427; 58368405 | + | ENST00000356151;ENST00000302779;ENST00000383716;ENST00000463280;ENST00000383715;ENST00000484288;ENST00000479241;ENST00000477308;ENST00000491164 | TAF |
| 14% | chr3 | 58365254 | 58365321 | + | chr3 | 58368241 | 58368427; 58368405 | + | ENST00000356151;ENST00000302779;ENST00000383716;ENST00000463280;ENST00000383715;ENST00000484288;ENST00000479241;ENST00000477308;ENST00000491164 | TAF |
| 14% | chr3 | 58365254 | 58365321 | + | chr3 | 58368241 | 58368427; 58368405 | + | ENST00000356151;ENST00000302779;ENST00000383716;ENST00000463280;ENST00000383715;ENST00000484288;ENST00000479241;ENST00000477308;ENST00000491164 | TAF |
| 14% | chr3 | 58365254 | 58365321 | + | chr3 | 58368241 | 58368427; 58368405 | + | ENST00000356151;ENST00000302779;ENST00000383716;ENST00000463280;ENST00000383715;ENST00000484288;ENST00000479241;ENST00000477308;ENST00000491164 | TAF |
| 14% | chr3 | 58365254 | 58365321 | + | chr3 | 58368241 | 58368427; 58368405 | + | ENST00000356151;ENST00000302779;ENST00000383716;ENST00000463280;ENST00000 | TAF |

TABLE 28-continued

Transcript fusion for Kidney Chromophobe (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | 000383715;ENST00000484288;ENST00000479241;ENST00000477308;ENST00000491164 | |
| 14% | chr1 | 236534342 | 236534395 | + | chr1 | 236572516 | 236572574 | + | ENST00000334232;ENST00000359362 | TAF |
| 14% | chr3 | 45030340 | 45030346 | + | chr3 | 45030632 | 45030733 | + | ENST00000265564 | TAF |
| 14% | chr7 | 150938296 | 150938250 | − | chr7 | 150937608 | 150937511 | − | ENST00000262188;ENST00000392811;ENST00000356800 | TAF |
| 14% | chr4 | 491211 | 490916 | − | chr4 | 466490 | 466364 | − | ENST00000515578;ENST00000506646;ENST00000505900 | TAF |
| 14% | chr4 | 491211 | 490916 | − | chr4 | 466490 | 466364 | − | ENST00000515578;ENST00000506646;ENST00000505900 | TAF |
| 14% | chr4 | 491211 | 490916 | − | chr4 | 466490 | 466364 | − | ENST00000515578;ENST00000506646;ENST00000505900 | TAF |
| 14% | chr14 | 78042174 | 78042075 | − | chr14 | 78036851 | 78036727 | − | ENST00000216484;ENST00000554901 | TAF |
| 14% | chr14 | 78042174 | 78042075 | − | chr14 | 78036851 | 78036727 | − | ENST00000216484;ENST00000554901 | TAF |
| 14% | chr10 | 4986182 | 4986518 | + | chr10 | 5008106 | 5008273 | + | ENST00000434459;ENST00000380872;ENST00000380859 | TSF |
| 14% | chr10 | 4986182 | 4986518 | + | chr10 | 5008106 | 5008273 | + | ENST00000434459;ENST00000380872;ENST00000380859 | TSF |
| 14% | chr4 | 10533364 | 10533137 | − | chr4 | 10529718 | 10529700 | − | ENST00000226951 | TSF |
| 12% | chr2 | 47552899 | 47553008 | + | chr2 | 47600602 | 47600709 | + | ENST00000405271;ENST00000456133;ENST00000263735;ENST00000419334 | TAF |
| 12% | chr2 | 47552899 | 47553008 | + | chr2 | 47600602 | 47600709 | + | ENST00000405271;ENST00000456133;ENST00000263735;ENST00000419334 | TAF |
| 12% | chr19 | 1600051 | 1599987 | − | chr19 | 1599559 | 1599439 | − | ENST00000585937;ENST00000591899;ENST00000589880;ENST00000585671 | TAF |
| 12% | chr8 | 39710096 | 39709999 | − | chr8 | 39694731 | 39694655 | − | ENST00000347580;ENST00000379853;ENST00000265708;ENST00000521880 | TAF |
| 12% | chr8 | 39710096 | 39709999 | − | chr8 | 39694731 | 39694655 | − | ENST00000347580;ENST00000379853;ENST00000265708;ENST00000521880 | TAF |
| 12% | chr8 | 39710096 | 39709999 | − | chr8 | 39694731 | 39694655 | − | ENST00000347580;ENST00000379853;ENST00000265708;ENST00000521880 | TAF |
| 12% | chr8 | 39710096 | 39709999 | − | chr8 | 39694731 | 39694655 | − | ENST00000347580;ENST00000379853;ENST00000265708;ENST00000521880 | TAF |
| 12% | chr14 | 70466641 | 70466673 | + | chr14 | 70477471 | 70477663 | + | ENST00000361956;ENST00000381280 | TSF |
| 12% | chr14 | 70466641 | 70466673 | + | chr14 | 70477471 | 70477663 | + | ENST00000361956;ENST00000381280 | TSF |
| 12% | chr10 | 4990318 | 4992053 | + | chr10 | 5008196 | 5008273 | + | ENST00000434459;ENST00000380872;ENST00000380859 | TSF |
| 12% | chr10 | 4990318 | 4992053 | + | chr10 | 5008196 | 5008273 | + | ENST00000434459;ENST00000380872;ENST00000380859 | TSF |
| 12% | chr12 | 15087626 | 15087625 | − | chr12 | 15073982 | 15073866 | − | ENST00000266397;ENST00000540097 | TSF |
| 12% | chr6 | 129918031 | 129917934 | − | chr6 | 129905257 | 129905133 | − | ENST00000368149 | TSF |
| 11% | chr14 | 24107624 | 24107626 | + | chr14 | 24108388 | 24108565 | + | ENST00000432832;ENST00000250383;ENST00000344777 | TAF |
| 11% | chr14 | 24107624 | 24107626 | + | chr14 | 24108388 | 24108565 | + | ENST00000432832;ENST00000250383;ENST00000344777 | TAF |
| 11% | chr14 | 24107624 | 24107626 | + | chr14 | 24108388 | 24108565 | + | ENST00000432832;ENST00000250383;ENST00000344777 | TAF |
| 11% | chr15 | 69682891 | 69682983 | + | chr15 | 69689807 | 69689903 | + | ENST00000395407;ENST00000561153;ENST00000340965 | TAF |
| 11% | chr10 | 4990318 | 4992053 | + | chr10 | 5009119 | 5009235 | + | ENST00000434459;ENST00000380872;ENST00000442997;ENST00000380859 | TAF |
| 11% | chr10 | 4990318 | 4992053 | + | chr10 | 5009119 | 5009235 | + | ENST00000434459;ENST00000380872;ENST00000442997;ENST00000380859 | TAF |
| 11% | chr10 | 4990318 | 4992053 | + | chr10 | 5009119 | 5009235 | + | ENST00000434459;ENST00000380872;ENST00000442997;ENST00000380859 | TAF |
| 11% | chr7 | 27687049 | 27686771 | − | chr7 | 27672045 | 27671955; 27672036 | − | ENST00000265395;ENST00000428288;ENST00000425715 | TAF |
| 11% | chr7 | 27687049 | 27686771 | − | chr7 | 27672045 | 27671955; 27672036 | − | ENST00000265395;ENST00000428288;ENST00000425715 | TAF |
| 11% | chr7 | 27687049 | 27686771 | − | chr7 | 27672045 | 27671955; 27672036 | − | ENST00000265395;ENST00000428288;ENST00000425715 | TAF |
| 11% | chr10 | 101185022 | 101184972 | − | chr10 | 101180562 | 101180381 | − | ENST00000370508;ENST00000543866 | TAF |
| 11% | chr11 | 72412362 | 72412165 | − | chr11 | 72410597 | 72410462 | − | ENST00000359373;ENST00000455638;ENST00000393605;ENST00000334211;ENST00000393609;ENST00000426523;ENST00000429686;ENST00000427971;ENST00000452383 | TAF |
| 11% | chr11 | 72412362 | 72412165 | − | chr11 | 72410597 | 72410462 | − | ENST00000359373;ENST00000455638;ENST00000393605;ENST00000334211;ENST00000393609;ENST00000426523;ENST00000429686;ENST00000427971;ENST00000452383 | TAF |
| 11% | chr11 | 72412362 | 72412165 | − | chr11 | 72410597 | 72410462 | − | ENST00000359373;ENST00000455638;ENST00000393605;ENST00000334211;ENST00 | TAF |

TABLE 28-continued

Transcript fusion for Kidney Chromophobe (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 11% | chr11 | 72412362 | 72412165 | – | chr11 | 72410597 | 72410462 | – | 000393609;ENST00000426523;ENST00000429686;ENST00000427971;ENST00000452383 ENST00000359373;ENST00000455638;ENST00000393605;ENST00000334211;ENST00000393609;ENST00000426523;ENST00000429686;ENST00000427971;ENST00000452383 | TAF |
| 11% | chr9 | 35846065 | 35846070 | + | chr9 | 35846255 | 35846378 | + | ENST00000377996;ENST00000439587;ENST00000377991;ENST00000377988 | TSF |
| 11% | chr9 | 35846065 | 35846070 | + | chr9 | 35846255 | 35846378 | + | ENST00000377996;ENST00000439587;ENST00000377991;ENST00000377988 | TSF |
| 11% | chr18 | 29076431 | 29076818 | + | chr18 | 29098202 | 29098237 | + | ENST00000261590;ENST00000585206 | TSF |
| 11% | chr18 | 29076431 | 29076818 | + | chr18 | 29098202 | 29098237 | + | ENST00000261590;ENST00000585206 | TSF |
| 11% | chr14 | 58545088 | 58544802 | – | chr14 | 58478868 | 58478837 |   | ENST00000267485 | TSF |
| 11% | chr20 | 30457064 | 30457004 | – | chr20 | 30454956 | 30454874 | – | ENST00000278979;ENST00000375966;ENST00000339738;ENST00000428829 | TSF |
| 11% | chr20 | 30457064 | 30457004 | – | chr20 | 30454956 | 30454874 | – | ENST00000278979;ENST00000375966;ENST00000339738;ENST00000428829 | TSF |
| 11% | chr20 | 30457064 | 30457004 | – | chr20 | 30454956 | 30454874 | – | ENST00000278979;ENST00000375966;ENST00000339738;ENST00000428829 | TSF |
| 9% | chr4 | 68436241 | 68436356 | + | chr4 | 68436802 | 68436873 | + | ENST00000265404;ENST00000396225 | TSF |
| 9% | chr19 | 1232978 | 1232910 | – | chr19 | 1231274 | 1230892; 1231100 | – | ENST00000590083;ENST00000382477;ENST00000215376 | TSF |
| 9% | chr19 | 1232978 | 1232910 | – | chr19 | 1231274 | 1230892; 1231100 | – | ENST00000590083;ENST00000382477;ENST00000215376 | TSF |
| 9% | chr | 80022917 | 80022085 | – | chr6 | 79924739 | 79924689 | – | ENST00000275036;ENST00000344726 | TSF |
| 9% | chr6 | 80022917 | 80022085 | – | chr6 | 79924739 | 79924689 | – | ENST00000275036;ENST00000344726 | TSF |
| 9% | chr4 | 10546721 | 10546658 | – | chr4 | 10543904 | 10543879 | – | ENST00000226951;ENST00000442825;ENST00000507719 | TSF |
| 9% | chr4 | 10546721 | 10546658 | – | chr4 | 10543904 | 10543879 | – | ENST00000226951;ENST00000442825;ENST00000507719 | TSF |
| 9% | chr4 | 10546721 | 10546658 | – | chr4 | 10543904 | 10543879 | – | ENST00000226951;ENST00000442825;ENST00000507719 | TSF |
| 9% | chrX | 119449588 | 119449552 | – | chrX | 119438268 | 119438204 | – | ENST00000309720;ENST00000371369;ENST00000440464;ENST00000519908 | TSF |
| 9% | chrX | 119449588 | 119449552 | – | chrX | 119438268 | 119438204 | – | ENST00000309720;ENST00000371369;ENST00000440464; ENST00000519908 | TSF |
| 9% | chrX | 119449588 | 119449552 | – | chrX | 119438268 | 119438204 | – | ENST00000309720;ENST00000371369;ENST00000440464;ENST00000519908 | TSF |
| 9% | chr> | 119449588 | 119449552 | – | chrX | 119438268 | 119438204 | – | ENST00000309720;ENST00000371369;ENST00000440464; ENST00000519908 | TSF |

TABLE 29

Transcript fusion for Kidney Renal Clear Cell Carcinoma (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 53% | chr1 | 60370730 | 60370543 | – | ENST00000371204 | chr1 | 60370188 | 60370144 | – | TAF |
| 47% | chr10 | 14709690 | 14709633 | – | ENST00000181796;ENST00000487335 | chr10 | 14664173 | 14664120 | – | TAF |
| 41% | chr3 | 122658317 | 122658272 | – | ENST00000357599;ENST00000475244;ENST000001 95173;ENST00000451055;ENST00000393583 | chr3 | 122652101 | 122651901 | – | TAF |
| 41% | chr3 | 122658317 | 122658272 | – | ENST00000357599;ENST00000475244;ENST000001 95173;ENST00000451055;ENST00000393583 | chr3 | 122652101 | 122651901 | – | TAF |
| 36% | chr5 | 156464372 | 156464258 | – | ENST00000522693;ENST00000523175;ENST0000033 9252;ENST00000425854;ENST00000544197 | chr5 | 156429918 | 156429891 | – | TSF |
| 29% | chr15 | 85467216 | 85467341 | + | ENST00000538177;ENST00000537216;ENST0000053 7624;ENST00000286749;ENST00000537703;ENST00000394573 | chr15 | 85472528 | 85472791 | + | TAF |
| 29% | chr15 | 85467216 | 85467341 | + | ENST00000538177;ENST00000537216;ENST0000053 7624;ENST00000286749;ENST00000537703;ENST00000394573 | chr15 | 85472528 | 85472791 | + | TAF |
| 27% | chr6 | 25849692; 25849622 | 25849602 | – | ENST00000481949;ENST00000505420;ENST0000039 7060;ENST00000361703;ENST00000360657 | chr6 | 25847464 | 25847164 | – | TAF |
| 27% | chr6 | 25849692; 25849622 | 25849602 | – | ENST00000481949;ENST00000505420;ENST0000039 7060;ENST00000361703;ENST00000360657 | chr6 | 25847464 | 25847164 | + | TAF |
| 27% | chr6 | 25849692; 25849622 | 25849602 | – | ENST00000481949;ENST00000505420;ENST0000039 7060;ENST00000361703;ENST00000360657 | chr6 | 25847464 | 25847164 | + | TAF |

TABLE 29-continued

Transcript fusion for Kidney Renal Clear Cell Carcinoma (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 27% | chr6 | 25849692; 25849622 | 25849602 | − | ENST00000481949;ENST00000505420;ENST00000397060;ENST00000361703;ENST00000360657 | chr6 | 25847464 | 25847164 | − | TAF |
| 19% | chr5 | 177657100; 177657074 | 177656941 | − | ENST00000308158;ENST00000510913;ENST00000323594;ENST00000476170 | chr5 | 177656721 | 177656690 | − | TAF |
| 19% | chr5 | 177657100; 177657074 | 177656941 | − | ENST00000308158;ENST00000510913;ENST00000323594;ENST00000476170 | chr5 | 177656721 | 177656690 | − | TAF |
| 19% | chr5 | 177657100; 177657074 | 177656941 | − | ENST00000308158;ENST00000510913;ENST00000323594;ENST00000476170 | chr5 | 177656721 | 177656690 | − | TAF |
| 19% | chr5 | 147649636 | 147649705 | + | ENST00000512953;ENST00000398450 | chr5 | 147650360 | 147650640 | + | TAF |
| 18% | chr5 | 147649636 | 147649705 | + | ENST00000512953;ENST00000398450 | chr5 | 147650500 | 147650640 | + | TAF |
| 18% | chr7 | 27582719 | 27582586 | − | ENST00000265395;ENST00000425715 | chr7 | 27581374 | 27579272 | − | TAF |
| 18% | chr7 | 27582719 | 27582586 | − | ENST00000265395;ENST00000425715 | chr7 | 27581374 | 27579272 | | TAF |
| 18% | chr5 | 1409240 | 1409141 | − | ENST00000270349;ENST00000453492 | chr5 | 1406873 | 1406748 | − | TSF |
| 17% | chr5 | 147281336 | 147281192 | − | ENST00000318315;ENST00000515291 | chr5 | 147260657 | 147260560 | − | TAF |
| 14% | chr19 | 39433391 | 39433350 | − | ENST00000448145;ENST00000599996;ENST00000292852;ENST00000595329 | chr19 | 39432008 | 39431967 | − | TAF |
| 14% | chr19 | 39433391 | 39433350 | − | ENST00000448145;ENST00000599996;ENST00000292852;ENST00000595329 | chr19 | 39432008 | 39431967 | − | TAF |
| 14% | chr19 | 39433391 | 39433350 | − | ENST00000448145;ENST00000599996;ENST00000292852;ENST00000595329 | chr19 | 39432008 | 39431967 | − | TAF |
| 13% | chr2 | 27320371 | 27320517 | + | ENST00000260599;ENST00000260598;ENST00000429697 | chr2 | 27321791 | 27321916 | + | TAF |
| 13% | chr2 | 27320371 | 27320517 | + | ENST00000260599;ENST00000260598;ENST00000429697 | chr2 | 27321791 | 27321916 | + | TAF |
| 13% | chr2 | 27320371 | 27320517 | + | ENST00000260599;ENST00000260598;ENST00000429697 | chr2 | 27321791 | 27321916 | + | TAF |
| 13% | chr5 | 147281336 | 147281192 | − | ENST00000318315;ENST00000515291 | chr5 | 147230105 | 147229718 | − | TSF |
| 12% | chrX | 152730513 | 152730446 | − | ENST00000370211;ENST00000370212;ENST00000370210 | chrX | 152728559 | 152728505 | − | TAF |
| 12% | chrX | 152730513 | 152730446 | − | ENST00000370211;ENST00000370212;ENST00000370210 | chrX | 152728559 | 152728505 | − | TAF |
| 12% | chr10 | 17061982 | 17061832 | − | ENST00000377833 | chr10 | 17054170 | 17053931 | − | TAF |
| 12% | chr19 | 39435744 | 39435609 | − | ENST00000448145;ENST00000599996;ENST00000292852;ENST00000595329;ENST00000599598 | chr19 | 39434842 | 39434530 | − | TAF |
| 12% | chr19 | 39435744 | 39435609 | − | ENST00000448145;ENST00000599996;ENST00000292852;ENST00000595329;ENST00000599598 | chr19 | 39434842 | 39434530 | − | TAF |
| 12% | chr19 | 39435744 | 39435609 | − | ENST00000448145;ENST00000599996;ENST00000292852;ENST00000595329;ENST00000599598 | chr19 | 39434842 | 39434530 | − | TAF |
| 12% | chr19 | 39435744 | 39435609 | − | ENST00000448145;ENST00000599996;ENST00000292852;ENST00000595329;ENST00000599598 | chr19 | 39434842 | 39434530 | − | TAF |
| 12% | chr4 | 25759228 | 25759156 | − | ENST00000399878;ENST00000264868;ENST00000502949;ENST00000510448 | chr4 | 25723603 | 25723555 | − | TSF |
| 12% | chr4 | 25759228 | 25759156 | − | ENST00000399878;ENST00000264868;ENST00000502949;ENST00000510448 | chr4 | 25723603 | 25723555 | − | TSF |
| 12% | chr4 | 25759228 | 25759156 | − | ENST00000399878;ENST00000264868;ENST00000502949;ENST00000510448 | chr4 | 25723603 | 25723555 | − | TSF |
| 12% | chr4 | 25759228 | 25759156 | − | ENST00000399878;ENST00000264868;ENST00000502949;ENST00000510448 | chr4 | 25723603 | 25723555 | − | TSF |
| 10% | chr6 | 36762426 | 36762367 | − | ENST00000244751 | chr6 | 36760223 | 36760189 | − | TAF |
| 10% | chr16 | 1728314 | 1728357 | + | ENST00000248098;ENST00000562684;ENST00000561516;ENST00000566742;ENST00000566925;ENST00000569765 | chr16 | 1729780 | 1730066 | + | TAF |
| 10% | chr5 | 121405863 | 121405748 | − | ENST00000231004 | chr5 | 121403052 | 121403016 | + | TSF |
| 8% | chr6 | 25691284 | 25691352 | + | ENST00000377961 | chr6 | 25718996 | 25719185 | + | TSF |
| 6% | chr3 | 48716169 | 48715997 | − | ENST00000341520;ENST00000416649;ENST00000294129;ENST00000413374 | chr3 | 48702393 | 48702198 | − | TSF |
| 6% | chr3 | 48716169 | 48715997 | − | ENST00000341520;ENST00000416649;ENST00000294129;ENST00000413374 | chr3 | 48702393 | 48702198 | − | TSF |
| 6% | chr3 | 48716169 | 48715997 | − | ENST00000341520;ENST00000416649;ENST00000294129;ENST00000413374 | chr3 | 48702393 | 48702198 | − | TSF |
| 5% | chr17 | 25934940 | 25935036 | + | ENST00000509603;ENST00000319524;ENST00000268763;ENST00000398988;ENST00000398982 | chr17 | 25936150 | 25936175 | + | TSF |
| 5% | chr17 | 25934940 | 25935036 | + | ENST00000509603;ENST00000319524;ENST00000268763;ENST00000398988;ENST00000398982 | chr17 | 25936150 | 25936175 | + | TSF |
| 5% | chr17 | 25934940 | 25935036 | + | ENST00000509603;ENST00000319524;ENST00000268763;ENST00000398988;ENST00000398982 | chr17 | 25936150 | 25936175 | + | TSF |

TABLE 29-continued

Transcript fusion for Kidney Renal Clear Cell Carcinoma (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 5% | chr17 | 25934940 | 25935036 | + | 68763;ENST00000398988;ENST00000398982 ENST00000509603;ENST00000319524;ENST000002 68763;ENST00000398988;ENST00000398982 | chr17 | 25936150 | 25936175 | + | TSF |
| 5% | chr17 | 18880167 | 18880302 | + | ENST00000317977;ENST00000395642;ENST000003 95647;ENST00000417251;ENST00000395643;ENST0 0000395645 | chr17 | 18897052 | 18897057 | + | TSF |
| 5% | chr17 | 18880167 | 18880302 | + | ENST00000317977;ENST00000395642;ENST000003 95647;ENST00000417251;ENST00000395643;ENST0 0000395645 | chr17 | 18897052 | 18897057 | + | TSF |
| 5% | chr17 | 18880167 | 18880302 | + | ENST00000317977;ENST00000395642;ENST000003 95647;ENST00000417251;ENST00000395643;ENST0 0000395645 | chr17 | 18897052 | 18897057 | + | TSF |
| 5% | chr5 | 147649636 | 147649705 | + | ENST00000512953;ENST00000398450 | chr5 | 147650327 | 147650640 | + | TSF |
| 4% | chr6 | 167352496 | 167352383 | − | ENST00000507747;ENST00000366855;ENST000005 08775;ENST00000476238;ENST00000478180 | chr6 | 167351170 | 167351130 | − | TSF |
| 4% | chr6 | 167352496 | 167352383 | − | ENST00000507747;ENST00000366855;ENST000005 08775;ENST00000476238;ENST00000478180 | chr6 | 167351170 | 167351130 | + | TSF |
| 4% | chr6 | 167352496 | 167352383 | − | ENST00000507747;ENST00000366855;ENST000005 08775;ENST00000476238;ENST00000478180 | chr6 | 167351170 | 167351130 | − | TSF |
| 4% | chr12 | 28636985 | 28637098 | + | ENST00000539107;ENST00000545336;ENST000003 81256;ENST00000381259;ENST00000306172;ENST0 0000535212;ENST00000542801 | chr12 | 28732785 | 28732895 | + | TSF |
| 4% | chr12 | 28636985 | 28637098 | + | ENST00000539107;ENST00000545336;ENST000003 81256;ENST00000381259;ENST00000306172;ENST0 0000535212;ENST00000542801 | chr12 | 28732785 | 28732895 | + | TSF |
| 4% | chr12 | 28636985 | 28637098 | + | ENST00000539107;ENST00000545336;ENST000003 81256;ENST00000381259;ENST00000306172;ENST0 0000535212;ENST00000542801 | chr12 | 28732785 | 28732895 | + | TSF |
| 4% | chr12 | 28636985 | 28637098 | + | ENST00000539107;ENST00000545336;ENST000003 81256;ENST00000381259;ENST00000306172;ENST0 0000535212;ENST00000542801 | chr12 | 28732785 | 28732895 | + | TSF |
| 4% | chr12 | 28636985 | 28637098 | + | ENST00000539107;ENST00000545336;ENST000003 81256;ENST00000381259;ENST00000306172;ENST0 0000535212;ENST00000542801 | chr12 | 28732785 | 28732895 | + | TSF |
| 4% | chr18 | 32650166; 32650159 | 32650286 | + | ENST00000591734;ENST00000413393;ENST000005 87359;ENST00000436190;ENST00000588349;ENST0 0000300249;ENST00000588910;ENST00000589699 | chr18 | 32670836 | 32671096 | + | TSF |
| 4% | chr18 | 32650166; 32650159 | 32650286 | + | ENST00000591734;ENST00000413393;ENST000005 87359;ENST00000436190;ENST00000588349;ENST0 0000300249;ENST00000588910;ENST00000589699 | chr18 | 32670836 | 32671096 | + | TSF |
| 4% | chr18 | 32650166; 32650159 | 32650286 | + | ENST00000591734;ENST00000413393;ENST000005 87359;ENST00000436190;ENST00000588349;ENST0 0000300249;ENST00000588910;ENST00000589699 | chr18 | 32670836 | 32671096 | + | TSF |
| 3% | chr11 | 58480322; 58480359 | 58480233 | − | ENST00000586098;ENST00000344743;ENST000005 29732;ENST00000278400 | chr11 | 58467960 | 58463759 | + | TSF |
| 3% | chr11 | 58480322; 58480359 | 58480233 | − | ENST00000586098;ENST00000344743;ENST000005 29732;ENST00000278400 | chr11 | 58467960 | 58463759 | − | TSF |
| 2% | chr12 | 58024115 | 58023935 | − | ENST00000341156;ENST00000418555;ENST000005 52798;ENST00000549391;ENST00000449184;ENST0 0000550764;ENST00000552350;ENST00000548888 | chr12 | 58023079 | 58022983 | − | TSF |
| 2% | chr12 | 58024115 | 58023935 | − | ENST00000341156;ENST00000418555;ENST000005 52798;ENST00000549391;ENST00000449184;ENST0 0000550764;ENST00000552350;ENST00000548888 | chr12 | 58023079 | 58022983 | + | TSF |
| 2% | chr12 | 58024115 | 58023935 | − | ENST00000341156;ENST00000418555;ENST000005 52798;ENST00000549391;ENST00000449184;ENST0 0000550764;ENST00000552350;ENST00000548888 | chr12 | 58023079 | 58022983 | − | TSF |
| 2% | chr12 | 58024115 | 58023935 | − | ENST00000341156;ENST00000418555;ENST000005 52798;ENST00000549391;ENST00000449184;ENST0 0000550764;ENST00000552350;ENST00000548888 | chr12 | 58023079 | 58022983 | + | TSF |
| 2% | chr7 | 55270210 | 55270401 | + | ENST00000455089 | chr7 | 55272949 | 55272949 | + | TSF |
| 2% | chr2 | 214228800 | 214228869 | + | ENST00000331683;ENST00000413312;ENST000002 72898;ENST00000447990;ENST00000374309 | chr2 | 214233538 | 214233723 | + | TSF |
| 2% | chr2 | 214228800 | 214228869 | + | ENST00000331683;ENST00000413312;ENST000002 72898;ENST00000447990;ENST00000374309 | chr2 | 214233538 | 214233723 | + | TSF |
| 2% | chr2 | 214228800 | 214228869 | + | ENST00000331683;ENST00000413312;ENST000002 72898;ENST00000447990;ENST00000374309 | chr2 | 214233538 | 214233723 | + | TSF |
| 2% | chr15 | 85478552 | 85478749 | + | ENST00000537216;ENST00000537624;ENST000002 86749;ENST00000394573 | chr15 | 85494311 | 85494404 | + | TSF |
| 2% | chr1 | 2492063 | 2492153 | + | ENST00000426449;ENST00000434817;ENST000004 35221;ENST00000451778;ENST00000409119;ENST0 0000355716 | chr1 | 2508457 | 2508463 | + | TSF |
| 2% | chr4 | 25759228 | 25759156 | − | ENST00000399878;ENST00000264868;ENST000005 02949;ENST00000510448 | chr4 | 25732727 | 25732722 | − | TSF |

TABLE 29-continued

Transcript fusion for Kidney Renal Clear Cell Carcinoma (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr4 | 25759228 | 25759156 | − | ENST00000399878;ENST00000264868;ENST00000502949;ENST00000510448 | chr4 | 25732727 | 25732722 | − | TSF |
| 2% | chr4 | 25759228 | 25759156 | − | ENST00000399878;ENST00000264868;ENST00000502949;ENST00000510448 | chr4 | 25732727 | 25732722 | − | TSF |
| 2% | chr4 | 25759228 | 25759156 | − | ENST00000399878;ENST00000264868;ENST00000502949;ENST00000510448 | chr4 | 25732727 | 25732722 | − | TSF |
| 2% | chr3 | 145788954 | 145788829 | − | ENST00000461497;ENST00000282903;ENST00000360060;ENST00000494950 | chr3 | 145784472 | 145784175 | + | TSF |
| 2% | chr3 | 145788954 | 145788829 | − | ENST00000461497;ENST00000282903;ENST00000360060;ENST00000494950 | chr3 | 145784472 | 145784175 | − | TSF |
| 2% | chr3 | 145788954 | 145788829 | − | ENST00000461497;ENST00000282903;ENST00000360060;ENST00000494950 | chr3 | 145784472 | 145784175 | − | TSF |
| 2% | chr3 | 145788954 | 145788829 | − | ENST00000461497;ENST00000282903;ENST00000360060;ENST00000494950 | chr3 | 145784472 | 145784175 | − | TSF |
| 2% | chr3 | 145788954 | 145788829 | − | ENST00000461497;ENST00000282903;ENST00000360060;ENST00000494950 | chr3 | 145784468 | 145784175 | − | TSF |
| 2% | chr3 | 145788954 | 145788829 | − | ENST00000461497;ENST00000282903;ENST00000360060;ENST00000494950 | chr3 | 145784468 | 145784175 | − | TSF |
| 2% | chr3 | 145788954 | 145788829 | − | ENST00000461497;ENST00000282903;ENST00000360060;ENST00000494950 | chr3 | 145784468 | 145784175 | − | TSF |
| 2% | chr3 | 145788954 | 145788829 | − | ENST00000461497;ENST00000282903;ENST00000360060;ENST00000494950 | chr3 | 145784468 | 145784175 | − | TSF |
| 2% | chr3 | 194325174; 194325170 | 194325016 | − | ENST00000392432;ENST00000273580;ENST00000432352;ENST00000381975;ENST00000347147;ENST00000473092;ENST00000452358 | chr3 | 194296178 | 194295847 | − | TSF |
| 2% | chr3 | 194325174; 194325170 | 194325016 | − | ENST00000392432;ENST00000273580;ENST00000432352;ENST00000381975;ENST00000347147;ENST00000473092;ENST00000452358 | chr3 | 194296178 | 194295847 | − | TSF |
| 2% | chr3 | 194325174; 194325170 | 194325016 | − | ENST00000392432;ENST00000273580;ENST00000432352;ENST00000381975;ENST00000347147;ENST00000473092;ENST00000452358 | chr3 | 194296178 | 194295847 | − | TSF |
| 2% | chr3 | 194325174; 194325170 | 194325016 | − | ENST00000392432;ENST00000273580;ENST00000432352;ENST00000381975;ENST00000347147;ENST00000473092;ENST00000452358 | chr3 | 194296178 | 194295847 | − | TSF |
| 2% | chr3 | 194325174; 194325170 | 194325016 | − | ENST00000392432;ENST00000273580;ENST00000432352;ENST00000381975;ENST00000347147;ENST00000473092;ENST00000452358 | chr3 | 194296178 | 194295847 | − | TSF |
| 2% | chr10 | 3177928 | 3178030 | + | ENST00000381125;ENST00000381075;ENST00000381072;ENST00000433193 | chr10 | 3202810 | 3202810 | + | TSF |
| 2% | chr10 | 3177928 | 3178030 | + | ENST00000381125;ENST00000381075;ENST00000381072;ENST00000433193 | chr10 | 3202810 | 3202810 | + | TSF |
| 2% | chr10 | 3177928 | 3178030 | + | ENST00000381125;ENST00000381075;ENST00000381072;ENST00000433193 | chr10 | 3202810 | 3202810 | + | TSF |
| 2% | chr10 | 3177928 | 3178030 | + | ENST00000381125;ENST00000381075;ENST00000381072;ENST00000433193 | chr10 | 3202810 | 3202810 | + | TSF |
| 2% | chr2 | 110671988 | 110672054 | + | ENST00000553749 | chr2 | 110672249 | 110672374 | + | TSF |
| 2% | chr11 | 27147201 | 27147367 | + | ENST00000529202;ENST00000263182;ENST00000528583;ENST00000525090 | chr11 | 27153068 | 27153143 | + | TSF |
| 2% | chr3 | 98600611; 98600498 | 98600384 | − | ENST00000326840;ENST00000326857;ENST00000449482 | chr3 | 98586282 | 98584565 | − | TSF |
| 2% | chr3 | 98600611; 98600498 | 98600384 | − | ENST00000326840;ENST00000326857;ENST00000449482 | chr3 | 98586282 | 98584565 | − | TSF |
| 2% | chr4 | 25759228 | 25759156 | − | ENST00000399878;ENST00000264868;ENST00000502949;ENST00000510448 | chr4 | 25716488 | 25716212 | − | TSF |
| 2% | chr4 | 25759228 | 25759156 | − | ENST00000399878;ENST00000264868;ENST00000502949;ENST00000510448 | chr4 | 25716488 | 25716212 | − | TSF |
| 2% | chr4 | 25759228 | 25759156 | − | ENST00000399878;ENST00000264868;ENST00000502949;ENST00000510448 | chr4 | 25716488 | 25716212 | − | TSF |
| 2% | chr4 | 25759228 | 25759156 | − | ENST00000399878;ENST00000264868;ENST00000502949;ENST00000510448 | chr4 | 25716488 | 25716212 | − | TSF |
| 2% | chr22 | 47071365 | 47071449 | + | ENST00000406902;ENST00000361034;ENST00000408031 | chr22 | 47078308 | 47078350 | + | TSF |
| 2% | chr22 | 47071365 | 47071449 | 1 | ENST00000406902;ENST00000361034;ENST00000408031 | chr22 | 47078308 | 47078350 | + | TSF |
| 2% | chr10 | 64416156 | 64416246 | + | ENST00000410046;ENST00000395251 | chr10 | 64417763 | 64418650 | + | TSF |
| 2% | chr10 | 64416156 | 64416246 | + | ENST00000410046;ENST00000395251 | chr10 | 64417763 | 64418650 | + | TSF |
| 2% | chr16 | 20492144 | 20492243 | + | ENST00000417235;ENST00000536134;ENST00000573854;ENST00000219054;ENST00000575690;ENST00000396104 | chr16 | 20492741 | 20493191 | + | TSF |
| 2% | chr16 | 20492144 | 20492243 | + | ENST00000417235;ENST00000536134;ENST00000573854;ENST00000219054;ENST00000575690;ENST00000396104 | chr16 | 20492741 | 20493191 | + | TSF |

TABLE 29-continued

Transcript fusion for Kidney Renal Clear Cell Carcinoma (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr16 | 20492144 | 20492243 | + | ENST00000417235;ENST00000536134;ENST000005 73854;ENST00000219054;ENST00000575690;ENST0 0000396104 | chr16 | 20492741 | 20493191 | + | TSF |
| 2% | chr17 | 36288631 | 36288740 | + | ENST00000327454;ENST00000378174;ENST000005 05415;ENST00000539424 | chr17 | 36289142 | 36289609 | + | TSF |
| 2% | chr17 | 36288631 | 36288740 | + | ENST00000327454;ENST00000378174;ENST000005 05415;ENST00000539424 | chr17 | 36289142 | 36289609 | + | TSF |
| 2% | chr6 | 25691284 | 25691352 | + | ENST00000377961 | chr6 | 25737488 | 25737845 | + | TSF |
| 2% | chr7 | 151573705 | 151573592 | − | ENST00000287878;ENST00000488258 | chr7 | 151532195 | 151531867 | − | TSF |
| 2% | chr18 | 56182313 | 56182225 | − | ENST00000361673 | chr18 | 56171854 | 56171790 | − | TSF |
| 2% | chr19 | 23556639 | 23556544 | − | ENST00000599743;ENST00000300619 | chr19 | 23491899 | 23491588 | − | TSF |
| 2% | chr12 | 56742407 | 56742313 | − | ENST00000314128;ENST00000557235 | chr12 | 56740986 | 56740975 | − | TSF |
| 2% | chr12 | 56742407 | 56742313 | − | ENST00000314128;ENST00000557235 | chr12 | 56740986 | 56740975 | − | TSF |
| 2% | chr2 | 111214673 | 111214607 | − | ENST00000603767;ENST00000447537 | chr2 | 111214412 | 111214287 | − | TSF |
| 1% | chr15 | 85487987 | 85488098 | + | ENST00000538177;ENST00000537624;ENST000002 86749;ENST00000394573 | chr15 | 85494311 | 85494404 | + | TSF |
| 1% | chr15 | 85487987 | 85488098 | + | ENST00000538177;ENST00000537624;ENST000002 86749;ENST00000394573 | chr15 | 85494311 | 85494404 | + | TSF |
| 1% | chr18 | 72179683 | 72179767 | + | ENST00000324262;ENST00000579847;ENST000005 83785;ENST00000324301;ENST00000579624 | chr18 | 72180493 | 72180593 | + | TSF |
| 1% | chr18 | 72179683 | 72179767 | + | ENST00000324262;ENST00000579847;ENST000005 83785;ENST00000324301;ENST00000579624 | chr18 | 72180493 | 72180593 | + | TSF |
| 1% | chr18 | 72179683 | 72179767 | + | ENST00000324262;ENST00000579847;ENST000005 83785;ENST00000324301;ENST00000579624 | chr18 | 72180493 | 72180593 | + | TSF |
| 1% | chr6 | 25851105 | 25850987 | − | ENST00000397060;ENST00000361703;ENST000003 60657 | chr6 | 25836733 | 25836517 | − | TSF |
| 1% | chr6 | 25851105 | 25850987 | − | ENST00000397060;ENST00000361703;ENST000003 60657 | chr6 | 25836733 | 25836517 | − | TSF |
| 1% | chr19 | 39435744 | 39435609 | − | ENST00000448145;ENST00000599996;ENST000002 92852;ENST00000595329;ENST00000599598 | chr19 | 39435141 | 39434931 | − | TSF |
| 1% | chr19 | 39435744 | 39435609 | − | ENST00000448145;ENST00000599996;ENST000002 92852;ENST00000595329;ENST00000599598 | chr19 | 39435141 | 39434931 | − | TSF |
| 1% | chr19 | 39435744 | 39435609 | − | ENST00000448145;ENST00000599996;ENST000002 92852;ENST00000595329;ENST00000599598 | chr19 | 39435141 | 39434931 | − | TSF |
| 1% | chr19 | 39435744 | 39435609 | − | ENST00000448145;ENST00000599996;ENST000002 92852;ENST00000595329;ENST00000599598 | chr19 | 39435141 | 39434931 | − | TSF |
| 1% | chr3 | 132322171 | 132322073 | − | ENST00000355458;ENST00000264990;ENST000005 45291;ENST00000510100 | chr3 | 132321769 | 132321649 | − | TSF |
| 1% | chr3 | 132322171 | 132322073 | − | ENST00000355458;ENST00000264990;ENST000005 45291;ENST00000510100 | chr3 | 132321769 | 132321649 | − | TSF |
| 1% | chr3 | 132322171 | 132322073 | − | ENST00000355458;ENST00000264990;ENST000005 45291;ENST00000510100 | chr3 | 132321769 | 132321649 | − | TSF |
| 1% | chr17 | 36343995 | 36343886 | − | ENST00000518551;ENST00000354664;ENST000003 39023;ENST00000519532;ENST00000537432 | chr17 | 36343484 | 36343017 | − | TSF |
| 1% | chr17 | 36343995 | 36343886 | − | ENST00000518551;ENST00000354664;ENST000003 39023;ENST00000519532;ENST00000537432 | chr17 | 36343484 | 36343017 | − | TSF |
| 1% | chr17 | 80656472 | 80656331 | − | ENST00000571995;ENST00000538809 | chr17 | 80634662 | 80634498 | − | TSF |
| 1% | chr1 | 163172625 | 163172582 | − | ENST00000313961;ENST00000530507;ENST000005 31476 | chr1 | 163138964 | 163138652 | − | TSF |
| 1% | chr17 | 19470409 | 19470541 | + | ENST00000571335;ENST00000436810;ENST000004 57293;ENST00000270570;ENST00000395585 | chr17 | 19482057 | 19482370 | + | TSF |
| 1% | chr17 | 19470409 | 19470541 | + | ENST00000571335;ENST00000436810;ENST000004 57293;ENST00000270570;ENST00000395585 | chr17 | 19482057 | 19482370 | + | TSF |
| 1% | chr17 | 19470409 | 19470541 | + | ENST00000571335;ENST00000436810;ENST000004 57293;ENST00000270570;ENST00000395585 | chr17 | 19482057 | 19482370 | + | TSF |
| 1% | chr1 | 59811919 | 59812070 | + | ENST00000413489;ENST00000371218;ENST000003 03721;ENST00000430447 | chr1 | 59840819 | 59840959 | + | TSF |
| 1% | chr16 | 3118181 | 3118240 | + | ENST00000325568;ENST00000534507;ENST000005 31965;ENST00000396887;ENST00000526464;ENST0 0000440815;ENST00000529550;ENST00000551122;E NST00000525643;ENST00000548807;ENST00000528 163;ENST00000530890;ENST00000444393;ENST000 00533097;ENST00000008180;ENST00000396890;EN ST00000525228;ENST00000548652;ENST000005253 77;ENST00000530538;ENST00000549213;ENST0000 0552936;ENST00000548476;ENST00000552664;ENS T00000552356;ENST00000551513;ENST0000038221 | chr16 | 3135449 | 3135770 | + | TSF |

TABLE 29-continued

Transcript fusion for Kidney Renal Clear Cell Carcinoma (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr16 | 3118181 | 3118240 | + | ENST00000325568;ENST00000534507;ENST00000531965;ENST00000396887;ENST00000526464;ENST00000440815;ENST00000529550;ENST00000551122;ENST00000525643;ENST00000548807;ENST00000528163;ENST00000530890;ENST00000444393;ENST00000533097;ENST00000008180;ENST00000396890;ENST00000525228;ENST00000548652;ENST00000525377;ENST00000530538;ENST00000549213;ENST00000552936;ENST00000548476;ENST00000552664;ENST00000552356;ENST00000551513;ENST00000382213 | chr16 | 3135449 | 3135770 | + | TSF |
| 1% | chr16 | 3118181 | 3118240 | + | ENST00000325568;ENST00000534507;ENST00000531965;ENST00000396887;ENST00000526464;ENST00000440815;ENST00000529550;ENST00000551122;ENST00000525643;ENST00000548807;ENST00000528163;ENST00000530890;ENST00000444393;ENST00000533097;ENST00000008180;ENST00000396890;ENST00000525228;ENST00000548652;ENST00000525377;ENST00000530538;ENST00000549213;ENST00000552936;ENST00000548476;ENST00000552664;ENST00000552356;ENST00000551513;ENST00000382213 | chr16 | 3135449 | 3135770 | + | TSF |
| 1% | chr16 | 3118181 | 3118240 | + | ENST00000325568;ENST00000534507;ENST00000531965;ENST00000396887;ENST00000526464;ENST00000440815;ENST00000529550;ENST00000551122;ENST00000525643;ENST00000548807;ENST00000528163;ENST00000530890;ENST00000444393;ENST00000533097;ENST00000008180;ENST00000396890;ENST00000525228;ENST00000548652;ENST00000525377;ENST00000530538;ENST00000549213;ENST00000552936;ENST00000548476;ENST00000552664;ENST00000552356;ENST00000551513;ENST00000382213 | chr16 | 3135449 | 3135770 | + | TSF |
| 1% | chr16 | 3118181 | 3118240 | + | ENST00000325568;ENST00000534507;ENST00000531965;ENST00000396887;ENST00000526464;ENST00000440815;ENST00000529550;ENST00000551122;ENST00000525643;ENST00000548807;ENST00000528163;ENST00000530890;ENST00000444393;ENST00000533097;ENST00000008180;ENST00000396890;ENST00000525228;ENST00000548652;ENST00000525377;ENST00000530538;ENST00000549213;ENST00000552936;ENST00000548476;ENST00000552664;ENST00000552356;ENST00000551513;ENST00000382213 | chr16 | 3135449 | 3135770 | + | TSF |
| 1% | chr16 | 3118181 | 3118240 | + | ENST00000325568;ENST00000534507;ENST00000531965;ENST00000396887;ENST00000526464;ENST00000440815;ENST00000529550;ENST00000551122;ENST00000525643;ENST00000548807;ENST00000528163;ENST00000530890;ENST00000444393;ENST00000533097;ENST00000008180;ENST00000396890;ENST00000525228;ENST00000548652;ENST00000525377;ENST00000530538;ENST00000549213;ENST00000552936;ENST00000548476;ENST00000552664;ENST00000552356;ENST00000551513;ENST00000382213 | chr16 | 3135449 | 3135770 | + | TSF |
| 1% | chr16 | 3118181 | 3118240 | + | ENST00000325568;ENST00000534507;ENST00000531965;ENST00000396887;ENST00000526464;ENST00000440815;ENST00000529550;ENST00000551122;ENST00000525643;ENST00000548807;ENST00000528163;ENST00000530890;ENST00000444393;ENST00000533097;ENST00000008180;ENST00000396890;ENST00000525228;ENST00000548652;ENST00000525377;ENST00000530538;ENST00000549213;ENST00000552936;ENST00000548476;ENST00000552664;ENST00000552356;ENST00000551513;ENST00000382213 | chr16 | 3135449 | 3135770 | + | TSF |
| 1% | chr16 | 3118181 | 3118240 | + | ENST00000325568;ENST00000534507;ENST00000531965;ENST00000396887;ENST00000526464;ENST00000440815;ENST00000529550;ENST00000551122;ENST00000525643;ENST00000548807;ENST00000528163;ENST00000530890;ENST00000444393;ENST00000533097;ENST00000008180;ENST00000396890;ENST00000525228;ENST00000548652;ENST00000525377;ENST00000530538;ENST00000549213;ENST0000 | chr16 | 3135449 | 3135770 | + | TSF |

TABLE 29-continued

Transcript fusion for Kidney Renal Clear Cell Carcinoma (KICH) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
|   |   |   |   |   | 0552936;ENST00000548476;ENST00000552664;ENST00000552356;ENST00000551513;ENST00000382213 |   |   |   |   |   |
| 1% | chr10 | 124172436 | 124172561 | + | ENST00000368990;ENST00000368988;ENST00000368989;ENST00000538022;ENST00000392799;ENST00000433307 | chr10 | 124173949 | 124175132 | + | TSF |
| 1% | chr20 | 61300282 | 61300430 | + | ENST00000217159;ENST00000370507;ENST00000451793 | chr20 | 61301309 | 61301456 | + | TSF |
| 1% | chr20 | 61300282 | 61300430 | + | ENST00000217159;ENST00000370507;ENST00000451793 | chr20 | 61301309 | 61301456 | + | TSF |
| 1% | chr8 | 26265743 | 26265892 | + | ENST00000380629;ENST00000523949;ENST00000523515;ENST00000520409;ENST00000518611 | chr8 | 26317396 | 26317454 | + | TSF |
| 1% | chr8 | 26265743 | 26265892 | + | ENST00000380629;ENST00000523949;ENST00000523515;ENST00000520409;ENST00000518611 | chr8 | 26317396 | 26317454 | + | TSF |
| 1% | chr8 | 26265743 | 26265892 | + | ENST00000380629;ENST00000523949;ENST00000523515;ENST00000520409;ENST00000518611 | chr8 | 26317396 | 26317454 | + | TSF |
| 1% | chr9 | 125054028 | 125054119 | + | ENST00000297908;ENST00000344641;ENST00000373723;ENST00000373729;ENST00000394315 | chr9 | 125068067 | 125068171 | + | TSF |
| 1% | chr9 | 125054028 | 125054119 | + | ENST00000297908;ENST00000344641;ENST00000373723;ENST00000373729;ENST00000394315 | chr | 125068067 | 125068171 | + | TSF |
| 1% | chr9 | 125054028 | 125054119 | + | ENST00000297908;ENST00000344641;ENST00000373723;ENST00000373729;ENST00000394315 | chr9 | 125068067 | 125068171 | + | TSF |
| 1% | chr12 | 28605411; 28605475 | 28605587 | + | ENST00000536154;ENST00000539107;ENST00000545336;ENST00000381256;ENST00000381259;ENST00000306172;ENST00000535212;ENST00000542801 | chr12 | 28624332 | 28624630 | + | TSF |
| 1% | chr12 | 28605411; 28605475 | 28605587 | + | ENST00000536154;ENST00000539107;ENST00000545336;ENST00000381256;ENST00000381259;ENST00000306172;ENST00000535212;ENST00000542801 | chr12 | 28624332 | 28624630 | + | TSF |
| 1% | chr12 | 28605411; 28605475 | 28605587 | + | ENST00000536154;ENST00000539107;ENST00000545336;ENST00000381256;ENST00000381259;ENST00000306172;ENST00000535212;ENST00000542801 | chr12 | 28624332 | 28624630 | + | TSF |
| 1% | chr12 | 28605411; 28605475 | 28605587 | + | ENST00000536154;ENST00000539107;ENST00000545336;ENST00000381256;ENST00000381259;ENST00000306172;ENST00000535212;ENST00000542801 | chr12 | 28624332 | 28624630 | + | TSF |
| 1% | chr12 | 28605411; 28605475 | 28605587 | + | ENST00000536154;ENST00000539107;ENST00000545336;ENST00000381256;ENST00000381259;ENST00000306172;ENST00000535212;ENST00000542801 | chr12 | 28624332 | 28624630 | + | TSF |
| 1% | chr12 | 28605411; 28605475 | 28605587 | + | ENST00000536154;ENST00000539107;ENST00000545336;ENST00000381256;ENST00000381259;ENST00000306172;ENST00000535212;ENST00000542801 | chr12 | 28624332 | 28624630 | + | TSF |
| 1% | chr5 | 54993786 | 54993674 | − | ENST00000396865;ENST00000539768;ENST00000318672;ENST00000508124;ENST00000511233;ENST00000503891;ENST00000513993;ENST00000505563;ENST00000506624;ENST00000507109 | chr5 | 54993040 | 54992544 | − | TSF |
| 1% | chr6 | 25861939 | 25861852 | − | ENST00000397060;ENST00000361703;ENST00000360657 | chr6 | 25836733 | 25836517 | − | TSF |
| 1% | chr6 | 25861939 | 25861852 | − | ENST00000397060;ENST00000361703;ENST00000360657 | chr6 | 25836733 | 25836517 | − | TSF |

TABLE 30

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 62% | chr1 | 46797740 | 46797497 | − | chr1 | 46764042 | 46763956 | − | ENST00000343304 | TAF |
| 53% | chr5 | 1407127 | 1406781 | − | chr5 | 1406403 | 1406303 | − | ENST00000270349; ENST00000453492 | TAF |
| 45% | chr4 | 69814157 | 69813728 | − | chr4 | 69811168 | 69811024 | − | ENST00000251566; ENST00000503012 | TAF |
| 45% | chr4 | 69814157 | 69813728 | − | chr4 | 69811168 | 69811024 | − | ENST00000251566; ENST00000503012 | TAF |
| 43% | chr9 | 19118990 | 19118890 | − | chr9 | 19118453 | 19118319 | − | ENST00000411567; ENST00000276914 | TAF |
| 35% | chr6 | 31154067 | 31153803 | − | chr6 | 31133824 | 31133704 | − | ENST00000259915 | TAF |
| 35% | chr10 | 124091515 | 124091773 | + | chr10 | 124091951 | 124092028 | + | ENST00000368994; ENST00000260723 | TAF |
| 29% | chr5 | 176950300 | 176950160 | − | chr5 | 176949072 | 176948976 | − | ENST00000514747; ENST00000329540; ENST00000443375; ENST00000524677 | TAF |
| 29% | chr4 | 111471988 | 111472030 | + | chr4 | 111474471 | 111474611 | + | ENST00000265162 | TAF |
| 24% | chr5 | 176950016 | 176949956 | − | chr5 | 176949072 | 176948976 | − | ENST00000514747; ENST00000329540; ENST00000443375; ENST00000524677 | TAF |
| 23% | chr9 | 75695610 | 75695283 | − | chr | 75555168 | 75555064 | − | ENST00000297785; ENST00000376939; ENST00000419959; ENST00000446946 | TAF |
| 23% | chr9 | 75695610 | 75695283 | − | chr9 | 75555168 | 75555064 | − | ENST00000297785; ENST00000376939; ENST00000419959; ENST00000446946 | TAF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 23% | chr9 | 75695610 | 75695283 | − | chr9 | 75555168 | 75555064 | − | ENST00000297785; ENST00000376939; ENST00000419959; ENST00000446946 | TAF |
| 23% | chr9 | 75695610 | 75695283 | − | chr9 | 75555168 | 75555064 | − | ENST00000297785; ENST00000376939; ENST00000419959; ENST00000446946 | TAF |
| 23% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 23% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 23% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 23% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 23% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 23% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 23% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 21% | chr10 | 3122429 | 3122494 | + | chr10 | 3124580 | 3124653 | + | ENST00000381125; ENST00000381075 | TAF |
| 21% | chr10 | 3122429 | 3122494 | + | chr10 | 3124580 | 3124653 | + | ENST00000381125; ENST00000381075 | TAF |
| 20% | chr10 | 90305421 | 90305214 | − | chr10 | 90122482 | 90122309 | − | ENST00000371947; ENST00000437752; ENST00000331772 | TAF |
| 20% | chr10 | 90305421 | 90305214 | − | chr10 | 90122482 | 90122309 | − | ENST00000371947; ENST00000437752; ENST00000331772 | TAF |
| 20% | chr3 | 195444683 | 195445067 | + | chr3 | 195451551 | 195453443; 195452030 | + | ENST00000447234; ENST00000320736; ENST00000436408 | TAF |
| 20% | chr3 | 195444683 | 195445067 | + | chr3 | 195451551 | 195453443; 195452030 | + | ENST00000447234; ENST00000320736; ENST00000436408 | TAF |
| 20% | chr3 | 195444683 | 195445067 | + | chr3 | 195451551 | 195453443; 195452030 | + | ENST00000447234; ENST00000320736; ENST00000436408 | TAF |
| 20% | chr8 | 28226049 | 28225966 | − | chr8 | 28218659 | 28218493 | − | ENST00000521548 | TSF |
| 20% | chr10 | 3133726 | 3133857 | + | chr10 | 3141467 | 3141544 | + | ENST00000607886; ENST00000381125; ENST00000381075; ENST00000407806 | TSF |
| 20% | chr10 | 3133726 | 3133857 | + | chr10 | 3141467 | 3141544 | + | ENST00000607886; ENST00000381125; ENST00000381075; ENST00000407806 | TSF |
| 20% | chr10 | 3133726 | 3133857 | + | chr10 | 3141467 | 3141544 | + | ENST00000607886; ENST00000381125; ENST00000381075; ENST00000407806 | TSF |
| 20% | chr10 | 3133726 | 3133857 | + | chr10 | 3141467 | 3141544 | + | ENST00000607886; ENST00000381125; ENST00000381075; ENST00000407806 | TSF |
| 18% | chr8 | 72937377 | 72937669 | + | chr8 | 72964774 | 72964806 | + | ENST00000524152; ENST00000519068 | TAF |
| 16% | chr2 | 162903347 | 162903212 | − | chr2 | 162902122 | 162902042 | − | ENST00000360534; ENST00000434918 | TAF |
| 16% | chr2 | 162903347 | 162903212 | − | chr2 | 162902122 | 162902042 | − | ENST00000360534; ENST00000434918 | TAF |
| 16% | chr5 | 135398466 | 135398602 | + | chr5 | 135398875 | 135398915; 135398898 | + | ENST00000442011; ENST00000305126; ENST00000514554; ENST00000508076; ENST00000503087 | TAF |
| 16% | chr5 | 135398466 | 135398602 | + | chr5 | 135398875 | 135398915; 135398898 | + | ENST00000442011; ENST00000305126; ENST00000514554; ENST00000508076; ENST00000503087 | TAF |
| 16% | chr10 | 90305421 | 90305146 | − | chr10 | 90122482 | 90122309 | − | ENST00000371947; ENST00000437752; ENST00000331772 | TAF |
| 16% | chr10 | 90305421 | 90305146 | − | chr10 | 90122482 | 90122309 | − | ENST00000371947; ENST00000437752; ENST00000331772 | TAF |
| 16% | chr6 | 123083025 | 123083103 | + | chr6 | 123101436 | 123101608 | + | ENST00000368444; ENST00000356535 | TSF |
| 16% | chr6 | 123083025 | 123083103 | + | chr6 | 123101436 | 123101608 | + | ENST00000368444; ENST00000356535 | TSF |
| 15% | chr6 | 123101055 | 123101091 | + | chr6 | 123101436 | 123101608 | + | ENST00000368444; ENST00000356535 | TSF |
| 15% | chr6 | 123101055 | 123101091 | + | chr6 | 123101436 | 123101608 | + | ENST00000368444; ENST00000356535 | TSF |
| 14% | chr3 | 122863450 | 122863676 | + | chr3 | 122864369 | 122864384; 122864439 | + | ENST00000489923; ENST00000316218 | TAF |
| 14% | chr3 | 122863450 | 122863676 | + | chr3 | 122864369 | 122864384; | + | ENST00000489923; ENST00000316218 | TAF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 14% | chr9 | 131002678 | 131002811 | + | chr9 | 122864439 131004511 | 131004624 | + | ENST00000475805; ENST00000341179; ENST00000372923; ENST00000393594; ENST00000486160 | TAF |
| 14% | chr9 | 131002678 | 131002811 | + | chr9 | 131004511 | 131004624 | + | ENST00000475805; ENST00000341179; ENST00000372923; ENST00000393594; ENST00000486160 | TAF |
| 14% | chr5 | 172281405 | 172281729 | + | chr5 | 172315702 | 172315763 | + | ENST00000393784; ENST00000520326; ENST00000520642; ENST00000523291 | TAF |
| 14% | chr5 | 172281405 | 172281729 | + | chr5 | 172315702 | 172315763 | + | ENST00000393784; ENST00000520326; ENST00000520642; ENST00000523291 | TAF |
| 14% | chr5 | 172281405 | 172281729 | + | chr5 | 172315702 | 172315763 | + | ENST00000393784; ENST00000520326; ENST00000520642; ENST00000523291 | TAF |
| 14% | chr5 | 172281405 | 172281729 | + | chr5 | 172315702 | 172315763 | + | ENST00000393784; ENST00000520326; ENST00000520642; ENST00000523291 | TAF |
| 14% | chr1 | 236326774 | 236327054 | + | chr1 | 236332006 | 236332055 | + | ENST00000366592; ENST00000454895 | TSF |
| 14% | chr1 | 236326774 | 236327054 | + | chr1 | 236332006 | 236332055 | + | ENST00000366592; ENST00000454895 | TSF |
| 12% | chr15 | 85472494 | 85472633 | + | chr15 | 85478257 | 85478425 | + | ENST00000537216; ENST00000537624; ENST00000286749; ENST00000394573 | TAF |
| 12% | chr15 | 85472494 | 85472633 | + | chr15 | 85478257 | 85478425 | + | ENST00000537216; ENST00000537624; ENST00000286749; ENST00000394573 | TAF |
| 12% | chr15 | 85472494 | 85472633 | + | chr15 | 85478257 | 85478425 | + | ENST00000537216; ENST00000537624; ENST00000286749; ENST00000394573 | TAF |
| 12% | chr9 | 19120331 | 19120171 | − | chr9 | 19119829 | 19119782; 19119648 | − | ENST00000411567; ENST00000276914 | TSF |
| 12% | chr9 | 19120331 | 19120171 | − | chr9 | 19119829 | 19119782; 19119648 | − | ENST00000411567; ENST00000276914 | TSF |
| 11% | chr2 | 218764168 | 218764162 | − | chr2 | 218762692 | 218762521; 218762518 | − | ENST00000446903; ENST00000413554; ENST00000310858; ENST00000423413 | TAF |
| 11% | chr2 | 218764168 | 218764162 | − | chr2 | 218762692 | 218762521; 218762518 | − | ENST00000446903; ENST00000413554; ENST00000310858; ENST00000423413 | TAF |
| 11% | chr2 | 218764168 | 218764162 | − | chr2 | 218762692 | 218762521; 218762518 | − | ENST00000446903; ENST00000413554; ENST00000310858; ENST00000423413 | TAF |
| 11% | chr2 | 218764168 | 218764162 | − | chr2 | 218762692 | 218762521; 218762518 | − | ENST00000446903; ENST00000413554; ENST00000310858; ENST00000423413 | TAF |
| 11% | chr11 | 114177915 | 114178747 | + | chr11 | 114182767 | 114183199 | + | ENST00000535401; ENST00000299964 | TAF |
| 11% | chr4 | 187060473 | 187060762 | + | chr4 | 187070327 | 187070437 | + | ENST00000356371 | TSF |
| 10% | chr2 | 201253013 | 201253278 | + | chr2 | 201253946 | 201254006 | + | ENST00000409755; ENST00000409151 | TAF |
| 10% | chr8 | 22271215 | 22271219 | + | chr8 | 22272293 | 22272415 | + | ENST00000359741; ENST00000240095; ENST00000381237; ENST00000289952; ENST00000517370 | TAF |
| 10% | chr8 | 22271215 | 22271219 | + | chr8 | 22272293 | 22272415 | + | ENST00000359741; ENST00000240095; ENST00000381237; ENST00000289952; ENST00000517370 | TAF |
| 10% | chr8 | 22271215 | 22271219 | + | chr8 | 22272293 | 22272415 | + | ENST00000359741; ENST00000240095; ENST00000381237; ENST00000289952; ENST00000517370 | TAF |
| 10% | chr1 | 9128508 | 9128439 | − | chr1 | 9118309 | 9118211 | − | ENST00000377424; ENST00000377414; ENST00000484798; ENST00000474145; ENST00000479813; ENST00000486632; ENST00000487835; ENST00000464985; ENST00000473209 | TAF |
| 10% | chr1 | 9128508 | 9128439 | − | chr1 | 9118309 | 9118211 | − | ENST00000377424; ENST00000377414; ENST00000484798; ENST00000474145; ENST00000479813; ENST00000486632; ENST00000487835; ENST00000464985; ENST00000473209 | TAF |
| 10% | chr1 | 9128508 | 9128439 | − | chr1 | 9118309 | 9118211 | − | ENST00000377424; ENST00000377414; ENST00000484798; ENST00000474145; ENST00000479813; ENST00000486632; ENST00000487835; ENST00000464985; ENST00000473209 | TAF |
| 10% | chr1 | 9128508 | 9128439 | − | chr1 | 9118309 | 9118211 | − | ENST00000377424; ENST00000377414; ENST00000484798; ENST00000474145; ENST00000479813; ENST00000486632; ENST00000487835; ENST00000464985; ENST00000473209 | TAF |
| 10% | chr1 | 9128508 | 9128439 | − | chr1 | 9118309 | 9118211 | − | ENST00000377424; ENST00000377414; ENST00000484798; ENST00000474145; ENST00000479813; | TAF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 9% | chr7 | 50763323 | 50763289 | − | chr7 | 50742355 | 50742133 | − | ENST00000486632; ENST00000487835; ENST00000464985; ENST00000473209 ENST00000439599; ENST00000398812; ENST00000403097; ENST00000357271; ENST00000401949; ENST00000439044 | TSF |
| 9% | chr7 | 50763323 | 50763289 | − | chr7 | 50742355 | 50742133 | − | ENST00000439599; ENST00000398812; ENST00000403097; ENST00000357271; ENST00000401949; ENST00000439044 | TSF |
| 9% | chr7 | 50763323 | 50763289 | − | chr7 | 50742355 | 50742133 | − | ENST00000439599; ENST00000398812; ENST00000403097; ENST00000357271; ENST00000401949; ENST00000439044 | TSF |
| 9% | chr17 | 39976225 | 39976301 | + | chr17 | 39976521 | 39976713 | + | ENST00000321562; ENST00000455106; ENST00000544340 | TSF |
| 9% | chr4 | 111332609 | 111332609 | + | chr4 | 111409697 | 111409838 | + | ENST00000265162 | TSF |
| 9% | chr3 | 182757105 | 182757101 | − | chr3 | 182756923 | 182756814 | − | ENST00000265594; ENST00000492597; ENST00000497959; ENST00000539926; ENST00000476176 | TSF |
| 9% | chr3 | 182757105 | 182757101 | − | chr3 | 182756923 | 182756814 | − | ENST00000265594; ENST00000492597; ENST00000497959; ENST00000539926; ENST00000476176 | TSF |
| 9% | chr3 | 182757105 | 182757101 | − | chr3 | 182756923 | 182756814 | − | ENST00000265594; ENST00000492597; ENST00000497959; ENST00000539926; ENST00000476176 | TSF |
| 9% | chr3 | 182757105 | 182757101 | − | chr3 | 182756923 | 182756814 | − | ENST00000265594; ENST00000492597; ENST00000497959; ENST00000539926; ENST00000476176 | TSF |
| 7% | chr5 | 31298457 | 31298554 | + | chr5 | 31299571 | 31299738 | + | ENST00000514738; ENST00000265071 | TSF |
| 7% | chr5 | 31298457 | 31298554 | + | chr5 | 31299571 | 31299738 | + | ENST00000514738; ENST00000265071 | TSF |
| 7% | chr10 | 124091515 | 124091773 | + | chr10 | 124094396 | 124094494 | + | ENST00000368994; ENST00000260723 | TSF |
| 7% | chr17 | 39974832 | 39974893 | + | chr17 | 39975462 | 39975651 | + | ENST00000321562 | TSF |
| 7% | chr6 | 123097008 | 123097454 | + | chr6 | 123101436 | 123101608 | + | ENST00000368444; ENST00000356535 | TSF |
| 7% | chr6 | 123097008 | 123097454 | + | chr6 | 123101436 | 123101608 | + | ENST00000368444; ENST00000356535 | TSF |
| 6% | chr16 | 53780019 | 53780292 | + | chr16 | 53844052 | 53844129 | + | ENST00000471389; ENST00000464071 | TSF |
| 6% | chr16 | 53780019 | 53780292 | + | chr16 | 53844052 | 53844129 | + | ENST00000471389; ENST00000464071 | TSF |
| 6% | chr19 | 8438007 | 8438075 | + | chr19 | 8438589 | 8438770 | + | ENST00000301455; ENST00000541807; ENST00000393962; ENST00000593998 | TSF |
| 6% | chrX | 123618682 | 123617816 | − | chrX | 123615814 | 123615582 | − | ENST00000371130; ENST00000422452 | TSF |
| 6% | chr5 | 54280783 | 54280736 | − | chr5 | 54277974 | 54277825 | − | ENST00000381405 | TSF |
| 6% | chr6 | 26370093 | 26370250 | + | chr6 | 26370550 | 26370831; 26370588 | + | ENST00000532865; ENST00000530653; ENST00000527422; ENST00000356386; ENST0000396934; ENST00000377708; ENST00000396948; ENST00000508906 | TSF |
| 6% | chr6 | 26370093 | 26370250 | + | chr6 | 26370550 | 26370831; 26370588 | + | ENST00000532865; ENST00000530653; ENST00000527422; ENST00000356386; ENST00000396934; ENST00000377708; ENST00000396948; ENST00000508906 | TSF |
| 6% | chr6 | 26370093 | 26370250 | + | chr6 | 26370550 | 26370831; 26370588 | + | ENST00000532865; ENST00000530653; ENST00000527422; ENST00000356386; ENST00000396934; ENST00000377708; ENST00000396948; ENST00000508906 | TSF |
| 6% | chr11 | 74751425 | 74751690 | + | chr11 | 74873700 | 74873830 | + | ENST00000289575 | TSF |
| 6% | chr7 | 126136473 | 126136413 | − | chr7 | 126086426 | 126086180; 126086130 | − | ENST00000444921; ENST00000339582; ENST00000358373; ENST00000472701 | TSF |
| 6% | chr7 | 126136473 | 126136413 | − | chr7 | 126086426 | 126086180; 126086130 | − | ENST00000444921; ENST00000339582; ENST00000358373; ENST00000472701 | TSF |
| 5% | chr12 | 58023123 | 58023062 | − | chr12 | 58022929 | 58022831; 58022905 | − | ENST00000341156; ENST00000418555; ENST00000552798; ENST00000549391 | TSF |
| 5% | chr12 | 58023123 | 58023062 | − | chr12 | 58022929 | 58022831; 58022905 | − | ENST00000341156; ENST00000418555; ENST00000552798; ENST00000549391 | TSF |
| 5% | chr12 | 28565851 | 28565871 | + | chr12 | 28603094 | 28603186 | + | ENST00000540794; ENST00000539107; ENST00000536442; ENST00000545336; ENST00000545737; ENST00000381256; ENST00000381259; ENST00000306172 | TSF |
| 5% | chr12 | 28565851 | 28565871 | + | chr12 | 28603094 | 28603186 | + | ENST00000540794; ENST00000539107; ENST00000536442; ENST00000545336; ENST00000545737; ENST00000381256; ENST00000381259; ENST00000306172 | TSF |
| 5% | chr12 | 28565851 | 28565871 | + | chr12 | 28603094 | 28603186 | + | ENST00000540794; ENST00000539107; ENST00000536442; ENST00000545336; ENST00000545737; ENST00000381256; ENST00000381259; ENST00000306172 | TSF |
| 5% | chr12 | 28565851 | 28565871 | + | chr12 | 28603094 | 28603186 | + | ENST00000540794; ENST00000539107; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
|  |  |  |  |  |  |  |  |  | ENST00000536442; ENST00000545336; ENST00000545737; ENST00000381256; ENST00000381259; ENST00000306172 |  |
| 5% | chr1 | 12002791 | 12002835 | + | chr1 | 12008033 | 12008124 | + | ENST00000449038; ENST00000376369; ENST00000429000; ENST00000196061 | TSF |
| 5% | chr1 | 12002791 | 12002835 | + | chr1 | 12008033 | 12008124 | + | ENST00000449038; ENST00000376369; ENST00000429000; ENST00000196061 | TSF |
| 5% | chr1 | 12002791 | 12002835 | + | chr1 | 12008033 | 12008124 | + | ENST00000449038; ENST00000376369; ENST00000429000; ENST00000196061 | TSF |
| 5% | chr5 | 177187536 | 177187438 | − | chr5 | 177175700 | 177175642; 177175700 | − | ENST00000515787; ENST00000503845; ENST00000504518 | TSF |
| 5% | chr5 | 177187536 | 177187438 | − | chr5 | 177175700 | 177175642; 177175700 | − | ENST00000515787; ENST00000503845; ENST00000504518 | TSF |
| 5% | chr5 | 177187536 | 177187438 | − | chr5 | 177175700 | 177175642; 177175700 | − | ENST00000515787; ENST00000503845; ENST00000504518 | TSF |
| 5% | chr2 | 26947307 | 26947428 | + | chr2 | 26950535 | 26951436 | + | ENST00000302909 | TSF |
| 5% | chr3 | 187088030 | 187088050 | + | chr3 | 187088576 | 187089161 | + | ENST00000259030 | TSF |
| 4% | chr5 | 177450235 | 177450333 | + | chr5 | 177462097 | 177462155 | + | ENST00000511856; ENST00000511189 | TSF |
| 4% | chr5 | 177450235 | 177450333 | + | chr5 | 177462097 | 177462155 | + | ENST00000511856; ENST00000511189 | TSF |
| 4% | chr4 | 22601350 | 22601612 | + | chr4 | 22737604 | 22737831 | + | ENST00000508166; ENST00000503442 | TSF |
| 4% | chr4 | 22601350 | 22601612 | + | chr4 | 22737604 | 22737831 | + | ENST00000508166; ENST00000503442 | TSF |
| 4% | chr16 | 84676629 | 84676456 | − | chr16 | 84623868 | 84623711 | − | ENST00000262428 | TSF |
| 4% | chr9 | 19118990 | 19118815 | − | chr9 | 19118453 | 19118319 | − | ENST00000411567; ENST00000276914 | TSF |
| 4% | chr13 | 114503037 | 114503038 | + | chr13 | 114503800 | 114503885 | + | ENST00000375353 | TSF |
| 4% | chr4 | 69919044 | 69920610 | + | chr4 | 69964258 | 69964406 | + | ENST00000305231; ENST00000508661 | TSF |
| 4% | chr4 | 69919044 | 69920610 | + | chr4 | 69964258 | 69964406 | + | ENST00000305231; ENST00000508661 | TSF |
| 4% | chr17 | 80812047 | 80812141 | + | chr17 | 80828100 | 80828256 | + | ENST00000355528; ENST00000397466; ENST00000539345 | TSF |
| 4% | chr17 | 80812047 | 80812141 | + | chr17 | 80828100 | 80828256 | + | ENST00000355528; ENST00000397466; ENST00000539345 | TSF |
| 4% | chr17 | 80812047 | 80812141 | + | chr17 | 80828100 | 80828256 | + | ENST00000355528; ENST00000397466; ENST00000539345 | TSF |
| 4% | chr5 | 175504615 | 175504713 | + | chr5 | 175516466 | 175516524 | + | ENST00000253490 | TSF |
| 4% | chr1 | 162768504 | 162768725 | + | chr1 | 162769533 | 162769727 | + | ENST00000367917; ENST00000254521 | TSF |
| 4% | chr1 | 162768504 | 162768725 | + | chr1 | 162769533 | 162769727 | + | ENST00000367917; ENST00000254521 | TSF |
| 4% | chr1 | 59980221 | 59980497 | + | chr1 | 60019796 | 60019899 | + | ENST00000371218; ENST00000303721; ENST00000430447; ENST00000371212 | TSF |
| 4% | chr1 | 59980221 | 59980497 | + | chr1 | 60019796 | 60019899 | + | ENST00000371218; ENST00000303721; ENST00000430447; ENST00000371212 | TSF |
| 4% | chr1 | 59980221 | 59980497 | + | chr1 | 60019796 | 60019899 | + | ENST00000371218; ENST00000303721; ENST00000430447; ENST00000371212 | TSF |
| 3% | chr3 | 187087097 | 187087144 | + | chr3 | 187088576 | 187089161 | + | ENST00000259030 | TSF |
| 3% | chr19 | 35551883 | 35551974 | + | chr19 | 35556154 | 35556249 | + | ENST00000262626; ENST00000392226; ENST00000597419 | TSF |
| 3% | chr2 | 201327365 | 201327459 | + | chr2 | 201332013 | 201332122; 201332101 | + | ENST00000409718; ENST00000358677; ENST00000409988; ENST00000409385; ENST00000451764; ENST00000360760; ENST00000409140; ENST00000409397; ENST00000409755; ENST00000409151; ENST00000438761 | TSF |
| 3% | chr2 | 201327365 | 201327459 | + | chr2 | 201332013 | 201332122; 201332101 | + | ENST00000409718; ENST00000358677; ENST00000409988; ENST00000409385; ENST00000451764; ENST00000360760; ENST00000409140; ENST00000409397; ENST00000409755; ENST00000409151; ENST00000438761 | TSF |
| 3% | chr2 | 201327365 | 201327459 | + | chr2 | 201332013 | 201332122; 201332101 | + | ENST00000409718; ENST00000358677; ENST00000409988; ENST00000409385; ENST00000451764; ENST00000360760; ENST00000409140; ENST00000409397; ENST00000409755; ENST00000409151; ENST00000438761 | TSF |
| 3% | chr14 | 34409875 | 34409759 | − | chr14 | 34400421 | 34400302 | − | ENST00000250457; ENST00000553215; ENST00000487915 | TSF |
| 3% | chr14 | 34409875 | 34409759 | − | chr14 | 34400421 | 34400302 | − | ENST00000250457; ENST00000553215; ENST00000487915 | TSF |
| 3% | chr6 | 31152226 | 31150660 | − | chr6 | 31133824 | 31133704 | − | ENST00000259915 | TSF |
| 3% | chr12 | 58023123 | 58023062 | − | chr12 | 58022686 | 58022496; 58022484 | − | ENST00000341156; ENST00000418555; ENST00000449184 | TSF |
| 3% | chr12 | 58023123 | 58023062 | − | chr12 | 58022686 | 58022496; 58022484 | − | ENST00000341156; ENST00000418555; ENST00000449184 | TSF |
| 3% | chr1 | 60384788 | 60384761 | − | chr1 | 60381772 | 60381610 | − | ENST00000371204 | TSF |
| 3% | chr1 | 60374334 | 60374278 | − | chr1 | 60373599 | 60373458 | − | ENST00000371204 | TSF |
| 3% | chr1 | 163139462 | 163138881 | − | chr1 | 163138158 | 163138048 | − | ENST00000313961; ENST00000367903; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr1 | 163139462 | 163138881 | − | chr1 | 163138158 | 163138048 | − | ENST00000530507 ENST00000313961; ENST00000367903; ENST00000530507 | TSF |
| 3% | chr11 | 114171770 | 114171954 | + | chr11 | 114182767 | 114183199 | + | ENST00000535401; ENST0000299964 | TSF |
| 3% | chr5 | 156483240 | 156483190 | − | chr5 | 156482544 | 156482212 | − | ENST00000522693; ENST00000523175; ENST00000339252; ENST00000425854; ENST00000544197; ENST00000518745 | TSF |
| 3% | chr5 | 156483240 | 156483190 | − | chr5 | 156482544 | 156482212 | − | ENST00000522693; ENST00000523175; ENST00000339252; ENST00000425854; ENST00000544197; ENST00000518745 | TSF |
| 3% | chr5 | 156483240 | 156483190 | − | chr5 | 156482544 | 156482212 | − | ENST00000522693; ENST00000523175; ENST00000339252; ENST00000425854; ENST00000544197; ENST00000518745 | TSF |
| 3% | chr1 | 85845282 | 85845264 | − | chr1 | 85824530 | 85824431 | − | ENST00000284031; ENST00000539042; ENST00000426972; ENST00000542148 | TSF |
| 3% | chr5 | 1408454 | 1408358 | − | chr5 | 1406403 | 1406303 | − | ENST00000270349; ENST00000453492 | TSF |
| 3% | chr1 | 8924664 | 8924519 | − | chr1 | 8924151 | 8923950 | − | ENST00000234590 | TSF |
| 3% | chr5 | 176950016 | 176949947 | − | chr5 | 176949072 | 176948976 | − | ENST00000514747; ENST00000329540; ENST00000443375; ENST00000524677 | TSF |
| 2% | chr9 | 35678063 | 35678160 | + | chr9 | 35679182 | 35679339 | + | ENST00000378357 | TSF |
| 2% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 2% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 2% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 2% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 2% | chr1 | 161177275 | 161177330 | + | chr1 | 161178983 | 161179103 | + | ENST00000367993; ENST00000392179; ENST00000476409 | TSF |
| 2% | chr1 | 161177275 | 161177330 | + | chr1 | 161178983 | 161179103 | + | ENST00000367993; ENST00000392179; ENST00000476409 | TSF |
| 2% | chr1 | 161177275 | 161177330 | + | chr1 | 161178983 | 161179103 | + | ENST00000367993; ENST00000392179; ENST00000476409 | TSF |
| 2% | chr7 | 139441888 | 139441762 | − | chr7 | 139416814 | 139415731 | − | ENST00000406875; ENST00000428878; ENST00000342645 | TSF |
| 2% | chr7 | 139441888 | 139441762 | − | chr7 | 139416814 | 139415731 | − | ENST00000406875; ENST00000428878; ENST00000342645 | TSF |
| 2% | chr7 | 139441888 | 139441762 | − | chr7 | 139416814 | 139415731 | − | ENST00000406875; ENST00000428878; ENST00000342645 | TSF |
| 2% | chr2 | 31156138 | 31156092 | − | chr2 | 31155060 | 31154934 | − | ENST00000324589; ENST00000349752; ENST00000406653; ENST00000356174; ENST00000420311; ENST00000430167 | TSF |
| 2% | chr2 | 31156138 | 31156092 | − | chr2 | 31155060 | 31154934 | − | ENST00000324589; ENST00000349752; ENST00000406653; ENST00000356174; ENST00000420311; ENST00000430167 | TSF |
| 2% | chr6 | 167367994 | 167367904 | − | chr6 | 167366036 | 167365976 | − | ENST00000507747; ENST00000508775; ENST00000421787; ENST00000476238; ENST00000028008; ENST00000478180 | TSF |
| 2% | chr6 | 167367994 | 167367904 | − | chr6 | 167366036 | 167365976 | − | ENST00000507747; ENST00000508775; ENST00000421787; ENST00000476238; ENST00000028008; ENST00000478180 | TSF |
| 2% | chr6 | 167367994 | 167367904 | − | chr6 | 167366036 | 167365976 | − | ENST00000507747; ENST00000508775; ENST00000421787; ENST00000476238; ENST00000028008; ENST00000478180 | TSF |
| 2% | chr6 | 167367994 | 167367904 | | chr6 | 167366036 | 167365976 | − | ENST00000507747; ENST00000508775; ENST00000421787; ENST00000476238; ENST00000028008; ENST00000478180 | TSF |
| 2% | chr6 | 167367994 | 167367904 | − | chr6 | 167366036 | 167365976 | − | ENST00000507747; ENST00000508775; ENST00000421787; ENST00000476238; ENST00000028008; ENST00000478180 | TSF |
| 2% | chr12 | 15812051 | 15811892 | − | chr12 | 15811519 | 15811431 | − | ENST00000543523; ENST00000281172; ENST00000543612; ENST00000540613; ENST00000542903 | TSF |
| 2% | chr2 | 210938033 | 210937924 | − | chr2 | 210908828 | 210908663; 210908637 | − | ENST00000281772; ENST00000418791; ENST00000457374; ENST00000452086; ENST00000428655 | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr2 | 210938033 | 210937924 | − | chr2 | 210908828 | 210908663; 210908637 | − | ENST00000281772; ENST00000418791; ENST00000457374; ENST00000452086; ENST00000428655 | TSF |
| 2% | chr2 | 210938033 | 210937924 | − | chr2 | 210908828 | 210908663; 210908637 | − | ENST00000281772; ENST00000418791; ENST00000457374; ENST00000452086; ENST00000428655 | TSF |
| 2% | chr2 | 210938033 | 210937924 | − | chr2 | 210908828 | 210908663; 210908637 | − | ENST00000281772; ENST00000418791; ENST00000457374; ENST00000452086; ENST00000428655 | TSF |
| 2% | chr12 | 28378695 | 28378794 | + | chr12 | 28458582 | 28458727; 28458739 | + | ENST00000538586; ENST00000539107; ENST00000536442; ENST00000545336; ENST00000543534; ENST00000543809; ENST00000545737; ENST00000381256; ENST00000381259; ENST00000306172 | TSF |
| 2% | chr12 | 28378695 | 28378794 | + | chr12 | 28458582 | 28458727; 28458739 | + | ENST00000538586; ENST00000539107; ENST00000536442; ENST00000545336; ENST00000543534; ENST00000543809; ENST00000545737; ENST00000381256; ENST00000381259; ENST00000306172 | TSF |
| 2% | chr12 | 28378695 | 28378794 | + | chr12 | 28458582 | 28458727; 28458739 | + | ENST00000538586; ENST00000539107; ENST00000536442; ENST00000545336; ENST00000543534; ENST00000543809; ENST00000545737; ENST00000381256; ENST00000381259; ENST00000306172 | TSF |
| 2% | chr12 | 28378695 | 28378794 | + | chr12 | 28458582 | 28458727; 28458739 | + | ENST00000538586; ENST00000539107; ENST00000536442; ENST00000545336; ENST00000543534; ENST00000543809; ENST00000545737; ENST00000381256; ENST00000381259; ENST00000306172 | TSF |
| 2% | chr12 | 28378695 | 28378794 | + | chr12 | 28458582 | 28458727; 28458739 | + | ENST00000538586; ENST00000539107; ENST00000536442; ENST00000545336; ENST00000543534; ENST00000543809; ENST00000545737; ENST00000381256; ENST00000381259; ENST00000306172 | TSF |
| 2% | chr12 | 28378695 | 28378794 | + | chr12 | 28458582 | 28458727; 28458739 | + | ENST00000538586; ENST00000539107; ENST00000536442; ENST00000545336; ENST00000543534; ENST00000543809; ENST00000545737; ENST00000381256; ENST00000381259; ENST00000306172 | TSF |
| 2% | chr9 | 127110792 | 127110909 | + | chr9 | 127113116 | 127113226 | + | ENST00000540326; ENST00000373603; ENST00000373600; ENST00000320246; ENST00000545174; ENST00000394199; ENST00000546191; ENST00000539416 | TSF |
| 2% | chr19 | 18506969 | 18506886 | − | chr19 | 18502935 | 18502797 | − | ENST00000339007; ENST00000595840 | TSF |
| 2% | chr21 | 42609094 | 42609191 | + | chr21 | 42609440 | 42609656 | + | ENST00000328735; ENST00000330333; ENST00000347667 | TSF |
| 2% | chr21 | 42609094 | 42609191 | + | chr21 | 42609440 | 42609656 | + | ENST00000328735; ENST00000330333; ENST00000347667 | TSF |
| 2% | chr21 | 42609094 | 42609191 | + | chr21 | 42609440 | 42609656 | + | ENST00000328735; ENST00000330333; ENST00000347667 | TSF |
| 2% | chr4 | 52913536 | 52913266 | − | chr4 | 52899806 | 52899597 | − | ENST00000381431; ENST00000506357; ENST00000514133 | TSF |
| 2% | chr4 | 52913536 | 52913266 | − | chr4 | 52899806 | 52899597 | − | ENST00000381431; ENST00000506357; ENST00000514133 | TSF |
| 2% | chrX | 119449588 | 119449548 | − | chrX | 119438346 | 119438204 | − | ENST00000309720; ENST00000371369; ENST00000440464; ENST00000519908 | TSF |
| 2% | chrX | 119449588 | 119449548 | − | chrX | 119438346 | 119438204 | − | ENST00000309720; ENST00000371369; ENST00000440464; ENST00000519908 | TSF |
| 2% | chrX | 119449588 | 119449548 | − | chrX | 119438346 | 119438204 | − | ENST00000309720; ENST00000371369; ENST00000440464; ENST00000519908 | TSF |
| 2% | chrX | 119449588 | 119449548 | − | chrX | 119438346 | 119438204 | − | ENST00000309720; ENST00000371369; ENST00000440464; ENST00000519908 | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 2% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 2% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 2% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 2% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 2% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 2% | chr4 | 6959398 | 6959457 | + | chr4 | 6969031 | 6969151 | + | ENST00000448507; ENST00000409757; ENST00000410031 | TSF |
| 2% | chr2 | 71895365 | 71895374 | + | chr2 | 71895884 | 71895972 | + | ENST00000409582; ENST00000409762; ENST00000413539; ENST00000429174; ENST00000258104; ENST00000394120; ENST00000409366; ENST00000409651; ENST00000409744; ENST00000410020; ENST00000410041 | TSF |
| 2% | chr8 | 39778739 | 39778956 | + | chr8 | 39780071 | 39780173; 39780170; 39780150 | + | ENST00000519154; ENST00000522495; ENST00000518237; ENST00000253513 | TSF |
| 2% | chr8 | 39778739 | 39778956 | + | chr8 | 39780071 | 39780173; 39780170; 39780150 | + | ENST00000519154; ENST00000522495; ENST00000518237; ENST00000253513 | TSF |
| 2% | chr8 | 39778739 | 39778956 | + | chr8 | 39780071 | 39780173; 39780170; 39780150 | + | ENST00000519154; ENST00000522495; ENST00000518237; ENST00000253513 | TSF |
| 2% | chr2 | 132237131 | 132237231 | + | chr2 | 132237642 | 132238322 | + | ENST00000321253 | TSF |
| 2% | chr1 | 156337404 | 156337862 | + | chr1 | 156339110 | 156339227 | + | ENST00000537040; ENST00000544720; ENST00000368246; ENST00000368247; ENST00000368249; ENST00000446171; ENST00000368245 | TSF |
| 2% | chr1 | 156337404 | 156337862 | + | chr1 | 156339110 | 156339227 | + | ENST00000537040; ENST00000544720; ENST00000368246; ENST00000368247; ENST00000368249; ENST00000446171; ENST00000368245 | TSF |
| 2% | chr1 | 156337404 | 156337862 | + | chr1 | 156339110 | 156339227 | + | ENST00000537040; ENST00000544720; ENST00000368246; ENST00000368247; ENST00000368249; ENST00000446171; ENST00000368245 | TSF |
| 2% | chr1 | 156337404 | 156337862 | + | chr1 | 156339110 | 156339227 | + | ENST00000537040; ENST00000544720; ENST00000368246; ENST00000368247; ENST00000368249; ENST00000446171; ENST00000368245 | TSF |
| 2% | chr1 | 156337404 | 156337862 | + | chr1 | 156339110 | 156339227 | + | ENST00000537040; ENST00000544720; ENST00000368246; ENST00000368247; ENST00000368249; ENST00000446171; ENST00000368245 | TSF |
| 2% | chr4 | 10533364 | 10533137 | − | chr4 | 10527546 | 10527465 | − | ENST00000226951 | TSF |
| 2% | chr3 | 122652679 | 122652013 | − | chr3 | 122647905 | 122647843 | − | ENST00000357599; ENST00000475244; ENST00000195173; ENST00000451055; ENST00000393583 | TSF |
| 2% | chr3 | 122652679 | 122652013 | − | chr3 | 122647905 | 122647843 | − | ENST00000357599; ENST00000475244; ENST00000195173; ENST00000451055; ENST00000393583 | TSF |
| 2% | chr3 | 122652679 | 122652013 | − | chr3 | 122647905 | 122647843 | − | ENST00000357599; ENST00000475244; ENST00000195173; ENST00000451055; ENST00000393583 | TSF |
| 2% | chr3 | 122652679 | 122652013 | − | chr3 | 122647905 | 122647843 | − | ENST00000357599; ENST00000475244; ENST00000195173; ENST00000451055; ENST00000393583 | TSF |
| 2% | chr4 | 10546721 | 10546658 | − | chr4 | 10543904 | 10543879 | − | ENST00000226951; ENST00000442825; ENST00000507719 | TSF |
| 2% | chr4 | 10546721 | 10546658 | − | chr4 | 10543904 | 10543879 | − | ENST00000226951; ENST00000442825; ENST00000507719 | TSF |
| 2% | chr4 | 10546721 | 10546658 | − | chr4 | 10543904 | 10543879 | − | ENST00000226951; ENST00000442825; ENST00000507719 | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chrX | 119449588 | 119449552 | − | chrX | 119438346 | 119438204 | − | ENST00000309720; ENST00000371369; ENST00000440464; ENST00000519908 | TSF |
| 2% | chrX | 119449588 | 119449552 | − | chrX | 119438346 | 119438204 | − | ENST00000309720; ENST00000371369; ENST00000440464; ENST00000519908 | TSF |
| 2% | chrX | 119449588 | 119449552 | − | chrX | 119438346 | 119438204 | − | ENST00000309720; ENST00000371369; ENST00000440464; ENST00000519908 | TSF |
| 2% | chrX | 119449588 | 119449552 | − | chrX | 119438346 | 119438204 | − | ENST00000309720; ENST00000371369; ENST00000440464; ENST00000519908 | TSF |
| 2% | chr10 | 124173941 | 124174189 | + | chr10 | 124175375 | 124175518 | + | ENST00000368990; ENST00000368988; ENST00000368989; ENST00000538022; ENST00000392799; ENST00000433307 | TSF |
| 2% | chr10 | 124173941 | 124174189 | + | chr10 | 124175375 | 124175518 | + | ENST00000368990; ENST00000368988; ENST00000368989; ENST00000538022; ENST00000392799; ENST00000433307 | TSF |
| 2% | chr10 | 124173941 | 124174189 | + | chr10 | 124175375 | 124175518 | + | ENST00000368990; ENST00000368988; ENST00000368989; ENST00000538022; ENST00000392799; ENST00000433307 | TSF |
| 2% | chr16 | 4702240 | 4702316 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702316 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702316 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702316 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702316 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702316 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702316 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702316 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702316 | + | chr16 | 4702679 | 4702825 | + | ENST00000591895; ENST00000262370; ENST00000415496; ENST00000536343; ENST00000587747; ENST00000399577; ENST00000588994; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | ENST00000586183; ENST00000590790; ENST00000593224 | |
| 2% | chr7 | 33006587 | 33006627 | + | chr7 | 33014229 | 33014374 | + | ENST00000242209; ENST00000538336 | TSF |
| 2% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 2% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 2% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 2% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 2% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 2% | chr4 | 111332609 | 111332609 | + | chr4 | 111397768 | 111398214 | + | ENST00000265162 | TSF |
| 2% | chr1 | 60391887 | 60391853 | − | chr1 | 60381772 | 60381610 | − | ENST00000371204 | TSF |
| 2% | chr6 | 25865287 | 25864286 | − | chr6 | 25862672 | 25862461 | − | ENST00000397060; ENST00000361703; ENST00000360657; ENST00000506105; ENST00000449356 | TSF |
| 2% | chr6 | 25865287 | 25864286 | − | chr6 | 25862672 | 25862461 | − | ENST00000397060; ENST00000361703; ENST00000360657; ENST00000506105; ENST00000449356 | TSF |
| 2% | chr6 | 25865287 | 25864286 | − | chr6 | 25862672 | 25862461 | − | ENST00000397060; ENST00000361703; ENST00000360657; ENST00000506105; ENST00000449356 | TSF |
| 2% | chr7 | 120447469 | 120447344 | − | chr7 | 120446746 | 120446603 | − | ENST00000222747; ENST00000415871 | TSF |
| 2% | chr1 | 161519332 | 161519206 | − | chr1 | 161518821 | 161518801 | − | ENST00000367969; ENST00000443193; ENST00000436743; ENST00000367967; ENST00000426740; ENST00000442336 | TSF |
| 2% | chr1 | 161519332 | 161519206 | − | chr1 | 161518821 | 161518801 | − | ENST00000367969; ENST00000443193; ENST00000436743; ENST00000367967; ENST00000426740; ENST00000442336 | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr1 | 161519332 | 161519206 | − | chr1 | 161518821 | 161518801 | − | ENST00000367969; ENST00000443193; ENST00000436743; ENST00000367967; ENST00000426740; ENST00000442336 | TSF |
| 2% | chr16 | 4702240 | 4702295 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702295 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702295 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702295 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702295 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702295 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702295 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702295 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr16 | 4702240 | 4702295 | + | chr16 | 4702679 | 4702825 | + | ENST00000591895; ENST00000262370; ENST00000415496; ENST00000536343; ENST00000587747; ENST00000399577; ENST00000588994; ENST00000586183; ENST00000590790; ENST00000593224 | TSF |
| 2% | chr12 | 123070929 | 123070983 | + | chr12 | 123071248 | 123071304 | + | ENST00000333479 | TSF |
| 2% | chr16 | 30057952 | 30057991 | + | chr16 | 30078595 | 30078687; 30078611; 30078654 | + | ENST00000338110; ENST00000395248; ENST00000566897; ENST00000568435; ENST00000562168; ENST00000569545; ENST00000563060; ENST00000412304; ENST00000563987; ENST00000564546; ENST00000564595; ENST00000569798; ENST00000395240; ENST00000566846; ENST00000562679 | TSF |
| 2% | chr16 | 30057952 | 30057991 | + | chr16 | 30078595 | 30078687; 30078611; 30078654 | + | ENST00000338110; ENST00000395248; ENST00000566897; ENST00000568435; ENST00000562168; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | ENST00000569545; ENST00000563060; ENST00000412304; ENST00000563987; ENST00000564546; ENST00000564595; ENST00000569798; ENST00000395240; ENST00000566846; ENST00000562679 | |
| 2% | chr16 | 30057952 | 30057991 | + | chr16 | 30078595 | 30078687; 30078611; 30078654 | + | ENST00000338110; ENST00000395248; ENST00000566897; ENST00000568435; ENST00000562168; ENST00000569545; ENST00000563060; ENST00000412304; ENST00000563987; ENST00000564546; ENST00000564595; ENST00000569798; ENST00000395240; ENST00000566846; ENST00000562679 | TSF |
| 2% | chr16 | 30057952 | 30057991 | + | chr16 | 30078595 | 30078687; 30078611; 30078654 | + | ENST00000338110; ENST00000395248; ENST00000566897; ENST00000568435; ENST00000562168; ENST00000569545; ENST00000563060; ENST00000412304; ENST00000563987; ENST00000564546; ENST00000564595; ENST00000569798; ENST00000395240; ENST00000566846; ENST00000562679 | TSF |
| 2% | chr16 | 30057952 | 30057991 | + | chr16 | 30078595 | 30078687; 30078611; 30078654 | + | ENST00000338110; ENST00000395248; ENST00000566897; ENST00000568435; ENST00000562168; ENST00000569545; ENST00000563060; ENST00000412304; ENST00000563987; ENST00000564546; ENST00000564595; ENST00000569798; ENST00000395240; ENST00000566846; ENST00000562679 | TSF |
| 2% | chr16 | 30057952 | 30057991 | + | chr16 | 30078595 | 30078687; 30078611; 30078654 | + | ENST00000338110; ENST00000395248; ENST00000566897; ENST00000568435; ENST00000562168; ENST00000569545; ENST00000563060; ENST00000412304; ENST00000563987; ENST00000564546; ENST00000564595; ENST00000569798; ENST00000395240; ENST00000566846; ENST00000562679 | TSF |
| 2% | chr16 | 30057952 | 30057991 | + | chr16 | 30078595 | 30078687; 30078611; 30078654 | + | ENST00000338110; ENST00000395248; ENST00000566897; ENST00000568435; ENST00000562168; ENST00000569545; ENST00000563060; ENST00000412304; ENST00000563987; ENST00000564546; ENST00000564595; ENST00000569798; ENST00000395240; ENST00000566846; ENST00000562679 | TSF |
| 2% | chr16 | 30057952 | 30057991 | + | chr16 | 30078595 | 30078687; 30078611; 30078654 | + | ENST00000338110; ENST00000395248; ENST00000566897; ENST00000568435; ENST00000562168; ENST00000569545; ENST00000563060; ENST00000412304; ENST00000563987; ENST00000564546; ENST00000564595; ENST00000569798; ENST00000395240; ENST00000566846; ENST00000562679 | TSF |
| 2% | chr18 | 668506 | 668576 | + | chr18 | 669072 | 669173 | + | ENST00000323274; ENST00000323250 | TSF |
| 2% | chr8 | 104389530 | 104389536 | + | chr8 | 104390255 | 104390471 | + | ENST00000330295; ENST00000520337 | TSF |
| 2% | chr4 | 22715811 | 22716168 | + | chr4 | 22737604 | 22737831 | + | ENST00000508166; ENST00000503442 | TSF |
| 2% | chr4 | 22715811 | 22716168 | + | chr4 | 22737604 | 22737831 | + | ENST00000508166; ENST00000503442 | TSF |
| 2% | chr20 | 389765 | 390021 | + | chr20 | 390525 | 390669 | + | ENST00000411647; ENST00000382214; ENST00000356286; ENST00000415942; ENST00000475269 | TSF |
| 2% | chr20 | 389765 | 390021 | + | chr20 | 390525 | 390669 | + | ENST00000411647; ENST00000382214; ENST00000356286; ENST00000415942; ENST00000475269 | TSF |
| 2% | chr20 | 389765 | 390021 | + | chr20 | 390525 | 390669 | + | ENST00000411647; ENST00000382214; ENST00000356286; ENST00000415942; ENST00000475269 | TSF |
| 2% | chr20 | 389765 | 390021 | + | chr20 | 390525 | 390669 | + | ENST00000411647; ENST00000382214; ENST00000356286; ENST00000415942; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr20 | 389765 | 390021 | + | chr20 | 390525 | 390669 | + | ENST00000475269 ENST00000411647; ENST00000382214; ENST00000356286; ENST00000415942; ENST00000475269 | TSF |
| 2% | chr19 | 1114930 | 1114676 | − | chr19 | 1114421 | 1114230 | − | ENST00000361757; ENST00000587024; ENST00000438103 | TSF |
| 2% | chr15 | 63668307 | 63668160 | − | chr15 | 63667877 | 63667857 | − | ENST00000178638; ENST00000344366; ENST00000422263 | TSF |
| 2% | chr15 | 63668307 | 63668160 | − | chr15 | 63667877 | 63667857 | − | ENST00000178638; ENST00000344366; ENST00000422263 | TSF |
| 2% | chr15 | 63668307 | 63668160 | − | chr15 | 63667877 | 63667857 | − | ENST00000178638; ENST00000344366; ENST00000422263 | TSF |
| 2% | chr20 | 10628319 | 10628254 | − | chr20 | 10627751 | 10627587 | − | ENST00000254958; ENST00000423891 | TSF |
| 2% | chr1 | 42660454 | 42660441 | − | chr1 | 42657390 | 42656974; 42657077 | − | ENST00000372572; ENST00000372573; ENST00000361346; ENST00000361776; ENST00000545068; ENST00000445886 | TSF |
| 2% | chr1 | 42660454 | 42660441 | − | chr1 | 42657390 | 42656974; 42657077 | − | ENST00000372572; ENST00000372573; ENST00000361346; ENST00000361776; ENST00000545068; ENST00000445886 | TSF |
| 2% | chr4 | 122175026 | 122174730 | − | chr4 | 122137655 | 122137570 | − | ENST00000509841 | TSF |
| 1% | chr8 | 24354477 | 24354747 | + | chr8 | 24356749 | 24356829 | + | ENST00000175238; ENST00000380789; ENST00000520720 | TSF |
| 1% | chr8 | 24354477 | 24354747 | + | chr8 | 24356749 | 24356829 | + | ENST00000175238; ENST00000380789; ENST00000520720 | TSF |
| 1% | chr8 | 24354477 | 24354747 | + | chr8 | 24356749 | 24356829 | + | ENST00000175238; ENST00000380789; ENST00000520720 | TSF |
| 1% | chr12 | 28378695 | 28378794 | + | chr12 | 28544237 | 28544344 | + | ENST00000540794; ENST00000536442; ENST00000545336; ENST00000543809; ENST00000545737; ENST00000381259; ENST00000306172 | TSF |
| 1% | chr12 | 28378695 | 28378794 | + | chr12 | 28544237 | 28544344 | + | ENST00000540794; ENST00000536442; ENST00000545336; ENST00000543809; ENST00000545737; ENST00000381259; ENST00000306172 | TSF |
| 1% | chr12 | 28378695 | 28378794 | + | chr12 | 28544237 | 28544344 | + | ENST00000540794; ENST00000536442; ENST00000545336; ENST00000543809; ENST00000545737; ENST00000381259; ENST00000306172 | TSF |
| 1% | chr12 | 28378695 | 28378794 | + | chr12 | 28544237 | 28544344 | + | ENST00000540794; ENST00000536442; ENST00000545336; ENST00000543809; ENST00000545737; ENST00000381259; ENST00000306172 | TSF |
| 1% | chr12 | 28378695 | 28378794 | + | chr12 | 28544237 | 28544344 | + | ENST00000540794; ENST00000536442; ENST00000545336; ENST00000543809; ENST00000545737; ENST00000381259; ENST00000306172 | TSF |
| 1% | chr22 | 25020098 | 25020113 | + | chr22 | 25023399 | 25023586; 25023457 | + | ENST00000248923; ENST00000412658; ENST00000400382; ENST00000400383; ENST00000400380; ENST00000406383; ENST00000425895 | TSF |
| 1% | chr22 | 25020098 | 25020113 | + | chr22 | 25023399 | 25023586; 25023457 | + | ENST00000248923; ENST00000412658; ENST00000400382; ENST00000400383; ENST00000400380; ENST00000406383; ENST00000425895 | TSF |
| 1% | chr22 | 25020098 | 25020113 | + | chr22 | 25023399 | 25023586; 25023457 | + | ENST00000248923; ENST00000412658; ENST00000400382; ENST00000400383; ENST00000400380; ENST00000406383; ENST00000425895 | TSF |
| 1% | chr15 | 85469743 | 85469889 | + | chr15 | 85478257 | 85478425 | + | ENST00000537216; ENST00000537624; ENST00000286749; ENST00000394573 | TSF |
| 1% | chr15 | 85469743 | 85469889 | + | chr15 | 85478257 | 85478425 | + | ENST00000537216; ENST00000537624; ENST00000286749; ENST00000394573 | TSF |
| 1% | chr15 | 85469743 | 85469889 | + | chr15 | 85478257 | 85478425 | + | ENST00000537216; ENST00000537624; ENST00000286749; ENST00000394573 | TSF |
| 1% | chr13 | 102181928 | 102182187 | + | chr13 | 102220050 | 102220196 | + | ENST00000376180; ENST00000376162 | TSF |
| 1% | chr7 | 76921651 | 76921792 | + | chr7 | 76922269 | 76922517 | + | ENST00000285871; ENST00000431197 | TSF |
| 1% | chr7 | 98448201 | 98448151 | − | chr7 | 98446318 | 98446206 | − | ENST00000416379; ENST00000339375; ENST00000450876; ENST00000345589; ENST00000546258 | TSF |
| 1% | chr7 | 98448201 | 98448151 | − | chr7 | 98446318 | 98446206 | − | ENST00000416379; ENST00000339375; ENST00000450876; ENST00000345589; ENST00000546258 | TSF |
| 1% | chrX | 152937975 | 152937874 | − | chrX | 152937655 | 152937581; 152937592; 152937597 | − | ENST00000340888; ENST00000370150; ENST00000393831; ENST00000370142; ENST00000370145; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chrX | 152937975 | 152937874 | − | chrX | 152937655 | 152937581; 152937592; 152937597 | − | ENST00000447676; ENST00000439087; ENST00000433470; ENST00000422811; ENST00000411968; ENST00000418241; ENST00000434652 ENST00000340888; ENST00000370150; ENST00000393831; ENST00000370142; ENST00000370145; | TSF |
| 1% | chrX | 152937975 | 152937874 | − | chrX | 152937655 | 152937581; 152937592; 152937597 | − | ENST00000447676; ENST00000439087; ENST00000433470; ENST00000422811; ENST00000411968; ENST00000418241; ENST00000434652 ENST00000340888; ENST00000370150; ENST00000393831; ENST00000370142; ENST00000370145; | TSF |
| 1% | chrX | 152937975 | 152937874 | − | chrX | 152937655 | 152937581; 152937592; 152937597 | − | ENST00000447676; ENST00000439087; ENST00000433470; ENST00000422811; ENST00000411968; ENST00000418241; ENST00000434652 ENST00000340888; ENST00000370150; ENST00000393831; ENST00000370142; ENST00000370145; | TSF |
| 1% | chrX | 152937975 | 152937874 | − | chrX | 152937655 | 152937581; 152937592; 152937597 | − | ENST00000340888; ENST00000370150; ENST00000393831; ENST00000370142; ENST00000370145; ENST00000447676; ENST00000439087; ENST00000433470; ENST00000422811; ENST00000411968; ENST00000418241; ENST00000434652 | TSF |
| 1% | chrX | 152937975 | 152937874 | − | chrX | 152937655 | 152937581; 152937592; 152937597 | − | ENST00000340888; ENST00000370150; ENST00000393831; ENST00000370142; ENST00000370145; ENST00000447676; ENST00000439087; ENST00000433470; ENST00000422811; ENST00000411968; ENST00000418241; ENST00000434652 | TSF |
| 1% | chrX | 152937975 | 152937874 | − | chrX | 152937655 | 152937581; 152937592; 152937597 | − | ENST00000340888; ENST00000370150; ENST00000393831; ENST00000370142; ENST00000370145; ENST00000447676; ENST00000439087; ENST00000433470; ENST00000422811; ENST00000411968; ENST00000418241; ENST00000434652 | TSF |
| 1% | chr5 | 121403097 | 121403017 | − | chr5 | 121402444 | 121402438 | − | ENST00000231004 | TSF |
| 1% | chr7 | 102146992 | 102146893 | − | chr7 | 102143691 | 102143610 | − | ENST00000541662; ENST00000465829; ENST00000306682 | TSF |
| 1% | chr7 | 102146992 | 102146893 | − | chr7 | 102143691 | 102143610 | − | ENST00000541662; ENST00000465829; ENST00000306682 | TSF |
| 1% | chr17 | 8713706 | 8713434 | − | chr17 | 8707471 | 8707359 | − | ENST00000311434 | TSF |
| 1% | chr1 | 205496165 | 205496185 | + | chr1 | 205496922 | 205497045; 205497001; 205496953 | + | ENST00000429964; ENST00000506784; ENST00000360066; ENST00000478560; ENST00000419301 | TSF |
| 1% | chr1 | 205496165 | 205496185 | + | chr1 | 205496922 | 205497045; 205497001; 205496953 | + | ENST00000429964; ENST00000506784; ENST00000360066; ENST00000478560; ENST00000419301 | TSF |
| 1% | chr1 | 205496165 | 205496185 | + | chr1 | 205496922 | 205497045; 205497001; 205496953 | + | ENST00000429964; ENST00000506784; ENST00000360066; ENST00000478560; ENST00000419301 | TSI |
| 1% | chr10 | 64280004 | 64280356 | + | chr10 | 64382863 | 64383010 | + | ENST00000410046 | TSF |
| 1% | chr3 | 195447345 | 195447395 | + | chr3 | 195451551 | 195453443; 195452030 | + | ENST00000447234; ENST00000320736; ENST00000436408 | TSF |
| 1% | chr3 | 195447345 | 195447395 | + | chr3 | 195451551 | 195453443; 195452030 | + | ENST00000447234; ENST00000320736; ENST00000436408 | TSF |
| 1% | chr3 | 195447345 | 195447395 | + | chr3 | 195451551 | 195453443; 195452030 | + | ENST00000447234; ENST00000320736; ENST00000436408 | TSF |
| 1% | chr1 | 101189453 | 101189853 | + | chr1 | 101190180 | 101190446 | + | ENST00000370119; ENST00000347652; ENST00000294728; ENST00000370115 | TSF |
| 1% | chr1 | 101189453 | 101189853 | + | chr1 | 101190180 | 101190446 | + | ENST00000370119; ENST00000347652; ENST00000294728; ENST00000370115 | TSF |
| 1% | chr1 | 101189453 | 101189853 | + | chr1 | 101190180 | 101190446 | + | ENST00000370119; ENST00000347652; ENST00000294728; ENST00000370115 | TSF |
| 1% | chr9 | 127083090 | 127083134 | + | chr9 | 127083738 | 127083848 | + | ENST00000540326; ENST00000373603; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr9 | 127083090 | 127083134 | + | chr9 | 127083738 | 127083848 | + | ENST00000540326; ENST00000373603; ENST00000373600; ENST00000320246; ENST00000545174; ENST00000444973; ENST00000454453; ENST00000373596; ENST00000425237; ENST00000423785; ENST00000394199; ENST00000546191; ENST00000422297; ENST00000539416; ENST00000447379 | TSF |
| 1% | chr9 | 127083090 | 127083134 | + | chr9 | 127083738 | 127083848 | + | ENST00000540326; ENST00000373603; ENST00000373600; ENST00000320246; ENST00000545174; ENST00000444973; ENST00000454453; ENST00000373596; ENST00000425237; ENST00000423785; ENST00000394199; ENST00000546191; ENST00000422297; ENST00000539416; ENST00000447379 | TSP |
| 1% | chr9 | 127083090 | 127083134 | + | chr9 | 127083738 | 127083848 | + | ENST00000540326; ENST00000373603; ENST00000373600; ENST00000320246; ENST00000545174; ENST00000444973; ENST00000454453; ENST00000373596; ENST00000425237; ENST00000423785; ENST00000394199; ENST00000546191; ENST00000422297; ENST00000539416; ENST00000447379 | TSF |
| 1% | chr9 | 127083090 | 127083134 | + | chr9 | 127083738 | 127083848 | + | ENST00000540326; ENST00000373603; ENST00000373600; ENST00000320246; ENST00000545174; ENST00000444973; ENST00000454453; ENST00000373596; ENST00000425237; ENST00000423785; ENST00000394199; ENST00000546191; ENST00000422297; ENST00000539416; ENST00000447379 | TSF |
| 1% | chr9 | 127083090 | 127083134 | + | chr9 | 127083738 | 127083848 | + | ENST00000540326; ENST00000373603; ENST00000373600; ENST00000320246; ENST00000545174; ENST00000444973; ENST00000454453; ENST00000373596; ENST00000425237; ENST00000423785; ENST00000394199; ENST00000546191; ENST00000422297; ENST00000539416; ENST00000447379 | TSF |
| 1% | chr9 | 127083090 | 127083134 | + | chr9 | 127083738 | 127083848 | + | ENST00000540326; ENST00000373603; ENST00000373600; ENST00000320246; ENST00000545174; ENST00000444973; ENST00000454453; ENST00000373596; ENST00000425237; ENST00000423785; ENST00000394199; ENST00000546191; ENST00000422297; ENST00000539416; ENST00000447379 | TSF |
| 1% | chr9 | 127083090 | 127083134 | + | chr9 | 127083738 | 127083848 | + | ENST00000540326; ENST00000373603; ENST00000373600; ENST00000320246; ENST00000545174; ENST00000444973; ENST00000454453; ENST00000373596; ENST00000425237; ENST00000423785; ENST00000394199; ENST00000546191; ENST00000422297; ENST00000539416; ENST00000447379 | TSF |
| 1% | chr2 | 85823332 | 85823377 | + | chr2 | 85823642 | 85823772 | + | ENST00000441634; ENST00000306368; ENST00000414390; ENST00000443647; ENST00000456023 | TSF |
| 1% | chr2 | 85823332 | 85823377 | + | chr2 | 85823642 | 85823772 | + | ENST00000441634; ENST00000306368; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr2 | 85823332 | 85823377 | + | chr2 | 85823642 | 85823772 | + | ENST00000414390; ENST00000443647; ENST00000456023 ENST00000441634; ENST00000306368; ENST00000414390; ENST00000443647; ENST00000456023 | TSF |
| 1% | chr2 | 85823332 | 85823377 | + | chr2 | 85823642 | 85823772 | + | ENST00000441634; ENST00000306368; ENST00000414390; ENST00000443647; ENST00000456023 | TSF |
| 1% | chr2 | 85823332 | 85823377 | + | chr2 | 85823642 | 85823772 | + | ENST00000441634; ENST00000306368; ENST00000414390; ENST00000443647; ENST00000456023 | TSF |
| 1% | chr17 | 3401396 | 3401426 | + | chr17 | 3402185 | 3402382 | + | ENST00000456349; ENST00000263080 | TSF |
| 1% | chr5 | 179021483 | 179021552 | + | chr5 | 179021867 | 179021964; 179021899 | + | ENST00000319449; ENST00000437570; ENST00000393438; ENST00000508609; ENST00000502434 | TSF |
| 1% | chr5 | 179021483 | 179021552 | + | chr5 | 179021867 | 179021964; 179021899 | + | ENST00000319449; ENST00000437570; ENST00000393438; ENST00000508609; ENST00000502434 | TSF |
| 1% | chr5 | 179021483 | 179021552 | + | chr5 | 179021867 | 179021964; 179021899 | + | ENST00000319449; ENST00000437570; ENST00000393438; ENST00000508609; ENST00000502434 | TSF |
| 1% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 1% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 1% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 1% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 1% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 1% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 1% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 1% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 1% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 1% | chr2 | 28191829 | 28192099 | + | chr2 | 28210860 | 28210954 | + | ENST00000436924; ENST00000344773; ENST00000379624; ENST00000342045; ENST00000361704; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr2 | 28191829 | 28192099 | + | chr2 | 28210860 | 28210954 | + | ENST00000379632; ENST00000379629; ENST00000604932 ENST00000436924; ENST00000344773; ENST00000379624; ENST00000342045; ENST00000361704; | TSF |
| 1% | chr2 | 28191829 | 28192099 | + | chr2 | 28210860 | 28210954 | + | ENST00000379632; ENST00000379629; ENST00000604932 ENST00000436924; ENST00000344773; ENST00000379624; ENST00000342045; ENST00000361704; | TSF |
| 1% | chr2 | 28191829 | 28192099 | + | chr2 | 28210860 | 28210954 | + | ENST00000379632; ENST00000379629; ENST00000604932 ENST00000436924; ENST00000344773; ENST00000379624; ENST00000342045; ENST00000361704; | TSF |
| 1% | chr1 | 101189453 | 101189677 | + | chr1 | 101190180 | 101190446 | + | ENST00000370119; ENST00000347652; ENST00000294728; ENST00000370115 | TSF |
| 1% | chr1 | 101189453 | 101189677 | + | chr1 | 101190180 | 101190446 | + | ENST00000370119; ENST00000347652; ENST00000294728; ENST00000370115 | TSF |
| 1% | chr1 | 101189453 | 101189677 | + | chr1 | 101190180 | 101190446 | + | ENST00000370119; ENST00000347652; ENST00000294728; ENST00000370115 | TSF |
| 1% | chr17 | 13442614 | 13442384 | − | chr17 | 13400135 | 13399514 | − | ENST00000284110 | TSF |
| 1% | chr20 | 48328930 | 48328898 | − | chr20 | 48273239 | 48273105 | − | ENST00000371711 | TSF |
| 1% | chr1 | 48256717 | 48256707 | − | chr1 | 48244216 | 48244126 | − | ENST00000606738 | TSF |
| 1% | chr17 | 30185561 | 30185499 | − | chr17 | 30183884 | 30183818 | − | ENST00000302362; ENST00000378634; ENST00000496655 | TSF |
| 1% | chr17 | 30185561 | 30185499 | − | chr17 | 30183884 | 30183818 | − | ENST00000302362; ENST00000378634; ENST00000496655 | TSF |
| 1% | chr | 206288369 | 206288105 | − | chr1 | 206243250 | 206243150 | − | ENST00000331555 | TSF |
| 1% | chr9 | 130732697 | 130732597 | − | chr9 | 130716204 | 130716084 | − | ENST00000373095 | TSF |
| 1% | chr3 | 59842786 | 59842708 | − | chr3 | 59738047 | 59737952 | − | ENST00000476844; ENST00000492590; ENST00000468189; ENST00000341848 | TSF |
| 1% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 1% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 1% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 1% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 1% | chr7 | 50723014 | 50722961 | − | chr7 | 50694675 | 50694519 | − | ENST00000398810; ENST00000439599; ENST00000398812; ENST00000335866; ENST00000402578; ENST00000403097; ENST00000406641; ENST00000357271; ENST00000407526; ENST00000401949; ENST00000402497 | TSF |
| 1% | chr7 | 50723014 | 50722961 | − | chr7 | 50694675 | 50694519 | − | ENST00000398810; ENST00000439599; ENST00000398812; ENST00000335866; ENST00000402578; ENST00000403097; ENST00000406641; ENST00000357271; ENST00000407526; ENST00000401949; ENST00000402497 | TSF |
| 1% | chr7 | 102246155 | 102246056 | − | chr7 | 102242852 | 102242771 | − | ENST00000262940; ENST00000461209; ENST00000449970; ENST00000462172; ENST00000522801; ENST00000520042; ENST00000521076 | TSF |
| 1% | chr7 | 102246155 | 102246056 | − | chr7 | 102242852 | 102242771 | − | ENST00000262940; ENST00000461209; ENST00000449970; ENST00000462172; ENST00000522801; ENST00000520042; ENST00000521076 | TSF |
| 1% | chr7 | 102246155 | 102246056 | − | chr7 | 102242852 | 102242771 | − | ENST00000262940; ENST00000461209; ENST00000449970; ENST00000462172; ENST00000522801; ENST00000520042; ENST00000521076 | TSF |
| 1% | chr7 | 102246155 | 102246056 | − | chr7 | 102242852 | 102242771 | − | ENST00000262940; ENST00000461209; | TSF |

TABLE 30-continued

Transcript fusion for Kidney Renal Clear Cell Carcinoma (KICH) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr1 | 60406096 | 60405910 | – | chr1 | 60381772 | 60381610 | – | ENST00000449970; ENST00000462172; ENST00000522801; ENST00000520042; ENST00000521076 ENST00000371204 | TSF |
| 1% | chr3 | 133881128 | 133880716 | – | chr3 | 133878217 | 133878081 | – | ENST00000460933; ENST00000296084; ENST00000427044 | TSF |
| 1% | chr8 | 95431039 | 95430884 | – | chr8 | 95423543 | 95423349; 95423528; 95423520; 95423471 | – | ENST00000336148; ENST00000517506; ENST00000463267; ENST00000518998; ENST00000523839 | TSF |
| 1% | chr8 | 95431039 | 95430884 | – | chr8 | 95423543 | 95423349; 95423528; 95423520; 95423471 | – | ENST00000336148; ENST00000517506; ENST00000463267; ENST00000518998; ENST00000523839 | TSF |
| 1% | chr8 | 95431039 | 95430884 | – | chr8 | 95423543 | 95423349; 95423528; 95423520; 95423471 | – | ENST00000336148; ENST00000517506; ENST00000463267; ENST00000518998; ENST00000523839 | TSF |
| 1% | chr8 | 95431039 | 95430884 | – | chr8 | 95423543 | 95423349; 95423528; 95423520; 95423471 | – | ENST00000336148; ENST00000517506; ENST00000463267; ENST00000518998; ENST00000523839 | TSF |
| 1% | chr2 | 170206045 | 170205691 | – | chr2 | 170177394 | 170177287 | – | ENST00000263816; ENST00000443831 | TSF |
| 1% | chr2 | 170206045 | 170205691 | – | chr2 | 170177394 | 170177287 | – | ENST00000263816; ENST00000443831 | TSF |
| 1% | chr12 | 7277801 | 7277662 | – | chr12 | 7277326 | 7277225 | – | ENST00000266560 | TSF |
| 1% | chr3 | 132377006 | 132376938 | – | chr3 | 132363740 | 132363641 | – | ENST00000355458; ENST00000264990; ENST00000485198; ENST00000481970 | TSF |
| 1% | chr3 | 132377006 | 132376938 | – | chr3 | 132363740 | 132363641 | – | ENST00000355458; ENST00000264990; ENST00000485198; ENST00000481970 | TSF |
| 1% | chr3 | 132377006 | 132376938 | – | chr3 | 132363740 | 132363641 | – | ENST00000355458; ENST00000264990; ENST00000485198; ENST00000481970 | TSF |
| 1% | chr3 | 132377006 | 132376938 | – | chr3 | 132363740 | 132363641 | – | ENST00000355458; ENST00000264990; ENST00000485198; ENST00000481970 | TSF |
| 1% | chr17 | 8715603 | 8715333 | – | chr17 | 8707471 | 8707359 | – | ENST00000311434 | TSF |

TABLE 31

Transcript fusion for Cervical Kidney renal papillary cell carcinoma (KIRP) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 54% | chr19 | 50984141 | 50984234 | + | ENST00000334976; ENST00000376918; ENST00000598585 | chr19 | 51009025 | 51009080 | + | TAF |
| 41% | chr9 | 131002264 | 131002275 | + | ENST00000475805; ENST00000341179; ENST00000372923; ENST00000393594; ENST00000486160 | chr9 | 131002706 | 131002973 | + | TAF |
| 41% | chr9 | 131002264 | 131002275 | + | ENST00000475805; ENST00000341179; ENST00000372923; ENST00000393594; ENST00000486160 | chr9 | 131002706 | 131002973 | + | TAF |
| 41% | chr5 | 156464372 | 156464258 | – | ENST00000522693; ENST00000523175; ENST00000339252; ENST00000425854; ENST00000544197 | chr5 | 156429918 | 156429891 | – | TSF |
| 27% | chr7 | 27582719 | 27582586 | – | ENST00000265395; ENST00000425715 | chr7 | 27581374 | 27579272 | – | TAF |
| 27% | chr7 | 27582719 | 27582586 | – | ENST00000265395; ENST00000425715 | chr7 | 27581374 | 27579272 | – | TAF |
| 23% | chr4 | 25759228 | 25759156 | – | ENST00000399878; ENST00000264868; ENST00000502949; ENST00000510448 | chr4 | 25723603 | 25723555 | – | TSF |
| 23% | chr4 | 25759228 | 25759156 | – | ENST00000399878; ENST00000264868; ENST00000502949; ENST00000510448 | chr4 | 25723603 | 25723555 | – | TSF |
| 23% | chr4 | 25759228 | 25759156 | – | ENST00000399878; ENST00000264868; ENST00000502949; ENST00000510448 | chr4 | 25723603 | 25723555 | – | TSF |
| 23% | chr4 | 25759228 | 25759156 | – | ENST00000399878; ENST00000264868; ENST00000502949; ENST00000510448 | chr4 | 25723603 | 25723555 | – | TSF |
| 22% | chr19 | 3544937 | 3544807 | – | ENST00000389395; ENST00000398558; ENST00000588918; ENST00000355415; ENST00000589063 | chr19 | 3538708 | 3538306 | – | TAF |
| 22% | chr19 | 3544937 | 3544807 | – | ENST00000389395; ENST00000398558; ENST00000588918; ENST00000355415; ENST00000589063 | chr19 | 3538708 | 3538306 | – | TAF |
| 22% | chr19 | 3544937 | 3544807 | – | ENST00000389395; ENST00000398558; ENST00000588918; ENST00000355415; ENST00000589063 | chr19 | 3538708 | 3538306 | – | TAF |

TABLE 31-continued

Transcript fusion for Cervical Kidney renal papillary cell carcinoma (KIRP)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 21% | chr6 | 25849692; 25849622 | 25849602 | − | ENST00000481949; ENST00000505420; ENST00000397060; ENST00000361703; ENST00000360657 | chr6 | 25847464 | 25847164 | − | TAF |
| 21% | chr6 | 25849692; 25849622 | 25849602 | − | ENST00000481949; ENST00000505420; ENST00000397060; ENST00000361703; ENST00000360657 | chr6 | 25847464 | 25847164 | − | TAF |
| 21% | chr6 | 25849692; 25849622 | 25849602 | − | ENST00000481949; ENST00000505420; ENST00000397060; ENST00000361703; ENST00000360657 | chr6 | 25847464 | 25847164 | − | TAF |
| 21% | chr6 | 25849692; 25849622 | 25849602 | − | ENST00000481949; ENST00000505420; ENST00000397060; ENST00000361703; ENST00000360657 | chr6 | 25847464 | 25847164 | − | TAF |
| 19% | chr9 | 131002007 | 131002058 | + | ENST00000475805; ENST00000341179; ENST00000372923; ENST00000393594; ENST00000486160 | chr9 | 131002706 | 131002973 | + | TSF |
| 19% | chr9 | 131002007 | 131002058 | + | ENST00000475805; ENST00000341179; ENST00000372923; ENST00000393594; ENST00000486160 | chr9 | 131002706 | 131002973 | + | TSF |
| 18% | chrX | 152730513 | 152730446 | − | ENST00000370211; ENST00000370212; ENST00000370210 | chrX | 152728559 | 152728505 | − | TAF |
| 18% | chrX | 152730513 | 152730446 | − | ENST00000370211; ENST00000370212; ENST00000370210 | chrX | 152728559 | 152728505 | − | TAF |
| 14% | chr20 | 53092486 | 53092551 | + | ENST00000262593 | chr20 | 53111339 | 53111426 | + | TAF |
| 13% | chr15 | 58724232 | 58724319 | + | ENST00000356113; ENST00000414170; ENST00000299022; ENST00000433326 | chr15 | 58787321 | 58787441 | + | TAF |
| 13% | chr1 | 171252283 | 171252355 | + | ENST00000367750; ENST00000402921; ENST00000354841 | chr1 | 171253062 | 171253076 | + | TAF |
| 13% | chr1 | 171252283 | 171252355 | + | ENST00000367750; ENST00000402921; ENST00000354841 | chr1 | 171253062 | 171253076 | + | TAF |
| 13% | chr10 | 5040939 | 5040817 | − | ENST00000380753; ENST00000421196; ENST00000407674; ENST00000604507 | chr10 | 5002427 | 5002117 | − | TAF |
| 13% | chr10 | 5040939 | 5040817 | − | ENST00000380753; ENST00000421196; ENST00000407674; ENST00000604507 | chr10 | 5002427 | 5002117 | − | TAF |
| 13% | chr11 | 2940537 | 2940637 | + | ENST00000347936; ENST00000312221; ENST00000449793; ENST00000380574 | chr11 | 2940968 | 2941017 | + | TAF |
| 13% | chr11 | 2940537 | 2940637 | + | ENST00000347936; ENST00000312221; ENST00000449793; ENST00000380574 | chr11 | 2940968 | 2941017 | + | TAF |
| 12% | chr17 | 43215280; 43215290 | 43215355 | + | ENST00000431281; ENST00000591859; ENST00000586346; ENST00000398322; ENST00000592162; ENST00000376955; ENST00000321854 | chr17 | 43215643 | 43215745 | + | TAF |
| 12% | chr17 | 43215280; 43215290 | 43215355 | + | ENST00000431281; ENST00000591859; ENST00000586346; ENST00000398322; ENST00000592162; ENST00000376955; ENST00000321854 | chr17 | 43215643 | 43215745 | + | TAF |
| 12% | chr17 | 43215280; 43215290 | 43215355 | + | ENST00000431281; ENST00000591859; ENST00000586346; ENST00000398322; ENST00000592162; ENST00000376955; ENST00000321854 | chr17 | 43215643 | 43215745 | + | TAF |
| 11% | chr7 | 1037440 | 1037282 | − | ENST00000357429; ENST00000397100; ENST00000397098; ENST00000412051; ENST00000444428; ENST00000491163 | chr7 | 1018697 | 1018446 | − | TAF |
| 11% | chr7 | 1037440 | 1037282 | − | ENST00000357429; ENST00000397100; ENST00000397098; ENST00000412051; ENST00000444428; ENST00000491163 | chr7 | 1018697 | 1018446 | − | TAF |
| 11% | chr7 | 1037440 | 1037282 | − | ENST00000357429; ENST00000397100; ENST00000397098; ENST00000412051; ENST00000444428; ENST00000491163 | chr7 | 1018697 | 1018446 | − | TAF |
| 11% | chr4 | 25759228 | 25759156 | − | ENST00000399878; ENST00000264868; ENST00000502949; ENST00000510448 | chr4 | 25716488 | 25716212 | − | TSF |
| 11% | chr4 | 25759228 | 25759156 | − | ENST00000399878; ENST00000264868; ENST00000502949; ENST00000510448 | chr4 | 25716488 | 25716212 | − | TSF |
| 11% | chr4 | 25759228 | 25759156 | − | ENST00000399878; ENST00000264868; ENST00000502949; ENST00000510448 | chr4 | 25716488 | 25716212 | − | TSF |
| 11% | chr4 | 25759228 | 25759156 | − | ENST00000399878; ENST00000264868; ENST00000502949; ENST00000510448 | chr4 | 25716488 | 25716212 | − | TSF |
| 10% | chr9 | 71155730 | 71155453 | − | ENST00000377311 | chr9 | 71141327 | 71141315 | − | TSF |
| 7% | chr7 | 151810331; 151810330 | 151810483 | + | ENST00000430044; ENST00000452146; ENST00000434507; ENST00000320311; ENST00000431940 | chr7 | 151813950 | 151814077 | + | TSF |
| 7% | chr7 | 151810331; 151810330 | 151810483 | + | ENST00000430044; ENST00000452146; ENST00000434507; ENST00000320311; ENST00000431940 | chr7 | 151813950 | 151814077 | + | TSF |
| 7% | chr7 | 151810331; 151810330 | 151810483 | + | ENST00000430044; ENST00000452146; ENST00000434507; ENST00000320311; | chr7 | 151813950 | 151814077 | + | TSF |

TABLE 31-continued

Transcript fusion for Cervical Kidney renal papillary cell carcinoma (KIRP)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 6% | chr9 | 125054028 | 125054119 | + | ENST00000431940 ENST00000297908; ENST00000344641; ENST00000373723; ENST00000373729; ENST00000394315 | chr9 | 125068067 | 125068171 | + | TSF |
| 6% | chr9 | 125054028 | 125054119 | + | ENST00000297908; ENST00000344641; ENST00000373723; ENST00000373729; ENST00000394315 | chr9 | 125068067 | 125068171 | + | TSF |
| 6% | chr9 | 125054028 | 125054119 | + | ENST00000297908; ENST00000344641; ENST00000373723; ENST00000373729; ENST00000394315 | chr9 | 125068067 | 125068171 | + | TSF |
| 4% | chr17 | 19470409 | 19470541 | + | ENST00000571335; ENST00000436810; ENST00000457293; ENST00000270570; ENST00000395585 | chr17 | 19482057 | 19482370 | + | TSF |
| 4% | chr17 | 19470409 | 19470541 | + | ENST00000571335; ENST00000436810; ENST00000457293; ENST00000270570; ENST00000395585 | chr17 | 19482057 | 19482370 | + | TSF |
| 4% | chr17 | 19470409 | 19470541 | + | ENST00000571335; ENST00000436810; ENST00000457293; ENST00000270570; ENST00000395585 | chr17 | 19482057 | 19482370 | + | TSF |
| 4% | chr20 | 43752906 | 43752748 | − | ENST00000372785 | chr20 | 43744893 | 43744813 | − | TSF |
| 4% | chr9 | 131004511 | 131004624 | + | ENST00000475805; ENST00000341179; ENST00000372923; ENST00000393594; ENST00000486160 | chr9 | 131004898 | 131005047 | + | TSF |
| 4% | chr9 | 131004511 | 131004624 | + | ENST00000475805; ENST00000341179; ENST00000372923; ENST00000393594; ENST00000486160 | chr9 | 131004898 | 131005047 | + | TSF |
| 4% | chr22 | 23955517 | 23955476 | − | ENST00000317749 | chr22 | 23925665 | 23925612 | − | TSF |
| 4% | chr3 | 98600611; 98600498 | 98600384 | − | ENST00000326840; ENST00000326857; ENST00000449482 | chr3 | 98586282 | 98584565 | − | TSF |
| 4% | chr3 | 98600611; 98600498 | 98600384 | − | ENST00000326840; ENST00000326857; ENST00000449482 | chr3 | 98586282 | 98584565 | − | TSF |
| 4% | chr17 | 45473200 | 45473343 | + | ENST00000331493; ENST00000517484; ENST00000523842 | chr17 | 45474435 | 45476216 | + | TSF |
| 4% | chr17 | 45473200 | 45473343 | + | ENST00000331493; ENST00000517484; ENST00000523842 | chr17 | 45474435 | 45476216 | + | TSF |
| 4% | chr17 | 45473200 | 45473343 | + | ENST00000331493; ENST00000517484; ENST00000523842 | chr17 | 45474435 | 45476216 | + | TSF |
| 4% | chr17 | 36288631 | 36288740 | + | ENST00000327454; ENST00000378174; ENST00000505415; ENST00000539424 | chr17 | 36289142 | 36289609 | + | TSF |
| 4% | chr17 | 36288631 | 36288740 | + | ENST00000327454; ENST00000378174; ENST00000505415; ENST00000539424 | chr17 | 36289142 | 36289609 | + | TSF |
| 4% | chr2 | 28352138 | 28352247 | + | ENST00000344773; ENST00000379624; ENST00000342045; ENST00000361704; ENST00000379632; ENST00000379629 | chr2 | 28362015 | 28362218 | + | TSF |
| 3% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 3% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 3% | chr16 | 30783410 | 30783511 | + | ENST00000324685; ENST00000402121; ENST00000563683; ENST00000357890 | chr16 | 30785136 | 30785155 | + | TSF |
| 3% | chr16 | 30783410 | 30783511 | + | ENST00000324685; ENST00000402121; ENST00000563683; ENST00000357890 | chr16 | 30785136 | 30785155 | + | TSF |
| 3% | chr16 | 30783410 | 30783511 | + | ENST00000324685; ENST00000402121; ENST00000563683; ENST00000357890 | chr16 | 30785136 | 30785155 | + | TSF |
| 3% | chr16 | 30783410 | 30783511 | + | ENST00000324685; ENST00000402121; ENST00000563683; ENST00000357890 | chr16 | 30785136 | 30785155 | + | TSF |
| 3% | chr17 | 19605987 | 19605918 | − | ENST00000325411; ENST00000350657 | chr17 | 19600213 | 19600058 | − | TSF |
| 3% | chr17 | 19605987 | 19605918 | − | ENST00000325411; ENST00000350657 | chr17 | 19600213 | 19600058 | − | TSF |
| 3% | chr17 | 36343995 | 36343886 | − | ENST00000518551; ENST00000354664; ENST00000339023; ENST00000519532; ENST00000537432 | chr17 | 36343484 | 36343017 | − | TSF |
| 3% | chr17 | 36343995 | 36343886 | − | ENST00000518551; ENST00000354664; ENST00000339023; ENST00000519532; ENST00000537432 | chr17 | 36343484 | 36343017 | − | TSF |
| 2% | chr14 | 73733431 | 73733539 | + | ENST00000427855; ENST00000340738; ENST00000554301; ENST00000555445 | chr14 | 73734835 | 73734859 | + | TSF |
| 2% | chr14 | 73733431 | 73733539 | + | ENST00000427855; ENST00000340738; ENST00000554301; ENST00000555445 | chr14 | 73734835 | 73734859 | + | TSF |
| 2% | chr14 | 73733431 | 73733539 | + | ENST00000427855; ENST00000340738; ENST00000554301; ENST00000555445 | chr14 | 73734835 | 73734859 | + | TSF |
| 2% | chr11 | 59562845 | 59562955 | + | ENST00000300150; ENST00000337979; ENST00000529177; ENST00000530221 | chr11 | 59605243 | 59605700 | + | TSF |
| 2% | chr11 | 59562845 | 59562955 | + | ENST00000300150; ENST00000337979 | chr11 | 59605243 | 59605700 | + | TSF |

TABLE 31-continued

Transcript fusion for Cervical Kidney renal papillary cell carcinoma (KIRP)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr11 | 59562845 | 59562955 | + | ENST00000529177; ENST00000530221 ENST00000300150; ENST00000337979; | chr11 | 59605243 | 59605700 | + | TSF |
| 2% | chr1 | 2492063 | 2492153 | + | ENST00000529177; ENST00000530221 ENST00000426449; ENST00000434817; ENST00000435221; ENST00000451778; ENST00000409119; ENST00000355716 | chr1 | 2508457 | 2508463 | + | TSF |
| 2% | chr11 | 118882859 | 118882964 | + | ENST00000334418 | chr11 | 118884956 | 118885003 | + | TSF |
| 2% | chr17 | 45473200 | 45473343 | + | ENST00000331493; ENST00000517484; ENST00000523842 | chr17 | 45474497 | 45476216 | + | TSF |
| 2% | chr17 | 45473200 | 45473343 | + | ENST00000331493; ENST00000517484; ENST00000523842 | chr17 | 45474497 | 45476216 | + | TSF |
| 2% | chr17 | 45473200 | 45473343 | + | ENST00000331493; ENST00000517484; ENST00000523842 | chr17 | 45474497 | 45476216 | + | TSF |
| 2% | chr7 | 93516743; 93516667 | 93516573 | − | ENST00000222543; ENST00000451238 | chr7 | 93492029 | 93491711 | − | TSF |
| 2% | chr7 | 93516743; 93516667 | 93516573 | − | ENST00000222543; ENST00000451238 | chr7 | 93492029 | 93491711 | − | TSF |
| 2% | chr16 | 29913136; 29912293 | 29913241 | + | ENST00000563177; ENST00000483405; ENST00000308748; ENST00000414952; ENST00000566693 | chr16 | 29915825 | 29915953 | + | TSF |
| 2% | chr16 | 29913136; 29912293 | 29913241 | + | ENST00000563177; ENST00000483405; ENST00000308748; ENST00000414952; ENST00000566693 | chr16 | 29915825 | 29915953 | + | TSF |
| 2% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 2% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 2% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 2% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 2% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 2% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 2% | chr15 | 58724232 | 58724319 | + | ENST00000356113; ENST00000414170; ENST00000299022; ENST00000433326 | chr15 | 58748060 | 58748095 | + | TSF |
| 2% | chr8 | 63502273 | 63502353 | + | ENST00000523211; ENST00000328472 | chr8 | 63546747 | 63547118 | + | TSF |
| 2% | chr17 | 62479116 | 62479036 | − | ENST00000539111; ENST00000581355 | chr17 | 62478351 | 62478214 | − | TSF |
| 2% | chr17 | 62479116 | 62479036 | − | ENST00000539111; ENST00000581355 | chr17 | 62478351 | 62478214 | − | TSF |

TABLE 32

Transcript fusion for Cervical Kidney renal papillary cell carcinoma (KIRP) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 53% | chr9 | 131002678 | 131002811 | + | chr9 | 131004511 | 131004624 | + | ENST00000475805; ENST00000341179; ENST00000372923; ENST00000393594; ENST00000486160 | TAF |
| 53% | chr9 | 131002678 | 131002811 | + | chr | 131004511 | 131004624 | + | ENST00000475805; ENST00000341179; ENST00000372923; ENST00000393594; ENST00000486160 | TAF |
| 40% | chr4 | 69814157 | 69813728 | − | chr4 | 69811168 | 69811024 | − | ENST00000251566; ENST00000503012 | TAF |
| 40% | chr4 | 69814157 | 69813728 | − | chr4 | 69811168 | 69811024 | − | ENST00000251566; ENST00000503012 | TAF |
| 37% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENS T00000426255; ENST00000512079; | TAF |

TABLE 32-continued

Transcript fusion for Cervical Kidney renal papillary cell carcinoma (KIRP) Coordinates of the fusion sequences for which the donor is the TE.

| 1' | 2' | 3' | 4' | 5 | 6' | 7' | 8' | 9' | 10' | 11' |
|---|---|---|---|---|---|---|---|---|---|---|
| 37% | chr5 | 34006954 | 34006922 | − | chr5 | 34006004 | 34005861 | − | ENST00000382068 ENST00000335606; ENST00000382072; ENST00000382079; ENST00000506639; ENST00000382085; ENST00000502637; ENST00000441713; ENST00000426255; ENST00000512079; ENST00000382068 | TAF |
| 37% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENS T00000426255; ENST00000512079; ENST00000382068 | TAF |
| 37% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 37% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENS T00000426255; ENST00000512079; ENST00000382068 | TAF |
| 37% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENS T00000426255; ENST00000512079; ENST00000382068 | TAF |
| 37% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENS T00000426255; ENST00000512079; ENST00000382068 | TAF |
| 37% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENS T00000426255; ENST00000512079; ENST00000382068 | TAF |
| 37% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENS T00000426255; ENST00000512079; ENST00000382068 | TAF |
| 34% | chr6 | 31154067 | 31153803 | − | chr6 | 31133824 | 31133704 | − | ENST00000259915 | TAF |
| 32% | chr17 | 79214190 | 79214239 | + | chr17 | 79214787 | 79214816; 79214953 | + | ENST00000431388; ENST00000576002 | TAF |
| 32% | chr17 | 79214190 | 79214239 | + | chr17 | 79214787 | 79214816; 79214953 | + | ENST00000431388; ENST00000576002 | TAF |
| 29% | chr1 | 46797740 | 46797497 | − | chr1 | 46764042 | 46763956 | − | ENST00000343304 | TAF |
| 28% | chr7 | 150938296 | 150938250 | − | chr7 | 150937608 | 150937511 | − | ENST00000262188; ENST00000392811; ENST00000356800 | TAF |
| 28% | chr8 | 30395124 | 30395240 | + | chr8 | 30402011 | 30402141; 30402288; 30402073 | + | ENST00000397323; ENST00000339877; ENST00000320203; ENST00000287771; ENST00000517860; ENST00000520161; ENST00000523115; ENS T00000519647; ENST00000520191; ENST00000522694 | TAF |
| 28% | chr8 | 30395124 | 30395240 | + | chr8 | 30402011 | 30402141; 30402288; 30402073 | + | ENST00000397323; ENST00000339877; ENST00000320203; ENST00000287771; ENST00000517860; ENST00000520161; ENST00000523115; ENST00000519647; ENST00000520191; ENST00000522694 | TAF |
| 28% | chr8 | 30395124 | 30395240 | + | chr8 | 30402011 | 30402141; 30402288; 30402073 | + | ENST00000397323; ENST00000339877; ENST00000320203; ENST00000287771; ENST00000517860; ENST00000520161; ENST00000523115; ENS T00000519647; ENST00000520191; ENST00000522694 | TAF |
| 28% | chr8 | 30395124 | 30395240 | + | chr8 | 30402011 | 30402141; 30402288; 30402073 | + | ENST00000397323; ENST00000339877; ENST00000320203; ENST00000287771; ENST00000517860; ENST00000520161; ENST00000523115; ENS T00000519647; ENST00000520191; ENST00000522694 | TAF |
| 28% | chr8 | 30395124 | 30395240 | + | chr8 | 30402011 | 30402141; 30402288; 30402073 | + | ENST00000397323; ENST00000339877; ENST00000320203; ENST00000287771; ENST00000517860; ENST00000520161; ENST00000523115; ENS T00000519647; ENST00000520191; ENST00000522694 | TAF |
| 28% | chr8 | 30395124 | 30395240 | + | chr8 | 30402011 | 30402141; 30402288; 30402073 | + | ENST00000397323; ENST00000339877; ENST00000320203; ENST00000287771; ENST00000517860; ENST00000520161; ENST00000523115; ENS T00000519647; ENST00000520191; ENST00000522694 | TAF |
| 27% | chr10 | 60376682 | 60376727 | + | chr10 | 60380615 | 60380661 | + | ENST00000373886 | TAF |
| 24% | chr17 | 48164136 | 48164357 | + | chr17 | 48165108 | 48165233 | + | ENST00000320031; ENST00000007722 | TAF |
| 24% | chr17 | 48164136 | 48164357 | + | chr17 | 48165108 | 48165233 | + | ENST00000320031; ENST00000007722 | TAF |
| 24% | chr16 | 29915789 | 29915910 | + | chr16 | 29916173 | 29916286 | + | ENST00000563177; ENST00000483405; ENST00000308748; ENST00000414952; ENST00000566693 | TAF |
| 24% | chr16 | 29915789 | 29915910 | + | chr16 | 29916173 | 29916286 | + | ENST00000563177; ENST00000483405; ENST00000308748; ENST00000414952; ENST00000566693 | TAF |
| 23% | chr14 | 102691697 | 102691432 | − | chr14 | 102691131 | 102691116 | − | ENST00000559838 | TAF |
| 22% | chr19 | 55558521 | 55558473 | − | chr19 | 55556677 | 55556442 | − | ENST00000415061; ENST00000396247 | TAF |
| 21% | chr5 | 176950300 | 176950160 | − | chr5 | 176949072 | 176948976 | − | ENST00000514747; ENST00000329540; ENST00000443375; ENST00000524677 | TAF |
| 18% | chr2 | 201253013 | 201253278 | + | chr2 | 201253946 | 201254006 | + | ENST00000409755; ENST00000409151 | TAF |

TABLE 32-continued

Transcript fusion for Cervical Kidney renal papillary cell carcinoma (KIRP) Coordinates of the fusion sequences for which the donor is the TE.

| 1' | 2' | 3' | 4' | 5 | 6' | 7' | 8' | 9' | 10' | 11' |
|---|---|---|---|---|---|---|---|---|---|---|
| 18% | chr8 | 15274514 | 15274814 | + | chr8 | 15480589 | 15480758 | + | ENST00000382020; ENST00000515859; ENST00000506802; ENST00000510836; ENST00000509380; ENST00000503731; ENST00000511783 | TAF |
| 18% | chr8 | 15274514 | 15274814 | + | chr8 | 15480589 | 15480758 | + | ENST00000382020; ENST00000515859; ENST00000506802; ENST00000510836; ENST00000509380; ENST00000503731; ENST00000511783 | TAF |
| 18% | chr8 | 15274514 | 15274814 | + | chr8 | 15480589 | 15480758 | + | ENST00000382020; ENST00000515859; ENST00000506802; ENST00000510836; ENST00000509380; ENST00000503731; ENST00000511783 | TAF |
| 18% | chr8 | 15274514 | 15274814 | + | chr8 | 15480589 | 15480758 | + | ENST00000382020; ENST00000515859; ENST00000506802; ENST00000510836; ENST00000509380; ENST00000503731; ENST00000511783 | TAF |
| 18% | chr8 | 15274514 | 15274814 | + | chr8 | 15480589 | 15480758 | + | ENST00000382020; ENST00000515859; ENST00000506802; ENST00000510836; ENST00000509380; ENST00000503731; ENST00000511783 | TAF |
| 17% | chr10 | 90305421 | 90305214 | − | chr10 | 90122482 | 90122309 | − | ENST00000371947; ENST00000437752; ENST00000331772 | TAF |
| 17% | chr10 | 90305421 | 90305214 | − | chr10 | 90122482 | 90122309 | − | ENST00000371947; ENST00000437752; ENST00000331772 | TAF |
| 16% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 16% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 16% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 16% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 16% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 16% | chr8 | 30356797 | 30356857 | + | chr8 | 30361803 | 30361953 | + | ENST00000538486; ENST00000397323; ENST00000339877; ENST00000320203; ENST00000287771; ENST00000517860; ENST00000519359; ENST00000522694 | TSF |
| 15% | chr10 | 100147690 | 100147622 | − | chr10 | 100147064 | 100146958 | − | ENST00000370575 | TAF |
| 15% | chr6 | 111995513 | 111995484 | − | chr6 | 111983150 | 111982942 | − | ENST00000368682; ENST00000354650; ENST00000229471; ENST00000368667; ENST00000368678; ENST00000538466; ENST00000229470; ENST00000356013 | TSF |
| 14% | chr5 | 176950016 | 176949956 | − | chr5 | 176949072 | 176948976 | − | ENST00000514747; ENST00000329540; ENST00000443375; ENST00000524677 | TAF |
| 14% | chr4 | 5788948 | 5789351 | + | chr4 | 5795335 | 5795444 | + | ENST00000264956; ENST00000382674 | TAF |
| 14% | chr10 | 90305421 | 90305146 | − | chr10 | 90122482 | 90122309 | − | ENST00000371947; ENST00000437752; ENST00000331772 | TAF |
| 14% | chr10 | 90305421 | 90305146 | − | chr10 | 90122482 | 90122309 | − | ENST00000371947; ENST00000437752; ENST00000331772 | TAF |
| 14% | chr7 | 74158449 | 74158566 | + | chr7 | 74159097 | 74159280 | + | ENST00000324896; ENST00000346152; ENST00000353920; ENST00000416070 | TAF |
| 14% | chr1 | 206288369 | 206288105 | − | chr1 | 206243250 | 206243150 | − | ENST00000331555 | TSF |
| 13% | chr19 | 55559415 | 55559414 | − | chr19 | 55558856 | 55558755 | − | ENST00000415061; ENST00000396247 | TAF |
| 12% | chr10 | 120902016 | 120901765 | − | chr10 | 120900831 | 120900754 | − | ENST00000355697; ENST00000330036 | TAF |
| 12% | chr20 | 33850895 | 33851310 | + | chr20 | 33851594 | 33851755 | + | ENST00000246186 | TAF |
| 12% | chrX | 129264697 | 129264593 | − | chrX | 129264141 | 129263945 | − | ENST00000440263; ENST00000460436; ENST00000346424; ENST00000319908; ENST00000287295 | TAF |
| 12% | chr19 | 1114930 | 1114676 | − | chr19 | 1114421 | 1114230 | − | ENST00000361757; ENST00000587024; ENST00000438103 | TSF |
| 12% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 12% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 12% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 12% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 11% | chrX | 2178048 | 2177670 | − | chrX | 2161271 | 2161064; 2161103 | − | ENST00000334651; ENST00000412516 | TAF |
| 11% | chrX | 2178048 | 2177670 | − | chrX | 2161271 | 2161064; 2161103 | − | ENST00000334651; ENST00000412516 | TAF |
| 11% | chr17 | 62480131 | 62480081 | − | chr17 | 62479116 | 62479036 | − | ENST00000539111; ENST00000581355 | TAF |
| 11% | chr17 | 62480131 | 62480081 | − | chr17 | 62479116 | 62479036 | − | ENST00000539111; ENST00000581355 | TAF |
| 11% | chr16 | 20474655 | 20474981 | + | chr16 | 20476839 | 20476978; 20477049; | + | ENST00000576361; ENST00000424070; ENST00000573854; ENST00000219054; ENST00000575690; ENST00000574692; | TAF |

TABLE 32-continued

Transcript fusion for Cervical Kidney renal papillary cell carcinoma (KIRP) Coordinates of the fusion sequences for which the donor is the TE.

| 1' | 2' | 3' | 4' | 5 | 6' | 7' | 8' | 9' | 10' | 11' |
|---|---|---|---|---|---|---|---|---|---|---|
| 11% | chr16 | 20474655 | 20474981 | + | chr16 | 20476839 | 20477015 20476978; 20477049; 20477015 | + | ENST00000571894; ENS T00000396104 ENST00000576361; ENST00000424070; ENST00000573854; ENST00000219054; ENST00000575690; ENST00000574692; | TAF |
| 11% | chr16 | 20474655 | 20474981 | + | chr16 | 20476839 | 20477015 20476978; 20477049; 20477015 | + | ENST00000571894; ENS T00000396104 ENST00000576361; ENST00000424070; ENST00000573854; ENST00000219054; ENST00000575690; ENST00000574692; | TAF |
| 11% | chr16 | 20474655 | 20474981 | + | chr16 | 20476839 | 20477015 20476978; 20477049; 20477015 | + | ENST00000571894; ENS T00000396104 ENST00000576361; ENST00000424070; ENST00000573854; ENST00000219054; ENST00000575690; ENST00000574692; | TAF |
| 11% | chr16 | 89649823 | 89649851 | + | chr16 | 89650105 | 89650179 | + | ENST00000268720; ENST00000319518 | TSF |
| 9% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 9% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 9% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 9% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 9% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 9% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 8% | chr3 | 159455523 | 159455690 | + | chr3 | 159482232 | 159482251; 159482927; 159482401; 159482495; 159482300; 159482888 | + | ENST00000471575; ENST00000476809; ENST00000485419; ENST00000483486; ENST000000481715; ENST00000488898; ENST00000337808; ENST00000412423 | TSF |
| 8% | chr3 | 159455523 | 159455690 | + | chr3 | 159482232 | 159482251; 159482927; 159482401; 159482495; 159482300; 159482888 | + | ENST00000471575; ENST00000476809; ENST00000485419; ENST00000483486; ENST00000481715; ENST00000488898; ENST00000337808; ENST00000412423 | TSF |
| 8% | chr3 | 159455523 | 159455690 | + | chr3 | 159482232 | 159482251; 159482927; 159482401; 159482495; 159482300; 159482888 | + | ENST00000471575; ENST00000476809; ENST00000485419; ENST00000483486; ENST00000481715; ENST00000488898; ENST00000337808; ENST00000412423 | TSF |
| 8% | chr3 | 159455523 | 159455690 | + | chr3 | 159482232 | 159482251; 159482927; 159482401; 159482495; 159482300; 159482888 | + | ENST00000471575; ENST00000476809; ENST00000485419; ENST00000483486; ENST00000481715; ENST00000488898; ENST00000337808; ENST00000412423 | TSF |
| 8% | chr3 | 159455523 | 159455690 | + | chr3 | 159482232 | 159482251; 159482927; 159482401; 159482495; 159482300; 159482888 | + | ENST00000471575; ENST00000476809; ENST00000485419; ENST00000483486; ENST00000481715; ENST00000488898; ENST00000337808; ENST00000412423 | TSF |
| 8% | chr3 | 159455523 | 159455690 | + | chr3 | 159482232 | 159482251; 159482927; 159482401; 159482495; 159482300; 159482888 | + | ENST00000471575; ENST00000476809; ENST00000485419; ENST00000483486; ENST00000481715; ENST00000488898; ENST00000337808; ENST00000412423 | TSF |
| 7% | chr4 | 22601350 | 22601612 | + | chr4 | 22737604 | 22737831 | + | ENST00000508166; ENST00000503442 | TSF |
| 7% | chr4 | 22601350 | 22601612 | + | chr4 | 22737604 | 22737831 | + | ENST00000508166; ENST00000503442 | TSF |
| 6% | chr7 | 100850556 | 100850506 | − | chr7 | 100850185 | 100850060 | − | ENST00000454310; ENST00000223127 | TSF |
| 5% | chr8 | 24354477 | 24354747 | + | chr8 | 24356749 | 24356829 | + | ENST00000175238; ENST00000380789; ENST00000520720 | TSF |
| 5% | chr8 | 24354477 | 24354747 | + | chr8 | 24356749 | 24356829 | + | ENST00000175238; ENST00000380789; ENST00000520720 | TSF |
| 5% | chr8 | 24354477 | 24354747 | + | chr8 | 24356749 | 24356829 | + | ENST00000175238; ENST00000380789; ENST00000520720 | TSF |
| 5% | chr1 | 236326774 | 236327054 | + | chr1 | 236332006 | 236332055 | + | ENST00000366592; ENST00000454895 | TSF |
| 5% | chr1 | 236326774 | 236327054 | + | chr1 | 236332006 | 236332055 | + | ENST00000366592; ENST00000454895 | TSF |
| 5% | chr22 | 23978396 | 23978123 | − | chr22 | 23974160 | 23974003 | − | ENST00000317749 | TSF |
| 5% | chr6 | 51817315 | 51817226 | − | chr6 | 51799120 | 51798908 | − | ENST00000371117; ENST00000340994 | TSF |
| 5% | chr6 | 51817315 | 51817226 | − | chr6 | 51799120 | 51798908 | − | ENST00000371117; ENST00000340994 | TSF |
| 5% | chr5 | 31298457 | 31298554 | + | chr5 | 31299571 | 31299738 | + | ENST00000514738; ENST00000265071 | TSF |
| 5% | chr5 | 31298457 | 31298554 | + | chr5 | 31299571 | 31299738 | + | ENST00000514738; ENST00000265071 | TSF |
| 5% | chr4 | 69919044 | 69920610 | + | chr4 | 69964258 | 69964406 | + | ENST00000305231; ENST00000508661 | TSF |
| 5% | chr4 | 69919044 | 69920610 | + | chr4 | 69964258 | 69964406 | + | ENST00000305231; ENST00000508661 | TSF |
| 4% | chr1 | 25125118 | 25125844 | + | chr1 | 25140585 | 25140710 | + | ENST00000374379; ENST00000488683 | TSF |
| 4% | chr3 | 1442010 | 1442077 | + | chr3 | 1443117 | 1443229 | + | ENST00000446702; ENST00000539053; ENST00000350110 | TSF |

TABLE 32-continued

Transcript fusion for Cervical Kidney renal papillary cell carcinoma (KIRP) Coordinates of the fusion sequences for which the donor is the TE.

| 1' | 2' | 3' | 4' | 5 | 6' | 7' | 8' | 9' | 10' | 11' |
|---|---|---|---|---|---|---|---|---|---|---|
| 4% | chr20 | 48328930 | 48328898 | − | chr20 | 48273239 | 48273105 | − | ENST00000371711 | TSF |
| 4% | chr10 | 3133726 | 3133857 | + | chr10 | 3141467 | 3141544 | + | ENST00000607886; ENST00000381125; ENST00000381075; ENST00000407806 | TSF |
| 4% | chr10 | 3133726 | 3133857 | + | chr10 | 3141467 | 3141544 | + | ENST00000607886; ENST00000381125; ENST00000381075; ENST00000407806 | TSF |
| 4% | chr10 | 3133726 | 3133857 | + | chr10 | 3141467 | 3141544 | + | ENST00000607886; ENST00000381125; ENST00000381075; ENST00000407806 | TSF |
| 4% | chr10 | 3133726 | 3133857 | + | chr10 | 3141467 | 3141544 | + | ENST00000607886; ENST00000381125; ENST00000381075; ENST00000407806 | TSF |
| 4% | chr7 | 107598095 | 107598030 | − | chr7 | 107596075 | 107595912 | − | ENST00000393561; ENST00000222399 | TSF |
| 4% | chr2 | 43963431 | 43963670 | + | chr2 | 43965480 | 43965659 | + | ENST00000282406 | TSF |
| 4% | chr1 | 48256717 | 48256707 | − | chr1 | 48244216 | 48244126 | − | ENST00000606738 | TSF |
| 4% | chr3 | 182757105 | 182757101 | − | chr3 | 182756923 | 182756814 | − | ENST00000265594; ENST00000492597; ENST00000497959; ENST00000539926; ENST00000476176 | TSF |
| 4% | chr3 | 182757105 | 182757101 | − | chr3 | 182756923 | 182756814 | − | ENST00000265594; ENST00000492597; ENST00000497959; ENST00000539926; ENST00000476176 | TSF |
| 4% | chr3 | 182757105 | 182757101 | − | chr3 | 182756923 | 182756814 | − | ENST00000265594; ENST00000492597; ENST00000497959; ENST00000539926; ENST00000476176 | TSF |
| 4% | chr3 | 182757105 | 182757101 | − | chr3 | 182756923 | 182756814 | − | ENST00000265594; ENST00000492597; ENST00000497959; ENST00000539926; ENST00000476176 | TSF |
| 3% | chr16 | 20474655 | 20474796 | + | chr16 | 20476839 | 20476978; 20477049; 20477015 | + | ENST00000576361; ENST00000424070; ENST00000573854; ENST00000219054; ENST0000057590; ENST00000574692; ENST00000571894; ENST00000396104 | TSF |
| 3% | chr16 | 20474655 | 20474796 | + | chr16 | 20476839 | 20476978; 20477049; 20477015 | + | ENST00000576361; ENST00000424070; ENST00000573854; ENST00000219054; ENST0000057590; ENST00000574692; ENST00000571894; ENST00000396104 | TSF |
| 3% | chr16 | 20474655 | 20474796 | + | chr16 | 20476839 | 20476978; 20477049; 20477015 | + | ENST00000576361; ENST00000424070; ENST00000573854; ENST00000219054; ENST0000057590; ENST00000574692; ENST00000571894; ENST00000396104 | TSF |
| 3% | chr16 | 20474655 | 20474796 | + | chr16 | 20476839 | 20476978; 20477049; 20477015 | + | ENST00000576361; ENST00000424070; ENST00000573854; ENST00000219054; ENST0000057590; ENST00000574692; ENST00000571894; ENST00000396104 | TSF |
| 3% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr22 | 25020098 | 25020113 | + | chr22 | 25023399 | 25023586; 25023457 | + | ENST00000248923; ENST00000412658; ENST00000400382; ENST00000400383; ENST0000040080; ENST00000406383; ENST0000425895 | TSF |
| 3% | chr22 | 25020098 | 25020113 | + | chr22 | 25023399 | 25023586; 25023457 | + | ENST00000248923; ENST00000412658; ENST00000400382; ENST00000400383; ENST0000040080; ENST00000406383; ENST0000425895 | TSF |
| 3% | chr22 | 25020098 | 25020113 | + | chr22 | 25023399 | 25023586; 25023457 | + | ENST00000248923; ENST00000412658; ENST00000400382; ENST00000400383; ENST0000040080; ENST00000406383; | TSF |

TABLE 32-continued

Transcript fusion for Cervical Kidney renal papillary cell carcinoma (KIRP) Coordinates of the fusion sequences for which the donor is the TE.

| 1' | 2' | 3' | 4' | 5 | 6' | 7' | 8' | 9' | 10' | 11' |
|---|---|---|---|---|---|---|---|---|---|---|
| | | | | | | | | | ENST00000425895 | |
| 3% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 3% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 3% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 3% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 3% | chr7 | 23290404 | 23290481 | + | chr7 | 23292926 | 23293078 | + | ENST00000258733; ENST00000381990; ENST00000409458; ENST00000453162 | TSF |
| 3% | chr7 | 23290404 | 23290481 | + | chr7 | 23292926 | 23293078 | + | ENST00000258733; ENST00000381990; ENST00000409458; ENST00000453162 | TSF |
| 3% | chr7 | 23290404 | 23290481 | + | chr7 | 23292926 | 23293078 | + | ENST00000258733; ENST00000381990; ENST00000409458; ENST00000453162 | TSF |
| 3% | chr7 | 23290404 | 23290481 | + | chr7 | 23292926 | 23293078 | + | ENST00000258733; ENST00000381990; ENST00000409458; ENST00000453162 | TSF |
| 3% | chr19 | 50174724 | 50174836 | + | chr19 | 50176955 | 50177005; 50177034 | + | ENST00000441864; ENST00000246785; ENST00000600947; ENST00000598306 | TSF |
| 3% | chr19 | 50174724 | 50174836 | + | chr19 | 50176955 | 50177005; 50177034 | + | ENST00000441864; ENST00000246785; ENST00000600947; ENST00000598306 | TSF |
| 3% | chr20 | 45138455 | 45138244 | − | chr20 | 45133379 | 45133253 | − | ENST00000593880; ENST00000347606 | TSF |
| 3% | chr20 | 45138455 | 45138244 | − | chr20 | 45133379 | 45133253 | − | ENST00000593880; ENST00000347606 | TSF |
| 3% | chr4 | 52913536 | 52913266 | − | chr4 | 52899806 | 52899597 | − | ENST00000381431; ENST00000506357; ENST00000514133 | TSF |
| 3% | chr4 | 52913536 | 52913266 | − | chr4 | 52899806 | 52899597 | − | ENST00000381431; ENST00000506357; ENST00000514133 | TSF |
| 3% | chr6 | 80022917 | 80022085 | − | chr6 | 79924739 | 79924689 | − | ENST00000275036; ENST00000344726 | TSF |
| 3% | chr6 | 80022917 | 80022085 | − | chr6 | 79924739 | 79924689 | − | ENST00000275036; ENST00000344726 | TSF |
| 3% | chr3 | 98586295 | 98586135 | − | chr3 | 98568442 | 98568305; 98568232 | − | ENST00000326840; ENST00000326857; ENST00000449482 | TSF |
| 3% | chr3 | 98586295 | 98586135 | − | chr3 | 98568442 | 98568305; 98568232 | − | ENST00000326840; ENST00000326857; ENST00000449482 | TSF |
| 3% | chr3 | 98586295 | 98586135 | − | chr3 | 98568442 | 98568305; 98568232 | − | ENST00000326840; ENST00000326857; ENST00000449482 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr1 | 48271615 | 48271527 | − | chr1 | 48267291 | 48267145 | − | ENST00000606738 | TSF |
| 2% | chr5 | 156483240 | 156483190 | − | chr5 | 156482544 | 156482212 | − | ENST00000522693; ENST00000523175; ENST00000339252; ENST00000425854; ENST00000544197; ENST00000518745 | TSF |
| 2% | chr5 | 156483240 | 156483190 | − | chr5 | 156482544 | 156482212 | − | ENST00000522693; ENST00000523175; ENST00000339252; ENST00000425854; ENST00000544197; ENST00000518745 | TSF |
| 2% | chr5 | 156483240 | 156483190 | − | chr5 | 156482544 | 156482212 | − | ENST00000522693; ENST00000523175; ENST00000339252; ENST00000425854; ENST00000544197; ENST00000518745 | TSF |
| 2% | chr4 | 187060473 | 187060762 | + | chr4 | 187070327 | 187070437 | + | ENST00000356371 | TSF |
| 2% | chr12 | 112169907 | 112169999 | + | chr12 | 112171727 | 112171872; 112171851 | + | ENST00000392636; ENST00000549590; ENST00000455480; ENST00000313698; ENST00000552706 | TSF |
| 2% | chr12 | 112169907 | 112169999 | + | chr12 | 112171727 | 112171872; 112171851 | + | ENST00000392636; ENST00000549590; ENST00000455480; ENST00000313698; ENST00000552706 | TSF |
| 2% | chr12 | 112169907 | 112169999 | + | chr12 | 112171727 | 112171872; 112171851 | + | ENST00000392636; ENST00000549590; ENST00000455480; ENST00000313698; ENST00000552706 | TSF |
| 2% | chr12 | 112169907 | 112169999 | + | chr12 | 112171727 | 112171872; | + | ENST00000392636; ENST00000549590; ENST00000455480; | TSF |

TABLE 32-continued

Transcript fusion for Cervical Kidney renal papillary cell carcinoma (KIRP) Coordinates of the fusion sequences for which the donor is the TE.

| 1' | 2' | 3' | 4' | 5 | 6' | 7' | 8' | 9' | 10' | 11' |
|---|---|---|---|---|---|---|---|---|---|---|
|  |  |  |  |  |  |  | 112171851 | | ENST00000313698; ENST00000552706 | |
| 2% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 2% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 2% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 2% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 2% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 2% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 2% | chr7 | 107568061 | 107568012 | − | chr7 | 107566804 | 107566628 | − | ENST00000393561; ENST00000222399 | TSF |
| 2% | chr2 | 210938033 | 210937924 | − | chr2 | 210908828 | 210908663; 210908637 | − | ENST00000281772; ENST00000418791; ENST00000457374; ENST00000452086; ENST00000428655 | TSF |
| 2% | chr2 | 210938033 | 210937924 | − | chr2 | 210908828 | 210908663; 210908637 | − | ENST00000281772; ENST00000418791; ENST00000457374; ENST00000452086; ENST00000428655 | TSF |
| 2% | chr2 | 210938033 | 210937924 | − | chr2 | 210908828 | 210908663; 210908637 | − | ENST00000281772; ENST00000418791; ENST00000457374; ENST00000452086; ENST00000428655 | TSF |
| 2% | chr2 | 210938033 | 210937924 | − | chr2 | 210908828 | 210908663; 210908637 | − | ENST00000281772; ENST00000418791; ENST00000457374; ENST00000452086; ENST00000428655 | TSF |

TABLE 33

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 98% | chr17 | 40812657 | 40812725 | + | ENST00000251412 | chr17 | 40813219 | 40813265 | + | TAF |
| 92% | chr11 | 73589824 | 73589864 | + | ENST00000310571 | chr11 | 73598085 | 73598225 | + | TAF |
| 90% | chrX | 64743587; 64743497 | 64743440 | − | ENST00000374807; ENST00000374811; ENST00000374804; ENST00000469091 | chrX | 64742373 | 64741630 | − | TAF |
| 90% | chrX | 64743587; 64743497 | 64743440 | − | ENST00000374807; ENST00000374811; ENST00000374804; ENST00000469091 | chrX | 64742373 | 64741630 | − | TAF |
| 90% | chrX | 64743587; 64743497 | 64743440 | − | ENST00000374807; ENST00000374811; ENST00000374804; ENST00000469091 | chrX | 64742373 | 64741630 | − | TAF |
| 90% | chrX | 64743587; 64743497 | 64743440 | − | ENST00000374807; ENST00000374811; ENST00000374804; ENST00000469091 | chrX | 64742373 | 64741630 | − | TAF |
| 81% | chr5 | 146460699; 146460671 | 146460622 | − | ENST00000504198; ENST00000394409 | chr5 | 146414803 | 146414648 |  | TAF |
| 81% | chr5 | 146460699; 146460671 | 146460622 | − | ENST00000504198; ENST00000394409 | chr5 | 146414803 | 146414648 |  | TAF |
| 80% | chr6 | 36762426 | 36762367 | − | ENST00000244751 | chr6 | 36760223 | 36760189 | − | TAF |
| 77% | chr19 | 39390161 | 39390146 | − | ENST00000249396; ENST00000358931; ENST00000443898 | chr19 | 39389554 | 39389434 | − | TAF |
| 51% | chr17 | 63173850 | 63173921 | + | ENST00000584234; ENST00000262406 | chr17 | 63176114 | 63176128 | + | TAF |
| 40% | chr11 | 73589824 | 73589864 | + | ENST00000310571 | chr11 | 73598076 | 73598225 | + | TAF |
| 39% | chr5 | 146435301; 146435306 | 146435228 | − | ENST00000394414; ENST00000336640; ENST00000522831; ENST00000515880; ENST00000512011 | chr5 | 146414803 | 146414648 | − | TAF |
| 39% | chr5 | 146435301; 146435306 | 146435228 | − | ENST00000394414; ENST00000336640; ENST00000522831; ENST00000515880; ENST00000512011 | chr5 | 146414803 | 146414648 | − | TAF |
| 38% | chr7 | 99821698 | 99821505 | − | ENST00000436886 | chr7 | 99810756 | 99810604 | − | TAF |
| 35% | chr1 | 1237426 | 1237368 | − | ENST00000354700; ENST00000353662 | chr1 | 1236310 | 1236145 | − | TAF |
| 35% | chr1 | 1237426 | 1237368 | − | ENST00000354700; ENST00000353662 | chr1 | 1236310 | 1236145 | − | TAF |
| 29% | chr14 | 77606081 | 77605556 | − | ENST00000319374 | chr14 | 77602889 | 77602820 | − | TAF |
| 28% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 28% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 28% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 28% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 28% | chr6 | 36762426 | 36762367 | − | ENST00000244751 | chr6 | 36760220 | 36760189 | − | TAF |
| 25% | chr11 | 61197619 | 61197654 | + | ENST00000542794; ENST00000541135; ENST00000301761; ENST00000542074; | chr11 | 61240217 | 61240660 | + | TAF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
|  |  |  |  |  | ENST00000534878; ENST00000359614; ENST00000537782; ENST00000538594; ENST00000544801; ENST00000536250; ENST00000543265 |  |  |  |  |  |
| 25% | chr19 | 1235564 | 1235500 | − | ENST00000590083; ENST00000382477; ENST00000215376; ENST00000589260 | chr19 | 1235389 | 1235290 | − | TAF |
| 25% | chr19 | 1235564 | 1235500 | − | ENST00000590083; ENST00000382477; ENST00000215376; ENST00000589260 | chr19 | 1235389 | 1235290 | − | TAF |
| 25% | chr3 | 125271523 | 125271025 | − | ENST00000296220 | chr3 | 125268456 | 125268341 | − | TAF |
| 22% | chr18 | 72250797 | 72250944 | + | ENST00000358821; ENST00000582365 | chr18 | 72256555 | 72256578 | + | TAF |
| 22% | chr18 | 72250797 | 72250944 | + | ENST00000358821; ENST00000582365 | chr18 | 72256555 | 72256578 | + | TAF |
| 18% | chr4 | 134084132 | 134084437 | + | ENST00000264360 | chr4 | 134129231 | 134129518 | + | TAF |
| 17% | chr9 | 131002264 | 131002275 | + | ENST00000475805; ENST00000341179; ENST00000372923; ENST00000393594; ENST00000486160 | chr9 | 131002706 | 131002973 | + | TAF |
| 17% | chr9 | 131002264 | 131002275 | + | ENST00000475805; ENST00000341179; ENST00000372923; ENST00000393594; ENST00000486160 | chr9 | 131002706 | 131002973 | + | TAF |
| 17% | chr3 | 9476508; 9476512 | 9476566 | + | ENST00000450326; ENST00000402198; ENST00000402466; ENST00000406341; ENST00000407969; ENST00000442373; ENST00000302463 | chr3 | 9476688 | 9476952 | + | TAF |
| 17% | chr3 | 9476508; 9476512 | 9476566 | + | ENST00000450326; ENST00000402198; ENST00000402466; ENST00000406341; ENST00000407969; ENST00000442373; ENST00000302463 | chr3 | 9476688 | 9476952 | + | TAF |
| 17% | chr3 | 9476508; 9476512 | 9476566 | + | ENST00000450326; ENST00000402198; ENST00000402466; ENST00000406341; ENST00000407969; ENST00000442373; ENST00000302463 | chr3 | 9476688 | 9476952 | + | TAF |
| 16% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chr16| | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chrX | 49054298 | 49054174 | − | ENST00000263233; ENST00000479808; ENST00000469389; ENST00000466635 | chrX | 49053735 | 49053463 | − | TSF |
| 15% | chr1 | 60370730 | 60370543 | − | ENST00000371204 | chr1 | 60370188 | 60370144 | − | TAF |
| 15% | chr1 | 160012322 | 160011624 | − | ENST00000368089 | chr1 | 159969284 | 159968914 | − | TSF |
| 14% | chr9 | 139872031 | 139872144 | + | ENST00000224167; ENST00000457950; ENST00000371625; ENST00000371623; ENST00000471521 | chr9 | 139873283 | 139873345 | + | TAF |
| 14% | chr19 | 44129402 | 44129230 | − | ENST00000222374 | chr19 | 44129055 | 44128921 | − | TAF |
| 14% | chr9 | 100308467 | 100308623 | + | ENST00000395211; ENST00000259365 | chr9 | 100309531 | 100309681 | + | TAF |
| 14% | chr4 | 159620139 | 159620282 | + | ENST00000511912; ENST00000307738 | chr4 | 159622027 | 159622060 | + | TSF |
| 14% | chr4 | 159620139 | 159620282 | + | ENST00000511912; ENST00000307738 | chr4 | 159622027 | 159622060 | + | TSF |
| 13% | chr1 | 99380476 | 99380342 | − | ENST00000263177 | chr1 | 99378537 | 99378478 | − | TSF |
| 13% | chr9 | 98766802 | 98766983 | + | ENST00000407474; ENST00000320486 | chr9 | 98801158 | 98801481 | + | TSF |
| 13% | chr9 | 98766802 | 98766983 | + | ENST00000407474; ENST00000320486 | chr9 | 98801158 | 98801481 | + | TSF |
| 13% | chr2 | 230377652 | 230377499 | − | ENST00000341772 | chr2 | 230370969 | 230370811 | − | TSF |
| 12% | chr2 | 85991114 | 85991305 | + | ENST00000306279 | chr2 | 86045431 | 86045447 | + | TAF |
| 12% | chr19 | 6444312 | 6444162 | − | ENST00000598704; ENST00000595810; ENST00000598908; ENST00000264088; ENST00000601322; ENST00000301454; ENST00000593600; ENST00000414491; ENST00000600682; ENST00000334510 | chr19 | 6436479 | 6436108 | − | TAF |
| 12% | chr19 | 6444312 | 6444162 | − | ENST00000598704; ENST00000595810; ENST00000598908; ENST00000264088; ENST00000601322; ENST00000301454; ENST00000593600; ENST00000414491; ENST00000600682; ENST00000334510 | chr19 | 6436479 | 6436108 | − | TAF |
| 12% | chr19 | 6444312 | 6444162 | − | ENST00000598704; ENST00000595810; ENST00000598908; ENST00000264088; ENST00000601322; ENST00000301454; ENST00000593600; ENST00000414491; ENST00000600682; ENST00000334510 | chr19 | 6436479 | 6436108 | − | TAF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 12% | chr19 | 6444312 | 6444162 | − | ENST00000598704; ENST00000595810; ENST00000598908; ENST00000264088; ENST00000601322; ENST00000301454; ENST00000593600; ENST00000414491; ENST00000600682; ENST00000334510 | chr19 | 6436479 | 6436108 | − | TAF |
| 12% | chr19 | 6444312 | 6444162 | − | ENST00000598704; ENST00000595810; ENST00000598908; ENST00000264088; ENST00000601322; ENST00000301454; ENST00000593600; ENST00000414491; ENST00000600682; ENST00000334510 | chr19 | 6436479 | 6436108 | − | TAF |
| 12% | chr19 | 6444312 | 6444162 | − | ENST00000598704; ENST00000595810; ENST00000598908; ENST00000264088; ENST00000601322; ENST00000301454; ENST00000593600; ENST00000414491; ENST00000600682; ENST00000334510 | chr19 | 6436479 | 6436108 | − | TAF |
| 12% | chr19 | 6444312 | 6444162 | − | ENST00000598704; ENST00000595810; ENST00000598908; ENST00000264088; ENST00000601322; ENST00000301454; ENST00000593600; ENST00000414491; ENST00000600682; ENST00000334510 | chr19 | 6436479 | 6436108 | − | TAF |
| 12% | chr19 | 6444312 | 6444162 | − | ENST00000598704; ENST00000595810; ENST00000598908; ENST00000264088; ENST00000601322; ENST00000301454; ENST00000593600; ENST00000414491; ENST00000600682; ENST00000334510 | chr19 | 6436479 | 6436108 | − | TAF |
| 12% | chr19 | 6444312 | 6444162 | − | ENST00000598704; ENST00000595810; ENST00000598908; ENST00000264088; ENST00000601322; ENST00000301454; ENST00000593600; ENST00000414491; ENST00000600682; ENST00000334510 | chr19 | 6436479 | 6436108 | − | TAF |
| 12% | chr2 | 230135759 | 230135730 | − | ENST00000409462; ENST00000392055; ENST00000534952 | chr2 | 230127609 | 230127321 | − | TAF |
| 12% | chr10 | 55943353 | 55943204 | − | ENST00000373965; ENST00000414778; ENST00000395438; ENST00000409834; ENST00000395445; ENST00000395446; ENST00000395432; ENST00000361849; ENST00000395433; ENST00000373957; ENST00000320301; ENST00000395430; ENST00000448885; ENST00000437009; ENST00000373955 | chr10 | 55933689 | 55933395 | − | TSF |
| 12% | chr10 | 55943353 | 55943204 | − | ENST00000373965; ENST00000414778; ENST00000395438; ENST00000409834; ENST00000395445; ENST00000395446; ENST00000395432; ENST00000361849; ENST00000395433; ENST00000373957; ENST00000320301; ENST00000395430; ENST00000448885; ENST00000437009; ENST00000373955 | chr10 | 55933689 | 55933395 | − | TSF |
| 12% | chr10 | 55943353 | 55943204 | − | ENST00000373965; ENST00000414778; ENST00000395438; ENST00000409834; ENST00000395445; ENST00000395446; ENST00000395432; ENST00000361849; ENST00000395433; ENST00000373957; ENST00000320301; ENST00000395430; ENST00000448885; ENST00000437009; ENST00000373955 | chr10 | 55933689 | 55933395 | − | TSF |
| 12% | chr10 | 55943353 | 55943204 | − | ENST00000373965; ENST00000414778; ENST00000395438; ENST00000409834; ENST00000395445; ENST00000395446; ENST00000395432; ENST00000361849; ENST00000395433; ENST00000373957; ENST00000320301; ENST00000395430; ENST00000448885; ENST00000437009; ENST00000373955 | chr10 | 55933689 | 55933395 | − | TSF |
| 12% | chr10 | 55943353 | 55943204 | − | ENST00000373965; ENST00000414778; ENST00000395438; ENST00000409834; ENST00000395445; ENST00000395446; ENST00000395432; ENST00000361849; ENST00000395433; ENST00000373957; ENST00000320301; ENST00000395430; ENST00000448885; ENST00000437009; ENST00000373955 | chr10 | 55933689 | 55933395 | − | TSF |
| 12% | chr10 | 55943353 | 55943204 | − | ENST00000373965; ENST00000414778; ENST00000395438; ENST00000409834; ENST00000395445; ENST00000395446; ENST00000395432; ENST00000361849; | chr10 | 55933689 | 55933395 | − | TSF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| | | | | | ENST00000395433; ENST00000373957; ENST00000320301; ENST00000395430; ENST00000448885; ENST00000437009; ENST00000373955 | | | | | |
| 11% | chr14 | 93799274 | 93799166 | − | ENST00000554565 | chr14 | 93791211 | 93791104 | − | TAF |
| 11% | chr1 | 11718793 | 11718928 | + | ENST00000251546; ENST00000376770; ENST00000376768; ENST00000251547; ENST00000376760; ENST00000376762; ENST00000475435; ENST00000471895 | chr1 | 11719303 | 11719464 | + | TAF |
| 11% | chr1 | 11718793 | 11718928 | + | ENST00000251546; ENST00000376770; ENST00000376768; ENST00000251547; ENST00000376760; ENST00000376762; ENST00000475435; ENST00000471895 | chr1 | 11719303 | 11719464 | + | TAF |
| 11% | chr1 | 11718793 | 11718928 | + | ENST00000251546; ENST00000376770; ENST00000376768; ENST00000251547; ENST00000376760; ENST00000376762; ENST00000475435; ENST00000471895 | chr1 | 11719303 | 11719464 | + | TAF |
| 11% | chr1 | 11718793 | 11718928 | + | ENST00000251546; ENST00000376770; ENST00000376768; ENST00000251547; ENST00000376760; ENST00000376762; ENST00000475435; ENST00000471895 | chr1 | 11719303 | 11719464 | + | TAF |
| 10% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 10% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 10% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 10% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 10% | chr19 | 5208068 | 5207933 | − | ENST00000262963; ENST00000348075; ENST00000353284; ENST00000357368; ENST00000372412; ENST00000587303; ENST00000588012; ENST00000592099 | chr19 | 5159115 | 5158876 | − | TAF |
| 10% | chr2 | 175809671 | 175809616 | − | ENST00000409900; ENST00000409156 | chr2 | 175805622 | 175805109 | | TAF |
| 9% | chr5 | 152873488; 152873613 | 152873625 | + | ENST00000285900; ENST00000518142; ENST00000340592; ENST00000521843; ENST00000448073; ENST00000518783 | chr5 | 152889310 | 152889396 | + | TSF |
| 9% | chr5 | 152873488; 152873613 | 152873625 | + | ENST00000285900; ENST00000518142; ENST00000340592; ENST00000521843; ENST00000448073; ENST00000518783 | chr5 | 152889310 | 152889396 | + | TSF |
| 9% | chr5 | 152873488; 152873613 | 152873625 | + | ENST00000285900; ENST00000518142; ENST00000340592; ENST00000521843; ENST00000448073; ENST00000518783 | chr5 | 152889310 | 152889396 | + | TSF |
| 9% | chr8 | 63502273 | 63502353 | + | ENST00000523211; ENST00000328472 | chr8 | 63546747 | 63547118 | + | TSF |
| 9% | chr19 | 1461962 | 1462176 | + | ENST00000590469; ENST00000233607; ENST00000238483; ENST00000535453 | chr19 | 1462374 | 1462680 | + | TSF |
| 9% | chr19 | 1461962 | 1462176 | + | ENST00000590469; ENST00000233607; ENST00000238483; ENST00000535453 | chr19 | 1462374 | 1462680 | + | TSF |
| 8% | chr16 | 30783410 | 30783511 | + | ENST00000324685; ENST00000402121; ENST00000563683; ENST00000357890 | chr16 | 30785136 | 30785155 | + | TSF |
| 8% | chr16 | 30783410 | 30783511 | + | ENST00000324685; ENST00000402121; ENST00000563683; ENST00000357890 | chr16 | 30785136 | 30785155 | + | TSF |
| 8% | chr16 | 30783410 | 30783511 | + | ENST00000324685; ENST00000402121; ENST00000563683; ENST00000357890 | chr16 | 30785136 | 30785155 | + | TSF |
| 8% | chr16 | 30783410 | 30783511 | + | ENST00000324685; ENST00000402121; ENST00000563683; ENST00000357890 | chr16 | 30785136 | 30785155 | + | TSF |
| 8% | chr1 | 156618360 | 156618653 | + | ENST00000329117; ENST00000361588 | chr1 | 156620746 | 156620747 | + | TSF |
| 8% | chr1 | 160109683; 160109716 | 160109774 | + | ENST00000361216; ENST00000392233; ENST00000447527 | chr1 | 160110441 | 160110463 | + | TSF |
| 8% | chr1 | 160109683; 160109716 | 160109774 | + | ENST00000361216; ENST00000392233; ENST00000447527 | chr1 | 160110441 | 160110463 | + | TSF |
| 8% | chr1 | 160109683; 160109716 | 160109774 | + | ENST00000361216; ENST00000392233; ENST00000447527 | chr1 | 160110441 | 160110463 | + | TSF |
| 7% | chr19 | 19351412 | 19351494 | + | ENST00000252575; ENST00000538881 | chr19 | 19353543 | 19353658 | + | TSF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 7% | chr19 | 19351412 | 19351494 | + | ENST00000588231 ENST00000252575; ENST00000538881;chr19 | | 19353543 | 19353658 | + | TSF |
| 7% | chr19 | 19351412 | 19351494 | + | ENST00000588231 ENST00000252575; ENST00000538881;chr19 | | 19353543 | 19353658 | + | TSF |
| 7% | chr1 | 31347435 | 31347144 | − | ENST00000588231 ENST00000336798; ENST00000339394 chr1 | | 31340352 | 31340311 | − | TSF |
| 7% | chr1 | 31347435 | 31347144 | − | ENST00000336798; ENST00000339394 chr1 | | 31340352 | 31340311 | − | TSF |
| 7% | chr22 | 39772057 | 39772202 | + | ENST00000318801; ENST00000406293;chr22 ENST00000328933; ENST00000381535 | | 39775891 | 39775926 | + | TSF |
| 7% | chr22 | 39772057 | 39772202 | + | ENST00000318801; ENST00000406293;chr22 ENST00000328933; ENST00000381535 | | 39775891 | 39775926 | + | TSF |
| 6% | chr11 | 117710545 | 117710496 | − | ENST00000532984; ENST00000584394;chr11 ENST00000529335 | | 117703821 | 117703741 | − | TSF |
| 6% | chr11 | 117710545 | 117710496 | − | ENST00000532984; ENST00000584394;chr11 ENST00000529335 | | 117703821 | 117703741 | − | TSF |
| 6% | chr11 | 117710545 | 117710496 | − | ENST00000532984; ENST00000584394;chr11 ENST00000529335 | | 117703821 | 117703741 1 | − | TSF |
| 6% | chr17 | 1028702; 1028625 | 1028518 | − | ENST00000302538; ENST00000544583;chr17 ENST00000574437; ENST00000575934; ENST00000574139; ENST00000570525; ENST00000574266 | | 1005267 | 1004964 | − | TSF |
| 6% | chr17 | 1028702; 1028625 | 1028518 | − | ENST00000302538; ENST00000544583;chr17 ENST00000574437; ENST00000575934; ENST00000574139; ENST00000570525; ENST00000574266 | | 1005267 | 1004964 | − | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | − | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | − | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | − | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | − | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | − | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | − | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | − | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | − | TSF |
| 6% | chr8 | 145001050 | 145000952 | − | ENST00000345136; ENST00000357649;chr8 ENST00000354589; ENST00000398774; ENST00000322810; ENST00000354958; ENST00000356346; ENST00000436759; ENST00000527096; ENST00000527303 | | 144977746 | 144977671 | − | TSF |
| 5% | chr13 | 115057109 | 115057267 | + | ENST00000375299; ENST00000351487 chr13 | | 115063902 | 115064025 | + | TSF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 5% | chr13 | 115057109 | 115057267 | + | ENST00000375299; ENST00000351487 | chr13 | 115063902 | 115064025 | + | TSF |
| 5% | chr7 | 102249269 | 102249208 | − | ENST00000262940; ENST00000461209; ENST00000449970; ENST00000462172; ENST00000522801; ENST00000520042; ENST00000521076 | chr7 | 102248714 | 102248385 | − | TSF |
| 5% | chr7 | 102249269 | 102249208 | − | ENST00000262940; ENST00000461209; ENST00000449970; ENST00000462172; ENST00000522801; ENST00000520042; ENST00000521076 | chr7 | 102248714 | 102248385 | − | TSF |
| 5% | chr7 | 102249269 | 102249208 | − | ENST00000262940; ENST00000461209; ENST00000449970; ENST00000462172; ENST00000522801; ENST00000520042; ENST00000521076 | chr7 | 102248714 | 102248385 | − | TSF |
| 5% | chr1 | 156384545 | 156384446 | − | ENST00000368242; ENST00000310027; ENST00000368243; ENST00000357975 | chr1 | 156374431 | 156374430 | − | TSF |
| 5% | chr1 | 156384545 | 156384446 | − | ENST00000368242; ENST00000310027; ENST00000368243; ENST00000357975 | chr1 | 156374431 | 156374430 | − | TSF |
| 5% | chr1 | 156384545 | 156384446 | − | ENST00000368242; ENST00000310027; ENST00000368243; ENST00000357975 | chr1 | 156374431 | 156374430 | − | TSF |
| 5% | chr1 | 156384545 | 156384446 | − | ENST00000368242; ENST00000310027; ENST00000368243; ENST00000357975 | chr1 | 156374431 | 156374430 | − | TSF |
| 5% | chr7 | 55270210 | 55270401 | + | ENST00000455089 | chr7 | 55272949 | 55272949 | + | TSF |
| 5% | chr20 | 29978286 | 29978226 | − | ENST00000339144; ENST00000376321; ENST00000376315 | chr20 | 29976162 | 29976126 | − | TSF |
| 5% | chr7 | 102150107 | 102150046 | − | ENST00000541662; ENST00000465829; ENST00000306682 | chr7 | 102149552 | 102149223 | − | TSF |
| 5% | chr7 | 102150107 | 102150046 | − | ENST00000541662; ENST00000465829; ENST00000306682 | chr7 | 102149552 | 102149223 | − | TSF |
| 5% | chr20 | 62612599 | 62612669 | + | ENST00000535781; ENST00000266079 | chr20 | 62612803 | 62612943 | + | TSF |
| 5% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 5% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 5% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 4% | chr1 | 99380476 | 99380357 | − | ENST00000370188; ENST00000263177 | chr1 | 99378537 | 99378478 | − | TSF |
| 4% | chr19 | 44129402 | 44129230 | − | ENST00000222374 | chr19 | 44129101 | 44128921 | − | TSF |
| 4% | chr10 | 55826645 | 55826517 | − | ENST00000373965; ENST00000414778; ENST00000395438; ENST00000409834; ENST00000395445; ENST00000395432; ENST00000361849; ENST00000395433; ENST00000373957; ENST00000320301; ENST00000395430; ENST00000437009; ENST00000373955 | chr10 | 55816578 | 55816423 | − | TSF |
| 4% | chr10 | 55826645 | 55826517 | − | ENST00000373965; ENST00000414778; ENST00000395438; ENST00000409834; ENST00000395445; ENST00000395432; ENST00000361849; ENST00000395433; ENST00000373957; ENST00000320301; ENST00000395430; ENST00000437009; ENST00000373955 | chr10 | 55816578 | 55816423 | − | TSF |
| 4% | chr10 | 55826645 | 55826517 | − | ENST00000373965; ENST00000414778; ENST00000395438; ENST00000409834; ENST00000395445; ENST00000395432; ENST00000361849; ENST00000395433; ENST00000373957; ENST00000320301; ENST00000395430; ENST00000437009; ENST00000373955 | chr10 | 55816578 | 55816423 | − | TSF |
| 4% | chr10 | 55826645 | 55826517 | − | ENST00000373965; ENST00000414778; ENST00000395438; ENST00000409834; ENST00000395445; ENST00000395432; ENST00000361849; ENST00000395433; ENST00000373957; ENST00000320301; ENST00000395430; ENST00000437009; ENST00000373955 | chr10 | 55816578 | 55816423 | − | TSF |
| 4% | chr10 | 55826645 | 55826517 | − | ENST00000373965; ENST00000414778; ENST00000395438; ENST00000409834; ENST00000395445; ENST00000395432; ENST00000361849; ENST00000395433; ENST00000373957; ENST00000320301; ENST00000395430; ENST00000437009; ENST00000373955 | chr10 | 55816578 | 55816423 | − | TSF |
| 4% | chr10 | 55826645 | 55826517 | − | ENST00000373965; ENST00000414778 | chr10 | 55816578 | 55816423 | − | TSF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
|  |  |  |  |  | ENST00000395438; ENST00000409834; ENST00000395445; ENST00000395432; ENST00000361849; ENST00000395433; ENST00000373957; ENST00000320301; ENST00000395430; ENST00000437009; ENST00000373955 |  |  |  |  |  |
| 4% | chr10 | 55826645 | 55826517 | − | ENST00000373965; ENST00000414778; ENST00000395438; ENST00000409834; ENST00000395445; ENST00000395432; ENST00000361849; ENST00000395433; ENST00000373957; ENST00000320301; ENST00000395430; ENST00000437009; ENST00000373955 | chr10 | 55816578 | 55816423 | − | TSF |
| 4% | chr19 | 3905432 | 3905653 | + | ENST00000450849; ENST00000301260; ENST00000398448; ENST00000600960 | chr19 | 3906655 | 3906700 | + | TSF |
| 4% | chr19 | 3905432 | 3905653 | + | ENST00000450849; ENST00000301260; ENST00000398448; ENST00000600960 | chr19 | 3906655 | 3906700 | + | TSF |
| 4% | chr11 | 17429000 | 17428901 | − | ENST00000389817; ENST00000302539 | chr11 | 17428722 | 17428716 | − | TSF |
| 4% | chr11 | 17429000 | 17428901 | − | ENST00000389817; ENST00000302539 | chr11 | 17428722 | 17428716 | − | TSF |
| 4% | chr3 | 98304342; 98304503 | 98304285 | − | ENST00000512905; ENST00000264193 | chr3 | 98292414 | 98292298 | − | TSF |
| 4% | chr3 | 98304342; 98304503 | 98304285 | − | ENST00000512905; ENST00000264193 | chr3 | 98292414 | 98292298 | − | TSF |
| 4% | chr5 | 90398036 | 90398157 | + | ENST00000405460; ENST00000425867 | chr5 | 90412152 | 90412249 | + | TSF |
| 4% | chr5 | 90398036 | 90398157 | + | ENST00000405460; ENST00000425867 | chr5 | 90412152 | 90412249 | + | TSF |
| 4% | chr16 | 50659396 | 50659491 | + | ENST00000268459 | chr16 | 50663933 | 50663990 | + | TSF |
| 4% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 4% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 4% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 4% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 4% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; | chr3 | 98228614 | 98228468 | − | TSF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 4% | chr3 | 98236033; 98236004 | 98235896 | − | ENST00000513287; ENST00000511667; ENST00000513452; ENST00000502299; ENST00000512147; ENST00000508902; ENST00000510541; ENST00000514537; ENST00000515620 ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 4% | chr3 | 98236033; 98236004 | 98235896 | − | ENST00000502288; ENST00000507874; ENST00000341181; ENST00000437922; ENST00000394180; ENST00000506885; ENST00000503004; ENST00000394185; ENST00000394181; ENST00000513873; ENST00000510545; ENST00000511081; ENST00000513287; ENST00000511667; ENST00000513452; ENST00000502299; ENST00000512147; ENST00000508902; ENST00000510541; ENST00000514537; ENST00000515620 | chr3 | 98228614 | 98228468 | − | TSF |
| 3% | chr3 | 120068090 | 120067591 | − | ENST00000295628 | chr3 | 120067161 | 120067151 | − | TSF |
| 3% | chr2 | 220379066 | 220380028 | + | ENST00000347842; ENST00000358078 | chr2 | 220383470 | 220383510 | + | TSF |
| 3% | chr14 | 94594329 | 94594183 | − | ENST00000238609; ENST00000556727 | chr14 | 94591218 | 94590919 | − | TSF |
| 3% | chr14 | 94594329 | 94594183 | − | ENST00000238609; ENST00000556727 | chr14 | 94591218 | 94590919 | − | TSF |
| 3% | chr8 | 104778455 | 104778765 | + | ENST00000504942; ENST00000406091 | chr8 | 104821508 | 104821527 | + | TSF |
| 3% | chr15 | 64444837 | 64444941 | + | ENST00000325881; ENST00000558466 | chr15 | 64445122 | 64445138 | + | TSF |
| 3% | chr22 | 26747018; 26747020 | 26747209 | + | ENST00000404234; ENST00000529632; ENST00000248933; ENST00000343706; ENST00000402979; ENST00000403121; ENST00000411842 | chr22 | 26750424 | 26750495 | + | TSF |
| 3% | chr22 | 26747018; 26747020 | 26747209 | + | ENST00000404234; ENST00000529632; ENST00000248933; ENST00000343706; ENST00000402979; ENST00000403121; ENST00000411842 | chr22 | 26750424 | 26750495 | + | TSF |
| 3% | chr22 | 26747018; 26747020 | 26747209 | + | ENST00000404234; ENST00000529632; ENST00000248933; ENST00000343706; ENST00000402979; ENST00000403121; ENST00000411842 | chr22 | 26750424 | 26750495 | + | TSF |
| 3% | chr14 | 31922550 | 31922481 | − | ENST00000549185; ENST00000547378; ENST00000310850; ENST00000356180 | chr14 | 31907346 | 31905965 | − | TSF |
| 3% | chr20 | 1144962 | 1145120 | + | ENST00000381898; ENST00000333082; ENST00000246015; ENST00000335877; ENST00000438768; ENST00000435720 | chr20 | 1166984 | 1167052 | + | TSF |
| 3% | chr20 | 1144962 | 1145120 | + | ENST00000381898; ENST00000333082; ENST00000246015; ENST00000335877; ENST00000438768; ENST00000435720 | chr20 | 1166984 | 1167052 | + | TSF |
| 3% | chr20 | 1144962 | 1145120 | + | ENST00000381898; ENST00000333082; ENST00000246015; ENST00000335877; ENST00000438768; ENST00000435720 | chr20 | 1166984 | 1167052 | + | TSF |
| 3% | chr20 | 1144962 | 1145120 | + | ENST00000381898; ENST00000333082; ENST00000246015; ENST00000335877; ENST00000438768; ENST00000435720 | chr20 | 1166984 | 1167052 | + | TSF |
| 3% | chr5 | 65310497 | 65310553 | + | ENST00000284037; ENST00000380943; ENST00000416865; ENST00000380935; ENST00000380936; ENST00000380939; ENST00000380938; ENST00000511297; ENST00000506030; ENST00000508515 | chr5 | 65311417 | 65311436 | + | TSF |
| 3% | chr6 | 102483216 | 102483441 | + | ENST00000369138; ENST00000413795; ENST00000421544; ENST00000318991; ENST00000369137; ENST00000369134 | chr6 | 102495349 | 102495644 | + | TSF |
| 3% | chr6 | 102483216 | 102483441 | + | ENST00000369138; ENST00000413795; ENST00000421544; ENST00000318991; ENST00000369137; ENST00000369134 | chr6 | 102495349 | 102495644 | + | TSF |
| 3% | chr6 | 102483216 | 102483441 | + | ENST00000369138; ENST00000413795; ENST00000421544; ENST00000318991; ENST00000369137; ENST00000369134 | chr6 | 102495349 | 102495644 | + | TSF |
| 3% | chrX | 13956629 | 13956626 | − | ENST00000454189 | chrX | 13952867 | 13952865 | − | TSF |
| 3% | chr4 | 83626566 | 83626436 | − | ENST00000319540; ENST00000273908; ENST00000282709 | chr4 | 83616020 | 83615829 | − | TSF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr8 | 27472298 | 27472172 | − | ENST00000560366 | chr8 | 27471250 | 27471189 | − | TSF |
| 2% | chr11 | 117342751 | 117342584 | − | ENST00000527706; ENST00000321322 | chr11 | 117342050 | 117341882 | − | TSF |
| 2% | chr11 | 117342751 | 117342584 | − | ENST00000527706; ENST00000321322 | chr11 | 117342050 | 117341882 | − | TSF |
| 2% | chr4 | 151124947 | 151125041 | + | ENST00000296550; ENST00000411937; ENST00000506325; ENST00000302176 | chr4 | 151135817 | 151135831 | + | TSF |
| 2% | chr4 | 151124947 | 151125041 | + | ENST00000296550; ENST00000411937; ENST00000506325; ENST00000302176 | chr4 | 151135817 | 151135831 | + | TSF |
| 2% | chr19 | 19349062; 19349068 | 19349220 | + | ENST00000252575; ENST00000538881; ENST00000588231 | chr19 | 19350543 | 19350866 | + | TSF |
| 2% | chr19 | 19349062; 19349068 | 19349220 | + | ENST00000252575; ENST00000538881; ENST00000588231 | chr19 | 19350543 | 19350866 | + | TSF |
| 2% | chr19 | 19349062; 19349068 | 19349220 | + | ENST00000252575; ENST00000538881; ENST00000588231 | chr19 | 19350543 | 19350866 | + | TSF |
| 2% | chr18 | 32650166; 32650159 | 32650286 | + | ENST00000591734; ENST00000413393; ENST00000587359; ENST00000436190; ENST00000588349; ENST00000300249; ENST00000588910; ENST00000589699 | chr18 | 32670836 | 32671096 | + | TSF |
| 2% | chr18 | 32650166; 32650159 | 32650286 | + | ENST00000591734; ENST00000413393; ENST00000587359; ENST00000436190; ENST00000588349; ENST00000300249; ENST00000588910; ENST00000589699 | chr18 | 32670836 | 32671096 | + | TSF |
| 2% | chr18 | 32650166; 32650159 | 32650286 | + | ENST00000591734; ENST00000413393; ENST00000587359; ENST00000436190; ENST00000588349; ENST00000300249; ENST00000588910; ENST00000589699 | chr18 | 32670836 | 32671096 | + | TSF |
| 2% | chr15 | 65687596 | 65687432 | − | ENST00000352385 | chr15 | 65687004 | 65686908 | − | TSF |
| 2% | chr1 | 160106691 | 160106821 | + | ENST00000361216; ENST00000392233; ENST00000447527 | chr1 | 160108093 | 160108301 | + | TSF |
| 2% | chr1 | 160106691 | 160106821 | + | ENST00000361216; ENST00000392233; ENST00000447527 | chr1 | 160108093 | 160108301 | + | TSF |
| 2% | chr17 | 30611678 | 30611836 | + | ENST00000431505; ENST00000269051; ENST00000538145 | chr17 | 30615251 | 30615440 | + | TSF |
| 2% | chr17 | 30611678 | 30611836 | + | ENST00000431505; ENST00000269051; ENST00000538145 | chr17 | 30615251 | 30615440 | + | TSF |
| 2% | chr7 | 103969270; 103969228 | 103969672 | + | ENST00000424859; ENST00000535008; ENST00000401970; ENST00000543266 | chr7 | 103974311 | 103974541 | + | TSF |
| 2% | chr7 | 103969270; 103969228 | 103969672 | + | ENST00000424859; ENST00000535008; ENST00000401970; ENST00000543266 | chr7 | 103974311 | 103974541 | + | TSF |
| 2% | chr4 | 83557976 | 83557744 | − | ENST00000319540 | chr4 | 83554583 | 83554006 | − | TSF |
| 2% | chr9 | 140261084; 140260993 | 140260945 | − | ENST00000491734; ENST00000340951; ENST00000478344; ENST00000479452 | chr9 | 140253058 | 140252867 | − | TSF |
| 2% | chr9 | 140261084; 140260993 | 140260945 | − | ENST00000491734; ENST00000340951; ENST00000478344; ENST00000479452 | chr9 | 140253058 | 140252867 | − | TSF |
| 2% | chr9 | 140261084; 140260993 | 140260945 | − | ENST00000491734; ENST00000340951; ENST00000478344; ENST00000479452 | chr9 | 140253058 | 140252867 | − | TSF |
| 2% | chr19 | 55178148; 55178145 | 55178200 | + | ENST00000391736; ENST00000270452; ENST00000430952;E NST00000391734; ENST00000391733; ENST00000434286 | chr19 | 55178294 | 55178458 | + | TSF |
| 2% | chr19 | 55178148; 55178145 | 55178200 | + | ENST00000391736; ENST00000270452; ENST00000430952;E NST00000391734; ENST00000391733; ENST00000434286 | chr19 | 55178294 | 55178458 | + | TSF |
| 2% | chr19 | 55178148; 55178145 | 55178200 | + | ENST00000391736; ENST00000270452; ENST00000430952;E NST00000391734; ENST00000391733; ENST00000434286 | chr19 | 55178294 | 55178458 | + | TSF |
| 2% | chr3 | 16216659; | 16217197 | + | ENST00000339732; ENST00000437509; ENST00000430410 | chr3 | 16224220 | 16224358 | + | TSF |
| 2% | chr3 | 16216659; | 16217197 | + | ENST00000339732; ENST00000437509; ENST00000430410 | chr3 | 16224220 | 16224358 | + | TSF |
| 2% | chr15 | 80883909 | 80884045 | + | ENST00000303329; ENST00000533983; ENST00000527771 | chr15 | 80885236 | 80885386 | + | TSF |
| 2% | chr15 | 80883909 | 80884045 | + | ENST00000303329; ENST00000533983; ENST00000527771 | chr15 | 80885236 | 80885386 | + | TSF |
| 2% | chr16 | 50666192 | 50666319 | + | ENST00000268459 | chr16 | 50682755 | 50682972 | + | TSF |
| 2% | chr22 | 48885405 | 48885516 | + | ENST00000402357; ENST00000336769 | chr22 | 48915770 | 48916108 | + | TSF |
| 2% | chr2 | 155115534 | 155115651 | + | ENST00000392825; ENST00000409237 | chr2 | 155142972 | 155143021 | + | TSF |
| 2% | chr1 | 156384545 | 156384446 | − | ENST00000368242; ENST00000310027; ENST00000368243; ENST00000357975 | chr1 | 156349478 | 156349429 | | TSF |
| 2% | chr1 | 156384545 | 156384446 | − | ENST00000368242; ENST00000310027; ENST00000368243; ENST00000357975 | chr1 | 156349478 | 156349429 | − | TSF |
| 2% | chr1 | 156384545 | 156384446 | − | ENST00000368242; ENST00000310027; ENST00000368243; ENST00000357975 | chr1 | 156349478 | 156349429 | − | TSF |
| 2% | chr1 | 156384545 | 156384446 | − | ENST00000368242; ENST00000310027; ENST00000368243; ENST00000357975 | chr1 | 156349478 | 156349429 | − | TSF |
| 2% | chr19 | 23556639 | 23556544 | − | ENST00000599743; ENST00000300619 | chr19 | 23491899 | 23491588 | − | TSF |
| 2% | chr1 | 12476713 | 12476880 | + | ENST00000356315; ENST00000358136; ENST00000011700; ENST00000543766 | chr1 | 12510638 | 12510871 | + | TSF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr1 | 12476713 | 12476880 | + | ENST00000356315; ENST00000358136; ENST00000011700; ENST00000543766 | chr1 | 12510638 | 12510871 | + | TSF |
| 2% | chr1 | 12476713 | 12476880 | + | ENST00000356315; ENST00000358136; ENST00000011700; ENST00000543766 | chr1 | 12510638 | 12510871 | + | TSF |
| 2% | chr1 | 12476713 | 12476880 | + | ENST00000356315; ENST00000358136; ENST00000011700; ENST00000543766 | chr1 | 12510638 | 12510871 | + | TSF |
| 2% | chr6 | 36922537 | 36922707 | + | ENST00000373674 | chr6 | 36924759 | 36925208 | + | TSF |
| 2% | chr21 | 45222155 | 45222268 | + | ENST00000497547 | chr21 | 45240407 | 45240709 | + | TSF |
| 2% | chr11 | 105623707 | 105623946 | + | ENST00000393125; ENST00000282499; ENST00000393127; ENST00000428631; ENST00000531011; ENST00000525187; ENST00000530497 | chr11 | 105628730 | 105628963 | + | TSF |
| 2% | chr1 | 48771550 | 48771459 | − | ENST00000371847; ENST00000371843; ENST00000396199 | chr1 | 48730486 | 48730045 | − | TSF |
| 2% | chr1 | 48771550 | 48771459 | − | ENST00000371847; ENST00000371843; ENST00000396199 | chr1 | 48730486 | 48730045 | − | TSF |
| 2% | chr1 | 48771550 | 48771459 | − | ENST00000371847; ENST00000371843; ENST00000396199 | chr1 | 48730486 | 48730045 | − | TSF |
| 2% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 2% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 2% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 2% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 2% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 2% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 2% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 2% | chr7 | 127953327 | 127953228 | − | ENST00000223073; ENST00000415472 | chr7 | 127921205 | 127920177 | − | TSF |
| 2% | chr7 | 127953327 | 127953228 | − | ENST00000223073; ENST00000415472 | chr7 | 127921205 | 127920177 | − | TSF |
| 2% | chr1 | 40313763; 40313769; 40313673; 40313734 | 40313658 | − | ENST00000441669; ENST00000462797; ENST00000316891; ENST00000372818; ENST00000537223; ENST00000537440; ENST00000545233 | chr1 | 40313419 | 40313374 | − | TSF |
| 2% | chr1 | 40313763; 40313769; 40313673; 40313734 | 40313658 | − | ENST00000441669; ENST00000462797; ENST00000316891; ENST00000372818; ENST00000537223; ENST00000537440; ENST00000545233 | chr1 | 40313419 | 40313374 | − | TSF |
| 2% | chr1 | 40313763; 40313769; 40313673; 40313734 | 40313658 | − | ENST00000441669; ENST00000462797; ENST00000316891; ENST00000372818; ENST00000537223; ENST00000537440; ENST00000545233 | chr1 | 40313419 | 40313374 | − | TSF |
| 2% | chr1 | 40313763; 40313769; 40313673; 40313734 | 40313658 | − | ENST00000441669; ENST00000462797; ENST00000316891; ENST00000372818; ENST00000537223; ENST00000537440; ENST00000545233 | chr1 | 40313419 | 40313374 | − | TSF |
| 1% | chr15 | 23810930 | 23811234 | + | ENST00000314520; ENST00000568252; ENST00000564592 | chr15 | 23872913 | 23873108 | + | TSF |
| 1% | chr7 | 73731877 | 73731997 | + | ENST00000361545; ENST00000223398; ENST00000395060 | chr7 | 73734711 | 73734869 | + | TSF |
| 1% | chr9 | 125054028 | 125054119 | + | ENST00000297908; ENST00000344641; ENST00000373723; ENST00000373729; ENST00000394315 | chr9 | 125068067 | 125068171 | + | TSF |
| 1% | chr9 | 125054028 | 125054119 | + | ENST00000297908; ENST00000344641; ENST00000373723; ENST00000373729; ENST00000394315 | chr9 | 125068067 | 125068171 | + | TSF |
| 1% | chr9 | 125054028 | 125054119 | + | ENST00000297908; ENST00000344641; ENST00000373723; ENST00000373729; ENST00000394315 | chr9 | 125068067 | 125068171 | + | TSF |
| 1% | chr16 | 15675074 | 15675188 | + | ENST00000300006; ENST00000566490; ENST00000452191; ENST00000564389; ENST00000561692; ENST00000565857 | chr16 | 15676435 | 15676574 | + | TSF |
| 1% | chr16 | 15675074 | 15675188 | + | ENST00000300006; ENST00000566490; ENST00000452191; ENST00000564389; ENST00000561692; ENST00000565857 | chr16 | 15676435 | 15676574 | + | TSF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr16 | 15675074 | 15675188 | + | ENST00000300006; ENST00000566490; ENST00000452191; ENST00000564389; ENST00000561692; ENST00000565857 | chr16 | 15676435 | 15676574 | + | TSF |
| 1% | chr16 | 15675074 | 15675188 | + | ENST00000300006; ENST00000566490; ENST00000452191; ENST00000564389; ENST00000561692; ENST00000565857 | chr16 | 15676435 | 15676574 | + | TSF |
| 1% | chr16 | 15675074 | 15675188 | + | ENST00000300006; ENST00000566490; ENST00000452191; ENST00000564389; ENST00000561692; ENST00000565857 | chr16 | 15676435 | 15676574 | + | TSF |
| 1% | chr5 | 146460699; 146460671 | 146460622 | − | ENST00000504198; ENST00000394409 | chr5 | 146321615 | 146321345 | − | TSF |
| 1% | chr5 | 146460699; 146460671 | 146460622 | − | ENST00000504198; ENST00000394409 | chr5 | 146321615 | 146321345 | − | TSF |
| 1% | chr7 | 4955710 | 4955636 | − | ENST00000406755; ENST00000404774; ENST00000401401 | chr7 | 4953019 | 4952706 | − | TSF |
| 1% | chr19 | 45991775 | 45991729 | − | ENST00000245923; ENST00000430715; ENST00000344680; ENST00000590526 | chr19 | 45990601 | 45990291 | − | TSF |
| 1% | chr19 | 45991775 | 45991729 | − | ENST00000245923; ENST00000430715; ENST00000344680; ENST00000590526 | chr19 | 45990601 | 45990291 | − | TSF |
| 1% | chr19 | 45991775 | 45991729 | − | ENST00000245923; ENST00000430715; ENST00000344680; ENST00000590526 | chr19 | 45990601 | 45990291 | − | TSF |
| 1% | chr19 | 45991775 | 45991729 | − | ENST00000245923; ENST00000430715; ENST00000344680; ENST00000590526 | chr19 | 45990601 | 45990291 | − | TSF |
| 1% | chr13 | 31531010 | 31531166 | + | ENST00000380473 | chr13 | 31534099 | 31534280 | + | TSF |
| 1% | chr19 | 4210262 | 4210369 | + | ENST00000600132; ENST00000318934; ENST00000597689; ENST00000262970 | chr19 | 4210493 | 4210815 | + | TSF |
| 1% | chr19 | 4210262 | 4210369 | + | ENST00000600132; ENST00000318934; ENST00000597689; ENST00000262970 | chr19 | 4210493 | 4210815 | + | TSF |
| 1% | chr19 | 4210262 | 4210369 | + | ENST00000600132; ENST00000318934; ENST00000597689; ENST00000262970 | chr19 | 4210493 | 4210815 | + | TSF |
| 1% | chr6 | 84772612 | 84772711 | + | ENST00000257776 | chr6 | 84849189 | 84849246 | + | TSF |
| 1% | chr10 | 126205749 | 126205840 | + | ENST00000368842 | chr10 | 126251911 | 126252288 | + | TSF |
| 1% | chr3 | 142769781 | 142769891 | + | ENST00000397933; ENST00000473835; ENST00000493598; ENST00000480029; ENST00000467348 | chr3 | 142772077 | 142772316 | + | TSF |
| 1% | chr3 | 142769781 | 142769891 | + | ENST00000397933; ENST00000473835; ENST00000493598; ENST00000480029; ENST00000467348 | chr3 | 142772077 | 142772316 | + | TSF |
| 1% | chr3 | 142769781 | 142769891 | + | ENST00000397933; ENST00000473835; ENST00000493598; ENST00000480029; ENST00000467348 | chr3 | 142772077 | 142772316 | + | TSF |
| 1% | chr3 | 142769781 | 142769891 | + | ENST00000397933; ENST00000473835; ENST00000493598; ENST00000480029; ENST00000467348 | chr3 | 142772077 | 142772316 | + | TSF |
| 1% | chr3 | 142769781 | 142769891 | + | ENST00000397933; ENST00000473835; ENST00000493598; ENST00000480029; ENST00000467348 | chr3 | 142772077 | 142772316 | + | TSF |
| 1% | chr16 | 29913136; 29912293 | 29913241 | + | ENST00000563177; ENST00000483405; ENST00000308748; ENST00000414952; ENST00000566693 | chr16 | 29930852 | 29930945 | + | TSF |
| 1% | chr16 | 29913136; 29912293 | 29913241 | + | ENST00000563177; ENST00000483405; ENST00000308748; ENST00000414952; ENST00000566693 | chr16 | 29930852 | 29930945 | + | TSF |
| 1% | chr7 | 121513554 | 121513611 | + | ENST00000393386; ENST00000449182 | chr7 | 121549265 | 121550027 | + | TSF |
| 1% | chr18 | 54318306 | 54318248 | − | ENST00000587613 | chr18 | 54314766 | 54314664 | − | TSF |
| 1% | chr5 | 151052777 | 151052751 | − | ENST00000231061; ENST00000539687; ENST00000522348 | chr5 | 150931801 | 150931704 | − | TSF |
| 1% | chr1 | 156396664 | 156396590 | − | ENST00000400991; ENST00000310027; ENST00000357975 | chr1 | 156374431 | 156374430 |  | TSF |
| 1% | chr1 | 156396664 | 156396590 | − | ENST00000400991; ENST00000310027; ENST00000357975 | chr1 | 156374431 | 156374430 | − | TSF |
| 1% | chr1 | 156396664 | 156396590 | − | ENST00000400991; ENST00000310027; ENST00000357975 | chr1 | 156374431 | 156374430 | − | TSF |
| 1% | chr14 | 51446267 | 51446105 | − | ENST00000298355; ENST00000338969 | chr14 | 51433184 | 51433141 | − | TSF |
| 1% | chr14 | 51446267 | 51446105 | − | ENST00000298355; ENST00000338969 | chr14 | 51433184 | 51433141 | − | TSF |
| 1% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023225 | 58023117 | − | TSF |
| 1% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023225 | 58023117 | − | TSF |
| 1% | chr12 | 58024115 | 58023935 | − | ENST00000341156; ENST00000418555; ENST00000552798; ENST00000549391; ENST00000449184; ENST00000550764; | chr12 | 58023225 | 58023117 | − | TSF |

TABLE 33-continued

Transcript fusion for Low Grade Glioma (LGG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr12 | 58024115 | 58023935 | − | ENST00000552350; ENST00000548888 ENST00000341156; ENST00000418555; ENST00000552798; ENST00000549391; ENST00000449184; ENST00000550764; ENST00000552350; ENST00000548888 | chr12 | 58023225 | 58023117 | − | TSF |
| 1% | chr11 | 17429000 | 17428901 | − | ENST00000389817; ENST00000302539 | chr11 | 17428756 | 17428716 | − | TSF |
| 1% | chr11 | 17429000 | 17428901 | − | ENST00000389817; ENST00000302539 | chr11 | 17428756 | 17428716 | − | TSF |
| 1% | chr1 | 226825451 | 226825380 | − | ENST00000272117; ENST00000429204 | chr1 | 226799389 | 226799188 | | TSF |
| 1% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 1% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 1% | chr8 | 27461912 | 27461808 | | ENST00000316403; ENST00000546343; ENST00000560366; ENST00000405140; ENST00000523500; ENST00000522098 | chr8 | 27458611 | 27458570 | − | TSF |
| 1% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 1% | chr20 | 62070073 | 62069978 | − | ENST00000357249; ENST00000359125; ENST00000354587; ENST00000359689; ENST00000360480; ENST00000370224; ENST00000344462; ENST00000344425 | chr20 | 62066140 | 62065806 | − | TSF |
| 1% | chr17 | 26938813 | 26938786 | | ENST00000494272; ENST00000301037 | chr17 | 26932233 | 26930495 | − | TSF |
| 1% | chr17 | 26938813 | 26938786 | − | ENST00000494272; ENST00000301037 | chr17 | 26932233 | 26930495 | − | TSF |

TABLE 34

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 100% | chr17 | 42989790 | 42989722 | − | chr17 | 42989165 | 42989040; 42989042; 42989065 | − | ENST00000253408; ENST00000435360; ENST00000586793; ENST00000587997; ENST00000588957; ENST00000588316 | TAF |
| 93% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 93% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 93% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 93% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 93% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 93% | chr19 | 54930702 | 54930716 | + | chr19 | 54932451 | 54932562 | + | ENST00000423529; ENST00000301194; ENST00000376530; ENST00000445095; ENST00000391739; ENST00000376531 | TAF |
| 88% | chr1 | 156374721 | 156374537 | − | chr1 | 156374393 | 156374318; 156374346 | − | ENST00000409991; ENST00000368242; ENST00000368243; ENST00000310027; ENST00000357975 | TAF |
| 88% | chr1 | 156374721 | 156374537 | − | chr1 | 156374393 | 156374318; 156374346 | − | ENST00000400991; ENST00000368242; ENST00000310027; ENST00000357975 | TAF |
| 87% | chr4 | 174310858 | 174310746 | − | chr4 | 174309546 | 174309492 | − | ENST00000296506 | TAF |
| 70% | chr2 | 230409549 | 230409481 | − | chr2 | 230377652 | 230377499 | − | ENST00000341772 | TAF |
| 65% | chr1 | 151683281 | 151683172 | − | chr1 | 151682267 | 151682219 | − | ENST00000290585; ENST00000290583 | TAF |
| 65% | chr1 | 151683281 | 151683172 | − | chr1 | 151682267 | 151682219 | − | ENST00000290585; ENST00000290583 | TAF |
| 65% | chr1 | 151683281 | 151683172 | − | chr1 | 151682267 | 151682219 | − | ENST00000290585; ENST00000290583; ENST00000420342 | TAF |
| 65% | chr1 | 151683281 | 151683172 | − | chr1 | 151682267 | 151682219 | − | ENST00000290585; ENST00000290583; ENST00000420342 | TAF |
| 63% | chrX | 13804185 | 13804092 | − | chrX | 13803927 | 13803741 | − | ENST00000316715; ENST00000454189; ENST00000493677; ENST00000355135; ENST00000356942; ENST00000475307 | TAF |
| 63% | chrX | 13804185 | 13804092 | − | chrX | 13803927 | 13803741 | − | ENST00000316715; ENST00000454189; ENST00000493677; ENST00000355135; ENST00000356942; ENST00000475307 | TAF |
| 63% | chrX | 13804185 | 13804092 | − | chrX | 13803927 | 13803741 | − | ENST00000316715; ENST00000454189; ENST00000493677; ENST00000355135; ENST00000356942; ENST00000475307 | TAF |
| 61% | chr3 | 39544232 | 39544405 | + | chr3 | 39554874 | 39554913; 39554874 | + | ENST00000428261; ENST00000415443; ENST00000447324; ENST00000383754; ENST00000311042; ENST00000452959; ENST00000396228; ENST00000442631 | TAF |
| 61% | chr3 | 39544232 | 39544405 | + | chr3 | 39554874 | 39554913; 39554874 | + | ENST00000428261; ENST00000415443; ENST00000447324; ENST00000383754; ENST00000311042; ENST00000452959; ENST00000396228; ENST00000442631 | TAF |
| 60% | chr16 | 19886067 | 19886054 | − | chr16 | 19884168 | 19883138 | − | ENST00000537135 | TAF |
| 56% | chr20 | 43919547 | 43919514 | − | chr20 | 43882374 | 43882216 | − | ENST00000338380 | TAF |
| 47% | chrX | 13907696 | 13907571 | − | chrX | 13803927 | 13803741 | − | ENST00000316715; ENST00000454189; ENST00000493677; ENST00000355135; ENST00000356942; ENST00000475307 | TAF |
| 47% | chrX | 13907696 | 13907571 | − | chrX | 13803927 | 13803741 | − | ENST00000316715; ENST00000454189; ENST00000493677; ENST00000355135; ENST00000356942; ENST00000475307 | TAF |
| 47% | chrX | 13907696 | 13907571 | − | chrX | 13803927 | 13803741 | − | ENST00000316715; ENST00000454189; ENST00000493677; ENST00000355135; ENST00000356942; ENST00000475307 | TAF |
| 46% | chr7 | 150938296 | 150938250 | − | chr7 | 150937608 | 150937511 | − | ENST00000262188; ENST00000392811; ENST00000356800 | TAF |
| 42% | chr17 | 42395269 | 42395306 | + | chr17 | 42395464 | 42395606 | + | ENST00000426726 | TAF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 41% | chr12 | 21478885 | 21477528 | – | chr12 | 21471857 | 21471716; 21471765 | – | ENST00000307378; ENST00000453443; ENST00000544020; ENST00000421294; ENST00000452078; ENST00000450590; ENST00000435179; ENST00000390670; ENST00000445053; ENST00000422327; ENST00000421287 | TAF |
| 41% | chr12 | 21478885 | 21477528 | – | chr12 | 21471857 | 21471716; 21471765 | – | ENST00000307378; ENST00000453443; ENST00000544020; ENST00000421294; ENST00000452078; ENST00000450590; ENST00000435179; ENST00000390670; ENST00000445053; ENST00000422327; ENST00000421287 | TAF |
| 41% | chr12 | 21478885 | 21477528 | – | chr12 | 21471857 | 21471716; 21471765 | – | ENST00000307378; ENST00000453443; ENST00000544020; ENST00000421294; ENST00000452078; ENST00000450590; ENST00000435179; ENST00000390670; ENST00000445053; ENST00000422327; ENST00000421287 | TAF |
| 41% | chr12 | 21478885 | 21477528 | – | chr12 | 21471857 | 21471716; 21471765 | – | ENST00000307378; ENST00000453443; ENST00000544020; ENST00000421294; ENST00000452078; ENST00000450590; ENST00000435179; ENST00000390670; ENST00000445053; ENST00000422327; ENST00000421287 | TAF |
| 41% | chr12 | 21478885 | 21477528 | – | chr12 | 21471857 | 21471716; 21471765 | – | ENST00000307378; ENST00000453443; ENST00000544020; ENST00000421294; ENST00000452078; ENST00000450590; ENST00000435179; ENST00000390670; ENST00000445053; ENST00000422327; ENST00000421287 | TAF |
| 41% | chr12 | 21478885 | 21477528 | – | chr12 | 21471857 | 21471716; 21471765 | – | ENST00000307378; ENST00000453443; ENST00000544020; ENST00000421294; ENST00000452078; ENST00000450590; ENST00000435179; ENST00000390670; ENST00000445053; ENST00000422327; ENST00000421287 | TAF |
| 41% | chr12 | 21478885 | 21477528 | – | chr12 | 21471857 | 21471716; 21471765 | – | ENST00000307378; ENST00000453443; ENST00000544020; ENST00000421294; ENST00000452078; ENST00000450590; ENST00000435179; ENST00000390670; ENST00000445053; ENST00000422327; ENST00000421287 | TAF |
| 41% | chr12 | 21478885 | 21477528 | – | chr12 | 21471857 | 21471716; 21471765 | – | ENST00000307378; ENST00000453443; ENST00000544020; ENST00000421294; ENST00000452078; ENST00000450590; ENST00000435179; ENST00000390670; ENST00000445053; ENST00000422327; ENST00000421287 | TAF |
| 41% | chr12 | 21478885 | 21477528 | – | chr12 | 21471857 | 21471716; 21471765 | – | ENST00000307378; ENST00000453443; ENST00000544020; ENST00000421294; ENST00000452078; ENST00000450590; ENST00000435179; ENST00000390670; ENST00000445053; ENST00000422327; ENST00000421287 | TAF |
| 40% | chr16 | 75685621 | 75685636 | + | chr16 | 75688171 | 75688295; 75688183 | + | ENST00000300086; ENST00000569234 | TAF |
| 40% | chr16 | 75685621 | 75685636 | + | chr16 | 75688171 | 75688295; 75688183 | + | ENST00000300086; ENST00000569234 | TAF |
| 40% | chr6 | 3247564 | 3247553 | – | chr6 | 3226903 | 3226795 | – | ENST00000259818 | TAF |
| 40% | chr4 | 55109748 | 55109839 | + | chr4 | 55124924 | 55124984 | + | ENST00000512143 | TAF |
| 40% | chr4 | 55096091 | 55096106 | + | chr4 | 55124924 | 55124984 | + | ENST00000512143 | TAF |
| 39% | chr2 | 65243329 | 65243368 | + | chr2 | 65243574 | 65243807 | + | ENST00000234256 | TSF |
| 39% | chr16 | 70714570 | 70714506 | – | chr16 | 70713958 | 70713874 | – | ENST00000338779 | TSF |
| 38% | chr4 | 151135833 | 151135882 | + | chr4 | 151141858 | 151141930 | + | ENST00000296550; ENST00000411937; ENST00000506325; ENST00000302176 | TSF |
| 38% | chr4 | 151135833 | 151135882 | + | chr4 | 151141858 | 151141930 | + | ENST00000296550; ENST00000411937; ENST00000506325; ENST00000302176 | TSF |
| 33% | chr14 | 21515206 | 21515025 | – | chr14 | 21491480 | 21491400 | – | ENST00000336798; ENST00000339394 | TAF |
| 32% | chr1 | 31346734 | 31346686 | – | chr1 | 31346224 | 31346058 | – | ENST00000403829 | TAF |
| 30% | chr19 | 13127972 | 13127986 | + | chr19 | 13135835 | 13136366; 13135976; 13136309 | + | ENST00000591028; ENST00000397661; ENST00000592199; ENST00000587760; ENST00000587260; ENST00000358552 | TAF |
| 30% | chr19 | 13127972 | 13127986 | + | chr19 | 13135835 | 13136366; 13135976; 13136309 | + | ENST00000591028; ENST00000397661; ENST00000592199; ENST00000587760; ENST00000587260; ENST00000358552 | ENST00000360105; ENST00000586797; TAF |
| 30% | chr19 | 13127972 | 13127986 | + | chr19 | 13135835 | 13136366; 13135976; 13136309 | + | ENST00000591028; ENST00000397661; ENST00000592199; ENST00000587760; ENST00000587260; ENST00000358552 | ENST00000360105; ENST00000586797; TAF |
| 30% | chr19 | 13127972 | 13127986 | + | chr19 | 13135835 | 13136366; 13135976; 13136309 | + | ENST00000591028; ENST00000397661; ENST00000592199; ENST00000587760; ENST00000587260; ENST00000358552 | ENST00000360105; ENST00000586797; TAF |
| 30% | chr19 | 13127972 | 13127986 | + | chr19 | 13135835 | 13136366; 13135976; 13136309 | + | ENST00000591028; ENST00000397661; ENST00000592199; ENST00000587760; ENST00000587260; ENST00000358552 | ENST00000360105; ENST00000586797; TAF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 30% | chr19 | 13127972 | 13127986 | + | chr19 | 13135835 | 13136309 13136366; 13136309 | + | ENST00000397661; ENST00000592199; ENST00000587760; ENST00000585575; ENST00000386797; ENST00000591028; ENST00000587260; ENST00000358552 | TAF |
| 30% | chr7 | 102208027 | 102207972 | − | chr7 | 102207530 | 102207498; 102207444 | − | ENST00000379340; ENST00000486319; ENST00000508848; ENST00000513506; ENST00000514917; ENST00000507355; ENST00000608621; ENST00000511313 | TSF |
| 30% | chr7 | 102208027 | 102207972 | − | chr7 | 102207530 | 102207498; 102207444 | − | ENST00000379340; ENST00000486319; ENST00000508848; ENST00000513506; ENST00000514917; ENST00000507355; ENST00000608621; ENST00000511313 | TSF |
| 30% | chr7 | 102208027 | 102207972 | − | chr7 | 102207530 | 102207498; 102207444; 102207440 | − | ENST00000379340; ENST00000486319; ENST00000508848; ENST00000513506; ENST00000514917; ENST00000507355; ENST00000608621; ENST00000511313 | TSF |
| 30% | chr7 | 102208027 | 102207972 | − | chr7 | 102207530 | 102207498; 102207444; 102207440 | − | ENST00000379340; ENST00000486319; ENST00000508848; ENST00000513506; ENST00000514917; ENST00000507355; ENST00000608621; ENST00000511313 | TSF |
| 30% | chr7 | 102208027 | 102207972 | − | chr7 | 102207530 | 102207498; 102207444; 102207440 | − | ENST00000379340; ENST00000486319; ENST00000508848; ENST00000513506; ENST00000514917; ENST00000507355; ENST00000608621; ENST00000511313 | TSF |
| 29% | chr19 | 18653186 | 18653179 | − | chr19 | 18652805 | 18652489 | − | ENST00000453489 | TAF |
| 29% | chr20 | 62066436 | 62065933 | − | chr20 | 62065256 | 62065162; 62065098 | − | ENST00000357249; ENST00000359125; ENST00000344462; ENST00000344425 | TSF |
| 29% | chr20 | 62066436 | 62065933 | − | chr20 | 62065256 | 62065162; 62065098 | − | ENST00000357249; ENST00000359125; ENST00000344462; ENST00000344425 | TSF |
| 29% | chr20 | 62066436 | 62065933 | − | chr20 | 62065256 | 62065162; 62065098 | − | ENST00000357249; ENST00000359125; ENST00000344462; ENST00000344425 | TSF |
| 29% | chr20 | 62066436 | 62065933 | − | chr20 | 62065256 | 62065162; 62065098 | − | ENST00000357249; ENST00000359125; ENST00000344462; ENST00000344425 | TSF |
| 29% | chr20 | 62066436 | 62065933 | − | chr20 | 62065256 | 62065162; 62065098 | − | ENST00000357249; ENST00000359125; ENST00000344462; ENST00000344425 | TSF |
| 29% | chr20 | 62066436 | 62065933 | − | chr20 | 62065256 | 62065162; 62065098 | − | ENST00000357249; ENST00000359125; ENST00000344462; ENST00000344425 | TSF |
| 29% | chr20 | 62066436 | 62065933 | − | chr20 | 62065256 | 62065162; 62065098 | − | ENST00000357249; ENST00000359125; ENST00000344462; ENST00000344425 | TSF |
| 28% | chr11 | 113094670 | 113094766 | + | chr11 | 113102367 | 113102517 | + | ENST00000533760; ENST00000524665; ENST00000534015; ENST00000401611; ENST00000316851 | TAF |
| 28% | chr11 | 113094670 | 113094766 | + | chr11 | 113102367 | 113102517 | + | ENST00000533760; ENST00000524665; ENST00000534015; ENST00000401611; ENST00000316851 | TAF |
| 28% | chr11 | 113094670 | 113094766 | + | chr11 | 113102367 | 113102517 | + | ENST00000533760; ENST00000524665; ENST00000534015; ENST00000401611; ENST00000316851 | TAF |
| 28% | chr11 | 113094670 | 113094766 | + | chr11 | 113102367 | 113102517 | + | ENST00000533760; ENST00000524665; ENST00000534015; ENST00000401611; ENST00000316851 | TAF |
| 28% | chr11 | 113094670 | 113094766 | + | chr11 | 113102367 | 113102517 | + | ENST00000533760; ENST00000524665; ENST00000534015; ENST00000401611; ENST00000316851 | TAF |
| 27% | chr2 | 79731998 | 79732308 | + | chr2 | 79878678 | 79878784 | + | ENST00000361291 | TAF |
| 27% | chr5 | 92920103 | 92920128 | + | chr5 | 92921107 | 92921192 | + | ENST00000327111 | TSF |
| 26% | chr20 | 25841506 | 25840376 | − | chr20 | 25755948 | 25755497; | − | ENST00000376403; ENST00000584071 | TSF |
| 26% | chr20 | 25841506 | 25840376 | − | chr20 | 25755948 | 25755497; | − | ENST00000376403; ENST00000584071 | TSF |
| 25% | chr7 | 74158449 | 74158566 | + | chr7 | 74159097 | 74159280 | + | ENST00000324896; ENST00000346152; ENST00000353920; ENST00000416070 | TAF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 25% | chr7 | 102307107 | 102307052 | – | chr7 | 102306610 | 102306578; 102306524 | – | ENST00000591000; ENST00000476151; ENST00000333432 | TSF |
| 25% | chr7 | 102307107 | 102307052 | – | chr7 | 102306610 | 102306578; 102306524 | – | ENST00000591000; ENST00000476151; ENST00000333432 | TSF |
| 25% | chr20 | 25843181 | 25842039 | – | chr20 | 25755948 | 25755497; 25755659 | – | ENST00000376403; ENST00000584071 | TSF |
| 25% | chr20 | 25843181 | 25842039 | – | chr20 | 25755948 | 25755497; 25755659 | – | ENST00000376403; ENST00000584071 | TSF |
| 24% | chr11 | 73367079 | 73367447 | + | chr11 | 73371798 | 73371897; 73371801; 73371811; 73371815; 73371918; 73371840 | + | ENST00000354190; ENST00000546251; ENST00000542389; ENST00000540431 | TAF |
| 24% | chr11 | 73367079 | 73367447 | + | chr11 | 73371798 | 73371897; 73371801; 73371811; 73371815; 73371918; 73371840 | + | ENST00000354190; ENST00000546251; ENST00000542389; ENST00000540431 | TAF |
| 24% | chr11 | 73367079 | 73367447 | + | chr11 | 73371798 | 73371897; 73371801; 73371811; 73371815; 73371918; 73371840 | + | ENST00000354190; ENST00000546251; ENST00000542389; ENST00000540431 | TAF |
| 24% | chr11 | 73367079 | 73367447 | + | chr11 | 73371798 | 73371897; 73371801; 73371811; 73371815; 73371918; 73371840 | + | ENST00000354190; ENST00000546251; ENST00000542389; ENST00000540431 | TAF |
| 24% | chr11 | 73367079 | 73367447 | + | chr11 | 73371798 | 73371897; 73371801; 73371811; 73371815; 73371918; 73371840 | + | ENST00000354190; ENST00000546251; ENST00000542389; ENST00000540431 | TAF |
| 24% | chr11 | 73367079 | 73367447 | + | chr11 | 73371798 | 73371897; 73371801; 73371811; 73371815; 73371918; 73371840 | + | ENST00000354190; ENST00000546251; ENST00000542389; ENST00000540431 | TAF |
| 24% | chr11 | 73367079 | 73367447 | + | chr11 | 73371798 | 73371897; 73371801; 73371811; 73371815; 73371918; 73371840 | + | ENST00000354190; ENST00000546251; ENST00000542389; ENST00000540431 | TAF |

Note: The 10' column for rows with TAF additionally includes: ENST00000398492; ENST00000535582; ENST00000540431 and ENST00000398494; ENST00000543524; ENST00000272214; ENST00000538227; ENST00000543085; ENST00000541597; ENST00000539157; ENST00000535129

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 24% | chr11 | 73367079 | 73367447 | + | chr11 | 73371798 | 73371840 73371897; 73371801; 73371811; 73371815; 73371918; 73371840 | + | ENST00000354190; ENST00000398492; ENST00000227214; ENST00000398494; ENST00000543085; ENST00000539157; ENST00000546251; ENST00000533582; ENST00000538227; ENST00000543524; ENST00000541597; ENST00000535129; ENST00000542389; ENST00000540431 | TAF |
| 24% | chr11 | 73367079 | 73367447 | + | chr11 | 73371798 | 73371840 73371897; 73371801; 73371811; 73371815; 73371918; 73371840 | + | ENST00000354190; ENST00000398492; ENST00000227214; ENST00000398494; ENST00000543085; ENST00000539157; ENST00000546251; ENST00000533582; ENST00000538227; ENST00000543524; ENST00000541597; ENST00000535129; ENST00000542389; ENST00000540431 | TAF |
| 23% | chr19 | 41816860 | 41816920 | + | chr19 | 41822289 | 41822744 | + | ENST00000269967 | TAF |
| 23% | chr1 | 125351332 | 125351294 | − | chr1 | 125333466 | 125333380 | − | ENST00000278919; ENST00000577924 | TAF |
| 23% | chr1 | 125351332 | 125351294 | − | chr1 | 125333466 | 125333380 | − | ENST00000278919; ENST00000577924 | TAF |
| 23% | chr12 | 55350849 | 55350538 | − | chr12 | 55344174 | 55343992; 55344114 | − | ENST00000528240; ENST00000532757 | TAF |
| 23% | chr12 | 55350849 | 55350538 | − | chr12 | 55344174 | 55343992; 55344114 | − | ENST00000528240; ENST00000532757 | TAF |
| 23% | chr20 | 25844836 | 25843696 | − | chr20 | 25755948 | 25755497; 25755659 | − | ENST00000376403; ENST00000584071 | TSF |
| 23% | chr20 | 25844836 | 25843696 | − | chr20 | 25755948 | 25755497; 25755659 | − | ENST00000376403; ENST00000584071 | TSF |
| 22% | chr9 | 131002678 | 131002811 | + | chr9 | 131004511 | 131004624 | + | ENST00000475805; ENST00000341179; ENST00000393594; ENST00000486160 | TAF |
| 22% | chr9 | 131002678 | 131002811 | + | chr9 | 131004511 | 131004624 | + | ENST00000475805; ENST00000341179; ENST00000393594; ENST00000486160 | TAF |
| 22% | chr4 | 166400036 | 166400127 | + | chr4 | 166403394 | 166403474; 166403511; 166403499 | + | ENST00000513982; ENST00000402744; ENST00000431967; ENST00000511992 | TAF |
| 22% | chr4 | 166400036 | 166400127 | + | chr4 | 166403394 | 166403474; 166403511; 166403499 | + | ENST00000513982; ENST00000402744; ENST00000431967; ENST00000511992 | TAF |
| 22% | chr4 | 166400036 | 166400127 | + | chr4 | 166403394 | 166403474; 166403511; 166403499 | + | ENST00000513982; ENST00000402744; ENST00000431967; ENST00000511992 | TAF |
| 22% | chr4 | 166400036 | 166400127 | + | chr4 | 166403394 | 166403474; 166403511; 166403499 | + | ENST00000513982; ENST00000402744; ENST00000431967; ENST00000511992 | TAF |
| 22% | chr7 | 149571552 | 149571710 | + | chr7 | 149572687 | 149572734 | + | ENST00000421974; ENST00000456496; ENST00000464683; ENST00000606024; ENST00000471877; ENST00000464662; ENST00000425642 | TAF |
| 22% | chr7 | 149571552 | 149571710 | + | chr7 | 149572687 | 149572734 | + | ENST00000421974; ENST00000456496; ENST00000464683; ENST00000606024; ENST00000471877; ENST00000464662; ENST00000425642 | TAF |
| 22% | chr7 | 149571552 | 149571710 | + | chr7 | 149572687 | 149572734 | + | ENST00000421974; ENST00000456496; ENST00000464683; ENST00000606024; ENST00000471877; ENST00000464662; ENST00000425642 | TAF |
| 22% | chr7 | 149571552 | 149571710 | + | chr7 | 149572687 | 149572734 | + | ENST00000421974; ENST00000456496; ENST00000464683; ENST00000606024; ENST00000471877; ENST00000464662; ENST00000425642 | TAF |
| 22% | chr17 | 45908775 | 45908677 | − | chr17 | 45906036 | 45905867 | − | ENST00000351111; ENST00000290208; ENST00000414011 | TAF |
| 22% | chr16 | 29915789 | 29915910 | + | chr16 | 29916173 | 29916286 | + | ENST00000563177; ENST00000483405; ENST00000308748; ENST00000414952; ENST00000566693 | TAF |
| 22% | chr16 | 29915789 | 29915910 | + | chr16 | 29916173 | 29916286 | + | ENST00000563177; ENST00000483405; ENST00000308748; ENST00000414952; ENST00000566693 | TAF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 21% | chr9 | 131189761 | 131190058 | + | chr9 | 131190581 | 131190700; 131190702 | + | ENST00000372842; ENST00000420512; ENST00000372838 | TAF |
| 21% | chr9 | 131189761 | 131190058 | + | chr9 | 131190581 | 131190700; 131190702 | + | ENST00000372842; ENST00000420512; ENST00000372838 | TAF |
| 21% | chr17 | 21476521 | 21476490 | − | chr17 | 21438799 | 21438561; 21438772 | − | ENST00000391411; ENST00000412778 | TAF |
| 21% | chr17 | 21476521 | 21476490 | − | chr17 | 21438799 | 21438561; 21438772 | − | ENST00000391411; ENST00000412778 | TAF |
| 21% | chr3 | 33550559 | 33550447 | − | chr3 | 33543260 | 33543144 | − | ENST00000468888; ENST00000399362; ENST00000359576; ENST00000480013; ENST00000461133; ENST00000487553 | TAF |
| 20% | chr16 | 56616788 | 56616837 | + | chr16 | 56623782 | 56623847; 56624029 | + | ENST00000561640; ENST00000565838; ENST00000200691; ENST00000570176 | TAF |
| 20% | chr16 | 56616788 | 56616837 | + | chr16 | 56623782 | 56623847; 56624029 | + | ENST00000561640; ENST00000565838; ENST00000200691; ENST00000570176 | TAF |
| 20% | chr3 | 9368437 | 9367694 | − | chr3 | 9166601 | 9166409 | − | ENST00000383836; ENST00000360413 | TAF |
| 20% | chr3 | 9368437 | 9367694 | − | chr3 | 9166601 | 9166409 | − | ENST00000383836; ENST00000360413 | TAF |
| 20% | chr1 | 155839652 | 155839730 | + | chr1 | 155850291 | 155850414 | + | ENST00000368324 | TAF |
| 19% | chr14 | 93425387 | 93425269 | − | chr14 | 93424711 | 93424546; 93424579; 93424616 | − | ENST00000267615; ENST00000354313; ENST00000555495; ENST00000556603; ENST00000554999; ENST00000556185; ENST00000555553 | TAF |
| 19% | chr14 | 93425387 | 93425269 | − | chr14 | 93424711 | 93424546; 93424579; 93424616 | − | ENST00000267615; ENST00000354313; ENST00000555495; ENST00000556603; ENST00000554999; ENST00000556185; ENST00000555553 | TAF |
| 19% | chr14 | 93425387 | 93425269 | − | chr14 | 93424711 | 93424546; 93424579; 93424616 | − | ENST00000267615; ENST00000354313; ENST00000555495; ENST00000556603; ENST00000554999; ENST00000556185; ENST00000555553 | TAF |
| 19% | chr14 | 93425387 | 93425269 | − | chr14 | 93424711 | 93424546; 93424579; 93424616 | − | ENST00000267615; ENST00000354313; ENST00000555495; ENST00000556603; ENST00000554999; ENST00000556185; ENST00000555553 | TAF |
| 19% | chr1 | 246581335 | 246580598 | − | chr1 | 246518396 | 246518333 | − | ENST00000388985; ENST00000403792 | TSF |
| 19% | chr1 | 246581335 | 246580598 | − | chr1 | 246518396 | 246518333 | − | ENST00000388985; ENST00000403792 | TSF |
| 18% | chr9 | 130569975 | 130570054 | + | chr9 | 130570513 | 130570590; 130570580 | + | ENST00000373247; ENST00000373245; ENST00000373228; ENST00000373225; ENST00000431857 | TAF |
| 18% | chr9 | 130569975 | 130570054 | + | chr9 | 130570513 | 130570590; 130570580 | + | ENST00000373247; ENST00000373245; ENST00000373228; ENST00000373225; ENST00000431857 | TAF |
| 18% | chr9 | 130569975 | 130570054 | + | chr9 | 130570513 | 130570590; 130570580 | + | ENST00000373247; ENST00000373245; ENST00000373228; ENST00000373225; ENST00000431857 | TAF |
| 18% | chr9 | 130569975 | 130570054 | + | chr9 | 130570513 | 130570590; 130570580 | + | ENST00000373247; ENST00000373245; ENST00000373228; ENST00000373225; ENST00000431857 | TAF |
| 17% | chr10 | 101952336 | 101952216 | − | chr10 | 101950725 | 101950626 | − | ENST00000370397; ENST00000251412 | TAF |
| 17% | chr17 | 40813377 | 40813974 | + | chr17 | 40814991 | 40815070 | + | ENST00000367534; ENST00000359856; ENST00000294742 | TAF |
| 17% | chr1 | 183600359 | 183599874 | − | chr1 | 183599772 | 183599596 | − | ENST00000367534; ENST00000359856; ENST00000294742 | TAF |
| 17% | chr1 | 183600359 | 183599874 | − | chr1 | 183599772 | 183599596 | − | ENST00000367534; ENST00000359856; ENST00000294742 | TAF |
| 17% | chr17 | 42991959 | 42991849 | − | chr17 | 42991456 | 42991396 | − | ENST00000253408; ENST00000435360; ENST00000586793; ENST00000592320; ENST00000588316; ENST00000588037 | TSF |
| 17% | chr17 | 42991959 | 42991849 | − | chr17 | 42991456 | 42991396 | − | ENST00000253408; ENST00000435360; ENST00000586793; ENST00000592320; ENST00000588316; ENST00000588037 | TSF |
| 17% | chr17 | 42991959 | 42991849 | − | chr17 | 42991456 | 42991396 | − | ENST00000253408; ENST00000435360; ENST00000586793; ENST00000592320; ENST00000588316; ENST00000588037 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 17% | chr17 | 42991959 | 42991849 | - | chr17 | 42991456 | 42991396 | - | ENST00000253408; ENST00000435360; ENST00000586793; ENST00000592320; ENST00000588316; ENST00000588037 | TSF |
| 17% | chr17 | 42991959 | 42991849 | - | chr17 | 42991456 | 42991396 | - | ENST00000253408; ENST00000435360; ENST00000586793; ENST00000592320; ENST00000588316; ENST00000588037 | TSF |
| 17% | chr17 | 42991959 | 42991849 | - | chr17 | 42991456 | 42991396 | - | ENST00000253408; ENST00000435360; ENST00000586793; ENST00000592320; ENST00000588316; ENST00000588037 | TAF |
| 16% | chr9 | 108112857 | 108112906 | + | chr9 | 108118493 | 108118662 | + | ENST00000374720; ENST00000374723; ENST00000470972; ENST00000374724 | TAF |
| 16% | chr9 | 108112857 | 108112906 | + | chr9 | 108118493 | 108118662 | + | ENST00000374720; ENST00000374723; ENST00000470972; ENST00000374724 | TAF |
| 16% | chr16 | 2564319 | 2564396 | + | chr16 | 2569219 | 2569384; 2569402 | + | ENST00000564543; ENST00000330398; ENST00000568562 | TAF |
| 16% | chr16 | 2564319 | 2564396 | + | chr16 | 2569219 | 2569384; 2569402 | + | ENST00000564543; ENST00000330398; ENST00000568562 | TAF |
| 16% | chr20 | 2633768 | 2633819 | + | chr20 | 2634039 | 2634039 | + | ENST00000329276; ENST00000445139 | TAF |
| 16% | chr20 | 2633768 | 2633819 | + | chr20 | 2634039 | 2634039 | + | ENST00000329276; ENST00000445139 | TAF |
| 16% | chr20 | 25777823 | 25776681 | - | chr20 | 25755948 | 25755497; 25755659 | - | ENST00000376403; ENST00000584071 | TSF |
| 16% | chr20 | 25777823 | 25776681 | - | chr20 | 25755948 | 25755497; 25755659 | - | ENST00000376403; ENST00000584071 | TAF |
| 16% | chr2 | 175806110 | 175805544 | - | chr2 | 175783293 | 175783262 | - | ENST00000409900; ENST00000409156 | TAF |
| 16% | chr2 | 175806110 | 175805544 | - | chr2 | 175783293 | 175783262 | - | ENST00000409900; ENST00000409156 | TAF |
| 16% | chr7 | 102307107 | 102307052 | - | chr7 | 102207530 | 102207444; 102207440 | - | ENST00000379340; ENST00000608621; ENST00000511313 | TSF |
| 16% | chr7 | 102307107 | 102307052 | - | chr7 | 102207530 | 102207498; 102207444; 102207440 | - | ENST00000379340; ENST00000486319; ENST00000608621; ENST00000511313 | TSF |
| 16% | chr7 | 102307107 | 102307052 | - | chr7 | 102207530 | 102207498; 102207444; 102207440 | - | ENST00000379340; ENST00000486319; ENST00000608621; ENST00000511313 | TSF |
| 16% | chr7 | 102307107 | 102307052 | - | chr7 | 102207530 | 102207498; 102207444; 102207440 | - | ENST00000379340; ENST00000486319; ENST00000608621; ENST00000511313 | TSF |
| 16% | chr7 | 102307107 | 102307052 | - | chr7 | 102207530 | 102207498; 102207444; 102207440 | - | ENST00000379340; ENST00000486319; ENST00000608621; ENST00000511313 | TSF |
| 16% | chr8 | 82356115 | 82355982 | - | chr8 | 82355683 | 82355633; 82355676 | - | ENST00000256103; ENST00000519260 | TSF |
| 16% | chr8 | 82356115 | 82355982 | - | chr8 | 82355683 | 82355633; 82355676 | - | ENST00000256103; ENST00000519260 | TSF |
| 15% | chr4 | 176868864 | 176868796 | - | chr4 | 176622918 | 176622726; 176622736 | - | ENST00000280187; ENST00000505304 | TAF |
| 15% | chr4 | 176868864 | 176868796 | - | chr4 | 176622918 | 176622726; 176622736 | - | ENST00000280187; ENST00000505304 | TAF |
| 15% | chr4 | 176868864 | 176868796 | - | chr4 | 176622918 | 176622726; 176622736 | - | ENST00000280187; ENST00000505304 | TAF |
| 15% | chr4 | 176868864 | 176868796 | - | chr4 | 176622918 | 176622726; 176622736 | - | ENST00000280187; ENST00000505304 | TAF |
| 15% | chr17 | 11973110 | 11973166 | + | chr17 | 11984673 | 11984847; | + | ENST00000353533; ENST00000415385; ENST00000602811; ENST00000602537; ENST00000602686 | TAF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 15% | chr17 | 11973110 | 11973166 | + | chr17 | 11984673 | 11984683; 11984847; 11984683 | | ENST00000353533; ENST00000415385; ENST00000602811; ENST00000602537; ENST00000602686 | TAF |
| 14% | chr3 | 180632728 | 180632783 | + | chr3 | 180651122 | 180651174 | + | ENST00000357559; ENST00000445140; ENST00000480918; ENST00000484042 | TAF |
| 14% | chr3 | 180632728 | 180632783 | + | chr3 | 180651122 | 180651174 | + | ENST00000357559; ENST00000445140; ENST00000480918; ENST00000484042 | TAF |
| 14% | chr3 | 180632728 | 180632783 | + | chr3 | 180651122 | 180651174 | + | ENST00000357559; ENST00000445140; ENST00000480918; ENST00000484042 | TAF |
| 14% | chr18 | 48249804 | 48249890 | + | chr18 | 48252332 | 48252545 | + | ENST00000400384; ENST00000540640 | TAF |
| 14% | chr6 | 111651498 | 111651389 | − | chr6 | 111650941 | 111650735 | − | ENST00000368802; ENST00000368805; ENST00000435970 | TAF |
| 14% | chr9 | 75695610 | 75695283 | − | chr9 | 75555168 | 75555064 | − | ENST00000297785; ENST00000376939; ENST00000419959; ENST00000446946 | TAF |
| 14% | chr9 | 75695610 | 75695283 | − | chr9 | 75555168 | 75555064 | − | ENST00000297785; ENST00000376939; ENST00000419959; ENST00000446946 | TAF |
| 14% | chr9 | 75695610 | 75695283 | − | chr9 | 75555168 | 75555064 | − | ENST00000297785; ENST00000376939; ENST00000419959; ENST00000446946 | TAF |
| 14% | chr9 | 75695610 | 75695283 | − | chr9 | 75555168 | 75555064 | − | ENST00000297785; ENST00000376939; ENST00000419959; ENST00000446946 | TAF |
| 14% | chr11 | 46670360 | 46670417 | + | chr11 | 46670687 | 46670733 | + | ENST00000312040; ENST00000434074; ENST00000451945; ENST00000529655; ENST00000533325; ENST00000395549 | TAF |
| 14% | chr11 | 46670360 | 46670417 | + | chr11 | 46670687 | 46670733 | + | ENST00000312040; ENST00000434074; ENST00000451945; ENST00000526308; ENST00000524625; ENST00000359513; ENST00000528494; ENST00000395549 | TAF |
| 14% | chr11 | 46670360 | 46670417 | + | chr11 | 46670687 | 46670733 | + | ENST00000312040; ENST00000434074; ENST00000451945; ENST00000526308; ENST00000524625; ENST00000359513; ENST00000528494; ENST00000529655; ENST00000533325; ENST00000395549 | TAF |
| 14% | chr11 | 46670360 | 46670417 | + | chr11 | 46670687 | 46670733 | + | ENST00000312040; ENST00000434074; ENST00000451945; ENST00000526308; ENST00000524625; ENST00000359513; ENST00000528494; ENST00000529655; ENST00000533325; ENST00000395549 | TAF |
| 14% | chr11 | 46670360 | 46670417 | + | chr11 | 46670687 | 46670733 | + | ENST00000312040; ENST00000434074; ENST00000451945; ENST00000526308; ENST00000524625; ENST00000359513; ENST00000528494; ENST00000529655; ENST00000533325; ENST00000395549 | TAF |
| 13% | chr9 | 140012434 | 140012371 | − | chr9 | 140009028 | 140008915 | − | ENST00000371579; ENST00000472306; ENST00000497375 | TAF |
| 13% | chr9 | 140012434 | 140012371 | − | chr9 | 140009028 | 140008915 | − | ENST00000371579; ENST00000472306; ENST00000497375 | TAF |
| 13% | chr9 | 140012434 | 140012371 | − | chr9 | 140009028 | 140008915 | − | ENST00000371579; ENST00000472306; ENST00000497375 | TAF |
| 13% | chrX | 13921681 | 13921670 | − | chrX | 13803927 | 13803741 | − | ENST00000316715; ENST00000454189; ENST00000493677; ENST00000355135; ENST00000356942; ENST00000475307 | TAF |
| 13% | chrX | 13921681 | 13921670 | − | chrX | 13803927 | 13803741 | − | ENST00000316715; ENST00000454189; ENST00000493677; ENST00000355135; ENST00000356942; ENST00000475307 | TAF |
| 13% | chrX | 13921681 | 13921670 | − | chrX | 13803927 | 13803741 | − | ENST00000316715; ENST00000454189; ENST00000493677; ENST00000355135; ENST00000356942; ENST00000475307 | TAF |
| 13% | chr19 | 58515808 | 58516068 | + | chr19 | 58517275 | 58517367; 58517363 | + | ENST00000550135; ENST00000553254 | TAF |
| 13% | chr19 | 58515808 | 58516068 | + | chr19 | 58517275 | 58517367; 58517363 | + | ENST00000550135; ENST00000553254 | TAF |
| 13% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513 | TAF |
| 13% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513 | TAF |
| 13% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513 | TAF |
| 13% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513 | TSF |
| 13% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513 | TSF |
| 12% | chr10 | 104164273 | 104164216 | − | chr10 | 104163742 | 104163599 | − | ENST00000020673; ENST00000406432 | TAF |
| 12% | chr19 | 19353662 | 19353712 | + | chr19 | 19356122 | 19356266 | + | ENST00000252575; ENST00000538881; ENST00000588231 | TSF |
| 12% | chr19 | 19353662 | 19353712 | + | chr19 | 19356122 | 19356266 | + | ENST00000252575; ENST00000538881; ENST00000588231 | TSF |
| 12% | chr4 | 151135833 | 151135882 | + | chr4 | 151141855 | 151141930 | + | ENST00000296550; ENST00000302176 | TSF |
| 11% | chr11 | 73359298 | 73359321 | + | chr11 | 73360057 | 73360132 | + | ENST00000354190; ENST00000398492 | TAF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 11% | chr11 | 73359298 | 73359321 | + | chr11 | 73360057 | 73360132 | + | ENST00000354190; ENST00000398492 | TAF |
| 11% | chr14 | 70421994 | 70422072 | + | chr14 | 70442432 | 70442531 | + | ENST00000361956; ENST00000381280 | TAF |
| 11% | chr14 | 70421994 | 70422072 | + | chr14 | 70442432 | 70442531 | + | ENST00000361956; ENST00000381280 | TAF |
| 11% | chr8 | 23127459 | 23127756 | + | chr8 | 23146019 | 23146146 | + | ENST00000411463 | TAF |
| 11% | chr2 | 50264840 | 50264776 | − | chr2 | 50264436 | 50264287; 50264314; 50264356 | − | ENST00000320634; ENST00000550890; ENST00000552669; ENST00000552863 | TAF |
| 11% | chr2 | 50264840 | 50264776 | − | chr2 | 50264436 | 50264287; 50264314; 50264356 | − | ENST00000320634; ENST00000550890; ENST00000552669; ENST00000552863 | TAF |
| 11% | chr2 | 50264840 | 50264776 | − | chr2 | 50264436 | 50264287; 50264314; 50264356 | − | ENST00000320634; ENST00000550890; ENST00000552669; ENST00000552863 | TAF |
| 11% | chr10 | 102260069 | 102259867 | − | chr10 | 102259355 | 102259281 | − | ENST00000370345 | TAF |
| 11% | chr5 | 79293955 | 79294198 | + | chr5 | 79335900 | 79336103 | + | ENST00000350881 | TSF |
| 11% | chr3 | 66502660 | 66502653 | − | chr3 | 66502057 | 66501983 | − | ENST00000273261; ENST00000383703 | TSF |
| 11% | chr3 | 66502660 | 66502653 | − | chr3 | 66502057 | 66501983 | − | ENST00000273261; ENST00000383703 | TSF |
| 11% | chr17 | 42991959 | 42991941 | − | chr17 | 42991456 | 42991396 | − | ENST00000253408; ENST00000435360; ENST00000586793; ENST00000592320; ENST00000588316; ENST00000588037 | TSF |
| 11% | chr17 | 42991959 | 42991941 | − | chr17 | 42991456 | 42991396 | − | ENST00000253408; ENST00000435360; ENST00000586793; ENST00000592320; ENST00000588316; ENST00000588037 | TSF |
| 11% | chr17 | 42991959 | 42991941 | − | chr17 | 42991456 | 42991396 | − | ENST00000253408; ENST00000435360; ENST00000586793; ENST00000592320; ENST00000588316; ENST00000588037 | TSF |
| 11% | chr17 | 42991959 | 42991941 | − | chr17 | 42991456 | 42991396 | − | ENST00000253408; ENST00000435360; ENST00000586793; ENST00000592320; ENST00000588316; ENST00000588037 | TSF |
| 11% | chr17 | 42991959 | 42991941 | − | chr17 | 42991456 | 42991396 | − | ENST00000253408; ENST00000435360; ENST00000586793; ENST00000592320; ENST00000588316; ENST00000588037 | TSF |
| 10% | chr17 | 40813377 | 40813974 | + | chr17 | 40815395 | 40815521 | + | ENST00000251412 | TAF |
| 10% | chr18 | 60573526 | 60573623 | + | chr18 | 60582146 | 60582241 | + | ENST00000400316; ENST00000262719; ENST00000591386 | TSF |
| 10% | chr18 | 60573526 | 60573623 | + | chr18 | 60582146 | 60582241 | + | ENST00000400316; ENST00000262719; ENST00000591386 | TSF |
| 10% | chr3 | 115350112 | 115350159 | + | chr3 | 115394860 | 115395457 | + | ENST00000305124; ENST00000393780 | TSF |
| 9% | chr1 | 24645232 | 24645398 | + | chr1 | 24657916 | 24658102 | + | ENST00000361548; ENST00000350501; ENST00000236255 | TSF |
| 9% | chr1 | 24645232 | 24645398 | + | chr1 | 24657916 | 24658102 | + | ENST00000361545; ENST00000223398; ENST00000395060; ENST00000487447 | TSF |
| 9% | chr7 | 73811611 | 73818214 | + | chr7 | 73818167 | 73818178 | + | ENST00000376403; ENST00000584071 | TSF |
| 9% | chr20 | 25780351 | 25778939 | − | chr20 | 25755948 | 25755497; 25755659 | − | ENST00000376403; ENST00000584071 | TSF |
| 9% | chr20 | 25780351 | 25778939 | − | chr20 | 25755948 | 25755497; 25755659 | − | ENST00000376403; ENST00000584071 | TSF |
| 9% | chr11 | 62651471 | 62651559 | + | chr11 | 62651929 | 62651997 | + | ENST00000377892; ENST00000377890; ENST00000377891; ENST00000338663 | TSF |
| 8% | chr7 | 29899867 | 29900179 | + | chr7 | 29915446 | 29915578 | + | ENST00000409123; ENST00000242140; ENST00000409290 | TSF |
| 8% | chr7 | 29899867 | 29900179 | + | chr7 | 29915446 | 29915578 | + | ENST00000409123; ENST00000242140; ENST00000409290 | TSF |
| 8% | chr3 | 186989069 | 186988983 | − | chr3 | 186980508 | 186980331; 186980469; 186980502 | − | ENST00000337774; ENST00000296280; ENST00000169293; ENST00000392470; ENST00000392475; ENST00000439271; ENST00000425937 | ITSF |
| 8% | chr3 | 186989069 | 186988983 | − | chr3 | 186980508 | 186980331; 186980469; 186980502 | − | ENST00000337774; ENST00000296280; ENST00000169293; ENST00000392470; ENST00000392475; ENST00000439271; ENST00000425937 | TSF |
| 8% | chr3 | 186989069 | 186988983 | − | chr3 | 186980508 | 186980331; 186980469; 186980502 | − | ENST00000337774; ENST00000296280; ENST00000169293; ENST00000392470; ENST00000392475; ENST00000439271; ENST00000425937 | TSF |
| 8% | chr3 | 186989069 | 186988983 | − | chr3 | 186980508 | 186980331; 186980469; 186980502 | − | ENST00000337774; ENST00000296280; ENST00000169293; ENST00000392470; ENST00000392475; ENST00000439271; ENST00000425937 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 8% | chr3 | 186989069 | 186988983 | – | chr3 | 186980508 | 186980331; 186980469; 186980502 | – | ENST00000337774; ENST00000296280; ENST00000392470; ENST00000392475; ENST00000439271; ENST00000425937 | TSF |
| 8% | chr3 | 186989069 | 186988983 | – | chr3 | 186980508 | 186980331; 186980469; 186980502 | – | ENST00000337774; ENST00000296280; ENST00000392470; ENST00000392475; ENST00000439271; ENST00000425937 | TSF |
| 8% | chr14 | 77240992 | 77241058 | + | chr14 | 77242235 | 77242616 | + | ENST00000167106 | TSF |
| 8% | chr17 | 73847069 | 73847024 | – | chr17 | 73845820 | 73845685 | – | ENST00000254806; ENST00000585462; ENST00000591399; ENST00000591831; ENST00000590221; ENST00000344296; ENST00000433525; ENST00000593002 | ITSF |
| 8% | chr17 | 73847069 | 73847024 | – | chr17 | 73845820 | 73845685 | – | ENST00000254806; ENST00000585462; ENST00000591399; ENST00000591831; ENST00000590221; ENST00000344296; ENST00000433525; ENST00000593002 | TSF |
| 8% | chr17 | 73847069 | 73847024 | – | chr17 | 73845820 | 73845685 | – | ENST00000254806; ENST00000585462; ENST00000591399; ENST00000591831; ENST00000590221; ENST00000344296; ENST00000433525; ENST00000593002 | TSF |
| 8% | chr17 | 73847069 | 73847024 | – | chr17 | 73845820 | 73845685 | – | ENST00000254806; ENST00000585462; ENST00000591399; ENST00000591831; ENST00000590221; ENST00000344296; ENST00000433525; ENST00000593002 | TSF |
| 7% | chr2 | 230371170 | 230370928 | – | chr2 | 230341969 | 230341856 | – | ENST00000341772 | TSF |
| 7% | chr7 | 102146992 | 102146893 | – | chr7 | 102143691 | 102143610 | – | ENST00000541662; ENST00000465829; ENST00000306682 | TSF |
| 7% | chr7 | 102146992 | 102146893 | – | chr7 | 102143691 | 102143610 | – | ENST00000541662; ENST00000465829; ENST00000306682 | TSF |
| 7% | chr19 | 13183453 | 13183471 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 7% | chr19 | 13183453 | 13183471 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 7% | chr19 | 13183453 | 13183471 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 7% | chr19 | 13183453 | 13183471 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 7% | chr4 | 5830600 | 5830583 | + | chr4 | 5830395 | 5830216 | + | ENST00000324989; ENST00000397890; ENST00000512574 | TSF |
| 7% | chr17 | 38243904 | 38243929 | + | chr17 | 38244495 | 38244753 | + | ENST00000394121; ENST00000264637; ENST00000584985; ENST00000450525; ENST00000546243 | TSF |
| 7% | chr17 | 38243904 | 38243929 | + | chr17 | 38244495 | 38244753 | + | ENST00000394121; ENST00000264637; ENST00000584985; ENST00000450525; ENST00000546243 | TSF |
| 7% | chr17 | 38243904 | 38243929 | + | chr17 | 38244495 | 38244753 | + | ENST00000394121; ENST00000264637; ENST00000584985; ENST00000450525; ENST00000546243 | TSF |
| 6% | chr2 | 101024262 | 101024202 | – | chr2 | 101023169 | 101023038 | – | ENST00000542617; ENST00000448989 | TSF |
| 6% | chr2 | 101024262 | 101024202 | – | chr2 | 101023169 | 101023038 | – | ENST00000542617; ENST00000448989 | TSF |
| 6% | chr7 | 102246155 | 102246056 | – | chr7 | 102242852 | 102242771 | – | ENST00000262940; ENST00000461209; ENST00000449970; ENST00000462172; ENST00000522801; ENST00000520042; ENST00000521076 | TSF |
| 6% | chr7 | 102246155 | 102246056 | – | chr7 | 102242852 | 102242771 | – | ENST00000262940; ENST00000461209; ENST00000449970; ENST00000462172; ENST00000522801; ENST00000520042; ENST00000521076 | TSF |
| 6% | chr7 | 102246155 | 102246056 | – | chr7 | 102242852 | 102242771 | – | ENST00000262940; ENST00000461209; ENST00000449970; ENST00000462172; ENST00000522801; ENST00000520042; ENST00000521076 | TSF |
| 6% | chr7 | 102246155 | 102246056 | – | chr7 | 102242852 | 102242771 | – | ENST00000262940; ENST00000461209; ENST00000449970; ENST00000462172; ENST00000522801; ENST00000520042; ENST00000521076 | TSF |
| 6% | chr19 | 18991807 | 18991757 | – | chr19 | 18991244 | 18991083 | – | ENST00000427170; ENST00000429504; ENST00000542296; ENST00000596048 | TSF |
| 6% | chr19 | 18991807 | 18991757 | – | chr19 | 18991244 | 18991083 | – | ENST00000427170; ENST00000429504; ENST00000542296; ENST00000596048 | TSF |
| 6% | chr19 | 18991807 | 18991757 | – | chr19 | 18991244 | 18991083 | – | ENST00000427170; ENST00000429504; ENST00000542296; ENST00000596048 | TSF |
| 6% | chr20 | 25841506 | 25840376 | – | chr20 | 25755972 | 25755659 | – | ENST00000584071 | TSF |
| 6% | chr12 | 50292609 | 50292556 | – | chr12 | 50291869 | 50291770 | – | ENST00000320634; ENST00000550890; ENST00000550195; ENST00000552669; ENST00000547871 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 6% | chr12 | 50292609 | 50292556 | − | chr12 | 50291869 | 50291770 | − | ENST00000320634; ENST00000550890; ENST00000550195; ENST00000552669; ENST00000550635; ENST00000547871 | TSF |
| 6% | chr12 | 50292609 | 50292556 | − | chr12 | 50291869 | 50291770 | − | ENST00000320634; ENST00000550890; ENST00000550195; ENST00000552669; ENST00000550635; ENST00000547871 | TSF |
| 6% | chr12 | 50292609 | 50292556 | − | chr12 | 50291869 | 50291770 | − | ENST00000320634; ENST00000550890; ENST00000550195; ENST00000552669; ENST00000550635; ENST00000547871 | TSF |
| 6% | chr12 | 50292609 | 50292556 | − | chr12 | 50291869 | 50291770 | − | ENST00000320634; ENST00000550890; ENST00000550195; ENST00000552669; ENST00000550635; ENST00000547871 | TSF |
| 6% | chr20 | 25843181 | 25842039 | − | chr20 | 25755972 | 25755659 | − | ENST00000084071 | TSF |
| 5% | chr19 | 7895176 | 7895267 | + | chr19 | 7911468 | 7911565 | + | ENST00000270530; ENST00000538904 | TSF |
| 5% | chr19 | 7895176 | 7895267 | + | chr19 | 7911468 | 7911565 | + | ENST00000270530; ENST00000538904 | TSF |
| 5% | chr19 | 54944914 | 54945078 | + | chr19 | 54946722 | 54946864 | + | ENST00000301194; ENST00000376530; ENST00000391739; ENST00000376531 | TSF |
| 5% | chr19 | 54944914 | 54945078 | + | chr19 | 54946722 | 54946864 | + | ENST00000301194; ENST00000376530; ENST00000391739; ENST00000376531 | TSF |
| 5% | chr19 | 54944914 | 54945078 | + | chr19 | 54946722 | 54946864 | + | ENST00000301194; ENST00000376530; ENST00000391739; ENST00000376531 | TSF |
| 5% | chr17 | 40813111 | 40813245 | + | chr17 | 40815395 | 40815521 | + | ENST00000251412 | TSF |
| 5% | chr6 | 3229888 | 3229779 | − | chr6 | 3226903 | 3226795 | − | ENST00000259818 | TSF |
| 5% | chr20 | 29976260 | 29976126 | − | chr20 | 29966194 | 29966155 | − | ENST00000339144 | TSF |
| 5% | chr2 | 220383535 | 220383613 | + | chr2 | 220396480 | 220396624 | + | ENST00000347842; ENST00000358078 | TSF |
| 5% | chr2 | 220383535 | 220383613 | + | chr2 | 220396480 | 220396624 | + | ENST00000347842; ENST00000358078 | TSF |
| 5% | chr7 | 4949365 | 4949360 | − | chr7 | 4947230 | 4947027 | − | ENST00000401401 | TSF |
| 5% | chr1 | 175324477 | 175324412 | − | chr1 | 175323639 | 175323527 | − | ENST00000367674; ENST00000263525 | TSF |
| 5% | chr20 | 25844836 | 25843696 | − | chr20 | 25755972 | 25755659 | − | ENST00000584071 | TSF |
| 4% | chr19 | 11469032 | 11469050 | + | chr19 | 11470208 | 11470396; 11470395 | + | ENST00000251473; ENST00000591329 | TSF |
| 4% | chr19 | 11469032 | 11469050 | + | chr19 | 11470208 | 11470396; 11470395 | + | ENST00000251473; ENST00000591329 | TSF |
| 4% | chr7 | 102208027 | 102207815 | − | chr7 | 102207530 | 102207498; 102207444; 102207440 | − | ENST00000379340; ENST00000486319; ENST00000508848; ENST00000513506; ENST00000514917; ENST00000507355; ENST00000660862l; ENST00000511313 | TSF |
| 4% | chr7 | 102208027 | 102207815 | − | chr7 | 102207530 | 102207498; 102207444; 102207440 | − | ENST00000379340; ENST00000486319; ENST00000508848; ENST00000513506; ENST00000514917; ENST00000507355; ENST00000660862l; ENST00000511313 | TSF |
| 4% | chr7 | 102208027 | 102207815 | − | chr7 | 102207530 | 102207498; 102207444; 102207440 | − | ENST00000379340; ENST00000486319; ENST00000508848; ENST00000513506; ENST00000514917; ENST00000507355; ENST00000660862l; ENST00000511313 | TSF |
| 4% | chr7 | 102208027 | 102207815 | − | chr7 | 102207530 | 102207498; 102207444; 102207440 | − | ENST00000379340; ENST00000486319; ENST00000508848; ENST00000513506; ENST00000514917; ENST00000507355; ENST00000660862l; ENST00000511313 | TSF |
| 4% | chr7 | 102208027 | 102207815 | − | chr7 | 102207530 | 102207498; 102207444; 102207440 | − | ENST00000379340; ENST00000486319; ENST00000508848; ENST00000513506; ENST00000514917; ENST00000507355; ENST00000660862l; ENST00000511313 | TSF |
| 4% | chr12 | 4948345 | 4948527 | + | chr12 | 4959904 | 4960077 | + | ENST00000542998 | TSF |
| 4% | chr7 | 117376632 | 117376519 | − | chr7 | 117375475 | 117375323; 117375385 | − | ENST00000160373; ENST00000446636; ENST00000435233 | TSF |
| 4% | chr7 | 117376632 | 117376519 | − | chr7 | 117375475 | 117375323; 117375385 | − | ENST00000160373; ENST00000446636; ENST00000435233 | TSF |
| 4% | chr2 | 198536292 | 198536266 | − | chr2 | 198511390 | 198511207 | − | ENST00000295049; ENST00000429081 | TSF |
| 4% | chr2 | 198536292 | 198536266 | − | chr2 | 198511390 | 198511207 | − | ENST00000295049; ENST00000429081 | TSF |
| 4% | chr12 | 49602693 | 49602732 | + | chr12 | 49621874 | 49621949 | + | ENST00000541364; ENST00000549818; ENST00000552448; ENST00000552125 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 4% | chr12 | 49602693 | 49602732 | + | chr12 | 49621874 | 49621949 | + | ENST00000541364; ENST00000541364; ENST00000549818; ENST00000549818; ENST00000552448; ENST00000552448; ENST00000552125 ENST00000552125 | TSF |
| 4% | chr12 | 49602693 | 49602732 | + | chr12 | 49621874 | 49621949 | + | ENST00000307378; ENST00000452078; ENST00000458504; ENST00000537524 | TSF |
| 4% | chr2 | 21426370 | 21426215 | − | chr2 | 21422701 | 21422482 | − | ENST00000524419; ENST00000528989; ENST00000315571 | TSF |
| 4% | chr11 | 36219316 | 36219321 | + | chr11 | 36248635 | 36248980 | + | ENST00000382110; ENST00000324266; ENST00000417243; ENST00000415624 | TSF |
| 4% | chr2 | 3462278 | 3462286 | + | chr2 | 3464034 | 3464107; 3464074 | + | ENST00000382110; ENST00000324266; ENST00000417243; ENST00000415624 | TSF |
| 4% | chr2 | 3462278 | 3462286 | + | chr2 | 3464034 | 3464107; 3464074 | + | ENST00000382110; ENST00000324266; ENST00000417243; ENST00000415624 | TSF |
| 4% | chr2 | 3462278 | 3462286 | + | chr2 | 3464034 | 3464107; 3464074 | + | ENST00000382110; ENST00000324266; ENST00000417243; ENST00000415624 | TSF |
| 4% | chr15 | 93592614 | 93592599 | − | chr15 | 93588935 | 93588228; 93588877 | − | ENST00000425933; ENST00000543599; ENST00000542321; ENST00000538818; ENST00000565857 ENST00000557420; ENST00000556658 | TSF |
| 4% | chr15 | 93592614 | 93592599 | − | chr15 | 93588935 | 93588228; 93588877 | − | ENST00000425933; ENST00000543599; ENST00000542321; ENST00000538818; ENST00000565857 ENST00000557420; ENST00000556658 | TSF |
| 4% | chr16 | 15624455 | 15624694 | + | chr16 | 15661840 | 15661913 | + | ENST00000300006; ENST00000566490; ENST00000452191; ENST00000561692; ENST00000565857 | TSF |
| 4% | chr16 | 15624455 | 15624694 | + | chr16 | 15661840 | 15661913 | + | ENST00000300006; ENST00000566490; ENST00000452191; ENST00000561692; ENST00000565857 | TSF |
| 4% | chr16 | 15624455 | 15624694 | + | chr16 | 15661840 | 15661913 | + | ENST00000300006; ENST00000566490; ENST00000452191; ENST00000561692; ENST00000565857 | TSF |
| 4% | chr16 | 15624455 | 15624694 | + | chr16 | 15661840 | 15661913 | + | ENST00000300006; ENST00000566490; ENST00000452191; ENST00000561692; ENST00000565857 | TSF |
| 4% | chr11 | 60694460 | 60694542 | + | chr11 | 60694676 | 60694890 | + | ENST00000453848; ENST00000005286 | TSF |
| 4% | chr11 | 60694460 | 60694542 | + | chr11 | 60694676 | 60694890 | + | ENST00000453848; ENST00000005286 | TSF |
| 4% | chr2 | 79924995 | 79925043 | + | chr2 | 79971513 | 79971708; 79971609 | + | ENST00000466387; ENST00000496558; ENST00000451966; ENST00000402739; ENST00000540488; ENST00000541047 | TSF |
| 4% | chr2 | 79924995 | 79925043 | + | chr2 | 79971513 | 79971708; 79971609 | + | ENST00000466387; ENST00000496558; ENST00000451966; ENST00000402739; ENST00000540488; ENST00000541047 | TSF |
| 4% | chr2 | 79924995 | 79925043 | + | chr2 | 79971513 | 79971708; 79971609 | + | ENST00000466387; ENST00000496558; ENST00000451966; ENST00000402739; ENST00000540488; ENST00000541047 | TSF |
| 4% | chr2 | 79924995 | 79925043 | + | chr2 | 79971513 | 79971708; 79971609 | + | ENST00000466387; ENST00000496558; ENST00000451966; ENST00000402739; ENST00000540488; ENST00000541047 | TSF |
| 4% | chr17 | 64988088 | 64988129 | + | chr17 | 65014305 | 65014388 | + | ENST00000262138 | TSF |
| 4% | chr1 | 156628571 | 156628662 | + | chr1 | 156628819 | 156628926 | + | ENST00000329117 | TSF |
| 4% | chr1 | 121570168 | 121570258 | + | chr7 | 121608005 | 121608184 | + | ENST00000393386; ENST00000449182 | TSF |
| 4% | chr7 | 121570168 | 121570258 | + | chr7 | 121608005 | 121608184 | + | ENST00000393386; ENST00000449182 | TSF |
| 4% | chr16 | 75683160 | 75683228 | + | chr16 | 75688171 | 75688295; 75688183 | + | ENST00000300086; ENST00000569234 | TSF |
| 4% | chr16 | 75683160 | 75683228 | + | chr16 | 75688171 | 75688295; 75688183 | + | ENST00000300086; ENST00000569234 | TSF |
| 3% | chr12 | 51101579 | 51101831 | + | chr12 | 51102231 | 51102345 | + | ENST00000301180 | TSF |
| 3% | chr1 | 99718539 | 99718543 | + | chr1 | 99753521 | 99753706 | + | ENST00000370185; ENST00000457765 | TSF |
| 3% | chr1 | 99718539 | 99718543 | + | chr1 | 99753521 | 99753706 | + | ENST00000370185; ENST00000457765 | TSF |
| 3% | chr7 | 87600681 | 87600690 | + | chr7 | 87607651 | 87607727 | + | ENST00000398204; ENST00000439864; ENST00000398201; ENST00000412441; ENST00000398209; ENST00000398203 | TSF |
| 3% | chr7 | 87600681 | 87600690 | + | chr7 | 87607651 | 87607727 | + | ENST00000398204; ENST00000439864; ENST00000398201; ENST00000412441; ENST00000265727; ENST00000315984; ENST00000398209; ENST00000398203 | TSF |
| 3% | chr7 | 87600681 | 87600690 | + | chr7 | 87607651 | 87607727 | + | ENST00000398204; ENST00000439864; ENST00000398201; ENST00000412441; ENST00000265727; ENST00000315984; ENST00000398209; ENST00000398203 | TSF |
| 3% | chr7 | 87600681 | 87600690 | + | chr7 | 87607651 | 87607727 | + | ENST00000398204; ENST00000439864; ENST00000398201; ENST00000412441; ENST00000265727; ENST00000315984 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 3% | chr7 | 87600681 | 87600690 | + | chr7 | 87607651 | 87607727 | + | ENST00000398209; ENST00000398203 | TSF |
| 3% | chr7 | 87600681 | 87600690 | + | chr7 | 87607651 | 87607727 | + | ENST00000398204; ENST00000439864; ENST00000398201; ENST00000265727; ENST00000315984; ENST00000398209; ENST00000398203 | TSF |
| 3% | chr7 | 87600681 | 87600690 | + | chr7 | 87607651 | 87607727 | + | ENST00000398204; ENST00000439864; ENST00000398201; ENST00000265727; ENST00000315984; ENST00000398209; ENST00000398203 | TSF |
| 3% | chr7 | 87600681 | 87600690 | + | chr7 | 87607651 | 87607727 | + | ENST00000398204; ENST00000439864; ENST00000398201; ENST00000265727; ENST00000315984; ENST00000398209; ENST00000398203 | TSF |
| 3% | chr7 | 87600681 | 87600690 | + | chr7 | 87607651 | 87607727 | + | ENST00000398204; ENST00000439864; ENST00000398201; ENST00000265727; ENST00000315984; ENST00000398209; ENST00000398203 | TSF |
| 3% | chr3 | 195593372 | 195593261 | − | chr3 | 195591058 | 195591052 | − | ENST00000416152; ENST00000381916; ENST00000333602; ENST00000392400 | TSF |
| 3% | chr8 | 104220609 | 104220725 | + | chr8 | 104225147 | 104225313 | + | ENST00000309982; ENST00000429574 | TSF |
| 3% | chr8 | 51556816 | 51557016 | + | chr8 | 51569469 | 51569585 | + | ENST00000518864; ENST00000522124; ENST00000517473; ENST00000520825; ENST00000276467; ENST00000524004 | TSF |
| 3% | chr8 | 51556816 | 51557016 | + | chr8 | 51569469 | 51569585 | + | ENST00000518864; ENST00000522124; ENST00000517473; ENST00000520825; ENST00000276467; ENST00000524004 | TSF |
| 3% | chr8 | 51556816 | 51557016 | + | chr8 | 51569469 | 51569585 | + | ENST00000518864; ENST00000522124; ENST00000517473; ENST00000520825; ENST00000276467; ENST00000524004 | TSF |
| 3% | chr1 | 10404970 | 10404975 | + | chr1 | 10405903 | 10406011 | + | ENST00000263934; ENST00000377086; ENST00000377081 | TSF |
| 3% | chr1 | 10404970 | 10404975 | + | chr1 | 10405903 | 10406011 | + | ENST00000263934; ENST00000377086; ENST00000377081 | TSF |
| 3% | chr19 | 4211130 | 4211271 | + | chr19 | 4212472 | 4212510 | + | ENST00000600132; ENST00000597689; ENST00000262970 | TSF |
| 3% | chr19 | 4211130 | 4211271 | + | chr19 | 4212472 | 4212510 | + | ENST00000600132; ENST00000597689; ENST00000262970 | TSF |
| 3% | chr1 | 243727680 | 243727587 | − | chr1 | 243727150 | 243727022 | − | ENST00000318934; ENST00000366199; ENST00000366540; ENST00000263826 | TSF |
| 3% | chr1 | 243727680 | 243727587 | − | chr1 | 243727150 | 243727022 | − | ENST00000318934; ENST00000366199; ENST00000366540; ENST00000263826 | TSF |
| 3% | chr14 | 60107035 | 60106250 | − | chr14 | 60074210 | 60074003 | − | ENST00000395090; ENST00000342503; ENST00000267484 | TSF |
| 3% | chr3 | 9476647 | 9476785 | + | chr3 | 9477412 | 9477509; 9477590 | + | ENST00000450326; ENST00000402198; ENST00000402466; ENST00000406341; ENST00000407969; ENST00000442373; ENST00000302463 | TSF |
| 3% | chr3 | 9476647 | 9476785 | + | chr3 | 9477412 | 9477509; 9477590 | + | ENST00000450326; ENST00000402198; ENST00000402466; ENST00000406341; ENST00000407969; ENST00000442373; ENST00000302463 | TSF |
| 3% | chr3 | 9476647 | 9476785 | + | chr3 | 9477412 | 9477509; 9477590 | + | ENST00000450326; ENST00000402198; ENST00000402466; ENST00000406341; ENST00000407969; ENST00000442373; ENST00000302463 | ITSF |
| 3% | chr3 | 9476647 | 9476785 | + | chr3 | 9477412 | 9477509; 9477590 | + | ENST00000450326; ENST00000402198; ENST00000402466; ENST00000406341; ENST00000407969; ENST00000442373; ENST00000302463 | TSF |
| 3% | chr16 | 47350611 | 47350483 | − | chr16 | 47347734 | 47347640 | − | ENST00000320640; ENST00000544001 | TSF |
| 3% | chr16 | 47350611 | 47350483 | − | chr16 | 47347734 | 47347640 | − | ENST00000320640; ENST00000544001 | TSF |
| 3% | chr22 | 39228782 | 39228705 | − | chr22 | 39224514 | 39224292 | − | ENST00000333039 | TSF |
| 3% | chr1 | 176882517 | 176882366 | − | chr1 | 176863966 | 176863698 | − | ENST00000367657; ENST00000361833; ENST00000424564 | TSF |
| 3% | chr1 | 176882517 | 176882366 | − | chr1 | 176863966 | 176863698 | − | ENST00000367657; ENST00000361833; ENST00000424564 | TSF |
| 3% | chr1 | 176882517 | 176882366 | − | chr1 | 176863966 | 176863698 | − | ENST00000367657; ENST00000361833; ENST00000424564 | TSF |
| 3% | chr13 | 51289548 | 51289014 | − | chr13 | 51287376 | 51287353 | − | ENST00000400393 | TSF |
| 3% | chr10 | 98821635 | 98821532 | − | chr10 | 98820544 | 98820397 | − | ENST00000266058; ENST00000371070; ENST00000314867; ENST00000371041 | TSF |
| 3% | chr10 | 98821635 | 98821532 | − | chr10 | 98820544 | 98820397 | − | ENST00000266058; ENST00000371070; ENST00000314867; ENST00000371041 | TSF |
| 3% | chr10 | 98821635 | 98821532 | − | chr10 | 98820544 | 98820397 | − | ENST00000266058; ENST00000371070; ENST00000314867; ENST00000371041 | TSF |
| 3% | chr2 | 216976986 | 216977153 | + | chr2 | 216977739 | 216977852 | + | ENST00000392133; ENST00000392132 | TSF |
| 3% | chr20 | 24951582 | 24951515 | − | chr20 | 24951007 | 24950833 | − | ENST00000451442; ENST00000217456; ENST00000447138 | TSF |
| 3% | chr20 | 24951582 | 24951515 | − | chr20 | 24951007 | 24950833 | − | ENST00000451442; ENST00000217456; ENST00000447138 | TSF |
| 3% | chr20 | 24951582 | 24951515 | − | chr20 | 24951007 | 24950833 | − | ENST00000451442; ENST00000217456; ENST00000447138 | TSF |
| 3% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 3% | chr3 | 11645847 | 11645798 | − | chr3 | 11643496 | 11643307 | − | ENST00000273038; ENST00000417206; ENST00000404339; ENST00000445411; ENST00000418000; ENST00000458499; ENST00000419541 | TSF |
| 3% | chr3 | 11645847 | 11645798 | − | chr3 | 11643496 | 11643307 | − | ENST00000273038; ENST00000417206; ENST00000404339; ENST00000445411; ENST00000418000; ENST00000458499; ENST00000419541 | TSF |
| 3% | chr3 | 11645847 | 11645798 | − | chr3 | 11643496 | 11643307 | − | ENST00000273038; ENST00000417206; ENST00000404339; ENST00000445411; ENST00000418000; ENST00000458499; ENST00000419541 | TSF |
| 3% | chr3 | 11645847 | 11645798 | − | chr3 | 11643496 | 11643307 | − | ENST00000273038; ENST00000417206; ENST00000404339; ENST00000445411; ENST00000418000; ENST00000458499; ENST00000419541 | TSF |
| 3% | chr8 | 82357757 | 82357691 | − | chr8 | 82357224 | 82357052 | − | ENST00000256103 | TSF |
| 3% | chr15 | 43802603 | 43802568 | − | chr15 | 43784666 | 43784482 | − | ENST00000382039; ENST00000450115; ENST00000413546 | TSF |
| 3% | chr15 | 43802603 | 43802568 | − | chr15 | 43784666 | 43784482 | − | ENST00000382039; ENST00000450115; ENST00000413546 | TSF |
| 3% | chr15 | 43802603 | 43802568 | − | chr15 | 43784666 | 43784482 | − | ENST00000382039; ENST00000450115; ENST00000413546 | TSF |
| 3% | chr15 | 43802603 | 43802568 | − | chr15 | 43784666 | 43784482 | − | ENST00000382039; ENST00000450115; ENST00000413546 | TSF |
| 3% | chr14 | 26959896 | 26959460 | − | chr14 | 26949349 | 26949183 | − | ENST00000465357; ENST00000549571; ENST00000449198; ENST00000539517; ENST00000574031 | TSF |
| 3% | chr14 | 26959896 | 26959460 | − | chr14 | 26949349 | 26949183 | − | ENST00000465357; ENST00000549571; ENST00000449198; ENST00000539517; ENST00000574031 | TSF |
| 3% | chr14 | 26959896 | 26959460 | − | chr14 | 26949349 | 26949183 | − | ENST00000465357; ENST00000549571; ENST00000449198; ENST00000539517; ENST00000574031 | TSF |
| 3% | chr14 | 26959896 | 26959460 | − | chr14 | 26949349 | 26949183 | − | ENST00000465357; ENST00000549571; ENST00000449198; ENST00000539517; ENST00000574031 | TSF |
| 3% | chr14 | 26959896 | 26959460 | − | chr14 | 26949349 | 26949183 | − | ENST00000465357; ENST00000549571; ENST00000449198; ENST00000539517; ENST00000574031 | TSF |
| 3% | chr4 | 70495075 | 70495153 | + | chr4 | 70496962 | 70496975 | + | ENST00000361956; ENST00000381280 | TSF |
| 3% | chr4 | 107241932 | 107242046 | + | chr4 | 107246142 | 107246275 | + | ENST00000394701 | TSF |
| 3% | chr19 | 54945134 | 54945169 | + | chr19 | 54946722 | 54946864 | + | ENST00000301194; ENST00000391739; ENST00000376530; ENST00000376531 | TSF |
| 3% | chr19 | 54945134 | 54945169 | + | chr19 | 54946722 | 54946864 | + | ENST00000301194; ENST00000391739; ENST00000376530; ENST00000376531 | TSF |
| 3% | chr19 | 54945134 | 54945169 | + | chr19 | 54946722 | 54946864 | + | ENST00000301194; ENST00000391739; ENST00000376530; ENST00000376531 | TSF |
| 3% | chr3 | 11060777 | 11060955 | + | chr3 | 11061899 | 11062008 | + | ENST00000287766 | TSF |
| 3% | chr7 | 121556048 | 121556146 | + | chr7 | 121568210 | 121568275 | + | ENST00000393386; ENST00000449182 | TSF |
| 3% | chr7 | 121556048 | 121556146 | + | chr7 | 121568210 | 121568275 | + | ENST00000393386; ENST00000449182 | TSF |
| 3% | chr6 | 123101055 | 123101091 | + | chr6 | 123101436 | 123101608 | + | ENST00000368444; ENST00000356535 | TSF |
| 3% | chr6 | 123101055 | 123101091 | + | chr6 | 123101436 | 123101608 | + | ENST00000368444; ENST00000356535 | TSF |
| 3% | chr10 | 118751278 | 118750845 | − | chr10 | 118738819 | 118738767 | − | ENST00000392903; ENST00000260777; ENST00000355371 | TSF |
| 3% | chr10 | 118751278 | 118750845 | − | chr10 | 118738819 | 118738767 | − | ENST00000392903; ENST00000260777; ENST00000355371 | TSF |
| 3% | chr10 | 118751278 | 118750845 | − | chr10 | 118738819 | 118738767 | − | ENST00000392903; ENST00000260777; ENST00000355371 | TSF |
| 3% | chr4 | 5869106 | 5868912 | − | chr4 | 5868483 | 5868395 | − | ENST00000324989; ENST00000397890; ENST00000512574 | TSF |
| 3% | chr5 | 152889167 | 152889366 | + | chr5 | 153026488 | 153026727 | + | ENST00000285900; ENST00000340592; ENST00000521843; ENST00000448073; ENST00000518783 | TSF |
| 3% | chr5 | 152889167 | 152889366 | + | chr5 | 153026488 | 153026727 | + | ENST00000285900; ENST00000340592; ENST00000521843; ENST00000448073; ENST00000518783 | TSF |
| 3% | chr7 | 121570168 | 121570251 | + | chr7 | 121608005 | 121608184 | + | ENST00000393386; ENST00000449182 | TSF |
| 3% | chr7 | 121570168 | 121570251 | + | chr7 | 121608005 | 121608184 | + | ENST00000393386; ENST00000449182 | TSF |
| 3% | chr9 | 126117506 | 126117568 | + | chr9 | 126125144 | 126125467 | + | ENST00000359999; ENST00000373631 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 3% | chr9 | 126117506 | 126117568 | + | chr9 | 126125144 | 126125467 | + | ENST00000359999; ENST00000373631 | TSF |
| 3% | chr7 | 55985644 | 55985990 | + | chr7 | 55990855 | 55990981 | + | ENST00000426595; ENST00000429591 | TSF |
| 3% | chr7 | 55985644 | 55985990 | − | chr7 | 55990855 | 55990981 | + | ENST00000426595; ENST00000429591 | TSF |
| 3% | chr1 | 226599484 | 226599358 | − | chr1 | 226590080 | 226589915; 226589733 | − | ENST00000366794; ENST00000366792; ENST00000366791; ENST00000366790 | TSF |
| 3% | chr1 | 226599484 | 226599358 | − | chr1 | 226590080 | 226589915; 226589733 | − | ENST00000366794; ENST00000366792; ENST00000366791; ENST00000366790 | TSF |
| 3% | chr1 | 226599484 | 226599358 | − | chr1 | 226590080 | 226589915; 226589733 | − | ENST00000366794; ENST00000366792; ENST00000366791; ENST00000366790 | TSF |
| 3% | chr18 | 74710407 | 74710247 | − | chr18 | 74702016 | 74701912; 74701967; 74701932; 74701935 | − | ENST00000382582; ENST00000359645; ENST00000580402; ENST00000578873; ENST00000355994; ENST00000397869; ENST00000579129; ENST00000459948; ENST00000397875; ENST00000531144; ENST00000578193; ENST00000498683; ENST00000397866; ENST00000583474; ENST00000447114; ENST00000527041; ENST00000533278; ENST00000473302; ENST00000526111; ENST00000493623 | TSF |
| 3% | chr18 | 74710407 | 74710247 | − | chr18 | 74702016 | 74701912; 74701967; 74701932; 74701935 | − | ENST00000382582; ENST00000359645; ENST00000580402; ENST00000578873; ENST00000355994; ENST00000397869; ENST00000579129; ENST00000459948; ENST00000397875; ENST00000531144; ENST00000578193; ENST00000498683; ENST00000397866; ENST00000583474; ENST00000447114; ENST00000527041; ENST00000533278; ENST00000473302; ENST00000526111; ENST00000493623 | TSF |
| 3% | chr18 | 74710407 | 74710247 | − | chr18 | 74702016 | 74701912; 74701967; 74701932; 74701935 | − | ENST00000382582; ENST00000359645; ENST00000580402; ENST00000578873; ENST00000355994; ENST00000397869; ENST00000579129; ENST00000459948; ENST00000397875; ENST00000531144; ENST00000578193; ENST00000498683; ENST00000397866; ENST00000583474; ENST00000447114; ENST00000527041; ENST00000533278; ENST00000473302; ENST00000526111; ENST00000493623 | TSF |
| 3% | chr18 | 74710407 | 74710247 | − | chr18 | 74702016 | 74701912; 74701967; 74701932; 74701935 | − | ENST00000382582; ENST00000359645; ENST00000580402; ENST00000578873; ENST00000355994; ENST00000397869; ENST00000579129; ENST00000459948; ENST00000397875; ENST00000531144; ENST00000578193; ENST00000498683; ENST00000397866; ENST00000583474; ENST00000447114; ENST00000527041; ENST00000533278; ENST00000473302; ENST00000526111; ENST00000493623 | TSF |
| 3% | chr18 | 74710407 | 74710247 | − | chr18 | 74702016 | 74701912; 74701967; 74701932; 74701935 | − | ENST00000382582; ENST00000359645; ENST00000580402; ENST00000578873; ENST00000355994; ENST00000397869; ENST00000579129; ENST00000459948; ENST00000397875; ENST00000531144; ENST00000578193; ENST00000498683; ENST00000397866; ENST00000583474; ENST00000447114; ENST00000527041; ENST00000533278; ENST00000473302; ENST00000526111; ENST00000493623 | TSF |
| 3% | chr18 | 74710407 | 74710247 | − | chr18 | 74702016 | 74701912; 74701967; 74701932; 74701935 | − | ENST00000382582; ENST00000359645; ENST00000580402; ENST00000578873; ENST00000355994; ENST00000397869; ENST00000579129; ENST00000459948; ENST00000397875; ENST00000531144; ENST00000578193; ENST00000498683; ENST00000397866; ENST00000583474; ENST00000447114; ENST00000527041; ENST00000533278; ENST00000473302; ENST00000526111; ENST00000493623 | TSF |
| 3% | chr18 | 74710407 | 74710247 | − | chr18 | 74702016 | 74701912; 74701967; 74701932; 74701935 | − | ENST00000382582; ENST00000359645; ENST00000580402; ENST00000578873; ENST00000355994; ENST00000397869; ENST00000579129; ENST00000459948; ENST00000397875; ENST00000531144; ENST00000578193; ENST00000498683; ENST00000397866; ENST00000583474; ENST00000447114; ENST00000527041; ENST00000533278; ENST00000473302; ENST00000526111; ENST00000493623 | TSF |
| 3% | chr18 | 74710407 | 74710247 | − | chr18 | 74702016 | 74701912; 74701967; 74701932; 74701935 | − | ENST00000382582; ENST00000359645; ENST00000580402; ENST00000578873; ENST00000355994; ENST00000397869; ENST00000579129; ENST00000459948; ENST00000397875; ENST00000531144; ENST00000578193; ENST00000498683; ENST00000397866; ENST00000583474; ENST00000447114; ENST00000527041; ENST00000533278; ENST00000473302; ENST00000526111; ENST00000493623 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 3% | chr18 | 74710407 | 74710247 | – | chr18 | 74702016 | 74701912; 74701967; 74701932; 7401935 | – | ENST00000382582; ENST00000355994; ENST00000397865; ENST00000397866; ENST00000527041; ENST00000359645; ENST00000397869; ENST00000531144; ENST00000583474; ENST00000526111; ENST00000580402; ENST00000579129; ENST00000578193; ENST00000447114; ENST00000473302; ENST00000493623; ENST00000578873; ENST00000459948; ENST00000498683 | TSF |
| 3% | chr18 | 74710407 | 74710247 | – | chr18 | 74702016 | 74701912; 74701967; 74701932; 7401935 | – | ENST00000382582; ENST00000355994; ENST00000397865; ENST00000397866; ENST00000527041; ENST00000359645; ENST00000397869; ENST00000531144; ENST00000583474; ENST00000526111; ENST00000580402; ENST00000579129; ENST00000578193; ENST00000447114; ENST00000473302; ENST00000493623; ENST00000578873; ENST00000459948; ENST00000498683 | TSF |
| 3% | chr18 | 74710407 | 74710247 | – | chr18 | 74702016 | 74701912; 74701967; 74701932; 7401935 | – | ENST00000382582; ENST00000355994; ENST00000397865; ENST00000397866; ENST00000527041; ENST00000359645; ENST00000397869; ENST00000531144; ENST00000583474; ENST00000526111; ENST00000580402; ENST00000579129; ENST00000578193; ENST00000447114; ENST00000473302; ENST00000493623; ENST00000578873; ENST00000459948; ENST00000498683 | TSF |
| 3% | chr18 | 74710407 | 74710247 | – | chr18 | 74702016 | 74701912; 74701967; 74701932; 7401935 | – | ENST00000382582; ENST00000355994; ENST00000397865; ENST00000397866; ENST00000527041; ENST00000359645; ENST00000397869; ENST00000531144; ENST00000583474; ENST00000526111; ENST00000580402; ENST00000579129; ENST00000578193; ENST00000447114; ENST00000473302; ENST00000493623; ENST00000578873; ENST00000459948; ENST00000498683 | TSF |
| 2% | chr5 | 152870891 | 152870892 | + | chr5 | 152873488 | 152873625 | + | ENST00000285900; ENST00000518142; ENST00000340592; ENST00000448073; ENST00000518783 | TSF |
| 2% | chr5 | 152870891 | 152870892 | + | chr5 | 152873488 | 152873625 | + | ENST00000285900; ENST00000518142; ENST00000340592; ENST00000448073; ENST00000518783 | TSF |
| 2% | chr5 | 152870891 | 152870892 | + | chr5 | 152873488 | 152873625 | + | ENST00000285900; ENST00000518142; ENST00000340592; ENST00000448073; ENST00000518783 | TSF |
| 2% | chr18 | 60453659 | 60453726 | + | chr18 | 60497268 | 60497464 | + | ENST00000400316; ENST00000262719 | TSF |
| 2% | chr7 | 95037343 | 95037151 | – | chr7 | 95035559 | 95035431 | – | ENST00000536183; ENST00000443091; ENST00000222572 | TSF |
| 2% | chr11 | 10549538 | 10549023 | – | chr11 | 10546920 | 10546739 | – | ENST00000265981; ENST00000528665; ENST00000533412 | TSF |
| 2% | chr11 | 10549538 | 10549023 | – | chr11 | 10546920 | 10546739 | – | ENST00000265981; ENST00000528665; ENST00000533412 | TSF |
| 2% | chr11 | 10549538 | 10549023 | – | chr11 | 10546920 | 10546739 | – | ENST00000265981; ENST00000528665; ENST00000533412 | TSF |
| 2% | chr7 | 102307107 | 102306895 | – | chr7 | 102306610 | 102306578; 102306524 | – | ENST00000591000; ENST00000476151; ENST00000333432 | TSF |
| 2% | chr7 | 102307107 | 102306895 | – | chr7 | 102306610 | 102306578; 102306524 | – | ENST00000591000; ENST00000476151; ENST00000333432 | TSF |
| 2% | chr20 | 25053246 | 25053172 | – | chr20 | 25052654 | 25052557; 25052571 | – | ENST00000429762; ENST00000444511 | TSF |
| 2% | chr20 | 25053246 | 25053172 | – | chr20 | 25052654 | 25052557; 25052571 | – | ENST00000429762; ENST00000444511 | TSF |
| 2% | chr7 | 55477082 | 55477474 | + | chr7 | 55479600 | 55479782 | + | ENST00000254770 | TSF |
| 2% | chr13 | 78324032 | 78324377 | + | chr13 | 78327338 | 78327493; 78327417; 78327376 | + | ENST00000466548; ENST00000441784; ENST00000314070; ENST00000418532; ENST00000442759; ENST00000474663; ENST00000488699; ENST00000267219; ENST00000351546; ENST00000358679 | TSF |
| 2% | chr13 | 78324032 | 78324377 | + | chr13 | 78327338 | 78327493; 78327417; 78327376 | + | ENST00000466548; ENST00000441784; ENST00000314070; ENST00000418532; ENST00000442759; ENST00000474663; ENST00000488699; ENST00000267219; ENST00000351546; ENST00000358679 | TSF |
| 2% | chr13 | 78324032 | 78324377 | + | chr13 | 78327338 | 78327493; 78327417; 78327376 | + | ENST00000466548; ENST00000441784; ENST00000314070; ENST00000418532; ENST00000442759; ENST00000474663; ENST00000488699; ENST00000267219; ENST00000351546; ENST00000358679 | TSF |
| 2% | chr13 | 78324032 | 78324377 | + | chr13 | 78327338 | 78327493; 78327417; 78327376 | + | ENST00000466548; ENST00000441784; ENST00000314070; ENST00000418532; ENST00000442759; ENST00000474663; ENST00000488699; ENST00000267219; ENST00000351546; ENST00000358679 | TSF |
| 2% | chr7 | 121663316 | 121663441 | + | chr7 | 121668606 | 121668697 | + | ENST00000393386; ENST00000449182 | TSF |
| 2% | chr7 | 121663316 | 121663441 | + | chr7 | 121668606 | 121668697 | + | ENST00000393386; ENST00000449182 | TSF |
| 2% | chr20 | 25777823 | 25776681 | – | chr20 | 25755972 | 25755659 | – | ENST00000584071 | TSF |
| 2% | chrX | 48752918 | 48752631 | – | chrX | 48751504 | 48751380 | – | ENST00000465150; ENST00000376582; ENST00000396779; ENST00000495490; ENST00000490755 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 2% | chrX | 48752918 | 48752631 | − | chrX | 48751504 | 48751380 | − | ENST00000465150; ENST00000376582; ENST00000396779; ENST00000495490; ENST00000490755 | TSF |
| 2% | chr9 | 101249511 | 101249441 | − | chr9 | 101243279 | 101243214 | − | ENST00000259455 | TSF |
| 2% | chr11 | 9172687 | 9172677 | − | chr11 | 9172311 | 9172227; 9172252 | − | ENST00000328194; ENST00000530044; ENST00000527700; ENST00000526707 | TSF |
| 2% | chr11 | 9172687 | 9172677 | − | chr11 | 9172311 | 9172227; 9172252 | − | ENST00000328194; ENST00000527700; ENST00000526707 | TSF |
| 2% | chr11 | 9172687 | 9172677 | − | chr11 | 9172311 | 9172227; 9172252 | − | ENST00000328194; ENST00000527700; ENST00000526707 | TSF |
| 2% | chr7 | 99810933 | 99810670 | − | chr7 | 99773988 | 99773830 | − | ENST00000292377 | TSF |
| 2% | chr15 | 80691014 | 80690949 | − | chr15 | 80690348 | 80690286 | − | ENST00000559008 | TSF |
| 2% | chr4 | 83652035 | 83651970 | − | chr4 | 83626566 | 83626436 | − | ENST00000319540; ENST00000273908; ENST00000282709 | TSF |
| 2% | chr4 | 83652035 | 83651970 | − | chr4 | 83626566 | 83626436 | − | ENST00000319540; ENST00000273908; ENST00000282709 | TSF |
| 2% | chr4 | 83652035 | 83651970 | − | chr4 | 83626566 | 83626436 | − | ENST00000319540; ENST00000273908; ENST00000282709 | TSF |
| 2% | chr7 | 55435136 | 55435321 | + | chr7 | 55459486 | 55459603 | + | ENST00000254770 | TSF |
| 2% | chr5 | 90248993 | 90249033 | + | chr5 | 90261232 | 90261348 | + | ENST00000405460; ENST00000425867 | TSF |
| 2% | chr3 | 133466701 | 133466865 | + | chr3 | 133467256 | 133467428; 133467513; 133467369 | + | ENST00000402696; ENST00000414694; ENST00000494430; ENST00000485977 | TSF |
| 2% | chr3 | 133466701 | 133466865 | + | chr3 | 133467256 | 133467428; 133467513; 133467369 | + | ENST00000402696; ENST00000414694; ENST00000494430; ENST00000485977 | TSF |
| 2% | chr3 | 133466701 | 133466865 | + | chr3 | 133467256 | 133467428; 133467513; 133467369 | + | ENST00000402696; ENST00000414694; ENST00000494430; ENST00000485977 | TSF |
| 2% | chr6 | 13616316 | 13616338 | + | chr6 | 13616695 | 13616753 | + | ENST00000451315; ENST00000420088 | TSF |
| 2% | chr6 | 13616316 | 13616338 | + | chr6 | 13616695 | 13616753 | + | ENST00000451315; ENST00000420088 | TSF |
| 2% | chr7 | 148982749 | 148982787 | + | chr7 | 148984656 | 148984699; 148984867 | + | ENST00000378052; ENST00000476295; ENST00000418158 | TSF |
| 2% | chr7 | 148982749 | 148982787 | + | chr7 | 148984656 | 148984699; 148984867 | + | ENST00000378052; ENST00000418158 | TSF |
| 2% | chr17 | 39974832 | 39974893 | + | chr17 | 39975462 | 39975651 | + | ENST00000321562 | TSF |
| 2% | chr10 | 31755851 | 31757459 | + | chr10 | 31784708 | 31784767 | + | ENST00000320985; ENST00000361642; ENST00000424869; ENST00000561212; ENST00000428815; ENST00000446923; ENST00000559476 | TSF |
| 2% | chr10 | 31755851 | 31757459 | + | chr10 | 31784708 | 31784767 | + | ENST00000320985; ENST00000361642; ENST00000424869; ENST00000561212; ENST00000428815; ENST00000446923; ENST00000559476 | TSF |
| 2% | chr10 | 31755851 | 31757459 | + | chr10 | 31784708 | 31784767 | + | ENST00000320985; ENST00000361642; ENST00000424869; ENST00000561212; ENST00000428815; ENST00000446923; ENST00000559476 | TSF |
| 2% | chr14 | 70495075 | 70495153 | + | chr14 | 70496959 | 70496975 | + | ENST00000480740; ENST00000471696; ENST00000361956; ENST00000485923 | TSF |
| 2% | chr3 | 150344303 | 150344471 | + | chr3 | 150344797 | 150344921 | + | ENST00000258767; ENST00000399322; ENST00000399351; ENST00000402815; ENST00000402700 | TSF |
| 2% | chr7 | 14309025 | 14308524 | − | chr7 | 14217776 | 14217656 | − | ENST00000406247 | TSF |
| 2% | chr7 | 14309025 | 14308524 | − | chr7 | 14217776 | 14217656 | − | ENST00000258767; ENST00000399322; ENST00000399351; ENST00000402815; ENST00000407950; ENST00000444700 | TSF |
| 2% | chr20 | 52615231 | 52614848 | − | chr20 | 52612589 | 52612431 | − | ENST00000406247; ENST00000448484; ENST00000371440; ENST00000371435; ENST00000395961 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 2% | chr20 | 52615231 | 52614848 | − | chr20 | 52612589 | 52612431 | − | ENST00000448484; ENST00000371440; ENST00000371435; ENST00000395961 | TSF |
| 2% | chr20 | 52615231 | 52614848 | − | chr20 | 52612589 | 52612431 | − | ENST00000448484; ENST00000371440; ENST00000371435; ENST00000395961 | TSF |
| 2% | chr4 | 174310858 | 174310746 | − | chr4 | 174309544 | 174309492 | − | ENST00000296506 | TSF |
| 2% | chr3 | 139244518 | 139244462 | − | chr3 | 139237364 | 139237263 | − | ENST00000232219 | TSF |
| 2% | chr13 | 51414162 | 51414079 | − | chr13 | 51397656 | 51397450 | − | ENST00000504404 | TSF |
| 2% | chr12 | 50285408 | 50285280 | − | chr12 | 50284897 | 50284860 | − | ENST00000320634; ENST00000550890; ENST00000552669; ENST00000552863; ENST00000550635; ENST00000547871 | TSF |
| 2% | chr12 | 50285408 | 50285280 | − | chr12 | 50284897 | 50284860 | − | ENST00000320634; ENST00000550890; ENST00000552669; ENST00000552863; ENST00000550635; ENST00000547871 | TSF |
| 2% | chr12 | 50285408 | 50285280 | − | chr12 | 50284897 | 50284860 | − | ENST00000320634; ENST00000550890; ENST00000552669; ENST00000552863; ENST00000550635; ENST00000547871 | TSF |
| 2% | chr12 | 50285408 | 50285280 | − | chr12 | 50284897 | 50284860 | − | ENST00000320634; ENST00000550890; ENST00000552669; ENST00000552863; ENST00000550635; ENST00000547871 | TSF |
| 2% | chr12 | 50285408 | 50285280 | − | chr12 | 50284897 | 50284860 | − | ENST00000320634; ENST00000550890; ENST00000552669; ENST00000552863; ENST00000550635; ENST00000547871 | TSF |
| 2% | chr9 | 104030196 | 104030320 | + | chr9 | 104032162 | 104032350 | + | ENST00000374874; ENST00000456287; ENST00000395056 | TSF |
| 2% | chr9 | 104030196 | 104030320 | + | chr9 | 104032162 | 104032350 | + | ENST00000374874; ENST00000456287; ENST00000395056 | TSF |
| 2% | chr2 | 173902425 | 173902474 | + | chr2 | 173913328 | 173913382 | + | ENST00000264111; ENST00000397081; ENST00000409036; ENST00000397087; ENST00000538974; ENST00000540783; ENST00000539331; ENST00000535187 | TSF |
| 2% | chr11 | 47435494 | 47435767 | + | chr11 | 47435976 | 47436026 | + | ENST00000533076; ENST00000531865; ENST00000362021; ENST00000354884 | TSF |
| 2% | chr11 | 47435494 | 47435767 | + | chr11 | 47435976 | 47436026 | + | ENST00000533076; ENST00000531865; ENST00000362021; ENST00000354884 | TSF |
| 2% | chr11 | 47435494 | 47435767 | + | chr11 | 47435976 | 47436026 | + | ENST00000533076; ENST00000531865; ENST00000362021; ENST00000354884 | TSF |
| 2% | chr11 | 47435494 | 47435767 | + | chr11 | 47435976 | 47436026 | + | ENST00000533076; ENST00000531865; ENST00000362021; ENST00000354884 | TSF |
| 2% | chr3 | 170144282 | 170144403 | + | chr3 | 170150312 | 170150544 | + | ENST00000393386; ENST00000449182 | TSF |
| 2% | chr18 | 60485771 | 60485978 | + | chr18 | 60497268 | 60497464 | + | ENST00000400316; ENST00000262719 | TSF |
| 2% | chr7 | 55464873 | 55464924 | + | chr7 | 55466116 | 55466323 | + | ENST00000254770 | TSF |
| 2% | chr20 | 35861188 | 35861289 | + | chr20 | 35862423 | 35862498 | + | ENST00000237530; ENST00000373622; ENST00000437329; ENST00000456400 | TSF |
| 2% | chr20 | 35861188 | 35861289 | + | chr20 | 35862423 | 35862498 | + | ENST00000237530; ENST00000373622; ENST00000437329; ENST00000456400 | TSF |
| 2% | chr20 | 35861188 | 35861289 | + | chr20 | 35862423 | 35862498 | + | ENST00000237530; ENST00000373622; ENST00000437329; ENST00000456400 | TSF |
| 2% | chr7 | 121614961 | 121615144 | + | chr7 | 121616227 | 121616322 | + | ENST00000393386; ENST00000449182 | TSF |
| 2% | chr7 | 121614961 | 121615144 | + | chr7 | 121616227 | 121616322 | + | ENST00000393386; ENST00000449182 | TSF |
| 2% | chr15 | 75891737 | 75891599 | − | chr15 | 75891022 | 75890699 | − | ENST00000567134; ENST00000308588; ENST00000371091; ENST00000564644; ENST00000564675 | TSF |
| 2% | chr18 | 58558391 | 58558348 | − | chr18 | 58555592 | 58555418 | − | ENST00000474531; ENST00000447756 | TSF |
| 2% | chr3 | 33556001 | 33556042 | − | chr3 | 33552256 | 33552050 | − | ENST00000468888; ENST00000399362; ENST00000307312; ENST00000359576; ENST00000480013; ENST00000461133 | TSF |
| 2% | chr12 | 58023123 | 58023062 | − | chr12 | 58022929 | 58022831; 58022905 | − | ENST00000341156; ENST00000552798; ENST00000549391 | TSF |
| 2% | chr12 | 58023123 | 58023062 | − | chr12 | 58022929 | 58022831; 58022905 | − | ENST00000341156; ENST00000552798; ENST00000549391 | TSF |
| 2% | chr17 | 27415371 | 274127415 | − | chr17 | 27414139 | 27413954 | − | ENST00000354329; ENST00000533112; ENST00000531253; ENST00000527372 | TSF |
| 2% | chr17 | 27415371 | 274127415 | − | chr17 | 27414139 | 27413954 | − | ENST00000354329; ENST00000533112; ENST00000531253; ENST00000527372 | TSF |
| 2% | chr18 | 48347181 | 48347090 | − | chr18 | 48346072 | 48345951 | − | ENST00000585524; ENST00000431965; ENST00000436348 | TSF |
| 2% | chr18 | 48347181 | 48347090 | − | chr18 | 48346072 | 48345951 | − | ENST00000585524; ENST00000431965; ENST00000436348 | TSF |
| 2% | chr18 | 48347181 | 48347090 | − | chr18 | 48346072 | 48345951 | − | ENST00000585524; ENST00000431965; ENST00000436348 | TSF |
| 2% | chr6 | 36924636 | 36924925 | + | chr6 | 36926921 | 36927142 | + | ENST00000373674 | TSF |
| 2% | chr5 | 140889477 | 140889480 | + | chr5 | 140890514 | 140890740 | + | ENST00000517417; ENST00000394576; ENST00000253812; ENST00000523390; ENST00000522605; ENST00000518069; ENST00000576222; ENST00000517434; ENST00000518325; ENST00000519479; ENST00000398604; ENST00000573521; ENST00000520790; ENST00000398610; ENST00000398594; ENST00000398587; ENST00000518882; | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 2% | chr3 | 134857832 | 134857845 | + | chr3 | 134872994 | 134873118 | + | ENST00000252085; ENST00000308177; ENST00000306593; ENST00000252087 | TSF |
| 2% | chr2 | 79872412 | 79872487 | + | chr2 | 79878678 | 79878784 | + | ENST00000398015 | TSF |
| 2% | chr9 | 17779355 | 17779564 | + | chr9 | 17786379 | 17786522 | + | ENST00000380607; ENST00000361291 | TSF |
| 2% | chr7 | 150783303 | 150783304 | + | chr7 | 150784009 | 150784159 | + | ENST00000473312; ENST00000479901; ENST00000397238 | TSF |
| 2% | chr7 | 150783303 | 150783304 | + | chr7 | 150784009 | 150784159 | + | ENST00000473312; ENST00000479901; ENST00000397238 | TSF |
| 2% | chr7 | 150783303 | 150783304 | + | chr7 | 150784009 | 150784159 | + | ENST00000473312; ENST00000479901; ENST00000397238 | TSF |
| 2% | chr10 | 124238815 | 124238992 | + | chr10 | 124248418 | 124248517 | + | ENST00000368984 | TSF |
| 2% | chr2 | 220381821 | 220381889 | + | chr2 | 220396480 | 220396624 | + | ENST00000347842; ENST00000358078 | TSF |
| 2% | chr2 | 220381821 | 220381889 | + | chr2 | 220396480 | 220396624 | + | ENST00000347842; ENST00000358078 | TSF |
| 2% | chr11 | 113094670 | 113100589 | + | chr11 | 113102367 | 113102517 | + | ENST00000533760; ENST00000524665; ENST00000534015; ENST00000401611; ENST00000316851 | TSF |
| 2% | chr11 | 113094670 | 113100589 | + | chr11 | 113102367 | 113102517 | + | ENST00000533760; ENST00000524665; ENST00000534015; ENST00000401611; ENST00000316851 | TSF |
| 2% | chr11 | 113094670 | 113100589 | + | chr11 | 113102367 | 113102517 | + | ENST00000533760; ENST00000524665; ENST00000534015; ENST00000401611; ENST00000316851 | ITSF |
| 2% | chr11 | 113094670 | 113100589 | + | chr11 | 113102367 | 113102517 | + | ENST00000533760; ENST00000524665; ENST00000534015; ENST00000401611; ENST00000316851 | TSF |
| 2% | chr8 | 9629642 | 9629933 | + | chr8 | 9634160 | 9634246 | + | ENST00000310430; ENST00000518281 | TSF |
| 2% | chr17 | 7549704 | 7550019 | + | chr17 | 7557159 | 7557263 | + | ENST00000250111 | TSF |
| 2% | chr7 | 73816311 | 73816411 | + | chr7 | 73818167 | 73818178 | + | ENST00000361545; ENST00000223398; ENST00000395060; ENST00000487447 | ITSF |
| 2% | chr15 | 52850366 | 52850214 | − | chr15 | 52849419 | 52849297 | − | ENST00000566423; ENST00000249822; ENST00000567669; ENST00000569281; ENST00000561971 | TSF |
| 2% | chr8 | 80686236 | 80686056 | − | chr8 | 80678931 | 80678886 | − | ENST00000354724; ENST00000377919; ENST00000518733 | TSF |
| 2% | chr8 | 80686236 | 80686056 | − | chr8 | 80678931 | 80678886 | − | ENST00000354724; ENST00000377919; ENST00000518733 | TSF |
| 2% | chr6 | 131913985 | 131913952 | − | chr6 | 131913600 | 131913528 | − | ENST00000354577; ENST00000403834; ENST00000368068; ENST00000368060; ENST00000368058; ENST00000545957 | TSF |
| 2% | chr6 | 131913985 | 131913952 | − | chr6 | 131913600 | 131913528 | − | ENST00000354577; ENST00000403834; ENST00000368068; ENST00000368060; ENST00000368058; ENST00000545957 | TSF |
| 2% | chr6 | 131913985 | 131913952 | − | chr6 | 131913600 | 131913528 | − | ENST00000354577; ENST00000403834; ENST00000368068; ENST00000368060; ENST00000368058; ENST00000545957 | TSF |
| 2% | chr6 | 131913985 | 131913952 | − | chr6 | 131913600 | 131913528 | − | ENST00000354577; ENST00000403834; ENST00000368068; ENST00000368060; ENST00000368058; ENST00000545957 | TSF |
| 2% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 2% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 2% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 2% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 2% | chr11 | 124800143 | 124799875 | − | chr11 | 124794965 | 124794624 | − | ENST00000298251 | TSF |
| 2% | chr10 | 5454793 | 5454849 | + | chr10 | 5468618 | 5468684 | + | ENST00000355029 | TSF |
| 2% | chr11 | 66048968 | 66049045 | + | chr11 | 66049730 | 66049798; 66049824 | + | ENST00000528852; ENST00000311445; ENST00000528063 | TSF |
| 1% | chr11 | 66048968 | 66049045 | + | chr11 | 66049730 | 66049798; 66049824 | + | ENST00000528852; ENST00000311445; ENST00000528063 | TSF |
| 1% | chr11 | 66048968 | 66049045 | + | chr11 | 66049730 | 66049798; 66049824 | + | ENST00000528852; ENST00000311445; ENST00000528063 | TSF |
| 1% | chr10 | 86006670 | 86006726 | + | chr10 | 86007347 | 86007503 | + | ENST00000359452; ENST00000358110 | TSF |
| 1% | chr10 | 86006670 | 86006726 | + | chr10 | 86007347 | 86007503 | + | ENST00000359452; ENST00000358110 | TSF |
| 1% | chr1 | 120257032 | 120257108 | + | chr1 | 120263793 | 120263944 | + | ENST00000369409; ENST00000369407 | TSF |
| 1% | chr18 | 32400184 | 32400289 | + | chr18 | 32400755 | 32400879 | + | ENST00000283365; ENST00000315456; ENST00000598334; ENST00000554864; ENST00000348997; ENST00000598142; ENST00000598774; ENST00000399121; ENST00000597599; ENST00000269190; ENST00000269191; ENST00000444659; ENST00000595022; ENST00000399113; ENST00000590727 | TSF |
| 1% | chr18 | 32400184 | 32400289 | + | chr18 | 32400755 | 32400879 | + | ENST00000283365; ENST00000315456; ENST00000598334; ENST00000554864; ENST00000348997; ENST00000598142; ENST00000598774; ENST00000399121; ENST00000597599; ENST00000269190; ENST00000269191; ENST00000444659; ENST00000595022; ENST00000399113; ENST00000590727 | TSF |
| 1% | chr18 | 32400184 | 32400289 | + | chr18 | 32400755 | 32400879 | + | ENST00000283365; ENST00000315456; ENST00000598334; ENST00000554864; ENST00000348997; ENST00000598142; ENST00000598774; ENST00000399121; ENST00000597599; ENST00000269190; ENST00000269191; ENST00000444659; ENST00000595022; ENST00000399113; ENST00000590727 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 1% | chr18 | 32400184 | 32400289 | + | chr18 | 32400755 | 32400879 | + | ENST00000283365; ENST00000595022; ENST00000444659; | ENST00000315456; ENST00000598774; ENST00000399113; | ENST00000598334; ENST00000598142; ENST00000590727 | ENST00000554864; ENST00000348997; | ENST00000399121; ENST00000597599; | ENST00000269190; ENST00000269191; | TSF |
| 1% | chr18 | 32400184 | 32400289 | + | chr18 | 32400755 | 32400879 | + | ENST00000283365; ENST00000595022; ENST00000444659; ENST00000315456; ENST00000598774; ENST00000399113; ENST00000598334; ENST00000598142; ENST00000590727 ENST00000554864; ENST00000348997; ENST00000399121; ENST00000597599; ENST00000269190; ENST00000269191; | TSF |
| 1% | chr18 | 32400184 | 32400289 | + | chr18 | 32400755 | 32400879 | + | ENST00000283365; ENST00000595022; ENST00000444659; ENST00000315456; ENST00000598774; ENST00000399113; ENST00000598334; ENST00000598142; ENST00000590727 ENST00000554864; ENST00000348997; ENST00000399121; ENST00000597599; ENST00000269190; ENST00000269191; | TSF |
| 1% | chr18 | 32400184 | 32400289 | + | chr18 | 32400755 | 32400879 | + | ENST00000283365; ENST00000595022; ENST00000444659; ENST00000315456; ENST00000598774; ENST00000399113; ENST00000598334; ENST00000598142; ENST00000590727 ENST00000554864; ENST00000348997; ENST00000399121; ENST00000597599; ENST00000269190; ENST00000269191; | TSF |
| 1% | chr18 | 32400184 | 32400289 | + | chr18 | 32400755 | 32400879 | + | ENST00000283365; ENST00000595022; ENST00000444659; ENST00000315456; ENST00000598774; ENST00000399113; ENST00000598334; ENST00000598142; ENST00000590727 ENST00000554864; ENST00000348997; ENST00000399121; ENST00000597599; ENST00000269190; ENST00000269191; | TSF |
| 1% | chr18 | 32400184 | 32400289 | + | chr18 | 32400755 | 32400879 | + | ENST00000283365; ENST00000595022; ENST00000444659; ENST00000315456; ENST00000598774; ENST00000399113; ENST00000598334; ENST00000598142; ENST00000590727 ENST00000554864; ENST00000348997; ENST00000399121; ENST00000597599; ENST00000269190; ENST00000269191; | TSF |
| 1% | chr18 | 32400184 | 32400289 | + | chr18 | 32400755 | 32400879 | + | ENST00000283365; ENST00000595022; ENST00000444659; ENST00000315456; ENST00000598774; ENST00000399113; ENST00000598334; ENST00000598142; ENST00000590727 ENST00000554864; ENST00000348997; ENST00000399121; ENST00000597599; ENST00000269190; ENST00000269191; | TSF |
| 1% | chr3 | 10973219 | 10973389 | + | chr3 | 10974837 | 10974939 | + | ENST00000254488 | TSF |
| 1% | chr21 | 40851014 | 40851064 | + | chr21 | 40871749 | 40871841 | + | ENST00000380637; ENST00000447939 | ENST00000380634; ENST00000440288; ENST00000333634; ENST00000423596; | TSF |
| 1% | chr21 | 40851014 | 40851064 | + | chr21 | 40871749 | 40871841 | + | ENST00000380637; ENST00000447939 | ENST00000380634; ENST00000440288; ENST00000333634; ENST00000423596; | ITSF |
| 1% | chr21 | 40851014 | 40851064 | + | chr21 | 40871749 | 40871841 | + | ENST00000380637; ENST00000447939 | ENST00000380634; ENST00000440288; ENST00000333634; ENST00000423596; | TSF |
| 1% | chr20 | 44019144 | 44019785 | + | chr20 | 44037100 | 44037106; 44037101; 44037246 | + | ENST00000419593; | ENST00000458187; ENST00000452133; ENST00000380631; ENST00000372710; ENST00000443296 | TSF |
| 1% | chr20 | 44019144 | 44019785 | + | chr20 | 44037100 | 44037106; 44037101; 44037246 | + | ENST00000419593; | ENST00000458187; ENST00000452133; ENST00000372720; ENST00000372710; ENST00000443296 | TSF |
| 1% | chr20 | 44019144 | 44019785 | + | chr20 | 44037100 | 44037106; 44037101; 44037246 | + | ENST00000419593; | ENST00000458187; ENST00000452133; ENST00000372720; ENST00000372710; ENST00000443296 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 1% | chr10 | 31755851 | 31756382 | + | chr10 | 31784708 | 31784767 | + | ENST00000320985; ENST00000559476 | TSF |
| 1% | chr10 | 31755851 | 31756382 | + | chr10 | 31784708 | 31784767 | + | ENST00000320985; ENST00000559476 | TSF |
| 1% | chr10 | 31755851 | 31756382 | + | chr10 | 31784708 | 31784767 | + | ENST00000320985; ENST00000559476 | TSF |
| 1% | chr10 | 31755851 | 31756382 | + | chr10 | 31784708 | 31784767 | + | ENST00000320985; ENST00000559476 | TSF |
| 1% | chr1 | 32264516 | 32264490 | − | chr1 | 32264202 | 32264043; 32264174 | − | ENST00000257100; ENST00000559476 | TSF |
| 1% | chr1 | 32264516 | 32264490 | − | chr1 | 32264202 | 32264043; 32264174 | − | ENST00000257100 | TSF |
| 1% | chr1 | 32264516 | 32264490 | − | chr1 | 32264202 | 32264043; 32264174 | − | ENST00000257100 | ITSF |
| 1% | chr1 | 32264516 | 32264490 | − | chr1 | 32264202 | 32264043; 32264174 | − | ENST00000257100 | TSF |
| 1% | chr1 | 32264516 | 32264490 | − | chr1 | 32264202 | 32264043; 32264174 | − | ENST00000257100 | TSF |
| 1% | chrX | 123618682 | 123617816 | − | chrX | 123615814 | 123615582 | − | ENST00000371130; ENST00000422452 | TSF |
| 1% | chr10 | 1100230 | 1100108 | − | chr10 | 1089333 | 1089241 | − | ENST00000381344; ENST00000427898 | TSF |
| 1% | chr10 | 1100230 | 1100108 | − | chr10 | 1089333 | 1089241 | − | ENST00000381344; ENST00000427898 | TSF |
| 1% | chr10 | 1100230 | 1100108 | − | chr10 | 1089333 | 1089241 | − | ENST00000381344; ENST00000427898 | TSF |
| 1% | chr22 | 31359261 | 31359211 | − | chr22 | 31354680 | 31354627 | − | ENST00000397641 | TSF |
| 1% | chr7 | 96380645 | 96380353 | − | chr7 | 96324203 | 96324110 | − | ENST00000417009; ENST00000449279; ENST00000413065; ENST00000248566 | TSF |
| 1% | chr7 | 96380645 | 96380353 | − | chr7 | 96324203 | 96324110 | − | ENST00000417009; ENST00000449279; ENST00000413065; ENST00000248566 | TSF |
| 1% | chr7 | 96380645 | 96380353 | − | chr7 | 96324203 | 96324110 | − | ENST00000417009; ENST00000449279; ENST00000413065; ENST00000248566 | TSF |
| 1% | chr7 | 96380645 | 96380353 | − | chr7 | 96324203 | 96324110 | − | ENST00000417009; ENST00000449279; ENST00000413065; ENST00000248566 | TSF |
| 1% | chr19 | 18982032 | 18981924 | − | chr19 | 18981428 | 18981386 | − | ENST00000427170 | TSF |
| 1% | chr11 | 60663653 | 60661987 | − | chr11 | 60658735 | 60658638 | − | ENST00000275524; ENST00000296220 | TSF |
| 1% | chr3 | 125267022 | 125266880 | − | chr3 | 125266436 | 125266250 | − | ENST00000520777; ENST00000505820; ENST00000487053; ENST00000357210; ENST00000378712 | TSF |
| 1% | chr1 | 1562829 | 1562926 | + | chr1 | 1563053 | 1563209 | + | ENST00000520777; ENST00000505820; ENST00000487053; ENST00000357210; ENST00000378712 | TSF |
| 1% | chr1 | 1562829 | 1562926 | + | chr1 | 1563053 | 1563209 | + | ENST00000520777; ENST00000505820; ENST00000487053; ENST00000357210; ENST00000378712 | TSF |
| 1% | chr1 | 1562829 | 1562926 | + | chr1 | 1563053 | 1563209 | + | ENST00000520777; ENST00000505820; ENST00000487053; ENST00000357210; ENST00000378712 | TSF |
| 1% | chr10 | 70433076 | 70433244 | + | chr10 | 70441156 | 70441245 | + | ENST00000373644 | TSF |
| 1% | chr16 | 7555906 | 7555956 | + | chr16 | 7568149 | 7568391 | + | ENST00000547605; ENST00000550418; ENST00000553186; ENST00000551752; ENST00000340209; ENST00000570626 | TSF |
| 1% | chr16 | 7555906 | 7555956 | + | chr16 | 7568149 | 7568391 | + | ENST00000547605; ENST00000552089; ENST00000550418; ENST00000551752; ENST00000340209; ENST00000570626 | |
| 1% | chr16 | 7555906 | 7555956 | + | chr16 | 7568149 | 7568391 | + | ENST00000547605; ENST00000552089; ENST00000550418; ENST00000551752; ENST00000340209; ENST00000570626 | TSF |
| 1% | chr16 | 7555906 | 7555956 | + | chr16 | 7568149 | 7568391 | + | ENST00000547605; ENST00000552089; ENST00000550418; ENST00000551752; ENST00000340209; ENST00000570626 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 1% | chr16 | 7555906 | 7555956 | + | chr16 | 7568149 | 7568391 | + | ENST00000547605; ENST00000552089; ENST00000340209; ENST00000550418; ENST00000551752; ENST00000570626 | ENST00000553186; ENST00000547338; ENST00000547372; ENST00000436368; ENST00000422070; ENST00000311745; ENST00000535565; ENST00000355637; | TSF |
| 1% | chr16 | 7555906 | 7555956 | + | chr16 | 7568149 | 7568391 | + | ENST00000547605; ENST00000552089; ENST00000340209; ENST00000550418; ENST00000551752; ENST00000570626 | ENST00000553186; ENST00000547338; ENST00000547372; ENST00000436368; ENST00000422070; ENST00000311745; ENST00000535565; ENST00000355637; | TSF |
| 1% | chr16 | 7555906 | 7555956 | + | chr16 | 7568149 | 7568391 | + | ENST00000547605; ENST00000552089; ENST00000340209; ENST00000550418; ENST00000551752; ENST00000570626 | ENST00000553186; ENST00000547338; ENST00000547372; ENST00000436368; ENST00000422070; ENST00000311745; ENST00000535565; ENST00000355637; | TSF |
| 1% | chr16 | 7555906 | 7555956 | + | chr16 | 7568149 | 7568391 | + | ENST00000547605; ENST00000552089; ENST00000340209; ENST00000550418; ENST00000551752; ENST00000570626 | ENST00000553186; ENST00000547338; ENST00000547372; ENST00000436368; ENST00000422070; ENST00000311745; ENST00000535565; ENST00000355637; | TSF |
| 1% | chr16 | 7555906 | 7555956 | + | chr16 | 7568149 | 7568391 | + | ENST00000547605; ENST00000552089; ENST00000340209; ENST00000550418; ENST00000551752; ENST00000570626 | ENST00000553186; ENST00000547338; ENST00000547372; ENST00000436368; ENST00000422070; ENST00000311745; ENST00000535565; ENST00000355637; | TSF |
| 1% | chr16 | 7555906 | 7555956 | + | chr16 | 7568149 | 7568391 | + | ENST00000547605; ENST00000552089; ENST00000340209; ENST00000550418; ENST00000551752; ENST00000570626 | ENST00000553186; ENST00000547338; ENST00000547372; ENST00000436368; ENST00000422070; ENST00000311745; ENST00000535565; ENST00000355637; | TSF |
| 1% | chr16 | 7555906 | 7555956 | + | chr16 | 7568149 | 7568391 | + | ENST00000547605; ENST00000552089; ENST00000340209; ENST00000550418; ENST00000551752; ENST00000570626 | ENST00000553186; ENST00000547338; ENST00000547372; ENST00000436368; ENST00000422070; ENST00000311745; ENST00000535565; ENST00000355637; | TSF |
| 1% | chr19 | 4288851 | 4288919 | + | chr19 | 4290444 | 4290630 | + | ENST00000543264; ENST00000599689 | | TSF |
| 1% | chr5 | 79371074 | 79371193 | + | chr5 | 79372678 | 79372871 | + | ENST00000350881; ENST00000511733 | | TSF |
| 1% | chr15 | 57573646 | 57573990 | + | chr15 | 57574643 | 57574785; 57574674 | + | ENST00000559609; ENST00000333725; ENST00000559703; ENST00000559710; ENST00000560836 | ENST00000267811; ENST00000557843; ENST00000452095; | TSF |
| 1% | chr15 | 57573646 | 57573990 | + | chr15 | 57574643 | 57574785; 57574674 | + | ENST00000559609; ENST00000333725; ENST00000559703; ENST00000559710; ENST00000560836 | ENST00000557843; ENST00000543579; ENST00000537840; ENST00000343827; | TSF |
| 1% | chr6 | 163875469 | 163875527 | + | chr6 | 163876311 | 163876453 | + | ENST00000361758; ENST00000275262; ENST00000424802 | ENST00000453779; ENST00000392127; ENST00000361752; ENST00000361195; | TSF |
| 1% | chr6 | 163875469 | 163875527 | + | chr6 | 163876311 | 163876453 | + | ENST00000361758; ENST00000275262; ENST00000424802 | ENST00000453779; ENST00000392127; ENST00000361752; ENST00000361195; | TSF |
| 1% | chr6 | 163875469 | 163875527 | + | chr6 | 163876311 | 163876453 | + | ENST00000361758; ENST00000275262; ENST00000424802 | ENST00000453779; ENST00000392127; ENST00000361752; ENST00000361195; | TSF |
| 1% | chr6 | 163875469 | 163875527 | + | chr6 | 163876311 | 163876453 | + | ENST00000361758; ENST00000275262; ENST00000424802 | ENST00000453779; ENST00000392127; ENST00000361752; ENST00000361195; | TSF |
| 1% | chr1 | 1562829 | 1562875 | + | chr1 | 1563053 | 1563209 | + | ENST00000520777; ENST00000505820; ENST00000357210; ENST00000487053; ENST00000378712; ENST00000378708; ENST00000424802 | ENST00000360522; ENST00000378710; ENST00000378708; ENST00000504599; ENST00000355826; ENST00000518681; ENST00000514234 | TSF |
| 1% | chr1 | 1562829 | 1562875 | + | chr1 | 1563053 | 1563209 | + | ENST00000520777; ENST00000505820; ENST00000357210; ENST00000487053; ENST00000378712; | ENST00000360522; ENST00000378710; ENST00000504599; ENST00000355826; ENST00000518681; ENST00000514234 | TSF |
| 1% | chr1 | 1562829 | 1562875 | + | chr1 | 1563053 | 1563209 | + | ENST00000520777; ENST00000505820; ENST00000357210; ENST00000487053; ENST00000378712; | ENST00000360522; ENST00000378710; ENST00000504599; ENST00000355826; ENST00000518681; ENST00000514234 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 1% | chr5 | 135216301 | 135216599 | + | chr5 | 135223721 | 135223773 | + | ENST00000412661 | TSF |
| 1% | chr6 | 36850815 | 36851128 | + | chr6 | 36867202 | 36867409 | + | ENST00000355190 | TSF |
| 1% | chr11 | 60694460 | 60694539 | + | chr11 | 60694676 | 60694890 | + | ENST00000453848; ENST00000005286 | TSF |
| 1% | chr11 | 60694460 | 60694539 | + | chr11 | 60694676 | 60694890 | + | ENST00000453848; ENST00000005286 | TSF |
| 1% | chr9 | 72500819 | 72501289 | + | chr9 | 72501754 | 72501811 | + | ENST00000377197 | TSF |
| 1% | chr11 | 62649715 | 62649740 | + | chr11 | 62650380 | 62650471 | + | ENST00000377892; ENST00000377890; ENST00000377889; ENST00000338663 | TSF |
| 1% | chr18 | 32426045 | 32426197 | + | chr18 | 32428260 | 32428347 | + | ENST00000283365; ENST00000598334; ENST00000598142; ENST00000598190; ENST00000269190; ENST00000399121; ENST00000399097; ENST00000595022; ENST00000348997; ENST00000597599; ENST00000269191; ENST00000444659; ENST00000399113; ENST00000591182; ENST00000269192; ENST00000597674; ENST00000556414; ENST00000599844; ENST00000587723 | TSF |
| 1% | chr18 | 32426045 | 32426197 | + | chr18 | 32428260 | 32428347 | + | ENST00000283365; ENST00000598334; ENST00000598142; ENST00000598190; ENST00000269190; ENST00000399121; ENST00000399097; ENST00000595022; ENST00000348997; ENST00000597599; ENST00000269191; ENST00000444659; ENST00000399113; ENST00000591182; ENST00000269192; ENST00000597674; ENST00000556414; ENST00000599844; ENST00000587723 | TSF |
| 1% | chr18 | 32426045 | 32426197 | + | chr18 | 32428260 | 32428347 | + | ENST00000283365; ENST00000598334; ENST00000598142; ENST00000598190; ENST00000269190; ENST00000399121; ENST00000399097; ENST00000595022; ENST00000348997; ENST00000597599; ENST00000269191; ENST00000444659; ENST00000399113; ENST00000591182; ENST00000269192; ENST00000597674; ENST00000556414; ENST00000599844; ENST00000587723 | TSF |
| 1% | chr18 | 32426045 | 32426197 | + | chr18 | 32428260 | 32428347 | + | ENST00000283365; ENST00000598334; ENST00000598142; ENST00000598190; ENST00000269190; ENST00000399121; ENST00000399097; ENST00000595022; ENST00000348997; ENST00000597599; ENST00000269191; ENST00000444659; ENST00000399113; ENST00000591182; ENST00000269192; ENST00000597674; ENST00000556414; ENST00000599844; ENST00000587723 | TSF |
| 1% | chr18 | 32426045 | 32426197 | + | chr18 | 32428260 | 32428347 | + | ENST00000283365; ENST00000598334; ENST00000598142; ENST00000598190; ENST00000269190; ENST00000399121; ENST00000399097; ENST00000595022; ENST00000348997; ENST00000597599; ENST00000269191; ENST00000444659; ENST00000399113; ENST00000591182; ENST00000269192; ENST00000597674; ENST00000556414; ENST00000599844; ENST00000587723 | TSF |
| 1% | chr20 | 44540290 | 44540197 | − | chr20 | 44540102 | 44539992 | − | ENST00000542937 | TSF |
| 1% | chr20 | 29976260 | 29976126 | − | chr20 | 29965242 | 29965212; 29965049 | − | ENST00000339144; ENST00000376321 | TSF |
| 1% | chr20 | 29976260 | 29976126 | − | chr20 | 29965242 | 29965212; 29965049 | − | ENST00000339144; ENST00000376321 | TSF |
| 1% | chr11 | 82551957 | 82551841 | − | chr11 | 82550467 | 82550303; 82550373 | − | ENST00000313010; ENST00000393399; ENST00000535099; ENST00000531801 | TSF |
| 1% | chr11 | 82551957 | 82551841 | − | chr11 | 82550467 | 82550303; 82550373 | − | ENST00000313010; ENST00000393399; ENST00000535099; ENST00000531801 | TSF |
| 1% | chr16 | 19893258 | 19893237 | − | chr16 | 19884168 | 19883138 | − | ENST00000537135 | TSF |
| 1% | chr19 | 19015073 | 19015005 | − | chr19 | 19014232 | 19014077; 19014082 | − | ENST00000262812; ENST00000600932; ENST00000351079; ENST00000593827 | TSF |
| 1% | chr19 | 19015073 | 19015005 | − | chr19 | 19014232 | 19014077; 19014082 | − | ENST00000262812; ENST00000600932; ENST00000351079; ENST00000593827 | TSF |
| 1% | chr20 | 25780351 | 25778939 | − | chr20 | 25755972 | 25755659 | − | ENST00000584071 | TSF |
| 1% | chr17 | 73847069 | 73846895 | − | chr17 | 73845820 | 73845685 | − | ENST00000254806; ENST00000585462; ENST00000591399; ENST00000591831; ENST00000590221; ENST00000344296; ENST00000433525; ENST00000593002 | TSF |
| 1% | chr17 | 73847069 | 73846895 | − | chr17 | 73845820 | 73845685 | − | ENST00000254806; ENST00000585462; ENST00000591399; ENST00000591831; ENST00000590221; ENST00000344296; ENST00000433525; ENST00000593002 | TSF |

TABLE 34-continued

Transcript fusion for Low Grade Glioma (LGG) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 1% | chr17 | 73847069 | 73846895 | – | chr17 | 73845820 | 73845685 | – | ENST00000254806; ENST00000585462; ENST00000591399; ENST00000591831; ENST00000590221; ENST00000344296; ENST00000433525; ENST00000593002 | TSF |
| 1% | chr17 | 73847069 | 73846895 | – | chr17 | 73845820 | 73845685 | – | ENST00000254806; ENST00000585462; ENST00000591399; ENST00000591831; ENST00000590221; ENST00000344296; ENST00000433525; ENST00000593002 | TSF |
| 1% | chr17 | 73847069 | 73846895 | – | chr17 | 73845820 | 73845685 | – | ENST00000254806; ENST00000585462; ENST00000591399; ENST00000591831; ENST00000590221; ENST00000344296; ENST00000433525; ENST00000593002 | TSF |
| 1% | chr19 | 13080090 | 13079995 | – | chr19 | 13065340 | 13065022 | – | ENST00000316939 | TSF |
| 1% | chr10 | 1100230 | 1100074 | – | chr10 | 1089333 | 1089241 | – | ENST00000381344; ENST00000427898; ENST00000429642 | TSF |
| 1% | chr10 | 1100230 | 1100074 | – | chr10 | 1089333 | 1089241 | – | ENST00000381344; ENST00000427898; ENST00000429642 | TSF |
| 1% | chr10 | 1100230 | 1100074 | – | chr10 | 1089333 | 1089241 | – | ENST00000381344; ENST00000427898; ENST00000429642 | TSF |
| 1% | chr15 | 75650395 | 75650345 | – | chr15 | 75649243 | 75649134 | – | ENST00000569482; ENST00000565683; ENST00000563622; ENST00000267978 | TSF |
| 1% | chr15 | 75650395 | 75650345 | – | chr15 | 75649243 | 75649134 | – | ENST00000569482; ENST00000565683; ENST00000563622; ENST00000267978 | TSF |
| 1% | chr17 | 42991959 | 42991849 | – | chr17 | 42991449 | 42991396 | – | ENST00000253408; ENST00000435360; ENST00000586793; ENST00000592320; ENST00000588316; ENST00000588037 | TSF |
| 1% | chr17 | 42991959 | 42991849 | – | chr17 | 42991449 | 42991396 | – | ENST00000253408; ENST00000435360; ENST00000586793; ENST00000592320; ENST00000588316; ENST00000588037 | TSF |
| 1% | chr17 | 42991959 | 42991849 | – | chr17 | 42991449 | 42991396 | – | ENST00000253408; ENST00000435360; ENST00000586793; ENST00000592320; ENST00000588316; ENST00000588037 | TSF |
| 1% | chr17 | 42991959 | 42991849 | – | chr17 | 42991449 | 42991396 | – | ENST00000253408; ENST00000435360; ENST00000586793; ENST00000592320; ENST00000588316; ENST00000588037 | TSF |
| 1% | chr17 | 42991959 | 42991849 | – | chr17 | 42991449 | 42991396 | – | ENST00000253408; ENST00000435360; ENST00000586793; ENST00000592320; ENST00000588316; ENST00000588037 | TSF |
| 1% | chr1 | 175328580 | 175328513 | – | chr1 | 175325598 | 175325455 | – | ENST00000367674; ENST00000263525 | TSF |
| 1% | chr7 | 44158417 | 44158351 | – | chr7 | 44157663 | 44157542 | – | ENST00000406581; ENST00000223361; ENST00000452185; ENST00000433715; ENST00000456038; ENST00000418438 | TSF |
| 1% | chr7 | 44158417 | 44158351 | – | chr7 | 44157663 | 44157542 | – | ENST00000406581; ENST00000223361; ENST00000452185; ENST00000433715; ENST00000456038; ENST00000418438 | TSF |
| 1% | chr7 | 44158417 | 44158351 | – | chr7 | 44157663 | 44157542 | – | ENST00000406581; ENST00000223361; ENST00000452185; ENST00000433715; ENST00000456038; ENST00000418438 | TSF |
| 1% | chr7 | 44158417 | 44158351 | – | chr7 | 44157663 | 44157542 | – | ENST00000406581; ENST00000223361; ENST00000452185; ENST00000433715; ENST00000456038; ENST00000418438 | TSF |
| 1% | chr7 | 44158417 | 44158351 | – | chr7 | 44157663 | 44157542 | – | ENST00000406581; ENST00000223361; ENST00000452185; ENST00000433715; ENST00000456038; ENST00000418438 | TSF |
| 1% | chr7 | 44158417 | 44158351 | – | chr7 | 44157663 | 44157542 | – | ENST00000406581; ENST00000223361; ENST00000452185; ENST00000433715; ENST00000456038; ENST00000418438 | TSF |

TABLE 35

Transcript fusion for Liver Hepatocellular Carcinoma (LIHC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 49% | chr16 | 16251666 | 16251520 | − | ENST00000205557 | chr16 | 16249711 | 16249633 | − | TAF |
| 33% | chr6 | 11000397 | 11000320 | − | ENST00000354666 | chr6 | 11000151 | 11000002 | − | TAF |
| 31% | chr20 | 3614958 | 3615036 | + | ENST00000262919 | chr20 | 3615708 | 3616042 | + | TSF |
| 29% | chr3 | 186337646 | 186337729 | + | ENST00000411641; ENST00000273784 | chr3 | 186345390 | 186345564 | + | TAF |
| 29% | chr3 | 186337646 | 186337729 | + | ENST00000411641; ENST00000273784 | chr3 | 186345390 | 186345564 | + | TAF |
| 25% | chr1 | 196748927 | 196749103 | + | ENST00000367425; ENST00000471440; ENST00000367427; ENST00000391985 | chr1 | 196835508 | 196835844 | + | TAF |
| 25% | chr16 | 83986867 | 83986975 | + | ENST00000561552 | chr16 | 83989608 | 83989764 | + | TAF |
| 25% | chr1 | 196659193 | 196659369 | + | ENST00000439155; ENST00000367429; ENST00000359637 | chr1 | 196835508 | 196835844 | + | TAF |
| 25% | chr1 | 196659193 | 196659369 | + | ENST00000439155; ENST00000367429; ENST00000359637 | chr1 | 196835508 | 196835844 | + | ITAF |
| 22% | chr9 | 104130604 | 104130402 | − | ENST00000259407; ENST00000395051 | chr9 | 104117689 | 104116763 | − | TAF |
| 21% | chr10 | 5040939 | 5040817 | − | ENST00000380753; ENST00000421196; ENST00000407674; ENST00000604507 | chr10 | 5002427 | 5002117 | − | TAF |
| 21% | chr10 | 5040939 | 5040817 | − | ENST00000380753; ENST00000421196; ENST00000407674; ENST00000604507 | chr10 | 5002427 | 5002117 | − | TAF |
| 21% | chr8 | 91057077 | 91057223 | + | ENST00000220764; ENST00000522161 | chr8 | 91058369 | 91063412 | + | TAF |
| 21% | chr8 | 91057077 | 91057223 | + | ENST00000220764; ENST00000522161 | chr8 | 91058369 | 91063412 | + | TAF |
| 20% | chr1 | 159683928 | 159683793 | − | ENST00000255030; ENST00000368112 | chr1 | 159682370 | 159682050 | − | TAF |
| 18% | chr3 | 149205406 | 149205542 | + | ENST00000305354 | chr3 | 149210784 | 149210892 | + | TAF |
| 18% | chr12 | 122284839 | 122284768 | − | ENST00000289004; ENST00000543163 | chr12 | 122282078 | 122281958 | − | TAF |
| 18% | chr12 | 122284839 | 122284768 | − | ENST00000289004; ENST00000543163 | chr12 | 122282078 | 122281958 | − | TAF |
| 17% | chr15 | 58724232 | 58724319 | + | ENST00000356113; ENST00000414170; ENST00000299022; ENST00000433326 | chr15 | 58787321 | 58787441 | + | TAF |
| 16% | chr1 | 156352539 | 156352660 | + | ENST00000451864; ENST00000255013; ENST00000368246; ENST00000400992; ENST00000368249 | chr1 | 156354102 | 156354192 | + | ITAF |
| 16% | chr1 | 156352539 | 156352660 | + | ENST00000451864; ENST00000255013; ENST00000368246; ENST00000400992; ENST00000368249 | chr1 | 156354102 | 156354192 | + | TAF |
| 16% | chr1 | 156352539 | 156352660 | + | ENST00000451864; ENST00000255013; ENST00000368246; ENST00000400992; ENST00000368249 | chr1 | 156354102 | 156354192 | + | TAF |
| 16% | chr1 | 156352539 | 156352660 | + | ENST00000451864; ENST00000255013; ENST00000368246; ENST00000400992; ENST00000368249 | chr1 | 156354102 | 156354192 | + | TAF |
| 15% | chr7 | 27582719 | 27582586 | − | ENST00000265395; ENST00000425715 | chr7 | 27581374 | 27579272 | − | TAF |
| 15% | chr7 | 27582719 | 27582586 | − | ENST00000265395; ENST00000425715 | chr7 | 27581374 | 27579272 | − | TAF |
| 14% | chr10 | 15151838 | 15151701 | − | ENST00000378165; ENST00000378150; ENST00000540259; ENST00000535341 | chr10 | 15148697 | 15148684 | − | TAF |
| 14% | chr10 | 15151838 | 15151701 | − | ENST00000378165; ENST00000378150; ENST00000540259; ENST00000535341 | chr10 | 15148697 | 15148684 | − | TAF |
| 14% | chr10 | 15151838 | 15151701 | − | ENST00000378165; ENST00000378150; ENST00000540259; ENST00000535341 | chr10 | 15148697 | 15148684 | − | TAF |
| 14% | chr10 | 15151838 | 15151701 | − | ENST00000378165; ENST00000378150; ENST00000540259; ENST00000535341 | chr10 | 15148697 | 15148684 | − | ITAF |
| 14% | chr2 | 27320371 | 27320517 | + | ENST00000260599; ENST00000260598; ENST00000429697 | chr2 | 27321791 | 27321916 | + | TAF |
| 14% | chr2 | 27320371 | 27320517 | + | ENST00000260599; ENST00000260598; ENST00000429697 | chr2 | 27321791 | 27321916 | + | TAF |
| 14% | chr2 | 27320371 | 27320517 | + | ENST00000260599; ENST00000260598; ENST00000429697 | chr2 | 27321791 | 27321916 | + | TAF |
| 13% | chr12 | 122284839 | 122284768 | − | ENST00000289004; ENST00000543163 | chr12 | 122282086 | 122281958 | − | TAF |
| 13% | chr12 | 122284839 | 122284768 | − | ENST00000289004; ENST00000543163 | chr12 | 122282086 | 122281958 | − | TAF |
| 13% | chr3 | 125828952 | 125828787 | − | ENST00000273450; ENST00000472186; ENST00000452905; ENST00000393434 | chr3 | 125828416 | 125828224 | − | TAF |
| 13% | chr3 | 125828952 | 125828787 | − | ENST00000273450; ENST00000472186; ENST00000452905; ENST00000393434 | chr3 | 125828416 | 125828224 | − | TAF |
| 13% | chr3 | 125828952 | 125828787 | − | ENST00000273450; ENST00000472186; ENST00000452905; ENST00000393434 | chr3 | 125828416 | 125828224 | − | ITAF |
| 13% | chr1 | 159683928 | 159683797 | − | ENST00000255030; ENST00000368112; ENST00000368111; ENST00000368110; ENST00000343919 | chr1 | 159682370 | 159682050 | − | TAF |
| 13% | chr3 | 39942308 | 39942417 | + | ENST00000444716; ENST00000302541; ENST00000425621; ENST00000458292; ENST00000458441 | chr3 | 40032343 | 40032651 | + | TAF |
| 12% | chr20 | 6015110 | 6015201 | + | ENST00000378863; ENST00000378868 | chr20 | 6020406 | 6020676 | + | TAF |
| 12% | chr20 | 6015110 | 6015201 | + | ENST00000378863; ENST00000378868 | chr20 | 6020406 | 6020676 | + | TAF |
| 12% | chrX | 117900807 | 117900939 | + | ENST00000371666 | chrX | 117938895 | 117939267 | + | TAF |
| 12% | chr9 | 123716146 | 123716008 | − | ENST00000223642 | chr9 | 123705787 | 123705454 | − | TAF |
| 12% | chr15 | 101845560 | 101845467 | − | ENST00000398185; ENST00000348070; ENST00000358417 | chr15 | 101841074 | 101840901 | − | TAF |
| 12% | chr15 | 101845560 | 101845467 | − | ENST00000398185; ENST00000348070; ENST00000358417 | chr15 | 101841074 | 101840901 | − | TAF |

TABLE 35-continued

Transcript fusion for Liver Hepatocellular Carcinoma (LIHC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 12% | chr15 | 101845560 | 101845467 | − | ENST00000398185; ENST00000348070; ENST00000358417 | chr15 | 101841074 | 101840901 | − | TAF |
| 12% | chr3 | 186334976; 186334973 | 186335139 | + | ENST00000411641; ENST00000273784 | chr3 | 186345390 | 186345564 | + | TSF |
| 12% | chr3 | 186334976; 186334973 | 186335139 | + | ENST00000411641; ENST00000273784 | chr3 | 186345390 | 186345564 | + | TSF |
| 11% | chr19 | 45451958 | 45452117 | + | ENST00000589057; ENST00000252490; ENST00000590360; ENST00000585786 | chr19 | 45452371 | 45452396 | + | TAF |
| 11% | chr19 | 45451958 | 45452117 | + | ENST00000589057; ENST00000252490; ENST00000590360; ENST00000585786 | chr19 | 45452371 | 45452396 | + | TAF |
| 11% | chr17 | 66538306 | 66538126 | − | ENST00000592554 | chr17 | 66537704 | 66537648 | − | TAF |
| 11% | chr20 | 37002581 | 37002657 | + | ENST00000217407 | chr20 | 37003944 | 37004237 | + | TAF |
| 10% | chr9 | 117085414 | 117085527 | + | ENST00000259396; ENST00000538816 | chr9 | 117092629 | 117092673 | + | TAF |
| 10% | chr1 | 156352539 | 156352660 | + | ENST00000451864; ENST00000255013; ENST00000368246; ENST00000400992; ENST00000368249 | chr1 | 156354082 | 156354192 | + | TSF |
| 10% | chr1 | 156352539 | 156352660 | + | ENST00000451864; ENST00000255013; ENST00000368246; ENST00000400992; ENST00000368249 | chr1 | 156354082 | 156354192 | + | TSF |
| 10% | chr1 | 156352539 | 156352660 | + | ENST00000451864; ENST00000255013; ENST00000368246; ENST00000400992; ENST00000368249 | chr1 | 156354082 | 156354192 | + | TSF |
| 10% | chr1 | 156352539 | 156352660 | + | ENST00000451864; ENST00000255013; ENST00000368246; ENST00000400992; ENST00000368249 | chr1 | 156354082 | 156354192 | + | TSF |
| 10% | chr19 | 49335016 | 49334925 | − | ENST00000263278; ENST00000595764 | chr19 | 49322122 | 49322095 | − | TSF |
| 10% | chr19 | 49335016 | 49334925 | − | ENST00000263278; ENST00000595764 | chr19 | 49322122 | 49322095 | − | TSF |
| 9% | chr1 | 204183034 | 204183010 | − | ENST00000308302 | chr1 | 204178313 | 204177989 | − | TSF |
| 9% | chr17 | 79912179 | 79912132 | − | ENST00000409678 | chr17 | 79911834 | 79911647 | − | TSF |
| 9% | chr7 | 44198719 | 44198672 | − | ENST00000345378 | chr7 | 44197795 | 44197675 | − | TSF |
| 8% | chr22 | 47071365 | 47071449 | + | ENST00000406902; ENST00000361034; ENST00000408031 | chr22 | 47078308 | 47078350 | + | TSF |
| 8% | chr22 | 47071365 | 47071449 | + | ENST00000406902; ENST00000361034; ENST00000408031 | chr22 | 47078308 | 47078350 | + | TSF |
| 8% | chrX | 119708472 | 119708406 | − | ENST00000404115 | chrX | 119705855 | 119705820 | − | TSF |
| 7% | chr20 | 29632611 | 29632721 | + | ENST00000278882; ENST00000358464 | chr20 | 29652086 | 29652324 | + | TSF |
| 7% | chr19 | 35540379 | 35540420 | + | ENST00000262626; ENST00000392226; ENST00000600390 | chr19 | 35547041 | 35547341 | + | TSF |
| 7% | chr1 | 225156461 | 225156576 | + | ENST00000430092; ENST00000400952; ENST00000366849; ENST00000439375 | chr1 | 225157336 | 225158402 | + | TSF |
| 7% | chr1 | 225156461 | 225156576 | + | ENST00000430092; ENST00000400952; ENST00000366849; ENST00000439375 | chr1 | 225157336 | 225158402 | + | TSF |
| 6% | chr16 | 50583333 | 50583466 | + | ENST00000268459 | chr16 | 50614862 | 50614981 | + | TSF |
| 6% | chr4 | 57319769 | 57319927 | + | ENST00000514888; ENST00000264221; ENST00000505164; ENST00000399688; ENST00000512576 | chr4 | 57321183 | 57321327 | + | TSF |
| 6% | chr4 | 57319769 | 57319927 | + | ENST00000514888; ENST00000264221; ENST00000505164; ENST00000399688; ENST00000512576 | chr4 | 57321183 | 57321327 | + | TSF |
| 6% | chr4 | 57319769 | 57319927 | + | ENST00000514888; ENST00000264221; ENST00000505164; ENST00000399688; ENST00000512576 | chr4 | 57321183 | 57321327 | + | TSF |
| 6% | chr1 | 196659193 | 196659369 | + | ENST00000439155; ENST00000367429; ENST00000359637 | chr1 | 196678901 | 196678922 | + | TSF |
| 6% | chr1 | 196659193 | 196659369 | + | ENST00000439155; ENST00000367429; ENST00000359637 | chr1 | 196678901 | 196678922 | + | TSF |
| 5% | chr22 | 21133601 | 21134489 | + | ENST00000215727; ENST00000406799 | chr22 | 21136178 | 21136264 | + | TSF |
| 5% | chr10 | 127483547 | 127483449 | − | ENST00000368797; ENST00000368786 | chr10 | 127473829 | 127473633 | − | TSF |
| 5% | chr3 | 186336325 | 186336426 | + | ENST00000411641; ENST00000273784 | chr3 | 186345404 | 186345564 | + | TSF |
| 5% | chr3 | 186336325 | 186336426 | + | ENST00000411641; ENST00000273784 | chr3 | 186345401 | 186345564 | + | TSF |
| 4% | chr22 | 50639466 | 50640019 | + | ENST00000380903 | chr22 | 50643348 | 50643731 | + | TSF |
| 4% | chr3 | 52823669 | 52823870 | + | ENST00000273283; ENST00000540715; ENST00000537050; ENST00000428133; ENST00000405128 | chr3 | 52824522 | 52824594 | + | TSF |
| 4% | chr3 | 52823669 | 52823870 | + | ENST00000273283; ENST00000540715; ENST00000537050; ENST00000428133; ENST00000405128 | chr3 | 52824522 | 52824594 | + | TSF |
| 4% | chr3 | 52823669 | 52823870 | + | ENST00000273283; ENST00000540715; ENST00000537050; ENST00000428133; ENST00000405128 | chr3 | 52824522 | 52824594 | + | TSF |
| 4% | chr3 | 52823669 | 52823870 | + | ENST00000273283; ENST00000540715; ENST00000537050; ENST00000428133; ENST00000405128 | chr3 | 52824522 | 52824594 | + | TSF |
| 4% | chr3 | 52823669 | 52823870 | + | ENST00000273283; ENST00000540715; ENST00000537050; ENST00000428133; | chr3 | 52824522 | 52824594 | + | TSF |

TABLE 35-continued

Transcript fusion for Liver Hepatocellular Carcinoma (LIHC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| | | | | | ENST00000405128 | | | | | |
| 4% | chr2 | 211452782 | 211452871 | + | ENST00000430249; ENST00000233072 | chr2 | 211454033 | 211454053 | + | TSF |
| 4% | chr2 | 211452782 | 211452871 | + | ENST00000430249; ENST00000233072 | chr2 | 211454033 | 211454053 | + | TSF |
| 4% | chr9 | 104133686 | 104133221 | − | ENST00000259407; ENST00000395051 | chr9 | 104117689 | 104116763 | − | TSF |
| 4% | chr3 | 186334232 | 186334316 | + | ENST00000411641; ENST00002273784 | chr3 | 186345390 | 186345564 | + | TSF |
| 4% | chr3 | 48716169 | 48715997 | − | ENST00000341520; ENST00000416649; ENST00000294129; ENST00000413374 | chr3 | 48702393 | 48702198 | − | TSF |
| 4% | chr3 | 48716169 | 48715997 | − | ENST00000341520; ENST00000416649; ENST00000294129; ENST00000413374 | chr3 | 48702393 | 48702198 | − | TSF |
| 4% | chr3 | 48716169 | 48715997 | − | ENST00000341520; ENST00000416649; ENST00000294129; ENST00000413374 | chr3 | 48702393 | 48702198 | − | TSF |
| 4% | chr12 | 103237557 | 103237424 | − | ENST00000553106; ENST00000307000 | chr12 | 103236886 | 103236826 | − | TSF |
| 4% | chr12 | 103237557 | 103237424 | − | ENST00000553106; ENST00000307000 | chr12 | 103236886 | 103236826 | − | TSF |
| 3% | chr12 | 71928895 | 71928966 | + | ENST00000266674; ENST00000536515; ENST00000540815 | chr12 | 71938771 | 71938901 | + | TSF |
| 3% | chr10 | 96731861 | 96732002 | + | ENST00000260682 | chr10 | 96735182 | 96735858 | + | TSF |
| 3% | chr12 | 113623819 | 113623826 | + | ENST00000552495 | chr12 | 113623998 | 113624117 | + | TSF |
| 3% | chr9 | 104133686 | 104133600 | − | ENST00000259407; ENST00000395051 | chr9 | 104117689 | 104116763 | − | TSF |
| 3% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 3% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 3% | chr10 | 126205749 | 126205840 | + | ENST00000368842 | chr10 | 126251911 | 126252288 | + | TSF |
| 3% | chr22 | 48885405 | 48885516 | + | ENST00000402357; ENST00000336769 | chr22 | 48915770 | 48916108 | + | TSF |
| 3% | chr12 | 21377656 | 21377773 | + | ENST00000256958 | chr12 | 21420585 | 21420936 | + | TSF |
| 3% | chr19 | 48382387 | 48382293 | − | ENST00000222002 | chr19 | 48379566 | 48379257 | − | TSF |
| 3% | chr11 | 62987493 | 62987404 | − | ENST00000528239 | chr11 | 62986972 | 62986804 | − | TSF |
| 2% | chr3 | 195956786; 195956876 | 195956932 | + | ENST00000296327; ENST00000415111 | chr3 | 195970598 | 195971983 | + | TSF |
| 2% | chr3 | 195956786; 195956876 | 195956932 | + | ENST00000296327; ENST00000415111 | chr3 | 195970598 | 195971983 | + | TSF |
| 2% | chr9 | 17143286 | 17143374 | + | ENST00000380647; ENST00000262360; ENST00000425824; ENST00000380641 | chr9 | 17166816 | 17167136 | + | TSF |
| 2% | chr16 | 50666192 | 50666319 | + | ENST00000268459 | chr16 | 50682755 | 50682972 | + | TSF |
| 2% | chr6 | 24533735 | 24533915 | + | ENST00000546278; ENST00000357578; ENST00000491546; ENST00000348925 | chr6 | 24536738 | 24536757 | + | TSF |
| 2% | chr6 | 24533735 | 24533915 | + | ENST00000546278; ENST00000357578; ENST00000491546; ENST00000348925 | chr6 | 24536738 | 24536757 | + | TSF |
| 2% | chr6 | 24533735 | 24533915 | + | ENST00000546278; ENST00000357578; ENST00000491546; ENST00000348925 | chr6 | 24536738 | 24536757 | + | TSF |
| 2% | chr6 | 24533735 | 24533915 | + | ENST00000546278; ENST00000357578; ENST00000491546; ENST00000348925 | chr6 | 24536738 | 24536757 | + | TSF |
| 2% | chr7 | 91509397 | 91509369 | − | ENST00000351870; ENST00000442961 | chr7 | 91430582 | 91429696 | − | TSF |
| 2% | chr22 | 37492755 | 37492688 | − | ENST00000381792; ENST00000346753; ENST00000406725; ENST00000406856; ENST00000442782; ENST00000423761 | chr22 | 37492292 | 37492206 | − | TSF |
| 2% | chr22 | 37492755 | 37492688 | − | ENST00000381792; ENST00000346753; ENST00000406725; ENST00000406856; ENST00000442782; ENST00000423761 | chr22 | 37492292 | 37492206 | − | TSF |
| 2% | chr5 | 176830398 | 176830255 | − | ENST00000253496 | chr5 | 176829864 | 176829767 | − | TSF |
| 2% | chr11 | 116701489 | 116701612 | + | ENST00000227667; ENST00000375345 | chr11 | 116704332 | 116704408 | + | TSF |
| 2% | chr11 | 116701489 | 116701612 | + | ENST00000227667; ENST00000375345 | chr11 | 116704332 | 116704408 | + | TSF |
| 2% | chr1 | 226016431 | 226016613 | + | ENST00000445856; ENST00000272167; ENST00000448202; ENST00000366837 | chr1 | 226018885 | 226018904 | + | TSF |
| 2% | chr22 | 47072497 | 47072565 | + | ENST00000406902; ENST00000361034; | chr22 | 47078308 | 47078350 | + | TSF |

TABLE 35-continued

Transcript fusion for Liver Hepatocellular Carcinoma (LIHC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr22 | 47072497 | 47072565 | + | ENST00000408031 ENST00000406902; ENST00000361034; ENST00000408031 | chr22 | 47078308 | 47078350 | + | TSF |
| 2% | chr4 | 107237705 | 107237751 | + | ENST00000394701 | chr4 | 107242023 | 107243452 | + | TSF |
| 2% | chr9 | 116825038 | 116824957 | − | ENST00000265132; ENST00000466610 | chr9 | 116823895 | 116823894 | − | TSF |
| 2% | chr9 | 116825038 | 116824957 | − | ENST00000265132; ENST00000466610 | chr9 | 116823895 | 116823894 | − | TSF |
| 2% | chr19 | 6718175 | 6718105 | − | ENST00000245907 | chr19 | 6716545 | 6716239 | − | TSF |
| 2% | chr12 | 122292698 | 122292609 | − | ENST00000289004; ENST00000543163 | chr12 | 122289515 | 122289239 | − | TSF |
| 2% | chr12 | 122292698 | 122292609 | − | ENST00000289004; ENST00000543163 | chr12 | 122289515 | 122289239 | − | TSF |
| 2% | chr19 | 45418149 | 45418206 | + | ENST00000588750; ENST00000588802; ENST00000592535; ENST00000252491; ENST00000592885; ENST00000589781; ENST00000589078; ENST00000590334; ENST00000586638; ENST00000592176 | chr19 | 45430934 | 45430990 | + | TSF |
| 2% | chr10 | 96443577 | 96443744 | + | ENST00000339022; ENST00000285979 | chr10 | 96698194 | 96698222 | + | TSF |
| 2% | chr1 | 161207850 | 161207831 | − | ENST00000512372; ENST00000437437; ENST00000412844; ENST00000508740; ENST00000506018; ENST00000367981; ENST00000504010; ENST00000507215; ENST00000508387; ENST00000510951; ENST00000511676; ENST00000511748; ENST00000512340; ENST00000506209 | chr1 | 161204494 | 161204367 | − | TSF |
| 2% | chr12 | 120966944 | 120966743 | − | ENST00000288532; ENST00000445328; ENST00000547943 | chr12 | 120965181 | 120964888 | − | TSF |
| 2% | chr14 | 24768312 | 24768163 | − | ENST00000288111; ENST00000396813; ENST00000558340 | chr14 | 24767944 | 24767783 | − | TSF |
| 2% | chr19 | 12987177 | 12986994 | − | ENST00000222219; ENST00000538460 | chr19 | 12986142 | 12986038 | − | TSF |
| 2% | chr19 | 12987177 | 12986994 | − | ENST00000222219; ENST00000538460 | chr19 | 12986142 | 12986038 | − | TSF |
| 2% | chr15 | 101858627 | 101858524 | − | ENST00000398185; ENST00000348070; ENST00000358417 | chr15 | 101841074 | 101840901 | − | TSF |
| 2% | chr15 | 101858627 | 101858524 | − | ENST00000398185; ENST00000348070; ENST00000358417 | chr15 | 101841074 | 101840901 | − | TSF |
| 2% | chr15 | 101858627 | 101858524 | − | ENST00000398185; ENST00000348070; ENST00000358417 | chr15 | 101841074 | 101840901 | − | TSF |
| 2% | chr6 | 44200080 | 44200165 | + | ENST00000393844; ENST00000313248; ENST00000427851; ENST00000371740; ENST00000371755; ENST00000371731; ENST00000393841; ENST00000371713; ENST00000371724; ENST00000371708 | chr6 | 44209921 | 44210213 | + | TSF |
| 2% | chr6 | 44200080 | 44200165 | + | ENST00000393844; ENST00000313248; ENST00000427851; ENST00000371740; ENST00000371755; ENST00000371731; ENST00000393841; ENST00000371713; ENST00000371724; ENST00000371708 | chr6 | 44209921 | 44210213 | + | TSF |
| 2% | chr8 | 71619168 | 71619388 | + | ENST00000408926; ENST00000520030 | chr8 | 71625661 | 71625673 | + | TSF |
| 2% | chr6 | 24533735 | 24533915 | + | ENST00000546278; ENST00000357578; ENST00000491546; ENST00000348925 | chr6 | 24543356 | 24543371 | + | lTSF |
| 2% | chr6 | 24533735 | 24533915 | + | ENST00000546278; ENST00000357578; ENST00000491546; ENST00000348925 | chr6 | 24543356 | 24543371 | + | TSF |
| 2% | chr6 | 24533735 | 24533915 | + | ENST00000546278; ENST00000357578; ENST00000491546; ENST00000348925 | chr6 | 24543356 | 24543371 | + | TSF |
| 2% | chr6 | 24533735 | 24533915 | + | ENST00000546278; ENST00000357578; ENST00000491546; ENST00000348925 | chr6 | 24543356 | 24543371 | + | TSF |
| 2% | chr19 | 45419447 | 45419582 | + | ENST00000588750; ENST00000588802; ENST00000592535; ENST00000252491; ENST00000592885; ENST00000590334; ENST00000586638 | chr19 | 45420139 | 45420241 | + | TSF |
| 2% | chr8 | 36780008 | 36780147 | + | ENST00000399881; ENST00000522372 | chr8 | 36786424 | 36786484 | + | TSF |
| 2% | chr14 | 32020101 | 32020133 | + | ENST00000550005 | chr14 | 32027031 | 32027274 | + | TSF |
| 2% | chr20 | 6017720 | 6017789 | + | ENST00000378863; ENST00000378868 | chr20 | 6020406 | 6020676 | + | TSF |
| 2% | chr20 | 6017720 | 6017789 | + | ENST00000378863; ENST00000378868 | chr20 | 6020406 | 6020676 | + | TSF |
| 2% | chr5 | 79410474 | 79410337 | − | ENST00000509193 | chr5 | 79407525 | 79407007 | − | TSF |
| 2% | chr17 | 79912179 | 79912132 | − | ENST00000409678 | chr17 | 79911819 | 79911647 | − | TSF |
| 2% | chr12 | 49317635 | 49317565 | − | ENST00000444214; ENST00000550765; ENST00000552878; ENST00000453172 | chr12 | 49310033 | 49308894 | − | TSF |
| 2% | chr12 | 49317635 | 49317565 | − | ENST00000444214; ENST00000550765; ENST00000552878; ENST00000453172 | chr12 | 49310033 | 49308894 | − | TSF |

TABLE 36

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 46% | chr16 | 16249761 | 16249649 | − | chr16 | 16248888 | 16248730 | − | ENST00000205557 | TAF |
| 46% | chr1 | 207263335 | 207263385 | + | chr1 | 207263653 | 207263826 | + | ENST00000367078; ENST00000452902; ENST00000243611; ENST00000391923 | TAF |
| 46% | chr1 | 207263335 | 207263385 | + | chr1 | 207263653 | 207263826 | + | ENST00000367078; ENST00000452902; ENST00000243611; ENST00000391923 | TAF |
| 44% | chr19 | 51854024 | 51853970 | − | chr19 | 51853645 | 51853583 | − | ENST00000354232; ENST00000309244; ENST00000596253 | TAF |
| 44% | chr19 | 51854024 | 51853970 | − | chr19 | 51853645 | 51853583 | − | ENST00000354232; ENST00000309244; ENST00000596253 | TAF |
| 36% | chr1 | 59980221 | 59980497 | + | chr1 | 60019796 | 60019899 | + | ENST00000371218; ENST00000303721; ENST00000430447; ENST00000371212 | TSF |
| 36% | chr1 | 59980221 | 59980497 | + | chr1 | 60019796 | 60019899 | + | ENST00000371218; ENST00000303721; ENST00000430447; ENST00000371212 | TSF |
| 36% | chr1 | 59980221 | 59980497 | + | chr1 | 60019796 | 60019899 | + | ENST00000371218; ENST00000303721; ENST00000430447; ENST00000371212 | TSF |
| 30% | chr19 | 51854233 | 51854037 | − | chr19 | 51853645 | 51853583 | − | ENST00000354232; ENST00000309244; ENST00000596253 | TAF |
| 30% | chr19 | 51854233 | 51854037 | − | chr19 | 51853645 | 51853583 | − | ENST00000354232; ENST00000309244; ENST00000596253 | TAF |
| 29% | chr16 | 72098678 | 72105593 | + | chr16 | 72107791 | 72107876 | + | ENST00000356967; ENST00000540303; ENST00000561690; ENST00000228226 | TAF |
| 29% | chr16 | 72098678 | 72105593 | + | chr16 | 72107791 | 72107876 | + | ENST00000356967; ENST00000540303; ENST00000561690; ENST00000228226 | TAF |
| 29% | chr9 | 117089333 | 117089580 | + | chr9 | 117092714 | 117092856; 117092769 | + | ENST00000431067; ENST00000412657 | TAF |
| 29% | chr9 | 117089333 | 117089580 | + | chr9 | 117092714 | 117092856; 117092769 | + | ENST00000431067; ENST00000412657 | TAF |
| 27% | chr17 | 56612963 | 56612799 | − | chr17 | 56603674 | 56603581; 56603614 | − | ENST00000393086; ENST00000426861; ENST00000579371; ENST00000317268; ENST00000457347; ENST00000580844; ENST00000317256; ENST00000412945; ENST00000580809; ENST00000577729; ENST00000581615; ENST00000578131; ENST00000583291 | TAF |
| 27% | chr17 | 56612963 | 56612799 | − | chr17 | 56603674 | 56603581; 56603614 | − | ENST00000393086; ENST00000426861; ENST00000579371; ENST00000317268; ENST00000457347; ENST00000580844; ENST00000317256; ENST00000412945; ENST00000580809; ENST00000577729; ENST00000581615; ENST00000578131; ENST00000583291 | TAF |
| 27% | chr17 | 56612963 | 56612799 | − | chr17 | 56603674 | 56603581; 56603614 | − | ENST00000393086; ENST00000426861; ENST00000579371; ENST00000317268; ENST00000457347; ENST00000580844; ENST00000317256; ENST00000412945; ENST00000580809; ENST00000577729; ENST00000581615; ENST00000578131; ENST00000583291 | TAF |
| 27% | chr17 | 56612963 | 56612799 | − | chr17 | 56603674 | 56603581; 56603614 | − | ENST00000393086; ENST00000426861; ENST00000579371; ENST00000317268; ENST00000457347; ENST00000580844; ENST00000317256; ENST00000412945; ENST00000580809; ENST00000577729; ENST00000581615; ENST00000578131; ENST00000583291 | TAF |
| 27% | chr17 | 56612963 | 56612799 | − | chr17 | 56603674 | 56603581; 56603614 | − | ENST00000393086; ENST00000426861; ENST00000579371; ENST00000317268; ENST00000457347; ENST00000580844; ENST00000317256; ENST00000412945; ENST00000580809; ENST00000577729; ENST00000581615; ENST00000578131; ENST00000583291 | TAF |
| 27% | chr17 | 56612963 | 56612799 | − | chr17 | 56603674 | 56603581; 56603614 | − | ENST00000393086; ENST00000426861; ENST00000579371; ENST00000317268; ENST00000457347; ENST00000580844; ENST00000317256; ENST00000412945; ENST00000580809; ENST00000577729; ENST00000581615; ENST00000578131; ENST00000583291 | TAF |
| 27% | chr1 | 207268999 | 207269340 | + | chr1 | 207269867 | 207269960 | + | ENST00000367078; ENST00000452902; ENST00000243611; ENST00000367076; ENST00000391923 | TAF |
| 27% | chr1 | 207268999 | 207269340 | + | chr1 | 207269867 | 207269960 | + | ENST00000367078; ENST00000452902; ENST00000243611; ENST00000367076; ENST00000391923 | TAF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 24% | chr16 | 72098678 | 72105852 | + | chr16 | 72107791 | 72107876 | + | ENST00000356967; ENST00000540303; ENST00000561690; ENST00000228226 | TAF |
| 24% | chr16 | 72098678 | 72105852 | + | chr16 | 72107791 | 72107876 | + | ENST00000356967; ENST00000540303; ENST00000561690; ENST00000228226 | TAF |
| 23% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 23% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 23% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 23% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 23% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 23% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 23% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 23% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 22% | chr16 | 83989605 | 83989746 | + | chr16 | 83991245 | 83991255; 83991343 | + | ENST00000561552; ENST00000343939 | TSF |
| 22% | chr16 | 83989605 | 83989746 | + | chr16 | 83991245 | 83991255; 83991343 | + | ENST00000561552; ENST00000343939 | TSF |
| 20% | chr10 | 71851150 | 71851334 | + | chr10 | 71851513 | 71851710 | + | ENST00000373255 | TAF |
| 20% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 20% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 20% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 20% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 20% | chr8 | 17722594 | 17722494 | − | chr8 | 17722260 | 17722101 | − | ENST00000398056; ENST00000522444; ENST00000381840; ENST00000398054; ENST00000381841; ENST00000427924; ENST00000518650 | TAF |
| 20% | chr17 | 79911953 | 79911734 | − | chr17 | 79911143 | 79910837 | − | ENST00000409678 | TAF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 19% | chr22 | 24899415 | 24899562 | + | chr22 | 24906717 | 24906811 | + | ENST00000413389; ENST00000326010 | TAF |
| 19% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 19% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 19% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 19% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 19% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 19% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 19% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 19% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 19% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 18% | chr4 | 73969917 | 73969720 | − | chr4 | 73968264 | 73968093; 73968180 | − | ENST00000358602; ENST00000558247; ENST00000509867; ENST00000330838; ENST00000561029 | TAF |
| 18% | chr4 | 73969917 | 73969720 | − | chr4 | 73968264 | 73968093; 73968180 | − | ENST00000358602; ENST00000558247; ENST00000509867; ENST00000330838; ENST00000561029 | TAF |
| 17% | chr16 | 20553998 | 20553701 | − | chr16 | 20552095 | 20551976 | − | ENST00000329697; ENST00000565322; ENST00000565232; ENST00000567001 | TAF |
| 16% | chr10 | 5241290 | 5241827 | + | chr10 | 5242144 | 5242311 | + | ENST00000380448; ENST00000263126 | TSF |
| 15% | chr3 | 125898576 | 125898558 | − | chr3 | 125879845 | 125879696 | − | ENST00000273450 | TAF |
| 15% | chr14 | 24105943 | 24105981 | + | chr14 | 24112361 | 24112428 | + | ENST00000432832; ENST00000250383; ENST00000344777; ENST00000557535; ENST00000553600 | TAF |
| 15% | chr14 | 24105943 | 24105981 | + | chr14 | 24112361 | 24112428 | + | ENST00000432832; ENST00000250383; ENST00000344777; ENST00000557535; ENST00000553600 | TAF |
| 15% | chr14 | 24105943 | 24105981 | + | chr14 | 24112361 | 24112428 | + | ENST00000432832; ENST00000250383; ENST00000344777; ENST00000557535; ENST00000553600 | TAF |
| 15% | chr14 | 24105943 | 24105981 | + | chr14 | 24112361 | 24112428 | + | ENST00000432832; ENST00000250383; ENST00000344777; ENST00000557535; ENST00000553600 | TAF |
| 15% | chr14 | 24105943 | 24105981 | + | chr14 | 24112361 | 24112428 | + | ENST00000432832; ENST00000250383; ENST00000344777; ENST00000557535; ENST00000553600 | TAF |
| 15% | chr4 | 72608401 | 72608377 | − | chr4 | 72607587 | 72607552 | − | ENST00000513476 | TAF |
| 15% | chr19 | 1600051 | 1599987 | − | chr19 | 1599559 | 1599439 | − | ENST00000585937; ENST00000591899; ENST00000589880; ENST00000585671 | TAF |
| 15% | chr10 | 5241290 | 5241755 | + | chr10 | 5242144 | 5242311 | + | ENST00000380448; ENST00000263126 | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 14% | chr1 | 23721341 | 23721341 | – | chr1 | 23720514 | 23720372 | – | ENST00000450454 | TAF |
| 13% | chr3 | 133465755 | 133465758 | + | chr3 | 133467256 | 133467428; 133467513; 133467369 | + | ENST00000402696; ENST00000414694; ENST00000494430; ENST00000485977 | TAF |
| 13% | chr3 | 133465755 | 133465758 | + | chr3 | 133467256 | 133467428; 133467513; 133467369 | + | ENST00000402696; ENST00000414694; ENST00000494430; ENST00000485977 | TAF |
| 13% | chr3 | 133465755 | 133465758 | + | chr3 | 133467256 | 133467428; 133467513; 133467369 | + | ENST00000402696; ENST00000414694; ENST00000494430; ENST00000485977 | TAF |
| 13% | chr3 | 133465755 | 133465758 | + | chr3 | 133467256 | 133467428; 133467513; 133467369 | + | ENST00000402696; ENST00000414694; ENST00000494430; ENST00000485977 | TAF |
| 13% | chr17 | 79214190 | 79214239 | + | chr17 | 79214787 | 79214816; 79214953 | + | ENST00000431388; ENST00000576002 | TAF |
| 13% | chr17 | 79214190 | 79214239 | + | chr17 | 79214787 | 79214816; 79214953 | + | ENST00000431388; ENST00000576002 | TAF |
| 13% | chr5 | 147210961 | 147210946 | – | chr5 | 147209193 | 147209162 | – | ENST00000296695; ENST00000510027 | TAF |
| 13% | chr5 | 147210961 | 147210946 | – | chr5 | 147209193 | 147209162 | – | ENST00000296695; ENST00000510027 | TAF |
| 12% | chr10 | 13337060 | 13336880 | – | chr10 | 13336596 | 13336428 | – | ENST00000263038; ENST00000396920; ENST00000479604 | TAF |
| 12% | chr10 | 13337060 | 13336880 | – | chr10 | 13336596 | 13336428 | – | ENST00000263038; ENST00000396920; ENST00000479604 | TAF |
| 12% | chr10 | 13337060 | 13336880 | – | chr10 | 13336596 | 13336428 | – | ENST00000263038; ENST00000396920; ENST00000479604 | TAF |
| 12% | chr10 | 120902016 | 120901765 | – | chr10 | 120900831 | 120900754 | – | ENST00000355697; ENST00000330036 | TAF |
| 12% | chr7 | 99394816 | 99394725 | – | chr7 | 99250402 | 99250176 | – | ENST00000222982; ENST00000343703 | TAF |
| 12% | chr6 | 160522124 | 160522271 | + | chr6 | 160523551 | 160523703 | + | ENST00000356956 | TAF |
| 12% | chr4 | 48013268 | 48012811 | – | chr4 | 47954720 | 47954600 | – | ENST00000402813 | TAF |
| 12% | chr10 | 5241290 | 5241368 | + | chr10 | 5242144 | 5242311 | + | ENST00000380448; ENST00000263126 | TSF |
| 11% | chr7 | 1193171 | 1193154 | – | chr7 | 1192860 | 1192709; 1192543; 1192705 | – | ENST00000401903; ENST00000397083; ENST00000316495 | TAF |
| 11% | chr7 | 1193171 | 1193154 | – | chr7 | 1192860 | 1192709; 1192543; 1192705 | – | ENST00000401903; ENST00000397083; ENST00000316495 | TAF |
| 11% | chr7 | 1193171 | 1193154 | – | chr7 | 1192860 | 1192709; 1192543; 1192705 | – | ENST00000401903; ENST00000397083; ENST00000316495 | TAF |
| 11% | chr17 | 76192772 | 76192809 | + | chr17 | 76198580 | 76198684 | + | ENST00000409257; ENST00000591256; ENST00000588199; ENST00000327898; ENST00000586542 | TAF |
| 11% | chr17 | 76192772 | 76192809 | + | chr17 | 76198580 | 76198684 | + | ENST00000409257; ENST00000591256; ENST00000588199; ENST00000327898; ENST00000586542 | TAF |
| 11% | chr17 | 76192772 | 76192809 | + | chr17 | 76198580 | 76198684 | + | ENST00000409257; ENST00000591256; ENST00000588199; ENST00000327898; ENST00000586542 | TAF |
| 11% | chr17 | 76192772 | 76192809 | + | chr17 | 76198580 | 76198684 | + | ENST00000409257; ENST00000591256; ENST00000588199; ENST00000327898; ENST00000586542 | TAF |
| 11% | chr17 | 76192772 | 76192809 | + | chr17 | 76198580 | 76198684 | + | ENST00000409257; ENST00000591256; ENST00000588199; ENST00000327898; ENST00000586542 | TAF |
| 11% | chr7 | 99401376 | 99401279 | – | chr7 | 99250402 | 99250176 | – | ENST00000222982; ENST00000343703 | TAF |
| 11% | chr3 | 125869700 | 125869634 | – | chr3 | 125869374 | 125869249 | – | ENST00000273450; ENST00000472186; ENST00000452905; ENST00000393434; ENST00000393431 | TAF |
| 11% | chr3 | 125869700 | 125869634 | – | chr3 | 125869374 | 125869249 | – | ENST00000273450; ENST00000472186; ENST00000452905; ENST00000393434; ENST00000393431 | TAF |
| 11% | chr8 | 144638103 | 144638200 | + | chr8 | 144640548 | 144640621 | + | ENST00000533063 | TAF |
| 11% | chr9 | 111648536 | 111648048 | – | chr9 | 111644467 | 111644405 | – | ENST00000495759; ENST00000374647; ENST00000537196 | TAF |
| 11% | chr9 | 111648536 | 111648048 | – | chr9 | 111644467 | 111644405 | – | ENST00000495759; ENST00000374647; ENST00000537196 | TAF |
| 10% | chr3 | 149210772 | 149210837 | + | chr3 | 149216509 | 149216698 | + | ENST00000305354 | TAF |
| 10% | chr11 | 322262 | 322206 | – | chr11 | 320772 | 320565 | – | ENST00000399808 | TAF |
| 10% | chr11 | 321450 | 321426 | – | chr11 | 320772 | 320565 | – | ENST00000399808 | TAF |
| 10% | chr11 | 321638 | 321543 | – | chr11 | 320772 | 320565 | – | ENST00000399808 | TAF |
| 10% | chr11 | 321638 | 321504 | – | chr11 | 320772 | 320565 | – | ENST00000399808 | TAF |
| 10% | chr11 | 322457 | 322401 | – | chr11 | 320772 | 320565 | – | ENST00000399808 | TAF |
| 10% | chr11 | 321911 | 321855 | – | chr11 | 320772 | 320565 | – | ENST00000399808 | TAF |
| 10% | chr11 | 321488 | 321465 | – | chr11 | 320772 | 320565 | – | ENST00000399808 | TAF |
| 10% | chr11 | 322580 | 322557 | – | chr11 | 320772 | 320565 | – | ENST00000399808 | TAF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 10% | chr11 | 321410 | 321387 | − | chr11 | 320772 | 320565 | − | ENST00000399808 | TAF |
| 10% | chr11 | 321638 | 321582 | − | chr11 | 320772 | 320565 | − | ENST00000399808 | TAF |
| 10% | chr11 | 321716 | 321660 | − | chr11 | 320772 | 320565 | − | ENST00000399808 | TAF |
| 10% | chr11 | 322067 | 322011 | − | chr11 | 320772 | 320565 | − | ENST00000399808 | TAF |
| 9% | chr1 | 59980753 | 59980969 | + | chr1 | 60019796 | 60019899 | + | ENST00000371218; ENST00000303721; ENST00000430447; ENST00000371212 | TSF |
| 9% | chr1 | 59980753 | 59980969 | + | chr1 | 60019796 | 60019899 | + | ENST00000371218; ENST00000303721; ENST00000430447; ENST00000371212 | TSF |
| 9% | chr1 | 59980753 | 59980969 | + | chr1 | 60019796 | 60019899 | + | ENST00000371218; ENST00000303721; ENST00000430447; ENST00000371212 | TSF |
| 7% | chr16 | 72098678 | 72105626 | + | chr16 | 72107791 | 72107876 | + | ENST00000356967; ENST00000540303; ENST00000561690; ENST00000228226 | TSF |
| 7% | chr16 | 72098678 | 72105626 | + | chr16 | 72107791 | 72107876 | + | ENST00000356967; ENST00000540303; ENST00000561690; ENST00000228226 | TSF |
| 6% | chr11 | 46744446 | 46744531 | + | chr11 | 46744730 | 46744835 | + | ENST00000311907; ENST00000530231; ENST00000442468 | TSF |
| 6% | chr11 | 46744446 | 46744531 | + | chr11 | 46744730 | 46744835 | + | ENST00000311907; ENST00000530231; ENST00000442468 | TSF |
| 6% | chr11 | 46744446 | 46744531 | + | chr11 | 46744730 | 46744835 | + | ENST00000311907; ENST00000530231; ENST00000442468 | TSF |
| 6% | chr1 | 60092543 | 60093457 | + | chr1 | 60103900 | 60104047 | + | ENST00000371218; ENST00000303721; ENST00000430447; ENST00000371212; ENST00000371210 | TSF |
| 6% | chr1 | 60092543 | 60093457 | + | chr1 | 60103900 | 60104047 | + | ENST00000371218; ENST00000303721; ENST00000430447; ENST00000371212; ENST00000371210 | TSF |
| 6% | chr1 | 60092543 | 60093457 | + | chr1 | 60103900 | 60104047 | + | ENST00000371218; ENST00000303721; ENST00000430447; ENST00000371212; ENST00000371210 | TSF |
| 6% | chr15 | 75030988 | 75030728 | − | chr15 | 75014682 | 75014614; 75014676 | − | ENST00000395048; ENST00000379727; ENST00000567032; ENST00000395049; ENST00000562201; ENST00000569630 | TSF |
| 6% | chr15 | 75030988 | 75030728 | − | chr15 | 75014682 | 75014614; 75014676 | − | ENST00000395048; ENST00000379727; ENST00000567032; ENST00000395049; ENST00000562201; ENST00000569630 | TSF |
| 6% | chr15 | 75030988 | 75030728 | − | chr15 | 75014682 | 75014614; 75014676 | − | ENST00000395048; ENST00000379727; ENST00000567032; ENST00000395049; ENST00000562201; ENST00000569630 | TSF |
| 6% | chrX | 133098739 | 133098673 | − | chrX | 133087238 | 133087077 | − | ENST00000370818; ENST00000394299 | TSF |
| 6% | chrX | 133098739 | 133098673 | − | chrX | 133087238 | 133087077 | − | ENST00000370818; ENST00000394299 | TSF |
| 6% | chr7 | 134212336 | 134212386 | + | chr7 | 134215479 | 134215562 | + | ENST00000359579 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr1 | 161205595 | 161205477 | − | chr1 | 161203128 | 161202959 | − | ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr1 | 161205595 | 161205477 | − | chr1 | 161203128 | 161202959 | − | ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr1 | 161205595 | 161205477 | − | chr1 | 161203128 | 161202959 | − | ENST00000506209; ENST00000515452 ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; | TSF |
| 5% | chr1 | 161205595 | 161205477 | − | chr1 | 161203128 | 161202959 | − | ENST00000506209; ENST00000515452 ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; | TSF |
| 5% | chr1 | 161205595 | 161205477 | − | chr1 | 161203128 | 161202959 | − | ENST00000506209; ENST00000515452 ENST00000512372; ENST00000367980; ENST00000367983; ENST00000437437; ENST00000412844; ENST00000428574; ENST00000442691; ENST00000505005; ENST00000508740; ENST00000367982; ENST00000506018; ENST00000367981; ENST00000504010; ENST00000511676; ENST00000515621; ENST00000367984; ENST00000367985; ENST00000367979; ENST00000506209; ENST00000515452 | TSF |
| 5% | chr11 | 118892255 | 118892263 | + | chr11 | 118892470 | 118892596; 118892500 | + | ENST00000533632; ENST00000528230; ENST00000525303; ENST00000434101; ENST00000533058; ENST00000533012 | TSF |
| 5% | chr11 | 118892255 | 118892263 | + | chr11 | 118892470 | 118892596; 118892500 | + | ENST00000533632; ENST00000528230; ENST00000525303; ENST00000434101; ENST00000533058; ENST00000533012 | TSF |
| 5% | chr11 | 118892255 | 118892263 | + | chr11 | 118892470 | 118892596; 118892500 | + | ENST00000533632; ENST00000528230; ENST00000525303; ENST00000434101; ENST00000533058; ENST00000533012 | TSF |
| 5% | chr1 | 169819657 | 169819707 | + | chr1 | 169820958 | 169821077 | + | ENST00000359326; ENST00000286031 | TSF |
| 5% | chr17 | 56612963 | 56612799 | − | chr17 | 56604339 | 56604043; 56604293; 56604126 | − | ENST00000393086; ENST00000426861; ENST00000317268; ENST00000457347; ENST00000317256; ENST00000412945; ENST00000581615; ENST00000578131; ENST00000583291; ENST00000581607 | TSF |
| 5% | chr17 | 56612963 | 56612799 | − | chr17 | 56604339 | 56604043; 56604293; 56604126 | − | ENST00000393086; ENST00000426861; ENST00000317268; ENST00000457347; ENST00000317256; ENST00000412945; ENST00000581615; ENST00000578131; ENST00000583291; ENST00000581607 | TSF |
| 5% | chr17 | 56612963 | 56612799 | − | chr17 | 56604339 | 56604043; 56604293; 56604126 | − | ENST00000393086; ENST00000426861; ENST00000317268; ENST00000457347; ENST00000317256; ENST00000412945; ENST00000581615; ENST00000578131; ENST00000583291; ENST00000581607 | TSF |
| 5% | chr17 | 56612963 | 56612799 | − | chr17 | 56604339 | 56604043; 56604293; 56604126 | − | ENST00000393086; ENST00000426861; ENST00000317268; ENST00000457347; ENST00000317256; ENST00000412945; ENST00000581615; ENST00000578131; ENST00000583291; ENST00000581607 | TSF |
| 5% | chr17 | 56612963 | 56612799 | − | chr17 | 56604339 | 56604043; 56604293; 56604126 | − | ENST00000393086; ENST00000426861; ENST00000317268; ENST00000457347; ENST00000317256; ENST00000412945; ENST00000581615; ENST00000578131; ENST00000583291; ENST00000581607 | TSF |
| 5% | chr22 | 37408003 | 37407942 | − | chr22 | 37407366 | 37407068 | − | ENST00000403892; ENST00000249042 | TSF |
| 5% | chr19 | 45439440 | 45439575 | + | chr19 | 45448006 | 45448147; 45448151 | + | ENST00000592954; ENST00000419266; ENST00000585685; ENST00000589057; ENST00000591600 | TSF |
| 5% | chr19 | 45439440 | 45439575 | + | chr19 | 45448006 | 45448147; 45448151 | + | ENST00000592954; ENST00000419266; ENST00000585685; ENST00000589057; ENST00000591600 | TSF |
| 5% | chr19 | 45439440 | 45439575 | + | chr19 | 45448006 | 45448147; 45448151 | + | ENST00000592954; ENST00000419266; ENST00000585685; ENST00000589057; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr1 | 31218846 | 31218765 | − | chr1 | 31215396 | 31215303 | − | ENST00000591600 ENST00000294507 | TSF |
| 5% | chr7 | 100230492 | 100230403 | − | chr7 | 100229568 | 100229429 | − | ENST00000223051; ENST00000490084; ENST00000462107 | TSF |
| 5% | chr7 | 100230492 | 100230403 | − | chr7 | 100229568 | 100229429 | − | ENST00000223051; ENST00000490084; ENST00000462107 | TSF |
| 5% | chr8 | 63949410 | 63948932 | − | chr8 | 63948329 | 63948215 | − | ENST00000260118 | TSF |
| 4% | chr17 | 42085560 | 42085588 | + | chr17 | 42085816 | 42085969 | + | ENST00000293404; ENST00000589767 | TSF |
| 4% | chr19 | 35551883 | 35551974 | + | chr19 | 35556154 | 35556249 | + | ENST00000262626; ENST00000392226; ENST00000597419 | TSF |
| 4% | chr9 | 117089333 | 117089631 | + | chr9 | 117092819 | 117092856 | + | ENST00000431067 | TSF |
| 4% | chr10 | 101180795 | 101180714 | − | chr10 | 101180381 | 101180562 | − | ENST00000370508; ENST00000543866 | TSF |
| 4% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 4% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 4% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 4% | chr16 | 20463435 | 20463788 | + | chr16 | 20476839 | 20476978; 20477049; 20477015 | + | ENST00000576361; ENST00000424070; ENST00000573854; ENST00000219054; ENST00000575690; ENST00000574692; ENST00000571894; ENST00000396104 | TSF |
| 4% | chr1 | 59980753 | 59981111 | + | chr1 | 60019796 | 60019899 | + | ENST00000371218; ENST00000303721; ENST00000430447; ENST00000371212 | TSF |
| 4% | chr1 | 59980753 | 59981111 | + | chr1 | 60019796 | 60019899 | + | ENST00000371218; ENST00000303721; ENST00000430447; ENST00000371212 | TSF |
| 4% | chr1 | 59980753 | 59981111 | + | chr1 | 60019796 | 60019899 | + | ENST00000371218; ENST00000303721; ENST00000430447; ENST00000371212 | TSF |
| 4% | chr5 | 80703954 | 80703677 | − | chr5 | 80681645 | 80681576 | − | ENST00000307624; ENST00000513751 | TSF |
| 4% | chr5 | 80703954 | 80703677 | − | chr5 | 80681645 | 80681576 | − | ENST00000307624; ENST00000513751 | TSF |
| 4% | chr6 | 161637963 | 161637691 | − | chr6 | 161587449 | 161587280; 161587148 | − | ENST00000320285; ENST00000366908; ENST00000436279; ENST00000366905 | TSF |
| 4% | chr6 | 161637963 | 161637691 | − | chr6 | 161587449 | 161587280; 161587148 | − | ENST00000320285; ENST00000366908; ENST00000436279; ENST00000366905 | TSF |
| 4% | chr6 | 161637963 | 161637691 | − | chr6 | 161587449 | 161587280; 161587148 | − | ENST00000320285; ENST00000366908; ENST00000436279; ENST00000366905 | TSF |
| 4% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 4% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 4% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 4% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 4% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 4% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 4% | chr8 | 63958276 | 63958130 | − | chr8 | 63948329 | 63948215 | − | ENST00000260118 | TSF |
| 4% | chr3 | 182757105 | 182757101 | − | chr3 | 182756923 | 182756814 | − | ENST00000265594; ENST00000492597; ENST00000497959; ENST00000539926; ENST00000476176 | TSF |
| 4% | chr3 | 182757105 | 182757101 | − | chr3 | 182756923 | 182756814 | − | ENST00000265594; ENST00000492597; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | ENST00000497959; ENST00000539926; ENST00000476176 | |
| 4% | chr3 | 182757105 | 182757101 | − | chr3 | 182756923 | 182756814 | − | ENST00000265594; ENST00000492597; ENST00000497959; ENST00000539926; ENST00000476176 | TSF |
| 4% | chr3 | 182757105 | 182757101 | − | chr3 | 182756923 | 182756814 | − | ENST00000265594; ENST00000492597; ENST00000497959; ENST00000539926; ENST00000476176 | TSF |
| 4% | chr1 | 50993149 | 50992877 | − | chr1 | 50957473 | 50957393 | − | ENST00000396153; ENST00000371778; ENST00000545823; ENST00000494400 | TSF |
| 4% | chr1 | 50993149 | 50992877 | − | chr1 | 50957473 | 50957393 | − | ENST00000396153; ENST00000371778; ENST00000545823; ENST00000494400 | TSF |
| 4% | chr19 | 45439440 | 45439575 | + | chr19 | 45451723 | 45451790 | + | ENST00000589057 | TSF |
| 4% | chr19 | 45420573 | 45420622 | + | chr19 | 45422430 | 45422487; 45422466; 45422480; 45422461 | + | ENST00000588750; ENST00000588802; ENST00000592535; ENST00000252491; ENST00000592885; ENST00000589781; ENST00000586638 | TSF |
| 4% | chr19 | 45420573 | 45420622 | + | chr19 | 45422430 | 45422487; 45422466; 45422480; 45422461 | + | ENST00000588750; ENST00000588802; ENST00000592535; ENST00000252491; ENST00000592885; ENST00000589781; ENST00000586638 | TSF |
| 4% | chr19 | 45420573 | 45420622 | + | chr19 | 45422430 | 45422487; 45422466; 45422480; 45422461 | + | ENST00000588750; ENST00000588802; ENST00000592535; ENST00000252491; ENST00000592885; ENST00000589781; ENST00000586638 | TSF |
| 4% | chr19 | 45420573 | 45420622 | + | chr19 | 45422430 | 45422487; 45422466; 45422480; 45422461 | + | ENST00000588750; ENST00000588802; ENST00000592535; ENST00000252491; ENST00000592885; ENST00000589781; ENST00000586638 | TSF |
| 4% | chr11 | 118083018 | 118082875 | − | chr11 | 118081427 | 118081202; 118081333 | − | ENST00000356289; ENST00000292067; ENST00000533261; ENST00000526595; ENST00000526620; ENST00000524477; ENST00000527877; ENST00000525565 | TSF |
| 4% | chr11 | 118083018 | 118082875 | − | chr11 | 118081427 | 118081202; 118081333 | − | ENST00000356289; ENST00000292067; ENST00000533261; ENST00000526595; ENST00000526620; ENST00000524477; ENST00000527877; ENST00000525565 | TSF |
| 4% | chr11 | 118083018 | 118082875 | − | chr11 | 118081427 | 118081202; 118081333 | − | ENST00000356289; ENST00000292067; ENST00000533261; ENST00000526595; ENST00000526620; ENST00000524477; ENST00000527877; ENST00000525565 | TSF |
| 4% | chr11 | 118083018 | 118082875 | − | chr11 | 118081427 | 118081202; 118081333 | − | ENST00000356289; ENST00000292067; ENST00000533261; ENST00000526595; ENST00000526620; ENST00000524477; ENST00000527877; ENST00000525565 | TSF |
| 4% | chr11 | 118083018 | 118082875 | − | chr11 | 118081427 | 118081202; 118081333 | − | ENST00000356289; ENST00000292067; ENST00000533261; ENST00000526595; ENST00000526620; ENST00000524477; ENST00000527877; ENST00000525565 | TSF |
| 4% | chr11 | 118083018 | 118082875 | − | chr11 | 118081427 | 118081202; 118081333 | − | ENST00000356289; ENST00000292067; ENST00000533261; ENST00000526595; ENST00000526620; ENST00000524477; ENST00000527877; ENST00000525565 | TSF |
| 4% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 4% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 4% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 4% | chr5 | 34006954 | 34006915 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 4% | chr5 | 34006954 | 34006915 | − | chr5 | 34006004 | 34005861 | − | ENST00000335606; ENST00000382072; ENST00000382079; ENST00000506639; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 4% | chr5 | 34006954 | 34006915 | − | chr5 | 34006004 | 34005861 | − | ENST00000382085; ENST00000502637; ENST00000441713; ENST00000426255; ENST00000512079; ENST00000382068 ENST00000335606; ENST00000382072; ENST00000382079; ENST00000506639; | TSF |
| 4% | chr5 | 34006954 | 34006915 | − | chr5 | 34006004 | 34005861 | − | ENST00000382085; ENST00000502637; ENST00000441713; ENST00000426255; ENST00000512079; ENST00000382068 ENST00000335606; ENST00000382072; ENST00000382079; ENST00000506639; | TSF |
| 4% | chr5 | 34006954 | 34006915 | − | chr5 | 34006004 | 34005861 | − | ENST00000382085; ENST00000502637; ENST00000441713; ENST00000426255; ENST00000512079; ENST00000382068 ENST00000335606; ENST00000382072; ENST00000382079; ENST00000506639; | TSF |
| 4% | chr5 | 34006954 | 34006915 | − | chr5 | 34006004 | 34005861 | − | ENST00000382085; ENST00000502637; ENST00000441713; ENST00000426255; ENST00000512079; ENST00000382068 ENST00000335606; ENST00000382072; ENST00000382079; ENST00000506639; | TSF |
| 3% | chr16 | 72098678 | 72105523 | + | chr16 | 72107791 | 72107876 | + | ENST00000356967; ENST00000540303; ENST00000561690; ENST00000228226 | TSF |
| 3% | chr16 | 72098678 | 72105523 | + | chr16 | 72107791 | 72107876 | + | ENST00000356967; ENST00000540303; ENST00000561690; ENST00000228226 | TSF |
| 3% | chr19 | 45409998 | 45410105 | + | chr19 | 45411017 | 45411209 | + | ENST00000252486; ENST00000446996; ENST00000434152; ENST00000425718 | TSF |
| 3% | chr19 | 45409998 | 45410105 | + | chr19 | 45411017 | 45411209 | + | ENST00000252486; ENST00000446996; ENST00000434152; ENST00000425718 | TSF |
| 3% | chr19 | 45409998 | 45410105 | + | chr19 | 45411017 | 45411209 | + | ENST00000252486; ENST00000446996; ENST00000434152; ENST00000425718 | TSF |
| 3% | chr19 | 45409998 | 45410105 | + | chr19 | 45411017 | 45411209 | + | ENST00000252486; ENST00000446996; ENST00000434152; ENST00000425718 | TSF |
| 3% | chr19 | 45450127 | 45450350 | + | chr19 | 45451723 | 45451790 | + | ENST00000589057 | TSF |
| 3% | chr1 | 59980221 | 59980497 | + | chr1 | 60073475 | 60073582 | + | ENST00000371218; ENST00000303721; ENST00000430447; ENST00000371212; ENST00000371210 | TSF |
| 3% | chr1 | 59980221 | 59980497 | + | chr1 | 60073475 | 60073582 | + | ENST00000371218; ENST00000303721; ENST00000430447; ENST00000371212; ENST00000371210 | TSF |
| 3% | chr1 | 59980221 | 59980497 | + | chr1 | 60073475 | 60073582 | + | ENST00000371218; ENST00000303721; ENST00000430447; ENST00000371212; ENST00000371210 | TSF |
| 3% | chr20 | 10400592 | 10400319 | − | chr20 | 10389451 | 10389276 | − | ENST00000347364; ENST00000399054 | TSF |
| 3% | chr2 | 85811874 | 85811992 | + | chr2 | 85818852 | 85818985 | + | ENST00000306384 | TSF |
| 3% | chr1 | 196673673 | 196675339 | + | chr1 | 196682865 | 196683047 | + | ENST00000367429 | TSF |
| 3% | chr6 | 5530387 | 5530482 | + | chr6 | 5545413 | 5545573 | + | ENST00000324331; ENST00000274680 | TSF |
| 3% | chr10 | 5060345 | 5060092 | − | chr10 | 5043777 | 5043706 | − | ENST00000380753; ENST00000421196; ENST00000407674; ENST00000604507; ENST00000455190 | TSF |
| 3% | chr10 | 5060345 | 5060092 | − | chr10 | 5043777 | 5043706 | − | ENST00000380753; ENST00000421196; ENST00000407674; ENST00000604507; ENST00000455190 | TSF |
| 3% | chr10 | 5060345 | 5060092 | − | chr10 | 5043777 | 5043706 | − | ENST00000380753; ENST00000421196; ENST00000407674; ENST00000604507; ENST00000455190 | TSF |
| 3% | chr10 | 5060345 | 5060092 | − | chr10 | 5043777 | 5043706 | − | ENST00000380753; ENST00000421196; ENST00000407674; ENST00000604507; ENST00000455190 | TSF |
| 3% | chr5 | 34014243 | 34013950 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34014243 | 34013950 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34014243 | 34013950 | − | chr5 | 34006004 | 34005861 | − | ENST00000335606; ENST00000382072; ENST00000382079; ENST00000506639; ENST00000382085; ENST00000502637; ENST00000441713; ENST00000426255; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr5 | 34014243 | 34013950 | − | chr5 | 34006004 | 34005861 | − | ENST00000512079; ENST00000382068 ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34014243 | 34013950 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34014243 | 34013950 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34014243 | 34013950 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34014243 | 34013950 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr5 | 34014243 | 34013950 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 3% | chr6 | 80022917 | 80022085 | − | chr6 | 79924739 | 79924689 | − | ENST00000275036; ENST00000344726 | TSF |
| 3% | chr6 | 80022917 | 80022085 | − | chr6 | 79924739 | 79924689 | − | ENST00000275036; ENST00000344726 | TSF |
| 3% | chr5 | 1257846 | 1257816 | − | chr5 | 1255526 | 1255402 | − | ENST00000310581; ENST00000334602 | TSF |
| 3% | chr9 | 99067886 | 99067556 | − | chr9 | 99064349 | 99064233 | − | ENST00000375263; ENST00000375262 | TSF |
| 3% | chr9 | 99067886 | 99067556 | − | chr9 | 99064349 | 99064233 | − | ENST00000375263; ENST00000375262 | TSF |
| 3% | chr7 | 100230492 | 100230403 | − | chr7 | 100229772 | 100229705 | − | ENST00000223051; ENST00000490084; ENST00000462107 | TSF |
| 3% | chr7 | 100230492 | 100230403 | − | chr7 | 100229772 | 100229705 | − | ENST00000223051; ENST00000490084; ENST00000462107 | TSF |
| 3% | chr4 | 107241932 | 107242046 | + | chr4 | 107246142 | 107246275 | + | ENST00000394701 | TSF |
| 3% | chr2 | 234733211 | 234733401 | + | chr2 | 234737276 | 234737425 | + | ENST00000389758 | TSF |
| 3% | chr7 | 65545998 | 65546064 | + | chr7 | 65546790 | 65546984 | + | ENST00000304874; ENST00000380839; ENST00000395332; ENST00000395331 | TSF |
| 3% | chr7 | 65545998 | 65546064 | + | chr7 | 65546790 | 65546984 | + | ENST00000304874; ENST00000380839; ENST00000395332; ENST00000395331 | TSF |
| 3% | chr7 | 65545998 | 65546064 | + | chr7 | 65546790 | 65546984 | + | ENST00000304874; ENST00000380839; ENST00000395332; ENST00000395331 | TSF |
| 3% | chr9 | 117090746 | 117090775 | + | chr9 | 117092714 | 117092856; 117092769 | + | ENST00000431067; ENST00000412657 | TSF |
| 3% | chr9 | 117090746 | 117090775 | + | chr9 | 117092714 | 117092856; 117092769 | + | ENST00000431067; ENST00000412657 | TSF |
| 3% | chr17 | 40029733 | 40029683 | − | chr17 | 40028435 | 40028285 | − | ENST00000352035; ENST00000590151; ENST00000353196; ENST00000537919; ENST00000393896 | TSF |
| 3% | chr3 | 58508590 | 58508545 | − | chr3 | 58508328 | 58508223 | − | ENST00000459701; ENST00000302819 | TSF |
| 3% | chr9 | 116860197 | 116860071 | − | chr9 | 116840393 | 116840373 | − | ENST00000265132; ENST00000603230 | TSF |
| 3% | chr9 | 116860197 | 116860071 | − | chr9 | 116840393 | 116840373 | − | ENST00000265132; ENST00000603230 | TSF |
| 2% | chr1 | 182406436 | 182406465 | + | chr1 | 182423093 | 182423175 | + | ENST00000542961; ENST00000294854; ENST00000443996; ENST00000416676; ENST00000422241 | TSF |
| 2% | chr1 | 182406436 | 182406465 | + | chr1 | 182423093 | 182423175 | + | ENST00000542961; ENST00000294854; ENST00000443996; ENST00000416676; ENST00000422241 | TSF |
| 2% | chr1 | 182406436 | 182406465 | + | chr1 | 182423093 | 182423175 | + | ENST00000542961; ENST00000294854; ENST00000443996; ENST00000416676; ENST00000422241 | TSF |
| 2% | chr1 | 182406436 | 182406465 | + | chr1 | 182423093 | 182423175 | + | ENST00000542961; ENST00000294854; ENST00000443996; ENST00000416676; ENST00000422241 | TSF |
| 2% | chr8 | 91057494 | 91058452 | + | chr8 | 91063905 | 91063967; 91063912 | + | ENST00000220764; ENST00000522161; ENST00000520148 | TSF |
| 2% | chr8 | 91057494 | 91058452 | + | chr8 | 91063905 | 91063967; 91063912 | + | ENST00000220764; ENST00000522161; ENST00000520148 | TSF |
| 2% | chr21 | 39513161 | 39513404 | + | chr21 | 39528398 | 39528496 | + | ENST00000357704; ENST00000400477 | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr17 | 27373782 | 27373865 | + | chr17 | 27380431 | 27380613; 27380610 | + | ENST00000323372; ENST00000466889; ENST00000469082 | TSF |
| 2% | chr17 | 27373782 | 27373865 | + | chr17 | 27380431 | 27380613; 27380610 | + | ENST00000323372; ENST00000466889; ENST00000469082 | TSF |
| 2% | chr17 | 27373782 | 27373865 | + | chr17 | 27380431 | 27380613; 27380610 | + | ENST00000323372; ENST00000466889; ENST00000469082 | TSF |
| 2% | chr5 | 139976114 | 139976476 | + | chr5 | 140021250 | 140021365; 140021408; 140021344 | + | ENST00000394671; ENST00000511410; ENST00000515653; ENST00000252100 | TSF |
| 2% | chr5 | 139976114 | 139976476 | + | chr5 | 140021250 | 140021365; 140021408; 140021344 | + | ENST00000394671; ENST00000511410; ENST00000515653; ENST00000252100 | TSF |
| 2% | chr5 | 139976114 | 139976476 | + | chr5 | 140021250 | 140021365; 140021408; 140021344 | + | ENST00000394671; ENST00000511410; ENST00000515653; ENST00000252100 | TSF |
| 2% | chr5 | 139976114 | 139976476 | + | chr5 | 140021250 | 140021365; 140021408; 140021344 | + | ENST00000394671; ENST00000511410; ENST00000515653; ENST00000252100 | TSF |
| 2% | chr12 | 122293286 | 122293120 | − | chr12 | 122292698 | 122292609 | − | ENST00000289004; ENST00000543163 | TSF |
| 2% | chr10 | 5060345 | 5060092 | − | chr10 | 5043783 | 5043706 | − | ENST00000380753; ENST00000421196; ENST00000407674; ENST00000604507; ENST00000455190 | TSF |
| 2% | chr10 | 5060345 | 5060092 | − | chr10 | 5043783 | 5043706 | − | ENST00000380753; ENST00000421196; ENST00000407674; ENST00000604507; ENST00000455190 | TSF |
| 2% | chr10 | 5060345 | 5060092 | − | chr10 | 5043783 | 5043706 | − | ENST00000380753; ENST00000421196; ENST00000407674; ENST00000604507; ENST00000455190 | TSF |
| 2% | chr10 | 5060345 | 5060092 | − | chr10 | 5043783 | 5043706 | − | ENST00000380753; ENST00000421196; ENST00000407674; ENST00000604507; ENST00000455190 | TSF |
| 2% | chr7 | 99257824 | 99251951 | − | chr7 | 99250402 | 99250176 | − | ENST00000222982; ENST00000343703 | TSF |
| 2% | chr12 | 54862718 | 54862609 | − | chr12 | 54858951 | 54858851 | − | ENST00000546931; ENST00000552397; ENST00000305879 | TSF |
| 2% | chr12 | 54862718 | 54862609 | − | chr12 | 54858951 | 54858851 | − | ENST00000546931; ENST00000552397; ENST00000305879 | TSF |
| 2% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 2% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 2% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 2% | chr16 | 20587097 | 20586744 | − | chr16 | 20570769 | 20570559; 20570593; 20570630 | − | ENST00000329697; ENST00000565232; ENST00000567001; ENST00000569327; ENST00000414188; ENST00000566384; ENST00000569344 | TSF |
| 2% | chr17 | 80070847 | 80070635 | − | chr17 | 80059742 | 80059558; 08005967 | − | ENST00000389641; ENST00000392347; ENST00000392345 | TSF |
| 2% | chr17 | 80070847 | 80070635 | − | chr17 | 80059742 | 80059558; 80059607 | − | ENST00000389641; ENST00000392347; ENST00000392345 | TSF |
| 2% | chr5 | 34010561 | 34010327 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010327 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010327 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010327 | − | chr5 | 34006004 | 34005861 | − | ENST00000335606; ENST00000382072; ENST00000382079; ENST00000506639; ENST00000382085; ENST00000502637; ENST00000441713; ENST00000426255; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr5 | 34010561 | 34010327 | − | chr5 | 34006004 | 34005861 | − | ENST00000512079; ENST00000382068 ENST00000335606; ENST00000382072; ENST00000382079; ENST00000506639; ENST00000382085; ENST00000502637; ENST00000441713; ENST00000426255; | TSF |
| 2% | chr5 | 34010561 | 34010327 | − | chr5 | 34006004 | 34005861 | − | ENST00000512079; ENST00000382068 ENST00000335606; ENST00000382072; ENST00000382079; ENST00000506639; ENST00000382085; ENST00000502637; ENST00000441713; ENST00000426255; | TSF |
| 2% | chr5 | 34010561 | 34010327 | − | chr5 | 34006004 | 34005861 | − | ENST00000512079; ENST00000382068 ENST00000335606; ENST00000382072; ENST00000382079; ENST00000506639; ENST00000382085; ENST00000502637; ENST00000441713; ENST00000426255; | TSF |
| 2% | chr5 | 34010561 | 34010327 | − | chr5 | 34006004 | 34005861 | − | ENST00000512079; ENST00000382068 ENST00000335606; ENST00000382072; ENST00000382079; ENST00000506639; ENST00000382085; ENST00000502637; ENST00000441713; ENST00000426255; | TSF |
| 2% | chr5 | 34010561 | 34010327 | − | chr5 | 34006004 | 34005861 | − | ENST00000512079; ENST00000382068 ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr1 | 207263335 | 207263401 | + | chr1 | 207263653 | 207263826 | + | ENST00000367078; ENST00000452902; ENST00000243611; ENST00000391923 | TSF |
| 2% | chr1 | 207263335 | 207263401 | + | chr1 | 207263653 | 207263826 | + | ENST00000367078; ENST00000452902; ENST00000243611; ENST00000391923 | TSF |
| 2% | chr16 | 72098678 | 72098893 | + | chr16 | 72108183 | 72108284 | + | ENST00000356967; ENST00000540303; ENST00000561690; ENST00000228226 | TSF |
| 2% | chr16 | 72098678 | 72098893 | + | chr16 | 72108183 | 72108284 | + | ENST00000356967; ENST00000540303; ENST00000561690; ENST00000228226 | TSF |
| 2% | chr16 | 84000773 | 84000932 | + | chr16 | 84005756 | 84005780 | + | ENST00000305202 | TSF |
| 2% | chr4 | 74314427 | 74314578 | + | chr4 | 74315052 | 74315184 | + | ENST00000395792; ENST00000226359 | TSF |
| 2% | chr4 | 74314427 | 74314578 | + | chr4 | 74315052 | 74315184 | + | ENST00000395792; ENST00000226359 | TSF |
| 2% | chr16 | 25189880 | 25189933 | + | chr16 | 25232778 | 25232904 | + | ENST00000566125; ENST00000219660 | TSF |
| 2% | chr15 | 51649563 | 51649596 | + | chr15 | 51669646 | 51669697 | + | ENST00000335449; ENST00000558426 | TSF |
| 2% | chr15 | 51649563 | 51649596 | + | chr15 | 51669646 | 51669697 | + | ENST00000335449; ENST00000558426 | TSF |
| 2% | chr20 | 634541 | 634468 | − | chr20 | 629561 | 629358; 629500 | − | ENST00000381962; ENST00000488788 | TSF |
| 2% | chr20 | 634541 | 634468 | − | chr20 | 629561 | 629358; 629500 | − | ENST00000381962; ENST00000488788 | TSF |
| 2% | chr2 | 216905778 | 216905772 | − | chr2 | 216904083 | 216903998 | − | ENST00000265322 | TSF |
| 2% | chr9 | 123165858 | 123165617 | − | chr9 | 123165349 | 123165084 | − | ENST00000359309; ENST00000360822; ENST00000349780; ENST00000360190; ENST00000416449; ENST00000425647 | TSF |
| 2% | chr10 | 74704869 | 74704617 | − | chr10 | 74702498 | 74702410 | − | ENST00000373032 | TSF |
| 2% | chr19 | 48387733 | 48387636 | − | chr19 | 48387042 | 48386834 | − | ENST00000222002 | TSF |
| 2% | chr12 | 21426370 | 21426215 | − | chr12 | 21422701 | 21422482 | − | ENST00000307378; ENST00000452078; ENST00000458504; ENST00000537524 | TSF |
| 2% | chr16 | 20553998 | 20553656 | − | chr16 | 20552095 | 20551976 | − | ENST00000329697; ENST00000565322; ENST00000565232; ENST00000567001 | TSF |
| 2% | chr4 | 72625242 | 72624879 | − | chr4 | 72623888 | 72623759 | − | ENST00000273951; ENST00000504199; ENST00000513476; ENST00000509740 | TSF |
| 2% | chr4 | 72625242 | 72624879 | − | chr4 | 72623888 | 72623759 | − | ENST00000273951; ENST00000504199; ENST00000513476; ENST00000509740 | TSF |
| 2% | chr4 | 72625242 | 72624879 | − | chr4 | 72623888 | 72623759 | − | ENST00000273951; ENST00000504199; ENST00000513476; ENST00000509740 | TSF |
| 2% | chr19 | 14129234 | 14129243 | + | chr19 | 14141522 | 14141760; 14141549 | + | ENST00000431365; ENST00000585987 | TSF |
| 2% | chr19 | 14129234 | 14129243 | + | chr19 | 14141522 | 14141760; 14141549 | + | ENST00000431365; ENST00000585987 | TSF |
| 2% | chr1 | 182374948 | 182375081 | + | chr1 | 182423093 | 182423175 | + | ENST00000542961; ENST00000294854; ENST00000443996; ENST00000416676; ENST00000422241 | TSF |
| 2% | chr1 | 182374948 | 182375081 | + | chr1 | 182423093 | 182423175 | + | ENST00000542961; ENST00000294854; ENST00000443996; ENST00000416676; ENST00000422241 | TSF |
| 2% | chr1 | 182374948 | 182375081 | + | chr1 | 182423093 | 182423175 | + | ENST00000542961; ENST00000294854; ENST00000443996; ENST00000416676; ENST00000422241 | TSF |
| 2% | chr1 | 182374948 | 182375081 | + | chr1 | 182423093 | 182423175 | + | ENST00000542961; ENST00000294854; ENST00000443996; ENST00000416676; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr1 | 226013104 | 226013146 | + | chr1 | 226019533 | 226019660 | + | ENST00000422241 ENST00000445856; ENST00000272167; ENST00000448202; ENST00000366837 | TSF |
| 2% | chr1 | 226013104 | 226013146 | + | chr1 | 226019533 | 226019660 | + | ENST00000445856; ENST00000272167; ENST00000448202; ENST00000366837 | TSF |
| 2% | chr1 | 226013104 | 226013146 | + | chr1 | 226019533 | 226019660 | + | ENST00000445856; ENST00000272167; ENST00000448202; ENST00000366837 | TSF |
| 2% | chr22 | 24967426 | 24967475 | + | chr22 | 24967884 | 24967945 | + | ENST00000215829; ENST00000404603 | TSF |
| 2% | chrX | 106007615 | 106007873 | + | chrX | 106016143 | 106016390 | + | ENST00000418562; ENST00000324342; ENST00000255499 | TSF |
| 2% | chrX | 106007615 | 106007873 | + | chrX | 106016143 | 106016390 | + | ENST00000418562; ENST00000324342; ENST00000255499 | TSF |
| 2% | chr9 | 104030196 | 104030320 | + | chr9 | 104032162 | 104032350 | + | ENST00000374874; ENST00000456287; ENST00000395056 | TSF |
| 2% | chr9 | 104030196 | 104030320 | + | chr9 | 104032162 | 104032350 | + | ENST00000374874; ENST00000456287; ENST00000395056 | TSF |
| 2% | chr9 | 33033420 | 33033436 | + | chr9 | 33034214 | 33034328 | + | ENST00000330899; ENST00000544625 | TSF |
| 2% | chr16 | 72106207 | 72106386 | + | chr16 | 72107791 | 72107876 | + | ENST00000356967; ENST00000540303; ENST00000561690; ENST00000228226 | TSF |
| 2% | chr16 | 72106207 | 72106386 | + | chr16 | 72107791 | 72107876 | + | ENST00000356967; ENST00000540303; ENST00000561690; ENST00000228226 | TSF |
| 2% | chr2 | 234967204 | 234967342 | + | chr2 | 234967480 | 234967602 | + | ENST00000373368; ENST00000168148 | TSF |
| 2% | chr19 | 35548506 | 35548655 | + | chr19 | 35556802 | 35556936 | + | ENST00000262626; ENST00000392226; ENST00000597419 | TSF |
| 2% | chr1 | 226013104 | 226013146 | + | chr1 | 226016587 | 226016613 | + | ENST00000445856; ENST00000272167; ENST00000448202; ENST00000366837 | TSF |
| 2% | chr1 | 226013104 | 226013146 | + | chr1 | 226016587 | 226016613 | + | ENST00000445856; ENST00000272167; ENST00000448202; ENST00000366837 | TSF |
| 2% | chr1 | 226013104 | 226013146 | + | chr1 | 226016587 | 226016613 | + | ENST00000445856; ENST00000272167; ENST00000448202; ENST00000366837 | TSF |
| 2% | chr19 | 6692279 | 6692148 | − | chr19 | 6690738 | 6690640 | − | ENST00000245907 | TSF |
| 2% | chr3 | 49725746 | 49725728 | − | chr3 | 49725330 | 49725183 | − | ENST00000449682; ENST00000545762 | TSF |
| 2% | chr3 | 49725746 | 49725728 | − | chr3 | 49725330 | 49725183 | − | ENST00000449682; ENST00000545762 | TSF |
| 2% | chr5 | 34010561 | 34010259 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010259 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010259 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010259 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010259 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010259 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010259 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010259 | − | chr5 | 34006004 | 34005861 | − | ENST00000335606; ENST00000382072; ENST00000382079; ENST00000506639; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | ENST00000382085; ENST00000502637; ENST00000441713; ENST00000426255; ENST00000512079; ENST00000382068 | |
| 2% | chr9 | 85967664 | 85967460 | − | chr9 | 85964672 | 85964594 | − | ENST00000376438; ENST00000304195 | TSF |
| 2% | chr9 | 85967664 | 85967460 | | chr9 | 85964672 | 85964594 | | ENST00000376438; ENST00000304195 | TSF |
| 2% | chr10 | 7735189 | 7733712 | − | chr10 | 7697638 | 7697594 | − | ENST00000256861; ENST00000397146; ENST00000397145 | TSF |
| 2% | chr10 | 7735189 | 7733712 | | chr10 | 7697638 | 7697594 | | ENST00000256861; ENST00000397146; ENST00000397145 | TSF |
| 2% | chr10 | 7735189 | 7733712 | | chr10 | l7697638 | 7697594 | | ENST00000256861; ENST00000397146; ENST00000397145 | TSF |
| 2% | chr2 | 77256752 | 77256391 | − | chr2 | 76976042 | 76975821 | − | ENST00000409911; ENST00000409884; ENST00000409093 | TSF |
| 2% | chr3 | 186352354 | 186352397 | + | chr3 | 186362540 | 186362709; 186362563 | + | ENST00000450521; ENST00000382134; ENST00000265029; ENST00000435961; ENST00000382136 | TSF |
| 2% | chr3 | 186352354 | 186352397 | + | chr3 | 186362540 | 186362709; 186362563 | + | ENST00000450521; ENST00000382134; ENST00000265029; ENST00000435961; ENST00000382136 | TSF |
| 2% | chr1 | 41465686 | 41465756 | + | chr1 | 41466701 | 41466789 | + | ENST00000372621; ENST00000541520; ENST00000372616 | TSF |
| 2% | chr12 | 133264718 | 133264790 | + | chr12 | 133266849 | 133266962 | + | ENST00000317479; ENST00000543589 | TSF |
| 2% | chr12 | 133264718 | 133264790 | + | chr12 | 133266849 | 133266962 | + | ENST00000317479; ENST00000543589 | TSF |
| 2% | chr10 | 18179688 | 18180042 | + | chr10 | 18183139 | 18183241 | + | ENST00000239761 | TSF |
| 2% | chr12 | 133264718 | 133264751 | + | chr12 | 133266849 | 133266962 | + | ENST00000317479; ENST00000543589 | TSF |
| 2% | chr12 | 133264718 | 133264751 | + | chr12 | 133266849 | 133266962 | + | ENST00000317479; ENST00000543589 | TSF |
| 2% | chr1 | 64652641 | 64652652 | + | chr1 | 64671322 | 64671403 | + | ENST00000371077; ENST00000371076 | TSF |
| 2% | chr1 | 64652641 | 64652652 | + | chr1 | 64671322 | 64671403 | + | ENST00000371077; ENST00000371076 | TSF |
| 2% | chr22 | 37423933 | 37423947 | + | chr22 | 37425305 | 37425555 | + | ENST00000401419; ENST00000397129; ENST00000404802; ENST00000341116; ENST00000429360; ENST00000397225 | TSF |
| 2% | chr20 | 410407 | 410425 | + | chr20 | 410994 | 411074 | + | ENST00000356286; ENST00000353660; ENST00000382181 | TSF |
| 2% | chr12 | 133264718 | 133264868 | + | chr12 | 133266849 | 133266962 | + | ENST00000317479; ENST00000543589 | TSF |
| 2% | chr12 | 133264718 | 133264868 | + | chr12 | 133266849 | 133266962 | + | ENST00000317479; ENST00000543589 | TSF |
| 2% | chr1 | 226013104 | 226013120 | + | chr1 | 226030115 | 226030175 | + | ENST00000272167; ENST00000366837 | TSF |
| 2% | chr10 | 17932769 | 17933123 | + | chr10 | 17936221 | 17936323 | + | ENST00000331429 | TSF |
| 2% | chr9 | 124090761 | 124090761 | + | chr9 | 124091169 | 124091293 | + | ENST00000373823; ENST00000341272; ENST00000373808; ENST00000394353; ENST00000412819; ENST00000436847; ENST00000449733; ENST00000545652; ENST00000373818; ENST00000373807; ENST00000373806 | TSF |
| 2% | chr9 | 124090761 | 124090761 | + | chr9 | 124091169 | 124091293 | + | ENST00000373823; ENST00000341272; ENST00000373808; ENST00000394353; ENST00000412819; ENST00000436847; ENST00000449733; ENST00000545652; ENST00000373818; ENST00000373807; ENST00000373806 | TSF |
| 2% | chr1 | 226013104 | 226013120 | + | chr1 | 226016587 | 226016613 | + | ENST00000445856; ENST00000272167; ENST00000448202; ENST00000366837 | TSF |
| 2% | chr1 | 226013104 | 226013120 | + | chr1 | 226016587 | 226016613 | + | ENST00000445856; ENST00000272167; ENST00000448202; ENST00000366837 | TSF |
| 2% | chr1 | 226013104 | 226013120 | + | chr1 | 226016587 | 226016613 | + | ENST00000445856; ENST00000272167; ENST00000448202; ENST00000366837 | TSF |
| 2% | chr9 | 130866734 | 130866740 | + | chr9 | 130868008 | 130868160 | + | ENST00000373068; ENST00000373069; ENST00000373066; ENST00000432073; ENST00000373064; ENST00000433501 | TSF |
| 2% | chr1 | 27271260 | 27271351 | + | chr1 | 27271881 | 27271964 | + | ENST00000321265 | TSF |
| 2% | chr1 | 111960622 | 111960373 | − | chr1 | 111959080 | 111958945; 111959068 | − | ENST00000369732; ENST00000540696 | TSF |
| 2% | chr1 | 111960622 | 111960373 | − | chr1 | 111959080 | 111958945; 111959068 | − | ENST00000369732; ENST00000540696 | TSF |
| 2% | chr1 | 204110253 | 204110153 | − | chr1 | 204109246 | 204109163 | − | ENST00000367201; ENST00000367202; ENST00000367199; ENST00000367198; ENST00000422072; ENST00000422699; ENST00000452983; ENST00000444817 | TSF |
| 2% | chr1 | 204110253 | 204110153 | − | chr1 | 204109246 | 204109163 | − | ENST00000367201; ENST00000367202; ENST00000367199; ENST00000367198; ENST00000422072; ENST00000422699; ENST00000452983; ENST00000444817 | TSF |
| 2% | chr1 | 204110253 | 204110153 | − | chr1 | 204109246 | 204109163 | − | ENST00000367201; ENST00000367202; ENST00000367199; ENST00000367198; ENST00000422072; ENST00000422699; ENST00000452983; ENST00000444817 | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr1 | 204110253 | 204110153 | – | chr1 | 204109246 | 204109163 | – | ENST00000367201; ENST00000367202; ENST00000367199; ENST00000367198; ENST00000422072; ENST00000422699; ENST00000452983; ENST00000444817 | TSF |
| 2% | chr1 | 204110253 | 204110153 | – | chr1 | 204109246 | 204109163 | – | ENST00000367201; ENST00000367202; ENST00000367199; ENST00000367198; ENST00000422072; ENST00000422699; ENST00000452983; ENST00000444817 | TSF |
| 2% | chrX | 123618682 | 123617816 | – | chrX | 123615814 | 123615582 | – | ENST00000371130; ENST00000422452 | TSF |
| 2% | chr12 | 117498589 | 117498567 | – | chr12 | 117494691 | 117494611 | – | ENST00000470612; ENST00000335209; ENST00000392545; ENST00000462502 | TSF |
| 2% | chr12 | 117498589 | 117498567 | – | chr12 | 117494691 | 117494611 | – | ENST00000470612; ENST00000335209; ENST00000392545; ENST00000462502 | TSF |
| 2% | chr12 | 117498589 | 117498567 | – | chr12 | 117494691 | 117494611 | – | ENST00000470612; ENST00000335209; ENST00000392545; ENST00000462502 | TSF |
| 2% | chr4 | 39516601 | 39516501 | – | chr4 | 39515804 | 39515703; 39515713 | – | ENST00000316423; ENST00000501493; ENST00000506179; ENST00000515021; ENST00000514106; ENST00000509391; ENST00000505698 | TSF |
| 2% | chr4 | 39516601 | 39516501 | – | chr4 | 39515804 | 39515703; 39515713 | – | ENST00000316423; ENST00000501493; ENST00000506179; ENST00000515021; ENST00000514106; ENST00000509391; ENST00000505698 | TSF |
| 2% | chr4 | 39516601 | 39516501 | – | chr4 | 39515804 | 39515703; 39515713 | – | ENST00000316423; ENST00000501493; ENST00000506179; ENST00000515021; ENST00000514106; ENST00000509391; ENST00000505698 | TSF |
| 2% | chr4 | 39516601 | 39516501 | – | chr4 | 39515804 | 39515703; 39515713 | – | ENST00000316423; ENST00000501493; ENST00000506179; ENST00000515021; ENST00000514106; ENST00000509391; ENST00000505698 | TSF |
| 2% | chr4 | 39516601 | 39516501 | – | chr4 | 39515804 | 39515703; 39515713 | – | ENST00000316423; ENST00000501493; ENST00000506179; ENST00000515021; ENST00000514106; ENST00000509391; ENST00000505698 | TSF |
| 2% | chr4 | 39516601 | 39516501 | – | chr4 | 39515804 | 39515703; 39515713 | – | ENST00000316423; ENST00000501493; ENST00000506179; ENST00000515021; ENST00000514106; ENST00000509391; ENST00000505698 | TSF |
| 2% | chr8 | 3040579 | 3040513 | – | chr8 | 3038736 | 3038632 | – | ENST00000335551; ENST00000400186; ENST00000602723; ENST00000520002; ENST00000602557; ENST00000537824; ENST00000542608; ENST00000539096 | TSF |
| 2% | chr8 | 3040579 | 3040513 | – | chr8 | 3038736 | 3038632 | – | ENST00000335551; ENST00000400186; ENST00000602723; ENST00000520002; ENST00000602557; ENST00000537824; ENST00000542608; ENST00000539096 | TSF |
| 2% | chr8 | 3040579 | 3040513 | – | chr8 | 3038736 | 3038632 | – | ENST00000335551; ENST00000400186; ENST00000602723; ENST00000520002; ENST00000602557; ENST00000537824; ENST00000542608; ENST00000539096 | TSF |
| 2% | chr8 | 3040579 | 3040513 | – | chr8 | 3038736 | 3038632 | – | ENST00000335551; ENST00000400186; ENST00000602723; ENST00000520002; ENST00000602557; ENST00000537824; ENST00000542608; ENST00000539096 | TSF |
| 2% | chr7 | 27581923 | 27581188 | – | chr7 | 27578036 | 27577960 | – | ENST00000265395; ENST00000425715 | TSF |
| 2% | chr7 | 27581923 | 27581188 | – | chr7 | 27578036 | 27577960 | – | ENST00000265395; ENST00000425715 | TSF |
| 2% | chr5 | 34007349 | 34007048 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34007349 | 34007048 | – | chr5 | chr5 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34007349 | 34007048 | – | chr5 | chr5 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34007349 | 34007048 | – | chr5 | chr5 | 34005861 | – | ENST00000335606; ENST00000382072; ENST00000382079; ENST00000506639; ENST00000382085; ENST00000502637; | TSF |

TABLE 36-continued

Transcript fusion for Liver Hepatocellular Carcinoma (LIHC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr5 | 34007349 | 34007048 | − | chr5 | chr5 | 34005861 | − | ENST00000441713; ENST00000426255; ENST00000512079; ENST00000382068 ENST00000335606; ENST00000382072; ENST00000382079; ENST00000506639; ENST00000382085; ENST00000502637; | TSF |
| 2% | chr5 | 34007349 | 34007048 | − | chr5 | chr5 | 34005861 | − | ENST00000441713; ENST00000426255; ENST00000512079; ENST00000382068 ENST00000335606; ENST00000382072; ENST00000382079; ENST00000506639; ENST00000382085; ENST00000502637; | TSF |
| 2% | chr5 | 34007349 | 34007048 | − | chr5 | chr5 | 34005861 | − | ENST00000441713; ENST00000426255; ENST00000512079; ENST00000382068 ENST00000335606; ENST00000382072; ENST00000382079; ENST00000506639; ENST00000382085; ENST00000502637; | TSF |
| 2% | chr5 | 34007349 | 34007048 | − | chr5 | chr5 | 34005861 | − | ENST00000441713; ENST00000426255; ENST00000512079; ENST00000382068 ENST00000335606; ENST00000382072; ENST00000382079; ENST00000506639; ENST00000382085; ENST00000502637; | TSE |
| 2% | chr5 | 34007349 | 34007048 | − | chr5 | chr5 | 34005861 | − | ENST00000441713; ENST00000426255; ENST00000512079; ENST00000382068 ENST00000335606; ENST00000382072; ENST00000382079; ENST00000506639; ENST00000382085; ENST00000502637; | TSF |
| 2% | chr9 | 75517880 | 75517763 | − | chr9 | 75516196 | 75516124 | − | ENST00000297785 | TSF |
| 2% | chr4 | 100304888 | 100304649 | − | chr4 | 100268301 | 100268163 | − | ENST00000515683 | TSF |
| 2% | chr10 | 7735546 | 7735278 | − | chr10 | 7697638 | 7697594 | − | ENST00000256861; ENST00000397146; ENST00000397145 | TSF |
| 2% | chr10 | 7735546 | 7735278 | − | chr10 | 7697638 | 7697594 | − | ENST00000256861; ENST00000397146; ENST00000397145 | TSF |
| 2% | chr10 | 7735546 | 7735278 | − | chr10 | 7697638 | 7697594 | − | ENST00000256861; ENST00000397146; ENST00000397145 | TSF |
| 2% | chr9 | 123541039 | 123540941 | − | chr9 | 123540823 | 123540629 | − | ENST00000608872; ENST00000453291 | TSF |
| 2% | chr9 | 123541039 | 123540941 | − | chr9 | 123540823 | 123540629 | − | ENST00000608872; ENST00000453291 | TSF |
| 2% | chr12 | 122293286 | 122293243 | − | chr12 | 122292698 | 122292609 | − | ENST00000289004; ENST00000543163 | TSF |
| 2% | chr7 | 100850556 | 100850506 | − | chr7 | 100850185 | 100850060 | − | ENST00000454310; ENST00000223127 | TSF |
| 2% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 2% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 2% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 2% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 2% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 2% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 2% | chr19 | 9974212 | 9974055 | − | chr19 | 9971470 | 9971321 | − | ENST00000264833; ENST00000593091 | TSF |
| 2% | chr19 | 9974212 | 9974055 | − | chr19 | 9971470 | 9971321 | − | ENST00000264833; ENST00000593091 | TSF |

TABLE 37

Transcript fusion for Lung Adenocarcinoma (LUAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 17% | chr12 | 71509738 | 71509630 | − | ENST00000549357 | chr12 | 71504233 | 71503634 | − | TAF |
| 15% | chr3 | 49927493 | 49927357 | − | ENST00000296474; ENST00000344206 | chr3 | 49927248 | 49927201 | − | TAF |
| 15% | chr3 | 49927493 | 49927357 | − | ENST00000296474; ENST00000344206 | chr3 | 49927248 | 49927204 | − | TAF |
| 12% | chr5 | 82554349 | 82554496 | + | ENST00000282268; ENST00000338635; ENST00000396027; ENST00000511817 | chr5 | 82606608 | 82606935 | + | TAF |
| 12% | chrX | 117900807 | 117900939 | + | ENST00000371666 | chrX | 117938895 | 117939267 | + | TAF |
| 12% | chr19 | 1147419 | 1147308 | − | ENST00000361757; ENST00000587024; ENST00000590998; ENST00000590176; ENST00000587655 | chr19 | 1143923 | 1143814 | − | TAF |
| 11% | chr11 | 428199 | 428088 | − | ENST00000332826 | chr11 | 424187 | 423924 | − | TAF |
| 10% | chr6 | 117700322 | 117700222 | − | ENST00000368507; ENST00000368508 | chr6 | 117693892 | 117693601 | − | TAF |
| 10% | chr6 | 117700322 | 117700222 | − | ENST00000368507; ENST00000368508 | chr6 | 117693892 | 117693601 | − | TAF |
| 10% | chr3 | 98600498; 98600611 | 98600384 | − | ENST00000449482; ENST00000326840; ENST00000326857 | chr3 | 98586282 | 98584565 | − | TSF |
| 10% | chr3 | 98600498; 98600611 | 98600384 | − | ENST00000449482; ENST00000326840; ENST00000326857 | chr3 | 98586282 | 98584565 | − | TSF |
| 8% | chrX | 100170072 | 100169610 | − | ENST00000328526; ENST00000372956 | chrX | 100143801 | 100143669 | − | TSF |
| 8% | chrX | 100170072 | 100169610 | − | ENST00000328526; ENST00000372956 | chrX | 100143801 | 1001436 69 | − | TSF |
| 7% | chrX | 100178050 | 100177782 | − | ENST00000328526; ENST00000372956 | chrX | 100143801 | 100143669 | − | TSF |
| 7% | chrX | 100178050 | 100177782 | − | ENST00000328526; ENST00000372956 | chrX | 100143801 | 100143669 | − | TSF |
| 6% | chr1 | 225156461 | 225156576 | + | ENST00000430092; ENST00000400952; ENST00000366849; ENST00000439375 | chr1 | 225157336 | 225158402 | + | TSF |
| 6% | chr1 | 225156461 | 225156576 | + | ENST00000430092; ENST00000400952; ENST00000366849; ENST00000439375 | chr1 | 225157336 | 225158402 | + | TSF |
| 6% | chr8 | 63502273 | 63502353 | + | ENST00000523211; ENST00000328472 | chr8 | 63546747 | 63547118 | + | TSF |
| 4% | chr4 | 57319769 | 57319927 | + | ENST00000514888; ENST00000264221; ENST00000505164; ENST00000399688; ENST00000512576 | chr4 | 57321183 | 57321327 | + | TSF |
| 4% | chr4 | 57319769 | 57319927 | + | ENST00000514888; ENST00000264221; ENST00000505164; ENST00000399688; ENST00000512576 | chr4 | 57321183 | 57321327 | + | TSF |
| 4% | chr4 | 57319769 | 57319927 | + | ENST00000514888; ENST00000264221; ENST00000505164; ENST00000399688; ENST00000512576 | chr4 | 57321183 | 57321327 | + | TSF |
| 4% | chr12 | 113623819 | 113623826 | + | ENST00000552495 | chr12 | 113623998 | 113624117 | + | TSF |
| 4% | chr3 | 32280465 | 32280611 | + | ENST00000458535; ENST00000307526 | chr3 | 32324083 | 32324625 | + | TSF |
| 4% | chr4 | 56230241 | 56230438 | + | ENST00000264228 | chr4 | 56252510 | 56252750 | + | TSF |
| 4% | chr19 | 3869013; 3869015 | 3868963 | − | ENST00000586578; ENST00000262961; ENST00000438164; ENST00000587212; ENST00000439086 | chr19 | 3855694 | 3855445 | − | TSF |
| 4% | chr19 | 3869013; 3869015 | 3868963 | − | ENST00000586578; ENST00000262961; ENST00000438164; ENST00000587212; ENST00000439086 | chr19 | 3855694 | 3855445 | − | TSF |
| 3% | chr10 | 126205749 | 126205840 | + | ENST00000368842 | chr10 | 126251911 | 126252288 | + | TSF |
| 3% | chr1 | 241803556 | 241803184 | − | ENST00000366554; ENST00000331838 | chr1 | 241771682 | 241771633 | − | TSF |
| 3% | chr12 | 56742407 | 56742313 | − | ENST00000314128; ENST00000557235 | chr12 | 56740986 | 56740975 | − | TSF |
| 3% | chr12 | 56742407 | 56742313 | − | ENST00000314128; ENST00000557235 | chr12 | 56740986 | 56740975 | − | TSF |
| 3% | chr1 | 234546277 | 234546191 | − | ENST00000040877 | chr1 | 234545319 | 234545287 | − | TSF |
| 3% | chr7 | 81964567 | 81964451 | − | ENST00000356860; ENST00000356253; ENST00000423588 | chr7 | 81929467 | 81929190 | − | TSF |
| 3% | chr2 | 89160434 | 89160398 | − | ENST00000390239 | chr2 | 89129384 | 89129304 | − | TSF |
| 3% | chr11 | 20981978 | 20982106 | + | ENST00000298925; ENST00000357134; ENST00000325319; ENST00000532434 | chr11 | 21041136 | 21041271 | + | TSF |
| 3% | chr11 | 20981978 | 20982106 | + | ENST00000298925; ENST00000357134; ENST00000325319; ENST00000532434 | chr11 | 21041136 | 21041271 | + | TSF |
| 3% | chr11 | 20981978 | 20982106 | + | ENST00000298925; ENST00000357134; ENST00000325319; ENST00000532434 | chr11 | 21041136 | 21041271 | + | TSF |
| 3% | chr5 | 54993786 | 54993674 | − | ENST00000396865; ENST00000539768; ENST00000318672; ENST00000508124; ENST00000511233; ENST00000503891; ENST00000513993; ENST00000505563; ENST00000506624; ENST00000507109 | chr5 | 54993040 | 54992544 | − | TSF |
| 3% | chrX | 119708472 | 119708406 | − | ENST00000404115 | chrX | 119705855 | 119705820 | − | TSF |
| 3% | chr2 | 135223796 | 135223685 | − | ENST00000281924 | chr2 | 135216236 | 135216223 | − | TSF |
| 2% | chr5 | 23976106 | 23976159 | + | ENST00000512559; ENST00000507936 | chr5 | 24177946 | 24178380 | + | TSF |
| 2% | chr9 | 125054028 | 125054119 | + | ENST00000297908; ENST00000344641; ENST00000373723; ENST00000373729; ENST00000394315 | chr9 | 125068067 | 125068171 | + | TSF |
| 2% | chr9 | 125054028 | 125054119 | + | ENST00000297908; ENST00000344641; ENST00000373723; ENST00000373729; ENST00000394315 | chr9 | 125068067 | 125068171 | + | TSF |
| 2% | chr9 | 125054028 | 125054119 | + | ENST00000297908; ENST00000344641; ENST00000373723; ENST00000373729; ENST00000394315 | chr9 | 125068067 | 125068171 | + | TSF |
| 2% | chrX | 117900807 | 117900939 | + | ENST00000371666 | chrX | 117902549 | 117902902 | + | TSF |
| 2% | chr13 | 53307473; 53307354 | | − | ENST00000431550; ENST00000448904; | chr13 | 53304269 | 53303967 | − | TSF |

TABLE 37-continued

Transcript fusion for Lung Adenocarcinoma (LUAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr13 | 53307473; 53307494 | 53307354 | – | ENST00000377962 ENST00000431550; ENST00000448904; ENST00000377962 | chr13 | 53304269 | 53303967 | – | TSF |
| 2% | chr3 | 138289340 | 138289160 | – | ENST00000264982; ENST00000542237; ENST00000484888; ENST00000474781; ENST00000481834; ENST00000468900; ENST00000462419; ENST00000464035 | chr3 | 138261631 | 138260784 | – | TSF |
| 2% | chr3 | 138289340 | 138289160 | – | ENST00000264982; ENST00000542237; ENST00000484888; ENST00000474781; ENST00000481834; ENST00000468900; ENST00000462419; ENST00000464035 | chr3 | 138261631 | 138260784 | – | TSF |
| 2% | chr3 | 138289340 | 138289160 | – | ENST00000264982; ENST00000542237; ENST00000484888; ENST00000474781; ENST00000481834; ENST00000468900; ENST00000462419; ENST00000464035 | chr3 | 138261631 | 138260784 | – | TSF |
| 2% | chr3 | 138289340 | 138289160 | – | ENST00000264982; ENST00000542237; ENST00000484888; ENST00000474781; ENST00000481834; ENST00000468900; ENST00000462419; ENST00000464035 | chr3 | 138261631 | 138260784 | – | TSF |
| 2% | chr1 | 1255909 | 1255836 | – | ENST00000435064; ENST00000540437; ENST00000450926; ENST00000545578; ENST00000528879; ENST00000434694; ENST00000526797; ENST00000527719; ENST00000530031; ENST00000534345; ENST00000498476 | chr1 | 1255085 | 1254988 | – | TSF |
| 2% | chr1 | 1255909 | 1255836 | – | ENST00000435064; ENST00000540437; ENST00000450926; ENST00000545578; ENST00000528879; ENST00000434694; ENST00000526797; ENST00000527719; ENST00000530031; ENST00000534345; ENST00000498476 | chr1 | 1255085 | 1254988 | – | TSF |
| 2% | chr1 | 1255909 | 1255836 | – | ENST00000435064; ENST00000540437; ENST00000450926; ENST00000545578; ENST00000528879; ENST00000434694; ENST00000526797; ENST00000527719; ENST00000530031; ENST00000534345; ENST00000498476 | chr1 | 1255085 | 1254988 | – | TSF |
| 2% | chr1 | 1255909 | 1255836 | – | ENST00000435064; ENST00000540437; ENST00000450926; ENST00000545578; ENST00000528879; ENST00000434694; ENST00000526797; ENST00000527719; ENST00000530031; ENST00000534345; ENST00000498476 | chr1 | 1255085 | 1254988 | – | TSF |
| 2% | chr1 | 1255909 | 1255836 | – | ENST00000435064; ENST00000540437; ENST00000450926; ENST00000545578; ENST00000528879; ENST00000434694; ENST00000526797; ENST00000527719; ENST00000530031; ENST00000534345; ENST00000498476 | chr1 | 1255085 | 1254988 | – | TSF |
| 2% | chr1 | 1255909 | 1255836 | – | ENST00000435064; ENST00000540437; ENST00000450926; ENST00000545578; ENST00000528879; ENST00000434694; ENST00000526797; ENST00000527719; ENST00000530031; ENST00000534345; ENST00000498476 | chr1 | 1255085 | 1254988 | – | TSF |
| 2% | chr2 | 135470889 | 135470770 | – | ENST00000281924 | chr2 | 135443800 | 135443742 | – | TSF |
| 2% | chr5 | 31493400 | 31493314 | – | ENST00000511367; ENST00000344624; ENST00000442743; ENST00000513349 | chr5 | 31489188 | 31488661 | – | TSF |
| 2% | chr5 | 31493400 | 31493314 | – | ENST00000511367; ENST00000344624; ENST00000442743; ENST00000513349 | chr5 | 31489188 | 31488661 | – | TSF |
| 2% | chr20 | 29632611 | 29632721 | + | ENST00000278882; ENST00000358464 | chr20 | 29652086 | 29652324 | + | TSF |
| 2% | chr14 | 66096210; 66096217 | 66096324 | + | ENST00000360689; ENST00000394586; ENST00000342677; ENST00000394585; ENST00000358307; ENST00000557164 | chr14 | 66099743 | 66101298 | + | TSF |
| 2% | chr14 | 66096210; 66096217 | 66096324 | + | ENST00000360689; ENST00000394586; ENST00000342677; ENST00000394585; ENST00000358307; ENST00000557164 | chr14 | 66099743 | 66101298 | + | TSF |
| 2% | chr14 | 66096210; 66096217 | 66096324 | + | ENST00000360689; ENST00000394586; ENST00000342677; ENST00000394585; ENST00000358307; ENST00000557164 | chr14 | 66099743 | 66101298 | + | TSF |
| 2% | chr2 | 89417128 | 89416936 | – | ENST00000490686 | chr2 | 89370042 | 89366766 | – | TSF |
| 2% | chr9 | 130678698 | 130678687 | – | ENST00000335791 | chr9 | 130678449 | 130678449 | – | TSF |
| 2% | chr1 | 180283857 | 180283827 | – | ENST00000367595 | chr1 | 180281457 | 180281103 | – | TSF |
| 2% | chr20 | 44333200 | 44333136 | – | ENST00000335769 | chr20 | 44322980 | 44322621 | – | TSF |
| 2% | chr7 | 55270210 | 55270401 | + | ENST00000455089 | chr7 | 55272949 | 55272949 | + | TSF |
| 2% | chr8 | 42924698; | 42924802 | + | ENST00000534420; ENST00000302279; | chr8 | 42925245 | 42925476 | + | TSF |

TABLE 37-continued

Transcript fusion for Lung Adenocarcinoma (LUAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 2% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 2% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 2% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 2% | chr8 | 42924698; 42924750 | 42924802 | + | ENST00000534420; ENST00000302279; ENST00000533998; ENST00000342116; ENST00000531266; ENST00000533336; ENST00000525699; ENST00000529687 | chr8 | 42925245 | 42925476 | + | TSF |
| 2% | chr2 | 89513203 | 89512947 | − | ENST00000498435 | chr2 | 89389297 | 89388194 | − | TSF |
| 2% | chr8 | 62546286 | 62546242 | − | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544521 | 62544342 | − | TSF |
| 2% | chr8 | 62546286 | 62546242 | − | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544521 | 62544342 | − | TSF |
| 2% | chr8 | 62546286 | 62546242 | − | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544521 | 62544342 | − | TSF |
| 2% | chr8 | 62546286 | 62546242 | − | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544521 | 62544342 | − | TSF |
| 2% | chr8 | 62546286 | 62546242 | − | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544521 | 62544342 | − | TSF |
| 2% | chr8 | 62546286 | 62546242 | − | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544521 | 62544342 | − | TSF |
| 2% | chr8 | 62546286 | 62546242 | − | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544521 | 62544342 | − | TSF |
| 2% | chr8 | 62546286 | 62546242 | − | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544521 | 62544342 | − | TSF |
| 2% | chr4 | 1102192 | 1102131 | − | ENST00000382968; ENST00000433731; ENST00000511620; ENST00000510715; ENST00000333673 | chr4 | 1101132 | 1100845 | − | TSF |
| 2% | chr6 | 24551753 | 24551662 | − | ENST00000430948; ENST00000535378; ENST00000378214; ENST00000543707 | chr6 | 24548828 | 24548413 | − | TSF |
| 2% | chr6 | 24551753 | 24551662 | − | ENST00000430948; ENST00000535378; ENST00000378214; ENST00000543707 | chr6 | 24548828 | 24548413 | − | TSF |
| 2% | chr6 | 24551753 | 24551662 | − | ENST00000430948; ENST00000535378; ENST00000378214; ENST00000543707 | chr6 | 24548828 | 24548413 | − | TSF |
| 2% | chr1 | 11115877; 11115983 | 11115838 | − | ENST00000490101; ENST00000376957 | chr1 | 11115464 | 11115178 | − | TSF |
| 2% | chr1 | 11115877; | 11115838 | − | ENST00000490101; ENST00000376957 | chr1 | 11115464 | 11115178 | − | TSF |

TABLE 37-continued

Transcript fusion for Lung Adenocarcinoma (LUAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr2 | 11115983 176860292; 176860312 | 176860286 | − | ENST00000392540; ENST00000272748; ENST00000544803; ENST00000445472 | chr2 | 176859008 | 176858934 | − | TSF |
| 2% | chr2 | 176860292; 176860312 | 176860286 | − | ENST00000392540; ENST00000272748; ENST00000544803; ENST00000445472 | chr2 | 176859008 | 176858934 | − | TSF |
| 2% | chr19 | 55178145; 55178148 | 55178200 | + | ENST00000391733; ENST00000391736; ENST00000270452; ENST00000430952; ENST00000391734; ENST00000434286 | chr19 | 55178294 | 55178458 | + | TSF |
| 2% | chr19 | 55178145; 55178148 | 55178200 | + | ENST00000391733; ENST00000391736; ENST00000270452; ENST00000430952; ENST00000391734; ENST00000434286 | chr19 | 55178294 | 55178458 | + | TSF |
| 2% | chr19 | 55178145; 55178148 | 55178200 | + | ENST00000391733; ENST00000391736; ENST00000270452; ENST00000430952; ENST00000391734; ENST00000434286 | chr19 | 55178294 | 55178458 | + | TSF |
| 2% | chr3 | 137906397; 137906427 | 137906441 | + | ENST00000469044; ENST00000461600; ENST00000461822; ENST00000470821; ENST00000471709; ENST00000538260; ENST00000463485; ENST00000393058 | chr3 | 137907243 | 137907252 | + | TSF |
| 2% | chr3 | 137906397; 137906427 | 137906441 | + | ENST00000469044; ENST00000461600; ENST00000461822; ENST00000470821; ENST00000471709; ENST00000538260; ENST00000463485; ENST00000393058 | chr3 | 137907243 | 137907252 | + | TSF |
| 2% | chr1 | 63955889 | 63955754 | − | ENST00000371092; ENST00000271002; ENST00000489099; ENST00000283568 | chr1 | 63952444 | 63951983 | − | TSF |
| 2% | chr1 | 63955889 | 63955754 | − | ENST00000371092; ENST00000271002; ENST00000489099; ENST00000283568 | chr1 | 63952444 | 63951983 | − | TSF |
| 2% | chr16 | 2825557; 2825626 | 2825452 | − | ENST00000262306; ENST00000409906; ENST00000409477; ENST00000494946 | chr16 | 2823822 | 2823809 | − | TSF |
| 2% | chr16 | 2825557; 2825626 | 2825452 | − | ENST00000262306; ENST00000409906; ENST00000409477; ENST00000494946 | chr16 | 2823822 | 2823809 | − | TSF |
| 2% | chr16 | 2825557; 2825626 | 2825452 | − | ENST00000262306; ENST00000409906; ENST00000409477; ENST00000494946 | chr16 | 2823822 | 2823809 | − | TSF |
| 2% | chr7 | 16900207 | 16900124 | − | ENST00000402239; ENST00000310398; ENST00000414935 | chr7 | 16894536 | 16894260 | − | TSF |
| 2% | chr7 | 16900207 | 16900124 | − | ENST00000402239; ENST00000310398; ENST00000414935 | chr7 | 16894536 | 16894260 | − | TSF |
| 2% | chr17 | 79532633; 79532593 | 79532531 | − | ENST00000374747; ENST00000539314; ENST00000572760; ENST00000573876; ENST00000331134; ENST00000573519; ENST00000571714; ENST00000572824; ENST00000573212 | chr17 | 79527702 | 79527690 | − | TSF |
| 2% | chr17 | 79532633; 79532593 | 79532531 | − | ENST00000374747; ENST00000539314; ENST00000572760; ENST00000573876; ENST00000331134; ENST00000573519; ENST00000571714; ENST00000572824; ENST00000573212 | chr17 | 79527702 | 79527690 | − | TSF |
| 2% | chr17 | 79532633; 79532593 | 79532531 | − | ENST00000374747; ENST00000539314; ENST00000572760; ENST00000573876; ENST00000331134; ENST00000573519; ENST00000571714; ENST00000572824; ENST00000573212 | chr17 | 79527702 | 79527690 | − | TSF |
| 2% | chr17 | 79532633; 79532593 | 79532531 | − | ENST00000374747; ENST00000539314; ENST00000572760; ENST00000573876; ENST00000331134; ENST00000573519; ENST00000571714; ENST00000572824; ENST00000573212 | chr17 | 79527702 | 79527690 | − | TSF |
| 2% | chr17 | 79532633; 79532593 | 79532531 | − | ENST00000374747; ENST00000539314; ENST00000572760; ENST00000573876; ENST00000331134; ENST00000573519; ENST00000571714; ENST00000572824; ENST00000573212 | chr17 | 79527702 | 79527690 | − | TSF |
| 2% | chr17 | 79532633; 79532593 | 79532531 | − | ENST00000374747; ENST00000539314; ENST00000572760; ENST00000573876; ENST00000331134; ENST00000573519; ENST00000571714; ENST00000572824; ENST00000573212 | chr17 | 79527702 | 79527690 | − | TSF |
| 2% | chr17 | 79532633; 79532593 | 79532531 | − | ENST00000374747; ENST00000539314; ENST00000572760; ENST00000573876; ENST00000331134; ENST00000573519; ENST00000571714; ENST00000572824; ENST00000573212 | chr17 | 79527702 | 79527690 | − | TSF |
| 2% | chr3 | 48716169 | 48715997 | − | ENST00000413374; ENST00000341520; ENST00000416649; ENST00000294129 | chr3 | 48702393 | 48702198 | − | TSF |
| 2% | chr3 | 48716169 | 48715997 | − | ENST00000413374; ENST00000341520; ENST00000416649; ENST00000294129 | chr3 | 48702393 | 48702198 | − | TSF |
| 2% | chr3 | 48716169 | 48715997 | − | ENST00000413374; ENST00000341520; ENST00000416649; ENST00000294129 | chr3 | 48702393 | 48702198 | − | TSF |

TABLE 37-continued

Transcript fusion for Lung Adenocarcinoma (LUAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr12 | 93873164 | 93873248 | + | ENST00000416649; ENST00000294129 ENST00000549982; ENST00000361630; ENST00000552217; ENST00000393128; ENST00000547098; ENST00000549561; ENST00000548545 | chr12 | 93876129 | 93876286 | + | TSF |
| 2% | chr12 | 93873164 | 93873248 | + | ENST00000549982; ENST00000361630; ENST00000552217; ENST00000393128; ENST00000547098; ENST00000549561; ENST00000548545 | chr12 | 93876129 | 93876286 | + | TSF |
| 2% | chr2 | 143743517 | 143743590 | + | ENST00000264170; ENST00000375773; ENST00000409512 | chr2 | 143745513 | 143745682 | + | TSF |
| 2% | chr1 | 53558459 | 53558226 | − | ENST00000371494 | chr1 | 53556655 | 53556632 | − | TSF |
| 1% | chr5 | 1802435 | 1802488 | + | ENST00000274137; ENST00000469176 | chr5 | 1811112 | 1811428 | + | TSF |
| 1% | chr22 | 47071365 | 47071449 | + | ENST00000406902; ENST00000361034; ENST00000408031 | chr22 | 47078308 | 47078350 | + | TSF |
| 1% | chr22 | 47071365 | 47071449 | + | ENST00000406902; ENST00000361034; ENST00000408031 | chr22 | 47078308 | 47078350 | + | TSF |
| 1% | chr16 | 16381600 | 16381719 | + | ENST00000399336; ENST00000263012; ENST00000538468 | chr16 | 16382422 | 16382605 | + | TSF |
| 1% | chr16 | 16381600 | 16381719 | + | ENST00000399336; ENST00000263012; ENST00000538468 | chr16 | 16382422 | 16382605 | + | TSF |
| 1% | chr18 | 56807181 | 56807267 | + | ENST00000587834; ENST00000299714; ENST00000588875 | chr18 | 56814218 | 56814267 | + | TSF |
| 1% | chr22 | 48885405 | 48885516 | + | ENST00000402357; ENST00000336769 | chr22 | 48915770 | 48916108 | + | TSF |
| 1% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 1% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 1% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 1% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 1% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 1% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 1% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 1% | chr12 | 117537087; 117537246 | 117537030 | − | ENST00000470612; ENST00000335209; ENST00000541210; ENST00000462502; ENST00000392545 | chr12 | 117513606 | 117513469 | − | TSF |
| 1% | chr12 | 117537087; 117537246 | 117537030 | − | ENST00000470612; ENST00000335209; ENST00000541210; ENST00000462502; ENST00000392545 | chr12 | 117513606 | 117513469 | − | TSF |
| 1% | chr11 | 63365635 | 63365533 | − | ENST00000323646; ENST00000415826 | chr11 | 63360665 | 63360559 | − | TSF |
| 1% | chr16 | 14782128 | 14782022 | − | ENST00000438167; ENST00000567462 | chr16 | 14779702 | 14779542 | − | TSF |
| 1% | chr7 | 22532348 | 22532184 | − | ENST00000406890; ENST00000404369; ENST00000424363 | chr7 | 22512853 | 22512669 | − | TSF |
| 1% | chr7 | 22532348 | 22532184 | − | ENST00000406890; ENST00000404369; ENST00000424363 | chr7 | 22512853 | 22512669 | − | TSF |

TABLE 37-continued

Transcript fusion for Lung Adenocarcinoma (LUAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr7 | 93516667; 93516743 | 93516573 | − | ENST00000451238; ENST00000222543 | chr7 | 93492029 | 93491711 | − | TSF |
| 1% | chr7 | 93516667; 93516743 | 93516573 | − | ENST00000451238; ENST00000222543 | chr7 | 93492029 | 93491711 | − | TSF |
| 1% | chr14 | 106235896 | 106235574 | − | ENST00000390551 | chr14 | 106216701 | 106216511 | − | TSF |
| 1% | chr7 | 22532348 | 22532184 | − | ENST00000406890; ENST00000404369; ENST00000424363 | chr7 | 22531483 | 2253137 0 | − | TSF |
| 1% | chr7 | 22532348 | 22532184 | − | ENST00000406890; ENST00000404369; ENST00000424363 | chr7 | 22531483 | 22531370 | − | TSF |
| 1% | chr8 | 17872093 | 17872349 | + | ENST00000325083; ENST00000519253; ENST00000327578; ENST00000522275 | chr8 | 17873210 | 17873221 | + | TSF |
| 1% | chr8 | 17872093 | 17872349 | + | ENST00000325083; ENST00000519253; ENST00000327578; ENST00000522275 | chr8 | 17873210 | 17873221 | + | TSF |
| 1% | chr8 | 17872093 | 17872349 | + | ENST00000325083; ENST00000519253; ENST00000327578; ENST00000522275 | chr8 | 17873210 | 17873221 | + | TSF |
| 1% | chr8 | 17872093 | 17872349 | + | ENST00000325083; ENST00000519253; ENST00000327578; ENST00000522275 | chr8 | 17873210 | 17873221 | + | TSF |
| 1% | chr2 | 192546672; 192546682 | 192546743 | + | ENST00000307849; ENST00000451500; ENST00000425611; ENST00000435931; ENST00000307834; ENST00000410026; ENST00000409510 | chr2 | 192548016 | 192548103 | + | TSF |
| 1% | chr2 | 192546672; 192546682 | 192546743 | + | ENST00000307849; ENST00000451500; ENST00000425611; ENST00000435931; ENST00000307834; ENST00000410026; ENST00000409510 | chr2 | 192548016 | 192548103 | + | TSF |
| 1% | chr2 | 192546672; 192546682 | 192546743 | + | ENST00000307849; ENST00000451500; ENST00000425611; ENST00000435931; ENST00000307834; ENST00000410026; ENST00000409510 | chr2 | 192548016 | 192548103 | + | TSF |
| 1% | chr11 | 67786242 | 67786362 | + | ENST00000539229; ENST00000316367; ENST00000007633; ENST00000342456 | chr11 | 67786535 | 67786588 | + | TSF |
| 1% | chr11 | 67786242 | 67786362 | + | ENST00000539229; ENST00000316367; ENST00000007633; ENST00000342456 | chr11 | 67786535 | 67786588 | + | TSF |
| 1% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 1% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 1% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 1% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 1% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 1% | chr10 | 79796952 | 79797062 | + | ENST00000435275; ENST00000440692; ENST00000372360; ENST00000360830 | chr4 | 176584518 | 176584519 | + | TSF |
| 1% | chr20 | 37384500 | 37384682 | + | ENST0000243903 | chr20 | 37390296 | 37390409 | + | TSF |
| 1% | chr4 | 169086398 | 169086477 | + | ENST00000359299 | chr4 | 169090666 | 169090754 | + | TSF |
| 1% | chr22 | 23165476 | 23165642 | + | ENST00000390317 | chr22 | 23175722 | 23175755 | + | TSF |
| 1% | chr16 | 4401235; 4401294 | 4401233 | − | ENST00000577031; ENST00000318059; ENST00000571986; ENST00000576217; ENST00000571178 | chr16 | 4398819 | 4398660 | − | TSF |
| 1% | chr16 | 4401235; 4401294 | 4401233 | − | ENST00000577031; ENST00000318059; ENST00000571986; ENST00000576217; ENST00000571178 | chr16 | 4398819 | 4398660 | − | TSF |
| 1% | chr1 | 220240735 | 220240644 | − | ENST00000322067; ENST00000469520; ENST00000354807; ENST00000544404; ENST00000414869; ENST00000463953; ENST00000498791; ENST00000480959 | chr1 | 220237757 | 220237680 | − | TSF |
| 1% | chr1 | 220240735 | 220240644 | − | ENST00000322067; ENST00000469520; ENST00000354807; ENST00000544404; ENST00000414869; ENST00000463953; ENST00000498791; ENST00000480959 | chr1 | 220237757 | 220237680 | − | TSF |
| 1% | chr1 | 220240735 | 220240644 | − | ENST00000322067; ENST00000469520; ENST00000354807; ENST00000544404; ENST00000414869; ENST00000463953; ENST00000498791; ENST00000480959 | chr1 | 220237757 | 220237680 | − | TSF |

TABLE 37-continued

Transcript fusion for Lung Adenocarcinoma (LUAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr14 | 106092403 | 106092109 | – | ENST00000390543 | chr14 | 105470421 | 105470286 | – | TSF |
| 1% | chr1 | 53569240 | 53569018 | – | ENST00000371494 | chr1 | 53568657 | 53568616 | – | TSF |
| 1% | chr9 | 5164265 | 5164179 | – | ENST00000381641 | chr9 | 4992433 | 4991945 | – | TSF |
| 1% | chr7 | 8198282 | 8198157 | – | ENST00000402384; ENST00000406470; ENST00000265577; ENST00000396675; ENST00000339809; ENST00000401396; ENST00000422063; ENST00000407906; ENST00000317367 | chr7 | 8197727 | 8197714 | – | TSF |
| 1% | chr7 | 8198282 | 8198157 | – | ENST00000402384; ENST00000406470; ENST00000265577; ENST00000396675; ENST00000339809; ENST00000401396; ENST00000422063; ENST00000407906; ENST00000317367 | chr7 | 8197727 | 8197714 | – | TSF |
| 1% | chr7 | 8198282 | 8198157 | – | ENST00000402384; ENST00000406470; ENST00000265577; ENST00000396675; ENST00000339809; ENST00000401396; ENST00000422063; ENST00000407906; ENST00000317367 | chr7 | 8197727 | 8197714 | – | TSF |
| 1% | chr8 | 62546286 | 62546242 | – | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544404 | 62544342 | – | TSF |
| 1% | chr8 | 62546286 | 62546242 | – | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544404 | 62544342 | – | TSF |
| 1% | chr8 | 62546286 | 62546242 | – | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544401 | 62544342 | – | TSF |
| 1% | chr8 | 62546286 | 62546242 | – | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544404 | 62544342 | – | TSF |
| 1% | chr8 | 62546286 | 62546242 | – | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544404 | 62544342 | – | TSF |
| 1% | chr8 | 62546286 | 62546242 | – | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544404 | 62544342 | – | TSF |
| 1% | chr8 | 62546286 | 62546242 | – | ENST00000541428; ENST00000379454; ENST00000522919; ENST00000356457; ENST00000519234; ENST00000518068; ENST00000517903; ENST00000445642; ENST00000517847; ENST00000522835 | chr8 | 62544404 | 62544342 | – | TSF |
| 1% | chr19 | 18710656 | 18710375 | – | ENST00000392386 | chr19 | 18709961 | 18709918 | – | TSF |
| 1% | chrX | 41598709 | 41598637 | – | ENST00000421587; ENST00000318588; ENST00000361962; ENST00000378163; ENST00000378158; ENST00000378166; ENST00000442742; ENST00000378154 | chrX | 41557348 | 41557057 | – | TSF |
| 1% | chr10 | 5037676 | 5037511 | – | ENST00000380753; ENST00000421196; ENST00000407674 | chr10 | 5023140 | 5022655 | – | TSF |
| 1% | chr10 | 5037676 | 5037511 | – | ENST00000380753; ENST00000421196; ENST00000407674 | chr10 | 5023140 | 5022655 | – | TSF |
| 1% | chr4 | 25759228 | 25759156 | – | ENST00000399878; ENST00000264868; ENST00000502949; ENST00000510448 | chr4 | 25723603 | 25723555 | – | TSF |
| 1% | chr4 | 25759228 | 25759156 | – | ENST00000399878; ENST00000264868; ENST00000502949; ENST00000510448 | chr4 | 25723603 | 25723555 | – | TSF |
| 1% | chr4 | 25759228 | 25759156 | – | ENST00000399878; ENST00000264868; ENST00000502949; ENST00000510448 | chr4 | 25723603 | 25723555 | – | TSF |
| 1% | chr4 | 25759228 | 25759156 | – | ENST00000399878; ENST00000264868; ENST00000502949; ENST00000510448 | chr4 | 25723603 | 25723555 | – | TSF |

TABLE 38

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 42% | chr8 | 104389530 | 104389551 | + | chr8 | 104390255 | 104390471 | + | ENST00000330295; ENST00000520337 | TAF |
| 36% | chr12 | 122430912 | 122431615 | + | chr12 | 122437622 | 122437850 | + | ENST00000288912 | TAF |
| 36% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513; ENST00000412079 | TAF |
| 36% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513; ENST00000412079 | TAF |
| 36% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513; ENST00000412079 | TAF |
| 36% | chr17 | 80440912 | 80441180 | + | chr17 | 80441592 | 80441655; 80441659 | + | ENST00000390006; ENST00000309794; ENST00000345415; ENST00000457415; ENST00000577432; ENST00000584513; ENST00000412079 | TAF |
| 32% | chr20 | 44420870 | 44421070 | + | chr20 | 44421316 | 44421386 | + | ENST00000372622; ENST00000449078; ENST00000456939 | TAF |
| 32% | chr20 | 44420870 | 44421070 | + | chr20 | 44421316 | 44421386 | + | ENST00000372622; ENST00000449078; ENST00000456939 | TAF |
| 32% | chr20 | 44420870 | 44421070 | + | chr20 | 44421316 | 44421386 | + | ENST00000372622; ENST00000449078; ENST00000456939 | TAF |
| 32% | chr6 | 80022917 | 80022085 | − | chr6 | 79924739 | 79924689 | − | ENST00000275036; ENST00000344726 | TSF |
| 32% | chr6 | 80022917 | 80022085 | − | chr6 | 79924739 | 79924689 | − | ENST00000275036; ENST00000344726 | TSF |
| 24% | chr7 | 116364854 | 116364901 | + | chr7 | 116371722 | 116371913 | + | ENST00000397752; ENST00000318493; ENST00000436117 | TAF |
| 24% | chr7 | 116364854 | 116364901 | + | chr7 | 116371722 | 116371913 | + | ENST00000397752; ENST00000318493; ENST00000436117 | TAF |
| 24% | chr7 | 116364854 | 116364901 | + | chr7 | 116371722 | 116371913 | + | ENST00000397752; ENST00000318493; ENST00000436117 | TAF |
| 23% | chr17 | 70713894 | 70713885 | − | chr17 | 70645407 | 70645309 | − | ENST00000255559; ENST00000542342; ENST00000582769 | TSF |
| 23% | chr17 | 70713894 | 70713885 | − | chr17 | 70645407 | 70645309 | − | ENST00000255559; ENST00000542342; ENST00000582769 | TSF |
| 22% | chr10 | 5077666 | 5077808 | + | chr10 | 5138602 | 5138769 | + | ENST00000602997; ENST00000605149; ENST00000380554 | TAF |
| 22% | chr10 | 5077666 | 5077808 | + | chr10 | 5138602 | 5138769 | + | ENST00000602997; ENST00000605149; ENST00000380554 | TAF |
| 18% | chr11 | 424193 | 423942 | − | chr11 | 421198 | 421141 | − | ENST00000332826 | TAF |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TAF |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TAF |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TAF |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TAF |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TAF |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; | TAF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 17% | chr5 | 66178759 | 66178848 | + | chr5 | 66195779 | 66195810 | + | ENST00000450827 ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TAF |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TAF |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TAF |
| 17% | chr5 | 66178759 | 66178848 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TAF |
| 16% | chr4 | 100021143 | 100021056 | − | chr4 | 100006367 | 100006266 | − | ENST00000296412; ENST00000512659; ENST00000503130; ENST00000502590; ENST00000505652 | TAF |
| 16% | chr4 | 100021143 | 100021056 | − | chr4 | 100006367 | 100006266 | − | ENST00000296412; ENST00000512659; ENST00000503130; ENST00000502590; ENST00000505652 | TAF |
| 16% | chr4 | 100021143 | 100021056 | − | chr4 | 100006367 | 100006266 | − | ENST00000296412; ENST00000512659; ENST00000503130; ENST00000502590; ENST00000505652 | TAF |
| 16% | chr4 | 100021143 | 100021056 | − | chr4 | 100006367 | 100006266 | − | ENST00000296412; ENST00000512659; ENST00000503130; ENST00000502590; ENST00000505652 | TAF |
| 16% | chr4 | 100021143 | 100021056 | − | chr4 | 100006367 | 100006266 | − | ENST00000296412; ENST00000512659; ENST00000503130; ENST00000502590; ENST00000505652 | |TAF |
| 16% | chr11 | 93468219 | 93468129 | − | chr11 | 93467826 | 93467791; 93467814 | − | ENST00000393259; ENST00000527169 | TAF |
| 16% | chr11 | 93468219 | 93468129 | − | chr11 | 93467826 | 93467791; 93467814 | − | ENST00000393259; ENST00000527169 | TAF |
| 15% | chr5 | 54528691 | 54528595 | − | chr5 | 54528374 | 54528189 | − | ENST00000282572 | TAF |
| 15% | chr17 | 70671026 | 70670643 | − | chr17 | 70645407 | 70645309 | − | ENST00000255559; ENST00000542342; ENST00000582769 | TAF |
| 15% | chr17 | 70671026 | 70670643 | − | chr17 | 70645407 | 70645309 | − | ENST00000255559; ENST00000542342; ENST00000582769 | TAF |
| 14% | chr5 | 823586 | 823504 | − | chr5 | 822010 | 821976 | − | ENST00000424784; ENST00000283441 | TAF |
| 13% | chr7 | 98974090 | 98974197 | + | chr7 | 98983325 | 98983401 | + | ENST00000432884 | TAF |
| 12% | chr20 | 31764878 | 31764929 | + | chr20 | 31765953 | 31766034 | + | ENST00000253362; ENST00000354932 | TAF |
| 11% | chr1 | 224551810 | 224551900 | + | chr1 | 224553581 | 224553693 | + | ENST00000465271; ENST00000366858; ENST00000366857; ENST00000366856 | TAF |
| 11% | chr1 | 224551810 | 224551900 | + | chr1 | 224553581 | 224553693 | + | ENST00000465271; ENST00000366858; ENST00000366857; ENST00000366856 | TAF |
| 11% | chr1 | 224551810 | 224551900 | + | chr1 | 224553581 | 224553693 | + | ENST00000465271; ENST00000366858; ENST00000366857; ENST00000366856 | TAF |
| 11% | chr1 | 224551810 | 224551900 | + | chr1 | 224553581 | 224553693 | + | ENST00000465271; ENST00000366858; ENST00000366857; ENST00000366856 | TAF |
| 10% | chr19 | 45347212 | 45347340 | + | chr19 | 45368528 | 45368917 | + | ENST00000252485; ENST00000252483 | TAF |
| 10% | chr19 | 45347212 | 45347340 | + | chr19 | 45368528 | 45368917 | + | ENST00000252485; ENST00000252483 | TAF |
| 10% | chr3 | 172098199 | 172098266 | +chr3 | | 172098756 | 172098883 | + | ENST00000415807; ENST00000336824; ENST00000416957 | TAF |
| 10% | chr5 | 1475119 | 1475076 | − | chr5 | 1474800 | 1474675 | − | ENST00000475622; ENST00000283415 | TSF |
| 9% | chr19 | 14129234 | 14129243 | + | chr19 | 14141522 | 14141549; 14141760 | + | ENST00000585987; ENST00000431365 | TSF |
| 9% | chr19 | 14129234 | 14129243 | + | chr19 | 14141522 | 14141549; 14141760 | + | ENST00000585987; ENST00000431365 | TSF |
| 9% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 9% | chr7 | 48039730 | 48039725 | − | chr7 | 48035743 | 48035628 | − | ENST00000453071; ENST00000297325; ENST00000412371; ENST00000412142; ENST00000395572; ENST00000453192; | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 9% | chr7 | 48039730 | 48039725 | − | chr7 | 48035743 | 48035628 | − | ENST00000438771 ENST00000453071; ENST00000297325; ENST00000412371; ENST00000412142; ENST00000395572; ENST00000453192; ENST00000438771 | TSF |
| 8% | chr10 | 33505669 | 33505616 | − | chr10 | 33502645 | 33502134; 33502314 | − | ENST00000432372; ENST00000374875; ENST00000265371; ENST00000374867; ENST00000395995; ENST00000374821; ENST00000374822; ENST00000374823; ENST00000374816 | TSF |
| 8% | chr10 | 33505669 | 33505616 | − | chr10 | 33502645 | 33502134; 33502314 | − | ENST00000432372; ENST00000374875; ENST00000265371; ENST00000374867; ENST00000395995; ENST00000374821; ENST00000374822; ENST00000374823; ENST00000374816 | TSF |
| 8% | chr10 | 33505669 | 33505616 | − | chr10 | 33502645 | 33502134; 33502314 | − | ENST00000432372; ENST00000374875; ENST00000265371; ENST00000374867; ENST00000395995; ENST00000374821; ENST00000374822; ENST00000374823; ENST00000374816 | TSF |
| 8% | chr10 | 33505669 | 33505616 | − | chr10 | 33502645 | 33502134; 33502314 | − | ENST00000432372; ENST00000374875; ENST00000265371; ENST00000374867; ENST00000395995; ENST00000374821; ENST00000374822; ENST00000374823; ENST00000374816 | TSF |
| 8% | chr10 | 33505669 | 33505616 | − | chr10 | 33502645 | 33502134; 33502314 | − | ENST00000432372; ENST00000374875; ENST00000265371; ENST00000374867; ENST00000395995; ENST00000374821; ENST00000374822; ENST00000374823; ENST00000374816 | TSF |
| 8% | chr10 | 33505669 | 33505616 | − | chr10 | 33502645 | 33502134; 33502314 | − | ENST00000432372; ENST00000374875; ENST00000265371; ENST00000374867; ENST00000395995; ENST00000374821; ENST00000374822; ENST00000374823; ENST00000374816 | TSF |
| 8% | chr10 | 33505669 | 33505616 | − | chr10 | 33502645 | 33502134; 33502314 | − | ENST00000432372; ENST00000374875; ENST00000265371; ENST00000374867; ENST00000395995; ENST00000374821; ENST00000374822; ENST00000374823; ENST00000374816 | TSF |
| 8% | chr10 | 33505669 | 33505616 | − | chr10 | 33502645 | 33502134; 33502314 | − | ENST00000432372; ENST00000374875; ENST00000265371; ENST00000374867; ENST00000395995; ENST00000374821; ENST00000374822; ENST00000374823; ENST00000374816 | TSF |
| 7% | chrX | 107293989 | 107294242 | + | chrX | 107301268 | 107301431 | + | ENST00000415430; ENST00000217957; ENST00000458383 | TSF |
| 7% | chrX | 107293989 | 107294242 | + | chrX | 107301268 | 107301431 | + | ENST00000415430; ENST00000217957; ENST00000458383 | TSF |
| 7% | chrX | 107293989 | 107294242 | + | chrX | 107301268 | 107301431 | + | ENST00000415430; ENST00000217957; ENST00000458383 | TSF |
| 5% | chr7 | 7559044 | 7558760 | − | chr7 | 7557468 | 7557427 | − | ENST00000399429; ENST00000444268 | TSF |
| 5% | chr7 | 7559044 | 7558760 | − | chr7 | 7557468 | 7557427 | − | ENST00000399429; ENST00000444268 | TSF |
| 5% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 5% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 5% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 5% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 5% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 5% | chr3 | 98586295 | 98586135 | − | chr3 | 98568442 | 98568232; 98568305 | − | ENST00000449482; ENST00000326840; ENST00000326857 | TSF |
| 5% | chr3 | 98586295 | 98586135 | − | chr3 | 98568442 | 98568232; | − | ENST00000449482; ENST00000326840; | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 5% | chr3 | 98586295 | 98586135 | – | chr3 | 98568442 | 98568305 98568232; 98568305 | – | ENST00000326857 ENST00000449482; ENST00000326840; ENST00000326857 | TSF |
| 4% | chr2 | 143794737 | 143794842 | + | chr2 | 143797997 | 143798227 | + | ENST00000264170; ENST00000409512 | TSF |
| 4% | chr10 | 5057417 | 5057095 | – | chr10 | 5043873 | 5043706 | – | ENST00000380753; ENST00000421196; ENST00000407674; ENST00000604507; ENST00000455190 | TSF |
| 4% | chr10 | 5057417 | 5057095 | – | chr10 | 5043873 | 5043706 | – | ENST00000380753; ENST00000421196; ENST00000407674; ENST00000604507; ENST00000455190 | TSF |
| 4% | chr10 | 5057417 | 5057095 | – | chr10 | 5043873 | 5043706 | – | ENST00000380753; ENST00000421196; ENST00000407674; ENST00000604507; ENST00000455190 | TSF |
| 4% | chr10 | 5057417 | 5057095 | – | chr10 | 5043873 | 5043706 | – | ENST00000380753; ENST00000421196; ENST00000407674; ENST00000604507; ENST00000455190 | TSF |
| 4% | chr12 | 122430912 | 122432103 | + | chr12 | 122437622 | 122437850 | + | ENST00000288912 | TSF |
| 4% | chr12 | 122430912 | 122431795 | + | chr12 | 122437622 | 122437850 | + | ENST00000288912 | TSF |
| 4% | chr22 | 22899971 | 22899965 | – | chr22 | 22893511 | 22893185; 22893189; 22893274; 22893481 | – | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | – | chr22 | 22893511 | 22893185; 22893189; 22893274; 22893481 | – | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | – | chr22 | 22893511 | 22893185; 22893189; 22893274; 22893481 | – | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | – | chr22 | 22893511 | 22893185; 22893189; 22893274; 22893481 | – | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | – | chr22 | 22893511 | 22893185; 22893189; 22893274; 22893481 | – | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | – | chr22 | 22893511 | 22893185; 22893189; 22893274; 22893481 | – | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr22 | 22899971 | 22899965 | – | chr22 | 22893511 | 22893185; 22893189; 22893274; 22893481 | – | ENST00000406503; ENST00000398743; ENST00000398741; ENST00000543184; ENST00000405655; ENST00000402697; ENST00000439106; ENST00000438888; ENST00000420709; ENST00000403441; ENST00000442481 | TSF |
| 4% | chr8 | 104389530 | 104389536 | + | chr8 | 104390255 | 104390471 | + | ENST00000330295; ENST00000520337 | TSF |
| 4% | chr12 | 117498589 | 117498567 | – | chr12 | 117494691 | 117494611 | – | ENST00000470612; ENST00000335209; ENST00000392545; ENST00000462502 | TSF |
| 4% | chr12 | 117498589 | 117498567 | – | chr12 | 117494691 | 117494611 | – | ENST00000470612; ENST00000335209; ENST00000392545; ENST00000462502 | TSF |
| 4% | chr12 | 117498589 | 117498567 | – | chr12 | 117494691 | 117494611 | – | ENST00000470612; ENST00000335209; ENST00000392545; ENST00000462502 | TSF |
| 4% | chr2 | 38983894 | 38983253 | – | chr2 | 38977336 | 38977156 | – | ENST00000313117; ENST00000425778; ENST00000425941; ENST00000446327; ENST00000409276; ENST00000431066; ENST00000443213 | TSF |
| 4% | chr2 | 38983894 | 38983253 | – | chr2 | 38977336 | 38977156 | – | ENST00000313117; ENST00000425778; ENST00000425941; ENST00000446327; ENST00000409276; ENST00000431066; ENST00000443213 | TSF |
| 4% | chr2 | 38983894 | 38983253 | – | chr2 | 38977336 | 38977156 | – | ENST00000313117; ENST00000425778; | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 4% | chr2 | 38983894 | 38983253 | − | chr2 | 38977336 | 38977156 | − | ENST00000425941; ENST00000446327; ENST00000409276; ENST00000431066; ENST00000443213 ENST00000313117; ENST00000425778; | TSF |
| 4% | chr2 | 38983894 | 38983253 | − | chr2 | 38977336 | 38977156 | − | ENST00000425941; ENST00000446327; ENST00000409276; ENST00000431066; ENST00000443213 ENST00000313117; ENST00000425778; | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr5 | 66178759 | 66179020 | + | chr5 | 66195779 | 66195810 | + | ENST00000404260; ENST00000403625; ENST00000406374; ENST00000406039; ENST00000452953; ENST00000432817; ENST00000434115; ENST00000411628; ENST00000490016; ENST00000403666; ENST00000450827 | TSF |
| 4% | chr20 | 45337040 | 45337192 | + | chr20 | 45353680 | 45354963 | + | ENST00000359271 | TSF |
| 4% | chr7 | 56018506 | 56018522 | + | chr7 | 56020872 | 56021011 | + | ENST00000426595 | TSF |
| 4% | chr4 | 57560508 | 57559845 | − | chr4 | 57522178 | 57522023; 57522025 | − | ENST00000420433; ENST00000554144; ENST00000508121; ENST00000557328 | TSF |
| 4% | chr4 | 57560508 | 57559845 | − | chr4 | 57522178 | 57522023; | − | ENST00000420433; ENST00000554144; | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 4% | chr4 | 57560508 | 57559845 | − | chr4 | 57522178 | 57522025 57522023; 57522025 | − | ENST00000508121; ENST00000557328 ENST00000420433; ENST00000554144; ENST00000508121; ENST00000557328 | TSF |
| 4% | chr6 | 117763870 | 117763597 | − | chr6 | 117739669 | 117739625 | − | ENST00000368507; ENST00000368508 | TSF |
| 4% | chr6 | 117763870 | 117763597 | − | chr6 | 117739669 | 117739625 | − | ENST00000368507; ENST00000368508 | TSF |
| 3% | chr5 | 147244208 | 147245387 | + | chr5 | 147261009 | 147261211 | + | ENST00000296694 | TSF |
| 3% | chr17 | 39974832 | 39974893 | + | chr17 | 39975462 | 39975651 | + | ENST00000321562 | TSF |
| 3% | chr12 | 122430912 | 122432282 | + | chr12 | 122437622 | 122437850 | + | ENST00000288912 | TSF |
| 3% | chr19 | 1114930 | 1114676 | − | chr19 | 1114421 | 1114230 | − | ENST00000361757; ENST00000587024; ENST00000438103 | TSF |
| 3% | chr4 | 57560508 | 57559885 | − | chr4 | 57522178 | 57522023; 57522025 | − | ENST00000420433; ENST00000554144; ENST00000508121; ENST00000557328 | TSF |
| 3% | chr4 | 57560508 | 57559885 | − | chr4 | 57522178 | 57522023; 57522025 | − | ENST00000420433; ENST00000554144; ENST00000508121; ENST00000557328 | TSF |
| 3% | chr4 | 57560508 | 57559885 | − | chr4 | 57522178 | 57522023; 57522025 | − | ENST00000420433; ENST00000554144; ENST00000508121; ENST00000557328 | TSF |
| 3% | chr4 | 873272 | 873014 | − | chr4 | 871597 | 871403 | − | ENST00000314167; ENST00000511163 | TSF |
| 3% | chr22 | 42511426 | 42511212 | − | chr22 | 42483179 | 42483064 | − | ENST00000602404; ENST00000498737 | TSF |
| 3% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 3% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 3% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 3% | chr22 | |29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 3% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000402731; ENST00000403642; ENST00000439200; ENST00000448511 | TSF |
| 3% | chr8 | 117816470 | 117816753 | + | chr8 | 117861127 | 117861256; 117861276 | + | ENST00000517820; ENST00000520733 | TSF |
| 3% | chr8 | 117816470 | 117816753 | + | chr8 | 117861127 | 117861256; 117861276 | + | ENST00000517820; ENST00000520733 | TSF |
| 3% | chr16 | 66461229 | 66461334 | + | chr16 | 66503505 | 66503768 | + | ENST00000536005 | TSF |
| 3% | chr17 | 39976225 | 39976301 | + | chr17 | 39976521 | 39976713 | + | ENST00000321562; ENST00000455106; ENST00000544340 | TSF |
| 3% | chr17 | 70713894 | 70713885 | − | chr17 | 70709120 | 70709075 | − | ENST00000581581 | TSF |
| 3% | chr1 | 223720576 | 223720355 | − | chr1 | 223718212 | 223718134 | − | ENST00000430824; ENST00000366872 | TSF |
| 3% | chrX | 151410500 | 151410406 | − | chrX | 151393317 | 151393235 | − | ENST00000370314; ENST00000535043 | TSF |
| 3% | chr16 | 74833301 | 74833256 | − | chr16 | 74774013 | 74773921 | − | ENST00000219368; ENST00000567683; ENST00000569949 | TSF |
| 3% | chr16 | 74833301 | 74833256 | − | chr16 | 74774013 | 74773921 | − | ENST00000219368; ENST00000567683; ENST00000569949 | TSF |
| 3% | chr16 | 74833301 | 74833256 | − | chr16 | 74774013 | 74773921 | − | ENST00000219368; ENST00000567683; ENST00000569949 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 2% | chr1 | 1422590 | 1422685 | + | chr1 | 1423243 | 1423294 | + | ENST00000308647 | TSF |
| 2% | chr15 | 43467899 | 43467988 | + | chr15 | 43470805 | 43470909 | + | ENST00000260403 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr10 | 5060345 | 5060092 | − | chr10 | 5043777 | 5043706 | − | ENST00000380753; ENST00000421196; ENST00000407674; ENST00000604507; ENST00000455190 | TSF |
| 2% | chr10 | 5060345 | 5060092 | − | chr10 | 5043777 | 5043706 | − | ENST00000380753; ENST00000421196; ENST00000407674; ENST00000604507; ENST00000455190 | TSF |
| 2% | chr10 | 5060345 | 5060092 | − | chr10 | 5043777 | 5043706 | − | ENST00000380753; ENST00000421196; ENST00000407674; ENST00000604507; ENST00000455190 | TSF |
| 2% | chr10 | 5060345 | 5060092 | − | chr10 | 5043777 | 5043706 | − | ENST00000380753; ENST00000421196; ENST00000407674; ENST00000604507; ENST00000455190 | TSF |
| 2% | chr8 | 121662427 | 121662337 | − | chr8 | 121644891 | 121644684 | − | ENST00000395601; ENST00000517992 | TSF |
| 2% | chr5 | 58596952 | 58596862 | − | chr5 | 58511794 | 58511603 | − | ENST00000340635; ENST00000360047; ENST00000507116; ENST00000503258; ENST00000405755; ENST00000502484; ENST00000546160; ENST00000309641; ENST00000502575 | TSF |
| 2% | chr5 | 58596952 | 58596862 | − | chr5 | 58511794 | 58511603 | − | ENST00000340635; ENST00000360047; ENST00000507116; ENST00000503258; ENST00000405755; ENST00000502484; ENST00000546160; ENST00000309641; ENST00000502575 | TSF |
| 2% | chr5 | 58596952 | 58596862 | − | chr5 | 58511794 | 58511603 | − | ENST00000340635; ENST00000360047; ENST00000507116; ENST00000503258; ENST00000405755; ENST00000502484; ENST00000546160; ENST00000309641; ENST00000502575 | TSF |
| 2% | chr14 | 106258982 | 106258725 | − | chr14 | 106209234 | 106209114 | − | ENST00000390548; ENST00000390549; ENST00000390542 | TSF |
| 2% | chr14 | 106258982 | 106258725 | − | chr14 | 106209234 | 106209114 | − | ENST00000390548; ENST00000390549; ENST00000390542 | TSF |
| 2% | chr14 | 106258982 | 106258725 | − | chr14 | 106209234 | 106209114 | − | ENST00000390548; ENST00000390549; ENST00000390542 | TSF |
| 2% | chrX | 149997009 | 149996779 | − | chrX | 149963959 | 149963891 | − | ENST00000370377; ENST00000466436; ENST00000418547 | TSF |
| 2% | chrX | 149997009 | 149996779 | − | chrX | 149963959 | 149963891 | − | ENST00000370377; ENST00000466436; ENST00000418547 | TSF |
| 2% | chr14 | 106258982 | 106258725 | − | chr14 | 106237569 | 106237449 | − | ENST00000390551 | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 2% | chrX | 123618682 | 123617816 | − | chrX | 123615814 | 123615582 | − | ENST00000371130; ENST00000422452 | TSF |
| 2% | chrX | 100655477 | 100654732 | − | chrX | 100653934 | 100653773 | − | ENST00000218516 | TSF |
| 2% | chr1 | 156716197 | 156716133 | − | chr1 | 156715165 | 156715089 | − | ENST00000357325; ENST00000537739; ENST00000368209; ENST00000368206 | TSF |
| 2% | chr1 | 224527533 | 224527861 | + | chr1 | 224553581 | 224553693 | + | ENST00000465271; ENST00000366858; ENST00000366857; ENST00000366856 | TSF |
| 2% | chr1 | 224527533 | 224527861 | + | chr1 | 224553581 | 224553693 | + | ENST00000465271; ENST00000366858; ENST00000366857; ENST00000366856 | TSF |
| 2% | chr1 | 224527533 | 224527861 | + | chr1 | 224553581 | 224553693 | + | ENST00000465271; ENST00000366858; ENST00000366857; ENST00000366856 | TSF |
| 2% | chr1 | 224527533 | 224527861 | + | chr1 | 224553581 | 224553693 | + | ENST00000465271; ENST00000366858; ENST00000366857; ENST00000366856 | TSF |
| 2% | chr18 | 70840904 | 70840073 | − | chr18 | 70829208 | 70829180 | − | ENST00000581011; ENST00000581862 | TSF |
| 2% | chr5 | 132737340 | 132737281 | − | chr5 | 132736678 | 132736430 | − | ENST00000265342; ENST00000510685 | TSF |
| 2% | chr5 | 132737340 | 132737281 | − | chr5 | 132736678 | 132736430 | − | ENST00000265342; ENST00000510685 | TSF |
| 2% | chr2 | 89370075 | 89370031 | − | chr2 | 89292018 | 89291928 | − | ENST00000495489 | TSF |
| 2% | chr6 | 32746812 | 32746483 | − | chr6 | 32731247 | 32731151 | − | ENST00000411527; ENST00000435145; ENST00000437316 | TSF |
| 2% | chr6 | 32746812 | 32746483 | − | chr6 | 32731247 | 32731151 | − | ENST00000411527; ENST00000435145; ENST00000437316 | TSF |
| 2% | chr6 | 32746812 | 32746483 | − | chr6 | 32731247 | 32731151 | − | ENST00000411527; ENST00000435145; ENST00000437316 | TSF |
| 2% | chr1 | 236485958 | 236485567 | − | chr1 | 236433294 | 236433175 | − | ENST00000354619; ENST00000327333 | TSF |
| 2% | chr1 | 236485958 | 236485567 | − | chr1 | 236433294 | 236433175 | − | ENST00000354619; ENST00000327333 | TSF |
| 2% | chr16 | 74834658 | 74834274 | − | chr16 | 74774013 | 74773921 | − | ENST00000219368; ENST00000567683; ENST00000569949 | TSF |
| 2% | chr16 | 74834658 | 74834274 | − | chr16 | 74774013 | 74773921 | − | ENST00000219368; ENST00000567683; ENST00000569949 | TSF |
| 2% | chr16 | 74834658 | 74834274 | − | chr16 | 74774013 | 74773921 | − | ENST00000219368; ENST00000567683; ENST00000569949 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr12 | 104681506 | 104681628 | + | chr12 | 104682709 | 104682818 | + | ENST00000378070; ENST00000525566; ENST00000429002; ENST00000526691; ENST00000388854; ENST00000542918 | TSF |
| 2% | chr12 | 104681506 | 104681628 | + | chr12 | 104682709 | 104682818 | + | ENST00000378070; ENST00000525566; ENST00000429002; ENST00000526691; ENST00000388854; ENST00000542918 | TSF |
| 2% | chr12 | 104681506 | 104681628 | + | chr12 | 104682709 | 104682818 | + | ENST00000378070; ENST00000525566; ENST00000429002; ENST00000526691; ENST00000388854; ENST00000542918 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr11 | 60694460 | 60694542 | + | chr11 | 60694676 | 60694890 | + | ENST00000453848; ENST00000005286 | TSF |
| 2% | chr11 | 60694460 | 60694542 | + | chr11 | 60694676 | 60694890 | + | ENST00000453848; ENST00000005286 | TSF |
| 2% | chr19 | 11140024 | 11140045 | + | chr19 | 11141406 | 11141569 | + | ENST00000358026; ENST00000344626; ENST00000429416; ENST00000541122; ENST00000589677; ENST00000444061; ENST00000590574; ENST00000413806; | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 2% | chr19 | 11140024 | 11140045 | + | chr19 | 11141406 | 11141569 | + | ENST00000450717; ENST00000358026; ENST00000344626; ENST00000429416; ENST00000541122; ENST00000589677; ENST00000444061; ENST00000590574; ENST00000413806; | TSF |
| 2% | chr19 | 11140024 | 11140045 | + | chr19 | 11141406 | 11141569 | + | ENST00000450717; ENST00000358026; ENST00000344626; ENST00000429416; ENST00000541122; ENST00000589677; ENST00000444061; ENST00000590574; ENST00000413806; | TSF |
| 2% | chr19 | 11140024 | 11140045 | + | chr19 | 11141406 | 11141569 | + | ENST00000450717; ENST00000358026; ENST00000344626; ENST00000429416; ENST00000541122; ENST00000589677; ENST00000444061; ENST00000590574; ENST00000413806; | TSF |
| 2% | chr19 | 11140024 | 11140045 | + | chr19 | 11141406 | 11141569 | + | ENST00000450717; ENST00000358026; ENST00000344626; ENST00000429416; ENST00000541122; ENST00000589677; ENST00000444061; ENST00000590574; ENST00000413806; | TSF |
| 2% | chr19 | 11140024 | 11140045 | + | chr19 | 11141406 | 11141569 | + | ENST00000450717; ENST00000358026; ENST00000344626; ENST00000429416; ENST00000541122; ENST00000589677; ENST00000444061; ENST00000590574; ENST00000413806; | TSF |
| 2% | chr18 | 71977251 | 71977013 | − | chr18 | 71930712 | 71930584 | − | ENST00000340533; ENST00000494131; ENST00000397914 | TSF |
| 2% | chr18 | 71977251 | 71977013 | − | chr18 | 71930712 | 71930584 | − | ENST00000340533; ENST00000494131; ENST00000397914 | TSF |
| 2% | chr18 | 71977251 | 71977013 | − | chr18 | 71930712 | 71930584 | − | ENST00000340533; ENST00000494131; ENST00000397914 | TSF |
| 2% | chr14 | 92120138 | 92119864 | − | chr14 | 92105594 | 92105440; 92105508 | − | ENST00000256343; ENST00000557036 | TSF |
| 2% | chr14 | 92120138 | 92119864 | − | chr14 | 92105594 | 92105440; 92105508 | − | ENST00000256343; ENST00000557036 | TSF |
| 2% | chr4 | 57560508 | 57559962 | − | chr4 | 57522178 | 57522023; 57522025 | − | ENST00000420433; ENST00000554144; ENST00000508121; ENST00000557328 | TSF |
| 2% | chr4 | 57560508 | 57559962 | − | chr4 | 57522178 | 57522023; 57522025 | − | ENST00000420433; ENST00000554144; ENST00000508121; ENST00000557328 | TSF |
| 2% | chr4 | 57560508 | 57559962 | − | chr4 | 57522178 | 57522023; 57522025 | − | ENST00000420433; ENST00000554144; ENST00000508121; ENST00000557328 | TSF |
| 2% | chr8 | 144691011 | 144690934 | − | chr8 | 144690296 | 144690232 | − | ENST00000220966; ENST00000433751 | TSF |
| 2% | chr8 | 144691011 | 144690934 | − | chr8 | 144690296 | 144690232 | − | ENST00000220966; ENST00000433751 | TSF |
| 2% | chr1 | 23762222 | 23762216 | − | chr1 | 23761111 | 23761026 | − | ENST00000495646; ENST00000336689; ENST00000437606 | TSF |
| 2% | chr7 | 50763323 | 50763289 | − | chr7 | 50742355 | 50742133 | − | ENST00000439599; ENST00000398812; ENST00000403097; ENST00000357271; ENST00000401949; ENST00000439044 | TSF |
| 2% | chr7 | 50763323 | 50763289 | − | chr7 | 50742355 | 50742133 | − | ENST00000439599; ENST00000398812; ENST00000403097; ENST00000357271; ENST00000401949; ENST00000439044 | TSF |
| 2% | chr7 | 50763323 | 50763289 | − | chr7 | 50742355 | 50742133 | − | ENST00000439599; ENST00000398812; ENST00000403097; ENST00000357271; ENST00000401949; ENST00000439044 | TSF |
| 2% | chr15 | 34453644 | 34453416 | − | chr15 | 34446885 | 34446845 | − | ENST00000256544; ENST00000557877; ENST00000560108; ENST00000559515 | TSF |
| 2% | chr15 | 34453644 | 34453416 | − | chr15 | 34446885 | 34446845 | − | ENST00000256544; ENST00000557877; ENST00000560108; ENST00000559515 | TSF |
| 2% | chr15 | 34453644 | 34453416 | − | chr15 | 34446885 | 34446845 | − | ENST00000256544; ENST00000557877; ENST00000560108; ENST00000559515 | TSF |
| 2% | chr15 | 34453644 | 34453416 | − | chr15 | 34446885 | 34446845 | − | ENST00000256544; ENST00000557877; ENST00000560108; ENST00000559515 | TSF |
| 2% | chr12 | 6459191 | 6458996 | − | chr12 | 6458387 | 6458330 | − | ENST00000360168; ENST00000358945; ENST00000540037; ENST00000228916; ENST00000543768 | TSF |
| 2% | chr7 | 95053394 | 95053104 | − | chr7 | 95045609 | 95045554 | − | ENST00000536183; ENST00000455123; ENST00000433091; ENST00000222572 | TSF |
| 2% | chr7 | 95053394 | 95053104 | − | chr7 | 95045609 | 95045554 | − | ENST00000536183; ENST00000455123; ENST00000433091; ENST00000222572 | TSF |
| 2% | chr7 | 95053394 | 95053104 | − | chr7 | 95045609 | 95045554 | − | ENST00000536183; ENST00000455123; ENST00000433091; ENST00000222572 | TSF |
| 2% | chr12 | 58189709 | 58189746 | + | chr12 | 58189960 | 58189980; 58190044; 58190366 | + | ENST00000540550; ENST00000457189; ENST00000454289; ENST00000323833; ENST00000350762 | TSF |
| 2% | chr12 | 58189709 | 58189746 | + | chr12 | 58189960 | 58189980; | + | ENST00000540550; ENST00000457189; | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| | | | | | | | 58190044;<br>58190366 | ENST00000454289; ENST00000323833;<br>ENST00000350762 | |
| 2% | chr12 | 58189709 | 58189746 | + | chr12 | 58189960 | 58189980; | + | ENST00000540550; ENST00000457189;<br>ENST00000454289; ENST00000323833;<br>ENST00000350762 | TSF |
| | | | | | | | 58190044;<br>58190366 | | | |
| 2% | chr14 | 70466641 | 70466673 | + | chr14 | 70477471 | 70477663 | + | ENST00000361956; ENST00000381280 | TSF |
| 2% | chr14 | 70466641 | 70466673 | + | chr14 | 70477471 | 70477663 | + | ENST00000361956; ENST00000381280 | TSF |
| 2% | chr10 | 3133726 | 3133857 | + | chr10 | 3141467 | 3141544 | + | ENST00000607886; ENST00000381125;<br>ENST00000381075; ENST00000407806 | TSF |
| 2% | chr10 | 3133726 | 3133857 | + | chr10 | 3141467 | 3141544 | + | ENST00000607886; ENST00000381125;<br>ENST00000381075; ENST00000407806 | TSF |
| 2% | chr10 | 3133726 | 3133857 | + | chr10 | 3141467 | 3141544 | + | ENST00000607886; ENST00000381125;<br>ENST00000381075; ENST00000407806 | TSF |
| 2% | chr10 | 3133726 | 3133857 | + | chr10 | 3141467 | 3141544 | + | ENST00000607886; ENST00000381125;<br>ENST00000381075; ENST00000407806 | TSF |
| 2% | chr7 | 134212336 | 134212386 | + | chr7 | 134215479 | 134215562 | + | ENST00000359579 | TSF |
| 2% | chr2 | 135250933 | 135250213 | − | chr2 | 135223796 | 135223685 | − | ENST00000281924 | TSF |
| 2% | chr7 | 30468250 | 30468120 | − | chr7 | 30465326 | 30465254 | − | ENST00000222823 | TSF |
| 2% | chr17 | 90541 | 90313 | − | chr17 | 69527 | 69414 | − | ENST00000331302; ENST00000323434;<br>ENST00000536489 | TSF |
| 1% | chr7 | 6423751 | 6423803 | + | chr7 | 6426843 | 6426914 | + | ENST00000348035; ENST00000356142 | TSF |
| 1% | chr7 | 6423751 | 6423803 | + | chr7 | 6426843 | 6426914 | + | ENST00000348035; ENST00000356142 | TSF |
| 1% | chr15 | 43431174 | 43431330 | + | chr15 | 43440953 | 43441077 | + | ENST00000564698; ENST00000260403;<br>ENST00000564494 | TSF |
| 1% | chr15 | 43431174 | 43431330 | + | chr15 | 43440953 | 43441077 | + | ENST00000564698; ENST00000260403;<br>ENST00000564494 | TSF |
| 1% | chr15 | 43431174 | 43431330 | + | chr15 | 43440953 | 43441077 | + | ENST00000564698; ENST00000260403;<br>ENST00000564494 | TSF |
| 1% | chr1 | 26595323 | 26595855 | + | chr1 | 26595951 | 26596105 | + | ENST00000451429; ENST00000476272;<br>ENST00000252992; ENST00000453146 | TSF |
| 1% | chr1 | 26595323 | 26595855 | + | chr1 | 26595951 | 26596105 | + | ENST00000451429; ENST00000476272;<br>ENST00000252992; ENST00000453146 | TSF |
| 1% | chr20 | 43561150 | 43561175 | + | chr20 | 43561713 | 43561826 | + | ENST00000255136; ENST00000217073 | TSF |
| 1% | chr2 | 26947307 | 26947428 | + | chr2 | 26950535 | 26951436 | + | ENST00000302909 | TSF |
| 1% | chr10 | 99600727 | 99601513 | + | chr10 | 99619215 | 99619340 | + | ENST00000370602 | TSF |
| 1% | chr20 | 58402976 | 58403213 | + | chr20 | 58411560 | 58411615 | + | ENST00000359926; ENST00000371015;<br>ENST00000395639; ENST00000541461;<br>ENST00000355648; ENST00000361300;<br>ENST00000395636 | TSF |
| 1% | chr7 | 95053394 | 95053140 | − | chr7 | 95045609 | 95045554 | − | ENST00000536183; ENST00000455123;<br>ENST00000433091; ENST00000222572 | TSF |
| 1% | chr7 | 95053394 | 95053140 | − | chr7 | 95045609 | 95045554 | − | ENST00000536183; ENST00000455123;<br>ENST00000433091; ENST00000222572 | TSF |
| 1% | chr7 | 95053394 | 95053140 | − | chr7 | 95045609 | 95045554 | − | ENST00000536183; ENST00000455123;<br>ENST00000433091; ENST00000222572 | TSF |
| 1% | chr10 | 5050548 | 5050220 | − | chr10 | 5043873 | 5043706 | − | ENST00000380753; ENST00000421196;<br>ENST00000407674; ENST00000604507;<br>ENST00000455190 | TSF |
| 1% | chr10 | 5050548 | 5050220 | − | chr10 | 5043873 | 5043706 | − | ENST00000380753; ENST00000421196;<br>ENST00000407674; ENST00000604507;<br>ENST00000455190 | TSF |
| 1% | chr10 | 5050548 | 5050220 | − | chr10 | 5043873 | 5043706 | − | ENST00000380753; ENST00000421196;<br>ENST00000407674; ENST00000604507;<br>ENST00000455190 | TSF |
| 1% | chr10 | 5050548 | 5050220 | − | chr10 | 5043873 | 5043706 | − | ENST00000380753; ENST00000421196;<br>ENST00000407674; ENST00000604507;<br>ENST00000455190 | TSF |
| 1% | chr19 | 50492224 | 50492051 | − | chr19 | 50491749 | 50491625;<br>50491629 | − | ENST00000593919; ENST00000316763;<br>ENST00000377011; ENST00000599538;<br>ENST00000443401; ENST00000601341;<br>ENST00000594948; ENST00000601912;<br>ENST00000594092; ENST00000593912 | TSF |
| 1% | chr19 | 50492224 | 50492051 | − | chr19 | 50491749 | 50491625;<br>50491629 | − | ENST00000593919; ENST00000316763;<br>ENST00000377011; ENST00000599538;<br>ENST00000443401; ENST00000601341;<br>ENST00000594948; ENST00000601912;<br>ENST00000594092; ENST00000593912 | TSF |
| 1% | chr19 | 50492224 | 50492051 | − | chr19 | 50491749 | 50491625;<br>50491629 | − | ENST00000593919; ENST00000316763;<br>ENST00000377011; ENST00000599538;<br>ENST00000443401; ENST00000601341;<br>ENST00000594948; ENST00000601912;<br>ENST00000594092; ENST00000593912 | TSF |
| 1% | chr19 | 50492224 | 50492051 | − | chr19 | 50491749 | 50491625;<br>50491629 | − | ENST00000593919; ENST00000316763;<br>ENST00000377011; ENST00000599538;<br>ENST00000443401; ENST00000601341;<br>ENST00000594948; ENST00000601912; | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 1% | chr10 | 5060345 | 5060092 | − | chr1 | 5043783 | 5043706 | − | ENST00000594092; ENST00000593912 ENST00000380753; ENST00000421196; ENST00000407674; ENST00000604507; ENST00000455190 | TSF |
| 1% | chr10 | 5060345 | 5060092 | − | chr10 | 5043783 | 5043706 | − | ENST00000380753; ENST00000421196; ENST00000407674; ENST00000604507; ENST00000455190 | TSF |
| 1% | chr10 | 5060345 | 5060092 | − | chr10 | 5043783 | 5043706 | − | ENST00000380753; ENST00000421196; ENST00000407674; ENST00000604507; ENST00000455190 | TSF |
| 1% | chr10 | 5060345 | 5060092 | − | chr10 | 5043783 | 5043706 | − | ENST00000380753; ENST00000421196; ENST00000407674; ENST00000604507; ENST00000455190 | TSF |
| 1% | chr14 | 105642036 | 105641815 | − | chr14 | 105639598 | 105639358 | − | ENST00000392568 | TSF |
| 1% | chr5 | 34914125 | 34914032 | − | chr5 | 34913683 | 34913575 | − | ENST00000382038; ENST00000341754 | TSF |
| 1% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 1% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 1% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 1% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 1% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 1% | chr4 | 39516601 | 39516533 | − | chr4 | 39515804 | 39515703; 39515713 | − | ENST00000316423; ENST00000501493; ENST00000506179; ENST00000515021; ENST00000514106; ENST00000509391; ENST00000505698 | TSF |
| 1% | chr20 | 44442461 | 44442685 | + | chr20 | 44443023 | 44443109 | + | ENST00000356455; ENST00000405520; ENST00000335046; ENST00000372568 | TSF |
| 1% | chr20 | 44442461 | 44442685 | + | chr20 | 44443023 | 44443109 | + | ENST00000356455; ENST00000405520; ENST00000335046; ENST00000372568 | TSF |
| 1% | chr17 | 66244121 | 66244199 | + | chr17 | 66244785 | 66244846 | + | ENST00000584837 | TSF |
| 1% | chr17 | 17051276 | 17051346 | + | chr17 | 17053458 | 17053547 | + | ENST00000395811; ENST00000444976; ENST00000395804; ENST00000341712; ENST00000584067 | TSF |
| 1% | chr17 | 17051276 | 17051346 | + | chr17 | 17053458 | 17053547 | + | ENST00000395811; ENST00000444976; ENST00000395804; ENST00000341712; ENST00000584067 | TSF |
| 1% | chr2 | 90168849 | 90168893 | + | chr2 | 90193334 | 90193424 | + | ENST00000390275 | TSF |
| 1% | chr19 | 50174724 | 50174836 | + | chr19 | 50176955 | 50177005; 50177034 | + | ENST00000441864; ENST00000246785; ENST00000598306; ENST00000600947 | TSF |
| 1% | chr19 | 50174724 | 50174836 | + | chr19 | 50176955 | 50177005; 50177034 | + | ENST00000441864; ENST00000246785; ENST00000598306; ENST00000600947 | TSF |
| 1% | chr11 | 85339945 | 85340247 | + | chr11 | 85342731 | 85342852 | + | ENST00000358867; ENST00000534341 | TSF |
| 1% | chr11 | 85339945 | 85340247 | + | chr1 | 85342731 | 85342852 | + | ENST00000358867; ENST00000534341 | TSF |
| 1% | chr19 | 17421511 | 17421655 | + | chr19 | 17424832 | 17424912 | + | ENST00000593466; ENST00000359866; ENST00000596582 | TSF |
| 1% | chr3 | 32323981 | 32324151 | + | chr3 | 32398865 | 32399038 | + | ENST00000307526 | TSF |
| 1% | chrX | 107265928 | 107266261 | + | chrX | 107301268 | 107301431 | + | ENST00000415430; ENST00000217957; ENST00000458383 | TSF |
| 1% | chrX | 107265928 | 107266261 | + | chrX | 107301268 | 107301431 | + | ENST00000415430; ENST00000217957; ENST00000458383 | TSF |
| 1% | chrX | 107265928 | 107266261 | + | chrX | 107301268 | 107301431 | + | ENST00000415430; ENST00000217957; ENST00000458383 | TSF |
| 1% | chr2 | 143715736 | 143715823 | + | chr2 | 143718193 | 143718339 | + | ENST00000264170; ENST00000375773; ENST00000409512 | TSF |
| 1% | chr2 | 143715736 | 143715823 | + | chr2 | 143718193 | 143718339 | + | ENST00000264170; ENST00000375773; ENST00000409512 | TSF |
| 1% | chr8 | 98817265 | 98817331 | + | chr8 | 98817581 | 98817692 | + | ENST00000445593; ENST00000521545; ENST00000517924 | TSF |
| 1% | chr8 | 98817265 | 98817331 | + | chr8 | 98817581 | 98817692 | + | ENST00000445593; ENST00000521545; ENST00000517924 | TSF |
| 1% | chr17 | 45698288 | 45698367 | + | chr17 | 45699134 | 45699286 | + | ENST00000530173; ENST00000322157; ENST00000544660; ENST00000528565 | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 1% | chr4 | 40352026 | 40352049 | + | chr4 | 40355996 | 40356537 | + | ENST00000310169 | TSF |
| 1% | chr21 | 39513161 | 39513404 | + | chr21 | 39528398 | 39528496 | + | ENST00000357704; ENST00000400477 | TSF |
| 1% | chr8 | 63314966 | 63315263 | + | chr8 | 63492098 | 63492235 | + | ENST00000523211; ENST00000524201; ENST00000328472 | TSF |
| 1% | chr8 | 63314966 | 63315263 | + | chr8 | 63492098 | 63492235 | + | ENST00000523211; ENST00000524201; ENST00000328472 | TSF |
| 1% | chr12 | 8864869 | 8864879 | + | chr12 | 8866407 | 8866637 | + | ENST00000537189 | TSF |
| 1% | chr7 | 65418154 | 65418399 | + | chr7 | 65419061 | 65419287; 65419400 | + | ENST00000360768; ENST00000434382 | TSF |
| 1% | chr7 | 65418154 | 65418399 | + | chr7 | 65419061 | 65419287; 65419400 | + | ENST00000360768; ENST00000434382 | TSF |
| 1% | chr4 | 186461046 | 186460994 | − | chr22 | 23243156 | 23243475 | + | ENST00000390323 | TSF |
| 1% | chr8 | 140818443 | 140818376 | − | chr8 | 140744445 | 140744222 | − | ENST00000389327; ENST00000389328; ENST00000520857; ENST00000438773 | TSF |
| 1% | chr6 | 39268199 | 39268149 | − | chr6 | 39267513 | 39267203 | − | ENST00000373231 | TSF |
| 1% | chr20 | 25841506 | 25840376 | − | chr20 | 25755948 | 25755497; 25755659 | − | ENST00000376403; ENST00000584071 | TSF |
| 1% | chr20 | 25841506 | 25840376 | − | chr20 | 25755948 | 25755497; 25755659 | − | ENST00000376403; ENST00000584071 | TSF |
| 1% | chr4 | 57560508 | 57559925 | − | chr4 | 57522178 | 57522023; 57522025 | − | ENST00000420433; ENST00000554144; ENST00000508121; ENST00000557328 | TSF |
| 1% | chr4 | 57560508 | 57559925 | − | chr4 | 57522178 | 57522023; 57522025 | − | ENST00000420433; ENST00000554144; ENST00000508121; ENST00000557328 | TSF |
| 1% | chr4 | 57560508 | 57559925 | − | chr4 | 57522178 | 57522023; 57522025 | − | ENST00000420433; ENST00000554144; ENST00000508121; ENST00000557328 | TSF |
| 1% | chr20 | 25843181 | 25842039 | − | chr20 | 25755948 | 25755497; 25755659 | − | ENST00000376403; ENST00000584071 | TSF |
| 1% | chr20 | 25843181 | 25842039 | − | chr20 | 25755948 | 25755497; 25755659 | − | ENST00000376403; ENST00000584071 | TSF |
| 1% | chr19 | 46194689 | 46194670 | − | chr19 | 46191824 | 46191645 | − | ENST00000342669; ENST00000588301; ENST00000590212 | TSF |
| 1% | chr19 | 46194689 | 46194670 | − | chr19 | 46191824 | 46191645 | − | ENST00000342669; ENST00000588301; ENST00000590212 | TSF |
| 1% | chr21 | 38273278 | 38272892 | − | chr21 | 38269431 | 38269160 | − | ENST00000336648; ENST00000399120 | TSF |
| 1% | chr4 | 162586244 | 162585968 | − | chr4 | 162577646 | 162577480 | − | ENST00000306100; ENST00000379164; ENST00000536695; ENST00000427802 | TSF |
| 1% | chr4 | 162586244 | 162585968 | − | chr4 | 162577646 | 162577480 | − | ENST00000306100; ENST00000379164; ENST00000536695; ENST00000427802 | TSF |
| 1% | chr20 | 25844836 | 25843696 | − | chr20 | 25755948 | 25755497; 25755659 | − | ENST00000376403; ENST00000584071 | TSF |
| 1% | chr20 | 25844836 | 25843696 | − | chr20 | 25755948 | 25755497; 25755659 | − | ENST00000376403; ENST00000584071 | TSF |
| 1% | chrX | 138072952 | 138072670 | − | chrX | 137939841 | 137939674 | − | ENST00000370603; ENST00000436198; ENST00000455663; ENST00000448673 | TSF |
| 1% | chrX | 138072952 | 138072670 | − | chrX | 137939841 | 137939674 | − | ENST00000370603; ENST00000436198; ENST00000455663; ENST00000448673 | TSF |
| 1% | chrX | 138072952 | 138072670 | − | chrX | 137939841 | 137939674 | − | ENST00000370603; ENST00000436198; ENST00000455663; ENST00000448673 | TSF |
| 1% | chrX | 138072952 | 138072670 | − | chrX | 137939841 | 137939674 | − | ENST00000370603; ENST00000436198; ENST00000455663; ENST00000448673 | TSF |
| 1% | chr2 | 97561135 | 97560977 | − | chr2 | 97559788 | 97559663 | − | ENST00000327896; ENST00000417561; ENST00000490605 | TSF |
| 1% | chr11 | 60934781 | 60933962 | − | chr11 | 60901679 | 60901508 | − | ENST00000301765; ENST00000538036 | TSF |
| 1% | chr11 | 60934781 | 60933962 | − | chr11 | 60901679 | 60901508 | − | ENST00000301765; ENST00000538036 | TSF |
| 1% | chr9 | 130929922 | 130929818 | − | chr9 | 130929443 | 130929374 | − | ENST00000372954; ENST00000393608; ENST00000541172; ENST00000325721; ENST00000357558; ENST00000538431; ENST00000277465; ENST00000372948; ENST00000372938; ENST00000415526 | TSF |
| 1% | chr10 | 5060345 | 5060040 | − | chr10 | 5043873 | 5043706 | − | ENST00000380753; ENST00000421196; ENST00000407674; ENST00000604507; ENST00000455190 | TSF |
| 1% | chr10 | 5060345 | 5060040 | − | chr10 | 5043873 | 5043706 | − | ENST00000380753; ENST00000421196; ENST00000407674; ENST00000604507; ENST00000455190 | TSF |
| 1% | chr10 | 5060345 | 5060040 | − | chr10 | 5043873 | 5043706 | − | ENST00000380753; ENST00000421196; ENST00000407674; ENST00000604507; ENST00000455190 | TSF |
| 1% | chr10 | 5060345 | 5060040 | − | chr10 | 5043873 | 5043706 | − | ENST00000380753; ENST00000421196; ENST00000407674; ENST00000604507; ENST00000455190 | TSF |
| 1% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 1% | chr1 | 156305455 | 156305264 | − | chr1 | 156304709 | 156304659 | − | ENST00000295688; ENST00000368258; ENST00000413555; ENST00000496684; | TSF |

TABLE 38-continued

Transcript fusion for Lung Adenocarcinoma (LUAD) Coordinates of the fusion sequences for which the donor is the TE.

| 1 | 2' | 3' | 4' | 5' | 6' | 7' | 8' | 9' | 10 | 11' |
|---|---|---|---|---|---|---|---|---|---|---|
| 1% | chr1 | 156305455 | 156305264 | − | chr1 | 156304709 | 156304659 | − | ENST00000478640; ENST00000415548 ENST00000295688; ENST00000368258; ENST00000413555; ENST00000496684; | TSF |
| 1% | chr1 | 156305455 | 156305264 | − | chr1 | 156304709 | 156304659 | − | ENST00000478640; ENST00000415548 ENST00000295688; ENST00000368258; ENST00000413555; ENST00000496684; | TSF |
| 1% | chr1 | 156305455 | 156305264 | − | chr1 | 156304709 | 156304659 | − | ENST00000478640; ENST00000415548 ENST00000295688; ENST00000368258; ENST00000413555; ENST00000496684; | TSF |
| 1% | chr1 | 156305455 | 156305264 | − | chr1 | 156304709 | 156304659 | − | ENST00000478640; ENST00000415548 ENST00000295688; ENST00000368258; ENST00000413555; ENST00000496684; | TSF |

TABLE 39

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 49% | chr12 | 71509738 | 71509630 | − | ENST00000549357 | chr12 | 71504233 | 71503634 | − | TAF |
| 31% | chr10 | 5040939 | 5040817 | − | ENST00000380753; ENST00000421196; ENST00000407674; ENST00000604507 | chr10 | 5002427 | 5002117 | − | TAF |
| 31% | chr10 | 5040939 | 5040817 | − | ENST00000380753; ENST00000421196; ENST00000407674; ENST00000604507 | chr10 | 5002427 | 5002117 | − | TAF |
| 27% | chr5 | 54993786 | 54993674 | − | ENST00000396865; ENST00000539768; ENST00000318672; ENST00000508124; ENST00000511233; ENST00000503891; ENST00000513993; ENST00000505563; ENST00000506624; ENST00000507109 | chr5 | 54993040 | 54992544 | − | TSF |
| 26% | chr3 | 118943092 | 118942905 | − | ENST00000483209; ENST00000467604; ENST00000359213; ENST00000393765; ENST00000480814 | chr3 | 118938512 | 118938188 | − | TAF |
| 23% | chr3 | 196230044 | 196229744 | − | ENST00000318037; ENST00000437070 | chr3 | 196223342 | 196223041 | − | TAF |
| 22% | chrX | 152864474 | 152864420 | − | ENST00000406277 | chrX | 152863164 | 152862704 | − | TAF |
| 20% | chr3 | 182566264 | 182566345 | + | ENST00000323116; ENST00000498086 | chr3 | 182566968 | 182567869 | + | TAF |
| 20% | chr3 | 182566264 | 182566345 | + | ENST00000323116; ENST00000498086 | chr3 | 182566968 | 182567869 | + | TAF |
| 19% | chr10 | 47747112 | 47747132 | + | ENST00000340243; ENST00000374277; ENST00000449464; ENST00000538825 | chr10 | 48278725 | 48278896 | + | TAF |
| 15% | chr1 | 153534067 | 153533988 | − | ENST00000368708; ENST00000487430; ENST00000497140; ENST00000368710; ENST00000368709 | chr1 | 153532853 | 153532704 | − | TAF |
| 15% | chr1 | 153534067 | 153533988 | − | ENST00000368708; ENST00000487430; ENST00000497140; ENST00000368710; ENST00000368709 | chr1 | 153532853 | 153532704 | − | TAF |
| 14% | chr7 | 4026818 | 4026954 | + | ENST00000404826; ENST00000389531 | chr7 | 4027977 | 4028157 | + | TAF |
| 14% | chr20 | 35842163 | 35842268 | + | ENST00000237530; ENST00000373622 | chr20 | 35844460 | 35844765 | + | TAF |
| 14% | chr20 | 35842163 | 35842268 | + | ENST00000237530; ENST00000373622 | chr20 | 35844460 | 35844765 | + | TAF |
| 14% | chrX | 41598709 | 41598637 | − | ENST00000421587; ENST00000318588; ENST00000361962; ENST00000378163; ENST00000378158; ENST00000378166; ENST00000442742; ENST00000378154 | chrX | 41557348 | 41557057 | − | TSF |
| 13% | chr19 | 35612126 | 35612149 | + | ENST00000454903; ENST00000406242; ENST00000604404; ENST00000435734; ENST00000603181; ENST00000604255; ENST00000344013; ENST00000346446; ENST00000603449; ENST00000406988; ENST00000605550; ENST00000604804; ENST00000605552; ENST00000535103; ENST00000603524; ENST00000604621; ENST00000605677 | chr19 | 35613565 | 35613610 | + | TAF |
| 13% | chr19 | 35612126 | 35612149 | + | ENST00000454903; ENST00000406242; ENST00000604404; ENST00000435734; ENST00000603181; ENST00000604255; ENST00000344013; ENST00000346446; ENST00000603449; ENST00000406988; ENST00000605550; ENST00000604804; ENST00000605552; ENST00000535103; ENST00000603524; ENST00000604621; ENST00000605677 | chr19 | 35613565 | 35613610 | + | TAF |
| 13% | chr14 | 104040444 | 104040507 | + | ENST00000409074; ENST00000472726; ENST00000556253; ENST00000247618; | chr14 | 104051201 | 104051490 | + | TAF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 13% | chr14 | 104040444 | 104040507 | + | ENST00000495778 ENST00000409074; ENST00000472726; ENST00000556253; ENST00000247618; | chr14 | 104051201 | 104051490 | + | TAF |
| 13% | chr14 | 104040444 | 104040507 | + | ENST00000495778 ENST00000409074; ENST00000472726; ENST00000556253; ENST00000247618; ENST00000495778 | chr14 | 104051201 | 104051490 | + | TAF |
| 13% | chr7 | 81964567 | 81964451 | − | ENST00000356860; ENST00000356253; ENST00000423588 | chr7 | 81929467 | 81929190 | − | TSF |
| 12% | chr9 | 33001602; 33001577 | 33001565 | − | ENST00000379825; ENST00000309615; ENST00000397172; ENST00000379819; ENST00000474658; ENST00000476858; ENST00000379812; ENST00000473221; ENST00000464632; ENST00000478279 | chr9 | 32997346 | 32997346 | − | TAF |
| 12% | chr9 | 33001602; 33001577 | 33001565 | − | ENST00000379825; ENST00000309615; ENST00000397172; ENST00000379819; ENST00000474658; ENST00000476858; ENST00000379812; ENST00000473221; ENST00000464632; ENST00000478279 | chr9 | 32997346 | 32997346 | − | TAF |
| 12% | chr6 | 139363856 | 139363999 | + | ENST00000367660 | chr6 | 139372258 | 139372516 | + | TAF |
| 11% | chr3 | 182804576; 182804522; 182804572 | 182804481 | − | ENST00000265594; ENST00000492597; ENST00000497959; ENST00000476176 | chr3 | 182797071 | 182796912 | − | TAF |
| 11% | chr3 | 182804576; 182804522; 182804572 | 182804481 | − | ENST00000265594; ENST00000492597; ENST00000497959; ENST00000476176 | chr3 | 182797071 | 182796912 | − | TAF |
| 11% | chr3 | 182804576; 182804522; 182804572 | 182804481 | − | ENST00000265594; ENST00000492597; ENST00000497959; ENST00000476176 | chr3 | 182797071 | 182796912 | − | TAF |
| 11% | chr3 | 182804576; 182804522; 182804572 | 182804481 | − | ENST00000265594; ENST00000492597; ENST00000497959; ENST00000476176 | chr3 | 182797071 | 182796912 | − | TAF |
| 11% | chr12 | 64833024 | 64833095 | + | ENST00000332707 | chr12 | 64833417 | 64833459 | + | TAF |
| 10% | chr5 | 1802435 | 1802488 | + | ENST00000274137; ENST00000469176 | chr5 | 1811023 | 1811428 | + | TAF |
| 10% | chr4 | 57319769 | 57319927 | + | ENST00000514888; ENST00000264221; ENST00000505164; ENST00000399688; ENST00000512576 | chr4 | 57321183 | 57321327 | + | TSF |
| 10% | chr4 | 57319769 | 57319927 | + | ENST00000514888; ENST00000264221; ENST00000505164; ENST00000399688; ENST00000512576 | chr4 | 57321183 | 57321327 | + | TSF |
| 10% | chr4 | 57319769 | 57319927 | + | ENST00000514888; ENST00000264221; ENST00000505164; ENST00000399688; ENST00000512576 | chr4 | 57321183 | 57321327 | + | TSF |
| 9% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 9% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 7% | chr16 | 16149949 | 16150152 | + | ENST00000399410; ENST00000345148; ENST00000346370; ENST00000349029; ENST00000351154; ENST00000399408; ENST00000572882 | chr16 | 16151288 | 16151380 | + | TSF |
| 7% | chr16 | 16149949 | 16150152 | + | ENST00000399410; ENST00000345148; ENST00000346370; ENST00000349029; ENST00000351154; ENST00000399408; ENST00000572882 | chr16 | 16151288 | 16151380 | + | TSF |
| 7% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 7% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 7% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 7% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| | | | | | ENST00000541394; ENST00000358383; ENST00000392911; ENST00000412715; ENST00000417507; ENST00000457614 | | | | | |
| 7% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 6% | chr3 | 185414451 | 185414400 | − | ENST00000382199; ENST00000421047; ENST00000457616; ENST00000346192 | chr3 | 185411016 | 185410789 | − | TSF |
| 6% | chr3 | 185414451 | 185414400 | − | ENST00000382199; ENST00000421047; ENST00000457616; ENST00000346192 | chr3 | 185411016 | 185410789 | − | TSF |
| 6% | chr1 | 225156461 | 225156576 | + | ENST00000430092; ENST00000400952; ENST00000366849; ENST00000439375 | chr1 | 225157336 | 225158402 | + | TSF |
| 6% | chr1 | 225156461 | 225156576 | + | ENST00000430092; ENST00000400952; ENST00000366849; ENST00000439375 | chr1 | 225157336 | 225158402 | + | TSF |
| 6% | chr22 | 35819207 | 35819334 | + | ENST00000216122; ENST00000382011 | chr22 | 35846150 | 35846200 | + | TSF |
| 6% | chr22 | 35819207 | 35819334 | + | ENST00000216122; ENST00000382011 | chr22 | 35846150 | 35846200 | + | TSF |
| 6% | chr7 | 22532348 | 22532184 | − | ENST00000406890; ENST00000404369; ENST00000424363 | chr7 | 22512853 | 22512669 | − | TSF |
| 6% | chr7 | 22532348 | 22532184 | − | ENST00000406890; ENST00000404369; ENST00000424363 | chr7 | 22512853 | 22512669 | − | TSF |
| 5% | chr12 | 86272123 | 86272347 | + | ENST00000256010 | chr12 | 86274455 | 86274746 | + | TSF |
| 5% | chr5 | 1802435 | 1802488 | + | ENST00000274137; ENST0000469176 | chr5 | 1811082 | 1811428 | + | TSF |
| 5% | chr2 | 176860312; 176860292 | 176860286 | − | ENST00000272748; ENST00000544803; ENST00000392540; ENST00000445472 | chr2 | 176859008 | 176858934 | − | TSF |
| 5% | chr2 | 176860312; 176860292 | 176860286 | − | ENST00000272748; ENST00000544803; ENST00000392540; ENST00000445472 | chr2 | 176859008 | 176858934 | − | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr12 | 71509738 | 71509630 | − | ENST00000549357 | chr12 | 71507025 | 71506982 | − | TSF |
| 5% | chr1 | 234546277 | 234546191 | − | ENST00000040877 | chr1 | 234545319 | 234545287 | − | TSF |
| 4% | chr1 | 63955889 | 63955754 | − | ENST00000371092; ENST00000271002; ENST00000489099; ENST00000283568 | chr1 | 63952444 | 63951983 | − | TSF |
| 4% | chr1 | 63955889 | 63955754 | − | ENST00000371092; ENST00000271002; ENST00000489099; ENST00000283568 | chr1 | 63952444 | 63951983 | − | TSF |
| 4% | chr3 | 190030825 | 190030661 | − | ENST00000295522 | chr3 | 190030018 | 190029730 | − | TSF |
| 4% | chr7 | 55270210 | 55270401 | + | ENST00000455089 | chr7 | 55272949 | 55272949 | + | TSF |
| 4% | chr20 | 29632611 | 29632721 | + | ENST00000278882; ENST00000358464 | chr20 | 29652086 | 29652324 | + | TSF |
| 4% | chr7 | 95668589 | 95668733 | + | ENST00000447467; ENST00000324972; ENST00000537881; ENST00000437599; ENST00000359388; ENST00000457059 | chr7 | 95670774 | 95671058 | + | TSF |
| 4% | chr7 | 95668589 | 95668733 | + | ENST00000447467; ENST00000324972; ENST00000537881; ENST00000437599; ENST00000359388; | chr7 | 95670774 | 95671058 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 4% | chr7 | 95668589 | 95668733 | + | ENST00000457059 ENST00000447467; ENST00000324972; ENST00000537881; ENST00000437599; ENST00000359388; | chr7 | 95670774 | 95671058 | + | TSF |
| 4% | chr7 | 95668589 | 95668733 | + | ENST00000457059 ENST00000447467; ENST00000324972; ENST00000537881; ENST00000437599; ENST00000359388; | chr7 | 95670774 | 95671058 | + | TSF |
| 4% | chr5 | 80769589 | 80769519 | − | ENST00000457059 ENST00000320672; ENST00000509053; ENST00000514493; ENST00000504985; ENST00000512923; ENST00000505980; ENST00000515395; ENST00000509013 | chr5 | 80769370 | 80769065 | − | TSF |
| 4% | chr5 | 80769589 | 80769519 | − | ENST00000320672; ENST00000509053; ENST00000514493; ENST00000504985; ENST00000512923; ENST00000505980; ENST00000515395; ENST00000509013 | chr5 | 80769370 | 80769065 | − | TSF |
| 4% | chr5 | 80769589 | 80769519 | − | ENST00000320672; ENST00000509053; ENST00000514493; ENST00000504985; ENST00000512923; ENST00000505980; ENST00000515395; ENST00000509013 | chr5 | 80769370 | 80769065 | − | TSF |
| 4% | chr5 | 80769589 | 80769519 | − | ENST00000320672; ENST00000509053; ENST00000514493; ENST00000504985; ENST00000512923; ENST00000505980; ENST00000515395; ENST00000509013 | chr5 | 80769370 | 80769065 | − | TSF |
| 4% | chr5 | 80769589 | 80769519 | − | ENST00000320672; ENST00000509053; ENST00000514493; ENST00000504985; ENST00000512923; ENST00000505980; ENST00000515395; ENST00000509013 | chr5 | 80769370 | 80769065 | − | TSF |
| 3% | chr8 | 109468102 | 109468159 | + | ENST00000220853; ENST00000519642 | chr8 | 109468381 | 109468590 | + | TSF |
| 3% | chr8 | 109468102 | 109468159 | + | ENST00000220853; ENST00000519642 | chr8 | 109468381 | 109468590 | + | TSF |
| 3% | chr9 | 125054028 | 125054119 | + | ENST00000297908; ENST00000344641; ENST00000373723; ENST00000373729; ENST00000394315 | chr9 | 125068067 | 125068171 | + | TSF |
| 3% | chr9 | 125054028 | 125054119 | + | ENST00000297908; ENST00000344641; ENST00000373723; ENST00000373729; ENST00000394315 | chr9 | 125068067 | 125068171 | + | TSF |
| 3% | chr9 | 125054028 | 125054119 | + | ENST00000297908; ENST00000344641; ENST00000373723; ENST00000373729; ENST00000394315 | chr9 | 125068067 | 125068171 | + | TSF |
| 3% | chr19 | 15289752 | 15289634 | − | ENST00000263388; ENST00000601011 | chr19 | 15289244 | 15289201 | − | TSF |
| 3% | chr19 | 15289752 | 15289634 | − | ENST00000263388; ENST00000601011 | chr19 | 15289244 | 15289201 | − | TSF |
| 3% | chr2 | 89160434 | 89160398 | − | ENST00000390239 | chr2 | 89129384 | 89129304 | − | TSF |
| 3% | chr6 | 84772612 | 84772711 | + | ENST00000257776 | chr6 | 84775517 | 84775723 | + | TSF |
| 3% | chr20 | 3614958 | 3615036 | + | ENST00000262919 | chr20 | 3615708 | 3616042 | + | TSF |
| 3% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 3% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 3% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 3% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 3% | chr19 | 46627413 | 46627143 | − | ENST00000341415 | chr19 | 46623577 | 46622963 | − | TSF |
| 3% | chr7 | 23300075 | 23300392 | + | ENST00000258733; ENST00000381990; ENST00000539136; ENST00000453162 | chr7 | 23300981 | 23301414 | + | TSF |
| 3% | chr7 | 23300075 | 23300392 | + | ENST00000258733; ENST00000381990; ENST00000539136; ENST00000453162 | chr7 | 23300981 | 23301414 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr7 | 23300075 | 23300392 | + | ENST00000258733; ENST00000381990; ENST00000539136; ENST00000453162 | chr7 | 23300981 | 23301414 | + | TSF |
| 3% | chr1 | 11115983; 11115877 | 11115838 | − | ENST00000376957; ENST00000490101 | chr1 | 11115464 | 11115178 | − | TSF |
| 3% | chr1 | 11115983; 11115877 | 11115838 | − | ENST00000376957; ENST00000490101 | chr1 | 11115464 | 11115178 | − | TSF |
| 3% | chr12 | 113403549; 113403702 | 113403834 | + | ENST00000228928; ENST00000546973 | chr12 | 113404028 | 113404051 | + | TSF |
| 3% | chr12 | 113403549; 113403702 | 113403834 | + | ENST00000228928; ENST00000546973 | chr12 | 113404028 | 113404051 | + | TSF |
| 3% | chr20 | 60578330 | 60578216 | − | ENST00000252996; ENST00000488539 | chr20 | 60576919 | 60576839 | − | TSF |
| 3% | chr20 | 60578330 | 60578216 | − | ENST00000252996; ENST00000488539 | chr20 | 60576919 | 60576839 | − | TSF |
| 3% | chr1 | 180283857 | 180283827 | − | ENST00000367595 | chr1 | 180281457 | 180281103 | − | TSF |
| 3% | chr16 | 16381600 | 16381719 | + | ENST00000399336; ENST00000263012; ENST00000538468 | chr16 | 16382422 | 16382605 | + | TSF |
| 3% | chr16 | 16381600 | 16381719 | + | ENST00000399336; ENST00000263012; ENST00000538468 | chr16 | 16382422 | 16382605 | + | TSF |
| 3% | chrX | 119708472 | 119708406 | − | ENST00000404115 | chrX | 119705855 | 119705820 | − | TSF |
| 3% | chr6 | 37611719 | 37611585 | − | ENST00000297153; ENST00000434837; ENST00000505425; ENST00000418178 | chr6 | 37611139 | 37611040 | − | TSF |
| 3% | chr6 | 37611719 | 37611585 | − | ENST00000297153; ENST00000434837; ENST00000505425; ENST00000418178 | chr6 | 37611139 | 37611040 | − | TSF |
| 3% | chr6 | 37611719 | 37611585 | − | ENST00000297153; ENST00000434837; ENST00000505425; ENST00000418178 | chr6 | 37611139 | 37611040 | − | TSF |
| 3% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 3% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 3% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 3% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 3% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 3% | chr5 | 31493400 | 31493314 | − | ENST00000511367; ENST00000344624; ENST00000442743; ENST00000513349 | chr5 | 31489188 | 31488661 | − | TSF |
| 3% | chr5 | 31493400 | 31493314 | − | ENST00000511367; ENST00000344624; ENST00000442743; ENST00000513349 | chr5 | 31489188 | 31488661 | − | TSF |
| 2% | chr11 | 60701014 | 60701216 | + | ENST00000453848; ENST00000005286; ENST00000536409 | chr11 | 60701443 | 60701575 | + | TSF |
| 2% | chr11 | 60701014 | 60701216 | + | ENST00000453848; ENST00000005286; ENST00000536409 | chr11 | 60701443 | 60701575 | + | TSF |
| 2% | chr11 | 60701014 | 60701216 | + | ENST00000453848; ENST00000005286; ENST00000536409 | chr11 | 60701443 | 60701575 | + | TSF |
| 2% | chr2 | 231236313 | 231236366 | + | ENST00000444636; ENST00000415673; ENST00000243810; ENST00000396563; ENST00000458341 | chr2 | 231236728 | 231236962 | + | TSF |
| 2% | chr2 | 231236313 | 231236366 | + | ENST00000444636; ENST00000415673; ENST00000243810; ENST00000396563; | chr2 | 231236728 | 231236962 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr12 | 71928895 | 71928966 | + | ENST00000458341; ENST00000266674; ENST00000536515; ENST00000540815 | chr12 | 71938771 | 71938901 | + | TSF |
| 2% | chr18 | 61627392 | 61627509 | + | ENST00000408945 | chr18 | 61628870 | 61629168 | + | TSF |
| 2% | chr7 | 135635430 | 135635347 | − | ENST00000393085 | chr7 | 135585557 | 135585512 | − | TSF |
| 2% | chr19 | 53352466; 53352373 | 53352340 | − | ENST00000595646; ENST00000243639; ENST00000597924; ENST00000601847 | chr19 | 53339322 | 53339166 | − | TSF |
| 2% | chr19 | 53352466; 53352373 | 53352340 | − | ENST00000595646; ENST00000243639; ENST00000597924; ENST00000601847 | chr19 | 53339322 | 53339166 | − | TSF |
| 2% | chr3 | 196214449 | 196214270 | − | ENST00000318037 | chr3 | 196213499 | 196213226 | − | TSF |
| 2% | chr7 | 22532348 | 22532184 | − | ENST00000406890; ENST00000404369; ENST00000424363 | chr7 | 22531483 | 22531370 | − | TSF |
| 2% | chr7 | 22532348 | 22532184 | − | ENST00000406890; ENST00000404369; ENST00000424363 | chr7 | 22531483 | 22531370 | − | TSF |
| 2% | chr9 | 94991408 | 94991283 | − | ENST00000375643; ENST00000443024; ENST00000447699 | chr9 | 94990268 | 94989087 | − | TSF |
| 2% | chr9 | 94991408 | 94991283 | − | ENST00000375643; ENST00000443024; ENST00000447699 | chr9 | 94990268 | 94989087 | − | TSF |
| 2% | chr8 | 71619168 | 71619388 | + | ENST00000408926; ENST00000520030 | chr8 | 71625661 | 71625673 | + | TSF |
| 2% | chr4 | 86491695 | 86491874 | + | ENST00000395184; ENST00000503995 | chr4 | 86580201 | 86580368 | + | TSF |
| 2% | chr7 | 23313140 | 23313233 | + | ENST00000258733; ENST00000381990; ENST00000539136; ENST00000453162 | chr7 | 23322924 | 23323223 | + | TSF |
| 2% | chr7 | 23313140 | 23313233 | + | ENST00000258733; ENST00000381990; ENST00000539136; ENST00000453162 | chr7 | 23322924 | 23323223 | + | TSF |
| 2% | chr7 | 23313140 | 23313233 | + | ENST00000258733; ENST00000381990; ENST00000539136; ENST00000453162 | chr7 | 23322924 | 23323223 | + | TSF |
| 2% | chr7 | 23313140 | 23313233 | + | ENST00000258733; ENST00000381990; ENST00000539136; ENST00000453162 | chr7 | 23322924 | 23323223 | + | TSF |
| 2% | chr19 | 40711028 | 40711203 | + | ENST00000253055; ENST00000593502; ENST00000597986 | chr19 | 40711395 | 40711597 | + | TSF |
| 2% | chr19 | 40711028 | 40711203 | + | ENST00000253055; ENST00000593502; ENST00000597986 | chr19 | 40711395 | 40711597 | + | TSF |
| 2% | chr19 | 40711028 | 40711203 | + | ENST00000253055; ENST00000593502; ENST00000597986 | chr19 | 40711395 | 40711597 | + | TSF |
| 2% | chr12 | 93873164 | 93873248 | + | ENST00000549982; ENST00000361630; ENST00000552217; ENST00000393128; ENST00000547098; ENST00000549561; ENST00000548545 | chr12 | 93876129 | 93876286 | + | TSF |
| 2% | chr12 | 93873164 | 93873248 | + | ENST00000549982; ENST00000361630; ENST00000552217; ENST00000393128; ENST00000547098; ENST00000549561; ENST00000548545 | chr12 | 93876129 | 93876286 | + | TSF |
| 2% | chr6 | 20758826 | 20758874 | + | ENST00000274695; ENST00000378624; ENST00000378610 | chr6 | 20772038 | 20772218 | + | TSF |
| 2% | chr6 | 20758826 | 20758874 | + | ENST00000274695; ENST00000378624; ENST00000378610 | chr6 | 20772038 | 20772218 | + | TSF |
| 2% | chr2 | 89513203 | 89512947 | − | ENST00000498435 | chr2 | 89389297 | 89388194 | − | TSF |
| 2% | chr19 | 15289752 | 15289634 | − | ENST00000263388; ENST00000601011 | chr19 | 15289358 | 15289201 | − | TSF |
| 2% | chr19 | 15289752 | 15289634 | − | ENST00000263388; ENST00000601011 | chr19 | 15289358 | 15289201 | − | TSF |
| 2% | chr2 | 153003822 | 153003676 | − | ENST00000263904 | chr2 | 153001350 | 153001066 | − | TSF |
| 2% | chr3 | 48716169 | 48715997 | − | ENST00000341520; ENST00000416649; ENST00000294129; ENST00000413374 | chr3 | 48702393 | 48702198 | − | TSF |
| 2% | chr3 | 48716169 | 48715997 | − | ENST00000341520; ENST00000416649; ENST00000294129; ENST00000413374 | chr3 | 48702393 | 48702198 | − | TSF |
| 2% | chr3 | 48716169 | 48715997 | − | ENST00000341520; ENST00000416649; ENST00000294129; ENST00000413374 | chr3 | 48702393 | 48702198 | − | TSF |
| 2% | chr2 | 197662632 | 197662521 | − | ENST00000263956; ENST00000409364 | chr2 | 197661554 | 197661227 | − | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; | chr12 | 53865082 | 53865327 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
|   |   |   |   |   | ENST00000549863; ENST00000359462; ENST00000546463; ENST00000552296; ENST00000552819; ENST00000455667; ENST00000439930; ENST00000548933; ENST00000562264; ENST00000553064; ENST00000547859 |   |   |   |   |   |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | chr12 | 53865082 | 53865327 | + | TSF |
| 2% | chr12 | 53862561; 53862564 | 53862616 | + | ENST00000359282; ENST00000437231; ENST00000447282; ENST00000603815; ENST00000549863; ENST00000359462; ENST00000546463; ENST00000552296; ENST00000552819; ENST00000455667; | chr12 | 53865082 | 53865327 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 2% | chr16 | 78143675 | 78143732 | + | ENST00000439930; ENST00000548933; ENST00000562264; ENST00000553064; ENST00000547859 ENST00000566780; ENST00000402655; ENST00000406884; ENST00000539474; ENST00000355860; ENST00000408984 | chr16 | 78145717 | 78146057 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 2% | chr5 | 41934235 | 41934410 | + | ENST00000296812; ENST00000281623; ENST00000509134 | chr5 | 41935724 | 41936388 | + | |
| 2% | chr2 | 172725333; 172725194 | 172725191 | − | ENST00000422440; ENST00000263812; ENST00000392592; ENST00000426896; ENST00000475360 | chr2 | 172723793 | 172722363 | − | TSF |
| 2% | chr2 | 172725333; 172725194 | 172725191 | − | ENST00000422440; ENST00000263812; ENST00000392592; ENST00000426896; ENST00000475360 | chr2 | 172723793 | 172722363 | − | TSF |
| 2% | chr2 | 172725333; 172725194 | 172725191 | − | ENST00000422440; ENST00000263812; ENST00000392592; ENST00000426896; ENST00000475360 | chr2 | 172723793 | 172722363 | − | TSF |
| 2% | chr19 | 16024719 | 16024559 | − | ENST00000248041; ENST00000402119; ENST00000591841 | chr19 | 16023994 | 16023778 | − | TSF |
| 2% | chr19 | 16024719 | 16024559 | − | ENST00000248041; ENST00000402119; ENST00000591841 | chr19 | 16023994 | 16023778 | − | TSF |
| 2% | chr19 | 46627413 | 46627143 | − | ENST00000341415 | chr19 | 46623564 | 46622963 | − | TSF |
| 2% | chr8 | 141762086 | 141762002 | − | ENST00000524202 | chr8 | 141760508 | 141760403 | − | TSF |
| 2% | chr10 | 5037676 | 5037511 | − | ENST00000380753; ENST00000421196; ENST00000407674 | chr10 | 5023140 | 5022655 | − | TSF |
| 2% | chr10 | 5037676 | 5037511 | − | ENST00000380753; ENST00000421196; ENST00000407674 | chr10 | 5023140 | 5022655 | − | TSF |
| 2% | chr13 | 114157811 | 114157903 | + | ENST00000434316; ENST00000375391 | chr13 | 114159741 | 114159770 | + | TSF |
| 2% | chr7 | 23300075 | 23300392 | + | ENST00000258733; ENST00000381990; ENST00000539136; ENST00000453162 | chr7 | 23301185 | 23301414 | + | TSF |
| 2% | chr7 | 23300075 | 23300392 | + | ENST00000258733; ENST00000381990; ENST00000539136; ENST00000453162 | chr7 | 23301185 | 23301414 | + | TSF |
| 2% | chr7 | 23300075 | 23300392 | + | ENST00000258733; ENST00000381990; ENST00000539136; ENST00000453162 | chr7 | 23301185 | 23301414 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr17 | 36288631 | 36288740 | + | ENST00000327454; ENST00000378174; ENST00000505415; ENST00000539424 | chr17 | 36289142 | 36289609 | + | TSF |
| 2% | chr17 | 36288631 | 36288740 | + | ENST00000327454; ENST00000378174; ENST00000505415; ENST00000539424 | chr17 | 36289142 | 36289609 | + | TSF |
| 2% | chr11 | 65222908 | 65223052 | + | ENST00000309775 | chr11 | 65223772 | 65224450 | + | TSF |
| 2% | chr8 | 42932359 | 42932507 | + | ENST00000302279; ENST00000342116; ENST00000529687; ENST00000533336 | chr8 | 42934165 | 42935743 | + | TSF |
| 2% | chr8 | 42932359 | 42932507 | + | ENST00000302279; ENST00000342116; ENST00000529687; ENST00000533336 | chr8 | 42934165 | 42935743 | + | TSF |
| 2% | chr8 | 42932359 | 42932507 | + | ENST00000302279; ENST00000342116; ENST00000529687; ENST00000533336 | chr8 | 42934165 | 42935743 | + | TSF |
| 2% | chr8 | 42932359 | 42932507 | + | ENST00000302279; ENST00000342116; ENST00000529687; ENST00000533336 | chr8 | 42934165 | 42935743 | + | TSF |
| 2% | chr12 | 28605411; 28605475 | 28605587 | + | ENST00000536154; ENST00000539107; ENST00000545336; ENST00000381256; ENST00000381259; ENST00000306172; ENST00000535212; ENST00000542801 | chr12 | 28624332 | 28624630 | + | TSF |
| 2% | chr12 | 28605411; 28605475 | 28605587 | + | ENST00000536154; ENST00000539107; ENST00000545336; ENST00000381256; ENST00000381259; ENST00000306172; ENST00000535212; ENST00000542801 | chr12 | 28624332 | 28624630 | + | TSF |
| 2% | chr12 | 28605411; 28605475 | 28605587 | + | ENST00000536154; ENST00000539107; ENST00000545336; ENST00000381256; ENST00000381259; ENST00000306172; ENST00000535212; ENST00000542801 | chr12 | 28624332 | 28624630 | + | TSF |
| 2% | chr12 | 28605411; 28605475 | 28605587 | + | ENST00000536154; ENST00000539107; ENST00000545336; ENST00000381256; ENST00000381259; ENST00000306172; ENST00000535212; ENST00000542801 | chr12 | 28624332 | 28624630 | + | TSF |
| 2% | chr12 | 28605411; 28605475 | 28605587 | + | ENST00000536154; ENST00000539107; ENST00000545336; ENST00000381256; ENST00000381259; ENST00000306172; ENST00000535212; ENST00000542801 | chr12 | 28624332 | 28624630 | + | TSF |
| 2% | chr12 | 28605411; 28605475 | 28605587 | + | ENST00000536154; ENST00000539107; ENST00000545336; ENST00000381256; ENST00000381259; ENST00000306172; ENST00000535212; ENST00000542801 | chr12 | 28624332 | 28624630 | + | TSF |
| 2% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 2% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 2% | chr10 | 127483547 | 127483449 | − | ENST00000368797; ENST00000368786 | chr10 | 127473829 | 127473633 | − | TSF |
| 2% | chr16 | 88873689 | 88873890 | + | ENST00000301019 | chr16 | 88875475 | 88875490 | + | TSF |
| 2% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 2% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 2% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 2% | chr10 | 126205749 | 126205840 | + | ENST00000368842 | chr10 | 126251911 | 126252288 | + | TSF |
| 2% | chr12 | 113623819 | 113623826 | + | ENST00000552495 | chr12 | 113623998 | 113624117 | + | TSF |
| 2% | chr17 | 75303223 | 75303279 | + | ENST00000427177 | chr17 | 75307415 | 75307459 | + | TSF |
| 2% | chr15 | 74219125 | 74220226 | + | ENST00000566011; ENST0000261921 | chr15 | 74234853 | 74234966 | + | TSF |
| 2% | chr9 | 5689959 | 5690038 | + | ENST00000251879; ENST00000414202; ENST00000381532; ENST00000418622; ENST00000449720; ENST00000545641 | chr9 | 5712361 | 5712559 | + | TSF |
| 2% | chr9 | 5689959 | 5690038 | + | ENST00000251879; ENST00000414202; ENST00000381532; ENST00000418622; ENST00000449720; ENST00000545641 | chr9 | 5712361 | 5712559 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr9 | 5689959 | 5690038 | + | ENST00000251879; ENST00000414202; ENST00000381532; ENST00000418622; ENST00000449720; ENST00000545641 | chr9 | 5712361 | 5712559 | + | TSF |
| 2% | chr1 | 25891664 | 25891698 | + | ENST00000374338 | chr1 | 25916660 | 25916675 | + | TSF |
| 2% | chrX | 117900807 | 117900939 | + | ENST00000371666 | chrX | 117902549 | 117902902 | + | TSF |
| 2% | chr4 | 56230241 | 56230438 | + | ENST00000264228 | chr4 | 56252510 | 56252750 | + | TSF |
| 2% | chr19 | 19313690; 19313653 | 19313600 | − | ENST00000420605; ENST00000331552; ENST00000544883; ENST00000538165; ENST00000539678 | chr19 | 19313030 | 19312992 | − | TSF |
| 2% | chr19 | 19313690; 19313653 | 19313600 | − | ENST00000420605; ENST00000331552; ENST00000544883; ENST00000538165; ENST00000539678 | chr19 | 19313030 | 19312992 | − | TSF |
| 2% | chr17 | 36343995 | 36343886 | − | ENST00000518551; ENST00000354664; ENST00000339023; ENST00000519532; ENST00000537432 | chr17 | 36343484 | 36343017 | − | TSF |
| 2% | chr17 | 36343995 | 36343886 | − | ENST00000518551; ENST00000354664; ENST00000339023; ENST00000519532; ENST00000537432 | chr17 | 36343484 | 36343017 | − | TSF |
| 2% | chr12 | 56742407 | 56742313 | − | ENST00000314128; ENST00000557235 | chr12 | 56740986 | 56740975 | − | TSF |
| 2% | chr12 | 56742407 | 56742313 | − | ENST00000314128; ENST00000557235 | chr12 | 56740986 | 56740975 | − | TSF |
| 1% | chr8 | 120220779 | 120220844 | + | ENST00000276681 | chr8 | 120233190 | 120233225 | + | TSF |
| 1% | chr22 | 35819207 | 35819334 | + | ENST00000216122; ENST00000382011 | chr22 | 35822985 | 35823438 | + | TSF |
| 1% | chr22 | 35819207 | 35819334 | + | ENST00000216122; ENST00000382011 | chr22 | 35822985 | 35823438 | + | TSF |
| 1% | chr3 | 196443740; 196443729 | 196443792 | + | ENST00000426755; ENST00000392391; ENST00000314118; ENST00000296333; ENST00000457284; ENST00000453218; ENST00000421265; ENST00000415832; ENST00000451319 | chr3 | 196444680 | 196444763 | + | TSF |
| 1% | chr3 | 196443740; 196443729 | 196443792 | + | ENST00000426755; ENST00000392391; ENST00000314118; ENST00000296333; ENST00000457284; ENST00000453218; ENST00000421265; ENST00000415832; ENST00000451319 | chr3 | 196444680 | 196444763 | + | TSF |
| 1% | chr3 | 196443740; 196443729 | 196443792 | + | ENST00000426755; ENST00000392391; ENST00000314118; ENST00000296333; ENST00000457284; ENST00000453218; ENST00000421265; ENST00000415832; ENST00000451319 | chr3 | 196444680 | 196444763 | + | TSF |
| 1% | chr11 | 65222908 | 65223052 | + | ENST00000309775 | chr11 | 65224109 | 65224450 | + | TSF |
| 1% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |
| 1% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |
| 1% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |
| 1% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |
| 1% | chrX | 153786747; 153786750 | 153786865 | + | ENST00000440286; ENST00000422680; ENST00000369609; ENST00000369607; ENST00000369606; ENST00000413620; ENST00000263518; ENST00000470142; ENST00000393549; ENST00000455588; ENST00000369602; ENST00000424839; ENST00000369601 | chrX | 153788357 | 153788357 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr2 | 110671988 | 110672054 | + | ENST00000553749 | chr2 | 110672249 | 110672374 | + | TSF |
| 1% | chr16 | 57115439 | 57115522 | + | ENST00000262510; ENST00000308149; ENST00000539144 | chr16 | 57116257 | 57116272 | + | TSF |
| 1% | chr16 | 57115439 | 57115522 | + | ENST00000262510; ENST00000308149; ENST00000539144 | chr16 | 57116257 | 57116272 | + | TSF |
| 1% | chr1 | 32560385 | 32560572 | + | ENST00000336294; ENST00000373634; ENST00000427288 | chr1 | 32561261 | 32561358 | + | TSF |
| 1% | chr1 | 32560385 | 32560572 | + | ENST00000336294; ENST00000373634; ENST00000427288 | chr1 | 32561261 | 32561358 | + | TSF |
| 1% | chr1 | 32560385 | 32560572 | + | ENST00000336294; ENST00000373634; ENST00000427288 | chr1 | 32561261 | 32561358 | + | TSF |
| 1% | chr5 | 23976106 | 23976159 | + | ENST00000512559; ENST00000507936 | chr5 | 24177946 | 24178380 | + | TSF |
| 1% | chr4 | 169086398 | 169086477 | + | ENST00000359299 | chr4 | 169090666 | 169090754 | + | TSF |
| 1% | chr11 | 20981978 | 20982106 | + | ENST00000298925; ENST00000357134; ENST00000325319; ENST00000532434 | chr11 | 21041136 | 21041271 | + | TSF |
| 1% | chr11 | 20981978 | 20982106 | + | ENST00000298925; ENST00000357134; ENST00000325319; ENST00000532434 | chr11 | 21041136 | 21041271 | + | TSF |
| 1% | chr11 | 20981978 | 20982106 | + | ENST00000298925; ENST00000357134; ENST00000325319; ENST00000532434 | chr11 | 21041136 | 21041271 | + | TSF |
| 1% | chr5 | 179315312 | 179315103 | − | ENST00000355235; ENST00000356834 | chr5 | 179312136 | 179312132 | − | TSF |
| 1% | chr11 | 10050104 | 10049999 | − | ENST00000256190 | chr11 | 10038326 | 10038049 | − | TSF |
| 1% | chr4 | 139135783 | 139135739 | − | ENST00000280612; ENST00000509248 | chr4 | 139120225 | 139120178 | − | TSF |
| 1% | chr4 | 139135783 | 139135739 | − | ENST00000280612; ENST00000509248 | chr4 | 139120225 | 139120178 | − | TSF |
| 1% | chr22 | 32802748 | 32802649 | − | ENST00000216038; ENST00000451746 | chr22 | 32801674 | 32801574 | − | TSF |
| 1% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 1% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 1% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 1% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 1% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 1% | chr17 | 26105817 | 26105716 | − | ENST00000313735 | chr17 | 26105322 | 26105316 | − | TSF |
| 1% | chr2 | 111214673 | 111214607 | − | ENST00000603767; ENST00000447537 | chr2 | 111214412 | 111214287 | − | TSF |
| 1% | chr4 | 1696567 | 1696501 | − | ENST00000429429; ENST00000489418; ENST00000318386; ENST00000483348; ENST00000488267 | chr4 | 1692954 | 1692622 | − | TSF |
| 1% | chr4 | 1696567 | 1696501 | − | ENST00000429429; ENST00000489418; ENST00000318386; ENST00000483348; ENST00000488267 | chr4 | 1692954 | 1692622 | − | TSF |
| 1% | chr4 | 1696567 | 1696501 | − | ENST00000429429; ENST00000489418; ENST00000318386; ENST00000483348; ENST00000488267 | chr4 | 1692954 | 1692622 | − | TSF |
| 1% | chr4 | 1696567 | 1696501 | − | ENST00000429429; ENST00000489418; ENST00000318386; ENST00000483348; ENST00000488267 | chr4 | 1692954 | 1692622 | − | TSF |
| 1% | chr4 | 1696567 | 1696501 | − | ENST00000429429; ENST00000489418; ENST00000318386; ENST00000483348; ENST00000488267 | chr4 | 1692954 | 1692622 | − | TSF |
| 1% | chr16 | 16225646 | 16225792 | + | ENST00000399410; ENST00000345148; ENST00000346370; ENST00000349029; ENST00000351154; ENST00000399408; ENST00000572882 | chr16 | 16227957 | 16228051 | + | TSF |
| 1% | chr16 | 16225646 | 16225792 | + | ENST00000399410; ENST00000345148; ENST00000346370; ENST00000349029; ENST00000351154; ENST00000399408; ENST00000572882 | chr16 | 16227957 | 16228051 | + | TSF |
| 1% | chr16 | 16225646 | 16225792 | + | ENST00000399410; ENST00000345148; ENST00000346370; ENST00000349029; | chr16 | 16227957 | 16228051 | + | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr16 | 16225646 | 16225792 | + | ENST00000351154; ENST00000399408; ENST00000572882 ENST00000399410; ENST00000345148; ENST00000346370; ENST00000349029; | chr16 | 16227957 | 16228051 | + | TSF |
| 1% | chr16 | 16225646 | 16225792 | + | ENST00000351154; ENST00000399408; ENST00000572882 ENST00000399410; ENST00000345148; ENST00000346370; ENST00000349029; | chr16 | 16227957 | 16228051 | + | TSF |
| 1% | chr16 | 16225646 | 16225792 | + | ENST00000351154; ENST00000399408; ENST00000572882 ENST00000399410; ENST00000345148; ENST00000346370; ENST00000349029; | chr16 | 16227957 | 16228051 | + | TSF |
| 1% | chr4 | 146617711 | 146617784 | + | ENST00000438731; ENST00000511965 | chr4 | 146620339 | 146620424 | + | TSF |
| 1% | chr4 | 146617711 | 146617784 | + | ENST00000438731; ENST00000511965 | chr4 | 146620339 | 146620424 | + | TSF |
| 1% | chr19 | 38872757 | 38872868 | + | ENST00000215071; ENST00000602911; ENST00000592561; ENST00000592035 | chr19 | 38873037 | 38873046 | + | TSF |
| 1% | chr19 | 38872757 | 38872868 | + | ENST00000215071; ENST00000602911; ENST00000592561; ENST00000592035 | chr19 | 38873037 | 38873046 | + | TSF |
| 1% | chr19 | 38872757 | 38872868 | + | ENST00000215071; ENST00000602911; ENST00000592561; ENST00000592035 | chr19 | 38873037 | 38873046 | + | TSF |
| 1% | chr19 | 38872757 | 38872868 | + | ENST00000215071; ENST00000602911; ENST00000592561; ENST00000592035 | chr19 | 38873037 | 38873046 | + | TSF |
| 1% | chr1 | 151537001 | 151537090 | + | ENST00000353024; ENST00000368849; ENST00000368848; ENST00000538902 | chr1 | 151537646 | 151537693 | + | TSF |
| 1% | chr1 | 151537001 | 151537090 | + | ENST00000353024; ENST00000368849; ENST00000368848; ENST00000538902 | chr1 | 151537646 | 151537693 | + | TSF |
| 1% | chr1 | 151537001 | 151537090 | + | ENST00000353024; ENST00000368849; ENST00000368848; ENST00000538902 | chr1 | 151537646 | 151537693 | + | TSF |
| 1% | chr1 | 151537001 | 151537090 | + | ENST00000353024; ENST00000368849; ENST00000368848; ENST00000538902 | chr1 | 151537646 | 151537693 | + | TSF |
| 1% | chr6 | 20781376 | 20781496 | + | ENST00000274695; ENST00000378624; ENST00000378610 | chr6 | 20805885 | 20806219 | + | TSF |
| 1% | chr6 | 20781376 | 20781496 | + | ENST00000274695; ENST00000378624; ENST00000378610 | chr6 | 20805885 | 20806219 | + | TSF |
| 1% | chr9 | 17143286 | 17143374 | + | ENST00000380647; ENST00000262360; ENST00000425824; ENST00000380641 | chr9 | 17166816 | 17167136 | + | TSF |
| 1% | chr5 | 1802435 | 1802488 | + | ENST00000274137; ENST00000469176 | chr5 | 1811112 | 1811428 | + | TSF |
| 1% | chr22 | 38321668; 38321854 | 38322050 | + | ENST00000215957; ENST00000454685 | chr22 | 38322963 | 38322967 | + | TSF |
| 1% | chr22 | 38321668; 38321854 | 38322050 | + | ENST00000215957; ENST00000454685 | chr22 | 38322963 | 38322967 | + | TSF |
| 1% | chr2 | 217366064 | 217366082 | + | ENST00000491306; ENST00000456586 | chr2 | 217393993 | 217394327 | + | TSF |
| 1% | chr2 | 217366064 | 217366082 | + | ENST00000491306; ENST00000456586 | chr2 | 217393993 | 217394327 | + | TSF |
| 1% | chr2 | 47690170 | 47690293 | + | ENST00000233146; ENST00000543555; ENST00000406134 | chr2 | 47691419 | 47691669 | + | TSF |
| 1% | chr2 | 47690170 | 47690293 | + | ENST00000233146; ENST00000543555; ENST00000406134 | chr2 | 47691419 | 47691669 | + | TSF |
| 1% | chr7 | 150065992 | 150066030 | + | ENST00000466559; ENST00000475514; ENST00000488943; ENST00000467980; ENST00000518514; ENST00000522266 | chr7 | 150067849 | 150067901 | + | TSF |
| 1% | chr6 | 20781376 | 20781496 | + | ENST00000274695; ENST00000378624; ENST00000378610 | chr6 | 20797829 | 20797991 | + | TSF |
| 1% | chr6 | 20781376 | 20781496 | + | ENST00000274695; ENST00000378624; ENST00000378610 | chr6 | 20797829 | 20797991 | + | TSF |
| 1% | chr8 | 126194345 | 126194498 | + | ENST00000523741; ENST00000517532; ENST00000287437; ENST00000522563; ENST00000517315 | chr8 | 126207297 | 126207395 | + | TSF |
| 1% | chr8 | 126194345 | 126194498 | + | ENST00000523741; ENST00000517532; ENST00000287437; ENST00000522563; ENST00000517315 | chr8 | 126207297 | 126207395 | + | TSF |
| 1% | chr22 | 22786497 | 22786736 | + | ENST00000390301 | chr22 | 22832893 | 22833352 | + | TSF |
| 1% | chr2 | 89417128 | 89416936 | − | ENST00000490686 | chr2 | 89370042 | 89366766 | − | TSF |
| 1% | chr8 | 42302280 | 42302164 | − | ENST00000342228; ENST00000520262; ENST00000520179 | chr8 | 42301552 | 42301149 | − | TSF |
| 1% | chr14 | 106092403 | 106092109 | − | ENST00000390543 | chr14 | 105470421 | 105470286 | − | TSF |
| 1% | chr6 | 65098733 | 65098583 | − | ENST00000503581; ENST00000370621; ENST00000370616 | chr6 | 65097495 | 65097442 | − | TSF |
| 1% | chr1 | 40313763; 40313769; 40313673; 40313734 | 40313658 | − | ENST00000441669; ENST0000462797; ENST00000316891; ENST00000372818; ENST00000537223; ENST00000537440; ENST00000545233 | chr1 | 40313419 | 40313374 | − | TSF |
| 1% | chr1 | 40313763; | 40313658 | − | ENST00000441669; ENST00000462797; | chr1 | 40313419 | 40313374 | − | TSF |

TABLE 39-continued

Transcript fusion for Lung Squamous Cell Carcinoma (LUSC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr1 | 40313769; 40313673; 40313734 40313763; 40313769; 40313673; 40313734 | 40313658 | − | ENST00000316891; ENST00000372818; ENST00000537223; ENST00000537440; ENST00000545233 ENST00000441669; ENST00000462797; ENST00000316891; ENST00000372818; ENST00000537223; ENST00000537440; ENST00000545233 | chr1 | 40313419 | 40313374 | − | TSF |
| 1% | chr1 | 40313763; 40313769; 40313673; 40313734 | 40313658 | − | ENST00000441669; ENST00000462797; ENST00000316891; ENST00000372818; ENST00000537223; ENST00000537440; ENST00000545233 | chr1 | 40313419 | 40313374 | − | TSF |
| 1% | chr1 | 180283857 | 180283827 | − | ENST00000367595 | chr1 | 180281120 | 180281103 | − | TSF |
| 1% | chr17 | 80656472 | 80656331 | − | ENST00000571995; ENST00000538809 | chr17 | 80634662 | 80634498 | − | TSF |
| 1% | chr21 | 46306817 | 46306651 | − | ENST00000397852; ENST00000397857; ENST00000397854; ENST00000355153; ENST00000397850; ENST00000302347 | chr21 | 46302588 | 46302215 | − | TSF |
| 1% | chr21 | 46306817 | 46306651 | − | ENST00000397852; ENST00000397857; ENST00000397854; ENST00000355153; ENST00000397850; ENST00000302347 | chr21 | 46302588 | 46302215 | − | TSF |
| 1% | chr4 | 1102192 | 1102131 | − | ENST00000382968; ENST00000433731; ENST00000511620; ENST00000510715; ENST00000333673 | chr4 | 1101132 | 1100845 | − | TSF |
| 1% | chr3 | 194325174; 194325170 | 194325016 | − | ENST00000392432; ENST00000273580; ENST00000432352; ENST00000381975; ENST00000347147; ENST00000473092; ENST00000452358 | chr3 | 194296178 | 194295847 | − | TSF |
| 1% | chr3 | 194325174; 194325170 | 194325016 | − | ENST00000392432; ENST00000273580; ENST00000432352; ENST00000381975; ENST00000347147; ENST00000473092; ENST00000452358 | chr3 | 194296178 | 194295847 | − | TSF |
| 1% | chr3 | 194325174; 194325170 | 194325016 | − | ENST00000392432; ENST00000273580; ENST00000432352; ENST00000381975; ENST00000347147; ENST00000473092; ENST00000452358 | chr3 | 194296178 | 194295847 | − | TSF |
| 1% | chr3 | 194325174; 194325170 | 194325016 | − | ENST00000392432; ENST00000273580; ENST00000432352; ENST00000381975; ENST00000347147; ENST00000473092; ENST00000452358 | chr3 | 194296178 | 194295847 | − | TSF |
| 1% | chr5 | 176830398 | 176830255 | − | ENST00000253496 | chr5 | 176829864 | 176829767 | − | TSF |
| 1% | chr6 | 99781423 | 99781227 | − | ENST00000389677 | chr6 | 99774039 | 99774006 | − | TSF |
| 1% | chr19 | 49335016 | 49334925 | − | ENST00000263278; ENST00000595764 | chr19 | 49322122 | 49322095 | − | TSF |
| 1% | chr19 | 49335016 | 49334925 | − | ENST00000263278; ENST00000595764 | chr19 | 49322122 | 49322095 | − | TSF |
| 1% | chr2 | 27610025 | 27609956 | − | ENST00000344034; ENST00000350803 | chr2 | 27609703 | 27609426 | − | TSF |
| 1% | chr1 | 40319740 | 40319642 | − | ENST00000462797; ENST00000316891; ENST00000372818; ENST00000492612; ENST00000489945; ENST00000469476; ENST00000544981 | chr1 | 40318623 | 40318602 | − | TSF |
| 1% | chr1 | 40319740 | 40319642 | − | ENST00000462797; ENST00000316891; ENST00000372818; ENST00000492612; ENST00000489945; ENST00000469476; ENST00000544981 | chr1 | 40318623 | 40318602 | − | TSF |
| 1% | chr1 | 40319740 | 40319642 | − | ENST00000462797; ENST00000316891; ENST00000372818; ENST00000492612; ENST00000489945; ENST00000469476; ENST00000544981 | chr1 | 40318623 | 40318602 | − | TSF |

TABLE 40

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 60% | chr11 | 93468219 | 93468129 | − | chr11 | 93467826 | 93467791; 93467814 | − | ENST00000393259; ENST00000527169 | TAF |
| 60% | chr11 | 93468219 | 93468129 | − | chr11 | 93467826 | 93467791; 93467814 | − | ENST00000393259; ENST00000527169 | TAF |
| 51% | chr12 | 122430912 | 122431615 | + | chr12 | 122437622 | 122437850 | + | ENST00000288912 | TAF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 48% | chr7 | 116364854 | 116364901 | + | chr7 | 116371722 | 116371913 | + | ENST00000397752; ENST00000318493; ENST00000436117 | TAF |
| 48% | chr7 | 116364854 | 116364901 | + | chr7 | 116371722 | 116371913 | + | ENST00000397752; ENST00000318493; ENST00000436117 | TAF |
| 48% | chr7 | 116364854 | 116364901 | + | chr7 | 116371722 | 116371913 | + | ENST00000397752; ENST00000318493; ENST00000436117 | TAF |
| 42% | chr8 | 104389530 | 104389551 | + | chr8 | 104390255 | 104390471 | + | ENST00000330295; ENST00000520337 | TAF |
| 40% | chr12 | 86274449 | 86274547 | + | chr12 | 86276001 | 86276153 | + | ENST00000551529; ENST00000256010 | TAF |
| 36% | chr3 | 185411133 | 185410965 | − | chr3 | 185410550 | 185410487 | − | ENST00000382199; ENST00000421047; ENST00000457616; ENST00000346192 | TAF |
| 36% | chr3 | 185411133 | 185410965 | − | chr3 | 185410550 | 185410487 | − | ENST00000382199; ENST00000421047; ENST00000457616; ENST00000346192 | TAF |
| 34% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 34% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 34% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 34% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 34% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 32% | chr12 | 64687157 | 64687061 | − | chr12 | 64679840 | 64679734 | − | ENST00000543942; ENST00000333722 | TAF |
| 32% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 32% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 32% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 32% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 32% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 31% | chr12 | 122387836 | 122388242 | + | chr12 | 122389386 | 122389436 | + | ENST00000288912; ENST00000397454 | TSF |
| 31% | chr12 | 122387836 | 122388242 | + | chr12 | 122389386 | 122389436 | + | ENST00000288912; ENST00000397454 | TSF |
| 30% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 30% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 30% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 30% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 30% | chr6 | 80022917 | 80022085 | − | chr6 | 79924739 | 79924689 | − | ENST00000275036; ENST00000344726 | TSF |
| 30% | chr6 | 80022917 | 80022085 | − | chr6 | 79924739 | 79924689 | − | ENST00000275036; ENST00000344726 | TSF |
| 29% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 29% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 29% | chr19 | 49121994 | 49121817 | − | chr19 | 49121134 | 49121048 | − | ENST00000549920; ENST00000547897; | TAF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 29% | chr19 | 49121994 | 49121817 | − | chr19 | 49121134 | 49121048 | − | ENST00000084795; ENST00000550645; ENST00000549370; ENST00000549273 ENST00000549920; ENST00000547897; | TAF |
| 29% | chr19 | 49121994 | 49121817 | − | chr19 | 49121134 | 49121048 | − | ENST00000084795; ENST00000550645; ENST00000549370; ENST00000549273 ENST00000549920; ENST00000547897; | TAF |
| 29% | chr9 | 123165858 | 123165594 | − | chr9 | 123165349 | 123165084 | − | ENST00000359309; ENST00000360822; ENST00000349780; ENST00000360190; ENST00000416449; ENST00000425647 | TAF |
| 27% | chr17 | 30771499 | 30771536 | + | chr17 | 30773963 | 30774064 | + | ENST00000261712; ENST00000457654; ENST00000579451 | TAF |
| 27% | chr17 | 30771499 | 30771536 | + | chr17 | 30773963 | 30774064 | + | ENST00000261712; ENST00000457654; ENST00000579451 | TAF |
| 24% | chr21 | 19289273 | 19289717 | + | chr21 | 19628826 | 19629135 | + | ENST00000299295; ENST00000543733 | TAF |
| 24% | chr12 | 6602868 | 6602840 | − | chr12 | 6602138 | 6602028 | − | ENST00000229238 | TAF |
| 24% | chr12 | 122387836 | 122388242 | + | chr12 | 122392026 | 122392240 | + | ENST00000288912; ENST00000397454 | TSF |
| 24% | chr12 | 122387836 | 122388242 | + | chr12 | 122392026 | 122392240 | + | ENST00000288912; ENST00000397454 | TSF |
| 19% | chr3 | 180632728 | 180632783 | + | chr3 | 180651122 | 180651174 | + | ENST00000357559; ENST00000445140; ENST00000480918; ENST00000484042 | TAF |
| 19% | chr3 | 180632728 | 180632783 | + | chr3 | 180651122 | 180651174 | + | ENST00000357559; ENST00000445140; ENST00000480918; ENST00000484042 | TAF |
| 19% | chr3 | 180632728 | 180632783 | + | chr3 | 180651122 | 180651174 | + | ENST00000357559; ENST00000445140; ENST00000480918; ENST00000484042 | TAF |
| 19% | chr10 | 5077666 | 5077808 | + | chr10 | 5138602 | 5138769 | + | ENST00000602997; ENST00000605149; ENST00000380554 | TAF |
| 19% | chr10 | 5077666 | 5077808 | + | chr10 | 5138602 | 5138769 | + | ENST00000602997; ENST00000605149; ENST00000380554 | TAF |
| 18% | chr11 | 752380 | 752481 | + | chr11 | 755879 | 756002 | + | ENST00000319006; ENST00000528097; ENST00000530440 | TAF |
| 18% | chr11 | 752380 | 752481 | + | chr11 | 755879 | 756002 | + | ENST00000319006; ENST00000528097; ENST00000530440 | TAF |
| 18% | chr11 | 752380 | 752481 | + | chr11 | 755879 | 756002 | + | ENST00000319006; ENST00000528097; ENST00000530440 | TAF |
| 17% | chr17 | 79214190 | 79214239 | + | chr17 | 79214787 | 79214816; 79214953 | + | ENST00000431388; ENST00000576002 | TAF |
| 17% | chr17 | 79214190 | 79214239 | + | chr17 | 79214787 | 79214816; 79214953 | + | ENST00000431388; ENST00000576002 | TAF |
| 17% | chr7 | 99747312 | 99747315 | + | chr7 | 99751023 | 99751140; 99751352 | + | ENST00000341942; ENST00000441173 | TAF |
| 17% | chr7 | 99747312 | 99747315 | + | chr7 | 99751023 | 99751140; 99751352 | + | ENST00000341942; ENST00000441173 | TAF |
| 17% | chr11 | 87906665 | 87906580 | − | chr11 | 87883123 | 87882843 | − | ENST00000243662; ENST00000526372 | TAF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 17% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 16% | chr2 | 65243329 | 65243368 | + | chr2 | 65243574 | 65243807 | + | ENST00000234256 | TSF |
| 16% | chr5 | 76107394 | 76108135 | + | chr5 | 76128515 | 76129626 | + | ENST00000296677 | TSF |
| 16% | chr19 | 56811235 | 56811344 | + | chr19 | 56813337 | 56813464 | + | ENST00000588026 | TSF |
| 15% | chr6 | 138423138 | 138423021 | − | chr6 | 138417631 | 138417491 | − | ENST00000421351 | TAF |
| 15% | chr11 | 60694460 | 60694542 | + | chr11 | 60694676 | 60694890 | + | ENST00000453848; ENST00000005286 | TSF |
| 15% | chr11 | 60694460 | 60694542 | + | chr11 | 60694676 | 60694890 | + | ENST00000453848; ENST00000005286 | TSF |
| 14% | chr7 | 56018506 | 56018522 | + | chr7 | 56020872 | 56021011 | + | ENST00000426595 | TSF |
| 13% | chr5 | 1811001 | 1811176 | + | chr5 | 1814453 | 1814575; 1814785 | + | ENST00000274137; ENST00000469176 | TAF |
| 13% | chr5 | 1811001 | 1811176 | + | chr5 | 1814453 | 1814575; 1814785 | + | ENST00000274137; ENST00000469176 | TAF |
| 13% | chr4 | 15791827 | 15792541 | + | chr4 | 15818134 | 15818263 | + | ENST00000502843; ENST00000226279 | TAF |
| 13% | chr4 | 15791827 | 15792541 | + | chr4 | 15818134 | 15818263 | + | ENST00000502843; ENST00000226279 | TAF |
| 13% | chr5 | 823586 | 823504 | − | chr5 | 822010 | 821976 | − | ENST00000424784; ENST00000283441 | TAF |
| 12% | chr1 | 171237955 | 171238225 | + | chr1 | 171244485 | 171244647 | + | ENST00000433267; ENST00000367750; ENST00000402921; ENST00000354841 | TAF |
| 12% | chr1 | 171237955 | 171238225 | + | chr1 | 171244485 | 171244647 | + | ENST00000433267; ENST00000367750; | TAF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 12% | chr3 | 197680391 | 197680531 | + | chr3 | 197680874 | 197681018; 197680991 | + | ENST00000402921; ENST00000354841 ENST00000464167; ENST00000448864; ENST00000442341 | TAF |
| 12% | chr3 | 197680391 | 197680531 | + | chr3 | 197680874 | 197681018; 197680991 | + | ENST00000464167; ENST00000448864; ENST00000442341 | TAF |
| 12% | chr3 | 141642134 | 141642345 | + | chr3 | 141644373 | 141644543 | + | ENST00000286371; ENST00000462082 | TAF |
| 12% | chr3 | 183973543 | 183973607 | + | chr3 | 183975261 | 183975544 | + | ENST00000324557; ENST00000402825 | TSF |
| 12% | chr3 | 183973543 | 183973607 | + | chr3 | 183975261 | 183975544 | + | ENST00000324557; ENST00000402825 | TSF |
| 11% | chr11 | 424193 | 423942 | − | chr11 | 421198 | 421141 | − | ENST00000332826 | TAF |
| 11% | chr19 | 39347374 | 39346206 | − | chr19 | 39338074 | 39337956 | − | ENST00000221419; ENST00000601449; ENST00000600233; ENST00000601813 | TSF |
| 11% | chr19 | 39347374 | 39346206 | − | chr19 | 39338074 | 39337956 | − | ENST00000221419; ENST00000601449; ENST00000600233; ENST00000601813 | TSF |
| 11% | chr19 | 39347374 | 39346206 | − | chr19 | 39338074 | 39337956 | − | ENST00000221419; ENST00000601449; ENST00000600233; ENST00000601813 | TSF |
| 11% | chr19 | 39347374 | 39346430 | − | chr19 | 39338074 | 39337956 | − | ENST00000221419; ENST00000601449; ENST00000600233; ENST00000601813 | TSF |
| 11% | chr19 | 39347374 | 39346430 | − | chr19 | 39338074 | 39337956 | − | ENST00000221419; ENST00000601449; ENST00000600233; ENST00000601813 | TSF |
| 11% | chr19 | 39347374 | 39346430 | − | chr19 | 39338074 | 39337956 | − | ENST00000221419; ENST00000601449; ENST00000600233; ENST00000601813 | TSF |
| 11% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 11% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 11% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 11% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 11% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 11% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 10% | chr3 | 183371827 | 183371877 | + | chr3 | 183381246 | 183381430 | + | ENST00000242810; ENST00000454652; ENST00000476808 | TAF |
| 10% | chr3 | 183371827 | 183371877 | + | chr3 | 183381246 | 183381430 | + | ENST00000242810; ENST00000454652; ENST00000476808 | TAF |
| 10% | chr1 | 165863702 | 165863816 | + | chr1 | 165865427 | 165865569 | + | ENST00000367879 | TAF |
| 10% | chr20 | 33191661 | 33190934 | − | chr20 | 33176411 | 33176257; 33176344 | − | ENST00000217446; ENST00000374820; ENST00000452740; ENST00000438215 | TAF |
| 10% | chr20 | 33191661 | 33190934 | − | chr20 | 33176411 | 33176257; 33176344 | − | ENST00000217446; ENST00000374820; ENST00000452740; ENST00000438215 | TAF |
| 10% | chr20 | 33191661 | 33190934 | − | chr20 | 33176411 | 33176257; 33176344 | − | ENST00000217446; ENST00000374820; ENST00000452740; ENST00000438215 | TAF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 10% | chr19 | 51854024 | 51853970 | – | chr19 | 51853645 | 51853583 | – | ENST00000354232; ENST00000309244; ENST00000596253 | TAF |
| 10% | chr19 | 51854024 | 51853970 | – | chr19 | 51853645 | 51853583 | – | ENST00000354232; ENST00000309244; ENST00000596253 | TAF |
| 10% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 10% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 10% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 10% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 10% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 10% | chr9 | 123165858 | 123165577 | – | chr9 | 123165349 | 123165084 | – | ENST00000359309; ENST00000360822; ENST00000349780; ENST00000360190; ENST00000416449; ENST00000425647 | TSF |
| 10% | chr9 | 123165858 | 123165617 | – | chr9 | 123165349 | 123165084 | – | ENST00000359309; ENST00000360822; ENST00000349780; ENST00000360190; ENST00000416449; ENST00000425647 | TSF |
| 9% | chrX | 151410500 | 151410406 | – | chrX | 151393317 | 151393235 | – | ENST00000370314; ENST00000535043 | TSF |
| 9% | chr22 | 29117574 | 29117506 | – | chr22 | 29115473 | 29115383; 29115458 | – | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 9% | chr22 | 29117574 | 29117506 | – | chr22 | 29115473 | 29115383; 29115458 | – | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 9% | chr22 | 29117574 | 29117506 | – | chr22 | 29115473 | 29115383; 29115458 | – | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 9% | chr22 | 29117574 | 29117506 | – | chr22 | 29115473 | 29115383; 29115458 | – | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 9% | chr22 | 29117574 | 29117506 | – | chr22 | 29115473 | 29115383; 29115458 | – | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 8% | chr10 | 5057417 | 5057095 | – | chr10 | 5043873 | 5043706 | – | ENST00000380753; ENST00000421196; ENST00000407674; ENST00000604507; ENST00000455190 | TSF |
| 8% | chr10 | 5057417 | 5057095 | – | chr10 | 5043873 | 5043706 | – | ENST00000380753; ENST00000421196; ENST00000407674; ENST00000604507; ENST00000455190 | TSF |
| 8% | chr10 | 5057417 | 5057095 | – | chr10 | 5043873 | 5043706 | – | ENST00000380753; ENST00000421196; ENST00000407674; ENST00000604507; ENST00000455190 | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 8% | chr10 | 5057417 | 5057095 | − | chr10 | 5043873 | 5043706 | − | ENST00000380753; ENST00000421196; ENST00000407674; ENST00000604507; ENST00000455190 | TSF |
| 8% | chr12 | 122430912 | 122432103 | + | chr12 | 122437622 | 122437850 | + | ENST00000288912 | TSF |
| 8% | chr12 | 122430912 | 122431795 | + | chr12 | 122437622 | 122437850 | + | ENST00000288912 | TSF |
| 8% | chr7 | 134212336 | 134212386 | + | chr7 | 134215479 | 134215562 | + | ENST00000359579 | TSF |
| 7% | chrX | 134954053 | 134953756 | − | chrX | 134950187 | 134950078 | − | ENST00000420087; ENST00000463085; ENST00000370724; ENST00000491480 | TSF |
| 7% | chrX | 134954053 | 134953756 | − | chrX | 134950187 | 134950078 | − | ENST00000420087; ENST00000463085; ENST00000370724; ENST00000491480 | TSF |
| 7% | chrX | 134971303 | 134971006 | − | chrX | 134950187 | 134950078 | − | ENST00000420087; ENST00000463085; ENST00000370724; ENST00000491480 | TSF |
| 7% | chrX | 134971303 | 134971006 | − | chrX | 134950187 | 134950078 | − | ENST00000420087; ENST00000463085; ENST00000370724; ENST00000491480 | TSF |
| 7% | chrX | 134971303 | 134971006 | − | chrX | 134967437 | 134967328 | − | ENST00000491002; ENST00000448053; ENST00000472834 | TSF |
| 7% | chr7 | 23290404 | 23290481 | + | chr7 | 23292926 | 23293078 | + | ENST00000258733; ENST00000381990; ENST00000409458; ENST00000453162 | TSF |
| 7% | chr7 | 23290404 | 23290481 | + | chr7 | 23292926 | 23293078 | + | ENST00000258733; ENST00000381990; ENST00000409458; ENST00000453162 | TSF |
| 7% | chr7 | 23290404 | 23290481 | + | chr7 | 23292926 | 23293078 | + | ENST00000258733; ENST00000381990; ENST00000409458; ENST00000453162 | TSF |
| 7% | chr7 | 23290404 | 23290481 | + | chr7 | 23292926 | 23293078 | + | ENST00000258733; ENST00000381990; ENST00000409458; ENST00000453162 | TSF |
| 7% | chr15 | 40187476 | 40186733 | − | chr15 | 40099459 | 40099207 | − | ENST00000561100; ENST00000543580 | TSF |
| 7% | chr10 | 5060345 | 5060092 | − | chr10 | 5043777 | 5043706 | − | ENST00000380753; ENST00000421196; ENST00000407674; ENST00000604507; ENST00000455190 | TSF |
| 7% | chr10 | 5060345 | 5060092 | − | chr10 | 5043777 | 5043706 | − | ENST00000380753; ENST00000421196; ENST00000407674; ENST00000604507; ENST00000455190 | |
| 7% | chr10 | 5060345 | 5060092 | − | chr10 | 5043777 | 5043706 | − | ENST00000380753; ENST00000421196; ENST00000407674; ENST00000604507; ENST00000455190 | |
| 7% | chr10 | 5060345 | 5060092 | − | chr10 | 5043777 | 5043706 | − | ENST00000380753; ENST00000421196; ENST00000407674; ENST00000604507; ENST00000455190 | |
| 7% | chrX | 134866155 | 134866452 | + | chrX | 134870023 | 134870132 | + | ENST00000370736; ENST00000471213; ENST00000495729 | TSF |
| 7% | chrX | 134866155 | 134866452 | + | chrX | 134887292 | 134887401 | + | ENST00000370734; ENST00000485366; ENST00000443882 | TSF |
| 7% | chrX | 134883429 | 134883726 | + | chrX | 134887292 | 134887401 | + | ENST00000370734; ENST00000485366; ENST00000443882 | TSF |
| 7% | chr12 | 58023123 | 58023062 | − | chr12 | 58022929 | 58022831; 58022905 | − | ENST00000341156; ENST00000418555; ENST00000552798; ENST00000549391 | TSF |
| 7% | chr12 | 58023123 | 58023062 | − | chr12 | 58022929 | 58022831; 58022905 | − | ENST00000341156; ENST00000418555; ENST00000552798; ENST00000549391 | TSF |
| 7% | chrX | 134954053 | 134953756 | − | chrX | 134932924 | 134932815 | − | ENST00000487941; ENST00000434966; ENST00000494421 | TSF |
| 7% | chrX | 134936794 | 134936497 | − | chrX | 134932924 | 134932815 | − | ENST00000487941; ENST00000434966; ENST00000494421 | TSF |
| 7% | chr2 | 143794737 | 143794842 | + | chr2 | 143797997 | 143798227 | + | ENST00000264170; ENST00000409512 | TSF |
| 7% | chr17 | 39974832 | 39974893 | + | chr17 | 39975462 | 39975651 | + | ENST00000321562 | TSF |
| 7% | chr20 | 634541 | 634468 | − | chr20 | 629561 | 629358; 629500 | − | ENST00000381962; ENST00000488788 | TSF |
| 7% | chr20 | 634541 | 634468 | − | chr20 | 629561 | 629358; 629500 | − | ENST00000381962; ENST00000488788 | TSF |
| 6% | chrX | 134971303 | 134971006 | − | chrX | 134932924 | 134932815 | − | ENST00000487941; ENST00000434966; ENST00000494421 | TSF |
| 6% | chr3 | 184749371 | 184749503 | + | chr3 | 184766267 | 184766347 | + | ENST00000287546; ENST00000437079; ENST00000436792; ENST00000446204 | TSF |
| 6% | chrX | 154534914 | 154534817 | − | chrX | 154528458 | 154528349 | − | ENST00000369449; ENST00000321926 | TSF |
| 6% | chrX | 154534914 | 154534817 | − | chrX | 154528458 | 154528349 | − | ENST00000369449; ENST00000321926 | TSF |
| 6% | chr6 | 161637963 | 161637691 | − | chr6 | 161587449 | 161587280; 161587148 | − | ENST00000320285; ENST00000366908; ENST00000436279; ENST00000366905 | TSF |
| 6% | chr6 | 161637963 | 161637691 | − | chr6 | 161587449 | 161587280; 161587148 | − | ENST00000320285; ENST00000366908; ENST00000436279; ENST00000366905 | TSF |
| 6% | chr6 | 161637963 | 161637691 | − | chr6 | 161587449 | 161587280; 161587148 | − | ENST00000320285; ENST00000366908; ENST00000436279; ENST00000366905 | TSF |
| 6% | chr10 | 125606103 | 125605751 | − | chr10 | 125602004 | 125601865 | − | ENST00000241305 | TSF |
| 6% | chr10 | 5060345 | 5060040 | − | chr10 | 5043873 | 5043706 | − | ENST00000380753; ENST00000421196; ENST00000407674; ENST00000604507; ENST00000455190 | TSF |
| 6% | chr10 | 5060345 | 5060040 | − | chr10 | 5043873 | 5043706 | − | ENST00000380753; ENST00000421196; ENST00000407674; ENST00000604507; ENST00000455190 | TSF |
| 6% | chr10 | 5060345 | 5060040 | − | chr10 | 5043873 | 5043706 | − | ENST00000380753; ENST00000421196; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 6% | chr10 | 5060345 | 5060040 | − | chr10 | 5043873 | 5043706 | − | ENST00000407674; ENST00000604507; ENST00000455190 ENST00000380753; ENST00000421196; ENST00000407674; ENST00000604507; ENST00000455190 | TSF |
| 6% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 6% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 6% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 6% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 6% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 6% | chr12 | 122430912 | 122432282 | + | chr12 | 122437622 | 122437850 | + | ENST00000288912 | TSF |
| 6% | chr12 | 6602868 | 6602754 | − | chr12 | 6602138 | 6602028 | − | ENST00000229238 | TSF |
| 5% | chr6 | 37326936 | 37327118 | + | chr6 | 37328222 | 37328350 | + | ENST00000373479; ENST00000229866; ENST00000394443; ENST00000469316; ENST00000469731 | TSF |
| 5% | chr6 | 37326936 | 37327118 | + | chr6 | 37328222 | 37328350 | + | ENST00000373479; ENST00000229866; ENST00000394443; ENST00000469316; ENST00000469731 | TSF |
| 5% | chr6 | 37326936 | 37327118 | + | chr6 | 37328222 | 37328350 | + | ENST00000373479; ENST00000229866; ENST00000394443; ENST00000469316; ENST00000469731 | TSF |
| 5% | chr6 | 37326936 | 37327118 | + | chr6 | 37328222 | 37328350 | + | ENST00000373479; ENST00000229866; ENST00000394443; ENST00000469316; ENST00000469731 | TSF |
| 5% | chr1 | 165854440 | 165854616 | + | chr1 | 165859441 | 165859600 | + | ENST00000367879; ENST00000372212 | TSF |
| 5% | chr1 | 165854440 | 165854616 | + | chr1 | 165859441 | 165859600 | + | ENST00000367879; ENST00000372212 | TSF |
| 5% | chr20 | 45337040 | 45337192 | + | chr20 | 45353680 | 45354963 | + | ENST00000359271 | TSF |
| 5% | chr21 | 19399995 | 19400289 | + | chr21 | 19628826 | 19629135 | + | ENST00000299295; ENST00000543733 | TSF |
| 5% | chr1 | 41465686 | 41465756 | + | chr1 | 41466701 | 41466789 | + | ENST00000372621; ENST00000541520; ENST00000372616 | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr5 | 76107394 | 76108212 | + | chr5 | 76128515 | 76129626 | + | ENST00000296677 | TSF |
| 5% | chr9 | 117824597 | 117824593 | − | chr9 | 117822281 | 117822009 | − | ENST00000350763; ENST00000341037; ENST00000423613 | TSF |
| 5% | chr9 | 117824597 | 117824593 | − | chr9 | 117822281 | 117822009 | − | ENST00000350763; ENST00000341037; ENST00000423613 | TSF |
| 5% | chr9 | 117824597 | 117824593 | − | chr9 | 117822281 | 117822009 | − | ENST00000350763; ENST00000341037; ENST00000423613 | TSF |
| 5% | chr10 | 79700435 | 79700428 | − | chr10 | 79628955 | 79628887 | − | ENST00000372391; ENST00000372388; ENST00000468332 | TSF |
| 5% | chr10 | 79700435 | 79700428 | − | chr10 | 79628955 | 79628887 | − | ENST00000372391; ENST00000372388; ENST00000468332 | TSF |
| 5% | chr10 | 79700435 | 79700428 | − | chr10 | 79628955 | 79628887 | − | ENST00000372391; ENST00000372388; ENST00000468332 | TSF |
| 5% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 5% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 5% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 5% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 5% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 5% | chr3 | 183460031 | 183460733 | + | chr3 | 183465460 | 183465504 | + | ENST00000305135 | TSF |
| 5% | chr6 | 124669760 | 124669850 | + | chr6 | 124676413 | 124676493 | + | ENST00000368416; ENST00000368417; ENST00000546092; ENST00000545433 | TSF |
| 5% | chr6 | 124669760 | 124669850 | + | chr6 | 124676413 | 124676493 | + | ENST00000368416; ENST00000368417; ENST00000546092; ENST00000545433 | TSF |
| 5% | chr6 | 124669760 | 124669850 | + | chr6 | 124676413 | 124676493 | + | ENST00000368416; ENST00000368417; ENST00000546092; ENST00000545433 | TSF |
| 5% | chr6 | 124669760 | 124669850 | + | chr6 | 124676413 | 124676493 | + | ENST00000368416; ENST00000368417; ENST00000546092; ENST00000545433 | TSF |
| 5% | chr17 | 39976225 | 39976301 | + | chr17 | 39976521 | 39976713 | + | ENST00000321562; ENST00000455106; ENST00000544340 | TSF |
| 5% | chr19 | 46194689 | 46194670 | − | chr19 | 46191824 | 46191645 | − | ENST00000342669; ENST00000588301; ENST00000590212 | TSF |
| 5% | chr19 | 46194689 | 46194670 | − | chr19 | 46191824 | 46191645 | − | ENST00000342669; ENST00000588301; ENST00000590212 | TSF |
| 4% | chr12 | 96340433 | 96341255 | + | chr12 | 96346495 | 96346601 | + | ENST00000266736; ENST00000548310 | TSF |
| 4% | chr12 | 96340433 | 96341255 | + | chr12 | 96346495 | 96346601 | + | ENST00000266736; ENST00000548310 | TSF |
| 4% | chr8 | 104389530 | 104389536 | + | chr8 | 104390255 | 104390471 | + | ENST00000330295; ENST00000520337 | TSF |
| 4% | chr1 | 45988716 | 45988450 | − | chr1 | 45981479 | 45981326 | − | ENST00000262746; ENST00000319248; ENST00000447184; ENST00000424390 | TSF |
| 4% | chr1 | 45988716 | 45988450 | − | chr1 | 45981479 | 45981326 | − | ENST00000262746; ENST00000319248; ENST00000447184; ENST00000424390 | TSF |
| 4% | chr10 | 5060345 | 5060092 | − | chr10 | 5040939 | 5040817 | − | ENST00000380753; ENST00000421196; ENST00000407674; ENST00000604507 | TSF |
| 4% | chr10 | 5060345 | 5060092 | − | chr10 | 5040939 | 5040817 | − | ENST00000380753; ENST00000421196; ENST00000407674; ENST00000604507 | TSF |
| 4% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chrX | 154534914 | 154534773 | − | chrX | 154528458 | 154528349 | − | ENST00000369449; ENST00000321926 | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chrX | 154534914 | 154534773 | − | chrX | 154528458 | 154528349 | − | ENST00000369449; ENST00000321926 | TSF |
| 4% | chr12 | 28565851 | 28565871 | + | chr12 | 28603094 | 28603186 | + | ENST00000540794; ENST00000539107; ENST00000536442; ENST00000545336; ENST00000545737; ENST00000381256; ENST00000381259; ENST00000306172 | TSF |
| 4% | chr12 | 28565851 | 28565871 | + | chr12 | 28603094 | 28603186 | + | ENST00000540794; ENST00000539107; ENST00000536442; ENST00000545336; ENST00000545737; ENST00000381256; ENST00000381259; ENST00000306172 | TSF |
| 4% | chr12 | 28565851 | 28565871 | + | chr12 | 28603094 | 28603186 | + | ENST00000540794; ENST00000539107; ENST00000536442; ENST00000545336; ENST00000545737; ENST00000381256; ENST00000381259; ENST00000306172 | TSF |
| 4% | chr12 | 28565851 | 28565871 | + | chr12 | 28603094 | 28603186 | + | ENST00000540794; ENST00000539107; ENST00000536442; ENST00000545336; ENST00000545737; ENST00000381256; ENST00000381259; ENST00000306172 | TSF |
| 4% | chr11 | 60694460 | 60694539 | + | chr11 | 60694676 | 60694890 | + | ENST00000453848; ENST00000005286 | TSF |
| 4% | chr11 | 60694460 | 60694539 | + | chr11 | 60694676 | 60694890 | + | ENST00000453848; ENST00000005286 | TSF |
| 4% | chr3 | 115829645 | 115827368 | − | chr3 | 115805403 | 115805171 | − | ENST00000490035; ENST00000333617; ENST00000539563; ENST00000474851 | TSF |
| 4% | chr3 | 115829645 | 115827368 | − | chr3 | 115805403 | 115805171 | − | ENST00000490035; ENST00000333617; ENST00000539563; ENST00000474851 | TSF |
| 4% | chr3 | 115829645 | 115827368 | − | chr3 | 115805403 | 115805171 | − | ENST00000490035; ENST00000333617; ENST00000539563; ENST00000474851 | TSF |
| 4% | chr9 | 123165858 | 123165677 | − | chr9 | 123165349 | 123165084 | − | ENST00000359309; ENST00000360822; ENST00000349780; ENST00000360190; ENST00000416449; ENST00000425647 | TSF |
| 4% | chr9 | 132580720 | 132580632 | − | chr9 | 132576501 | 132576251 | − | ENST00000351698 | TSF |
| 4% | chr3 | 191873117 | 191872988 | − | chr3 | 191861916 | 191861798; 191861849 | − | ENST00000445105; ENST00000264730; ENST00000454309; ENST00000440901; ENST00000450716; ENST00000430714; ENST00000448795 | TSF |
| 4% | chr3 | 191873117 | 191872988 | − | chr3 | 191861916 | 191861798; 191861849 | − | ENST00000445105; ENST00000264730; ENST00000454309; ENST00000440901; ENST00000450716; ENST00000430714; ENST00000448795 | TSF |
| 4% | chr12 | 122387836 | 122388242 | + | chr12 | 122394980 | 122395174 | + | ENST00000288912; ENST00000397454 | TSF |
| 4% | chr12 | 122387836 | 122388242 | + | chr12 | 122394980 | 122395174 | + | ENST00000288912; ENST00000397454 | TSF |
| 4% | chr1 | 31218846 | 31218765 | − | chr1 | 31215396 | 31215303 | − | ENST00000294507 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 4% | chr3 | 197640178 | 197640160 | − | chr3 | 197639620 | 197639546 | − | ENST00000265239; ENST00000455191 | TSF |
| 4% | chr8 | 130855946 | 130855855 | − | chr8 | 130854451 | 130854388 | − | ENST00000519824; ENST00000522746; ENST00000523509; ENST00000401979; ENST00000519110; ENST00000522250; ENST00000517654; ENST00000519540; ENST00000522941 | TSF |
| 4% | chr16 | 83989605 | 83989746 | + | chr16 | 83991245 | 83991255; 83991343 | + | ENST00000561552; ENST00000343939 | TSF |
| 4% | chr16 | 83989605 | 83989746 | + | chr16 | 83991245 | 83991255; 83991343 | + | ENST00000561552; ENST00000343939 | TSF |
| 4% | chr7 | 56020443 | 56020541 | + | chr7 | 56020872 | 56021011 | + | ENST00000426595 | TSF |
| 4% | chr10 | 5060345 | 5060092 | − | chr10 | 5043783 | 5043706 | − | ENST00000380753; ENST00000421196; ENST00000407674; ENST00000604507; ENST00000455190 | TSF |
| 4% | chr10 | 5060345 | 5060092 | − | chr10 | 5043783 | 5043706 | − | ENST00000380753; ENST00000421196; ENST00000407674; ENST00000604507; ENST00000455190 | TSF |
| 4% | chr10 | 5060345 | 5060092 | − | chr10 | 5043783 | 5043706 | − | ENST00000380753; ENST00000421196; ENST00000407674; ENST00000604507; ENST00000455190 | TSF |
| 4% | chr10 | 5060345 | 5060092 | − | chr10 | 5043783 | 5043706 | − | ENST00000380753; ENST00000421196; ENST00000407674; ENST00000604507; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr1 | 59980221 | 59980497 | + | chr1 | 60019796 | 60019899 | + | ENST00000455190 ENST00000371218; ENST00000303721; ENST00000430447; ENST00000371212 | TSF |
| 3% | chr1 | 59980221 | 59980497 | + | chr1 | 60019796 | 60019899 | + | ENST00000371218; ENST00000303721; ENST00000430447; ENST00000371212 | TSF |
| 3% | chr1 | 59980221 | 59980497 | + | chr1 | 60019796 | 60019899 | + | ENST00000371218; ENST00000303721; ENST00000430447; ENST00000371212 | TSF |
| 3% | chr7 | 56018506 | 56018522 | + | chr7 | 56022602 | 56022871; 56022865 | + | ENST00000426595; ENST00000285298; ENST00000443449 | TSF |
| 3% | chr7 | 56018506 | 56018522 | + | chr7 | 56022602 | 56022871; 56022865 | + | ENST00000426595; ENST00000285298; ENST00000443449 | TSF |
| 3% | chr3 | 190065748 | 190065532 | − | chr3 | 190030825 | 190030661 | − | ENST00000295522 | TSF |
| 3% | chr11 | 93468219 | 93468129 | − | chr11 | 93466563 | 93466528 | − | ENST00000393259 | TSF |
| 3% | chrX | 154751709 | 154751612 | − | chrX | 154528458 | 154528349 | − | ENST00000369449; ENST00000321926 | TSF |
| 3% | chrX | 154751709 | 154751612 | − | chrX | 154528458 | 154528349 | − | ENST00000369449; ENST00000321926 | TSF |
| 3% | chr14 | 51360331 | 51362440 | + | chr14 | 51368547 | 51368629 | + | ENST00000337334; ENST00000353130; ENST00000395752 | TSF |
| 3% | chr1 | 1422590 | 1422685 | + | chr1 | 1423243 | 1423294 | + | ENST00000308647 | TSF |
| 3% | chr1 | 168348640 | 168349020 | + | chr1 | 168549301 | 168549415 | + | ENST00000367818 | TSF |
| 3% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 3% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 3% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 3% | chr7 | 33006587 | 33006627 | + | chr7 | 33014229 | 33014374 | + | ENST00000242209; ENST00000538336 | TSF |
| 3% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 3% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 3% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 3% | chr2 | 17876171 | 17876059 | − | chr2 | 17865030 | 17864905 | − | ENST00000448223; ENST00000351948; ENST00000381272; ENST00000402989 | TSF |
| 3% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 3% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 3% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 3% | chr19 | 48654965 | 48654725 | − | chr19 | 48654596 | 48654489 | − | ENST00000263274; ENST00000601091; ENST00000542460 | TSF |
| 3% | chr19 | 48654965 | 48654725 | − | chr19 | 48654596 | 48654489 | − | ENST00000263274; ENST00000601091; ENST00000542460 | TSF |
| 3% | chr19 | 48654965 | 48654725 | − | chr19 | 48654596 | 48654489 | − | ENST00000263274; ENST00000601091; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr2 | 29353781 | 29353921 | + | chr2 | 29354124 | 29354263 | + | ENST00000542460 ENST00000401605; ENST00000415891; ENST00000404424; ENST00000456385; ENST00000320081; ENST00000449202 | TSF |
| 3% | chr2 | 29353781 | 29353921 | + | chr2 | 29354124 | 29354263 | + | ENST00000401605; ENST00000415891; ENST00000404424; ENST00000456385; ENST00000320081; ENST00000449202 | TSF |
| 3% | chr2 | 29353781 | 29353921 | + | chr2 | 29354124 | 29354263 | + | ENST00000401605; ENST00000415891; ENST00000404424; ENST00000456385; ENST00000320081; ENST00000449202 | TSF |
| 3% | chr2 | 29353781 | 29353921 | + | chr2 | 29354124 | 29354263 | + | ENST00000401605; ENST00000415891; ENST00000404424; ENST00000456385; ENST00000320081; ENST00000449202 | TSF |
| 3% | chr2 | 29353781 | 29353921 | + | chr2 | 29354124 | 29354263 | + | ENST00000401605; ENST00000415891; ENST00000404424; ENST00000456385; ENST00000320081; ENST00000449202 | TSF |
| 3% | chrX | 134847126 | 134847423 | + | chrX | 134852761 | 134852870 | + | ENST00000370741; ENST00000497301; ENST00000482795 | TSF |
| 3% | chr17 | 66244121 | 66244199 | + | chr17 | 66244785 | 66244846 | + | ENST00000584837 | TSF |
| 3% | chr1 | 169819657 | 169819707 | + | chr1 | 169820958 | 169821077 | + | ENST00000359326; ENST00000286031 | TSF |
| 3% | chr17 | 45698288 | 45698367 | + | chr17 | 45699134 | 45699286 | + | ENST00000530173; ENST00000322157; ENST00000544660; ENST00000528565 | TSF |
| 3% | chr10 | 5120335 | 5120493 | + | chr10 | 5138602 | 5138769 | + | ENST00000602997; ENST00000605149; ENST00000380554 | TSF |
| 3% | chr10 | 5120335 | 5120493 | + | chr10 | 5138602 | 5138769 | + | ENST00000602997; ENST00000605149; ENST00000380554 | TSF |
| 3% | chrX | 134847126 | 134847423 | + | chrX | 134887292 | 134887401 | + | ENST00000370734; ENST00000485366; ENST00000443882 | TSF |
| 3% | chr7 | 55464873 | 55464924 | + | chr7 | 55466116 | 55466323 | + | ENST00000254770 | TSF |
| 3% | chrX | 134847126 | 134847423 | + | chrX | 134870023 | 134870132 | + | ENST00000370736; ENST00000471213; ENST00000495729 | TSF |
| 3% | chr3 | 196453456 | 196453642 | + | chr3 | 196454798 | 196455007; 196455051; 196454981 | + | ENST00000426755; ENST00000392391; ENST00000314118; ENST00000296333; ENST00000421265; ENST00000451319 | TSF |
| 3% | chr3 | 196453456 | 196453642 | + | chr3 | 196454798 | 196455007; 196455051; 196454981 | + | ENST00000426755; ENST00000392391; ENST00000314118; ENST00000296333; ENST00000421265; ENST00000451319 | TSF |
| 3% | chr3 | 196453456 | 196453642 | + | chr3 | 196454798 | 196455007; 196455051; 196454981 | + | ENST00000426755; ENST00000392391; ENST00000314118; ENST00000296333; ENST00000421265; ENST00000451319 | TSF |
| 3% | chr3 | 196453456 | 196453642 | + | chr3 | 196454798 | 196455007; 196455051; 196454981 | + | ENST00000426755; ENST00000392391; ENST00000314118; ENST00000296333; ENST00000421265; ENST00000451319 | TSF |
| 3% | chr3 | 196453456 | 196453642 | + | chr3 | 196454798 | 196455007; 196455051; 196454981 | + | ENST00000426755; ENST00000392391; ENST00000314118; ENST00000296333; ENST00000421265; ENST00000451319 | TSF |
| 3% | chr2 | 9695192 | 9695025 | − | chr2 | 9683414 | 9683282 | − | ENST00000310823; ENST00000497134 | TSF |
| 3% | chr2 | 9695192 | 9695025 | − | chr2 | 9683414 | 9683282 | − | ENST00000310823; ENST00000497134 | TSF |
| 3% | chr12 | 58023123 | 58023062 | − | chr12 | 58022686 | 58022496; 58022484 | − | ENST00000341156; ENST00000418555; ENST00000449184 | TSF |
| 3% | chr12 | 58023123 | 58023062 | − | chr12 | 58022686 | 58022496; 58022484 | − | ENST00000341156; ENST00000418555; ENST00000449184 | TSF |
| 3% | chr6 | 117763870 | 117763597 | − | chr6 | 117739669 | 117739625 | − | ENST00000368507; ENST00000368508 | TSF |
| 3% | chr6 | 117763870 | 117763597 | − | chr6 | 117739669 | 117739625 | − | ENST00000368507; ENST00000368508 | TSF |
| 3% | chr12 | 97286062 | 97286334 | + | chr12 | 97303530 | 97303673 | + | ENST00000554226; ENST00000557644 | TSF |
| 3% | chr12 | 97286062 | 97286334 | + | chr12 | 97303530 | 97303673 | + | ENST00000554226; ENST00000557644 | TSF |
| 3% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 3% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 3% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 3% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 3% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 3% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr1 | 1562829 | 1562973 | + | chr1 | 1563053 | 1563209 | + | ENST00000520777; ENST00000360522; ENST00000355826; ENST00000505820; ENST00000378712; ENST00000378708; | ENST00000357210; ENST00000378710; ENST00000518681; ENST00000487053; ENST00000504599; ENST00000514234 | TSF |
| 3% | chr1 | 1562829 | 1562973 | + | chr1 | 1563053 | 1563209 | + | ENST00000520777; ENST00000360522; ENST00000355826; ENST00000505820; ENST00000378712; ENST00000378708; | ENST00000357210; ENST00000378710; ENST00000518681; ENST00000487053; ENST00000504599; ENST00000514234 | TSF |
| 3% | chr1 | 1562829 | 1562973 | + | chr1 | 1563053 | 1563209 | + | ENST00000520777; ENST00000360522; ENST00000355826; ENST00000505820; ENST00000378712; ENST00000378708; | ENST00000357210; ENST00000378710; ENST00000518681; ENST00000487053; ENST00000504599; ENST00000514234 | TSF |
| 3% | chr10 | 5060345 | 5060092 | − | chr10 | 5042858 | 5042742 | − | ENST00000380753; ENST00000407674; ENST00000455190 | ENST00000421196; ENST00000604507; | TSF |
| 3% | chr10 | 5060345 | 5060092 | − | chr10 | 5042858 | 5042742 | − | ENST00000380753; ENST00000407674; ENST00000455190 | ENST00000421196; ENST00000604507; | TSF |
| 3% | chr10 | 5060345 | 5060092 | − | chr10 | 5042858 | 5042742 | − | ENST00000380753; ENST00000407674; ENST00000455190 | ENST00000421196; ENST00000604507; | TSF |
| 3% | chr10 | 5060345 | 5060092 | − | chr10 | 5042858 | 5042742 | − | ENST00000380753; ENST00000407674; ENST00000455190 | ENST00000421196; ENST00000604507; | TSF |
| 3% | chr10 | 5060345 | 5060092 | − | chr10 | 5034105 | 5034023 | − | ENST00000380753; ENST00000407674 | ENST00000421196; | TSF |
| 3% | chr17 | 70713894 | 70713885 | − | chr17 | 70645407 | 70645309 | − | ENST00000255559; ENST00000582769 | ENST00000542342; | TSF |
| 3% | chr17 | 70713894 | 70713885 | − | chr17 | 70645407 | 70645309 | − | ENST00000255559; ENST00000582769 | ENST00000542342; | TSF |
| 3% | chr10 | 5000323 | 5000656 | + | chr10 | 5008106 | 5008273 | + | ENST00000434459; ENST00000380859 | ENST00000380872; | TSF |
| 3% | chr10 | 5000323 | 5000656 | + | chr10 | 5008106 | 5008273 | + | ENST00000434459; ENST00000380859 | ENST00000380872; | TSF |
| 3% | chr17 | 80544496 | 80544753 | + | chr17 | 80544939 | 80545148; 80545255 | + | ENST00000473637; ENST00000575578 | ENST00000335255; | TSF |
| 3% | chr17 | 80544496 | 80544753 | + | chr17 | 80544939 | 80545148; 80545255 | + | ENST00000473637; ENST00000575578 | ENST00000335255; | TSF |
| 3% | chr17 | 80544496 | 80544753 | + | chr17 | 80544939 | 80545148; 80545255 | + | ENST00000473637; ENST00000575578 | ENST00000335255; | TSF |
| 3% | chr6 | 20673784 | 20674067 | + | chr6 | 20739750 | 20739846 | + | ENST00000274695; ENST00000378610 | ENST00000378624; | TSF |
| 3% | chr6 | 20673784 | 20674067 | + | chr6 | 20739750 | 20739846 | + | ENST00000274695; ENST00000378610 | ENST00000378624; | TSF |
| 3% | chr11 | 70006969 | 70007088 | + | chr11 | 70007267 | 70007468 | + | ENST00000355303; ENST00000538023; ENST00000530676; ENST00000531300 | ENST00000398543; ENST00000316296; ENST00000531349; | TSF |
| 3% | chr11 | 70006969 | 70007088 | + | chr11 | 70007267 | 70007468 | + | ENST00000355303; ENST00000538023; ENST00000530676; ENST00000531300 | ENST00000398543; ENST00000316296; ENST00000531349; | TSF |
| 3% | chr11 | 70006969 | 70007088 | + | chr11 | 70007267 | 70007468 | + | ENST00000355303; ENST00000538023; ENST00000530676; ENST00000531300 | ENST00000398543; ENST00000316296; ENST00000531349; | TSF |
| 3% | chr22 | 22542244 | 22542331 | + | chr22 | 22550370 | 22550770 | + | ENST00000390285 | | TSF |
| 3% | chr15 | 74004214 | 74004264 | + | chr15 | 74005275 | 74005297 | + | ENST00000318443; ENST00000318424; ENST00000561176; ENST00000559073 | ENST00000537340; ENST00000564751; | TSF |
| 3% | chrX | 134866155 | 134866469 | + | chrX | 134870023 | 134870132 | + | ENST00000370736; ENST00000495729 | ENST00000471213; | TSF |
| 3% | chr4 | 186461046 | 186460994 | − | chr22 | 23243156 | 23243475 | + | ENST00000390323 | | TSF |
| 3% | chr4 | 22097850 | 22097560 | − | chr4 | 21764655 | 21764612 | − | ENST00000515786 | | TSF |
| 3% | chr10 | 5050548 | 5050220 | − | chr10 | 5043873 | 5043706 | − | ENST00000380753; ENST00000407674; ENST00000455190 | ENST00000421196; ENST00000604507; | TSF |
| 3% | chr10 | 5050548 | 5050220 | − | chr10 | 5043873 | 5043706 | − | ENST00000380753; ENST00000407674; | ENST00000421196; ENST00000604507; | |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr10 | 5050548 | 5050220 | − | chr10 | 5043873 | 5043706 | − | ENST00000380753; ENST00000421196; ENST00000407674; ENST00000604507; ENST00000455190 | TSF |
| 3% | chr10 | 5050548 | 5050220 | − | chr10 | 5043873 | 5043706 | − | ENST00000380753; ENST00000421196; ENST00000407674; ENST00000604507; ENST00000455190 | TSF |
| 3% | chrX | 134971303 | 134970989 | − | chrX | 134967437 | 134967328 | − | ENST00000491002; ENST00000448053; ENST00000472834 | TSF |
| 3% | chrX | 134954053 | 134953739 | − | chrX | 134950187 | 134950078 | − | ENST00000420087; ENST00000463085; ENST00000370724; ENST00000491480 | TSF |
| 3% | chrX | 134954053 | 134953739 | − | chrX | 134950187 | 134950078 | − | ENST00000420087; ENST00000463085; ENST00000370724; ENST00000491480 | TSF |
| 3% | chr3 | 195593372 | 195593261 | − | chr3 | 195591058 | 195591052 | − | ENST00000416152; ENST00000381916; ENST00000333602; ENST00000428187; ENST00000392400 | TSF |
| 3% | chrX | 134971303 | 134970989 | − | chrX | 134950187 | 134950078 | − | ENST00000420087; ENST00000463085; ENST00000370724; ENST00000491480 | TSF |
| 3% | chrX | 134971303 | 134970989 | − | chrX | 134950187 | 134950078 | − | ENST00000420087; ENST00000463085; ENST00000370724; ENST00000491480 | TSF |
| 3% | chrX | 138072952 | 138072670 | − | chrX | 137939841 | 137939674 | − | ENST00000370603; ENST00000436198; ENST00000455663; ENST00000448673 | TSF |
| 3% | chrX | 138072952 | 138072670 | − | chrX | 137939841 | 137939674 | − | ENST00000370603; ENST00000436198; ENST00000455663; ENST00000448673 | TSF |
| 3% | chrX | 138072952 | 138072670 | − | chrX | 137939841 | 137939674 | − | ENST00000370603; ENST00000436198; ENST00000455663; ENST00000448673 | TSF |
| 3% | chrX | 138072952 | 138072670 | − | chrX | 137939841 | 137939674 | − | ENST00000370603; ENST00000436198; ENST00000455663; ENST00000448673 | TSF |
| 3% | chr20 | 10628319 | 10628254 | − | chr20 | 10627751 | 10627587 | − | ENST00000254958; ENST00000423891 | TSF |
| 3% | chr19 | 48627094 | 48627044 | − | chr19 | 48626575 | 48626431 | − | ENST00000263274; ENST00000536218; ENST00000594759; ENST00000427526; ENST00000601091 | TSF |
| 3% | chr19 | 48627094 | 48627044 | − | chr19 | 48626575 | 48626431 | − | ENST00000263274; ENST00000536218; ENST00000594759; ENST00000427526; ENST00000601091 | TSF |
| 3% | chr8 | 91107662 | 91105645 | − | chr8 | 91094330 | 91094254 | − | ENST00000265431 | TSF |
| 3% | chr2 | 101024262 | 101024202 | − | chr2 | 101023169 | 101023038 | − | ENST00000542617; ENST00000448989 | TSF |
| 3% | chr2 | 101024262 | 101024202 | − | chr2 | 101023169 | 101023038 | − | ENST00000542617; ENST00000448989 | TSF |
| 3% | chr5 | 34914125 | 34914032 | − | chr5 | 34913683 | 34913575 | − | ENST00000382038; ENST00000341754 | TSF |
| 3% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 3% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 3% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 3% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 3% | chr1 | 156305455 | 156305264 | | chr1 | 156304709 | 156304659 | − | ENST00000295688; ENST00000368258; ENST00000413555; ENST00000496684; ENST00000478640; ENST00000415548 | TSF |
| 3% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 2% | chr12 | 97286062 | 97286334 | + | chr12 | 97311399 | 97311515; 97311469 | + | ENST00000266742; ENST00000429527; ENST00000554226; ENST00000557478; ENST00000557092; ENST00000557644 | TSF |
| 2% | chr12 | 97286062 | 97286334 | + | chr12 | 97311399 | 97311515; 97311469 | + | ENST00000266742; ENST00000429527; ENST00000554226; ENST00000557478; ENST00000557092; ENST00000557644 | TSF |
| 2% | chr12 | 97286062 | 97286334 | + | chr12 | 97311399 | 97311515; 97311469 | + | ENST00000266742; ENST00000429527; ENST00000554226; ENST00000557478; ENST00000557092; ENST00000557644 | TSF |
| 2% | chr12 | 97286062 | 97286334 | + | chr12 | 97311399 | 97311515; 97311469 | + | ENST00000266742; ENST00000429527; ENST00000554226; ENST00000557478; ENST00000557092; ENST00000557644 | TSF |
| 2% | chr2 | 217519962 | 217520258 | + | chr2 | 217525280 | 217525509 | + | ENST00000233809; ENST00000456764 | TSF |
| 2% | chr3 | 130586141 | 130586877 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr3 | 130586141 | 130586877 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586877 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586877 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586877 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586877 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586877 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr19 | 1114930 | 1114676 | − | chr19 | 1114421 | 1114230 | − | ENST00000361757; ENST00000587024; ENST00000438103 | TSF |
| 2% | chr8 | 91102885 | 91102521 | − | chr8 | 91094330 | 91094254 | − | ENST00000265431 | TSF |
| 2% | chr19 | 47343471 | 47343373 | − | chr19 | 47342835 | 47342722 | − | ENST00000352203; ENST00000601498; ENST00000599990; ENST00000593442; ENST00000263270; ENST00000597020 | TSF |
| 2% | chr1 | 33251116 | 33251115 | − | chr1 | 33248140 | 33248005 | − | ENST00000373477 | TSF |
| 2% | chr11 | 60934781 | 60933962 | − | chr11 | 60901679 | 60901508 | − | ENST00000301765; ENST00000538036 | TSF |
| 2% | chr11 | 60934781 | 60933962 | − | chr11 | 60901679 | 60901508 | − | ENST00000301765; ENST00000538036 | TSF |
| 2% | chr12 | 110306235 | 110306193 | − | chr12 | 110296546 | 110296488 | − | ENST00000318348; ENST00000544393; ENST00000540772; ENST00000536390; ENST00000537066 | TSF |
| 2% | chr12 | 110306235 | 110306193 | − | chr12 | 110296546 | 110296488 | − | ENST00000318348; ENST00000544393; ENST00000540772; ENST00000536390; ENST00000537066 | TSF |
| 2% | chr12 | 110306235 | 110306193 | − | chr12 | 110296546 | 110296488 | − | ENST00000318348; ENST00000544393; ENST00000540772; ENST00000536390; ENST00000537066 | TSF |
| 2% | chr12 | 110306235 | 110306193 | − | chr12 | 110296546 | 110296488 | − | ENST00000318348; ENST00000544393; ENST00000540772; ENST00000536390; ENST00000537066 | TSF |
| 2% | chr9 | 123159676 | 123159573 | − | chr9 | 123156916 | 123156790 | − | ENST00000359309; ENST00000360822; ENST00000349780; ENST00000360190; ENST00000416449; ENST00000425647 | TSF |
| 2% | chr3 | 184639788 | 184640271 | + | chr3 | 184642650 | 184642769 | + | ENST00000287546; ENST00000437079; ENST00000436792; ENST00000446204 | TSF |
| 2% | chrX | 134866155 | 134866469 | + | chrX | 134887292 | 134887401 | + | ENST00000370734; ENST00000485366; ENST00000443882 | TSF |
| 2% | chrX | 134883429 | 134883743 | + | chrX | 134887292 | 134887401 | + | ENST00000370734; ENST00000485366; ENST00000443882 | TSF |
| 2% | chr20 | 60878087 | 60878105 | + | chr20 | 60878775 | 60878837 | + | ENST00000253003 | TSF |
| 2% | chr1 | 15562769 | 15563257 | + | chr1 | 15578196 | 15578373 | + | ENST00000433640 | TSF |
| 2% | chr12 | 54862718 | 54862609 | − | chr12 | 54858951 | 54858851 | − | ENST00000546931; ENST00000552397; ENST00000305879 | TSF |
| 2% | chr12 | 54862718 | 54862609 | − | chr12 | 54858951 | 54858851 | − | ENST00000546931; ENST00000552397; ENST00000305879 | TSF |
| 2% | chr16 | 48451457 | 48450727 | − | chr16 | 48396341 | 48395491 | − | ENST00000356721 | TSF |
| 2% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 2% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 2% | chr15 | 91529041 | 91528993 | − | chr15 | 91528055 | 91527923 | − | ENST00000394249; ENST00000361919; ENST00000361188; ENST00000442656; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr15 | 91529041 | 91528993 | − | chr15 | 91528055 | 91527923 | − | | ENST00000557905; ENST00000559811; ENST00000394249; ENST00000361919;TSF ENST00000361188; ENST00000442656; |
| 2% | chr15 | 91529041 | 91528993 | − | chr15 | 91528055 | 91527923 | − | | ENST00000557905; ENST00000559811; ENST00000394249; ENST00000361919;TSF ENST00000361188; ENST00000442656; |
| 2% | chr15 | 91529041 | 91528993 | − | chr15 | 91528055 | 91527923 | − | | ENST00000557905; ENST00000559811; ENST00000394249; ENST00000361919;TSF ENST00000361188; ENST00000442656; |
| 2% | chr17 | 17816540 | 17815566 | − | chr17 | 17810845 | 17810761 | − | | ENST00000581396; ENST00000379504;TSF ENST00000318094; ENST00000395739; ENST00000535933; ENST00000540946; ENST00000542206 |
| 2% | chr17 | 17816540 | 17815566 | − | chr17 | 17810845 | 17810761 | − | | ENST00000581396; ENST00000379504;TSF ENST00000318094; ENST00000395739; ENST00000535933; ENST00000540946; ENST00000542206 |
| 2% | chr17 | 17816540 | 17815566 | − | chr17 | 17810845 | 17810761 | − | | ENST00000581396; ENST00000379504;TSF ENST00000318094; ENST00000395739; ENST00000535933; ENST00000540946; ENST00000542206 |
| 2% | chr17 | 17816540 | 17815566 | − | chr17 | 17810845 | 17810761 | − | | ENST00000581396; ENST00000379504;TSF ENST00000318094; ENST00000395739; ENST00000535933; ENST00000540946; ENST00000542206 |
| 2% | chr17 | 17816540 | 17815566 | − | chr17 | 17810845 | 17810761 | − | | ENST00000581396; ENST00000379504;TSF ENST00000318094; ENST00000395739; ENST00000535933; ENST00000540946; ENST00000542206 |
| 2% | chr17 | 17816540 | 17815566 | − | chr17 | 17810845 | 17810761 | − | | ENST00000581396; ENST00000379504;TSF ENST00000318094; ENST00000395739; ENST00000535933; ENST00000540946; ENST00000542206 |
| 2% | chr19 | 50167252 | 50167184 | − | chr19 | 50166771 | 50166600; 50166728; 50166630 | − | | ENST00000309877; ENST00000600911;TSF ENST00000601291; ENST00000377139; ENST00000597198; ENST00000597636; ENST00000599223; ENST00000377135; ENST00000596756; ENST00000598108; ENST00000593337; ENST00000601809; ENST00000596788; ENST00000600453 |
| 2% | chr19 | 50167252 | 50167184 | − | chr19 | 50166771 | 50166600; 50166728; 50166630 | − | | ENST00000309877; ENST00000600911;TSF ENST00000601291; ENST00000377139; ENST00000597198; ENST00000597636; ENST00000599223; ENST00000377135; ENST00000596756; ENST00000598108; ENST00000593337; ENST00000601809; ENST00000596788; ENST00000600453 |
| 2% | chr19 | 50167252 | 50167184 | − | chr19 | 50166771 | 50166600; 50166728; 50166630 | − | | ENST00000309877; ENST00000600911;TSF ENST00000601291; ENST00000377139; ENST00000597198; ENST00000597636; ENST00000599223; ENST00000377135; ENST00000596756; ENST00000598108; ENST00000593337; ENST00000601809; ENST00000596788; ENST00000600453 |
| 2% | chr19 | 50167252 | 50167184 | − | chr19 | 50166771 | 50166600; 50166728; 50166630 | − | | ENST00000309877; ENST00000600911;TSF ENST00000601291; ENST00000377139; ENST00000597198; ENST00000597636; ENST00000599223; ENST00000377135; ENST00000596756; ENST00000598108; ENST00000593337; ENST00000601809; ENST00000596788; ENST00000600453 |
| 2% | chr19 | 50167252 | 50167184 | − | chr19 | 50166771 | 50166600; 50166728; 50166630 | − | | ENST00000309877; ENST00000600911;TSF ENST00000601291; ENST00000377139; ENST00000597198; ENST00000597636; ENST00000599223; ENST00000377135; ENST00000596756; ENST00000598108; ENST00000593337; ENST00000601809; ENST00000596788; ENST00000600453 |
| 2% | chr19 | 50167252 | 50167184 | − | chr19 | 50166771 | 50166600; 50166728; 50166630 | − | | ENST00000309877; ENST00000600911;TSF ENST00000601291; ENST00000377139; ENST00000597198; ENST00000597636; ENST00000599223; ENST00000377135; ENST00000596756; ENST00000598108; ENST00000593337; ENST00000601809; |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr19 | 50167252 | 50167184 | − | chr19 | 50166771 | 50166600; 50166728; 50166630 | − | ENST00000596788; ENST00000600453 ENST00000309877; ENST00000600911; ENST00000601291; ENST00000377139; ENST00000597198; ENST00000597636; ENST00000599223; ENST00000377135; ENST00000596756; ENST00000598108; ENST00000593337; ENST00000601809; | TSF |
| 2% | chr19 | 50167252 | 50167184 | − | chr19 | 50166771 | 50166600; 50166728; 50166630 | − | ENST00000596788; ENST00000600453 ENST00000309877; ENST00000600911; ENST00000601291; ENST00000377139; ENST00000597198; ENST00000597636; ENST00000599223; ENST00000377135; ENST00000596756; ENST00000598108; ENST00000593337; ENST00000601809; | TSF |
| 2% | chr19 | 50167252 | 50167184 | − | chr19 | 50166771 | 50166600; 50166728; 50166630 | − | ENST00000596788; ENST00000600453 ENST00000309877; ENST00000600911; ENST00000601291; ENST00000377139; ENST00000597198; ENST00000597636; ENST00000599223; ENST00000377135; ENST00000596756; ENST00000598108; ENST00000593337; ENST00000601809; | TSF |
| 2% | chr19 | 50167252 | 50167184 | − | chr19 | 50166771 | 50166600; 50166728; 50166630 | − | ENST00000596788; ENST00000600453 ENST00000309877; ENST00000600911; ENST00000601291; ENST00000377139; ENST00000597198; ENST00000597636; ENST00000599223; ENST00000377135; ENST00000596756; ENST00000598108; ENST00000593337; ENST00000601809; | TSF |
| 2% | chr19 | 50167252 | 50167184 | − | chr19 | 50166771 | 50166600; 50166728; 50166630 | − | ENST00000596788; ENST00000600453 ENST00000309877; ENST00000600911; ENST00000601291; ENST00000377139; ENST00000597198; ENST00000597636; ENST00000599223; ENST00000377135; ENST00000596756; ENST00000598108; ENST00000593337; ENST00000601809; | TSF |
| 2% | chr19 | 35613389 | 35613502 | + | chr19 | 35613669 | 35613862; 35613743; 35613858 | + | ENST00000406242; ENST00000604404; ENST00000435734; ENST00000603181; ENST00000604255; ENST00000344013; ENST00000346446; ENST00000406988; ENST00000605550; ENST00000604804; ENST00000535103; ENST00000603524; ENST00000604621; ENST00000605677 | TSF |
| 2% | chr19 | 35613389 | 35613502 | + | chr19 | 35613669 | 35613862; 35613743; 35613858 | + | ENST00000406242; ENST00000604404; ENST00000435734; ENST00000603181; ENST00000604255; ENST00000344013; ENST00000346446; ENST00000406988; ENST00000605550; ENST00000604804; ENST00000535103; ENST00000603524; ENST00000604621; ENST00000605677 | TSF |
| 2% | chr19 | 35613389 | 35613502 | + | chr19 | 35613669 | 35613862; 35613743; 35613858 | + | ENST00000406242; ENST00000604404; ENST00000435734; ENST00000603181; ENST00000604255; ENST00000344013; ENST00000346446; ENST00000406988; ENST00000605550; ENST00000604804; ENST00000535103; ENST00000603524; ENST00000604621; ENST00000605677 | TSF |
| 2% | chr19 | 35613389 | 35613502 | + | chr19 | 35613669 | 35613862; 35613743; 35613858 | + | ENST00000406242; ENST00000604404; ENST00000435734; ENST00000603181; ENST00000604255; ENST00000344013; ENST00000346446; ENST00000406988; ENST00000605550; ENST00000604804; ENST00000535103; ENST00000603524; ENST00000604621; ENST00000605677 | TSF |
| 2% | chr22 | 24967426 | 24967475 | + | chr22 | 24967884 | 24967945 | + | ENST00000215829; ENST00000404603 | TSF |
| 2% | chr2 | 26666337 | 26666354 | + | chr2 | 26667090 | 26667224; 26667126 | + | ENST00000288710; ENST00000442810 | TSF |
| 2% | chr2 | 26666337 | 26666354 | + | chr2 | 26667090 | 26667224; 26667126 | + | ENST00000288710; ENST00000442810 | TSF |
| 2% | chr3 | 126601624 | 126602182 | + | chr3 | 126633523 | 126633593 | + | ENST00000290913; ENST00000508789; ENST00000513253 | TSF |
| 2% | chr3 | 126601624 | 126602182 | + | chr3 | 126633523 | 126633593 | + | ENST00000290913; ENST00000508789; ENST00000513253 | TSF |
| 2% | chr3 | 126601624 | 126602182 | + | chr3 | 126633523 | 126633593 | + | ENST00000290913; ENST00000508789; ENST00000513253 | TSF |
| 2% | chr16 | 53866877 | 53867152 | + | chr16 | 53878067 | 53878210; 53878156 | + | ENST00000471389; ENST00000464071 | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr16 | 53866877 | 53867152 | + | chr16 | 53878067 | 53878210; 53878156 | + | ENST00000471389; ENST00000464071 | TSF |
| 2% | chr16 | 16227557 | 16227839 | + | chr16 | 16228207 | 16228365 | + | ENST00000399410; ENST00000345148; ENST00000346370; ENST00000349029; ENST00000351154; ENST00000399408; ENST00000572882 | TSF |
| 2% | chr16 | 16227557 | 16227839 | + | chr16 | 16228207 | 16228365 | + | ENST00000399410; ENST00000345148; ENST00000346370; ENST00000349029; ENST00000351154; ENST00000399408; ENST00000572882 | TSF |
| 2% | chr1 | 27158561 | 27158563 | + | chr1 | 27158938 | 27159098 | + | ENST00000374142 | TSF |
| 2% | chr20 | 8624404 | 8625147 | + | chr20 | 8626749 | 8626828 | + | ENST00000378641; ENST00000338037; ENST00000378637; ENST00000404098 | TSF |
| 2% | chr20 | 8624404 | 8625147 | + | chr20 | 8626749 | 8626828 | + | ENST00000378641; ENST00000338037; ENST00000378637; ENST00000404098 | TSF |
| 2% | chr20 | 8624404 | 8625147 | + | chr20 | 8626749 | 8626828 | + | ENST00000378641; ENST00000338037; ENST00000378637; ENST00000404098 | TSF |
| 2% | chr2 | 216976986 | 216977153 | + | chr2 | 216977739 | 216977852 | + | ENST00000392133; ENST00000392132 | TSF |
| 2% | chr7 | 134215952 | 134215973 | + | chr7 | 134216660 | 134216776 | + | ENST00000359579 | TSF |
| 2% | chr6 | 30844573 | 30844673 | + | chr6 | 30856465 | 30856591 | + | ENST00000508312; ENST00000503495 | TSF |
| 2% | chr6 | 30844573 | 30844673 | + | chr6 | 30856465 | 30856591 | + | ENST00000508312; ENST00000503495 | TSF |
| 2% | chr12 | 96302230 | 96301326 | − | chr12 | 96300229 | 96300165 | − | ENST00000344280 | TSF |
| 2% | chr3 | 183680609 | 183680541 | − | chr3 | 183679442 | 183679299 | − | ENST00000334444; ENST00000265586 | TSF |
| 2% | chr3 | 183680609 | 183680541 | − | chr3 | 183679442 | 183679299 | − | ENST00000334444; ENST00000265586 | TSF |
| 2% | chr18 | 51273 | 49727 | − | chr18 | 49237 | 49129 | − | ENST00000308911 | TSF |
| 2% | chr1 | 180281096 | 180280936 | − | chr1 | 180257652 | 180257498 | − | ENST00000367595 | TSF |
| 2% | chr18 | 33076776 | 33076739 | − | chr18 | 33060527 | 33060417 | − | ENST00000592173; ENST00000334598; ENST00000441607; ENST00000591139 | TSF |
| 2% | chr18 | 33076776 | 33076739 | − | chr18 | 33060527 | 33060417 | − | ENST00000592173; ENST00000334598; ENST00000441607; ENST00000591139 | TSF |
| 2% | chr18 | 33076776 | 33076739 | − | chr18 | 33060527 | 33060417 | − | ENST00000592173; ENST00000334598; ENST00000441607; ENST00000591139 | TSF |
| 2% | chr1 | 156716197 | 156716133 | − | chr1 | 156715165 | 156715089 | − | ENST00000357325; ENST00000537739; ENST00000368209; ENST00000368206 | TSF |
| 2% | chr10 | 5060345 | 5060092 | − | chr10 | 5038057 | 5037948; 5038026 | − | ENST00000380753; ENST00000421196; ENST00000407674; ENST00000604507 | TSF |
| 2% | chr10 | 5060345 | 5060092 | − | chr10 | 5038057 | 5037948; 5038026 | − | ENST00000380753; ENST00000421196; ENST00000407674; ENST00000604507 | TSF |
| 2% | chr8 | 119918965 | 119919242 | + | chr8 | 120101919 | 120101990 | + | ENST00000332843 | TSF |
| 2% | chr18 | 20590293 | 20590383 | + | chr18 | 20596791 | 20596887 | + | ENST00000327155; ENST00000399722; ENST00000360790; ENST00000583057 | TSF |
| 2% | chr18 | 20590293 | 20590383 | + | chr18 | 20596791 | 20596887 | + | ENST00000327155; ENST00000399722; ENST00000360790; ENST00000583057 | TSF |
| 2% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586917 | + | chr3 | 130649260 | 130649370 | + | ENST00000393221; ENST00000533801; ENST00000510168; ENST00000508532; ENST00000505072; ENST00000509662; ENST00000328560; ENST00000428331; ENST00000359644; ENST00000422190 | TSF |
| 2% | chr3 | 130586141 | 130586917 | + | chr3 | 130649260 | 130649370 | + | ENST00000393221; ENST00000533801; ENST00000510168; ENST00000508532; ENST00000505072; ENST00000509662; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr12 | 50491053 | 50491120 | + | chr12 | 50492497 | 50492598 | + | ENST00000328560; ENST00000428331; ENST00000359644; ENST00000422190 ENST00000394963; ENST00000381513; ENST00000548573; ENST00000549274 | TSF |
| 2% | chr1 | 44446234 | 44446286 | + | chr1 | 44446781 | 44447145 | + | ENST00000309519 | TSF |
| 2% | chr20 | 110606 | 110697 | + | chr20 | 126056 | 126333 | + | ENST00000382398 | TSF |
| 2% | chr8 | 97343998 | 97344068 | + | chr8 | 97345685 | 97345794; 97345714 | + | ENST00000517309; ENST00000455950; ENST00000522072 | TSF |
| 2% | chr8 | 97343998 | 97344068 | + | chr8 | 97345685 | 97345794; 97345714 | + | ENST00000517309; ENST00000455950; ENST00000522072 | TSF |
| 2% | chr10 | 3133726 | 3133857 | + | chr10 | 3141467 | 3141544 | + | ENST00000607886; ENST00000381125; ENST00000381075; ENST00000407806 | TSF |
| 2% | chr10 | 3133726 | 3133857 | + | chr10 | 3141467 | 3141544 | + | ENST00000607886; ENST00000381125; ENST00000381075; ENST00000407806 | TSF |
| 2% | chr10 | 3133726 | 3133857 | + | chr10 | 3141467 | 3141544 | + | ENST00000607886; ENST00000381125; ENST00000381075; ENST00000407806 | TSF |
| 2% | chr10 | 3133726 | 3133857 | + | chr10 | 3141467 | 3141544 | + | ENST00000607886; ENST00000381125; ENST00000381075; ENST00000407806 | TSF |
| 2% | chr16 | 16233187 | 16233287 | + | chr16 | 16235030 | 16235138 | + | ENST00000399410; ENST00000345148; ENST00000346370; ENST00000349029; ENST00000351154; ENST00000399408; ENST00000572882 | TSF |
| 2% | chr8 | 120050383 | 120050389 | + | chr8 | 120101919 | 120101990 | + | ENST00000332843 | TSF |
| 2% | chr1 | 12002791 | 12002835 | + | chr1 | 12008033 | 12008124 | + | ENST00000449038; ENST00000376369; ENST00000429000; ENST00000196061 | TSF |
| 2% | chr1 | 12002791 | 12002835 | + | chr1 | 12008033 | 12008124 | + | ENST00000449038; ENST00000376369; ENST00000429000; ENST00000196061 | TSF |
| 2% | chr1 | 12002791 | 12002835 | + | chr1 | 12008033 | 12008124 | + | ENST00000449038; ENST00000376369; ENST00000429000; ENST00000196061 | TSF |
| 2% | chr5 | 1475119 | 1475076 | − | chr5 | 1474800 | 1474675 | − | ENST00000475622; ENST00000283415 | TSF |
| 2% | chr15 | 83667946 | 83667078 | − | chr15 | 83660798 | 83660684 | − | ENST00000451195 | TSF |
| 2% | chr1 | 8924664 | 8924519 | − | chr1 | 8924151 | 8923950 | − | ENST00000234590 | TSF |
| 2% | chr8 | 91108096 | 91107732 | − | chr8 | 91094330 | 91094254 | − | ENST00000265431 | TSF |
| 2% | chr1 | 203191927 | 203191877 | − | chr1 | 203191453 | 203191330 | − | ENST00000367229; ENST00000491855; ENST00000255427; ENST00000535569; ENST00000503786 | TSF |
| 2% | chr1 | 203191927 | 203191877 | − | chr1 | 203191453 | 203191330 | − | ENST00000367229; ENST00000491855; ENST00000255427; ENST00000535569; ENST00000503786 | TSF |
| 2% | chr1 | 203191927 | 203191877 | − | chr1 | 203191453 | 203191330 | − | ENST00000367229; ENST00000491855; ENST00000255427; ENST00000535569; ENST00000503786 | TSF |
| 2% | chr12 | 92826976 | 92826686 | − | chr12 | 92814949 | 92814786 | − | ENST00000378487; ENST00000538965 | TSF |
| 2% | chr1 | 23762222 | 23762216 | − | chr1 | 23761111 | 23761026 | − | ENST00000495646; ENST00000336689; ENST00000437606 | TSF |
| 2% | chr3 | 113450271 | 113449590 | − | chr3 | 113442939 | 113442806; 113442828 | − | ENST00000240922; ENST00000477813; ENST00000497255; ENST00000481432; ENST00000493900; ENST00000478020 | TSF |
| 2% | chr3 | 113450271 | 113449590 | − | chr3 | 113442939 | 113442806; 113442828 | − | ENST00000240922; ENST00000477813; ENST00000497255; ENST00000481432; ENST00000493900; ENST00000478020 | TSF |
| 2% | chr3 | 113450271 | 113449590 | − | chr3 | 113442939 | 113442806; 113442828 | − | ENST00000240922; ENST00000477813; ENST00000497255; ENST00000481432; ENST00000493900; ENST00000478020 | TSF |
| 2% | chr3 | 113450271 | 113449590 | − | chr3 | 113442939 | 113442806; 113442828 | − | ENST00000240922; ENST00000477813; ENST00000497255; ENST00000481432; ENST00000493900; ENST00000478020 | TSF |
| 2% | chr3 | 113450271 | 113449590 | − | chr3 | 113442939 | 113442806; 113442828 | − | ENST00000240922; ENST00000477813; ENST00000497255; ENST00000481432; ENST00000493900; ENST00000478020 | TSF |
| 2% | chr12 | 96302230 | 96301454 | − | chr12 | 96300229 | 96300165 | − | ENST00000344280 | TSF |
| 2% | chr10 | 4952037 | 4952123 | + | chr10 | 5014908 | 5014941; 5014939 | + | ENST00000434459; ENST00000380872; ENST00000442997 | TSF |
| 2% | chr10 | 4952037 | 4952123 | + | chr10 | 5014908 | 5014941; 5014939 | + | ENST00000434459; ENST00000380872; ENST00000442997 | TSF |
| 2% | chr7 | 6423751 | 6423803 | + | chr7 | 6426843 | 6426914 | + | ENST00000348035; ENST00000356142 | TSF |
| 2% | chr7 | 6423751 | 6423803 | + | chr7 | 6426843 | 6426914 | + | ENST00000348035; ENST00000356142 | TSF |
| 2% | chr20 | 62647199 | 62647374 | + | chr20 | 62648076 | 62648198 | + | ENST00000535781; ENST00000266079 | TSF |
| 2% | chr20 | 62647199 | 62647374 | + | chr20 | 62648076 | 62648198 | + | ENST00000535781; ENST00000266079 | TSF |
| 2% | chr1 | 162768504 | 162768725 | + | chr1 | 162769533 | 162769727 | + | ENST00000367917; ENST00000254521 | TSF |
| 2% | chr1 | 162768504 | 162768725 | + | chr1 | 162769533 | 162769727 | + | ENST00000367917; ENST00000254521 | TSF |
| 2% | chr2 | 143763612 | 143763709 | + | chr2 | 143787196 | 143787248 | + | ENST00000264170; ENST00000409512 | TSF |
| 2% | chr22 | 38182207 | 38182899 | + | chr22 | 38206034 | 38206164 | + | ENST00000323205; ENST00000248924; ENST00000445195; ENST00000451984 | TSF |
| 2% | chr22 | 38182207 | 38182899 | + | chr22 | 38206034 | 38206164 | + | ENST00000323205; ENST00000248924; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr22 | 38182207 | 38182899 | + | chr22 | 38206034 | 38206164 | + | ENST00000445195; ENST00000451984 ENST00000323205; ENST00000248924; ENST00000445195; ENST00000451984 | TSF |
| 2% | chr14 | 70466641 | 70466673 | + | chr14 | 70477471 | 70477663 | + | ENST00000361956; ENST00000381280 | TSF |
| 2% | chr14 | 70466641 | 70466673 | + | chr14 | 70477471 | 70477663 | + | ENST00000361956; ENST00000381280 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr5 | 52897435; 52897700 | 52897704 | + | chr5 | 52899282 | 52899360 | + | ENST00000502423; ENST00000296684; ENST00000506974; ENST00000506765 | TSF |
| 2% | chr19 | 40709427 | 40709625 | + | chr19 | 40710392 | 40710540 | + | ENST00000253055; ENST00000597986 | TSF |
| 2% | chr19 | 40709427 | 40709625 | + | chr19 | 40710392 | 40710540 | + | ENST00000253055; ENST00000597986 | TSF |
| 2% | chr2 | 217506021 | 217506062 | + | chr2 | 217525280 | 217525509 | + | ENST00000233809; ENST00000456764 | TSF |
| 2% | chr4 | 99926272 | 99927003 | + | chr4 | 99950018 | 99950069 | + | ENST00000296411; ENST00000510107 | TSF |
| 2% | chr4 | 99926272 | 99927003 | + | chr4 | 99950018 | 99950069 | + | ENST00000296411; ENST00000510107 | TSF |
| 2% | chr12 | 97251345 | 97251620 | + | chr12 | 97303530 | 97303673 | + | ENST00000554226; ENST00000557644 | TSF |
| 2% | chr12 | 97251345 | 97251620 | + | chr12 | 97303530 | 97303673 | + | ENST00000554226; ENST00000557644 | TSF |
| 2% | chr8 | 128749913 | 128749923 | + | chr8 | 128750494 | 128751265 | + | ENST00000377970 | TSF |
| 2% | chr12 | 86274449 | 86274547 | + | chr12 | 86276010 | 86276153 | + | ENST00000551529; ENST00000256010 | TSF |
| 2% | chr7 | 96798362 | 96798524 | + | chr7 | 96810324 | 96810527 | + | ENST00000432641 | TSF |
| 2% | chr12 | 122430912 | 122431578 | + | chr12 | 122439403 | 122439504 | + | ENST00000288912 | TSF |
| 2% | chr11 | 66354487 | 66355279 | + | chr11 | 66361113 | 66361185 | + | ENST00000533244; ENST00000530961 | TSF |
| 2% | chr11 | 66354487 | 66355279 | + | chr11 | 66361113 | 66361185 | + | ENST00000533244; ENST00000530961 | TSF |
| 2% | chr4 | 185620772 | 185620691 | − | chr4 | 185618957 | 185618801; 185618919 | − | ENST00000281453; ENST00000510146 | TSF |
| 2% | chr4 | 185620772 | 185620691 | − | chr4 | 185618957 | 185618801; 185618919 | − | ENST00000281453; ENST00000510146 | TSF |
| 2% | chrX | 134936794 | 134936480 | − | chrX | 134932924 | 134932815 | − | ENST00000487941; ENST00000434966; ENST00000494421 | TSF |
| 2% | chr15 | 74475607 | 74475594 | − | chr15 | 74474801 | 74474684 | − | ENST00000395105; ENST00000423167; ENST00000323940; ENST00000449139; ENST00000416286; ENST00000535552; ENST00000563965; ENST00000574278; ENST00000572785 | TSF |
| 2% | chr15 | 74475607 | 74475594 | − | chr15 | 74474801 | 74474684 | − | ENST00000395105; ENST00000423167; ENST00000323940; ENST00000449139; ENST00000416286; ENST00000535552; ENST00000563965; ENST00000574278; ENST00000572785 | TSF |
| 2% | chr1 | 31744147 | 31744121 | − | chr1 | 31742087 | 31742005 | − | ENST00000263694; ENST00000373720; ENST00000446633 | TSF |
| 2% | chr1 | 31744147 | 31744121 | − | chr1 | 31742087 | 31742005 | − | ENST00000263694; ENST00000373720; ENST00000446633 | TSF |
| 2% | chr13 | 73295985 | 73295918 | − | chr13 | 73293235 | 73293090 | − | ENST00000377818 | TSF |
| 2% | chr21 | 38273278 | 38272892 | − | chr21 | 38269431 | 38269160 | − | ENST00000336648; ENST00000399120 | TSF |
| 2% | chr3 | 191873117 | 191873032 | − | chr3 | 191861916 | 191861798; 191861849 | − | ENST00000445105; ENST00000264730; ENST00000454309; ENST00000440901; ENST00000450716; ENST00000430714; ENST00000448795 | TSF |
| 2% | chr3 | 191873117 | 191873032 | − | chr3 | 191861916 | 191861798; 191861849 | − | ENST00000445105; ENST00000264730; ENST00000454309; ENST00000440901; ENST00000450716; ENST00000430714; ENST00000448795 | TSF |
| 2% | chrX | 134971303 | 134970989 | − | chrX | 134932924 | 134932815 | − | ENST00000487941; ENST00000434966; ENST00000494421 | TSF |
| 2% | chr21 | 30382014 | 30381948 | − | chr21 | 30380942 | 30380716 | − | ENST00000493196 | TSF |
| 2% | chrX | 134954053 | 134953739 | − | chrX | 134932924 | 134932815 | − | ENST00000487941; ENST00000434966; ENST00000494421 | TSF |
| 2% | chr1 | 52322378 | 52322114 | − | chr1 | 52306186 | 52305898 | − | ENST00000352171; ENST00000354831 | TSF |
| 2% | chr1 | 52322378 | 52322114 | − | chr1 | 52306186 | 52305898 | − | ENST00000352171; ENST00000354831 | TSF |
| 1% | chr18 | 33274343 | 33274542 | + | chr18 | 33282861 | 33282959 | + | ENST00000269195; ENST00000537549 | TSF |
| 1% | chr14 | 51360331 | 51360476 | + | chr14 | 51368547 | 51368629 | + | ENST00000337334; ENST00000353130; ENST00000395752 | TSF |
| 1% | chr2 | 28630786 | 28630878 | + | chr2 | 28631626 | 28631733 | + | ENST00000379619; ENST00000264716 | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr2 | 28630786 | 28630878 | + | chr2 | 28631626 | 28631733 | + | ENST00000436647; ENST00000545753 ENST00000379619; ENST00000264716; | TSF |
| 1% | chr2 | 28630786 | 28630878 | + | chr2 | 28631626 | 28631733 | + | ENST00000436647; ENST00000545753 ENST00000379619; ENST00000264716; | TSF |
| 1% | chr3 | 187088030 | 187088050 | + | chr3 | 187088576 | 187089161 | + | ENST00000259030 | TSF |
| 1% | chr10 | 27470588 | 27470654 | + | chr10 | 27475308 | 27475465 | + | ENST00000375946; ENST00000375940; ENST00000342386 | TSF |
| 1% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 1% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 1% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 1% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 1% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 1% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 1% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 1% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 1% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 1% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 1% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 1% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 1% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 1% | chr3 | 155605105 | 155605320 | + | chr3 | 155611307 | 155611488 | + | ENST00000496455 | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 1% | chr4 | 15791827 | 15792504 | + | chr4 | 15818134 | 15818263 | + | ENST00000502843; ENST00000226279 | TSF |
| 1% | chr4 | 15791827 | 15792504 | + | chr4 | 15818134 | 15818263 | + | ENST00000502843; ENST00000226279 | TSF |
| 1% | chr9 | 134363954 | 134364268 | + | chr9 | 134366812 | 134366967 | + | ENST00000405995; ENST00000357304; ENST00000458550; ENST00000372249; ENST00000320547 | TSF |
| 1% | chr9 | 134363954 | 134364268 | + | chr9 | 134366812 | 134366967 | + | ENST00000405995; ENST00000357304; ENST00000458550; ENST00000372249; ENST00000320547 | TSF |
| 1% | chr5 | 147155750 | 147156045 | + | chr5 | 147261009 | 147261211 | + | ENST00000296694 | TSF |
| 1% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 1% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 1% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 1% | chr7 | 134215952 | 134215973 | + | chr7 | 134217756 | 134217833 | + | ENST00000359579 | TSF |
| 1% | chr4 | 57321042 | 57321258 | + | chr4 | 57325538 | 57325704; 57325665 | + | ENST00000514888; ENST00000264221; ENST00000505164; ENST00000399688; ENST00000512576 | TSF |
| 1% | chr4 | 57321042 | 57321258 | + | chr4 | 57325538 | 57325704; 57325665 | + | ENST00000514888; ENST00000264221; ENST00000505164; ENST00000399688; ENST00000512576 | TSF |
| 1% | chr7 | 2287707 | 2287861 | + | chr7 | 2289492 | 2289637 | + | ENST00000356714; ENST00000397049; ENST00000397046; ENST00000397048; ENST00000339737; ENST00000343985 | TSF |
| 1% | chr11 | 118959557 | 118959558 | + | chr11 | 118959927 | 118959982 | + | ENST00000278715; ENST00000536813; ENST00000537841; ENST00000542729; ENST00000546302; ENST00000442944; ENST00000544387; ENST00000543090; ENST00000539986; ENST00000535253; ENST00000392841 | TSF |
| 1% | chr11 | 118959557 | 118959558 | + | chr11 | 118959927 | 118959982 | + | ENST00000278715; ENST00000536813; ENST00000537841; ENST00000542729; ENST00000546302; ENST00000442944; ENST00000544387; ENST00000543090; ENST00000539986; ENST00000535253; ENST00000392841 | TSF |
| 1% | chr11 | 118959557 | 118959558 | + | chr11 | 118959927 | 118959982 | + | ENST00000278715; ENST00000536813; ENST00000537841; ENST00000542729; ENST00000546302; ENST00000442944; ENST00000544387; ENST00000543090; ENST00000539986; ENST00000535253; ENST00000392841 | TSF |
| 1% | chr11 | 118959557 | 118959558 | + | chr11 | 118959927 | 118959982 | + | ENST00000278715; ENST00000536813; ENST00000537841; ENST00000542729; ENST00000546302; ENST00000442944; ENST00000544387; ENST00000543090; ENST00000539986; ENST00000535253; ENST00000392841 | TSF |
| 1% | chr11 | 118959557 | 118959558 | + | chr11 | 118959927 | 118959982 | + | ENST00000278715; ENST00000536813; ENST00000537841; ENST00000542729; ENST00000546302; ENST00000442944; ENST00000544387; ENST00000543090; ENST00000539986; ENST00000535253; ENST00000392841 | TSF |
| 1% | chr11 | 118959557 | 118959558 | + | chr11 | 118959927 | 118959982 | + | ENST00000278715; ENST00000536813; ENST00000537841; ENST00000542729; ENST00000546302; ENST00000442944; ENST00000544387; ENST00000543090; ENST00000539986; ENST00000535253; ENST00000392841 | TSF |
| 1% | chr8 | 39766308 | 39766549 | + | chr8 | 39775394 | 39775489; 39775448 | + | ENST00000518804; ENST00000519154; ENST00000522495; ENST00000522840; ENST00000518237; ENST00000253513 | TSF |
| 1% | chr8 | 39766308 | 39766549 | + | chr8 | 39775394 | 39775489; 39775448 | + | ENST00000518804; ENST00000519154; ENST00000522495; ENST00000522840; ENST00000518237; ENST00000253513 | TSF |
| 1% | chr8 | 39766308 | 39766549 | + | chr8 | 39775394 | 39775489; 39775448 | + | ENST00000518804; ENST00000519154; ENST00000522495; ENST00000522840; ENST00000518237; ENST00000253513 | TSF |
| 1% | chr8 | 39766308 | 39766549 | + | chr8 | 39775394 | 39775489; 39775448 | + | ENST00000518804; ENST00000519154; ENST00000522495; ENST00000522840; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr8 | 39766308 | 39766549 | + | chr8 | 39775394 | 39775489; 39775448 | + | ENST00000518237; ENST00000253513 ENST00000518804; ENST00000519154; ENST00000522495; ENST00000522840; ENST00000518237; ENST00000253513 | TSF |
| 1% | chr12 | 53865082 | 53865132 | + | chr12 | 53865422 | 53865591 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | TSF |
| 1% | chr12 | 53865082 | 53865132 | + | chr12 | 53865422 | 53865591 | + | ENST00000359282; ENST00000437231; ENST00000447282; ENST00000603815; ENST00000549863; ENST00000359462; ENST00000546463; ENST00000552296; ENST00000552819; ENST00000455667; ENST00000439930; ENST00000548933; ENST00000562264; ENST00000553064; ENST00000547859 | TSF |
| 1% | chr1 | 23397020 | 23397118 | + | chr1 | 23397718 | 23397852 | + | ENST00000356634; ENST00000400181; ENST00000542151 | TSF |
| 1% | chr8 | 42014292 | 42014390 | + | chr8 | 42015459 | 42015630; 42015603 | + | ENST00000518421; ENST00000174653; ENST00000396926; ENST00000530375; ENST00000522288; ENST00000517922; ENST00000517499 | TSF |
| 1% | chr8 | 42014292 | 42014390 | + | chr8 | 42015459 | 42015630; 42015603 | + | ENST00000518421; ENST00000174653; ENST00000396926; ENST00000530375; ENST00000522288; ENST00000517922; ENST00000517499 | TSF |
| 1% | chr8 | 42014292 | 42014390 | + | chr8 | 42015459 | 42015630; 42015603 | + | ENST00000518421; ENST00000174653; ENST00000396926; ENST00000530375; ENST00000522288; ENST00000517922; ENST00000517499 | TSF |
| 1% | chr8 | 42014292 | 42014390 | + | chr8 | 42015459 | 42015630; 42015603 | + | ENST00000518421; ENST00000174653; ENST00000396926; ENST00000530375; ENST00000522288; ENST00000517922; ENST00000517499 | TSF |
| 1% | chr8 | 42014292 | 42014390 | + | chr8 | 42015459 | 42015630; 42015603 | + | ENST00000518421; ENST00000174653; ENST00000396926; ENST00000530375; ENST00000522288; ENST00000517922; ENST00000517499 | TSF |
| 1% | chr7 | 74480763 | 74480881 | + | chr7 | 74528191 | 74528329 | + | ENST00000356115; ENST00000430511; ENST00000312575; ENST00000423666 | TSF |
| 1% | chr7 | 74480763 | 74480881 | + | chr7 | 74528191 | 74528329 | + | ENST00000356115; ENST00000430511; ENST00000312575; ENST00000423666 | TSF |
| 1% | chr7 | 74480763 | 74480881 | + | chr7 | 74528191 | 74528329 | + | ENST00000356115; ENST00000430511; ENST00000312575; ENST00000423666 | TSF |
| 1% | chr12 | 49659927 | 49660025 | + | chr12 | 49663248 | 49663470; 49663252 | + | ENST00000541364; ENST00000552125; ENST00000301072; ENST00000549183 | TSF |
| 1% | chr12 | 49659927 | 49660025 | + | chr12 | 49663248 | 49663470; 49663252 | + | ENST00000541364; ENST00000552125; ENST00000301072; ENST00000549183 | TSF |
| 1% | chr12 | 49659927 | 49660025 | + | chr12 | 49663248 | 49663470; 49663252 | + | ENST00000541364; ENST00000552125; ENST00000301072; ENST00000549183 | TSF |
| 1% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 1% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 1% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 1% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 1% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 1% | chr3 | 11645847 | 11645798 | − | chr3 | 11643496 | 11643307 | − | ENST00000273038; ENST00000430365; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr9 | 119603649 | 119602972 | − | chr9 | 119583062 | 119582896 | − | ENST00000404339; ENST00000445411; ENST00000418000; ENST00000458499; ENST00000417206; ENST00000419541 ENST00000373996; ENST00000313400; ENST00000373986; ENST00000361209 | TSF |
| 1% | chr9 | 130929922 | 130929818 | − | chr9 | 130929443 | 130929374 | − | ENST00000372954; ENST00000393608; ENST00000541172; ENST00000325721; ENST00000357558; ENST00000538431; ENST00000277465; ENST00000372948; ENST00000372938; ENST00000415526 | TSF |
| 1% | chr3 | 195798106 | 195797990 | − | chr3 | 195796439 | 195796326 | − | ENST00000420415; ENST00000360110; ENST00000392396 | TSF |
| 1% | chr17 | 30244937 | 30244908 | − | chr17 | 30226749 | 30226665 | − | ENST00000261708 | TSF |
| 1% | chr1 | 45988716 | 45988450 | − | chr1 | 45980667 | 45980545 | − | ENST00000262746; ENST00000319248; ENST00000447184; ENST00000424390 | TSF |
| 1% | chr1 | 45988716 | 45988450 | − | chr1 | 45980667 | 45980545 | − | ENST00000262746; ENST00000319248; ENST00000447184; ENST00000424390 | TSF |
| 1% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 1% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 1% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 1% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 1% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 1% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 1% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 1% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 1% | chr9 | 123165858 | 123165590 | − | chr9 | 123165349 | 123165084 | − | ENST00000359309; ENST00000360822; ENST00000349780; ENST00000360190; ENST00000416449; ENST00000425647 | TSF |
| 1% | chr5 | 72167664 | 72167716 | + | chr5 | 72168466 | 72168547; 72168521 | + | ENST00000337273; ENST00000454282; ENST00000447967; ENST00000520850; ENST00000523768; ENST00000506351 | TSF |
| 1% | chr5 | 72167664 | 72167716 | + | chr5 | 72168466 | 72168547; 72168521 | + | ENST00000337273; ENST00000454282; ENST00000447967; ENST00000520850; ENST00000523768; ENST00000506351 | TSF |
| 1% | chr12 | 97286062 | 97286334 | + | chr12 | 97328754 | 97328983; 97328758 | + | ENST00000266742; ENST00000429527; ENST00000557478; ENST00000411739; ENST00000553609; ENST00000557644; ENST00000457368 | TSF |
| 1% | chr12 | 97286062 | 97286334 | + | chr12 | 97328754 | 97328983; 97328758 | + | ENST00000266742; ENST00000429527; ENST00000557478; ENST00000411739; ENST00000553609; ENST00000557644; ENST00000457368 | TSF |
| 1% | chr12 | 97286062 | 97286334 | + | chr12 | 97328754 | 97328983; 97328758 | + | ENST00000266742; ENST00000429527; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
|  |  |  |  |  |  |  |  |  | ENST00000557478; ENST00000411739; ENST00000553609; ENST00000557644; ENST00000457368 |  |
| 1% | chr3 | 100461913 | 100462018 | + | chr3 | 100463677 | 100463775 | + | ENST00000418917; ENST00000490574; ENST00000240851; ENST00000476228 | TSF |
| 1% | chr19 | 55501071 | 55501120 | + | chr19 | 55501390 | 55501560; 55501464 | + | ENST00000543010; ENST00000391721; ENST00000339757; ENST00000448584; ENST00000537859; ENST00000427260; ENST00000538819; ENST00000263437; ENST00000543277 | TSF |
| 1% | chr19 | 55501071 | 55501120 | + | chr19 | 55501390 | 55501560; 55501464 | + | ENST00000543010; ENST00000391721; ENST00000339757; ENST00000448584; ENST00000537859; ENST00000427260; ENST00000538819; ENST00000263437; ENST00000543277 | TSF |
| 1% | chr22 | 43552142 | 43552306 | + | chr22 | 43557058 | 43557196 | + | ENST00000337554; ENST00000428336; ENST00000329563 | TSF |
| 1% | chr22 | 43552142 | 43552306 | + | chr22 | 43557058 | 43557196 | + | ENST00000337554; ENST00000428336; ENST00000329563 | TSF |
| 1% | chr8 | 39778739 | 39778956 | + | chr8 | 39780071 | 39780173; 39780170; 39780150 | + | ENST00000519154; ENST00000522495; ENST00000518237; ENST00000253513 | TSF |
| 1% | chr8 | 39778739 | 39778956 | + | chr8 | 39780071 | 39780173; 39780170; 39780150 | + | ENST00000519154; ENST00000522495; ENST00000518237; ENST00000253513 | TSF |
| 1% | chr8 | 39778739 | 39778956 | + | chr8 | 39780071 | 39780173; 39780170; 39780150 | + | ENST00000519154; ENST00000522495; ENST00000518237; ENST00000253513 | TSF |
| 1% | chr7 | 134213194 | 134213199 | + | chr7 | 134215395 | 134215562 | + | ENST00000359579 | TSF |
| 1% | chr12 | 56110428 | 56110523 | + | chr12 | 56112875 | 56113007; 56112894; 56113085 | + | ENST00000257899; ENST00000551946; ENST00000550412; ENST00000548925; ENST00000549147; ENST00000553100 | TSF |
| 1% | chr12 | 56110428 | 56110523 | + | chr12 | 56112875 | 56113007; 56112894; 56113085 | + | ENST00000257899; ENST00000551946; ENST00000550412; ENST00000548925; ENST00000549147; ENST00000553100 | TSF |
| 1% | chr12 | 56110428 | 56110523 | + | chr12 | 56112875 | 56113007; 56112894; 56113085 | + | ENST00000257899; ENST00000551946; ENST00000550412; ENST00000548925; ENST00000549147; ENST00000553100 | TSF |
| 1% | chr12 | 56110428 | 56110523 | + | chr12 | 56112875 | 56113007; 56112894; 56113085 | + | ENST00000257899; ENST00000551946; ENST00000550412; ENST00000548925; ENST00000549147; ENST00000553100 | TSF |
| 1% | chr15 | 43889497 | 43889601 | + | chr15 | 43990212 | 43990346 | + | ENST00000434505; ENST00000413453 | TSF |
| 1% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 1% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 1% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 1% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 1% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 1% | chr2 | 238935895 | 238935906 | + | chr2 | 238939197 | 238939220; 238939254; | + | ENST00000441728; ENST00000272930; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 238939236; 238939204 | | ENST00000448502; ENST00000416292; ENST00000409633; ENST00000449891; ENST00000455999; ENST00000445676; ENST00000414443; ENST00000409953; ENST00000409332; ENST00000434655; ENST00000434137 | |
| 1% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 1% | chr2 | 238935895 | 238935906 | + | chr2 | 238939197 | 238939220; 238939254; 238939236; 238939204 | + | ENST00000441728; ENST00000272930; TSF ENST00000448502; ENST00000416292; ENST00000409633; ENST00000449891; ENST00000455999; ENST00000445676; ENST00000414443; ENST00000409953; ENST00000409332; ENST00000434655; ENST00000434137 | |
| 1% | chr3 | 40465676 | 40465763 | + | chr3 | 40468763 | 40468999 | + | ENST00000301825; ENST00000456402 | TSF |
| 1% | chr11 | 66953459 | 66954052 | + | chr11 | 66974981 | 66975159 | + | ENST00000398645; ENST00000529006 | TSF |
| 1% | chr11 | 66953459 | 66954052 | + | chr11 | 66974981 | 66975159 | + | ENST00000398645; ENST00000529006 | TSF |
| 1% | chr19 | 36105129 | 36105133 | + | chr19 | 36105944 | 36106049 | + | ENST00000587439; ENST00000203166; ENST00000379045 | TSF |
| 1% | chr19 | 36105129 | 36105133 | + | chr19 | 36105944 | 36106049 | + | ENST00000587439; ENST00000203166; ENST00000379045 | TSF |
| 1% | chr8 | 82194688 | 82194723 | + | chr8 | 82195601 | 82195773 | + | ENST00000297258 | TSF |
| 1% | chr1 | 53070435 | 53070501 | + | chr1 | 53072356 | 53072617 | + | ENST00000361314 | TSF |
| 1% | chr22 | 22512559 | 22512867 | + | chr22 | 22516765 | 22517074 | + | ENST00000390284 | TSF |
| 1% | chr5 | 108341955 | 108342193 | + | chr5 | 108373123 | 108373179 | + | ENST00000281092; ENST00000438717 | TSF |
| 1% | chr12 | 58189709 | 58189746 | + | chr12 | 58189960 | 58190366; 58189980; 58190044 | + | ENST00000454289; ENST00000540550; ENST00000323833; ENST00000350762; ENST00000457189 | TSF |
| 1% | chr12 | 58189709 | 58189746 | + | chr12 | 58189960 | 58190366; 58189980; 58190044 | + | ENST00000454289; ENST00000540550; ENST00000323833; ENST00000350762; ENST00000457189 | TSF |
| 1% | chr12 | 58189709 | 58189746 | + | chr12 | 58189960 | 58190366; 58189980; 58190044 | + | ENST00000454289; ENST00000540550; ENST00000323833; ENST00000350762; ENST00000457189 | TSF |
| 1% | chr14 | 106258982 | 106258725 | − | chr14 | 106209234 | 106209114 | − | ENST00000390548; ENST00000390549; ENST00000390542 | TSF |
| 1% | chr14 | 106258982 | 106258725 | − | chr14 | 106209234 | 106209114 | − | ENST00000390548; ENST00000390549; ENST00000390542 | TSF |
| 1% | chr14 | 106258982 | 106258725 | − | chr14 | 106209234 | 106209114 | − | ENST00000390548; ENST00000390549; ENST00000390542 | TSF |
| 1% | chr3 | 169042432 | 169042361 | − | chr3 | 168861620 | 168861486 | − | ENST00000264674; ENST00000494292 | TSF |
| 1% | chr3 | 169042432 | 169042361 | − | chr3 | 168861620 | 168861486 | − | ENST00000264674; ENST00000494292 | TSF |
| 1% | chr3 | 185370915 | 185370866 | − | chr3 | 185369956 | 185369882 | − | ENST00000382199; ENST00000421047; ENST00000457616; ENST00000346192 | TSF |
| 1% | chr14 | 106258982 | 106258725 | − | chr14 | 106237569 | 106237449 | − | ENST00000390551 | TSF |
| 1% | chr19 | 282715 | 282661 | − | chr19 | 282310 | 282134; 282122 | − | ENST00000269812; ENST00000434325; ENST00000327790; ENST00000586998 | TSF |
| 1% | chr19 | 282715 | 282661 | − | chr19 | 282310 | 282134; 282122 | − | ENST00000269812; ENST00000434325; ENST00000327790; ENST00000586998 | |
| 1% | chr11 | 89098177 | 89098143 | − | chr11 | 89088211 | 89088130 | − | ENST00000535633; ENST00000424319; ENST00000343727; ENST00000534731; ENST00000263317; ENST00000532825; ENST00000527956; ENST00000542487; ENST00000527626; ENST00000528341; ENST00000413594; ENST00000375979; ENST00000531342 | TSF |
| 1% | chr11 | 89098177 | 89098143 | − | chr11 | 89088211 | 89088130 | − | ENST00000535633; ENST00000424319; ENST00000343727; ENST00000534731; ENST00000263317; ENST00000532825; ENST00000527956; ENST00000542487; ENST00000527626; ENST00000528341; ENST00000413594; ENST00000375979; ENST00000531342 | TSF |
| 1% | chr11 | 89098177 | 89098143 | − | chr11 | 89088211 | 89088130 | − | ENST00000535633; ENST00000424319; ENST00000343727; ENST00000534731; ENST00000263317; ENST00000532825; ENST00000527956; ENST00000542487; ENST00000527626; ENST00000528341; | TSF |

TABLE 40-continued

Transcript fusion for Lung Squamous Cell Carcinoma (LUSC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | ENST00000413594; ENST00000375979; ENST00000531342 | |
| 1% | chr22 | 21355965 | 21355835 | − | chr22 | 21355700 | 21355545 | − | ENST00000215742; ENST00000399133 | TSF |
| 1% | chr9 | 130732697 | 130732597 | − | chr9 | 130716204 | 130716084 | − | ENST00000373095 | TSF |
| 1% | chr2 | 89238917 | 89238677 | − | chr2 | 89157196 | 89156874 | − | ENST00000390237 | TSF |
| 1% | chr7 | 50763323 | 50763289 | − | chr7 | 50742355 | 50742133 | − | ENST00000439599; ENST00000398812; ENST00000403097; ENST00000357271; ENST00000401949; ENST00000439044 | TSF |
| 1% | chr7 | 50763323 | 50763289 | − | chr7 | 50742355 | 50742133 | − | ENST00000439599; ENST00000398812; ENST00000403097; ENST00000357271; ENST00000401949; ENST00000439044 | TSF |
| 1% | chr7 | 50763323 | 50763289 | − | chr7 | 50742355 | 50742133 | − | ENST00000439599; ENST00000398812; ENST00000403097; ENST00000357271; ENST00000401949; ENST00000439044 | TSF |
| 1% | chr15 | 83667946 | 83667078 | − | chr15 | 83657580 | 83657392 | − | ENST00000514272 | TSF |
| 1% | chr3 | 115829645 | 115829500 | − | chr3 | 115805403 | 115805171 | − | ENST00000490035; ENST00000333617; ENST00000539563; ENST00000474851 | TSF |
| 1% | chr3 | 115829645 | 115829500 | − | chr3 | 115805403 | 115805171 | − | ENST00000490035; ENST00000333617; ENST00000539563; ENST00000474851 | TSF |
| 1% | chr3 | 115829645 | 115829500 | − | chr3 | 115805403 | 115805171 | − | ENST00000490035; ENST00000333617; ENST00000539563; ENST00000474851 | TSF |
| 1% | chr3 | 139245547 | 139245400 | − | chr3 | 139237364 | 139237263 | − | ENST00000232219 | TSF |
| 1% | chr3 | 183966288 | 183966210 | − | chr3 | 183963600 | 183963501; 183963562 | − | ENST00000397676; ENST00000445626; ENST00000455059; ENST00000423996 | TSF |
| 1% | chr3 | 183966288 | 183966210 | − | chr3 | 183963600 | 183963501; 183963562 | − | ENST00000397676; ENST00000445626; ENST00000455059; ENST00000423996 | TSF |
| 1% | chrX | 133098739 | 133098673 | − | chrX | 133087238 | 133087077 | − | ENST00000370818; ENST00000394299 | TSF |
| 1% | chrX | 133098739 | 133098673 | − | chrX | 133087238 | 133087077 | − | ENST00000370818; ENST00000394299 | TSF |
| 1% | chr7 | 100850556 | 100850506 | − | chr7 | 100850185 | 100850060 | − | ENST00000454310; ENST00000223127 | TSF |
| 1% | chr19 | 47343471 | 47343460 | − | chr19 | 47342835 | 47342722 | − | ENST00000352203; ENST00000601498; ENST00000599990; ENST00000593442; ENST00000263270; ENST00000597020 | TSF |
| 1% | chr9 | 75580673 | 75580323 | − | chr9 | 75555168 | 75555064 | − | ENST00000297785; ENST00000376939; ENST00000419959; ENST00000446946 | TSF |
| 1% | chr9 | 75580673 | 75580323 | − | chr9 | 75555168 | 75555064 | − | ENST00000297785; ENST00000376939; ENST00000419959; ENST00000446946 | TSF |
| 1% | chr9 | 75580673 | 75580323 | − | chr9 | 75555168 | 75555064 | − | ENST00000297785; ENST00000376939; ENST00000419959; ENST00000446946 | TSF |
| 1% | chr9 | 75580673 | 75580323 | − | chr9 | 75555168 | 75555064 | − | ENST00000297785; ENST00000376939; ENST00000419959; ENST00000446946 | TSF |
| 1% | chr10 | 27051731 | 27051669 | − | chr10 | 27048164 | 27047991 | − | ENST00000376170; ENST00000359188; ENST00000376142; ENST00000376139; ENST00000376160; ENST00000376166; ENST00000376138; ENST00000346832; ENST00000355394; ENST00000376134; ENST00000376140 | TSF |
| 1% | chr10 | 27051731 | 27051669 | − | chr10 | 27048164 | 27047991 | − | ENST00000376170; ENST00000359188; ENST00000376142; ENST00000376139; ENST00000376160; ENST00000376166; ENST00000376138; ENST00000346832; ENST00000355394; ENST00000376134; ENST00000376140 | TSF |
| 1% | chr1 | 17371820 | 17371636 | − | chr1 | 17371383 | 17371256 | − | ENST00000375499 | TSF |
| 1% | chr12 | 48058419 | 48058373 | − | chr12 | 48057373 | 48057288 | − | ENST00000005386; ENST00000432584; ENST00000380650 | TSF |
| 1% | chr3 | 139086428 | 139086379 | − | chr3 | 139085987 | 139085857; 139085942 | − | ENST00000333188; ENST00000507777; ENST00000512309 | TSF |
| 1% | chr3 | 139086428 | 139086379 | − | chr3 | 139085987 | 139085857; 139085942 | − | ENST00000333188; ENST00000507777; ENST00000512309 | TSF |

TABLE 41

Transcript fusion for Mesothelioma (MESO) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 79% | chr10 | 47747112 | 47747132 | + | ENST00000340243;ENST00000374277;ENST00000449464; ENST00000538825 | chr10 | 48278725 | 48278896 | + | TAF |
| 53% | chr20 | 48124601 | 48124521 | − | ENST00000244043 | chr20 | 48123357 | 48123321 | − | TAF |
| 44% | chrX | 152730513 | 152730446 | − | ENST00000370211;ENST00000370212;ENST00000370210 | chrX | 152728559 | 152728505 | − | TAF |
| 44% | chrX | 152730513 | 152730446 | − | ENST00000370211;ENST00000370212;ENST00000370210 | chrX | 152728559 | 152728505 | − | TAF |

TABLE 41-continued

Transcript fusion for Mesothelioma (MESO) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 34% | chr4 | 110723127 | 110723071 | − | ENST00000394635;ENST00000394634;ENST00000512148; ENST00000510800 | chr4 | 110715581 | 110714981 | − | TAF |
| 31% | chr7 | 76144362 | 76144473 | + | ENST00000334348;ENST00000448265;ENST00000419923; ENST00000443097;ENST00000257632;ENST00000394849 | chr7 | 76648226 | 76648393 | + | TSF |
| 31% | chr7 | 76144362 | 76144473 | + | ENST00000334348;ENST00000448265;ENST00000419923; ENST00000443097;ENST00000257632;ENST00000394849 | chr7 | 76648226 | 76648393 | + | TSF |
| 31% | chr7 | 76144362 | 76144473 | + | ENST00000334348;ENST00000448265;ENST00000419923; ENST00000443097;ENST00000257632;ENST00000394849 | chr7 | 76648226 | 76648393 | + | TSF |
| 30% | chr20 | 53092486 | 53092551 | + | ENST00000262593 | chr20 | 53111339 | 53111426 | + | TAF |
| 30% | chr7 | 76144362 | 76144473 | + | ENST00000334348;ENST00000448265;ENST00000419923; ENST00000443097;ENST00000257632;ENST00000394849 | chr7 | 76676146 | 76676313 | + | TSF |
| 30% | chr7 | 76144362 | 76144473 | + | ENST00000334348;ENST00000448265;ENST00000419923; ENST00000443097;ENST00000257632;ENST00000394849 | chr7 | 76676146 | 76676313 | + | TSF |
| 30% | chr7 | 76144362 | 76144473 | + | ENST00000334348;ENST00000448265;ENST00000419923; ENST00000443097;ENST00000257632;ENST00000394849 | chr7 | 76676146 | 76676313 | + | TSF |
| 29% | chr3 | 124839669; 124839530; 124839525 | 124839443 | − | ENST00000430155;ENST00000393469;ENST00000423114; ENST00000469902;ENST00000314584;ENST00000479826 | chr3 | 124838735 | 124838686 | − | TAF |
| 29% | chr3 | 124839669; 124839530; 124839525 | 124839443 | − | ENST00000430155;ENST00000393469;ENST00000423114; ENST00000469902;ENST00000314584;ENST00000479826 | chr3 | 124838735 | 124838686 | − | TAF |
| 29% | chr3 | 124839669; 124839530; 124839525 | 124839443 | − | ENST00000430155;ENST00000393469;ENST00000423114; ENST00000469902;ENST00000314584;ENST00000479826 | chr3 | 124838735 | 124838686 | − | TAF |
| 29% | chr3 | 124839669; 124839530; 124839525 | 124839443 | − | ENST00000430155;ENST00000393469;ENST00000423114; ENST00000469902;ENST00000314584;ENST00000479826 | chr3 | 124838735 | 124838686 | − | TAF |
| 29% | chr3 | 124839669; 124839530; 124839525 | 124839443 | − | ENST00000430155;ENST00000393469;ENST00000423114; ENST00000469902;ENST00000314584;ENST00000479826 | chr3 | 124838735 | 124838686 | − | TAF |
| 26% | chr20 | 48184653 | 48184580 | − | ENST00000244043 | chr20 | 48177475 | 48177085 | − | TSF |
| 25% | chr3 | 118943092 | 118942905 | − | ENST00000483209;ENST00000467604;ENST00000359213; ENST00000393765;ENST00000480814 | chr3 | 118938512 | 118938188 | − | TAF |
| 24% | chr16 | 29916173 | 29916286 | + | ENST00000563177;ENST00000483405;ENST00000308748; ENST00000414952;ENST00000566693 | chr16 | 29930852 | 29930945 | + | TSF |
| 24% | chr16 | 29916173 | 29916286 | + | ENST00000563177;ENST00000483405;ENST00000308748; ENST00000414952;ENST00000566693 | chr16 | 29930852 | 29930945 | + | TSF |
| 22% | chr5 | 82554349 | 82554496 | + | ENST00000282268;ENST00000338635;ENST00000396027; ENST00000511817 | chr5 | 82606608 | 82606935 | + | TAF |
| 21% | chr8 | 74939024 | 74939076 | + | ENST00000284818;ENST00000518893 | chr8 | 74944554 | 74944936 | + | TAF |
| 21% | chr8 | 74939024 | 74939076 | + | ENST00000284818;ENST00000518893 | chr8 | 74944554 | 74944936 | + | TAF |
| 20% | chr9 | 101984828 | 101984925 | + | ENST00000223641 | chr9 | 101986374 | 101986588 | + | TAF |
| 20% | chr15 | 58957396 | 58957296 | − | ENST00000260408 | chr15 | 58947615 | 58947395 | − | TAF |
| 18% | chr15 | 84611655 | 84611834 | + | ENST00000286744;ENST00000567476 | chr15 | 84630325 | 84630701 | + | TAF |
| 18% | chr6 | 53778652 | 53778767 | + | ENST00000370888 | chr6 | 53783822 | 53783822 | + | TSF |
| 17% | chr6 | 10749855; 10749898 | 10749931 | + | ENST00000379542;ENST00000473166;ENST00000463448; ENST00000460341;ENST00000480294;ENST00000473807; ENST00000461342;ENST00000475942;ENST00000379530; ENST00000463100;ENST00000481240;ENST00000467317; ENST00000478732 | chr6 | 10829240 | 10829256 | + | TAF |
| 17% | chr6 | 10749855; 10749898 | 10749931 | + | ENST00000379542;ENST00000473166;ENST00000463448; ENST00000460341;ENST00000480294;ENST00000473807; ENST00000461342;ENST00000475942;ENST00000379530; ENST00000463100;ENST00000481240;ENST00000467317; ENST00000478732 | chr6 | 10829240 | 10829256 | + | TAF |
| 16% | chr7 | 1037440 | 1037282 | − | ENST00000357429;ENST00000397100;ENST00000397098; ENST00000412051;ENST00000444428;ENST00000491163 | chr7 | 1018697 | 1018446 | − | TAF |
| 16% | chr7 | 1037440 | 1037282 | − | ENST00000357429;ENST00000397100;ENST00000397098; ENST00000412051;ENST00000444428;ENST00000491163 | chr7 | 1018697 | 1018446 | − | TAF |
| 16% | chr7 | 1037440 | 1037282 | − | ENST00000357429;ENST00000397100;ENST00000397098; ENST00000412051;ENST00000444428;ENST00000491163 | chr7 | 1018697 | 1018446 | − | TAF |
| 16% | chr1 | 160854667 | 160854610 | − | ENST00000326245 | chr1 | 160853933 | 160853823 | − | TSF |
| 14% | chr3 | 49927493 | 49927357 | − | ENST00000296474;ENST00000344206 | chr3 | 49927248 | 49927204 | − | TAF |
| 14% | chr3 | 49927493 | 49927357 | − | ENST00000296474;ENST00000344206 | chr3 | 49927248 | 49927204 | − | TAF |
| 13% | chr4 | 47583977 | 47584081 | + | ENST00000273859 | chr4 | 47584886 | 47585171 | + | TAF |
| 13% | chr8 | 27516013 | 27517056 | + | ENST00000337221;ENST00000301904 | chr8 | 27555709 | 27555926 | + | TAF |
| 13% | chr16 | 29913136; 29912293 | 29913241 | + | ENST00000563177;ENST00000483405;ENST00000308748; ENST00000414952;ENST00000566693 | chr16 | 29930852 | 29930945 | + | TSF |
| 13% | chr16 | 29913136; 29912293 | 29913241 | + | ENST00000563177;ENST00000483405;ENST00000308748; ENST00000414952;ENST00000566693 | chr16 | 29930852 | 29930945 | + | TSF |
| 11% | chr2 | 220239744 | 220239577 | − | ENST00000273075;ENST00000373972;ENST00000523282 | chr2 | 220227530 | 220227195 | − | TAF |
| 11% | chr2 | 220239744 | 220239577 | − | ENST00000273075;ENST00000373972;ENST00000523282 | chr2 | 220227530 | 220227195 | − | TAF |
| 11% | chr2 | 220239744 | 220239577 | − | ENST00000273075;ENST00000373972;ENST00000523282 | chr2 | 220227530 | 220227195 | − | TAF |
| 11% | chr15 | 79054907 | 79054745 | − | ENST00000388820 | chr15 | 79054428 | 79054400 | − | TAF |
| 10% | chr16 | 81142298 | 81142167 | − | ENST00000533478;ENST00000525539 | chr16 | 81141929 | 81141855 | − | TAF |

TABLE 41-continued

Transcript fusion for Mesothelioma (MESO) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 10% | chr16 | 81142298 | 81142167 | − | ENST00000533478;ENST00000525539 | chr16 | 81141929 | 81141855 | − | TAF |
| 9% | chr16 | 29913136; 29912293 | 29913241 | + | ENST00000563177;ENST00000483405;ENST00000308748; ENST00000414952;ENST00000566693 | chr16 | 29915825 | 29915953 | + | TSF |
| 9% | chr16 | 29913136; 29912293 | 29913241 | + | ENST00000563177;ENST00000483405;ENST00000308748; ENST00000414952;ENST00000566693 | chr16 | 29915825 | 29915953 | + | TSF |
| 9% | chr19 | 3869015; 3869013 | 3868963 | − | ENST00000262961;ENST00000438164;ENST00000587212; ENST00000586578;ENST00000439086 | chr19 | 3855694 | 3855445 | − | TSF |
| 9% | chr19 | 3869015; 3869013 | 3868963 | − | ENST00000262961;ENST00000438164;ENST00000587212; ENST00000586578;ENST00000439086 | chr19 | 3855694 | 3855445 | − | TSF |
| 9% | chr1 | 11115983; 11115877 | 11115838 | − | ENST00000376957;ENST00000490101 | chr1 | 11115464 | 11115178 | − | TSF |
| 9% | chr1 | 11115983; 11115877 | 11115838 | − | ENST00000376957;ENST00000490101 | chr1 | 11115464 | 11115178 | − | TSF |
| 9% | chr5 | 121405863 | 121405748 | − | ENST00000231004 | chr5 | 121403052 | 121403016 | − | TSF |
| 8% | chr6 | 150239520 | 150239310 | − | ENST00000367360 | chr6 | 150238660 | 150237927 | − | TSF |
| 7% | chr10 | 47173918 | 47173898 | − | ENST00000358140;ENST00000359178;ENST00000545298; ENST00000414655 | chr10 | 47151097 | 47150900 | − | TSF |

TABLE 42

Transcript fusion for Mesothelioma (MESO) Coordinates of the fusion sequences for which the donor is the TE.

| 1 | 2' | 3' | 4' | 5' | 6' |
|---|---|---|---|---|---|
| 59% | chr2 | 174982998 | 174982711 | − | chr2 |
| 59% | chr2 | 174982998 | 174982711 | − | chr2 |
| 54% | chr16 | 29915789 | 29915910 | + | chr16 |
| 54% | chr16 | 29915789 | 29915910 | + | chr16 |
| 52% | chr3 | 124842655 | 124842374 | − | chr3 |
| 52% | chr3 | 124842655 | 124842374 | − | chr3 |
| 46% | chr2 | 174982998 | 174982666 | − | chr2 |
| 46% | chr2 | 174982998 | 174982666 | − | chr2 |
| 46% | chr7 | 33006587 | 33006627 | + | chr7 |
| 44% | chr1 | 44018824 | 44019043 | + | chr1 |
| 44% | chr1 | 44018824 | 44019043 | + | chr1 |
| 44% | chr1 | 44018824 | 44019043 | + | chr1 |
| 43% | chr8 | 104389530 | 104389551 | + | chr8 |
| 38% | chr7 | 100878007 | 100877907 | − | chr7 |
| 38% | chr7 | 100878007 | 100877907 | − | chr7 |
| 34% | chr7 | 100878007 | 100877859 | − | chr7 |
| 34% | chr7 | 100878007 | 100877859 | − | chr7 |
| 31% | chr1 | 160854025 | 160853835 | − | chr1 |
| 28% | chr7 | 98974090 | 98974197 | + | chr7 |
| 26% | chr4 | 38103597 | 38103648 | + | chr4 |
| 26% | chr4 | 38103597 | 38103648 | + | chr4 |
| 25% | chr3 | 124690942 | 124690838 | − | chr3 |
| 25% | chr19 | 4454954 | 4454819 | − | chr19 |
| 25% | chr19 | 4454954 | 4454819 | − | chr19 |
| 25% | chr19 | 4454954 | 4454819 | − | chr19 |
| 22% | chr3 | 69286305 | 69286248 | − | chr3 |
| 22% | chr3 | 69286305 | 69286248 | − | chr3 |
| 22% | chr3 | 69286305 | 69286248 | − | chr3 |
| 22% | chr3 | 69286305 | 69286248 | − | chr3 |
| 21% | chr5 | 135398466 | 135398602 | + | chr5 |
| 21% | chr5 | 135398466 | 135398602 | + | chr5 |
| 21% | chr7 | 150938296 | 150938250 | − | chr7 |
| 21% | chr1 | 183600359 | 183599874 | − | chr1 |
| 21% | chr1 | 183600359 | 183599874 | − | chr1 |
| 18% | chr7 | 2289080 | 2289115 | + | chr7 |
| 18% | chr14 | 102691697 | 102691432 | − | chr14 |
| 18% | chr2 | 86512770 | 86512698 | − | chr2 |
| 18% | chr2 | 86512770 | 86512698 | − | chr2 |
| 18% | chr2 | 86512770 | 86512698 | − | chr2 |
| 17% | chr14 | 24631729 | 24631779 | + | chr14 |
| 17% | chr14 | 24631729 | 24631779 | + | chr14 |
| 17% | chr14 | 24631729 | 24631779 | + | chr14 |
| 17% | chr11 | 24631729 | 24631779 | + | chr14 |
| 16% | chr7 | 130127044 | 130127065 | + | chr7 |
| 16% | chr7 | 130127044 | 270613015 | + | chr7 |
| 15% | chr11 | 114177915 | 114178747 | + | chr11 |

TABLE 42-continued

Transcript fusion for Mesothelioma (MESO) Coordinates of the fusion sequences for which the donor is the TE.

| | | | | |
|---|---|---|---|---|
| 15% | chr20 | 33850895 | 33851310 + | chr20 |
| 15% | chr11 | 322262 | 322206 − | chr11 |
| 15% | chr11 | 321450 | 321426 − | chr11 |
| 15% | chr11 | 321638 | 321543 − | chr11 |
| 15% | chr11 | 321638 | 321504 − | chr11 |
| 15% | chr11 | 321488 | 321465 − | chr11 |
| 15% | chr11 | 322580 | 322557 − | chr11 |
| 15% | chr11 | 321410 | 321387 − | chr11 |
| 15% | chr11 | 321638 | 321582 − | chr11 |
| 15% | chr11 | 321716 | 321660 − | chr11 |
| 15% | chr11 | 322067 | 322011 − | chr11 |
| 15% | chr11 | 322457 | 322401 | chr11 |
| 15% | chr11 | 321911 | 321855 − | chr11 |
| 14% | chr9 | 131189761 | 131190058 + | chr9 |
| 14% | chr9 | 131189761 | 131190058 + | chr9 |
| 14% | chr13 | 22253799 | 22254080 + | chr13 |
| 14% | chr11 | 93468219 | 93468129 − | chr11 |
| 14% | chr11 | 93468219 | 93468129 − | chr11 |
| 14% | chr15 | 76298180 | 76298078 − | chr15 |
| 14% | chr7 | 100877200 | 100877154 − | chr7 |
| 14% | chr7 | 100877200 | 100877154 − | chr7 |
| 14% | chr7 | 100877200 | 100877154 − | chr7 |
| 13% | chr17 | 79214190 | 79214239 + | chr17 |
| 13% | chr17 | 79214190 | 79214239 + | chr17 |
| 13% | chr2 | 56146377 | 56145988 − | chr2 |
| 13% | chr2 | 56146377 | 56145988 − | chr2 |
| 13% | chr2 | 56146377 | 56145988 − | chr2 |
| 13% | chr2 | 56146377 | 56145988 − | chr2 |
| 13% | chr2 | 56146377 | 56145988 − | chr2 |
| 13% | chr2 | 56146377 | 56145988 − | chr2 |
| 13% | chr2 | 174982998 | 174982866 − | chr2 |
| 13% | chr2 | 174982998 | 174982866 − | chr2 |
| 11% | chr17 | 48164136 | 48164357 + | chr17 |
| 11% | chr17 | 48164136 | 48164357 + | chr17 |
| 11% | chr9 | 123237538 | 123237484 − | chr9 |
| 11% | chr9 | 123237538 | 123237484 − | chr9 |
| 11% | chr9 | 123237538 | 123237484 − | chr9 |
| 11% | chr9 | 123237538 | 123237484 − | chr9 |
| 11% | chr9 | 123237538 | 123237484 − | chr9 |
| 11% | chr3 | 149090578 | 149090421 − | chr3 |
| 11% | chr3 | 149090578 | 149090421 − | chr3 |
| 11% | chr3 | 149090578 | 149090421 − | chr3 |
| 10% | chr5 | 92920103 | 92920128 + | chr5 |
| 10% | chr16 | 88878506 | 88878500 − | chr16 |
| 10% | chr16 | 88878506 | 88878500 − | chr16 |
| 10% | chr16 | 88878506 | 88878500 − | chr16 |
| 10% | chr16 | 88878506 | 88878500 − | chr16 |
| 10% | chr16 | 88878506 | 88878500 − | chr16 |
| 10% | chr16 | 88878506 | 88878500 − | chr16 |
| 10% | chr5 | 171488028 | 171487971 − | chr5 |
| 10% | chr5 | 171488028 | 171487971 − | chr5 |
| 10% | chr1 | 198208121 | 198208232 + | chr1 |
| 10% | chr1 | 198208121 | 198208232 + | chr1 |
| 10% | chr1 | 198208121 | 198208232 + | chr1 |
| 10% | chr1 | 198208121 | 198208232 + | chr1 |
| 10% | chr1 | 198208121 | 198208232 + | chr1 |
| 10% | chr4 | 56493122 | 56492923 − | chr4 |
| 10% | chr4 | 56493122 | 56492923 − | chr4 |
| 10% | chr4 | 56493122 | 56492923 − | chr4 |
| 9% | chr11 | 60694460 | 60694542 + | chr11 |
| 9% | chr11 | 60694460 | 60694542 + | chr11 |
| 9% | chr7 | 129960758 | 129960856 + | chr7 |
| 9% | chr19 | 13148192 | 13148316 + | chr19 |
| 9% | chr19 | 13148192 | 13148316 + | chr19 |
| 9% | chr19 | 13148192 | 13148316 + | chr19 |
| 9% | chr19 | 13148192 | 13148316 + | chr19 |
| 9% | chr19 | 13148192 | 13148316 + | chr19 |
| 9% | chr3 | 124842655 | 124842374 − | chr3 |
| 9% | chr3 | 124842655 | 124842374 − | chr3 |
| 9% | chr3 | 124842655 | 124842374 − | chr3 |
| 9% | chr3 | 124838831 | 124838710 − | chr3 |
| 9% | chr3 | 124838831 | 124838710 − | chr3 |
| 9% | chr3 | 124838831 | 124838710 − | chr3 |
| 8% | chr1 | 3424070 | 3423998 − | chr1 |
| 8% | chr1 | 3424070 | 3423998 − | chr1 |
| 8% | chr1 | 3424070 | 3423998 − | chr1 |

TABLE 42-continued

Transcript fusion for Mesothelioma (MESO) Coordinates of the fusion sequences for which the donor is the TE.

| 7' | 8' | 9' | 10' | 11' |
|---|---|---|---|---|
| 174946792 | 174946652; 174946738 | − | ENST00000284719;ENST00000344357;ENST00000409546;ENST0 0000429575 | TAF |
| 174946792 | 174946652; 174946738 | − | ENST00000284719;ENST00000344357;ENST00000409546;ENST0 0000429575 | TAF |
| 29916173 | 29916286 | + | ENST00000563177;ENST00000483405;ENST00000308748;ENST0 0000414952;ENST00000566693 | TAF |
| 29916173 | 29916286 | + | ENST00000563177;ENST00000483405;ENST00000308748;ENST0 0000414952;ENST00000566693 | TAF |
| 124839530 | 124839443 | − | ENST00000430155;ENST00000393469;ENST00000423114;ENST0 0000469902;ENST00000479826 | TAF |
| 124839530 | 124839443 | − | ENST00000430155;ENST00000393469;ENST00000423114;ENST0 0000469902;ENST00000479826 | TAF |
| 174946792 | 174946652; 174946738 | − | ENST00000284719;ENST00000344357;ENST00000409546;ENST0 0000429575 | TAF |
| 174946792 | 174946652; 174946738 | − | ENST00000284719;ENST00000344357;ENST00000409546;ENST0 0000429575 | TAF |
| 33014229 | 33014374 | + | ENST00000242209;ENST00000538336 | TSF |
| 44019163 | 44019308 | + | ENST00000359947;ENST00000438120;ENST00000372413;ENST0 0000372414;ENST00000437607 | TAF |
| 44019163 | 44019308 | + | ENST00000359947;ENST00000438120;ENST00000372413;ENST0 0000372414;ENST00000437607 | TAF |
| 44019163 | 44019308 | + | ENST00000359947;ENST00000438120;ENST00000372413;ENST0 0000372414;ENST00000437607 | TAF |
| 104390255 | 104390471 | + | ENST00000330295;ENST00000520337 | TAF |
| 100877723 | 100877559 | − | ENST00000308344;ENST00000401528;ENST00000433833 | TSF |
| 100877723 | 100877559 | − | ENST00000308344;ENST00000401528;ENST00000433833 | TSF |
| 100877723 | 100877559 | − | ENST00000308344;ENST00000401528;ENST00000433833 | TAF |
| 100877723 | 100877559 | − | ENST00000308344;ENST00000401528;ENST00000433833 | TAF |
| 160853316 | 160853218 | − | ENST00000326245 | TSF |
| 98983325 | 98983401 | + | ENST00000432884 | TAF |
| 38104620 | 38104778 | + | ENST00000508802;ENST00000261439 | TAF |
| 38104620 | 38104778 | + | ENST00000508802;ENST00000261439 | TAF |
| 124689645 | 124689496 | − | ENST00000311127;ENST00000487661 | TAF |
| 4454090 | 4453927 | − | ENST00000591919;ENST00000301281;ENST00000592515 | TSF |
| 4454090 | 4453927 | − | ENST00000591919;ENST00000301281;ENST00000592515 | TSF |
| 4454090 | 4453927 | − | ENST00000591919;ENST00000301281;ENST00000592515 | TSF |
| 69273841 | 69273758; 69273834 | − | ENST00000398540;ENST00000542259;ENST00000493880;ENST0 0000473029;ENST00000460709 | TAF |
| 69273841 | 69273758; 69273834 | − | ENST00000398540;ENST00000542259;ENST00000493880;ENST0 0000473029;ENST00000460709 | TAF |
| 69273841 | 69273758; 69273834 | − | ENST00000398540;ENST00000542259;ENST00000493880;ENST0 0000473029;ENST00000460709 | TAF |
| 69273841 | 69273758; 69273834 | − | ENST00000398540;ENST00000542259;ENST00000493880;ENST0 0000473029;ENST00000460709 | TAF |
| 135398875 | 135398915; 135398898 | + | ENST00000442011;ENST00000305126;ENST00000514554;ENST0 0000508076;ENST00000503087 | TAF |
| 135398875 | 135398915; 135398898 | + | ENST00000442011;ENST00000305126;ENST00000514554;ENST0 0000508076;ENST00000503087 | TAF |
| 150937608 | 150937511 | − | ENST00000262188;ENST00000392811;ENST00000356800 | TAF |
| 183599772 | 183599596 | − | ENST00000367534;ENST00000359856;ENST00000294742 | TAF |
| 183599772 | 183599596 | − | ENST00000367534;ENST00000359856;ENST00000294742 | TAF |
| 2289492 | 2289637 | + | ENST00000356714;ENST00000397049;ENST00000397046;ENST0 0000397048;ENST00000339737;ENST00000343985 | TAF |
| 102691131 | 102691116 | − | ENST00000559838 | TAF |
| 86509365 | 86509293 | − | ENST00000165698;ENST00000541910;ENST00000538924;ENST0 0000437769;ENST00000453231 | TSF |
| 86509365 | 86509293 | − | ENST00000165698;ENST00000541910;ENST00000538924;ENST0 0000437769;ENST00000453231 | TSF |
| 86509365 | 86509293 | − | ENST00000165698;ENST00000541910;ENST00000538924;ENST0 0000437769;ENST00000453231 | TSF |
| 86509365 | 86509293 | − | ENST00000165698;ENST00000541910;ENST00000538924;ENST0 0000437769;ENST00000453231 | TSF |
| 24632175 | 24632358; 24632191 | + | ENST00000396864;ENST00000561342;ENST00000559284;ENST0 0000560275;ENST00000560852 | TAF |
| 24632175 | 24632358; 24632191 | + | ENST00000396864;ENST00000561342;ENST00000559284;ENST0 0000560275;ENST00000560852 | TAF |
| 24632175 | 24632358; 24632191 | + | ENST00000396864;ENST00000561342;ENST00000559284;ENST0 0000560275;ENST00000560852 | TAF |
| 24632175 | 24632358; 24632191 | + | ENST00000396864;ENST00000561342;ENST00000559284;ENST0 0000560275;ENST00000560852 | TAF |
| 130135209 | 130135363 | + | ENST00000223215;ENST00000437945 | TAF |
| 130135209 | 130135363 | + | ENST00000223215;ENST00000437945 | TAF |

TABLE 42-continued

Transcript fusion for Mesothelioma (MESO) Coordinates of the fusion sequences for which the donor is the TE.

| | | | | |
|---|---|---|---|---|
| 114182767 | 114183199 | + | ENST00000535401;ENST00000299964 | TAF |
| 33851594 | 33851755 | + | ENST00000246186 | TAF |
| 320772 | 320565 | − | ENST00000399808 | TAF |
| 320772 | 320565 | − | ENST00000399808 | TAF |
| 320772 | 320565 | − | ENST00000399808 | TAF |
| 320772 | 320565 | − | ENST00000399808 | TAF |
| 320772 | 320565 | − | ENST00000399808 | TAF |
| 320772 | 320565 | − | ENST00000399808 | TAF |
| 320772 | 320565 | − | ENST00000399808 | TAF |
| 320772 | 320565 | − | ENST00000399808 | TAF |
| 320772 | 320565 | | ENST00000399808 | TAF |
| 320772 | 320565 | − | ENST00000399808 | TAF |
| 320772 | 320565 | − | ENST00000399808 | TAF |
| 320772 | 320565 | − | ENST00000399808 | TAF |
| 131190581 | 131190702 131190700; | + | ENST00000372842;ENST00000420512;ENST00000372838 | TAF |
| 131190581 | 131190700; 131190702 | + | ENST00000372842;ENST00000420512;ENST00000372838 | TAF |
| 22255181 | 22255284 | + | ENST00000382353 | TAF |
| 93467826 | 93467791; 93467814 | − | ENST00000393259;ENST00000527169 | TAF |
| 93467826 | 93467791; 93467814 | − | ENST00000393259;ENST00000527169 | TAF |
| 76261565 | 76261559 | − | ENST00000472094;ENST00000568073;ENST00000562114;ENST0 0000567936;ENST00000498750;ENST00000567126 | TAF |
| 100876195 | 100876114 | − | ENST00000308344;ENST00000401528;ENST00000414035;ENST0 0000412417 | TSF |
| 100876195 | 100876114 | − | ENST00000308344;ENST00000401528;ENST00000414035;ENST0 0000412417 | TSF |
| 100876195 | 100876114 | − | ENST00000308344;ENST00000401528;ENST00000414035;ENST0 0000412417 | TSF |
| 79214787 | 79214816; 79214953 | + | ENST00000431388;ENST00000576002 | TAF |
| 79214787 | 79214816; 79214953 | + | ENST00000431388;ENST00000576002 | TAF |
| 56145402 | 56145354 | − | ENST00000394555;ENST00000394554;ENST00000355426;ENST0 0000438672;ENST00000439193;ENST00000440439;ENST0000042 9909;ENST00000452337;ENST00000421664 | TAF |
| 56145402 | 56145354 | − | ENST00000394555;ENST00000394554;ENST00000355426;ENST0 0000438672;ENST00000439193;ENST00000440439;ENST0000042 9909;ENST00000452337;ENST00000421664 | TAF |
| 56145402 | 56145354 | − | ENST00000394555;ENST00000394554;ENST00000355426;ENST0 0000438672;ENST00000439193;ENST00000440439;ENST0000042 9909;ENST00000452337;ENST00000421664 | TAF |
| 56145402 | 56145354 | − | ENST00000394555;ENST00000394554;ENST00000355426;ENST0 0000438672;ENST00000439193;ENST00000440439;ENST0000042 9909;ENST00000452337;ENST00000421664 | TAF |
| 56145402 | 56145354 | − | ENST00000394555;ENST00000394554;ENST00000355426;ENST0 0000438672;ENST00000439193;ENST00000440439;ENST0000042 9909;ENST00000452337;ENST00000421664 | TAF |
| 56145402 | 56145354 | − | ENST00000394555;ENST00000394554;ENST00000355426;ENST0 0000438672;ENST00000439193;ENST00000440439;ENST0000042 9909;ENST00000452337;ENST00000421664 | TAF |
| 174946792 | 174946652; 174946738 | − | ENST00000284719;ENST00000344357;ENST00000409546;ENST0 0000429575 | TSF |
| 174946792 | 174946652; 174946738 | − | ENST00000284719;ENST00000344357;ENST00000409546;ENST0 0000429575 | TSF |
| 48165108 | 48165233 | + | ENST00000320031;ENST00000007722 | TAF |
| 48165108 | 48165233 | + | ENST00000320031;ENST00000007722 | TAF |
| 123234156 | 123234026 | − | ENST00000359309;ENST00000360822;ENST00000349780;ENST0 0000360190;ENST00000480112;ENST00000416449 | TAF |
| 123234156 | 123234026 | − | ENST00000359309;ENST00000360822;ENST00000349780;ENST0 0000360190;ENST00000480112;ENST00000416449 | TAF |
| 123234156 | 123234026 | − | ENST00000359309;ENST00000360822;ENST00000349780;ENST0 0000360190;ENST00000480112;ENST00000416449 | TAF |
| 123234156 | 123234026 | − | ENST00000359309;ENST00000360822;ENST00000349780;ENST0 0000360190;ENST00000480112;ENST00000416449 | TAF |
| 123234156 | 123234026 | − | ENST00000359309;ENST00000360822;ENST00000349780;ENST0 0000360190;ENST00000480112;ENST00000416449 | TAF |
| 149089654 | 149089474; 149089447; | − | ENST00000305366;ENST00000472441;ENST00000493348 | TSF |

TABLE 42-continued

Transcript fusion for Mesothelioma (MESO) Coordinates of the fusion sequences for which the donor is the TE.

| | | | | |
|---|---|---|---|---|
| 149089654 | 149089616 149089474; 149089447; 149089616 | | ENST00000305366;ENST00000472441;ENST00000493348 | TSF |
| 149089654 | 149089474; 149089447; 149089616 | – | ENST00000305366;ENST00000472441;ENST00000493348 | TSF |
| 92921107 | 92921192 | + | ENST00000327111 | TAF |
| 88878064 | 88877958; 88877905 | – | ENST00000378364;ENST00000567713;ENST00000426324;ENST0 0000567391;ENST00000568319;ENST00000563655;ENST0000056 9616 | TAF |
| 88878064 | 88877958; 88877905 | – | ENST00000378364;ENST00000567713;ENST00000426324;ENST0 0000567391;ENST00000568319;ENST00000563655;ENST0000056 9616 | TAF |
| 88878064 | 88877958; 88877905 | – | ENST00000378364;ENST00000567713;ENST00000426324;ENST0 0000567391;ENST00000568319;ENST00000563655;ENST0000056 9616 | TAF |
| 88878064 | 88877958; 88877905 | – | ENST00000378364;ENST00000567713;ENST00000426324;ENST0 0000567391;ENST00000568319;ENST00000563655;ENST0000056 9616 | TAF |
| 88878064 | 88877958; 88877905 | – | ENST00000378364;ENST00000567713;ENST00000426324;ENST0 0000567391;ENST00000568319;ENST00000563655;ENST0000056 9616 | TAF |
| 88878064 | 88877958; 88877905 | – | ENST00000378364;ENST00000567713;ENST00000426324;ENST0 0000567391;ENST00000568319;ENST00000563655;ENST0000056 9616 | TAF |
| 171484477 | 171484353 | – | ENST00000176763;ENST00000520476 | TAF |
| 171484477 | 171484353 | – | ENST00000176763;ENST00000520476 | TAF |
| 198222170 | 198222310; 198222208; 198222298 | + | ENST00000367385;ENST00000442588;ENST00000538004;ENST0 0000367383;ENST00000544035;ENST00000391974 | TSF |
| 198222170 | 198222310; 198222208; 198222298 | + | ENST00000367385;ENST00000442588;ENST00000538004;ENST0 0000367383;ENST00000544035;ENST00000391974 | TSF |
| 198222170 | 198222310; 198222208; 198222298 | + | ENST00000367385;ENST00000442588;ENST00000538004;ENST0 0000367383;ENST00000544035;ENST00000391974 | TSF |
| 198222170 | 198222310; 198222208; 198222298 | + | ENST00000367385;ENST00000442588;ENST00000538004;ENST0 0000367383;ENST00000544035;ENST00000391974 | TSF |
| 198222170 | 198222310; 198222208; 198222298 | + | ENST00000367385;ENST00000442588;ENST00000538004;ENST0 0000367383;ENST00000544035;ENST00000391974 | TSF |
| 56482552 | 56482505 | – | ENST00000264218;ENST00000505262;ENST00000507338 | TSF |
| 56482552 | 56482505 | – | ENST00000264218;ENST00000505262;ENST00000507338 | TSF |
| 56482552 | 56482505 | – | ENST00000264218;ENST00000505262;ENST00000507338 | TSF |
| 60694676 | 60694890 | + | ENST00000453848;ENST00000005286 | TSF |
| 60694676 | 60694890 | + | ENST00000453848;ENST00000005286 | TSF |
| 129962329 | 129962516 | + | ENST00000445470;ENST00000222482;ENST00000493259 | TSF |
| 13183861 | 13183923 | + | ENST00000397661;ENST00000592199;ENST00000585382;ENST0 0000587760;ENST00000585575;ENST00000360105;ENST0000058 8228;ENST00000587260;ENST00000358552 | TSF |
| 13183861 | 13183923 | + | ENST00000397661;ENST00000592199;ENST00000585382;ENST0 0000587760;ENST00000585575;ENST00000360105;ENST0000058 8228;ENST00000587260;ENST00000358552 | TSF |
| 13183861 | 13183923 | + | ENST00000397661;ENST00000592199;ENST00000585382;ENST0 0000587760;ENST00000585575;ENST00000360105;ENST0000058 8228;ENST00000587260;ENST00000358552 | TSF |
| 13183861 | 13183923 | + | ENST00000397661;ENST00000592199;ENST00000585382;ENST0 0000587760;ENST00000585575;ENST00000360105;ENST0000058 8228;ENST00000587260;ENST00000358552 | TSF |
| 13183861 | 13183923 | + | ENST00000397661;ENST00000592199;ENST00000585382;ENST0 0000587760;ENST00000585575;ENST00000360105;ENST0000058 8228;ENST00000587260;ENST00000358552 | TSF |
| 124829179 | 124829033; 124829116 | – | ENST00000430155;ENST00000393469;ENST00000423114;ENST0 0000469902;ENST00000314584;ENST00000479826 | TSF |
| 124829179 | 124829033; 124829116 | – | ENST00000430155;ENST00000393469;ENST00000423114;ENST0 0000469902;ENST00000314584;ENST00000479826 | TSF |
| 124829179 | 124829033; 124829116 | – | ENST00000430155;ENST00000393469;ENST00000423114;ENST0 0000469902;ENST00000314584;ENST00000479826 | TSF |
| 124837700 | 124837613 | – | ENST00000430155;ENST00000393469;ENST00000423114;ENST0 0000469902;ENST00000314584;ENST00000479826 | TSF |
| 124837700 | 124837613 | – | ENST00000430155;ENST00000393469;ENST00000423114;ENST0 0000469902;ENST00000314584;ENST00000479826 | TSF |
| 124837700 | 124837613 | – | ENST00000430155;ENST00000393469;ENST00000423114;ENST0 0000469902;ENST00000314584;ENST00000479826 | TSF |
| 3422800 | 3422672 | – | ENST00000294599;ENST00000356575;ENST00000485002 | TSF |

TABLE 42-continued

Transcript fusion for Mesothelioma (MESO) Coordinates of the fusion sequences for which the donor is the TE.

| 3422800 | 3422672 | − | ENST00000294599;ENST00000356575;ENST00000485002 | TSF |
| 3422800 | 3422672 | − | ENST00000294599;ENST00000356575;ENST00000485002 | TSF |

TABLE 43

Transcript fusion for avarian cancer (OV) Coordinates of the fusion sequences for whichich the donor is the exon.

| 1 | 2 | 3 | 4 | 5 | 6 |
|---|---|---|---|---|---|
| 84% | chr20 | 53092486 | 53092551 | + | ENST00000262593 |
| 84% | chr19 | 45323962 | 45324032 | + | ENST00000270233 |
| 51% | chr1 | 32696528 | 32696620 | + | ENST00000373586 |
| 50% | chr6 | 74228333 | 74228077 | − | ENST00000316292;ENST00000309268;ENST00000331523 |
| 40% | chr20 | 47768284 | 47768119 | − | ENST00000371828;ENST00000340954;ENST00000347458;ENST00000360426;ENST00000371792;ENST00000371802;ENST00000371856;ENST00000437404;ENST00000456866 |
| 40% | chr20 | 47768284 | 47768119 | − | ENST00000371828;ENST00000340954;ENST00000347458;ENST00000360426;ENST00000371792;ENST00000371802;ENST00000371856;ENST00000437404;ENST00000456866 |
| 40% | chr20 | 47768284 | 47768119 | − | ENST00000371828;ENST00000340954;ENST00000347458;ENST00000360426;ENST00000371792;ENST00000371802;ENST00000371856;ENST00000437404;ENST00000456866 |
| 38% | chr6 | 10749855; 10749898 | 10749931 | + | ENST00000379542;ENST00000473166;ENST00000463448;ENST00000460341;ENST00000480294;ENST00000473807;ENST00000461342;ENST00000475942;ENST00000379530;ENST00000463100;ENST00000481240;ENST00000467317;ENST00000478732 |
| 38% | chr6 | 10749855; 10749898 | 10749931 | + | ENST00000379542;ENST00000473166;ENST00000463448;ENST00000460341;ENST00000480294;ENST00000473807;ENST00000461342;ENST00000475942;ENST00000379530;ENST00000463100;ENST00000481240;ENST00000467317;ENST00000478732 |
| 38% | chr12 | 113623819 | 113623826 | + | ENST00000552495 |
| 36% | chr12 | 124810916 | 124810737 | − | ENST00000405201;ENST00000404621;ENST00000356219;ENST00000397355;ENST00000404121;ENST00000429285;ENST00000418829;ENST00000443451;ENST00000413172 |
| 36% | chr12 | 124810916 | 124810737 | − | ENST00000405201;ENST00000404621;ENST00000356219;ENST00000397355;ENST00000404121;ENST00000429285;ENST00000418829;ENST00000443451;ENST00000413172 |
| 36% | chr12 | 124810916 | 124810737 | − | ENST00000405201;ENST00000404621;ENST00000356219;ENST00000397355;ENST00000404121;ENST00000429285;ENST00000418829;ENST00000443451;ENST00000413172 |
| 36% | chr12 | 124810916 | 124810737 | − | ENST00000405201;ENST00000404621;ENST00000356219;ENST00000397355;ENST00000404121;ENST00000429285;ENST00000418829;ENST00000443451;ENST00000413172 |
| 36% | chr12 | 124810916 | 124810737 | − | ENST00000405201;ENST00000404621;ENST00000356219;ENST00000397355;ENST00000404121;ENST00000429285;ENST00000418829;ENST00000443451;ENST00000413172 |
| 36% | chr12 | 124810916 | 124810737 | − | ENST00000405201;ENST00000404621;ENST00000356219;ENST00000397355;ENST00000404121;ENST00000429285;ENST00000418829;ENST00000443451;ENST00000413172 |
| 36% | chr12 | 124810916 | 124810737 | − | ENST00000405201;ENST00000404621;ENST00000356219;ENST00000397355;ENST00000404121;ENST00000429285;ENST00000418829;ENST00000443451;ENST00000413172 |
| 36% | chr12 | 124810916 | 124810737 | − | ENST00000405201;ENST00000404621;ENST00000356219;ENST00000397355;ENST00000404121;ENST00000429285;ENST00000418829;ENST00000443451;ENST00000413172 |
| 36% | chr12 | 124810916 | 124810737 | − | ENST00000405201;ENST00000404621;ENST00000356219;ENST00000397355;ENST00000404121;ENST00000429285;ENST00000418829;ENST00000443451;ENST00000413172 |
| 35% | chr1 | 224544627 | 224544695 | + | ENST00000465271;ENST00000366858;ENST00000366857;ENST00000366856 |
| 31% | chr14 | 31922550 | 31922481 | − | ENST00000549185;ENST00000547378;ENST00000310850;ENST00000356180 |
| 30% | chr8 | 144102731 | 144102850 | + | ENST00000292494;ENST00000429120;ENST00000521699;ENST00000520531;ENST00000520466;ENST00000521003;ENST00000522971;ENST00000519611;ENST00000519546;ENST00000523847;ENST00000522024 |
| 30% | chr12 | 6463721 | 6463604 | − | ENST00000360168;ENST00000358945;ENST00000540037;ENST00000228916;ENST00000396966;ENST00000543768 |
| 30% | chr12 | 6463721 | 6463604 | − | ENST00000360168;ENST00000358945;ENST00000540037;ENST00000228916;ENST00000396966;ENST00000543768 |
| 30% | chr12 | 6463721 | 6463604 | − | ENST00000360168;ENST00000358945;ENST00000540037;ENST00000228916;ENST00000396966;ENST00000543768 |
| 30% | chr12 | 6463721 | 6463604 | − | ENST00000360168;ENST00000358945;ENST00000540037;ENST00000228916;ENST00000396966;ENST00000543768 |
| 29% | chr19 | 45322839 | 45322879 | + | ENST00000589651;ENST00000270233 |
| 27% | chr20 | 43881792 | 43881643 | − | ENST00000338380 |
| 26% | chr11 | 118888255 | 118888078 | − | ENST00000527673 |
| 25% | chr2 | 26624858 | 26625012 | + | ENST00000288710;ENST00000421869 |

TABLE 43-continued

| | | | | |
|---|---|---|---|---|
| 24% | chr9 | 91150350 | 91150651 + | ENST00000375854;ENST0000375855 |
| 24% | chr19 | 45315735 | 45315805 + | ENST00000589651;ENST0000270233;ENST00000591520 |
| 24% | chr19 | 45315735 | 45315805 + | ENST00000589651;ENST0000270233;ENST00000591520 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458 |

TABLE 43-continued

| | | | | |
|---|---|---|---|---|
| 21% | chr19 | 35996667 | 35996620 − | 071;ENST00000418261;ENST00000424570;ENST00000451297;ENST00000450261 ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 21% | chr19 | 35996667 | 35996620 − | ENST00000434389;ENST00000402589;ENST00000339686;ENST00000436012;ENST00000414866;ENST00000480502;ENST00000467637;ENST00000429837;ENST00000419602;ENST00000443640;ENST00000597212;ENST00000472252;ENST00000492341;ENST00000602781;ENST00000602679;ENST00000474928;ENST00000488892;ENST00000461300;ENST00000447113;ENST00000392206;ENST00000440396;ENST00000458071;ENST00000418261;ENST00000424570;ENST00000451297;ENST00000450261 |
| 20% | chr11 | 18536388 | 18536225 − | ENST00000536719;ENST00000251968 |
| 20% | chr15 | 66995597 | 66996413 + | ENST00000288840;ENST00000457357;ENST00000557916 |
| 20% | chr10 | 120905865 | 120905748 − | ENST00000355697;ENST00000330036 |
| 20% | chr10 | 120905865 | 120905748 − | ENST00000355697;ENST00000330036 |
| 19% | chr7 | 91771800 | 91771777 − | ENST00000435873 |
| 18% | chr19 | 13869914; 13869931; 13869925 | 13870086 + | ENST00000586600;ENST00000221554;ENST00000586666;ENST00000588809;ENST00000585844 |
| 18% | chr19 | 13869914; 13869931; 13869925 | 13870086 + | ENST00000586600;ENST00000221554;ENST00000586666;ENST00000588809;ENST00000585844 |
| 18% | chr19 | 13869914; 13869931; 13869925 | 13870086 + | ENST00000586600;ENST00000221554;ENST00000586666;ENST00000588809;ENST00000585844 |
| 18% | chr19 | 13869914; 13869931; 13869925 | 13870086 + | ENST00000586600;ENST00000221554;ENST00000586666;ENST00000588809;ENST00000585844 |
| 18% | chr15 | 82726234 | 82726553 + | ENST00000300515 |
| 18% | chr15 | 83102759 | 83103078 + | ENST00000561062;ENST00000358583 |
| 17% | chr8 | 27516013 | 27517056 + | ENST00000337221;ENST00000301904 |
| 17% | chr19 | 51452029 | 51451896 − | ENST00000391809;ENST00000336334;ENST00000593428 |
| 17% | chr9 | 133352258 | 133352273 − | ENST00000352480;ENST00000372394;ENST00000372393 |
| 17% | chr19 | 16204346; 16204382 | 16204408 + | ENST00000344824;ENST00000538887;ENST00000300933;ENST00000588032;ENST00000592822 |
| 17% | chr19 | 16204346; 16204382 | 16204408 + | ENST00000344824;ENST00000538887;ENST00000300933;ENST00000588032;ENST00000592822 |
| 17% | chr19 | 16204346; 16204382 | 16204408 + | ENST00000344824;ENST00000538887;ENST00000300933;ENST00000588032;ENST00000592822 |
| 17% | chr19 | 16204346; 16204382 | 16204408 + | ENST00000344824;ENST00000538887;ENST00000300933;ENST00000588032;ENST00000592822 |
| 15% | chr1 | 33272212 | 33272083 − | ENST00000373477 |
| 15% | chr19 | 46498683 | 46498762 + | ENST00000263284 |
| 15% | chr6 | 34386201 | 34386146 − | ENST00000605528;ENST00000344700;ENST00000326199 |
| 14% | chr4 | 17625224 | 17625417 + | ENST00000237380;ENST00000503945 |
| 14% | chr4 | 17625224 | 17625417 + | ENST00000237380;ENST00000503945 |
| 14% | chr12 | 71509738 | 71509630 − | ENST00000549357 |
| 14% | chr7 | 27582719 | 27582586 − | ENST00000265395;ENST00000425715 |
| 14% | chr7 | 27582719 | 27582586 − | ENST00000265395;ENST00000425715 |
| 14% | chr9 | 91150350 | 91150651 + | ENST00000375854;ENST00000375855 |
| 14% | chr11 | 66008898; 66008919 | 66008937 + | ENST00000320580;ENST00000529757;ENST00000529677 |
| 14% | chr11 | 66008898; 66008919 | 66008937 + | ENST00000320580;ENST00000529757;ENST00000529677 |
| 14% | chr11 | 66008898; 66008919 | 66008937 + | ENST00000320580;ENST00000529757;ENST00000529677 |
| 14% | chr11 | 66008898; 66008919 | 66008937 + | ENST00000320580;ENST00000529757;ENST00000529677 |
| 13% | chr2 | 132249597 | 132249449 − | ENST00000427024;ENST00000309451 |
| 13% | chr2 | 132249597 | 132249449 − | ENST00000427024;ENST00000309451 |
| 13% | chr6 | 42980766 | 42980664 − | ENST00000244711 |
| 12% | chr19 | 35514331 | 35514451 + | ENST00000599564;ENST00000317991;ENST00000504615;ENST00000411896 |
| 12% | chr19 | 35514331 | 35514451 + | ENST00000599564;ENST00000317991;ENST00000504615;ENST00000411896 |
| 12% | chr19 | 35514331 | 35514451 + | ENST00000599564;ENST00000317991;ENST00000504615;ENST00000411896 |
| 12% | chr19 | 35514331 | 35514451 + | ENST00000599564;ENST00000317991;ENST00000504615;ENST00000411896 |
| 12% | chr6 | 35314915 | 35314927 + | ENST00000448077 |
| 12% | chr18 | 33767503 | 33767644 + | ENST00000261326 |
| 12% | chr6 | 34210489 | 34210572 + | ENST00000447654;ENST00000311487;ENST00000347617;ENST00000401473;ENST00000374116 |
| 12% | chr6 | 34210489 | 34210572 + | ENST00000447654;ENST00000311487;ENST00000347617;ENST00000401473;ENST00000374116 |

TABLE 43-continued

| | | | | |
|---|---|---|---|---|
| 12% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 12% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 12% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 12% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 12% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 12% | chr8 | 42924698; 42924750 | 42924802 + | ENST00000534420;ENST00000302279;ENST00000533998;ENST00000342116;ENST00000531266;ENST00000525699;ENST00000529687;ENST00000533336 |
| 12% | chr1 | 153662760 | 153662858 + | ENST00000368680 |
| 12% | chr1 | 55319285 | 55319152 − | ENST00000371269;ENST00000436604;ENST00000537443;ENST00000535035 |
| 12% | chr1 | 55319285 | 55319152 − | ENST00000371269;ENST00000436604;ENST00000537443;ENST00000535035 |
| 12% | chr1 | 55319285 | 55319152 − | ENST00000371269;ENST00000436604;ENST00000537443;ENST00000535035 |
| 12% | chr1 | 55319285 | 55319152 − | ENST00000371269;ENST00000436604;ENST00000537443;ENST00000535035 |
| 11% | chr2 | 242275390; 242275258 | 222475513 + | ENST00000391973;ENST00000428282;ENST00000360051;ENST00000407017;ENST00000391971;ENST00000401990;ENST00000407971;ENST00000436795;ENST00000411484;ENST00000402092;ENST00000443492;ENST00000437066;ENST00000449239;ENST00000457874 |
| 11% | chr2 | 242275390; 242275258 | 222475513 + | ENST00000391973;ENST00000428282;ENST00000360051;ENST00000407017;ENST00000391971;ENST00000401990;ENST00000407971;ENST00000436795;ENST00000411484;ENST00000402092;ENST00000443492;ENST00000437066;ENST00000449239;ENST00000457874 |
| 11% | chr2 | 242275390; 242275258 | 222475513 + | ENST00000391973;ENST00000428282;ENST00000360051;ENST00000407017;ENST00000391971;ENST00000401990;ENST00000407971;ENST00000436795;ENST00000411484;ENST00000402092;ENST00000443492;ENST00000437066;ENST00000449239;ENST00000457874 |
| 11% | chr2 | 242275390; 242275258 | 222475513 + | ENST00000391973;ENST00000428282;ENST00000360051;ENST00000407017;ENST00000391971;ENST00000401990;ENST00000407971;ENST00000436795;ENST00000411484;ENST00000402092;ENST00000443492;ENST00000437066;ENST00000449239;ENST00000457874 |
| 11% | chr2 | 242275390; 242275258 | 222475513 + | ENST00000391973;ENST00000428282;ENST00000360051;ENST00000407017;ENST00000391971;ENST00000401990;ENST00000407971;ENST00000436795;ENST00000411484;ENST00000402092;ENST00000443492;ENST00000437066;ENST00000449239;ENST00000457874 |
| 11% | chr9 | 15506635 | 15506559 − | ENST00000380738;ENST00000380733;ENST00000380715;ENST00000380716;ENST00000397519 |
| 11% | chr12 | 57060050 | 57059988 − | ENST00000262033;ENST00000414274;ENST00000436399;ENST00000456859 |
| 11% | chr12 | 57060050 | 57059988 − | ENST00000262033;ENST00000414274;ENST00000436399;ENST00000456859 |
| 11% | chr12 | 57060050 | 57059988 − | ENST00000262033;ENST00000414274;ENST00000436399;ENST00000456859 |
| 11% | chr12 | 57060050 | 57059988 − | ENST00000262033;ENST00000414274;ENST00000436399;ENST00000456859 |
| 11% | chr19 | 14063948 | 14063931 − | ENST00000538517;ENST00000538371;ENST00000585607 |
| 11% | chr19 | 45316507 | 45316603 + | ENST00000589651;ENST00000270233;ENST00000591520 |
| 11% | chr19 | 45316507 | 45316603 + | ENST00000589651;ENST00000270233;ENST00000591520 |
| 11% | chr1 | 225156461 | 225156576 + | ENST00000430092;ENST00000400952;ENST00000366849;ENST00000439375 |
| 11% | chr1 | 225156461 | 225156576 + | ENST00000430092;ENST00000400952;ENST00000366849;ENST00000439375 |
| 11% | chr1 | 11805860 | 11805894 + | ENST00000476512;ENST00000400895;ENST00000376629;ENST00000376627;ENST00000314340;ENST00000452018;ENST00000510878 |
| 11% | chr1 | 11805860 | 11805894 + | ENST00000476512;ENST00000400895;ENST00000376629;ENST00000376627;ENST00000314340;ENST00000452018;ENST00000510878 |
| 11% | chr19 | 3869015; 3869013 | 3868963 − | ENST00000262961;ENST00000438164;ENST00000587212;ENST00000586578;ENST0000439086 |
| 11% | chr19 | 3869015; 3869013 | 3868963 − | ENST00000262961;ENST00000438164;ENST00000587212;ENST00000586578;ENST0000439086 |
| 11% | chr1 | 987108 | 987195 + | ENST00000379370;ENST00000419249 |
| 11% | chr1 | 987108 | 987195 + | ENST00000379370;ENST00000419249 |
| 11% | chr19 | 49497169 | 494971 + | ENST00000595090;ENST00000595811;ENST00000596247;ENST00000221413;ENST00000593570 |
| 11% | chr5 | 54993786 | 54993674 − | ENST00000396865;ENST00000539768;ENST00000318672;ENST00000508124;ENST00000511233;ENST00000503891;ENST00000513993;ENST00000505563;ENST00000506624;ENST00000507109 |
| 10% | chr6 | 10751366; 10751403 | 10751467 + | ENST00000379542;ENST00000475942;ENST00000467317;ENST00000478732;ENST00000467229 |
| 10% | chr6 | 10751366; 10751403 | 10751467 + | ENST00000379542;ENST00000475942;ENST00000467317;ENST00000478732;ENST00000467229 |
| 10% | chr6 | 10751366; 10751403 | 10751467 + | ENST00000379542;ENST00000475942;ENST00000467317;ENST00000478732;ENST00000467229 |
| 10% | chr6 | 42980766 | 48980664 − | ENST00000244711 |
| 10% | chr1 | 151239649 | 151239815 + | ENST00000368884;ENST00000368881;ENST00000445776;ENST00000453615 |
| 10% | chr1 | 151239649 | 151239815 + | ENST00000368884;ENST00000368881;ENST00000445776;ENST00000453615 |
| 10% | chr1 | 151239649 | 151239815 + | ENST00000368884;ENST00000368881;ENST00000445776;ENST00000453615 |
| 10% | chr1 | 151239649 | 151239815 + | ENST00000368884;ENST00000368881;ENST00000445776;ENST00000453615 |
| 10% | chr17 | 7214669 | 7214800 + | ENST00000336452;ENST00000336458;ENST00000576930;ENST00000572815;ENST00000573542;ENST00000419711;ENST00000571955;ENST00000573714;ENST00000416016 |
| 10% | chr17 | 7214669 | 7214800 + | ENST00000336452;ENST00000336458;ENST00000576930;ENST00000572815;ENST00000573542;ENST00000419711;ENST00000571955;ENST00000573714;ENST00000416016 |

TABLE 43-continued

| | | | | |
|---|---|---|---|---|
| 9% | chr2 | 133426110; 133426006 | 133425973 − | ENST00000397463;ENST00000345008 |
| 9% | chr2 | 133426110; 133426006 | 133425973 − | ENST00000397463;ENST00000345008 |
| 9% | chr12 | 71928895 | 71928966 + | ENST00000266674;ENST00000536515;ENST00000540815 |
| 9% | chr14 | 66096210; 66096217 | 66096324 + | ENST00000360689;ENST00000394586;ENST00000342677;ENST00000557164;ENST00000394585;ENST00000358307 |
| 9% | chr14 | 66096210; 66096217 | 66096324 + | ENST00000360689;ENST00000394586;ENST00000342677;ENST00000557164;ENST00000394585;ENST00000358307 |
| 9% | chr14 | 66096210; 66096217 | 66096324 + | ENST00000360689;ENST00000394586;ENST00000342677;ENST00000557164;ENST00000394585;ENST00000358307 |
| 8% | chr1 | 155036300 | 152036412 + | ENST00000368409;ENST00000359751;ENST00000556931;ENST00000505139;ENST00000427683 |
| 8% | chr18 | 72176075 | 72176163 + | ENST00000324262;ENST00000580672;ENST00000579847;ENST00000583785 |
| 8% | chr18 | 72176075 | 72176163 + | ENST00000324262;ENST00000580672;ENST00000579847;ENST00000583785 |
| 8% | chr12 | 102547647 | 102547754 + | ENST00000327680;ENST00000378128;ENST00000541394;ENST00000358383;ENST00000392911;ENST00000412715;ENST00000417507;ENST00000457614 |
| 8% | chr12 | 102547647 | 102547754 + | ENST00000327680;ENST00000378128;ENST00000541394;ENST00000358383;ENST00000392911;ENST00000412715;ENST00000417507;ENST00000457614 |
| 8% | chr12 | 102547647 | 102547754 + | ENST00000327680;ENST00000378128;ENST00000541394;ENST00000358383;ENST00000392911;ENST00000412715;ENST00000417507;ENST00000457614 |
| 8% | chr12 | 102547647 | 102547754 + | ENST00000327680;ENST00000378128;ENST00000541394;ENST00000358383;ENST00000392911;ENST00000412715;ENST00000417507;ENST00000457614 |
| 8% | chr12 | 102547647 | 102547754 + | ENST00000327680;ENST00000378128;ENST00000541394;ENST00000358383;ENST00000392911;ENST00000412715;ENST00000417507;ENST00000457614 |
| 8% | chr19 | 15289752 | 15289634 − | ENST00000263388;ENST00000601011 |
| 8% | chr19 | 15289752 | 15289634 − | ENST00000263388;ENST00000601011 |
| 8% | chr2 | 10671988 | 110672054 + | ENST00000553749 |
| 8% | chr22 | 36661197; 36661246 | 36661833 + | ENST00000397278;ENST00000422706;ENST00000426053;ENST00000319136;ENST00000347595;ENST00000397279 |
| 8% | chr22 | 36661197; 36661246 | 36661833 + | ENST00000397278;ENST00000422706;ENST00000426053;ENST00000319136;ENST00000347595;ENST00000397279 |
| 8% | chr22 | 36661197; 36661246 | 36661833 + | ENST00000397278;ENST00000422706;ENST00000426053;ENST00000319136;ENST00000347595;ENST00000397279 |
| 8% | chr22 | 36661197; 36661246 | 36661833 + | ENST00000397278;ENST00000422706;ENST00000426053;ENST00000319136;ENST00000347595;ENST00000397279 |
| 7% | chr19 | 45323962 | 45324032 + | ENST00000270233 |
| 7% | chr2 | 111214673 | 111214907 | ENST00000603767;ENST00000447537 |
| 7% | chr16 | 2867802; 2867880 | 2867967 + | ENST00000455114;ENST00000450020;ENST00000005995;ENST00000574813;ENST00000574265 |
| 7% | chr16 | 2867802; 2867880 | 2867967 + | ENST00000455114;ENST00000450020;ENST00000005995;ENST00000574813;ENST00000574265 |
| 7% | chr16 | 2867802; 2867880 | 2867967 + | ENST00000455114;ENST00000450020;ENST00000005995;ENST00000574813;ENST00000574265 |
| 7% | chr19 | 45322839 | 45322983 + | ENST00000589651;ENST00000270233 |
| 7% | chr19 | 45323962 | 45324032 + | ENST00000270233 |
| 7% | chr16 | 2825557; 2825626 | 2825452 − | ENST00000262306;ENST00000409906;ENST00000409477;ENST00000494946 |
| 7% | chr16 | 2825557; 2825626 | 2825452 − | ENST00000262306;ENST00000409906;ENST00000409477;ENST00000494946 |
| 7% | chr16 | 2825557; 2825626 | 2825452 − | ENST00000262306;ENST00000409906;ENST00000409477;ENST00000494946 |
| 7% | chr3 | 48716169 | 48715997 | ENST00000341520;ENST00000416649;ENST00000294129;ENST00000413374 |
| 7% | chr3 | 48716169 | 48715997 | ENST00000341520;ENST00000416649;ENST00000294129;ENST00000413374 |
| 7% | chr3 | 48716169 | 48715997 | ENST00000341520;ENST00000416649;ENST00000294129;ENST00000413374 |
| 7% | chr19 | 45317861 | 45318010 + | ENST00000589651;ENST00000270233 |
| 7% | chr7 | 76144362 | 76144473 + | ENST00000334348;ENST00000448265;ENST00000419923;ENST00000443097;ENST00000257632;ENST00000394849 |
| 7% | chr7 | 76144362 | 76144473 + | ENST00000334348;ENST00000448265;ENST00000419923;ENST00000443097;ENST00000257632;ENST00000394849 |
| 7% | chr7 | 76144362 | 76144473 + | ENST00000334348;ENST00000448265;ENST00000419923;ENST00000443097;ENST00000257632;ENST00000394849 |
| 7% | chr2 | 217366064 | 217366082 + | ENST00000491306;ENST00000456586 |
| 7% | chr2 | 217366064 | 217366082 + | ENST00000491306;ENST00000456586 |
| 6% | chr17 | 7214669 | 7214719 + | ENST00000336452;ENST00000336458;ENST00000576930;ENST00000572815;ENST00000573542;ENST00000419711;ENST00000571955;ENST00000573714;ENST00000416016 |
| 6% | chr17 | 7214669 | 7214719 + | ENST00000336452;ENST00000336458;ENST00000576930;ENST00000572815;ENST00000573542;ENST00000419711;ENST00000571955;ENST00000573714;ENST00000416016 |
| 6% | chr7 | 76144362 | 76144473 + | ENST00000334348;ENST00000448265;ENST00000419923;ENST00000443097;ENST00000257632;ENST00000394849 |
| 6% | chr7 | 76144362 | 76144473 + | ENST00000334348;ENST00000448265;ENST00000419923;ENST00000443097;ENST00000257632;ENST00000394849 |
| 6% | chr7 | 76144362 | 76144473 + | ENST00000334348;ENST00000448265;ENST00000419923;ENST00000443097;ENST00000257632;ENST00000394849 |
| 6% | chr7 | 76143264 | 76143393 + | ENST00000334348;ENST00000448265;ENST00000419923;ENST00000443097;ENST00000257632;ENST00000394849 |
| 6% | chr7 | 76143264 | 76143393 + | ENST00000334348;ENST00000448265;ENST00000419923;ENST00000443097;ENST00000257632;ENST00000394849 |

TABLE 43-continued

| | | | | |
|---|---|---|---|---|
| 6% | chr7 | 76143264 | 76143393 + | ENST00000334348;ENST00000448265;ENST00000419923;ENST00000443097;ENST00000257632;ENST00000394849 |
| 6% | chr20 | 29632611 | 29632721 + | ENST00000278882;ENST00000358464 |
| 6% | chr7 | 76143264 | 76143393 + | ENST00000334348;ENST00000448265;ENST00000419923;ENST00000443097;ENST00000257632;ENST00000394849 |
| 6% | chr7 | 76143264 | 76143393 + | ENST00000334348;ENST00000448265;ENST00000419923;ENST00000443097;ENST00000257632;ENST00000394849 |
| 6% | chr7 | 76143264 | 76143393 + | ENST00000334348;ENST00000448265;ENST00000419923;ENST00000443097;ENST00000257632;ENST00000394849 |
| 6% | chr1 | 183441756 | 183441784 + | ENST00000440812;ENST00000444547;ENST00000347615;ENST00000507469;ENST00000515829 |
| 6% | chr11 | 101937216; 101937273 | 101937382 + | ENST00000434758;ENST00000526781;ENST00000529204 |
| 6% | chr11 | 101937216; 101937273 | 101937382 + | ENST00000434758;ENST00000526781;ENST00000529204 |
| 6% | chr6 | 10755375 | 10755465 + | ENST00000379542;ENST00000461342;ENST00000475942;ENST00000379530;ENST00000473276;ENST00000481240;ENST00000467317;ENST00000467229 |
| 6% | chr6 | 10755375 | 10755465 + | ENST00000379542;ENST00000461342;ENST00000475942;ENST00000379530;ENST00000473276;ENST00000481240;ENST00000467317;ENST00000467229 |
| 6% | chr6 | 10755375 | 10755465 + | ENST00000379542;ENST00000461342;ENST00000475942;ENST00000379530;ENST00000473276;ENST00000481240;ENST00000467317;ENST00000467229 |
| 6% | chr6 | 10755375 | 10755465 + | ENST00000379542;ENST00000461342;ENST00000475942;ENST00000379530;ENST00000473276;ENST00000481240;ENST00000467317;ENST00000467229 |
| 6% | chr7 | 74168178 | 74168361 + | ENST00000324896;ENST00000346152;ENST00000353920;ENST00000416070 |
| 6% | chr7 | 74168178 | 74168361 + | ENST00000324896;ENST00000346152;ENST00000353920;ENST00000416070 |
| 6% | chr7 | 74168178 | 74168361 + | ENST00000324896;ENST00000346152;ENST00000353920;ENST00000416070 |
| 6% | chr7 | 74168178 | 74168361 + | ENST00000324896;ENST00000346152;ENST00000353920;ENST00000416070 |
| 6% | chr12 | 56744672 | 56744613 − | ENST00000314128;ENST00000557235;ENST00000418572 |
| 6% | chr12 | 56744672 | 56744613 − | ENST00000314128;ENST00000557235;ENST00000418572 |
| 5% | chr19 | 45349783 | 45349870 + | ENST00000252485;ENST00000252483 |
| 5% | chr3 | 185414451 | 185414400 − | ENST00000382199;ENST00000421047;ENST00000457616;ENST00000346192 |
| 5% | chr3 | 185414451 | 185414400 − | ENST00000382199;ENST00000421047;ENST00000457616;ENST00000346192 |
| 5% | chr22 | 36661197; 36661246 | 36661580 + | ENST00000397278;ENST00000422706;ENST00000426053;ENST00000319136;ENST00000347595;ENST00000397279 |
| 5% | chr22 | 36661197; 36661246 | 36661580 + | ENST00000397278;ENST00000422706;ENST00000426053;ENST00000319136;ENST00000347595;ENST00000397279 |
| 5% | chr22 | 36661197; 36661246 | 36661580 + | ENST00000397278;ENST00000422706;ENST00000426053;ENST00000319136;ENST00000347595;ENST00000397279 |
| 5% | chr22 | 36661197; 36661246 | 36661580 + | ENST00000397278;ENST00000422706;ENST00000426053;ENST00000319136;ENST00000347595;ENST00000397279 |
| 5% | chr9 | 3856184 | 3856009 − | ENST00000324333;ENST00000381971 |
| 5% | chr9 | 3856184 | 3856009 − | ENST00000324333;ENST00000381971 |
| 5% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 5% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 5% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 5% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 5% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 5% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 5% | chr4 | 1102192 | 1102131 − | ENST00000382968;ENST00000433731;ENST00000511620;ENST00000510715;ENST00000333673 |
| 5% | chr9 | 19378916 | 19378898 − | ENST00000380394;ENST00000380384;ENST00000315377 |
| 5% | chr9 | 19378916 | 19378898 − | ENST00000380394;ENST00000380384;ENST00000315377 |
| 5% | chr6 | 29910534 | 29910757 + | ENST00000396634;ENST00000376806;ENST00000376809;ENST00000376802 |
| 5% | chr1 | 40313763; 40313769; 40313673; 40313734 | 40313658 − | ENST00000441669;ENST00000462797;ENST00000316891;ENST00000372818;ENST00000537223;ENST00000537440;ENST00000545233 |
| 5% | chr1 | 40313763; 40313769; 40313673; 40313734 | 40313658 − | ENST00000441669;ENST00000462797;ENST00000316891;ENST00000372818;ENST00000537223;ENST00000537440;ENST00000545233 |
| 5% | chr1 | 40313763; 40313769; 40313673; 40313734 | 40313658 − | ENST00000441669;ENST00000462797;ENST00000316891;ENST00000372818;ENST00000537223;ENST00000537440;ENST00000545233 |
| 5% | chr1 | 40313763; 40313769; 40313673; | 40313658 − | ENST00000441669;ENST00000462797;ENST00000316891;ENST00000372818;ENST00000537223;ENST00000537440;ENST00000545233 |

TABLE 43-continued

| | | | | |
|---|---|---|---|---|
| | | 40313734 | | |
| 5% | chr1 | 44804994; 44804988 | 44804717 | − | ENST00000372257;ENST00000457571 |
| 5% | chr1 | 44804994; 44804988 | 44804717 | − | ENST00000372257;ENST00000457571 |
| 5% | chr1 | 20979220 | 20979114 | − | ENST00000602624;ENST00000375048;ENST00000415136 |
| 5% | chr1 | 20979220 | 20979114 | − | ENST00000602624;ENST00000375048;ENST00000415136 |
| 5% | chr1 | 20979220 | 20979114 | − | ENST00000602624;ENST00000375048;ENST00000415136 |
| 5% | chr20 | 3842901 | 3843060 | + | ENST00000416600;ENST00000428216 |
| 5% | chr20 | 3842901 | 3843060 | + | ENST00000416600;ENST00000428216 |
| 5% | chr8 | 71619168 | 71619388 | + | ENST00000408926;ENST00000520030 |
| 5% | chr17 | 7214669 | 7214719 | + | ENST00000336452;ENST00000336458;ENST00000576930;ENST00000572815;ENST00000573542;ENST00000419711;ENST00000571955;ENST00000573714;ENST00000416016 |
| 5% | chr17 | 7214669 | 7214719 | + | ENST00000336452;ENST00000336458;ENST00000576930;ENST00000572815;ENST00000573542;ENST00000419711;ENST00000571955;ENST00000573714;ENST00000416016 |
| 5% | chr19 | 45323962 | 45324053 | + | ENST00000270233 |
| 5% | chr16 | 2868684; 2868678 | 2868970 | + | ENST00000455114;ENST00000450020;ENST00000005995;ENST00000574813;ENST00000574265 |
| 5% | chr16 | 2868684; 2868678 | 2868970 | + | ENST00000455114;ENST00000450020;ENST00000005995;ENST00000574813;ENST00000574265 |
| 5% | chr16 | 2868684; 2868678 | 2868970 | + | ENST00000455114;ENST00000450020;ENST00000005995;ENST00000574813;ENST00000574265 |
| 5% | chr16 | 2868684; 2868678 | 2868970 | + | ENST00000455114;ENST00000450020;ENST00000005995;ENST00000574813;ENST00000574265 |
| 5% | chr18 | 72176075 | 72176163 | + | ENST00000324262;ENST00000580672;ENST00000579847;ENST00000583785 |
| 5% | chr18 | 72176075 | 72176163 | + | ENST00000324262;ENST00000580672;ENST00000579847;ENST00000583785 |
| 5% | chr10 | 75555297 | 75555421 | + | ENST00000604729;ENST00000603114;ENST00000604524;ENST00000398706;ENST00000605216;ENST00000433366;ENST00000492395;ENST00000603187;ENST00000412198;ENST00000604754 |
| 5% | chr10 | 75555297 | 75555421 | + | ENST00000604729;ENST00000603114;ENST00000604524;ENST00000398706;ENST00000605216;ENST00000433366;ENST00000492395;ENST00000603187;ENST00000412198;ENST00000604754 |
| 5% | chr10 | 75555297 | 75555421 | + | ENST00000604729;ENST00000603114;ENST00000604524;ENST00000398706;ENST00000605216;ENST00000433366;ENST00000492395;ENST00000603187;ENST00000412198;ENST00000604754 |
| 5% | chr10 | 75555297 | 75555421 | + | ENST00000604729;ENST00000603114;ENST00000604524;ENST00000398706;ENST00000605216;ENST00000433366;ENST00000492395;ENST00000603187;ENST00000412198;ENST00000604754 |
| 5% | chr10 | 75555297 | 75555421 | + | ENST00000604729;ENST00000603114;ENST00000604524;ENST00000398706;ENST00000605216;ENST00000433366;ENST00000492395;ENST00000603187;ENST00000412198;ENST00000604754 |
| 5% | chr10 | 75555297 | 75555421 | + | ENST00000604729;ENST00000603114;ENST00000604524;ENST00000398706;ENST00000605216;ENST00000433366;ENST00000492395;ENST00000603187;ENST00000412198;ENST00000604754 |
| 5% | chr10 | 75555297 | 75555421 | + | ENST00000604729;ENST00000603114;ENST00000604524;ENST00000398706;ENST00000605216;ENST00000433366;ENST00000492395;ENST00000603187;ENST00000412198;ENST00000604754 |
| 5% | chr10 | 75555297 | 75555421 | + | ENST00000604729;ENST00000603114;ENST00000604524;ENST00000398706;ENST00000605216;ENST00000433366;ENST00000492395;ENST00000603187;ENST00000412198;ENST00000604754 |
| 5% | chr1 | 33138392 | 33138502 | + | ENST00000414241;ENST00000373493;ENST00000544435;ENST00000373485;ENST00000458695;ENST00000475321;ENST00000463378;ENST00000460669;ENST00000481 2190 |
| 5% | chr1 | 33138392 | 33138502 | + | ENST00000414241;ENST00000373493;ENST00000544435;ENST00000373485;ENST00000458695;ENST00000475321;ENST00000463378;ENST00000460669;ENST00000481 2190 |
| 5% | chr1 | 33138392 | 33138502 | + | ENST00000414241;ENST00000373493;ENST00000544435;ENST00000373485;ENST00000458695;ENST00000475321;ENST00000463378;ENST00000460669;ENST00000481 2190 |
| 5% | chr1 | 33138392 | 33138502 | + | ENST00000414241;ENST00000373493;ENST00000544435;ENST00000373485;ENST00000458695;ENST00000475321;ENST00000463378;ENST00000460669;ENST00000481 2190 |
| 5% | chr1 | 33138392 | 33138502 | + | ENST00000414241;ENST00000373493;ENST00000544435;ENST00000373485;ENST00000458695;ENST00000475321;ENST00000463378;ENST00000460669;ENST00000481 2190 |
| 5% | chr1 | 33138392 | 33138502 | + | ENST00000414241;ENST00000373493;ENST00000544435;ENST00000373485;ENST00000458695;ENST00000475321;ENST00000463378;ENST00000460669;ENST00000481 2190 |
| 5% | chr1 | 33138392 | 33138502 | + | ENST00000414241;ENST00000373493;ENST00000544435;ENST00000373485;ENST00000458695;ENST00000475321;ENST00000463378;ENST00000460669;ENST00000481 2190 |
| 5% | chr1 | 33138392 | 33138502 | + | ENST00000414241;ENST00000373493;ENST00000544435;ENST00000373485;ENST00000458695;ENST00000475321;ENST00000463378;ENST00000460669;ENST00000481 2190 |
| 5% | chr19 | 53352466; 53352373 | 53352340 | − | ENST00000595646;ENST00000243639;ENST00000597924;ENST00000601847 |
| 5% | chr19 | 53352466; 53352373 | 53352340 | − | ENST00000595646;ENST00000243639;ENST00000597924;ENST00000601847 |

TABLE 43-continued

| | | | | |
|---|---|---|---|---|
| 5% | chr4 | 289322 | 299227 − | ENST00000419098 |
| 4% | chr14 | 93813615 | 938134740 + | ENST00000342144 |
| 4% | chr3 | 50153339 | 50153413 + | ENST00000347869 |
| 4% | chr3 | 137906397;<br>137906427 | 137906441 + | ENST00000469044;ENST00000461600;ENST00000461822;ENST00000470821;ENST00000471709;ENST00000393058;ENST00000538260;ENST00000463485 |
| 4% | chr3 | 137906397;<br>137906427 | 137906441 + | ENST00000469044;ENST00000461600;ENST00000461822;ENST00000470821;ENST00000471709;ENST00000393058;ENST00000538260;ENST00000463485 |
| 4% | chr19 | 17387632;<br>17387623 | 17387718 + | ENST00000598188;ENST00000359435;ENST00000596542;ENST00000447614;ENST00000601043;ENST00000595632;ENST00000601232 |
| 4% | chr19 | 17387632;<br>17387623 | 17387718 + | ENST00000598188;ENST00000359435;ENST00000596542;ENST00000447614;ENST00000601043;ENST00000595632;ENST00000601232 |
| 4% | chr19 | 17387632;<br>17387623 | 17387718 + | ENST00000598188;ENST00000359435;ENST00000596542;ENST00000447614;ENST00000601043;ENST00000595632;ENST00000601232 |
| 4% | chr19 | 17387632;<br>17387623 | 17387718 + | ENST00000598188;ENST00000359435;ENST00000596542;ENST00000447614;ENST00000601043;ENST00000595632;ENST00000601232 |
| 4% | chr19 | 17387632;<br>17387623 | 17387718 + | ENST00000598188;ENST00000359435;ENST00000596542;ENST00000447614;ENST00000601043;ENST00000595632;ENST00000601232 |
| 4% | chr19 | 45323962 | 45324032 + | ENST00000270233 |
| 4% | chr15 | 89456550 | 89456478 − | ENST00000558018;ENST00000268151;ENST00000268150;ENST00000566497;ENST00000542878;ENST00000558029 |
| 4% | chr9 | 5164265 | 5164179 − | ENST00000381641 |
| 4% | chr11 | 64088133 | 64808189 + | ENST00000265462 |
| 4% | chr19 | 18685867;<br>18685680;<br>18685913 | 18685937 + | ENST00000596304;ENST00000430157;ENST00000596273;ENST00000442744;ENST00000595683;ENST00000595158;ENST00000598780;ENST00000599551;ENST00000597451;ENST00000599595;ENST00000596272;ENST00000594527 |
| 4% | chr19 | 18685867;<br>18685680;<br>18685913 | 18685937 + | ENST00000596304;ENST00000430157;ENST00000596273;ENST00000442744;ENST00000595683;ENST00000595158;ENST00000598780;ENST00000599551;ENST00000597451;ENST00000599595;ENST00000596272;ENST00000594527 |
| 4% | chr19 | 18685867;<br>18685680;<br>18685913 | 18685937 + | ENST00000596304;ENST00000430157;ENST00000596273;ENST00000442744;ENST00000595683;ENST00000595158;ENST00000598780;ENST00000599551;ENST00000597451;ENST00000599595;ENST00000596272;ENST00000594527 |
| 4% | chr12 | 21445270 | 21445098 − | ENST00000307378;ENST00000452078;ENST00000458504;ENST00000537524;ENST00000390670 |
| 4% | chr12 | 21445270 | 21445098 − | ENST00000307378;ENST00000452078;ENST00000458504;ENST00000537524;ENST00000390670 |
| 4% | chr12 | 21445270 | 21445098 − | ENST00000307378;ENST00000452078;ENST00000458504;ENST00000537524;ENST00000390670 |
| 4% | chr7 | 116593595 | 116593745 + | ENST00000393446;ENST00000265437;ENST00000393451;ENST00000438863;ENST00000323984;ENST00000393449;ENST00000443979;ENST00000446490 |
| 4% | chr2 | 217364672 | 217364754 + | ENST00000491306;ENST00000600880;ENST00000446558;ENST00000456586;ENST00000598925;ENST00000427280;ENST00000441179 |
| 4% | chr2 | 217364672 | 217364754 + | ENST00000491306;ENST00000600880;ENST00000446558;ENST00000456586;ENST00000598925;ENST00000427280;ENST00000441179 |
| 4% | chr15 | 82726234 | 82726553 + | ENST00000300515 |
| 4% | chr19 | 39888097;<br>39888167 | 39888183 + | ENST00000315588;ENST00000594368;ENST00000599213;ENST00000596297 |
| 4% | chr19 | 39888097;<br>39888167 | 39888183 + | ENST00000315588;ENST00000594368;ENST00000599213;ENST00000596297 |
| 4% | chr19 | 39888097;<br>39888167 | 39888183 + | ENST00000315588;ENST00000594368;ENST00000599213;ENST00000596297 |
| 4% | chr19 | 39888097;<br>39888167 | 39888183 + | ENST00000315588;ENST00000594368;ENST00000599213;ENST00000596297 |
| 4% | chr1 | 54389620 | 54389577 − | ENST00000371378;ENST00000194214;ENST00000371377 |
| 4% | chr1 | 156721221 | 156721135 − | ENST00000357325;ENST00000537739 |
| 4% | chr19 | 58386594 | 58386524 − | ENST00000597348;ENST00000435989 |
| 4% | chr1 | 153701111 | 153701260 + | ENST00000318967;ENST00000435409 |
| 3% | chr19 | 45315735 | 45315805 + | ENST00000589651;ENST00000270233;ENST00000591520 |
| 3% | chr19 | 45315735 | 45315805 + | ENST00000589651;ENST00000270233;ENST00000591520 |
| 3% | chr5 | 23976106 | 23976159 + | ENST00000512559;ENST00000507936 |
| 3% | chr1 | 32696528 | 32696620 + | ENST00000373586 |
| 3% | chr12 | 52639196 | 52639416 + | ENST00000331817 |
| 3% | chr7 | 81964567 | 81964451 − | ENST00000356860;ENST00000356253;ENST00000423588 |
| 3% | chr7 | 75617128 | 75617036 − | ENST00000493111 |
| 3% | chr9 | 130213596 | 130213560 − | ENST00000361436;ENST00000536368 |
| 3% | chr1 | 32560385 | 32560572 + | ENST00000336294;ENST00000373634;ENST00000427288 |
| 3% | chr1 | 32560385 | 32560572 + | ENST00000336294;ENST00000373634;ENST00000427288 |
| 3% | chr1 | 32560385 | 32560572 + | ENST00000336294;ENST00000373634;ENST00000427288 |
| 3% | chr20 | 45644820;<br>45644887 | 45644936 + | ENST00000327619;ENST00000357410;ENST00000497062;ENST00000317304;ENST00000458636 |
| 3% | chr20 | 45644820;<br>45644887 | 45644936 + | ENST00000327619;ENST00000357410;ENST00000497062;ENST00000317304;ENST00000458636 |
| 3% | chr20 | 45644820;<br>45644887 | 45644936 + | ENST00000327619;ENST00000357410;ENST00000497062;ENST00000317304;ENST00000458636 |
| 3% | chr1 | 25891664 | 25891698 + | ENST00000374338 |
| 3% | chr4 | 17623210 | 17623322 + | ENST00000237380;ENST00000503945 |
| 3% | chr4 | 17623210 | 17623322 + | ENST00000237380;ENST00000503945 |
| 3% | chr19 | 17556093 | 17556008 − | ENST00000341130;ENST00000594663 |
| 3% | chr19 | 17556093 | 17556008 − | ENST00000341130;ENST00000594663 |
| 3% | chrX | 151996474 | 151996436 − | ENST00000370277 |
| 3% | chr19 | 11553201 | 11553248 + | ENST00000591462;ENST00000252455;ENST00000412601;ENST00000592741;ENST0 |

TABLE 43-continued

| | | | | |
|---|---|---|---|---|
| | | | | 0000587327;ENST00000589838 |
| 3% | chr8 | 144102731 | 144102850 + | ENST00000292494;ENST00000429120;ENST00000521699;ENST00000520531;ENST00000520466;ENST00000521003;ENST00000522971;ENST00000519611;ENST00000519546;ENST00000523847;ENST00000522024 |
| 3% | chr12 | 15087927 | 15087790 − | ENST00000266397 |
| 3% | chr20 | 36768056 | 36767968 − | ENST00000361475;ENST00000536701;ENST00000536724 |
| 3% | chr20 | 36768056 | 36767968 − | ENST00000361475;ENST00000536701;ENST00000536724 |
| 3% | chr20 | 36768056 | 36767968 − | ENST00000361475;ENST00000536701;ENST00000536724 |
| 3% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 3% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 3% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 3% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 3% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 3% | chr1 | 6531697 | 6531548 − | ENST00000400913;ENST00000340850;ENST00000377748;ENST00000377725;ENST00000377728;ENST00000377732;ENST00000400915;ENST00000377740;ENST00000535355;ENST00000377737;ENST00000537245;ENST00000544978 |
| 3% | chr8 | 27461912 | 27461808 | ENST00000316403;ENST00000546343;ENST00000560366;ENST00000405140;ENST00000523500;ENST00000522098 |
| 3% | chr8 | 27461912 | 27461808 | ENST00000316403;ENST00000546343;ENST00000560366;ENST00000405140;ENST00000523500;ENST00000522098 |
| 3% | chr8 | 27461912 | 27461808 | ENST00000316403;ENST00000546343;ENST00000560366;ENST00000405140;ENST00000523500;ENST00000522098 |
| 3% | chr8 | 27461912 | 27461808 | ENST00000316403;ENST00000546343;ENST00000560366;ENST00000405140;ENST00000523500;ENST00000522098 |
| 3% | chr7 | 91771800 | 91771777 − | ENST00000435873 |
| 3% | chr3 | 419501 | 419625 + | ENST00000256509;ENST00000397491 |
| 3% | chr3 | 419501 | 419625 + | ENST00000256509;ENST00000397491 |
| 3% | chr10 | 128594087 | 128594132 + | ENST00000280333 |
| 3% | chr20 | 45725724 | 45725807 + | ENST00000327619;ENST00000357410;ENST00000317304;ENST00000458636 |
| 3% | chr20 | 45725724 | 45725807 + | ENST00000327619;ENST00000357410;ENST00000317304;ENST00000458636 |
| 3% | chr19 | 45323962 | 453240553 + | ENST00000270233 |
| 3% | chr19 | 45322603 | 45322747 + | ENST00000589651;ENST00000270233 |
| 3% | chrX | 1505652 | 1505528 − | ENST00000381401 |
| 3% | chr7 | 135635430 | 135635347 − | ENST00000393085 |
| 3% | chr19 | 58427779 | 58427747 − | ENST00000312026;ENST00000595559 |
| 3% | chr7 | 74867341 | 74867229 − | ENST00000426327 |
| 3% | chr5 | 149782875 | 149782749 − | ENST00000518797;ENST00000009530 |
| 3% | chr5 | 149782875 | 149782749 − | ENST00000518797;ENST00000009530 |
| 2% | chr10 | 114207132 | 114207225 + | ENST00000432306;ENST00000393077 |
| 2% | chr11 | 76834734 | 76834775 + | ENST00000278559;ENST00000529629;ENST00000456580 |
| 2% | chr11 | 76834734 | 76834775 + | ENST00000278559;ENST00000529629;ENST00000456580 |
| 2% | chr14 | 75904624; 75904601 | 75904758 + | ENST00000419727;ENST00000559060;ENST00000437176;ENST00000435893;ENST00000267569 |
| 2% | chr14 | 75904624; 75904601 | 75904758 + | ENST00000419727;ENST00000559060;ENST00000437176;ENST00000435893;ENST00000267569 |
| 2% | chr7 | 150065992 | 150066030 + | ENST00000466559;ENST00000475514;ENST00000488943;ENST00000467980;ENST00000518514;ENST00000522266 |
| 2% | chr9 | 5689959 | 5690038 + | ENST00000251879;ENST00000414202;ENST00000381532;ENST00000418622;ENST00000449720;ENST00000545641 |
| 2% | chr9 | 5689959 | 5690038 + | ENST00000251879;ENST00000414202;ENST00000381532;ENST00000418622;ENST00000449720;ENST00000545641 |
| 2% | chr9 | 5689959 | 5690038 + | ENST00000251879;ENST00000414202;ENST00000381532;ENST00000418622;ENST00000449720;ENST00000545641 |
| 2% | chr19 | 45322839 | 45322864 + | ENST00000589651;ENST00000270233 |
| 2% | chr17 | 7214669 | 7214719 + | ENST00000336452;ENST00000336458;ENST00000576930;ENST00000572815;ENST00000573542;ENST00000419711;ENST00000571955;ENST00000573714;ENST00000416016 |
| 2% | chr17 | 7214669 | 7214719 + | ENST00000336452;ENST00000336458;ENST00000576930;ENST00000572815;ENST00000573542;ENST00000419711;ENST00000571955;ENST00000573714;ENST00000416016 |
| 2% | chr7 | 91509397 | 91509369 − | ENST00000351870;ENST00000442961 |
| 2% | chr17 | 80404572 | 80404499 − | ENST00000306645;ENST00000437807;ENST00000434650;ENST00000583617;ENST00000577436;ENST00000585064;ENST00000577732;ENST00000578919;ENST000005817 5080;ENST00000577888;ENST00000578913;ENST00000584408;ENST00000577696;ENST00000577471;ENST00000577834;ENST00000582545 |
| 2% | chr17 | 80404572 | 80404499 − | ENST00000306645;ENST00000437807;ENST00000434650;ENST00000583617;ENST00000577436;ENST00000585064;ENST00000577732;ENST00000578919;ENST000005817 5080;ENST00000577888;ENST00000578913;ENST00000584408;ENST00000577696;E |

TABLE 43-continued

| | | | | |
|---|---|---|---|---|
| 2% | chr17 | 80404572 | 80404499 − | NST00000577471;ENST00000577834;ENST00000582545 ENST00000306645;ENST00000437807;ENST00000434650;ENST00000583617;ENST00000577436;ENST00000585064;ENST00000577732;ENST00000578919; ENST000005817 5080;ENST00000577888;ENST00000578913;ENST00000584408;ENST00000577696;ENST00000577471;ENST00000577834;ENST00000582545 |
| 2% | chr4 | 25759228 | 25759156 − | ENST00000399878;ENST00000264868;ENST00000502949;ENST00000510448 |
| 2% | chr4 | 25759228 | 25759156 − | ENST00000399878;ENST00000264868;ENST00000502949;ENST00000510448 |
| 2% | chr4 | 25759228 | 25759156 − | ENST00000399878;ENST00000264868;ENST00000502949;ENST00000510448 |
| 2% | chr6 | 30459314 | 30459396 + | ENST00000376630 |
| 2% | chr4 | 107237705 | 107237751 + | ENST00000394701 |
| 2% | chr1 | 230203028 | 230203153 + | ENST00000366672 |
| 2% | chr8 | 117950483 | 117950806 + | ENST00000378279 |
| 2% | chr1 | 70820635 | 70820794 + | ENST00000359875;ENST00000370940;ENST00000531950;ENST00000432224 |
| 2% | chr5 | 70858101 | 70858347 + | ENST00000358731;ENST00000525844 |
| 2% | chr5 | 70858101 | 70858347 + | ENST00000358731;ENST00000525844 |
| 2% | chr19 | 2151333 | 2151238 − | ENST00000355272;ENST00000356926;ENST00000350812;ENST00000345016 |
| 2% | chr1 | 63955889 | 63955754 − | ENST00000371092;ENST00000271002;ENST00000489099;ENST00000283568 |
| 2% | chr1 | 63955889 | 63955754 − | ENST00000371092;ENST00000271002;ENST00000489099;ENST00000283568 |
| 2% | chr5 | 10748383 | 10748287 − | ENST00000230895;ENST00000432074 |
| 2% | chr6 | 110567463 | 110567335 − | ENST00000338882 |
| 2% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 2% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 2% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 2% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 2% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 2% | chr1 | 1255909 | 1255836 − | ENST00000435064;ENST00000540437;ENST00000450926;ENST00000545578;ENST00000528879;ENST00000434694;ENST00000526797;ENST00000527719;ENST00000530031;ENST00000534345;ENST00000498476 |
| 2% | chr6 | 51609340 | 51609183 − | ENST00000371117;ENST00000340994 |
| 2% | chr11 | 118888255 | 118888078 − | ENST00000527673 |
| 2% | chr8 | 109240620 | 109240496 − | ENST00000522352;ENST00000220849;ENST00000519030;ENST00000519627 |
| 2% | chr8 | 109240620 | 109240496 − | ENST00000522352;ENST00000220849;ENST00000519030;ENST00000519627 |
| 2% | chr8 | 109240620 | 109240496 − | ENST00000522352;ENST00000220849;ENST00000519030;ENST00000519627 |
| 2% | chr8 | 109240620 | 109240496 − | ENST00000522352;ENST00000220849;ENST00000519030;ENST00000519627 |
| 2% | chr17 | 27244467 | 27244303 − | ENST00000332830;ENST00000577226;ENST00000378879;ENST00000268756 |
| 2% | chr20 | 48184653 | 48184580 − | ENST00000244043 |
| 2% | chr8 | 11704677 | 11704561 − | ENST00000434271;ENST00000353047;ENST00000530640;ENST00000531089;ENST00000453527;ENST00000345125;ENST00000533455;ENST00000534510 |
| 2% | chr10 | 71990155 | 71990097 − | ENST00000373232;ENST00000373230;ENST00000608321 |
| 2% | chr9 | 7799734 | 7799461 − | ENST00000358227 |
| 2% | chr19 | 35505093 | 35505291 + | ENST00000599564;ENST00000317991;ENST00000504615;ENST00000411896 |
| 2% | chr19 | 35505093 | 35505291 + | ENST00000599564;ENST00000317991;ENST00000504615;ENST00000411896 |
| 2% | chr19 | 35505093 | 35505291 + | ENST00000599564;ENST00000317991;ENST00000504615;ENST00000411896 |
| 2% | chr19 | 35505093 | 35505291 + | ENST00000599564;ENST00000317991;ENST00000504615;ENST00000411896 |
| 2% | chr6 | 10759172 | 10759294 + | ENST00000481240;ENST00000467317 |
| 2% | chr6 | 10759172 | 10759294 + | ENST00000481240;ENST00000467317 |
| 2% | chr19 | 45322839 | 45322983 + | ENST00000589651;ENST00000270233 |
| 2% | chr2 | 219204752 | 219204864 + | ENST00000273077;ENST00000258362;ENST00000436005 |
| 2% | chr2 | 219204752 | 219204864 + | ENST00000273077;ENST00000258362;ENST00000436005 |
| 2% | chr2 | 219204752 | 219204864 + | ENST00000273077;ENST00000258362;ENST00000436005 |
| 2% | chr12 | 56503641 | 56503719 + | ENST00000303305;ENST00000552766 |
| 2% | chr22 | 47071365 | 47071449 + | ENST00000406902;ENST00000361034;ENST00000408031 |
| 2% | chr22 | 47071365 | 47071449 + | ENST00000406902;ENST00000361034;ENST00000408031 |
| 2% | chr3 | 32280465 | 32280611 + | ENST00000458535;ENST00000307526 |
| 2% | chr15 | 74219125 | 74220226 + | ENST00000566011;ENST00000261921 |
| 2% | chr6 | 30458914 | 30459146 + | ENST00000376630 |
| 2% | chr6 | 30458914 | 30459146 + | ENST00000376630 |
| 2% | chr16 | 2811562; 2817723 | 2818262 + | ENST00000301740;ENST00000572883 |
| 2% | chr16 | 2811562; 2817723 | 2818262 + | ENST00000301740;ENST00000572883 |
| 2% | chr11 | 113857547; 113857240 | 113857768 + | ENST00000504030;ENST00000355556;ENST00000375498;ENST00000506841;ENST00000535865;ENST00000299961 |
| 2% | chr11 | 113857547; 113857240 | 113857768 + | ENST00000504030;ENST00000355556;ENST00000375498;ENST00000506841;ENST00000535865;ENST00000299961 |
| 2% | chr11 | 113857547; 113857240 | 113857768 + | ENST00000504030;ENST00000355556;ENST00000375498;ENST00000506841;ENST00000535865;ENST00000299961 |
| 2% | chr11 | 113857547; | 113857768 + | ENST00000504030;ENST00000355556;ENST00000375498;ENST00000506841;ENST0 |

TABLE 43-continued

| | | | | |
|---|---|---|---|---|
| 2% | | 113857240 | | 0000535865;ENST00000299961 |
| 2% | chr11 | 113857547; 113857240 | 113857768 + | ENST00000504030;ENST00000355556;ENST00000375498;ENST00000506841;ENST0 0000535865;ENST00000299961 |
| 2% | chr11 | 113857547; 113857240 | 113857768 + | ENST00000504030;ENST00000355556;ENST00000375498;ENST00000506841;ENST0 0000535865;ENST00000299961 |
| 2% | chrX | 153284238; 153284089 | 153284050 − | ENST00000369980;ENST00000369974;ENST00000393682;ENST00000369973;ENST0 0000393687;ENST00000429936;ENST00000443220 |
| 2% | chrX | 153284238; 153284089 | 153284050 − | ENST00000369980;ENST00000369974;ENST00000393682;ENST00000369973;ENST0 0000393687;ENST00000429936;ENST00000443220 |
| 2% | chrX | 153284238; 153284089 | 153284050 − | ENST00000369980;ENST00000369974;ENST00000393682;ENST00000369973;ENST0 0000393687;ENST00000429936;ENST00000443220 |
| 2% | chr1 | 117712793 | 117712729 − | ENST00000359008;ENST00000328189;ENST00000369458 |
| 2% | chr1 | 117712793 | 117712729 − | ENST00000359008;ENST00000328189;ENST00000369458 |
| 2% | chr1 | 55341720 | 55341615 − | ENST00000371269;ENST00000535035 |
| 2% | chr1 | 55341720 | 55341615 − | ENST00000371269;ENST00000535035 |
| 2% | chr17 | 74622000 | 74621901 − | ENST00000156626 |
| 2% | chr1 | 55331119 | 55330976 − | ENST00000371269;ENST00000535035 |
| 2% | chr1 | 55331119 | 55330976 − | ENST00000371269;ENST00000535035 |
| 2% | chr19 | 58423461; 58423535; 58423557; 58423554 | 58423428 − | ENST00000602124;ENST00000594396;ENST00000312026;ENST00000595559;ENST0 0000597515;ENST00000598526;ENST00000598629;ENST00000599251 |
| 2% | chr19 | 58423461; 58423535; 58423557; 58423554 | 58423428 − | ENST00000602124;ENST00000594396;ENST00000312026;ENST00000595559;ENST0 0000597515;ENST00000598526;ENST00000598629;ENST00000599251 |
| 2% | chr19 | 58423461; 58423535; 58423557; 58423554 | 58423428 − | ENST00000602124;ENST00000594396;ENST00000312026;ENST00000595559;ENST0 0000597515;ENST00000598526;ENST00000598629;ENST00000599251 |
| 2% | chr19 | 58423461; 58423535; 58423557; 58423554 | 58423428 − | ENST00000602124;ENST00000594396;ENST00000312026;ENST00000595559;ENST0 0000597515;ENST00000598526;ENST00000598629;ENST00000599251 |
| 2% | chr19 | 40328483 | 40328341 − | ENST00000595545;ENST00000221801;ENST00000597224;ENST00000601274;ENST0 0000597634 |
| 2% | chr19 | 40328483 | 40328341 − | ENST00000595545;ENST00000221801;ENST00000597224;ENST00000601274;ENST0 0000597634 |
| 2% | chr19 | 40328483 | 40328341 − | ENST00000595545;ENST00000221801;ENST00000597224;ENST00000601274;ENST0 0000597634 |
| 2% | chr19 | 40328483 | 40328341 − | ENST00000595545;ENST00000221801;ENST00000597224;ENST00000601274;ENST0 0000597634 |
| 2% | chr19 | 40328483 | 40328341 − | ENST00000595545;ENST00000221801;ENST00000597224;ENST00000601274;ENST0 0000597634 |
| 2% | chr8 | 120220779 | 120220844 + | ENST00000276681 |
| 2% | chr19 | 45317409 | 45317445 + | ENST00000589651;ENST00000270233;ENST00000591520 |
| 2% | chr19 | 45317409 | 45317445 + | ENST00000589651;ENST00000270233;ENST00000591520 |
| 2% | chr9 | 80932592 | 80932720 + | ENST00000347159;ENST00000376588 |
| 2% | chr11 | 64087206 | 64087232 + | ENST00000265462;ENST00000352435 |
| 2% | chr10 | 116020945 | 116021054 + | ENST00000603594;ENST00000392982 |
| 2% | chr5 | 175723254 | 175723323 + | ENST00000341199;ENST00000430704;ENST00000443967;ENST00000429602 |
| 2% | chr5 | 175723254 | 175723323 + | ENST00000341199;ENST00000430704;ENST00000443967;ENST00000429602 |
| 2% | chr5 | 175723254 | 175723323 + | ENST00000341199;ENST00000430704;ENST00000443967;ENST00000429602 |
| 2% | chr19 | 45322603 | 45322630 + | ENST00000589651;ENST00000270233 |
| 2% | chr15 | 81436003 | 81436161 + | ENST00000286732 |
| 2% | chr11 | 73075497 | 73075645 + | ENST00000263674 |
| 2% | chr19 | 16381600 | 19381719 + | ENST00000399336;ENST00000263012;ENST00000538468 |
| 2% | chr16 | 16381600 | 16381719 + | ENST00000399336;ENST00000263012;ENST00000538468 |
| 2% | chr12 | 113403549; 113403702 | 113403834 + | ENST00000228928;ENST00000546973 |
| 2% | chr12 | 113403549; 113403702 | 113403834 + | ENST00000228928;ENST00000546973 |
| 2% | chr12 | 53691634 | 53691705 + | ENST00000551018;ENST00000351500;ENST00000334478;ENST00000549759 |
| 2% | chr12 | 53691634 | 53691705 + | ENST00000551018;ENST00000351500;ENST00000334478;ENST00000549759 |
| 2% | chr12 | 53691634 | 53691705 + | ENST00000551018;ENST00000351500;ENST00000334478;ENST00000549759 |
| 2% | chr14 | 75904624; 75904601 | 75904716 + | ENST00000419727;ENST00000559060;ENST00000437176;ENST00000435893;ENST0 0000267569 |
| 2% | chr14 | 75904624; 75904601 | 75904716 + | ENST00000419727;ENST00000559060;ENST00000437176;ENST00000435893;ENST0 0000267569 |
| 2% | chr9 | 5689959 | 5690038 + | ENST00000251879;ENST00000414202;ENST00000381532;ENST00000418622;ENST0 0000449720;ENST00000545641 |
| 2% | chr9 | 5689959 | 5690038 + | ENST00000251879;ENST00000414202;ENST00000381532;ENST00000418622;ENST0 0000449720;ENST00000545641 |
| 2% | chr9 | 5689959 | 5690038 + | ENST00000251879;ENST00000414202;ENST00000381532;ENST00000418622;ENST0 0000449720;ENST00000545641 |
| 2% | chr9 | 100774703 | 100774754 + | ENST00000339399 |
| 2% | chr4 | 56230241 | 56230438 + | ENST00000264228 |
| 2% | chr11 | 16769644 | 16769704 + | ENST00000228136;ENST00000524439;ENST00000422258;ENST00000528634 |
| 2% | chr11 | 16769644 | 16769704 + | ENST00000228136;ENST00000524439;ENST00000422258;ENST00000528634 |
| 2% | chr11 | 16769644 | 16769704 + | ENST00000228136;ENST00000524439;ENST00000422258;ENST00000528634 |

TABLE 43-continued

| | | | | |
|---|---|---|---|---|
| 2% | chr16 | 1735440; 1735444; 1735501 | 1735588 + | ENST00000248098;ENST00000562684;ENST00000561516;ENST00000382711;ENST00000566742;ENST00000569765;ENST00000566691;ENST00000382710;ENST00000565851;ENST00000562569 |
| 2% | chr16 | 1735440; 1735444; 1735501 | 1735588 + | ENST00000248098;ENST00000562684;ENST00000561516;ENST00000382711;ENST00000566742;ENST00000569765;ENST00000566691;ENST00000382710;ENST00000565851;ENST00000562569 |
| 2% | chr16 | 1735440; 1735444; 1735501 | 1735588 + | ENST00000248098;ENST00000562684;ENST00000561516;ENST00000382711;ENST00000566742;ENST00000569765;ENST00000566691;ENST00000382710;ENST00000565851;ENST00000562569 |
| 2% | chr16 | 1735440; 1735444; 1735501 | 1735588 + | ENST00000248098;ENST00000562684;ENST00000561516;ENST00000382711;ENST00000566742;ENST00000569765;ENST00000566691;ENST00000382710;ENST00000565851;ENST00000562569 |
| 2% | chr16 | 1735440; 1735444; 1735501 | 1735588 + | ENST00000248098;ENST00000562684;ENST00000561516;ENST00000382711;ENST00000566742;ENST00000569765;ENST00000566691;ENST00000382710;ENST00000565851;ENST00000562569 |
| 2% | chr2 | 160176929 | 160176785 − | ENST00000343439;ENST00000355831;ENST00000392782;ENST00000392783 |
| 2% | chr2 | 160176929 | 160176785 − | ENST00000343439;ENST00000355831;ENST00000392782;ENST00000392783 |
| 2% | chr2 | 160176929 | 160176785 − | ENST00000343439;ENST00000355831;ENST00000392782;ENST00000392783 |
| 2% | chr2 | 160176929 | 160176785 − | ENST00000343439;ENST00000355831;ENST00000392782;ENST00000392783 |
| 2% | chr22 | 39711560 | 39711495 − | ENST00000401609;ENST00000216146;ENST00000402527;ENST00000453303;ENST00000427905 |
| 2% | chr22 | 39711560 | 39711495 − | ENST00000401609;ENST00000216146;ENST00000402527;ENST00000453303;ENST00000427905 |
| 2% | chr22 | 39711560 | 39711495 − | ENST00000401609;ENST00000216146;ENST00000402527;ENST00000453303;ENST00000427905 |
| 2% | chr22 | 39711560 | 39711495 − | ENST00000401609;ENST00000216146;ENST00000402527;ENST00000453303;ENST00000427905 |
| 2% | chr12 | 21427520 | 21427403 − | ENST00000307378;ENST00000452078;ENST00000458504;ENST00000537524 |
| 2% | chr12 | 21427520 | 21427403 − | ENST00000307378;ENST00000452078;ENST00000458504;ENST00000537524 |
| 2% | chr1 | 55352792 | 55352562 − | ENST00000371269 |
| 2% | chr16 | 2835172 | 2835003 − | ENST00000293851;ENST00000570702;ENST00000571674 |
| 2% | chr16 | 2835172 | 2835003 − | ENST00000293851;ENST00000570702;ENST00000571674 |
| 2% | chr11 | 77784187; 77784118 | 77784044 − | ENST00000530054;ENST00000281031;ENST00000525085;ENST00000528164 |
| 2% | chr11 | 77784187; 77784118 | 77784044 − | ENST00000530054;ENST00000281031;ENST00000525085;ENST00000528164 |
| 2% | chr14 | 106235896 | 106235574 − | ENST00000390551 |
| 2% | chr6 | 75953546; 75953450; 75953503 | 75953433 − | ENST00000370081;ENST00000230459;ENST00000370089;ENST00000459637;ENST00000509698;ENST00000460985;ENST00000472311;ENST00000377978 |
| 2% | chr6 | 75953546; 75953450; 75953503 | 75953433 − | ENST00000370081;ENST00000230459;ENST00000370089;ENST00000459637;ENST00000509698;ENST00000460985;ENST00000472311;ENST00000377978 |
| 2% | chr6 | 75953546; 75953450; 75953503 | 75953433 − | ENST00000370081;ENST00000230459;ENST00000370089;ENST00000459637;ENST00000509698;ENST00000460985;ENST00000472311;ENST00000377978 |
| 2% | chr5 | 79410474 | 79410337 − | ENST00000509193 |
| 2% | chr1 | 20979464 | 20979344 − | ENST00000602624;ENST00000375048;ENST00000415136 |
| 2% | chr1 | 20979464 | 20979344 − | ENST00000602624;ENST00000375048;ENST00000415136 |
| 2% | chr1 | 20979464 | 20979344 − | ENST00000602624;ENST00000375048;ENST00000415136 |
| 2% | chr1 | 47101642 | 47101569 − | ENST00000576409;ENST00000371937;ENST00000574428;ENST00000492233;ENST00000526821;ENST00000542495;ENST00000329231;ENST00000534216;ENST00000532925 |
| 2% | chr1 | 47101642 | 47101569 − | ENST00000576409;ENST00000371937;ENST00000574428;ENST00000492233;ENST00000526821;ENST00000542495;ENST00000329231;ENST00000534216;ENST00000532925 |
| 2% | chr1 | 47101642 | 47101569 − | ENST00000576409;ENST00000371937;ENST00000574428;ENST00000492233;ENST00000526821;ENST00000542495;ENST00000329231;ENST00000534216;ENST00000532925 |
| 2% | chr1 | 47101642 | 47101569 − | ENST00000576409;ENST00000371937;ENST00000574428;ENST00000492233;ENST00000526821;ENST00000542495;ENST00000329231;ENST00000534216;ENST00000532925 |
| 2% | chr1 | 47101642 | 47101569 − | ENST00000576409;ENST00000371937;ENST00000574428;ENST00000492233;ENST00000526821;ENST00000542495;ENST00000329231;ENST00000534216;ENST00000532925 |
| 2% | chr1 | 47101642 | 47101569 − | ENST00000576409;ENST00000371937;ENST00000574428;ENST00000492233;ENST00000526821;ENST00000542495;ENST00000329231;ENST00000534216;ENST00000532925 |
| 2% | chr1 | 47101642 | 47101569 − | ENST00000576409;ENST00000371937;ENST00000574428;ENST00000492233;ENST00000526821;ENST00000542495;ENST00000329231;ENST00000534216;ENST00000532925 |
| 2% | chr1 | 47101642 | 47101569 − | ENST00000576409;ENST00000371937;ENST00000574428;ENST00000492233;ENST00000526821;ENST00000542495;ENST00000329231;ENST00000534216;ENST00000532925 |
| 2% | chr1 | 47101642 | 47101569 − | ENST00000576409;ENST00000371937;ENST00000574428;ENST00000492233;ENST00000526821;ENST00000542495;ENST00000329231;ENST00000534216;ENST00000532925 |
| 2% | chr20 | 30060816 | 30060759 − | ENST00000317676 |
| 2% | chr3 | 156262228 | 156262097 − | ENST00000265044;ENST00000467789;ENST00000476217;ENST00000463503;ENST00000496050 |

TABLE 43-continued

| | | | | |
|---|---|---|---|---|
| 2% | chr3 | 156262228 | 156262097 − | ENST00000265044;ENST00000467789;ENST00000476217;ENST00000463503;ENST00000496050 |
| 2% | chr3 | 156262228 | 156262097 − | ENST00000265044;ENST00000467789;ENST00000476217;ENST00000463503;ENST00000496050 |
| 2% | chr19 | 8962031 | 8961952 − | ENST00000397910;ENST00000599436;ENST00000380951 |
| 2% | chr19 | 8962031 | 8961952 − | ENST00000397910;ENST00000599436;ENST00000380951 |
| 2% | chr19 | 8962031 | 8961952 − | ENST00000397910;ENST00000599436;ENST00000380951 |
| 2% | chr10 | 127483547 | 127483449 − | ENST00000368797;ENST00000368786 |
| 1% | chr19 | 40478053 | 40478151 + | ENST00000157812;ENST00000455878 |
| 1% | chr18 | 12720509 | 12720682 + | ENST00000585331;ENST00000586445;ENST00000317615;ENST00000590217 |
| 1% | chr18 | 12720509 | 12720682 + | ENST00000585331;ENST00000586445;ENST00000317615;ENST00000590217 |
| 1% | chr18 | 12720509 | 12720682 + | ENST00000585331;ENST00000586445;ENST00000317615;ENST00000590217 |
| 1% | chr19 | 45323962 | 45324079 + | ENST00000270233 |
| 1% | chr3 | 50153339 | 50153413 + | ENST00000347869 |
| 1% | chrX | 49358721 | 49358846 + | ENST00000362097 |
| 1% | chr3 | 50153339 | 50153413 + | ENST00000347869 |
| 1% | chr22 | 35819207 | 35819334 + | ENST00000216122;ENST00000382011 |
| 1% | chr22 | 35819207 | 35819334 + | ENST00000216122;ENST00000382011 |
| 1% | chr1 | 82372702 | 82372915 + | ENST00000370721;ENST00000370723;ENST00000370725;ENST00000370727;ENST00000370728;ENST00000370730;ENST00000359929;ENST00000319517;ENST00000370713;ENST00000370715;ENST00000271029;ENST00000335786;ENST00000370717;ENST00000394879 |
| 1% | chr2 | 130940200 | 130940348 + | ENST00000425361;ENST00000457492;ENST00000281871;ENST00000409255 |
| 1% | chr2 | 130940200 | 130940348 + | ENST00000425361;ENST00000457492;ENST00000281871;ENST00000409255 |
| 1% | chr2 | 130940200 | 130940348 + | ENST00000425361;ENST00000457492;ENST00000281871;ENST00000409255 |
| 1% | chr22 | 24200187 | 24200216 + | ENST00000436643;ENST00000316185 |
| 1% | chr19 | 45316507 | 45316603 + | ENST00000589651;ENST00000270233;ENST00000591520 |
| 1% | chr19 | 45316507 | 45316603 + | ENST00000589651;ENST00000270233;ENST00000591520 |
| 1% | chr3 | 23960687; 23960694 | 23960737 + | ENST00000307839;ENST00000422218;ENST00000434031;ENST00000413699;ENST00000456530;ENST00000412097;ENST00000415719;ENST00000435882;ENST00000354811 |
| 1% | chr3 | 23960687; 23960694 | 23960737 + | ENST00000307839;ENST00000422218;ENST00000434031;ENST00000413699;ENST00000456530;ENST00000412097;ENST00000415719;ENST00000435882;ENST00000354811 |
| 1% | chr22 | 24236959 | 24237131 + | ENST00000433835;ENST00000215754 |
| 1% | chr22 | 24236959 | 24237131 + | ENST00000433835;ENST00000215754 |
| 1% | chr1 | 25883644 | 25883758 + | ENST00000374338 |
| 1% | chr10 | 81111243 | 81111329 + | ENST00000472580;ENST00000394579;ENST00000225174;ENST00000448165 |
| 1% | chr10 | 81111243 | 81111329 + | ENST00000472580;ENST00000394579;ENST00000225174;ENST00000448165 |
| 1% | chr11 | 64088479 | 64088540 + | ENST00000265462;ENST00000352435;ENST00000347941 |
| 1% | chr11 | 64088479 | 64088540 + | ENST00000265462;ENST00000352435;ENST00000347941 |
| 1% | chr11 | 64088479 | 64088540 + | ENST00000265462;ENST00000352435;ENST00000347941 |
| 1% | chr11 | 60701014 | 60701216 + | ENST00000453848;ENST00000005286;ENST00000536409 |
| 1% | chr11 | 60701014 | 60701216 + | ENST00000453848;ENST00000005286;ENST00000536409 |
| 1% | chr11 | 60701014 | 60701216 + | ENST00000453848;ENST00000005286;ENST00000536409 |
| 1% | chr6 | 21594766 | 21595236 + | ENST00000543472 |
| 1% | chr16 | 30783410 | 30783511 + | ENST00000324685;ENST00000402121;ENST00000563683;ENST00000357890 |
| 1% | chr16 | 30783410 | 30783511 + | ENST00000324685;ENST00000402121;ENST00000563683;ENST00000357890 |
| 1% | chr16 | 30783410 | 30783511 + | ENST00000324685;ENST00000402121;ENST00000563683;ENST00000357890 |
| 1% | chr16 | 30783410 | 30783511 + | ENST00000324685;ENST00000402121;ENST00000563683;ENST00000357890 |
| 1% | chr19 | 45316507 | 45316581 + | ENST00000589651;ENST00000270233;ENST00000591520 |
| 1% | chr19 | 45316507 | 45316581 + | ENST00000589651;ENST00000270233;ENST00000591520 |
| 1% | chr8 | 146279404 | 146279527 + | ENST00000331434 |
| 1% | chrX | 134852702 | 134852722 + | ENST00000370741;ENST00000497301;ENST00000482795 |
| 1% | chr6 | 30458017 | 30458292 + | ENST00000376630 |
| 1% | chr19 | 17628519 | 17628659 + | ENST00000252603 |
| 1% | chr7 | 71142196 | 71142291 + | ENST00000333538 |
| 1% | chr20 | 52831839 | 52831979 + | ENST00000371419;ENST00000441080 |
| 1% | chrX | 49368271 | 49368396 + | ENST00000381709;ENST00000381700 |
| 1% | chr22 | 36661197; 36661246 | 36661833 + | ENST00000397278;ENST00000422706;ENST00000426053;ENST00000319136;ENST00000347595;ENST00000397279 |
| 1% | chr22 | 36661197; 36661246 | 36661833 + | ENST00000397278;ENST00000422706;ENST00000426053;ENST00000319136;ENST00000347595;ENST00000397279 |
| 1% | chr22 | 36661197; 36661246 | 36661833 + | ENST00000397278;ENST00000422706;ENST00000426053;ENST00000319136;ENST00000347595;ENST00000397279 |
| 1% | chr22 | 36661197; 36661246 | 36661833 + | ENST00000397278;ENST00000422706;ENST00000426053;ENST00000319136;ENST00000347595;ENST00000397279 |
| 1% | chr14 | 24615449 | 24615417 − | ENST00000216802;ENST00000558273;ENST00000560370 |
| 1% | chr12 | 71509738 | 71509630 − | ENST00000549357 |
| 1% | chrX | 134950246 | 134950226 − | ENST00000420087;ENST00000463085;ENST00000370724;ENST00000491480 |
| 1% | chr2 | 71216946 | 71216879 − | ENST00000606025;ENST00000272438 |
| 1% | chrX | 153277368 | 153277177 − | ENST00000455690 |
| 1% | chr19 | 54666021 | 54665838 − | ENST00000301187;ENST00000416963;ENST00000376591 |
| 1% | chr19 | 54666021 | 54665838 − | ENST00000301187;ENST00000416963;ENST00000376591 |
| 1% | chr19 | 54666021 | 54665838 − | ENST00000301187;ENST00000416963;ENST00000376591 |
| 1% | chr6 | 65098733 | 65098583 − | ENST00000503581;ENST00000370621;ENST00000370616 |
| 1% | chr7 | 150939064 | 150939023 − | ENST00000262188;ENST00000392811;ENST00000356800 |
| 1% | chr7 | 150939064 | 150939023 − | ENST00000262188;ENST00000392811;ENST00000356800 |
| 1% | chr1 | 152006276 | 152006124 − | ENST00000271638 |
| 1% | chrX | 118923974 | 118923871 − | ENST00000361575 |

TABLE 43-continued

| | | | | | |
|---|---|---|---|---|---|
| 1% | chr19 | 54687563; 54687517 | 54687404 | − | ENST00000431666;ENST00000338624;ENST00000245615;ENST00000449249;ENST00000391754;ENST00000495279;ENST00000414665;ENST00000453320 |
| 1% | chr19 | 54687563; 54687517 | 54687404 | − | ENST00000431666;ENST00000338624;ENST00000245615;ENST00000449249;ENST00000391754;ENST00000495279;ENST00000414665;ENST00000453320 |
| 1% | chr19 | 54687563; 54687517 | 54687404 | − | ENST00000431666;ENST00000338624;ENST00000245615;ENST00000449249;ENST00000391754;ENST00000495279;ENST00000414665;ENST00000453320 |
| 1% | chr19 | 54687563; 54687517 | 54687404 | − | ENST00000431666;ENST00000338624;ENST00000245615;ENST00000449249;ENST00000391754;ENST00000495279;ENST00000414665;ENST00000453320 |
| 1% | chr12 | 8808043 | 8808011 | − | ENST00000535411;ENST00000359478;ENST00000433590;ENST00000396549;ENST00000543369;ENST00000544211;ENST00000535336;ENST00000540087;ENST00000537009;ENST00000544889 |
| 1% | chr12 | 8808043 | 8808011 | − | ENST00000535411;ENST00000359478;ENST00000433590;ENST00000396549;ENST00000543369;ENST00000544211;ENST00000535336;ENST00000540087;ENST00000537009;ENST00000544889 |
| 1% | chr12 | 8808043 | 8808011 | − | ENST00000535411;ENST00000359478;ENST00000433590;ENST00000396549;ENST00000543369;ENST00000544211;ENST00000535336;ENST00000540087;ENST00000537009;ENST00000544889 |
| 1% | chr9 | 130678698 | 130678687 | − | ENST00000335791 |
| 1% | chr11 | 75917451 | 75917369 | − | ENST00000322563 |
| 1% | chr12 | 56744974 | 56744882 | − | ENST00000314128;ENST00000557235;ENST00000418572 |
| 1% | chr12 | 56744974 | 56744882 | − | ENST00000314128;ENST00000557235;ENST00000418572 |
| 1% | chrX | 134967496 | 134967476 | − | ENST00000491002;ENST00000448053;ENST00000472834 |
| 1% | chr19 | 49335016 | 49334925 | − | ENST00000263278;ENST00000595764 |
| 1% | chr19 | 49335016 | 49334925 | − | ENST00000263278;ENST00000595764 |
| 1% | chr1 | 85279854 | 85279558 | − | ENST00000440886;ENST00000370611 |
| 1% | chr20 | 55803477 | 55803285 | − | ENST00000395863;ENST00000395864;ENST00000450594;ENST00000433911 |
| 1% | chr20 | 55803477 | 55803285 | − | ENST00000395863;ENST00000395864;ENST00000450594;ENST00000433911 |
| 1% | chr19 | 6422447 | 6422351 | − | ENST00000398148;ENST00000599395 |
| 1% | chr19 | 6422447 | 6422351 | − | ENST00000398148;ENST00000599395 |
| 1% | chr4 | 980639 | 980594 | − | ENST00000510286 |
| 1% | chr8 | 144919471 | 144919421 | − | ENST00000442628;ENST00000327830 |
| 1% | chr8 | 144919471 | 144919421 | − | ENST00000442628;ENST00000327830 |
| 1% | chr15 | 40849571; 40849518 | 40849415 | − | ENST00000560305;ENST00000559153;ENST00000561011;ENST00000559291;ENST00000559911;ENST00000558113;ENST00000358005;ENST00000416810;ENST00000558750;ENST00000558918;ENST00000559103;ENST00000558871 |
| 1% | chr15 | 40849571; 40849518 | 40849415 | − | ENST00000560305;ENST00000559153;ENST00000561011;ENST00000559291;ENST00000559911;ENST00000558113;ENST00000358005;ENST00000416810;ENST00000558750;ENST00000558918;ENST00000559103;ENST00000558871 |
| 1% | chr15 | 40849571; 40849518 | 40849415 | − | ENST00000560305;ENST00000559153;ENST00000561011;ENST00000559291;ENST00000559911;ENST00000558113;ENST00000358005;ENST00000416810;ENST00000558750;ENST00000558918;ENST00000559103;ENST00000558871 |
| 1% | chrX | 134967496 | 134967476 | − | ENST00000491002;ENST00000448053;ENST00000472834 |
| 7 | 8 | | 9 | 10 | 11 |
| | chr20 | 53111339 | 53111426 | + | TAF |
| | chr19 | 45324388 | 45324391 | + | TSF |
| | chr1 | 32696861 | 32697110 | + | TAF |
| | chr6 | 74195910 | 74195882 | − | TSF |
| | chr20 | 47761186 | 47760181 | − | TAF |
| | chr20 | 47761186 | 47760181 | − | TAF |
| | chr20 | 47761186 | 47760181 | − | TAF |
| | chr6 | 10829240 | 10829256 | + | TAF |
| | chr6 | 10829240 | 10829256 | + | TAF |
| | chr12 | 113623998 | 113624117 | + | TSF |
| | chr12 | 124767376 | 124767267 | − | TAF |
| | chr12 | 124767376 | 124767267 | − | TAF |
| | chr12 | 124767376 | 124767267 | − | TAF |
| | chr12 | 124767376 | 124767267 | − | TAF |
| | chr12 | 124767376 | 124767267 | − | TAF |
| | chr12 | 124767376 | 124767267 | − | TAF |
| | chr12 | 124767376 | 124767267 | − | TAF |
| | chr1 | 224551811 | 224551931 | + | TAF |
| | chr14 | 31907346 | 31905965 | − | TSF |
| | chr8 | 144113283 | 144113885 | + | TAF |
| | chr12 | 6364053 | 5462746 | − | TAF |
| | chr12 | 6364053 | 5462746 | − | TAF |
| | chr12 | 6364053 | 5462746 | − | TAF |
| | chr12 | 6364053 | 5462746 | − | TAF |
| | chr19 | 45324388 | 45324391 | + | TSF |
| | chr20 | 43880953 | 43880903 | − | TAF |
| | chr11 | 118861152 | 118861045 | − | TSF |
| | chr2 | 26630464 | 26631004 | + | TAF |
| | chr9 | 91198914 | 91198934 | + | TAF |
| | chr19 | 45316049 | 45316236 | + | TAF |
| | chr19 | 45316049 | 45316236 | + | TAF |
| | chr19 | 35995923 | 35995655 | − | TAF |
| | chr19 | 35995923 | 35995655 | − | TAF |
| | chr19 | 35995923 | 35995655 | − | TAF |
| | chr19 | 35995923 | 35995655 | − | TAF |

TABLE 43-continued

| | | | |
|---|---|---|---|
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr19 | 35995923 | 35995655 − | TAF |
| chr11 | 18534149 | 18533862 − | TAF |
| chr15 | 67000837 | 67001281 + | TAF |
| chr10 | 120901885 | 120901741 − | TAF |
| chr10 | 120901885 | 120901741 − | TAF |
| chr7 | 91767155 | 91766808 − | TSF |
| chr19 | 13872305 | 13872412 + | TAF |
| chr19 | 13872305 | 13872412 + | TAF |
| chr19 | 13872305 | 13872412 + | TAF |
| chr19 | 13872305 | 13872412 + | TAF |
| chr15 | 82808796 | 82808882 + | TAF |
| chr15 | 83193141 | 83193227 + | TSF |
| chr8 | 27555709 | 27555926 + | TAF |
| chr19 | 51445160 | 51445047 − | TAF |
| chr9 | 133421349 | 133421406 + | TSF |
| chr19 | 16213047 | 16213167 + | TSF |
| chr19 | 16213047 | 16213167 + | TSF |
| chr19 | 16213047 | 16213167 + | TSF |
| chr19 | 16213047 | 16213167 + | TSF |
| chr1 | 33270534 | 33269340 − | TAF |
| chr19 | 46499503 | 46499685 + | TSF |
| chr6 | 34385704 | 34385695 − | TSF |
| chr4 | 17629629 | 17629638 + | TAF |
| chr4 | 17629629 | 17629638 + | TAF |
| chr12 | 71504233 | 71503634 − | TAF |
| chr7 | 27581374 | 27579272 − | TAF |
| chr7 | 27581374 | 27579272 − | TAF |
| chr9 | 91198917 | 91198934 + | TAF |
| chr11 | 66010931 | 66010981 + | TSF |
| chr11 | 66010931 | 66010981 + | TSF |
| chr11 | 66010931 | 66010981 + | TSF |
| chr11 | 66010931 | 66010981 + | TSF |
| chr2 | 132245283 | 132245193 − | TAF |
| chr2 | 132245283 | 132245193 − | TAF |
| chr6 | 42973204 | 42973029 − | TSF |
| chr19 | 35514601 | 35514631 + | TAF |
| chr19 | 35514601 | 35514631 + | TAF |
| chr19 | 35514601 | 35514631 + | TAF |
| chr19 | 35514601 | 35514631 + | TAF |
| chr6 | 35351354 | 35351915 + | TAF |
| chr18 | 33773430 | 33773774 + | TAF |
| chr6 | 34212756 | 34212817 + | TSF |
| chr6 | 34212756 | 34212817 + | TSF |
| chr8 | 42925245 | 42925476 + | TSF |
| chr8 | 42925245 | 42925476 + | TSF |
| chr8 | 42925245 | 42925476 + | TSF |
| chr8 | 42925245 | 42925476 + | TSF |
| chr8 | 42925245 | 42925476 + | TSF |
| chr1 | 153663274 | 153663445 + | TSF |
| chr1 | 55317584 | 55317525 − | TSF |
| chr1 | 55317584 | 55317525 − | TSF |
| chr1 | 55317584 | 55317525 − | TSF |
| chr2 | 242276200 | 242276228 + | TAF |
| chr2 | 242276200 | 242276228 + | TAF |
| chr2 | 242276200 | 242276228 + | TAF |
| chr2 | 242276200 | 242276228 + | TAF |
| chr9 | 15492223 | 15492056 − | TAF |
| chr12 | 57059571 | 57059432 − | TAF |
| chr12 | 57059571 | 57059432 − | TAF |
| chr12 | 57059571 | 57059432 − | TAF |
| chr12 | 57059571 | 57059432 − | TAF |
| chr19 | 14060442 | 14060422 − | TAF |
| chr19 | 45324388 | 45324391 + | TSF |
| chr19 | 45324388 | 45324391 + | TSF |
| chr1 | 225157336 | 225158402 + | TSF |
| chr1 | 225157336 | 225158402 + | TSF |

TABLE 43-continued

| | | | |
|---|---|---|---|
| chr1 | 11805987 | 11806151 + | TSF |
| chr1 | 11805987 | 11806151 + | TSF |
| chr19 | 3855694 | 3855445 − | TSF |
| chr19 | 3855694 | 3855445 − | TSF |
| chr1 | 992542 | 992691 + | TSF |
| chr1 | 992542 | 992691 + | TSF |
| chr19 | 494980 | 494981 + | TSF |
| chr5 | 54993040 | 54992544 − | TSF |
| chr6 | 10829243 | 10829256 + | TAF |
| chr6 | 10829243 | 10829256 + | TAF |
| chr6 | 10829243 | 10829256 + | TAF |
| chr6 | 42948581 | 42948550 − | TAF |
| chr1 | 151245243 | 151245553 + | TAF |
| chr1 | 151245243 | 151245553 + | TAF |
| chr1 | 151245243 | 151245553 + | TAF |
| chr1 | 151245243 | 151245553 + | TAF |
| chr17 | 7215641 | 7215651 + | TSF |
| chr17 | 7215641 | 7215651 + | TSF |
| chr2 | 133381838 | 133381614 − | TSF |
| chr2 | 133381838 | 133381614 − | TSF |
| chr12 | 71938771 | 71938901 + | TSF |
| chr14 | 66099743 | 66101298 + | TSF |
| chr14 | 66099743 | 66101298 + | TSF |
| chr14 | 66099743 | 66101298 + | TSF |
| chr1 | 155036918 | 155037085 + | TSF |
| chr | 72187682 | 72187899 + | TSF |
| chr | 72187682 | 72187899 + | TSF |
| chr12 | 102548605 | 102548938 + | TSF |
| chr12 | 102548605 | 102548938 + | TSF |
| chr12 | 102548605 | 102548938 + | TSF |
| chr12 | 102548605 | 102548938 + | TSF |
| chr12 | 102548605 | 102548938 + | TSF |
| chr19 | 15289244 | 15289201 − | TSF |
| chr19 | 15289244 | 15289201 − | TSF |
| chr2 | 110672249 | 110672374 + | TSF |
| chr22 | 36662881 | 36662970 + | TSF |
| chr22 | 36662881 | 36662970 + | TSF |
| chr22 | 36662881 | 36662970 + | TSF |
| chr22 | 36662881 | 36662970 + | TSF |
| chr19 | 45324358 | 45324391 + | TSF |
| chr2 | 111214412 | 111214287 − | TSF |
| chr16 | 2875971 | 2876154 + | TSF |
| chr16 | 2875971 | 2876154 + | TSF |
| chr16 | 2875971 | 2876154 + | TSF |
| chr19 | 45323867 | 453239109 + | TSF |
| chr19 | 45324372 | 45324391 + | TSF |
| chr16 | 2823822 | 2823809 − | TSF |
| chr16 | 2823822 | 2823809 − | TSF |
| chr16 | 2823822 | 2823809 − | TSF |
| chr3 | 48702393 | 48702198 − | TSF |
| chr3 | 48702393 | 48702198 − | TSF |
| chr3 | 48702393 | 48702198 − | TSF |
| chr19 | 45324388 | 45324391 + | TSF |
| chr7 | 76648226 | 76648393 + | TSF |
| chr7 | 76648226 | 76648393 + | TSF |
| chr7 | 76648226 | 76648393 + | TSF |
| chr2 | 217393993 | 217394327 + | TSF |
| chr2 | 217393993 | 217394327 + | TSF |
| chr17 | 7215648 | 7215651 + | TSF |
| chr17 | 7215648 | 7215651 + | TSF |
| chr7 | 76676146 | 76676313 + | TSF |
| chr7 | 76676146 | 76676313 + | TSF |
| chr7 | 76676146 | 76676313 + | TSF |
| chr7 | 76676146 | 76676313 + | TSF |
| chr7 | 76676146 | 76676313 + | TSF |
| chr20 | 29652086 | 29652324 + | TSF |
| chr7 | 76648226 | 76648393 + | TSF |
| chr7 | 76648226 | 76648393 + | TSF |
| chr7 | 76648226 | 76648393 + | TSF |
| chr1 | 183470266 | 183470283 + | TSF |
| chr11 | 101937956 | 101938097 + | TSF |
| chr11 | 101937956 | 101938097 + | TSF |
| chr6 | 10829240 | 10829256 + | TSF |
| chr6 | 10829240 | 10829256 + | TSF |
| chr6 | 10829240 | 10829256 + | TSF |
| chr6 | 10829240 | 10829256 + | TSF |
| chr7 | 74168612 | 74168748 + | TSF |
| chr7 | 74168612 | 74168748 + | TSF |
| chr7 | 74168612 | 74168748 + | TSF |

TABLE 43-continued

| | | | |
|---|---|---|---|
| chr7 | 74168612 | 74168748 + | TSF |
| chr12 | 56736879 | 56736779 − | TSF |
| chr12 | 56736879 | 56736779 − | TSF |
| chr19 | 45365316 | 45365390 + | TSF |
| chr3 | 185411016 | 185410789 − | TSF |
| chr3 | 185411016 | 185410789 − | TSF |
| chr22 | 36663327 | 36663652 + | TSF |
| chr22 | 36663327 | 36663652 + | TSF |
| chr22 | 36663327 | 36663652 + | TSF |
| chr22 | 36663327 | 36663652 + | TSF |
| chr9 | 3855631 | 3855480 − | TSF |
| chr9 | 3855631 | 3855480 − | TSF |
| chr1 | 1255223 | 1254988 − | TSF |
| chr1 | 1255223 | 1254988 − | TSF |
| chr1 | 1255223 | 1254988 − | TSF |
| chr1 | 1255223 | 1254988 − | TSF |
| chr1 | 1255223 | 1254988 − | TSF |
| chr4 | 1101132 | 1100845 − | TSF |
| chr9 | 19269457 | 19269457 − | TSF |
| chr9 | 19269457 | 19269457 − | TSF |
| chr6 | 30349606 | 30349643 + | TSF |
| chr1 | 40313419 | 40313374 − | TSF |
| chr1 | 40313419 | 40313374 − | TSF |
| chr1 | 40313419 | 40313374 − | TSF |
| chr1 | 40313419 | 40313374 − | TSF |
| chr1 | 44801643 | 44801548 − | TSF |
| chr1 | 44801643 | 44801548 − | TSF |
| chr1 | 20978611 | 20978295 − | TSF |
| chr1 | 20978611 | 20978295 − | TSF |
| chr1 | 20978611 | 20978295 − | TSF |
| chr20 | 3854441 | 3854475 + | TSF |
| chr20 | 3854441 | 3854475 + | TSF |
| chr8 | 71625661 | 71625673 + | TSF |
| chr17 | 7215628 | 7215651 + | TSF |
| chr17 | 7215628 | 7215651 + | TSF |
| chr19 | 45324388 | 45324381 + | TSF |
| chr16 | 2875971 | 2876154 + | TSF |
| chr16 | 2875971 | 2876154 + | TSF |
| chr16 | 2875971 | 2876154 + | TSF |
| chr16 | 2875971 | 2876154 + | TSF |
| chr18 | 72187799 | 72187899 + | TSF |
| chr18 | 72187799 | 72187899 + | TSF |
| chr10 | 75556079 | 75556138 + | TSF |
| chr10 | 75556079 | 75556138 + | TSF |
| chr10 | 75556079 | 75556138 + | TSF |
| chr10 | 75556079 | 75556138 + | TSF |
| chr10 | 75556079 | 75556138 + | TSF |
| chr10 | 75556079 | 75556138 + | TSF |
| chr10 | 75556079 | 75556138 + | TSF |
| chr1 | 33145073 | 33145159 + | TSF |
| chr1 | 33145073 | 33145159 + | TSF |
| chr1 | 33145073 | 33145159 + | TSF |
| chr1 | 33145073 | 33145159 + | TSF |
| chr1 | 33145073 | 33145159 + | TSF |
| chr1 | 33145073 | 33145159 + | TSF |
| chr1 | 33145073 | 33145159 + | TSF |
| chr19 | 53339322 | 53339166 − | TSF |
| chr19 | 53339322 | 53339166 − | TSF |
| chr4 | 227073 | 226784 − | TSF |
| chr14 | 93864129 | 93864243 + | TSF |
| chr3 | 50155909 | 50155909 + | TSF |
| chr3 | 137907243 | 137907252 + | TSF |
| chr3 | 137907243 | 137907252 + | TSF |
| chr19 | 17388878 | 17389009 + | TSF |
| chr19 | 17388878 | 17389009 + | TSF |
| chr19 | 17388878 | 17389009 + | TSF |
| chr19 | 17388878 | 17389009 + | TSF |
| chr19 | 17388878 | 17389009 + | TSF |
| chr19 | 45324363 | 45324391 + | TSF |
| chr15 | 89453897 | 89453853 − | TSF |
| chr9 | 4992433 | 4991945 − | TSF |
| chr11 | 64089177 | 64089204 + | TSF |
| chr19 | 18717523 | 18717557 + | TSF |
| chr19 | 18717523 | 18717557 + | TSF |
| chr19 | 18717523 | 18717557 + | TSF |
| chr12 | 21387233 | 21386864 − | TSF |
| chr12 | 21387233 | 21386864 − | TSF |

TABLE 43-continued

| | | | |
|---|---|---|---|
| chr12 | 21387233 | 21386864 − | TSF |
| chr7 | 116738667 | 116738692 + | TSF |
| chr2 | 217393976 | 217394327 + | TSF |
| chr2 | 217393976 | 217394327 + | TSF |
| chr15 | 83193141 | 83193227 + | TSF |
| chr19 | 39890782 | 39891028 + | TSF |
| chr19 | 39890782 | 39891028 + | TSF |
| chr19 | 39890782 | 39891028 + | TSF |
| chr19 | 39890782 | 39891028 + | TSF |
| chr1 | 54362523 | 54362446 − | TSF |
| chr1 | 156716225 | 156716218 − | TSF |
| chr19 | 58361929 | 58361580 − | TSF |
| chr1 | 153703418 | 153703434 + | TSF |
| chr19 | 45324388 | 45324391 + | TSF |
| chr19 | 45324388 | 45324391 + | TSF |
| chr5 | 24177946 | 24178380 + | TSF |
| chr1 | 32696865 | 32697110 + | TSF |
| chr12 | 52659397 | 52659518 + | TSF |
| chr7 | 81929467 | 81929190 − | TSF |
| chr7 | 75603302 | 75603295 − | TSF |
| chr9 | 130213398 | 130213359 − | TSF |
| chr1 | 32561261 | 32561358 + | TSF |
| chr1 | 32561261 | 32561358 + | TSF |
| chr1 | 32561261 | 32561358 + | TSF |
| chr20 | 45656785 | 45656967 + | TSF |
| chr20 | 45656785 | 45656967 + | TSF |
| chr20 | 45656785 | 45656967 + | TSF |
| chr1 | 25916660 | 25916675 + | TSF |
| chr4 | 17629629 | 17629638 + | TSF |
| chr4 | 17629629 | 17629638 + | TSF |
| chr19 | 17551332 | 17551032 − | TSF |
| chr19 | 17551332 | 17551032 − | TSF |
| chrX | 151994427 | 151994098 − | TSF |
| chr19 | 11561222 | 11561319 + | TSF |
| chr8 | 144113354 | 144113885 + | TSF |
| chr12 | 15086263 | 15086233 − | TSF |
| chr20 | 36757686 | 36757563 − | TSF |
| chr20 | 36757686 | 36757563 − | TSF |
| chr20 | 36757686 | 36757563 | |
| | | | TSF |
| chr1 | 6531300 | 6531188 − | TSF |
| chr1 | 6531300 | 6531188 − | TSF |
| chr1 | 6531300 | 6531188 − | TSF |
| chr1 | 6531300 | 6531188 − | TSF |
| chr1 | 6531300 | 6531188 − | TSF |
| chr1 | 6531300 | 6531188 − | TSF |
| chr8 | 27458611 | 27458570 − | TSF |
| chr8 | 27458611 | 27458570 − | TSF |
| chr8 | 27458611 | 27458570 − | TSF |
| chr8 | 27458611 | 27458570 − | TSF |
| chr7 | 91767179 | 91766808 − | TSF |
| chr3 | 420259 | 420361 + | TSF |
| chr3 | 420259 | 420361 + | TSF |
| chr10 | 128608404 | 128608409 + | TSF |
| chr20 | 45728490 | 45728598 + | TSF |
| chr20 | 45728490 | 45728598 + | TSF |
| chr19 | 45324372 | 45324391 + | ITSF |
| chr19 | 45324388 | 45324391 + | TSF |
| chrX | 1481917 | 1481663 − | TSF |
| chr7 | 135585557 | 135585512 − | TSF |
| chr19 | 58361929 | 58361580 − | TSF |
| chr7 | 74856485 | 74856184 − | TSF |
| chr5 | 149709118 | 149709023 − | TSF |
| chr5 | 149709118 | 149709023 − | TSF |
| chr10 | 114208140 | 114208243 + | TSF |
| chr11 | 76834999 | 76835082 + | TSF |
| chr11 | 76834999 | 76835082 + | TSF |
| chr14 | 75936196 | 75936249 + | TSF |
| chr14 | 75936196 | 75936249 + | TSF |
| chr7 | 150067849 | 150067901 + | TSF |
| chr9 | 5712361 | 5712559 + | TSF |
| chr9 | 5712361 | 5712559 + | TSF |
| chr9 | 5712361 | 5712559 + | TSF |
| chr19 | 45324388 | 45324391 + | TSF |
| chr17 | 7215638 | 7215651 + | TSF |
| chr17 | 7215638 | 7215651 + | TSF |
| chr7 | 91430582 | 91429696 − | TSF |
| chr | 80401028 | 80400962 − | TSF |
| chr | 80401028 | 80400962 − | TSF |
| chr | 80401028 | 80400962 − | TSF |

TABLE 43-continued

| | | | |
|---|---|---|---|
| chr4 | 25723603 | 25723555 − | TSF |
| chr4 | 25723603 | 25723555 − | TSF |
| chr4 | 25723603 | 25723555 − | TSF |
| chr4 | 25723603 | 25723555 − | TSF |
| chr6 | 30461007 | 30461101 + | TSF |
| chr4 | 107242023 | 107243452 + | TSF |
| chr1 | 230227336 | 230227441 + | TSF |
| chr8 | 117960753 | 117961020 + | TSF |
| chr1 | 70831829 | 70831848 + | TSF |
| chr5 | 70868141 | 70868205 + | TSF |
| chr5 | 70868141 | 70868205 + | TSF |
| chr19 | 2141056 | 2140753 − | TSF |
| chr1 | 63952444 | 63951983 − | TSF |
| chr1 | 63952444 | 63951983 − | TSF |
| chr5 | 10732796 | 10732287 − | TSF |
| chr6 | 11056581 | 110565664 − | TSF |
| chr1 | 1255085 | 1254988 − | TSF |
| chr1 | 1255085 | 1254988 − | TSF |
| chr1 | 1255085 | 1254988 − | TSF |
| chr1 | 1255085 | 1254988 − | TSF |
| chr1 | 1255085 | 1254988 − | TSF |
| chr1 | 1255085 | 1254988 − | TSF |
| chr6 | 51608386 | 51607435 − | TSF |
| chr11 | 118739656 | 118739455 − | TSF |
| chr8 | 109233832 | 109233552 − | TSF |
| chr8 | 109233832 | 109233552 − | TSF |
| chr8 | 109233832 | 109233552 − | TSF |
| chr8 | 109233832 | 109233552 − | TSF |
| chr17 | 27242466 | 27242238 − | TSF |
| chr20 | 48177475 | 48177085 − | TSF |
| chr8 | 11700371 | 11700139 − | TSF |
| chr10 | 71982750 | 71982433 − | TSF |
| chr9 | 7798658 | 7798645 − | TSF |
| chr19 | 35505459 | 35505647 + | TSF |
| chr19 | 35505459 | 35505647 + | TSF |
| chr19 | 35505459 | 35505647 + | TSF |
| chr19 | 35505459 | 35505647 + | TSF |
| chr6 | 10760279 | 10760632 + | TSF |
| chr6 | 10760249 | 10790632 + | TSF |
| chr19 | 45324388 | 45324391 + | ITSF |
| chr2 | 219211310 | 219211505 + | TSF |
| chr2 | 219211310 | 219211505 + | TSF |
| chr2 | 219211310 | 219211505 + | TSF |
| chr12 | 56503862 | 56504158 + | TSF |
| chr22 | 47078308 | 47078350 + | TSF |
| chr22 | 47078308 | 47078350 + | TSF |
| chr3 | 32324083 | 32324625 + | TSF |
| chr15 | 74234853 | 74234966 + | TSF |
| chr6 | 30461539 | 30461850 + | TSF |
| chr6 | 30461539 | 30461850 + | TSF |
| chr16 | 2818542 | 2818580 + | TSF |
| chr16 | 2818542 | 2818580 + | TSF |
| chr11 | 113858309 | 11358477 + | TSF |
| chr11 | 113858309 | 11358477 + | TSF |
| chr11 | 113858309 | 11358477 + | TSF |
| chr11 | 113858309 | 11358477 + | TSF |
| chr11 | 113858309 | 11358477 + | TSF |
| chr11 | 113858309 | 11358477 + | TSF |
| chrX | 153276645 | 153276543 − | TSF |
| chrX | 153276645 | 153276543 − | TSF |
| chrX | 153276645 | 153276543 − | TSF |
| chr1 | 117702007 | 117701826 − | TSF |
| chr1 | 117702007 | 117701826 − | TSF |
| chr1 | 55317750 | 55317525 − | TSF |
| chr1 | 55317750 | 55317525 − | TSF |
| chr17 | 74615240 | 74615040 − | TSF |
| chr1 | 55317750 | 55317525 − | TSF |
| chr1 | 55317750 | 55317525 − | TSF |
| chr19 | 58361929 | 58361580 − | TSF |
| chr19 | 58361929 | 58361580 − | TSF |
| chr19 | 58361929 | 58361580 − | TSF |
| chr19 | 58361929 | 58361580 − | TSF |
| chr19 | 40327613 | 10327527 − | TSF |
| chr19 | 40327613 | 10327527 − | TSF |
| chr19 | 40327613 | 10327527 − | TSF |
| chr19 | 40327613 | 10327527 − | TSF |
| chr19 | 40327613 | 10327527 − | TSF |
| chr8 | 120233190 | 120233225 + | TSF |
| chr19 | 45324388 | 45324391 + | TSF |
| chr19 | 45324388 | 45324391 + | TSF |

TABLE 43-continued

| | | | |
|---|---|---|---|
| chr9 | 81037010 | 81037166 + | TSF |
| chr11 | 64089165 | 64089204 + | TSF |
| chr10 | 116030863 | 116030985 + | TSF |
| chr5 | 175731557 | 175732243 + | TSF |
| chr5 | 175731557 | 175732243 + | TSF |
| chr5 | 175731557 | 175732243 + | TSF |
| chr19 | 45324372 | 45324391 + | TSF |
| chr15 | 81439636 | 81439809 + | TSF |
| chr11 | 73076139 | 73076217 + | TSF |
| chr16 | 16382422 | 16382605 + | TSF |
| chr16 | 16382422 | 16382605 + | TSF |
| chr12 | 11340402 | 113404051 + | TSF |
| chr12 | 11340402 | 113404051 + | TSF |
| chr12 | 53716024 | 53716124 + | TSF |
| chr12 | 53716024 | 53716124 + | TSF |
| chr12 | 53716024 | 53716124 + | TSF |
| chr14 | 75936196 | 75936249 + | TSF |
| chr14 | 75936196 | 75936249 + | TSF |
| chr9 | 5710416 | 5711239 + | TSF |
| chr9 | 5710416 | 5711239 + | TSF |
| chr9 | 5710416 | 5711239 + | TSF |
| chr9 | 100777715 | 100777715 + | TSF |
| chr4 | 56252510 | 56252750 + | TSF |
| chr11 | 16771716 | 16772764 + | TSF |
| chr11 | 16771716 | 16772764 + | TSF |
| chr11 | 16771716 | 16772764 + | TSF |
| chr16 | 1740010 | 1740018 + | TSF |
| chr16 | 1740010 | 1740018 + | TSF |
| chr16 | 1740010 | 1740018 + | TSF |
| chr16 | 1740010 | 1740018 + | TSF |
| chr16 | 1740010 | 1740018 + | TSF |
| chr2 | 160172085 | 160171780 − | TSF |
| chr2 | 160172085 | 160171780 − | TSF |
| chr2 | 160172085 | 160171780 − | TSF |
| chr2 | 160172085 | 160171780 − | TSF |
| chr22 | 39689975 | 39689898 − | TSF |
| chr22 | 39689975 | 39689898 − | TSF |
| chr22 | 39689975 | 39689898 − | TSF |
| chr22 | 39689975 | 39689898 − | TSF |
| chr12 | 21387233 | 21386864 − | TSF |
| chr12 | 21387233 | 21386864 − | TSF |
| chr1 | 55317546 | 55317525 − | TSF |
| chr16 | 2834278 | 2833911 − | TSF |
| chr16 | 2834278 | 2833911 − | TSF |
| chr11 | 77763913 | 77763811 − | TSF |
| chr11 | 77763913 | 77763811 − | TSF |
| chr14 | 106216701 | 106216511 − | TSF |
| chr6 | 75951015 | 75951009 − | TSF |
| chr6 | 75951015 | 75951009 − | TSF |
| chr6 | 75951015 | 75951009 − | TSF |
| chr5 | 79409445 | 79409319 − | TSF |
| chr1 | 20978562 | 20978295 − | TSF |
| chr1 | 20978562 | 20978295 − | TSF |
| chr1 | 20978562 | 20978295 − | TSF |
| chr1 | 47098528 | 47098433 − | TSF |
| chr1 | 47098528 | 47098433 − | TSF |
| chr1 | 47098528 | 47098433 − | TSF |
| chr1 | 47098528 | 47098433 − | TSF |
| chr1 | 47098528 | 47098433 − | TSF |
| chr1 | 47098528 | 47098433 − | TSF |
| chr1 | 47098528 | 47098433 − | TSF |
| chr1 | 47098528 | 47098433 − | TSF |
| chr20 | 30059856 | 30059283 − | TSF |
| chr3 | 156246256 | 156246164 − | TSF |
| chr3 | 156246256 | 156246164 − | TSF |
| chr3 | 156246256 | 156246164 − | TSF |
| chr19 | 8958092 | 8957538 − | TSF |
| chr19 | 8958092 | 8957538 − | TSF |
| chr19 | 8958092 | 8957538 − | TSF |
| chr10 | 127473829 | 127473633 − | TSF |
| chr19 19 | 40491610 | 49491685 + | TSF |
| chr18 | 12728047 | 12728839 + | TSF |
| chr18 | 12728047 | 12728839 + | TSF |
| chr18 | 12728047 | 12728839 + | TSF |
| chr19 | 45324388 | 45324391 + | TSF |
| chr3 | 50155897 | 50155909 + | TSF |
| chrX | 49452063 | 49452091 + | TSF |
| chr3 | 50155901 | 50155909 + | TSF |

TABLE 43-continued

| | | | |
|---|---|---|---|
| chr22 | 35846150 | 35846200 + | TSF |
| chr22 | 35846150 | 35846200 + | TSF |
| chr1 | 82386280 | 82386482 + | TSF |
| chr2 | 130944553 | 130944643 + | TSF |
| chr2 | 130944553 | 130944643 + | TSF |
| chr2 | 130944553 | 130944643 + | TSF |
| chr22 | 24200767 | 24200784 + | TSF |
| chr19 | 45323220 | 45323361 + | TSF |
| chr19 | 45323220 | 45323361 + | TSF |
| chr3 | 23965495 | 23965511 + | TSF |
| chr3 | 23965495 | 23965511 + | TSF |
| chr22 | 24237181 | 24237187 + | TSF |
| chr22 | 24237181 | 24237187 + | TSF |
| chr1 | 25916660 | 25916675 + | TSF |
| chr10 | 81114803 | 81115129 + | TSF |
| chr10 | 81114803 | 81115129 + | TSF |
| chr11 | 64089177 | 64089204 + | TSF |
| chr11 | 64089177 | 64089204 + | TSF |
| chr11 | 64089177 | 64089204 + | TSF |
| chr11 | 60701443 | 60701575 + | TSF |
| chr11 | 60701443 | 60701575 + | TSF |
| chr11 | 60701443 | 60701575 + | TSF |
| chr6 | 21596236 | 21596314 + | TSF |
| chr16 | 30785136 | 30785155 + | TSF |
| chr16 | 30785136 | 30785155 + | TSF |
| chr16 | 30785136 | 30785155 + | TSF |
| chr16 | 30785136 | 30785155 + | TSF |
| chr19 | 45324388 | 45324391 + | TSF |
| chr19 | 45324388 | 45324391 + | TSF |
| chr8 | 146280809 | 146281504 + | TSF |
| chrX | 134866428 | 134866512 + | TSF |
| chr6 | 30461503 | 30461850 + | TSF |
| chr19 | 17631427 | 17631563 + | TSF |
| chr7 | 71169493 | 71170639 + | TSF |
| chr20 | 52835531 | 52835553 + | TSF |
| chrX | 49452063 | 49452091 + | TSF |
| chr22 | 36663327 | 36663652 + | TSF |
| chr22 | 36663327 | 36663652 + | TSF |
| chr22 | 36663327 | 36663652 + | TSF |
| chr22 | 36663327 | 36663652 + | TSF |
| chr14 | 24615120 | 24615007 − | TSF |
| chr12 | 71507025 | 71506982 − | TSF |
| chrX | 134936521 | 134936437 − | TSF |
| chr2 | 71213835 | 71213417 − | TSF |
| chrX | 153276642 | 153276543 − | TSF |
| chr19 | 54665366 | 54665264 − | TSF |
| chr19 | 54665366 | 54665264 − | TSF |
| chr19 | 54665366 | 54665264 − | TSF |
| chr6 | 65097495 | 65097442 − | TSF |
| chr7 | 150938275 | 150938099 − | TSF |
| chr7 | 15093827 | 150938099 − | TSF |
| chr1 | 152005339 | 152005310 − | TSF |
| chrX | 118884131 | 118883802 − | TSF |
| chr19 | 54687313 | 54687206 − | TSF |
| chr19 | 54687313 | 54687206 − | TSF |
| chr19 | 54687313 | 54687206 − | TSF |
| chr19 | 54687313 | 54687206 − | TSF |
| chr12 | 8793960 | 8793803 − | TSF |
| chr12 | 8793960 | 8793803 − | TSF |
| chr12 | 8793960 | 8793803 − | TSF |
| chr9 | 130678527 | 130678449 − | TSF |
| chr11 | 75917186 | 75917166 − | TSF |
| chr12 | 56736937 | 56736779 − | TSF |
| chr12 | 56736937 | 56736779 − | TSF |
| chrX | 134953780 | 134953696 − | TSF |
| chr19 | 49322122 | 49322095 − | TSF |
| chr19 | 49322122 | 49322095 − | TSF |
| chr1 | 85278179 | 85278107 − | TSF |
| chr20 | 55781390 | 55781345 − | TSF |
| chr20 | 55781390 | 55781345 − | TSF |
| chr19 | 6414524 | 6414481 − | TSF |
| chr19 | 6414524 | 6414481 − | TSF |
| chr4 | 973292 | 973258 − | TSF |
| chr8 | 144916987 | 144916867 − | TSF |
| chr8 | 144916987 | 144916867 − | TSF |
| chr15 | 40813374 | 40812967 − | TSF |
| chr15 | 40813374 | 40812967 − | TSF |
| chr15 | 40813374 | 40812967 − | TSF |
| chrX | 134936521 | 134936437 − | TSF |

TABLE 44

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 81% | chr17 | 74261446 | 74261484 | + | chr17 | 74261988 | 74262050 | + | ENST00000327490 | TAF |
| 70% | chr12 | 66102868 | 6602840 | − | chr12 | 6602138 | 6602028 | − | ENST00000229238 | TAF |
| 69% | chr4 | 39699858 | 39699922 | + | chr4 | 39739040 | 39739133 | + | ENST00000261427; ENST00000510934; ENST00000295963; ENST00000445950 | TAF |
| 69% | chr4 | 39699858 | 39699922 | + | chr4 | 39739040 | 39739133 | + | ENST00000261427; ENST00000510934; ENST00000295963; ENST00000445950 | TAF |
| 69% | chr4 | 39699858 | 39699922 | + | chr4 | 39739040 | 39739133 | + | ENST00000261427; ENST00000510934; ENST00000295963; ENST00000445950 | TAF |
| 69% | chr4 | 39699858 | 39699922 | + | chr4 | 39739040 | 39739133 | + | ENST00000261427; ENST00000510934; ENST00000295963; ENST00000445950 | TAF |
| 59% | chr21 | 19289273 | 19289717 | + | chr21 | 19628826 | 19629135 | + | ENST00000299295; ENST00000543733 | TAF |
| 58% | chr12 | 64687157 | 64687061 | − | chr12 | 64679840 | 64679734 | − | ENST00000543942; ENST00000333722 | TAF |
| 54% | chr11 | 78075071 | 78075062 | − | chr11 | 77991947 | 77991647 | − | ENST00000361507 | TAF |
| 53% | chr7 | 150938296 | 150938250 | − | chr7 | 150937608 | 150937511 | − | ENST00000262188; ENST00000392811; ENST00000356800 | TAF |
| 49% | chr17 | 75318693 | 75318752 | + | chr17 | 75398141 | 75398484; 75398785; 75398497; 75398565 | + | ENST00000589070; ENST00000427177; ENST00000591198; ENST00000329047; ESNT00000590294; ENST00000591934; ENST00000423034; ENST00000589140 | TAF |
| 49% | chr17 | 75318693 | 75318752 | + | chr17 | 75398141 | 75398484; 75398785; 75398497; 75398565 | + | ENST00000589070; ENST00000427177; ENST00000591198; ENST00000329047; ESNT00000590294; ENST00000591934; ENST00000423034; ENST00000589140 | TAF |
| 49% | chr17 | 75318693 | 75318752 | + | chr17 | 75398141 | 75398484; 75398785; 75398497; 75398565 | + | ENST00000589070; ENST00000427177; ENST00000591198; ENST00000329047; ESNT00000590294; ENST00000591934; ENST00000423034; ENST00000589140 | TAF |
| 49% | chr17 | 75318693 | 75318752 | + | chr17 | 75398141 | 75398484; 75398785; 75398497; 75398565 | + | ENST00000589070; ENST00000427177; ENST00000591198; ENST00000329047; ESNT00000590294; ENST00000591934; ENST00000423034; ENST00000589140 | TAF |
| 48% | chr1 | 46797740 | 46797497 | − | chr1 | 46764042 | 46763956 | − | ENST00000343304 | TAF |
| 44% | chr3 | 128359904 | 128359849 | − | chr3 | 128356948 | 128356642 | − | ENST00000296255 | TAF |
| 43% | chr12 | 6602868 | 6602754 | − | chr12 | 6602138 | 6602028 | − | ENST00000229238 | TSF |
| 42% | chr11 | 93468219 | 93468129 | − | chr11 | 93467826 | 93467791; 93467814 | − | ENST00000393259; ENST00000527169 | TAF |
| 42% | chr11 | 93468219 | 93468129 | − | chr11 | 93467826 | 93467791; 93467814 | − | ENST00000393259; ENST00000527169 | TAF |
| 41% | chr2 | 133363747 | 133363763 | + | chr2 | 133402674 | 133403179 | + | ENST00000329321 | TAF |
| 39% | chr19 | 56187371 | 56187420 | + | chr19 | 56189893 | 56190221 | + | ENST00000411543 | TAF |
| 39% | chr21 | 46238665 | 46238584 | − | chr21 | 46234019 | 46233891; 46233777 | − | ENST00000397898; ENST00000332859; ENST00000411651; ENST00000397893 | TAF |
| 39% | chr21 | 46238665 | 46238584 | − | chr21 | 46234019 | 46233891; 46233777 | − | ENST00000397898; ENST00000332859; ENST00000411651; ENST00000397893 | TAF |
| 39% | chr21 | 46238665 | 46238584 | − | chr21 | 46234019 | 46233891; 46233777 | − | ENST00000397898; ENST00000332859; ENST00000411651; ENST00000397893 | TAF |
| 39% | chr21 | 46238665 | 46238584 | − | chr21 | 46234019 | 46233891; 46233777 | − | ENST00000397898; ENST00000332859; ENST00000411651; ENST00000397893 | TAF |
| 39% | chr4 | 39585352 | 39585284 | − | chr4 | 39459881 | 39459814 | − | ENST00000295955; ENST00000449470; ENST00000508595; ENST00000503040; ENST00000504470 | TSF |
| 39% | chr4 | 39585352 | 39585284 | − | chr4 | 39459881 | 39459814 | − | ENST00000295955; ENST00000449470; ENST00000508595; ENST00000503040; ENST00000504470 | TSF |
| 39% | chr4 | 39585352 | 39585284 | − | chr4 | 39459881 | 39459814 | − | ENST00000295955; ENST00000449470; ENST00000508595; ENST00000503040; ENST00000504470 | TSF |
| 35% | chr21 | 19399995 | 19400289 | + | chr21 | 19628826 | 19629135 | + | ENST00000299295; ENST00000543733 | TSF |
| 33% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 33% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 33% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 33% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 33% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 32% | chr14 | 105944002 | 105944214 | + | chr14 | 10594603 | 105944697 | + | ENST00000483017; ENST00000329146 | TAF |
| 32% | chr9 | 130924283 | 130924301 | + | chr9 | 130925722 | 130925894 | + | ENST00000372994 | TAF |
| 30% | chr2 | 28190037 | 28190310 | + | chr2 | 28210860 | 28210954 | + | ENST00000436924; ENST00000344773; | TAF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 30% | chr2 | 28190037 | 28190310 | + | chr2 | 28210860 | 28210954 | + | ENST00000379624; ENST00000342045; ENST00000361704; ENST00000379632; ENST00000379629; ENST00000604932 ENST00000436924; ENST00000344773; | TAF |
| 30% | chr2 | 28190037 | 28190310 | + | chr2 | 28210860 | 28210954 | + | ENST00000379624; ENST00000342045; ENST00000361704; ENST00000379632; ENST00000379629; ENST00000604932 ENST00000436924; ENST00000344773; | TAF |
| 30% | chr2 | 28190037 | 28190310 | + | chr2 | 28210860 | 28210954 | + | ENST00000379624; ENST00000342045; ENST00000361704; ENST00000379632; ENST00000379629; ENST00000604932 ENST00000436924; ENST00000344773; | TAF |
| 30% | chr2 | 28190037 | 28190310 | + | chr2 | 28210860 | 28210954 | + | ENST00000379624; ENST00000342045; ENST00000361704; ENST00000379632; ENST00000379629; ENST00000604932 ENST00000436924; ENST00000344773; | TAF |
| 30% | chr2 | 28190037 | 28190310 | + | chr2 | 28210860 | 28210954 | + | ENST00000379624; ENST00000342045; ENST00000361704; ENST00000379632; ENST00000379629; ENST00000604932 ENST00000436924; ENST00000344773; | TAF |
| 30% | chr19 | 17971608 | 17971652 | + | chr19 | 17972102 | 17972281; 17972116 | + | ENST00000222247; ENST00000600147; ENST00000599898 | TAF |
| 30% | chr19 | 17971608 | 17971652 | + | chr19 | 17972102 | 17972281; 17972116 | + | ENST00000222247; ENST00000600147; ENST00000599898 | TAF |
| 30% | chr19 | 17971608 | 17971652 | + | chr19 | 17972102 | 17972281; 17972116 | + | ENST00000222247; ENST00000600147; ENST00000599898 | TAF |
| 30% | chr12 | 53342573 | 53342523 | − | chr12 | 53298811 | 53298442; 53298460 | − | ENST00000552150; ENST00000546542; | TAF |
| 30% | chr12 | 53342573 | 53342523 | − | chr12 | 53298811 | 53298442; 53298460 | − | ENST00000552150; ENST00000546542; | TAF |
| 30% | chr12 | 53342573 | 53342523 | − | chr12 | 53298811 | 53298442; 53298460 | − | ENST00000552150; ENST00000546542; | TAF |
| 30% | chr19 | 50391349 | 50391391 | + | chr19 | 50391488 | 50391574 | + | ENST00000221543; ENST00000535102 | TAF |
| 28% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 28% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 28% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 28% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 28% | chr3 | 124842655 | 124842374 | − | chr3 | 124839530 | 124839443 | − | ENST00000430155; ENST00000393469; ENST00000423114; ENST00000469902; ENST00000479826 | TAF |
| 28% | chr3 | 124842655 | 124842374 | − | chr3 | 124839530 | 124839443 | − | ENST00000430155; ENST00000393469; ENST00000423114; ENST00000469902; ENST00000479826 | TAF |
| 27% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 27% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 27% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 27% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 27% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 27% | chr19 | 35995931 | 35995843 | − | chr19 | 35994349 | 35994323; 35994334 | − | ENST00000474928; ENST00000488892; ENST00000461300; ENST00000447113; ENST00000392206; ENST00000440396; | TAF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 27% | chr19 | 35995931 | 35995843 | − | chr19 | 35994349 | 35994323; 35994334 | − | ENST00000458071; ENST00000418261; ENST00000424570; ENST00000451297; ENST00000450261 ENST00000474928; ENST00000488892; ENST00000461300; ENST00000447113; ENST00000392206; ENST00000440396; ENST00000458071; ENST00000418261; ENST00000424570; ENST00000451297; ENST00000450261 | TAF |
| 27% | chr21 | 42597177 | 42597622 | + | chr21 | 42598193 | 42598281 | + | ENST00000328735; ENST00000330333; ENST00000347667 | TAF |
| 27% | chr21 | 42597177 | 42597622 | + | chr21 | 42598193 | 42598281 | + | ENST00000328735; ENST00000330333; ENST00000347667 | TAF |
| 27% | chr21 | 42597177 | 42597622 | + | chr21 | 42598193 | 42598281 | + | ENST00000328735; ENST00000330333; ENST00000347667 | TAF |
| 27% | chr14 | 69863275 | 69863209 | − | chr14 | 69861629 | 69861542 | − | ENST00000557016; ENST00000555373 | TAF |
| 27% | chr14 | 69863275 | 69863209 | − | chr14 | 69861629 | 69861542 | − | ENST00000557016; ENST00000555373 | TAF |
| 26% | chr11 | 321638 | 321504 | − | chr11 | 320772 | 320565 | − | ENST00000399808 | TAF |
| 26% | chr11 | 321488 | 321465 | − | chr11 | 320772 | 320565 | − | ENST00000399808 | TAF |
| 26% | chr11 | 321410 | 321387 | − | chr11 | 320772 | 320565 | − | ENST00000399808 | TAF |
| 26% | chr11 | 321450 | 321426 | − | chr11 | 320772 | 320565 | − | ENST00000399808 | TAF |
| 26% | chr11 | 321638 | 321543 | − | chr11 | 320772 | 320565 | − | ENST00000399808 | TAF |
| 26% | chr3 | 47700203 | 47700048 | − | chr3 | 47680270 | 47680215 | − | ENST00000254480 | TAF |
| 25% | chr11 | 322580 | 322557 | − | chr11 | 320772 | 320565 | − | ENST00000399808 | TAF |
| 25% | chr11 | 321638 | 321582 | − | chr11 | 320772 | 320565 | − | ENST00000399808 | TAF |
| 25% | chr11 | 321716 | 321660 | − | chr11 | 320772 | 320565 | − | ENST00000399808 | TAF |
| 25% | chr11 | 322067 | 322011 | − | chr11 | 320772 | 320565 | − | ENST00000399808 | TAF |
| 25% | chr11 | 322262 | 322206 | − | chr11 | 320772 | 320565 | − | ENST00000399808 | TAF |
| 25% | chr11 | 321911 | 321855 | − | chr11 | 320772 | 320565 | − | ENST00000399808 | TAF |
| 25% | chr14 | 105944002 | 105944268 | + | chr14 | 105944603 | 105944697 | + | ENST00000483017; ENST00000329146 | TAF |
| 25% | chr6 | 31154067 | 31153803 | − | chr6 | 31133824 | 31133704 | − | ENST00000259915 | TAF |
| 24% | chr14 | 105944002 | 105944250 | + | chr14 | 105944603 | 105944697 | + | ENST00000483017; ENST00000329146 | TAF |
| 24% | chr14 | 105944002 | 105944232 | + | chr14 | 105944603 | 105944697 | + | ENST00000483017; ENST00000329146 | TAF |
| 24% | chr10 | 126455800 | 126455793 | − | chr10 | 126454177 | 126453961 | − | ENST00000494792; ENST00000368836 | TAF |
| 24% | chr10 | 126455800 | 126455793 | − | chr10 | 126454177 | 126453961 | − | ENST00000494792; ENST00000368836 | TAF |
| 24% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 24% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 24% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 24% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 24% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 24% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 24% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 23% | chr10 | 120902016 | 120901765 | − | chr10 | 120900831 | 120900754 | − | ENST00000403441 ENST00000355697; ENST00000330036 | TAF |
| 23% | chr3 | 185411133 | 185410965 | − | chr3 | 18541087 | 185410487 | − | ENST00000382199; ENST00000421047; ENST00000457616; ENST00000346192 | TAF |
| 23% | chr3 | 185411133 | 185410965 | − | chr3 | 18541087 | 185410487 | − | ENST00000382199; ENST00000421047; ENST00000457616; ENST00000346192 | TAF |
| 23% | chr20 | 110606 | 110697 | + | chr20 | 126056 | 126333 | + | ENST00000382398 | TSF |
| 23% | chr2 | 150044073 | 150044093 | + | chr2 | 150061767 | 150061918 | + | ENST00000409642; ENST00000409876; ENST00000409029; ENST00000442722; ENST00000280115 | TSF |
| 23% | chr2 | 150044073 | 150044093 | + | chr2 | 150061767 | 150061918 | + | ENST00000409642; ENST00000409876; ENST00000409029; ENST00000442722; ENST00000280115 | TSF |
| 22% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 22% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 22% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 22% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 22% | chr10 | 89682344 | 89682384 | + | chr10 | 89685270 | 89685314 | + | ENST00000371953 | TAF |
| 21% | chr1 | 33142637 | 33142971 | + | chr1 | 33145241 | 33145306; 33145415; 33145299 | + | ENST00000414241; ENST00000373493; ENST00000544435; ENST00000458695; ENST00000463378; ENST00000460669; ENST00000482190 | TAF |
| 21% | chr1 | 33142637 | 33142971 | + | chr1 | 33145241 | 33145306; 33145415; 33145299 | + | ENST00000414241; ENST00000373493; ENST00000544435; ENST00000458695; ENST00000463378; ENST00000460669; ENST00000482190 | TAF |
| 21% | chr1 | 33142637 | 33142971 | + | chr1 | 33145241 | 33145306; 33145415; 33145299 | + | ENST00000414241; ENST00000373493; ENST00000544435; ENST00000458695; ENST00000463378; ENST00000460669; ENST00000482190 | TAF |
| 21% | chr19 | 39110121 | 39110170 | + | chr19 | 39110977 | 39111075 | + | ENST00000248342; ENST00000588934; ENST00000545173; ENST00000586513; ENST00000592558 | TAF |
| 21% | chr19 | 39110121 | 39110170 | + | chr19 | 39110977 | 39111075 | + | ENST00000248342; ENST00000588934; ENST00000545173; ENST00000586513; ENST00000592558 | TAF |
| 21% | chr19 | 39110121 | 39110170 | + | chr19 | 39110977 | 39111075 | + | ENST00000248342; ENST00000588934; ENST00000545173; ENST00000586513; ENST00000592558 | TAF |
| 21% | chr19 | 39110121 | 39110170 | + | chr19 | 39110977 | 39111075 | + | ENST00000248342; ENST00000588934; ENST00000545173; ENST00000586513; ENST00000592558 | TAF |
| 21% | chr19 | 39110121 | 39110170 | + | chr19 | 39110977 | 39111075 | + | ENST00000248342; ENST00000588934; ENST00000545173; ENST00000586513; ENST00000592558 | TAF |
| 21% | chr10 | 5826921 | 5825287 | − | chr10 | 5815904 | 5815805 | − | ENST00000380191; ENST00000447751; ENST00000380132; ENST00000380181; ENST00000456041 | TAF |
| 21% | chr10 | 5826921 | 5825287 | − | chr10 | 5815904 | 5815805 | − | ENST00000380191; ENST00000447751; ENST00000380132; ENST00000380181; ENST00000456041 | TAF |
| 21% | chr10 | 5826921 | 5825287 | − | chr10 | 5815904 | 5815805 | − | ENST00000380191; ENST00000447751; ENST00000380132; ENST00000380181; ENST00000456041 | TAF |
| 21% | chr20 | 110606 | 110697 | + | chr20 | 126220 | 126333 | + | ENST00000382398 | TSF |
| 20% | chr19 | 50188651 | 50188743 | + | chr19 | 50189350 | 50189500 | + | ENST00000532489; ENST00000391851; ENST00000454376 | TAF |
| 20% | chr19 | 1600051 | 1599987 | − | chr19 | 1599559 | 1599439 | − | ENST00000585937; ENST0000591899; ENST00000589880; ENST00000585671 | TAF |
| 20% | chr1 | 55368856 | 55366719 | − | chr1 | 55349446 | 55349291 | − | ENST00000371269; ENST00000535035 | TSF |
| 20% | chr11 | 32453241 | 32453220 | − | chr11 | 32450165 | 32450043 | − | ENST00000379079; ENST00000379077; ENST00000332351; ENST00000530998; ENST00000452863; ENST00000448076 | TSF |
| 20% | chr11 | 32453241 | 32324520 | − | chr11 | 32450165 | 32450043 | − | ENST00000379079; ENST00000379077; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 20% | chr11 | 32453241 | 32324520 | − | chr11 | 32450165 | 32450043 | − | ENST00000332351; ENST00000530998; ENST00000452863; ENST00000448076 ENST00000379079; ENST00000379077 | TSF |
| 20% | chr11 | 32453241 | 32324520 | − | chr11 | 32450165 | 32450043 | − | ENST00000332351; ENST00000530998; ENST00000452863; ENST00000448076 ENST00000379079; ENST00000379077 | TSF |
| 20% | chr11 | 32453241 | 32324520 | − | chr11 | 32450165 | 32450043 | − | ENST00000332351; ENST00000530998; ENST00000452863; ENST00000448076 ENST00000379079; ENST00000379077 | TSF |
| 20% | chr6 | 71556614 | 71556625 | + | chr6 | 71562243 | 71562367 | + | ENST00000316999; ENST00000370452; ENST00000370455 | TSF |
| 20% | chr6 | 71556614 | 71556625 | + | chr6 | 71562243 | 71562367 | + | ENST00000316999; ENST00000370452; ENST00000370455 | TSF |
| 18% | chr1 | 40781678 | 40781517 | − | chr1 | 40781336 | 40781262 | − | ENST00000372748; ENST00000417105; ENST00000372736 | TAF |
| 18% | chr1 | 40781678 | 40781517 | − | chr1 | 40781336 | 40781262 | − | ENST00000372748; ENST00000417105; ENST00000372736 | TAF |
| 18% | chr1 | 40781678 | 40781517 | − | chr1 | 40781336 | 40781262 | − | ENST00000372748; ENST00000417105; ENST00000372736 | TAF |
| 18% | chr5 | 10732874 | 10732658 | − | chr5 | 10683683 | 10683641 | − | ENST00000230895 | TAF |
| 17% | chr1 | 21901654 | 21901670 | + | chr1 | 21902226 | 21902417 | + | ENST00000539907; ENST00000540617; ENST00000374840; ENST00000374832; ENST00000425315 | TAF |
| 17% | chr1 | 155036912 | 155037036 | + | chr1 | 155039206 | 155039492 | + | ENST00000368409; ENST00000359751; ENST00000427683 | TAF |
| 17% | chr1 | 155036912 | 155037036 | + | chr1 | 155039206 | 155039492 | + | ENST00000368409; ENST00000359751; ENST00000427683 | TAF |
| 17% | chr1 | 155036912 | 155037036 | + | chr1 | 155039206 | 155039492 | + | ENST00000368409; ENST00000359751; ENST00000427683 | TAF |
| 17% | chr19 | 55649945 | 55649877 | − | chr19 | 55649442 | 55649329; 55649344; 55649386 | − | ENST00000587758; ENST00000291901; ENST00000356783; ENST00000588426; ENST00000536926; ENST00000588981; ENST00000593194; ENST00000589745; ENST00000587465; ENST00000585321; ENST00000593046; ENST00000589226; ENST00000588147 | TAF |
| 17% | chr19 | 55649945 | 55649877 | − | chr19 | 55649442 | 55649329; 55649344; 55649386 | − | ENST00000587758; ENST00000291901; ENST00000356783; ENST00000588426; ENST00000536926; ENST00000588981; ENST00000593194; ENST00000589745; ENST00000587465; ENST00000585321; ENST00000593046; ENST00000589226; ENST00000588147 | TAF |
| 17% | chr19 | 55649945 | 55649877 | − | chr19 | 55649442 | 55649329; 55649344; 55649386 | − | ENST00000587758; ENST00000291901; ENST00000356783; ENST00000588426; ENST00000536926; ENST00000588981; ENST00000593194; ENST00000589745; ENST00000587465; ENST00000585321; ENST00000593046; ENST00000589226; ENST00000588147 | TAF |
| 17% | chr19 | 55649945 | 55649877 | − | chr19 | 55649442 | 55649329; 55649344; 55649386 | − | ENST00000587758; ENST00000291901; ENST00000356783; ENST00000588426; ENST00000536926; ENST00000588981; ENST00000593194; ENST00000589745; ENST00000587465; ENST00000585321; ENST00000593046; ENST00000589226; ENST00000588147 | TAF |
| 17% | chr19 | 55649945 | 55649877 | − | chr19 | 55649442 | 55649329; 55649344; 55649386 | − | ENST00000587758; ENST00000291901; ENST00000356783; ENST00000588426; ENST00000536926; ENST00000588981; ENST00000593194; ENST00000589745; ENST00000587465; ENST00000585321; ENST00000593046; ENST00000589226; ENST00000588147 | TAF |
| 17% | chr12 | 123873690 | 123873729 | + | chr12 | 123873980 | 123874101 | + | ENST00000330479; ENST00000402868 | TSF |
| 17% | chr1 | 44446234 | 44446286 | + | chr1 | 44446781 | 44447145 | + | ENST00000309519 | TSF |
| 16% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 16% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 16% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 16% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 16% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 16% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 16% | chr8 | 104389530 | 104389551 | + | chr8 | 104390255 | 104390471 | + | ENST00000330295; ENST00000520337 | TAF |
| 16% | chr5 | 179238653 | 179238682 | + | chr5 | 179249989 | 179250053 | + | ENST00000389805; ENST00000504627; ENST00000510187 | TAF |
| 16% | chr5 | 179238653 | 179238682 | + | chr5 | 179249989 | 179250053 | + | ENST00000389805; ENST00000504627; ENST00000510187 | TAF |
| 16% | chr5 | 179238653 | 179238682 | + | chr5 | 179249989 | 179250053 | + | ENST00000389805; ENST00000504627; ENST00000510187 | TAF |
| 16% | chr7 | 99747312 | 99747315 | + | chr7 | 99751023 | 99751140; 99751352 | + | ENST00000341942; ENST00000441173 | TAF |
| 16% | chr7 | 99747312 | 99747315 | + | chr7 | 99751023 | 99751140; 99751352 | + | ENST00000341942; ENST00000441173 | TAF |
| 16% | chr1 | 27228495 | 27228857 | + | chr1 | 27250580 | 27250657 | + | ENST00000435827; ENST00000321265 | TAF |
| 16% | chr1 | 27228495 | 27228857 | + | chr1 | 27250580 | 27250657 | + | ENST00000435827; ENST00000321265 | TAF |
| 16% | chr2 | 62197111 | 62197160 | + | chr2 | 62227836 | 62228117 | + | ENST00000311832; ENST00000538736 | TAF |
| 16% | chr2 | 62197111 | 62197160 | + | chr2 | 62227836 | 62228117 | + | ENST00000311832; ENST00000538736 | TAF |
| 16% | chr15 | 66170740 | 66170790 | + | chr15 | 66172009 | 66172089; 66172017 | + | ENST00000564910; ENST00000261890; ENST00000569896; ENST00000567671 | TSF |
| 16% | chr15 | 66170740 | 66170790 | + | chr15 | 66172009 | 66172089; 66172017 | + | ENST00000564910; ENST00000261890; ENST00000569896; ENST00000567671 | TSF |
| 16% | chr15 | 66170740 | 66170790 | + | chr15 | 66172009 | 66172089; 66172017 | + | ENST00000564910; ENST00000261890; ENST00000569896; ENST00000567671 | TSF |
| 16% | chr7 | 56018506 | 56018522 | + | chr7 | 56020872 | 56021011 | + | ENST00000426595 | TSF |
| 15% | chr7 | 130127044 | 130127065 | + | chr7 | 130135209 | 130135363 | + | ENST00000223215; ENST00000437945 | TAF |
| 15% | chr7 | 130127044 | 130127065 | + | chr7 | 130135209 | 130135363 | + | ENST00000223215; ENST00000437945 | TAF |
| 15% | chr13 | 43628887 | 43629679 | + | chr13 | 43639822 | 43639873 | + | ENST00000379221 | TAF |
| 15% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 15% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 15% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 15% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 15% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 15% | chr19 | 5902574 | 5902426 | − | chr19 | 5897008 | 5896916 | − | ENST00000592091; ENST00000585661; ENST00000586349; ENST00000418389; ENST00000592634; ENST00000308961 | TAF |
| 15% | chr2 | 9737072 | 9736908 | − | chr2 | 9731644 | 9731521 | − | ENST00000381844; ENST00000238081; ENST00000446619 | TAF |
| 15% | chr2 | 9737072 | 9736908 | − | chr2 | 9731644 | 9731521 | − | ENST00000381844; ENST00000238081; ENST00000446619 | TAF |
| 14% | chr19 | 41816860 | 41816920 | + | chr19 | 41822289 | 41822744 | + | ENST00000269967 | |
| 14% | chr3 | 195444683 | 195445067 | + | chr3 | 195451551 | 195453443; 195452030 | + | ENST00000447234; ENST00000320736; ENST00000436408 | TAF |
| 14% | chr3 | 195444683 | 195445067 | + | chr3 | 195451551 | 195453443; 195452030 | + | ENST00000447234; ENST00000320736; ENST00000436408 | TAF |
| 14% | chr3 | 195444683 | 195445067 | + | chr3 | 195451551 | 195453443; 195452030 | + | ENST00000447234; ENST00000320736; ENST00000436408 | TAF |
| 14% | chr20 | 55970013 | 55970039 | + | chr20 | 55982599 | 55982902; 55982603 | + | ENST00000356208; ENST00000440234; ENST00000371219 | TAF |
| 14% | chr20 | 55970013 | 55970039 | + | chr20 | 55982599 | 55982902; 55982603 | + | ENST00000356208; ENST00000440234; ENST00000371219 | TAF |
| 14% | chr5 | 823586 | 823504 | − | chr5 | 822010 | 821976 | − | ENST00000424784; ENST00000283441 | |
| 14% | chr19 | 17384225 | 17384260 | + | chr19 | 17384713 | 17384833; | + | ENST00000598188; ENST00000594247; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 17384754; 17384789 | | ENST00000359435; ENST00000596542; ENST00000599474; ENST00000599057; ENST00000447614; ENST00000601043; ENST00000596335; ENST00000601436; ENST00000601938; ENST00000602066; ENST00000598567 | |
| 14% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 14% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 14% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 14% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 14% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 14% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 14% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 14% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 14% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 14% | chr1 | 53070435 | 53070501 | + | chr1 | 53072356 | 53072617 | + | ENST00000361314 | TSF |
| 14% | chr19 | 39347374 | 39346206 | − | chr19 | 39338074 | 39337956 | − | ENST00000221419; ENST00000601449; ENST00000600233; ENST00000601813 | TSF |
| 14% | chr19 | 39347374 | 39346206 | − | chr19 | 39338074 | 39337956 | − | ENST00000221419; ENST00000601449; ENST00000600233; ENST00000601813 | TSF |
| 14% | chr19 | 39347374 | 39346206 | − | chr19 | 39338074 | 39337956 | − | ENST00000221419; ENST00000601449; ENST00000600233; ENST00000601813 | TSF |
| 14% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 14% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 14% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 14% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 14% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 14% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 14% | chr1 | 206288369 | 206288105 | − | chr1 | 206243250 | 206243150 | − | ENST00000331555 | TSF |
| 13% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 13% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 13% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 13% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 13% | chr8 | 126162241 | 126168340 | + | chr8 | 126194345 | 126194498 | + | ENST00000523741; ENST00000517532; ENST00000287437; ENST00000522563; ENST00000517315 | TAF |
| 13% | chr8 | 126162241 | 126168340 | + | chr8 | 126194345 | 126194498 | + | ENST00000523741; ENST00000517532; ENST00000287437; ENST00000522563; ENST00000517315 | TAF |
| 13% | chr8 | 126162241 | 126168340 | + | chr8 | 126194345 | 126194498 | + | ENST00000523741; ENST00000517532; ENST00000287437; ENST00000522563; ENST00000517315 | TAF |
| 13% | chr11 | 424193 | 423942 | − | chr11 | 421198 | 421141 | − | ENST00000332826 | TAF |
| 13% | chr1 | 2124338 | 2124284 | − | chr1 | 2121196 | 2121152; 2121148 | − | ENST00000414253; ENST00000378546; ENST00000378545 | TAF |
| 13% | chr1 | 2124338 | 2124284 | − | chr1 | 2121196 | 2121152; 2121148 | − | ENST00000414253; ENST00000378546; ENST00000378545 | TAF |
| 13% | chr12 | 56110428 | 56110523 | + | chr12 | 56110717 | 56110789 | + | ENST00000257899; ENST00000550412; ENST00000548925; ENST00000549147 | TAF |
| 13% | chr12 | 56110428 | 56110523 | + | chr12 | 56110717 | 56110789 | + | ENST00000257899; ENST00000550412; ENST00000548925; ENST00000549147 | TAF |
| 13% | chr12 | 56110428 | 56110523 | + | chr12 | 56110717 | 56110789 | + | ENST00000257899; ENST00000550412; ENST00000548925; ENST00000549147 | TAF |
| 13% | chr3 | 197680391 | 197680531 | + | chr | 197680874 | 197681018; 197680991 | + | ENST00000464167; ENST00000448864; ENST00000442341 | TAF |
| 13% | chr3 | 197680391 | 197680531 | + | chr3 | 197680874 | 197681018; 197680991 | + | ENST00000464167; ENST00000448864; ENST00000442341 | TAF |
| 13% | chr12 | 120900591 | 12098393 | − | chr12 | 120899965 | 120899822 | − | ENST00000229390 | TAF |
| 13% | chr11 | 61196480 | 61196370 | − | chr11 | 61189080 | 61188862 | − | ENST00000340437; ENST00000394888; ENST00000439958; ENST00000448745; ENST00000477890; ENST00000539952; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 13% | chr11 | 61196480 | 61196370 | – | chr11 | 61189080 | 61188862 | – | ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 13% | chr11 | 61196480 | 61196370 | – | chr11 | 61189080 | 61188862 | – | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 13% | chr11 | 61196480 | 61196370 | – | chr11 | 61189080 | 61188862 | – | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 13% | chr11 | 61196480 | 61196370 | – | chr11 | 61189080 | 61188862 | – | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 13% | chr11 | 61196480 | 61196370 | – | chr11 | 61189080 | 61188862 | – | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 13% | chr11 | 61196480 | 61196370 | – | chr11 | 61189080 | 61188862 | – | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 13% | chr11 | 61196480 | 61196370 | – | chr11 | 61189080 | 61188862 | – | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 13% | chr11 | 61196480 | 61196370 | – | chr11 | 61189080 | 61188862 | – | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 13% | chr11 | 61196480 | 61196370 | – | chr11 | 61189080 | 61188862 | – | ENST00000450000; ENST00000449811; ENST00000413184; ENST00000536145 ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; | TSF |
| 13% | chr11 | 61196480 | 61196370 | – | chr11 | 61189080 | 61188862 | – | ENST00000450000; ENST00000449811; ENST00000413184; ENST00000536145 ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; | TSF |
| 13% | chr11 | 61196480 | 61196370 | – | chr11 | 61189080 | 61188862 | – | ENST00000450000; ENST00000449811; ENST00000413184; ENST00000536145 ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; | TSF |
| 13% | chr11 | 61196480 | 61196370 | – | chr11 | 61189080 | 61188862 | – | ENST00000450000; ENST00000449811; ENST00000413184; ENST00000536145 ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; | TSF |
| 13% | chr11 | 61196480 | 61196370 | – | chr11 | 61189080 | 61188862 | – | ENST00000450000; ENST00000449811; ENST00000413184; ENST00000536145 ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; | TSF |
| 13% | chr11 | 61196480 | 61196370 | – | chr11 | 61189080 | 61188862 | – | ENST00000450000; ENST00000449811; ENST00000413184; ENST00000536145 ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; | TSF |
| 12% | chr3 | 146238022 | 146237953 | – | chr3 | 146234951 | 146234793; 146234876; 146234936; 146234945 | – | ENST00000342435; ENST00000487389; ENST00000448787; ENST00000483300; ENST00000462666; ENST00000486631; ENST00000472349 | TAF |
| 12% | chr3 | 146238022 | 146237953 | – | chr3 | 146234951 | 146234793; 146234876; 146234936; 146234945 | – | ENST00000342435; ENST00000487389; ENST00000448787; ENST00000483300; ENST00000462666; ENST00000486631; ENST00000472349 | TAF |
| 12% | chr3 | 146238022 | 146237953 | – | chr3 | 146234951 | 146234793; 146234876; 146234936; 146234945 | – | ENST00000342435; ENST00000487389; ENST00000448787; ENST00000483300; ENST00000462666; ENST00000486631; ENST00000472349 | TAF |
| 12% | chr3 | 146238022 | 146237953 | – | chr3 | 146234951 | 146234793; 146234876; 146234936; 146234945 | – | ENST00000342435; ENST00000487389; ENST00000448787; ENST00000483300; ENST00000462666; ENST00000486631; ENST00000472349 | TAF |
| 12% | chr3 | 146238022 | 146237953 | – | chr3 | 146234951 | 146234793; 146234876; 146234936; 146234945 | – | ENST00000342435; ENST00000487389; ENST00000448787; ENST00000483300; ENST00000462666; ENST00000486631; ENST00000472349 | TAF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 12% | chr22 | 45064651 | 45064685 | + | chr22 | 45098488 | 45098488 | + | ENST00000403581; ENST00000336985; ENST00000403696; ENST00000431834; ENST00000361473; ENST00000352766; ENST00000517296 | TAF |
| 12% | chr22 | 45064651 | 45064685 | + | chr22 | 45098488 | 45098488 | + | ENST00000403581; ENST00000336985; ENST00000403696; ENST00000431834; ENST00000361473; ENST00000352766; ENST00000517296 | TAF |
| 12% | chr22 | 45064651 | 45064685 | + | chr22 | 45098488 | 45098488 | + | ENST00000403581; ENST00000336985; ENST00000403696; ENST00000431834; ENST00000361473; ENST00000352766; ENST00000517296 | TAF |
| 12% | chr22 | 45064651 | 45064685 | + | chr22 | 45098488 | 45098488 | + | ENST00000403581; ENST00000336985; ENST00000403696; ENST00000431834; ENST00000361473; ENST00000352766; ENST00000517296 | TAF |
| 12% | chr22 | 45064651 | 45064685 | + | chr22 | 45098488 | 45098488 | + | ENST00000403581; ENST00000336985; ENST00000403696; ENST00000431834; ENST00000361473; ENST00000352766; ENST00000517296 | TAF |
| 12% | chr17 | 79214190 | 79214239 | + | chr17 | 79214787 | 79214816; 79214953 | + | ENST00000431388; ENST00000576002 | TAF |
| 12% | chr17 | 79214190 | 79214239 | + | chr17 | 79214787 | 79214816; 79214953 | + | ENST00000431388; ENST00000576002 | TAF |
| 12% | chr10 | 3122429 | 3122494 | + | chr10 | 3124580 | 3124653 | + | ENST00000381125; ENST00000381075 | TAF |
| 12% | chr10 | 3122429 | 3122494 | + | chr10 | 3124580 | 3124653 | + | ENST00000381125; ENST00000381075 | TAF |
| 12% | chr2 | 242174499 | 242174121 | − | chr2 | 242173378 | 242173235; 242173268 | − | ENST00000391975; ENST00000391976; ENST00000310931; ENST00000427183; ENST00000373292 | TAF |
| 12% | chr2 | 242174499 | 242174121 | − | chr2 | 242173378 | 242173235; 242173268 | − | ENST00000391975; ENST00000391976; ENST00000310931; ENST00000427183; ENST00000373292 | TAF |
| 12% | chr2 | 161411930 | 161411748 | − | chr2 | 161223902 | 161223727 | − | ENST00000348849; ENST00000392753 | TAF |
| 12% | chr2 | 161411930 | 161411748 | − | chr2 | 161223902 | 161223727 | − | ENST00000348849; ENST00000392753 | TAF |
| 12% | chr3 | 69286305 | 69286248 | − | chr3 | 69273841 | 69273758; 69273834 | − | ENST00000398540; ENST00000542259; ENST00000493880; ENST00000473029; ENST00000460709 | TAF |
| 12% | chr3 | 69286305 | 69286248 | − | chr3 | 69273841 | 69273758; 69273834 | − | ENST00000398540; ENST00000542259; ENST00000493880; ENST00000473029; ENST00000460709 | TAF |
| 12% | chr3 | 69286305 | 69286248 | − | chr3 | 69273841 | 69273758; 69273834 | − | ENST00000398540; ENST00000542259; ENST00000493880; ENST00000473029; ENST00000460709 | TAF |
| 12% | chr3 | 69286305 | 69286248 | − | chr3 | 69273841 | 69273758; 69273834 | − | ENST00000398540; ENST00000542259; ENST00000493880; ENST00000473029; ENST00000460709 | TAF |
| 12% | chr19 | 39347374 | 39346430 | − | chr19 | 39338074 | 39337956 | − | ENST00000221419; ENST00000601449; ENST00000600233; ENST00000601813 | TSF |
| 12% | chr19 | 39347374 | 39346430 | − | chr19 | 39338074 | 39337956 | − | ENST00000221419; ENST00000601449; ENST00000600233; ENST00000601813 | TSF |
| 12% | chr19 | 39347374 | 39346430 | − | chr19 | 39338074 | 39337956 | − | ENST00000221419; ENST00000601449; ENST00000600233; ENST00000601813 | TSF |
| 12% | chrX | 151410500 | 151410406 | − | chrX | 151393317 | 151393235 | − | ENST00000370314; ENST00000535043 | TSF |
| 11% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 11% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 11% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 11% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 11% | chr22 | 37419605 | 37419606 | + | chr22 | 37420233 | 37420851 | + | ENST00000397129 | TAF |
| 11% | chr1 | 154190418 | 154190416 | − | chr1 | 154187050 | 154186933 | − | ENST00000368521; ENST00000362076; ENST00000350592; ENST00000368519; ENST00000368518; ENST00000368516 | TAF |
| 11% | chr1 | 154190418 | 154190416 | − | chr1 | 154187050 | 154186933 | − | ENST00000368521; ENST00000362076; ENST00000350592; ENST00000368519; ENST00000368518; ENST00000368516 | TAF |
| 11% | chr1 | 154190418 | 154190416 | − | chr1 | 154187050 | 154186933 | − | ENST00000368521; ENST00000362076; ENST00000350592; ENST00000368519; ENST00000368518; ENST00000368516 | TAF |
| 11% | chr15 | 41968651 | 41968463 | − | chr15 | 41815513 | 41815443 | − | ENST00000561603; ENST00000304330; | TAF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 11% | chr15 | 41968651 | 41968463 | − | chr15 | 41815513 | 41815443 | − | ENST00000561603; ENST00000304330; ENST00000562303 | TAF |
| 11% | chr15 | 41968651 | 41968463 | − | chr15 | 41815513 | 41815443 | − | ENST00000561603; ENST00000304330; ENST00000562303 | TAF |
| 11% | chr17 | 28178819 | 2879069 | + | chr17 | 2883581 | 2883659 | + | ENST00000540393; ENST00000254695; ENST00000366401; ENST00000542807 | TAF |
| 11% | chr2 | 99797199 | 90797170 | − | chr2 | 99790479 | 99790378 | − | ENST00000422537; ENST00000289359; ENST00000409107 | TAF |
| 11% | chr2 | 99797199 | 90797170 | − | chr2 | 99790479 | 99790378 | − | ENST00000422537; ENST00000289359; ENST00000409107 | TAF |
| 11% | chr8 | 74871473 | 74871320 | − | chr8 | 74868289 | 74868146 | − | ENST00000602840; ENST00000518127; ENST00000520242; ENST00000519487; ENST00000284811; ENST00000522337; ENST00000523815; ENST00000519082 | TAF |
| 11% | chr8 | 74871473 | 74871320 | − | chr8 | 74868289 | 74868146 | − | ENST00000602840; ENST00000518127; ENST00000520242; ENST00000519487; ENST00000284811; ENST00000522337; ENST00000523815; ENST00000519082 | TAF |
| 11% | chr8 | 74871473 | 74871320 | − | chr8 | 74868289 | 74868146 | − | ENST00000602840; ENST00000518127; ENST00000520242; ENST00000519487; ENST00000284811; ENST00000522337; ENST00000523815; ENST00000519082 | TAF |
| 11% | chr9 | 130213440 | 130213384 | − | chr9 | 130213083 | 130213010 | − | ENST00000361436; ENST00000536368 | TAF |
| 11% | chr9 | 130213440 | 130213384 | − | chr9 | 130213083 | 130213010 | − | ENST00000361436; ENST00000536368 | TAF |
| 11% | chr6 | 24710791 | 24710723 | − | chr6 | 24709139 | 24709005 | − | ENST00000378119; ENST00000540769; ENST00000378102 | TAF |
| 11% | chr9 | 131002678 | 131002811 | + | chr9 | 131004511 | 131004624 | + | ENST00000475805; ENST00000341179; ENST00000372923; ENST00000393594; ENST00000486160 | TAF |
| 11% | chr9 | 131002678 | 131002811 | + | chr9 | 131004511 | 131004624 | + | ENST00000475805; ENST00000341179; ENST00000372923; ENST00000393594; ENST00000486160 | TAF |
| 10% | chr16 | 603045 | 603077 | + | chr16 | 603343 | 603516 | + | ENST00000219611 | TAF |
| 10% | chr16 | 603045 | 603077 | + | chr16 | 603343 | 603516 | + | ENST00000219611 | TAF |
| 10% | chr16 | 29915789 | 29915910 | + | chr16 | 29916173 | 29916286 | + | ENST00000563177; ENST00000483405; ENST00000308748; ENST00000414952; ENST00000566693 | TAF |
| 10% | chr16 | 29915789 | 29915910 | + | chr16 | 29916173 | 29916286 | + | ENST00000563177; ENST00000483405; ENST00000308748; ENST00000414952; ENST00000566693 | TAF |
| 9% | chr9 | 130921922 | 130922014 | + | chr9 | 130925722 | 130925894 | + | ENST00000372994 | TSF |
| 9% | chr9 | 140122334 | 140122359 | + | chr9 | 140123074 | 140123538 | + | ENST00000445101 | TSF |
| 9% | chr10 | 74437735 | 35744391 | + | chr10 | 35772332 | 35772406 | + | ENST00000374704 | TSF |
| 8% | chr11 | 60978221 | 60978370 | + | chr11 | 60978562 | 60978706 | + | ENST00000325558; ENST00000543505; ENST00000543125 | TSF |
| 8% | chr11 | 60978221 | 60978370 | + | chr11 | 60978562 | 60978706 | + | ENST00000325558; ENST00000543505; ENST00000543125 | TSF |
| 8% | chr11 | 99705060 | 60997199 | + | chr11 | 60997391 | 60997535 | + | ENST00000378149; ENST00000537932 | TSF |
| 8% | chr2 | 19182928 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 8% | chr2 | 19182928 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 8% | chr2 | 19182928 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 8% | chr2 | 19182928 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 8% | chr2 | 19182928 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 8% | chr2 | 19182928 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 8% | chrX | 495405313 | 134953756 | − | chrX | 134950187 | 134950078 | − | ENST00000420087; ENST00000463085; ENST00000370724; ENST00000491480 | TSF |
| 8% | chrX | 495405313 | 134953756 | − | chrX | 134950187 | 134950078 | − | ENST00000420087; ENST00000463085; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 7% | chr12 | 53835137 | 53835233 | + | chr12 | 53836479 | 53836517 | + | ENST00000370724; ENST00000491480 ENST00000547368 | TSF |
| 7% | chr15 | 74004214 | 74004264 | + | chr15 | 74005275 | 74005297 | + | ENST00000318443; ENST00000537340; ENST00000318424; ENST00000564751; ENST00000561176; ENST00000559073 | TSF |
| 7% | chr2 | 135414144 | 135414047 | − | chr2 | 135308232 | 135308141 | − | ENST00000281924 | TSF |
| 7% | chr19 | 17551333 | 1755123517 | − | chr19 | 171547736 | 17547267; | − | ENST00000341130; ENST00000594663 | TSF |
| 7% | chr19 | 17551333 | 1755123517 | − | chr19 | 171547736 | 17547267; | − | ENST00000341130; ENST00000594663 | TSF |
| 7% | chr7 | 66386440 | 66386448 | + | chr7 | 66409963 | 66410248; 66410147; 66410019; 66410221; 66410085 | + | ENST00000341567; ENST00000607045; ENST00000433271; ENST00000413593; ENST00000424964; ENST00000418375 | TSF |
| 7% | chr7 | 66386440 | 66386448 | + | chr7 | 66409963 | 66410248; 66410147; 66410019; 66410221; 66410085 | + | ENST00000341567; ENST00000607045; ENST00000433271; ENST00000413593; ENST00000424964; ENST00000418375 | TSF |
| 7% | chr7 | 66386440 | 66386448 | + | chr7 | 66409963 | 66410248; 66410147; 66410019; 66410221; 66410085 | + | ENST00000341567; ENST00000607045; ENST00000433271; ENST00000413593; ENST00000424964; ENST00000418375 | TSF |
| 7% | chr7 | 66386440 | 66386448 | + | chr7 | 66409963 | 66410248; 66410147; 66410019; 66410221; 66410085 | + | ENST00000341567; ENST00000607045; ENST00000433271; ENST00000413593; ENST00000424964; ENST00000418375 | TSF |
| 7% | chr7 | 66386440 | 66386448 | + | chr7 | 66409963 | 66410248; 66410147; 66410019; 66410221; 66410085 | + | ENST00000341567; ENST00000607045; ENST00000433271; ENST00000413593; ENST00000424964; ENST00000418375 | TSF |
| 7% | chr7 | 66386440 | 66386448 | + | chr7 | 66409963 | 66410248; 66410147; 66410019; 66410221; 66410085 | + | ENST00000341567; ENST00000607045; ENST00000433271; ENST00000413593; ENST00000424964; ENST00000418375 | TSF |
| 7% | chr10 | 116126443 | 116126388 | − | chr10 | 116100490 | 116100362 | − | ENST00000304129; ENST00000369271; ENST00000545353; ENST00000419268 | TSF |
| 7% | chr10 | 116126443 | 116126388 | − | chr10 | 116100490 | 116100362 | − | ENST00000304129; ENST00000369271; ENST00000545353; ENST00000419268 | TSF |
| 7% | chr10 | 116126443 | 116126388 | − | chr10 | 116100490 | 116100362 | − | ENST00000304129; ENST00000369271; ENST00000545353; ENST00000419268 | TSF |
| 7% | chr10 | 116126443 | 116126388 | − | chr10 | 116100490 | 116100362 | − | ENST00000304129; ENST00000369271; ENST00000545353; ENST00000419268 | TSF |
| 7% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 7% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 7% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 7% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 7% | chrX | 134971303 | 134971306 | − | chrX | 134950187 | 134950078 | − | ENST00000420087; ENST00000463085; ENST00000370724; ENST00000491480 | TSF |
| 7% | chrX | 134971303 | 134971306 | − | chrX | 134950187 | 134950078 | − | ENST00000420087; ENST00000463085; ENST00000370724; ENST00000491480 | TSF |
| 7% | chrX | 134971303 | 134971306 | − | chrX | 134950187 | 134950078 | − | ENST00000420087; ENST00000463085; ENST00000370724; ENST00000491480 | TSF |
| 7% | chrX | 134971303 | 134971006 | − | chrX | 134967437 | 134967328 | − | ENST00000491002; ENST00000448053; ENST00000472834 | TSF |
| 7% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 7% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 7% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 7% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 7% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 7% | chr11 | 47013185 | 47013198 | + | chr11 | 47073939 | 47074069 | + | ENST00000528488; ENST00000278460; ENST00000378618; ENST00000395460; ENST00000378615; ENST00000525895 | TSF |
| 6% | chr7 | 33006587 | 33006627 | + | chr7 | 33014229 | 33014374 | + | ENST00000242209; ENST00000538336 | TSF |
| 6% | chr1 | 111960622 | 111960373 | − | chr1 | 111959080 | 111958945; 111959068 | − | ENST00000369732; ENST00000540696 | TSF |
| 6% | chr1 | 111960622 | 111960373 | − | chr1 | 111959080 | 111958945; 111959068 | − | ENST00000369732; ENST00000540696 | TSF |
| 6% | chrX | 134883429 | 134883726 | + | chrX | 134887292 | 134887401 | + | ENST00000370734; ENST00000485366; ENST00000443882 | TSF |
| 6% | chr14 | 105172936 | 105173038 | + | chr14 | 105173247 | 105173388 | + | ENST00000330634; ENST00000392634 | TSF |
| 6% | chr14 | 105172936 | 105173038 | + | chr14 | 105173247 | 105173388 | + | ENST00000330634; ENST00000392634 | TSF |
| 6% | chr3 | 100461913 | 100462018 | + | chr3 | 100463677 | 100463775 | + | ENST00000418917; ENST00000490574; ENST00000240851; ENST00000476228 | TSF |
| 6% | chr20 | 60878087 | 60878105 | + | chr20 | 60882884 | 60882884 | + | ENST00000253003 | TSF |
| 6% | chr16 | 21060024 | 21059927 | − | chr16 | 21053525 | 21053349 | − | ENST00000261383; ENST00000415178 | TSF |
| 6% | chr16 | 21060024 | 21059927 | − | chr16 | 21053525 | 21053349 | − | ENST00000261383; ENST00000415178 | TSF |
| 6% | chr1 | 33270876 | 33270146 | − | chr1 | 33263444 | 33263364 | − | ENST00000373477 | TSF |
| 6% | chrX | 134954053 | 134953756 | − | chrX | 134932924 | 134932815 | − | ENST00000487941; ENST00000434966; ENST00000494421 | TSF |
| 6% | chr14 | 24686795 | 24686695 | − | chr14 | 24686429 | 24686392; 24686333 | − | ENST00000605847; ENST00000250495 | TSF |
| 6% | chr14 | 24686795 | 24686695 | − | chr14 | 24686429 | 24686392; 24686333 | − | ENST00000605847; ENST00000250495 | TSF |
| 6% | chr17 | 42400590 | 42400540 | − | chr17 | 42400220 | 42400176 | − | ENST00000225308; ENST00000377095; ENST00000590194; ENST00000588049; ENST00000586633; ENST00000592857; ENST00000585523 | TSF |
| 6% | chr17 | 42400590 | 42400540 | − | chr17 | 42400220 | 42400176 | − | ENST00000225308; ENST00000377095; ENST00000590194; ENST00000588049; ENST00000586633; ENST00000592857; ENST00000585523 | TSF |
| 6% | chr17 | 42400590 | 42400540 | − | chr17 | 42400220 | 42400176 | − | ENST00000225308; ENST00000377095; ENST00000590194; ENST00000588049; ENST00000586633; ENST00000592857; ENST00000585523 | TSF |
| 6% | chr17 | 42400590 | 42400540 | − | chr17 | 42400220 | 42400176 | − | ENST00000225308; ENST00000377095; ENST00000590194; ENST00000588049; ENST00000586633; ENST00000592857; ENST00000585523 | TSF |
| 6% | chr17 | 42400590 | 42400540 | − | chr17 | 42400220 | 42400176 | − | ENST00000225308; ENST00000377095; ENST00000590194; ENST00000588049; ENST00000586633; ENST00000592857; ENST00000585523 | TSF |
| 6% | chr17 | 42400590 | 42400540 | − | chr17 | 42400220 | 42400176 | − | ENST00000225308; ENST00000377095; ENST00000590194; ENST00000588049; ENST00000586633; ENST00000592857; ENST00000585523 | TSF |
| 6% | chrX | 134936794 | 134936497 | − | chrX | 134932924 | 134932815 | − | ENST00000487941; ENST00000434966; ENST00000494421 | TSF |
| 6% | chr17 | 39976225 | 39976301 | + | chr17 | 39976521 | 39976713 | + | ENST00000321562; ENST00000455106; ENST00000544340 | TSF |
| 5% | chr5 | 31298457 | 31298554 | + | chr5 | 31299571 | 31299738 | + | ENST00000514738; ENST00000265071 | TSF |
| 5% | chr5 | 31298457 | 31298554 | + | chr5 | 31299571 | 31299738 | + | ENST00000514738; ENST00000265071 | TSF |
| 5% | chr11 | 77945120 | 77945089 | − | chr11 | 77938097 | 77937511 | − | ENST00000340149; ENST00000361507 | TSF |
| 5% | chrX | 134866155 | 134866452 | + | chrX | 134870023 | 134870132 | + | ENST00000370736; ENST00000471213; ENST00000495729 | TSF |
| 5% | chr13 | 114996946 | 114997117 | + | chr13 | 115002120 | 115002174 | + | ENST00000360383; ENST00000356221; ENST00000252457 | TSF |
| 5% | chr13 | 114996946 | 114997117 | + | chr13 | 115002120 | 115002174 | + | ENST00000360383; ENST00000356221; ENST00000252457 | TSF |
| 5% | chr17 | 78344149 | 78344187 | + | chr17 | 78345674 | 78345785 | + | ENST00000508628; ENST00000582970; ENST00000336301 | TSF |
| 5% | chr8 | 125535738 | 125535448 | − | chr8 | 125535243 | 125535178 | − | ENST00000276692; ENST00000523214; ENST00000522810; ENST00000519776; ENST00000605953; ENST00000522310; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr8 | 125535738 | 125535448 | – | chr8 | 125535243 | 125535178 | – | ENST00000519232 ENST00000276692; ENST00000523214; ENST00000522810; ENST00000519776; ENST00000605953; ENST00000522310; ENST00000519232 | TSF |
| 5% | chr8 | 125535738 | 125535448 | – | chr8 | 125535243 | 125535178 | – | ENST00000276692; ENST00000523214; ENST00000522810; ENST00000519776; ENST00000605953; ENST00000522310; ENST00000519232 | TSF |
| 5% | chr8 | 125535738 | 125535448 | – | chr8 | 125535243 | 125535178 | – | ENST00000276692; ENST00000523214; ENST00000522810; ENST00000519776; ENST00000605953; ENST00000522310; ENST00000519232 | TSF |
| 5% | chr8 | 125535738 | 125535448 | – | chr8 | 125535243 | 125535178 | – | ENST00000276692; ENST00000523214; ENST00000522810; ENST00000519776; ENST00000605953; ENST00000522310; ENST00000519232 | TSF |
| 5% | chr8 | 125535738 | 125535448 | – | chr8 | 125535243 | 125535178 | – | ENST00000276692; ENST00000523214; ENST00000522810; ENST00000519776; ENST00000605953; ENST00000522310; ENST00000519232 | TSF |
| 5% | chr8 | 125535738 | 125535448 | – | chr8 | 125535243 | 125535178 | – | ENST00000276692; ENST00000523214; ENST00000522810; ENST00000519776; ENST00000605953; ENST00000522310; ENST00000519232 | TSF |
| 5% | chr21 | 34902064 | 34901873 | – | chr21 | 34901243 | 34901156 | – | ENST00000381815; ENST00000381831; ENST00000381839; ENST00000424203; ENST00000361093 | TSF |
| 5% | chr21 | 34902064 | 34901873 | – | chr21 | 34901243 | 34901156 | – | ENST00000381815; ENST00000381831; ENST00000381839; ENST00000424203; ENST00000361093 | TSF |
| 5% | chr21 | 34902064 | 34901873 | – | chr21 | 34901243 | 34901156 | – | ENST00000381815; ENST00000381831; ENST00000381839; ENST00000424203; ENST00000361093 | TSF |
| 5% | chr3 | 150463581 | 150463483 | – | chr3 | 150460485 | 150459928; 150460275 | – | ENST00000312960; ENST00000482706 | TSF |
| 5% | chr3 | 150463581 | 150463483 | – | chr3 | 150460485 | 150459928; 150460275 | – | ENST00000312960; ENST00000482706 | TSF |
| 5% | chr17 | 66244121 | 66244199 | + | chr17 | 66244785 | 66244846 | + | ENST00000584837 | TSF |
| 5% | chrX | 134866155 | 134866452 | + | chrX | 134887292 | 134887401 | + | ENST00000370734; ENST00000485366; ENST00000443882 | TSF |
| 5% | chr17 | 42149044 | 42149179 | + | chr17 | 42151528 | 42151634; 42151597 | + | ENST00000269097; ENST00000591696 | TSF |
| 5% | chr17 | 42149044 | 42149179 | + | chr17 | 42151528 | 42151634; 42151597 | + | ENST00000269097; ENST00000591696 | TSF |
| 5% | chr22 | 21972574 | 21972670 | + | chr22 | 21975804 | 21975958 | + | ENST00000458578; ENST00000342192; ENST00000545681 | TSF |
| 5% | chr10 | 12277215 | 12277329 | + | chr10 | 12279143 | 12279265; 12279223 | + | ENST00000281141; ENST00000442050; ENST00000440613 | TSF |
| 5% | chr10 | 12277215 | 12277329 | + | chr10 | 12279143 | 12279265; 12279223 | + | ENST00000281141; ENST00000442050; ENST00000440613 | TSF |
| 5% | chr10 | 12277215 | 12277329 | + | chr10 | 12279143 | 12279265; 12279223 | + | ENST00000281141; ENST00000442050; ENST00000440613 | TSF |
| 5% | chr4 | 56493122 | 29564923 | – | chr4 | 56482552 | 56482505 | – | ENST00000264218; ENST00000505262; ENST00000507338 | TSF |
| 5% | chr4 | 56493122 | 29564923 | – | chr4 | 56482552 | 56482505 | – | ENST00000264218; ENST00000505262; ENST00000507338 | TSF |
| 5% | chr4 | 56493122 | 29564923 | – | chr4 | 56482552 | 56482505 | – | ENST00000264218; ENST00000505262; ENST00000507338 | TSF |
| 5% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 5% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 5% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 5% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 5% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 5% | chr19 | 11528445 | 11528379 | – | chr19 | 11527733 | 11527510 | – | ENST00000562663; ENST00000563726; ENST00000380456; ENST00000393423; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr11 | 60934781 | 60933962 | − | chr11 | 60901679 | 60901508 | − | ENST00000567431; ENST00000567080 ENST00000301765; ENST00000538036 | TSF |
| 5% | chr11 | 60934781 | 60933962 | − | chr11 | 60901679 | 60901508 | − | ENST00000301765; ENST00000538036 | TSF |
| 5% | chr1 | 156716197 | 156716133 | − | chr1 | 156715165 | 156715089 | − | ENST00000357325; ENST00000537739; ENST00000368209; ENST00000368206 | TSF |
| 5% | chr2 | 27667813 | 27667765 | − | chr2 | 27667388 | 27667299 | − | ENST00000260570 | TSF |
| 5% | chr1 | 33593993 | 33594050 | + | chr1 | 33741701 | 33741764 | + | ENST00000539719; ENST00000373428 | TSF |
| 5% | chr20 | 62631560 | 62631735 | + | chr20 | 62632430 | 62632592 | + | ENST00000535781; ENST00000266079 | TSF |
| 5% | chr20 | 62631560 | 62631735 | + | chr20 | 62632430 | 62632592 | + | ENST00000535781; ENST00000266079 | TSF |
| 5% | chr5 | 64050585 | 64050405 | − | chr5 | 64050189 | 64050142 | − | ENST00000513458 | TSF |
| 4% | chr19 | 45365391 | 45365456 | + | chr19 | 45368528 | 45368917 | + | ENST00000252485; ENST00000252483 | TSF |
| 4% | chr19 | 45365391 | 45365456 | + | chr19 | 45368528 | 45368917 | + | ENST00000252485; ENST00000252483 | TSF |
| 4% | chr6 | 31941780 | 31941829 | + | chr6 | 31946680 | 31946775; 31946787; 31946759 | + | ENST00000375331; ENST00000375333; ENST00000483801; ENST00000519179 | TSF |
| 4% | chr6 | 31941780 | 31941829 | + | chr6 | 31946680 | 31946775; 31946787; 31946759 | + | ENST00000375331; ENST00000375333; ENST00000483801; ENST00000519179 | TSF |
| 4% | chr6 | 31941780 | 31941829 | + | chr6 | 31946680 | 31946775; 31946787; 31946759 | + | ENST00000375331; ENST00000375333; ENST00000483801; ENST00000519179 | TSF |
| 4% | chr19 | 13880454 | 13880520 | + | chr19 | 13882935 | 13883095 | + | ENST00000319545; ENST00000040663 | TSF |
| 4% | chr1 | 165854440 | 165854616 | + | chr1 | 165859441 | 165859600 | + | ENST00000367879; ENST00000372212 | TSF |
| 4% | chr1 | 165854440 | 165854616 | + | chr1 | 165859441 | 165859600 | + | ENST00000367879; ENST00000372212 | TSF |
| 4% | chr9 | 35790327 | 35790337 | + | chr9 | 35799615 | 35799728 | + | ENST00000342694 | TSF |
| 4% | chr9 | 140499260 | 140499389 | + | chr9 | 140507348 | 140507458; 140507601 | + | ENST00000371421; ENST00000431925; ENST00000461627; ENST00000419386 | TSF |
| 4% | chr9 | 140499260 | 140499389 | + | chr9 | 140507348 | 140507458; 140507601 | + | ENST00000371421; ENST00000431925; ENST00000461627; ENST00000419386 | TSF |
| 4% | chr9 | 140499260 | 140499389 | + | chr9 | 140507348 | 140507458; 140507601 | + | ENST00000371421; ENST00000431925; ENST00000461627; ENST00000419386 | TSF |
| 4% | chr9 | 140499260 | 140499389 | + | chr9 | 140507348 | 140507458; 140507601 | + | ENST00000371421; ENST00000431925; ENST00000461627; ENST00000419386 | TSF |
| 4% | chr19 | 51464315 | 51464269 | − | chr19 | 51462572 | 51462420; 51462407 | − | ENST00000376851; ENST00000310157; ENST00000391808; ENST00000456750; ENST00000376853; ENST00000594641 | TSF |
| 4% | chr19 | 51464315 | 51464269 | − | chr19 | 51462572 | 51462420; 51462407 | − | ENST00000376851; ENST00000310157; ENST00000391808; ENST00000456750; ENST00000376853; ENST00000594641 | TSF |
| 4% | chr2 | 135414144 | 135414047 | − | chr2 | 135309662 | 135309619 | − | ENST00000281924 | TSF |
| 4% | chr14 | 105944002 | 105944196 | + | chr14 | 105944603 | 105944697 | + | ENST00000483017; ENST00000329146 | TSF |
| 4% | chr1 | 15562769 | 15563257 | + | chr1 | 15578267 | 15578373 | + | ENST00000433640 | TSF |
| 4% | chr11 | 66219706 | 66219444 | − | chr11 | 66205730 | 66205635 | − | ENST00000310999; ENST00000430466; ENST00000534488; ENST00000329819 | TSF |
| 4% | chr11 | 66219706 | 66219444 | − | chr11 | 66205730 | 66205635 | − | ENST00000310999; ENST00000430466; ENST00000534488; ENST00000329819 | TSF |
| 4% | chr11 | 66219706 | 66219444 | − | chr11 | 66205730 | 66205635 | − | ENST00000310999; ENST00000430466; ENST00000534488; ENST00000329819 | TSF |
| 4% | chr11 | 15114123 | 15112973 | − | chr6 | 32497961 | 32497902 | − | ENST00000374975 | TSF |
| 4% | chr20 | 32693720 | 32693709 | − | chr20 | 32693351 | 32693174 | − | ENST00000374980 | TSF |
| 4% | chr18 | 51273 | 49727 | − | chr18 | 49237 | 49129 | − | ENST00000308911 | TSF |
| 4% | chr19 | 50167252 | 50167184 | − | chr19 | 50166771 | 50166600; 50166728; 50166630 | − | ENST00000309877; ENST00000600911; ENST00000601291; ENST00000377139; ENST00000597198; ENST00000597636; ENST00000599223; ENST00000377135; ENST00000596756; ENST00000598108; ENST00000593337; ENST00000601809; ENST00000596788; ENST00000600453 | TSF |
| 4% | chr19 | 50167252 | 50167184 | − | chr19 | 50166771 | 50166600; 50166728; 50166630 | − | ENST00000309877; ENST00000600911; ENST00000601291; ENST00000377139; ENST00000597198; ENST00000597636; ENST00000599223; ENST00000377135; ENST00000596756; ENST00000598108; ENST00000593337; ENST00000601809; ENST00000596788; ENST00000600453 | TSF |
| 4% | chr19 | 50167252 | 50167184 | − | chr19 | 50166771 | 50166600; 50166728; 50166630 | − | ENST00000309877; ENST00000600911; ENST00000601291; ENST00000377139; ENST00000597198; ENST00000597636; ENST00000599223; ENST00000377135; ENST00000596756; ENST00000598108; ENST00000593337; ENST00000601809; ENST00000596788; ENST00000600453 | TSF |
| 4% | chr19 | 50167252 | 50167184 | − | chr19 | 50166771 | 50166600; 50166728; 50166630 | − | ENST00000309877; ENST00000600911; ENST00000601291; ENST00000377139; ENST00000597198; ENST00000597636; ENST00000599223; ENST00000377135; | |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr19 | 50167252 | 50167184 | − | chr19 | 50166771 | 50166600; 50166728; 50166630 | − | ENST00000596756; ENST00000598108; ENST00000593337; ENST00000601809; ENST00000596788; ENST00000600453 ENST00000309877; ENST00000600911; ENST00000601291; ENST00000377139; ENST00000597198; ENST00000597636; ENST00000599223; ENST00000377135; | TSF |
| 4% | chr19 | 50167252 | 50167184 | − | chr19 | 50166771 | 50166600; 50166728; 50166630 | − | ENST00000596756; ENST00000598108; ENST00000593337; ENST00000601809; ENST00000596788; ENST00000600453 ENST00000309877; ENST00000600911; ENST00000601291; ENST00000377139; ENST00000597198; ENST00000597636; ENST00000599223; ENST00000377135; | TSF |
| 4% | chr19 | 50167252 | 50167184 | − | chr19 | 50166771 | 50166600; 50166728; 50166630 | − | ENST00000596756; ENST00000598108; ENST00000593337; ENST00000601809; ENST00000596788; ENST00000600453 ENST00000309877; ENST00000600911; ENST00000601291; ENST00000377139; ENST00000597198; ENST00000597636; ENST00000599223; ENST00000377135; | TSF |
| 4% | chr19 | 50167252 | 50167184 | − | chr19 | 50166771 | 50166600; 50166728; 50166630 | − | ENST00000596756; ENST00000598108; ENST00000593337; ENST00000601809; ENST00000596788; ENST00000600453 ENST00000309877; ENST00000600911; ENST00000601291; ENST00000377139; ENST00000597198; ENST00000597636; ENST00000599223; ENST00000377135; | TSF |
| 4% | chr19 | 50167252 | 50167184 | − | chr19 | 50166771 | 50166600; 50166728; 50166630 | − | ENST00000596756; ENST00000598108; ENST00000593337; ENST00000601809; ENST00000596788; ENST00000600453 ENST00000309877; ENST00000600911; ENST00000601291; ENST00000377139; ENST00000597198; ENST00000597636; ENST00000599223; ENST00000377135; | TSF |
| 4% | chr19 | 50167252 | 50167184 | − | chr19 | 50166771 | 50166600; 50166728; 50166630 | − | ENST00000596756; ENST00000598108; ENST00000593337; ENST00000601809; ENST00000596788; ENST00000600453 ENST00000309877; ENST00000600911; ENST00000601291; ENST00000377139; ENST00000597198; ENST00000597636; ENST00000599223; ENST00000377135; | TSF |
| 4% | chr19 | 50167252 | 50167184 | − | chr19 | 50166771 | 50166600; 50166728; 50166630 | − | ENST00000596756; ENST00000598108; ENST00000593337; ENST00000601809; ENST00000596788; ENST00000600453 ENST00000309877; ENST00000600911; ENST00000601291; ENST00000377139; ENST00000597198; ENST00000597636; ENST00000599223; ENST00000377135; | TSF |
| 4% | chr2 | 25015386 | 25015253 | − | chr2 | 25013450 | 25013280 | − | ENST00000328379 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 4% | chr12 | 120877048 | 120877098 | + | chr12 | 120878257 | 120878340 | + | ENST00000229379 | TSF |
| 4% | chr20 | 57466589 | 57466605 | + | chr20 | 57480438 | 57480535 | + | ENST00000371100; ENST00000371102; ENST00000450130; ENST00000349036; ENST00000604005; ENST00000371095; ENST00000354359; ENST00000371085; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr20 | 57466589 | 57466605 | + | chr20 | 57480438 | 57480535 | + | ENST00000265620; ENST00000306090; ENST00000603546 ENST00000371100; ENST00000371102; ENST00000450130; ENST00000349036; ENST00000604005; ENST00000371095; ENST00000354359; ENST00000371085; | TSF |
| 4% | chr20 | 57466589 | 57466605 | + | chr20 | 57480438 | 57480535 | + | ENST00000265620; ENST00000306090; ENST00000603546 ENST00000371100; ENST00000371102; ENST00000450130; ENST00000349036; ENST00000604005; ENST00000371095; ENST00000354359; ENST00000371085; | TSF |
| 4% | chr20 | 57466589 | 57466605 | + | chr20 | 57480438 | 57480535 | + | ENST00000265620; ENST00000306090; ENST00000603546 ENST00000371100; ENST00000371102; ENST00000450130; ENST00000349036; ENST00000604005; ENST00000371095; ENST00000354359; ENST00000371085; | TSF |
| 4% | chr20 | 57466589 | 57466605 | + | chr20 | 57480438 | 57480535 | + | ENST00000265620; ENST00000306090; ENST00000603546 ENST00000371100; ENST00000371102; ENST00000450130; ENST00000349036; ENST00000604005; ENST00000371095; ENST00000354359; ENST00000371085; | TSF |
| 4% | chr19 | 35760074 | 35760261 | + | chr19 | 35760349 | 35760395; 35760602 | + | ENST00000343550; ENST00000222305; ENST00000595068; ENST00000379134; ENST00000602164; ENST00000594064; ENST00000598058 | TSF |
| 4% | chr19 | 35760074 | 35760261 | + | chr19 | 35760349 | 35760395; 35760602 | + | ENST00000343550; ENST00000222305; ENST00000595068; ENST00000379134; ENST00000602164; ENST00000594064; ENST00000598058 | TSF |
| 4% | chr19 | 35760074 | 35760261 | + | chr19 | 35760349 | 35760395; 35760602 | + | ENST00000343550; ENST00000222305; ENST00000595068; ENST00000379134; ENST00000602164; ENST00000594064; ENST00000598058 | TSF |
| 4% | chr19 | 35760074 | 35760261 | + | chr19 | 35760349 | 35760395; 35760602 | + | ENST00000343550; ENST00000222305; ENST00000595068; ENST00000379134; ENST00000602164; ENST00000594064; ENST00000598058 | TSF |
| 4% | chr19 | 35760074 | 35760261 | + | chr19 | 35760349 | 35760395; 35760602 | + | ENST00000343550; ENST00000222305; ENST00000595068; ENST00000379134; ENST00000602164; ENST00000594064; ENST00000598058 | TSF |
| 4% | chr19 | 35760074 | 35760261 | + | chr19 | 35760349 | 35760395; 35760602 | + | ENST00000343550; ENST00000222305; ENST00000595068; ENST00000379134; ENST00000602164; ENST00000594064; ENST00000598058 | TSF |
| 4% | chr11 | 32453241 | 32453188 | − | chr11 | 32450165 | 32450043 | − | ENST00000379079; ENST00000379077; ENST00000332351; ENST00000530998; ENST00000452863; ENST00000448076 | TSF |
| 4% | chr11 | 32453241 | 32453188 | − | chr11 | 32450165 | 32450043 | − | ENST00000379079; ENST00000379077; ENST00000332351; ENST00000530998; ENST00000452863; ENST00000448076 | TSF |
| 4% | chr11 | 32453241 | 32453188 | − | chr11 | 32450165 | 32450043 | − | ENST00000379079; ENST00000379077; ENST00000332351; ENST00000530998; ENST00000452863; ENST00000448076 | TSF |
| 4% | chr11 | 32453241 | 32453188 | − | chr11 | 32450165 | 32450043 | − | ENST00000379079; ENST00000379077; ENST00000332351; ENST00000530998; ENST00000452863; ENST00000448076 | TSF |
| 4% | chr11 | 32453241 | 32453188 | − | chr11 | 32450165 | 32450043 | − | ENST00000379079; ENST00000379077; ENST00000332351; ENST00000530998; ENST00000452863; ENST00000448076 | TSF |
| 4% | chrX | 134971303 | 134971006 | − | chrX | 134932924 | 134932815 | − | ENST00000487941; ENST00000434966; ENST00000494421 | TSF |
| 4% | chr22 | 29194595 | 29194546 | − | chr22 | 29193193 | 29193065 | − | ENST00000216037; ENST00000403532; ENST00000405219; ENST00000344347 | TSF |
| 4% | chr22 | 29194595 | 29194546 | − | chr22 | 29193193 | 29193065 | − | ENST00000216037; ENST00000403532; ENST00000405219; ENST00000344347 | TSF |
| 4% | chr1 | 206278006 | 206277067 | − | chr1 | 206243250 | 206243150 | − | ENST00000331555 | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr13 | 43628887 | 43629679 | + | chr13 | 43681314 | 43681384 | + | ENST00000379221 | TSF |
| 4% | chr5 | 175697409 | 175697523 | + | chr5 | 175716657 | 175717958 | + | ENST00000443967; ENST00000429602 | TSF |
| 4% | chr5 | 175697409 | 175697523 | + | chr5 | 175716657 | 175717958 | + | ENST00000443967; ENST00000429602 | TSF |
| 4% | chr14 | 105944002 | 105944027 | + | chr14 | 105944603 | 105944697 | + | ENST00000483017; ENST00000329146 | TSF |
| 4% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 4% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 4% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 4% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 4% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 4% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 4% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 4% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 4% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 4% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 4% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 4% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 4% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 4% | chr16 | 28836248 | 28836298 | + | chr16 | 28836687 | 28836723 | + | ENST00000340394; ENST00000325215; ENST00000336783; ENST00000382686; ENST00000395547; ENST00000564304; ENST00000570200; ENST00000568266 | TSF |
| 4% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 4% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 4% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 4% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 4% | chr20 | 34133027 | 34133127 | + | chr20 | 34135163 | 34135256 | + | ENST00000348547; ENST00000357394; ENST00000279052; ENST00000447986; ENST00000416206; ENST00000413587 | TSF |
| 4% | chr20 | 34133027 | 34133127 | + | chr20 | 34135163 | 34135256 | + | ENST00000348547; ENST00000357394; ENST00000279052; ENST00000447986; ENST00000416206; ENST00000413587 | TSF |
| 4% | chr20 | 34133027 | 34133127 | + | chr20 | 34135163 | 34135256 | + | ENST00000348547; ENST00000357394; ENST00000279052; ENST00000447986; ENST00000416206; ENST00000413587 | TSF |
| 4% | chr20 | 34133027 | 34133127 | + | chr20 | 34135163 | 34135256 | + | ENST00000348547; ENST00000357394; ENST00000279052; ENST00000447986; ENST00000416206; ENST00000413587 | TSF |
| 4% | chr20 | 34133027 | 34133127 | + | chr20 | 34135163 | 34135256 | + | ENST00000348547; ENST00000357394; ENST00000279052; ENST00000447986; ENST00000416206; ENST00000413587 | TSF |
| 4% | chr10 | 133791239 | 133791188 | − | chr10 | 133787447 | 133787297 | − | ENST00000368636; ENST00000540159 | TSF |
| 4% | chr10 | 133791239 | 133791188 | − | chr10 | 133787447 | 133787297 | − | ENST00000368636; ENST00000540159 | TSF |
| 4% | chr17 | 72951257 | 72951178 | − | chr17 | 72950460 | 72950233 | − | ENST00000425042 | TSF |
| 4% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 4% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 4% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 4% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 4% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 4% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 4% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 3% | chr21 | 46927878 | 46927878 | + | chr21 | 46929270 | 46929515 | + | ENST00000400337; ENST00000355480; ENST00000359759; ENST00000342220; ENST00000423214 | TSF |
| 3% | chr21 | 46927878 | 46927878 | + | chr21 | 46929270 | 46929515 | + | ENST00000400337; ENST00000355480; ENST00000359759; ENST00000342220; ENST00000423214 | TSF |
| 3% | chr7 | 148982749 | 148982787 | + | chr7 | 148984656 | 148984699; 148984867 | + | ENST00000378052; ENST00000476295; ENST00000418158 | TSF |
| 3% | chr7 | 148982749 | 148982787 | + | chr7 | 148984656 | 148984699; 148984867 | + | ENST00000378052; ENST00000476295; ENST00000418158 | TSF |
| 3% | chr14 | 105944002 | 105944067 | + | chr14 | 105944603 | 105944697 | + | ENST00000483017; ENST00000329146 | TSF |
| 3% | chr17 | 39974832 | 39974893 | + | chr17 | 39975462 | 39975651 | + | ENST00000321562 | TSF |
| 3% | chr9 | 21974190 | 21974089 | − | chr9 | 21971207 | 21971002; 21970901; 21970975 | − | ENST00000361570; ENST00000304494; ENST00000579755; ENST00000579122; ENST00000530628; ENST00000498124; ENST00000446177 | TSF |
| 3% | chr9 | 21974190 | 21974089 | − | chr9 | 21971207 | 21971002; 21970901; 21970975 | − | ENST00000361570; ENST00000304494; ENST00000579755; ENST00000579122; ENST00000530628; ENST00000498124; ENST00000446177 | TSF |
| 3% | chr9 | 21974190 | 21974089 | − | chr9 | 21971207 | 21971002; 21970901; 21970975 | − | ENST00000361570; ENST00000304494; ENST00000579755; ENST00000579122; ENST00000530628; ENST00000498124; ENST00000446177 | TSF |
| 3% | chr9 | 21974190 | 21974089 | − | chr9 | 21971207 | 21971002; 21970901; 21970975 | − | ENST00000361570; ENST00000304494; ENST00000579755; ENST00000579122; ENST00000530628; ENST00000498124; ENST00000446177 | TSF |
| 3% | chr6 | 80092917 | 80022085 | − | chr6 | 79924739 | 79924689 | − | ENST00000275036; ENST00000344726 | TSF |
| 3% | chr6 | 80092917 | 80022085 | − | chr6 | 79924739 | 79924689 | − | ENST00000275036; ENST00000344726 | TSF |
| 3% | chr22 | 38620420 | 38620354 | − | chr22 | 38617717 | 38617476 | − | ENST00000361906; ENST00000361684 | TSF |
| 3% | chr20 | 44246144 | 44442685 | + | chr20 | 44443023 | 44443109 | + | ENST00000356455; ENST00000405520; ENST00000335046; ENST00000372568 | TSF |
| 3% | chr20 | 44246144 | 44442685 | + | chr20 | 44443023 | 44443109 | + | ENST00000356455; ENST00000405520; ENST00000335046; ENST00000372568 | TSF |
| 3% | chr1 | 33228913 | 33229103 | + | chr | 33233388 | 33233558 | + | ENST00000401073; ENST00000373481; ENST00000294521; ENST00000373480 | TSF |
| 3% | chr1 | 33228913 | 33229103 | + | chr | 33233388 | 33233558 | + | ENST00000401073; ENST00000373481; ENST00000294521; ENST00000373480 | TSF |
| 3% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 3% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 3% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 3% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 3% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 3% | chr6 | 125440425 | 125440534 | + | chr6 | 125541224 | 125541339 | + | ENST00000304877; ENST00000534000; ENST00000368402; ENST00000368388; ENST00000527711; ENST00000528193 | TSF |
| 3% | chr2 | 47596424 | 47596600 | + | chr2 | 47596660 | 47596720; | + | ENST00000263735; ENST00000419334 | TSF |
| 3% | chr2 | 47596424 | 47596600 | + | chr2 | 47596660 | 47596720; | + | ENST00000263735; ENST00000419334 | TSF |
| 3% | chr17 | 37898260 | 37898291 | + | chr17 | 37898505 | 37898709 | + | ENST00000445327 | TSF |
| 3% | chr3 | 39374892 | 39374955 | + | chr3 | 39453486 | 39453552; 39453550 | + | ENST00000301821; ENST00000458478; ENST00000443003 | TSF |
| 3% | chr3 | 39374892 | 39374955 | + | chr3 | 39453486 | 39453552; 39453550 | + | ENST00000301821; ENST00000458478; ENST00000443003 | TSF |
| 3% | chr17 | 37897992 | 37898081 | + | chr17 | 37898505 | 37898709 | + | ENST00000445327 | TSF |
| 3% | chr21 | 42822313 | 42822398 | + | chr21 | 42823094 | 42823170 | + | ENST00000398600; ENST00000398598; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr10 | 135208151 | 135208232 | + | chr10 | 135209217 | 135209281 | + | ENST00000455164; ENST00000288383 ENST00000468317; ENST00000317502; ENST00000432508 | TSF |
| 3% | chr10 | 135208151 | 135208232 | + | chr10 | 135209217 | 135209281 | + | ENST00000455164; ENST00000288383 ENST00000468317; ENST00000317502; ENST00000432508 | TSF |
| 3% | chr1 | 153636090 | 153635838 | − | chr1 | 153635752 | 153635691 | − | ENST00000361891 | TSF |
| 3% | chr8 | 74036014 | 74035742 | − | chr8 | 73993448 | 73993254 | − | ENST00000297354 | TSF |
| 3% | chr2 | 40465767 | 40465674 | − | chr2 | 40404995 | 40404892; 40404907 | − | ENST00000406785; ENST00000407929; ENST00000402441; ENST00000405269; ENST00000406391; ENST00000408028; ENST00000542024 | TSF |
| 3% | chr2 | 40465767 | 40465674 | − | chr2 | 40404995 | 40404892; 40404907 | − | ENST00000406785; ENST00000407929; ENST00000402441; ENST00000405269; ENST00000406391; ENST00000408028; ENST00000542024 | TSF |
| 3% | chr2 | 40465767 | 40465674 | − | chr2 | 40404995 | 40404892; 40404907 | − | ENST00000406785; ENST00000407929; ENST00000402441; ENST00000405269; ENST00000406391; ENST00000408028; ENST00000542024 | TSF |
| 3% | chr2 | 40465767 | 40465674 | − | chr2 | 40404995 | 40404892; 40404907 | − | ENST00000406785; ENST00000407929; ENST00000402441; ENST00000405269; ENST00000406391; ENST00000408028; ENST00000542024 | TSF |
| 3% | chr8 | 38320722 | 38320623 | − | chr | 38315052 | 38314874 | − | ENST00000425967 | TSF |
| 3% | chrX | 47013218 | 47013188 | − | chrX | 47002143 | 47002013; 47001983 | − | ENST00000377811; ENST00000276062 | TSF |
| 3% | chrX | 47013218 | 47013188 | − | chrX | 47002143 | 47002013; 47001983 | − | ENST00000377811; ENST00000276062 | TSF |
| 3% | chr7 | 72059372 | 72720556 | − | chr7 | 72719094 | 72718956; 72719042 | − | ENST00000428206; ENST00000252594; ENST00000438747; ENST00000310326; ENST00000455763 | TSF |
| 3% | chr7 | 72059372 | 72720556 | − | chr7 | 72719094 | 72718956; 72719042 | − | ENST00000428206; ENST00000252594; ENST00000438747; ENST00000310326; ENST00000455763 | TSF |
| 3% | chr7 | 72059372 | 72720556 | − | chr7 | 72719094 | 72718956; 72719042 | − | ENST00000428206; ENST00000252594; ENST00000438747; ENST00000310326; ENST00000455763 | TSF |
| 3% | chr7 | 72059372 | 72720556 | − | chr7 | 72719094 | 72718956; 72719042 | − | ENST00000428206; ENST00000252594; ENST00000438747; ENST00000310326; ENST00000455763 | TSF |
| 3% | chr9 | 130213440 | 130213384 | − | chr9 | 130213062 | 130213010 | − | ENST00000361436; ENST00000536368 | TSF |
| 3% | chr9 | 130213440 | 130213384 | − | chr9 | 130213062 | 130213010 | − | ENST00000361436; ENST00000536368 | TSF |
| 3% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 3% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 3% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 3% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr9 | 131902050 | 131902148 | + | chr9 | 131904724 | 131904831; 131905179 | + | ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 3% | chr1 | 168348640 | 168349020 | + | chr1 | 168549301 | 168549415 | + | ENST00000367818 | TSF |
| 3% | chr9 | 130921922 | 1309221177 | + | chr9 | 130925722 | 130925894 | + | ENST00000372994 | TSF |
| 3% | chr7 | 56020443 | 56020541 | + | chr7 | 56020872 | 56021011 | + | ENST00000426595 | TSF |
| 3% | chr20 | 42231978 | 42232068 | + | chr20 | 42232400 | 42232529 | + | ENST00000373030; ENST00000373039 | TSF |
| 3% | chr20 | 389765 | 390021 | + | chr20 | 390525 | 390669 | + | ENST00000411647; ENST00000382214; ENST00000356286; ENST00000415942; ENST00000475269 | TSF |
| 3% | chr20 | 389765 | 390021 | + | chr20 | 390525 | 390669 | + | ENST00000411647; ENST00000382214; ENST00000356286; ENST00000415942; ENST00000475269 | TSF |
| 3% | chr20 | 389765 | 390021 | + | chr20 | 390525 | 390669 | + | ENST00000411647; ENST00000382214; ENST00000356286; ENST00000415942; ENST00000475269 | TSF |
| 3% | chr20 | 389765 | 390021 | + | chr20 | 390525 | 390669 | + | ENST00000411647; ENST00000382214; ENST00000356286; ENST00000415942; ENST00000475269 | TSF |
| 3% | chr20 | 389765 | 390021 | + | chr20 | 390525 | 390669 | + | ENST00000411647; ENST00000382214; ENST00000356286; ENST00000415942; ENST00000475269 | TSF |
| 3% | chr11 | 118917082 | 118917078 | − | chr11 | 118916543 | 118916493 | − | ENST00000404233; ENST00000529972; ENST00000525859 | TSF |
| 3% | chr3 | 124597514 | 124597450 | − | chr3 | 124592378 | 124592293 | − | ENST00000296181 | TSF |
| 3% | chr19 | 51502251 | 51502209 | − | chr19 | 51501140 | 51501007 | − | ENST00000391806; ENST00000291726; ENST00000600767; ENST00000347619 | TSF |
| 3% | chr1 | 36604350 | 36604261 | − | chr1 | 36603579 | 36603397 | − | ENST00000373166; ENST00000373163; ENST00000373162 | TSF |
| 3% | chr11 | 324821 | 324180 | − | chr11 | 320772 | 320565 | − | ENST00000399808 | TSF |
| 3% | chr8 | 144691011 | 144690934 | − | chr8 | 149690296 | 144690232 | − | ENST00000220966; ENST00000433751 | TSF |
| 3% | chr8 | 144691011 | 144690934 | − | chr8 | 149690296 | 144690232 | − | ENST00000220966; ENST00000433751 | TSF |
| 3% | chr4 | 1101138 | 1101040 | − | chr4 | 1090627 | 1090578; 1090553 | − | ENST00000506730; ENST00000382968; ENST00000433731; ENST00000511620; ENST00000508428; ENST00000333673 | TSF |
| 3% | chr4 | 1101138 | 1101040 | − | chr4 | 1090627 | 1090578; 1090553 | − | ENST00000506730; ENST00000382968; ENST00000433731; ENST00000511620; ENST00000508428; ENST00000333673 | TSF |
| 3% | chr4 | 1101138 | 1101040 | − | chr4 | 1090627 | 1090578; 1090553 | − | ENST00000506730; ENST00000382968; ENST00000433731; ENST00000511620; ENST00000508428; ENST00000333673 | TSF |
| 3% | chr4 | 1101138 | 1101040 | − | chr4 | 1090627 | 1090578; 1090553 | − | ENST00000506730; ENST00000382968; ENST00000433731; ENST00000511620; ENST00000508428; ENST00000333673 | TSF |
| 3% | chr4 | 1101138 | 1101040 | − | chr4 | 1090627 | 1090578; 1090553 | − | ENST00000506730; ENST00000382968; ENST00000433731; ENST00000511620; ENST00000508428; ENST00000333673 | TSF |
| 3% | chr3 | 191873117 | 191872988 | − | chr3 | 191861916 | 191861798; 191861849 | − | ENST00000445105; ENST00000264730; ENST00000454309; ENST00000440901; ENST00000450716; ENST00000430714; ENST00000448795 | TSF |
| 3% | chr3 | 191873117 | 191872988 | − | chr3 | 191861916 | 191861798; 191861849 | − | ENST00000445105; ENST00000264730; ENST00000454309; ENST00000440901; ENST00000450716; ENST00000430714; ENST00000448795 | TSF |
| 3% | chr1 | 43634418 | 43634409 | − | chr1 | 43632906 | 43632831 | − | ENST00000431635; ENST00000236051 | TSF |
| 3% | chr2 | 99224680 | 99224660 | − | chr2 | 99220654 | 99220571 | − | ENST00000328709; ENST00000409997 | TSF |
| 3% | chr2 | 99224680 | 99224660 | − | chr2 | 99220654 | 99220571 | − | ENST00000328709; ENST00000409997 | TSF |
| 3% | chr3 | 139086428 | 139086379 | − | chr3 | 139085987 | 139085857; 139085942 | − | ENST00000333188; ENST00000507777; ENST00000512309 | TSF |
| 3% | chr3 | 139086428 | 139086379 | − | chr3 | 139085987 | 139085857; 139085942 | − | ENST00000333188; ENST00000507777; ENST00000512309 | TSF |
| 3% | chr2 | 238921636 | 238921737 | + | chr2 | 238925208 | 238925275 | + | ENST00000272930; ENST00000448502; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | ENST00000416292; ENST00000409633; ENST00000455999; ENST00000414443; ENST00000439780; ENST00000449191; ENST00000433241; ENST00000409953; ENST00000409332; ENST00000434655; ENST00000434137 | |
| 3% | chr2 | 238921636 | 238921737 | + | chr2 | 238925208 | 238925275 | + | ENST00000272930; ENST00000448502; ENST00000416292; ENST00000409633; ENST00000455999; ENST00000414443; ENST00000439780; ENST00000449191; ENST00000433241; ENST00000409953; ENST00000409332; ENST00000434655; ENST00000434137 | TSF |
| 3% | chr2 | 238921636 | 238921737 | + | chr2 | 238925208 | 238925275 | + | ENST00000272930; ENST00000448502; ENST00000416292; ENST00000409633; ENST00000455999; ENST00000414443; ENST00000439780; ENST00000449191; ENST00000433241; ENST00000409953; ENST00000409332; ENST00000434655; ENST00000434137 | TSF |
| 3% | chr2 | 238921636 | 238921737 | + | chr2 | 238925208 | 238925275 | + | ENST00000272930; ENST00000448502; ENST00000416292; ENST00000409633; ENST00000455999; ENST00000414443; ENST00000439780; ENST00000449191; ENST00000433241; ENST00000409953; ENST00000409332; ENST00000434655; ENST00000434137 | TSF |
| 3% | chr2 | 238921636 | 238921737 | + | chr2 | 238925208 | 238925275 | + | ENST00000272930; ENST00000448502; ENST00000416292; ENST00000409633; ENST00000455999; ENST00000414443; ENST00000439780; ENST00000449191; ENST00000433241; ENST00000409953; ENST00000409332; ENST00000434655; ENST00000434137 | TSF |
| 3% | chr2 | 238921636 | 238921737 | + | chr2 | 238925208 | 238925275 | + | ENST00000272930; ENST00000448502; ENST00000416292; ENST00000409633; ENST00000455999; ENST00000414443; ENST00000439780; ENST00000449191; ENST00000433241; ENST00000409953; ENST00000409332; ENST00000434655; ENST00000434137 | TSF |
| 3% | chr2 | 238921636 | 238921737 | + | chr2 | 238925208 | 238925275 | + | ENST00000272930; ENST00000448502; ENST00000416292; ENST00000409633; ENST00000455999; ENST00000414443; ENST00000439780; ENST00000449191; ENST00000433241; ENST00000409953; ENST00000409332; ENST00000434655; ENST00000434137 | TSF |
| 3% | chr2 | 238921636 | 238921737 | + | chr2 | 238925208 | 238925275 | + | ENST00000272930; ENST00000448502; ENST00000416292; ENST00000409633; ENST00000455999; ENST00000414443; ENST00000439780; ENST00000449191; ENST00000433241; ENST00000409953; ENST00000409332; ENST00000434655; ENST00000434137 | TSF |
| 3% | chr2 | 238921636 | 238921737 | + | chr2 | 238925208 | 238925275 | + | ENST00000272930; ENST00000448502; ENST00000416292; ENST00000409633; ENST00000455999; ENST00000414443; ENST00000439780; ENST00000449191; ENST00000433241; ENST00000409953; ENST00000409332; ENST00000434655; ENST00000434137 | TSF |
| 3% | chr14 | 95047992 | 95048047 | + | chr14 | 95053957 | 95054215; 95054318; 95053971; 95053957; 95054132; 95054170 | + | ENST00000554220; ENST00000553780; ENST00000554760; ENST00000554866; ENST00000329597; ENST00000556775; ENST00000553511; ENST00000554633; ENST00000555681; ENST00000554276; ENST00000557598 | TSF |
| 3% | chr14 | 95047992 | 95048047 | + | chr14 | 95053957 | 95054215; | + | ENST00000554220; ENST00000553780; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
|  |  |  |  |  |  |  | 95054318; 95053971; 95053957; 95054132; 95054170 4170 | | ENST00000554760; ENST00000554866; ENST00000329597; ENST00000556775; ENST00000553511; ENST00000554633; ENST00000555681; ENST00000554276; ENST00000557598 ENST00000554276; ENST00000557598 |  |
| 3% | chr14 | 95047992 | 95048047 | + | chr14 | 95053957 | 95054215; 95054318; 95053971; 95053957; 95054132; 95054170 | + | ENST00000554220; ENST00000553780; ENST00000554760; ENST00000554866; ENST00000329597; ENST00000556775; ENST00000553511; ENST00000554633; ENST00000555681; ENST00000554276; ENST00000557598 | TSF |
| 3% | chr14 | 95047992 | 95048047 | + | chr14 | 95053957 | 95054215; 95054318; 95053971; 95053957; 95054132; 95054170 | + | ENST00000554220; ENST00000553780; ENST00000554760; ENST00000554866; ENST00000329597; ENST00000556775; ENST00000553511; ENST00000554633; ENST00000555681; ENST00000554276; ENST00000557598 | TSF |
| 3% | chr14 | 95047992 | 95048047 | + | chr14 | 95053957 | 95054215; 95054318; 95053971; 95053957; 95054132; 95054170 | + | ENST00000554220; ENST00000553780; ENST00000554760; ENST00000554866; ENST00000329597; ENST00000556775; ENST00000553511; ENST00000554633; ENST00000555681; ENST00000554276; ENST00000557598 | TSF |
| 3% | chr14 | 95047992 | 95048047 | + | chr14 | 95053957 | 95054215; 95054318; 95053971; 95053957; 95054132; 95054170 | + | ENST00000554220; ENST00000553780; ENST00000554760; ENST00000554866; ENST00000329597; ENST00000556775; ENST00000553511; ENST00000554633; ENST00000555681; ENST00000554276; ENST00000557598 | TSF |
| 3% | chr14 | 95047992 | 95048047 | + | chr14 | 95053957 | 95054215; 95054318; 95053971; 95053957; 95054132; 95054170 | + | ENST00000554220; ENST00000553780; ENST00000554760; ENST00000554866; ENST00000329597; ENST00000556775; ENST00000553511; ENST00000554633; ENST00000555681; ENST00000554276; ENST00000557598 | TSF |
| 3% | chr14 | 95047992 | 95048047 | + | chr14 | 95053957 | 95054215; 95054318; 95053971; 95053957; 95054132; 95054170 | + | ENST00000554220; ENST00000553780; ENST00000554760; ENST00000554866; ENST00000329597; ENST00000556775; ENST00000553511; ENST00000554633; ENST00000555681; ENST00000554276; ENST00000557598 | TSF |
| 3% | chr19 | 13148192 | 13148316 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 3% | chr19 | 13148192 | 13148316 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 3% | chr19 | 13148192 | 13148316 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 3% | chr19 | 13148192 | 13148316 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 3% | chr19 | 13148192 | 13148316 | + | chr19 | 13183861 | 13183923 | + | ENST00000397661; ENST00000592199; ENST00000585382; ENST00000587760; ENST00000585575; ENST00000360105; ENST00000588228; ENST00000587260; ENST00000358552 | TSF |
| 3% | chr5 | 179238653 | 179238682 | + | chr5 | 179250858 | 179251087; 179251057 | + | ENST00000376929; ENST00000514093; ENST00000422245; ENST00000389805; ENST00000504627; ENST00000402874; ENST00000510187; ENST00000360718 | TSF |
| 3% | chr5 | 179238653 | 179238682 | + | chr5 | 179250858 | 179251087; 179251057 | + | ENST00000376929; ENST00000514093; ENST00000422245; ENST00000389805; ENST00000504627; ENST00000402874; ENST00000510187; ENST00000360718 | TSF |
| 3% | chr5 | 179238653 | 179238682 | + | chr5 | 179250858 | 179251087; | + | ENST00000376929; ENST00000514093; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr5 | 179238653 | 179238682 | + | chr5 | 179250858 | 179251087; 179251057 | + | ENST00000422245; ENST00000389805; ENST00000504627; ENST00000402874; ENST00000510187; ENST00000360718 ENST00000376929; ENST00000514093; | TSF |
| 3% | chr5 | 179238653 | 179238682 | + | chr5 | 179250858 | 179251087; 179251057 | + | ENST00000422245; ENST00000389805; ENST00000504627; ENST00000402874; ENST00000510187; ENST00000360718 ENST00000376929; ENST00000514093; | TSF |
| 3% | chr2 | 26947307 | 26947428 | + | chr2 | 26950532 | 26951436 | + | ENST00000302909 | TSF |
| 3% | chr12 | 12966683 | 12966871 | + | chr12 | 12967065 | 12967158 | + | ENST00000352940; ENST00000358007; ENST00000544400 | TSF |
| 3% | chr12 | 12966683 | 12966871 | + | chr12 | 12967065 | 12967158 | + | ENST00000352940; ENST00000358007; ENST00000544400 | TSF |
| 3% | chr12 | 12966683 | 12966871 | + | chr12 | 12967065 | 12967158 | + | ENST00000352940; ENST00000358007; ENST00000544400 | TSF |
| 3% | chr20 | 62631560 | 62631628 | + | chr20 | 62632430 | 62632592 | + | ENST00000535781; ENST00000266079 | TSF |
| 3% | chr20 | 62631560 | 62631628 | + | chr20 | 62632430 | 62632592 | + | ENST00000535781; ENST00000266079 | TSF |
| 3% | chr4 | 56227367 | 56227417 | + | chr4 | 56235999 | 56236258 | + | ENST00000264228; ENST00000505210 | TSF |
| 3% | chr2 | 232340741 | 232340940 | + | chr2 | 232576646 | 232576693 | + | ENST00000409321; ENST00000409115; ENST00000341369; ENST00000409683; ENST00000410064; ENST00000412128 | TSF |
| 3% | chr2 | 232340741 | 232340940 | + | chr2 | 232576646 | 232576693 | + | ENST00000409321; ENST00000409115; ENST00000341369; ENST00000409683; ENST00000410064; ENST00000412128 | TSF |
| 3% | chr4 | 6592494 | 6592648 | + | chr4 | 6594900 | 6595077; 6595011 | + | ENST00000285599; ENST00000504248; ENST00000505907 | TSF |
| 3% | chr4 | 6592494 | 6592648 | + | chr4 | 6594900 | 6595077; 6595011 | + | ENST00000285599; ENST00000504248; ENST00000505907 | TSF |
| 3% | chr4 | 6592494 | 6592648 | + | chr4 | 6594900 | 6595077; 6595011 | + | ENST00000285599; ENST00000504248; ENST00000505907 | TSF |
| 3% | chr11 | 67803205 | 67803255 | + | chr11 | 67803929 | 67804060; 67803981 | + | ENST00000313468; ENST00000528492; ENST00000526339 | TSF |
| 3% | chr11 | 67803205 | 67803255 | + | chr11 | 67803929 | 67804060; 67803981 | + | ENST00000313468; ENST00000528492; ENST00000526339 | TSF |
| 3% | chr12 | 48166180 | 48166365 | + | chr12 | 48172811 | 48172978; 48172837 | + | ENST00000442218; ENST00000551301 | TSF |
| 3% | chr12 | 48166180 | 48166365 | + | chr12 | 48172811 | 48172978; 48172837 | + | ENST00000442218; ENST00000551301 | TSF |
| 3% | chr14 | 20787221 | 20787171 | − | chr14 | 20784719 | 20784573 | − | ENST00000556563 | TSF |
| 3% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 3% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 3% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 3% | chr7 | 102118425 | 102118421 | − | chr7 | 102116717 | 102116628 | − | ENST00000292614; ENST00000393794 | TSF |
| 3% | chr7 | 102118425 | 102118421 | − | chr7 | 102116717 | 102116628 | − | ENST00000292614; ENST00000393794 | TSF |
| 3% | chr12 | 54862718 | 54862609 | − | chr12 | 54858951 | 54858851 | − | ENST00000546931; ENST00000552397; ENST00000305879 | TSF |
| 3% | chr12 | 54862718 | 54862609 | − | chr12 | 54858951 | 54858851 | − | ENST00000546931; ENST00000552397; ENST00000305879 | TSF |
| 3% | chr1 | 8924664 | 8924519 | − | chr1 | 8924151 | 8923950 | − | ENST00000234590 | TSF |
| 3% | chr11 | 60720029 | 60719973 | − | chr11 | 60718838 | 60718466 | − | ENST00000541505; ENST00000227880 | TSF |
| 3% | chr11 | 60720029 | 60719973 | − | chr11 | 60718838 | 60718466 | − | ENST00000541505; ENST00000227880 | TSF |
| 3% | chr15 | 67546688 | 67546562 | − | chr15 | 67529158 | 67528968 | − | ENST00000261880 | TSF |
| 2% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 2% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 2% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 2% | chr19 | 16267516 | 16267584 | + | chr19 | 16268020 | 16268208; 16268205; 16268448; | + | ENST00000253680; ENST00000397372; ENST00000593154; ENST00000588246; ENST00000593031 | |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr22 | 38253087 | 38253185 | + | chr22 | 38254686 | 16268139 38254747 | + | ENST00000412331; ENST00000381683; ENST00000414316; ENST00000406934; ENST00000451427 | TSF |
| 2% | chr22 | 38253087 | 38253185 | + | chr22 | 38254686 | 38254747 | + | ENST00000412331; ENST00000381683; ENST00000414316; ENST00000406934; ENST00000451427 | TSF |
| 2% | chr22 | 38253087 | 38253185 | + | chr22 | 38254686 | 38254747 | + | ENST00000412331; ENST00000381683; ENST00000414316; ENST00000406934; ENST00000451427 | TSF |
| 2% | chr22 | 38253087 | 38253185 | + | chr22 | 38254686 | 38254747 | + | ENST00000412331; ENST00000381683; ENST00000414316; ENST00000406934; ENST00000451427 | TSF |
| 2% | chr2 | 3624355 | 3624441 | + | chr2 | 3625300 | 3625364 | + | ENST00000304921; ENST00000407445; ENST00000403564; ENST00000406376 | TSF |
| 2% | chr2 | 3624355 | 3624441 | + | chr2 | 3625300 | 3625364 | + | ENST00000304921; ENST00000407445; ENST00000403564; ENST00000406376 | TSF |
| 2% | chr16 | 89884404 | 89884946 | + | chr16 | 89911730 | 89911773 | + | ENST00000393062; ENST00000378247; ENST00000563972 | TSF |
| 2% | chr16 | 89884404 | 89884946 | + | chr16 | 89911730 | 89911773 | + | ENST00000393062; ENST00000378247; ENST00000563972 | TSF |
| 2% | chr16 | 89884404 | 89884946 | + | chr16 | 89911730 | 89911773 | + | ENST00000393062; ENST00000378247; ENST00000563972 | TSF |
| 2% | chr4 | 56227367 | 56227417 | + | chr4 | 56230241 | 56230438 | + | ENST00000264228 | TSF |
| 2% | chr9 | 97766976 | 97767010 | + | chr9 | 97767440 | 97767502 | + | ENST00000297979; ENST00000375315; ENST00000424143; ENST00000428313; ENST00000451893; ENST00000425634; ENST00000445181; ENST00000478473 | TSF |
| 2% | chr9 | 97766976 | 97767010 | + | chr9 | 97767440 | 97767502 | + | ENST00000297979; ENST00000375315; ENST00000424143; ENST00000428313; ENST00000451893; ENST00000425634; ENST00000445181; ENST00000478473 | TSF |
| 2% | chr9 | 97766976 | 97767010 | + | chr9 | 97767440 | 97767502 | + | ENST00000297979; ENST00000375315; ENST00000424143; ENST00000428313; ENST00000451893; ENST00000425634; ENST00000445181; ENST00000478473 | TSF |
| 2% | chr2 | 26309164 | 26309272 | + | chr2 | 26321531 | 26321591 | + | ENST00000264710 | TSF |
| 2% | chr2 | 150015354 | 150015745 | + | chr2 | 150017278 | 150017349 | + | ENST00000409642; ENST00000450639; ENST00000280115 | TSF |
| 2% | chr2 | 150015354 | 150015745 | + | chr2 | 150017278 | 150017349 | + | ENST00000409642; ENST00000450639; ENST00000280115 | TSF |
| 2% | chr16 | 30011417 | 30011504 | + | chr16 | 30012079 | 30012157 | + | ENST00000563197; ENST00000304516; ENST00000567254; ENST00000567065; ENST00000562441; ENST00000567705; ENST00000567987 | TSF |
| 2% | chr16 | 30011417 | 30011504 | + | chr16 | 30012079 | 30012157 | + | ENST00000563197; ENST00000304516; ENST00000567254; ENST00000567065; ENST00000562441; ENST00000567705; ENST00000567987 | TSF |
| 2% | chr16 | 30011417 | 30011504 | + | chr16 | 30012079 | 30012157 | + | ENST00000563197; ENST00000304516; ENST00000567254; ENST00000567065; ENST00000562441; ENST00000567705; ENST00000567987 | TSF |
| 2% | chr16 | 30011417 | 30011504 | + | chr16 | 30012079 | 30012157 | + | ENST00000563197; ENST00000304516; ENST00000567254; ENST00000567065; ENST00000562441; ENST00000567705; ENST00000567987 | TSF |
| 2% | chr16 | 30011417 | 30011504 | + | chr16 | 30012079 | 30012157 | + | ENST00000563197; ENST00000304516; ENST00000567254; ENST00000567065; ENST00000562441; ENST00000567705; ENST00000567987 | TSF |
| 2% | chr16 | 30011417 | 30011504 | + | chr16 | 30012079 | 30012157 | + | ENST00000563197; ENST00000304516; ENST00000567254; ENST00000567065; ENST00000562441; ENST00000567705; ENST00000567987 | TSF |
| 2% | chr6 | 35258663 | 35258760 | + | chr6 | 35259055 | 35259180 | + | ENST00000469195; ENST00000373953; ENST00000440666; ENST00000339411 | TSF |
| 2% | chr6 | 35258663 | 35258760 | + | chr6 | 35259055 | 35259180 | + | ENST00000469195; ENST00000373953; ENST00000440666; ENST00000339411 | TSF |
| 2% | chr6 | 35258663 | 35258760 | + | chr6 | 35259055 | 35259180 | + | ENST00000469195; ENST00000373953; ENST00000440666; ENST00000339411 | TSF |
| 2% | chr11 | 102045048 | 102045146 | + | chr11 | 102056749 | 102056862 | + | ENST00000282441; ENST00000537274; ENST00000531439; ENST00000524575 | TSF |
| 2% | chr11 | 102045048 | 102045146 | + | chr11 | 102056749 | 102056862 | + | ENST00000282441; ENST00000537274; ENST00000531439; ENST00000524575 | TSF |
| 2% | chr11 | 102045048 | 102045146 | + | chr11 | 102056749 | 102056862 | + | ENST00000282441; ENST00000537274; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr4 | 111332609 | 111332609 | + | chr4 | 111409697 | 111409838 | + | ENST00000531439; ENST00000524575 ENST00000265162 | TSF |
| 2% | chr9 | 35846065 | 35846070 | + | chr9 | 35846255 | 35846378 | + | ENST00000377996; ENST00000439587; ENST00000377991; ENST00000377988 | TSF |
| 2% | chr9 | 35846065 | 35846070 | + | chr9 | 35846255 | 35846378 | + | ENST00000377996; ENST00000439587; ENST00000377991; ENST00000377988 | TSF |
| 2% | chr3 | 139251153 | 139250891 | − | chr3 | 139237364 | 139237263 | − | ENST00000232219 | TSF |
| 2% | chr1 | 49723490 | 49723396 | − | chr1 | 49711536 | 49711442 | − | ENST00000371839; ENST00000371838; ENST00000371836 | TSF |
| 2% | chr1 | 49723490 | 49723396 | − | chr1 | 49711536 | 49711442 | − | ENST00000371839; ENST00000371838; ENST00000371836 | TSF |
| 2% | chr1 | 49723490 | 49723396 | − | chr1 | 49711536 | 49711442 | − | ENST00000371839; ENST00000371838; ENST00000371836 | TSF |
| 2% | chr1 | 43409712 | 43409704 | − | chr1 | 43408992 | 43408897 | − | ENST00000426263; ENST00000415851; ENST00000372500 | TSF |
| 2% | chr1 | 43409712 | 43409704 | − | chr1 | 43408992 | 43408897 | − | ENST00000426263; ENST00000415851; ENST00000372500 | TSF |
| 2% | chr1 | 43409712 | 43409704 | − | chr1 | 43408992 | 43408897 | − | ENST00000426263; ENST00000415851; ENST00000372500 | TSF |
| 2% | chr7 | 102212088 | 102212084 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212088 | 102212084 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212088 | 102212084 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212088 | 102212084 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212088 | 102212084 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212088 | 102212084 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212088 | 102212084 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212088 | 102212084 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr19 | 47347459 | 47347409 | − | chr19 | 47342835 | 47342722 | − | ENST00000352203; ENST00000601498; ENST00000599990; ENST00000593442; ENST00000263270; ENST00000597020 | TSF |
| 2% | chr11 | 323767 | 323324 | − | chr11 | 320772 | 320565 | − | ENST00000399808 | TSF |
| 2% | chr19 | 46194689 | 46194670 | − | chr19 | 46191824 | 46191645 | − | ENST00000342669; ENST00000588301; ENST00000590212 | TSF |
| 2% | chr19 | 46194689 | 46194670 | − | chr19 | 46191824 | 46191645 | − | ENST00000342669; ENST00000588301; ENST00000590212 | TSF |
| 2% | chr17 | 30185561 | 30185499 | − | chr17 | 30183884 | 30183818 | − | ENST00000302362; ENST00000378634; ENST00000496655 | TSF |
| 2% | chr17 | 30185567 | 30185499 | − | chr17 | 30183884 | 30183818 | − | ENST00000302362; ENST00000378634; ENST00000496655 | TSF |
| 2% | chr19 | 2141057 | 2140989 | − | chr19 | 2138713 | 2138618 | − | ENST00000355272; ENST00000356926; ENST00000350812; ENST00000345016 | TSF |
| 2% | chr19 | 2141057 | 2140989 | − | chr19 | 2138713 | 2138618 | − | ENST00000355272; ENST00000356926; ENST00000350812; ENST00000345016 | TSF |
| 2% | chr19 | 2141057 | 2140989 | − | chr19 | 2138713 | 2138618 | − | ENST00000355272; ENST00000356926; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr19 | 2141057 | 2140989 | – | chr19 | 2138713 | 2138618 | – | ENST00000350812; ENST00000345016 ENST00000355272; ENST00000356926; | TSF |
| 2% | chr2 | 38983894 | 38983253 | – | chr2 | 38977336 | 38977156 | – | ENST00000350812; ENST00000345016 ENST00000313117; ENST00000425778; ENST00000425941; ENST00000446327; ENST00000409276; ENST00000431066; ENST00000443213 | TSF |
| 2% | chr2 | 38983894 | 38983253 | – | chr2 | 38977336 | 38977156 | – | ENST00000313117; ENST00000425778; ENST00000425941; ENST00000446327; ENST00000409276; ENST00000431066; ENST00000443213 | TSF |
| 2% | chr2 | 38983894 | 38983253 | – | chr2 | 38977336 | 38977156 | – | ENST00000313117; ENST00000425778; ENST00000425941; ENST00000446327; ENST00000409276; ENST00000431066; ENST00000443213 | TSF |
| 2% | chr2 | 38983894 | 38983253 | – | chr2 | 38977336 | 38977156 | – | ENST00000313117; ENST00000425778; ENST00000425941; ENST00000446327; ENST00000409276; ENST00000431066; ENST00000443213 | TSF |
| 2% | chr2 | 38983894 | 38983253 | – | chr2 | 38977336 | 38977156 | – | ENST00000313117; ENST00000425778; ENST00000425941; ENST00000446327; ENST00000409276; ENST00000431066; ENST00000443213 | TSF |
| 2% | chr2 | 38983894 | 38983253 | – | chr2 | 38977336 | 38977156 | – | ENST00000313117; ENST00000425778; ENST00000425941; ENST00000446327; ENST00000409276; ENST00000431066; ENST00000443213 | TSF |
| 2% | chr4 | 83774285 | 83774211 | – | chr4 | 83772757 | 83772584; 83772667 | – | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 2% | chr4 | 83774285 | 83774211 | – | chr4 | 83772757 | 83772584; 83772667 | – | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 2% | chr4 | 83774285 | 83774211 | – | chr4 | 83772757 | 83772584; 83772667 | – | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 2% | chr4 | 83774285 | 83774211 | – | chr4 | 83772757 | 83772584; 83772667 | – | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 2% | chr4 | 83774285 | 83774211 | – | chr4 | 83772757 | 83772584; 83772667 | – | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 2% | chr4 | 83774285 | 83774211 | – | chr4 | 83772757 | 83772584; 83772667 | – | ENST00000348405; ENST00000513858; ENST00000395310; ENST00000443462; ENST00000509142; ENST00000311785; ENST00000326950; ENST00000432794; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr4 | 83774285 | 83774211 | − | chr4 | 83772757 | 83772584; 83772667 | − | ENST00000448323; ENST00000505472; ENST00000500777; ENST00000508502; ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; | TSF |
| 2% | chr4 | 83774285 | 83774211 | − | chr4 | 83772757 | 83772584; 83772667 | − | ENST00000448323; ENST00000505472; ENST00000500777; ENST00000508502; ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; | TSF |
| 2% | chr4 | 83774285 | 83774211 | − | chr4 | 83772757 | 83772584; 83772667 | − | ENST00000448323; ENST00000505472; ENST00000500777; ENST00000508502; ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 2% | chr14 | 92112577 | 92112481 | − | chr14 | 92105594 | 92105508; 92105440 | − | ENST00000557036; ENST00000256343 | TSF |
| 2% | chr14 | 92112577 | 92112481 | − | chr14 | 92105594 | 92105508; 92105440 | − | ENST00000557036; ENST00000256343 | TSF |
| 2% | chr7 | 22858195 | 22858099 | − | chr7 | 22857667 | 22857619 | − | ENST00000358435; ENST00000405021; ENST00000372879 | TSF |
| 2% | chr7 | 22858195 | 22858099 | − | chr7 | 22857667 | 22857619 | − | ENST00000358435; ENST00000405021; ENST00000372879 | TSF |
| 2% | chr11 | 100156479 | 100156572 | + | chr11 | 100168357 | 100168427 | + | ENST00000527185; ENST00000528682; ENST00000524871; ENST00000418526; ENST00000279463 | TSF |
| 2% | chr11 | 100156479 | 100156572 | + | chr11 | 100168357 | 100168427 | + | ENST00000527185; ENST00000528682; ENST00000524871; ENST00000418526; ENST00000279463 | TSF |
| 2% | chr20 | 60878087 | 60878105 | + | chr20 | 60878778 | 60878837 | + | ENST00000253003 | TSF |
| 2% | chr2 | 171572610 | 171572614 | + | chr2 | 171572769 | 171573914 | + | ENST00000375281 | TSF |
| 2% | chr11 | 40331346 | 46403329 | + | chr11 | 46403844 | 46404011; 46403914 | + | ENST00000405308; ENST00000441869; ENST00000359803; ENST00000533952; ENST00000395566; ENST00000489525; ENST00000407067; ENST00000395565 | TSF |
| 2% | chr11 | 40331346 | 46403329 | + | chr11 | 46403844 | 46404011; 46403914 | + | ENST00000405308; ENST00000441869; ENST00000359803; ENST00000533952; ENST00000395566; ENST00000489525; ENST00000407067; ENST00000395565 | TSF |
| 2% | chr11 | 40331346 | 46403329 | + | chr11 | 46403844 | 46404011; 46403914 | + | ENST00000405308; ENST00000441869; ENST00000359803; ENST00000533952; ENST00000395566; ENST00000489525; ENST00000407067; ENST00000395565 | TSF |
| 2% | chr11 | 40331346 | 46403329 | + | chr11 | 46403844 | 46404011; 46403914 | + | ENST00000405308; ENST00000441869; ENST00000359803; ENST00000533952; ENST00000395566; ENST00000489525; ENST00000407067; ENST00000395565 | TSF |
| 2% | chr21 | 42597177 | 42597622 | + | chr21 | 42598199 | 42598281 | + | ENST00000328735; ENST00000330333; ENST00000347667 | TSF |
| 2% | chr21 | 42597177 | 42597622 | + | chr21 | 42598199 | 42598281 | + | ENST00000328735; ENST00000330333; ENST00000347667 | TSF |
| 2% | chr21 | 42597177 | 42597622 | + | chr21 | 42598199 | 42598281 | + | ENST00000328735; ENST00000330333; ENST00000347667 | TSF |
| 2% | chr3 | 183973543 | 183973607 | + | chr3 | 183975261 | 183975544 | + | ENST00000324557; ENST00000402825 | TSF |
| 2% | chr3 | 183973543 | 183973607 | + | chr3 | 183975261 | 183975544 | + | ENST00000324557; ENST00000402825 | TSF |
| 2% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 2% | chr3 | 184083167 | 184083362 | + | chr3 | 184084505 | 184084588 | + | ENST00000456318; ENST00000438240; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr3 | 184083167 | 184083362 | + | chr3 | 184084505 | 184084588 | + | ENST00000455712; ENST00000452961; ENST00000296223; ENST00000429568 ENST00000456318; ENST00000438240; ENST00000455712; ENST00000452961; ENST00000296223; ENST00000429568 | TSF |
| 2% | chr2 | 133324902 | 133325151 | + | chr2 | 133402674 | 133403179 | + | ENST00000329321 | TSF |
| 2% | chr7 | 56020443 | 56020509 | + | chr7 | 56020872 | 56021011 | + | ENST00000426595 | TSF |
| 2% | chr19 | 17524027 | 17524114 | + | chr19 | 17531122 | 17531220 | + | ENST00000317040; ENST00000528659; ENST00000392702; ENST00000529939; ENST00000528515; ENST00000543795 | TSF |
| 2% | chr19 | 17524027 | 17524114 | + | chr19 | 17531122 | 17531220 | + | ENST00000317040; ENST00000528659; ENST00000392702; ENST00000529939; ENST00000528515; ENST00000543795 | TSF |
| 2% | chr19 | 17524027 | 17524114 | + | chr19 | 17531122 | 17531220 | + | ENST00000317040; ENST00000528659; ENST00000392702; ENST00000529939; ENST00000528515; ENST00000543795 | TSF |
| 2% | chr19 | 17524027 | 17524114 | + | chr19 | 17531122 | 17531220 | + | ENST00000317040; ENST00000528659; ENST00000392702; ENST00000529939; ENST00000528515; ENST00000543795 | TSF |
| 2% | chr19 | 17524027 | 17524114 | + | chr19 | 17531122 | 17531220 | + | ENST00000317040; ENST00000528659; ENST00000392702; ENST00000529939; ENST00000528515; ENST00000543795 | TSF |
| 2% | chr4 | 125071 | 125178 | + | chr4 | 337571 | 337697 | + | ENST00000512994; ENST00000505939; ENST00000240499 | TSF |
| 2% | chr4 | 125071 | 125178 | + | chr4 | 337571 | 337697 | + | ENST00000512994; ENST00000505939; ENST00000240499 | TSF |
| 2% | chr4 | 125071 | 125178 | + | chr4 | 337571 | 337697 | + | ENST00000512994; ENST00000505939; ENST00000240499 | TSF |
| 2% | chr6 | 71556614 | 71556620 | + | chr6 | 71562243 | 71562367 | + | ENST00000316999; ENST00000370452; ENST00000370455 | TSF |
| 2% | chr6 | 71556614 | 71556620 | + | chr6 | 71562243 | 71562367 | + | ENST00000316999; ENST00000370452; ENST00000370455 | TSF |
| 2% | chr6 | 13616316 | 13616338 | + | chr6 | 13616695 | 13616753 | + | ENST00000451315; ENST00000420088 | TSF |
| 2% | chr6 | 13616316 | 13616338 | + | chr6 | 13616695 | 13616753 | + | ENST00000451315; ENST00000420088 | TSF |
| 2% | chr11 | 121357068 | 121357166 | + | chr11 | 121358741 | 121358902 | + | ENST00000260197 | TSF |
| 2% | chr1 | 23397020 | 23397118 | + | chr1 | 23397718 | 23397852 | + | ENST00000356634; ENST00000400181; ENST00000542151 | TSF |
| 2% | chr16 | 2556075 | 2556125 | + | chr16 | 2569219 | 2569384; 2569402 | + | ENST00000564543; ENST00000330398; ENST00000568562 | TSF |
| 2% | chr16 | 2556075 | 2556125 | + | chr16 | 2569219 | 2569384; 2569402 | + | ENST00000564543; ENST00000330398; ENST00000568562 | TSF |
| 2% | chr2 | 232340741 | 232340940 | + | chr2 | 2325777 | 232577226 | + | ENST00000409321; ENST00000409115; ENST00000341369; ENST00000409683; ENST00000410064; ENST00000412128 | TSF |
| 2% | chr2 | 132286104 | 132286168 | + | chr2 | 132287220 | 132287264 | + | ENST00000295171; ENST00000409856; ENST00000434330 | TSF |
| 2% | chr2 | 132286104 | 132286168 | + | chr2 | 132287220 | 132287264 | + | ENST00000295171; ENST00000409856; ENST00000434330 | TSF |
| 2% | chr2 | 132286104 | 132286168 | + | chr2 | 132287220 | 132287264 | + | ENST00000295171; ENST00000409856; ENST00000434330 | TSF |
| 2% | chr8 | 145516361 | 145516371 | + | chr8 | 145532592 | 145532700 | + | ENST00000528838 | TSF |
| 2% | chr22 | 38166164 | 38166230 | + | chr22 | 38167657 | 38167743 | + | ENST00000406386; ENST00000403663 | TSF |
| 2% | chr12 | 25062633 | 25062524 | − | chr12 | 25054819 | 25054748 | − | ENST00000261192; ENST00000538118; ENST00000539282; ENST00000539780 | TSF |
| 2% | chr12 | 25062633 | 25062524 | − | chr12 | 25054819 | 25054748 | − | ENST00000261192; ENST00000538118; ENST00000539282; ENST00000539780 | TSF |
| 2% | chr14 | 24682072 | 24681871 | − | chr14 | 24681035 | 24680886 | − | ENST00000530611; ENST00000556387; ENST00000347519; ENST00000533523; ENST00000609024; ENST00000533011; ENST00000534106 | TSF |
| 2% | chr14 | 24682072 | 24681871 | − | chr14 | 24681035 | 24680886 | − | ENST00000530611; ENST00000556387; ENST00000347519; ENST00000533523; ENST00000609024; ENST00000533011; ENST00000534106 | TSF |
| 2% | chr14 | 24682072 | 24681871 | − | chr14 | 24681035 | 24680886 | − | ENST00000530611; ENST00000556387; ENST00000347519; ENST00000533523; ENST00000609024; ENST00000533011; ENST00000534106 | TSF |
| 2% | chr14 | 24682072 | 24681871 | − | chr14 | 24681035 | 24680886 | − | ENST00000530611; ENST00000556387; ENST00000347519; ENST00000533523; ENST00000609024; ENST00000533011; ENST00000534106 | TSF |
| 2% | chr14 | 24682072 | 24681871 | − | chr14 | 24681035 | 24680886 | − | ENST00000530611; ENST00000556387; ENST00000347519; ENST00000533523; ENST00000609024; ENST00000533011; ENST00000534106 | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 2% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 2% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 2% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 2% | chrX | 134954053 | 134953756 | − | chrX | 134950133 | 134950078 | − | ENST00000420087; ENST00000463085; ENST00000370724; ENST00000491480 | TSF |
| 2% | chrX | 134954053 | 134953756 | − | chrX | 134950133 | 134950078 | − | ENST00000420087; ENST00000463085; ENST00000370724; ENST00000491480 | TSF |
| 2% | chr7 | 130130176 | 130130254 | + | chr7 | 130135209 | 130135363 | + | ENST00000223215; ENST00000437945 | TSF |
| 2% | chr7 | 130130176 | 130130254 | + | chr7 | 130135209 | 130135363 | + | ENST00000223215; ENST00000437945 | TSF |
| 2% | chr9 | 42254026 | 42254270 | + | chr9 | 42671887 | 42671946 | + | ENST00000456520; ENST00000377391 | TSF |
| 2% | chr9 | 42254026 | 42254270 | + | chr9 | 42671887 | 42671946 | + | ENST00000456520; ENST00000377391 | TSF |
| 2% | chr6 | 151188691 | 151188718 | + | chr6 | 151197226 | 151197310 | + | ENST00000367321; ENST00000367307; ENST00000367308 | TSF |
| 2% | chr6 | 151188691 | 151188718 | + | chr6 | 151197226 | 151197310 | + | ENST00000367321; ENST00000367307; ENST00000367308 | TSF |
| 2% | chr6 | 151188691 | 151188718 | + | chr6 | 151197226 | 151197310 | + | ENST00000367321; ENST00000367307; ENST00000367308 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr11 | 61544394 | 61544423 | + | chr11 | 61544736 | 61544936 | + | ENST00000278836; ENST00000265460; ENST00000327797 | TSF |
| 2% | chr11 | 61544394 | 61544423 | + | chr11 | 61544736 | 61544936 | + | ENST00000278836; ENST00000265460; ENST00000327797 | TSF |
| 2% | chr11 | 61544394 | 61544423 | + | chr11 | 61544736 | 61544936 | + | ENST00000278836; ENST00000265460; ENST00000327797 | TSF |
| 2% | chr11 | 65037941 | 65038313 | + | chr11 | 65043363 | 65043469 | + | ENST00000265465; ENST00000532391 | TSF |
| 2% | chr11 | 65037941 | 65038313 | + | chr11 | 65043363 | 65043469 | + | ENST00000265465; ENST00000532391 | TSF |
| 2% | chr2 | 177035648 | 177035647 | + | chr2 | 177036245 | 177037002 | + | ENST00000468418; ENST00000410016; ENST00000249440 | TSF |
| 2% | chr6 | 124669760 | 124669850 | + | chr6 | 124676413 | 124676493 | + | ENST00000368416; ENST00000368417; ENST00000546092; ENST00000545433 | TSF |
| 2% | chr6 | 124669760 | 124669850 | + | chr6 | 124676413 | 124676493 | + | ENST00000368416; ENST00000368417; ENST00000546092; ENST00000545433 | TSF |
| 2% | chr6 | 124669760 | 124669850 | + | chr6 | 124676413 | 124676493 | + | ENST00000368416; ENST00000368417; ENST00000546092; ENST00000545433 | TSF |
| 2% | chr6 | 124669760 | 124669850 | + | chr6 | 124676413 | 124676493 | + | ENST00000368416; ENST00000368417; ENST00000546092; ENST00000545433 | TSF |
| 2% | chr8 | 128749913 | 128749923 | + | chr8 | 128750494 | 128751265 | + | ENST00000377970 | TSF |
| 2% | chr19 | 39973016 | 39973114 | + | chr19 | 39973525 | 39973556; 39973603 | + | ENST00000314349; ENST00000601358; ENST00000607714; ENST00000597666; ENST00000602028; ENST00000597782; ENST00000599733; ENST00000602265; ENST00000594583 | TSF |
| 2% | chr19 | 39973016 | 39973114 | + | chr19 | 39973525 | 39973556; 39973603 | + | ENST00000314349; ENST00000601358; ENST00000607714; ENST00000597666; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 2% | chr19 | 39973016 | 39973114 | + | chr19 | 39973525 | 39973556; 39973603 | + | ENST00000602028; ENST00000597782; ENST00000599733; ENST00000602265; ENST00000594583 ENST00000314349; ENST00000601358; ENST00000607714; ENST00000597666; ENST00000602028; ENST00000597782; ENST00000599733; ENST00000602265; ENST00000594583 | TSF |
| 2% | chr19 | 39973016 | 39973114 | + | chr19 | 39973525 | 39973556; 39973603 | + | ENST00000314349; ENST00000601358; ENST00000607714; ENST00000597666; ENST00000602028; ENST00000597782; ENST00000599733; ENST00000602265; ENST00000594583 | TSF |
| 2% | chr19 | 39973016 | 39973114 | + | chr19 | 39973525 | 39973556; 39973603 | + | ENST00000314349; ENST00000601358; ENST00000607714; ENST00000597666; ENST00000602028; ENST00000597782; ENST00000599733; ENST00000602265; ENST00000594583 | TSF |
| 2% | chr19 | 39973016 | 39973114 | + | chr19 | 39973525 | 39973556; 39973603 | + | ENST00000314349; ENST00000601358; ENST00000607714; ENST00000597666; ENST00000602028; ENST00000597782; ENST00000599733; ENST00000602265; ENST00000594583 | TSF |
| 2% | chr19 | 39973016 | 39973114 | + | chr19 | 39973525 | 39973556; 39973603 | + | ENST00000314349; ENST00000601358; ENST00000607714; ENST00000597666; ENST00000602028; ENST00000597782; ENST00000599733; ENST00000602265; ENST00000594583 | TSF |
| 2% | chr7 | 73098580 | 73098709 | + | chr7 | 73100966 | 73101061 | + | ENST00000265758; ENST00000432522; ENST00000421744; ENST00000428163; ENST00000423166; ENST00000423497 | TSF |
| 2% | chr7 | 73098580 | 73098709 | + | chr7 | 73100966 | 73101061 | + | ENST00000265758; ENST00000432522; ENST00000421744; ENST00000428163; ENST00000423166; ENST00000423497 | TSF |
| 2% | chr7 | 73098580 | 73098709 | + | chr7 | 73100966 | 73101061 | + | ENST00000265758; ENST00000432522; ENST00000421744; ENST00000428163; ENST00000423166; ENST00000423497 | TSF |
| 2% | chr7 | 73098580 | 73098709 | + | chr7 | 73100966 | 73101061 | + | ENST00000265758; ENST00000432522; ENST00000421744; ENST00000428163; ENST00000423166; ENST00000423497 | TSF |
| 2% | chr7 | 73098580 | 73098709 | + | chr7 | 73100966 | 73101061 | + | ENST00000265758; ENST00000432522; ENST00000421744; ENST00000428163; ENST00000423166; ENST00000423497 | TSF |
| 2% | chr2 | 232340741 | 232340940 | + | chr2 | 232576105 | 232576119; 232576129 | + | ENST00000448874; ENST00000409321; ENST00000409115; ENST00000341369; ENST00000409683; ENST00000410064; ENST00000412128 | TSF |
| 2% | chr2 | 232340741 | 232340940 | + | chr2 | 232576105 | 232576119; 232576129 | + | ENST00000448874; ENST00000409321; ENST00000409115; ENST00000341369; ENST00000409683; ENST00000410064; ENST00000412128 | TSF |
| 2% | chr2 | 232340741 | 232340940 | + | chr2 | 232576105 | 232576119; 232576129 | + | ENST00000448874; ENST00000409321; ENST00000409115; ENST00000341369; ENST00000409683; ENST00000410064; ENST00000412128 | TSF |
| 2% | chr2 | 232340741 | 232340940 | + | chr2 | 232576105 | 232576119; 232576129 | + | ENST00000448874; ENST00000409321; ENST00000409115; ENST00000341369; ENST00000409683; ENST00000410064; ENST00000412128 | TSF |
| 2% | chr8 | 145134058 | 145134124 | + | chr8 | 145134846 | 145135052; 145134924 | + | ENST00000316052; ENST00000525936; ENST00000527954 | TSF |
| 2% | chr8 | 145134058 | 145134124 | + | chr8 | 145134846 | 145135052; 145134924 | + | ENST00000316052; ENST00000525936; ENST00000527954 | TSF |
| 2% | chr8 | 145134058 | 145134124 | + | chr8 | 145134846 | 145135052; 145134924 | + | ENST00000316052; ENST00000525936; ENST00000527954 | TSF |
| 2% | chr12 | 49659927 | 4966025 | + | chr12 | 49663248 | 49663470; 49663252 | + | ENST00000541364; ENST00000552125; ENST00000301072; ENST00000549183 | TSF |
| 2% | chr12 | 49659927 | 4966025 | + | chr12 | 49663248 | 49663470; 49663252 | + | ENST00000541364; ENST00000552125; ENST00000301072; ENST00000549183 | TSF |
| 2% | chr12 | 49659927 | 4966025 | + | chr12 | 49663248 | 49663470; 49663252 | + | ENST00000541364; ENST00000552125; ENST00000301072; ENST00000549183 | TSF |
| 2% | chr15 | 72464154 | 72463983 | − | chr15 | 72462280 | 72462188 | − | ENST00000309731; ENST00000564129; ENST00000568594; ENST00000570275; ENST00000562288 | TSF |
| 2% | chr15 | 72464154 | 72463983 | − | chr15 | 72462280 | 72462188 | − | ENST00000309731; ENST00000564129; ENST00000568594; ENST00000570275; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr15 | 72464154 | 72463983 | − | chr15 | 72462280 | 72462188 | − | ENST00000562288 ENST00000309731; ENST00000564129; ENST00000568594; ENST00000570275; ENST00000562288 | TSF |
| 2% | chr15 | 72464154 | 72463983 | − | chr15 | 72462280 | 72462188 | − | ENST00000309731; ENST00000564129; ENST00000568594; ENST00000570275; ENST00000562288 | TSF |
| 2% | chr15 | 72464154 | 72463983 | − | chr15 | 72462280 | 72462188 | − | ENST00000309731; ENST00000564129; ENST00000568594; ENST00000570275; ENST00000562288 | TSF |
| 2% | chrX | 134971303 | 134971006 | − | chrX | 134950133 | 134950078 | − | ENST00000420087; ENST00000463085; ENST00000370724; ENST00000491480 | TSF |
| 2% | chrX | 134971303 | 134971006 | − | chrX | 134950133 | 134950078 | − | ENST00000420087; ENST00000463085; ENST00000370724; ENST00000491480 | TSF |
| 2% | chr3 | 128352356 | 1283523306 | − | chr3 | 128351000 | 128350791 | − | ENST00000296255; ENST00000497289 | TSF |
| 2% | chr20 | 48264330 | 48264298 | − | chr20 | 48263615 | 48263502 | − | ENST00000371711 | TSF |
| 2% | chr6 | 33544821 | 33544801 | − | chr6 | 33543643 | 33543570 | − | ENST00000374467; ENST00000442998; ENST00000360661 | TSF |
| 2% | chr6 | 33544821 | 33544801 | − | chr6 | 33543643 | 33543570 | − | ENST00000374467; ENST00000442998; ENST00000360661 | TSF |
| 2% | chr19 | 45681322 | 45681186 | − | chr19 | 45668452 | 45668385 | − | ENST00000006275; ENST00000585934 | TSF |
| 2% | chr19 | 48654965 | 48654725 | − | chr19 | 48654596 | 48654489 | − | ENST00000263274; ENST00000601091; ENST00000542460 | TSF |
| 2% | chr19 | 48654965 | 48654725 | − | chr19 | 48654596 | 48654489 | − | ENST00000263274; ENST00000601091; ENST00000542460 | TSF |
| 2% | chr19 | 48654965 | 48654725 | − | chr19 | 48654596 | 48654489 | − | ENST00000263274; ENST00000601091; ENST00000542460 | TSF |
| 2% | chr3 | 191873117 | 191873032 | − | chr3 | 191861916 | 191861798; 191861849 | − | ENST00000445105; ENST00000264730; ENST00000454309; ENST00000440901; ENST00000450716; ENST00000430714; ENST00000448795 | TSF |
| 2% | chr3 | 191873117 | 191873032 | − | chr3 | 191861916 | 191861798; 191861849 | − | ENST00000445105; ENST00000264730; ENST00000454309; ENST00000440901; ENST00000450716; ENST00000430714; ENST00000448795 | TSF |
| 2% | chr4 | 1079284 | 1079281 | − | chr4 | 1075407 | 1075355 | − | ENST00000382968; ENST00000433731 | TSF |
| 2% | chr4 | 1079284 | 1079281 | − | chr4 | 1075407 | 1075355 | − | ENST00000382968; ENST00000433731 | TSF |
| 2% | chr4 | 1101138 | 1101040 | − | chr4 | 1093715 | 1093539 | − | ENST00000510715 | TSF |
| 2% | chr5 | 59983652 | 59983552 | − | chr5 | 59983054 | 59982789 | − | ENST00000265036; ENST00000453022 | TSF |
| 2% | chr5 | 59983652 | 59983552 | − | chr5 | 59983054 | 59982789 | − | ENST00000265036; ENST00000453022 | TSF |
| 2% | chrX | 103287465 | 103287369 | − | chrX | 103267320 | 103267284 | − | ENST00000217926 | TSF |
| 2% | chr13 | 95233957 | 95233815 | − | chr13 | 95233443 | 95233345 | − | ENST00000261296 | TSF |
| 2% | chr22 | 38253087 | 38253153 | + | chr22 | 38254686 | 38254747 | + | ENST00000412331; ENST00000381683; ENST00000414316; ENST00000406934; ENST00000451427 | TSF |
| 2% | chr22 | 38253087 | 38253153 | + | chr22 | 38254686 | 38254747 | + | ENST00000412331; ENST00000381683; ENST00000414316; ENST00000406934; ENST00000451427 | TSF |
| 2% | chr22 | 38253087 | 38253153 | + | chr22 | 38254686 | 38254747 | + | ENST00000412331; ENST00000381683; ENST00000414316; ENST00000406934; ENST00000451427 | TSF |
| 2% | chr22 | 38253087 | 38253153 | + | chr22 | 38254686 | 38254747 | + | ENST00000412331; ENST00000381683; ENST00000414316; ENST00000406934; ENST00000451427 | TSF |
| 2% | chr11 | 32617857 | 32617922 | + | chr11 | 32622235 | 32622378 | + | ENST00000531120; ENST00000524896; ENST00000526267 | TSF |
| 2% | chr11 | 32617857 | 32617922 | + | chr11 | 32622235 | 32622378 | + | ENST00000531120; ENST00000524896; ENST00000526267 | TSF |
| 2% | chr11 | 122699762 | 122700370 | + | chr11 | 122720776 | 122720922 | + | ENST00000227348 | TSF |
| 2% | chr21 | 42801857 | 42802535 | + | chr21 | 42811621 | 42811775 | + | ENST00000398600; ENST00000398598; ENST00000455164; ENST00000424365; ENST00000417963; ENST00000288383 | TSF |
| 2% | chr21 | 42801857 | 42802535 | + | chr21 | 42811621 | 42811775 | + | ENST00000398600; ENST00000398598; ENST00000455164; ENST00000424365; ENST00000417963; ENST00000288383 | TSF |
| 2% | chr21 | 42801857 | 42802535 | + | chr21 | 42811621 | 42811775 | + | ENST00000398600; ENST00000398598; ENST00000455164; ENST00000424365; ENST00000417963; ENST00000288383 | TSF |
| 2% | chr16 | 66587343 | 66587382 | + | chr16 | 66597025 | 66597120 | + | ENST00000264001; ENST00000351137; ENST00000417030; ENST00000532838 | TSF |
| 2% | chr16 | 66587343 | 66587382 | + | chr16 | 66597025 | 66597120 | + | ENST00000264001; ENST00000351137; ENST00000417030; ENST00000532838 | TSF |
| 2% | chr16 | 2819422 | 2820027 | + | chr16 | 2820353 | 2820466 | + | ENST00000301740 | TSF |
| 2% | chr20 | 33107223 | 33107303 | + | chr20 | 33122432 | 33122599; 33122718 | + | ENST00000357156; ENST00000417166; ENST00000374846 | TSF |
| 2% | chr20 | 33107223 | 33107303 | + | chr20 | 33122432 | 33122599; | + | ENST00000357156; ENST00000417166; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr19 | 17667441 | 17667488 | + | chr19 | 17670120 | 33122718 17670230 | + | ENST00000374846 ENST00000252599 | TSF |
| 2% | chr8 | 125551665 | 125551665 | + | chr8 | 125555328 | 125555520 | + | ENST00000276689; ENST00000518008; ENST00000522532 | TSF |
| 2% | chr8 | 125551665 | 125551665 | + | chr8 | 125555328 | 125555520 | + | ENST00000276689; ENST00000518008; ENST00000522532 | TSF |
| 2% | chr8 | 125551665 | 125551665 | + | chr8 | 125555328 | 125555520 | + | ENST00000276689; ENST00000518008; ENST00000522532 | TSF |
| 2% | chr11 | 64853798 | 64852846 | + | chr11 | 64853887 | 64854027; 64853914; 64854080 | + | ENST00000531761; ENST00000453524; ENST00000294258; ENST00000526334; ENST00000526945; ENST00000532200 | TSF |
| 2% | chr11 | 64853798 | 64852846 | + | chr11 | 64853887 | 64854027; 64853914; 64854080 | + | ENST00000531761; ENST00000453524; ENST00000294258; ENST00000526334; ENST00000526945; ENST00000532200 | TSF |
| 2% | chr11 | 64853798 | 64852846 | + | chr11 | 64853887 | 64854027; 64853914; 64854080 | + | ENST00000531761; ENST00000453524; ENST00000294258; ENST00000526334; ENST00000526945; ENST00000532200 | TSF |
| 2% | chr11 | 64853798 | 64852846 | + | chr11 | 64853887 | 64854027; 64853914; 64854080 | + | ENST00000531761; ENST00000453524; ENST00000294258; ENST00000526334; ENST00000526945; ENST00000532200 | TSF |
| 2% | chr11 | 64853798 | 64852846 | + | chr11 | 64853887 | 64854027; 64853914; 64854080 | + | ENST00000531761; ENST00000453524; ENST00000294258; ENST00000526334; ENST00000526945; ENST00000532200 | TSF |
| 2% | chr11 | 64853798 | 64852846 | + | chr11 | 64853887 | 64854027; 64853914; 64854080 | + | ENST00000531761; ENST00000453524; ENST00000294258; ENST00000526334; ENST00000526945; ENST00000532200 | TSF |
| 2% | chr12 | 56110428 | 56110523 | + | chr12 | 56112875 | 56113007; 56112894; 56113085 | + | ENST00000257899; ENST00000551946; ENST00000550412; ENST00000548925; ENST00000549147; ENST00000553100 | TSF |
| 2% | chr12 | 56110428 | 56110523 | + | chr12 | 56112875 | 56113007; 56112894; 56113085 | + | ENST00000257899; ENST00000551946; ENST00000550412; ENST00000548925; ENST00000549147; ENST00000553100 | TSF |
| 2% | chr12 | 56110428 | 56110523 | + | chr12 | 56112875 | 56113007; 56112894; 56113085 | + | ENST00000257899; ENST00000551946; ENST00000550412; ENST00000548925; ENST00000549147; ENST00000553100 | TSF |
| 2% | chr12 | 56110428 | 56110523 | + | chr12 | 56112875 | 56113007; 56112894; 56113085 | + | ENST00000257899; ENST00000551946; ENST00000550412; ENST00000548925; ENST00000549147; ENST00000553100 | TSF |
| 2% | chrX | 118371254 | 118371371 | + | chrX | 118374272 | 118374427 | + | ENST00000217971 | TSF |
| 2% | chr5 | 142190974 | 142191055 | + | chr5 | 142252965 | 142253060 | + | ENST00000274498; ENST00000378004; ENST00000378013 | TSF |
| 2% | chr5 | 142190974 | 142191055 | + | chr5 | 142252965 | 142253060 | + | ENST00000274498; ENST00000378004; ENST00000378013 | TSF |
| 2% | chr5 | 142190974 | 142191055 | + | chr5 | 142252965 | 142253060 | + | ENST00000274498; ENST00000378004; ENST00000378013 | TSF |
| 2% | chr2 | 3431377 | 3431530 | + | chr2 | 3624220 | 3624220 | + | ENST00000304921; ENST00000407445; ENST00000403564; ENST00000406376 | TSF |
| 2% | chr2 | 3431377 | 3431530 | + | chr2 | 3624220 | 3624220 | + | ENST00000304921; ENST00000407445; ENST00000403564; ENST00000406376 | TSF |
| 2% | chr13 | 43670805 | 43671144 | + | chr13 | 43381314 | 43681384 | + | ENST00000379221 | TSF |
| 2% | chr20 | 45337040 | 45337192 | + | chr20 | 45353680 | 45354963 | + | ENST00000359271 | TSF |
| 2% | chr1 | 28199269 | 28199387 | + | chr1 | 28203099 | 28203239 | + | ENST00000328928; ENST00000373925; ENST00000373927; ENST00000442118; ENST00000373921 | TSF |
| 2% | chr1 | 28199269 | 28199387 | + | chr1 | 28203099 | 28203239 | + | ENST00000328928; ENST00000373925; ENST00000373927; ENST00000442118; ENST00000373921 | TSF |
| 2% | chr1 | 28199269 | 28199387 | + | chr1 | 28203099 | 28203239 | + | ENST00000328928; ENST00000373925; ENST00000373927; ENST00000442118; ENST00000373921 | TSF |
| 2% | chr1 | 28199269 | 28199387 | + | chr1 | 28203099 | 28203239 | + | ENST00000328928; ENST00000373925; ENST00000373927; ENST00000442118; ENST00000373921 | TSF |
| 2% | chr1 | 28199269 | 28199387 | + | chr1 | 28203099 | 28203239 | + | ENST00000328928; ENST00000373925; ENST00000373927; ENST00000442118; ENST00000373921 | TSF |
| 2% | chr20 | 33111081 | 33111436 | + | chr20 | 33114073 | 33114148 | + | ENST00000357156; ENST00000417166; ENST00000300469; ENST00000374846 | TSF |
| 2% | chr20 | 33111081 | 33111436 | + | chr20 | 33114073 | 33114148 | + | ENST00000357156; ENST00000417166; ENST00000300469; ENST00000374846 | TSF |
| 2% | chr20 | 33111081 | 33111436 | + | chr20 | 33114073 | 33114148 | + | ENST00000357156; ENST00000417166; ENST00000300469; ENST00000374846 | TSF |
| 2% | chr5 | 108341955 | 1083421993 | + | chr5 | 108373123 | 108373179 | + | ENST00000281092; ENST00000438717 | TSF |
| 2% | chrX | 69366031 | 69366077 | + | chrX | 69366595 | 69366678 | + | ENST00000342206; ENST00000356413 | TSF |
| 2% | chr7 | 74128471 | 74128505 | + | chr7 | 74165693 | 74165748 | + | ENST00000324896; ENST00000346152; ENST00000353920; ENST00000416070 | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr8 | 100905650 | 100954057 | − | chr8 | 100899846 | 100899733 | − | ENST00000522934; ENST00000520517; ENST00000520468; ENST00000297564; ENST00000520271; ENST00000517682; ENST00000524245; ENST00000522940; ENST00000518171; ENST00000523016 | TSF |
| 2% | chr19 | 1114930 | 1114676 | − | chr19 | 1114421 | 1114230 | − | ENST00000361757; ENST00000587024; ENST00000438103 | TSF |
| 2% | chr9 | 132580720 | 132580632 | − | chr9 | 132576501 | 132576251 | − | ENST00000351698 | TSF |
| 2% | chr10 | 71990523 | 71990251 | − | chr10 | 71990155 | 71990097 | − | ENST00000373232; ENST00000373230; ENST00000608321 | TSF |
| 2% | chr10 | 71990523 | 71990251 | − | chr10 | 71990155 | 71990097 | − | ENST00000373232; ENST00000373230; ENST00000608321 | TSF |
| 2% | chrX | 134971303 | 13497186 | − | chrX | 134932870 | 134932815 | − | ENST00000487941; ENST00000434966; ENST00000494421 | TSF |
| 2% | chr12 | 27144384 | 27144286 | − | chr12 | 27143560 | 27143383 | − | ENST00000343028; ENST00000545303; ENST00000535260; ENST00000543882; ENST00000543655; ENST00000535819 | TSF |
| 2% | chr12 | 27144384 | 27144286 | − | chr12 | 27143560 | 27143383 | − | ENST00000343028; ENST00000545303; ENST00000535260; ENST00000543882; ENST00000543655; ENST00000535819 | TSF |
| 2% | chr12 | 27144384 | 27144286 | − | chr12 | 27143560 | 27143383 | − | ENST00000343028; ENST00000545303; ENST00000535260; ENST00000543882; ENST00000543655; ENST00000535819 | TSF |
| 2% | chr12 | 27144384 | 27144286 | − | chr12 | 27143560 | 27143383 | − | ENST00000343028; ENST00000545303; ENST00000535260; ENST00000543882; ENST00000543655; ENST00000535819 | TSF |
| 2% | chr12 | 27144384 | 27144286 | − | chr12 | 27143560 | 27143383 | − | ENST00000343028; ENST00000545303; ENST00000535260; ENST00000543882; ENST00000543655; ENST00000535819 | TSF |
| 2% | chrX | 134971303 | 134971006 | − | chrX | 134967383 | 134967328 | − | ENST00000491002; ENST00000448053; ENST00000472834 | TSF |
| 2% | chr8 | 143834800 | 143834786 | − | chr8 | 143832588 | 143832469 | − | ENST00000359228 | TSF |
| 2% | chr7 | 48039730 | 48039725 | − | chr7 | 48035743 | 48035628 | − | ENST00000453071; ENST00000297325; ENST00000412371; ENST00000453192; ENST00000395572; ENST00000438771 | TSF |
| 2% | chr7 | 48039730 | 48039725 | − | chr7 | 48035743 | 48035628 | − | ENST00000453071; ENST00000297325; ENST00000412371; ENST00000453192; ENST00000395572; ENST00000438771 | TSF |
| 2% | chr7 | 48039730 | 48039725 | − | chr7 | 48035743 | 48035628 | − | ENST00000453071; ENST00000297325; ENST00000412371; ENST00000453192; ENST00000395572; ENST00000438771 | TSF |
| 2% | chr1 | 206278006 | 206276891 | − | chr1 | 206243250 | 206243150 | − | ENST00000331555 | TSF |
| 2% | chr3 | 197640178 | 197640160 | − | chr3 | 197639671 | 197639546 | − | ENST00000265239; ENST00000455191 | TSF |
| 2% | chr14 | 35063866 | 35063813 | − | chr14 | 35062356 | 35062251 | − | ENST00000396526; ENST00000396534; ENST00000362031; ENST00000355110; ENST00000557265 | TSF |
| 2% | chr14 | 35063866 | 35063813 | − | chr14 | 35062356 | 35062251 | − | ENST00000396526; ENST00000396534; ENST00000362031; ENST00000355110; ENST00000557265 | TSF |
| 2% | chr1 | 33251116 | 33251115 | − | chr1 | 33248140 | 33248005 | − | ENST00000373477 | TSF |
| 2% | chr4 | 162586244 | 162585968 | − | chr4 | 162577646 | 162577480 | − | ENST00000306100; ENST00000379164; ENST00000536695; ENST00000427802 | TSF |
| 2% | chr4 | 162586244 | 162585968 | − | chr4 | 162577646 | 162577480 | − | ENST00000306100; ENST00000379164; ENST00000536695; ENST00000427802 | TSF |
| 2% | chr6 | 31660537 | 31660355 | − | chr6 | 31659695 | 31659581 | − | ENST00000395952; ENST00000440843 | TSF |
| 2% | chr9 | 130213440 | 130213384 | − | chr9 | 130211635 | 130211560 | − | ENST00000361436; ENST00000536368 | TSF |
| 2% | chr6 | 41744299 | 41744159 | − | chr6 | 41743343 | 41743157; 41743301 | − | ENST00000259748; ENST00000373018; ENST00000426290; ENST00000422888 | TSF |
| 2% | chr6 | 41744299 | 41744159 | − | chr6 | 41743343 | 41743157; 41743301 | − | ENST00000259748; ENST00000373018; ENST00000426290; ENST00000422888 | TSF |
| 2% | chr6 | 41744299 | 41744159 | − | chr6 | 41743343 | 41743157; 41743301 | − | ENST00000259748; ENST00000373018; ENST00000426290; ENST00000422888 | TSF |
| 2% | chr22 | 21355965 | 21355835 | − | chr22 | 21355700 | 21355545 | − | ENST00000215742; ENST00000399133 | |
| 2% | chr12 | 15490399 | 15490311 | − | chr12 | 15274053 | 15273997; 15273999 | − | ENST00000256953; ENST00000538313; ENST00000536465; ENST00000545567; ENST00000537647; ENST00000393736 | TSF |
| 2% | chr12 | 15490399 | 15490311 | − | chr12 | 15274053 | 15273997; 15273999 | − | ENST00000256953; ENST00000538313; ENST00000536465; ENST00000545567; ENST00000537647; ENST00000393736 | TSF |
| 2% | chr12 | 15490399 | 15490311 | − | chr12 | 15274053 | 15273997; 15273999 | − | ENST00000256953; ENST00000538313; ENST00000536465; ENST00000545567; ENST00000537647; ENST00000393736 | TSF |
| 2% | chr12 | 15490399 | 15490311 | − | chr12 | 15274053 | 15273997; | − | ENST00000256953; ENST00000538313; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 15273999 | | ENST00000536465; ENST00000545567; ENST00000537647; ENST00000393736 | |
| 2% | chr12 | 15490399 | 15490311 | – | chr12 | 15274053 | 15273997; 15273999 | – | ENST00000256953; ENST00000538313; ENST00000536465; ENST00000545567; ENST00000537647; ENST00000393736 | TSF |
| 2% | chr12 | 15490399 | 15490311 | – | chr12 | 15274053 | 15273997; 15273999 | – | ENST00000256953; ENST00000538313; ENST00000536465; ENST00000545567; ENST00000537647; ENST00000393736 | TSF |
| 2% | chrX | 134954053 | 134953756 | – | chrX | 134932870 | 134932815 | – | ENST00000487941; ENST00000434966; ENST00000494421 | TSF |
| 2% | chr3 | 18283330 | 182833262 | – | chr3 | 182812393 | 182812347 | – | ENST00000265594; ENST00000497830; ENST00000495767; ENST00000476176; ENST00000487634; ENST00000466650; ENST00000486226 | TSF |
| 2% | chr3 | 18283330 | 182833262 | – | chr3 | 182812393 | 182812347 | – | ENST00000265594; ENST00000497830; ENST00000495767; ENST00000476176; ENST00000487634; ENST00000466650; ENST00000486226 | TSF |
| 2% | chr3 | 18283330 | 182833262 | – | chr3 | 182812393 | 182812347 | – | ENST00000265594; ENST00000497830; ENST00000495767; ENST00000476176; ENST00000487634; ENST00000466650; ENST00000486226 | TSF |
| 2% | chr3 | 18283330 | 182833262 | – | chr3 | 182812393 | 182812347 | – | ENST00000265594; ENST00000497830; ENST00000495767; ENST00000476176; ENST00000487634; ENST00000466650; ENST00000486226 | TSF |
| 2% | chr3 | 18283330 | 182833262 | – | chr3 | 182812393 | 182812347 | – | ENST00000265594; ENST00000497830; ENST00000495767; ENST00000476176; ENST00000487634; ENST00000466650; ENST00000486226 | TSF |
| 2% | chrX | 134936794 | 134936497 | – | chrX | 134932870 | 134932815 | – | ENST00000487941; ENST00000434966; ENST00000494421 | TSF |
| 1% | chr10 | 27470588 | 27470654 | + | chr10 | 27476308 | 27475465 | + | ENST00000375946; ENST00000375940; ENST00000342386 | TSF |
| 1% | chr2 | 101518034 | 101518064 | + | chr2 | 101521195 | 101521248 | + | ENST00000427413; ENST00000542504 | TSF |
| 1% | chr2 | 101518034 | 101518064 | + | chr2 | 101521195 | 101521248 | + | ENST00000427413; ENST00000542504 | TSF |
| 1% | chr17 | 37902588 | 37902638 | + | chr17 | 37903004 | 37903150 | + | ENST00000309156; ENST00000394211; ENST00000445327; ENST00000394209 | TSF |
| 1% | chr9 | 130921922 | 130921962 | + | chr9 | 13092572 | 130925894 | + | ENST00000372994 | TSF |
| 1% | chr19 | 16198411 | 16198509 | + | chr19 | 16198837 | 16198907; 16198903; 16198876 | + | ENST00000344824; ENST00000538887; ENST00000586499; ENST00000586833; ENST00000588507; ENST00000300933; ENST00000588410; ENST00000592138 | TSF |
| 1% | chr19 | 16198411 | 16198509 | + | chr19 | 16198837 | 16198907; 16198903; 16198876 | + | ENST00000344824; ENST00000538887; ENST00000586499; ENST00000586833; ENST00000588507; ENST00000300933; ENST00000588410; ENST00000592138 | TSF |
| 1% | chr19 | 16198411 | 16198509 | + | chr19 | 16198837 | 16198907; 16198903; 16198876 | + | ENST00000344824; ENST00000538887; ENST00000586499; ENST00000586833; ENST00000588507; ENST00000300933; ENST00000588410; ENST00000592138 | TSF |
| 1% | chr19 | 16198411 | 16198509 | + | chr19 | 16198837 | 16198907; 16198903; 16198876 | + | ENST00000344824; ENST00000538887; ENST00000586499; ENST00000586833; ENST00000588507; ENST00000300933; ENST00000588410; ENST00000592138 | TSF |
| 1% | chr19 | 16198411 | 16198509 | + | chr19 | 16198837 | 16198907; 16198903; 16198876 | + | ENST00000344824; ENST00000538887; ENST00000586499; ENST00000586833; ENST00000588507; ENST00000300933; ENST00000588410; ENST00000592138 | TSF |
| 1% | chr19 | 16198411 | 16198509 | + | chr19 | 16198837 | 16198907; 16198903; 16198876 | + | ENST00000344824; ENST00000538887; ENST00000586499; ENST00000586833; ENST00000588507; ENST00000300933; ENST00000588410; ENST00000592138 | TSF |
| 1% | chr19 | 16201364 | 16201431 | + | chr19 | 16204346 | 16204408; 16204354; 16204374; 16204391 | + | ENST00000344824; ENST00000538887; ENST00000586833; ENST00000588507; ENST00000300933; ENST00000592138; ENST00000588032 | TSF |
| 1% | chr19 | 16201364 | 16201431 | + | chr19 | 16204346 | 16204408; 16204354; 16204374; 16204391 | + | ENST00000344824; ENST00000538887; ENST00000586833; ENST00000588507; ENST00000300933; ENST00000592138; ENST00000588032 | TSF |
| 1% | chr19 | 16201364 | 16201431 | + | chr19 | 16204346 | 16204408; 16204354; 16204374; 16204391 | + | ENST00000344824; ENST00000538887; ENST00000586833; ENST00000588507; ENST00000300933; ENST00000592138; ENST00000588032 | TSF |
| 1% | chr19 | 16201364 | 16201431 | + | chr19 | 16204346 | 16204408; | + | ENST00000344824; ENST00000538887; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 16204354; 16204374; 16204391 | | ENST00000586833; ENST00000588507; ENST00000300933; ENST00000592138; ENST00000588032 | |
| 1% | chr17 | 65894489 | 65894534 | + | chr17 | 65899905 | 65900034 | + | ENST00000544778; ENST00000321892; ENST00000335221; ENST00000306378; ENST00000424123 | TSF |
| 1% | chr17 | 65894489 | 65894534 | + | chr17 | 65899905 | 65900034 | + | ENST00000544778; ENST00000321892; ENST00000335221; ENST00000306378; ENST00000424123 | TSF |
| 1% | chr17 | 65894489 | 65894534 | + | chr17 | 65899905 | 65900034 | + | ENST00000544778; ENST00000321892; ENST00000335221; ENST00000306378; ENST00000424123 | TSF |
| 1% | chr2 | 232340741 | 232340940 | + | chr2 | 232576649 | 232576693 | + | ENST00000409321; ENST00000409115; ENST00000341369; ENST00000409683; ENST00000410064; ENST00000412128 | TSF |
| 1% | chr2 | 232340741 | 232340940 | + | chr2 | 232576649 | 232576693 | + | ENST00000409321; ENST00000409115; ENST00000341369; ENST00000409683; ENST00000410064; ENST00000412128 | TSF |
| 1% | chr1 | 43234653 | 43234703 | + | chr1 | 43239234 | 43239320 | + | ENST00000372525 | TSF |
| 1% | chr21 | 42801857 | 42802535 | + | chr21 | 42807910 | 42807956 | + | ENST00000398600; ENST00000398598; ENST00000455164; ENST00000424365; ENST00000417963 | TSF |
| 1% | chr21 | 42801857 | 42802535 | + | chr21 | 42807910 | 42807956 | + | ENST00000398600; ENST00000398598; ENST00000455164; ENST00000424365; ENST00000417963 | TSF |
| 1% | chr21 | 42801857 | 42802535 | + | chr21 | 42807910 | 42807956 | + | ENST00000398600; ENST00000398598; ENST00000455164; ENST00000424365; ENST00000417963 | TSF |
| 1% | chr1 | 155179310 | 155179341 | + | chr1 | 155180137 | 155180206; 155180226 | + | ENST00000368376; ENST00000316721; ENST00000424959; ENST00000609421 | TSF |
| 1% | chr1 | 155179310 | 155179341 | + | chr1 | 155180137 | 155180206; 155180226 | + | ENST00000368376; ENST00000316721; ENST00000424959; ENST00000609421 | TSF |
| 1% | chr1 | 155179310 | 155179341 | + | chr1 | 155180137 | 155180206; 155180226 | + | ENST00000368376; ENST00000316721; ENST00000424959; ENST00000609421 | TSF |
| 1% | chr12 | 49105350 | 50491120 | + | chr12 | 50492497 | 50492598 | + | ENST00000394963; ENST00000381513; ENST00000548573; ENST00000549274 | TSF |
| 1% | chr3 | 54946412 | 54946415 | + | chr3 | 55002477 | 55002538 | + | ENST00000415676; ENST00000288197; ENST00000474759; ENST00000490478 | TSF |
| 1% | chr12 | 133288092 | 133288275 | + | chr12 | 133291444 | 133291498; 133291622 | + | ENST00000537262; ENST00000545677; ENST00000317555; ENST00000498926 | TSF |
| 1% | chr12 | 133288092 | 133288275 | + | chr12 | 133291444 | 133291498; 133291622 | + | ENST00000537262; ENST00000545677; ENST00000317555; ENST00000498926 | TSF |
| 1% | chr12 | 133288092 | 133288275 | + | chr12 | 133291444 | 133291498; 133291622 | + | ENST00000537262; ENST00000545677; ENST00000317555; ENST00000498926 | TSF |
| 1% | chr12 | 133288092 | 133288275 | + | chr12 | 133291444 | 133291498; 133291622 | + | ENST00000537262; ENST00000545677; ENST00000317555; ENST00000498926 | TSF |
| 1% | chr17 | 64988088 | 64988129 | + | chr17 | 65014305 | 65014388 | + | ENST00000262138 | TSF |
| 1% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 1% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 1% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 1% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 1% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 1% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 1% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 1% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 1% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 1% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 1% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 1% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 1% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 1% | chr17 | 79936116 | 79936215 | + | chr17 | 79937060 | 79937115 | + | ENST00000581484; ENST00000306729; ENST00000306739; ENST00000344865; ENST00000581647; ENST00000583503; ENST00000579684 | TSF |
| 1% | chrX | 71397824 | 71398498 | + | chrX | 71416635 | 71416778; 71416754 | + | ENST00000218432; ENST00000423432; ENST00000373669; ENST00000496835; ENST00000439980; ENST00000446576 | TSF |
| 1% | chrX | 71397824 | 71398498 | + | chrX | 71416635 | 71416778; 71416754 | + | ENST00000218432; ENST00000423432; ENST00000373669; ENST00000496835; ENST00000439980; ENST00000446576 | TSF |
| 1% | chrX | 71397824 | 71398498 | + | chrX | 71416635 | 71416778; 71416754 | + | ENST00000218432; ENST00000423432; ENST00000373669; ENST00000496835; ENST00000439980; ENST00000446576 | TSF |
| 1% | chrX | 71397824 | 71398498 | + | chrX | 71416635 | 71416778; 71416754 | + | ENST00000218432; ENST00000423432; ENST00000373669; ENST00000496835; ENST00000439980; ENST00000446576 | TSF |
| 1% | chr8 | 143592075 | 143592168 | + | chr8 | 143592293 | 143592434 | + | ENST00000517894; ENST00000521208; ENST00000323289 | TSF |
| 1% | chr8 | 143592075 | 143592168 | + | chr8 | 143592293 | 143592434 | + | ENST00000517894; ENST00000521208; ENST00000323289 | TSF |
| 1% | chr2 | 101567739 | 101568117 | + | chr2 | 101580520 | 101580638 | + | ENST00000335681; ENST00000542504 | TSF |
| 1% | chr7 | 76921651 | 76921749 | + | chr7 | 76922269 | 76922517 | + | ENST00000285871; ENST00000431197 | TSF |
| 1% | chr16 | 28838911 | 28839140 | + | chr16 | 288407 | 28840813 | + | ENST00000340394; ENST00000325215; ENST00000336783; ENST00000382686; ENST00000395547; ENST00000564304; ENST00000570200; ENST00000568266 | TSF |
| 1% | chr16 | 28838911 | 28839140 | + | chr16 | 288407 | 28840813 | + | ENST00000340394; ENST00000325215; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr16 | 28838911 | 28839140 | + | chr16 | 288407 | 28840813 | + | ENST00000336783; ENST00000382686; ENST00000395547; ENST00000564304; ENST00000570200; ENST00000568266 ENST00000340394; ENST00000325215; | TSF |
| 1% | chr16 | 28838911 | 28839140 | + | chr16 | 288407 | 28840813 | + | ENST00000336783; ENST00000382686; ENST00000395547; ENST00000564304; ENST00000570200; ENST00000568266 ENST00000340394; ENST00000325215; | TSF |
| 1% | chr16 | 28838911 | 28839140 | + | chr16 | 288407 | 28840813 | + | ENST00000336783; ENST00000382686; ENST00000395547; ENST00000564304; ENST00000570200; ENST00000568266 ENST00000340394; ENST00000325215; | TSF |
| 1% | chr16 | 28838911 | 28839140 | + | chr16 | 288407 | 28840813 | + | ENST00000336783; ENST00000382686; ENST00000395547; ENST00000564304; ENST00000570200; ENST00000568266 ENST00000340394; ENST00000325215; | TSF |
| 1% | chr16 | 28838911 | 28839140 | + | chr16 | 288407 | 28840813 | + | ENST00000336783; ENST00000382686; ENST00000395547; ENST00000564304; ENST00000570200; ENST00000568266 ENST00000340394; ENST00000325215; | TSF |
| 1% | chr16 | 28838911 | 28839140 | + | chr16 | 288407 | 28840813 | + | ENST00000336783; ENST00000382686; ENST00000395547; ENST00000564304; ENST00000570200; ENST00000568266 ENST00000340394; ENST00000325215; | TSF |
| 1% | chr8 | 95716710 | 95716810 | + | chr8 | 95718153 | 95718173; 95718159 | + | ENST00000423620; ENST00000454170; ENST00000517610 | TSF |
| 1% | chr8 | 95716710 | 95716810 | + | chr8 | 95718153 | 95718173; 95718159 | + | ENST00000423620; ENST00000454170; ENST00000517610 | TSF |
| 1% | chr5 | 79293955 | 79294198 | + | chr5 | 79335900 | 79336103 | + | ENST00000350881 | TSF |
| 1% | chr7 | 150777427 | 150777296 | − | chr7 | 150775179 | 150775103; 150774966 | − | ENST00000540185; ENST00000353841; ENST00000297532; ENST00000482571 | TSF |
| 1% | chr7 | 150777427 | 150777296 | − | chr7 | 150775179 | 150775103; 150774966 | − | ENST00000540185; ENST00000353841; ENST00000297532; ENST00000482571 | TSF |
| 1% | chr5 | 151074528 | 151074519 | − | chr5 | 151046027 | 151045922; 151045934 | − | ENST00000231061; ENST00000538026 | TSF |
| 1% | chr5 | 151074528 | 151074519 | − | chr5 | 151046027 | 151045922; 151045934 | − | ENST00000231061; ENST00000538026 | TSF |
| 1% | chr8 | 140818443 | 140818376 | − | chr8 | 140744445 | 140744222 | − | ENST00000389327; ENST00000389328; ENST00000520857; ENST00000438773 | TSF |
| 1% | chr12 | 54064392 | 54064161 | − | chr12 | 54063732 | 54063655 | − | ENST00000602871; ENST00000394349; ENST00000549164; ENST00000338662 | TSF |
| 1% | chr20 | 49556441 | 49556310 | − | chr20 | 49552799 | 49552685 | − | ENST00000371588; ENST00000371582; ENST00000371584; ENST00000371583; ENST00000413082 | TSF |
| 1% | chr20 | 49556441 | 49556310 | − | chr20 | 49552799 | 49552685 | − | ENST00000371588; ENST00000371582; ENST00000371584; ENST00000371583; ENST00000413082 | TSF |
| 1% | chr19 | 36405278 | 36405224 | − | chr19 | 36398166 | 36398120 | − | ENST00000585901; ENST00000544690; ENST00000262629 | TSF |
| 1% | chr19 | 8382856 | 8382806 | − | chr19 | 8381529 | 8381380; 8381494 | − | ENST00000598884; ENST00000593729; ENST00000595856; ENST00000301457 | TSF |
| 1% | chr19 | 8382856 | 8382806 | − | chr19 | 8381529 | 8381380; 8381494 | − | ENST00000598884; ENST00000593729; ENST00000595856; ENST00000301457 | TSF |
| 1% | chr20 | 45138455 | 45138244 | − | chr20 | 4513379 | 45133253 | − | ENST00000593880; ENST00000347606 | TSF |
| 1% | chr20 | 45138455 | 45138244 | − | chr20 | 4513379 | 45133253 | − | ENST00000593880; ENST00000347606 | TSF |
| 1% | chr12 | 34257353 | 53342475 | − | chr12 | 53298811 | 53298442; 53298460 | − | ENST00000552150; ENST00000548998; ENST00000546542 | TSF |
| 1% | chr12 | 34257353 | 53342475 | − | chr12 | 53298811 | 53298442; 53298460 | − | ENST00000552150; ENST00000548998; ENST00000546542 | TSF |
| 1% | chr12 | 34257353 | 53342475 | − | chr12 | 53298811 | 53298442; 53298460 | − | ENST00000552150; ENST00000548998; ENST00000546542 | TSF |
| 1% | chr1 | 154581117 | 154581067 | − | chr1 | 154575102 | 154573517 | − | ENST00000292205; ENST00000368474; ENST00000529168 | TSF |
| 1% | chr1 | 154581117 | 154581067 | − | chr1 | 154575102 | 154573517 | − | ENST00000292205; ENST00000368474; ENST00000529168 | TSF |
| 1% | chr3 | 122652679 | 122652013 | − | chr3 | 122647905 | 122647843 | − | ENST00000357599; ENST00000475244; ENST00000195173; ENST00000451055; ENST00000393583 | TSF |
| 1% | chr3 | 122652679 | 122652013 | − | chr3 | 122647905 | 122647843 | − | ENST00000357599; ENST00000475244; ENST00000195173; ENST00000451055; ENST00000393583 | TSF |
| 1% | chr3 | 122652679 | 122652013 | − | chr3 | 122647905 | 122647843 | − | ENST00000357599; ENST00000475244; ENST00000195173; ENST00000451055; | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr3 | 122652679 | 122652013 | – | chr3 | 122647905 | 122647843 | – | ENST00000393583 ENST00000357599; ENST00000475244; ENST00000195173; ENST00000451055; ENST00000393583 | TSF |
| 1% | chr1 | 153533056 | 153532824 | – | chr1 | 153517203 | 153517130 | – | ENST00000368715; ENST00000354332; ENST00000368716; ENST00000368714 | TSF |
| 1% | chr3 | 52007496 | 52007451 | – | chr3 | 52004200 | 52003959; | – | ENST00000483233; ENST00000395008; ENST00000361143; ENST00000461108; ENST00000525795 | TSF |
| 1% | chr3 | 52007496 | 52007451 | – | chr3 | 52004200 | 52003959; | – | ENST00000483233; ENST00000395008; ENST00000361143; ENST00000461108; ENST00000525795 | TSF |
| 1% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 1% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 1% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 1% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 1% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 1% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 1% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 1% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr11 | 93468219 | 93468129 | − | chr11 | 93466563 | 93466528 | − | ENST00000393259 | TSF |
| 1% | chr11 | 61558725 | 61558538 | − | chr11 | 61558074 | 61557965; 61557928 | − | ENST00000537328; ENST00000541893; ENST00000545210; ENST00000257262; ENST00000535297 | TSF |
| 1% | chr11 | 61558725 | 61558538 | − | chr11 | 61558074 | 61557965; 61557928 | − | ENST00000537328; ENST00000541893; ENST00000545210; ENST00000257262; ENST00000535297 | TSF |
| 1% | chr11 | 65629362 | 65629337 | − | chr11 | 65623713 | 65623406; 65623445 | − | ENST00000525451; ENST00000308162; ENST00000534769; ENST00000532134; ENST00000526975 | TSF |
| 1% | chr11 | 65629362 | 65629337 | − | chr11 | 65623713 | 65623406; 65623445 | − | ENST00000525451; ENST00000308162; ENST00000534769; ENST00000532134; ENST00000526975 | TSF |
| 1% | chr11 | 65629362 | 65629337 | − | chr11 | 65623713 | 65623406; 65623445 | − | ENST00000525451; ENST00000308162; ENST00000534769; ENST00000532134; ENST00000526975 | TSF |
| 1% | chr19 | 5714928 | 5714878 | − | chr19 | 5714282 | 5714194 | − | ENST00000360614; ENST00000590558; ENST00000585374; ENST00000593119; ENST00000590729 | TSF |
| 1% | chr19 | 5714928 | 5714878 | − | chr19 | 5714282 | 5714194 | − | ENST00000360614; ENST00000590558; ENST00000585374; ENST00000593119; ENST00000590729 | TSF |
| 1% | chr19 | 5714928 | 5714878 | − | chr19 | 5714282 | 5714194 | − | ENST00000360614; ENST00000590558; ENST00000585374; ENST00000593119; ENST00000590729 | TSF |
| 1% | chr1 | 31208485 | 31208427 | − | chr1 | 31208112 | 31208020 | − | ENST00000294507 | TSF |
| 1% | chr19 | 36397290 | 36397240 | − | chr19 | 36395536 | 36395471 | − | ENST00000424586; ENST00000585901; ENST00000544690; ENST00000262629; ENST00000589517 | TSF |
| 1% | chr3 | 32535582 | 32535322 | − | chr3 | 32533378 | 32533202 | − | ENST00000205636 | TSF |
| 1% | chr14 | 105642036 | 105642815 | − | chr14 | 105639598 | 105639358 | − | ENST00000392568 | TSF |
| 1% | chr1 | 206278006 | 206277271 | − | chr1 | 206243250 | 206243150 | − | ENST00000331555 | TSF |
| 1% | chr19 | 46194689 | 46194421 | − | chr19 | 46191824 | 46191645 | − | ENST00000342669; ENST00000588301; ENST00000590212 | TSF |
| 1% | chr19 | 46194689 | 46194421 | − | chr19 | 46191824 | 46191645 | − | ENST00000342669; ENST00000588301; ENST00000590212 | TSF |
| 1% | chr4 | 83762275 | 83761993 | − | chr4 | 83750211 | 83750153 | − | ENST00000503937; ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000511338 | TSF |
| 1% | chr4 | 83762275 | 83761993 | − | chr4 | 83750211 | 83750153 | − | ENST00000503937; ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000511338 | TSF |
| 1% | chr20 | 5090931 | 5090905 | − | chr20 | 5090091 | 5089978 | − | ENST00000342308 | TSF |
| 1% | chr11 | 57328392 | 57328294 | − | chr11 | 57327905 | 57327810 | − | ENST00000287156; ENST00000526659 | TSF |
| 1% | chr11 | 57328392 | 57328294 | − | chr11 | 57327905 | 57327810 | − | ENST00000287156; ENST00000526659 | TSF |
| 1% | chr8 | 101933557 | 101933272 | − | chr8 | 101932980 | 101932921; 101932944 | − | ENST00000395957; ENST00000395958; ENST00000457309; ENST00000395956; ENST00000353245; ENST00000523848; ENST00000522542; ENST00000521309; ENST00000522819; ENST00000395953; ENST00000395948; ENST00000395951; ENST00000419477; ENST00000521607 | TSF |
| 1% | chr8 | 101933557 | 101933272 | − | chr8 | 101932980 | 101932921; 101932944 | − | ENST00000395957; ENST00000395958; ENST00000457309; ENST00000395956; ENST00000353245; ENST00000523848; ENST00000522542; ENST00000521309; ENST00000522819; ENST00000395953; ENST00000395948; ENST00000395951; ENST00000419477; ENST00000521607 | TSF |
| 1% | chr12 | 6459191 | 6458996 | − | chr12 | 6458387 | 6458330 | − | ENST00000360168; ENST00000358945; ENST00000540037; ENST00000228916; ENST00000543768 | TSF |
| 1% | chr1 | 9850138 | 9850120 | − | chr1 | 9833452 | 9833330 | − | ENST00000377298; ENST00000361311; ENST00000377288 | TSF |

TABLE 44-continued

Transcript fusion for ovarian cancer (OV) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr1 | 9850138 | 9850120 | – | chr1 | 9833452 | 9833330 | – | ENST00000377298; ENST00000361311; ENST00000377288 | TSF |
| 1% | chr1 | 9850138 | 9850120 | – | chr1 | 9833452 | 9833330 | – | ENST00000377298; ENST00000361311; ENST00000377288 | TSF |
| 1% | chr19 | 14243138 | 14242881 | – | chr19 | 14237049 | 14236934 | – | ENST00000263382; ENST00000592798; ENST00000590835; ENST00000474890 | TSF |
| 1% | chr19 | 14243138 | 14242881 | – | chr19 | 14237049 | 14236934 | – | ENST00000263382; ENST00000592798; ENST00000590835; ENST00000474890 | TSF |
| 1% | chr19 | 14243138 | 14242881 | – | chr19 | 14237049 | 14236934 | – | ENST00000263382; ENST00000592798; ENST00000590835; ENST00000474890 | TSF |
| 1% | chr19 | 14243138 | 14242881 | – | chr19 | 14237049 | 14236934 | – | ENST00000263382; ENST00000592798; ENST00000590835; ENST00000474890 | TSF |

TABLE 45

Transcript fusion for Pancreatic adenocarcinoma (PAAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 43% | chr3 | 49927493 | 49927357 | – | ENST00000296474; ENST00000344206 | chr3 | 49927248 | 49927204 | – | TAF |
| 43% | chr3 | 49927493 | 49927357 | – | ENST00000296474; ENST00000344206 | chr3 | 49927248 | 49927204 | – | TAF |
| 21% | chr5 | 147207691 | 147207585 | – | ENST00000296695; ENST00000510027 | chr5 | 147185494 | 147185375 | – | TAF |
| 20% | chr5 | 82554349 | 82554496 | + | ENST00000282268; ENST00000338635; ENST00000396027; ENST00000511817 | chr5 | 82606608 | 82606935 | + | TAF |
| 19% | chr3 | 118943092 | 118942905 | – | ENST00000483209; ENST00000467604; ENST00000359213; ENST00000393765; ENST00000480814 | chr3 | 118938512 | 118938188 | – | TAF |
| 18% | chr1 | 22313024 | 22313176 | + | ENST00000337107; ENST00000400277 | chr1 | 22321959 | 22322031 | + | TAF |
| 18% | chr1 | 22313024 | 22313176 | + | ENST00000337107; ENST00000400277 | chr1 | 22321959 | 22322031 | + | TAF |
| 17% | chr4 | 169086398 | 169086477 | + | ENST00000359299 | chr4 | 169090666 | 169090754 | + | TSF |
| 13% | chr20 | 53092486 | 53092551 | + | ENST00000262593 | chr20 | 53111339 | 53111426 | + | TAF |
| 12% | chr1 | 15813780 | 15813932 | + | ENST00000375910 | chr1 | 15814741 | 15814890 | + | TSF |
| 11% | chr19 | 50984141 | 50984234 | + | ENST00000334976; ENST00000376918; ENST00000598585 | chr19 | 51009025 | 51009080 | + | TAF |
| 11% | chr3 | 149205406 | 149205542 | + | ENST00000305354 | chr3 | 149210784 | 149210892 | + | TAF |
| 10% | chr15 | 32976758; 32976761 | 32976870 | + | ENST00000300175; ENST00000413748; ENST00000494364; ENST00000497208; ENST00000471027 | chr15 | 32977789 | 32977906 | + | TAF |
| 10% | chr15 | 32976758; 32976761 | 32976870 | + | ENST00000300175; ENST00000413748; ENST00000494364; ENST00000497208; ENST00000471027 | chr15 | 32977789 | 32977906 | + | TAF |
| 10% | chr15 | 32976758; 32976761 | 32976870 | + | ENST00000300175; ENST00000413748; ENST00000494364; ENST00000497208; ENST00000471027 | chr15 | 32977789 | 32977906 | + | TAF |
| 10% | chr10 | 118310610 | 118310744 | + | ENST00000369221 | chr10 | 118311742 | 118312116 | + | TSF |
| 10% | chr1 | 15802952; 15802960 | 15803040 | + | ENST00000375910; ENST00000422901 | chr1 | 15807450 | 15807521 | + | TSF |
| 10% | chr1 | 15802952; 15802960 | 15803040 | + | ENST00000375910; ENST00000422901 | chr1 | 15807450 | 15807521 | + | TSF |
| 10% | chr3 | 49928739 | 49928630 | – | ENST00000296474; ENST00000344206; ENST00000434765; ENST00000440292 | chr3 | 49928452 | 49928163 | – | TSF |
| 10% | chr3 | 49928739 | 49928630 | – | ENST00000296474; ENST00000344206; ENST00000434765; ENST00000440292 | chr3 | 49928452 | 49928163 | – | TSF |
| 10% | chr3 | 49928739 | 49928630 | – | ENST00000296474; ENST00000344206; ENST00000434765; ENST00000440292 | chr3 | 49928452 | 49928163 | – | TSF |
| 10% | chr3 | 49928739 | 49928630 | – | ENST00000296474; ENST00000344206; ENST00000434765; ENST00000440292 | chr3 | 49928452 | 49928163 | – | TSF |
| 9% | chr3 | 148563211 | 148563413 | + | ENST00000491148; ENST00000282957 | chr3 | 148570090 | 148570266 | + | TSF |
| 8% | chr11 | 17429000 | 17428901 | – | ENST00000389817; ENST00000302539 | chr11 | 17428722 | 17428716 | – | TSF |
| 8% | chr11 | 17429000 | 17428901 | – | ENST00000389817; ENST00000302539 | chr11 | 17428722 | 17428716 | – | TSF |
| 8% | chr1 | 15783581 | 15783669 | + | ENST00000359621 | chr1 | 15807450 | 15807521 | + | TSF |
| 8% | chr17 | 43475413 | 43475315 | – | ENST00000532038; ENST00000376922; ENST00000528384; ENST00000455881; ENST00000428638; ENST00000442348; ENST00000532891 | chr17 | 43474814 | 43474703 | – | TSF |
| 8% | chr17 | 43475413 | 43475315 | – | ENST00000532038; ENST00000376922; ENST00000528384; ENST00000455881; ENST00000428638; ENST00000442348; ENST00000532891 | chr17 | 43474814 | 43474703 | – | TSF |
| 8% | chr17 | 43475413 | 43475315 | – | ENST00000532038; ENST00000376922; ENST00000528384; ENST00000455881; ENST00000428638; ENST00000442348; ENST00000532891 | chr17 | 43474814 | 43474703 | – | TSF |
| 8% | chr17 | 43475413 | 43475315 | – | ENST00000532038; ENST00000376922; ENST00000528384; ENST00000455881; ENST00000428638; ENST00000442348; ENST00000532891 | chr17 | 43474814 | 43474703 | – | TSF |
| 8% | chr17 | 43475413 | 43475315 | – | ENST00000532038; ENST00000376922; ENST00000528384; ENST00000455881; ENST00000428638; ENST00000442348; ENST00000532891 | chr17 | 43474814 | 43474703 | – | TSF |
| 8% | chr17 | 43475413 | 43475315 | – | ENST00000532038; ENST00000376922; ENST00000528384; ENST00000455881; ENST00000428638; ENST00000442348; | chr17 | 43474814 | 43474703 | – | TSF |

TABLE 45-continued

Transcript fusion for Pancreatic adenocarcinoma (PAAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 7% | chr9 | 33796641 | 33796800 | + | ENST00000532891; ENST00000361005; ENST00000457896; ENST00000342836; ENST00000429677; ENST00000379405 | chr9 | 33797121 | 33797225 | + | TSF |
| 7% | chr9 | 33796641 | 33796800 | + | ENST00000361005; ENST00000457896; ENST00000342836; ENST00000429677; ENST00000379405 | chr9 | 33797121 | 33797225 | + | TSF |
| 7% | chr9 | 33796641 | 33796800 | + | ENST00000361005; ENST00000457896; ENST00000342836; ENST00000429677; ENST00000379405 | chr9 | 33797121 | 33797225 | + | TSF |
| 7% | chr9 | 33796641 | 33796800 | + | ENST00000361005; ENST00000457896; ENST00000342836; ENST00000429677; ENST00000379405 | chr9 | 33797121 | 33797225 | + | TSF |
| 7% | chr9 | 33796641 | 33796800 | + | ENST00000361005; ENST00000457896; ENST00000342836; ENST00000429677; ENST00000379405 | chr9 | 33797121 | 33797225 | + | TSF |
| 6% | chr16 | 75239411 | 75239269 | − | ENST00000303037; ENST00000562106; ENST00000567767; ENST00000562387 | chr16 | 75081811 | 75081640 | − | TSF |
| 6% | chr16 | 75239411 | 75239269 | − | ENST00000303037; ENST00000562106; ENST00000567767; ENST00000562387 | chr16 | 75081811 | 75081640 | − | TSF |
| 6% | chr16 | 75239411 | 75239269 | − | ENST00000303037; ENST00000562106; ENST00000567767; ENST00000562387 | chr16 | 75081811 | 75081640 | − | TSF |
| 6% | chr16 | 75239411 | 75239269 | − | ENST00000303037; ENST00000562106; ENST00000567767; ENST00000562387 | chr16 | 75081811 | 75081640 | − | TSF |
| 6% | chr11 | 17429000 | 17428901 | − | ENST00000389817; ENST00000302539 | chr11 | 17428756 | 17428716 | − | TSF |
| 6% | chr11 | 17429000 | 17428901 | − | ENST00000389817; ENST00000302539 | chr11 | 17428756 | 17428716 | − | TSF |
| 5% | chr16 | 29913136; 29912293 | 29913241 | + | ENST00000563177; ENST00000483405; ENST00000308748; ENST00000414952; ENST00000566693 | chr16 | 29915825 | 29915953 | + | TSF |
| 5% | chr16 | 29913136; 29912293 | 29913241 | + | ENST00000563177; ENST00000483405; ENST00000308748; ENST00000414952; ENST00000566693 | chr16 | 29915825 | 29915953 | + | TSF |
| 4% | chr1 | 15764961 | 15765000 | + | ENST00000375949; ENST00000375943 | chr1 | 15765777 | 15765949 | + | TSF |
| 4% | chr10 | 118386375 | 118386509 | + | ENST00000537242; ENST00000433618 | chr10 | 118386790 | 118386809 | + | TSF |
| 4% | chr10 | 118386375 | 118386509 | + | ENST00000537242; ENST00000433618 | chr10 | 118386790 | 118386809 | + | TSF |
| 4% | chr19 | 54501493 | 54501567 | + | ENST00000252729; ENST00000346968 | chr19 | 54502685 | 54502767 | + | TSF |
| 3% | chr19 | 504745 | 504908 | + | ENST00000587541; ENST00000215637; ENST00000346144; ENST00000382683 | chr19 | 505078 | 505370 | + | TSF |
| 3% | chr19 | 504745 | 504908 | + | ENST00000587541; ENST00000215637; ENST00000346144; ENST00000382683 | chr19 | 505078 | 505370 | + | TSF |
| 3% | chr19 | 504745 | 504908 | + | ENST00000587541; ENST00000215637; ENST00000346144; ENST00000382683 | chr19 | 505078 | 505370 | + | TSF |
| 3% | chr19 | 504745 | 504908 | + | ENST00000587541; ENST00000215637; ENST00000346144; ENST00000382683 | chr19 | 505078 | 505370 | + | TSF |
| 3% | chr9 | 33798484 | 33798593 | + | ENST00000361005; ENST00000342836; ENST00000429677; ENST00000379405 | chr4 | 144494223 | 144494466 | + | TSF |
| 3% | chr9 | 33798484 | 33798593 | + | ENST00000361005; ENST00000342836; ENST00000429677; ENST00000379405 | chr4 | 144494223 | 144494466 | + | TSF |
| 3% | chr9 | 33798484 | 33798593 | + | ENST00000361005; ENST00000342836; ENST00000429677; ENST00000379405 | chr4 | 144494223 | 144494466 | + | TSF |
| 3% | chr9 | 33798484 | 33798593 | + | ENST00000361005; ENST00000342836; ENST00000429677; ENST00000379405 | chr4 | 144494223 | 144494466 | + | TSF |
| 3% | chr1 | 15793881 | 15794033 | + | ENST00000359621 | chr1 | 15795560 | 15795701 | + | TSF |
| 3% | chr8 | 71619168 | 71619388 | + | ENST00000408926; ENST00000520030 | chr8 | 71625661 | 71625673 | + | TSF |
| 3% | chr6 | 84772612 | 84772711 | + | ENST00000257776 | chr6 | 84849189 | 84849246 | + | TSF |
| 3% | chr10 | 96443577 | 96443744 | + | ENST00000339022; ENST00000285979 | chr10 | 96698194 | 96698222 | + | TSF |
| 3% | chr3 | 98600611; 98600498 | 98600384 | − | ENST00000326840; ENST00000326857; ENST00000449482 | chr3 | 98586282 | 98584565 | − | TSF |
| 3% | chr3 | 98600611; 98600498 | 98600384 | − | ENST00000326840; ENST00000326857; ENST00000449482 | chr3 | 98586282 | 98584565 | − | TSF |

TABLE 46

Transcript fusion for Pancreatic adenocarcinoma (PAAD) Coordinates of the fusion sequences for which the donor is the TE.

| 1 | 2' | 3' | 4' | 5' | 6' | 7' | 8' | 9' | 10' | 11 |
|---|---|---|---|---|---|---|---|---|---|---|
| 81% | chr8 | 104389530 | 104389551 | + | chr8 | 104390255 | 104390471 | + | ENST00000330295; ENST00000520337 | TAF |
| 31% | chr17 | 70713894 | 70713885 | − | chr17 | 70645407 | 70645309 | − | ENST00000255559; ENST00000542342; ENST00000582769 | TSF |
| 31% | chr17 | 70713894 | 70713885 | − | chr17 | 70645407 | 70645309 | − | ENST00000255559; ENST00000542342; ENST00000582769 | TSF |
| 29% | chr16 | 29915789 | 29915910 | + | chr16 | 29916173 | 29916286 | + | ENST00000563177; ENST00000483405; ENST00000308748; ENST00000414952; ENST00000566693 | TAF |
| 29% | chr16 | 29915789 | 29915910 | + | chr16 | 29916173 | 29916286 | + | ENST00000563177; ENST00000483405; ENST00000308748; ENST00000414952; ENST00000566693 | TAF |
| 29% | chr9 | 130900342 | 130900452 | + | chr9 | 130913917 | 130913996 | + | ENST00000373017; ENST00000540948; ENST00000277480; ENST00000373013 | TAF |
| 29% | chr9 | 130900342 | 130900452 | + | chr9 | 130913917 | 130913996 | + | ENST00000373017; ENST00000540948; ENST00000277480; ENST00000373013 | TAF |
| 26% | chr5 | 147210961 | 147210946 | − | chr5 | 147209193 | 147209162 | − | ENST0000296695; ENST00000510027 | TAF |
| 26% | chr5 | 147210961 | 147210946 | − | chr5 | 147209193 | 147209162 | − | ENST0000296695; ENST00000510027 | TAF |

TABLE 46-continued

Transcript fusion for Pancreatic adenocarcinoma (PAAD) Coordinates of the fusion sequences for which the donor is the TE.

| 1 | 2' | 3' | 4' | 5' | 6' | 7' | 8' | 9' | 10' | 11 |
|---|---|---|---|---|---|---|---|---|---|---|
| 23% | chr | 22321930 | 22322006 | + | chr1 | 22324644 | 22324682 | + | ENST00000400277 | TAF |
| 21% | chr14 | 102691697 | 102691432 | − | chr14 | 102691131 | 102691116 | − | ENST00000559838 | TAF |
| 20% | chr19 | 55558521 | 55558473 | − | chr19 | 55556677 | 55556442 | − | ENST00000415061; ENST00000396247 | TAF |
| 19% | chr1 | 17568772 | 17568900 | + | chr1 | 17570505 | 17570738 | + | ENST00000375471; ENST00000537499; ENST00000413717; ENST00000536552 | TAF |
| 16% | chr20 | 44420870 | 44421070 | + | chr20 | 44421316 | 44421386 | + | ENST00000372622; ENST00000449078; ENST00000456939 | TAF |
| 16% | chr20 | 44420870 | 44421070 | + | chr20 | 44421316 | 44421386 | + | ENST00000372622; ENST00000449078; ENST00000456939 | TAF |
| 16% | chr20 | 44420870 | 44421070 | + | chr20 | 44421316 | 44421386 | + | ENST00000372622; ENST00000449078; ENST00000456939 | TAF |
| 16% | chr10 | 99548701 | 99548695 | − | chr10 | 99529502 | 99529425 | − | ENST00000266066 | TAF |
| 15% | chr7 | 150938296 | 150938250 | − | chr7 | 150937608 | 150937511 | − | ENST00000262188; ENST00000392811; ENST00000356800 | TAF |
| 15% | chr1 | 22296254 | 22296330 | + | chr1 | 22324644 | 22324682 | + | ENST00000400277 | TSF |
| 13% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 13% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 13% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 13% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 13% | chr21 | 42597177 | 42597622 | + | chr21 | 42598193 | 42598281 | + | ENST00000328735; ENST00000330333; ENST00000347667 | TAF |
| 13% | chr21 | 42597177 | 42597622 | + | chr21 | 42598193 | 42598281 | + | ENST00000328735; ENST00000330333; ENST00000347667 | TAF |
| 13% | chr21 | 42597177 | 42597622 | + | chr21 | 42598193 | 42598281 | + | ENST00000328735; ENST00000330333; ENST00000347667 | TAF |
| 13% | chr9 | 135665394 | 135665131 | − | chr9 | 135602921 | 135602841 | − | ENST00000298545 | TAF |
| 12% | chr9 | 131189761 | 131190058 | + | chr9 | 131190581 | 131190700; 131190702 | + | ENST00000372842; ENST00000420512; ENST00000372838 | TAF |
| 12% | chr9 | 131189761 | 131190058 | + | chr9 | 131190581 | 131190700; 131190702 | + | ENST00000372842; ENST00000420512; ENST00000372838 | TAF |
| 11% | Ichr8 | 143751981 | 143751986 | + | chr8 | 143762745 | 143762852; 143762884 | + | ENST00000301258; ENST00000513264 | TAF |
| 11% | chr8 | 143751981 | 143751986 | + | chr8 | 143762745 | 143762852; 143762884 | + | ENST00000301258; ENST00000513264 | TAF |
| 11% | chr17 | 79214190 | 79214239 | + | chr17 | 79214787 | 79214816; 79214953 | + | ENST00000431388; ENST00000576002 | TAF |
| 11% | chr17 | 79214190 | 79214239 | + | chr17 | 79214787 | 79214816; 79214953 | + | ENST00000431388; ENST00000576002 | TAF |
| 11% | chr17 | 48749939 | 48750209 | + | chr17 | 48750332 | 48750499 | + | ENST00000285238; ENST00000505699 | TAF |
| 11% | chr17 | 48749939 | 48750209 | + | chr17 | 48750332 | 48750499 | + | ENST00000285238; ENST00000505699 | TAF |
| 11% | chr7 | 116364854 | 116364901 | + | chr7 | 116371722 | 116371913 | + | ENST00000397752; ENST00000318493; ENST00000436117 | TAF |
| 11% | chr7 | 116364854 | 116364901 | + | chr7 | 116371722 | 116371913 | + | ENST00000397752; ENST00000318493; ENST00000436117 | TAF |
| 11% | chr7 | 116364854 | 116364901 | + | chr7 | 116371722 | 116371913 | + | ENST00000397752; ENST00000318493; ENST00000436117 | TAF |
| 11% | chr1 | 15807396 | 15807482 | + | chr1 | 15807593 | 15807690 | + | ENST00000375910; ENST00000422901 | TSF |
| 11% | chr1 | 15807396 | 15807482 | + | chr1 | 15807593 | 15807690 | + | ENST00000375910; ENST00000422901 | TSF |
| 11% | chr10 | 118308042 | 118308051 | + | chr10 | 118310610 | 118310744 | + | ENST00000369221 | TSF |
| 10% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 10% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 10% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 10% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 10% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 10% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 10% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 10% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 10% | chr6 | 31154067 | 31153803 | − | chr6 | 31133824 | 31133704 | − | ENST00000259915 | TAF |

TABLE 46-continued

Transcript fusion for Pancreatic adenocarcinoma (PAAD) Coordinates of the fusion sequences for which the donor is the TE.

| 1 | 2' | 3' | 4' | 5' | 6' | 7' | 8' | 9' | 10' | 11 |
|---|---|---|---|---|---|---|---|---|---|---|
| 8% | chr12 | 117498589 | 117498567 | − | chr12 | 117494691 | 117494611 | − | ENST00000470612; ENST00000335209; ENST00000392545; ENST00000462502 | TSF |
| 8% | chr12 | 117498589 | 117498567 | − | chr12 | 117494691 | 117494611 | − | ENST00000470612; ENST00000335209; ENST00000392545; ENST00000462502 | TSF |
| 8% | chr12 | 117498589 | 117498567 | − | chr12 | 117494691 | 117494611 | − | ENST00000470612; ENST00000335209; ENST00000392545; ENST00000462502 | TSF |
| 7% | chr19 | 1114930 | 1114676 | − | chr19 | 1114421 | 1114230 | − | ENST00000361757; ENST00000587024; ENST00000438103 | TSF |
| 7% | chr9 | 33797054 | 33797162 | + | chr9 | 33797827 | 33798080 | + | ENST00000361005; ENST00000457896; ENST00000342836; ENST00000429677; ENST00000379405 | TSF |
| 7% | chr9 | 33797054 | 33797162 | + | chr9 | 33797827 | 33798080 | + | ENST00000361005; ENST00000457896; ENST00000342836; ENST00000429677; ENST00000379405 | TSF |
| 7% | chr16 | 20336354 | 20336269 | − | chr16 | 20557833 | 20335138; 20335289 | − | ENST00000302555; ENST00000381362; ENST00000575449 | TSF |
| 7% | chr16 | 20336354 | 20336269 | − | chr16 | 20335578 | 20335138; 20335289 | | ENST00000302555; ENST00000381362; ENST00000575449 | TSF |
| 7% | chr16 | 20336354 | 20336269 | − | chr16 | 20335578 | 20335138; 20335289 | − | ENST00000302555; ENST00000381362; ENST00000575449 | TSF |
| 6% | chr10 | 118312917 | 118313077 | + | chr10 | 118313239 | 118313350 | + | ENST00000369221 | TSF |
| 6% | chr1 | 200882539 | 200882562 | + | chr1 | 200882665 | 200882757 | + | ENST00000367342; ENST00000413687 | TSF |
| 6% | chr7 | 100850556 | 100850506 | − | chr7 | 100850185 | 100850060 | − | ENST00000454310; ENST00000223127 | TSF |
| 5% | chr3 | 148570083 | 148570155 | + | chr3 | 148575244 | 148575328 | + | ENST00000491148; ENST00000282957 | TSF |
| 4% | chr1 | 15791260 | 15791412 | + | chr1 | 15792494 | 15792639 | + | ENST00000359621 | TSF |
| 4% | chr20 | 43941352 | 43941632 | + | chr20 | 43942108 | 43942245 | + | ENST00000372741; ENST00000372743; ENST00000343694 | TSF |
| 4% | chr20 | 43941352 | 43941632 | + | chr20 | 43942108 | 43942245 | + | ENST00000372741; ENST00000372743; ENST00000343694 | TSF |
| 4% | chr20 | 43941352 | 43941632 | + | chr20 | 43942108 | 43942245 | + | ENST00000372741; ENST00000372743; ENST00000343694 | TSF |
| 4% | chr | 22296254 | 22296400 | + | chr1 | 22324644 | 22324682 | + | ENST00000400277 | TSF |
| 4% | chr16 | 20328511 | 20328487 | − | chr16 | 20327362 | 20327278 | − | ENST00000302555; ENST00000341642; ENST00000381362; ENST00000381360 | TSF |
| 4% | chr4 | 142977397 | 142977072 | − | chr4 | 142950067 | 142949935 | − | ENST00000513000; ENST00000262992; ENST00000308502; ENST00000508116 | TSF |
| 4% | chr9 | 35678063 | 35678160 | + | chr9 | 35679182 | 35679339 | + | ENST00000378357 | TSF |
| 3% | chr1 | 15795401 | 15795527 | + | chr1 | 15798485 | 15798502 | + | ENST00000359621 | TSF |
| 3% | chr20 | 45337040 | 45337192 | + | chr20 | 45353680 | 45354963 | + | ENST00000359271 | TSF |
| 3% | chr16 | 75251739 | 75251839 | + | chr16 | 75256666 | 75256769 | + | ENST00000361017; ENST00000495583 | TSF |
| 3% | chr16 | 75251739 | 75251839 | + | chr16 | 75256666 | 75256769 | + | ENST00000361017; ENST00000495583 | TSF |
| 3% | chr11 | 59621007 | 59620878 | − | chr11 | 59620794 | 59620676 | − | ENST00000257264 | TSF |
| 3% | chr12 | 120764491 | 120764436 | − | chr12 | 120763823 | 120763664 | − | ENST00000308366; ENST00000423423 | TSF |
| 3% | chr12 | 120764491 | 120764436 | − | chr12 | 120763823 | 120763664 | − | ENST00000308366; ENST00000423423 | TSF |

TABLE 47

Transcript fusion for Pheochromocytoma and Paraganglioma (PCPG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 84% | chr14 | 101200486 | 101200513 | + | ENST00000341267; ENST00000331224 | chr14 | 101473144 | 101473392 | + | TAF |
| 65% | chr6 | 84772612 | 84772711 | + | ENST00000257776 | chr6 | 84849189 | 84849246 | + | TSF |
| 61% | chr20 | 9453926 | 9454012 | + | ENST00000334005; ENST00000378473; ENST00000278655; ENST00000414679; ENST00000378493; ENST00000378501 | chr20 | 9484605 | 9485169 | + | TAF |
| 61% | chr20 | 9453926 | 9454012 | + | ENST00000334005; ENST00000378473; ENST00000278655; ENST00000414679; ENST00000378493; ENST00000378501 | chr20 | 9484605 | 9485169 | + | TAF |
| 59% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 59% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 59% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 59% | chr3 | 33636460 | 33636443 | − | ENST00000468888; ENST00000399362; ENST00000307312; ENST00000359576; ENST00000480013; ENST00000461133 | chr3 | 33635629 | 33635332 | − | TAF |
| 51% | chr9 | 136518062 | 136518121 | + | ENST00000393056 | chr9 | 136521413 | 136521506 | + | TSF |
| 49% | chr12 | 6943089 | 6943213 | + | ENST00000251761; ENST00000396725; ENST00000606935 | chr12 | 6943989 | 6944119 | + | TAF |
| 49% | chr12 | 6943089 | 6943213 | + | ENST00000251761; ENST00000396725; ENST00000606935 | chr12 | 6943989 | 6944119 | + | TAF |
| 49% | chr12 | 6943089 | 6943213 | + | ENST00000251761; ENST00000396725; ENST00000606935 | chr12 | 6943989 | 6944119 | + | TAF |
| 47% | chrX | 49054298 | 49054174 | − | ENST00000263233; ENST00000479808; ENST00000469389; ENST00000466635 | chrX | 49053735 | 49053463 | − | TSF |
| 41% | chr19 | 44129402 | 44129230 | − | ENST00000222374 | chr19 | 44129055 | 44128921 | − | TAF |
| 41% | chr3 | 54157540 | 54157621 | + | ENST00000415676; ENST00000288197; ENST00000474759 | chr3 | 54326852 | 54327228 | + | TSF |
| 32% | chr9 | 100308467 | 100308623 | + | ENST00000395211; ENST00000259365 | chr9 | 100309531 | 100309647 | + | TAF |
| 31% | chr19 | 1235564 | 1235500 | − | ENST00000590083; ENST00000382477; ENST00000215376; ENST00000589260 | chr19 | 1235389 | 1235290 | − | TAF |
| 31% | chr19 | 1235564 | 1235500 | − | ENST00000590083; ENST00000382477; ENST00000215376; ENST00000589260 | chr19 | 1235389 | 1235290 | − | TAF |
| 31% | chr20 | 5902981 | 5904677 | + | ENST00000378961 | chr20 | 5911058 | 5911312 | + | TSF |

TABLE 47-continued

Transcript fusion for Pheochromocytoma and Paraganglioma (PCPG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 28% | chr10 | 43601824 | 43602019 | + | ENST00000355710; ENST0000340058 | chr10 | 43602522 | 43602638 | + | TSF |
| 27% | chr15 | 32976758; 32976761 | 32976870 | + | ENST00000300175; ENST00000413748; ENST00000494364; ENST00000497208; ENST00000471027 | chr15 | 32977789 | 32977906 | + | TAF |
| 27% | chr15 | 32976758; 32976761 | 32976870 | + | ENST00000300175; ENST00000413748; ENST00000494364; ENST00000497208; ENST00000471027 | chr15 | 32977789 | 32977906 | + | TAF |
| 27% | chr15 | 32976758; 32976761 | 32976870 | + | ENST00000300175; ENST00000413748; ENST00000494364; ENST00000497208; ENST00000471027 | chr15 | 32977789 | 32977906 | + | TAF |
| 27% | chr2 | 219849027 | 219848953 | − | ENST00000295727 | chr2 | 219847374 | 219847276 | − | TSF |
| 26% | chr17 | 26938813 | 26938786 | − | ENST00000494272; ENST00000301037 | chr17 | 26932233 | 26930495 | − | TSF |
| 26% | chr17 | 26938813 | 26938786 | − | ENST00000494272; ENST00000301037 | chr17 | 26932233 | 26930495 | − | TSF |
| 22% | chr15 | 74476330 | 74476197 | − | ENST00000395105; ENST00000423167; ENST00000323940; ENST00000449139; ENST00000416286; ENST00000535552; ENST00000563965; ENST00000574278; ENST00000569936 | chr15 | 74475723 | 74475630 | − | TSF |
| 22% | chr15 | 74476330 | 74476197 | − | ENST00000395105; ENST00000423167; ENST00000323940; ENST00000449139; ENST00000416286; ENST00000535552; ENST00000563965; ENST00000574278; ENST00000569936 | chr15 | 74475723 | 74475630 | − | TSF |
| 22% | chr15 | 74476330 | 74476197 | − | ENST00000395105; ENST00000423167; ENST00000323940; ENST00000449139; ENST00000416286; ENST00000535552; ENST00000563965; ENST00000574278; ENST00000569936 | chr15 | 74475723 | 74475630 | − | TSF |
| 22% | chr15 | 74476330 | 74476197 | − | ENST00000395105; ENST00000423167; ENST00000323940; ENST00000449139; ENST00000416286; ENST00000535552; ENST00000563965; ENST00000574278; ENST00000569936 | chr15 | 74475723 | 74475630 | − | TSF |
| 22% | chr15 | 74476330 | 74476197 | − | ENST00000395105; ENST00000423167; ENST00000323940; ENST00000449139; ENST00000416286; ENST00000535552; ENST00000563965; ENST00000574278; ENST00000569936 | chr15 | 74475723 | 74475630 | − | TSF |
| 22% | chr15 | 74476330 | 74476197 | − | ENST00000395105; ENST00000423167; ENST00000323940; ENST00000449139; ENST00000416286; ENST00000535552; ENST00000563965; ENST00000574278; ENST00000569936 | chr15 | 74475723 | 74475630 | − | TSF |
| 22% | chr15 | 74476330 | 74476197 | − | ENST00000395105; ENST00000423167; ENST00000323940; ENST00000449139; ENST00000416286; ENST00000535552; ENST00000563965; ENST00000574278; ENST00000569936 | chr15 | 74475723 | 74475630 | − | TSF |
| 20% | chr19 | 50984141 | 50984234 | + | ENST00000334976; ENST00000376918; ENST00000598585 | chr19 | 51009025 | 51009080 | + | TAF |
| 17% | chr10 | 33197462; 33197431 | 33197296 | − | ENST00000423113; ENST00000396033; ENST00000302278; ENST00000374956; ENST00000488427 | chr10 | 33039666 | 33039198 | − | TSF |
| 17% | chr10 | 33197462; 33197431 | 33197296 | − | ENST00000423113; ENST00000396033; ENST00000302278; ENST00000374956; ENST00000488427 | chr10 | 33039666 | 33039198 | − | TSF |
| 16% | chr3 | 54786626 | 54786704 | + | ENST00000415676; ENST00000288197; ENST00000474759; ENST00000471363; ENST00000490478; ENST00000477024 | chr3 | 54787473 | 54787673 | + | TSF |
| 16% | chr3 | 54786626 | 54786704 | + | ENST00000415676; ENST00000288197; ENST00000474759; ENST00000471363; ENST00000490478; ENST00000477024 | chr3 | 54787473 | 54787673 | + | TSF |
| 14% | chr15 | 45464200; 45464276 | 45464081 | − | ENST00000290894; ENST00000318390; ENST00000458022; ENST00000558294; ENST00000559566 | chr15 | 45462680 | 45462661 | − | TSF |
| 14% | chr15 | 45464200; 45464276 | 45464081 | − | ENST00000290894; ENST00000318390; ENST00000458022; ENST00000558294; ENST00000559566 | chr15 | 45462680 | 45462661 | − | TSF |
| 14% | chr15 | 45464200; 45464276 | 45464081 | − | ENST00000290894; ENST00000318390; ENST00000458022; ENST00000558294; ENST00000559566 | chr15 | 45462680 | 45462661 | − | TSF |
| 14% | chr15 | 45464200; 45464276 | 45464081 | − | ENST00000290894; ENST00000318390; ENST00000458022; ENST00000558294; ENST00000559566 | chr15 | 45462680 | 454162661 | − | TSF |
| 14% | chr15 | 45464200; 45464276 | 45464081 | − | ENST00000290894; ENST00000318390; ENST00000458022; ENST00000558294; ENST00000559566 | chr15 | 45462680 | 45462661 | − | TSF |
| 13% | chr6 | 37611719 | 37611585 | − | ENST00000297153; ENST00000434837; ENST00000505425; ENST00000418178 | chr6 | 37611139 | 37611040 | − | TSF |
| 13% | chr6 | 37611719 | 37611585 | − | ENST00000297153; ENST00000434837; ENST00000505425; ENST00000418178 | chr6 | 37611139 | 37611040 | − | TSF |
| 13% | chr6 | 37611719 | 37611585 | − | ENST00000297153; ENST00000434837; ENST00000505425; ENST00000418178 | chr6 | 37611139 | 37611040 | − | TSF |
| 13% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 13% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 13% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 12% | chr6 | 107908284 | 107908379 | + | ENST00000317357 | chr6 | 107948590 | 107948666 | + | TSF |
| 12% | chr7 | 102249269 | 102249208 | − | ENST00000262940; ENST00000461209; ENST00000449970; ENST00000462172; ENST00000522801; ENST00000520042; ENST00000521076 | chr7 | 102248714 | 102248385 | − | TSF |
| 12% | chr7 | 102249269 | 102249208 | − | ENST00000262940; ENST00000461209; ENST00000449970; ENST00000462172; ENST00000522801; ENST00000520042; ENST00000521076 | chr7 | 102248714 | 102248385 | − | TSF |
| 12% | chr7 | 102249269 | 102249208 | − | ENST00000262940; ENST00000461209; ENST00000449970; ENST00000462172; ENST00000522801; ENST00000520042; ENST00000521076 | chr7 | 102248714 | 102248385 | − | TSF |
| 12% | chr8 | 139626163 | 139626110 | − | ENST00000303045; ENST00000435777 | chr8 | 139623600 | 139623460 | − | TSF |
| 12% | chr8 | 139626163 | 139626110 | − | ENST00000303045; ENST00000435777 | chr8 | 139623600 | 139623460 | − | TSF |
| 11% | chr7 | 102141240 | 102141146 | − | ENST00000541662; ENST00000465829; ENST00000306682 | chr7 | 102139087 | 102139007 | − | TAF |
| 11% | chr7 | 102141240 | 102141146 | − | ENST00000541662; ENST00000465829; ENST00000306682 | chr7 | 102139087 | 102139007 | − | TAF |

TABLE 47-continued

Transcript fusion for Pheochromocytoma and Paraganglioma (PCPG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 11% | chr7 | 102240401 | 102240307 | − | ENST00000262940; ENST00000461209; ENST00000449970; ENST00000462172; ENST00000519539; ENST00000522801 | chr7 | 102238252 | 102238172 | − | TAF |
| 11% | chr7 | 102240401 | 102240307 | − | ENST00000262940; ENST00000461209; ENST00000449970; ENST00000462172; ENST00000519539; ENST00000522801 | chr7 | 102238252 | 102238172 | − | TAF |
| 11% | chr7 | 102240401 | 102240307 | − | ENST00000262940; ENST00000461209; ENST00000449970; ENST00000462172; ENST00000519539; ENST00000522801 | chr7 | 102238252 | 102238172 | − | TAF |
| 11% | chr7 | 102240401 | 102240307 | − | ENST00000262940; ENST00000461209; ENST00000449970; ENST00000462172; ENST00000519539; ENST00000522801 | chr7 | 102238252 | 102238172 | − | TAF |
| 10% | chrX | 64743587; 64743497 | 64743440 | − | ENST00000374807; ENST00000374811; ENST00000374804; ENST00000469091 | chrX | 64742373 | 64741630 | − | TAF |
| 10% | chrX | 64743587; 64743497 | 64743440 | − | ENST00000374807; ENST00000374811; ENST00000374804; ENST00000469091 | chrX | 64742373 | 64741630 | − | TAF |
| 10% | chrX | 64743587; 64743497 | 64743440 | − | ENST00000374807; ENST00000374811; ENST00000374804; ENST00000469091 | chrX | 64742373 | 64741630 | − | TAF |
| 10% | chrX | 64743587; 64743497 | 64743440 | − | ENST00000374807; ENST00000374811; ENST00000374804; ENST00000469091 | chrX | 64742373 | 64741630 | − | TAF |
| 10% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 10% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 10% | chr16 | 4409386 | 4409297 | − | ENST00000572467; ENST00000251166; ENST00000539968; ENST00000537233; ENST00000574025; ENST00000576637 | chr16 | 4409070 | 8944405 | − | TAF |
| 10% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 10% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 10% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 10% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 10% | chr3 | 48716169 | 48715997 | − | ENST00000341520; ENST00000416649; ENST00000294129; ENST00000413374 | chr3 | 48702393 | 48702198 | − | TSF |
| 10% | chr3 | 48716169 | 48715997 | − | ENST00000341520; ENST00000416649; ENST00000294129; ENST00000413374 | chr3 | 48702393 | 48702198 | − | TSF |
| 10% | chr3 | 48716169 | 48715997 | − | ENST00000341520; ENST00000416649; ENST00000294129; ENST00000413374 | chr3 | 48702393 | 02148798 | − | TSF |
| 9% | chr7 | 102150107 | 102150046 | − | ENST00000541662; ENST00000465829; ENST00000306682 | chr7 | 102149552 | 149102223 | − | TSF |
| 9% | chr7 | 102150107 | 102150046 | − | ENST00000541662; ENST00000465829; ENST00000306682 | chr7 | 102149552 | 102149223 | − | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 734603177 | + | TSF |
| 7% | chr14 | 93397595 | 93397666 | + | ENST00000216492 | chr14 | 93414485 | 93414702 | + | TSF |
| 6% | chr7 | 102240401 | 102240307 | − | ENST00000262940; ENST00000461209; ENST00000449970; ENST00000462172; ENST00000519539; ENST00000522801 | chr7 | 102237809 | 102237686 | − | TSF |
| 6% | chr7 | 102240401 | 102240307 | − | ENST00000262940; ENST00000461209; ENST00000449970; ENST00000462172; ENST00000519539; ENST00000522801 | chr7 | 102237809 | 102237686 | − | TSF |
| 6% | chr7 | 102240401 | 102240307 | − | ENST00000262940; ENST00000461209; ENST00000449970; ENST00000462172; ENST00000519539; ENST00000522801 | chr7 | 102237809 | 102237686 | − | TSF |
| 6% | chr7 | 102240401 | 102240307 | − | ENST00000262940; ENST00000461209; ENST00000449970; ENST00000462172; ENST00000519539; ENST00000522801 | chr7 | 102237809 | 102237686 | − | TSF |
| 6% | chr19 | 42471492 | 42471401 | − | ENST00000441343; ENST00000302102; ENST00000545399; ENST00000543770; ENST00000602133 | chr19 | 42470173 | 70042426 | − | TSF |
| 6% | chr19 | 42471492 | 42471401 | − | ENST00000441343; ENST00000302102; ENST00000545399; ENST00000543770; ENST00000602133 | chr19 | 42470173 | 42470026 | − | TSF |

TABLE 47-continued

Transcript fusion for Pheochromocytoma and Paraganglioma (PCPG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 6% | chr19 | 42471492 | 42471401 | − | ENST00000441343; ENST00000302102; ENST00000545399; ENST00000543770; ENST00000602133 | chr19 | 42470173 | 70042426 | − | TSF |
| 6% | chr19 | 42471492 | 42471401 | − | ENST00000441343; ENST00000302102; ENST00000545399; ENST00000543770; ENST00000602133 | chr19 | 42470173 | 42470026 | − | TSF |
| 6% | chr7 | 102141240 | 102141146 | − | ENST00000541662; ENST00000465829; ENST00000306682 | chr7 | 102138644 | 102138521 | − | TSF |
| 6% | chr7 | 102141240 | 102141146 | − | ENST00000541662; ENST00000465829; ENST00000306682 | chr7 | 102138644 | 102138521 | − | TSF |
| 6% | chr6 | 110567463 | 110567335 | − | ENST00000338882 | chr6 | 110565813 | 110565664 | − | TSF |
| 6% | chr22 | 25202408 | 25202451 | + | ENST00000400358; ENST00000400359 | chr22 | 25209976 | 25210040 | + | TSF |
| 6% | chr2 | 207146574 | 207146633 | + | ENST00000374423 | chr2 | 207156738 | 207157223 | + | TSF |
| 6% | chrX | 53407651 | 53407541 | − | ENST00000322213; ENST00000470241 | chrX | 53388629 | 53388408 | − | TSF |
| 6% | chrX | 53407651 | 53407541 | − | ENST00000322213; ENST00000470241 | chrX | 53388629 | 53388408 | − | TSF |
| 6% | chr19 | 23556639 | 23556544 | − | ENST00000599743; ENST00000300619 | chr19 | 23491899 | 23491588 | − | TSF |
| 5% | chr8 | 104778455 | 104778765 | + | ENST00000504942; ENST00000406091 | chr8 | 104821508 | 104527821 | + | TSF |
| 5% | chr11 | 117710545 | 117710496 | − | ENST00000532984; ENST00000584394; ENST00000529335 | chr11 | 117703821 | 117703741 | − | TSF |
| 5% | chr11 | 117710545 | 117710496 | − | ENST00000532984; ENST00000584394; ENST00000529335 | chr11 | 117703821 | 117703741 | − | TSF |
| 5% | chr11 | 117710545 | 117710496 | − | ENST00000532984; ENST00000584394; ENST00000529335 | chr11 | 117703821 | 117703741 | − | TSF |
| 4% | chr10 | 73056335 | 73056499 | + | ENST00000335350; ENST00000373192 | chr10 | 73057337 | 730573178 | + | TSF |
| 4% | chr10 | 73056335 | 73056499 | + | ENST00000335350; ENST00000373192 | chr10 | 73057337 | 73057378 | + | TSF |
| 4% | chr15 | 32976758; 32976761 | 3297670 | + | ENST00000300175; ENST00000413748; ENST00000494364; ENST00000497208; ENST00000471027 | chr15 | 32977335 | 132977906 | + | TSF |
| 4% | chr15 | 32976758; 32976761 | 32976870 | + | ENST00000300175; ENST00000413748; ENST00000494364; ENST00000497208; ENST00000471027 | chr15 | 32977335 | 32977906 | + | TSF |
| 4% | chr15 | 32976758; 32976761 | 32976870 | + | ENST00000300175; ENST00000413748; ENST00000494364; ENST00000497208; ENST00000471027 | chr15 | 32977335 | 32977906 | + | TSF |
| 4% | chr19 | 49335016 | 49334925 | − | ENST00000263278; ENST00000595764 | chr19 | 49322122 | 49322095 | − | TSF |
| 4% | chr19 | 49335016 | 49334925 | − | ENST00000263278; ENST00000595764 | chr19 | 49322122 | 49322095 | − | TSF |
| 4% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 4% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 4% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 56175538 | + | TSF |
| 4% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 4% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 4% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 4% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 4% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 175556079 | 75556138 | + | TSF |
| 4% | chr10 | 23399171 | 23399247 | + | ENST00000376510; ENST00000472663 | chr10 | 23428951 | 23429096 | + | TSF |
| 4% | chr10 | 23399171 | 23399247 | + | ENST00000376510; ENST00000472663 | chr10 | 23428951 | 23429096 | + | TSF |
| 4% | chr7 | 81964567 | 81964451 | − | ENST00000356860; ENST00000356253; ENST00000423588 | chr7 | 81929467 | 29181990 | − | TSF |
| 4% | chr19 | 19371984 | 19371622 | − | ENST00000291481 | chr19 | 19371465 | 19371326 | − | TSF |
| 3% | chr10 | 84718705 | 84718831 | + | ENST00000372141; ENST00000404547; ENST00000372142; ENST00000404576; ENST00000556918; ENST00000537893; ENST00000545131 | chr10 | 84720295 | 84720298 | + | TSF |
| 3% | chr10 | 84718705 | 84718831 | + | ENST00000372141; ENST00000404547; ENST00000372142; ENST00000404576; ENST00000556918; ENST00000537893; ENST00000545131 | chr10 | 84720295 | 84720298 | + | TSF |
| 3% | chr10 | 84718705 | 84718831 | + | ENST00000372141; ENST00000404547; ENST00000372142; ENST00000404576; ENST00000556918; ENST00000537893; ENST00000545131 | chr10 | 84720295 | 84720298 | + | TSF |
| 3% | chr10 | 84718705 | 84718831 | + | ENST00000372141; ENST00000404547; ENST00000372142; ENST00000404576; ENST00000556918; ENST00000537893; ENST00000545131 | chr10 | 84720295 | 84720298 | + | TSF |
| 3% | chr10 | 84718705 | 84718831 | + | ENST00000372141; ENST00000404547; ENST00000372142; ENST00000404576; ENST00000556918; ENST00000537893; | chr10 | 84720295 | 84720298 | + | TSF |

TABLE 47-continued

Transcript fusion for Pheochromocytoma and Paraganglioma (PCPG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr9 | 136518062 | 136518121 | + | ENST00000545131; ENST00000393056 | chr9 | 136521502 | 136521506 | + | TSF |
| 3% | chr14 | 24845500; 24845580 | 24846084 | + | ENST00000413692; ENST00000555590; ENST00000424781; ENST00000539237; ENST00000556279; ENST00000250373; ENST00000553708; ENST00000553879; ENST00000554344; ENST00000422617; ENST00000557451; ENST00000555453; ENST00000556759; ENST00000555167; ENST00000555393; ENST00000555802 | chr14 | 24854777 | 24855120 | + | TSF |
| 3% | chr14 | 24845500; 24845580 | 24846084 | + | ENST00000413692; ENST00000555590; ENST00000424781; ENST00000539237; ENST00000556279; ENST00000250373; ENST00000553708; ENST00000553879; ENST00000554344; ENST00000422617; ENST00000557451; ENST00000555453; ENST00000556759; ENST00000555167; ENST00000555393; ENST00000555802 | chr14 | 24854777 | 24855120 | + | TSF |
| 3% | chr14 | 24845500; 24845580 | 24846084 | + | ENST00000413692; ENST00000555590; ENST00000424781; ENST00000539237; ENST00000556279; ENST00000250373; ENST00000553708; ENST00000553879; ENST00000554344; ENST00000422617; ENST00000557451; ENST00000555453; ENST00000556759; ENST00000555167; ENST00000555393; ENST00000555802 | chr14 | 24854777 | 24855120 | + | TSF |
| 3% | chr14 | 24845500; 24845580 | 24846084 | + | ENST00000413692; ENST00000555590; ENST00000424781; ENST00000539237; ENST00000556279; ENST00000250373; ENST00000553708; ENST00000553879; ENST00000554344; ENST00000422617; ENST00000557451; ENST00000555453; ENST00000556759; ENST00000555167; ENST00000555393; ENST00000555802 | chr14 | 24854777 | 24855120 | + | TSF |
| 3% | chr14 | 24845500; 24845580 | 24846084 | + | ENST00000413692; ENST00000555590; ENST00000424781; ENST00000539237; ENST00000556279; ENST00000250373; ENST00000553708; ENST00000553879; ENST00000554344; ENST00000422617; ENST00000557451; ENST00000555453; ENST00000556759; ENST00000555167; ENST00000555393; ENST00000555802 | chr14 | 24854777 | 24855120 | + | TSF |
| 3% | chr14 | 24845500; 24845580 | 24846084 | + | ENST00000413692; ENST00000555590; ENST00000424781; ENST00000539237; ENST00000556279; ENST00000250373; ENST00000553708; ENST00000553879; ENST00000554344; ENST00000422617; ENST00000557451; ENST00000555453; ENST00000556759; ENST00000555167; ENST00000555393; ENST00000555802 | chr14 | 24854777 | 24855120 | + | TSF |
| 3% | chr14 | 24845500; 24845580 | 24846084 | + | ENST00000413692; ENST00000555590; ENST00000424781; ENST00000539237; ENST00000556279; ENST00000250373; ENST00000553708; ENST00000553879; ENST00000554344; ENST00000422617; ENST00000557451; ENST00000555453; ENST00000556759; ENST00000555167; ENST00000555393; ENST00000555802 | chr14 | 24854777 | 24855120 | + | TSF |
| 3% | chr14 | 24845500; 24845580 | 24846084 | + | ENST00000413692; ENST00000555590; ENST00000424781; ENST00000539237; ENST00000556279; ENST00000250373; ENST00000553708; ENST00000553879; ENST00000554344; ENST00000422617; ENST00000557451; ENST00000555453; ENST00000556759; ENST00000555167; ENST00000555393; ENST00000555802 | chr14 | 24854777 | 24855120 | + | TSF |
| 3% | chr17 | 26940164 | 26940096 | − | ENST00000481916; ENST00000531839; ENST00000584196; ENST00000534850; ENST00000301037; ENST00000525510 | chr17 | 26932233 | 26930495 | − | TSF |
| 3% | chr17 | 26940164 | 26940096 | − | ENST00000481916; ENST00000531839; ENST00000584196; ENST00000534850; ENST00000301037; ENST00000525510 | chr17 | 26932233 | 26930495 | − | TSF |
| 3% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 3% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 3% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 3% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 3% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 3% | chr19 | 11567963 | 11567925 | − | ENST00000359227; ENST00000438662 | chr19 | 11567647 | 11567483 | − | TSF |
| 3% | chr19 | 45991775 | 45991729 | − | ENST00000245923; ENST00000430715; ENST00000344680; ENST00000590526 | chr19 | 45990601 | 45990291 | − | TSF |
| 3% | chr19 | 45991775 | 45991729 | − | ENST00000245923; ENST00000430715; ENST00000344680; ENST00000590526 | chr19 | 45990601 | 45990291 | − | TSF |
| 3% | chr19 | 45991775 | 45991729 | − | ENST00000245923; ENST00000430715; ENST00000344680; ENST00000590526 | chr19 | 45990601 | 45990291 | − | TSF |

TABLE 47-continued

Transcript fusion for Pheochromocytoma and Paraganglioma (PCPG) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr19 | 45991775 | 45991729 | − | ENST00000245923; ENST00000430715; ENST00000344680; ENST00000590526 | chr19 | 45990601 | 45990291 | − | TSF |
| 3% | chr1 | 163122506; 163122399 | 163122340 | − | ENST00000313961; ENST00000367903; ENST00000530507; ENST00000527988 | chr1 | 163022553 | 163022549 | − | TSF |
| 3% | chr1 | 163122506; 163122399 | 163122340 | − | ENST00000313961; ENST00000367903; ENST00000530507; ENST00000527988 | chr1 | 163022553 | 163022549 | − | TSF |
| 3% | chr1 | 163122506; 163122399 | 163122340 | − | ENST00000313961; ENST00000367903; ENST00000530507; ENST00000527988 | chr1 | 163022553 | 163022549 | − | TSF |

TABLE 48

Transcript fusion for Pheochromocytoma and Paraganglioma (PCPG) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 88% | chr1 | 151683281 | 151683172 | − | chr1 | 151682267 | 151682219 | − | ENST00000290585; ENST00000290583; ENST00000420342 | TAF |
| 88% | chr1 | 151683281 | 151683172 | − | chr1 | 151682267 | 151682219 | − | ENST00000290585; ENST00000290583; ENST00000420342 | TAF |
| 88% | chr1 | 151683281 | 151683172 | − | chr1 | 151682267 | 151682219 | − | ENST00000290585; ENST00000290583; ENST00000420342 | TAF |
| 76% | chr14 | 93399634 | 93399750 | + | chr14 | 93401146 | 93401229 | + | ENST00000216492; ENST00000334654 | TSF |
| 64% | chr17 | 42395269 | 42395306 | + | chr17 | 42395464 | 42395606 | + | ENST00000426726 | TAF |
| 54% | chr11 | 66048968 | 66049045 | + | chr11 | 66049730 | 66049798; 66049824 | + | ENST00000528852; ENST00000311445; ENST00000528063 | TSF |
| 54% | chr11 | 66048968 | 66049045 | + | chr11 | 66049730 | 66049798; 66049824 | + | ENST00000528852; ENST00000311445; ENST00000528063 | TSF |
| 54% | chr11 | 66048968 | 66049045 | + | chr11 | 66049730 | 66049798; 66049824 | + | ENST00000528852; ENST00000311445; ENST00000528063 | TSF |
| 52% | chr15 | 93221696 | 93221360 | − | chr15 | 93173575 | 93173444 | − | ENST00000327355 | TAF |
| 51% | chr16 | 29915789 | 29915910 | + | chr16 | 29916173 | 29916286 | + | ENST00000563177; ENST00000483405; ENST00000308748; ENST00000414952; ENST00000566693 | TAF |
| 51% | chr16 | 29915789 | 29915910 | − | chr16 | 29916173 | 29916286 | + | ENST00000563177; ENST00000483405; 5ENST00000308748; ENST0000041492; ENST00000566693 | TAF |
| 44% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 44% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 44% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 44% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 44% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 44% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 44% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 44% | chr20 | 62066436 | 62065933 | − | chr20 | 62065256 | 62065162; 62065098 | − | ENST00000357249; ENST00000359125; ENST00000354587; ENST00000359689; ENST00000360480; ENST00000370224; ENST00000344462; ENST00000344425 | TSF |
| 39% | chr15 | 74475607 | 74475594 | − | chr15 | 74474801 | 74474684 | − | ENST00000395105; ENST00000423167; ENST00000323940; ENST00000449139; ENST00000416286; ENST00000535552; ENST00000563965; ENST00000574278; ENST00000572785 | TSF |

TABLE 48-continued

Transcript fusion for Pheochromocytoma and Paraganglioma (PCPG) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 39% | chr15 | 74475607 | 744175594 | − | chr15 | 74474801 | 74474684 | − | ENST00000395105; ENST00000423167; ENST00000323940; ENST00000449139; ENST00000416286; ENST00000535552; ENST00000563965; ENST00000574278; ENST00000572785 | TSF |
| 36% | chr2 | 230409549 | 230409481 | − | chr2 | 230377652 | 230377499 | − | ENST00000341772 | TAF |
| 35% | chr12 | 50264840 | 50264776 | − | chr12 | 50264436 | 50264287; 50264314; 50264356 | − | ENST00000320634; ENST00000550890; ENST00000552669; ENST00000552863 | TAF |
| 35% | chr12 | 50264840 | 50264776 | − | chr12 | 50264436 | 50264287; 50264314; 50264356 | − | ENST00000320634; ENST00000550890; ENST00000552669; ENST00000552863 | TAF |
| 35% | chr12 | 50264840 | 50264776 | − | chr12 | 50264436 | 50264287; 50264314; 50264356 | − | ENST00000320634; ENST00000550890; ENST00000552669; ENST00000552863 | TAF |
| 30% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 30% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 30% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 30% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 28% | chr9 | 100309652 | 100309653 | + | chr9 | 100315563 | 100315682 | + | ENST00000395211; ENST00000259365 | TAF |
| 26% | chr10 | 72618870 | 72618877 | + | chr10 | 72619128 | 72619256; 72619307 | + | ENST00000373202; ENST00000299297; ENST00000409118 | TSF |
| 26% | chr10 | 72618870 | 72618877 | + | chr10 | 72619128 | 72619256; 72619307 | + | ENST00000373202; ENST00000299297; ENST00000409118 | TSF |
| 26% | chr10 | 72618870 | 72618877 | + | chr10 | 72619128 | 72619256; 72619307 | + | ENST00000373202; ENST00000299297; ENST00000409118 | TSF |
| 25% | chr14 | 94518197 | 94518094 | − | chr14 | 94517808 | 94517537 | − | ENST00000330836; ENST00000544005; ENST00000555054 | TAF |
| 25% | chr21 | 47278635 | 47278724 | + | chr21 | 47316122 | 47316276 | + | ENST00000400314; ENST00000400310; ENST00000449640; ENST00000400308; ENST00000400309 | TSF |
| 25% | chr21 | 47278635 | 472178724 | + | chr21 | 47316122 | 47316276 | + | ENST00000400314; ENST00000400310; ENST00000449640; ENST00000400308; ENST00000400309 | TSF |
| 25% | chr21 | 47278635 | 47278724 | + | chr21 | 47316122 | 47316276 | + | ENST00000400314; ENST00000400310; ENST00000449640; ENST00000400308; ENST00000400309 | TSF |
| 25% | chr21 | 47278635 | 47278724 | + | chr21 | 47316122 | 47316276 | + | ENST00000400314; ENST00000400310; ENST00000449640; ENST00000400308; ENST00000400309 | TSF |
| 24% | chr12 | 102411559 | 102411498 | − | chr12 | 102406970 | 102406886 | − | ENST00000240079; ENST00000545679; ENST00000542923 | TAF |
| 23% | chr16 | 75685621 | 75685636 | + | chr16 | 75688171 | 75688295; 75688183 | + | ENST00000300086; ENST00000569234 | TAF |
| 23% | chr16 | 75685621 | 75685636 | + | chr16 | 75688171 | 75688295; 75688183 | + | ENST00000300086; ENST00000569234 | TAF |
| 21% | chr17 | 41171108 | 41170991 | − | chr17 | 41170816 | 41170609; 41170766 | − | ENST00000355653; ENST00000587173; ENST00000587062 | TAF |
| 21% | chr17 | 41171108 | 41170991 | − | chr17 | 41170816 | 41170609; 41170766 | − | ENST00000355653; ENST00000587173; ENST00000587062 | TAF |
| 20% | chr10 | 104164273 | 104164216 | − | chr10 | 104163742 | 104163599 | − | ENST00000000673; ENST00000406432 | TAF |
| 20% | chr12 | 7284013 | 7284070 | + | chr12 | 7285620 | 7285742 | + | ENST00000541953; ENST00000266546; ENST00000539982; ENST00000537408 | TAF |
| 20% | chr12 | 7284013 | 7284070 | + | chr12 | 7285620 | 7285742 | + | ENST00000541953; ENST00000266546; ENST00000539982; ENST00000537408 | TAF |
| 20% | chr12 | 7284013 | 7284070 | + | chr12 | 7285620 | 7285742 | + | ENST00000541953; ENST00000266546; ENST00000539982; ENST00000537408 | TAF |
| 17% | chr17 | 42388704 | 42388881 | + | chr17 | 42389948 | 42390063 | + | ENST00000426726; ENST00000590941; ENST00000225441 | TAF |
| 17% | chr17 | 42388704 | 42388881 | + | chr17 | 42389948 | 42390063 | + | ENST00000426726; ENST00000590941; ENST00000225441 | TAF |
| 17% | chr17 | 42388704 | 42388881 | + | chr17 | 42389948 | 42390063 | + | ENST00000426726; ENST00000590941; ENST00000225441 | TAF |
| 17% | chr7 | 54611995 | 54612029 | + | chr7 | 54612315 | 54612481 | + | ENST00000302287; ENST00000407838; | TAF |

TABLE 48-continued

Transcript fusion for Pheochromocytoma and Paraganglioma (PCPG) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 17% | chr7 | 54611995 | 54612029 | + | chr7 | 54612315 | 54612481 | + | ENST00000404951; ENST00000402026; ENST00000402613 ENST00000302287; ENST00000407838; ENST00000404951; ENST00000402026; ENST00000402613 | TAF |
| 17% | chr7 | 54611995 | 54612029 | + | chr7 | 54612315 | 54612481 | + | ENST00000302287; ENST00000407838; ENST00000404951; ENST00000402026; ENST00000402613 | TAF |
| 17% | chr7 | 54611995 | 54612029 | + | chr7 | 54612315 | 54612481 | + | ENST00000302287; ENST00000407838; ENST00000404951; ENST00000402026; ENST00000402613 | TAF |
| 16% | chr2 | 238626962 | 238627008 | + | chr2 | 238628166 | 238628210 | + | ENST00000308482; ENST00000244815; ENST00000420665; ENST00000392000 | TAF |
| 16% | chr2 | 238626962 | 238627008 | + | chr2 | 238628166 | 238628210 | + | ENST00000308482; ENST00000244815; ENST00000420665; ENST00000392000 | TAF |
| 16% | chr2 | 238626962 | 238627008 | + | chr2 | 238628166 | 238628210 | + | ENST00000308482; ENST00000244815; ENST00000420665; ENST00000392000 | TAF |
| 16% | chr2 | 238626962 | 238627008 | + | chr2 | 238628166 | 238628210 | + | ENST00000308482; ENST00000244815; ENST00000420665; ENST00000392000 | TAF |
| 15% | chr16 | 2564319 | 2564396 | + | chr16 | 2569219 | 2569384; 2569402 | + | ENST00000564543; ENST00000330398; ENST00000568562 | TAF |
| 15% | chr16 | 2564319 | 2564396 | + | chr16 | 2569219 | 2569384; 2569402 | + | ENST00000564543; ENST00000330398; ENST00000568562 | TAF |
| 15% | chr12 | 63962410 | 63961380 | − | chr12 | 63954442 | 63954292 | − | ENST00000324472; ENST00000413230 | TAF |
| 15% | chr5 | 54528691 | 54528595 | − | chr5 | 54528374 | 54528189 | − | ENST00000282572 | TAF |
| 14% | chrX | 148577156 | 148576990 | − | chrX | 148571971 | 148571845 | − | ENST00000340855; ENST00000422081; ENST00000541269; ENST00000370441 | TAF |
| 14% | chrX | 148577156 | 148576990 | − | chrX | 148571971 | 148571845 | − | ENST00000340855; ENST00000422081; ENST00000541269; ENST00000370441 | TAF |
| 14% | chr20 | 25053246 | 25053172 | − | chr20 | 25052654 | 25052557; 25052571 | − | ENST00000429762; ENST00000444511 | TSF |
| 14% | chr20 | 25053246 | 25053172 | − | chr20 | 25052654 | 25052557; 25052571 | − | ENST00000429762; ENST00000444511 | TSF |
| 13% | chr12 | 4948345 | 4948527 | + | chr12 | 4959904 | 4960077 | + | ENST00000542998 | TSF |
| 12% | chr11 | 17895953 | 17895767 | − | chr11 | 17809960 | 17809632; 17809702 | − | ENST00000265965; ENST00000529151 | TAF |
| 12% | chr11 | 17895953 | 17895767 | − | chr11 | 17809960 | 17809632; 17809702 | − | ENST00000265965; ENST00000529151 | TAF |
| 12% | chr12 | 94167005 | 94167262 | + | chr12 | 94243746 | 94244047 | + | ENST00000332896; ENST00000542893 | TAF |
| 12% | chr17 | 21476521 | 21476490 | − | chr17 | 21438799 | 21438561; 21438772 | − | ENST00000391411; ENST00000412778 | TAF |
| 12% | chr17 | 21476521 | 21476490 | − | chr17 | 21438799 | 21438561; 21438772 | − | ENST00000391411; ENST00000412778 | TAF |
| 12% | chr7 | 95670520 | 95670949 | + | chr7 | 95705369 | 95705509 | + | ENST00000447467; ENST00000324972; ENST00000537881; ENST00000437599; ENST00000359388; ENST00000457059 | TSF |
| 12% | chr7 | 95670520 | 95670949 | + | chr7 | 95705369 | 95705509 | + | ENST00000447467; ENST00000324972; ENST00000537881; ENST00000437599; ENST00000359388; ENST00000457059 | TSF |
| 12% | chr2 | 74762302 | 74762039 | − | chr2 | 74761901 | 74761658 | − | ENST00000264094; ENST00000393937; ENST00000409549; ENST00000409986 | TSF |
| 12% | chr2 | 74762302 | 74762039 | − | chr2 | 74761901 | 74761658 | − | ENST00000264094; ENST00000393937; ENST00000409549; ENST00000409986 | TSF |
| 11% | chr2 | 207156598 | 207156840 | + | chr2 | 207161970 | 207162097 | + | ENST00000374423 | TAF |
| 11% | chr5 | 38458801 | 38458851 | + | chr5 | 38463010 | 38463113 | + | ENST00000354891; ENST00000322350; ENST00000336740; ENST00000397202; ENST00000397210; ENST00000506135; ENST00000508131; ENST00000514476 | TAF |
| 11% | chr5 | 38458801 | 38458851 | + | chr5 | 38463010 | 38463113 | + | ENST00000354891; ENST00000322350; ENST00000336740; ENST00000397202; ENST00000397210; ENST00000506135; ENST00000508131; ENST00000514476 | TAF |
| 11% | chr5 | 176950016 | 176949956 | − | chr5 | 176949072 | 176948976 | − | ENST00000514747; ENST00000329540; ENST00000443375; ENST00000524677 | TAF |
| 11% | chr8 | 20011376 | 20011370 | − | chr8 | 20008255 | 20008177 | − | ENST00000265808; ENST00000276373; ENST00000437980; ENST00000440926; ENST00000517776; ENST00000519026; ENST00000381608 | TSF |
| 11% | chr8 | 20011376 | 20011370 | − | chr8 | 20008255 | 20008177 | − | ENST00000265808; ENST00000276373; ENST00000437980; ENST00000440926; ENST00000517776; ENST00000519026; ENST00000381608 | TSF |
| 11% | chr8 | 20011376 | 20011370 | − | chr8 | 20008255 | 20008177 | − | ENST00000265808; ENST00000276373; ENST00000437980; ENST00000440926; ENST00000517776; ENST00000519026; ENST00000381608 | TSF |

TABLE 48-continued

Transcript fusion for Pheochromocytoma and Paraganglioma (PCPG) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 11% | chr15 | 74475607 | 74475594 | − | chr15 | 74474784 | 74474684 | − | ENST00000395105; ENST00000423167; ENST00000323940; ENST00000449139; ENST00000416286; ENST00000535552; ENST00000563965; ENST00000574278; ENST00000572785 | TSF |
| 11% | chr15 | 74475607 | 74475594 | − | chr15 | 74474784 | 74474684 | − | ENST00000395105; ENST00000423167; ENST00000323940; ENST00000449139; ENST00000416286; ENST00000535552; ENST00000563965; ENST00000574278; ENST00000572785 | TSF |
| 11% | chr5 | 38304257 | 38305719 | + | chr5 | 38337622 | 38337731 | + | ENST00000354891; ENST00000322350 | TSF |
| 11% | chr5 | 38304257 | 38305719 | + | chr5 | 38337622 | 38337731 | + | ENST00000354891; ENST00000322350 | TSF |
| 11% | chr15 | 72540647 | 72540602 | − | chr15 | 72535040 | 72534961; 72534975; 72535001 | − | ENST00000569795; ENST00000260376; ENST00000287196; ENST00000564610; ENST00000567974; ENST00000565443; ENST00000567263; ENST00000419739 | TSF |
| 11% | chr15 | 72540647 | 72540602 | − | chr15 | 72535040 | 72534961; 72534975; 72535001 | − | ENST00000569795; ENST00000260376; ENST00000287196; ENST00000564610; ENST00000567974; ENST00000565443; ENST00000567263; ENST00000419739 | TSF |
| 11% | chr15 | 72540647 | 72540602 | − | chr15 | 72535040 | 72534961; 72534975; 72535001 | − | ENST00000569795; ENST00000260376; ENST00000287196; ENST00000564610; ENST00000567974; ENST00000565443; ENST00000567263; ENST00000419739 | TSF |
| 11% | chr15 | 72540647 | 72540602 | − | chr15 | 72535040 | 72534961; 72534975; 72535001 | − | ENST00000569795; ENST00000260376; ENST00000287196; ENST00000564610; ENST00000567974; ENST00000565443; ENST00000567263; ENST00000419739 | TSF |
| 11% | chr14 | 91013189 | 91013107 | − | chr14 | 91007933 | 91007712; 91007626 | − | ENST00000328459; ENST00000357056; ENST00000553972; ENST00000555894; ENST00000557292 | TSF |
| 11% | chr14 | 91013189 | 91013107 | − | chr14 | 91007933 | 91007712; 91007626 | − | ENST00000328459; ENST00000357056; ENST00000553972; ENST00000555894; ENST00000557292 | TSF |
| 10% | chr3 | 98482258 | 98482283 | + | chr3 | 98487274 | 98487373 | + | ENST00000492254 | TAF |
| 10% | chr1 | 40041312 | 40041229 | − | chr1 | 40038258 | 40038065 | − | ENST00000372862; ENST00000372858; ENST00000372857; ENST00000372856; ENST00000470443; ENST00000451091 | TAF |
| 10% | chr1 | 40041312 | 40041229 | − | chr1 | 40038258 | 40038065 | − | ENST00000372862; ENST00000372858; ENST00000372857; ENST00000372856; ENST00000470443; ENST00000451091 | TAF |
| 10% | chr1 | 40041312 | 40041229 | − | chr1 | 40038258 | 40038065 | − | ENST00000372862; ENST00000372858; ENST00000372857; ENST00000372856; ENST00000470443; ENST00000451091 | TAF |
| 10% | chr1 | 40041312 | 40041229 | − | chr1 | 40038258 | 40038065 | − | ENST00000372862; ENST00000372858; ENST00000372857; ENST00000372856; ENST00000470443; ENST00000451091 | TAF |
| 10% | chr1 | 40041312 | 40041229 | − | chr1 | 40038258 | 40038065 | − | ENST00000372862; ENST00000372858; ENST00000372857; ENST00000372856; ENST00000470443; ENST00000451091 | TAF |
| 10% | chr1 | 40041312 | 40041229 | − | chr1 | 40038258 | 40038065 | − | ENST00000372862; ENST00000372858; ENST00000372857; ENST00000372856; ENST00000470443; ENST00000451091 | TAF |
| 10% | chr19 | 18653186 | 18653179 | − | chr19 | 18652805 | 18652489 | − | ENST00000453489 | TAF |
| 9% | chrX | 63029112 | 63029083 | − | chrX | 62944591 | 62944412 | − | ENST00000253401; ENST00000374878 | TSF |
| 9% | chrX | 63029112 | 63029083 | − | chrX | 62944591 | 62944412 | − | ENST00000253401; ENST00000374878 | TSF |
| 9% | chr7 | 50595425 | 50595367 | − | chr7 | 50571757 | 50571691 | − | ENST00000357936; ENST00000431062; ENST00000426377; ENST00000444733; ENST00000444124; ENST00000430300; ENST00000380984 | TSF |
| 9% | chr7 | 50595425 | 50595367 | − | chr7 | 50571757 | 50571691 | − | ENST00000357936; ENST00000431062; ENST00000426377; ENST00000444733; ENST00000444124; ENST00000430300; ENST00000380984 | TSF |
| 9% | chr7 | 50595425 | 50595367 | − | chr7 | 50571757 | 50571691 | − | ENST00000357936; ENST00000431062; ENST00000426377; ENST00000444733; ENST00000444124; ENST00000430300; ENST00000380984 | TSF |
| 9% | chr14 | 93396861 | 93396958 | + | chr14 | 93397595 | 93398047 | + | ENST00000216492 | TSF |
| 8% | chr3 | 99883880 | 99884005 | + | chr3 | 99885179 | 99885238 | + | ENST00000421999; ENST00000489081; ENST00000478909; ENST00000497345 | TSF |
| 8% | chr3 | 99883880 | 99884005 | + | chr3 | 99885179 | 99885238 | + | ENST00000421999; ENST00000489081; ENST00000478909; ENST00000497345 | TSF |
| 8% | chr3 | 99883880 | 99884005 | + | chr3 | 99885179 | 99885238 | + | ENST00000421999; ENST00000489081; ENST00000478909; ENST00000497345 | TSF |
| 8% | chr3 | 54853592 | 54853855 | + | chr3 | 54871186 | 54871257 | + | ENST00000415676; ENST00000288197; | TSF |

TABLE 48-continued

Transcript fusion for Pheochromocytoma and Paraganglioma (PCPG) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 8% | chr3 | 54853592 | 54853855 | + | chr3 | 54871186 | 54871257 | + | ENST00000474759; ENST00000471363; ENST00000490478; ENST00000477024 ENST00000415676; ENST00000288197; | TSF |
| 8% | chr4 | 48897704 | 48897441 | – | chr4 | 48896070 | 48896023 | – | ENST00000474759; ENST00000471363; ENST00000490478; ENST00000477024 ENST00000508632; ENST00000273860; ENST00000381464 | TSF |
| 8% | chr4 | 48897704 | 48897441 | – | chr4 | 48896070 | 48896023 | – | ENST00000508632; ENST00000273860; ENST00000381464 | TSF |
| 8% | chr4 | 48897704 | 48897441 | | chr4 | 48896070 | 48896023 | – | ENST00000508632; ENST00000273860; ENST00000381464 | TSF |
| 8% | chr17 | 61518950 | 61518901 | – | chr17 | 61514921 | 61514707; 61514733 | – | ENST00000542042; ENST00000580691; ENST00000582997; ENST00000580592 | TSF |
| 8% | chr17 | 61518950 | 61518901 | – | chr17 | 61514921 | 61514707; 61514733 | – | ENST00000542042; ENST00000580691; ENST00000582997; ENST00000580592 | TSF |
| 8% | chr11 | 71954010 | 71953910 | – | chr11 | 71952333 | 71952146 | – | ENST00000298231 | TSF |
| 7% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 7% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 7% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 7% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 7% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 7% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 7% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 7% | chr20 | 5874978 | 5874991 | + | chr20 | 5903286 | 5904746; 5903719 | + | ENST00000378961; ENST00000455042 | TSF |
| 7% | chr20 | 5874978 | 5874991 | + | chr20 | 5903286 | 5904746; 5903719 | + | ENST00000378961; ENST00000455042 | TSF |
| 7% | chr7 | 5340608 | 5340708 | + | chr7 | 5342428 | 5342570 | + | ENST00000396872; ENST00000297195; ENST00000406453 | TSF |
| 7% | chr20 | 57466178 | 57466186 | + | chr20 | 57485409 | 57485456 | + | ENST00000371100; ENST00000371102; ENST00000371095; ENST00000354359; ENST00000371085; ENST00000265620; ENST00000306090 | TSF |
| 7% | chr3 | 183904878 | 183904948 | + | chr3 | 183905185 | 183905231 | + | ENST00000429586; ENST00000292808 | TSF |
| 6% | chr1 | 110168535 | 110168634 | + | chr1 | 110168782 | 110168820; 110168850 | + | ENST00000531734; ENST00000342115; ENST00000528667; ENST00000531203; ENST00000256578; ENST00000358729; ENST00000369840; ENST00000527846; ENST00000528454; ENST00000393688 | TSF |
| 6% | chr1 | 110168535 | 110168634 | + | chr1 | 110168782 | 110168820; 110168850 | + | ENST00000531734; ENST00000342115; ENST00000528667; ENST00000531203; ENST00000256578; ENST00000358729; ENST00000369840; ENST00000527846; ENST00000528454; ENST00000393688 | TSF |
| 6% | chr1 | 110168535 | 110168634 | + | chr1 | 110168782 | 110168820; 110168850 | + | ENST00000531734; ENST00000342115; ENST00000528667; ENST00000531203; ENST00000256578; ENST00000358729; ENST00000369840; ENST00000527846; | TSF |

TABLE 48-continued

Transcript fusion for Pheochromocytoma and Paraganglioma (PCPG) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 6% | chr1 | 110168535 | 110168634 | + | chr1 | 110168782 | 110168820; 110168508 | + | ENST00000528454; ENST00000393688 ENST00000531734; ENST00000342115; ENST00000528667; ENST00000531203; ENST00000256578; ENST00000358729; ENST00000369840; ENST00000527846; ENST00000528454; ENST00000393688 | TSF |
| 6% | chr1 | 110168535 | 110168634 | + | chr1 | 110168782 | 110168820; 110168850 | + | ENST00000531734; ENST00000342115; ENST00000528667; ENST00000531203; ENST00000256578; ENST00000358729; ENST00000369840; ENST00000527846; ENST00000528454; ENST00000393688 | TSF |
| 6% | chr8 | 139623662 | 139623508 | − | chr8 | 139620232 | 139620179 | − | ENST00000303045; ENST00000435777 | TSF |
| 6% | chr4 | 5830600 | 5830583 | − | chr4 | 5830395 | 5830216 | − | ENST00000324989; ENST00000397890; ENST00000512574 | TSF |
| 6% | chr14 | 101195452 | 101195584 | + | chr14 | 101198379 | 101198407; 101198520 | + | ENST00000392848; ENST00000341267; ENST00000331224 | TSF |
| 6% | chr14 | 101195452 | 101195584 | + | chr14 | 101198379 | 101198407; 101198520 | + | ENST00000392848; ENST00000341267; ENST00000331224 | TSF |
| 6% | chr14 | 101195452 | 101195584 | + | chr14 | 101198379 | 101198407; 101198520 | + | ENST00000392848; ENST00000341267; ENST00000331224 | TSF |
| 6% | chr7 | 100818527 | 100818318 | − | chr7 | 100806798 | 100806277 | − | ENST00000249330; ENST00000445482 | TSF |
| 6% | chr7 | 50595425 | 50595367 | − | chr7 | 50563115 | 50563048; 50563093 | − | ENST00000357936; ENST00000431062; ENST00000426377; ENST00000444733; ENST00000444124; ENST00000430300; ENST00000380984 | TSF |
| 6% | chr7 | 50595425 | 50595367 | − | chr7 | 50563115 | 50563048; 50563093 | − | ENST00000357936; ENST00000431062; ENST00000426377; ENST00000444733; ENST00000444124; ENST00000430300; ENST00000380984 | TSF |
| 6% | chr7 | 50595425 | 50595367 | − | chr7 | 50563115 | 50563048; 50563093 | − | ENST00000357936; ENST00000431062; ENST00000426377; ENST00000444733; ENST00000444124; ENST00000430300; ENST00000380984 | TSF |
| 6% | chr2 | 165806067 | 165805999 | − | chr2 | 165802237 | 165802103 | − | ENST00000303735; ENST00000409149; ENST00000409058; ENST00000409662 | TSF |
| 6% | chr2 | 165806067 | 165805999 | − | chr2 | 165802237 | 165802103 | − | ENST00000303735; ENST00000409149; ENST00000409058; ENST00000409662 | TSF |
| 6% | chr17 | 61517244 | 61517092 | − | chr17 | 61514921 | 61514707; 61514733 | − | ENST00000542042; ENST00000580691; ENST00000582997; ENST00000580592 | TSF |
| 6% | chr17 | 61517244 | 61517092 | − | chr17 | 61514921 | 61514707; 61514733 | − | ENST00000542042; ENST00000580691; ENST00000582997; ENST00000580592 | TSF |
| 6% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 6% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 6% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 6% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 6% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 6% | chr12 | 50285408 | 50285280 | − | chr12 | 50284897 | 50284847; 50284860 | − | ENST00000320634; ENST00000550890; ENST00000550195; ENST00000552669; ENST00000552863; ENST00000550635; ENST00000547871 | TSF |
| 5% | chr17 | 61517244 | 61517029 | − | chr17 | 61514921 | 61514707; 61514733 | − | ENST00000542042; ENST00000580691; ENST00000582997; ENST00000580592 | TSF |
| 5% | chr17 | 61517244 | 61517029 | − | chr17 | 61514921 | 61514707; 61514733 | − | ENST00000542042; ENST00000580691; ENST00000582997; ENST00000580592 | TSF |
| 5% | chr6 | 32490932 | 32490383 | − | chr6 | 32489951 | 32489682 | − | ENST00000374975 | TSF |
| 4% | chr21 | 39513161 | 39513404 | + | chr21 | 39528398 | 39528496 | + | ENST00000357704; ENST00000400477 | TSF |
| 4% | chr16 | 75683160 | 75683228 | + | chr16 | 75688171 | 75688295; 75688183 | + | ENST00000300086; ENST00000569234 | TSF |
| 4% | chr16 | 75683160 | 75683228 | + | chr16 | 75688171 | 75688295; 75688183 | + | ENST00000300086; ENST00000569234 | TSF |
| 4% | chr3 | 31046348 | 31045927 | − | chr3 | 30903257 | 30903085 | − | ENST00000282538; ENST00000454381 | TSF |

TABLE 48-continued

Transcript fusion for Pheochromocytoma and Paraganglioma (PCPG) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr3 | 31046348 | 31045927 | − | chr3 | 30903257 | 30903085 | − | ENST00000282538; ENST00000454381 | TSF |
| 4% | chr7 | 50595425 | 50595367 | − | chr7 | 50547561 | 50547485 | − | ENST00000357936; ENST00000431062; ENST00000426377; ENST00000444124; ENST00000430300 | TSF |
| 4% | chr7 | 102146992 | 102146893 | − | chr7 | 102143691 | 102143610 | − | ENST00000541662; ENST00000465829; ENST00000306682 | TSF |
| 4% | chr7 | 102146992 | 102146893 | − | chr7 | 102143691 | 102143610 | − | ENST00000541662; ENST00000465829; ENST00000306682 | TSF |
| 4% | chr15 | 74490750 | 74490651 | − | chr15 | 74490159 | 74490093; 74490009 | − | ENST00000395105; ENST00000423167; ENST00000323940; ENST00000449139; ENST00000416286; ENST00000535552; ENST00000563965; ENST00000574278; ENST00000569936; ENST00000432245; ENST00000571341; ENST00000573391 | TSF |
| 4% | chr15 | 74490750 | 74490651 | − | chr15 | 74490159 | 74490093; 74490009 | − | ENST00000395105; ENST00000423167; ENST00000323940; ENST00000449139; ENST00000416286; ENST00000535552; ENST00000563965; ENST00000574278; ENST00000569936; ENST00000432245; ENST00000571341; ENST00000573391 | TSF |
| 4% | chr15 | 74490750 | 74490651 | − | chr15 | 74490159 | 74490093; 74490009 | − | ENST00000395105; ENST00000423167; ENST00000323940; ENST00000449139; ENST00000416286; ENST00000535552; ENST00000563965; ENST00000574278; ENST00000569936; ENST00000432245; ENST00000571341; ENST00000573391 | TSF |
| 4% | chr15 | 74490750 | 74490651 | − | chr15 | 74490159 | 74490093; 74490009 | − | ENST00000395105; ENST00000423167; ENST00000323940; ENST00000449139; ENST00000416286; ENST00000535552; ENST00000563965; ENST00000574278; ENST00000569936; ENST00000432245; ENST00000571341; ENST00000573391 | TSF |
| 4% | chr15 | 74490750 | 74490651 | − | chr15 | 74490159 | 74490093; 74490009 | − | ENST00000395105; ENST00000423167; ENST00000323940; ENST00000449139; ENST00000416286; ENST00000535552; ENST00000563965; ENST00000574278; ENST00000569936; ENST00000432245; ENST00000571341; ENST00000573391 | TSF |
| 4% | chr15 | 74490750 | 74490651 | − | chr15 | 74490159 | 74490093; 74490009 | − | ENST00000395105; ENST00000423167; ENST00000323940; ENST00000449139; ENST00000416286; ENST00000535552; ENST00000563965; ENST00000574278; ENST00000569936; ENST00000432245; ENST00000571341; ENST00000573391 | TSF |
| 4% | chr15 | 74490750 | 74490651 | − | chr15 | 74490159 | 74490093; 74490009 | − | ENST00000395105; ENST00000423167; ENST00000323940; ENST00000449139; ENST00000416286; ENST00000535552; ENST00000563965; ENST00000574278; ENST00000569936; ENST00000432245; ENST00000571341; ENST00000573391 | TSF |
| 4% | chr20 | 5741057 | 5741274 | + | chr20 | 5903657 | 5904746; 5903719 | + | ENST00000378961; ENST00000455042 | TSF |
| 4% | chr20 | 5741057 | 5741274 | + | chr20 | 5903657 | 5904746; 5903719 | + | ENST00000378961; ENST00000455042 | TSF |
| 4% | chr10 | 119009835 | 119009901 | + | chr10 | 119012910 | 119012968 | + | ENST00000298472 | TSF |
| 4% | chr9 | 130424996 | 130425055 | + | chr9 | 130425484 | 130425632 | + | ENST00000373302; ENST00000373299 | TSF |
| 4% | chr9 | 130424996 | 130425055 | + | chr9 | 130425484 | 130425632 | + | ENST00000373302; ENST00000373299 | TSF |
| 4% | chr7 | 92778284 | 92778372 | + | chr7 | 92869179 | 92869247; 92869263 | + | ENST00000251739; ENST00000305866; ENST00000438395; ENST00000441602; ENST00000458530; ENST00000436177; ENST00000535481 | TSF |
| 4% | chr7 | 92778284 | 92778372 | + | chr7 | 92869179 | 92869247; 92869263 | + | ENST00000251739; ENST00000305866; ENST00000438395; ENST00000441602; ENST00000458530; ENST00000436177; ENST00000535481 | TSF |
| 4% | chr7 | 92778284 | 92778372 | + | chr7 | 92869179 | 92869247; 92869263 | + | ENST00000251739; ENST00000305866; ENST00000438395; ENST00000441602; ENST00000458530; ENST00000436177; ENST00000535481 | TSF |
| 4% | chr7 | 92778284 | 92778372 | + | chr7 | 92869179 | 92869247; 92869263 | + | ENST00000251739; ENST00000305866; ENST00000438395; ENST00000441602; ENST00000458530; ENST00000436177; ENST00000535481 | TSF |
| 4% | chr7 | 92778284 | 92778372 | + | chr7 | 92869179 | 92869247; 92869263 | + | ENST00000251739; ENST00000305866; ENST00000438395; ENST00000441602; ENST00000458530; ENST00000436177; | TSF |

TABLE 48-continued

Transcript fusion for Pheochromocytoma and Paraganglioma (PCPG) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr7 | 92778284 | 92778372 | + | chr7 | 92869179 | 92869247; 92869263 | + | ENST00000535481 ENST00000251739; ENST00000305866; ENST00000438395; ENST00000441602; ENST00000458530; ENST00000436177; ENST00000535481 | TSF |
| 4% | chr7 | 92778284 | 92778372 | + | chr7 | 92869179 | 92869247; 92869263 | + | ENST00000251739; ENST00000305866; ENST00000438395; ENST00000441602; ENST00000458530; ENST00000436177; ENST00000535481 | TSF |
| 4% | chr20 | 5874978 | 5874991 | + | chr20 | 5903856 | 5904746 | + | ENST00000378961 | TSF |
| 4% | chr7 | 98448201 | 98448151 | − | chr7 | 98446318 | 98446206 | − | ENST00000416379; ENST00000339375; ENST00000450876; ENST00000345589; ENST00000546258 | TSF |
| 4% | chr7 | 98448201 | 98448151 | − | chr7 | 198446318 | 98446206 | − | ENST00000416379; ENST00000339375; ENST00000450876; ENST00000345589; ENST00000546258 | TSF |
| 4% | chr7 | 102246155 | 102246056 | − | chr7 | 102242852 | 102242771 | − | ENST00000262940; ENST00000461209; ENST00000449970; ENST00000462172; ENST00000522801; ENST00000520042; ENST00000521076 | TSF |
| 4% | chr7 | 102246155 | 102246056 | − | chr7 | 102242852 | 102242771 | − | ENST00000262940; ENST00000461209; ENST00000449970; ENST00000462172; ENST00000522801; ENST00000520042; ENST00000521076 | TSF |
| 4% | chr7 | 102246155 | 102246056 | − | chr7 | 102242852 | 102242771 | − | ENST00000262940; ENST00000461209; ENST00000449970; ENST00000462172; ENST00000522801; ENST00000520042; ENST00000521076 | TSF |
| 4% | chr7 | 102246155 | 102246056 | − | chr7 | 102242852 | 102242771 | − | ENST00000262940; ENST00000461209; ENST00000449970; ENST00000462172; ENST00000522801; ENST00000520042; ENST00000521076 | TSF |
| 4% | chr10 | 87362982 | 87362906 | − | chr10 | 87362458 | 87362030 | − | ENST00000327946; ENST00000536331 | TSF |
| 4% | chr15 | 78467446 | 78467436 | − | chr15 | 78466866 | 78466727 | − | ENST00000258873; ENST00000541759; ENST00000560817 | TSF |
| 3% | chr9 | 35846065 | 35846070 | + | chr9 | 35846255 | 35846378 | + | ENST00000377996; ENST00000439587; ENST00000377991; ENST00000377988 | TSF |
| 3% | chr9 | 35846065 | 35846070 | + | chr9 | 35846255 | 35846378 | + | ENST00000377996; ENST00000439587; ENST00000377991; ENST00000377988 | TSF |
| 3% | chr20 | 15874978 | 5874991 | + | chr20 | 5903727 | 5904746 | + | ENST00000378961 | TSF |
| 3% | chr12 | 50292609 | 50292556 | − | chr12 | 50291869 | 50291770 | − | ENST00000320634; ENST00000550890; ENST00000550195; ENST00000552669; ENST00000550635; ENST00000547871 | TSF |
| 3% | chr12 | 50292609 | 50292556 | − | chr12 | 50291869 | 50291770 | − | ENST00000320634; ENST00000550890; ENST00000550195; ENST00000552669; ENST00000550635; ENST00000547871 | TSF |
| 3% | chr12 | 50292609 | 50292556 | − | chr12 | 50291869 | 50291770 | − | ENST00000320634; ENST00000550890; ENST00000550195; ENST00000552669; ENST00000550635; ENST00000547871 | TSF |
| 3% | chr12 | 50292609 | 50292556 | − | chr12 | 50291869 | 50291770 | − | ENST00000320634; ENST00000550890; ENST00000550195; ENST00000552669; ENST00000550635; ENST00000547871 | TSF |
| 3% | chr12 | 50292609 | 50292556 | − | chr12 | 50291869 | 50291770 | − | ENST00000320634; ENST00000550890; ENST00000550195; ENST00000552669; ENST00000550635; ENST00000547871 | TSF |

TABLE 49

Transcript fusion for Prostate Adenocarcinoma (PRAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 61% | chr11 | 49229961 | 49229844 | − | ENST00000256999; ENST00000356696; ENST00000525826; ENST00000533510; ENST00000529648 | chr11 | 49228426 | 49228367 | − | TAF |
| 60% | chr13 | 95768255 | 95768176 | − | ENST00000412704; ENST00000376887; ENST00000536256; ENST00000431522 | chr13 | 95757357 | 95757136 | − | TAF |
| 50% | chr13 | 95768255 | 95768176 | − | ENST00000412704; ENST00000376887; ENST00000536256; ENST00000431522 | chr13 | 95757357 | 95757136 | − | TAF |
| 60% | chr13 | 95768255 | 95768176 | − | ENST00000412704; ENST00000376887; ENST00000536256; ENST00000431522 | chr13 | 95757357 | 95757136 | − | TAF |
| 49% | chr6 | 34512232 | 34511797 | − | ENST00000374037; ENST00000544425 | chr6 | 34511385 | 34511028 | − | TAF |
| 29% | chr5 | 34008124 | 34007878 | − | ENST00000335606; ENST00000382072; | chr5 | 34007194 | 34006954 | − | TAF |

TABLE 49-continued

Transcript fusion for Prostate Adenocarcinoma (PRAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
|  |  |  |  |  | ENST00000506639; ENST00000382085; ENST00000502637; ENST00000441713; ENST00000426255; ENST00000512079; ENST00000382068 |  |  |  |  |  |
| 18% | chr10 | 120905865 | 120905748 | − | ENST00000355697; ENST00000330036 | chr10 | 120901885 | 120901741 | − | TAF |
| 18% | chr10 | 120905865 | 120905748 | − | ENST00000355697; ENST00000330036 | chr10 | 120901885 | 120901741 | − | TAF |
| 17% | chr1 | 46876486 | 46876526 | + | ENST00000243167 | chr1 | 46877130 | 46877147 | + | TAF |
| 16% | chr19 | 51359567; 51359496; 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | chr19 | 51360009 | 51360064 | + | TAF |
| 16% | chr19 | 51359567; 51359496; 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | chr19 | 51360009 | 51360064 | + | TAF |
| 16% | chr19 | 51359567; 51359496; 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | chr19 | 51360009 | 51360064 | + | TAF |
| 16% | chr19 | 51359567; 51359496; 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | chr19 | 51360009 | 51360064 | + | TAF |
| 15% | chr19 | 44129402 | 44129230 | − | ENST00000222374 | chr19 | 44129055 | 44128921 | − | TAF |
| 14% | chr5 | 33998932; 33998887 | 33998746 | − | ENST00000335606; ENST00000382072; ENST00000506639; ENST00000382085; ENST00000502637; ENST00000441713; ENST00000426255; ENST00000512079; ENST00000382068 | chr5 | 33993480 | 33992996 | − | TSF |
| 14% | chr5 | 33998932; 33998887 | 33998746 | − | ENST00000335606; ENST00000382072; ENST00000506639; ENST00000382085; ENST00000502637; ENST00000441713; ENST00000426255; ENST00000512079; ENST00000382068 | chr5 | 33993480 | 33992996 | − | TSF |
| 14% | chr5 | 33998932; 33998887 | 33998746 | − | ENST00000335606; ENST00000382072; ENST00000506639; ENST00000382085; ENST00000502637; ENST00000441713; ENST00000426255; ENST00000512079; ENST00000382068 | chr5 | 33993480 | 33992996 | − | TSF |
| 13% | chr3 | 122103113 | 122103146 | + | ENST00000477892; ENST00000469967 | chr3 | 122112280 | 122112741 | + | TAF |
| 13% | chr9 | 5335597 | 5335468 | − | ENST00000223862 | chr9 | 5326315 | 5326232 | − | TAF |
| 11% | chr1 | 156256051 | 156256264 | + | ENST00000295694; ENST00000357501; ENST00000405535; ENST00000456810 | chr1 | 156259791 | 156259857 | + | TAF |
| 11% | chr1 | 156256051 | 156256264 | + | ENST00000295694; ENST00000357501; ENST00000405535; ENST00000456810 | chr1 | 156259791 | 156259857 | + | TAF |
| 11% | chr22 | 24323139 | 24323226 | + | ENST00000215780; ENST00000402588 | chr22 | 24324557 | 24324632 | + | TAF |
| 11% | chr6 | 11000397 | 11000320 | − | ENST00000354666 | chr6 | 11000151 | 11000002 | − | TAF |
| 10% | chr20 | 32247538; 32247356 | 32247303 | − | ENST00000246190; ENST00000375238; ENST00000480994 | chr20 | 32246861 | 32246725 | − | TAF |
| 10% | chr20 | 32247538; 32247356 | 32247303 | − | ENST00000246190; ENST00000375238; ENST00000480994 | chr20 | 32246861 | 32246725 | − | TAF |
| 10% | chr20 | 32247538; 32247356 | 32247303 | − | ENST00000246190; ENST00000375238; ENST00000480994 | chr20 | 32246861 | 32246725 | − | TAF |
| 10% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 10% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 10% | chr12 | 102074121 | 102074307 | + | ENST00000547405; ENST00000452455; ENST00000360610; ENST00000441232; ENST00000392934; ENST00000547509; | chr12 | 102089430 | 102089665 | + | TAF |

TABLE 49-continued

Transcript fusion for Prostate Adenocarcinoma (PRAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 10% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 10% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 10% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 10% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 10% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 10% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 10% | chr12 | 102074121 | 102074307 | + | ENST00000547405; ENST00000452455; ENST00000360610; ENST00000441232; ENST00000392934; ENST00000547509; ENST00000361685; ENST00000549145; ENST00000553190; ENST00000536007; ENST00000541119; ENST00000545503; ENST00000361466; ENST00000551300; ENST00000550270 | chr12 | 102089430 | 102089665 | + | TAF |
| 9% | chr13 | 95686993 | 95686859 | − | ENST00000412704; ENST00000376887 | chr13 | 95659886 | 95659840 | − | TSF |
| 9% | chr13 | 95686993 | 95686859 | − | ENST00000412704; ENST00000376887 | chr13 | 95659886 | 95659840 | − | TSF |
| 7% | chr3 | 53707050 | 53707153 | + | ENST00000350061; ENST00000422281; ENST00000481478 | chr3 | 53713021 | 53713326 | + | TSF |
| 7% | chr3 | 53707050 | 53707153 | + | ENST00000350061; ENST00000422281; ENST00000481478 | chr3 | 53713021 | 53713326 | + | TSF |
| 7% | chr3 | 132063771 | 132063903 | + | ENST00000336375; ENST00000475741; ENST00000351273 | chr3 | 132063998 | 132064153 | + | TSF |
| 7% | chr3 | 132063771 | 132063903 | + | ENST00000336375; ENST00000475741; ENST00000351273 | chr3 | 132063998 | 132064153 | + | TSF |
| 6% | chr19 | 49714421 | 49714526 | + | ENST00000252826; ENST00000427978; ENST00000355712 | chr19 | 49739844 | 49739922 | + | TSF |
| 6% | chr19 | 49714421 | 49714526 | + | ENST00000252826; ENST00000427978; ENST00000355712 | chr19 | 49739844 | 49739922 | + | TSF |
| 6% | chr19 | 49714421 | 49714526 | + | ENST00000252826; ENST00000427978; | chr19 | 49739844 | 49739922 | + | TSF |

TABLE 49-continued

Transcript fusion for Prostate Adenocarcinoma (PRAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 5% | chr7 | 151573705 | 151573592 | − | ENST00000355712; ENST00000287878; ENST00000488258 | chr7 | 151532195 | 531151867 | − | TSF |
| 5% | chr2 | 193044420 | 193044394 | − | ENST00000392314; ENST00000272771; ENST00000409056 | chr2 | 193026176 | 193025896 | − | TSF |
| 4% | chr1 | 11115983; 11115877 | 11115838 | − | ENST00000376957; ENST00000490101 | chr1 | 11115464 | 11115178 | − | TSF |
| 4% | chr1 | 11115983; 11115877 | 11115838 | − | ENST00000376957; ENST00000490101 | chr1 | 11115464 | 15111178 | − | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr19 | 51376730 | 51376775 | + | ENST00000325321; ENST00000600690; ENST00000594174; ENST00000597727; ENST00000595316; ENST00000599121; ENST00000358049; ENST00000597439 | chr19 | 51382148 | 51382280 | + | TSF |
| 4% | chr5 | 70944924 | 70945080 | + | ENST00000340941; ENST00000323375; ENST00000509539 | chr10 | 1662872 | 1663598 | + | TSF |
| 4% | chr5 | 70944924 | 70945080 | + | ENST00000340941; ENST00000323375; ENST00000509539 | chr10 | 1662872 | 1663598 | + | TSF |
| 4% | chr5 | 70944924 | 70945080 | + | ENST00000340941; ENST00000323375; ENST00000509539 | chr10 | 1662872 | 1663598 | + | TSF |
| 3% | chr18 | 56807181 | 56807267 | + | ENST0000587834; ENST00000299714; ENST00000588875 | chr18 | 56814218 | 56814267 | + | TSF |
| 3% | chr21 | 39762964 | 39762917 | − | ENST00000398905; ENST00000398907; ENST00000288319; ENST00000398897; ENST00000398911; ENST00000398910; ENST00000417133; ENST00000442448; ENST00000453032; ENST00000398919 | chr21 | 39739570 | 39739188 | − | TSF |
| 3% | chr21 | 39762964 | 39762917 | − | ENST00000398905; ENST00000398907; ENST00000288319; ENST00000398897; ENST00000398911; ENST00000398910; ENST00000417133; ENST00000442448; ENST00000453032; ENST00000398919 | chr21 | 39739570 | 39739188 | − | TSF |
| 3% | chr21 | 39762964 | 39762917 | − | ENST00000398905; ENST00000398907; ENST00000288319; ENST00000398897; ENST00000398911; ENST00000398910; ENST00000417133; ENST00000442448; ENST00000453032; ENST00000398919 | chr21 | 39739570 | 39739188 | − | TSF |
| 3% | chr21 | 39762964 | 39762917 | − | ENST00000398905; ENST00000398907; ENST00000288319; ENST00000398897; ENST00000398911; ENST00000398910; ENST00000417133; ENST00000442448; ENST00000453032; ENST00000398919 | chr21 | 39739570 | 39739188 | − | TSF |
| 3% | chr21 | 39762964 | 39762917 | − | ENST00000398905; ENST00000398907; ENST00000288319; ENST00000398897; ENST00000398911; ENST00000398910; ENST00000417133; ENST00000442448; ENST00000453032; ENST00000398919 | chr21 | 39739570 | 39739188 | − | TSF |
| 3% | chr21 | 39762964 | 39762917 | − | ENST00000398905; ENST00000398907; ENST00000288319; ENST00000398897; ENST00000398911; ENST00000398910; ENST00000417133; ENST00000442448; ENST00000453032; ENST00000398919 | chr21 | 39739570 | 39739188 | − | TSF |
| 3% | chr21 | 39762964 | 39762917 | − | ENST00000398905; ENST00000398907; ENST00000288319; ENST00000398897; | chr21 | 39739570 | 39739188 | − | TSF |

TABLE 49-continued

Transcript fusion for Prostate Adenocarcinoma (PRAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr21 | 39762964 | 39762917 | − | ENST00000398911; ENST00000398910; ENST00000417133; ENST00000442448; ENST00000453032; ENST00000398919 ENST00000398905; ENST00000398907; ENST00000288319; ENST00000398897; ENST00000398911; ENST00000398910; ENST00000417133; ENST00000442448; ENST00000453032; ENST00000398919 | chr21 | 39739570 | 39739188 | − | TSF |
| 3% | chr6 | 38851652 | 38851774 | + | ENST00000449981; ENST00000327475; ENST00000359357; ENST00000441566 | chr6 | 38852622 | 38852809 | + | TSF |
| 3% | chr6 | 38851652 | 38851774 | + | ENST00000449981; ENST00000327475; ENST00000359357; ENST00000441566 | chr6 | 38852622 | 38852809 | + | TSF |
| 3% | chr6 | 38851652 | 38851774 | + | ENST00000449981; ENST00000327475; ENST00000359357; ENST00000441566 | chr6 | 38852622 | 38852809 | + | TSF |
| 3% | chr6 | 38851652 | 38851774 | + | ENST00000449981; ENST00000327475; ENST00000359357; ENST00000441566 | chr6 | 38852622 | 38852809 | + | TSF |
| 3% | chr3 | 4927450 | 4927407 | − | ENST00000449914; ENST00000441894 | chr3 | 4898429 | 4898242 | − | TSF |
| 3% | chr5 | 79410474 | 79410337 | − | ENST00000509193 | chr5 | 79409445 | 79409319 | − | TSF |
| 3% | chr11 | 10050104 | 10049999 | − | ENST00000256190 | chr11 | 10038326 | 10038049 | − | TSF |
| 3% | chr11 | 49175479 | 49175398 | − | ENST00000256999; ENST00000356696; ENST00000343844; ENST00000340334; ENST00000533034 | chr11 | 49173831 | 49173562 | − | TSF |
| 3% | chr11 | 49175479 | 49175398 | − | ENST00000256999; ENST00000356696; ENST00000343844; ENST00000340334; ENST00000533034 | chr11 | 49173831 | 49173562 | − | TSF |
| 3% | chr11 | 49175479 | 49175398 | − | ENST00000256999; ENST00000356696; ENST00000343844; ENST00000340334; ENST00000533034 | chr11 | 49173831 | 49173562 | − | TSF |
| 3% | chr3 | 4872702 | 4872631 | − | ENST00000449914; ENST00000441894 | chr3 | 4871958 | 4871639 | − | TSF |
| 2% | chr17 | 11166683 | 11166843 | + | ENST00000432116; ENST00000441885; ENST00000409168; ENST00000343478 | chr17 | 11172072 | 11172130 | + | TSF |
| 2% | chr17 | 11166683 | 11166843 | + | ENST00000432116; ENST00000441885; ENST00000409168; ENST00000343478 | chr17 | 11172072 | 11172130 | + | TSF |
| 2% | chr12 | 63061109 | 63060958 | − | ENST00000228705 | chr12 | 63057027 | 63056997 | − | TSF |
| 2% | chr9 | 17143286 | 17143374 | + | ENST00000380647; ENST00000262360; ENST00000425824; ENST00000380641 | chr9 | 17166816 | 17167136 | + | TSF |
| 2% | chr19 | 51361715 | 51361851 | + | ENST00000326003; ENST00000597483; ENST00000593997; ENST00000595952; ENST00000360617; ENST00000598145 | chr19 | 51369527 | 51369763 | + | TSF |
| 2% | chr19 | 51361715 | 51361851 | + | ENST00000326003; ENST00000597483; ENST00000593997; ENST00000595952; ENST00000360617; ENST00000598145 | chr19 | 51369527 | 51369763 | + | TSF |
| 2% | chr19 | 51361715 | 51361851 | + | ENST00000326003; ENST00000597483; ENST00000593997; ENST00000595952; ENST00000360617; ENST00000598145 | chr19 | 51369527 | 51369763 | + | TSF |
| 2% | chr10 | 79796952 | 79797062 | + | ENST00000435275; ENST00000440692; ENST00000372360; ENST00000360830 | chr4 | 176584518 | 176584519 | + | TSF |
| 2% | chr20 | 29632611 | 29632721 | + | ENST00000278882; ENST00000358464 | chr20 | 29652086 | 29652324 | + | TSF |
| 2% | chr4 | 57319769 | 57319927 | + | ENST00000514888; ENST00000264221; ENST00000505164; ENST00000399688; ENST00000512576 | chr4 | 57321183 | 57321327 | + | TSF |
| 2% | chr4 | 57319769 | 57319927 | + | ENST00000514888; ENST00000264221; ENST00000505164; ENST00000399688; ENST00000512576 | chr4 | 57321183 | 57321327 | + | TSF |
| 2% | chr4 | 57319769 | 57319927 | + | ENST00000514888; ENST00000264221; ENST00000505164; ENST00000399688; ENST00000512576 | chr4 | 57321183 | 57321327 | + | TSF |
| 2% | chr5 | 172341717 | 172341841 | + | ENST00000393784; ENST00000520326; ENST00000523291; ENST00000518247; ENST00000326654; ENST00000519567 | chr5 | 172345344 | 172345395 | + | TSF |
| 2% | chr5 | 172341717 | 172341841 | + | ENST00000393784; ENST00000520326; ENST00000523291; ENST00000518247; ENST00000326654; ENST00000519567 | chr5 | 172345344 | 172345395 | + | TSF |
| 2% | chr5 | 172341717 | 172341841 | + | ENST00000393784; ENST00000520326; ENST00000523291; ENST00000518247; ENST00000326654; ENST00000519567 | chr5 | 172345344 | 172345395 | + | TSF |
| 2% | chr9 | 125054028 | 125054119 | + | ENST00000297908; ENST00000344641; ENST00000373723; ENST00000373729; ENST00000394315 | chr9 | 125068067 | 125068171 | + | TSF |
| 2% | chr9 | 125054028 | 125054119 | + | ENST00000297908; ENST00000344641; ENST00000373723; ENST00000373729; ENST00000394315 | chr9 | 125068067 | 125068171 | + | TSF |
| 2% | chr9 | 125054028 | 125054119 | + | ENST00000297908; ENST00000344641; ENST00000373723; ENST00000373729; ENST00000394315 | chr9 | 125068067 | 125068171 | + | TSF |
| 2% | chr21 | 43967213 | 43967250 | + | ENST00000398341; ENST00000352133 | chr21 | 43968760 | 43968869 | + | TSF |

TABLE 49-continued

Transcript fusion for Prostate Adenocarcinoma (PRAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 2% | chr1 | 227842037 | 227843464 | + | ENST00000397097; ENST00000343776 | chr1 | 227864880 | 227866572 | + | TSF |
| 2% | chr1 | 227842037 | 227843464 | + | ENST00000397097; ENST00000343776 | chr1 | 227864880 | 227866572 | + | TSF |
| 2% | chr6 | 43005749 | 43005597 | − | ENST00000265348; ENST00000535468 | chr6 | 43005086 | 43004995 | − | TSF |
| 2% | chr6 | 43005749 | 43005597 | − | ENST00000265348; ENST00000535468 | chr6 | 43005086 | 43004995 | − | TSF |
| 2% | chr16 | 450219 | 450294 | + | ENST00000397722; ENST00000444498; ENST00000382940; ENST00000219479; ENST00000450036 | chr16 | 452708 | 452993 | + | TSF |
| 2% | chr16 | 450219 | 450294 | + | ENST00000397722; ENST00000444498; ENST00000382940; ENST00000219479; ENST00000450036 | chr16 | 452708 | 452993 | + | TSF |
| 2% | chr16 | 450219 | 450294 | + | ENST00000397722; ENST00000444498; ENST00000382940; ENST00000219479; ENST00000450036 | chr16 | 452708 | 452993 | + | TSF |
| 2% | chr4 | 106557560 | 106557577 | + | ENST00000420470 | chr4 | 106563757 | 106563879 | + | TSF |
| 2% | chr4 | 106557560 | 106557577 | + | ENST00000420470 | chr4 | 106563763 | 106563879 | + | TSF |
| 2% | chr5 | 59481425 | 59481384 | − | ENST00000502484; ENST00000546160; ENST00000509368; ENST00000505507; ENST00000514552; ENST00000515835 | chr5 | 59443721 | 59443367 | − | TSF |
| 2% | chr19 | 52380630 | 52380535 | − | ENST00000412216; ENST00000301399; ENST00000420592; ENST00000451628; ENST00000458390 | chr19 | 52359220 | 52358662 | − | TSF |
| 2% | chr9 | 130213596 | 130213560 | − | ENST00000361436; ENST00000536368 | chr9 | 130213398 | 130213359 | − | TSF |
| 2% | chr7 | 14017105 | 14017052 | − | ENST00000430479; ENST00000399357; ENST00000405192; ENST00000405358; ENST00000403527; ENST00000405218; ENST00000443137; ENST00000443608; ENST00000421381; ENST00000431887 | chr7 | 14014711 | 14014667 | − | TSF |
| 2% | chr7 | 14017105 | 14017052 | − | ENST00000430479; ENST00000399357; ENST00000405192; ENST00000405358; ENST00000403527; ENST00000405218; ENST00000443137; ENST00000443608; ENST00000421381; ENST00000431887 | chr7 | 14014711 | 14014667 | − | TSF |
| 2% | chr7 | 14017105 | 14017052 | − | ENST00000430479; ENST00000399357; ENST00000405192; ENST00000405358; ENST00000403527; ENST00000405218; ENST00000443137; ENST00000443608; ENST00000421381; ENST00000431887 | chr7 | 14014711 | 14014667 | − | TSF |
| 1% | chr22 | 29884838 | 29886410 | + | ENST00000310624 | chr22 | 29909572 | 29909695 | + | TSF |
| 1% | chr19 | 58758112; 58758077 | 58758160 | + | ENST00000599227; ENST00000269829; ENST00000597240; ENST00000594384; ENST00000596825; ENST00000333581; ENST00000596652; ENST00000596677; ENST00000596929; ENST00000595981 | chr19 | 58785766 | 58786010 | + | TSF |
| 1% | chr19 | 58758112; 58758077 | 58758160 | + | ENST00000599227; ENST00000269829; ENST00000597240; ENST00000594384; ENST00000596825; ENST00000333581; ENST00000596652; ENST00000596677; ENST00000596929; ENST00000595981 | chr19 | 58785766 | 58786010 | + | TSF |
| 1% | chr1 | 2492063 | 2492153 | + | ENST00000426449; ENST00000434817; ENST00000435221; ENST00000451778; ENST00000409119; ENST00000355716 | chr1 | 2508457 | 2508463 | + | TSF |
| 1% | chr21 | 42720519 | 42720651 | + | ENST00000357985; ENST00000398647; ENST00000398652; ENST00000398646 | chr21 | 42720974 | 42721052 | + | TSF |
| 1% | chr21 | 42720519 | 42720651 | + | ENST00000357985; ENST00000398647; ENST00000398652; ENST00000398646 | chr21 | 42720974 | 42721052 | + | TSF |
| 1% | chr21 | 42720519 | 42720651 | + | ENST00000357985; ENST00000398647; ENST00000398652; ENST00000398646 | chr21 | 42720974 | 42721052 | + | TSF |
| 1% | chr21 | 42720519 | 42720651 | + | ENST00000357985; ENST00000398647; ENST00000398652; ENST00000398646 | chr21 | 42720974 | 42721052 | + | TSF |
| 1% | chr15 | 75105196 | 75105370 | + | ENST00000309664; ENST00000379709 | chr15 | 75108232 | 75108281 | + | TSF |
| 1% | chr11 | 49186324 | 49186257 | − | ENST00000256999; ENST00000356696; ENST00000343844; ENST00000340334; ENST00000533034 | chr11 | 49184464 | 49182294 | − | TSF |
| 1% | chr11 | 49186324 | 49186257 | − | ENST00000256999; ENST00000356696; ENST00000343844; ENST00000340334; ENST00000533034 | chr11 | 49184464 | 49182294 | − | TSF |
| 1% | chr11 | 49186324 | 49186257 | − | ENST00000256999; ENST00000356696; ENST00000343844; ENST00000340334; ENST00000533034 | chr11 | 49184464 | 49182294 | − | TSF |
| 1% | chr13 | 95686993 | 95686859 | − | ENST00000412704; ENST00000376887 | chr13 | 95659875 | 95659840 | − | TSF |
| 1% | chr13 | 95686993 | 95686859 | − | ENST00000412704; ENST00000376887 | chr13 | 95659875 | 95659840 | − | TSF |
| 1% | chr11 | 61290746 | 61290547 | − | ENST00000263846; ENST00000540677; ENST00000539008; ENST00000542836; ENST00000542670; ENST00000535826 | chr11 | 61289967 | 61289967 | − | TSF |
| 1% | chr11 | 61290746 | 61290547 | − | ENST00000263846; ENST00000540677; ENST00000539008; ENST00000542836; | chr11 | 61289967 | 61289967 | − | TSF |

TABLE 49-continued

Transcript fusion for Prostate Adenocarcinoma (PRAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr11 | 61290746 | 61290547 | − | ENST00000542670; ENST00000535826 ENST00000263846; ENST00000540677; ENST00000539008; ENST00000542836 | chr11 | 61289967 | 61289967 | − | TSF |
| 1% | chr11 | 61290746 | 61290547 | − | ENST00000542670; ENST00000535826 ENST00000263846; ENST00000540677; ENST00000539008; ENST00000542836 | chr11 | 61289967 | 61289967 | − | TSF |
| 1% | chr11 | 61290746 | 61290547 | − | ENST00000542670; ENST00000535826 ENST00000263846; ENST00000540677; ENST00000539008; ENST00000542836 | chr11 | 61289967 | 61289967 | − | TSF |
| 1% | chr11 | 61290746 | 61290547 | − | ENST00000542670; ENST00000535826 ENST00000263846; ENST00000540677; ENST00000539008; ENST00000542836 | chr11 | 61289967 | 61289967 | − | TSF |
| 1% | chr6 | 46673038 | 46672890 | − | ENST00000274793; ENST00000537365 | chr6 | 46667004 | 46666386 | − | TSF |
| 1% | chr6 | 144612965 | 144613043 | + | ENST00000433557; ENST00000367545 | chr6 | 144629111 | 144629489 | + | TSF |
| 1% | chr12 | 93873164 | 93873248 | + | ENST00000549982; ENST00000361630; ENST00000552217; ENST00000393128; ENST00000547098; ENST00000549561; ENST00000548545 | chr12 | 93876129 | 93876286 | + | TSF |
| 1% | chr12 | 93873164 | 93873248 | + | ENST00000549982; ENST00000361630; ENST00000552217; ENST00000393128; ENST00000547098; ENST00000549561; ENST00000548545 | chr12 | 93876129 | 93876286 | + | TSF |
| 1% | chr22 | 40760884; 40761043 | 40761060 | + | ENST00000216194; ENST00000454266; ENST00000498234 | chr22 | 40796700 | 40796751 | + | TSF |
| 1% | chr22 | 40760884; 40761043 | 40761060 | + | ENST00000216194; ENST00000454266; ENST00000498234 | chr22 | 40796700 | 40796751 | + | TSF |
| 1% | chr22 | 40760884; 40761043 | 40761060 | + | ENST00000216194; ENST00000454266; ENST00000498234 | chr22 | 40796700 | 40796751 | + | TSF |
| 1% | chr22 | 48885405 | 48885516 | + | ENST00000402357; ENST00000336769 | chr22 | 48915770 | 48916108 | + | TSF |
| 1% | chr2 | 131128772 | 131128860 | + | ENST00000175756; ENST00000347849; ENST00000409022 | chr2 | 131129120 | 131129406 | + | TSF |
| 1% | chr2 | 131128772 | 131128860 | + | ENST00000175756; ENST00000347849; ENST00000409022 | chr2 | 131129120 | 131129406 | + | TSF |
| 1% | chr2 | 131128772 | 131128860 | + | ENST00000175756; ENST00000347849; ENST00000409022 | chr2 | 131129120 | 131129406 | + | TSF |
| 1% | chr7 | 81964567 | 81964451 | − | ENST00000356860; ENST00000356253; ENST00000423588 | chr7 | 81929467 | 81929190 | − | TSF |
| 1% | chr15 | 55516210 | 55516087 | − | ENST00000396307; ENST00000336787; ENST00000564609; ENST00000569493; ENST00000566877 | chr15 | 55512776 | 55512769 | − | TSF |
| 1% | chr11 | 57256462 | 57256389 | − | ENST00000278426; ENST00000528450; ENST00000525764 | chr11 | 57255085 | 57254993 | − | TSF |
| 1% | chr11 | 57256462 | 57256389 | − | ENST00000278426; ENST00000528450; ENST00000525764 | chr11 | 57255085 | 57254993 | − | TSF |
| 1% | chr7 | 44294206 | 44294141 | − | ENST00000350811; ENST00000457475; ENST00000395749; ENST00000440254; ENST00000358707; ENST00000353625; ENST00000353185; ENST00000258682; ENST00000346990; ENST00000347193; ENST00000395747; ENST00000415369; ENST00000424197; ENST00000421607 | chr7 | 44293110 | 44292801 | − | TSF |
| 1% | chr7 | 44294206 | 44294141 | − | ENST00000350811; ENST00000457475; ENST00000395749; ENST00000440254; ENST00000358707; ENST00000353625; ENST00000353185; ENST00000258682; ENST00000346990; ENST00000347193; ENST00000395747; ENST00000415369; ENST00000424197; ENST00000421607 | chr7 | 44293110 | 44292801 | − | TSF |
| 1% | chr6 | 35547998 | 35547813 | − | ENST00000539068; ENST00000536438; ENST00000357266; ENST00000540787 | chr6 | 35531291 | 35531039 | − | TSF |
| 1% | chr6 | 35547998 | 35547813 | − | ENST00000539068; ENST00000536438; ENST00000357266; ENST00000540787 | chr6 | 35531291 | 31035539 | − | TSF |
| 1% | chr1 | 2340297 | 2339891 | − | ENST00000288774; ENST00000447513; ENST00000507596 | chr1 | 2339399 | 2339300 | − | TSF |
| 1% | chr1 | 40779939 | 40779877 | − | ENST00000372748; ENST00000417105 | chr1 | 40778630 | 40778617 | − | TSF |
| 1% | chr1 | 40779939 | 40779877 | − | ENST00000372748; ENST00000417105 | chr1 | 40778630 | 40778617 | − | TSF |
| 1% | chr11 | 49229961 | 49229844 | − | ENST00000256999; ENST00000356696; ENST00000525826; ENST00000533510; ENST00000529648 | chr11 | 49228751 | 49228576 | − | TSF |
| 1% | chr2 | 193044420 | 193044394 | − | ENST00000392314; ENST00000272771; ENST00000409056 | chr2 | 192957935 | 192957907 | − | TSF |
| 1% | chr5 | 79442057 | 79441913 | − | ENST00000507668; ENST00000509193; ENST00000512972; ENST00000512721 | chr5 | 79407525 | 79407007 | − | TSF |
| 1% | chr5 | 79442057 | 79441913 | − | ENST00000507668; ENST00000509193; ENST00000512972; ENST00000512721 | chr5 | 79407525 | 79407007 | − | TSF |

TABLE 49-continued

Transcript fusion for Prostate Adenocarcinoma (PRAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|

TABLE 50

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|----|----|----|----|----|----|----|----|-----|-----|
| 79% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 79% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 79% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 79% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 79% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 79% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 79% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 79% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 79% | chr5 | 34010561 | 34010276 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 70% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 70% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 70% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 70% | chr5 | 34006954 | 34006922 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TAF |
| 70% | chr5 | 34006954 | 34006922 | − | chr5 | 34006004 | 34005861 | − | ENST00000335606; ENST00000382072; | TAF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 70% | chr5 | 34006954 | 34006922 | – | chr5 | 34006004 | 34005861 | – | ENST00000382079; ENST00000506639; ENST00000382085; ENST00000502637; ENST00000441713; ENST00000426255; ENST00000512079; ENST00000382068 ENST00000335606; ENST00000382072; ENST00000382079; ENST00000506639; ENST00000382085; ENST00000502637; ENST00000441713; ENST00000426255; ENST00000512079; ENST00000382068 | TAF |
| 70% | chr5 | 34006954 | 34006922 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TAF |
| 70% | chr5 | 34006954 | 34006922 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TAF |
| 70% | chr5 | 34006954 | 34006922 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TAF |
| 69% | chr7 | 38312003 | 383111882 | – | chr7 | 38305279 | 38304950 | – | ENST00000443402 | TAF |
| 42% | chr7 | 38312003 | 38311882 | – | chr7 | 38289173 | 38288844 | – | ENST00000436911 | TAF |
| 40% | chr8 | 39710096 | 39709866 | – | chr8 | 39694731 | 39694655 | – | ENST00000347580; ENST00000379853; ENST00000265708; ENST00000521880 | TAF |
| 40% | chr8 | 39710096 | 39709866 | – | chr8 | 39694731 | 39694655 | – | ENST00000347580; ENST00000379853; ENST00000265708; ENST00000521880 | TAF |
| 40% | chr8 | 39710096 | 39709866 | – | chr8 | 39694731 | 39694655 | – | ENST00000347580; ENST00000379853; ENST00000265708; ENST00000521880 | TAF |
| 40% | chr8 | 39710096 | 39709866 | – | chr8 | 39694731 | 39694655 | – | ENST00000347580; ENST00000379853; ENST00000265708; ENST00000521880 | TAF |
| 39% | chr11 | 49228772 | 49228638 | – | chr11 | 49227724 | 49227619 | – | ENST00000256999; ENST00000356696; ENST00000525826; ENST00000340334; ENST00000533034 | TAF |
| 39% | chr11 | 49228772 | 49228638 | – | chr11 | 49227724 | 49227619 | – | ENST00000256999; ENST00000356696; ENST00000525826; ENST00000340334; ENST00000533034 | TAF |
| 39% | chr11 | 49228772 | 49228638 | – | chr11 | 49227724 | 49227619 | – | ENST00000256999; ENST00000356696; ENST00000525826; ENST00000340334; ENST00000533034 | TAF |
| 28% | chr10 | 135190204 | 135190164 | – | chr10 | 135184261 | 135184064 | – | ENST00000368547 | TAF |
| 26% | chr10 | 100147690 | 100147622 | – | chr10 | 100147064 | 100146958 | – | ENST00000370575 | TAF |
| 25% | chr1 | 40748073 | 40748159 | + | chr1 | 40751597 | 40751701 | + | ENST00000372759 | TAF |
| 23% | chr5 | 34006954 | 34006915 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 23% | chr5 | 34006954 | 34006915 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 23% | chr5 | 34006954 | 34006915 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 23% | chr5 | 34006954 | 34006915 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 23% | chr5 | 34006954 | 34006915 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 23% | chr5 | 34006954 | 34006915 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 23% | chr5 | 34006954 | 34006915 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 23% | chr5 | 34006954 | 34006915 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 23% | chr5 | 34006954 | 34006915 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 22% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 22% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 22% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TFA |
| 22% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 22% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 22% | chr10 | 120902016 | 120901765 | – | chr10 | 120900831 | 120900754 | – | ENST00000355697; ENST00000330036 | TAF |
| 21% | chr7 | 89911392 | 89911485 | + | chr7 | 89912206 | 89912370 | + | ENST00000316089; ENST00000389297; ENST00000497910; ENST00000457170; ENST00000449577 | TAF |
| 21% | chr7 | 89911392 | 89911485 | + | chr7 | 89912206 | 89912370 | + | ENST00000316089; ENST00000389297; ENST00000497910; ENST00000457170; ENST00000449577 | TAF |
| 21% | chr7 | 89911392 | 89911485 | + | chr7 | 89912206 | 89912370 | + | ENST00000316089; ENST00000389297; ENST00000497910; ENST00000457170; ENST00000449577 | TAF |
| 19% | chr1 | 40781678 | 40781517 | – | chr1 | 40781336 | 40781262 | – | ENST00000372748; ENST00000417105; ENST00000372736 | TAF |
| 19% | chr1 | 40781678 | 40781517 | – | chr1 | 40781336 | 40781262 | – | ENST00000372748; ENST00000417105; ENST00000372736 | TAF |
| 19% | chr1 | 40781678 | 40781517 | – | chr1 | 40781336 | 40781262 | – | ENST00000372748; ENST00000417105; ENST00000372736 | TAF |
| 18% | chr5 | 34010561 | 34010259 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 18% | chr5 | 34010561 | 34010259 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 18% | chr5 | 34010561 | 34010259 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 18% | chr5 | 34010561 | 34010259 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 18% | chr5 | 34010561 | 34010259 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 18% | chr5 | 34010561 | 34010259 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 18% | chr5 | 34010561 | 34010259 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 18% | chr5 | 34010561 | 34010259 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 18% | chr5 | 34010561 | 34010259 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 16% | chr11 | 118401084 | 118401227 | + | chr11 | 118401369 | 118401631 | + | ENST00000302783; ENST00000539546 | TAF |
| 16% | chr4 | 147298390 | 147297909 | – | chr4 | 147247148 | 147247113 | – | ENST00000432059; ENST00000335472; ENST00000507030; ENST00000394062 | TAF |
| 16% | chr4 | 147298390 | 147297909 | – | chr4 | 147247148 | 147247113 | – | ENST00000432059; ENST00000335472; ENST00000507030; ENST00000394062 | TAF |
| 16% | chr6 | 34509454 | 345 09380 | – | chr6 | 34508958 | 34508761 | – | ENST00000374037; ENST00000544425 | TAF |
| 16% | chr6 | 34509454 | 34509380 | – | chr6 | 34508958 | 34508761 | – | ENST00000374037; ENST00000544425 | TAF |
| 16% | chr5 | 34010561 | 34010327 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 16% | chr5 | 34010561 | 34010327 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 16% | chr5 | 34010561 | 34010327 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 16% | chr5 | 34010561 | 34010327 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 16% | chr5 | 34010561 | 34010327 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 16% | chr5 | 34010561 | 34010327 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 16% | chr5 | 34010561 | 34010327 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 16% | chr5 | 34010561 | 34010327 | – | chr5 | 34006004 | 34005861 | – | ENST00000335606; ENST00000382072; ENST00000382079; ENST00000506639; ENST00000382085; ENST00000502637; ENST00000441713; ENST00000426255; ENST00000512079; ENST00000382068 | TSF |
| 15% | chr22 | 36007706 | 36007617 | – | chr22 | 36007153 | 36006931; 36007017 | – | ENST00000397326; ENST00000397328; ENST00000359787; ENST00000406324; ENST00000443033; ENST00000451685; ENST00000447607; ENST00000419229 | TAF |
| 15% | chr22 | 36007706 | 36007617 | – | chr22 | 36007153 | 36007017 36006931; | – | ENST00000397326; ENST00000397328; ENST00000359787; ENST00000406324; ENST00000443033; ENST00000451685; ENST00000447607; ENST00000419229 | TAF |
| 15% | chr22 | 36007706 | 36007617 | – | chr22 | 36007153 | 36007017 | – | ENST00000397326; ENST00000397328; | TAF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| | | | | | | | 36006931; | ENST00000359787; ENST00000406324; ENST00000443033; ENST00000451685; ENST00000447607; ENST00000419229 | |
| 15% | chr22 | 36007706 | 36007617 | − | chr22 | 36007153 | 36007017; 36006931; | − | ENST00000397326; ENST00000397328; ENST00000359787; ENST00000406324; ENST00000443033; ENST00000451685; ENST00000447607; ENST00000419229 | TAF |
| 15% | chr4 | 95574306 | 95574522 | + | chr4 | 95575611 | 95575791 | + | ENST00000437932; ENST00000317968; ENST00000503974; ENST00000542407; ENST00000514743; ENST00000506632 | TAF |
| 15% | chr4 | 95574306 | 95574522 | + | chr4 | 95575611 | 95575791 | + | ENST00000437932; ENST00000317968; ENST00000503974; ENST00000542407; ENST00000514743; ENST00000506632 | TAF |
| 15% | chr4 | 95574306 | 95574522 | + | chr4 | 95575611 | 95575791 | + | ENST00000437932; ENST00000317968; ENST00000503974; ENST00000542407; ENST00000514743; ENST00000506632 | TAF |
| 15% | chr9 | 100831854 | 100832020 | + | chr9 | 100839200 | 100839299 | + | ENST00000210444 | TAF |
| 14% | chr11 | 76630955 | 76631299 | + | chr11 | 76637601 | 76637711; 76637616 | + | ENST00000532485; ENST00000525194; ENST00000525861; ENST00000531461; ENST00000531352; ENST00000278544 | TAF |
| 14% | chr11 | 76630955 | 76631299 | + | chr11 | 76637601 | 76637711; 76637616 | + | ENST00000532485; ENST00000525194; ENST00000525861; ENST00000531461; ENST00000531352; ENST00000278544 | TAF |
| 14% | chr11 | 76630955 | 76631299 | + | chr11 | 76637601 | 76637711; 76637616 | + | ENST00000532485; ENST00000525194; ENST00000525861; ENST00000531461; ENST00000531352; ENST00000278544 | TAF |
| 14% | chr11 | 76630955 | 76631299 | + | chr11 | 76637601 | 76637711; 76637616 | + | ENST00000532485; ENST00000525194; ENST00000525861; ENST00000531461; ENST00000531352; ENST00000278544 | TAF |
| 14% | chr11 | 76630955 | 76631299 | + | chr11 | 76637601 | 76637711; 76637616 | + | ENST00000532485; ENST00000525194; ENST00000525861; ENST00000531461; ENST00000531352; ENST00000278544 | TAF |
| 14% | chr14 | 52930122 | 52929530 | − | chr14 | 52923892 | 52923808 | − | ENST00000281741 | TAF |
| 14% | chr14 | 24631729 | 24631779 | + | chr14 | 24632175 | 24632358; 24632191 | + | ENST00000396864; ENST00000561342; ENST00000559284; ENST00000560275; ENST00000560852 | TAF |
| 14% | chr14 | 24631729 | 24631779 | + | chr14 | 24632175 | 24632358; 24632191 | + | ENST00000396864; ENST00000561342; ENST00000559284; ENST00000560275; ENST00000560852 | TAF |
| 14% | chr14 | 24631729 | 24631779 | + | chr14 | 24632175 | 24632358; 24632191 | + | ENST00000396864; ENST00000561342; ENST00000559284; ENST00000560275; ENST00000560852 | TAF |
| 14% | chr14 | 24631729 | 24631779 | + | chr14 | 24632175 | 24632358; 24632191 | + | ENST00000396864; ENST00000561342; ENST00000559284; ENST00000560275; ENST00000560852 | TAF |
| 14% | chr5 | 34007349 | 34007048 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 14% | chr5 | 34007349 | 34007048 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 14% | chr5 | 34007349 | 34007048 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 14% | chr5 | 34007349 | 34007048 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 14% | chr5 | 34007349 | 34007048 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 14% | chr5 | 34007349 | 34007048 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 14% | chr5 | 34007349 | 34007048 | − | chr5 | 34006004 | 34005861 | − | ENST00000335606; ENST00000382072; | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 14% | chr5 | 34007349 | 34007048 | − | chr5 | 34006004 | 34005861 | − | ENST00000382079; ENST00000506639; ENST00000382085; ENST00000502637; ENST00000441713; ENST00000426255; ENST00000512079; ENST00000382068 ENST00000335606; ENST00000382072; ENST00000382079; ENST00000506639; ENST00000382085; ENST00000502637; ENST00000441713; ENST00000426255; ENST00000512079; ENST00000382068 | TSF |
| 14% | chr5 | 34007349 | 34007048 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 13% | chr21 | 44307009 | 44307069 | + | chr21 | 44317037 | 44317157 | + | ENST00000354250; ENST00000340344 | TAF |
| 13% | chr21 | 44307009 | 44307069 | + | chr21 | 44317037 | 44317157 | + | ENST00000354250; ENST00000340344 | TAF |
| 12% | chr5 | 70927667 | 70927725 | + | chr5 | 70927948 | 70928012 | + | ENST00000512218; ENST00000340941; ENST00000509358; ENST00000323375; ENST00000509539 | TAF |
| 12% | chr5 | 70927667 | 70927725 | + | chr5 | 70927948 | 70928012 | + | ENST00000512218; ENST00000340941; ENST00000509358; ENST00000323375; ENST00000509539 | TAF |
| 12% | chr5 | 70927667 | 70927725 | + | chr5 | 70927948 | 70928012 | + | ENST00000512218; ENST00000340941; ENST00000509358; ENST00000323375; ENST00000509539 | TAF |
| 12% | chr5 | 70927667 | 70927725 | + | chr5 | 70927948 | 70928012 | + | ENST00000512218; ENST00000340941; ENST00000509358; ENST00000323375; ENST00000509539 | TAF |
| 12% | chr6 | 111205094 | 111205591 | + | chr6 | 111208708 | 111208794 | + | ENST00000368885 | TAF |
| 12% | chr21 | 42882831 | 42882786 | − | chr21 | 42870116 | 42870046 | − | ENST00000398585 | TAF |
| 12% | chr13 | 95757645 | 95757300 | − | chr13 | 95748433 | 95748389 | − | ENST00000536256; ENST00000431522 | TSF |
| 12% | chr3 | 131480308 | 131308085 | − | chr3 | 131306426 | 131306328 | − | ENST00000512055; ENST00000429747; ENST00000512332; ENST00000511604; ENST00000502818 | TSF |
| 12% | chr13 | 24331567 | 24331229 | − | chr13 | 24330757 | 24330684 | − | ENST00000433710; ENST00000382172 | TSF |
| 12% | chr13 | 24331567 | 24331229 | − | chr13 | 24330757 | 24330684 | − | ENST00000433710; ENST00000382172 | TSF |
| 11% | chr19 | 51340308 | 51340387 | + | chr19 | 51359496 | 51359655 | + | ENST00000326003; ENST00000422986; ENST00000597483; ENST00000593997; ENST00000595392; ENST00000595952; ENST00000360617; ENST00000598145 | TAF |
| 11% | chr19 | 51340308 | 51340387 | + | chr19 | 51359496 | 51359655 | + | ENST00000326003; ENST00000422986; ENST00000597483; ENST00000593997; ENST00000595392; ENST00000595952; ENST00000360617; ENST00000598145 | TAF |
| 11% | chr19 | 51340308 | 51340387 | + | chr19 | 51359496 | 51359655 | + | ENST00000326003; ENST00000422986; ENST00000597483; ENST00000593997; ENST00000595392; ENST00000595952; ENST00000360617; ENST00000598145 | TAF |
| 11% | chr19 | 51340308 | 51340387 | + | chr19 | 51359496 | 51359655 | + | ENST00000326003; ENST00000422986; ENST00000597483; ENST00000593997; ENST00000595392; ENST00000595952; ENST00000360617; ENST00000598145 | TAF |
| 11% | chr19 | 51340308 | 51340387 | + | chr19 | 51359496 | 51359655 | + | ENST00000326003; ENST00000422986; ENST00000597483; ENST00000593997; ENST00000595392; ENST00000595952; ENST00000360617; ENST00000598145 | TAF |
| 11% | chr19 | 51340308 | 51340387 | + | chr19 | 51359496 | 51359655 | + | ENST00000326003; ENST00000422986; ENST00000597483; ENST00000593997; ENST00000595392; ENST00000595952; ENST00000360617; ENST00000598145 | TAF |
| 11% | chr19 | 51340308 | 51340387 | + | chr19 | 51359496 | 51359655 | + | ENST00000326003; ENST00000422986; ENST00000597483; ENST00000593997; ENST00000595392; ENST00000595952; ENST00000360617; ENST00000598145 | TAF |
| 11% | chr19 | 51340308 | 51340387 | + | chr19 | 51359496 | 51359655 | + | ENST00000326003; ENST00000422986; ENST00000597483; ENST00000593997; ENST00000595392; ENST00000595952; ENST00000360617; ENST00000598145 | TAF |
| 11% | chr5 | 54722535 | 54722306 | − | chr5 | 54721867 | 54721691 | − | ENST00000264775; ENST00000307259 | TAF |
| 11% | chr8 | 82194688 | 82194727 | + | chr8 | 82195601 | 82195773 | + | ENST00000297258 | TAF |
| 11% | chr21 | 42884787 | 42883790 | − | chr21 | 42861520 | 42861434 | − | ENST00000332149; ENST00000398585; ENST00000458356; ENST00000454499; ENST00000424093 | TSF |
| 11% | chr21 | 42884787 | 42883790 | − | chr21 | 42861520 | 42861434 | − | ENST00000332149; ENST00000398585; ENST00000458356; ENST00000454499; ENST00000424093 | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 11% | chr21 | 42884787 | 42883790 | – | chr21 | 42861520 | 42861434 | – | ENST00000332149; ENST00000398585; ENST00000458356; ENST00000454499; ENST00000424093 | TSF |
| 11% | chr21 | 42884787 | 42883790 | – | chr21 | 42866505 | 42866283 | – | ENST00000332149; ENST00000398585; ENST00000458356; ENST00000454499; ENST00000424093; ENST00000455813 | TSF |
| 11% | chr21 | 42884787 | 42883790 | – | chr21 | 42866505 | 42866283 | – | ENST00000332149; ENST00000398585; ENST00000458356; ENST00000454499; ENST00000424093; ENST00000455813 | TSF |
| 11% | chr21 | 42884787 | 42883790 | – | chr21 | 42866505 | 42866283 | – | ENST00000332149; ENST00000398585; ENST00000458356; ENST00000454499; ENST00000424093; ENST00000455813 | TSF |
| 11% | chr21 | 42884787 | 42883790 | – | chr21 | 42866505 | 42866283 | – | ENST00000332149; ENST00000398585; ENST00000458356; ENST00000454499; ENST00000424093; ENST00000455813 | TSF |
| 11% | chr2 | 192947147 | 192946999 | – | chr2 | 192922501 | 192922405 | – | ENST00000392314; ENST00000272771 | TSF |
| 11% | chr2 | 192947147 | 192946999 | – | chr2 | 192922501 | 192922405 | – | ENST00000392314; ENST00000272771 | TSF |
| 10% | chr17 | 79057181 | 79057207 | + | chr17 | 79058632 | 79058693 | + | ENST00000575750; ENST00000575989; ENST00000321280; ENST00000572329; ENST00000428708; ENST00000575712; ENST00000575245; ENST00000435091; ENST00000321300; ENST00000571530; ENST00000572918; ENST00000575958; ENST00000573659; ENST00000572073; ENST00000573677; ENST00000574804 | TAF |
| 10% | chr17 | 79057181 | 79057207 | + | chr17 | 79058632 | 79058693 | + | ENST00000575750; ENST00000575989; ENST00000321280; ENST00000572329; ENST00000428708; ENST00000575712; ENST00000575245; ENST00000435091; ENST00000321300; ENST00000571530; ENST00000572918; ENST00000575958; ENST00000573659; ENST00000572073; ENST00000573677; ENST00000574804 | TAF |
| 10% | chr17 | 79057181 | 79057207 | + | chr17 | 79058632 | 79058693 | + | ENST00000575750; ENST00000575989; ENST00000321280; ENST00000572329; ENST00000428708; ENST00000575712; ENST00000575245; ENST00000435091; ENST00000321300; ENST00000571530; ENST00000572918; ENST00000575958; ENST00000573659; ENST00000572073; ENST00000573677; ENST00000574804 | TAF |
| 10% | chr17 | 79057181 | 79057207 | + | chr17 | 79058632 | 79058693 | + | ENST00000575750; ENST00000575989; ENST00000321280; ENST00000572329; ENST00000428708; ENST00000575712; ENST00000575245; ENST00000435091; ENST00000321300; ENST00000571530; ENST00000572918; ENST00000575958; ENST00000573659; ENST00000572073; ENST00000573677; ENST00000574804 | TAF |
| 10% | chr17 | 79057181 | 79057207 | + | chr17 | 79058632 | 79058693 | + | ENST00000575750; ENST00000575989; ENST00000321280; ENST00000572329; ENST00000428708; ENST00000575712; ENST00000575245; ENST00000435091; ENST00000321300; ENST00000571530; ENST00000572918; ENST00000575958; ENST00000573659; ENST00000572073; ENST00000573677; ENST00000574804 | TAF |
| 10% | chr17 | 79057181 | 79057207 | + | chr17 | 79058632 | 79058693 | + | ENST00000575750; ENST00000575989; ENST00000321280; ENST00000572329; ENST00000428708; ENST00000575712; ENST00000575245; ENST00000435091; ENST00000321300; ENST00000571530; ENST00000572918; ENST00000575958; ENST00000573659; ENST00000572073; ENST00000573677; ENST00000574804 | TAF |
| 10% | chr17 | 79057181 | 79057207 | + | chr17 | 79058632 | 79058693 | + | ENST00000575750; ENST00000575989; ENST00000321280; ENST00000572329; ENST00000428708; ENST00000575712; ENST00000575245; ENST00000435091; ENST00000321300; ENST00000571530; ENST00000572918; ENST00000575958; ENST00000573659; ENST00000572073; ENST00000573677; ENST00000574804 | TAF |
| 10% | chr17 | 79057181 | 79057207 | + | chr17 | 79058632 | 79058693 | + | ENST00000575750; ENST00000575989; ENST00000321280; ENST00000572329; ENST00000428708; ENST00000575712; | TAF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 10% | chr17 | 79057181 | 79057207 | + | chr17 | 79058632 | 79058693 | + | ENST00000575245; ENST00000435091; ENST00000321300; ENST00000571530; ENST00000572918; ENST00000575958; ENST00000573659; ENST00000572073; ENST00000573677; ENST00000574804 ENST00000575750; ENST00000575989; ENST00000321280; ENST00000572329; ENST00000428708; ENST00000575712; | TAF |
| 10% | chr17 | 79057181 | 79057207 | + | chr17 | 79058632 | 79058693 | + | ENST00000575245; ENST00000435091; ENST00000321300; ENST00000571530; ENST00000572918; ENST00000575958; ENST00000573659; ENST00000572073; ENST00000573677; ENST00000574804 ENST00000575750; ENST00000575989; ENST00000321280; ENST00000572329; ENST00000428708; ENST00000575712; | TAF |
| 10% | chr17 | 79057181 | 79057207 | + | chr17 | 79058632 | 79058693 | + | ENST00000575245; ENST00000435091; ENST00000321300; ENST00000571530; ENST00000572918; ENST00000575958; ENST00000573659; ENST00000572073; ENST00000573677; ENST00000574804 ENST00000575750; ENST00000575989; ENST00000321280; ENST00000572329; ENST00000428708; ENST00000575712; | TAF |
| 10% | chr17 | 79057181 | 79057207 | + | chr17 | 79058632 | 79058693 | + | ENST00000575245; ENST00000435091; ENST00000321300; ENST00000571530; ENST00000572918; ENST00000575958; ENST00000573659; ENST00000572073; ENST00000573677; ENST00000574804 ENST00000575750; ENST00000575989; ENST00000321280; ENST00000572329; ENST00000428708; ENST00000575712; | TAF |
| 10% | chr17 | 79057181 | 79057207 | + | chr17 | 79058632 | 79058693 | + | ENST00000575245; ENST00000435091; ENST00000321300; ENST00000571530; ENST00000572918; ENST00000575958; ENST00000573659; ENST00000572073; ENST00000573677; ENST00000574804 ENST00000575750; ENST00000575989; ENST00000321280; ENST00000572329; ENST00000428708; ENST00000575712; | TAF |
| 10% | chr17 | 79057181 | 79057207 | + | chr17 | 79058632 | 79058693 | + | ENST00000575245; ENST00000435091; ENST00000321300; ENST00000571530; ENST00000572918; ENST00000575958; ENST00000573659; ENST00000572073; ENST00000573677; ENST00000574804 | TAF |
| 10% | chr12 | 64687157 | 64687061 | − | chr12 | 64679840 | 64679734 | − | ENST00000543942; ENST00000333722 | TAF |
| 8% | chr13 | 95757645 | 57395700 | − | chr13 | 95735544 | 95735394 | − | ENST00000412704; ENST00000376887 | TSF |
| 8% | chr19 | 51410961 | 51410894 | − | chr19 | 51410342 | 51410190; 51410338 | − | ENST00000324041; ENST00000431178 | TSF |
| 8% | chr19 | 51410961 | 51410894 | − | chr19 | 51410342 | 51410190; 51410338 | − | ENST00000324041; ENST00000431178 | TSF |
| 7% | chrX | 123618682 | 123617816 | − | chrX | 123615814 | 123615582 | − | ENST00000371130; ENST00000422452 | TSF |
| 6% | chr20 | 45337040 | 45337192 | + | chr20 | 45353680 | 45354963 | + | ENST00000359271 | TSF |
| 6% | chr19 | 51360137 | 51360236 | + | chr19 | 51361285 | 51361342; 51361571; 51361430; 51361589 | + | ENST00000601503; ENST00000326003; ENST00000422986; ENST00000597286; ENST00000593997; ENST00000595392; ENST00000360617; ENST00000598145 | TSF |
| 6% | chr19 | 51360137 | 51360236 | + | chr19 | 51361285 | 51361571; 51361342; 51361430; 51361589 | + | ENST00000601503; ENST00000326003; ENST00000422986; ENST00000597286; ENST00000593997; ENST00000595392; ENST00000360617; ENST00000598145 | TSF |
| 6% | chr19 | 51360137 | 51360236 | + | chr19 | 51361285 | 51361571; 51361342; 51361430; 51361589 | + | ENST00000601503; ENST00000326003; ENST00000422986; ENST00000597286; ENST00000593997; ENST00000595392; ENST00000360617; ENST00000598145 | TSF |
| 6% | chr19 | 51360137 | 51360236 | + | chr19 | 51361285 | 51361571; 51361342; 51361430; | + | ENST00000601503; ENST00000326003; ENST00000422986; ENST00000597286; ENST00000593997; ENST00000595392; | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 6% | chr19 | 51360137 | 51360236 | + | chr19 | 51361285 | 51361589 51361342; 51361571; 51361430; 51361589 | + | ENST00000360617; ENST00000598145 ENST00000601503; ENST00000326003; ENST00000422986; ENST00000597286; ENST00000593997; ENST00000595392 | TSF |
| 6% | chr19 | 51360137 | 51360236 | + | chr19 | 51361285 | 51361571; 51361342; 51361430; 51361589 | + | ENST00000360617; ENST00000598145 ENST00000601503; ENST00000326003; ENST00000422986; ENST00000597286; ENST00000593997; ENST00000595392 | TSF |
| 6% | chr19 | 51360137 | 51360236 | + | chr19 | 51361285 | 51361342; 51361571; 51361430; 51361589 | + | ENST00000360617; ENST00000598145 ENST00000601503; ENST00000326003; ENST00000422986; ENST00000597286; ENST00000593997; ENST00000595392 | TSF |
| 6% | chr19 | 51360137 | 51360236 | + | chr19 | 51361285 | 51361342; 51361571; 51361430; 51361589 | + | ENST00000360617; ENST00000598145 ENST00000601503; ENST00000326003; ENST00000422986; ENST00000597286; ENST00000593997; ENST00000595392 | TSF |
| 6% | chr16 | 28932484 | 28932384 | − | chr16 | 28931264 | 28931107 | − | ENST00000357573; ENST00000358201; ENST00000544477; ENST00000568703; ENST00000567483 | TSF |
| 6% | chr16 | 28932484 | 28932384 | − | chr16 | 28931264 | 28931107 | − | ENST00000357573; ENST00000358201; ENST00000544477; ENST00000568703; ENST00000567483 | TSF |
| 6% | chr16 | 28932484 | 28932384 | − | chr16 | 28931264 | 28931107 | − | ENST00000357573; ENST00000358201; ENST00000544477; ENST00000568703; ENST00000567483 | TSF |
| 6% | chr16 | 28932484 | 28932384 | − | chr16 | 28931264 | 28931107 | − | ENST00000357573; ENST00000358201; ENST00000544477; ENST00000568703; ENST00000567483 | TSF |
| 5% | chr2 | 207633144 | 207633327 | + | chr2 | 207634815 | 207634918 | + | ENST00000236980; ENST00000402774; ENST00000403094 | TSF |
| 5% | chr21 | 42884787 | 42883790 | − | chr21 | 42852529 | 42852403 | − | ENST00000332149; ENST00000398585; ENST00000458356; ENST00000454499; ENST00000424093 | TSF |
| 5% | chr21 | 42884787 | 42883790 | − | chr21 | 42852529 | 42852403 | − | ENST00000332149; ENST00000398585; ENST00000458356; ENST00000454499; ENST00000424093 | TSF |
| 5% | chr21 | 42884787 | 42883790 | − | chr21 | 42852529 | 42852403 | − | ENST00000332149; ENST00000398585; ENST00000458356; ENST00000454499; ENST00000424093 | TSF |
| 5% | chr5 | 120012572 | 120012614 | + | chr5 | 120021649 | 120022404 | + | ENST00000407149; ENST00000379551 | TSF |
| 4% | chr13 | 95887439 | 95887439 | − | chr13 | 95887088 | 95886864 | − | ENST00000412704; ENST00000376887; ENST00000431522 | TSF |
| 4% | chr13 | 95887439 | 95887439 | − | chr13 | 95887088 | 95886864 | − | ENST00000412704; ENST00000376887; ENST00000431522 | TSF |
| 4% | chr13 | 95887439 | 95887439 | − | chr13 | 95887088 | 95886864 | − | ENST00000412704; ENST00000376887; ENST00000431522 | TSF |
| 4% | chr5 | 70911418 | 70912053 | + | chr5 | 70922467 | 70922580 | + | ENST00000340941; ENST00000509358 | TSF |
| 4% | chr5 | 70911418 | 12070953 | + | chr5 | 70922467 | 70922580 | + | ENST00000340941; ENST00000509358 | TSF |
| 4% | chr1 | 222838237 | 222838312 | + | chr1 | 222838651 | 222838961 | + | ENST00000344922; ENST00000344441; ENST00000340535 | TSF |
| 4% | chr21 | 44193636 | 44193728 | + | chr21 | 44195390 | 44195403 | + | ENST00000335512; ENST00000539837; ENST00000291539; ENST00000328862; ENST00000335440; ENST00000380328; ENST00000398225; ENST00000398227; ENST00000398229; ENST00000398232; ENST00000398234; ENST00000398236; ENST00000349112; ENST00000398224 | TSF |
| 4% | chr3 | 9823188 | 9823088 | − | chr3 | 9822233 | 9822041 | − | ENST00000301964; ENST00000440161 | TSF |
| 4% | chr6 | 111198749 | 111198849 | + | chr6 | 111208708 | 111208794 | + | ENST00000368885 | TSF |
| 4% | chr1 | 213316012 | 213316144 | + | chr1 | 213341201 | 213341316 | + | ENST00000543470; ENST00000366959; ENST00000366960 | TSF |
| 4% | chr1 | 213316012 | 213316144 | + | chr1 | 213341201 | 213341316 | + | ENST00000543470; ENST00000366959; ENST00000366960 | TSF |
| 3% | chr5 | 33993714 | 33993278 | − | chr5 | 33989607 | 33989198; 33989589; 33989216 | − | ENST00000335606; ENST00000382072; ENST00000382085; ENST00000502637 | TSF |
| 3% | chr5 | 33993714 | 33993278 | − | chr5 | 33989607 | 33989198; 33989589; 33989216 | − | ENST00000335606; ENST00000382072; ENST00000382085; ENST00000502637 | TSF |
| 3% | chr5 | 33993714 | 33993278 | − | chr5 | 33989607 | 33989198; 33989589; 33989216 | − | ENST00000335606; ENST00000382072; ENST00000382085; ENST00000502637 | TSF |
| 3% | chr5 | 33993714 | 33993278 | − | chr5 | 33989607 | 33989198; 33989589; 33989216 | − | ENST00000335606; ENST00000382072; ENST00000382085; ENST00000502637 | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 3% | chr5 | 33993714 | 33993278 | − | chr5 | 33989607 | 33989198; 33989589; 33989216 | − | ENST00000335606; ENST00000382072; ENST00000382085; ENST00000502637 | TSF |
| 3% | chr5 | 33993714 | 33993278 | − | chr5 | 33989607 | 33989198; 33989589; 33989216 | − | ENST00000335606; ENST00000382072; ENST00000382085; ENST00000502637 | TSF |
| 3% | chr5 | 70911418 | 70912053 | + | chr5 | 70927948 | 70928012 | + | ENST00000512218; ENST00000340941; ENST00000509358; ENST00000323375; ENST00000509539 | TSF |
| 3% | chr5 | 70911418 | 70912053 | + | chr5 | 70927948 | 70928012 | + | ENST00000512218; ENST00000340941; ENST00000509358; ENST00000323375; ENST00000509539 | TSF |
| 3% | chr5 | 70911418 | 70912053 | + | chr5 | 70927948 | 70928012 | + | ENST00000512218; ENST00000340941; ENST00000509358; ENST00000323375; ENST00000509539 | TSF |
| 3% | chr5 | 70911418 | 70912053 | + | chr5 | 70927948 | 70928012 | + | ENST00000512218; ENST00000340941; ENST00000509358; ENST00000323375; ENST00000509539 | TSF |
| 3% | chr12 | 21426370 | 21426215 | − | chr12 | 21422701 | 21422482 | − | ENST00000307378; ENST00000452078; ENST00000458504; ENST00000537524 | TSF |
| 3% | chr7 | 148982749 | 148982787 | + | chr7 | 148984656 | 148984699; 148984867 | + | ENST00000378052; ENST00000476295; ENST00000418158 | TSF |
| 3% | chr7 | 148982749 | 148982787 | + | chr7 | 148984656 | 148984699; 148984867 | + | ENST00000378052; ENST00000476295; ENST00000418158 | TSF |
| 3% | chr15 | 74004214 | 74004264 | + | chr15 | 74005275 | 74005297 | + | ENST00000318443; ENST00000537340; ENST00000318424; ENST00000564751; ENST00000561176; ENST00000559073 | TSF |
| 3% | chr3 | 4858133 | 4857857 | − | chr3 | 4856115 | 4856088 | − | ENST00000449914; ENST00000441894 | TSF |
| 3% | chr5 | 70945258 | 170945361 | + | chr5 | 70945896 | 70946010 | + | ENST00000340941; ENST00000323375; ENST00000509539 | TSF |
| 3% | chr5 | 70945258 | 70945361 | + | chr5 | 70945896 | 70946010 | + | ENST00000340941; ENST00000323375; ENST00000509539 | TSF |
| 3% | chr14 | 69855378 | 69855278 | − | chr14 | 69853800 | 69853680; 69853676 | − | ENST00000557016; ENST00000555373 | TSF |
| 3% | chr14 | 69855378 | 69855278 | − | chr14 | 69853800 | 69853676 69853680; | − | ENST00000557016; ENST00000555373 | TSF |
| 3% | chr1 | 246478956 | 246478829 | − | chr1 | 246093239 | 246093172; 246093200 | − | ENST00000541742; ENST00000490107; ENST00000388985; ENST00000453676 | TSF |
| 3% | chr1 | 246478956 | 246478829 | − | chr1 | 246093239 | 246093172; 246093200 | − | ENST00000541742; ENST00000490107; ENST00000388985; ENST00000453676 | TSF |
| 3% | chr3 | 4859338 | 4859117 | − | chr3 | 4856115 | 4856088 | − | ENST00000449914; ENST00000441894 | TSF |
| 3% | chr21 | 42882831 | 42882427 | − | chr21 | 42870116 | 42870046 | − | ENST00000398585 | TSF |
| 2% | chr3 | 132047242 | 132047426 | + | chr3 | 132050491 | 132050577 | + | ENST00000336375; ENST00000475741; ENST00000351273 | TSF |
| 2% | chr3 | 132047242 | 132047426 | + | chr3 | 132050491 | 132050577 | + | ENST00000336375; ENST00000475741; ENST00000351273 | TSF |
| 2% | chr3 | 132047242 | 132047426 | + | chr3 | 132050491 | 132050577 | + | ENST00000336375; ENST00000475741; ENST00000351273 | TSF |
| 2% | chr17 | 72951257 | 72951178 | − | chr17 | 72950460 | 72950233 | − | ENST00000425042 | TSF |
| 2% | chr14 | 68160667 | 68160511 | − | chr14 | 68159769 | 68159651; 68159690 | − | ENST00000381346; ENST00000553384; ENST00000428130; ENST00000557273; ENST00000557726 | TSF |
| 2% | chr14 | 68160667 | 68160511 | − | chr14 | 68159769 | 68159651; 68159690 | − | ENST00000381346; ENST00000553384; ENST00000428130; ENST00000557273; ENST00000557726 | TSF |
| 2% | chr14 | 68160667 | 68160511 | − | chr14 | 68159769 | 68159651; 68159690 | − | ENST00000381346; ENST00000553384; ENST00000428130; ENST00000557273; ENST00000557726 | TSF |
| 2% | chr14 | 68160667 | 68160511 | − | chr14 | 68159769 | 68159651; 68159690 | − | ENST00000381346; ENST00000553384; ENST00000428130; ENST00000557273; ENST00000557726 | TSF |
| 2% | chr14 | 68160667 | 68160511 | − | chr14 | 68159769 | 68159651; 68159690 | − | ENST00000381346; ENST00000553384; ENST00000428130; ENST00000557273; ENST00000557726 | TSF |
| 2% | chr11 | 114311118 | 114311184 | + | chr11 | 114311378 | 114311461 | + | ENST00000265881; ENST00000544196; ENST00000539754; ENST00000539275; ENST00000541703; ENST00000538198; ENST00000544827 | TSF |
| 2% | chr11 | 114311118 | 114311184 | + | chr11 | 114311378 | 114311461 | + | ENST00000265881; ENST00000544196; ENST00000539754; ENST00000539275; ENST00000541703; ENST00000538198; ENST00000544827 | TSF |
| 2% | chr11 | 114311118 | 114311184 | + | chr11 | 114311378 | 114311461 | + | ENST00000265881; ENST00000544196; ENST00000539754; ENST00000539275; ENST00000541703; ENST00000538198; ENST00000544827 | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 2% | chr11 | 114311118 | 114311184 | + | chr11 | 114311378 | 114311461 | + | ENST00000265881; ENST00000544196; ENST00000539754; ENST00000539275; ENST00000541703; ENST00000538198; ENST00000544827 | TSF |
| 2% | chr11 | 114311118 | 114311184 | + | chr11 | 114311378 | 114311461 | + | ENST00000265881; ENST00000544196; ENST00000539754; ENST00000539275; ENST00000541703; ENST00000538198; ENST00000544827 | TSF |
| 2% | chr11 | 114311118 | 114311184 | + | chr11 | 114311378 | 114311461 | + | ENST00000265881; ENST00000544196; ENST00000539754; ENST00000539275; ENST00000541703; ENST00000538198; ENST00000544827 | TSF |
| 2% | chr16 | 77234898 | 77235039 | + | chr16 | 77240338 | 77240397 | + | ENST00000378644 | TSF |
| 2% | chr19 | 51143477 | 51143477 | + | chr19 | 51159307 | 51159379 | + | ENST00000425202 | TSF |
| 2% | chr1 | 37979411 | 37979373 | − | chr1 | 37979139 | 37979024 | − | ENST00000373075; ENST00000296214; ENST00000373074; ENST00000373073; ENST00000448519 | TSF |
| 2% | chr1 | 37979411 | 37979373 | − | chr1 | 37979139 | 37979024 | − | ENST00000373075; ENST00000296214; ENST00000373074; ENST00000373073; ENST00000448519 | TSF |
| 2% | chr1 | 37979411 | 37979373 | − | chr1 | 37979139 | 37979024 | − | ENST00000373075; ENST00000296214; ENST00000373074; ENST00000373073; ENST00000448519 | TSF |
| 2% | chr1 | 37979411 | 37979373 | − | chr1 | 37979139 | 37979024 | − | ENST00000373075; ENST00000296214; ENST00000373074; ENST00000373073; ENST00000448519 | TSF |
| 2% | chr1 | 37979411 | 37979373 | − | chr1 | 37979139 | 37979024 | − | ENST00000373075; ENST00000296214; ENST00000373074; ENST00000373073; ENST00000448519 | TSF |
| 2% | chr1 | 37979411 | 37979373 | − | chr1 | 37979139 | 37979024 | − | ENST00000373075; ENST00000296214; ENST00000373074; ENST00000373073; ENST00000448519 | TSF |
| 2% | chr1 | 37979411 | 37979373 | − | chr1 | 37979139 | 37979024 | − | ENST00000373075; ENST00000296214; ENST00000373074; ENST00000373073; ENST00000448519 | TSF |
| 2% | chr1 | 37979411 | 37979373 | − | chr1 | 37979139 | 37979024 | − | ENST00000373075; ENST00000296214; ENST00000373074; ENST00000373073; ENST00000448519 | TSF |
| 2% | chr8 | 144691011 | 144690934 | − | chr8 | 144690296 | 144690232 | − | ENST00000220966; ENST00000433751 | TSF |
| 2% | chr8 | 144691011 | 144690934 | − | chr8 | 144690296 | 144690232 | − | ENST00000220966; ENST00000433751 | TSF |
| 2% | chr3 | 132052633 | 132052733 | + | chr3 | 132056300 | 132056398 | + | ENST00000336375; ENST00000495911; ENST00000351273 | TSF |
| 2% | chr3 | 132052633 | 132052733 | + | chr3 | 132056300 | 132056398 | + | ENST00000336375; ENST00000495911; ENST00000351273 | TSF |
| 2% | chr3 | 132052633 | 132052733 | + | chr3 | 132056300 | 132056398 | + | ENST00000336375; ENST00000495911; ENST00000351273 | TSF |
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |
| 2% | chr19 | 51340308 | 51340387 | + | chr19 | 51359590 | 51359655 | + | ENST00000601503; ENST00000326003; ENST00000422986; ENST00000597286; ENST00000597483; ENST00000593997; ENST00000595392; ENST00000595952; ENST00000360617; ENST00000598145 | TSF |
| 2% | chr1 | 222838237 | 222838358 | + | chr1 | 222838651 | 222838961 | + | ENST00000344922; ENST00000344441; ENST00000340535 | TSF |
| 2% | chr2 | 192851958 | 192851903 | − | chr2 | 192821104 | 192820981 | − | ENST00000392314; ENST00000272771 | TSF |
| 2% | chr2 | 192851958 | 192851903 | − | chr2 | 192821104 | 192820981 | − | ENST00000392314; ENST00000272771 | TSF |
| 2% | chr21 | 38273278 | 38272892 | − | chr21 | 38269431 | 38269160 | − | ENST00000336648; ENST00000399120 | TSF |
| 2% | chr22 | 43223671 | 43223414 | − | chr22 | 43223005 | 43222946 | − | ENST00000263245; ENST00000429508; ENST00000437119; ENST00000453516; ENST00000454099 | TSF |
| 2% | chr22 | 43223671 | 43223414 | − | chr22 | 43223005 | 43222946 | − | ENST00000263245; ENST00000429508; ENST00000437119; ENST00000453516; ENST00000454099 | TSF |
| 2% | chr22 | 43223671 | 43223414 | − | chr22 | 43223005 | 43222946 | − | ENST00000263245; ENST00000429508; ENST00000437119; ENST00000453516; ENST00000454099 | TSF |
| 2% | chr2 | 168968104 | 168968047 | − | chr2 | 168931741 | 168931619 | − | ENST00000355999 | TSF |
| 2% | chr11 | 49185698 | 49184098 | − | chr11 | 49179595 | 49179504 | − | ENST00000256999; ENST00000356696; ENST00000343844; ENST00000340334; ENST00000533034 | TSF |
| 2% | chr11 | 49185698 | 49184098 | − | chr11 | 49179595 | 49179504 | − | ENST00000256999; ENST00000356696; ENST00000343844; ENST00000340334; ENST00000533034 | TSF |
| 2% | chr1 | 55349965 | 55349772 | − | chr1 | 55349446 | 55349291 | − | ENST00000371269; ENST00000535035 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 2% | chr19 | 51363647 | 51363679 | + | chr19 | 51381765 | 51381815; 51381861 | + | ENST00000325321; ENST00000391810; ENST00000595050 | TSF |
| 2% | chr19 | 51363647 | 51363679 | + | chr19 | 51381765 | 51381815; 51381861 | + | ENST00000325321; ENST00000391810; ENST00000595050 | TSF |
| 2% | chrX | 21965424 | 21965489 | + | chrX | 21985314 | 21985434 | + | ENST00000404933; ENST00000379404; ENST00000457085 | TSF |
| 2% | chrX | 21965424 | 21965489 | + | chrX | 21985314 | 21985434 | + | ENST00000404933; ENST00000379404; ENST00000457085 | TSF |
| 2% | chrX | 21965424 | 21965489 | + | chrX | 21985314 | 21985434 | + | ENST00000404933; ENST00000379404; ENST00000457085 | TSF |
| 2% | chr19 | 51360137 | 51360205 | + | chr19 | 51361285 | 51361342; 51361571; 51361430; 51361589 | + | ENST00000601503; ENST00000326003; ENST00000422986; ENST00000597286; ENST00000593997; ENST00000595392; ENST00000360617; ENST00000598145 | TSF |
| 2% | chr19 | 51360137 | 51360205 | + | chr19 | 51361285 | 51361571; 51361342; 51361430; 51361589 | + | ENST00000601503; ENST00000326003; ENST00000422986; ENST00000597286; ENST00000593997; ENST00000595392; ENST00000360617; ENST00000598145 | TSF |
| 2% | chr19 | 51360137 | 51360205 | + | chr19 | 51361285 | 51361342; | + | ENST00000601503; ENST00000326003; | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 2% | chr19 | 51360137 | 51360205 | + | chr19 | 51361285 | 51361571; 51361430; 51361589 51361571; 51361342; 51361430; 51361589 | + | ENST00000422986; ENST00000597286; ENST00000593997; ENST00000595392; ENST00000360617; ENST00000598145 ENST00000601503; ENST00000326003; ENST00000422986; ENST00000597286; ENST00000593997; ENST00000595392; ENST00000360617; ENST00000598145 | TSF |
| 2% | chr19 | 51360137 | 51360205 | + | chr19 | 51361285 | 51361571; 51361342; 51361430; 51361589 | + | ENST00000601503; ENST00000326003; ENST00000422986; ENST00000597286; ENST00000593997; ENST00000595392; ENST00000360617; ENST00000598145 | TSF |
| 2% | chr19 | 51360137 | 51360205 | + | chr19 | 51361285 | 51361571; 51361342; 51361430; 51361589 | + | ENST00000601503; ENST00000326003; ENST00000422986; ENST00000597286; ENST00000593997; ENST00000595392; ENST00000360617; ENST00000598145 | TSF |
| 2% | chr19 | 51360137 | 51360205 | + | chr19 | 51361285 | 51361571; 51361342; 51361430; 51361589 | + | ENST00000601503; ENST00000326003; ENST00000422986; ENST00000597286; ENST00000593997; ENST00000595392; ENST00000360617; ENST00000598145 | TSF |
| 2% | chr19 | 51360137 | 51360205 | + | chr19 | 51361285 | 51361571; 51361342; 51361430; 51361589 | + | ENST00000601503; ENST00000326003; ENST00000422986; ENST00000597286; ENST00000593997; ENST00000595392; ENST00000360617; ENST00000598145 | TSF |
| 2% | chr1 | 109725208 | 109725274 | + | chr1 | 109727667 | 109727755 | + | ENST00000369939; ENST00000457623 | TSF |
| 2% | chr1 | 109725208 | 109725274 | + | chr1 | 109727667 | 109727755 | + | ENST00000369939; ENST00000457623 | TSF |
| 2% | chr2 | 207634479 | 207634640 | + | chr2 | 207634815 | 207634918 | + | ENST00000236980; ENST00000402774; ENST00000403094 | TSF |
| 2% | chr13 | 95872419 | 95872224 | − | chr13 | 95863035 | 95862946 | − | ENST00000412704; ENST00000376887; ENST00000536256; ENST00000431522 | TSF |
| 2% | chr13 | 95872419 | 95872224 | − | chr13 | 95863035 | 95862946 | − | ENST00000412704; ENST00000376887; ENST00000536256; ENST00000431522 | TSF |
| 2% | chr13 | 95872419 | 95872224 | − | chr13 | 95863035 | 95862946 | − | ENST00000412704; ENST00000376887; ENST00000536256; ENST00000431522 | TSF |
| 2% | chr5 | 34010561 | 34010287 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010287 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010287 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010287 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010287 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010287 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010287 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 2% | chr5 | 34010561 | 34010287 | − | chr5 | 34006004 | 34005861 | − | ENST00000335606; ENST00000382072; ENST00000382079; ENST00000506639; ENST00000382085; ENST00000502637; | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 2% | chr1 | 52306889 | 52306849 | − | chr1 | 52306186 | 52305898 | − | ENST00000441713; ENST00000426255; ENST00000512079; ENST00000382068 ENST00000352171; ENST00000354831 | TSF |
| 2% | chr1 | 52306889 | 52306849 | − | chr1 | 52306186 | 52305898 | − | ENST00000352171; ENST00000354831 | TSF |
| 2% | chr4 | 102080353 | 102080228 | − | chr4 | 102030235 | 102030111 | − | ENST00000394854; ENST00000323055; ENST00000394853; ENST00000523694; ENST00000529324; ENST00000525819 | TSF |
| 2% | chr4 | 102080353 | 102080228 | − | chr4 | 102030235 | 102030111 | − | ENST00000394854; ENST00000323055; ENST00000394853; ENST00000523694; ENST00000529324; ENST00000525819 | TSF |
| 2% | chr4 | 102080353 | 102080228 | − | chr4 | 102030235 | 102030111 | − | ENST00000394854; ENST00000323055; ENST00000394853; ENST00000523694; ENST00000529324; ENST00000525819 | TSF |
| 2% | chr4 | 102080353 | 102080228 | − | chr4 | 102030235 | 102030111 | − | ENST00000394854; ENST00000323055; ENST00000394853; ENST00000523694; ENST00000529324; ENST00000525819 | TSF |
| 2% | chr4 | 102080353 | 102080228 | − | chr4 | 102030235 | 102030111 | − | ENST00000394854; ENST00000323055; ENST00000394853; ENST00000523694; ENST00000529324; ENST00000525819 | TSF |
| 2% | chr11 | 49185698 | 49184443 | − | chr11 | 49179595 | 49179504 | − | ENST00000256999; ENST00000356696; ENST00000343844; ENST00000340334; ENST00000533034 | TSF |
| 2% | chr11 | 49185698 | 49184443 | − | chr11 | 49179595 | 49179504 | − | ENST00000256999; ENST00000356696; ENST00000343844; ENST00000340334; ENST00000533034 | TSF |
| 2% | chr8 | 117816470 | 117816753 | + | chr8 | 117861127 | 117861256; 117861276 | + | ENST00000517820; ENST00000520733 | TSF |
| 2% | chr8 | 117816470 | 117816753 | + | chr8 | 117861127 | 117861256; 117861276 | + | ENST00000517820; ENST00000520733 | TSF |
| 2% | chr5 | 118865267 | 118865382 | + | chr5 | 118865589 | 118865675 | + | ENST00000256216; ENST00000515320; ENST00000510025; ENST00000504811; ENST00000414835; ENST00000513628; ENST00000509514 | TSF |
| 2% | chr2 | 131117443 | 131117848 | + | chr2 | 131126706 | 131126774 | + | ENST00000175756; ENST00000347849 | TSF |
| 2% | chr5 | 54723913 | 54723765 | − | chr5 | 54721867 | 54721691 | − | ENST00000264775; ENST00000307259 | TSF |
| 2% | chr11 | 49229295 | 49229182 | − | chr11 | 49227724 | 49227619 | − | ENST00000256999; ENST00000356696; ENST00000525826; ENST00000340334; ENST00000533034 | TSF |
| 2% | chr11 | 49229295 | 49229182 | − | chr11 | 49227724 | 49227619 | − | ENST00000256999; ENST00000356696; ENST00000525826; ENST00000340334; ENST00000533034 | TSF |
| 2% | chr11 | 49229295 | 49229182 | − | chr11 | 49227724 | 49227619 | − | ENST00000256999; ENST00000356696; ENST00000525826; ENST00000340334; ENST00000533034 | TSF |
| 2% | chr13 | 95690828 | 95690729 | − | chr13 | 95686993 | 95686859 | − | ENST00000412704; ENST00000376887 | TSF |
| 1% | chr8 | 102609579 | 102609842 | + | chr8 | 102611285 | 102611379 | + | ENST00000251808; ENST00000395927 | TSF |
| 1% | chr1 | 228782545 | 228782677 | + | chr1 | 228873420 | 228873478 | + | ENST00000366691 | TSF |
| 1% | chr19 | 50174724 | 50174836 | + | chr19 | 50176955 | 50177034; 50177005; | + | ENST00000441864; ENST00000246785; ENST00000600947; ENST00000598306 | TSF |
| 1% | chr19 | 50174724 | 50174836 | + | chr19 | 50176955 | 50177005; 50177034 | + | ENST00000441864; ENST00000246785; ENST00000600947; ENST00000598306 | TSF |
| 1% | chr14 | 37888149 | 37888315 | + | chr14 | 37892060 | 37892154 | + | ENST00000536774; ENST00000327441; ENST00000539062; ENST00000556451; ENST00000555870; ENST00000396294; ENST00000545536; ENST00000537471 | TSF |
| 1% | chr14 | 37888149 | 37888315 | + | chr14 | 37892060 | 37892154 | + | ENST00000536774; ENST00000327441; ENST00000539062; ENST00000556451; ENST00000555870; ENST00000396294; ENST00000545536; ENST00000537471 | TSF |
| 1% | chr14 | 37888149 | 37888315 | + | chr14 | 37892060 | 37892154 | + | ENST00000536774; ENST00000327441; ENST00000539062; ENST00000556451; ENST00000555870; ENST00000396294; ENST00000545536; ENST00000537471 | TSF |
| 1% | chr2 | 44523867 | 44524132 | + | chr2 | 44527110 | 44527229 | + | ENST00000260649; ENST00000409387; ENST00000409741; ENST00000410056; ENST00000409229; ENST00000409380; ENST00000427285 | TSF |
| 1% | chr2 | 44523867 | 44524132 | + | chr2 | 44527110 | 44527229 | + | ENST00000260649; ENST00000409387; ENST00000410056; ENST00000409741; ENST00000409229; ENST00000409380; ENST00000427285 | TSF |
| 1% | chr2 | 44523867 | 44524132 | + | chr2 | 44527110 | 44527229 | + | ENST00000260649; ENST00000409387; ENST00000410056; ENST00000409741; ENST00000409229; ENST00000409380; ENST00000427285 | TSF |
| 1% | chr2 | 44523867 | 44524132 | + | chr2 | 44527110 | 44527229 | + | ENST00000260649; ENST00000409387; | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 1% | chr2 | 44523867 | 44524132 | + | chr2 | 44527110 | 44527229 | + | ENST00000410056; ENST00000409741; ENST00000409229; ENST00000409380; ENST00000427285 ENST00000260649; ENST00000409387; ENST00000410056; ENST00000409741; ENST00000409229; ENST00000409380; ENST00000427285 | TSF |
| 1% | chr2 | 44523867 | 44524132 | + | chr2 | 44527110 | 44527229 | + | ENST00000260649; ENST00000409387; ENST00000410056; ENST00000409741; ENST00000409229; ENST00000409380; ENST00000427285 | TSF |
| 1% | chr4 | 95574306 | 95574373 | + | chr4 | 95575611 | 95575791 | + | ENST00000437932; ENST00000317968; ENST00000503974; ENST00000542407; ENST00000514743; ENST00000506632 | TSF |
| 1% | chr4 | 95574306 | 95574373 | + | chr4 | 95575611 | 95575791 | + | ENST00000437932; ENST00000317968; ENST00000503974; ENST00000542407; ENST00000514743; ENST00000506632 | TSF |
| 1% | chr4 | 95574306 | 95574373 | + | chr4 | 95575611 | 95575791 | + | ENST00000437932; ENST00000317968; ENST00000503974; ENST00000542407; ENST00000514743; ENST00000506632 | TSF |
| 1% | chr5 | 34007349 | 34007309 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 1% | chr5 | 34007349 | 34007309 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 1% | chr5 | 34007349 | 34007309 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 1% | chr5 | 34007349 | 34007309 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 1% | chr5 | 34007349 | 34007309 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 1% | chr5 | 34007349 | 34007309 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 1% | chr5 | 34007349 | 34007309 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 1% | chr5 | 34007349 | 34007309 | − | chr5 | 34006004 | 34005861 | − | ENST00000335606; ENST00000382072; ENST00000382079; ENST00000506639; ENST00000382085; ENST00000502637; ENST00000441713; ENST0000512079; ENST00000382068 | TSF |
| 1% | chr5 | 34007349 | 34007309 | − | chr5 | 34006004 | 34005861 | − | ENST00000335606; ENST00000382072; ENST00000382079; ENST00000506639; ENST00000382085; ENST00000502637; ENST00000441713; ENST00000426255; ENST00000512079; ENST00000382068 | TSF |
| 1% | chr4 | 151647998 | 151647737 | − | chr4 | 151604869 | 151604703 | − | ENST00000535741; ENST00000510413; ENST00000357115; ENST00000509835; ENST00000507224 | TSF |
| 1% | chr4 | 151647998 | 151647737 | − | chr4 | 151604869 | 151604703 | − | ENST00000535741; ENST00000510413; ENST00000357115; ENST00000509835; ENST00000507224 | TSF |
| 1% | chr4 | 151647998 | 151647737 | − | chr4 | 151604869 | 151604703 | − | ENST00000535741; ENST00000510413; ENST00000357115; ENST00000509835; ENST00000507224 | TSF |
| 1% | chr4 | 151647998 | 151647737 | − | chr4 | 151604869 | 151604703 | − | ENST00000535741; ENST00000510413; ENST00000357115; ENST00000509835; | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 1% | chr2 | 165806067 | 165805999 | − | chr2 | 165802237 | 165802103 | − | ENST00000507224; ENST00000303735; ENST00000409149; ENST00000409058; ENST00000409662 | TSF |
| 1% | chr2 | 165806067 | 165805999 | − | chr2 | 165802237 | 165802103 | − | ENST00000303735; ENST00000409149; ENST00000409058; ENST00000409662 | TSF |
| 1% | chr1 | 37979411 | 37979375 | − | chr1 | 37979139 | 37979024 | − | ENST00000373075; ENST00000296214; ENST00000373074; ENST00000373073; ENST00000448519 | TSF |
| 1% | chr1 | 37979411 | 37979375 | − | chr1 | 37979139 | 37979024 | − | ENST00000373075; ENST00000296214; ENST00000373074; ENST00000373073; ENST00000448519 | TSF |
| 1% | chr1 | 37979411 | 37979375 | − | chr1 | 37979139 | 37979024 | − | ENST00000373075; ENST00000296214; ENST00000373074; ENST00000373073; ENST00000448519 | TSF |
| 1% | chr1 | 37979411 | 37979375 | − | chr1 | 37979139 | 37979024 | − | ENST00000373075; ENST00000296214; ENST00000373074; ENST00000373073; ENST00000448519 | TSF |
| 1% | chr8 | 19324621 | 19324413 | − | chr8 | 19316153 | 19315937 | − | ENST00000454498; ENST00000332246; ENST00000397998; ENST00000311540; ENST00000522854; ENST00000544602; ENST00000519222 | TSF |
| 1% | chr8 | 19324621 | 193 24413 | − | chr8 | 19316153 | 19315937 | − | ENST00000454498; ENST00000332246; ENST00000397998; ENST00000311540; ENST00000522854; ENST00000544602; ENST00000519222 | TSF |
| 1% | chr4 | 171005986 | 171005876 | − | chr4 | 170999734 | 170999660 | − | ENST00000337664; ENST00000509167; ENST00000515480; ENST00000353187; ENST00000510340; ENST00000507375; ENST00000502392 | TSF |
| 1% | chr4 | 171005986 | 171005876 | − | chr4 | 170999734 | 170999660 | − | ENST00000337664; ENST00000509167; ENST00000515480; ENST00000353187; ENST00000510340; ENST00000507375; ENST00000502392 | TSF |
| 1% | chr4 | 171005986 | 171005876 | − | chr4 | 170999734 | 170999660 | − | ENST00000337664; ENST00000509167; ENST00000515480; ENST00000353187; ENST00000510340; ENST00000507375; ENST00000502392 | TSF |
| 1% | chr4 | 171005986 | 171005876 | − | chr4 | 170999734 | 170999660 | − | ENST00000337664; ENST00000509167; ENST00000515480; ENST00000353187; ENST00000510340; ENST00000507375; ENST00000502392 | TSF |
| 1% | chr12 | 93806814 | 93806392 | − | chr12 | 93805075 | 93804829; 93804647; 93804902 | − | ENST00000318066; ENST00000550657; ENST00000549490; ENST00000552442 | TSF |
| 1% | chr12 | 93806814 | 93806392 | − | chr12 | 93805075 | 93804829; 93804647; 93804902 | − | ENST00000318066; ENST00000550657; ENST00000549490; ENST00000552442 | TSF |
| 1% | chr12 | 93806814 | 93806392 | − | chr12 | 93805075 | 93804829; 93804647; 93804902 | − | ENST00000318066; ENST00000550657; ENST00000549490; ENST00000552442 | TSF |
| 1% | chr12 | 93806814 | 93806392 | − | chr12 | 93805075 | 93804647; 93804829; 93804902 | − | ENST00000318066; ENST00000550657; ENST00000549490; ENST00000552442 | TSF |
| 1% | chr4 | 142977397 | 142977072 | − | chr4 | 142950067 | 142949935 | − | ENST00000513000; ENST00000262992; ENST00000308502; ENST00000508116 | TSF |
| 1% | chr15 | 73055826 | 73055759 | − | chr15 | 73052868 | 73052760; 73052748 | − | ENST00000569534; ENST00000311669; ENST00000563907; ENST00000565814 | TSF |
| 1% | chr15 | 73055826 | 73055759 | − | chr15 | 73052868 | 73052760; 73052748 | − | ENST00000569534; ENST00000311669; ENST00000563907; ENST00000565814 | TSF |
| 1% | chr15 | 73055826 | 73055759 | − | chr15 | 73052868 | 73052760; 73052748 | − | ENST00000569534; ENST00000311669; ENST00000563907; ENST00000565814 | TSF |
| 1% | chr15 | 73055826 | 73055759 | − | chr15 | 73052868 | 73052760; 73052748 | − | ENST00000569534; ENST00000311669; ENST00000563907; ENST00000565814 | TSF |
| 1% | chr3 | 141923156 | 141923059 | − | chr3 | 141917775 | 141917644 | − | ENST00000492097; ENST00000480757; ENST00000392993; ENST00000544571 | TSF |
| 1% | chr3 | 141923156 | 141923059 | − | chr3 | 141917775 | 141917644 | − | ENST00000492097; ENST00000480757; ENST00000392993; ENST00000544571 | TSF |
| 1% | chr12 | 56160733 | 56160521 | − | chr12 | 56154424 | 56154335; 56154284 | − | ENST00000546604; ENST00000444631; ENST00000336133; ENST00000546837; ENST00000552080 | TSF |
| 1% | chr12 | 56160733 | 561160521 | − | chr12 | 56154424 | 56154284 56154335; | − | ENST00000546604; ENST00000444631; ENST00000336133; ENST00000546837; ENST00000552080 | TSF |
| 1% | chr16 | 81057014 | 81057064 | + | chr16 | 81058320 | 81058383 | + | ENST00000305850; ENST00000439957; ENST00000393335; ENST00000428963 | TSF |
| 1% | chr16 | 81057014 | 81057064 | + | chr16 | 81058320 | 81058383 | + | ENST00000305850; ENST00000439957; | TSF |

TABLE 50-continued

Transcript fusion for Prostate Adenocarcinoma (PRAD) Coordinates of the fusion sequences for which the donor is the T

| 1 | 2' | 3' | 4' | 5' | 6' | 7' | 8' | 9' | 10' | 11' |
|---|---|---|---|---|---|---|---|---|---|---|
| 1% | chr17 | 7947105 | 7947155 | + | chr17 | 7948147 | 7948319 | + | ENST00000393335; ENST00000428963 ENST00000380183; ENST00000572022; ENST00000380173; ENST00000573359 | TSF |
| 1% | chr17 | 7947105 | 7947155 | + | chr17 | 7948147 | 7948319 | + | ENST00000380183; ENST00000572022; ENST00000380173; ENST00000573359 | TSF |
| 1% | chr17 | 7947105 | 7947155 | + | chr17 | 7948147 | 7948319 | + | ENST00000380183; ENST00000572022; ENST00000380173; ENST00000573359 | TSF |
| 1% | chr17 | 7947105 | 7947155 | + | chr17 | 7948147 | 7948319 | + | ENST00000380183; ENST00000572022; ENST00000380173; ENST00000573359 | TSF |
| 1% | chr5 | 79371074 | 79371193 | + | chr5 | 79372678 | 79372871 | + | ENST00000350881; ENST00000511733 | TSF |
| 1% | chr19 | 51345545 | 51345748 | + | chr19 | 51359496 | 51359655 | + | ENST00000326003; ENST00000422986; ENST00000597483; ENST00000593997; ENST00000595392; ENST00000595952; ENST00000360617; ENST00000598145 | TSF |
| 1% | chr19 | 51345545 | 51345748 | + | chr19 | 51359496 | 51359655 | + | ENST00000326003; ENST00000422986; ENST00000597483; ENST00000593997; ENST00000595392; ENST00000595952; ENST00000360617; ENST00000598145 | TSF |
| 1% | chr19 | 51345545 | 51345748 | + | chr19 | 51359496 | 51359655 | + | ENST00000326003; ENST00000422986; ENST00000597483; ENST00000593997; ENST00000595392; ENST00000595952; ENST00000360617; ENST00000598145 | TSF |
| 1% | chr19 | 51345545 | 51345748 | + | chr19 | 51359496 | 51359655 | + | ENST00000326003; ENST00000422986; ENST00000597483; ENST00000593997; ENST00000595392; ENST00000595952; ENST00000360617; ENST00000598145 | TSF |
| 1% | chr19 | 51345545 | 51345748 | + | chr19 | 51359496 | 51359655 | + | ENST00000326003; ENST00000422986; ENST00000597483; ENST00000593997; ENST00000595392; ENST00000595952; ENST00000360617; ENST00000598145 | TSF |
| 1% | chr19 | 51345545 | 51345748 | + | chr19 | 51359496 | 51359655 | + | ENST00000326003; ENST00000422986; ENST00000597483; ENST00000593997; ENST00000595392; ENST00000595952; ENST00000360617; ENST00000598145 | TSF |
| 1% | chr19 | 51345545 | 45513748 | + | chr19 | 51359496 | 51359655 | + | ENST00000326003; ENST00000422986; ENST00000597483; ENST00000593997; ENST00000595392; ENST00000595952; ENST00000360617; ENST00000598145 | TSF |
| 1% | chr19 | 51345545 | 51345748 | + | chr19 | 51359496 | 51359655 | + | ENST00000326003; ENST00000422986; ENST00000597483; ENST00000593997; ENST00000595392; ENST00000595952; ENST00000360617; ENST00000598145 | TSF |
| 1% | chr15 | 89717587 | 89717675 | + | chr15 | 89719043 | 89719226 | + | ENST00000352732; ENST00000565973; ENST00000355100 | TSF |
| 1% | chr9 | 100821079 | 100821131 | + | chr9 | 100823064 | 100823279 | + | ENST00000210444 | TSF |
| 1% | chr7 | 24325099 | 24325188 | + | chr7 | 24329118 | 24329198 | + | ENST00000242152; ENST00000407573; ENST00000405982 | TSF |
| 1% | chr19 | 35551883 | 35551974 | + | chr19 | 35556154 | 35556249 | + | ENST00000262626; ENST00000392226; ENST00000597419 | TSF |
| 1% | chr9 | 100807994 | 100808487 | + | chr9 | 100823064 | 100823279 | + | ENST00000210444 | TSF |
| 1% | chr8 | 128749913 | 128749923 | + | chr8 | 128750494 | 128751265 | + | ENST00000377970 | TSF |
| 1% | chr3 | 175506179 | 175506380 | + | chr3 | 175520793 | 175520991 | + | ENST00000454872 | TSF |
| 1% | chr8 | 19325038 | 19325000 | − | chr8 | 19316153 | 19315937 | − | ENST00000454498; ENST00000332246; ENST00000397998; ENST00000311540; ENST00000522854; ENST00000544602; ENST00000519222 | TSF |
| 1% | chr8 | 19325038 | 19325000 | − | chr8 | 19316153 | 19315937 | − | ENST00000454498; ENST00000332246; ENST00000397998; ENST00000311540; ENST00000522854; ENST00000544602; ENST00000519222 | TSF |
| 1% | chr13 | 95715443 | 95715253 | − | chr13 | 95715113 | 95714958 | − | ENST00000412704; ENST00000376887 | TSF |
| 1% | chr2 | 99311548 | 99315517 | − | chr2 | 99294934 | 99294767 | − | ENST00000264968; ENST00000393487; ENST00000409391 | TSF |
| 1% | chr6 | 46618224 | 46617893 | − | chr6 | 46610035 | 46609900 | − | ENST00000275016 | TSF |
| 1% | chr21 | 34823925 | 34823642 | − | chr21 | 34823170 | 34823125 | − | ENST00000420455; ENST00000542230 | TSF |
| 1% | chr2 | 25015386 | 25015253 | − | chr2 | 25013450 | 25013280 | − | ENST00000328379 | TSF |
| 1% | chr10 | 73858281 | 73858277 | − | chr10 | 73857208 | 73857092; 73857201 | − | ENST00000394919; ENST00000317168; ENST00000486689; ENST00000530394; ENST00000317126; ENST00000545550 | TSF |
| 1% | chr10 | 73858281 | 73858277 | − | chr10 | 73857208 | 73857092; 73857201 | − | ENST00000394919; ENST00000317168; ENST00000486689; ENST00000530394; ENST00000317126; ENST00000545550 | TSF |

TABLE 51

Transcript fusion for Rectum adenocarcinoma (READ) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 37% | chr12 | 71928895 | 71928966 | + | ENST00000266674; ENST00000536515; ENST00000540815 | chr12 | 71938771 | 71938901 | + | TSF |
| 34% | chr13 | 44433033 | 44432917 | − | ENST00000444614; ENST00000281508 | chr13 | 44413224 | 44412729 | − | TAF |
| 30% | chr13 | 43659904 | 43659974 | + | ENST00000379221 | chr13 | 43670953 | 43671210 | + | TAF |
| 28% | chr11 | 428199 | 428088 | − | ENST00000332826 | chr11 | 424187 | 423924 | − | TAF |
| 28% | chr3 | 49927493 | 49927357 | − | ENST00000296474; ENST00000344206 | chr3 | 49927248 | 49927204 | − | TAF |
| 28% | chr3 | 49927493 | 49927357 | − | ENST00000296474; ENST00000344206 | chr3 | 49927248 | 49927204 | − | TAF |
| 27% | chr1 | 24463799 | 24463621 | − | ENST00000270800 | chr1 | 24461426 | 24461370 | − | TAF |
| 24% | chr20 | 9453926 | 9454012 | + | ENST00000334005; ENST00000378473; ENST00000278655; ENST00000414679; ENST00000378493; ENST00000378501 | chr20 | 9484605 | 9485169 | + | TAF |
| 24% | chr20 | 9453926 | 9454012 | + | ENST00000334005; ENST00000378473; ENST00000278655; ENST00000414679; ENST00000378493; ENST00000378501 | chr20 | 9484605 | 9485169 | + | TAF |
| 23% | chr13 | 115030625 | 115030715 | + | ENST00000360383; ENST00000375312; ENST00000356221; ENST00000375310; ENST00000252457; ENST00000375308; ENST00000252458 | chr13 | 115035038 | 115035171 | + | TAF |
| 23% | chr13 | 115030625 | 115030715 | + | ENST00000360383; ENST00000375312; ENST00000356221; ENST00000375310; ENST00000252457; ENST00000375308; ENST00000252458 | chr13 | 115035038 | 115035171 | + | TAF |
| 23% | chr13 | 115030625 | 115030715 | + | ENST00000360383; ENST00000375312; ENST00000356221; ENST00000375310; ENST00000252457; ENST00000375308; ENST00000252458 | chr13 | 115035038 | 115035171 | + | TAF |
| 23% | chr13 | 115030625 | 115030715 | + | ENST00000360383; ENST00000375312; ENST00000356221; ENST00000375310; ENST00000252457; ENST00000375308; ENST00000252458 | chr13 | 115035038 | 115035171 | + | TAF |
| 23% | chr7 | 75442741 | 75442624 | − | ENST00000222902; ENST00000416943 | chr7 | 75441450 | 75441417 | − | TAF |
| 20% | chr20 | 47768284 | 47768119 | − | ENST00000371828; ENST00000340954; ENST00000347458; ENST00000360426; ENST00000371792; ENST00000371802; ENST00000371856; ENST00000437404; ENST00000456866 | chr20 | 47761186 | 47760181 | − | TAF |
| 20% | chr20 | 47768284 | 47768119 | − | ENST00000371828; ENST00000340954; ENST00000347458; ENST00000360426; ENST00000371792; ENST00000371802; ENST00000371856; ENST00000437404; ENST00000456866 | chr20 | 47761186 | 47760181 | − | TAF |
| 20% | chr20 | 47768284 | 47768119 | − | ENST00000371828; ENST00000340954; ENST00000347458; ENST00000360426; ENST00000371792; ENST00000371802; ENST00000371856; ENST00000437404; ENST00000456866 | chr20 | 47761186 | 47760181 | − | TAF |
| 19% | chr9 | 125054028 | 125054119 | + | ENST00000297908; ENST00000344641; ENST00000373723; ENST00000373729; ENST00000394315 | chr9 | 125068067 | 125068171 | + | TSF |
| 19% | chr9 | 125054028 | 125054119 | + | ENST00000297908; ENST00000344641; ENST00000373723; ENST00000373729; ENST00000394315 | chr9 | 125068067 | 125068171 | + | TSF |
| 19% | chr9 | 125054028 | 125054119 | + | ENST00000297908; ENST00000344641; ENST00000373723; ENST00000373729; ENST00000394315 | chr9 | 125068067 | 125068171 | + | TSF |
| 18% | chr20 | 33137782 | 33137833 | + | ENST00000374837 | chr20 | 33138384 | 33138773 | + | TSF |
| 17% | chr13 | 113849439 | 113849385 | − | ENST00000337344; ENST00000375477; ENST00000375479; ENST00000375459; ENST00000246505; ENST00000375457 | chr13 | 113848640 | 113848038 | − | TAF |
| 17% | chr13 | 113849439 | 113849385 | − | ENST00000337344; ENST00000375477; ENST00000375479; ENST00000375459; ENST00000246505; ENST00000375457 | chr13 | 113848640 | 113848038 | − | TAF |
| 17% | chr13 | 113849439 | 113849385 | − | ENST00000337344; ENST00000375477; ENST00000375479; ENST00000375459; ENST00000246505; ENST00000375457 | chr13 | 113848640 | 113848038 | − | TAF |
| 17% | chr20 | 9382137 | 9382237 | + | ENST00000334005; ENST00000378473; ENST00000278655; ENST00000414679; ENST00000378493; ENST00000378501 | chr20 | 9383648 | 9383757 | + | TSF |
| 15% | chr16 | 50583333 | 50583466 | + | ENST00000268459 | chr16 | 50614862 | 50614981 | + | TSF |
| 14% | chr6 | 1960205 | 1960101 | − | ENST00000530927; ENST00000380815 | chr6 | 1955184 | 1955013 | − | TAF |
| 14% | chr6 | 1960205 | 1960101 | − | ENST00000530927; ENST00000380815 | chr6 | 1955184 | 1955013 | − | TAF |
| 14% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 14% | chr16 | 4409386 | 4409297 | − | ENST00000572467; ENST00000251166; | chr16 | 4409070 | 4408945 | − | TAF |

TABLE 51-continued

Transcript fusion for Rectum adenocarcinoma (READ) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 14% | chr16 | 4409386 | 4409297 | − | ENST00000539968; ENST00000537233; ENST00000574025; ENST00000576637 ENST00000572467; ENST00000251166; ENST00000539968; ENST00000537233; ENST00000574025; ENST00000576637 | chr16 | 4409070 | 4408945 | − | TAF |
| 14% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 14% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 14% | chr16 | 50659396 | 50659491 | + | ENST00000268459 | chr16 | 50663933 | 50663990 | + | TSF |
| 13% | chr3 | 14520593 | 14520693 | + | ENST00000454876; ENST00000360861 | chr3 | 14521628 | 14521634 | + | TAF |
| 13% | chr5 | 82554349 | 82554496 | + | ENST00000282268; ENST00000338635; ENST00000396027; ENST00000511817 | chr5 | 82606608 | 82606935 | + | TAF |
| 13% | chr10 | 120905865 | 120905748 | − | ENST00000355697; ENST00000330036 | chr10 | 120901885 | 120901741 | − | TAF |
| 13% | chr10 | 120905865 | 120905748 | − | ENST00000355697; ENST00000330036 | chr10 | 120901885 | 120901741 | − | TAF |
| 12% | chr1 | 32696528 | 32696620 | + | ENST00000373586 | chr1 | 32696861 | 32697110 | + | TAF |
| 12% | chr9 | 99122503 | 99122436 | − | ENST00000253270; ENST00000375259; ENST00000375257 | chr9 | 99115925 | 99115627 | − | TAF |
| 11% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 11% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 9% | chr4 | 57319769 | 57319927 | + | ENST00000514888; ENST00000264221; ENST00000505164; ENST00000399688; ENST00000512576 | chr4 | 57321183 | 57321327 | + | TSF |
| 9% | chr4 | 57319769 | 57319927 | + | ENST00000514888; ENST00000264221; ENST00000505164; ENST00000399688; ENST00000512576 | chr4 | 57321183 | 57321327 | + | TSF |
| 9% | chr4 | 57319769 | 57319927 | + | ENST00000514888; ENST00000264221; ENST00000505164; ENST00000399688; ENST00000512576 | chr4 | 57321183 | 57321327 | + | TSF |
| 9% | chr8 | 42924698; 42924750 | 429248102 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr8 | 42924 698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 9% | chr16 | 72153988; 72154048 | 72153750 | − | ENST00000537465; ENST00000237353; ENST00000355636 | chr16 | 72150929 | 72150229 | − | TSF |
| 9% | chr16 | 72153988; 72154048 | 72153750 | − | ENST00000537465; ENST00000237353; ENST00000355636 | chr16 | 72150929 | 72150229 | − | TSF |
| 9% | chr16 | 72153988; 72154048 | 72153750 | − | ENST00000537465; ENST00000237353; ENST00000355636 | chr16 | 72150929 | 72150229 | − | TSF |
| 7% | chr16 | 50642205 | 50642271 | + | ENST00000268459 | chr16 | 50651664 | 50651770 | + | TSF |
| 7% | chr2 | 241555805 | 241555928 | + | ENST00000270364 | chr2 | 241556208 | 241556489 | + | TSF |

TABLE 51-continued

Transcript fusion for Rectum adenocarcinoma (READ) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 6% | chr7 | 73973957 | 73973985 | + | ENST00000265755; ENST00000455841; ENST00000424337; ENST00000476977; ENST00000470715 | chr7 | 73985447 | 73985582 | + | TSF |
| 6% | chr7 | 73973957 | 73973985 | + | ENST00000265755; ENST00000455841; ENST00000424337; ENST00000476977; ENST00000470715 | chr7 | 73985417 | 73985582 | + | TSF |
| 6% | chr7 | 73973957 | 73973985 | + | ENST00000265755; ENST00000455841; ENST00000424337; ENST00000476977; ENST00000470715 | chr7 | 73985447 | 73985582 | + | TSF |
| 6% | chr7 | 73973957 | 73973985 | + | ENST00000265755; ENST00000455841; ENST00000424337; ENST00000476977; ENST00000470715 | chr7 | 73985447 | 73985582 | + | TSF |

TABLE 52

Transcript fusion for Rectum adenocarcinoma (READ) Coordinates of the fusion sequences for which the donor is the exon.

| 1 | 2' | 3' | 4' | 5' | 6' | 7' | 8' | 9' | 10' | 11' |
|---|---|---|---|---|---|---|---|---|---|---|
| 55% | chr11 | 93468219 | 93468129 | − | chr11 | 93467826 | 93467791; 93467814 | − | ENST00000393259; ENST00000527169 | TAF |
| 55% | chr11 | 93468219 | 93468129 | − | chr11 | 93467826 | 93467791; 93467814 | − | ENST00000393259; ENST00000527169 | TAF |
| 51% | chr9 | 6248332 | 6248555 | + | chr9 | 6250474 | 6250599 | + | ENST00000456383; ENST00000381434 | TAF |
| 51% | chr9 | 6248332 | 6248555 | + | chr9 | 6250474 | 6250599 | + | ENST00000456383; ENST00000381434 | TAF |
| 36% | chr8 | 104389530 | 104389551 | + | chr8 | 104390255 | 104390471 | + | ENST00000330295; ENST00000520337 | TAF |
| 34% | chr13 | 28224759 | 28225489 | + | chr13 | 28239823 | 28240090 | + | ENST00000399697 | TAF |
| 33% | chr11 | 424193 | 423942 | − | chr11 | 421198 | 421141 | − | ENST00000332826 | TAF |
| 30% | chr13 | 43628887 | 43629679 | + | chr13 | 43643066 | 43643139 | + | ENST00000379221 | TAF |
| 28% | chr14 | 51360331 | 51362440 | + | chr14 | 51368547 | 51368629 | + | ENST00000337334; ENST00000353130; ENST00000395752 | TSF |
| 27% | chr17 | 79911953 | 79911734 | − | chr17 | 79911143 | 79910837 | − | ENST00000409678 | TAF |
| 24% | chr20 | 44420870 | 44421070 | + | chr20 | 44421316 | 44421386 | + | ENST00000372622; ENST00000449078; ENST00000456939 | TAF |
| 24% | chr20 | 44420870 | 44421070 | + | chr20 | 44421316 | 44421386 | + | ENST00000372622; ENST00000449078; ENST00000456939 | TAF |
| 24% | chr20 | 44420870 | 44421070 | + | chr20 | 44421316 | 44421386 | + | ENST00000372622; ENST00000449078; ENST00000456939 | TAF |
| 24% | chr13 | 43628887 | 43629679 | + | chr13 | 43639822 | 43639873 | + | ENST00000379221 | TAF |
| 24% | chr13 | 101090702 | 101090970 | + | chr13 | 101101506 | 101101559 | + | ENST00000376279; ENST00000376286; ENST00000376285; ENST00000458283; ENST00000413170 | TSF |
| 24% | chr13 | 101090702 | 101090970 | + | chr13 | 101101506 | 101101559 | + | ENST00000376279; ENST00000376286; ENST00000376285; ENST00000458283; ENST00000413170 | TSF |
| 24% | chr13 | 101090702 | 101090970 | + | chr13 | 101101506 | 101101559 | + | ENST00000376279; ENST00000376286; ENST00000376285; ENST00000458283; ENST00000413170 | TSF |
| 23% | chr14 | 65406849 | 65406835 | − | chr14 | 65406556 | 65406206 | − | ENST00000389614; ENST00000557049 | TAF |
| 20% | chr2 | 85053636 | 85053622 | − | chr2 | 85051328 | 85051077 | − | ENST00000335459; ENST00000409520 | TSF |
| 19% | chr5 | 135398466 | 135398602 | + | chr5 | 135398875 | 135398915; 135398898 | + | ENST00000442011; ENST00000305126; ENST00000514554; ENST00000508076; ENST00000503087 | TAF |
| 19% | chr5 | 135398466 | 135398602 | + | chr5 | 135398875 | 135398915; 135398898 | + | ENST00000442011; ENST00000305126; ENST00000514554; ENST00000508076; ENST00000503087 | TAF |
| 18% | chr13 | 76173531 | 76175706 | + | chr13 | 76178905 | 76178963 | + | ENST00000377595; ENST00000419068 | TAF |
| 18% | chrX | 100125243 | 100124234 | − | chrX | 100118584 | 100118474 | − | ENST00000372966; ENST00000372964; ENST00000217885 | TAF |
| 18% | chrX | 100125243 | 100124234 | − | chrX | 100118584 | 100118474 | − | ENST00000372966; ENST00000372964; ENST00000217885 | TAF |
| 18% | chrX | 100125243 | 100124234 | − | chrX | 100118584 | 100118474 | − | ENST00000372966; ENST00000372964; ENST00000217885 | TAF |
| 18% | chr1 | 59980221 | 59980497 | + | chr1 | 60019796 | 60019899 | + | ENST00000371218; ENST00000303721; ENST00000430447; ENST00000371212 | TSF |
| 18% | chr1 | 59980221 | 59980497 | + | chr1 | 60019796 | 60019899 | + | ENST00000371218; ENST00000303721; ENST00000430447; ENST00000371212 | TSF |
| 18% | chr1 | 59980221 | 59980497 | + | chr1 | 60019796 | 60019899 | + | ENST00000371218; ENST00000303721; ENST00000430447; ENST00000371212 | TSF |
| 17% | chr20 | 61301271 | 61301405 | + | chr20 | 61303102 | 61303245 | + | ENST00000217159; ENST00000370507; ENST00000451793 | TAF |

TABLE 52-continued

Transcript fusion for Rectum adenocarcinoma (READ) Coordinates of the fusion sequences for which the donor is the exon.

| 1 | 2' | 3' | 4' | 5' | 6' | 7' | 8' | 9' | 10' | 11' |
|---|---|---|---|---|---|---|---|---|---|---|
| 16% | chr12 | 20780314 | 20780410 | + | chr12 | 20782842 | 20783061 | + | ENST00000359062 | TAF |
| 15% | chr13 | 43659219 | 43659268 | + | chr13 | 43659904 | 43659974 | + | ENST00000379221 | TAF |
| 15% | chr7 | 116364854 | 116364901 | + | chr7 | 116371722 | 116371913 | + | ENST00000397752; ENST00000318493; ENST00000436117 | TAF |
| 15% | chr7 | 116364854 | 116364901 | + | chr7 | 116371722 | 116371913 | + | ENST00000397752; ENST00000318493; ENST00000436117 | TAF |
| 15% | chr7 | 116364854 | 116364901 | + | chr7 | 116371722 | 116371913 | + | ENST00000397752; ENST00000318493; ENST00000436117 | TAF |
| 15% | chr20 | 33601951 | 33601885 | − | chr20 | 33600869 | 33600811 | − | ENST00000451813; ENST00000252015; ENST00000539834; ENST00000432634 | TAF |
| 15% | chr7 | 100850556 | 100850506 | − | chr7 | 100850185 | 100850060 | − | ENST00000454310; ENST00000223127 | TSF |
| 14% | chr2 | 99797199 | 99797170 | − | chr2 | 99790479 | 99790378 | − | ENST00000422537; ENST00000289359; ENST00000409107 | TAF |
| 14% | chr2 | 99797199 | 99797170 | − | chr2 | 99790479 | 99790378 | − | ENST00000422537; ENST00000289359; ENST00000409107 | TAF |
| 14% | chr2 | 85059551 | 85059512 | − | chr2 | 85059269 | 85059179 | | ENST00000335459; ENST00000409520 | TAF |
| 13% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 13% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 13% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 13% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 13% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 13% | chr3 | 9953662 | 9953735 | + | chr3 | 9955640 | 9955708 | + | ENST00000421412; ENST00000295980; ENST00000383814; ENST00000454190 | TAF |
| 13% | chr3 | 9953662 | 9953735 | + | chr3 | 9955640 | 9955708 | + | ENST00000421412; ENST00000295980; ENST00000383814; ENST00000454190 | TAF |
| 13% | chr1 | 165863702 | 165863816 | + | chr1 | 165865427 | 165865569 | + | ENST00000367879 | TAF |
| 13% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 13% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 13% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 13% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 13% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 13% | chr10 | 120902016 | 120901765 | − | chr10 | 120900831 | 120900754 | − | ENST00000355697; ENST00000330036 | TAF |
| 13% | chr1 | 59843828 | 59844080 | + | chr1 | 59844421 | 59844509 | + | ENST00000413489; ENST00000371218; ENST00000303721; ENST00000430447; ENST00000371212 | TSF |
| 13% | chr1 | 59843828 | 59844080 | + | chr1 | 59844421 | 59844509 | + | ENST00000413489; ENST00000371218; ENST00000303721; ENST00000430447; ENST00000371212 | TSF |
| 13% | chr1 | 59843828 | 59844080 | + | chr1 | 59844421 | 59844509 | + | ENST00000413489; ENST00000371218; ENST00000303721; ENST00000430447; ENST00000371212 | TSF |
| 13% | chr1 | 59843828 | 59844080 | + | chr1 | 59844421 | 59844509 | + | ENST00000413489; ENST00000371218; ENST00000303721; ENST00000430447; ENST00000371212 | TSF |
| 13% | chr12 | 15701006 | 15701267 | + | chr12 | 15702028 | 15702160 | + | ENST00000281171; ENST00000348962; ENST00000535311 | TSF |

TABLE 52-continued

Transcript fusion for Rectum adenocarcinoma (READ) Coordinates of the fusion sequences for which the donor is the exon.

| 1 | 2' | 3' | 4' | 5' | 6' | 7' | 8' | 9' | 10' | 11' |
|---|---|---|---|---|---|---|---|---|---|---|
| 13% | chr12 | 15701006 | 15701267 | + | chr12 | 15702028 | 15702160 | + | ENST00000281171; ENST00000348962; ENST00000535311 | TSF |
| 13% | chr12 | 15701006 | 15701267 | + | chr12 | 15702028 | 15702160 | + | ENST00000281171; ENST00000348962; ENST00000535311 | TSF |
| 12% | chr4 | 107241932 | 107242850 | + | chr4 | 107246142 | 107246275 | + | ENST00000394701 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| 12% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; | TAF |

TABLE 52-continued

Transcript fusion for Rectum adenocarcinoma (READ) Coordinates of the fusion sequences for which the donor is the exon.

| 1 | 2' | 3' | 4' | 5' | 6' | 7' | 8' | 9' | 10' | 11' |
|---|---|---|---|---|---|---|---|---|---|---|
| 11% | chr21 | 42597177 | 42597622 | + | chr21 | 42598193 | 42598281 | + | ENST00000480611; ENST00000485433; ENST00000496368; ENST00000421861 ENST00000328735; ENST00000330333; ENST00000347667 | TAF |
| 11% | chr21 | 42597177 | 42597622 | + | chr21 | 42598193 | 42598281 | + | ENST00000328735; ENST00000330333; ENST00000347667 | TAF |
| 11% | chr21 | 42597177 | 42597622 | + | chr21 | 42598193 | 42598281 | + | ENST00000328735; ENST00000330333; ENST00000347667 | TAF |
| 11% | chr20 | 35844460 | 35844528 | + | chr20 | 35852281 | 35852372 | + | ENST00000237530; ENST00000373622 | TAF |
| 11% | chr20 | 35844460 | 35844528 | + | chr20 | 35852281 | 35852372 | + | ENST00000237530; ENST00000373622 | TAF |
| 11% | chr11 | 63953789 | 63953882 | + | chr11 | 63960550 | 63960759 | + | ENST00000358794; ENST00000305218; ENST00000536973; ENST00000538945; ENST00000543847 | TAF |
| 11% | chr11 | 63953789 | 63953882 | + | chr11 | 63960550 | 63960759 | + | ENST00000358794; ENST00000305218; ENST00000536973; ENST00000538945; ENST00000543847 | TAF |
| 11% | chr11 | 63953789 | 63953882 | + | chr11 | 63960550 | 63960759 | + | ENST00000358794; ENST00000305218; ENST00000536973; ENST00000538945; ENST00000543847 | TAF |
| 11% | chr11 | 63953789 | 63953882 | + | chr11 | 63960550 | 63960759 | + | ENST00000358794; ENST00000305218; ENST00000536973; ENST00000538945; ENST00000543847 | TAF |
| 11% | chr9 | 33787120 | 33787393 | + | chr9 | 33796641 | 33796800 | + | ENST00000361005; ENST00000457896; ENST00000342836; ENST00000429677; ENST00000379405 | TAF |
| 11% | chr9 | 33787120 | 33787393 | + | chr9 | 33796641 | 33796800 | + | ENST00000361005; ENST00000457896; ENST00000342836; ENST00000429677; ENST00000379405 | TAF |
| 11% | chr13 | 41835911 | 41835827 | − | chr13 | 41835051 | 41834629 | − | ENST00000430347 | TAF |
| 11% | chr5 | 173041966 | 173041919 | − | chr5 | 173040258 | 173040134 | − | ENST00000311086; ENST00000285908 | TAF |
| 11% | chr5 | 173041966 | 173041919 | − | chr5 | 173040258 | 173040134 | − | ENST00000311086; ENST00000285908 | TAF |
| 7% | chr13 | 34394352 | 34394605 | + | chr13 | 34395269 | 34395406 | + | ENST00000380071; ENST00000434425 | TSF |
| 7% | chr13 | 34394352 | 34394605 | + | chr13 | 34395269 | 34395406 | + | ENST00000380071; ENST00000434425 | TSF |
| 7% | chr14 | 51360331 | 51360476 | + | chr14 | 51368547 | 51368629 | + | ENST00000337334; ENST00000353130; ENST00000395752 | TSF |
| 6% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 6% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 6% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 6% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 6% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 6% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 6% | chr20 | 9311166 | 9311205 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 6% | chr7 | 117315827 | 117316035 | + | chr7 | 117355812 | 117355913 | + | ENST00000600166 | TSF |
| 6% | chr8 | 128749913 | 128749923 | + | chr8 | 128750494 | 128751265 | + | ENST00000377970 | TSF |
| 6% | chr21 | 40180090 | 40180187 | + | chr21 | 40181959 | 40182030 | + | ENST00000360214; ENST00000360938; ENST00000432278; ENST00000456966 | TSF |
| 6% | chr21 | 40180090 | 40180187 | + | chr21 | 40181959 | 40182030 | + | ENST00000360214; ENST00000360938; | TSF |

TABLE 52-continued

Transcript fusion for Rectum adenocarcinoma (READ) Coordinates of the fusion sequences for which the donor is the exon.

| 1 | 2' | 3' | 4' | 5' | 6' | 7' | 8' | 9' | 10' | 11' |
|---|---|---|---|---|---|---|---|---|---|---|
| 6% | chr21 | 40180090 | 40180187 | + | chr21 | 40181959 | 40182030 | + | ENST00000432278; ENST00000456966 ENST00000360214; ENST00000360938; ENST00000432278; ENST00000456966 | TSF |
| 6% | chr19 | 48627094 | 48627044 | − | chr19 | 48626575 | 48626431 | − | ENST00000263274; ENST00000536218; ENST00000594759; ENST00000427526; ENST00000601091 | TSF |
| 6% | chr19 | 48627094 | 48627044 | − | chr19 | 48626575 | 48626431 | − | ENST00000263274; ENST00000536218; ENST00000594759; ENST00000427526; ENST00000601091 | TSF |

TABLE 53

Transcript fusion for Sarcoma (SARC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 22% | chr12 | 6943089 | 6943213 | + | ENST00000251761; ENST00000396725; ENST00000606935 | chr12 | 6943989 | 6944119 | + | TAF |
| 22% | chr12 | 6943089 | 6943213 | + | ENST00000251761; ENST00000396725; ENST00000606935 | chr12 | 6943989 | 6944119 | + | TAF |
| 22% | chr12 | 6943089 | 6943213 | + | ENST00000251761; ENST00000396725; ENST00000606935 | chr12 | 6943989 | 6944119 | + | TAF |
| 20% | chr20 | 48124601 | 48124521 | − | ENST00000244043 | chr20 | 48123357 | 48123321 | − | TAF |
| 18% | chr15 | 79054907 | 79054745 | − | ENST00000388820 | chr15 | 79054428 | 79054400 | − | TAF |
| 18% | chr9 | 131002264 | 131002275 | + | ENST00000475805; ENST00000341179; ENST00000372923; ENST00000393594; ENST00000486160 | chr9 | 131002706 | 131002973 | + | TAF |
| 18% | chr9 | 131002264 | 131002275 | + | ENST00000475805; ENST00000341179; ENST00000372923; ENST00000393594; ENST00000486160 | chr9 | 131002706 | 131002973 | + | TAF |
| 18% | chr11 | 74414012 | 74413839 | − | ENST00000263671; ENST00000376332; ENST00000528789 | chr11 | 74412552 | 74412398 | − | TAF |
| 18% | chr11 | 74414012 | 74413839 | − | ENST00000263671; ENST00000376332; ENST00000528789 | chr11 | 74412552 | 74412398 | − | TAF |
| 16% | chr1 | 11115983; 11115877 | 11115838 | − | ENST00000376957; ENST00000490101 | chr1 | 11115464 | 11115178 | − | TSF |
| 16% | chr1 | 11115983; 11115877 | 11115838 | − | ENST00000376957; ENST00000490101 | chr1 | 11115464 | 11115178 | − | TSF |
| 15% | chr20 | 3654143 | 3654001 | − | ENST00000356518; ENST00000379861; ENST00000350009 | chr20 | 3653870 | 3653815 | − | TAF |
| 15% | chr16 | 15844188 | 15843995 | − | ENST00000396324; ENST00000452625; ENST00000576790; ENST00000300036 | chr16 | 15842631 | 15842472 | − | TAF |
| 15% | chr16 | 15844188 | 15843995 | − | ENST00000396324; ENST00000452625; ENST00000576790; ENST00000300036 | chr16 | 15842631 | 15842472 | − | TAF |
| 14% | chr22 | 38074490 | 38074661 | + | ENST00000215909 | chr22 | 38079136 | 38079241 | + | TAF |
| 14% | chr8 | 74939024 | 74939076 | + | ENST00000284818; ENST00000518893 | chr8 | 74944554 | 74944936 | + | TAF |
| 14% | chr8 | 74939024 | 74939076 | + | ENST00000284818; ENST00000518893 | chr8 | 74944554 | 74944936 | + | TAF |
| 14% | chr8 | 121282274 | 121282413 | + | ENST00000309791; ENST00000297848; ENST00000247781 | chr8 | 121289724 | 121290171 | + | TSF |
| 14% | chr8 | 121282274 | 121282413 | + | ENST00000309791; ENST00000297848; ENST00000247781 | chr8 | 121289724 | 121290171 | + | TSF |
| 12% | chrX | 152730513 | 152730446 | − | ENST00000370211; ENST00000370212; ENST00000370210 | chrX | 152728559 | 152728505 | − | TAF |
| 12% | chrX | 152730513 | 152730446 | − | ENST00000370211; ENST00000370212; ENST00000370210 | chrX | 152728559 | 152728505 | − | TAF |
| 12% | chr20 | 53092486 | 53092551 | + | ENST00000262593 | chr20 | 53111339 | 53111426 | + | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 11% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |

TABLE 53-continued

Transcript fusion for Sarcoma (SARC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 11% | chr20 | 35842163 | 35842268 | + | ENST00000237530; ENST00000373622 | chr20 | 35844460 | 35844765 | + | TAF |
| 11% | chr20 | 35842163 | 35842268 | + | ENST00000237530; ENST00000373622 | chr20 | 35844460 | 35844765 | + | TAF |
| 11% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST 00000379530; ENST00000463100; ENST00000481240; ENST00000467317; ENST00000478732 | chr6 | 10829240 | 10829256 | + | TAF |
| 11% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 10% | chr4 | 1742553 | 1742713 | + | ENST00000313288 | chr4 | 1745122 | 1745307 | + | TAF |
| 10% | chr9 | 101984828 | 101984925 | + | ENST00000223641 | chr9 | 101986374 | 101986588 | + | TAF |
| 10% | chr11 | 74412691 | 74412637 | − | ENST00000263671 | chr11 | 74412552 | 74412398 | − | TAF |
| 10% | chr13 | 111138002 | 111138183 | + | ENST00000360467 | chr13 | 111139687 | 111139825 | + | TSF |
| 8% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 8% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 8% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 8% | chr12 | 58024115 | 58023935 | − | ENST00000341156; ENST00000418555; ENST00000552798; ENST00000549391; ENST00000449184; ENST00000550764; ENST00000552350; ENST00000548888 | chr12 | 58023079 | 58022983 | − | TSF |
| 8% | chr15 | 74219125 | 74220226 | + | ENST00000566011; ENST00000261921 | chr15 | 74234853 | 74234966 | + | TSF |
| 8% | chr7 | 73459552 | 73459623 | + | ENST00000445912; ENST00000252034; ENST00000358929; ENST00000320492; ENST00000438906; ENST00000414324; ENST00000380562; ENST00000380575; ENST 00000380584; ENST00000458204; ENST00000357036; ENST00000429192; ENST00000380576; ENST00000320399 | chr7 | 73460337 | 73460377 | + | TSF |
| 8% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 8% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 8% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 8% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr3 | 48716169 | 48715997 | − | ENST00000341520; ENST00000416649; ENST00000294129; ENST00000413374 | chr3 | 48702393 | 48702198 | − | TSF |
| 7% | chr3 | 48716169 | 48715997 | − | ENST00000341520; ENST00000416649; | chr3 | 48702393 | 48702198 | − | TSF |

TABLE 53-continued

Transcript fusion for Sarcoma (SARC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 7% | chr3 | 48716169 | 48715997 | – | ENST00000294129; ENST00000413374; ENST00000341520; ENST00000416649; ENST00000294129; ENST00000413374 | chr3 | 48702393 | 48702198 | – | TSF |
| 7% | chr12 | 8807077 | 8807033 | – | ENST00000535411; ENST00000359478; ENST00000396549; ENST00000543369; ENST00000544211; ENST00000535336; ENST00000540087; ENST00000537009; ENST00000544889 | chr12 | 8793960 | 8793803 | – | TSF |
| 7% | chr12 | 8807077 | 8807033 | – | ENST00000535411; ENST00000359478; ENST00000396549; ENST00000543369; ENST00000544211; ENST00000535336; ENST00000540087; ENST00000537009; ENST00000544889 | chr12 | 8793960 | 8793803 | – | TSF |
| 7% | chr12 | 8807077 | 8807033 | – | ENST00000535411; ENST00000359478; ENST00000396549; ENST00000543369; ENST00000544211; ENST00000535336; ENST00000540087; ENST00000537009; ENST00000544889 | chr12 | 8793960 | 8793803 | – | TSF |
| 5% | chr1 | 25891664 | 25891698 | + | ENST00000374338 | chr1 | 25916660 | 25916675 | + | TSF |
| 5% | chr10 | 81901900; 81901838 | 81901935 | + | ENST00000372270; ENST00000372267; ENST00000372263 | chr10 | 81903525 | 81903598 | + | TSF |
| 5% | chr10 | 81901900; 81901838 | 81901935 | + | ENST00000372270; ENST00000372267; ENST00000372263 | chr10 | 81903525 | 81903598 | + | TSF |
| 5% | chr20 | 48184653 | 48184580 | – | ENST00000244043 | chr20 | 48177475 | 48177085 | – | TSF |
| 4% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 4% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 4% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 4% | chr1 | 225156461 | 225156576 | + | ENST00000430092; ENST00000400952; ENST00000366849; ENST00000439375 | chr1 | 225157336 | 225158402 | + | TSF |
| 4% | chr1 | 225156461 | 225156576 | + | ENST00000430092; ENST00000400952; ENST00000366849; ENST00000439375 | chr1 | 225157336 | 225158402 | + | TSF |
| 4% | chr2 | 28352138 | 28352247 | + | ENST00000344773; ENST00000379624; ENST00000342045; ENST00000361704; ENST00000379632; ENST00000379629 | chr2 | 28362015 | 28362218 | + | TSF |
| 4% | chr15 | 65687596 | 65687432 | – | ENST00000352385 | chr15 | 65687004 | 65686908 | – | TSF |
| 4% | chr6 | 85448309 | 85448215 | – | ENST00000606784; ENST00000369663 | chr6 | 85377422 | 85377053 | – | TSF |
| 4% | chr6 | 85448309 | 85448215 | – | ENST00000606784; ENST00000369663 | chr6 | 85377422 | 85377053 | – | TSF |
| 3% | chr3 | 13659576 | 13659785 | + | ENST00000535798; ENST00000404922; ENST00000295760; ENST00000492059 | chr3 | 13660222 | 13660288 | + | TSF |
| 3% | chr3 | 13659576 | 13659785 | + | ENST00000535798; ENST00000404922; ENST00000295760; ENST00000492059 | chr3 | 13660222 | 13660288 | + | TSF |
| 3% | chr2 | 112933291 | 112933416 | + | ENST00000331203; ENST00000409903; ENST00000409450; ENST00000441565 | chr2 | 112935633 | 112935771 | + | TSF |
| 3% | chr2 | 112933291 | 112933416 | + | ENST00000331203; ENST00000409903; ENST00000409450; ENST00000441565 | chr2 | 112935633 | 112935771 | + | TSF |
| 3% | chr20 | 29632611 | 29632721 | + | ENST00000278882; ENST00000358464 | chr20 | 29652086 | 29652324 | + | TSF |
| 3% | chr15 | 74234216 | 74234399 | + | ENST00000566011 | chr15 | 74234853 | 74234966 | + | TSF |
| 3% | chr1 | 161968139 | 161967615 | – | ENST00000294794; ENST00000367940 | chr1 | 161962049 | 161961535 | – | TSF |
| 3% | chr1 | 161968139 | 161967615 | – | ENST00000294794; ENST00000367940 | chr1 | 161962049 | 161961535 | – | TSF |
| 3% | chr17 | 66972154 | 66972092 | – | ENST00000340001; ENST00000453985 | chr17 | 66971441 | 66970995 | – | TSF |
| 3% | chr17 | 66972154 | 66972092 | – | ENST00000340001; ENST00000453985 | chr17 | 66971441 | 66970995 | – | TSF |
| 3% | chr10 | 127483547 | 127483449 | – | ENST00000368797; ENST00000368786 | chr10 | 127473829 | 127473633 | – | TSF |
| 3% | chr7 | 22532348 | 22532184 | – | ENST00000406890; ENST00000404369; ENST00000424363 | chr7 | 22512853 | 22512669 | – | TSF |
| 3% | chr7 | 22532348 | 22532184 | – | ENST00000406890; ENST00000404369; ENST00000424363 | chr7 | 22512853 | 22512669 | – | TSF |
| 3% | chr1 | 25883644 | 25883758 | + | ENST00000374338 | chr1 | 25916660 | 25916675 | + | TSF |
| 3% | chr3 | 13659576 | 13659785 | + | ENST00000535798; ENST00000404922; ENST00000295760; ENST00000492059 | chr3 | 13660219 | 13660288 | + | TSF |
| 3% | chr3 | 13659576 | 13659785 | + | ENST00000535798; ENST00000404922; ENST00000295760; ENST00000492059 | chr3 | 13660219 | 13660288 | + | TSF |
| 3% | chr1 | 2492063 | 2492153 | + | ENST00000426449; ENST00000434817; ENST00000435221; ENST00000451778; ENST00000409119; ENST00000355716 | chr1 | 2508457 | 2508463 | + | TSF |
| 3% | chr7 | 91509397 | 91509369 | – | ENST00000351870; ENST00000442961 | chr7 | 91430582 | 91429696 | – | TSF |
| 3% | chr5 | 121405863 | 121405748 | – | ENST00000231004 | chr5 | 121403052 | 121403016 | – | TSF |
| 3% | chr7 | 75617128 | 75617036 | – | ENST00000493111 | chr7 | 75603302 | 75603295 | – | TSF |
| 3% | chr8 | 52287291 | 52287157 | – | ENST00000522628; ENST00000356297; ENST00000543296 | chr8 | 52286772 | 52286772 | – | TSF |

TABLE 53-continued

Transcript fusion for Sarcoma (SARC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 3% | chr8 | 52287291 | 52287157 | − | ENST00000522628; ENST00000356297; ENST00000543296 | chr8 | 52286772 | 52286772 | − | TSF |
| 3% | chr4 | 83626566 | 83626436 | − | ENST00000319540; ENST00000273908; ENST0000282709 | chr4 | 83616035 | 83615829 | − | TSF |
| 3% | chr10 | 128019078 | 128018981 | − | ENST00000368679; ENST00000368676; ENST00000448723 | chr10 | 127981199 | 127981183 | − | TSF |
| 3% | chr17 | 73887428 | 73887358 | − | ENST00000591668; ENST00000592642; ENST00000269383; ENST00000543309 | chr17 | 73885428 | 73885139 | − | TSF |
| 3% | chr17 | 73887428 | 73887358 | − | ENST00000591668; ENST00000592642; ENST00000269383; ENST00000543309 | chr17 | 73885428 | 73885139 | − | TSF |
| 3% | chr17 | 73887428 | 73887358 | − | ENST00000591668; ENST00000592642; ENST00000269383; ENST00000543309 | chr17 | 73885428 | 73885139 | − | TSF |
| 3% | chr17 | 73887428 | 73887358 | − | ENST00000591668; ENST00000592642; ENST00000269383; ENST00000543309 | chr17 | 73885428 | 73885139 | − | TSF |
| 3% | chr19 | 41838186 | 41838033 | − | ENST00000598758; ENST00000221930 | chr19 | 41818843 | 41818697 | − | TSF |
| 3% | chr19 | 41838186 | 41838033 | − | ENST00000598758; ENST00000221930 | chr19 | 41818843 | 41818697 | − | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr16 | 30783410 | 30783511 | + | ENST00000324685; ENST00000402121; ENST00000563683; ENST00000357890 | chr16 | 30785136 | 30785155 | + | TSF |
| 2% | chr8 | 41387722 | 41387817 | + | ENST00000276533; ENST00000520354; ENST00000520710; ENST00000518671; ENST00000523277 | chr8 | 41388646 | 41388815 | + | TSF |
| 2% | chr9 | 17143286 | 17143374 | + | ENST00000380647; ENST00000262360; ENST00000425824; ENST00000380641 | chr9 | 17166816 | 17167136 | + | TSF |
| 2% | chr9 | 133301074 | 133301311 | + | ENST00000428715 | chr9 | 133302166 | 133302266 | + | TSF |
| 2% | chr13 | 114157811 | 114157903 | + | ENST00000434316; ENST00000375391 | chr13 | 114159741 | 114159770 | + | TSF |
| 2% | chr19 | 48830778 | 48830880 | + | ENST00000599704; ENST00000270221; ENST00000599255; ENST00000597279 | chr19 | 48832237 | 48832399 | + | TSF |
| 2% | chr12 | 69656249 | 69656342 | + | ENST00000551516 | chr12 | 69673004 | 69673309 | + | TSF |
| 2% | chr1 | 170705189 | 170705309 | + | ENST00000239461 | chr1 | 170706854 | 170706973 | + | TSF |
| 2% | chr12 | 113623819 | 113623826 | + | ENST00000552495 | chr12 | 113623998 | 113624117 | + | TSF |
| 2% | chr5 | 179315312 | 179315103 | − | ENST00000355235; ENST00000356834 | chr5 | 179312136 | 179312132 | − | TSF |
| 2% | chrX | 41598709 | 41598637 | − | ENST00000421587; ENST00000318588; ENST00000361962; ENST00000378163; ENST00000378158; ENST00000378166; ENST00000442742; ENST00000378154 | chrX | 41557348 | 41557057 | − | TSF |
| 2% | chr5 | 54993786 | 54993674 | − | ENST00000396865; ENST00000539768; ENST00000318672; ENST00000508124; ENST00000511233; ENST00000503891; ENST00000513993; ENST00000505563; ENST 00000506624; ENST00000507109 | chr5 | 54993040 | 54992544 | − | TSF |
| 2% | chr17 | 17127457 | 17127236 | − | ENST00000285071; ENST00000389169; ENST00000417064 | chr17 | 17126584 | 17126403 | − | TSF |
| 2% | chr17 | 17127457 | 17127236 | − | ENST00000285071; ENST00000389169; ENST00000417064 | chr17 | 17126584 | 17126403 | − | TSF |
| 2% | chr15 | 89456550 | 89456478 | − | ENST00000558018; ENST00000268151; ENST00000268150; ENST00000566497; ENST00000542878; ENST00000558029 | chr15 | 89453897 | 89453853 | − | TSF |
| 2% | chr5 | 147281336 | 147281192 | − | ENST00000318315; ENST00000515291 | chr5 | 147230105 | 147229718 | − | TSF |
| 2% | chr20 | 42789047 | 42788258 | − | ENST00000372980 | chr20 | 42726338 | 42726029 | − | TSF |
| 2% | chr4 | 28372431 | 28372322 | − | ENST00000507759 | chr4 | 28319160 | 28318916 | − | TSF |
| 2% | chr3 | 194325174; 194325170 | 194325016 | − | ENST00000392432; ENST00000273580; ENST00000432352; ENST00000381975; ENST00000347147; ENST00000473092; ENST00000452358 | chr3 | 194296178 | 194295847 | − | TSF |
| 2% | chr3 | 194325174; 194325170 | 194325016 | − | ENST00000392432; ENST00000273580; ENST00000432352; ENST00000381975; ENST00000347147; ENST00000473092; ENST00000452358 | chr3 | 194296178 | 194295847 | − | TSF |
| 2% | chr3 | 194325174; 194325170 | 194325016 | − | ENST00000392432; ENST00000273580; ENST00000432352; ENST00000381975; ENST00000347147; ENST00000473092; ENST00000452358 | chr3 | 194296178 | 194295847 | − | TSF |
| 2% | chr3 | 194325174; 194325170 | 194325016 | − | ENST00000392432; ENST00000273580; ENST00000432352; ENST00000381975; ENST00000347147; ENST00000473092; ENST00000452358 | chr3 | 194296178 | 194295847 | − | TSF |
| 2% | chr3 | 194325174; 194325170 | 194325016 | − | ENST00000392432; ENST00000273580; ENST00000432352; ENST00000381975; ENST00000347147; ENST00000473092; | chr3 | 194296178 | 194295847 | − | TSF |

TABLE 53-continued

Transcript fusion for Sarcoma (SARC) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| | | | | | ENST00000452358 | | | | | |

TABLE 54

Transcript fusion for Sarcoma (SARC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 57% | chr8 | 104389530 | 104389551 | + | chr8 | 104390255 | 104390471 | + | ENST00000330295; ENST00000520337 | TAF |
| 36% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 36% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 36% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 36% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 36% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 36% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 34% | chr9 | 131189761 | 131190058 | + | chr9 | 131190581 | 131190700; 131190702 | + | ENST00000372842; ENST00000420512; ENST00000372838 | TAF |
| 34% | chr9 | 131189761 | 131190058 | + | chr9 | 131190581 | 131190700; 131190702 | + | ENST00000372842; ENST00000420512; ENST00000372838 | TAF |
| 31% | chr7 | 2289080 | 2289115 | + | chr7 | 2289492 | 2289637 | + | ENST00000356714; ENST00000397049; ENST00000397046; ENST00000397048; ENST00000339737; ENST00000343985 | TAF |
| 23% | chr9 | 131002678 | 131002811 | + | chr9 | 131004511 | 131004624 | + | ENST00000475805; ENST00000341179; ENST00000372923; ENST00000393594; ENST00000486160 | TAF |
| 23% | chr9 | 131002678 | 131002811 | + | chr9 | 131004511 | 131004624 | + | ENST00000475805; ENST00000341179; ENST00000372923; ENST00000393594; ENST00000486160 | TAF |
| 22% | chr7 | 2289080 | 2289194 | + | chr7 | 2289492 | 2289637 | + | ENST00000356714; ENST00000397049; ENST00000397046; ENST00000397048; ENST00000339737; ENST00000343985 | TAF |
| 22% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 22% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 22% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 22% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 22% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 22% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 21% | chr17 | 79214190 | 79214239 | + | chr17 | 79214787 | 79214816; 79214953 | + | ENST00000431388; ENST00000576002 | TAF |
| 21% | chr17 | 79214190 | 79214239 | + | chr17 | 79214787 | 79214816; 79214953 | + | ENST00000431388; ENST00000576002 | TAF |
| 20% | chr7 | 150938296 | 150938250 | − | chr7 | 150937608 | 150937511 | − | ENST00000262188; ENST00000392811; ENST00000356800 | TAF |
| 19% | chr19 | 41732717 | 41732817 | + | chr19 | 41736872 | 41736952 | + | ENST00000301178; ENST00000359092 | TAF |
| 19% | chr19 | 41732717 | 41732817 | + | chr19 | 41736872 | 41736952 | + | ENST00000301178; ENST00000359092 | TAF |
| 19% | chr7 | 73466655 | 73466891 | + | chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 19% | chr7 | 73466655 | 73466891 | + | chr7 | 73467493 | 73467639 | + | ENST00000445912; ENST00000252034; ENST00000358929; ENST00000320492; ENST00000414324; ENST00000380562; | TAF |

TABLE 54-continued

Transcript fusion for Sarcoma (SARC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 19% | chr7 | 73466655 | 73466891 | + | chr7 | 73467493 | 73467639 | + | ENST00000380575; ENST00000380584; ENST00000458204; ENST00000357036; ENST00000429192; ENST00000380553; ENST00000380576; ENST00000320399 ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000 380553; ENST00000380576; ENST00000320399 | TAF |
| 19% | chr7 | 73466655 | 173466891 | + | chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000 380553; ENST00000380576; ENST00000320399 | TAF |
| 19% | chr7 | 73466655 | 73466891 | + | chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 19% | chr7 | 73466655 | 73466891 | + | chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 19% | chr7 | 73466655 | 73466891 | + | chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 19% | chr7 | 73466655 | 73466891 | + | chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000 380553; ENST00000380576; ENST00000320399 | TAF |
| 19% | chr7 | 73466655 | 73466891 | + | chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 17% | chr17 | 39974832 | 39974854 | + | chr17 | 39975462 | 39975651 | + | ENST00000321562 | TAF |
| 17% | chr1 | 246581335 | 246580598 | − | chr1 | 246518396 | 246518333 | − | ENST00000388985; ENST00000403792 | TSF |
| 17% | chr1 | 246581335 | 246580598 | − | chr1 | 246518396 | 246518333 | − | ENST00000388985; ENST00000403792 | TSF |
| 16% | chr6 | 5498702 | 5498789 | + | chr6 | 5545413 | 5545573 | + | ENST00000324331; ENST00000274680 | TSF |
| 15% | chr11 | 93468219 | 93468129 | − | chr11 | 93467826 | 93467791; 93467814 | − | ENST00000393259; ENST00000527169 | TAF |
| 15% | chr11 | 93468219 | 93468129 | − | chr11 | 93467826 | 93467791; 93467814 | | ENST00000393259; ENST00000527169 | TAF |
| 15% | chr6 | 26474324 | 26474624 | + | chr6 | 26476389 | 26476396 | + | ENST00000480218 | TAF |
| 14% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 14% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 14% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 14% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 14% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 14% | chr2 | 28200909 | 28201241 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 14% | chr9 | 131193013 | 131193223 | + | chr9 | 131193538 | 131193582 | + | ENST00000372842; ENST00000372838 | TAF |
| 14% | chr5 | 135398466 | 135398602 | + | chr5 | 135398875 | 135398915; 135398898 | + | ENST00000442011; ENST00000305126; ENST00000514554; ENST00000508076; ENST00000503087 | TAF |
| 14% | chr5 | 135398466 | 135398602 | + | chr5 | 135398875 | 135398915; 135398898 | | ENST00000442011; ENST00000305126; ENST00000514554; ENST00000508076; ENST00000503087 | TAF |
| 14% | chr17 | 39976225 | 39976301 | + | chr17 | 39976521 | 39976713 | + | ENST00000321562; ENST00000455106; ENST00000544340 | TSF |
| 14% | chr12 | 58023123 | 58023062 | − | chr12 | 58022929 | 58022831; 58022905 | − | ENST00000341156; ENST00000418555; ENST00000552798; ENST00000549391 | TSF |
| 14% | chr12 | 58023123 | 58023062 | − | chr12 | 58022929 | 58022831; 58022905 | − | ENST00000341156; ENST00000418555; ENST00000552798; ENST00000549391 | TSF |

TABLE 54-continued

Transcript fusion for Sarcoma (SARC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 14% | chr17 | 39974832 | 39974893 | + | chr17 | 39975462 | 39975651 | + | ENST00000321562 | TSF |
| 13% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 13% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 13% | chr17 | 80440912 | 80441180 | + | chr17 | 80441592 | 80441655; 48041659 | + | ENST00000390006; ENST00000309794; ENST00000345415; ENST00000457415; ENST00000412079; ENST00000577432; ENST00000584513 | TAF |
| 13% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 13% | chr12 | 6602868 | 6602840 | − | chr12 | 6602138 | 6602028 | − | ENST00000229238 | TAF |
| 12% | chr19 | 3966211 | 3966171 | − | chr19 | 3964989 | 3964629 | − | ENST00000545797; ENST00000301264; ENST00000596311; ENST00000601824; ENST00000593844 | TAF |
| 12% | chr19 | 3966211 | 3966171 | − | chr19 | 3964989 | 3964629 | − | ENST00000545797; ENST00000301264; ENST00000596311; ENST00000601824; ENST00000593844 | TAF |
| 12% | chr19 | 3966211 | 3966171 | − | chr19 | 3964989 | 3964629 | − | ENST00000545797; ENST00000301264; ENST00000596311; ENST00000601824; ENST00000593844 | TAF |
| 12% | chr19 | 3966211 | 3966171 | − | chr19 | 3964989 | 3964629 | − | ENST00000545797; ENST00000301264; ENST00000596311; ENST00000601824; ENST00000593844 | TAF |
| 12% | chr17 | 57885458 | 57885650 | + | chr17 | 57886157 | 57886237; 57886196 | + | ENST00000262291; ENST00000537567; ENST00000539763; ENST00000536180; ENST00000545362; ENST00000592619; ENST00000591877 | TSF |
| 12% | chr17 | 57885458 | 57885650 | + | chr17 | 57886157 | 57886237; 57886196 | + | ENST00000262291; ENST00000537567; ENST00000539763; ENST00000536180; ENST00000545362; ENST00000592619; ENST00000591877 | TSF |
| 12% | chr17 | 57885458 | 57885650 | + | chr17 | 57886157 | 57886237; 57886196 | + | ENST00000262291; ENST00000537567; ENST00000539763; ENST00000536180; ENST00000545362; ENST00000592619; ENST00000591877 | TSF |
| 12% | chr1 | 59843828 | 59844080 | + | chr1 | 59844421 | 59844509 | + | ENST00000413489; ENST00000371218; ENST00000303721; ENST00000430447; ENST00000371212 | TSF |
| 12% | chr1 | 59843828 | 59844080 | + | chr1 | 59844421 | 59844509 | + | ENST00000413489; ENST00000371218; ENST00000303721; ENST00000430447; ENST00000371212 | TSF |
| 12% | chr1 | 59843828 | 59844080 | + | chr1 | 59844421 | 59844509 | + | ENST00000413489; ENST00000371218; ENST00000303721; ENST00000430447; ENST00000371212 | TSF |
| 12% | chr1 | 59843828 | 59844080 | + | chr1 | 59844421 | 59844509 | + | ENST00000413489; ENST00000371218; ENST00000303721; ENST00000430447; ENST00000371212 | TSF |
| 12% | chr15 | 74004214 | 74004264 | + | chr15 | 74005275 | 74005297 | + | ENST00000318443; ENST00000537340; ENST00000318424; ENST00000564751; ENST00000561176; ENST00000559073 | TSF |
| 11% | chr4 | 55109748 | 55109839 | + | chr4 | 55124924 | 55124984 | + | ENST00000512143 | TAF |
| 11% | chr4 | 55096091 | 55096106 | + | chr4 | 55124924 | 55124984 | + | ENST00000512143 | TAF |
| 10% | chr19 | 48832400 | 48832441 | + | chr19 | 48832609 | 48832696; 34882749 | + | ENST00000599704; ENST00000270221; ENST00000597279; ENST00000593437 | TAF |
| 10% | chr19 | 48832400 | 48832441 | + | chr19 | 48832609 | 48832696; 48832749 | + | ENST00000599704; ENST00000270221; ENST00000597279; ENST00000593437 | TAF |
| 10% | chr19 | 48832400 | 48832441 | + | chr19 | 48832609 | 48832696; 48832749 | + | ENST00000599704; ENST00000270221; ENST00000597279; ENST00000593437 | TAF |
| 10% | chr1 | 40781678 | 40781517 | − | chr1 | 40781336 | 40781262 | − | ENST00000372748; ENST00000417105; ENST00000372736 | TAF |
| 10% | chr1 | 40781678 | 40781517 | − | chr1 | 40781336 | 40781262 | − | ENST00000372748; ENST00000417105; ENST00000372736 | TAF |
| 10% | chr1 | 40781678 | 40781517 | − | chr1 | 40781336 | 40781262 | − | ENST00000372748; ENST00000417105; ENST00000372736 | TAF |
| 10% | chr2 | 1675865 | 1675811 | − | chr2 | 1670258 | 1669986 | − | ENST00000252804; ENST00000433670 | TAF |
| 10% | chr2 | 1675865 | 1675811 | − | chr2 | 1670258 | 1669986 | − | ENST00000252804; ENST00000433670 | TAF |
| 10% | chr20 | 44410585 | 44410081 | − | chr20 | 44404241 | 44404056 | − | ENST00000337205; ENST00000243938; ENST00000372632; ENST00000372630 | TAF |
| 9% | chr9 | 117824597 | 117824593 | − | chr9 | 117822281 | 117822009 | − | ENST00000350763; ENST00000341037; ENST00000423613 | TSF |
| 9% | chr9 | 117824597 | 117824593 | − | chr9 | 117822281 | 117822009 | − | ENST00000350763; ENST00000341037; ENST00000423613 | TSF |
| 9% | chr9 | 117824597 | 117824593 | − | chr9 | 117822281 | 117822009 | − | ENST00000350763; ENST00000341037; ENST00000423613 | TSF |
| 8% | chr11 | 86380764 | 86380517 | − | chr11 | 86270855 | 86270732 | − | ENST00000393324; ENST00000359636; ENST00000543262; ENST00000524826; ENST00000526504; ENST00000530335 | TSF |
| 8% | chr11 | 86380764 | 86380517 | − | chr11 | 86270865 | 86270732 | − | ENST00000393324; ENST00000359636; ENST00000543262; ENST00000524826; ENST00000526504; ENST00000530335 | TSF |
| 8% | chr11 | 86380764 | 86380517 | − | chr11 | 86270865 | 86270732 | − | ENST00000393324; ENST00000359636; ENST00000543262; ENST00000524826; ENST00000526504; ENST00000530335 | TSF |
| 8% | chr11 | 86380764 | 86380517 | − | chr11 | 86270865 | 86270732 | − | ENST00000393324; ENST00000359636; ENST00000543262; ENST00000524826; ENST00000526504; ENST00000530335 | TSF |
| 8% | chr20 | 44409050 | 44409038 | − | chr20 | 44404241 | 44404056 | − | ENST00000337205; ENST00000243938; ENST00000372632; ENST00000372630 | TSF |
| 7% | chr8 | 104389530 | 104389536 | + | chr8 | 104390255 | 104390471 | + | ENST00000330295; ENST00000520337 | TSF |
| 7% | chr14 | 32035785 | 32036132 | + | chr14 | 32068495 | 32068585 | + | ENST00000281081; ENST00000547839; ENST00000549838; ENST00000551314; ENST00000536705 | TSF |
| 7% | chr14 | 32035785 | 32036132 | + | chr14 | 32068495 | 32068585 | + | ENST00000281081; ENST00000547839; ENST00000549838; ENST00000551314; ENST00000536705 | TSF |
| 7% | chr14 | 32035785 | 32036132 | + | chr14 | 32068495 | 32068585 | + | ENST00000281081; ENST00000547839; ENST00000549838; | TSF |

TABLE 54-continued

Transcript fusion for Sarcoma (SARC) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 7% | chr14 | 32035785 | 32036132 | + | chr14 | 32068495 | 32068585 | + | ENST00000551314; ENST00000536705 ENST00000281081; ENST00000547839; ENST00000549838; ENST00000551314; ENST00000536705 | TSF |
| 7% | chr9 | 124090761 | 124090761 | + | chr9 | 124091169 | 124091293 | + | ENST00000373823; ENST00000341272; ENST00000373808; ENST00000394353; ENST00000412819; ENST00000436847; ENST00000449733; ENST00000545652; ENST00000373818; ENST00000373807; ENST00000373806 | TSF |
| 7% | chr9 | 124090761 | 124090761 | + | chr9 | 124091169 | 124091293 | + | ENST00000373823; ENST00000341272; ENST00000373808; ENST00000394353; ENST00000412819; ENST00000436847; ENST00000449733; ENST00000545652; ENST00000373818; ENST00000373807; ENST00000373806 | TSF |
| 6% | chr2 | 74762302 | 74762039 | − | chr2 | 74761901 | 74761658 | − | ENST00000264094; ENST00000393937; ENST00000409549; ENST00000409986 | TSF |
| 6% | chr2 | 74762302 | 74762039 | − | chr2 | 74761901 | 74761658 | − | ENST00000264094; ENST00000393937; ENST00000409549; ENST00000409986 | TSF |
| 6% | chr11 | 74426175 | 74426167 | − | chr11 | 74424524 | 74424431 | − | ENST00000263671; ENST00000376332; ENST00000534276; ENST00000528789 | TSF |
| 6% | chr11 | 74426175 | 74426167 | − | chr11 | 74424524 | 74424431 | − | ENST00000263671; ENST00000376332; ENST00000534276; ENST00000528789 | TSF |
| 6% | chr11 | 74426175 | 74426167 | − | chr11 | 74424524 | 174424431 | − | ENST00000263671; ENST00000376332; ENST00000534276; ENST00000528789 | TSF |
| 6% | chr11 | 74426175 | 74426167 | − | chr11 | 74424524 | 174424431 | − | ENST00000263671; ENST00000376332; ENST00000534276; ENST00000528789 | TSF |
| 6% | chr15 | 82386123 | 82386575 | + | chr15 | 82387823 | 82387869 | + | ENST00000559788 | TSF |
| 5% | chr20 | 42754178 | 42754145 | − | chr20 | 42747263 | 42747145 | − | ENST00000372980 | TSF |
| 5% | chr3 | 133881128 | 133880716 | − | chr3 | 133878217 | 133878081 | − | ENST00000460933; ENST00000296084; ENST00000427044 | TSF |
| 5% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 5% | chr22 | 22899971 | 22899965 | − | chr22 | 22893511 | 22893189; 92283185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 5% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 5% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 5% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 5% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 5% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 5% | chr7 | 94018505 | 94018589 | + | chr7 | 94057748 | 94057789 | + | ENST00000297268 | TSF |
| 5% | chr5 | 79371074 | 79371193 | + | chr5 | 79372678 | 79372871 | + | ENST00000350881; ENST00000511733 | TSF |
| 5% | chr7 | 2059680 | 2059649 | − | chr7 | 2054277 | 2054137 | − | ENST00000402746; ENST00000399654; ENST00000406869; ENST00000265854; ENST00000438959 | TSF |
| 5% | chr7 | 2059680 | 2059649 | − | chr7 | 2054277 | 2054137 | − | ENST00000402746; ENST00000399654; ENST00000406869; ENST00000265854; ENST00000438959 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 91529041 | 91528993 | − | chr15 | 91528055 | 91527923 | − | ENST00000394249; ENST00000361919; ENST00000361188; ENST00000442656; ENST00000557905; ENST00000559811 | TSF |
| 5% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |

TABLE 54-continued

Transcript fusion for Sarcoma (SARC) Coordinates of the
fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 5% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 5% | chr15 | 69718867 | 69718995 | + | chr15 | 69721450 | 69721552 | + | ENST00000559279; ENST00000395392; ENST00000352331; ENST00000260363; ENST00000558585; ENST00000559283; ENST00000537891 | TSF |
| 5% | chr12 | 58023123 | 58023062 | − | chr12 | 58022686 | 58022496; 58022484 | − | ENST00000341156; ENST00000418555; ENST00000449184 | TSF |
| 5% | chr12 | 58023123 | 58023062 | − | chr12 | 58022686 | 58022496; 58022484 | − | ENST00000341156; ENST00000418555; ENST00000449184 | TSF |
| 5% | chr5 | 33794481 | 33794368 | − | chr5 | 33751653 | 33751509; 33751444 | | ENST00000504830; ENST00000352040; ENST00000515401 | TSF |
| 5% | chr5 | 33794481 | 33794368 | − | chr5 | 33751653 | 33751509; 33751444 | | ENST00000504830; ENST00000352040; ENST00000515401 | TSF |
| 5% | chr5 | 33794481 | 33794368 | − | chr5 | 33751653 | 33751509; 33751444 | − | ENST00000504830; ENST00000352040; ENST00000515401 | TSF |
| 4% | chr1 | 41465686 | 41465756 | + | chr1 | 41466701 | 41466789 | + | ENST00000372621; ENST00000541520; ENST00000372616 | TSF |
| 4% | chr1 | 53070435 | 530170501 | + | chr1 | 53072356 | 53072617 | + | ENST00000361314 | TSF |
| 4% | chr1 | 23762222 | 23762216 | − | chr1 | 23761111 | 23761026 | − | ENST00000495646; ENST00000336689; ENST00000437606 | TSF |
| 4% | chr12 | 6602868 | 6602754 | − | chr12 | 6602138 | 6602028 | − | ENST00000229238 | TSF |
| 4% | chr11 | 66048968 | 66049045 | + | chr11 | 66049730 | 66049798; 66049824 | + | ENST00000528852; ENST00000311445; ENST00000528063 | TSF |
| 4% | chr11 | 66048968 | 66049045 | + | chr11 | 66049730 | 66049798; 66049824 | + | ENST00000528852; ENST00000311445; ENST00000528063 | TSF |
| 4% | chr11 | 66048968 | 66049045 | + | chr11 | 66049730 | 66049798; 66049824 | + | ENST00000528852; ENST00000311445; ENST00000528063 | TSF |
| 4% | chr11 | 1891186 | 1891243 | + | chr11 | 1901317 | 1901454 | + | ENST00000311604; ENST00000381775; ENST00000457279; ENST00000429923; ENST00000418975 | TSF |
| 4% | chr11 | 1891186 | 1891243 | + | chr11 | 1901317 | 1901454 | + | ENST00000311604; ENST00000381775; ENST00000457279; ENST00000429923; ENST00000418975 | TSF |
| 4% | chr11 | 1891186 | 1891243 | + | chr11 | 1901317 | 1901454 | + | ENST00000311604; ENST00000381775; ENST00000457279; ENST00000429923; ENST00000418975 | TSF |
| 4% | chr11 | 1891186 | 1891243 | + | chr11 | 1901317 | 1901454 | − | ENST00000311604; ENST00000381775; ENST00000457279; ENST00000429923; ENST00000418975 | TSF |
| 4% | chr1 | 169819657 | 169819707 | + | chr1 | 169820958 | 169821077 | + | ENST00000359326; ENST00000286031 | TSF |
| 4% | chr17 | 13442614 | 13442384 | − | chr17 | 13400135 | 13399514 | − | ENST00000284110 | TSF |
| 4% | chr5 | 178696659 | 178696386 | − | chr5 | 178634716 | 178634514 | − | ENST00000251582; ENST00000274609 | TSF |
| 4% | chr5 | 178696659 | 178696386 | − | chr5 | 178634716 | 178634514 | − | ENST00000251582; ENST00000274609 | TSF |
| 4% | chr1 | 32152700 | 32152171 | − | chr1 | 32151880 | 32151845 | − | ENST00000271069; ENST00000373672; ENST00000373668 | TSF |
| 4% | chr1 | 32152700 | 32152171 | − | chr1 | 32151880 | 32151845 | − | ENST00000271069; ENST00000373672; ENST00000373668 | TSF |
| 4% | chr1 | 32152700 | 32152171 | − | chr1 | 32151880 | 32151845 | − | ENST00000271069; ENST00000373672; ENST00000373668 | TSF |
| 3% | chr4 | 1745002 | 1745264 | + | chr4 | 1746245 | 1746351 | + | ENST00000313288 | TSF |
| 3% | chr2 | 48949534 | 48949869 | + | chr2 | 49003419 | 49003454 | + | ENST00000402114 | TSF |
| 3% | chr14 | 70466641 | 70466673 | + | chr14 | 70477471 | 70477663 | + | ENST00000361956; ENST00000381280 | TSF |
| 3% | chr14 | 70466641 | 70466673 | + | chr14 | 70477471 | 70477663 | + | ENST00000361956; ENST00000381280 | TSF |
| 3% | chr3 | 111532965 | 111533310 | + | chr3 | 111564668 | 111564716 | + | ENST00000393934 | TSF |
| 3% | chr9 | 35657501 | 35657683 | + | chr9 | 35658573 | 35658724 | + | ENST00000378407; ENST00000378406; ENST00000426546; ENST00000327351; ENST00000421582; ENST00000378409 | TSF |
| 3% | chr9 | 35657501 | 35657683 | + | chr9 | 35658573 | 35658724 | + | ENST00000378407; ENST00000378406; ENST00000426546; ENST00000327351; ENST00000421582; ENST00000378409 | TSF |
| 3% | chr9 | 35657501 | 35657683 | + | chr9 | 35658573 | 35658724 | + | ENST00000378407; ENST00000378406; ENST00000426546; ENST00000327351; ENST00000421582; ENST00000378409 | TSF |
| 3% | chr9 | 35657501 | 35657683 | + | chr9 | 35658573 | 35658724 | + | ENST00000378407; ENST00000378406; ENST00000426546; ENST00000327351; ENST00000421582; ENST00000378409 | TSF |
| 3% | chr9 | 35657501 | 35657683 | + | chr9 | 35658573 | 35658724 | + | ENST00000378407; ENST00000378406; ENST00000426546; ENST00000327351; ENST00000421582; ENST00000378409 | TSF |
| 3% | chr9 | 35657501 | 356157683 | + | chr9 | 35658573 | 35658724 | + | ENST00000378407; ENST00000378406; ENST00000426546; ENST00000327351; ENST00000421582; ENST00000378409 | TSF |
| 3% | chr2 | 189864980 | 189865248 | + | chr2 | 189866123 | 189866176 | + | ENST00000304636; ENST00000317840 | TSF |
| 3% | chr2 | 189864980 | 189865248 | + | chr2 | 189866123 | 189866176 | + | ENST00000304636; ENST00000317840 | TSF |
| 3% | chr4 | 28378393 | 28378035 | − | chr4 | 28372431 | 28372322 | − | ENST00000507759 | TSF |
| 3% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 3% | chr1 | 246581335 | 246580598 | − | chr1 | 246498776 | 246498669 | − | ENST00000541742; ENST00000490107; ENST00000388985; ENST00000453676; ENST00000403792; ENST00000455277 | |
| 3% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 3% | chr1 | 246581335 | 246580598 | − | chr1 | 246498776 | 246498669 | − | ENST00000541742; ENST00000490107; ENST00000388985; ENST00000453676; ENST00000403792; ENST00000455277 | TSF |
| 3% | chr5 | 148770827 | 148770728 | − | chr5 | 148756588 | 148756299 | − | ENST00000261796 | TSF |
| 3% | chr17 | 17126706 | 17126441 | − | chr17 | 17125975 | 17125815 | − | ENST00000285071; ENST00000389169 | TSF |
| 3% | chr17 | 17126706 | 17126441 | − | chr17 | 17125975 | 17125815 | − | ENST00000285071; ENST00000389169 | TSF |

TABLE 54-continued

Transcript fusion for Sarcoma (SARC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr15 | 67546688 | 67546562 | − | chr15 | 67529158 | 67528968 | − | ENST00000261880 | TSF |
| 3% | chr2 | 85811874 | 85811992 | + | chr2 | 85818852 | 85818985 | + | ENST00000306384 | TSF |
| 3% | chrX | 48394106 | 48394426 | + | chrX | 48417285 | 48417412; 48417354 | + | ENST00000376771; ENST00000481090; ENST00000418627 | TSF |
| 3% | chrX | 48394106 | 48394426 | + | chrX | 48417285 | 48417412; 48417354 | + | ENST00000376771; ENST00000481090; ENST00000418627 | TSF |
| 3% | chrX | 48394106 | 48394426 | + | chrX | 48417285 | 48417412; 48417354 | + | ENST00000376771; ENST00000481090; ENST00000418627 | TSF |
| 3% | chr14 | 100942914 | 100942918 | + | chr14 | 100950331 | 100950461; 100950378 | + | ENST00000554998; ENST00000402312; ENST00000335290; ENST00000557710; ENST00000542471 | TSF |
| 3% | chr14 | 100942914 | 100942918 | + | chr14 | 100950331 | 100950461; 100950378 | + | ENST00000554998; ENST00000402312; ENST00000335290; ENST00000557710; ENST00000542471 | TSF |
| 3% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 3% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 3% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 3% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 3% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 3% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 3% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; ENST00000563584; ENST00000561416; ENST00000560995; ENST00000561260; ENST00000564751 | TSF |
| 3% | chr15 | 73976790 | 73976801 | + | chr15 | 73994596 | 73994914; 73994934; 73994926; 73994838; 73994671 | + | ENST00000567189; ENST00000318443; ENST00000318424; ENST00000558689; ENST00000560786; ENST00000561213; 1ENST00000563584; ENST0000056416; ENST00000560995; ENST00000561260; ENST00000564751 | TSF |
| 3% | chr10 | 23383125 | 23383689 | + | chr10 | 23393073 | 23393173 | + | ENST00000376510; ENST00000472663 | TSF |
| 3% | chr10 | 23383125 | 23383689 | + | chr10 | 23393073 | 23393173 | + | ENST00000376510; ENST00000472663 | TSF |
| 3% | chr6 | 45627086 | 45627095 | + | chr6 | 45630852 | 45631459 | + | ENST00000576263 | TSF |
| 3% | chr2 | 189861720 | 189861722 | + | chr2 | 189861891 | 189861944 | + | ENST00000304636; ENST00000317840 | TSF |
| 3% | chr2 | 189861720 | 189861722 | + | chr2 | 189861891 | 189861944 | + | ENST00000304636; ENST00000317840 | TSF |
| 3% | chr18 | 2873127 | 2873305 | + | chr18 | 2891239 | 2892484 | + | ENST00000254528 | TSF |
| 3% | chr8 | 27834814 | 27834547 | − | chr8 | 27779762 | 27779088 | − | ENST00000354914; ENST00000524352; ENST00000518030; ENST00000301906 | TSF |
| 3% | chr8 | 27834814 | 27834547 | − | chr8 | 27779762 | 27779088 | − | ENST00000354914; ENST00000524352; ENST00000518030; ENST00000301906 | TSF |
| 3% | chr7 | 82523973 | 82523713 | − | chr7 | 82508778 | 82508653 | − | ENST00000333891; ENST00000423517; ENST00000413807; ENST00000456006 | TSF |
| 3% | chr7 | 82523973 | 82523713 | − | chr7 | 82508778 | 82508653 | − | ENST00000333891; ENST00000423517; ENST00000413807; ENST00000456006 | TSF |
| 3% | chr7 | 82523973 | 82523713 | − | chr7 | 82508778 | 82508653 | − | ENST00000333891; ENST00000423517; ENST00000413807; ENST00000456006 | TSF |
| 3% | chr7 | 82523973 | 82523713 | − | chr7 | 82508778 | 82508653 | − | ENST00000333891; ENST00000423517; ENST00000413807; ENST00000456006 | TSF |

TABLE 54-continued

Transcript fusion for Sarcoma (SARC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr5 | 33794481 | 33794291 | − | chr5 | 33751653 | 33751509; 33751444 | − | ENST00000504830; ENST00000352040; ENST00000515401 | TSF |
| 3% | chr5 | 33794481 | 33794291 | − | chr5 | 33751653 | 33751509; 33751444 | − | ENST00000504830; ENST00000352040; ENST00000515401 | TSF |
| 3% | chr5 | 33794481 | 33794291 | − | chr5 | 33751653 | 33751509; 33751444 | − | ENST00000504830; ENST00000352040; ENST00000515401 | TSF |
| 3% | chrX | 19668715 | 19668432 | − | chrX | 19663593 | 19663518; 61963535 | − | ENST00000397821; ENST00000379716; ENST00000379698; ENST00000379726; ENST00000379697; ENST00000432234 | TSF |
| 3% | chrX | 19668715 | 19668432 | − | chrX | 19663593 | 19663518; 19663535 | − | ENST00000397821; ENST00000379716; ENST00000379698; ENST00000379726; ENST00000379697; ENST00000432234 | TSF |
| 3% | chrX | 19668715 | 19668432 | − | chrX | 19663593 | 19663518; 19663535 | − | ENST00000397821; ENST00000379716; ENST00000379698; ENST00000379726; ENST00000379697; ENST00000432234 | TSF |
| 3% | chrX | 19668715 | 19668468 | − | chrX | 19663593 | 19663518; 61963535 | − | ENST00000397821; ENST00000379716; ENST00000379698; ENST00000379726; ENST00000379697; ENST00000432234 | TSF |
| 3% | chrX | 19668715 | 19668468 | − | chrX | 19663593 | 19663518; 19663535 | − | ENST00000397821; ENST00000379716; ENST00000379698; ENST00000379726; ENST00000379697; ENST00000432234 | TSF |
| 3% | chrX | 19668715 | 19668468 | − | chrX | 19663593 | 19663518; 19663535 | − | ENST00000397821; ENST00000379716; ENST00000379698; ENST00000379726; ENST00000379697; ENST00000432234 | TSF |
| 3% | chr5 | 178594221 | 178594154 | − | chr5 | 178585880 | 178585724 | − | ENST00000251582; ENST00000274609 | TSF |
| 3% | chr5 | 178594221 | 178594154 | − | chr5 | 178585880 | 178585724 | − | ENST00000251582; ENST00000274609 | TSF |
| 3% | chr6 | 114321437 | 114321165 | − | chr6 | 114281182 | 114281070 | − | ENST00000519065; ENST00000398283; ENST00000425835; ENST00000521163 | TSF |
| 3% | chr6 | 114321437 | 114321165 | − | chr6 | 114281182 | 114281070 | − | ENST00000519065; ENST00000398283; ENST00000425835; ENST00000521163 | TSF |
| 3% | chr6 | 114321437 | 114321165 | − | chr6 | 114281182 | 114281070 | − | ENST00000519065; ENST00000398283; ENST00000425835; ENST00000521163 | TSF |
| 3% | chr7 | 100850556 | 100850506 | − | chr7 | 100850185 | 100850060 | − | ENST00000454310; ENST00000223127 | TSF |
| 3% | chr5 | 148780664 | 148780258 | − | chr5 | 148756588 | 148756299 | − | ENST00000261796 | TSF |
| 3% | chr19 | 18506969 | 18506886 | − | chr19 | 18502935 | 18502797 | − | ENST00000339007; ENST00000595840 | TSF |
| 2% | chr6 | 168927975 | 168928062 | + | chr6 | 168944305 | 168944352 | + | ENST00000354536; ENST00000356284 | TSF |
| 2% | chr6 | 168927975 | 168928062 | + | chr6 | 168944305 | 168944352 | + | ENST00000354536; ENST00000356284 | TSF |
| 2% | chr5 | 15934695 | 15934710 | + | chr5 | 15936559 | 15937295 | + | ENST00000504595; ENST00000510662; ENST00000329673 | TSF |
| 2% | chr10 | 118177984 | 118178265 | + | chr10 | 118202567 | 118202686 | + | ENST00000369230 | TSF |
| 2% | chr15 | 68577054 | 68577315 | + | chr15 | 68581945 | 68583580 | + | ENST00000306917 | TSF |
| 2% | chr2 | 36993390 | 36993533 | + | chr2 | 36994237 | 36994428 | + | ENST00000379242; ENST00000389975; ENST00000404084; ENST00000379241; ENST00000401530 | TSF |
| 2% | chr2 | 36993390 | 36993533 | + | chr2 | 36994237 | 36994428 | + | ENST00000379242; ENST00000389975; ENST00000404084; ENST00000379241; ENST00000401530 | TSF |
| 2% | chr2 | 36993390 | 36993533 | + | chr2 | 36994237 | 36994428 | + | ENST00000379242; ENST00000389975; ENST00000404084; ENST00000379241; ENST00000401530 | TSF |
| 2% | chr2 | 36993390 | 36993533 | + | chr2 | 36994237 | 36994428 | + | ENST00000379242; ENST00000389975; ENST00000404084; ENST00000379241; ENST00000401530 | TSF |
| 2% | chr2 | 36993390 | 36993533 | + | chr2 | 36994237 | 36994428 | + | ENST00000379242; ENST00000389975; ENST00000404084; ENST00000379241; ENST00000401530 | TSF |
| 2% | chrX | 80517692 | 80518225 | + | chrX | 80532483 | 80532668 | + | ENST00000373212 | TSF |
| 2% | chr7 | 23290404 | 23290481 | + | chr7 | 23292926 | 23293078 | + | ENST00000258733; ENST00000381990; ENST00000409458; ENST00000453162 | TSF |
| 2% | chr7 | 23290404 | 23290481 | + | chr7 | 23292926 | 23293078 | + | ENST00000258733; ENST00000381990; ENST00000409458; ENST00000453162 | TSF |
| 2% | chr7 | 23290404 | 23290481 | + | chr7 | 23292926 | 23293078 | + | ENST00000258733; ENST00000381990; ENST00000409458; ENST00000453162 | TSF |
| 2% | chr7 | 23290404 | 23290481 | + | chr7 | 23292926 | 23293078 | + | ENST00000258733; ENST00000381990; ENST00000409458; ENST00000453162 | TSF |
| 2% | chr11 | 46321227 | 46321229 | + | chr11 | 46321486 | 46321714 | + | ENST00000529193; ENST00000288400 | TSF |
| 2% | chr21 | 47278635 | 47278724 | + | chr21 | 47316122 | 47316276 | + | ENST00000400314; ENST00000400310; ENST00000449640; ENST00000400308; ENST00000400309 | TSF |
| 2% | chr21 | 47278635 | 47278724 | + | chr21 | 47316122 | 47316276 | + | ENST00000400314; ENST00000400310; ENST00000449640; ENST00000400308; ENST00000400309 | TSF |
| 2% | chr21 | 47278635 | 47278724 | + | chr21 | 47316122 | 47316276 | + | ENST00000400314; ENST00000400310; ENST00000449640; ENST00000400308; ENST00000400309 | TSF |
| 2% | chr21 | 47278635 | 47278724 | + | chr21 | 47316122 | 47316276 | + | ENST00000400314; ENST00000400310; ENST00000449640; ENST00000400308; ENST00000400309 | TSF |
| 2% | chr20 | 55815985 | 55815709 | − | chr20 | 55803477 | 55803285 | − | ENST00000395863; ENST00000395864; ENST00000450594; ENST00000433911 | TSF |
| 2% | chr20 | 55815985 | 55815709 | − | chr20 | 55803477 | 55803285 | − | ENST00000395863; ENST00000395864; ENST00000450594; ENST00000433911 | TSF |
| 2% | chr20 | 55815985 | 55815709 | − | chr20 | 55803477 | 55803285 | − | ENST00000395863; ENST00000395864; ENST00000450594; ENST00000433911 | TSF |
| 2% | chr20 | 55815985 | 55815709 | − | chr20 | 55803477 | 55803285 | − | ENST00000395863; ENST00000395864; ENST00000450594; ENST00000433911 | TSF |
| 2% | chr3 | 11645847 | 11645798 | − | chr3 | 11643496 | 11643307 | − | ENST00000273038; ENST00000430365; ENST00000404339; ENST00000445411; ENST00000418000; ENST00000458499; ENST00000417206; ENST00000419541 | TSF |
| 2% | chr3 | 11645847 | 11645798 | − | chr3 | 11643496 | 11643307 | − | ENST00000273038; ENST00000430365; ENST00000404339; ENST00000445411; ENST00000418000; ENST00000458499; | TSF |

TABLE 54-continued

Transcript fusion for Sarcoma (SARC) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr3 | 11645847 | 11645798 | − | chr3 | 11643496 | 11643307 | − | ENST00000417206; ENST00000419541 ENST00000273038; ENST00000430365; ENST00000404339; ENST00000445411; ENST00000418000; ENST00000458499; | TSF |
| 2% | chr3 | 11645847 | 11645798 | − | chr3 | 11643496 | 11643307 | − | ENST00000417206; ENST00000419541 ENST00000273038; ENST00000430365; ENST00000404339; ENST00000445411; ENST00000418000; ENST00000458499; | TSF |
| 2% | chr3 | 11645847 | 11645798 | − | chr3 | 11643496 | 11643307 | − | ENST00000417206; ENST00000419541 ENST00000273038; ENST00000430365; ENST00000404339; ENST00000445411; ENST00000418000; ENST00000458499; | TSF |
| 2% | chr3 | 11645847 | 11645798 | − | chr3 | 11643496 | 11643307 | − | ENST00000417206; ENST00000419541 ENST00000273038; ENST00000430365; ENST00000404339; ENST00000445411; ENST00000418000; ENST00000458499; ENST00000417206; ENST00000419541 | TSF |
| 2% | chr9 | 132580720 | 132580632 | − | chr9 | 132576501 | 132576251 | − | ENST00000351698 | TSF |
| 2% | chr22 | 21355965 | 21355808 | − | chr22 | 21355700 | 21355545 | − | ENST00000215742; ENST00000399133 | TSF |
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |

TABLE 55

Transcript fusion for skin cutaneous melanoma (SKCM) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 93% | chr11 | 88960991 | 88961138 | + | ENST00000263321 | chr11 | 88974422 | 88974649 | + | TAF |
| 68% | chr8 | 54793576 | 54793644 | + | ENST00000276500 | chr8 | 54826057 | 54826421 | + | TAF |
| 68% | chr19 | 3544937 | 3544807 | − | ENST00000389395; ENST00000398558; ENST00000588918; ENST00000355415; ENST00000589063 | chr19 | 3538708 | 3538306 | − | TAF |
| 68% | chr19 | 3544937 | 3544807 | − | ENST00000389395; ENST00000398558; ENST00000588918; ENST00000355415; ENST00000589063 | chr19 | 3538708 | 3538306 | − | TAF |
| 68% | chr19 | 3544937 | 3544807 | − | ENST00000389395; ENST00000398558; ENST00000588918; ENST00000355415; ENST00000589063 | chr19 | 3538708 | 3538306 | − | TAF |
| 67% | chr12 | 110511233 | 110511227 | − | ENST00000548191 | chr12 | 110496968 | 110496909 | − | TAF |
| 37% | chr11 | 89017941 | 89018122 | + | ENST00000263321 | chr11 | 89022608 | 89022727 | + | TSF |
| 33% | chr20 | 35842163 | 35842268 | + | ENST00000237530; ENST00000373622 | chr20 | 35844460 | 35844765 | + | TAF |
| 33% | chr20 | 35842163 | 35842268 | + | ENST00000237530; ENST00000373622 | chr20 | 35844460 | 35844765 | + | TAF |
| 27% | chr12 | 110495101 | 110494994 | − | ENST00000309050 | chr12 | 110493610 | 110493335 | − | TAF |
| 27% | chr8 | 54791818 | 54792162 | + | ENST00000297313 | chr8 | 54826057 | 54826421 | + | TSF |
| 24% | chr6 | 36762426 | 36762367 | − | ENST00000244751 | chr6 | 36760223 | 36760189 | − | TAF |
| 22% | chr7 | 98991652 | 98991742 | + | ENST00000252725; ENST00000451682 | chr7 | 98994840 | 98994900 | + | TAF |
| 21% | chr4 | 108999538 | 108999376 | − | ENST00000265165; ENST00000379951; ENST00000438313; ENST00000510624 | chr4 | 108994190 | 108994089 | − | TAF |
| 21% | chr4 | 108999538 | 108999376 | − | ENST00000265165; ENST00000379951; ENST00000438313; ENST00000510624 | chr4 | 108994190 | 108994089 | − | TAF |
| 21% | chr4 | 108999538 | 108999376 | − | ENST00000265165; ENST00000379951; ENST00000438313; ENST00000510624 | chr4 | 108994190 | 108994089 | − | TAF |
| 21% | chr11 | 57191501 | 57191455 | − | ENST00000395123; ENST00000395124; ENST00000352187; ENST00000529554; ENST00000533524; ENST00000530005; ENST00000529113; ENST00000525474; ENST00000529112; ENST00000528187 | chr11 | 57191196 | 57190890 | − | TAF |
| 21% | chr11 | 57191501 | 57191455 | − | ENST00000395123; ENST00000395124; ENST00000352187; ENST00000529554; ENST00000533524; ENST00000530005; ENST00000529113; ENST00000525474; ENST00000529112; ENST00000528187 | chr11 | 57191196 | 57190890 | − | TAF |
| 21% | chr11 | 57191501 | 57191455 | − | ENST00000395123; ENST00000395124; ENST00000352187; ENST00000529554; ENST00000533524; ENST00000530005; ENST00000529113; ENST00000525474; ENST00000529112; ENST00000528187 | chr11 | 57191196 | 57190890 | − | TAF |

TABLE 55-continued

Transcript fusion for skin cutaneous melanoma (SKCM) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 20% | chr7 | 22532348 | 22532184 | − | ENST00000406890; ENST00000404369; ENST00000424363 | chr7 | 22512853 | 22512669 | − | TSF |
| 20% | chr7 | 22532348 | 22532184 | − | ENST00000406890; ENST00000404369; ENST00000424363 | chr7 | 22512853 | 22512669 | − | TSF |
| 19% | chr1 | 32696528 | 32696620 | + | ENST00000373586 | chr1 | 32696861 | 32697110 | + | TAF |
| 18% | chr3 | 196753630 | 196753531 | − | ENST00000296350; ENST00000296351; ENST00000439320 | chr3 | 196753047 | 196752998 | − | TAF |
| 17% | chr1 | 12010414 | 12010577 | + | ENST00000449038; ENST00000376369; ENST00000429000; ENST00000196061 | chr1 | 12010679 | 12010856 | + | TAF |
| 17% | chr1 | 12010414 | 12010577 | + | ENST00000449038; ENST00000376369; ENST00000429000; ENST00000196061 | chr1 | 12010679 | 12010856 | + | TAF |
| 16% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 16% | chr19 | 14063948 | 14063931 | − | ENST00000538517; ENST00000538371; ENST00000585607 | chr19 | 14060442 | 14060422 | − | TAF |
| 16% | chr6 | 11000397 | 11000320 | − | ENST00000354666 | chr6 | 11000151 | 11000002 | − | TAF |
| 16% | chr11 | 88960991 | 88961082 | + | ENST00000263321 | chr11 | 88974422 | 88974649 | + | TSF |
| 16% | chr7 | 100854953; 100854997 | 100854872 | − | ENST00000454310; ENST00000223127; ENST00000440925; ENST00000421736 | chr7 | 100854207 | 100854151 | − | TSF |
| 16% | chr7 | 100854953; 100854997 | 100854872 | − | ENST00000454310; ENST00000223127; ENST00000440925; ENST00000421736 | chr7 | 100854207 | 100854151 | − | TSF |
| 16% | chr7 | 100854953; 100854997 | 100854872 | − | ENST00000454310; ENST00000223127; ENST00000440925; ENST00000421736 | chr7 | 100854207 | 100854151 | − | TSF |
| 16% | chr7 | 100854953; 100854997 | 100854872 | − | ENST00000454310; ENST00000223127; ENST00000440925; ENST00000421736 | chr7 | 100854207 | 100854151 | − | TSF |
| 15% | chr1 | 11115983; 11115877 | 11115838 | − | ENST00000376957; ENST00000490101 | chr1 | 11115464 | 11115178 | − | TSF |
| 15% | chr1 | 11115983; 11115877 | 11115838 | − | ENST00000376957; ENST00000490101 | chr1 | 11115464 | 11115178 | − | TSF |
| 14% | chr8 | 74939024 | 74939076 | + | ENST00000284818; ENST00000518893 | chr8 | 74944554 | 74944936 | + | TAF |
| 14% | chr8 | 74939024 | 74939076 | + | ENST00000284818; ENST00000518893 | chr8 | 74944554 | 74944936 | + | TAF |
| 14% | chr15 | 89011139 | 89011255 | + | ENST00000560708; ENST00000325844; ENST00000353598 | chr15 | 89011993 | 89012264 | + | TAF |
| 14% | chr4 | 57319769 | 57319927 | + | ENST00000514888; ENST00000264221; ENST00000505164; ENST00000399688; ENST00000512576 | chr4 | 57321183 | 57321327 | + | TSF |
| 14% | chr4 | 57319769 | 57319927 | + | ENST00000514888; ENST00000264221; ENST00000505164; ENST00000399688; ENST00000512576 | chr4 | 57321183 | 57321327 | + | TSF |
| 14% | chr4 | 57319769 | 57319927 | + | ENST00000514888; ENST00000264221; ENST00000505164; ENST00000399688; ENST00000512576 | chr4 | 57321183 | 57321327 | + | TSF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; | chr19 | 35995923 | 35995655 | − | TAF |

TABLE 55-continued

Transcript fusion for skin cutaneous melanoma (SKCM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 351995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |

TABLE 55-continued

Transcript fusion for skin cutaneous melanoma (SKCM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 13% | chr19 | 35996667 | 35996620 | − | ENST00000434389; ENST00000402589; ENST00000339686; ENST00000436012; ENST00000414866; ENST00000480502; ENST00000467637; ENST00000429837; ENST00000419602; ENST00000443640; ENST00000597212; ENST00000472252; ENST00000492341; ENST00000602781; ENST00000602679; ENST00000474928; ENST00000488892; ENST00000461300; ENST00000447113; ENST00000392206; ENST00000440396; ENST00000458071; ENST00000418261; ENST00000424570; ENST00000451297; ENST00000450261 | chr19 | 35995923 | 35995655 | − | TAF |
| 12% | chr11 | 88924370 | 88924586 | + | ENST00000263321 | chr11 | 88953763 | 88953776 | + | TSF |
| 12% | chr1 | 31347435 | 31347144 | − | ENST00000336798; ENST00000339394 | chr1 | 31340352 | 31340311 | − | TSF |
| 12% | chr1 | 31347435 | 31347144 | − | ENST00000336798; ENST00000339394 | chr1 | 31340352 | 31340311 | − | TSF |
| 12% | chr19 | 3546166 | 3546072 | − | ENST00000389395; ENST00000398558; ENST00000588918; ENST00000355415; ENST00000589063; ENST00000589995 | chr19 | 3538708 | 3538306 | − | TSF |
| 12% | chr19 | 3546166 | 3546072 | − | ENST00000389395; ENST00000398558; ENST00000588918; ENST00000355415; ENST00000589063; ENST00000589995 | chr19 | 3538708 | 3538306 | − | TSF |
| 12% | chr19 | 3546166 | 3546072 | − | ENST00000389395; ENST00000398558; ENST00000588918; ENST00000355415; ENST00000589063; ENST00000589995 | chr19 | 3538708 | 3538306 | − | TSF |
| 12% | chr19 | 3546166 | 3546072 | − | ENST00000389395; ENST00000398558; ENST00000588918; ENST00000355415; ENST00000589063; ENST00000589995 | chr19 | 3538708 | 3538306 | − | TSF |
| 11% | chr22 | 24323139 | 24323226 | + | ENST00000215780; ENST00000402588 | chr22 | 24324557 | 24324632 | + | TAF |
| 11% | chr12 | 121775196; 121775195 | 121775094 | − | ENST00000539079; ENST00000441917; ENST00000541887; ENST00000261819; ENST00000344395; ENST00000536366; ENST00000544442 | chr12 | 121766988 | 121766947 | − | TAF |
| 11% | chr12 | 121775196; 121775195 | 121775094 | − | ENST00000539079; ENST00000441917; ENST00000541887; ENST00000261819; ENST00000344395; ENST00000536366; ENST00000544442 | chr12 | 121766988 | 121766947 | − | TAF |
| 11% | chr12 | 121775196; 121775195 | 121775094 | − | ENST00000539079; ENST00000441917; ENST00000541887; ENST00000261819; ENST00000344395; ENST00000536366; ENST00000544442 | chr12 | 121766988 | 121766947 | − | TAF |
| 11% | chr12 | 121775196; 121775195 | 121775094 | − | ENST00000539079; ENST00000441917; ENST00000541887; ENST00000261819; ENST00000344395; ENST00000536366; ENST00000544442 | chr12 | 121766988 | 121766947 | − | TAF |
| 11% | chr15 | 28090198 | 28090105 | − | ENST00000353809; ENST00000354638 | chr15 | 27964474 | 27964338 | − | TSF |
| 11% | chr15 | 28090198 | 28090105 | − | ENST00000353809; ENST00000354638 | chr15 | 27964474 | 27964338 | − | TSF |
| 10% | chr12 | 56742407 | 56742313 | − | ENST00000314128; ENST00000557235 | chr12 | 56740986 | 56740975 | − | TSF |
| 10% | chr12 | 56742407 | 56742313 | − | ENST00000314128; ENST00000557235 | chr12 | 56740986 | 56740975 | − | TSF |
| 10% | chr13 | 95095891 | 95095690 | − | ENST00000377028; ENST00000446125 | chr13 | 95063527 | 95063301 | − | TSF |
| 10% | chr13 | 95095891 | 95095690 | − | ENST00000377028; ENST00000446125 | chr13 | 95063527 | 95063301 | − | TSF |
| 10% | chr3 | 98600611; 98600498 | 98600384 | − | ENST00000326840; ENST00000326857; ENST00000449482 | chr3 | 98586282 | 98584565 | − | TSF |
| 10% | chr3 | 98600611; 98600498 | 98600384 | − | ENST00000326840; ENST00000326857; ENST00000449482 | chr3 | 98586282 | 98584565 | − | TSF |
| 10% | chr15 | 33149308 | 33149216 | − | ENST00000334528; ENST00000561249; ENST00000559047; ENST00000559610 | chr15 | 33129775 | 33129703 | − | TSF |
| 10% | chr15 | 33149308 | 33149216 | − | ENST00000334528; ENST00000561249; ENST00000559047; ENST00000559610 | chr15 | 33129775 | 33129703 | − | TSF |
| 10% | chr15 | 33149308 | 33149216 | − | ENST00000334528; ENST00000561249; ENST00000559047; | chr15 | 33129775 | 33129703 | − | TSF |

TABLE 55-continued

Transcript fusion for skin cutaneous melanoma (SKCM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 10% | chr15 | 33149308 | 33149216 | − | ENST00000334528; ENST00000561249; ENST00000559047; ENST00000559610 | chr15 | 33129775 | 33129703 | − | TSF |
| 9% | chr21 | 42540191 | 42540502 | + | ENST00000328735; ENST00000330333; ENST00000347667 | chr21 | 42572645 | 42572848 | + | TSF |
| 9% | chr7 | 116660662 | 116660683 | + | ENST00000465133; ENST00000393444; ENST00000393447 | chr7 | 116738667 | 116738692 | + | TSF |
| 9% | chr3 | 48716169 | 48715997 | − | ENST00000341520; ENST00000416649; ENST00000294129; ENST00000413374 | chr3 | 48702393 | 48702198 | − | TSF |
| 9% | chr3 | 48716169 | 48715997 | − | ENST00000341520; ENST00000416649; ENST00000294129; ENST00000413374 | chr3 | 48702393 | 48702198 | − | TSF |
| 9% | chr3 | 48716169 | 48715997 | − | ENST00000341520; ENST00000416649; ENST00000294129; ENST00000413374 | chr3 | 48702393 | 48702198 | − | TSF |
| 9% | chr17 | 1028702; 1028625 | 1028518 | − | ENST00000302538; ENST00000544583; ENST00000574437; ENST00000575934; ENST00000574139; ENST00000570525; ENST00000574266 | chr17 | 1005267 | 1004964 | − | TSF |
| 9% | chr17 | 1028702; 1028625 | 1028518 | − | ENST00000302538; ENST00000544583; ENST00000574437; ENST00000575934; ENST00000574139; ENST00000570525; ENST00000574266 | chr17 | 1005267 | 1004964 | − | TSF |
| 8% | chr1 | 25891664 | 25891698 | + | ENST00000374338 | chr1 | 25916660 | 25916675 | + | TSF |
| 8% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 8% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 8% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 8% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 8% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 8% | chr8 | 42924698; 42924750 | 42924802 | + | ENST00000534420; ENST00000302279; ENST00000533998; 0ENST00000342116; ENST0000531266; ENST00000525699; ENST00000529687; ENST00000533336 | chr8 | 42925245 | 42925476 | + | TSF |
| 7% | chr19 | 48830778 | 48830880 | + | ENST00000599704; ENST00000270221; ENST00000599255; ENST00000597279 | chr19 | 48832237 | 48832399 | + | TSF |
| 7% | chr20 | 29632611 | 29632721 | + | ENST00000278882; ENST00000358464 | chr20 | 29652086 | 29652324 | + | TSF |
| 7% | chr7 | 23313140 | 23313233 | + | ENST00000258733; ENST00000381990; ENST00000539136; ENST00000453162 | chr7 | 23322924 | 23323223 | + | TSF |
| 7% | chr7 | 23313140 | 23313233 | + | ENST00000258733; ENST00000381990; ENST00000539136; ENST00000453162 | chr7 | 23322924 | 23323223 | + | TSF |
| 7% | chr7 | 23313140 | 23313233 | + | ENST00000258733; ENST00000381990; ENST00000539136; ENST00000453162 | chr7 | 23322924 | 23323223 | + | TSF |
| 7% | chr7 | 23313140 | 23313233 | + | ENST00000258733; ENST00000381990; ENST00000539136; ENST00000453162 | chr7 | 23322924 | 23323223 | + | TSF |
| 7% | chr8 | 11872558 | 11872340 | − | ENST00000527396 | chr8 | 11761114 | 11760831 | − | TSF |
| 7% | chr2 | 74762581 | 74762419 | − | ENST00000264094; ENST00000393937; ENST00000409549; ENST00000409986 | chr2 | 74762269 | 74761994 | − | TSF |
| 7% | chr2 | 74762581 | 74762419 | − | ENST00000264094; ENST00000393937; ENST00000409549; ENST00000409986 | chr2 | 74762269 | 74761994 | − | TSF |
| 7% | chr2 | 74762581 | 74762419 | − | ENST00000264094; ENST00000393937; ENST00000409549; ENST00000409986 | chr2 | 74762269 | 74761994 | − | TSF |
| 6% | chr7 | 23300075 | 23300392 | + | ENST00000258733; ENST00000381990; ENST00000539136; ENST00000453162 | chr7 | 23300981 | 23301414 | + | TSF |
| 6% | chr7 | 23300075 | 23300392 | + | ENST00000258733; ENST00000381990; ENST00000539136; ENST00000453162 | chr7 | 23300981 | 23301414 | + | TSF |
| 6% | chr7 | 23300075 | 23300392 | + | ENST00000258733; ENST00000381990; ENST00000539136; ENST00000453162 | chr7 | 23300981 | 23301414 | + | TSF |
| 6% | chr1 | 2492063 | 2492153 | + | ENST00000426449; ENST00000434817; ENST00000435221; ENST00000451778; ENST00000409119; ENST00000355716 | chr1 | 2508457 | 2508463 | + | TSF |
| 6% | chr2 | 127413840 | 127413888 | + | ENST00000259254; ENST00000409836 | chr2 | 127447276 | 127447440 | + | TSF |
| 6% | chr22 | 40258012 | 40257770 | − | ENST00000325157 | chr22 | 40254656 | 40253648 | − | TSF |
| 6% | chr15 | 89456550 | 89456478 | − | ENST00000558018; ENST00000268151; ENST00000268150; ENST00000566497; ENST00000542878; ENST00000558029 | chr15 | 89453897 | 89453853 | − | TSF |

TABLE 56

Transcript fusion for skin cutaneous melanoma (SKCM) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 83% | chr16 | 1521687 | 1521625 | − | chr16 | 1515339 | 1515268 | − | ENST00000382745; ENST00000564568 | TAF |
| 83% | chr16 | 1521687 | 1521625 | − | chr16 | 1515339 | 1515268 | − | ENST00000382745; ENST00000564568 | TAF |
| 66% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 66% | chr22 | 22899971 | 22899965 | − | chr22 | 22893511 | 22893189; 22893185; 22893481; 22893274 | − | ENST00000398743; ENST00000398741; ENST00000543184; ENST00000405655; ENS T00000402697; ENST00000439106; ENST00000438888; ENST00000420709; ENST00000406503; ENST00000442481; ENST00000403441 | TSF |
| 66% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 66% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 66% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 66% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 66% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 63% | chr8 | 104389530 | 104389551 | + | chr8 | 104390255 | 104390471 | + | ENST00000330295; ENST00000520337 | TAF |
| 61% | chr14 | 102691697 | 102691432 | − | chr14 | 102691131 | 102691116 | − | ENST00000559838 | TAF |
| 53% | chr11 | 87906665 | 87906580 | − | chr11 | 87883123 | 87882843 | − | ENST00000243662; ENST00000526372 | TAF |
| 52% | chr7 | 2289080 | 2289115 | + | chr7 | 2289492 | 2289637 | + | ENST00000356714; ENST00000397049; ENST00000397046; ENST00000397048; ENST00000339737; ENST00000343985 | TAF |
| 51% | chr12 | 110610148 | 110610836 | + | chr12 | 110618227 | 110618376 | + | ENST00000552912; ENST00000242591; ENST00000550156 | TAF |
| 51% | chr12 | 110610148 | 110610836 | + | chr12 | 110618227 | 110618376 | + | ENST00000552912; ENST00000242591; ENST00000550156 | TAF |
| 50% | chr21 | 42597177 | 42597622 | + | chr21 | 42598193 | 42598281 | + | ENST00000328735; ENST00000330333; ENST00000347667 | TAF |
| 50% | chr21 | 42597177 | 42597622 | + | chr21 | 42598193 | 42598281 | + | ENST00000328735; ENST00000330333; ENST00000347667 | TAF |
| 50% | chr21 | 42597177 | 42597622 | + | chr21 | 42598193 | 42598281 | + | ENST00000328735; ENST00000330333; ENST00000347667 | TAF |
| 50% | chr3 | 98482258 | 98482283 | + | chr3 | 98487274 | 98487373 | + | ENST00000492254 | TAF |
| 50% | chr15 | 93221696 | 93221360 | − | chr15 | 93173575 | 93173444 | − | ENST00000327355 | TAF |
| 42% | chr7 | 2289080 | 2289194 | + | chr7 | 2289492 | 2289637 | + | ENST00000356714; ENST00000397049; ENST00000397046; ENST00000397048; ENST00000339737; ENST00000343985 | TAF |
| 40% | chr17 | 30850448 | 30850415 | − | chr17 | 30821933 | 30821777 | − | ENST00000318217; ENST00000394649 | TSF |
| 39% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 39% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 39% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 39% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 35% | chr11 | 88974419 | 88974474 | − | chr11 | 89017941 | 89018122 | + | ENST00000263321 | TSF |
| 35% | chr12 | 110610148 | 110610701 | + | chr12 | 110618227 | 110618376 | + | ENST00000552912; ENST00000242591; ENST00000550156 | TSF |
| 35% | chr12 | 110610148 | 110610701 | + | chr12 | 110618227 | 110618376 | + | ENST00000552912; ENST00000242591; ENST00000550156 | TSF |
| 34% | chr9 | 5907671 | 5907721 | + | chr9 | 5908640 | 5908708 | + | ENST00000381477; ENST00000381476; ENST00000381471 | TSF |
| 34% | chr22 | 40270249 | 40269979 | − | chr22 | 40258012 | 40257770 | − | ENST00000325157 | TSF |
| 34% | chr22 | 140270249 | 40269979 | − | chr22 | 40231963 | 40231845 | − | ENST00000325157 | TSF |
| 33% | chr12 | 56363784 | 56363834 | + | chr12 | 56364828 | 56365031 | + | ENST00000266970; ENST00000553376; ENST00000440311; ENST00000354056 | TSF |
| 32% | chr12 | 56353740 | 56353706 | − | chr12 | 56352391 | 56352257; 56352273; 56352331 | − | ENST00000449260; ENST00000552882; ENST00000550464; ENST00000548747; ENST00000539511; ENST00000548493; ENST00000550447; ENST00000548803; ENST00000547137; ENST00000546543; ENST00000549418; ENST00000549233 | TSF |
| 32% | chr12 | 56353740 | 56353706 | − | chr12 | 56352391 | 56352257; 56352273; 56352331 | − | ENST00000449260; ENST00000552882; ENST00000550464; ENST00000548747; ENST00000539511; ENST00000548493; ENST00000550447; ENST00000548803; ENST00000547137; ENST00000546543; ENST00000549418; ENST00000549233 | TSF |
| 32% | chr12 | 56353740 | 56353706 | − | chr12 | 56352391 | 56352257; 56352273; | − | ENST00000449260; ENST00000552882; ENST00000550464; ENST00000548747; ENST00000539511; ENST00000548493; | TSF |

TABLE 56-continued

Transcript fusion for skin cutaneous melanoma (SKCM) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 32% | chr12 | 56353740 | 56353706 | − | chr12 | 56352391 | 56352257; 56352273; 56352331 | − | ENST00000550447; ENST00000548803; ENST00000547137; ENST00000546543; ENST00000549418; ENST00000549233 ENST00000449260; ENST00000552882; ENST00000550464; ENST00000548747; ENST00000539511; ENST00000548493 | TSF |
| 32% | chr12 | 56353740 | 56353706 | − | chr12 | 56352391 | 56352257; 56352273; 56352331 | − | ENST00000550447; ENST00000548803; ENST00000547137; ENST00000546543; ENST00000549418; ENST00000549233 ENST00000449260; ENST00000552882; ENST00000550464; ENST00000548747; ENST00000539511; ENST00000548493 | TSF |
| 32% | chr12 | 56353740 | 56353706 | − | chr12 | 56352391 | 56352257; 56352273; 56352331 | − | ENST00000550447; ENST00000548803; ENST00000547137; ENST00000546543; ENST00000549418; ENST00000549233 ENST00000449260; ENST00000552882; ENST00000550464; ENST00000548747; ENST00000539511; ENST00000548493 | TSF |
| 32% | chr12 | 56353740 | 56353706 | − | chr12 | 56352391 | 56352257; 56352273; 56352331 | − | ENST00000550447; ENST00000548803; ENST00000547137; ENST00000546543; ENST00000549418; ENST00000549233 ENST00000449260; ENST00000552882; ENST00000550464; ENST00000548747; ENST00000539511; ENST00000548493 | TSF |
| 32% | chr12 | 56353740 | 56353706 | − | chr12 | 56352391 | 56352257; 56352273; 56352331 | − | ENST00000550447; ENST00000548803; ENST00000547137; ENST00000546543; ENST00000549418; ENST00000549233 ENST00000449260; ENST00000552882; ENST00000550464; ENST00000548747; ENST00000539511; ENST00000548493 | TSF |
| 28% | chr7 | 98974090 | 98974197 | + | chr7 | 98983325 | 98983401 | + | ENST00000432884 | TAF |
| 28% | chr13 | 60978922 | 60979204 | + | chr13 | 61013822 | 61013906 | + | ENST00005535286 | TAF |
| 23% | chr1 | 31346734 | 31346686 | − | chr1 | 31346224 | 31346058 | − | ENST00000336798; ENST00000339394 | TAF |
| 23% | chr20 | 45199908 | 45199655 | − | chr20 | 45195029 | 45194868; 45194995 | − | ENST00000396360; ENST00000435032; ENST00000290317; ENST00000279027; ENST00000472148; ENST00000413164; ENST00000495082; ENST00000468915 | TSF |
| 23% | chr20 | 45199908 | 45199655 | − | chr20 | 45195029 | 45194868; 45194995 | − | ENST00000396360; ENST00000435032; ENST00000290317; ENST00000279027; ENST00000472148; ENST00000413164; ENST00000495082; ENST00000468915 | TSF |
| 22% | chr17 | 426168 | 426165 | − | chr17 | 424978 | 424841 | − | ENST00000437048 | TAF |
| 22% | chr7 | 23290404 | 23290481 | + | chr7 | 23292926 | 23293078 | + | ENST00000258733; ENST00000381990; ENST00000409458; ENST00000453162 | TSF |
| 22% | chr7 | 23290404 | 23290481 | + | chr7 | 23292926 | 23293078 | + | ENST00000258733; ENST00000381990; ENST00000409458; ENST00000453162 | TSF |
| 22% | chr7 | 23290404 | 23290481 | + | chr7 | 23292926 | 23293078 | + | ENST00000258733; ENST00000381990; ENST00000409458; ENST00000453162 | TSF |
| 22% | chr7 | 23290404 | 23290481 | + | chr7 | 23292926 | 23293078 | + | ENST00000258733; ENST00000381990; ENST00000409458; ENST00000453162 | TSF |
| 20% | chr11 | 126273341 | 126273381 | + | chr11 | 126275991 | 126276045 | + | ENST00000534733 | TAF |
| 20% | chr1 | 183600359 | 183599874 | − | chr1 | 183599772 | 183599596 | − | ENST00000367534; ENST00000359856; ENST00000294742 | TAF |
| 20% | chr1 | 183600359 | 183599874 | − | chr1 | 183599772 | 183599596 | − | ENST00000367534; ENST00000359856; ENST00000294742 | TAF |
| 20% | chr11 | 65378293 | 65378283 | − | chr11 | 65375919 | 65375739 | − | ENST00000309100 | TSF |
| 19% | chr8 | 143751981 | 143751986 | + | chr8 | 143762745 | 143762852; 143762884 | + | ENST00000301258; ENST00000513264 | TAF |
| 19% | chr8 | 143751981 | 143751986 | + | chr8 | 143762745 | 143762852; 143762884 | + | ENST00000301258; ENST00000513264 | TAF |
| 19% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 19% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 19% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 19% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 19% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 18% | chr1 | 240569724 | 240569786 | + | chr1 | 240601361 | 240601510 | + | ENST00000319653; ENST00000545751 | TAF |
| 18% | chr12 | 110654593 | 110654638 | + | chr12 | 110655849 | 110656031 | + | ENST00000552912; ENST00000242591 | TAF |
| 18% | chr12 | 94167005 | 94167262 | + | chr12 | 94243746 | 94244047 | + | ENST00000332896; ENST00000542893 | TAF |
| 18% | chr11 | 322262 | 322206 | − | chr11 | 320772 | 320565 | − | ENST00000399808 | TAF |
| 18% | chr11 | 321450 | 321426 | − | chr11 | 320772 | 320565 | − | ENST00000399808 | TAF |
| 18% | chr11 | 321638 | 321543 | − | chr11 | 320772 | 320565 | − | ENST00000399808 | TAF |
| 18% | chr11 | 321638 | 321504 | − | chr11 | 320772 | 320565 | − | ENST00000399808 | TAF |
| 18% | chr11 | 321488 | 321465 | − | chr11 | 320772 | 320565 | − | ENST00000399808 | TAF |
| 18% | chr11 | 322580 | 322557 | − | chr11 | 320772 | 320565 | − | ENST00000399808 | TAF |
| 18% | chr11 | 321410 | 321387 | − | chr11 | 320772 | 320565 | − | ENST00000399808 | TAF |
| 18% | chr11 | 321638 | 321582 | − | chr11 | 320772 | 320565 | − | ENST00000399808 | TAF |
| 18% | chr11 | 321716 | 321660 | − | chr11 | 320772 | 320565 | − | ENST00000399808 | TAF |
| 18% | chr11 | 322067 | 322011 | − | chr11 | 320772 | 320565 | − | ENST00000399808 | TAF |
| 18% | chr11 | 322457 | 322401 | − | chr11 | 320772 | 320565 | − | ENST00000399808 | TAF |
| 18% | chr11 | 321911 | 321855 | − | chr11 | 320772 | 320565 | − | ENST00000399808 | TAF |
| 17% | chr11 | 93468219 | 93468129 | − | chr11 | 93467826 | 93467791; 93467814 | − | ENST00000393259; ENST00000527169 | TAF |

TABLE 56-continued

Transcript fusion for skin cutaneous melanoma (SKCM) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 17% | chr11 | 93468219 | 93468129 | − | chr11 | 93467826 | 93467791; 93467814 | − | ENST00000393259; ENST00000527169 | TAF |
| 17% | chr5 | 171488028 | 171487971 | − | chr5 | 171484477 | 171484353 | − | ENST00000176763; ENST00000520476 | TAF |
| 17% | chr5 | 171488028 | 171487971 | − | chr5 | 171484477 | 171484353 | − | ENST00000176763; ENST00000520476 | TAF |
| 17% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 17% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 17% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 17% | chr7 | 150730019 | 150730148 | + | chr7 | 150730692 | 150730929; 150731004; 150730700 | + | ENST00000461373; ENST00000358849; ENST00000489192; ENST00000297504; ENS T00000356058; ENST00000498578; ENST00000477719; ENST00000477092 | TAF |
| 17% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 17% | chr7 | 150730019 | 150730148 | + | chr7 | 150730692 | 150730929; 150731004; 150730700 | + | ENST00000461373; ENST00000358849; ENST00000489192; ENST00000297504; ENS T00000356058; ENST00000498578; ENST00000477719; ENST00000477092 | TAF |
| 17% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 17% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 17% | chr1 | 6380703 | 6380649 | − | chr1 | 6378638 | 6378552 | − | ENST00000608083; ENST00000377842; ENST00000377845; ENST00000377855; ENS T00000377860; ENST00000418124; ENST00000545482; ENST00000361521; ENST00000473466; ENST00000541130 | TAF |
| 17% | chr1 | 6380703 | 6380649 | − | chr1 | 6378638 | 6378552 | − | ENST00000608083; ENST00000377842; ENST00000377845; ENST00000377855; ENS T00000377860; ENST00000418124; ENST00000545482; ENST00000361521; ENST00000473466; ENST00000541130 | TAF |
| 17% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 17% | chr1 | 6380703 | 6380649 | − | chr1 | 16378638 | 6378552 | − | ENST00000608083; ENST00000377842; ENST00000377845; ENST00000377855; ENS T00000377860; ENST00000418124; ENST00000545482; ENST00000361521; ENST00000473466; ENST00000541130 | TAF |
| 17% | chr17 | 39976225 | 39976301 | + | chr17 | 39976521 | 39976713 | + | ENST00000321562; ENST00000455106; ENST00000544340 | TSF |
| 17% | chr2 | 37569837 | 37570066 | + | chr2 | 37579932 | 37580078 | + | ENST00000338415 | TSF |
| 17% | chr19 | 48627094 | 48627044 | − | chr19 | 48626575 | 48626431 | − | ENST00000263274; ENST00000536218; ENST00000594759; ENST00000427526; ENST00000601091 | TSF |
| 17% | chr19 | 48627094 | 48627044 | − | chr19 | 48626575 | 48626431 | − | ENST00000263274; ENST00000536218; ENST00000594759; ENST00000427526; ENST00000601091 | TSF |
| 16% | chr19 | 46196448 | 46196481 | + | chr19 | 46196671 | 46196814 | + | ENST00000012049; ENST00000366382; ENST00000591606 | TSF |
| 16% | chr19 | 46196448 | 46196481 | + | chr19 | 46196671 | 46196814 | + | ENST00000012049; ENST00000366382; ENST00000591606 | TSF |
| 16% | chr19 | 46196448 | 46196481 | + | chr19 | 46196671 | 46196814 | + | ENST00000012049; ENST00000366382; ENST00000591606 | TSF |
| 16% | chr2 | 74762302 | 74762039 | − | chr2 | 74761901 | 74761658 | − | ENST00000264094; ENST00000393937; ENST00000409549; ENST00000409986 | TSF |
| 16% | chr2 | 74762302 | 74762039 | − | chr2 | 74761901 | 74761658 | − | ENST00000264094; ENST00000393937; ENST00000409549; ENST00000409986 | TSF |
| 15% | chr8 | 145134058 | 145134309 | + | chr8 | 145134846 | 145135052; 145134924 | + | ENST00000316052; ENST00000525936; ENST00000527954 | TAF |
| 15% | chr 8 | 145134058 | 145134309 | + | chr8 | 145134846 | 145135052; 145134924 | + | ENST00000316052; ENST00000525936; ENST00000527954 | TAF |
| 15% | chr8 | 145134058 | 145134309 | + | chr8 | 145134846 | 145135052; 145134924 | + | ENST00000316052; ENST00000525936; ENST00000527954 | TAF |
| 15% | chr10 | 100147690 | 100147622 | − | chr10 | 100147064 | 100146958 | − | ENST00000370575 | TAF |
| 15% | chr12 | 50380548 | 50380303 | − | chr12 | 50370842 | 50370733 | − | ENST00000548961 | TSF |
| 15% | chr7 | 100850556 | 100850506 | − | chr7 | 100850185 | 100850060 | − | ENST00000454310; ENST00000223127 | TSF |
| 14% | chr4 | 107241932 | 107242850 | + | chr4 | 107246142 | 107246275 | + | ENST00000394701 | TAF |
| 14% | chr17 | 39974832 | 39974854 | + | chr17 | 39975462 | 39975651 | + | ENST00000321562 | TAF |
| 14% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 14% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 14% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |

TABLE 56-continued

Transcript fusion for skin cutaneous melanoma (SKCM) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 14% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 14% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 14% | chr17 | 74583012 | 74582951 | − | chr17 | 74574898 | 74574838; 74574881 | | ENST00000225276; ENST00000585736 | TAF |
| 14% | chr17 | 74583012 | 74582951 | − | chr17 | 74574898 | 74574838; 74574881 | − | ENST00000225276; ENST00000585736 | TAF |
| 14% | chr12 | 64427856 | 64428169 | + | chr12 | 64436570 | 64436752 | + | ENST00000355086; ENST00000357825; ENST00000543397 | TSF |
| 14% | chr12 | 64427856 | 64428169 | + | chr12 | 64436570 | 64436752 | + | ENST00000355086; ENST00000357825; ENST00000543397 | TSF |
| 14% | chr5 | 113768197 | 113769626 | + | chr5 | 113798746 | 113798887 | + | ENST00000512097; ENST00000264773 | TSF |
| 13% | chr1 | 156095197 | 156095265 | + | chr1 | 156100408 | 156100564 | + | ENST00000368301; ENST00000361308; ENST00000347559; ENST00000368300; ENST00000368299; ENST00000448611; ENST00000368297; ENST00000504687; ENST00000473598; ENST00000392353 | TAF |
| 13% | chr1 | 156095197 | 155095265 | + | chr1 | 156100408 | 156100564 | + | ENST00000368301; ENST00000361308; ENST00000347559; ENST00000368300; ENS T00000368299; ENST00000448611; ENST00000368297; ENST00000504687; ENST00000473598; ENST00000392353 | TAF |
| 13% | chr1 | 156095197 | 155095265 | + | chr1 | 156100408 | 156100564 | + | ENST00000368301; ENST00000361308; ENST00000347559; ENST00000368300; ENS T00000368299; ENST00000448611; ENST00000368297; ENST00000504687; ENST00000473598; ENST00000392353 | TAF |
| 13% | chr1 | 156095197 | 156095265 | + | chr1 | 156100408 | 156100564 | + | ENST00000368301; ENST00000361308; ENST00000347559; ENST00000368300; ENS T00000368299; ENST00000448611; ENST00000368297; ENST00000504687; ENST00000473598; ENST00000392353 | TAF |
| 13% | chr1 | 156095197 | 155095265 | + | chr1 | 156100408 | 156100564 | + | ENST00000368301; ENST00000361308; ENST00000347559; ENST00000368300; ENST00000368299; ENST00000448611; ENST00000368297; ENST00000504687; ENST000 00473598; ENST00000392353 | TAF |
| 13% | chr1 | 156095197 | 156095265 | + | chr1 | 156100408 | 156100564 | + | ENST00000368301; ENST00000361308; ENST00000347559; ENST00000368300; ENST00000368299; ENST00000448611; ENST00000368297; ENST00000504687; ENST00000473598; ENST00000392353 | TAF |
| 13% | chr17 | 79214190 | 79214239 | + | chr17 | 79214787 | 79214816; 79214953 | + | ENST00000431388; ENST00000576002 | TAF |
| 13% | chr17 | 79214190 | 79214239 | + | chr17 | 79214787 | 79214816; 79214953 | + | ENST00000431388; ENST00000576002 | TAF |
| 13% | chr9 | 131189761 | 131190058 | + | chr9 | 131190581 | 131190700; 131190702 | + | ENST00000372842; ENST00000420512; ENST00000372838 | TAF |
| 13% | chr9 | 131189761 | 131190058 | + | chr9 | 131190581 | 131190700; 131190702 | + | ENST00000372842; ENST00000420512; ENST00000372838 | TAF |
| 13% | chr15 | 41968651 | 41968463 | − | chr15 | 41815513 | 41815443 | − | ENST00000561603; ENST00000304330; ENST00000562303 | TAF |
| 13% | chr15 | 41968651 | 41968463 | − | chr15 | 41815513 | 41815443 | − | ENST00000561603; ENST00000304330; ENST00000562303 | TAF |
| 13% | chr15 | 41968651 | 41968463 | − | chr15 | 41815513 | 41815443 | − | ENST00000561603; ENST00000304330; ENST00000562303 | TAF |
| 13% | chr1 | 45139523 | 45139439 | − | chr1 | 45125967 | 45125846 | − | ENST00000372242; ENST00000372243; ENST00000372237; ENST00000372235; ENST00000420706 | TAF |
| 13% | chr1 | 45139523 | 45139439 | − | chr1 | 45125967 | 45125846 | − | ENST00000372242; ENST00000372243; ENST00000372237; ENST00000372235; ENST00000420706 | TAF |
| 13% | chr1 | 45139523 | 45139439 | − | chr1 | 45125967 | 45125846 | − | ENST00000372242; ENST00000372243; ENST00000372237; ENST00000372235; ENST00000420706 | TAF |
| 13% | chr1 | 45139523 | 45139439 | − | chr1 | 45125967 | 45125846 | − | ENST00000372242; ENST00000372243; ENST00000372237; ENST00000372235; ENST00000420706 | TAF |
| 13% | chr1 | 45139523 | 45139439 | − | chr1 | 45125967 | 45125846 | − | ENST00000372242; ENST00000372243; ENST00000372237; ENST00000372235; ENST00000420706 | TAF |
| 13% | chr10 | 90305421 | 90305214 | − | chr10 | 90122482 | 90122309 | − | ENST00000371947; ENST00000437752; ENST00000331772 | TAF |
| 13% | chr10 | 90305421 | 90305214 | − | chr10 | 90122482 | 90122309 | − | ENST00000371947; ENST00000437752; ENST00000331772 | TAF |
| 13% | chr17 | 41171108 | 41170991 | − | chr17 | 41170816 | 41170609; 41170766 | − | ENST00000355653; ENST00000587173; ENST00000587062 | TAF |
| 13% | chr17 | 41171108 | 41170991 | − | chr17 | 41170816 | 41170609; 41170766 | − | ENST00000355653; ENST00000587173; ENST00000587062 | TAF |
| 13% | chr6 | 111651498 | 111651389 | − | chr6 | 111650941 | 111650735 | − | ENST00000368802; ENST00000368805; ENST00000358835; ENST00000435970 | TAF |
| 13% | chr1 | 236326774 | 236327054 | + | chr1 | 236332006 | 236332055 | + | ENST00000366592; ENST00000454895 | TSF |
| 13% | chr1 | 236326774 | 236327054 | + | chr1 | 236332006 | 236332055 | + | ENST00000366592; ENST00000454895 | TSF |
| 13% | chr4 | 142977397 | 142977072 | − | chr4 | 142950067 | 142949935 | − | ENST00000513000; ENST00000262992; ENST00000308502; ENST00000508116 | TSF |
| 12% | chr16 | 23575135 | 23575430 | + | chr16 | 23578308 | 23578390 | + | ENST00000219638; ENST00000395878; ENST00000567212 | TAF |
| 12% | chr19 | 54631006 | 54631115 | + | chr19 | 54631448 | 54631575 | + | ENST00000321030; ENST00000419967 | TAF |
| 12% | chr19 | 54631006 | 54631115 | + | chr19 | 54631448 | 54631575 | + | ENST00000321030; ENST00000419967 | TAF |
| 12% | chr1 | 212594935 | 212595005 | + | chr1 | 212615911 | 212615967 | + | ENST00000366988 | TAF |
| 12% | chr9 | 139611399 | 139611665 | + | chr9 | 139612029 | 139612163 | + | ENST00000371692 | TAF |
| 12% | chr4 | 171310858 | 174310746 | − | chr4 | 174309546 | 174309492 | − | ENST00000296506 | TAF |
| 12% | chr7 | 150938296 | 150938250 | − | chr7 | 150937608 | 150937511 | − | ENST00000262188; ENST00000392811; ENST00000356800 | TAF |

TABLE 56-continued

Transcript fusion for skin cutaneous melanoma (SKCM) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 12% | chr7 | 100854761 | 100854711 | − | chr7 | 100853725 | 100853612 | − | ENST00000454310; ENST00000223127 | TAF |
| 12% | chr7 | 100854761 | 100854711 | − | chr7 | 100853725 | 100853612 | − | ENST00000454310; ENST00000223127 | TAF |
| 12% | chr1 | 54879137 | 54879029 | − | chr1 | 54870603 | 54870531 | − | ENST00000371320; ENST00000371319; ENST00000357475 | TAF |
| 12% | chr1 | 54879137 | 54879029 | − | chr1 | 54870603 | 54870531 | − | ENST00000371320; ENST00000371319; ENST00000357475 | TAF |
| 12% | chr1 | 54879137 | 54879029 | − | chr1 | 54870603 | 54870531 | − | ENST00000371320; ENST00000371319; ENST00000357475 | TAF |
| 12% | chr5 | 54528691 | 54528595 | − | chr5 | 54528374 | 54528189 | − | ENST00000282572 | TAF |
| 12% | chr7 | 2276932 | 2276801 | − | chr7 | 2275199 | 2274757; 2275164 | − | ENST00000242257; ENST00000440306; ENST00000407040 | TAF |
| 12% | chr7 | 2276932 | 2276801 | − | chr7 | 2275199 | 2274757; 2275164 | − | ENST00000242257; ENST00000440306; ENST00000407040 | TAF |
| 12% | chr2 | 65243329 | 65243368 | + | chr2 | 65243574 | 65243807 | + | ENST00000234256 | TSF |
| 12% | chr11 | 88974419 | 88974474 | + | chr11 | 89028311 | 89028534 | + | ENST00000263321 | TSF |
| 11% | chr10 | 199667221 | 99666955 | − | chr10 | 99664571 | 99664426 | − | ENST00000413387; ENST00000370597; ENST00000298819; ENST00000309155; ENST00000370591 | TAF |
| 11% | chr10 | 199667221 | 99666955 | − | chr10 | 99664571 | 99664426 | − | ENST00000413387; ENST00000370597; ENST00000298819; ENST00000309155; ENST00000370591 | TAF |
| 11% | chr10 | 99667221 | 99666955 | − | chr10 | 99664571 | 99664426 | − | ENST00000413387; ENST00000370597; ENST00000298819; ENST00000309155; ENST00000370591 | TAF |
| 11% | chr10 | 90305421 | 90305146 | − | chr10 | 90122482 | 90122309 | − | ENST00000371947; ENST00000437752; ENST00000331772 | TAF |
| 11% | chr10 | 90305421 | 90305146 | − | chr10 | 90122482 | 90122309 | − | ENST00000371947; ENST00000437752; ENST00000331772 | TAF |
| 11% | chr21 | 47675413 | 47675316 | − | chr21 | 47674758 | 47674690 | − | ENST00000397708; ENST00000291688 | TAF |
| 11% | chr9 | 127176843 | 127176809 | − | chr9 | 127176284 | 127176187 | − | ENST00000259457; ENST00000536392; ENST00000441097 | TAF |
| 11% | chr9 | 127176843 | 127176809 | − | chr9 | 127176284 | 127176187 | − | ENST00000259457; ENST00000536392; ENST00000441097 | TAF |
| 11% | chr9 | 127176843 | 127176809 | − | chr9 | 127176284 | 127176187 | − | ENST00000259457; ENST00000536392; ENST00000441097 | TAF |
| 11% | chr5 | 113768197 | 113769590 | + | chr5 | 113798746 | 113798887 | + | ENST00000512097; ENST00000264773 | TSF |
| 11% | chr17 | 39974832 | 39974893 | + | chr17 | 39975462 | 39975651 | + | ENST00000321562 | TSF |
| 11% | chr7 | 20686966 | 20686997 | + | chr7 | 20687158 | 20687271 | + | ENST00000404938 | TSF |
| 11% | chr15 | 28127352 | 28127177 | − | chr15 | 28117068 | 28117009 | − | ENST00000353809; ENST00000354638 | TSF |
| 11% | chr7 | 82523973 | 82523713 | − | chr7 | 82508778 | 82508653 | − | ENST00000333891; ENST00000423517; ENST00000413807; ENST00000456006 | TSF |
| 11% | chr7 | 82523973 | 82523713 | − | chr7 | 82508778 | 82508653 | − | ENST00000333891; ENST00000423517; ENST00000413807; ENST00000456006 | TSF |
| 11% | chr7 | 82523973 | 82523713 | − | chr7 | 82508778 | 82508653 | − | ENST00000333891; ENST00000423517; ENST00000413807; ENST00000456006 | TSF |
| 11% | chr7 | 82523973 | 82523713 | − | chr7 | 82508778 | 82508653 | − | ENST00000333891; ENST00000423517; ENST00000413807; ENST00000456006 | TSF |
| 11% | chr6 | 13472490 | 13472213 | − | chr6 | 13470862 | 13470669 | − | ENST00000603223 | TSF |
| 10% | chr8 | 104389530 | 104389536 | + | chr8 | 104390255 | 104390471 | + | ENST00000330295; ENST00000520337 | TSF |
| 10% | chr2 | 97615730 | 97615723 | − | chr2 | 197613639 | 97613555 | | ENST00000327896; ENST00000417561; ENST00000490605 | TSF |
| 10% | chr14 | 102691697 | 102691557 | − | chr14 | 102691131 | 102691116 | − | ENST00000559838 | TSF |
| 10% | chr4 | 89198618 | 89198541 | − | chr4 | 89198395 | 89198295; 89198287 | | ENST00000608933; ENST00000295908; ENST00000315194; ENST00000514204 | TSF |
| 10% | chr4 | 89198618 | 89198541 | − | chr4 | 89198395 | 89198295; 89198287 | | ENST00000608933; ENST00000295908; ENST00000315194; ENST00000514204 | TSF |
| 10% | chr4 | 89198618 | 89198541 | − | chr4 | 89198395 | 89198295; 89198287 | − | ENST00000608933; ENST00000295908; ENST00000315194; ENST00000514204 | TSF |
| 10% | chr4 | 89198618 | 89198541 | − | chr4 | 89198395 | 89198295; 89198287 | − | ENST00000608933; ENST00000295908; ENST00000315194; ENST00000514204 | TSF |
| 10% | chr12 | 56357933 | 56357814 | − | chr12 | 56355516 | 56355406 | − | ENST00000449260; ENST00000552882; ENST00000548747; ENST00000360714; ENS T00000536427; ENST00000548493; ENST00000548803; ENST00000547137; ENST00000546543; ENST00000549418; ENST00000549233 | TSF |
| 10% | chr12 | 56357933 | 56357814 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 10% | chr12 | 56357933 | 56357814 | | chr12 | 56355516 | 56355406 | | ENST00000449260; ENST00000552882; ENST00000548747; ENST00000360714; ENS T00000536427; ENST00000548493; ENST00000548803; ENST00000547137; ENST00000546543; ENST00000549418; ENST00000549233 | TSF |
| 10% | chr12 | 56357933 | 56357814 | | chr12 | 56355516 | 56355406 | | ENST00000449260; ENST00000552882; ENST00000548747; ENST00000360714; ENS T00000536427; ENST00000548493; ENST00000548803; ENST00000547137; ENST00000546543; ENST00000549418; ENST00000549233 | TSF |
| 10% | chr12 | 56357933 | 56357814 | | chr12 | 56355516 | 56355406 | | ENST00000449260; ENST00000552882; ENST00000548747; ENST00000360714; ENS T00000536427; ENST00000548493; ENST00000548803; ENST00000547137; ENST00000546543; ENST00000549418; ENST00000549233 | TSF |
| 10% | chr12 | 56357933 | 56357814 | | chr12 | 56355516 | 56355406 | | ENST00000449260; ENST00000552882; ENST00000548747; ENST00000360714; ENS T00000536427; ENST00000548493; ENST00000548803; ENST00000547137; ENST00000546543; ENST00000549418; ENST00000549233 | TSF |
| 10% | chr12 | 56357933 | 56357814 | | chr12 | 56355516 | 56355406 | | ENST00000449260; ENST00000552882; ENST00000548747; ENST00000360714; ENST00000536427; ENST00000548493; ENST00000548803; ENST00000547137; ENST00000546543; | TSF |

TABLE 56-continued

Transcript fusion for skin cutaneous melanoma (SKCM) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 10% | chr12 | 56357933 | 56357814 | − | chr12 | 56355516 | 56355406 | − | ENST00000549418; ENST00000549233 ENST00000449260; ENST00000552882; ENST00000548747; ENST00000360714; ENST00000536427; ENST00000548493; ENST00000548803; ENST00000547137; ENST00000546543 | TSF |
| 10% | chr12 | 56357933 | 56357814 | − | chr12 | 56355516 | 56355406 | − | ENST00000549418; ENST00000549233 ENST00000449260; ENST00000552882; ENST00000548747; ENST00000360714; ENST00000536427; ENST00000548493; ENST00000548803; ENST00000547137; ENST00000546543 | TSF |
| 9% | chr12 | 110610148 | 110610745 | + | chr12 | 110618227 | 110618376 | + | ENST00000549418; ENST00000549233 ENST00000552912; ENST00000242591; ENST00000550156 | TSF |
| 9% | chr12 | 110610148 | 110610745 | + | chr12 | 110618227 | 110618376 | + | ENST00000552912; ENST00000242591; ENST00000550156 | TSF |
| 8% | chr9 | 5907671 | 5907771 | + | chr9 | 5908640 | 5908708 | + | ENST00000381477; ENST00000381476; ENST00000381471 | TSF |
| 8% | chr12 | 66314250 | 66314527 | + | chr12 | 66345163 | 66345195; 66345213 | + | ENST00000403681; ENST00000541363; ENST00000393577 | TSF |
| 8% | chr12 | 66314250 | 66314527 | + | chr12 | 66345163 | 66345195; 66345213 | + | ENST00000403681; ENST00000541363; ENST00000393577 | TSF |
| 8% | chr12 | 66314250 | 66314527 | + | chr12 | 66345163 | 66345195; 66345213 | + | ENST00000403681; ENST00000541363; ENST00000393577 | TSF |
| 8% | chr18 | 20777402 | 20777408 | + | chr18 | 20793941 | 20794018; 20794082 | + | ENST00000400473; ENST00000579963; ENST00000256925; ENST00000582882; ENST00000420687 | TSF |
| 8% | chr18 | 20777402 | 20777408 | + | chr18 | 20793941 | 20794018; 20794082 | + | ENST00000400473; ENST00000579963; ENST00000256925; ENST00000582882; ENST00000420687 | TSF |
| 8% | chr18 | 20777402 | 20777408 | + | chr18 | 20793941 | 20794018; 20794082 | + | ENST00000400473; ENST00000579963; ENST00000256925; ENST00000582882; ENST00000420687 | TSF |
| 8% | chr1 | 212596286 | 212598077 | + | chr1 | 212617681 | 212617784 | + | ENST00000366988 | TSF |
| 8% | chr7 | 22512874 | 22512791 | − | chr7 | 22459455 | 22459423 | − | ENST00000406890 | TSF |
| 8% | chr16 | 90158266 | 90158141 | − | chr16 | 90141431 | 90141324 | − | ENST00000449207; ENST00000568473; ENST00000564210 | TSF |
| 8% | chr16 | 90158266 | 90158141 | − | chr16 | 90141431 | 90141324 | − | ENST00000449207; ENST00000568473; ENST00000564210 | TSF |
| 8% | chr16 | 90158266 | 90158141 | − | chr16 | 90141431 | 90141324 | − | ENST00000449207; ENST00000568473; ENST00000564210 | TSF |
| 8% | chr15 | 52752877 | 52752312 | − | chr15 | 52725482 | 52725372 | − | ENST00000399231; ENST00000356338; ENST00000358212; ENST00000399233; ENST00000553916; ENST00000556196 | TSF |
| 8% | chr15 | 52752877 | 52752312 | − | chr15 | 52725482 | 52725372 | − | ENST00000399231; ENST00000356338; ENST00000358212; ENST00000399233; ENST00000553916; ENST00000556196 | TSF |
| 8% | chr15 | 52752877 | 52752312 | − | chr15 | 52725482 | 52725372 | − | ENST00000399231; ENST00000356338; ENST00000358212; ENST00000399233; ENST00000553916; ENST00000556196 | TSF |
| 8% | chr15 | 52752877 | 52752312 | − | chr15 | 52725482 | 52725372 | − | ENST00000399231; ENST00000356338; ENST00000358212; ENST00000399233; ENST00000553916; ENST00000556196 | TSF |
| 8% | chr15 | 52752877 | 52752312 | − | chr15 | 52725482 | 52725372 | − | ENST00000399231; ENST00000356338; ENST00000358212; ENST00000399233; ENST00000553916; ENST00000556196 | TSF |
| 8% | chr15 | 52752877 | 52752312 | − | chr15 | 52725482 | 52725372 | − | ENST00000399231; ENST00000356338; ENST00000358212; ENST00000399233; ENST00000553916; ENST00000556196 | TSF |
| 8% | chr5 | 178696659 | 178696386 | − | chr5 | 178634716 | 178634514 | − | ENST00000251582; ENST00000274609 | TSF |
| 8% | chr5 | 178696659 | 178696386 | − | chr5 | 178634716 | 178634514 | − | ENST00000251582; ENST00000274609 | TSF |
| 8% | chr15 | 31367719 | 31365913 | − | chr15 | 31362429 | 31362234; 31362036 | − | ENST00000397795; ENST00000256552; ENST00000542188; ENST00000558445; ENST00000559177; ENST00000560658; ENST00000559179 | TSF |
| 8% | chr15 | 31367719 | 31365913 | − | chr15 | 31362429 | 31362234; 31362036 | − | ENST00000397795; ENST00000256552; ENST00000542188; ENST00000558445; ENST00000559177; ENST00000560658; ENST00000559179 | TSF |
| 8% | chr15 | 31367719 | 31365913 | − | chr15 | 31362429 | 31362234; 31362036 | − | ENST00000397795; ENST00000256552; ENST00000542188; ENST00000558445; ENST00000559177; ENST00000560658; ENST00000559179 | TSF |
| 8% | chr15 | 31367719 | 31365913 | − | chr15 | 31362429 | 31362234; 31362036 | − | ENST00000397795; ENST00000256552; ENST00000542188; ENST00000558445; ENST00000559177; ENST00000560658; ENST00000559179 | TSF |
| 8% | chr2 | 42615588 | 42615585 | − | chr2 | 42580483 | 42580352; 42580316 | − | ENST00000468711; ENST00000378669; ENST00000234301; ENST00000463055 | TSF |
| 8% | chr2 | 42615588 | 42615585 | − | chr2 | 42580483 | 42580352; 42580316 | − | ENST00000468711; ENST00000378669; ENST00000234301; ENST00000463055 | TSF |
| 8% | chr2 | 42615588 | 42615585 | − | chr2 | 42580483 | 42580352; 42580316 | − | ENST00000468711; ENST00000378669; ENST00000234301; ENST00000463055 | TSF |
| 7% | chr2 | 144377158 | 144377460 | + | chr2 | 144381702 | 144381836 | + | ENST00000295095 | TSF |
| 7% | chr5 | 50095496 | 50095792 | + | chr5 | 50111266 | 50111358 | + | ENST00000514342; ENST00000505697; ENST00000503750; ENST00000281631; ENST00000514067; ENST00000505554 | TSF |
| 7% | chr5 | 50095496 | 50095792 | + | chr5 | 50111266 | 50111358 | + | ENST00000514342; ENST00000505697; ENST00000503750; ENST00000281631; ENST00000514067; ENST00000505554 | TSF |
| 7% | chr5 | 50095496 | 50095792 | + | chr5 | 50111266 | 50111358 | + | ENST00000514342; ENST00000505697; ENST00000503750; ENST00000281631; ENST00000514067; ENST00000505554 | TSF |
| 7% | chr6 | 151188691 | 151188718 | + | chr6 | 151197226 | 151197310 | + | ENST00000367321; ENST00000367307; ENST00000367308 | TSF |
| 7% | chr6 | 151188691 | 151188718 | + | chr6 | 151197226 | 151197310 | + | ENST00000367321; ENST00000367307; ENST00000367308 | TSF |
| 7% | chr6 | 151188691 | 151188718 | + | chr6 | 151197226 | 151197310 | + | ENST00000367321; ENST00000367307; ENST00000367308 | TSF |
| 7% | chr12 | 56350811 | 56350835 | + | chr12 | 56350794 | 56350733 | − | ENST00000449260; ENST00000552882; ENST00000550464; | TSF |

TABLE 56-continued

Transcript fusion for skin cutaneous melanoma (SKCM) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 7% | chr12 | 56350811 | 56350835 | + | chr12 | 56350794 | 56350733 | − | ENST00000548747; ENST00000360714; ENST00000536427; ENST00000539511; ENST00000548493; ENST00000549404; ENST00000548803 ENST00000449260; ENST00000552882; ENST00000550464; | TSF |
| 7% | chr12 | 56350811 | 56350835 | + | chr12 | 56350794 | 56350733 | − | ENST00000548747; ENST00000360714; ENST00000536427; ENST00000539511; ENST00000548493; ENST00000549404; ENST00000548803 ENST00000449260; ENST00000552882; ENST00000550464; | TSF |
| 7% | chr12 | 56350811 | 56350835 | + | chr12 | 56350794 | 56350733 | − | ENST00000548747; ENS T00000360714; ENST00000536427; ENST00000539511; ENST00000548493; ENST00000549404; ENST00000548803 ENST00000449260; ENST00000552882; ENST00000550464; | TSF |
| 7% | chr2 | 42615932 | 42615589 | − | chr2 | 42580483 | 42580352; 42580316 | − | ENST00000468711; ENST00000378669; ENST00000234301; ENST00000463055 | TSF |
| 7% | chr2 | 42615932 | 42615589 | − | chr2 | 42580483 | 42580352; 42580316 | − | ENST00000468711; ENST00000378669; ENST00000234301; ENST00000463055 | TSF |
| 7% | chr2 | 42615932 | 42615589 | − | chr2 | 42580483 | 42580352; 42580316 | − | ENST00000468711; ENST00000378669; ENST00000234301; ENST00000463055 | TSF |
| 7% | chr15 | 52752877 | 52752156 | − | chr15 | 52725482 | 52725372 | − | ENST00000399231; ENST00000356338; ENST00000358212; ENST00000399233; ENST00000553916; ENST00000556196 | TSF |
| 7% | chr15 | 52752877 | 52752156 | − | chr15 | 52725482 | 52725372 | − | ENST00000399231; ENST00000356338; ENST00000358212; ENST00000399233; ENST00000553916; ENST00000556196 | TSF |
| 7% | chr15 | 52752877 | 52752156 | − | chr15 | 52725482 | 52725372 | − | ENST00000399231; ENST00000356338; ENST00000358212; ENST00000399233; ENST00000553916; ENST00000556196 | TSF |
| 7% | chr15 | 52752877 | 52752156 | − | chr15 | 52725482 | 52725372 | − | ENST00000399231; ENST00000356338; ENST00000358212; ENST00000399233; ENST00000553916; ENST00000556196 | TSF |
| 7% | chr15 | 52752877 | 52752156 | − | chr15 | 52725482 | 52725372 | − | ENST00000399231; ENST00000356338; ENST00000358212; ENST00000399233; ENST00000553916; ENST00000556196 | TSF |
| 7% | chr15 | 52752877 | 52752156 | − | chr15 | 52725482 | 52725372 | − | ENST00000399231; ENST00000356338; ENST00000358212; ENST00000399233; ENST00000553916; ENST00000556196 | TSF |
| 7% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 7% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 7% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 7% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 7% | chr7 | 44158417 | 44158351 | − | chr7 | 44157663 | 44157542 | − | ENST00000406581; ENST00000223361; ENST00000452185; ENST00000433715; ENST00000456038; ENST00000418438 | TSF |
| 7% | chr13 | 78549747 | 78549606 | − | chr13 | 78492759 | 78492226 | − | ENST00000377211 | TSF |
| 6% | chr20 | 45199908 | 45199619 | − | chr20 | 45195029 | 45194868; 45194995 | − | ENST00000396360; ENST00000435032; ENST00000290317; ENST00000279027; ENST00000472148; ENST00000413164; ENST00000495082; ENST00000468915 | TSF |
| 6% | chr20 | 45199908 | 45199619 | − | chr20 | 45195029 | 45194868; 45194995 | − | ENST00000396360; ENST00000435032; ENST00000290317; ENST00000279027; ENST00000472148; ENST00000413164; ENST00000495082; ENST00000468915 | TSF |
| 6% | chr19 | 3552777 | 3552620 | − | chr19 | 3551192 | 3550982; 3551006 | − | ENST00000389395; ENST00000398558; ENST00000588918; ENST00000355415; ENST00000585814 | TSF |
| 6% | chr19 | 3552777 | 3552620 | − | chr19 | 3551192 | 3550982; 3551006 | − | ENST00000389395; ENST00000398558; ENST00000588918; ENST00000355415; ENST00000585814 | TSF |
| 6% | chr19 | 3552777 | 3552620 | − | chr19 | 3551192 | 3550982; 5351006 | − | ENST00000389395; ENST00000398558; ENST00000588918; ENST00000355415; ENST00000585814 | TSF |
| 6% | chr19 | 3552777 | 3552620 | − | chr19 | 3551192 | 3550982; 3551006 | − | ENST00000389395; ENST00000398558; ENST00000588918; ENST00000355415; ENST00000585814 | TSF |
| 6% | chr6 | 13321752 | 13321692 | − | chr6 | 13321327 | 13321140; 13320945; 13321064 | − | ENST00000606214; ENST00000421203; ENST00000356436; ENST00000379300; ENST00000379307; ENST00000343141; ENST00000607658; ENST00000450347; ENST00000452989; ENST00000422136; ENST00000446018; ENST00000420456; ENST00000428109; ENST00000416436; ENST00000379291; ENST00000606370; ENST00000606541 | TSF |
| 6% | chr6 | 13321752 | 13321692 | − | chr6 | 13321327 | 13321140; 13320945; 13321064 | − | ENST00000606214; ENST00000421203; ENST00000356436; ENST00000379300; ENS T00000379307; ENST00000343141; ENST00000607658; ENST00000450347; ENST00000452989; ENST00000422136; ENST00000446018; ENST00000420456; ENST0000042 8109; ENST00000416436; ENST00000379291; ENST00000606370; ENST00000606541 | TSF |
| 6% | chr6 | 13321752 | 13321692 | − | chr6 | 13321327 | 13321140; 13320945; 13321064 | − | ENST00000606214; ENST00000421203; ENST00000356436; ENST00000379300; ENST00000379307; ENST00000343141; ENST00000607658; ENST00000450347; ENST00000452989; ENST0000422136; ENST00000446018; ENST00000420456; ENST00000428109; ENST00000416436; ENST00000379291; | TSF |

TABLE 56-continued

Transcript fusion for skin cutaneous melanoma (SKCM) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 6% | chr6 | 13321752 | 13321692 | – | chr6 | 13321327 | 13321140; 13320945; 13321064 | – | ENST00000606214; ENST00000421203; ENST00000356436; ENST00000379300; ENST00000379307; ENST00000343141; ENST00000607658; ENST00000450347; ENST00000452989; ENST00000422136; ENST00000446018; ENST00000420456; ENST0000042 8109; ENST00000416436; ENST00000379291; ENST00000606370; ENST00000606541 | TSF |
| 6% | chr6 | 13321752 | 13321692 | – | chr6 | 13321327 | 13321140; 13320945; 13321064 | – | ENST00000606214; ENST00000421203; ENST00000356436; ENST00000379300; ENS T00000379307; ENST00000343141; ENST00000607658; ENST00000450347; ENST00000452989; ENST00000422136; ENST00000446018; ENST00000420456; ENST0000042 8109; ENST00000416436; ENST00000379291; ENST00000606370; ENST00000606541 | TSF |
| 6% | chr6 | 13321752 | 13321692 | – | chr6 | 13321327 | 13321140; 13320945; 13321064 | – | ENST00000606214; ENST00000421203; ENST00000356436; ENST00000379300; ENST00000379307; ENST00000343141; ENST00000607658; ENST00000450347; ENST00000452989; ENST00000422136; ENST00000446018; ENST00000420456; ENST0000042 8109; ENST00000416436; ENST00000379291; ENST00000606370; ENST00000606541 | TSF |
| 6% | chr6 | 13321752 | 13321692 | – | chr6 | 13321327 | 13321140; 13320945; 13321064 | – | ENST00000606214; ENST00000421203; ENST00000356436; ENST00000379300; ENS T00000379307; ENST00000343141; ENST00000607658; ENST00000450347; ENST00000452989; ENST00000422136; ENST00000446018; ENST00000420456; ENST00000428109; ENST00000416436; ENST00000379291; ENST00000606370; ENST00000606541 | TSF |
| 6% | chr6 | 13321752 | 13321692 | – | chr6 | 13321327 | 13321140; 13320945; 13321064 | – | ENST00000606214; ENST00000421203; ENST00000356436; ENST00000379300; ENST00000379307; ENST00000343141; ENST00000607658; ENST00000450347; ENST00000452989; ENST00000422136; ENST00000446018; ENST00000420456; ENST0000042 8109; ENST00000416436; ENST00000379291; ENST00000606370; ENST00000606541 | TSF |
| 6% | chr6 | 13321752 | 13321692 | – | chr6 | 13321327 | 13321140; 13320945; 13321064 | – | ENST00000606214; ENST00000421203; ENST00000356436; ENST00000379300; ENST00000379307; ENST00000343141; ENST00000607658; ENST00000450347; ENST00000452989; ENST00000422136; ENST00000446018; ENST00000420456; ENST0000042 8109; ENST00000416436; ENST00000379291; ENST00000606370; ENST00000606541 | TSF |
| 6% | chr6 | 13321752 | 13321692 | – | chr6 | 13321327 | 13321140; 13320945; 13321064 | – | ENST00000606214; ENST00000421203; ENST00000356436; ENST00000379300; ENST00000379307; ENST00000343141; ENST00000607658; ENST00000450347; ENST00000452989; ENST00000422136; ENST00000446018; ENST00000420456; ENST00000428109; ENST00000416436; ENST00000379291; ENST00000606370; ENST00000606541 | TSF |
| 6% | chr6 | 13321752 | 13321692 | – | chr6 | 13321327 | 13321140; 13320945; 13321064 | – | ENST00000606214; ENST00000421203; ENST00000356436; ENST00000379300; ENST00000379307; ENST00000343141; ENST00000607658; ENST00000450347; ENST00000452989; ENST00000422136; ENST00000446018; ENST00000420456; ENST00000428109; ENST00000416436; ENST00000379291; ENST00000606370; ENST00000606541 | TSF |
| 6% | chr6 | 13321752 | 13321692 | – | chr6 | 13321327 | 13321140; 13320945; 13321064 | – | ENST00000606214; ENST00000421203; ENST00000356436; ENST00000379300; ENST00000379307; ENST00000343141; ENST00000607658; ENST00000450347; ENST00000452989; ENST00000422136; ENST00000446018; ENST00000420456; ENST0000042 8109; ENST00000416436; ENST00000379291; ENST00000606370; ENST00000606541 | TSF |
| 6% | chr6 | 13321752 | 13321692 | – | chr6 | 13321327 | 13321140; 13320945; 13321064 | – | ENST00000606214; ENST00000421203; ENST00000356436; ENST00000379300; ENST00000379307; ENST00000343141; ENST00000607658; ENST00000450347; ENST00000452989; ENST00000422136; ENST00000446018; ENST00000420456; ENST00000428109; ENST00000416436; ENST00000379291; ENST00000606370; ENST00000606541 | TSF |
| 6% | chrX | 153207989 | 153207921 | – | chrX | 153207484 | 153207403 | – | ENST00000393700; ENST00000369997 | TSF |
| 6% | chr15 | 28123956 | 28123431 | – | chr15 | 28117068 | 28117009 | – | ENST00000353809; ENST00000354638 | TSF |
| 6% | chr17 | 28255620 | 28255510 | – | chr17 | 28252573 | 28252490 | – | ENST00000582084; ENST00000590153 | TSF |

TABLE 57

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 51% | chr20 | 47768284 | 47768119 | - | ENST00000371828; ENST00000340954; ENST00000347458; ENST00000360426; ENST00000371792; ENST00000371802; ENST00000371856; ENST00000437404; ENST00000456866 | chr20 | 47761186 | 47760181 | - | TAF |
| 51% | chr20 | 47768284 | 47768119 | - | ENST00000371828; ENST00000340954; ENST00000347458; ENST00000360426; ENST00000371792; ENST00000371802; ENST00000371856; ENST00000437404; ENST00000456866 | chr20 | 47761186 | 47760181 | - | TAF |
| 51% | chr20 | 47768284 | 47768119 | - | ENST00000371828; ENST00000340954; ENST00000347458; ENST00000360426; ENST00000371792; ENST00000371802; ENST00000371856; ENST00000437404; ENST00000456866 | chr20 | 47761186 | 47760181 | - | TAF |
| 46% | chr1 | 32696528 | 32696620 | + | ENST00000373586 | chr1 | 32696861 | 32697110 | + | TAF |
| 45% | chr1 | 24463799 | 24463621 | - | ENST00000270800 | chr1 | 24461426 | 24461370 | - | TAF |
| 37% | chr18 | 33767503 | 33767644 | + | ENST00000261326 | chr18 | 33773430 | 33773774 | + | TAF |
| 26% | chr3 | 57678745 | 57678509 | - | ENST00000311128 | chr3 | 57665452 | 57665436 | - | TAF |
| 24% | chr20 | 35842163 | 35842268 | + | ENST00000237530; ENST00000373622 | chr20 | 35844460 | 35844765 | + | TAF |
| 24% | chr20 | 35842163 | 35842268 | + | ENST00000237530; ENST00000373622 | chr20 | 35844460 | 35844765 | + | TAF |
| 22% | chr13 | 43659904 | 43659974 | + | ENST00000379221 | chr13 | 43670953 | 43671210 | + | TAF |
| 21% | chr19 | 42222047 | 42222099 | + | ENST00000398599; ENST00000221992; ENST00000405816 | chr19 | 42234250 | 42234353 | + | TSF |
| 21% | chr19 | 42222047 | 42222099 | + | ENST00000398599; ENST00000221992; ENST00000405816 | chr19 | 42234250 | 42234353 | + | TSF |
| 20% | chr11 | 118888255 | 118888078 | - | ENST00000527673 | chr11 | 118861152 | 118861045 | - | TSF |
| 20% | chr6 | 74228333 | 74228077 | - | ENST00000316292; ENST00000309268; ENST00000331523 | chr6 | 74195910 | 74195882 | - | TSF |
| 19% | chr6 | 1960205 | 1960101 | - | ENST00000530927; ENST00000380815 | chr6 | 1955184 | 1955013 | - | TAF |
| 19% | chr6 | 1960205 | 1960101 | - | ENST00000530927; ENST00000380815 | chr6 | 1955184 | 1955013 | - | TAF |
| 18% | chr21 | 45379563 | 45379740 | + | ENST00000291572; ENST00000448287; ENST00000398061; ENST00000327505; ENST00000445582; ENST00000398063; ENST00000398058; ENST00000457068; ENST00000422850; ENST00000546158 | chr21 | 45380513 | 45380695 | + | TAF |
| 17% | chr6 | 35314915 | 35314927 | + | ENST00000448077 | chr6 | 35351354 | 35351915 | + | TAF |
| 17% | chr2 | 24550951 | 24550921 | - | ENST00000361999; ENST00000355123; ENST00000406921; ENST00000412011 | chr2 | 24544749 | 24544681 | - | TAF |
| 17% | chr10 | 22171368 | 22171211 | - | ENST00000376980 | chr10 | 22168812 | 22168560 | - | TAF |
| 17% | chr19 | 16204346; 16204382 | 16204408 | + | ENST00000344824; ENST00000538887; ENST00000300933; ENST00000588032; ENST00000592822 | chr19 | 16213047 | 16213167 | + | TSF |
| 17% | chr19 | 16204346; 16204382 | 16204408 | + | ENST00000344824; ENST00000538887; ENST00000300933; ENST00000588032; ENST00000592822 | chr19 | 16213047 | 16213167 | + | TSF |
| 17% | chr19 | 16204346; 16204382 | 16204408 | + | ENST00000344824; ENST00000538887; ENST00000300933; ENST00000588032; ENST00000592822 | chr19 | 16213047 | 16213167 | + | TSF |
| 17% | chr19 | 16204346; 16204382 | 16204408 | + | ENST00000344824; ENST00000538887; ENST00000300933; ENST00000588032; ENST00000592822 | chr19 | 16213047 | 16213167 | + | TSF |
| 16% | chr12 | 57060050 | 57059988 | - | ENST00000262033; ENST00000414274; ENST00000436399; ENST00000456859 | chr12 | 57059571 | 57059432 | - | TAF |
| 16% | chr12 | 57060050 | 57059988 | - | ENST00000262033; ENST00000414274; ENST00000436399; ENST00000456859 | chr12 | 57059571 | 57059432 | - | TAF |
| 16% | chr12 | 57060050 | 57059988 | - | ENST00000262033; ENST00000414274; ENST00000436399; ENST00000456859 | chr12 | 57059571 | 57059432 | - | TAF |
| 16% | chr12 | 57060050 | 57059988 | - | ENST00000262033; ENST00000414274; ENST00000436399; ENST00000456859 | chr12 | 57059571 | 57059432 | - | TAF |
| 16% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 16% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 16% | chr10 | 75555297 | 75555421 | + | ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 16% | chr10 | 75555297 | 75555421 | + | ENST00000604729; ENST00000603114; | chr10 | 75556079 | 75556138 | + | TSF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 16% | chr10 | 75555297 | 75555421 | + | ENST00000604524; ENST00000398706; ENST00000605216; ENST00000433366; ENST00000492395; ENST00000603187; ENST00000412198; ENST00000604754 ENST00000604729; ENST00000603114; | chr10 | 75556079 | 75556138 | + | TSF |
| 16% | chr10 | 75555297 | 75555421 | + | ENST00000604524; ENST00000398706; ENST00000605216; ENST00000433366; ENST00000492395; ENST00000603187; ENST00000412198; ENST00000604754 ENST00000604729; ENST00000603114; | chr10 | 75556079 | 75556138 | + | TSF |
| 16% | chr10 | 75555297 | 75555421 | + | ENST00000604524; ENST00000398706; ENST00000605216; ENST00000433366; ENST00000492395; ENST00000603187; ENST00000412198; ENST00000604754 ENST00000604729; ENST00000603114; | chr10 | 75556079 | 75556138 | + | TSF |
| 16% | chr10 | 75555297 | 75555421 | + | ENST00000604524; ENST00000398706; ENST00000605216; ENST00000433366; ENST00000492395; ENST00000603187; ENST00000412198; ENST00000604754 ENST00000604729; ENST00000603114; ENST00000604524; ENST00000398706; ENST00000605216; ENST00000433366; ENST00000492395; ENST00000603187; ENST00000412198; ENST00000604754 | chr10 | 75556079 | 75556138 | + | TSF |
| 15% | chr5 | 147207691 | 147207585 | − | ENST00000296695; ENST00000510027 | chr5 | 147185494 | 147185375 | − | TAF |
| 15% | chr10 | 47747112 | 47747132 | + | ENST00000340243; ENST00000374277; ENST00000449464; ENST00000538825 | chr10 | 48278725 | 48278896 | + | TAF |
| 14% | chr1 | 33272212 | 33272083 | − | ENST00000373477 | chr1 | 33270534 | 33269340 | − | TAF |
| 14% | chr2 | 86769435 | 86769375 | − | ENST00000263856; ENST00000409727; ENST00000439940; ENST00000604011 ENST00000440757 | chr2 | 86768487 | 86767721 | − | TAF |
| 14% | chr2 | 86769435 | 86769375 | − | ENST00000263856; ENST00000409727; ENST00000439940; ENST00000604011; ENST00000440757 | chr2 | 86768487 | 86767721 | − | TAF |
| 14% | chr2 | 86769435 | 86769375 | − | ENST00000263856; ENST00000409727; ENST00000439940; ENST00000604011; ENST00000440757 | chr2 | 86768487 | 86767721 | − | TAF |
| 14% | chr20 | 48273239 | 48273105 | − | ENST00000371711 | chr20 | 48264429 | 48264382 | − | TAF |
| 14% | chr11 | 18536388 | 18536225 | − | ENST00000536719; ENST00000251968 | chr11 | 18534149 | 18533862 | − | TAF |
| 14% | chr8 | 71619168 | 71619388 | + | ENST00000408926; ENST00000520030 | chr8 | 71625661 | 71625673 | + | TSF |
| 13% | chr13 | 44433033 | 44432917 | − | ENST00000444614; ENST00000281508 | chr13 | 44413224 | 44412729 | − | TAF |
| 13% | chr7 | 27582719 | 27582586 | − | ENST00000265395; ENST00000425715 | chr7 | 27581374 | 27579272 | − | TAF |
| 13% | chr7 | 27582719 | 27582586 | − | ENST00000265395; ENST00000425715 | chr7 | 27581374 | 27579272 | − | TAF |
| 13% | chr12 | 71509738 | 71509630 | − | ENST00000549357 | chr12 | 71504233 | 71503634 | − | TAF |
| 13% | chr16 | 68849418 | 68849662 | + | ENST00000261769; ENST00000566612; ENST00000422392 | chr16 | 68851395 | 68851859 | + | TAF |
| 13% | chr16 | 68849418 | 68849662 | + | ENST00000261769; ENST00000566612; ENST00000422392 | chr16 | 68851395 | 68851859 | + | TAF |
| 13% | chr19 | 42222047 | 42222099 | + | ENST00000398599; ENST00000221992; ENST00000405816 | chr19 | 42234246 | 42234353 | + | TSF |
| 13% | chr19 | 42222047 | 42222099 | + | ENST00000398599; ENST00000221992; ENST00000405816 | chr19 | 42234246 | 42234353 | + | TSF |
| 13% | chr4 | 169086398 | 169086477 | + | ENST00000359299 | chr4 | 169090666 | 169090754 | + | TSF |
| 12% | chr2 | 211342488 | 211342490 | + | ENST00000523702; ENST00000430249 | chr2 | 211384275 | 211384452 | + | TAF |
| 12% | chr6 | 2116114 | 2116005 | − | ENST00000530927; ENST00000380815 | chr6 | 2109630 | 2109512 | − | TAF |
| 12% | chr6 | 2116114 | 2116005 | − | ENST00000530927; ENST00000380815 | chr6 | 2109630 | 2109512 | − | TAF |
| 12% | chr3 | 49927493 | 49927357 | − | ENST00000296474; ENST00000344206 | chr3 | 49927248 | 49927204 | − | TAF |
| 12% | chr3 | 49927493 | 49927357 | − | ENST00000296474; ENST00000344206 | chr3 | 49927248 | 49927204 | − | TAF |
| 11% | chr2 | 242275390; 242275258 | 242275513 | + | ENST00000391973; ENST00000428282; ENST00000360051; ENST00000407017; ENST00000391971; ENST00000401990; ENST00000407971; ENST00000436795; ENST00000411484; ENST00000402092; ENST00000443492; ENST00000437066; ENST00000449239; ENST00000457874 | chr2 | 242276200 | 242276228 | + | TAF |
| 11% | chr2 | 242275390; 242275258 | 242275513 | + | ENST00000391973; ENST00000428282; ENST00000360051; ENST00000407017; ENST00000391971; ENST00000401990; ENST00000407971; ENST00000436795; ENST00000411484; ENST00000402092; ENST00000443492; ENST00000437066; ENST00000449239; ENST00000457874 | chr2 | 242276200 | 242276228 | + | TAF |
| 11% | chr2 | 242275390; 242275258 | 242275513 | + | ENST00000391973; ENST00000428282; ENST00000360051; ENST00000407017; ENST00000391971; ENST00000401990; ENST00000407971; ENST00000436795; | chr2 | 242276200 | 242276228 | + | TAF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 11% | chr2 | 242275390; 242275258 | 242275513 | + | ENST00000411484; ENST00000402092; ENST00000443492; ENST00000437066; ENST00000449239; ENST00000457874 ENST00000391973; ENST00000428282; ENST00000360051; ENST00000407017; ENST00000391971; ENST00000401990; ENST00000407971; ENST00000436795; | chr2 | 242276200 | 242276228 | + | TAF |
| 11% | chr2 | 242275390; 242275258 | 242275513 | + | ENST00000411484; ENST00000402092; ENST00000443492; ENST00000437066; ENST00000449239; ENST00000457874 ENST00000391973; ENST00000428282; ENST00000360051; ENST00000407017; ENST00000391971; ENST00000401990; ENST00000407971; ENST00000436795; ENST00000411484; ENST00000402092; ENST00000443492; ENST00000437066; ENST00000449239; ENST00000457874 | chr2 | 242276200 | 242276228 | + | TAF |
| 11% | chr16 | 2825557; 2825626 | 2825452 | − | ENST00000262306; ENST00000409906; ENST00000409477; ENST00000494946 | chr16 | 2823834 | 2823809 | − | TAF |
| 11% | chr16 | 2825557; 2825626 | 2825452 | − | ENST00000262306; ENST00000409906; ENST00000409477; ENST00000494946 | chr16 | 2823834 | 2823809 | − | TAF |
| 11% | chr16 | 2825557; 2825626 | 2825452 | − | ENST00000262306; ENST00000409906; ENST00000409477; ENST00000494946 | chr16 | 2823834 | 2823809 | − | TAF |
| 11% | chr9 | 99122503 | 99122436 | − | ENST00000253270; ENST00000375259; ENST00000375257 | chr9 | 99115925 | 99115627 | − | TAF |
| 11% | chr1 | 183441756 | 183441784 | + | ENST00000440812; ENST00000444547; ENST00000347615; ENST00000507469; ENST00000515829 | chr1 | 183470266 | 183470283 | + | TSF |
| 11% | chr5 | 10748383 | 10748287 | − | ENST00000230895; ENST00000432074 | chr5 | 10732796 | 10732287 | − | TSF |
| 10% | chr6 | 34210489 | 34210572 | + | ENST00000447654; ENST00000311487; ENST00000347617; ENST00000401473; ENST00000374116 | chr6 | 34212756 | 34212817 | + | TSF |
| 10% | chr6 | 34210489 | 34210572 | + | ENST00000447654; ENST00000311487; ENST00000347617; ENST00000401473; ENST00000374116 | chr6 | 34212756 | 34212817 | + | TSF |
| 10% | chr1 | 20979220 | 20979114 | − | ENST00000602624; ENST00000375048; ENST00000415136 | chr1 | 20978611 | 20978295 | − | TSF |
| 10% | chr1 | 20979220 | 20979114 | − | ENST00000602624; ENST00000375048; ENST00000415136 | chr1 | 20978611 | 20978295 | − | TSF |
| 10% | chr1 | 20979220 | 20979114 | − | ENST00000602624; ENST00000375048; ENST00000415136 | chr1 | 20978611 | 20978295 |  | TSF |
| 10% | chr3 | 185414451 | 185414400 | − | ENST00000382199; ENST00000421047; ENST00000457616; ENST00000346192 | chr3 | 185411016 | 185410789 | − | TSF |
| 10% | chr3 | 185414451 | 185414400 | − | ENST00000382199; ENST00000421047; ENST00000457616; ENST00000346192 | chr3 | 185411016 | 185410789 | − | TSF |
| 10% | chr4 | 25759228 | 25759156 | − | ENST00000399878; ENST00000264868; ENST00000502949; ENST00000510448 | chr4 | 25723603 | 25723555 | − | TSF |
| 10% | chr4 | 25759228 | 25759156 | − | ENST00000399878; ENST00000264868; ENST00000502949; ENST00000510448 | chr4 | 25723603 | 25723555 | − | TSF |
| 10% | chr4 | 25759228 | 25759156 | − | ENST00000399878; ENST00000264868; ENST00000502949; ENST00000510448 | chr4 | 25723603 | 25723555 | − | TSF |
| 10% | chr4 | 25759228 | 25759156 | − | ENST00000399878; ENST00000264868; ENST00000502949; ENST00000510448 | chr4 | 25723603 | 25723555 | − | TSF |
| 10% | chr6 | 29910534 | 29910757 | + | ENST00000396634; ENST00000376806; ENST00000376809; ENST00000376802 | chr6 | 30349606 | 30349643 | + | TSF |
| 10% | chr12 | 113623819 | 113623826 | + | ENST00000552495 | chr12 | 113623998 | 113624117 | + | TSF |
| 10% | chr22 | 25202408 | 25202451 | + | ENST00000400358; ENST00000400359 | chr22 | 25209976 | 25210040 | + | TSF |
| 9% | chr14 | 31922550 | 31922481 | − | ENST00000549185; ENST00000547378; ENST00000310850; ENST00000356180 | chr14 | 31907346 | 31905965 | − | TSF |
| 9% | chr2 | 69173592 | 69173436 | − | ENST00000328895; ENST00000481498 | chr2 | 69171675 | 69168240 | − | TSF |
| 9% | chr1 | 32573732 | 32573735 | + | ENST00000373625; ENST00000471599 | chr1 | 32605356 | 32605563 | + | TSF |
| 8% | chr10 | 6019455 | 6019368 | − | ENST00000379977; ENST00000397251; ENST00000528354; ENST00000397250; ENST00000379971; ENST00000397255; ENST00000530685; ENST00000429135 | chr10 | 6010891 | 6010471 | − | TSF |
| 8% | chr16 | 2825557; 2825626 | 2825452 | − | ENST00000262306; ENST00000409906; ENST00000409477; ENST00000494946 | chr16 | 2823822 | 2823809 | − | TSF |
| 8% | chr16 | 2825557; 2825626 | 2825452 | − | ENST00000262306; ENST00000409906; ENST00000409477; ENST00000494946 | chr16 | 2823822 | 2823809 | − | TSF |
| 8% | chr16 | 2825557; 2825626 | 2825452 | − | ENST00000262306; ENST00000409906; ENST00000409477; ENST00000494946 | chr16 | 2823822 | 2823809 | − | TSF |
| 8% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 8% | chr12 | 102547647 | 102547754 | + | ENST00000327680; ENST00000378128; | chr12 | 102548605 | 102548938 | + | TSF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 8% | chr12 | 102547647 | 102547754 | + | ENST00000541394; ENST00000358383; ENST00000392911; ENST00000412715; ENST00000417507; ENST00000457614 ENST00000327680; ENST00000378128; | chr12 | 102548605 | 102548938 | + | TSF |
| 8% | chr12 | 102547647 | 102547754 | + | ENST00000541394; ENST00000358383; ENST00000392911; ENST00000412715; ENST00000417507; ENST00000457614 ENST00000327680; ENST00000378128; | chr12 | 102548605 | 102548938 | + | TSF |
| 8% | chr12 | 102547647 | 102547754 | + | ENST00000541394; ENST00000358383; ENST00000392911; ENST00000412715; ENST00000417507; ENST00000457614 ENST00000327680; ENST00000378128; | chr12 | 102548605 | 102548938 | + | TSF |
| 8% | chr2 | 241555805 | 241555928 | + | ENST00000270364 | chr2 | 241556208 | 241556489 | + | TSF |
| 7% | chr15 | 83102759 | 83103078 | + | ENST00000561062; ENST00000358583 | chr15 | 83193141 | 83193227 | + | TSF |
| 7% | chr12 | 71928895 | 71928966 | + | ENST00000266674; ENST00000536515; ENST00000540815 | chr12 | 71938771 | 71938901 | + | TSF |
| 7% | chr17 | 80656472 | 80656331 | − | ENST00000571995; ENST00000538809 | chr17 | 80634662 | 80634498 | − | TSF |
| 7% | chr16 | 15844188 | 15843995 | − | ENST00000396324; ENST00000452625; ENST00000576790; ENST00000300036 | chr16 | 15797541 | 15797467 | − | TSF |
| 7% | chr16 | 15844188 | 15843995 | − | ENST00000396324; ENST00000452625; ENST00000576790; ENST00000300036 | chr16 | 15797541 | 15797467 | − | TSF |
| 7% | chr19 | 45349783 | 45349870 | + | ENST00000252485; ENST00000252483 | chr19 | 45365316 | 45365390 | + | TSF |
| 7% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 7% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 7% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 7% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 7% | chr1 | 6531697 | 6531548 | − | ENST00000400913; ENST00000340850; ENST00000377748; ENST00000377725; ENST00000377728; ENST00000377732; ENST00000400915; ENST00000377740; ENST00000535355; ENST00000377737; ENST00000537245; ENST00000544978 | chr1 | 6531300 | 6531188 | − | TSF |
| 6% | chr22 | 50639466 | 50640019 | + | ENST00000380903 | chr22 | 50643348 | 50643731 | + | TSF |
| 6% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 6% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 6% | chr7 | 158282477 | 158282427 | − | ENST00000389413; ENST00000409483; ENST00000389418; ENST00000404321 | chr7 | 158229450 | 158229273 | − | TSF |
| 6% | chr7 | 158282477 | 158282427 | − | ENST00000389413; ENST00000409483; ENST00000389418; ENST00000404321 | chr7 | 158229450 | 158229273 | − | TSF |
| 6% | chrX | 14891811 | 14891880 | + | ENST00000380492; ENST00000482354; ENST00000497603 | chrX | 14899985 | 14900209 | + | TSF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 5% | chr19 | 42222047 | 42222099 | + | ENST00000398599; ENST00000221992; ENST00000405816 | chr19 | 42233309 | 42233421 | + | TSF |
| 5% | chr19 | 42222047 | 42222099 | + | ENST00000398599; ENST00000221992; ENST00000405816 | chr19 | 42233309 | 42233421 | + | TSF |
| 5% | chr6 | 74228333 | 74228077 | − | ENST00000316292; ENST00000309268; ENST00000331523 | chr6 | 74202961 | 74202718 | − | TSF |
| 5% | chr1 | 63955889 | 63955754 | − | ENST00000371092; ENST00000271002; ENST00000489099; ENST00000283568 | chr1 | 63952444 | 63951983 | − | TSF |
| 5% | chr1 | 63955889 | 63955754 | − | ENST00000371092; ENST00000271002; ENST00000489099; ENST00000283568 | chr1 | 63952444 | 63951983 | − | TSF |
| 5% | chr14 | 106208132 | 106207921 | − | ENST00000390548; ENST00000390549; ENST00000390542 | chr14 | 106043673 | 106043390 | − | TSF |
| 5% | chr14 | 106208132 | 106207921 | − | ENST00000390548; ENST00000390549; ENST00000390542 | chr14 | 106043673 | 106043390 | − | TSF |
| 5% | chr8 | 25240190 | 25240294 | + | ENST00000276440 | chr8 | 25246325 | 25246384 | + | TSF |
| 5% | chr12 | 111803370 | 111803368 | − | ENST00000361483 | chr12 | 111803267 | 111803247 | − | TSF |
| 5% | chr20 | 36768056 | 36767968 | − | ENST00000361475; ENST00000536701; ENST00000536724 | chr20 | 36757686 | 36757563 | − | TSF |
| 5% | chr20 | 36768056 | 36767968 | − | ENST00000361475; ENST00000536701; ENST00000536724 | chr20 | 36757686 | 36757563 | − | TSF |
| 5% | chr20 | 36768056 | 36767968 | − | ENST00000361475; ENST00000536701; ENST00000536724 | chr20 | 36757686 | 36757563 | − | TSF |
| 4% | chr7 | 34888095 | 34888275 | + | ENST00000360581; ENST00000381542; ENST00000359791; ENST00000531252; ENST00000381539 | chr7 | 34935732 | 34935887 | + | TSF |
| 4% | chr7 | 34888095 | 34888275 | + | ENST00000360581; ENST00000381542; ENST00000359791; ENST00000531252; ENST00000381539 | chr7 | 34935732 | 34935887 | + | TSF |
| 4% | chr7 | 34888095 | 34888275 | + | ENST00000360581; ENST00000381542; ENST00000359791; ENST00000531252; ENST00000381539 | chr7 | 34935732 | 34935887 | + | TSF |
| 4% | chr20 | 33137782 | 33137833 | + | ENST00000374837 | chr20 | 33138384 | 33138773 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr20 | 3614958 | 3615036 | + | ENST00000262919 | chr20 | 3615708 | 3616042 | + | TSF |
| 4% | chr7 | 81964567 | 81964451 | − | ENST00000356860; ENST00000356253; ENST00000423588 | chr7 | 81929467 | 81929190 | − | TSF |
| 4% | chr6 | 34386201 | 34386146 | − | ENST00000605528; ENST00000344700; ENST00000326199 | chr6 | 34385704 | 34385695 | − | TSF |
| 4% | chr2 | 176860312; 176860292 | 176860286 | − | ENST00000272748; ENST00000544803; ENST00000392540; ENST00000445472 | chr2 | 176859008 | 176858934 | − | TSF |
| 4% | chr2 | 176860312; 176860292 | 176860286 | − | ENST00000272748; ENST00000544803; ENST00000392540; ENST00000445472 | chr2 | 176859008 | 176858934 | − | TSF |
| 4% | chr1 | 206320201 | 206320319 | + | ENST00000358184; ENST00000361052; ENST00000360218; ENST00000432969 | chr1 | 206324771 | 206325084 | + | TSF |
| 4% | chr1 | 206320201 | 206320319 | + | ENST00000358184; ENST00000361052; ENST00000360218; ENST00000432969 | chr1 | 206324771 | 206325084 | + | TSF |
| 4% | chr18 | 59992586 | 59992660 | + | ENST00000269485; ENST00000586569 | chr18 | 60003547 | 60003575 | + | TSF |
| 4% | chrX | 24091208 | 24091333 | + | ENST00000253039 | chrX | 24091714 | 24091817 | + | TSF |
| 4% | chr12 | 113403549; 113403702 | 113403834 | + | ENST00000228928; ENST00000546973 | chr12 | 113404028 | 113404051 | + | TSF |
| 4% | chr12 | 113403549; 113403702 | 113403834 | + | ENST00000228928; ENST00000546973 | chr12 | 113404028 | 113404051 | + | TSF |
| 4% | chr17 | 79912179 | 79912132 | − | ENST00000409678 | chr17 | 79911834 | 79911647 | − | TSF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 4% | chr8 | 624047; 623326; 623657 | 623289 | − | ENST00000522706; ENST00000523415; ENST00000262109; ENST00000522893 | chr8 | 622204 | 621954 | − | TSF |
| 4% | chr8 | 624047; 623326; 623657 | 623289 | − | ENST00000522706; ENST00000523415; ENST00000262109; ENST00000522893 | chr8 | 622204 | 621954 | − | TSF |
| 4% | chr8 | 624047; 623326; 623657 | 623289 | − | ENST00000522706; ENST00000523415; ENST00000262109; ENST00000522893 | chr8 | 622204 | 621954 | − | TSF |
| 4% | chr8 | 624047; 623326; 623657 | 623289 | − | ENST00000522706; ENST00000523415; ENST00000262109; ENST00000522893 | chr8 | 622204 | 621954 | − | TSF |
| 4% | chrX | 107320278 | 107320560 | + | ENST00000415430; ENST00000217957 | chrX | 107321756 | 107321847 | + | TSF |
| 4% | chrX | 107320278 | 107320560 | + | ENST00000415430; ENST00000217957 | chrX | 107321756 | 107321847 | + | TSF |
| 4% | chr10 | 90435966 | 90436037 | + | ENST00000394375; ENST00000608620; ENST00000238983; ENST00000355843 | chr10 | 90437871 | 90438023 | + | TSF |
| 4% | chr10 | 90435966 | 90436037 | + | ENST00000394375; ENST00000608620; ENST00000238983; ENST00000355843 | chr10 | 90437871 | 90438023 | + | TSF |
| 4% | chr10 | 90435966 | 90436037 | + | ENST00000394375; ENST00000608620; ENST00000238983; ENST00000355843 | chr10 | 90437871 | 90438023 | + | TSF |
| 4% | chr10 | 90435966 | 90436037 | + | ENST00000394375; ENST00000608620; ENST00000238983; ENST00000355843 | chr10 | 90437871 | 90438023 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36662881 | 36662970 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36662881 | 36662970 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36662881 | 36662970 | + | TSF |
| 4% | chr22 | 36661197; 36661246 | 36661833 | + | ENST00000397278; ENST00000422706; ENST00000426053; ENST00000319136; ENST00000347595; ENST00000397279 | chr22 | 36662881 | 36662970 | + | TSF |
| 4% | chr19 | 53352466; 53352373 | 53352340 | − | ENST00000595646; ENST00000243639; ENST00000597924; ENST00000601847 | chr19 | 53339322 | 53339166 | − | TSF |
| 4% | chr19 | 53352466; 53352373 | 53352340 | − | ENST00000595646; ENST00000243639; ENST00000597924; ENST00000601847 | chr19 | 53339322 | 53339166 | − | TSF |
| 4% | chr17 | 38066177 | 38066009 | − | ENST00000360317; ENST00000394175; ENST00000309481; ENST00000520542; ENST00000394179; ENST00000418519; ENST00000523371; ENST00000524039; ENST00000468820 | chr17 | 38065588 | 38065521 | − | TSF |
| 4% | chr17 | 38066177 | 38066009 | − | ENST00000360317; ENST00000394175; ENST00000309481; ENST00000520542; ENST00000394179; ENST00000418519; ENST00000523371; ENST00000524039; ENST00000468820 | chr17 | 38065588 | 38065521 | − | TSF |
| 4% | chr16 | 72153988; 72154048 | 72153750 | − | ENST00000537465; ENST00000237353; ENST00000355636 | chr16 | 72150929 | 72150229 | − | TSF |
| 4% | chr16 | 72153988; 72154048 | 72153750 | − | ENST00000537465; ENST00000237353; ENST00000355636 | chr16 | 72150929 | 72150229 | − | TSF |
| 4% | chr16 | 72153988; 72154048 | 72153750 | − | ENST00000537465; ENST00000237353; ENST00000355636 | chr16 | 72150929 | 72150229 | − | TSF |
| 4% | chr10 | 48255429 | 48255449 | + | ENST00000357718; ENST00000344416; ENST00000535874; ENST00000456111 | chr10 | 48278725 | 48278896 | + | TSF |
| 4% | chr16 | 50583333 | 50583466 | + | ENST00000268459 | chr16 | 50614862 | 50614981 | + | TSF |
| 4% | chr16 | 50659396 | 50659491 | + | ENST00000268459 | chr16 | 50663933 | 50663990 | + | TSF |
| 4% | chr3 | 32280465 | 32280611 | + | ENST00000458535; ENST00000307526 | chr3 | 32324083 | 32324625 | + | TSF |
| 4% | chr21 | 42540191 | 42540502 | + | ENST00000328735; ENST00000330333; ENST00000347667 | chr21 | 42572645 | 42572848 | + | TSF |
| 4% | chr11 | 22204746 | 22204679 | − | ENST00000374695 | chr1 | 22204032 | 22203987 | − | TSF |
| 4% | chr19 | 15289752 | 15289634 | − | ENST00000263388; ENST00000601011 | chr19 | 15289244 | 15289201 | − | TSF |
| 4% | chr19 | 15289752 | 15289634 | − | ENST00000263388; ENST00000601011 | chr19 | 15289244 | 15289201 | − | TSF |
| 4% | chr7 | 5434226; 5434191 | 5434071 | − | ENST00000399537; ENST00000430969; ENST00000434361; ENST00000399434 | chr7 | 5433863 | 5433797 | − | TSF |
| 4% | chr7 | 5434226; 5434191 | 5434071 | − | ENST00000399537; ENST00000430969; ENST00000434361; ENST00000399434 | chr7 | 5433863 | 5433797 | − | TSF |
| 4% | chr10 | 47173918 | 47173898 | − | ENST00000358140; ENST00000359178; ENST00000545298; ENST00000414655 | chr10 | 47139994 | 47138925 | − | TSF |
| 4% | chr7 | 16900207 | 16900124 | − | ENST00000310398; ENST00000402239; ENST00000414935 | chr7 | 16894536 | 16894260 | − | TSF |
| 4% | chr7 | 16900207 | 16900124 | − | ENST00000310398; ENST00000402239; ENST00000414935 | chr7 | 16894536 | 16894260 | − | TSF |
| 4% | chr1 | 11115983; 11115877 | 11115838 | − | ENST00000376957; ENST00000490101 | chr1 | 11115464 | 11115178 | − | TSF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 4% | chr1 | 11115983; 11115877 | 11115838 | − | ENST00000376957; ENST00000490101 | chr1 | 11115464 | 15111178 | − | TSF |
| 3% | chr7 | 150065992 | 150066030 | + | ENST00000466559; ENST00000475514; ENST00000488943; ENST00000467980; ENST00000518514; ENST00000522266 | chr7 | 150067849 | 150067901 | + | TSF |
| 3% | chr19 | 49497169 | 49497180 | + | ENST00000595090; ENST00000595811; ENST00000596247; ENST00000221413; ENST00000593570 | chr19 | 49498033 | 49498189 | + | TSF |
| 3% | chr3 | 48716169 | 48715997 | − | ENST00000341520; ENST00000416649; ENST00000294129; ENST00000413374 | chr3 | 48702393 | 48702198 | − | TSF |
| 3% | chr3 | 48716169 | 48715997 | − | ENST00000341520; ENST00000416649; ENST00000294129; ENST00000413374 | chr3 | 48702393 | 48702198 | − | TSF |
| 3% | chr3 | 48716169 | 48715997 | − | ENST00000341520; ENST00000416649; ENST00000294129; ENST00000413374 | chr3 | 48702393 | 48702198 | − | TSF |
| 3% | chr14 | 67878776 | 67878735 | − | ENST00000216446; ENST00000553387 | chr14 | 67864772 | 67864768 | − | TSF |
| 3% | chr20 | 29632611 | 29632721 | + | ENST00000278882; ENST00000358464 | chr20 | 29652086 | 29652324 | + | TSF |
| 3% | chr19 | 42222047 | 42222099 | + | ENST00000398599; ENST00000221992; ENST00000405816 | chr19 | 42233313 | 42233421 | + | TSF |
| 3% | chr19 | 42222047 | 42222099 | + | ENST00000398599; ENST00000221992; ENST00000405816 | chr19 | 42233313 | 42233421 | + | TSF |
| 3% | chr16 | 30783410 | 30783511 | + | ENST00000324685; ENST00000402121; ENST00000563683; ENST00000357890 | chr16 | 30785136 | 30785155 | + | TSF |
| 3% | chr16 | 30783410 | 30783511 | + | ENST00000324685; ENST00000402121; ENST00000563683; ENST00000357890 | chr16 | 30785136 | 30785155 | + | TSF |
| 3% | chr16 | 30783410 | 30783511 | + | ENST00000324685; ENST00000402121; ENST00000563683; ENST00000357890 | chr16 | 30785136 | 30785155 | + | TSF |
| 3% | chr16 | 30783410 | 30783511 | + | ENST00000324685; ENST00000402121; ENST00000563683; ENST00000357890 | chr16 | 30785136 | 30785155 | + | TSF |
| 3% | chr16 | 50642205 | 50642271 | + | ENST00000268459 | chr16 | 50651664 | 50651770 | + | TSF |
| 3% | chr11 | 118888255 | 118888078 | − | ENST00000527673 | chr11 | 118739656 | 118739455 | − | TSF |
| 3% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 3% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 3% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 3% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 3% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 3% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 3% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 3% | chr8 | 145001050 | 145000952 | − | ENST00000345136; ENST00000357649; ENST00000354589; ENST00000398774; ENST00000322810; ENST00000354958; ENST00000356346; ENST00000436759; ENST00000527096; ENST00000527303 | chr8 | 144977746 | 144977671 | − | TSF |
| 3% | chr8 | 145001050 | 145000952 | − | ENST00000345136; ENST00000357649; | chr8 | 144977746 | 144977671 | − | TSF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| | | | | | ENST00000354589; ENST00000398774; ENST00000322810; ENST00000354958; ENST00000356346; ENST00000436759; ENST00000527096; ENST00000527303 | | | | | |
| 3% | chr6 | 30908777 | 30908858 | + | ENST00000462446 | chr6 | 30913176 | 30913422 | + | TSF |
| 3% | chr7 | 55270210 | 55270401 | + | ENST00000455089 | chr7 | 55272949 | 55272949 | + | TSF |
| 3% | chr9 | 133352258 | 133352273 | + | ENST00000352480; ENST00000372394; ENST00000372393 | chr9 | 133421349 | 133421406 | + | TSF |
| 3% | chr1 | 152006276 | 152006124 | − | ENST00000271638 | chr1 | 152005339 | 152005310 | − | TSF |
| 3% | chr14 | 106208559 | 106208462 | − | ENST00000390548; ENST00000390549; ENST00000390542 | chr14 | 106194471 | 106194382 | − | TSF |
| 3% | chr7 | 91771800 | 91771777 | − | ENST00000435873 | chr7 | 91767155 | 91766808 | − | TSF |
| 3% | chr5 | 176830398 | 176830255 | − | ENST00000253496 | chr5 | 176829864 | 176829767 | − | TSF |
| 3% | chr7 | 98741403 | 98741349 | − | ENST00000361368; ENST00000361125 | chr7 | 98680363 | 98679576 | − | TSF |
| 3% | chr14 | 66096210; 66096217 | 66096324 | + | ENST00000360689; ENST00000394586; ENST00000342677; ENST00000557164; ENST00000394585; ENST00000358307 | chr14 | 66099743 | 66101298 | + | TSF |
| 3% | chr14 | 66096210; 66096217 | 66096324 | + | ENST00000360689; ENST00000394586; ENST00000342677; ENST00000557164; ENST00000394585; ENST00000358307 | chr14 | 66099743 | 66101298 | + | TSF |
| 3% | chr14 | 66096210; 66096217 | 66096324 | + | ENST00000360689; ENST00000394586; ENST00000342677; ENST00000557164; ENST00000394585; ENST00000358307 | chr14 | 66099743 | 66101298 | + | TSF |
| 3% | chr10 | 90435966 | 90436037 | + | ENST00000394375; ENST00000608620; ENST00000238983; ENST00000355843 | chr10 | 90437884 | 90438023 | + | TSF |
| 3% | chr10 | 90435966 | 90436037 | + | ENST00000394375; ENST00000608620; ENST00000238983; ENST00000355843 | chr10 | 90437884 | 90438023 | + + | TSF TSF |
| 3% | chr10 | 90435966 | 90436037 | + | ENST00000394375; ENST00000608620; ENST00000238983; ENST00000355843 | chr10 | 90437884 | 90438023 | + | TSF |
| 3% | chr10 | 90435966 | 90436037 | + | ENST00000394375; ENST00000608620; ENST00000238983; ENST00000355843 | chr10 | 90437884 | 90438023 | + | TSF |
| 3% | chr22 | 36661197; 36661246 | 36661580 | + | ENST00000397278; ENST00000422706; ENST00000426053; ENST00000319136; ENST00000347595; ENST00000397279 | chr22 | 36663327 | 36663652 | + | TSF |
| 3% | chr22 | 36661197; 36661246 | 36661580 | + | ENST00000397278; ENST00000422706; ENST00000426053; ENST00000319136; ENST00000347595; ENST00000397279 | chr22 | 36663327 | 36663652 | + | TSF |
| 3% | chr22 | 36661197; 36661246 | 36661580 | + | ENST00000397278; ENST00000422706; ENST00000426053; ENST00000319136; ENST00000347595; ENST00000397279 | chr22 | 36663327 | 36663652 | + | TSF |
| 3% | chr22 | 36661197; 36661246 | 36661580 | + | ENST00000397278; ENST00000422706; ENST00000426053; ENST00000319136; ENST00000347595; ENST00000397279 | chr22 | 36663327 | 36663652 | + | TSF |
| 3% | chr16 | 57115439 | 57115522 | + | ENST00000262510; ENST00000308149; ENST00000539144 | chr16 | 57116257 | 57116272 | + | TSF |
| 3% | chr16 | 57115439 | 57115522 | + | ENST00000262510; ENST00000308149; ENST00000539144 | chr16 | 57116257 | 57116272 | + | TSF |
| 3% | chr1 | 225156461 | 225156576 | + | ENST00000430092; ENST00000400952; ENST00000366849; ENST00000439375 | chr1 | 225157336 | 225158402 | + | TSF |
| 3% | chr1 | 225156461 | 225156576 | + | ENST00000430092; ENST00000400952; ENST00000366849; ENST00000439375 | chr1 | 225157336 | 225158402 | + | TSF |
| 3% | chr5 | 54993786 | 54993674 | − | ENST00000396865; ENST00000539768; ENST00000318672; ENST00000508124; ENST00000511233; ENST00000503891; ENST00000513993; ENST00000505563; ENST00000506624; ENST00000507109 | chr5 | 54993040 | 54992544 | − | TSF |
| 3% | chr17 | 79912179 | 79912132 | − | ENST00000409678 | chr17 | 79911819 | 79911647 | − | TSF |
| 3% | chr11 | 6624732 | 6624634 | − | ENST00000254605; ENST00000534343; ENST00000533907; ENST00000530762 | chr11 | 6614053 | 6614046 | − | TSF |
| 3% | chrX | 119708472 | 119708406 | − | ENST00000404115 | chrX | 119705855 | 119705820 | − | TSF |
| 2% | chr2 | 217366064 | 217366082 | + | ENST00000491306; ENST00000456586 | chr2 | 217393993 | 217394327 | + | TSF |
| 2% | chr2 | 217366064 | 217366082 | + | ENST00000491306; ENST00000456586 | chr2 | 217393993 | 217394327 | + | TSF |
| 2% | chr11 | 61015891; 61015697 | 61016007 | + | ENST00000422676; ENST00000312403; ENST00000451616 | chr11 | 61016877 | 61016985 | + | TSF |
| 2% | chr11 | 61015891; 61015697 | 61016007 | + | ENST00000422676; ENST00000312403; ENST00000451616 | chr11 | 61016877 | 61016985 | + | TSF |
| 2% | chr6 | 84772612 | 84772711 | + | ENST00000257776 | chr6 | 84775517 | 84775723 | + | TSF |
| 2% | chr9 | 100774703 | 100774754 | + | ENST00000339399 | chr9 | 100777715 | 100777715 | + | TSF |
| 2% | chr4 | 39978197 | 39978060 | − | ENST00000303538; ENST00000503396 | chr4 | 39933249 | 39932944 | − | TSF |
| 2% | chr3 | 156262228 | 156262097 | − | ENST00000265044; ENST00000467789; ENST00000476217; ENST00000463503; ENST00000496050 | chr3 | 156246256 | 156246164 | − | TSF |
| 2% | chr3 | 156262228 | 156262097 | − | ENST00000265044; ENST00000467789; ENST00000476217; ENST00000463503; ENST00000496050 | chr3 | 156246256 | 156246164 | − | TSF |
| 2% | chr3 | 156262228 | 156262097 | − | ENST00000265044; ENST00000467789; | chr3 | 156246256 | 156246164 | − | TSF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| | | | | | ENST00000476217; ENST00000463503; ENST00000496050 | | | | | |
| 2% | chr7 | 74168178 | 74168361 | + | ENST00000324896; ENST00000346152; ENST00000353920; ENST00000416070 | chr7 | 74168612 | 74168748 | + | TSF |
| 2% | chr7 | 74168178 | 74168361 | + | ENST00000324896; ENST00000346152; ENST00000353920; ENST00000416070 | chr7 | 74168612 | 74168748 | + | TSF |
| 2% | chr7 | 74168178 | 74168361 | + | ENST00000324896; ENST00000346152; ENST00000353920; ENST00000416070 | chr7 | 74168612 | 74168748 | + | TSF |
| 2% | chr7 | 74168178 | 74168361 | + | ENST00000324896; ENST00000346152; ENST00000353920; ENST00000416070 | chr7 | 74168612 | 74168748 | + | TSF |
| 2% | chr8 | 63502273 | 63502353 | + | ENST00000523211; ENST00000328472 | chr8 | 63546747 | 63547118 | + | TSF |
| 2% | chr19 | 42265157 | 42265242 | + | ENST00000199764 | chr19 | 42274857 | 42275202 | + | TSF |
| 2% | chr20 | 9382137 | 9382237 | + | ENST00000334005; ENST00000378473; ENST00000278655; ENST00000414679; ENST00000378493; ENST00000378501 | chr20 | 9383648 | 9383757 | + | TSF |
| 2% | chr20 | 62328681 | 62328875 | + | ENST00000369996 | chr20 | 62334477 | 62334522 | + | TSF |
| 2% | chr19 | 42221377; 42221374 | 42221482 | + | ENST00000398599; ENST00000221992; ENST00000405816; ENST00000595113 | chr19 | 42233335 | 42233421 | + | TSF |
| 2% | chr19 | 42221377; 42221374 | 42221482 | + | ENST00000398599; ENST00000221992; ENST00000405816; ENST00000595113 | chr19 | 42233335 | 42233421 | + | TSF |
| 2% | chr19 | 42221377; 42221374 | 42221482 | + | ENST00000398599; ENST00000221992; ENST00000405816; ENST00000595113 | chr19 | 42233335 | 42233421 | + | TSF |
| 2% | chr16 | 50666192 | 50666319 | + | ENST00000268459 | chr16 | 50682755 | 50682972 | + | TSF |
| 2% | chr14 | 24615449 | 24615417 | − | ENST00000216802; ENST00000558273; ENST00000560370 | chr14 | 24615120 | 24615007 | − | TSF |
| 2% | chr2 | 71216946 | 71216879 | − | ENST00000606025; ENST00000272438 | chr2 | 71213852 | 71213417 | − | TSF |
| 2% | chr9 | 130678698 | 130678687 | − | ENST00000335791 | chr9 | 130678527 | 130678449 | − | TSF |
| 2% | chr7 | 74867341 | 74867229 | − | ENST00000426327 | chr7 | 74856485 | 74856184 | − | TSF |
| 2% | chr14 | 106208132 | 106207810 | − | ENST00000390549; ENST00000390542 | chr14 | 106097973 | 106097783 | − | TSF |
| 2% | chr14 | 106208132 | 106207810 | − | ENST00000390549; ENST00000390542 | chr14 | 106097973 | 106097783 | − | TSF |
| 2% | chr20 | 33356389 | 33356267 | − | ENST00000374796; ENST00000359003 | chr20 | 33350617 | 33350460 | − | TSF |
| 2% | chr22 | 42003865 | 42003844 | − | ENST00000263256 | chr22 | 42003633 | 42003499 | − | TSF |
| 2% | chr5 | 149782875 | 149782749 | − | ENST00000518797; ENST00000009530 | chr5 | 149709118 | 149709023 | − | TSF |
| 2% | chr5 | 149782875 | 149782749 | − | ENST00000518797; ENST00000009530 | chr5 | 149709118 | 149709023 | − | TSF |
| 2% | chr15 | 40849571; 40849518 | 40849415 | − | ENST00000560305; ENST00000559153; ENST00000561011; ENST00000559291; ENST00000559911; ENST00000558113; ENST00000358005; ENST00000416810; ENST00000558750; ENST00000558918; ENST00000559103; ENST00000558871 | chr15 | 40813374 | 40812967 | − | TSF |
| 2% | chr15 | 40849571; 40849518 | 40849415 | − | ENST00000560305; ENST00000559153; ENST00000561011; ENST00000559291; ENST00000559911; ENST00000558113; ENST00000358005; ENST00000416810; ENST00000558750; ENST00000558918; ENST00000559103; ENST00000558871 | chr15 | 40813374 | 40812967 | − | TSF |
| 2% | chr15 | 40849571; 40849518 | 40849415 | − | ENST00000560305; ENST00000559153; ENST00000561011; ENST00000559291; ENST00000559911; ENST00000558113; ENST00000358005; ENST00000416810; ENST00000558750; ENST00000558918; ENST00000559103; ENST00000558871 | chr15 | 40813374 | 40812967 | − | TSF |
| 2% | chr4 | 6698620 | 6698734 | + | ENST00000296370 | chr4 | 6720414 | 6720685 | + | TSF |
| 2% | chr11 | 60977314; 60977120 | 60977430 | + | ENST00000325558; ENST00000543349; ENST00000543505; ENST00000543125 | chr11 | 61016877 | 61016985 | + | TSF |
| 2% | chr11 | 60977314; 60977120 | 60977430 | + | ENST00000325558; ENST00000543349; ENST00000543505; ENST00000543125 | chr11 | 61016877 | 61016985 | + | TSF |
| 2% | chr11 | 60977314; 60977120 | 60977430 | + | ENST00000325558; ENST00000543349; ENST00000543505; ENST00000543125 | chr11 | 61016877 | 61016985 | + | TSF |
| 2% | chr7 | 92901947 | 92902045 | + | ENST00000251739; ENST00000305866; ENST00000541136; ENST00000544910; ENST00000458707 | chr7 | 92904706 | 92904974 | + | TSF |
| 2% | chr7 | 92901947 | 92902045 | + | ENST00000251739; ENST00000305866; ENST00000541136; ENST00000544910; ENST00000458707 | chr7 | 92904706 | 92904974 | + | TSF |
| 2% | chr7 | 92901947 | 92902045 | + | ENST00000251739; ENST00000305866; ENST00000541136; ENST00000544910; ENST00000458707 | chr7 | 92904706 | 92904974 | + | TSF |
| 2% | chr7 | 92901947 | 92902045 | + | ENST00000251739; ENST00000305866; ENST00000541136; ENST00000544910; ENST00000458707 | chr7 | 92904706 | 92904974 | + | TSF |
| 2% | chr11 | 60996143; 60995949 | 60996259 | + | ENST00000378149; ENST00000537932 | chr11 | 61016877 | 61016985 | + | TSF |
| 2% | chr11 | 60996143; 60995949 | 60996259 | + | ENST00000378149; ENST00000537932 | chr11 | 61016877 | 61016985 | + | TSF |
| 2% | chr11 | 61015891; | 61016007 | + | ENST00000422676; ENST00000312403; | chr11 | 61016873 | 61016985 | + | TSF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chr11 | 61015697 61015891; 61015697 | 61016007 | + | ENST00000451616 ENST00000422676; ENST00000312403; ENST00000451616 | chr11 | 61016873 | 61016985 | + | TSF |
| 2% | chr11 | 60975763 | 60975962 | + | ENST00000325558; ENST00000543349; ENST00000543505 | chr11 | 60977054 | 60977239 | + | TSF |
| 2% | chr11 | 60975763 | 60975962 | + | ENST00000325558; ENST00000543349; ENST00000543505 | chr11 | 60977054 | 60977239 | + | TSF |
| 2% | chr19 | 46498683 | 46498762 | + | ENST00000263284 | chr19 | 46499503 | 46499685 | + | TSF |
| 2% | chr11 | 64088133 | 64088189 | + | ENST00000265462 | chr11 | 64089177 | 64089204 | + | TSF |
| 2% | chr19 | 42223849 | 42223892 | + | ENST00000398599; ENST00000221992; ENST00000405816; ENST00000595403 | chr19 | 42233335 | 42233421 | + | TSF |
| 2% | chr19 | 42223849 | 42223892 | + | ENST00000398599; ENST00000221992; ENST00000405816; ENST00000595403 | chr19 | 42233335 | 42233421 | + | TSF |
| 2% | chr19 | 42223849 | 42223892 | + | ENST00000398599; ENST00000221992; ENST00000405816; ENST00000595403 | chr19 | 42233335 | 42233421 | + | TSF |
| 2% | chr17 | 38451608 | 38451708 | + | ENST00000209728 | chr17 | 38452940 | 38452953 | + | TSF |
| 2% | chrX | 133963256 | 133963312 | + | ENST00000370784; ENST00000370785 | chrX | 133972757 | 133974403 | + | TSF |
| 2% | chr1 | 32696528 | 32696620 | + | ENST00000373586 | chr1 | 32696865 | 32697110 | + | TSF |
| 2% | chr19 | 2151333 | 2151238 | − | ENST00000355272; ENST00000356926; ENST00000350812; ENST00000345016 | chr19 | 2141056 | 2140753 | − | TSF |
| 2% | chr13 | 43566301 | 43566114 | − | ENST00000313640; ENST00000313624; ENST00000398762; ENST00000538562 | chr13 | 43550258 | 43550168 | − | TSF |
| 2% | chr9 | 5164265 | 5164179 | − | ENST00000381641 | chr9 | 4992433 | 4991945 | − | TSF |
| 2% | chr14 | 92251705 | 92251506 | − | ENST00000435962; ENST00000340892; ENST00000360594; ENST00000556018; ENST00000556590 | chr14 | 92250314 | 92250292 | − | TSF |
| 2% | chr14 | 92251705 | 92251506 | − | ENST00000435962; ENST00000340892; ENST00000360594; ENST00000556018; ENST00000556590 | chr14 | 92250314 | 92250292 | − | TSF |
| 2% | chr14 | 92251705 | 92251506 | − | ENST00000435962; ENST00000340892; ENST00000360594; ENST00000556018; ENST00000556590 | chr14 | 92250314 | 92250292 | − | TSF |
| 2% | chr1 | 204183034 | 204183010 | − | ENST00000308302 | chr1 | 204178313 | 204177989 | − | TSF |
| 2% | chr16 | 52580635 | 52580549 | − | ENST00000219746; ENST00000568436 | chr16 | 52507504 | 52507494 | − | TSF |
| 2% | chr2 | 89160434 | 89160398 | − | ENST00000390239 | chr2 | 89129384 | 89129304 | − | TSF |
| 2% | chr2 | 131840219 | 131840150 | − | ENST00000409185; ENST00000389915 | chr2 | 131829827 | 131829686 | − | TSF |
| 2% | chr10 | 128594087 | 128594132 | + | ENST00000280333 | chr10 | 128608404 | 128608409 | + | TSF |
| 2% | chr20 | 3842901 | 3843060 | + | ENST00000416600; ENST00000428216 | chr20 | 3854441 | 3854475 | + | TSF |
| 2% | chr20 | 3842901 | 3843060 | + | ENST00000416600; ENST00000428216 | chr20 | 3854441 | 3854475 | + | TSF |
| 2% | chr3 | 45748376; 45748272 | 45748399 | + | ENST00000455997; ENST00000418611; ENST00000389061; ENST00000445499 | chr3 | 45748934 | 45748953 | + | TSF |
| 2% | chr3 | 45748376; 45748272 | 45748399 | + | ENST00000455997; ENST00000418611; ENST00000389061; ENST00000445499 | chr3 | 45748934 | 45748953 | + | TSF |
| 2% | chr4 | 146617711 | 146617784 | + | ENST00000438731; ENST00000511965 | chr4 | 146620339 | 146620424 | + | TSF |
| 2% | chr4 | 146617711 | 146617784 | + | ENST00000438731; ENST00000511965 | chr4 | 146620339 | 146620424 | + | TSF |
| 2% | chr3 | 50153339 | 50153413 | + | ENST00000347869 | chr3 | 50155909 | 50155909 | + | TSF |
| 2% | chr13 | 52586555 | 52586598 | + | ENST00000523764; ENST00000521508 | chr13 | 52589919 | 52589956 | + | TSF |
| 2% | chr19 | 45323962 | 45324032 | + | ENST00000270233 | chr19 | 45324388 | 45324391 | + | TSF |
| 2% | chr11 | 60975763 | 60975962 | + | ENST00000325558; ENST00000543349; ENST00000543505 | chr11 | 60995883 | 60996068 | + | TSF |
| 2% | chr11 | 60975763 | 60975962 | + | ENST00000325558; ENST00000543349; ENST00000543505 | chr11 | 60995883 | 60996068 | + | TSF |
| 2% | chr1 | 151239649 | 151239815 | + | ENST00000368884; ENST00000368881; ENST00000445776; ENST00000453615 | chr1 | 151245263 | 151245553 | + | TSF |
| 2% | chr1 | 151239649 | 151239815 | + | ENST00000368884; ENST00000368881; ENST00000445776; ENST00000453615 | chr1 | 151245263 | 151245553 | + | TSF |
| 2% | chr1 | 151239649 | 151239815 | + | ENST00000368884; ENST00000368881; ENST00000445776; ENST00000453615 | chr1 | 151245263 | 151245553 | + | TSF |
| 2% | chr1 | 151239649 | 151239815 | + | ENST00000368884; ENST00000368881; ENST00000445776; ENST00000453615 | chr1 | 151245263 | 151245553 | + | TSF |
| 2% | chr19 | 42223849 | 42223957 | + | ENST00000398599; ENST00000221992; ENST00000405816 | chr19 | 42233335 | 42233421 | + | TSF |
| 2% | chr19 | 42223849 | 42223957 | + | ENST00000398599; ENST00000221992; ENST00000405816 | chr19 | 42233335 | 42233421 | + | TSF |
| 2% | chr4 | 57319769 | 57319927 | + | ENST00000514888; ENST00000264221; ENST00000505164; ENST00000399688; ENST00000512576 | chr4 | 57321183 | 57321327 | + | TSF |
| 2% | chr4 | 57319769 | 57319927 | + | ENST00000514888; ENST00000264221; ENST00000505164; ENST00000399688; ENST00000512576 | chr4 | 57321183 | 57321327 | + | TSF |
| 2% | chr4 | 57319769 | 57319927 | + | ENST00000514888; ENST00000264221; ENST00000505164; ENST00000399688; ENST00000512576 | chr4 | 57321183 | 57321327 | + | TSF |
| 2% | chr17 | 80543780; 80544006 | 80544069 | + | ENST00000473637; ENST00000335255; ENST00000575578 | chr17 | 80544168 | 80544444 | + | TSF |
| 2% | chr17 | 80543780; | 80544069 | + | ENST00000473637; ENST00000335255; | chr17 | 80544168 | 80544444 | + | TSF |

TABLE 57-continued

Transcript fusion for Stomach adenocarcinoma (STAD) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
|   |   | 80544006 |  |  | ENST00000575578 |  |  |  |  |  |
| 2% | chr7 | 98961166 | 98961256 | + | ENST00000432884; ENST00000262942 | chr7 | 98963096 | 98963255 | + | TSF |
| 2% | chr7 | 98961166 | 98961256 | + | ENST00000432884; ENST00000262942 | chr7 | 98963096 | 98963255 | + | TSF |
| 2% | chr11 | 66949317 | 66949363 | + | ENST00000398645; ENST00000529006 | chr11 | 66953323 | 66953458 | + | TSF |
| 2% | chr11 | 60994592 | 60994791 | + | ENST00000378149; ENST00000422676 | chr11 | 60995883 | 60996068 | + | TSF |
| 2% | chr11 | 16769644 | 16769704 | + | ENST00000228136; ENST00000524439; ENST00000422258; ENST00000528634 | chr11 | 16771716 | 16772764 | + | TSF |
| 2% | chr11 | 16769644 | 16769704 | + | ENST00000228136; ENST00000524439; ENST00000422258; ENST00000528634 | chr11 | 16771716 | 16772764 | + | TSF |
| 2% | chr11 | 16769644 | 16769704 | + | ENST00000228136; ENST00000524439; ENST00000422258; ENST00000528634 | chr11 | 16771716 | 16772764 | + | TSF |
| 2% | chr14 | 54903155 | 54903087 | − | ENST00000395573; ENST00000216416; ENST00000557659; ENST00000557690; ENST00000556113 | chr14 | 54854962 | 54854914 | − | TSF |
| 2% | chr7 | 157903607 | 157903521 | − | ENST00000409483; ENST00000389416; ENST00000389418; ENST00000404321 | chr7 | 157893548 | 157892972 | − | TSF |
| 2% | chr7 | 157903607 | 157903521 | − | ENST00000409483; ENST00000389416; ENST00000389418; ENST00000404321 | chr7 | 157893548 | 157892972 | − | TSF |
| 2% | chr7 | 157903607 | 157903521 | − | ENST00000409483; ENST00000389416; ENST00000389418; ENST00000404321 | chr7 | 157893548 | 157892972 | − | TSF |
| 2% | chr7 | 157903607 | 157903521 | − | ENST00000409483; ENST00000389416; ENST00000389418; ENST00000404321 | chr7 | 157893548 | 157892972 | − | TSF |
| 2% | chr16 | 15813165 | 15813077 | − | ENST00000396324; ENST00000452625; ENST00000576790; ENST00000300036 | chr16 | 15797551 | 15797467 | − | TSF |
| 2% | chr16 | 15813165 | 15813077 | − | ENST00000396324; ENST00000452625; ENST00000576790; ENST00000300036 | chr16 | 15797551 | 15797467 | − | TSF |
| 2% | chr19 | 46088022 | 46087881 | − | ENST00000323060; ENST00000263275 | chr19 | 46085924 | 46085806 | − | TSF |
| 2% | chr1 | 160264383 | 160264318 | − | ENST00000368069; ENST00000241704 | chr1 | 160259468 | 160259379 | − | TSF |
| 2% | chr1 | 160264383 | 160264318 | − | ENST00000368069; ENST00000241704 | chr1 | 160259468 | 160259379 | − | TSF |
| 2% | chr8 | 28707790 | 28707730 | − | ENST00000523303; ENST00000521022; ENST00000416984; ENST00000521777; ENST00000522363; ENST00000523436; ENST00000518510; ENST00000524081; ENST00000520184 | chr8 | 28705226 | 28705209 | − | TSF |
| 2% | chr8 | 28707790 | 28707730 | − | ENST00000523303; ENST00000521022; ENST00000416984; ENST00000521777; ENST00000522363; ENST00000523436; ENST00000518510; ENST00000524081; ENST00000520184 | chr8 | 28705226 | 28705209 | − | TSF |
| 2% | chr8 | 28707790 | 28707730 | − | ENST00000523303; ENST00000521022; ENST00000416984; ENST00000521777; ENST00000522363; ENST00000523436; ENST00000518510; ENST00000524081; ENST00000520184 | chr8 | 28705226 | 28705209 | − | TSF |
| 2% | chr8 | 28707790 | 28707730 | − | ENST00000523303; ENST00000521022; ENST00000416984; ENST00000521777; ENST00000522363; ENST00000523436; ENST00000518510; ENST00000524081; ENST00000520184 | chr8 | 28705226 | 28705209 | − | TSF |
| 2% | chr6 | 105771643 | 105771540 | − | ENST00000369110; ENST00000448705 | chr6 | 105764464 | 105763345 | − | TSF |
| 2% | chr1 | 156721221 | 156721135 | − | ENST00000357325; ENST00000537739 | chr1 | 156716225 | 156716218 | − | TSF |
| 2% | chr14 | 106235896 | 106235574 | − | ENST00000390551 | chr14 | 106216701 | 106216511 | − | TSF |
| 2% | chrX | 41598709 | 41598637 | − | ENST00000421587; ENST00000318588; ENST00000361962; ENST00000378163; ENST00000378158; ENST00000378166; ENST00000442742; ENST00000378154 | chrX | 41557348 | 41557057 | − | TSF |
| 2% | chr6 | 2116114 | 2116005 | − | ENST00000530927; ENST00000380815 | chr6 | 2081017 | 2075510 | − | TSF |
| 2% | chr6 | 2116114 | 2116005 | − | ENST00000530927; ENST00000380815 | chr6 | 2081017 | 2075510 | − | TSF |
| 2% | chr13 | 111315865 | 111315798 | − | ENST00000257347; ENST00000487253; ENST00000537743 | chr13 | 111312615 | 111311877 | − | TSF |
| 2% | chr13 | 111315865 | 111315798 | − | ENST00000257347; ENST00000487253; ENST00000537743 | chr13 | 111312615 | 111311877 | − | TSF |
| 2% | chr13 | 111315865 | 111315798 | − | ENST00000257347; ENST00000487253; ENST00000537743 | chr13 | 111312615 | 111311877 | − | TSF |
| 2% | chr17 | 79912179 | 79912132 | − | ENST00000409678 | chr17 | 79911788 | 79911647 | − | TSF |
| 2% | chr19 | 39294191 | 39294162 | − | ENST00000307751; ENST00000600070 | chr19 | 39289106 | 39287788 | − | TSF |
| 2% | chr19 | 39294191 | 39294162 | − | ENST00000307751; ENST00000600070 | chr19 | 39289106 | 39287788 | − | TSF |
| 2% | chr17 | 48266371 | 48266269 | − | ENST00000225964 | chr17 | 48238174 | 48237883 | − | TSF |

TABLE 58

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 60% | chr4 | 39699858 | 39699922 | + | chr4 | 39739040 | 39739133 | + | ENST00000261427; ENST00000510934; ENST00000295963; ENST00000445950 | TAF |
| 60% | chr4 | 39699858 | 39699922 | + | chr4 | 39739040 | 39739133 | + | ENST00000261427; ENST00000510934; ENST00000295963; ENST00000445950 | TAF |
| 60% | chr4 | 39699858 | 39699922 | + | chr4 | 39739040 | 39739133 | + | ENST00000261427; ENST00000510934; ENST00000295963; ENST00000445950 | TAF |
| 60% | chr4 | 39699858 | 39699922 | + | chr4 | 39739040 | 39739133 | + | ENST00000261427; ENST00000510934; ENST00000295963; ENST00000445950 | TAF |
| 55% | chr19 | 56187371 | 56187420 | + | chr19 | 56189893 | 56190221 | + | ENST00000411543 | TAF |
| 53% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 53% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 53% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 53% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 48% | chr17 | 74261446 | 74261484 | + | chr17 | 74261988 | 74262050 | + | ENST00000327490 | TAF |
| 47% | chr21 | 42597177 | 42597622 | + | chr21 | 42598193 | 42598281 | + | ENST00000328735; ENST00000330333; ENST00000347667 | TAF |
| 47% | chr21 | 42597177 | 42597622 | + | chr21 | 42598193 | 42598281 | + | ENST00000328735; ENST00000330333; ENST00000347667 | TAF |
| 47% | chr21 | 42597177 | 42597622 | + | chr21 | 42598193 | 42598281 | + | ENST00000328735; ENST00000330333; ENST00000347667 | TAF |
| 45% | chr5 | 10732874 | 10732658 | − | chr5 | 10683683 | 10683641 | − | ENST00000230895 | TAF |
| 42% | chr7 | 116364854 | 116364901 | + | chr7 | 116371722 | 116371913 | + | ENST00000397752; ENST00000318493; ENST00000436117 | TAF |
| 42% | chr7 | 116364854 | 116364901 | + | chr7 | 116371722 | 116371913 | + | ENST00000397752; ENST00000318493; ENST00000436117 | TAF |
| 42% | chr7 | 116364854 | 116364901 | + | chr7 | 116371722 | 116371913 | + | ENST00000397752; ENST00000318493; ENST00000436117 | TAF |
| 38% | chr3 | 128359904 | 128359849 | − | chr3 | 128356948 | 128356642 | − | ENST00000296255 | TAF |
| 37% | chr3 | 47700203 | 47700048 | − | chr3 | 47680270 | 47680215 | − | ENST00000254480 | TAF |
| 36% | chr11 | 93468219 | 93468129 | − | chr11 | 93467826 | 93467791; 93467814 | − | ENST00000393259; ENST00000527169 | TAF |
| 36% | chr11 | 93468219 | 93468129 | − | chr11 | 93467826 | 93467791; 93467814 | − | ENST00000393259; ENST00000527169 | TAF |
| 34% | chr12 | 123873690 | 123873729 | + | chr12 | 123873980 | 123874101 | + | ENST00000330479; ENST00000402868 | TSF |
| 34% | chr4 | 39585332 | 39585284 | − | chr4 | 39459881 | 39459814 | − | ENST00000295955; ENST00000449470; ENST00000508595; ENST00000503040; ENST00000504470 | TSF |
| 34% | chr4 | 39585332 | 39585284 | − | chr4 | 39459881 | 39459814 | − | ENST00000295955; ENST00000449470; ENST00000508595; ENST00000503040; ENST00000504470 | TSF |
| 34% | chr4 | 39585332 | 39585284 | − | chr4 | 39459881 | 39459814 | − | ENST00000295955; ENST00000449470; ENST00000508595; ENST00000503040; ENST00000504470 | TSF |
| 33% | chr22 | 37419605 | 37419606 | + | chr22 | 37420233 | 37420851 | + | ENST00000397129 | TAF |
| 28% | chr9 | 100872455 | 100872351 | − | chr9 | 100872266 | 100872171 | − | ENST00000375098; ENST00000341469; ENST00000342043 | TAF |
| 27% | chr13 | 43628887 | 43629679 | + | chr13 | 43639822 | 43639873 | + | ENST00000379221 | TAF |
| 27% | chr7 | 56018506 | 56018522 | + | chr7 | 56020872 | 56021011 | + | ENST00000426595 | TSF |
| 26% | chr3 | 185411133 | 185410965 | − | chr3 | 185410550 | 185410487 | − | ENST00000382199; ENST00000421047; ENST00000457616; ENST00000346192 | TAF |
| 26% | chr3 | 185411133 | 185410965 | − | chr3 | 185410550 | 185410487 | − | ENST00000382199; ENST00000421047; ENST00000457616; ENST00000346192 | TAF |
| 25% | chr19 | 1600051 | 1599987 | − | chr19 | 1599559 | 1599439 | − | ENST00000585937; ENST00000591899; ENST00000589880; ENST00000585671 | TAF |
| 23% | chr2 | 24544896 | 24544683 | − | chr2 | 24538093 | 24538001 | − | ENST00000361999; ENST00000355123; ENST00000406921; ENST00000412011 | TAF |
| 23% | chr2 | 24544896 | 24544683 | − | chr2 | 24538093 | 24538001 | − | ENST00000361999; ENST00000355123; ENST00000406921; ENST00000412011 | TAF |
| 23% | chr2 | 24544896 | 24544683 | − | chr2 | 24538093 | 24538001 | − | ENST00000361999; ENST00000355123; ENST00000406921; ENST00000412011 | TAF |
| 23% | chr2 | 24544896 | 24544683 | − | chr2 | 24538093 | 24538001 | − | ENST00000361999; ENST00000355123; ENST00000406921; ENST00000412011 | TAF |
| 23% | chr13 | 98628730 | 98628756 | + | chr13 | 98628947 | 98629040; 98629046 | + | ENST00000460070; ENST00000481455; ENST00000261574; ENST00000493281; | TAF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| | 23% | chr13 | 98628730 | 98628756 | + | chr13 | 98628947 | 98629040; 98629046 | + | ENST00000490369; ENST00000463157; ENST00000489058; ENST00000481689; ENST00000480611; ENST00000485433; ENST00000496368; ENST00000421861 ENST00000460070; ENST00000481455; ENST00000261574; ENST00000493281; | TAF |
| | 23% | chr13 | 98628730 | 98628756 | + | chr13 | 98628947 | 98629040; 98629046 | + | ENST00000490369; ENST00000463157; ENST00000489058; ENST00000481689; ENST00000480611; ENST00000485433; ENST00000496368; ENST00000421861 ENST00000460070; ENST00000481455; ENST00000261574; ENST00000493281; | TAF |
| | 23% | chr13 | 98628730 | 98628756 | + | chr13 | 98628947 | 98629040; 98629046 | + | ENST00000490369; ENST00000463157; ENST00000489058; ENST00000481689; ENST00000480611; ENST00000485433; ENST00000496368; ENST00000421861 ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 23% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 23% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 23% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 23% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 23% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 23% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 23% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 23% | chr13 | 98628730 | 98628756 | + | chr13 | 98628947 | 98629040; 98629046 | + | ENST00000460070; ENST00000481455; ENST00000261574; ENST00000493281; ENST00000490369; ENST00000463157; ENST00000489058; ENST00000481689; ENST00000480611; ENST00000485433; ENST00000496368; ENST00000421861 | TAF |
| | 22% | chr10 | 5826921 | 5825287 | − | chr10 | 5815904 | 5815805 | − | ENST00000380191; ENST00000447751; ENST00000380132; ENST00000380181; ENST00000456041 | TAF |
| | 22% | chr10 | 5826921 | 5825287 | − | chr10 | 5815904 | 5815805 | − | ENST00000380191; ENST00000447751; ENST00000380132; ENST00000380181; ENST00000456041 | TAF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 22% | chr10 | 5826921 | 5825287 | − | chr10 | 5815904 | 5815805 | − | ENST00000380191; ENST00000447751; ENST00000380132; ENST00000380181; ENST00000456041 | TAF |
| 22% | chr10 | 89682344 | 89682384 | + | chr10 | 89685270 | 89685314 | + | ENST00000371953 | TSF |
| 21% | chr5 | 147210961 | 147210946 | − | chr5 | 147209193 | 147209162 | − | ENST00000296695; ENST00000510027 | TAF |
| 21% | chr5 | 147210961 | 147210946 | − | chr5 | 147209193 | 147209162 | − | ENST00000296695; ENST00000510027 | TAF |
| 20% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 20% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 20% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 20% | chr19 | 16267516 | 16267566 | + | chr19 | 16268020 | 16268208; 16268205; 16268448; 16268139 | + | ENST00000253680; ENST00000397372; ENST00000593154; ENST00000588246; ENST00000593031 | TAF |
| 20% | chr13 | 43659219 | 43659268 | + | chr13 | 43659904 | 43659974 | + | ENST00000379221 | TAF |
| 20% | chr5 | 147206892 | 147206839 | + | chr5 | 147204269 | 147204224 | − | ENST00000296695 | TAF |
| 19% | chr12 | 6602868 | 6602840 | − | chr12 | 6602138 | 6602028 | − | ENST00000229238 | TAF |
| 18% | chr7 | 66386440 | 66386448 | + | chr7 | 66409963 | 66410248; 66410147; 46610019; 66410221; 66410085 | + | ENST00000341567; ENST00000607045; ENST00000433271; ENST00000413593; ENST00000424964; ENST00000418375 | TSF |
| 18% | chr7 | 66386440 | 66386448 | + | chr7 | 66409963 | 66410248; 66410147; 46610019; 66410221; 66410085 | + | ENST00000341567; ENST00000607045; ENST00000433271; ENST00000413593; ENST00000424964; ENST00000418375 | TSF |
| 18% | chr7 | 66386440 | 66386448 | + | chr7 | 66409963 | 66410248; 66410147; 46610019; 66410221; 66410085 | + | ENST00000341567; ENST00000607045; ENST00000433271; ENST00000413593; ENST00000424964; ENST00000418375 | TSF |
| 18% | chr7 | 66386440 | 66386448 | + | chr7 | 66409963 | 66410248; 66410147; 46610019; 66410221; 66410085 | + | ENST00000341567; ENST00000607045; ENST00000433271; ENST00000413593; ENST00000424964; ENST00000418375 | TSF |
| 18% | chr7 | 66386440 | 66386448 | + | chr7 | 66409963 | 66410248; 66410147; 46610019; 66410221; 66410085 | + | ENST00000341567; ENST00000607045; ENST00000433271; ENST00000413593; ENST00000424964; ENST00000418375 | TSF |
| 18% | chr7 | 66386440 | 66386448 | + | chr7 | 66409963 | 66410248; 66410147; 46610019; 66410221; 66410085 | + | ENST00000341567; ENST00000607045; ENST00000433271; ENST00000413593; ENST00000424964; ENST00000418375 | TSF |
| 17% | chr5 | 179238653 | 179238682 | + | chr5 | 179249989 | 179250053 | + | ENST00000389805; ENST00000504627; ENST00000510187 | TAF |
| 17% | chr5 | 179238653 | 179238682 | + | chr5 | 179249989 | 179250053 | + | ENST00000389805; ENST00000504627; ENST00000510187 | TAF |
| 17% | chr5 | 179238653 | 179238682 | + | chr5 | 179249989 | 179250053 | + | ENST00000389805; ENST00000504627; ENST00000510187 | TAF |
| 17% | chr20 | 35844460 | 35844528 | + | chr20 | 35852281 | 35852372 | + | ENST00000237530; ENST00000373622 | TAF |
| 17% | chr20 | 35844460 | 35844528 | + | chr20 | 35852281 | 35852372 | + | ENST00000237530; ENST00000373622 | TAF |
| 17% | chr4 | 38696010 | 38696173 | + | chr4 | 38696367 | 38696527 | + | ENST00000261438 | TAF |
| 17% | chr22 | 45064651 | 45064685 | + | chr22 | 45098372 | 45098488 | + | ENST00000403581; ENST00000336985; ENST00000403696; ENST00000431834; ENST00000361473; ENST00000352766; ENST00000517296 | TAF |
| 17% | chr22 | 45064651 | 45064685 | + | chr22 | 45098372 | 45098488 | + | ENST00000403581; ENST00000336985; ENST00000403696; ENST00000431834; ENST00000361473; ENST00000352766; ENST00000517296 | TAF |
| 17% | chr22 | 45064651 | 45064685 | + | chr22 | 45098372 | 45098488 | + | ENST00000403581; ENST00000336985; ENST00000403696; ENST00000431834; ENST00000361473; ENST00000352766; ENST00000517296 | TAF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 17% | chr22 | 45064651 | 45064685 | + | chr22 | 45098372 | 45098488 | + | ENST00000403581; ENST00000336985; ENST00000403696; ENST00000431834; ENST00000361473; ENST00000352766; ENST00000517296 | TAF |
| 17% | chr22 | 45064651 | 45064685 | + | chr22 | 45098372 | 45098488 | + | ENST00000403581; ENST00000336985; ENST00000403696; ENST00000431834; ENST00000361473; ENST00000352766; ENST00000517296 | TAF |
| 17% | chr10 | 74501505 | 74501603 | + | chr10 | 74594117 | 74594186; 74594190 | + | ENST00000373053; ENST00000357157; ENST00000536019; ENST00000604152 | TSF |
| 17% | chr10 | 74501505 | 74501603 | + | chr10 | 74594117 | 74594186; 74594190 | + | ENST00000373053; ENST00000357157; ENST00000536019; ENST00000604152 | TSF |
| 17% | chr10 | 74501505 | 74501603 | + | chr10 | 74594117 | 74594186; 74594190 | + | ENST00000373053; ENST00000357157; ENST00000536019; ENST00000604152 | TSF |
| 17% | chr4 | 6592594 | 6592648 | + | chr4 | 6594900 | 6595077; 6595011 | + | ENST00002285599; ENST00000504248; ENST00000505907 | TSF |
| 17% | chr4 | 6592594 | 6592648 | + | chr4 | 6594900 | 6595077; 6595011 | + | ENST00002285599; ENST00000504248; ENST00000505907 | TSF |
| 17% | chr4 | 6592594 | 6592648 | + | chr4 | 6594900 | 6595077; 6595011 | + | ENST00002285599; ENST00000504248; ENST00000505907 | TSF |
| 16% | chr9 | 6248332 | 6248555 | + | chr9 | 6250474 | 6250599 | + | ENST00000456383; ENST00000381434 | TAF |
| 16% | chr9 | 6248332 | 6248555 | + | chr9 | 6250474 | 6250599 | + | ENST00000456383; ENST00000381434 | TAF |
| 16% | chr9 | 135665394 | 135665131 | − | chr9 | 135602921 | 135602841 | − | ENST00000298545 | TAF |
| 16% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 16% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 16% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 16% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 16% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 16% | chr14 | 65406849 | 65406835 | − | chr14 | 65406556 | 65406206 | − | ENST00000389614; ENST00000557049 | TAF |
| 16% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 16% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 16% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 16% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 16% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 16% | chr16 | 2991578 | 29915910 | + | chr16 | 29916173 | 29916286 | + | ENST00000563177; ENST00000483405; ENST00000308748; ENST00000414952; ENST00000566693 | TAF |
| 16% | chr16 | 2991578 | 29915910 | + | chr16 | 29916173 | 29916286 | + | ENST00000563177; ENST00000483405; ENST00000308748; ENST00000414952; ENST00000566693 | TAF |
| 16% | chr15 | 66170740 | 66170790 | + | chr15 | 66172009 | 66172089; 66172017 | + | ENST00000564910; ENST00000261890; ENST00000569896; ENST00000567671 | TSF |
| 16% | chr15 | 66170740 | 66170790 | + | chr15 | 66172009 | 66172089; 66172017 | + | ENST00000564910; ENST00000261890; ENST00000569896; ENST00000567671 | TSF |
| 16% | chr15 | 66170740 | 66170790 | + | chr15 | 66172009 | 66172089; 66172017 | + | ENST00000564910; ENST00000261890; ENST00000569896; ENST00000567671 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 15% | chr16 | 603045 | 603077 | + | chr16 | 603343 | 603516 | + | ENST00000219611 | TAF |
| 15% | chr16 | 603045 | 603138 | + | chr16 | 603343 | 603516 | + | ENST00000219611 | TAF |
| 15% | chr15 | 43889497 | 43889601 | + | chr15 | 43890391 | 43890525 | + | ENST00000300283; ENST00000441322 | TAF |
| 15% | chr22 | 21972574 | 21972670 | + | chr22 | 21975804 | 21975958 | + | ENST00000458578; ENST00000342192; ENST00000545681 | TSF |
| 14% | chr17 | 30771499 | 30771536 | + | chr17 | 30773963 | 30774064 | + | ENST00000261712; ENST00000457654; ENST00000579451 | TAF |
| 14% | chr17 | 30771499 | 30771536 | + | chr17 | 30773963 | 30774064 | + | ENST00000261712; ENST00000457654; ENST00000579451 | TAF |
| 14% | chr13 | 43628887 | 43629679 | + | chr13 | 43643066 | 43643139 | + | ENST00000379221 | TAF |
| 14% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 14% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 14% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 14% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 14% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 14% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 14% | chr7 | 150730019 | 150730148 | + | chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 14% | chr10 | 126455800 | 12645579 | − | chr10 | 126454177 | 126453961 | − | ENST00000494792; ENST00000368836 | TAF |
| 14% | chr10 | 126455800 | 12645579 | − | chr10 | 126454177 | 126453961 | − | ENST00000494792; ENST00000368836 | TAF |
| 14% | chr8 | 143751981 | 143751986 | + | chr8 | 143762745 | 143762852; 143762884 | + | ENST00000301258; ENST00000513264 | TAF |
| 14% | chr8 | 143751981 | 143751986 | + | chr8 | 143762745 | 143762852; 143762884 | + | ENST00000301258; ENST00000513264 | TAF |
| 14% | chr17 | 78344149 | 78344187 | + | chr17 | 78345674 | 78345785 | + | ENST00000508628; ENST00000582970; ENST00000336301 | TSF |
| 14% | chr4 | 39933437 | 39933081 | − | chr4 | 39929784 | 39929581 | − | ENST00000303538; ENST00000503396 | TSF |
| 14% | chr4 | 39933437 | 39933081 | − | chr4 | 39929784 | 39929581 | − | ENST00000303538; ENST00000503396 | TSF |
| 14% | chr5 | 64050585 | 64050405 | − | chr5 | 64050189 | 64050142 | − | ENST00000513458 | TSF |
| 13% | chr19 | 42217251 | 42217314 | + | chr19 | 42218890 | 42219168 | + | ENST00000398599; ENST00000221992; ENST00000405816; ENST00000595113 | TAF |
| 13% | chr19 | 42217251 | 42217314 | + | chr19 | 42218890 | 42219168 | + | ENST00000398599; ENST00000221992; ENST00000405816; ENST00000595113 | TAF |
| 13% | chr19 | 42217251 | 42217314 | + | chr19 | 42218890 | 42219168 | + | ENST00000398599; ENST00000221992; ENST00000405816; ENST00000595113 | TAF |
| 13% | chr4 | 73969917 | 73969720 | − | chr4 | 73968264 | 73968093; 73968180 | − | ENST00000358602; ENST00000558247; ENST00000509867; ENST00000330838; ENST00000561029 | TAF |
| 13% | chr4 | 73969917 | 73969720 | − | chr4 | 73968264 | 73968093; 73968180 | − | ENST00000358602; ENST00000558247; ENST00000509867; ENST00000330838; ENST00000561029 | TAF |
| 13% | chr13 | 41835911 | 41835827 | − | chr13 | 41835051 | 41834629 | − | ENST00000430347 | TAF |
| 13% | chr3 | 69286305 | 69286248 | − | chr3 | 69273841 | 69273758; 69273834 | − | ENST00000398540; ENST00000542259; ENST00000493880; ENST00000473029; ENST00000460709 | TAF |
| 13% | chr3 | 69286305 | 69286248 | − | chr3 | 69273841 | 69273758; 69273834 | − | ENST00000398540; ENST00000542259; ENST00000493880; ENST00000473029; ENST00000460709 | TAF |
| 13% | chr3 | 69286305 | 69286248 | − | chr3 | 69273841 | 69273758; 69273834 | − | ENST00000398540; ENST00000542259; ENST00000493880; ENST00000473029; ENST00000460709 | TAF |
| 13% | chr3 | 69286305 | 69286248 | − | chr3 | 69273841 | 69273758; 69273834 | − | ENST00000398540; ENST00000542259; ENST00000493880; ENST00000473029; ENST00000460709 | TAF |
| 13% | chr1 | 44446234 | 44446286 | + | chr1 | 44446781 | 44447145 | + | ENST00000309519 | TSF |
| 13% | chr10 | 90437871 | 90437988 | + | chr10 | 90438202 | 90438438 | + | ENST00000394375; ENST00000608620; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 12% | chr9 | 130924283 | 130924301 | + | chr9 | 130925722 | 130925894 | + | ENST00000238983; ENST00000355843 ENST00000372994 | TAF |
| 12% | chr2 | 201253013 | 201253278 | + | chr2 | 201253946 | 201254006 | + | ENST00000409755; ENST00000409151 | TAF |
| 12% | chr12 | 64687157 | 64687061 | − | chr12 | 64679840 | 64679734 | − | ENST00000543942; ENST00000333722 | TAF |
| 12% | chr14 | 65408081 | 65408080 | − | chr14 | 65406556 | 65406206 | − | ENST00000389614; ENST00000557049 | TAF |
| 12% | chr15 | 43989318 | 43989422 | + | chr15 | 43990212 | 43990346 | + | ENST00000434505; ENST00000413453 | TAF |
| 12% | chr19 | 42217251 | 42217314 | + | chr19 | 42223849 | 42224127; 42223947 | + | ENST00000398599; ENST00000221992; ENST00000405816; ENST00000595403 | TAF |
| 12% | chr19 | 42217251 | 42217314 | + | chr19 | 42223849 | 42224127; 42223947 | + | ENST00000398599; ENST00000221992; ENST00000405816; ENST00000595403 | TAF |
| 12% | chr19 | 55559415 | 55559414 | − | chr19 | 55558856 | 55558755 | − | ENST00000415061; ENST00000396247 | TAF |
| 11% | chr21 | 47410358 | 47410419 | + | chr21 | 47410687 | 47410740 | + | ENST00000361866 | TAF |
| 11% | chr5 | 175826144 | 175825958 | − | chr5 | 175825048 | 175824931; 175824945 | − | ENST00000310418; ENST00000345807; ENST00000508425 | TAF |
| 11% | chr5 | 175826144 | 175825958 | − | chr5 | 175825048 | 175824931; 175824945 | − | ENST00000310418; ENST00000345807; ENST00000508425 | TAF |
| 11% | chr5 | 175826144 | 175825958 | − | chr5 | 175825048 | 175824931; 175824945 | − | ENST00000310418; ENST00000345807; ENST00000508425 | TAF |
| 11% | chr20 | 19851935 | 19851939 | + | chr20 | 19870210 | 19870302 | + | ENST00000255006 | TAF |
| 11% | chr12 | 21011867 | 21011909 | + | chr12 | 21013951 | 21014072 | + | ENST00000540853; ENST00000261196; ENST00000381545; ENST00000540229; ENST00000553473 | TAF |
| 11% | chr12 | 21011867 | 21011909 | + | chr12 | 21013951 | 21014072 | + | ENST00000540853; ENST00000261196; ENST00000381545; ENST00000540229; ENST00000553473 | TAF |
| 11% | chr12 | 21011867 | 21011909 | + | chr12 | 21013951 | 21014072 | + | ENST00000540853; ENST00000261196; ENST00000381545; ENST00000540229; ENST00000553473 | TAF |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; ENST00000360760; ENST00000423749; ENST00000457757; ENST00000453663; ENST00000409140; ENST00000409397; ENST00000409755; ENST00000409151; ENST00000421573; ENST00000449647; ENST00000438761 | TAF |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; ENST00000360760; ENST00000423749; ENST00000457757; ENST00000453663; ENST00000409140; ENST00000409397; ENST00000409755; ENST00000409151; ENST00000421573; ENST00000449647; ENST00000438761 | TAF |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; ENST00000360760; ENST00000423749; ENST00000457757; ENST00000453663; ENST00000409140; ENST00000409397; ENST00000409755; ENST00000409151; ENST00000421573; ENST00000449647; ENST00000438761 | TAF |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; ENST00000360760; ENST00000423749; ENST00000457757; ENST00000453663; ENST00000409140; ENST00000409397; ENST00000409755; ENST00000409151; ENST00000421573; ENST00000449647; ENST00000438761 | TAF |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; | TAF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | ENST00000360760; ENST00000423749; ENST00000457757; ENST00000453663; ENST00000409140; ENST00000409397; ENST00000409755; ENST00000409151; ENST00000421573; ENST00000449647; ENST00000438761 | |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; ENST00000360760; ENST00000423749; ENST00000457757; ENST00000453663; ENST00000409140; ENST00000409397; ENST00000409755; ENST00000409151; ENST00000421573; ENST00000449647; ENST00000438761 | TAF |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; ENST00000360760; ENST00000423749; ENST00000457757; ENST00000453663; ENST00000409140; ENST00000409397; ENST00000409755; ENST00000409151; ENST00000421573; ENST00000449647; ENST00000438761 | TAF |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; ENST00000360760; ENST00000423749; ENST00000457757; ENST00000453663; ENST00000409140; ENST00000409397; ENST00000409755; ENST00000409151; ENST00000421573; ENST00000449647; ENST00000438761 | TAF |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; ENST00000360760; ENST00000423749; ENST00000457757; ENST00000453663; ENST00000409140; ENST00000409397; ENST00000409755; ENST00000409151; ENST00000421573; ENST00000449647; ENST00000438761 | TAF |
| 11% | chr2 | 201277501 | 201277593 | + | chr2 | 201281102 | 201281151 | + | ENST00000439084; ENST00000409718; ENST00000358677; ENST00000409988; ENST00000439395; ENST00000451764; ENST00000360760; ENST00000423749; ENST00000457757; ENST00000453663; ENST00000409140; ENST00000409397; ENST00000409755; ENST00000409151; ENST00000421573; ENST00000449647; ENST00000438761 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr3 | 146238022 | 146237953 | − | chr3 | 146234954 | 146234793; 146234876; 146234936; 146234945 | − | ENST00000342435; ENST00000487389; ENST00000448787; ENST00000483300; ENST00000462666; ENST00000486631; ENST00000472349 | TAF |
| 11% | chr17 | 79911953 | 79911734 | − | chr17 | 79911143 | 79910837 | − | ENST00000409678 | TAF |
| 11% | chr14 | 105172936 | 105173038 | + | chr14 | 105173247 | 105173388 | + | ENST00000330634; ENST00000392634 | TSF |
| 11% | chr14 | 105172936 | 105173038 | + | chr14 | 105173247 | 105173388 | + | ENST00000330634; ENST00000392634 | TSF |
| 10% | chr7 | 100850556 | 100850506 | − | chr7 | 100850185 | 100850060 | − | ENST00000454310; ENST00000223127 | TSF |
| 9% | chr20 | 45337040 | 45337192 | + | chr20 | 45353680 | 45354963 | + | ENST00000359271 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 9% | chrX | 107293989 | 107294242 | + | chrX | 107301268 | 107301431 | + | ENST00000415430; ENST00000217957; ENST00000458383 | TSF |
| 9% | chrX | 107293989 | 107294242 | + | chrX | 107301268 | 107301431 | + | ENST00000415430; ENST00000217957; ENST00000458383 | TSF |
| 9% | chrX | 107293989 | 107294242 | + | chrX | 107301268 | 107301431 | + | ENST00000415430; ENST00000217957; ENST00000458383 | TSF |
| 9% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 9% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 9% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 9% | chr1 | 19672366 | 19672295 | − | chr1 | 19671746 | 19671681 | − | ENST00000401084; ENST00000264203; ENST00000375144; ENST00000375142; ENST00000433834; ENST00000264202; ENST00000413711 | TSF |
| 9% | chr3 | 132014279 | 132014543 | + | chr3 | 132047111 | 132047206 | + | ENST00000336375; ENST00000495911; ENST00000475741; ENST00000351273 | TSF |
| 9% | chr3 | 132014279 | 132014543 | + | chr3 | 132047111 | 132047206 | + | ENST00000336375; ENST00000495911; ENST00000475741; ENST00000351273 | TSF |
| 9% | chr3 | 132014279 | 132014543 | + | chr3 | 132047111 | 132047206 | + | ENST00000336375; ENST00000495911; ENST00000475741; ENST00000351273 | TSF |
| 9% | chr3 | 132014279 | 132014543 | + | chr3 | 132047111 | 132047206 | + | ENST00000336375; ENST00000495911; ENST00000475741; ENST00000351273 | TSF |
| 9% | chr7 | 7559044 | 7558760 | − | chr7 | 7557468 | 7557427 | − | ENST00000399429; ENST00000444268 | TSF |
| 9% | chr7 | 7559044 | 7558760 | − | chr7 | 7557468 | 7557427 | − | ENST00000399429; ENST00000444268 | TSF |
| 8% | chr17 | 65894489 | 65894534 | + | chr17 | 65899905 | 65900034 | + | ENST00000544778; ENST00000321892; ENST00000335221; ENST00000306378; ENST00000424123 | TSF |
| 8% | chr17 | 65894489 | 65894534 | + | chr17 | 65899905 | 65900034 | + | ENST00000544778; ENST00000321892; ENST00000335221; ENST00000306378; ENST00000424123 | TSF |
| 8% | chr17 | 65894489 | 65894534 | + | chr17 | 65899905 | 65900034 | + | ENST00000544778; ENST00000321892; ENST00000335221; ENST00000306378; ENST00000424123 | TSF |
| 8% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 8% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 8% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 8% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 8% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 8% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 8% | chr1 | 156716197 | 156716133 | − | chr1 | 156715165 | 156715089 | − | ENST00000357325; ENST00000537739; ENST00000368209; ENST00000368206 | TSF |
| 8% | chr11 | 59608573 | 59608450 | − | chr11 | 59604824 | 59604647 | − | ENST00000257248; ENST00000541311 | TSF |
| 8% | chr2 | 232340741 | 232340940 | + | chr2 | 232577177 | 232577226 | + | ENST00000409321; ENST00000409115; ENST00000341369; ENST00000409683; ENST00000410064; ENST00000412128 | TSF |
| 8% | chr17 | 75338773 | 75338959 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 8% | chr17 | 75338773 | 75338959 | + | chr17 | 75398141 | 75398484; | + | ENST00000589070; ENST00000427177; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 8% | chr17 | 75338773 | 75338959 | + | chr17 | 75398141 | 75398785; 75398497; 75398565 75398484; 75398785; 75398497; 75398565 | + | ENST00000591198; ENST00000329047; ENST00000590294; ENST00000591934; ENST00000423034; ENST00000589140 ENST00000589070; ENST00000427177; ENST00000591198; ENST00000329047; ENST00000590294; ENST00000591934; ENST00000423034; ENST00000589140 | TSF |
| 8% | chr17 | 75338773 | 75338959 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| 8% | chr11 | 61196480 | 61196370 | − | chr11 | 61189080 | 61188862 | − | ENST00000340437; ENST00000394888; ENST00000439958; ENST00000448745; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | |
| | 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| | 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| | 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| | 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| | 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| | 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| | 8% | chr11 | 61196480 | 61196370 | − | chr11 | 61189080 | 61188862 | − | ENST00000340437; ENST00000394888; ENST00000439958; ENST00000448745; ENST00000477890; ENST00000539952; ENST00000535222; ENST00000544990; ENST00000544585; ENST00000413232; ENST00000537162; ENST00000543545; ENST00000541963; ENST00000536548; ENST00000450000; ENST00000449811; ENST00000413184; ENST00000536145 | TSF |
| | 7% | chr19 | 2141057 | 2140989 | − | chr19 | 2138713 | 2138618 | − | ENST00000355272; ENST00000356926; ENST00000350812; ENST00000345016 | TSF |
| | 7% | chr19 | 2141057 | 2140989 | − | chr19 | 2138713 | 2138618 | − | ENST00000355272; ENST00000356926; ENST00000350812; ENST00000345016 | TSF |
| | 7% | chr19 | 2141057 | 2140989 | − | chr19 | 2138713 | 2138618 | − | ENST00000355272; ENST00000356926; ENST00000350812; ENST00000345016 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 7% | chr19 | 2141057 | 2140989 | – | chr19 | 2138713 | 2138618 | – | ENST00000355272; ENST00000356926; ENST00000350812; ENST00000345016 | TSF |
| 7% | chr9 | 101730308 | 101730438 | + | chr9 | 101747847 | 101748394 | + | ENST0000375001 | TSF |
| 7% | chr17 | 75313396 | 75313709 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 7% | chr17 | 75313396 | 75313709 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 7% | chr17 | 75313396 | 75313709 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 7% | chr17 | 75313396 | 75313709 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TSF |
| 7% | chr7 | 100877200 | 100877154 | – | chr7 | 100876195 | 100876114 | – | ENST00000308344; ENST00000401528; ENST00000414035; ENST00000412417 | TSF |
| 7% | chr7 | 100877200 | 100877154 | – | chr7 | 100876195 | 100876114 | – | ENST00000308344; ENST00000401528; ENST00000414035; ENST00000412417 | TSF |
| 7% | chr7 | 100877200 | 100877154 | – | chr7 | 100876195 | 100876114 | – | ENST00000308344; ENST00000401528; ENST00000414035; ENST00000412417 | TSF |
| 7% | chr12 | 6602868 | 6602754 | – | chr12 | 6602138 | 6602028 | – | ENST00000229238 | TSF |
| 7% | chr20 | 48264330 | 48264298 | – | chr20 | 48263615 | 48263502 | – | ENST00000371711 | TSF |
| 7% | chr5 | 59968470 | 59968185 | – | chr5 | 59943360 | 59943225 | – | ENST00000265036; ENST00000453022; ENST00000545085 | TSF |
| 7% | chr5 | 59968470 | 59968185 | – | chr5 | 59943360 | 59943225 | – | ENST00000265036; ENST00000453022; ENST00000545085 | TSF |
| 6% | chr5 | 175697409 | 175697523 | + | chr5 | 175716657 | 175717958 | + | ENST00000443967; ENST00000429602 | TSF |
| 6% | chr5 | 175697409 | 175697523 | + | chr5 | 175716657 | 175717958 | + | ENST00000443967; ENST00000429602 | TSF |
| 6% | chr11 | 46321227 | 46321229 | + | chr11 | 46321486 | 46321714 | + | ENST00000529193; ENST00000288400 | TSF |
| 6% | chr21 | 34902064 | 34901873 | – | chr21 | 34901243 | 34901156 | – | ENST00000381815; ENST00000381831; ENST00000381839; ENST00000424203; ENST00000361093 | TSF |
| 6% | chr21 | 34902064 | 34901873 | – | chr21 | 34901243 | 34901156 | – | ENST00000381815; ENST00000381831; ENST00000381839; ENST00000424203; ENST00000361093 | TSF |
| 6% | chr21 | 34902064 | 34901873 | – | chr21 | 34901243 | 34901156 | – | ENST00000381815; ENST00000381831; ENST00000381839; ENST00000424203; ENST00000361093 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 6% | chr19 | 17384225 | 17384260 | + | chr19 | 17384713 | 17384833; 17384754; 17384789 | + | ENST00000601938; ENST00000602066; ENST00000598567 ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr19 | 17384225 | 17384260 | + | chr19 | 17384713 | 17384833; 17384754; 17384789 | + | ENST00000598188; ENST00000594247; ENST00000359435; ENST00000596542; ENST00000599474; ENST00000599057; ENST00000447614; ENST00000601043; ENST00000596335; ENST00000601436; ENST00000601938; ENST00000602066; ENST00000598567 | TSF |
| 6% | chr2 | 232340741 | 232340940 | + | chr2 | 232576646 | 232576693 | + | ENST00000409321; ENST00000409115; ENST00000341369; ENST00000409683; ENST00000410064; ENST00000412128 | TSF |
| 6% | chr2 | 232340741 | 232340940 | + | chr2 | 232576646 | 232576693 | + | ENST00000409321; ENST00000409115; ENST00000341369; ENST00000409683; ENST00000410064; ENST00000412128 | TSF |
| 6% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 6% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 6% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 6% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 6% | chr19 | 45365391 | 45365456 | + | chr19 | 45368528 | 45368917 | + | ENST00000252485; ENST00000252483 | TSF |
| 6% | chr19 | 45365391 | 45365456 | + | Ichr19 | 45368528 | 45368917 | + | ENST00000252485; ENST00000252483 | TSF |
| 6% | chr22 | 37963762 | 37963951 | + | chr22 | 37964115 | 37964827 | + | ENST00000249014 | TSF |
| 6% | chr12 | 50813695 | 50814670 | + | chr12 | 50821545 | 50821692 | + | ENST00000293618; ENST00000429001; ENST00000548174; ENST00000398473; ENST00000522085; ENST00000551886; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 6% | chr12 | 50813695 | 50814670 | + | chr12 | 50821545 | 50821692 | + | ENST00000347328 ENST00000293618; ENST00000429001; ENST00000548174; ENST00000398473; ENST00000522085; ENST00000551886; | TSF |
| 6% | chr12 | 50813695 | 50814670 | + | chr12 | 50821545 | 50821692 | + | ENST00000347328 ENST00000293618; ENST00000429001; ENST00000548174; ENST00000398473; ENST00000522085; ENST00000551886; | TSF |
| 6% | chr12 | 50813695 | 50814670 | + | chr12 | 50821545 | 50821692 | + | ENST00000347328 ENST00000293618; ENST00000429001; ENST00000548174; ENST00000398473; ENST00000522085; ENST00000551886; | TSF |
| 6% | chr12 | 50813695 | 50814670 | + | chr12 | 50821545 | 50821692 | + | ENST00000347328 ENST00000293618; ENST00000429001; ENST00000548174; ENST00000398473; ENST00000522085; ENST00000551886; | TSF |
| 6% | chr12 | 50813695 | 50814670 | + | chr12 | 50821545 | 50821692 | + | ENST00000347328 ENST00000293618; ENST00000429001; ENST00000548174; ENST00000398473; ENST00000522085; ENST00000551886; | TSF |
| 6% | chr12 | 50813695 | 50814670 | + | chr12 | 50821545 | 50821692 | + | ENST00000347328 ENST00000293618; ENST00000429001; ENST00000548174; ENST00000398473; ENST00000522085; ENST00000551886; | TSF |
| 6% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 6% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 6% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 6% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 6% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 6% | chr16 | 16100474 | 16100650 | + | chr16 | 16101673 | 16101849 | + | ENST00000399410; ENST00000345148; ENST00000346370; ENST00000349029; ENST00000351154; ENST00000399408 | TSF |
| 6% | chr12 | 133288092 | 133288275 | + | chr12 | 133291444 | 133291498; 133291622 | + | ENST00000537262; ENST00000545677; ENST00000317555; ENST00000498926 | TSF |
| 6% | chr12 | 133288092 | 133288275 | + | chr12 | 133291444 | 133291498; 133291622 | + | ENST00000537262; ENST00000545677; ENST00000317555; ENST00000498926 | TSF |
| 6% | chr12 | 133288092 | 133288275 | + | chr12 | 133291444 | 133291498; 133291622 | + | ENST00000537262; ENST00000545677; ENST00000317555; ENST00000498926 | TSF |
| 6% | chr12 | 133288092 | 133288275 | + | chr12 | 133291444 | 133291498; 133291622 | + | ENST00000537262; ENST00000545677; ENST00000317555; ENST00000498926 | TSF |
| 6% | chr11 | 14589824 | 14589773 | − | chr11 | 14540587 | 14540543 | − | ENST00000419365; ENST00000555531; ENST00000396394; ENST00000396393; ENST00000418988 | TSF |
| 6% | chr11 | 14589824 | 14589773 | − | chr11 | 14540587 | 14540543 | − | ENST00000419365; ENST00000555531; ENST00000396394; ENST00000396393; ENST00000418988 | TSF |
| 5% | chr14 | 93063213 | 93063281 | + | chr14 | 93081752 | 93081824 | + | ENST00000216487 | TSF |
| 5% | chr4 | 124087242 | 124087575 | + | chr4 | 124177171 | 124177335 | + | ENST00000274008 | TSF |
| 5% | chr7 | 5433736 | 5433673 | − | chr7 | 5430259 | 5430116; 5429988 | − | ENST00000399537; ENST00000430969; ENST00000434361; ENST00000399434 | TSF |
| 5% | chr7 | 5433736 | 5433673 | − | chr7 | 5430259 | 5430116; 5429988 | − | ENST00000399537; ENST00000430969; ENST00000434361; ENST00000399434 | TSF |
| 5% | chr7 | 5433736 | 5433673 | − | chr7 | 5430259 | 5430116; 5429988 | − | ENST00000399537; ENST00000430969; ENST00000434361; ENST00000399434 | TSF |
| 5% | chr7 | 5433736 | 5433673 | − | chr7 | 5430259 | 5430116; 5429988 | − | ENST00000399537; ENST00000430969; ENST00000434361; ENST00000399434 | TSF |
| 5% | chr10 | 74623670 | 74624174 | + | chr10 | 74628461 | 74628621; 74628570 | + | ENST00000373053; ENST00000536019; ENST00000604152 | TSF |
| 5% | chr10 | 74623670 | 74624174 | + | chr10 | 74628461 | 74628621; 74628570 | + | ENST00000373053; ENST00000536019; ENST00000604152 | TSF |
| 5% | chr7 | 56020443 | 56020541 | + | chr7 | 56020872 | 56021011 | + | ENST00000426595 | TSF |
| 5% | chr1 | 33270876 | 33270146 | − | chr1 | 33263444 | 33263364 | − | ENST00000373477 | TSF |
| 5% | chr3 | 100461912 | 100462018 | + | chr3 | 100463677 | 100463775 | + | ENST00000418917; ENST00000490574; ENST00000240851; ENST00000476228 | TSF |
| 5% | chr1 | 233789624 | 233790730 | + | chr1 | 233802341 | 233802736 | + | ENST00000366621; ENST00000366620; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr1 | 233789624 | 233790730 | + | chr1 | 233802341 | 233802736 | + | ENST00000446915 ENST00000366621; ENST00000366620; ENST00000446915 | |
| 5% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 5% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 5% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 5% | chr16 | 56972194 | 56972244 | + | chr16 | 56973149 | 56973271 | + | ENST00000439977; ENST00000300302; ENST00000379792; ENST00000569429; ENST00000563343; ENST00000568358 | TSF |
| 5% | chr19 | 1114930 | 1114676 | − | chr19 | 1114421 | 1114230 | − | ENST00000361757; ENST00000587024; ENST00000438103 | TSF |
| 5% | chr16 | 23606905 | 23606750 | − | chr16 | 23598640 | 23598518 | − | ENST00000007516; ENST00000570319 | TSF |
| 4% | chr10 | 101420120 | 101420239 | + | chr10 | 101421203 | 101421385 | + | ENST00000370489 | TSF |
| 4% | chr17 | 37898260 | 37898291 | + | chr17 | 37898505 | 37898709 | + | ENST00000445327 | TSF |
| 4% | chr12 | 52353922 | 52353971 | + | chr12 | 52369049 | 52369288 | + | ENST00000257963; ENST00000541224; ENST00000426655; ENST00000415850 | TSF |
| 4% | chr12 | 52353922 | 52353971 | + | chr12 | 52369049 | 52369288 | + | ENST00000257963; ENST00000541224; ENST00000426655; ENST00000415850 | TSF |
| 4% | chr12 | 52353922 | 52353971 | + | chr12 | 52369049 | 52369288 | + | ENST00000257963; ENST00000541224; ENST00000426655; ENST00000415850 | TSF |
| 4% | chr12 | 52353922 | 52353971 | + | chr12 | 52369049 | 52369288 | + | ENST00000257963; ENST00000541224; ENST00000426655; ENST00000415850 | TSF |
| 4% | chr5 | 59983652 | 59983552 | − | chr5 | 59983054 | 59982789 | − | ENST00000265036; ENST00000453022 | TSF |
| 4% | chr5 | 59983652 | 59983552 | − | chr5 | 59983054 | 59982789 | − | ENST00000265036; ENST00000453022 | TSF |
| 4% | chr1 | 201354798 | 201354740 | − | chr1 | 201353963 | 201353920 | − | ENST00000503578; ENST00000391967; ENST00000367313 | TSF |
| 4% | chr1 | 201354798 | 201354740 | − | chr1 | 201353963 | 201353920 | − | ENST00000503578; ENST00000391967; ENST00000367313 | TSF |
| 4% | chr1 | 172134550 | 172134843 | + | chr1 | 172222713 | 172222822; 172222718 | + | ENST00000358155; ENST00000355305; ENST00000367731; ENST00000520906; ENST00000523513 | TSF |
| 4% | chr1 | 172134550 | 172134843 | + | chr1 | 172222713 | 172222822; 172222718 | + | ENST00000358155; ENST00000355305; ENST00000367731; ENST00000520906; ENST00000523513 | TSF |
| 4% | chr1 | 172134550 | 172134843 | + | chr1 | 172222713 | 172222822; 172222718 | + | ENST00000358155; ENST00000355305; ENST00000367731; ENST00000520906; ENST00000523513 | TSF |
| 4% | chr1 | 172134550 | 172134843 | + | chr1 | 172222713 | 172222822; 172222718 | + | ENST00000358155; ENST00000355305; ENST00000367731; ENST00000520906; ENST00000523513 | TSF |
| 4% | chr2 | 232340741 | 232340940 | + | chr2 | 232576621 | 232576693 | + | ENST00000409321; ENST00000409115; ENST00000341369; ENST00000409683; ENST00000410064; ENST00000412128 | TSF |
| 4% | chr2 | 232340741 | 232340940 | + | chr2 | 232576621 | 232576693 | + | ENST00000409321; ENST00000409115; ENST00000341369; ENST00000409683; ENST00000410064; ENST00000412128 | TSF |
| 4% | chr10 | 35744377 | 35744391 | + | chr10 | 35772332 | 35772406 | + | ENST00000374704 | TSF |
| 4% | chr17 | 42149044 | 42149179 | + | chr17 | 42151528 | 42151634; 42151597 | + | ENST00000269097; ENST00000591696 | TSF |
| 4% | chr17 | 42149044 | 42149179 | + | chr17 | 42151528 | 42151634; 42151597 | + | ENST00000269097; ENST00000591696 | TSF |
| 4% | chr7 | 33006587 | 33006627 | + | chr7 | 33014229 | 33014374 | + | ENST00000242209; ENST00000538336 | TSF |
| 4% | chr16 | 58758969 | 58758792 | − | chr16 | 58757806 | 58757650 | − | ENST00000245206; ENST00000434819 | TSF |
| 4% | chr16 | 58758969 | 58758792 | − | chr16 | 58757806 | 58757650 | − | ENST00000245206; ENST00000434819 | TSF |
| 4% | chr14 | 51360331 | 51362440 | + | chr14 | 51368547 | 51368629 | + | ENST00000337334; ENST00000353130; ENST00000395752 | TSF |
| 4% | chr17 | 37902588 | 37902638 | + | chr17 | 37903004 | 37903150 | + | ENST00000309156; ENST00000394211; ENST00000445327; ENST00000394209 | TSF |
| 4% | chr12 | 50810162 | 50810217 | + | chr12 | 50821545 | 50821692 | + | ENST00000293618; ENST00000429001; ENST00000548174; ENST00000398473; ENST00000522085; ENST00000551886; ENST00000347328 | TSF |
| 4% | chr12 | 50810162 | 50810217 | + | chr12 | 50821545 | 50821692 | + | ENST00000293618; ENST00000429001; ENST00000548174; ENST00000398473; ENST00000522085; ENST00000551886; ENST00000347328 | TSF |
| 4% | chr12 | 50810162 | 50810217 | + | chr12 | 50821545 | 50821692 | + | ENST00000293618; ENST00000429001; ENST00000548174; ENST00000398473; ENST00000522085; ENST00000551886; ENST00000347328 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr12 | 50810162 | 50810217 | + | chr12 | 50821545 | 50821692 | + | ENST00000293618; ENST00000429001; ENST00000548174; ENST00000398473; ENST00000522085; ENST00000551886; ENST00000347328 | TSF |
| 4% | chr12 | 50810162 | 50810217 | + | chr12 | 50821545 | 50821692 | + | ENST00000293618; ENST00000429001; ENST00000548174; ENST00000398473; ENST00000522085; ENST00000551886; ENST00000347328 | TSF |
| 4% | chr12 | 50810162 | 50810217 | + | chr12 | 50821545 | 50821692 | + | ENST00000293618; ENST00000429001; ENST00000548174; ENST00000398473; ENST00000522085; ENST00000551886; ENST00000347328 | TSF |
| 4% | chr12 | 50810162 | 50810217 | + | chr12 | 50821545 | 50821692 | + | ENST00000293618; ENST00000429001; ENST00000548174; ENST00000398473; ENST00000522085; ENST00000551886; ENST00000347328 | TSF |
| 4% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 4% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 4% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 4% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 4% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 4% | chr20 | 34710617 | 34710669 | + | chr20 | 34761806 | 34761876 | + | ENST00000406771; ENST00000452261; ENST00000447825; ENST00000427533; ENST00000338074; ENST00000373941 | TSF |
| 4% | chr7 | 100878007 | 100877907 | − | chr7 | 100877723 | 100877559 | − | ENST00000308344; ENST00000401528; ENST00000433833 | TSF |
| 4% | chr7 | 100878007 | 100877907 | − | chr7 | 100877723 | 100877559 | − | ENST00000308344; ENST00000401528; ENST00000433833 | TSF |
| 4% | chr11 | 14589824 | 14589820 | − | chr11 | 14540587 | 14540543 | − | ENST00000419365; ENST00000555531; ENST00000396394; ENST00000396393; ENST00000418988 | TSF |
| 4% | chr11 | 14589824 | 14589820 | − | chr11 | 14540587 | 14540543 | − | ENST00000419365; ENST00000555531; ENST00000396394; ENST00000396393; ENST00000418988 | TSF |
| 4% | chr6 | 17994733 | 17994671 | − | chr6 | 17987375 | 17987285 | − | ENST00000378814; ENST00000259711; ENST00000378843; ENST00000378826; ENST00000378816; ENST00000502704 | TSF |
| 4% | chr6 | 17994733 | 17994671 | − | chr6 | 17987375 | 17987285 | − | ENST00000378814; ENST00000259711; ENST00000378843; ENST00000378826; ENST00000378816; ENST00000502704 | TSF |
| 4% | chr6 | 17994733 | 17994671 | − | chr6 | 17987375 | 17987285 | − | ENST00000378814; ENST00000259711; ENST00000378843; ENST00000378826; ENST00000378816; ENST00000502704 | TSF |
| 4% | chr6 | 17994733 | 17994671 | − | chr6 | 17987375 | 17987285 | − | ENST00000378814; ENST00000259711; ENST00000378843; ENST00000378826; ENST00000378816; ENST00000502704 | TSF |
| 4% | chr6 | 17994733 | 17994671 | − | chr6 | 17987375 | 17987285 | − | ENST00000378814; ENST00000259711; ENST00000378843; ENST00000378826; ENST00000378816; ENST00000502704 | TSF |
| 4% | chr6 | 17994733 | 17994671 | − | chr6 | 17987375 | 17987285 | − | ENST00000378814; ENST00000259711; ENST00000378843; ENST00000378826; ENST00000378816; ENST00000502704 | TSF |
| 4% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; ENST00000500777; ENST00000508502; ENST00000355196; ENST00000264405; ENST00000505984; ENST00000508479; ENST00000507828; ENST00000512664 | TSF |
| 4% | chr4 | 83774285 | 83774211 | − | chr4 | 83772757 | 83772584; 83772667 | − | ENST00000348405; ENST00000513858; ENST00000395310; ENST00000443462; ENST00000509142; ENST00000311785; ENST00000326950; ENST00000432794; ENST00000448323; ENST00000505472; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 4% | chr4 | 83774285 | 83774211 | − | chr4 | 83772757 | 83772584; 83772667 | − | ENST00000500777; ENST00000508502; ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; ENST00000448323; ENST00000505472; | TSF |
| 4% | chr4 | 83774285 | 83774211 | − | chr4 | 83772757 | 83772584; 83772667 | − | ENST00000500777; ENST00000508502; ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; ENST00000448323; ENST00000505472; | TSF |
| 4% | chr4 | 83774285 | 83774211 | − | chr4 | 83772757 | 83772584; 83772667 | − | ENST00000500777; ENST00000508502; ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; ENST00000448323; ENST00000505472; | TSF |
| 4% | chr4 | 83774285 | 83774211 | − | chr4 | 83772757 | 83772584; 83772667 | − | ENST00000500777; ENST00000508502; ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; ENST00000448323; ENST00000505472; | TSF |
| 4% | chr4 | 83774285 | 83774211 | − | chr4 | 83772757 | 83772584; 83772667 | − | ENST00000500777; ENST00000508502; ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; ENST00000448323; ENST00000505472; | TSF |
| 4% | chr4 | 83774285 | 83774211 | − | chr4 | 83772757 | 83772584; 83772667 | − | ENST00000500777; ENST00000508502; ENST00000355196; ENST00000264405; ENST00000505984; ENST00000508479; ENST00000507828; ENST00000512664 ENST00000348405; ENST00000513858; ENST00000395310; ENST00000443462; ENST00000509142; ENST00000311785; ENST00000326950; ENST00000432794; ENST00000448323; ENST00000505472; | TSF |
| 4% | chr17 | 18967449 | 18967302 | − | chr17 | 18881199 | 18880897 | − | ENST00000388995; ENST00000585154; ENST00000345041; ENST00000580115 | TSF |
| 4% | chr17 | 18967449 | 18967302 | − | chr17 | 18881199 | 18880897 | − | ENST00000388995; ENST00000585154; ENST00000345041; ENST00000580115 | |
| 4% | chr10 | 134665322 | 134665102 | − | chr10 | 134664809 | 134664621 | − | ENST00000368586; ENST00000263170 | TSF |
| 4% | chr7 | 100854761 | 10085471 | − | chr7 | 100853923 | 100853813; 100853876 | − | ENST00000454310; ENST00000223127; ENST00000421736 | TSF |
| 4% | chr7 | 100854761 | 10085471 | − | chr7 | 100853923 | 100853813; 100853876 | − | ENST00000454310; ENST00000223127; ENST00000421736 | TSF |
| 4% | chr7 | 100854761 | 10085471 | − | chr7 | 100853923 | 100853813; 100853876 | − | ENST00000454310; ENST00000223127; ENST00000421736 | TSF |
| 4% | chr16 | 67063021 | 67063052 | + | chr16 | 67063630 | 67063716 | + | ENST00000290858; ENST00000564034; ENST00000412916; ENST00000565389 | TSF |
| 4% | chr16 | 67063021 | 67063052 | + | chr16 | 67063630 | 67063716 | + | ENST00000290858; ENST00000564034; ENST00000412916; ENST00000565389 | TSF |
| 4% | chr16 | 67063021 | 67063052 | + | chr16 | 67063630 | 67063716 | + | ENST00000290858; ENST00000564034; ENST00000412916; ENST00000565389 | TSF |
| 4% | chr16 | 67063021 | 67063052 | + | chr16 | 67063630 | 67063716 | + | ENST00000290858; ENST00000564034; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 4% | chr12 | 53835137 | 53835233 | + | chr12 | 53836479 | 53836517 | + | ENST00000412916; ENST00000565389 ENST00000547368 | TSF |
| 4% | chr4 | 1708983 | 1709026 | + | chr4 | 1957892 | 1957915 | + | ENST00000508803; ENST00000382892; ENST00000382891; ENST00000382895; ENST00000514329; ENST00000382888 | TSF |
| 4% | chr4 | 1708983 | 1709026 | + | chr4 | 1957892 | 1957915 | + | ENST00000508803; ENST00000382892; ENST00000382891; ENST00000382895; ENST00000514329; ENST00000382888 | TSF |
| 4% | chr3 | 137719364 | 137719364 | + | chr3 | 137742500 | 137742664 | + | ENST00000343735; ENST00000183605; ENST00000479660 | TSF |
| 4% | chr3 | 137719364 | 137719364 | + | chr3 | 137742500 | 137742664 | + | ENST00000343735; ENST00000183605; ENST00000479660 | TSF |
| 4% | chr19 | 39131233 | 39131283 | + | chr19 | 39191240 | 39191354; 39191344 | + | ENST00000252699; ENST00000424234; ENST00000589528 | TSF |
| 4% | chr19 | 39131233 | 39131283 | + | chr19 | 39191240 | 39191354; 39191344 | + | ENST00000252699; ENST00000424234; ENST00000589528 | TSF |
| 4% | chr19 | 39131233 | 39131283 | + | chr19 | 39191240 | 39191354; 39191344 | + | ENST00000252699; ENST00000424234; ENST00000589528 | TSF |
| 4% | chr20 | 33351314 | 33350530 | − | chr20 | 33346736 | 33346608 | − | ENST00000374796; ENST00000359003 | TSF |
| 4% | chrX | 76851229 | 76851182 | − | chrX | 76849319 | 76849166 | − | ENST00000373344; ENST00000395603 | TSF |
| 3% | chr2 | 171572610 | 171572614 | + | chr2 | 171572769 | 171573914 | + | ENST00000375281 | TSF |
| 3% | chr16 | 14942551 | 14942561 | + | chr16 | 14942756 | 14942828 | + | ENST00000287667 | TSF |
| 3% | chr6 | 124669760 | 124669850 | + | chr6 | 124676413 | 124676493 | + | ENST00000368416; ENST00000368417; ENST00000546092; ENST00000545433 | TSF |
| 3% | chr6 | 124669760 | 124669850 | + | chr6 | 124676413 | 124676493 | + | ENST00000368416; ENST00000368417; ENST00000546092; ENST00000545433 | TSF |
| 3% | chr6 | 124669760 | 124669850 | + | chr6 | 124676413 | 124676493 | + | ENST00000368416; ENST00000368417; ENST00000546092; ENST00000545433 | TSF |
| 3% | chr6 | 124669760 | 124669850 | + | chr6 | 124676413 | 124676493 | + | ENST00000368416; ENST00000368417; ENST00000546092; ENST00000545433 | TSF |
| 3% | chr16 | 16341038 | 16341057 | + | chr16 | 16341252 | 16341324; 16341266 | + | ENST00000399336; ENST00000263012; ENST00000538468; ENST00000575225 | TSF |
| 3% | chr16 | 16341038 | 16341057 | + | chr16 | 16341252 | 16341324; 16341266 | + | ENST00000399336; ENST00000263012; ENST00000538468; ENST00000575225 | TSF |
| 3% | chr16 | 16341038 | 16341057 | + | chr16 | 16341252 | 16341324; 16341266 | + | ENST00000399336; ENST00000263012; ENST00000538468; ENST00000575225 | TSF |
| 3% | chr1 | 78389766 | 78390023 | + | chr1 | 78390873 | 78390914 | + | ENST00000401035; ENST00000330010; ENST00000334785; ENST00000342754 | TSF |
| 3% | chr1 | 78389766 | 78390023 | + | chr1 | 78390873 | 78390914 | + | ENST00000401035; ENST00000330010; ENST00000334785; ENST00000342754 | TSF |
| 3% | chr1 | 78389766 | 78390023 | + | chr1 | 78390873 | 78390914 | + | ENST00000401035; ENST00000330010; ENST00000334785; ENST00000342754 | TSF |
| 3% | chr17 | 39974832 | 39974893 | + | chr17 | 39975462 | 39975651 | + | ENST00000321562 | TSF |
| 3% | chr1 | 200882539 | 200882562 | + | chr1 | 200882665 | 200882757 | + | ENST00000367342; ENST00000413687 | TSF |
| 3% | chr9 | 130732697 | 130732597 | − | chr9 | 130716204 | 130716084 | − | ENST00000373095 | TSF |
| 3% | chr2 | 232340741 | 232340940 | + | chr2 | 232576658 | 232576693 | + | ENST00000409321; ENST00000409115; ENST00000341369; ENST00000409683; ENST00000410064; ENST00000412128 | TSF |
| 3% | chr2 | 232340741 | 232340940 | + | chr2 | 232576658 | 232576693 | + | ENST00000409321; ENST00000409115; ENST00000341369; ENST00000409683; ENST00000410064; ENST00000412128 | TSF |
| 3% | chr13 | 43628887 | 43629679 | + | chr13 | 43681314 | 43681384 | + | ENST00000379221 | TSF |
| 3% | chr2 | 85534293 | 85534401 | + | chr2 | 85534765 | 85534840 | + | ENST00000282111 | TSF |
| 3% | chr1 | 165854440 | 165854616 | + | chr1 | 165859441 | 165859600 | + | ENST00000367879; ENST00000372212 | TSF |
| 3% | chr1 | 165854440 | 165854616 | + | chr1 | 165859441 | 165859600 | + | ENST00000367879; ENST00000372212 | TSF |
| 3% | chr20 | 34710617 | 34710669 | + | chr20 | 34763473 | 34763637 | + | ENST00000406771; ENST00000452261; ENST00000447825; ENST00000373946; ENST00000338074; ENST00000373941 | TSF |
| 3% | chr20 | 34710617 | 34710669 | + | chr20 | 34763473 | 34763637 | + | ENST00000406771; ENST00000452261; ENST00000447825; ENST00000373946; ENST00000338074; ENST00000373941 | TSF |
| 3% | chr20 | 34710617 | 34710669 | + | chr20 | 34763473 | 34763637 | + | ENST00000406771; ENST00000452261; ENST00000447825; ENST00000373946; ENST00000338074; ENST00000373941 | TSF |
| 3% | chr20 | 34710617 | 34710669 | + | chr20 | 34763473 | 34763637 | + | ENST00000406771; ENST00000452261; ENST00000447825; ENST00000373946; ENST00000338074; ENST00000373941 | TSF |
| 3% | chr20 | 34710617 | 34710669 | + | chr20 | 34763473 | 34763637 | + | ENST00000406771; ENST00000452261; ENST00000447825; ENST00000373946; ENST00000338074; ENST00000373941 | TSF |
| 3% | chr20 | 34710617 | 34710669 | + | chr20 | 34763473 | 34763637 | + | ENST00000406771; ENST00000452261; ENST00000447825; ENST00000373946; ENST00000338074; ENST00000373941 | TSF |
| 3% | chr21 | 40180090 | 40180187 | + | chr21 | 40181959 | 40182030 | + | ENST00000360214; ENST00000360938; ENST00000432278; ENST00000456966 | TSF |
| 3% | chr21 | 40180090 | 40180187 | + | chr21 | 40181959 | 40182030 | + | ENST00000360214; ENST00000360938; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr21 | 40180090 | 40180187 | + | chr21 | 40181959 | 40182030 | + | ENST00000432278; ENST00000456966 ENST00000360214; ENST00000360938; ENST00000432278; ENST00000456966 | TSF |
| 3% | chrX | 53664297 | 53664254 | − | chrX | 53661250 | 53661188 | − | ENST00000342160; ENST00000262854; ENST00000218328 | TSF |
| 3% | chrX | 53664297 | 53664254 | − | chrX | 53661250 | 53661188 | − | ENST00000342160; ENST00000262854; ENST00000218328 | TSF |
| 3% | chr17 | 27441253 | 27441216 | − | chr17 | 27441115 | 27441029 | − | ENST00000354329; ENST00000533112; ENST00000531253; ENST00000527372 | TSF |
| 3% | chr17 | 27441253 | 27441216 | − | chr17 | 27441115 | 27441029 | − | ENST00000354329; ENST00000533112; ENST00000531253; ENST00000527372 | TSF |
| 3% | chr17 | 27441253 | 27441216 | − | chr17 | 27441115 | 27441029 | − | ENST00000354329; ENST00000533112; ENST00000531253; ENST00000527372 | TSF |
| 3% | chr17 | 43485811 | 43485601 | − | chr17 | 43483449 | 43483042; 43483213 | − | ENST00000532038; ENST00000428638; ENST00000442348; ENST00000532891; ENST00000528677 | TSF |
| 3% | chr17 | 43485811 | 43485601 | − | chr17 | 43483449 | 43483042; 43483213 | − | ENST00000532038; ENST00000428638; ENST00000442348; ENST00000532891; ENST00000528677 | TSF |
| 3% | chr17 | 43485811 | 43485601 | − | chr17 | 43483449 | 43483042; 43483213 | − | ENST00000532038; ENST00000428638; ENST00000442348; ENST00000532891; ENST00000528677 | TSF |
| 3% | chr17 | 43485811 | 43485601 | − | chr17 | 43483449 | 43483042; 43483213 | − | ENST00000532038; ENST00000428638; ENST00000442348; ENST00000532891; ENST00000528677 | TSF |
| 3% | chr13 | 95233957 | 95233815 | − | chr13 | 95233443 | 95233345 | − | ENST00000261296 | TSF |
| 3% | chr17 | 1005272 | 1005174 | − | chr17 | 1003975 | 1003877 | − | ENST00000302538; ENST00000544583; ENST00000574437; ENST00000291107; ENST00000574139; ENST00000570525; ENST00000574266 | TSF |
| 3% | chr17 | 1005272 | 1005174 | − | chr17 | 1003975 | 1003877 | − | ENST00000302538; ENST00000544583; ENST00000574437; ENST00000291107; ENST00000574139; ENST00000570525; ENST00000574266 | TSF |
| 3% | chr17 | 1005272 | 1005174 | − | chr17 | 1003975 | 1003877 | − | ENST00000302538; ENST00000544583; ENST00000574437; ENST00000291107; ENST00000574139; ENST00000570525; ENST00000574266 | TSF |
| 3% | chr17 | 1005272 | 1005174 | − | chr17 | 1003975 | 1003877 | − | ENST00000302538; ENST00000544583; ENST00000574437; ENST00000291107; ENST00000574139; ENST00000570525; ENST00000574266 | TSF |
| 3% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 3% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 3% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 3% | chr9 | 131902050 | 131902148 | + | chr9 | 131904724 | 131904831; 131905179 | + | ENST00000358994; ENST00000393370; ENST00000337738; ENST00000348141; ENST00000452489; ENST00000357197; ENST00000347048; ENST00000355007; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr9 | 131902050 | 131902148 | + | chr9 | 131904724 | 131904831; 131905179 | + | ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 ENST00000358994; ENST00000393370; ENST00000337738; ENST00000348141; ENST00000452489; ENST00000357197; ENST00000347048; ENST00000355007; ENST00000417728; ENST00000411917; ENST00000423100; ENST00000524946; ENST00000436883; ENST00000414510; ENST00000432124; ENST00000435305; ENST00000419582; ENST00000432651; ENST00000435132; ENST00000434095 | TSF |
| 3% | chr1 | 109695285 | 109695471 | + | chr1 | 109704516 | 109704636 | + | ENST00000533147; ENST00000531664; ENST00000534476; ENST00000526264; ENST00000369939; ENST00000457623; ENST00000529753 | TSF |
| 3% | chr1 | 109695285 | 109695471 | + | chr1 | 109704516 | 109704636 | + | ENST00000533147; ENST00000531664; ENST00000534476; ENST00000526264; ENST00000369939; ENST00000457623; ENST00000529753 | TSF |
| 3% | chr1 | 109695285 | 109695471 | + | chr1 | 109704516 | 109704636 | + | ENST00000533147; ENST00000531664; ENST00000534476; ENST00000526264; ENST00000369939; ENST00000457623; ENST00000529753 | TSF |
| 3% | chr1 | 109695285 | 109695471 | + | chr1 | 109704516 | 109704636 | + | ENST00000533147; ENST00000531664; ENST00000534476; ENST00000526264; ENST00000369939; ENST00000457623; ENST00000529753 | TSF |
| 3% | chr1 | 109695285 | 109695471 | + | chr1 | 109704516 | 109704636 | + | ENST00000533147; ENST00000531664; ENST00000534476; ENST00000526264; ENST00000369939; ENST00000457623; ENST00000529753 | TSF |
| 3% | chr1 | 109695285 | 109695471 | + | chr1 | 109704516 | 109704636 | + | ENST00000533147; ENST00000531664; ENST00000534476; ENST00000526264; ENST00000369939; ENST00000457623; ENST00000529753 | TSF |
| 3% | chr10 | 74643151 | 74643529 | + | chr10 | 74644024 | 74644140 | + | ENST00000373053; ENST00000357157; ENST00000536019 | TSF |
| 3% | chr5 | 179238653 | 179238682 | + | chr5 | 179250858 | 179251087; 179251057 | + | ENST00000376929; ENST00000514093; ENST00000422245; ENST00000389805; ENST00000504627; ENST00000402874; ENST00000510187; ENST00000360718 | TSF |
| 3% | chr5 | 179238653 | 179238682 | + | chr5 | 179250858 | 179251087; 179251057 | + | ENST00000376929; ENST00000514093; ENST00000422245; ENST00000389805; ENST00000504627; ENST00000402874; ENST00000510187; ENST00000360718 | TSF |
| 3% | chr5 | 179238653 | 179238682 | + | chr5 | 179250858 | 179251087; 179251057 | + | ENST00000376929; ENST00000514093; ENST00000422245; ENST00000389805; ENST00000504627; ENST00000402874; ENST00000510187; ENST00000360718 | TSF |
| 3% | chr5 | 179238653 | 179238682 | + | chr5 | 179250858 | 179251087; 179251057 | + | ENST00000376929; ENST00000514093; ENST00000422245; ENST00000389805; ENST00000504627; ENST00000402874; ENST00000510187; ENST00000360718 | TSF |
| 3% | chr5 | 179238653 | 179238682 | + | chr5 | 179250858 | 179251087; 179251057 | + | ENST00000376929; ENST00000514093; ENST00000422245; ENST00000389805; ENST00000504627; ENST00000402874; ENST00000510187; ENST00000360718 | TSF |
| 3% | chr2 | 232340741 | 232340940 | + | chr2 | 232576651 | 232576693 | + | ENST00000409321; ENST00000409115; ENST00000341369; ENST00000409683; ENST00000410064; ENST00000412128 | TSF |
| 3% | chr2 | 232340741 | 232340940 | + | chr2 | 232576651 | 232576693 | + | ENST00000409321; ENST00000409115; ENST00000341369; ENST00000409683; ENST00000410064; ENST00000412128 | TSF |
| 3% | chr7 | 56020443 | 56020509 | + | chr7 | 56020872 | 56021011 | + | ENST0000426595 | TSF |
| 3% | chr16 | 50663697 | 50663964 | + | chr16 | 50664097 | 50664244 | + | ENST00000268459 | TSF |
| 3% | chr16 | 28836248 | 28836298 | + | chr16 | 28836687 | 28836723 | + | ENST00000340394; ENST00000325215; ENST00000336783; ENST00000382686; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|----|----|
| 3% | chr16 | 28836248 | 28836298 | + | chr16 | 28836687 | 28836723 | + | ENST00000395547; ENST00000564304; ENST00000570200; ENST00000568266 ENST00000340394; ENST00000325215; ENST00000336783; ENST00000382686; | TSF |
| 3% | chr16 | 28836248 | 28836298 | + | chr16 | 28836687 | 28836723 | + | ENST00000395547; ENST00000564304; ENST00000570200; ENST00000568266 ENST00000340394; ENST00000325215; ENST00000336783; ENST00000382686; | TSF |
| 3% | chr16 | 28836248 | 28836298 | + | chr16 | 28836687 | 28836723 | + | ENST00000395547; ENST00000564304; ENST00000570200; ENST00000568266 ENST00000340394; ENST00000325215; ENST00000336783; ENST00000382686; | TSF |
| 3% | chr16 | 28836248 | 28836298 | + | chr16 | 28836687 | 28836723 | + | ENST00000395547; ENST00000564304; ENST00000570200; ENST00000568266 ENST00000340394; ENST00000325215; ENST00000336783; ENST00000382686; | TSF |
| 3% | chr16 | 28836248 | 28836298 | + | chr16 | 28836687 | 28836723 | + | ENST00000395547; ENST00000564304; ENST00000570200; ENST00000568266 ENST00000340394; ENST00000325215; ENST00000336783; ENST00000382686; | TSF |
| 3% | chr16 | 28836248 | 28836298 | + | chr16 | 28836687 | 28836723 | + | ENST00000395547; ENST00000564304; ENST00000570200; ENST00000568266 ENST00000340394; ENST00000325215; ENST00000336783; ENST00000382686; | TSF |
| 3% | chr16 | 28836248 | 28836298 | + | chr16 | 28836687 | 28836723 | + | ENST00000395547; ENST00000564304; ENST00000570200; ENST00000568266 ENST00000340394; ENST00000325215; ENST00000336783; ENST00000382686; | TSF |
| 3% | chr7 | 23722338 | 23722381 | + | chr7 | 23724118 | 23724291 | + | ENST00000409192; ENST00000344962; ENST00000429719; ENST00000446234 | TSF |
| 3% | chr7 | 23722338 | 23722381 | + | chr7 | 23724118 | 23724291 | + | ENST00000409192; ENST00000344962; ENST00000429719; ENST00000446234 | TSF |
| 3% | chr7 | 23722338 | 23722381 | + | chr7 | 23724118 | 23724291 | + | ENST00000409192; ENST00000344962; ENST00000429719; ENST00000446234 | TSF |
| 3% | chr7 | 23722338 | 23722381 | + | chr7 | 23724118 | 23724291 | + | ENST00000409192; ENST00000344962; ENST00000429719; ENST00000446234 | TSF |
| 3% | chr17 | 39976225 | 39976301 | + | chr17 | 39976521 | 39976713 | + | ENST00000321562; ENST00000455106; ENST00000544340 | TSF |
| 3% | chr15 | 44600951 | 44601046 | + | chr15 | 44615163 | 44615217 | + | ENST00000557945; ENST00000299957; ENST00000345795; ENST00000360824 | TSF |
| 3% | chr15 | 44600951 | 44601046 | + | chr15 | 44615163 | 44615217 | + | ENST00000557945; ENST00000299957; ENST00000345795; ENST00000360824 | TSF |
| 3% | chr15 | 44600951 | 44601046 | + | chr15 | 44615163 | 44615217 | + | ENST00000557945; ENST00000299957; ENST00000345795; ENST00000360824 | TSF |
| 3% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 3% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 3% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 3% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 3% | chr11 | 46390474 | 46390524 | + | chr11 | 46391044 | 46391100; 46391047 | + | ENST00000343674; ENST00000532868; ENST00000395574; ENST00000527911; ENST00000533376; ENST00000456247; ENST00000421244; ENST00000318201; ENST00000454345; ENST00000524448 | TSF |
| 3% | chr22 | 38166164 | 38166230 | + | chr22 | 38167657 | 38167743 | + | ENST00000406386; ENST00000403663 | TSF |
| 3% | chr12 | 117498589 | 117498567 | − | chr12 | 117494691 | 117494611 | − | ENST00000470612; ENST00000335209; ENST00000392545; ENST00000462502 | TSF |
| 3% | chr12 | 117498589 | 117498567 | − | chr12 | 117494691 | 117494611 | − | ENST00000470612; ENST00000335209; ENST00000392545; ENST00000462502 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr12 | 117498589 | 117498567 | − | chr12 | 117494691 | 117494611 | − | ENST00000470612; ENST00000335209; ENST00000392545; ENST00000462502 | TSF |
| 3% | chr16 | 21060024 | 21059927 | − | chr16 | 21053525 | 21053349 | − | ENST00000261383; ENST00000415178 | TSF |
| 3% | chr16 | 21060024 | 21059927 | − | chr16 | 21053525 | 21053349 | − | ENST00000261383; ENST00000415178 | TSF |
| 3% | chr17 | 38639751 | 38639593 | − | chr17 | 38638668 | 38638576 | − | ENST00000254051 | TSF |
| 3% | chr1 | 8924664 | 8924519 | − | chr1 | 8924151 | 8923950 | − | ENST00000234590 | TSF |
| 3% | chr7 | 22858195 | 22858099 | − | chr7 | 22857667 | 22857619 | − | ENST00000358435; ENST00000405021; ENST00000372879 | TSF TSF |
| 3% | chr17 | 17735107 | 17735071 | − | chr17 | 17723835 | 17723404 | − | ENST00000338854; ENST00000355815; ENST00000261646; ENST00000435530; ENST00000423161 | TSF |
| 3% | chr17 | 17735107 | 17735071 | − | chr17 | 17723835 | 17723404 | − | ENST00000338854; ENST00000355815; ENST00000261646; ENST00000435530; ENST00000423161 | TSF |
| 3% | chr17 | 17735107 | 17735071 | − | chr17 | 17723835 | 17723404 | − | ENST00000338854; ENST00000355815; ENST00000261646; ENST00000435530; ENST00000423161 | TSF |
| 3% | chr17 | 17735107 | 17735071 | − | chr17 | 17723835 | 17723404 | − | ENST00000338854; ENST00000355815; ENST00000261646; ENST00000435530; ENST00000423161 | TSF |
| 3% | chr7 | 97938760 | 97938714 | − | chr7 | 97937208 | 97937001 | − | ENST00000005260 | TSF |
| 3% | chr2 | 150044073 | 150044093 | + | chr2 | 150061767 | 150061918 | + | ENST00000409642; ENST00000409876; ENST00000409029; ENST00000442722; ENST00000280115 | TSF |
| 3% | chr2 | 150044073 | 150044093 | + | chr2 | 150061767 | 150061918 | + | ENST00000409642; ENST00000409876; ENST00000409029; ENST00000442722; ENST00000280115 | TSF |
| 3% | chr16 | 66461229 | 66461334 | + | chr16 | 66503505 | 66503768 | + | ENST00000536005 | TSF |
| 3% | chr2 | 101567739 | 101568117 | + | chr2 | 101580425 | 101580638 | + | ENST00000335681; ENST00000542504 | TSF |
| 3% | chr13 | 43670805 | 43671144 | + | chr13 | 43681314 | 43681384 | + | ENST00000379221 | TSF |
| 3% | chr7 | 56018506 | 56018522 | + | chr7 | 56022602 | 56022871; 56022865 | + | ENST00000426595; ENST00000285298; ENST00000443449 | TSF |
| 3% | chr7 | 56018506 | 56018522 | + | chr7 | 56022602 | 56022871; 56022865 | + | ENST00000426595; ENST00000285298; ENST00000443449 | TSF |
| 3% | chr1 | 15562769 | 15563257 | + | chr1 | 15578267 | 15578373 | + | ENST00000433640 | TSF |
| 3% | chr3 | 47772073 | 47772030 | − | chr3 | 47770584 | 47770515 | − | ENST00000254480 | TSF |
| 3% | chr17 | 70713894 | 70713885 | − | chr17 | 70645407 | 70645309 | − | ENST00000255559; ENST00000542342; ENST00000582769 | TSF |
| 3% | chr17 | 70713894 | 70713885 | − | chr17 | 70645407 | 70645309 | − | ENST00000255559; ENST00000542342; ENST00000582769 | TSF |
| 3% | chr11 | 93468219 | 93468129 | − | chr11 | 93466563 | 93466528 | − | ENST00000393259 | TSF |
| 3% | chr20 | 56265149 | 56265035 | − | chr20 | 56234753 | 56234599 | − | ENST00000341744; ENST00000347215; ENST00000414037; ENST00000395819 | TSF |
| 3% | chr20 | 56265149 | 56265035 | − | chr20 | 56234753 | 56234599 | − | ENST00000341744; ENST00000347215; ENST00000414037; ENST00000395819 | TSF |
| 3% | chr20 | 56265149 | 56265035 | − | chr20 | 56234753 | 56234599 | − | ENST00000341744; ENST00000347215; ENST00000414037; ENST00000395819 | TSF |
| 3% | chrX | 134954053 | 134953756 | − | chrX | 134932924 | 134932815 | − | ENST00000487941; ENST00000434966; ENST00000494421 | TSF |
| 3% | chr17 | 42400590 | 42400540 | − | chr17 | 42400220 | 42400176 | − | ENST00000225308; ENST00000377095; ENST00000590194; ENST00000590194; ENST00000588049; ENST00000586633; ENST00000592857; ENST00000585523 | TSF |
| 3% | chr17 | 42400590 | 42400540 | − | chr17 | 42400220 | 42400176 | − | ENST00000225308; ENST00000377095; ENST00000590194; ENST00000590194; ENST00000588049; ENST00000586633; ENST00000592857; ENST00000585523 | TSF |
| 3% | chr17 | 42400590 | 42400540 | − | chr17 | 42400220 | 42400176 | − | ENST00000225308; ENST00000377095; ENST00000590194; ENST00000590194; ENST00000588049; ENST00000586633; ENST00000592857; ENST00000585523 | TSF |
| 3% | chr17 | 42400590 | 42400540 | − | chr17 | 42400220 | 42400176 | − | ENST00000225308; ENST00000377095; ENST00000590194; ENST00000590194; ENST00000588049; ENST00000586633; ENST00000592857; ENST00000585523 | TSF |
| 3% | chr17 | 42400590 | 42400540 | − | chr17 | 42400220 | 42400176 | − | ENST00000225308; ENST00000377095; ENST00000590194; ENST00000590194; ENST00000588049; ENST00000586633; ENST00000592857; ENST00000585523 | TSF |
| 3% | chr17 | 42400590 | 42400540 | − | chr17 | 42400220 | 42400176 | − | ENST00000225308; ENST00000377095; ENST00000590194; ENST00000590194; ENST00000588049; ENST00000586633; ENST00000592857; ENST00000585523 | TSF |
| 3% | chrX | 134954053 | 134953756 | − | chrX | 134950187 | 134950078 | − | ENST00000420087; ENST00000463085; ENST00000370724; ENST00000491480 | TSF |
| 3% | chrX | 134954053 | 134953756 | − | chrX | 134950187 | 134950078 | − | ENST00000420087; ENST00000463085; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr22 | 22899971 | 22899965 | − | chr22 | 22893511 | 22893189; 22893185; 22893481; 22893274 | − | ENST00000370724; ENST00000491480 ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 3% | chrX | 134936794 | 134936497 | − | chrX | 134932924 | 134932815 | − | ENST00000487941; ENST00000434966; ENST00000494421 | TSF |
| 2% | chr7 | 2403615 | 2403665 | + | chr7 | 2404007 | 2404164; 2404031 | + | ENST00000431643; ENST00000360876; ENST00000413917; ENST00000397011 | TSF |
| 2% | chr7 | 2403615 | 2403665 | + | chr7 | 2404007 | 2404164; 2404031 | + | ENST00000431643; ENST00000360876; ENST00000413917; ENST00000397011 | TSF |
| 2% | chr7 | 2403615 | 2403665 | + | chr7 | 2404007 | 2404164; 2404031 | + | ENST00000431643; ENST00000360876; ENST00000413917; ENST00000397011 | TSF |
| 2% | chr20 | 44442461 | 44442685 | + | chr20 | 44443023 | 44443109 | + | ENST00000356455; ENST00000405520; ENST00000335046; ENST00000372568 | TSF |
| 2% | chr20 | 44442461 | 44442685 | + | chr20 | 44443023 | 44443109 | + | ENST00000356455; ENST00000405520; ENST00000335046; ENST00000372568 | TSF |
| 2% | chr21 | 42597177 | 42597622 | + | chr21 | 42598199 | 42598281 | + | ENST00000328735; ENST00000330333; ENST00000347667 | TSF |
| 2% | chr21 | 42597177 | 42597622 | + | chr21 | 42598199 | 42598281 | + | ENST00000328735; ENST00000330333; ENST00000347667 | TSF |
| 2% | chr21 | 42597177 | 42597622 | + | chr21 | 42598199 | 42598281 | + | ENST00000328735; ENST00000330333; ENST00000347667 | TSF |
| 2% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 2% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 2% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 2% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 2% | chr17 | 7479605 | 7479718 | + | chr17 | 7479842 | 7480008; | + | ENST00000582169; ENST00000293831; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 7480010; 7479924 | | ENST00000585024; ENST00000583802; ENST00000581544; ENST00000577269; ENST00000584784; ENST00000582746; ENST00000584860; ENST00000581384 | |
| 2% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 2% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 2% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 2% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 2% | chr17 | 7479605 | 7479718 | + | chr17 | 7479842 | 7480008; 7480010; 7479924 | + | ENST00000582169; ENST00000293831; ENST00000585024; ENST00000583802; ENST00000581544; ENST00000577269; ENST00000584784; ENST00000582746; ENST00000584860; ENST00000581384 | TSF |
| 2% | chr3 | 39374892 | 39374955 | + | chr3 | 39453486 | 39453552; 39453550 | + | ENST00000301821; ENST00000458478; ENST00000443003 | TSF |
| 2% | chr3 | 39374892 | 39374955 | + | chr3 | 39453486 | 39453552; 39453550 | + | ENST00000301821; ENST00000458478; ENST00000443003 | TSF |
| 2% | chr1 | 206326596 | 206326721 | + | chr1 | 206327474 | 206327596 | + | ENST00000358184; ENST00000361052; ENST00000360218; ENST00000432969 | TSF |
| 2% | chr1 | 206326596 | 206326721 | + | chr1 | 206327474 | 206327596 | + | ENST00000358184; ENST00000361052; ENST00000360218; ENST00000432969 | TSF |
| 2% | chr20 | 60878087 | 60878105 | + | chr20 | 60878775 | 60878837 | + | ENST00000253003 | TSF |
| 2% | chr11 | 66953459 | 66954052 | + | chr11 | 66974981 | 66975159 | + | ENST00000398645; ENST00000529006 | TSF |
| 2% | chr11 | 66953459 | 66954052 | + | chr11 | 66974981 | 66975159 | + | ENST00000398645; ENST00000529006 | TSF |
| 2% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276279 | + | chr2 | 242276797 | 242276931; | + | ENST00000391973; ENST00000428282; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
|   |    |    |    |    |    |    | 242276900; 242276863; 242276848 |    | ENST00000360051; ENST00000391971; ENST00000401990; ENST00000407971; ENST00000436795; ENST00000411484; ENST00000402092; ENST00000443492; ENST00000437066; ENST00000449239; ENST00000457874 |  |
| 2% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276279 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 189844524 | 189844751 | + | chr2 | 189849486 | 189849688 | + | ENST00000304636; ENST00000317840 | TSF |
| 2% | chr2 | 189844524 | 189844751 | + | chr2 | 189849486 | 189849688 | + | ENST00000304636; ENST00000317840 | TSF |
| 2% | chr6 | 30913142 | 30913271 | + | chr6 | 30916324 | 30920276 | + | ENST00000462446 | TSF |
| 2% | chr17 | 37897992 | 37898081 | + | chr17 | 37898505 | 37898709 | + | ENST00000445327 | TSF |
| 2% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 2% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 2% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 2% | chr8 | 9629642 | 9629933 | + | chr8 | 9634160 | 9634246 | + | ENST00000310430; ENST00000518281 | TSF |
| 2% | chr4 | 2041574 | 2041819 | + | chr4 | 2044463 | 2044551 | + | ENST00000382878; ENST00000409248; ENST00000409860 | TSF |
| 2% | chr14 | 106174427 | 106174466 | + | chr14 | 106173770 | 106173505 | − | ENST00000390547 | TSF |
| 2% | chr1 | 31218846 | 31218765 | − | chr1 | 31215396 | 31215303 | − | ENST00000294507 | TSF |
| 2% | chr11 | 118917082 | 118917078 | − | chr11 | 118916543 | 118916493 | − | ENST00000404233; ENST00000529972; ENST00000525859 | TSF |
| 2% | chr11 | 118917082 | 118917078 | − | chr11 | 118916543 | 118916493 | − | ENST00000404233; ENST00000529972; ENST00000525859 | TSF |
| 2% | chr11 | 118917082 | 118917078 | − | chr11 | 118916543 | 118916493 | − | ENST00000404233; ENST00000529972; ENST00000525859 | TSF |
| 2% | chr3 | 128352356 | 128352306 | − | chr3 | 128351000 | 128350791 | − | ENST00000296255; ENST00000497289 | TSF |
| 2% | chr1 | 52343673 | 52343655 | − | chr1 | 52306186 | 52305898 | − | ENST00000352171; ENST00000354831 | TSF |
| 2% | chr1 | 52343673 | 52343655 | − | chr1 | 52306186 | 52305898 | − | ENST00000352171; ENST00000354831 | TSF |
| 2% | chrX | 134971303 | 134971006 | − | chrX | 134950187 | 134950078 | − | ENST00000420087; ENST00000463085; ENST00000370724; ENST00000491480 | TSF |
| 2% | chrX | 134971303 | 134971006 | − | chrX | 134950187 | 134950078 | − | ENST00000420087; ENST00000463085; ENST00000370724; ENST00000491480 | TSF |
| 2% | chr19 | 47347459 | 47347409 | − | chr19 | 47342835 | 47342722 | − | ENST00000352203; ENST00000601498; ENST00000599990; ENST00000593442; ENST00000263270; ENST00000597020 | TSF |
| 2% | chr15 | 93592614 | 93592599 | − | chr15 | 93588935 | 93588228; 93588877 | − | ENST00000425933; ENST00000543599; ENST00000329082; ENST00000542321; ENST00000538818; ENST00000557301; ENST00000557420; ENST00000556658 | TSF |
| 2% | chr15 | 93592614 | 93592599 | − | chr15 | 93588935 | 93588228; 93588877 | − | ENST00000425933; ENST00000543599; ENST00000329082; ENST00000542321; ENST00000538818; ENST00000557301; ENST00000557420; ENST00000556658 | TSF |
| 2% | chr12 | 14670381 | 14670239 | − | chr12 | 14664645 | 14664445 | − | ENST00000240617 | TSF |
| 2% | chr17 | 19015949 | 19015802 | − | chr17 | 18881199 | 18880897 | − | ENST00000388995; ENST00000585154; ENST00000345041; ENST00000580115 | TSF |
| 2% | chr17 | 19015949 | 19015802 | − | chr17 | 18881199 | 18880897 | − | ENST00000388995; ENST00000585154; ENST00000345041; ENST00000580115 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chrX | 134971303 | 134971006 | − | chrX | 134967437 | 134967328 | − | ENST00000491002; ENST00000448053; ENST00000472834 | TSF |
| 2% | chr16 | 74833301 | 74833256 | − | chr16 | 74774013 | 74773921 | − | ENST00000219368; ENST00000567683; ENST00000569949 | TSF |
| 2% | chr16 | 74833301 | 74833256 | − | chr16 | 74774013 | 74773921 | − | ENST00000219368; ENST00000567683; ENST00000569949 | TSF |
| 2% | chr16 | 74833301 | 74833256 | − | chr16 | 74774013 | 74773921 | − | ENST00000219368; ENST00000567683; ENST00000569949 | TSF |
| 2% | chr9 | 130921922 | 130922014 | + | chr9 | 130925722 | 130925894 | + | ENST00000372994 | TSF |
| 2% | chr6 | 37326936 | 37327118 | + | chr6 | 37328222 | 37328350 | + | ENST00000373479; ENST00000229866; ENST00000394443; ENST00000469316; ENST00000469731 | TSF |
| 2% | chr6 | 37326936 | 37327118 | + | chr6 | 37328222 | 37328350 | + | ENST00000373479; ENST00000229866; ENST00000394443; ENST00000469316; ENST00000469731 | TSF |
| 2% | chr6 | 37326936 | 37327118 | + | chr6 | 37328222 | 37328350 | + | ENST00000373479; ENST00000229866; ENST00000394443; ENST00000469316; ENST00000469731 | TSF |
| 2% | chr6 | 37326936 | 37327118 | + | chr6 | 37328222 | 37328350 | + | ENST00000373479; ENST00000229866; ENST00000394443; ENST00000469316; ENST00000469731 | TSF |
| 2% | chr6 | 109426948 | 109427293 | + | chr6 | 109466422 | 109466584 | + | ENST00000523787 | TSF |
| 2% | chr19 | 45365700 | 45365943 | + | chr19 | 45368528 | 45368917 | + | ENST00000252485; ENST00000252483 | TSF |
| 2% | chr19 | 45365700 | 45365943 | + | chr19 | 45368528 | 45368917 | + | ENST00000252485; ENST00000252483 | TSF |
| 2% | chr6 | 31941780 | 31941829 | + | chr6 | 31946680 | 31946775; 31946787; 31946759 | + | ENST00000375331; ENST00000375333; ENST00000483801; ENST00000519179 | TSF |
| 2% | chr6 | 31941780 | 31941829 | + | chr6 | 31946680 | 31946775; 31946787; 31946759 | + | ENST00000375331; ENST00000375333; ENST00000483801; ENST00000519179 | TSF |
| 2% | chr6 | 31941780 | 31941829 | + | chr6 | 31946680 | 31946775; 31946787; 31946759 | + | ENST00000375331; ENST00000375333; ENST00000483801; ENST00000519179 | TSF |
| 2% | chr1 | 32605303 | 32605465 | + | chr1 | 32620189 | 32620322 | + | ENST00000373625; ENST00000471599; ENST00000545542 | TSF |
| 2% | chr1 | 32605303 | 32605465 | + | chr1 | 32620189 | 32620322 | + | ENST00000373625; ENST00000471599; ENST00000545542 | TSF |
| 2% | chr2 | 27666464 | 27666532 | + | chr2 | 27666816 | 27666923 | + | ENST00000543753; ENST00000288873; ENST00000407293; ENST00000452499 | TSF |
| 2% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 2% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 2% | chr3 | 184083167 | 184083362 | + | chr3 | 184084505 | 184084588 | + | ENST00000456318; ENST00000438240; ENST00000455712; ENST00000452961; ENST00000296223; ENST00000429568 | TSF |
| 2% | chrX | 69366031 | 69366077 | + | chrX | 69366483 | 69366678 | + | ENST00000342206; ENST00000356413 | TSF |
| 2% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 2% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 2% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 2% | chr2 | 211417526 | 211417732 | + | chr2 | 211421443 | 211421583 | + | ENST00000523702; ENST00000430249 | TSF |
| 2% | chr2 | 211417526 | 211417732 | + | chr2 | 211421443 | 211421583 | + | ENST00000523702; ENST00000430249 | TSF |
| 2% | chr17 | 78263107 | 78263365 | + | chr17 | 78263458 | 78263636 | + | ENST00000508628; ENST00000456466; ENST00000582970; ENST00000319921 | TSF |
| 2% | chr17 | 78263107 | 78263365 | + | chr17 | 78263458 | 78263636 | + | ENST00000508628; ENST00000456466; ENST00000582970; ENST00000319921 | TSF |
| 2% | chr17 | 78263107 | 78263365 | + | chr17 | 78263458 | 78263636 | + | ENST00000508628; ENST00000456466; ENST00000582970; ENST00000319921 | TSF |
| 2% | chr15 | 44051756 | 44051953 | + | chr15 | 44053622 | 44053729 | + | ENST00000300289; ENST00000538521 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr2 | 171572610 | 171572610 | + | chr2 | 171572769 | 171573914 | + | ENST00000375281 | TSF |
| 2% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 2% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 2% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 2% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 2% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 2% | chr2 | 28191829 | 28192099 | + | chr2 | 28210860 | 28210954 | + | ENST00000436924; ENST00000344773; ENST00000379624; ENST00000342045; ENST00000361704; ENST00000379632; ENST00000379629; ENST00000604932 | TSF |
| 2% | chr9 | 101724297 | 101724399 | + | chr9 | 101747847 | 101748394 | + | ENST00000375001 | TSF |
| 2% | chr15 | 74004214 | 74004264 | + | chr15 | 74005275 | 74005297 | + | ENST00000318443; ENST00000537340; ENST00000318424; ENST00000564751; ENST00000561176; ENST00000559073 | TSF |
| 2% | chrX | 17044209 | 17044386 | + | chrX | 17047649 | 17047746 | + | ENST00000357277; ENST00000303843; ENST00000380064 | TSF |
| 2% | chrX | 17044209 | 17044386 | + | chrX | 17047649 | 17047746 | + | ENST00000357277; ENST00000303843; ENST00000380064 | TSF |
| 2% | chr12 | 49659927 | 49660025 | + | chr12 | 49663248 | 49663470; 49663252 | + | ENST00000541364; ENST00000552125; ENST00000301072; ENST00000549183 | TSF |
| 2% | chr12 | 49659927 | 49660025 | + | chr12 | 49663248 | 49663470; 49663252 | + | ENST00000541364; ENST00000552125; ENST00000301072; ENST00000549183 | TSF |
| 2% | chr12 | 49659927 | 49660025 | + | chr12 | 49663248 | 49663470; 49663252 | + | ENST00000541364; ENST00000552125; ENST00000301072; ENST00000549183 | TSF |
| 2% | chr5 | 151074528 | 151074519 | − | chr5 | 151046027 | 151045922; 151045934 | − | ENST00000231061; ENST00000538026 | TSF |
| 2% | chr5 | 151074528 | 151074519 | − | chr5 | 151046027 | 151045922; 151045934 | − | ENST00000231061; ENST00000538026 | TSF |
| 2% | chr19 | 46395476 | 46395428 | − | chr19 | 46394581 | 46393881 | − | ENST00000322217 | TSF |
| 2% | chr3 | 45180920 | 45180844 | − | chr3 | 45160113 | 45159904 | − | ENST00000296129; ENST00000425231 | TSF |
| 2% | chr3 | 45180920 | 45180844 | − | chr3 | 45160113 | 45159904 | − | ENST00000296129; ENST00000425231 | TSF |
| 2% | chr8 | 74859521 | 74859471 | − | chr8 | 74859055 | 74858865; 74858935 | − | ENST00000518127; ENST00000520210; ENST00000520242; ENST00000519487; ENST00000284811; ENST00000522337; ENST00000523815; ENST00000519082 | TSF |
| 2% | chr8 | 74859521 | 74859471 | − | chr8 | 74859055 | 74858865; 74858935 | − | ENST00000518127; ENST00000520210; ENST00000520242; ENST00000519487; ENST00000284811; ENST00000522337; ENST00000523815; ENST00000519082 | TSF |
| 2% | chr4 | 873272 | 873014 | − | chr4 | 871597 | 871403 | − | ENST00000314167; ENST00000511163 | TSF |
| 2% | chr7 | 99257824 | 99257739 | − | chr7 | 99247855 | 99247696 | − | ENST00000222982; ENST00000343703 | TSF |
| 2% | chr17 | 30185561 | 30185499 | − | chr17 | 30183884 | 30183818 | − | ENST00000302362; ENST00000378634; ENST00000496655 | TSF |
| 2% | chr17 | 30185561 | 30185499 | − | chr17 | 30183884 | 30183818 | − | ENST00000302362; ENST00000378634; ENST00000496655 | TSF |
| 2% | chr19 | 36397290 | 36397240 | − | chr19 | 36395536 | 36395471 | − | ENST00000424586; ENST00000585901; ENST00000544690; ENST00000262629; ENST00000589517 | TSF |
| 2% | chr1 | 89663545 | 89663461 | − | chr1 | 89662987 | 89662793 | − | ENST00000355754 | TSF |
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 2% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 2% | chr14 | 92270099 | 92270000 | − | chr14 | 92268765 | 92268598 | − | ENST00000435962; ENST00000340892; ENST00000360594; ENST00000556018 | TSF |
| 2% | chr14 | 92270099 | 92270000 | − | chr14 | 92268765 | 92268598 | − | ENST00000435962; ENST00000340892; ENST00000360594; ENST00000556018 | TSF |
| 2% | chr2 | 27667813 | 27667765 | − | chr2 | 27667388 | 27667299 | − | ENST00000260570 | TSF |
| 2% | chr4 | 39699858 | 39699922 | + | chr4 | 39747372 | 39747430 | + | ENST00000261427; ENST00000510934; ENST00000295963; ENST00000445950 | TSF |
| 2% | chr4 | 39699858 | 39699922 | + | chr4 | 39747372 | 39747430 | + | ENST00000261427; ENST00000510934; ENST00000295963; ENST00000445950 | TSF |
| 2% | chr4 | 39699858 | 39699922 | + | chr4 | 39747372 | 39747430 | + | ENST00000261427; ENST00000510934; ENST00000295963; ENST00000445950 | TSF |
| 2% | chr4 | 39699858 | 39699922 | + | chr4 | 39747372 | 39747430 | + | ENST00000261427; ENST00000510934; ENST00000295963; ENST00000445950 | TSF |
| 2% | chr3 | 184639788 | 184640271 | + | chr3 | 184642650 | 184642769 | + | ENST00000287546; ENST00000437079; ENST00000436792; ENST00000446204 | TSF |
| 2% | chr7 | 6423751 | 6423803 | + | chr7 | 6426843 | 6426914 | + | ENST00000348035; ENST00000356142 | TSF |
| 2% | chr7 | 6423751 | 6423803 | + | chr7 | 6426843 | 6426914 | + | ENST00000348035; ENST00000356142 | TSF |
| 2% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 2% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 2% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 2% | chr19 | 16267516 | 16267584 | + | chr19 | 16268020 | 16268208; 16268205; 16268448; 16268139 | + | ENST00000253680; ENST00000397372; ENST00000593154; ENST00000588246; ENST00000593031 | TSF |
| 2% | chr17 | 66244121 | 66244199 | + | chr17 | 66244785 | 66244846 | + | ENST00000584837 | TSF |
| 2% | chr22 | 24967426 | 24967475 | + | chr22 | 24967884 | 24967945 | + | ENST00000215829; ENST00000404603 | TSF |
| 2% | chr2 | 219298180 | 219298229 | + | chr2 | 219299249 | 219299428 | + | ENST00000248444; ENST00000392114; ENST00000419986 | TSF |
| 2% | chr2 | 219298180 | 219298229 | + | chr2 | 219299249 | 219299428 | + | ENST00000248444; ENST00000392114; ENST00000419986 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr22 | 45098289 | 45098289 | + | chr22 | 45098372 | 45098488 | + | ENST00000403581; ENST00000336985; ENST00000403696; ENST00000431834; ENST00000361473; ENST00000352766; ENST00000517296 | TSF |
| 2% | chr8 | 71625721 | 71625811 | + | chr8 | 71646031 | 71646659 | + | ENST00000408926; ENST00000520030 | TSF |
| 2% | chr7 | 156960055 | 156960055 | + | chr7 | 156961742 | 156961816 | + | ENST00000348165 | TSF |
| 2% | chr9 | 130921922 | 130922117 | + | chr9 | 130925722 | 130925894 | + | ENST00000372994 | TSF |
| 2% | chr20 | 61437613 | 61437613 | + | chr20 | 61438889 | 61438957 | + | ENST00000290291 | TSF |
| 2% | chr1 | 236326774 | 236327054 | + | chr1 | 236332006 | 236332055 | + | ENST00000366592; ENST00000454895 | TSF |
| 2% | chr1 | 236326774 | 236327054 | + | chr1 | 236332006 | 236332055 | + | ENST00000366592; ENST00000454895 | TSF |
| 2% | chr5 | 66046112 | 66046208 | + | chr5 | 66055537 | 66055690 | + | ENST00000404260; ENST00000403625; ENST00000406374; ENST00000406039 | TSF |
| 2% | chr5 | 66046112 | 66046208 | + | chr5 | 66055537 | 66055690 | + | ENST00000404260; ENST00000403625; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr5 | 66046112 | 66046208 | + | chr5 | 66055537 | 66055690 | + | ENST00000406374; ENST00000406039 ENST00000404260; ENST00000403625; ENST00000406374; ENST00000406039 | TSF |
| 2% | chr5 | 66046112 | 66046208 | + | chr5 | 66055537 | 66055690 | + | ENST00000404260; ENST00000403625; ENST00000406374; ENST00000406039 | TSF |
| 2% | chr7 | 134212336 | 134212386 | + | chr7 | 134215479 | 134215562 | + | ENST00000359579 | TSF |
| 2% | chr4 | 56227367 | 56227417 | + | chr4 | 56235999 | 56236258 | + | ENST00000264228; ENST00000505210 | TSF |
| 2% | chr1 | 23397020 | 23397118 | + | chr1 | 23397718 | 23397852 | + | ENST00000356634; ENST00000400181; ENST00000542151 | TSF |
| 2% | chr19 | 39144921 | 39144970 | + | chr19 | 39191240 | 39191354; 39191344 | + | ENST00000252699; ENST00000424234; ENST00000589528 | TSF |
| 2% | chr19 | 39144921 | 39144970 | + | chr19 | 39191240 | 39191354; 39191344 | + | ENST00000252699; ENST00000424234; ENST00000589528 | TSF |
| 2% | chr19 | 39144921 | 39144970 | + | chr19 | 39191240 | 39191354; 39191344 | + | ENST00000252699; ENST00000424234; ENST00000589528 | TSF |
| 2% | chr7 | 55464873 | 55464924 | + | chr7 | 55466116 | 55466323 | + | ENST00000254770 | TSF |
| 2% | chr21 | 42609094 | 42609191 | + | chr21 | 42609440 | 42609656 | + | ENST00000328735; ENST00000330333; ENST00000347667 | TSF |
| 2% | chr21 | 42609094 | 42609191 | + | chr21 | 42609440 | 42609656 | + | ENST00000328735; ENST00000330333; ENST00000347667 | TSF |
| 2% | chr21 | 42609094 | 42609191 | + | chr21 | 42609440 | 42609656 | + | ENST00000328735; ENST00000330333; ENST00000347667 | TSF |
| 2% | chr2 | 232340741 | 232340940 | + | chr2 | 232576105 | 232576119; 232576129 | + | ENST00000448874; ENST00000409321; ENST00000409115; ENST00000341369; ENST00000409683; ENST00000410064; ENST00000412128 | TSF |
| 2% | chr2 | 232340741 | 232340940 | + | chr2 | 232576105 | 232576119; 232576129 | + | ENST00000448874; ENST00000409321; ENST00000409115; ENST00000341369; ENST00000409683; ENST00000410064; ENST00000412128 | TSF |
| 2% | chr2 | 232340741 | 232340940 | + | chr2 | 232576105 | 232576119; 232576129 | + | ENST00000448874; ENST00000409321; ENST00000409115; ENST00000341369; ENST00000409683; ENST00000410064; ENST00000412128 | TSF |
| 2% | chr2 | 232340741 | 232340940 | + | chr2 | 232576105 | 232576119; 232576129 | + | ENST00000448874; ENST00000409321; ENST00000409115; ENST00000341369; ENST00000409683; ENST00000410064; ENST00000412128 | TSF |
| 2% | chrX | 134971303 | 134971006 | − | chrX | 134932924 | 134932815 | − | ENST00000487941; ENST00000434966; ENST00000494421 | TSF |
| 2% | chr5 | 39217816 | 39217739 | − | chr5 | 39203089 | 39201928 | − | ENST00000540520 | TSF |
| 2% | chr14 | 106258982 | 106258725 | − | chr14 | 106209234 | 106209114 | − | ENST00000390548; ENST00000390549; ENST00000390542 | TSF |
| 2% | chr14 | 106258982 | 106258725 | − | chr14 | 106209234 | 106209114 | − | ENST00000390548; ENST00000390549; ENST00000390542 | TSF |
| 2% | chr14 | 106258982 | 106258725 | − | chr14 | 106209234 | 106209114 | − | ENST00000390548; ENST00000390549; ENST00000390542 | TSF |
| 2% | chr5 | 179234950 | 179234884 | − | chr5 | 179228969 | 179228784 | − | ENST00000337755; ENST00000292591; ENST00000520918; ENST00000523329 | TSF |
| 2% | chr5 | 179234950 | 179234884 | − | chr5 | 179228969 | 179228784 | − | ENST00000337755; ENST00000292591; ENST00000520918; ENST00000523329 | TSF |
| 2% | chr5 | 179234950 | 179234884 | − | chr5 | 179228969 | 179228784 | − | ENST00000337755; ENST00000292591; ENST00000520918; ENST00000523329 | TSF |
| 2% | chr6 | 137536317 | 137536205 | − | chr6 | 137528214 | 137528100 | − | ENST00000367739; ENST00000543628; ENST00000458076; ENST00000367735; ENST00000414770 | TSF |
| 2% | chr6 | 137536317 | 137536205 | − | chr6 | 137528214 | 137528100 | − | ENST00000367739; ENST00000543628; ENST00000458076; ENST00000367735; ENST00000414770 | TSF |
| 2% | chr6 | 137536317 | 137536205 | − | chr6 | 137528214 | 137528100 | − | ENST00000367739; ENST00000543628; ENST00000458076; ENST00000367735; ENST00000414770 | TSF |
| 2% | chr6 | 137536317 | 137536205 | − | chr6 | 137528214 | 137528100 | − | ENST00000367739; ENST00000543628; ENST00000458076; ENST00000367735; ENST00000414770 | TSF |
| 2% | chr11 | 15114123 | 15112973 | − | chr6 | 32497961 | 32497902 | − | ENST00000374975 | TSF |
| 2% | chr20 | 32693720 | 32693709 | − | chr20 | 32693351 | 32693174 | − | ENST00000374980 | TSF |
| 2% | chr5 | 145541009 | 145540727 | − | chr5 | 145540049 | 145539937 | − | ENST00000394434; ENST00000545646; ENST00000274562; ENST00000510191 | TSF |
| 2% | chr1 | 48839622 | 48839346 | − | chr1 | 48825442 | 48825258 | − | ENST00000371847; ENST00000371843; ENST00000396199; ENST00000371841 | TSF |
| 2% | chr1 | 48839622 | 48839346 | − | chr1 | 48825442 | 48825258 | − | ENST00000371847; ENST00000371843; ENST00000396199; ENST00000371841 | TSF |
| 2% | chr1 | 48839622 | 48839346 | − | chr1 | 48825442 | 48825258 | − | ENST00000371847; ENST00000371843; ENST00000396199; ENST00000371841 | TSF |
| 2% | chr14 | 106258982 | 106258725 | − | chr14 | 106237569 | 106237449 | − | ENST00000390551 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr19 | 48889673 | 48889623 | − | chr19 | 48887655 | 48887487; 48887496 | − | ENST00000330720; ENST00000597017; ENST00000600980 | TSF |
| 2% | chr19 | 48889673 | 48889623 | − | chr19 | 48887655 | 48887487; 48887496 | − | ENST00000330720; ENST00000597017; ENST00000600980 | TSF |
| 2% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 2% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 2% | chr7 | 48039730 | 48039725 | − | chr7 | 48035743 | 48035628 | − | ENST00000453071; ENST00000297325; ENST00000412371; ENST00000412142; ENST00000395572; ENST00000453192; ENST00000438771 | TSF |
| 2% | chr17 | 38649720 | 38649640 | − | chr17 | 38645221 | 38644798 | − | ENST00000254051 | TSF |
| 2% | chr19 | 39309918 | 39309912 | − | chr19 | 39308215 | 39308091; 39308111 | − | ENST00000221418; ENST00000601778; ENST00000595470; ENST00000594769; ENST00000602021 | TSF |
| 2% | chr19 | 39309918 | 39309912 | − | chr19 | 39308215 | 39308091; 39308111 | − | ENST00000221418; ENST00000601778; ENST00000595470; ENST00000594769; ENST00000602021 | TSF |
| 2% | chr19 | 39309918 | 39309912 | − | chr19 | 39308215 | 39308091; 39308111 | − | ENST00000221418; ENST00000601778; ENST00000595470; ENST00000594769; ENST00000602021 | TSF |
| 2% | chr19 | 39309918 | 39309912 | − | chr19 | 39308215 | 39308091; 39308111 | − | ENST00000221418; ENST00000601778; ENST00000595470; ENST00000594769; ENST00000602021 | TSF |
| 2% | chr6 | 31660537 | 31660355 | − | chr6 | 31659695 | 31659581 | − | ENST00000395952; ENST00000440843 | TSF |
| 2% | chr22 | 21355965 | 21355835 | − | chr22 | 21355700 | 21355545 | − | ENST00000215742; ENST00000399133 | TSF |
| 2% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 2% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 2% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 2% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 2% | chr17 | 37886362 | 37886333 | − | chr17 | 37886014 | 37885938; 37885851 | − | ENST00000394231; ENST00000577810 | TSF |
| 2% | chr17 | 37886362 | 37886333 | − | chr17 | 37886014 | 37885938; 37885851 | − | ENST00000394231; ENST00000577810 | TSF |
| 2% | chr1 | 109479016 | 109478866 | − | chr1 | 109477564 | 109477292 | − | ENST00000369968; ENST00000369969; ENST00000356970; ENST00000369971; ENST00000415331; ENST00000369970; ENST00000302500; ENST00000348264 | TSF |
| 2% | chr5 | 10728215 | 10728097 | − | chr5 | 10683683 | 10683641 | − | ENST00000230895 | TSF |
| 2% | chr8 | 101933557 | 101933272 | − | chr8 | 101932980 | 101932921; 101932944 | − | ENST00000395957; ENST00000395958; ENST00000457309; ENST00000395956; ENST00000353245; ENST00000523848; ENST00000522542; ENST00000521309; ENST00000522819; ENST00000395953; ENST00000395948; ENST00000395951; ENST00000419477; ENST00000521607 | TSF |
| 2% | chr8 | 101933557 | 101933272 | − | chr8 | 101932980 | 101932921; 101932944 | − | ENST00000395957; ENST00000395958; ENST00000457309; ENST00000395956; ENST00000353245; ENST00000523848; ENST00000522542; ENST00000521309; ENST00000522819; ENST00000395953; ENST00000395948; ENST00000395951; ENST00000419477; ENST00000521607 | TSF |
| 2% | chr14 | 50053298 | 50053490 | + | chr14 | 50166790 | 50166875 | + | ENST00000555704 | TSF |
| 2% | chr2 | 242276229 | 242276234 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr2 | 242276229 | 242276234 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276234 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276234 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276234 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276234 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276234 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr2 | 242276229 | 242276234 | + | chr2 | 242276797 | 242276931; 242276900; 242276863; 242276848 | + | ENST00000391973; ENST00000428282; ENST00000360051; ENST00000391971; ENST00000401990; ENST00000407971; ENST00000436795; ENST00000411484; ENST00000402092; ENST00000443492; ENST00000437066; ENST00000449239; ENST00000457874 | TSF |
| 2% | chr3 | 9476647 | 9476785 | + | chr3 | 9477412 | 9477509; 9477590 | + | ENST00000450326; ENST00000402198; ENST00000402466; ENST00000406341; ENST00000407969; ENST00000442373; ENST00000302463 | TSF |
| 2% | chr3 | 9476647 | 9476785 | + | chr3 | 9477412 | 9477509; 9477590 | + | ENST00000450326; ENST00000402198; ENST00000402466; ENST00000406341; ENST00000407969; ENST00000442373; ENST00000302463 | TSF |
| 2% | chr3 | 9476647 | 9476785 | + | chr3 | 9477412 | 9477509; 9477590 | + | ENST00000450326; ENST00000402198; ENST00000402466; ENST00000406341; ENST00000407969; ENST00000442373; ENST00000302463 | TSF |
| 2% | chr3 | 9476647 | 9476785 | + | chr3 | 9477412 | 9477509; 9477590 | + | ENST00000450326; ENST00000402198; ENST00000402466; ENST00000406341; ENST00000407969; ENST00000442373; ENST00000302463 | TSF |
| 2% | chr7 | 55477082 | 55477474 | + | chr7 | 55479600 | 55479782 | + | ENST00000254770 | TSF |
| 2% | chr16 | 2525097 | 2525171 | + | chr16 | 2569219 | 2569384; 2569402 | + | ENST00000564543; ENST00000330398; ENST00000568562 | TSF |
| 2% | chr16 | 2525097 | 2525171 | + | chr16 | 2569219 | 2569384; 2569402 | + | ENST00000564543; ENST00000330398; ENST00000568562 | TSF |
| 2% | chr3 | 170075519 | 170075551 | + | chr3 | 170099032 | 170099129 | + | ENST00000259119; ENST00000426052; ENST00000413427; ENST00000458537; ENST00000470571 | TSF |
| 2% | chr3 | 170075519 | 170075551 | + | chr3 | 170099032 | 170099129 | + | ENST00000259119; ENST00000426052; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr3 | 170075519 | 170075551 | + | chr3 | 170099032 | 170099129 | + | ENST00000413427; ENST00000458537; ENST00000470571 ENST00000259119; ENST00000426052; ENST00000413427; ENST00000458537; ENST00000470571 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr7 | 99779289 | 99779427 | + | chr7 | 99779713 | 99779815 | + | ENST00000426455; ENST00000394018; ENST00000416412; ENST00000317296; ENST00000422690; ENST00000439782 | TSF |
| 2% | chr8 | 21954408 | 21954458 | + | chr8 | 21955027 | 21955131 | + | ENST00000450006; ENST00000289921 | TSF |
| 2% | chr2 | 232340741 | 232340940 | + | chr2 | 232576649 | 232576693 | + | ENST00000409321; ENST00000409115; ENST00000341369; ENST00000409683; ENST00000410064; ENST00000412128 | TSF |
| 2% | chr2 | 232340741 | 232340940 | + | chr2 | 232576649 | 232576693 | + | ENST00000409321; ENST00000409115; ENST00000341369; ENST00000409683; ENST00000410064; ENST00000412128 | TSF |
| 2% | chr16 | 2205826 | 2205859 | + | chr16 | 2215880 | 2215937 | + | ENST00000326181; ENST00000564067; ENST00000567645 | TSF |
| 2% | chr16 | 2205826 | 2205859 | + | chr16 | 2215880 | 2215937 | + | ENST00000326181; ENST00000564067; ENST00000567645 | TSF |
| 2% | chr16 | 2205826 | 2205859 | + | chr16 | 2215880 | 2215937 | + | ENST00000326181; ENST00000564067; ENST00000567645 | TSF |
| 2% | chr20 | 3776424 | 3776526 | + | chr20 | 3779059 | 3779110 | + | ENST00000344256; ENST00000379598; ENST00000245960; ENST00000439880; ENST00000340833 | TSF |
| 2% | chr20 | 3776424 | 3776526 | + | chr20 | 3779059 | 3779110 | + | ENST00000344256; ENST00000379598; ENST00000245960; ENST00000439880; ENST00000340833 | TSF |
| 2% | chr20 | 3776424 | 3776526 | + | chr20 | 3779059 | 3779110 | + | ENST00000344256; ENST00000379598; ENST00000245960; ENST00000439880; ENST00000340833 | TSF |
| 2% | chr7 | 66414193 | 66414197 | + | chr7 | 66415939 | 66416122 | + | ENST00000341567 | TSF |
| 2% | chr20 | 25146273 | 25146366 | + | chr20 | 25249765 | 25249843 | + | ENST00000216962 | TSF |
| 2% | chrX | 134883429 | 134883726 | + | chrX | 134887292 | 134887401 | + | ENST00000370734; ENST00000485366; ENST00000443882 | TSF |
| 2% | chr12 | 4757939 | 4757967 | + | chr12 | 4763458 | 4763628 | + | ENST00000266544; ENST00000535050 | TSF |
| 2% | chr12 | 4757939 | 4757967 | + | chr12 | 4763458 | 4763628 | + | ENST00000266544; ENST00000535050 | TSF |
| 2% | chr7 | 73816114 | 73816214 | + | chr7 | 73818167 | 73818178 | + | ENST00000361545; ENST00000223398; ENST00000395060; ENST00000487447 | TSF |
| 2% | chr2 | 26309164 | 26309786 | + | chr2 | 26321531 | 26321591 | + | ENST00000264710 | TSF |
| 2% | chr20 | 44501760 | 44501827 | + | chr20 | 44520650 | 44520666 | + | ENST00000606788; ENST00000372484; ENST00000354880; ENST00000191018; ENST00000607482; ENST00000372459 | TSF |
| 2% | chr20 | 44501760 | 44501827 | + | chr20 | 44520650 | 44520666 | + | ENST00000606788; ENST00000372484; ENST00000354880; ENST00000191018; ENST00000607482; ENST00000372459 | TSF |
| 2% | chr20 | 44501760 | 44501827 | + | chr20 | 44520650 | 44520666 | + | ENST00000606788; ENST00000372484; ENST00000354880; ENST00000191018; ENST00000607482; ENST00000372459 | TSF |
| 2% | chr20 | 44501760 | 44501827 | + | chr20 | 44520650 | 44520666 | + | ENST00000606788; ENST00000372484; ENST00000354880; ENST00000191018; ENST00000607482; ENST00000372459 | TSF |
| 2% | chr3 | 170097741 | 170097776 | + | chr3 | 170099032 | 170099129 | + | ENST00000259119; ENST00000426052; ENST00000413427; ENST00000458537; ENST00000470571 | TSF |
| 2% | chr3 | 170097741 | 170097776 | + | chr3 | 170099032 | 170099129 | + | ENST00000259119; ENST00000426052; ENST00000413427; ENST00000458537; ENST00000470571 | TSF |
| 2% | chr3 | 170097741 | 170097776 | + | chr3 | 170099032 | 170099129 | + | ENST00000259119; ENST00000426052; ENST00000413427; ENST00000458537; ENST00000470571 | TSF |
| 2% | chr15 | 89717587 | 89717675 | + | chr15 | 89719043 | 89719226 | + | ENST00000352732; ENST00000565973; ENST00000355100 | TSF |
| 2% | chr16 | 28838911 | 28839140 | + | chr16 | 28840722 | 28840813 | + | ENST00000340394; ENST00000325215; ENST00000336783; ENST00000382686; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr16 | 28838911 | 28839140 | + | chr16 | 28840722 | 28840813 | + | ENST00000395547; ENST00000564304; ENST00000570200; ENST00000568266 ENST00000340394; ENST00000325215; ENST00000336783; ENST00000382686; | TSF |
| 2% | chr16 | 28838911 | 28839140 | + | chr16 | 28840722 | 28840813 | + | ENST00000395547; ENST00000564304; ENST00000570200; ENST00000568266 ENST00000340394; ENST00000325215; ENST00000336783; ENST00000382686; | TSF |
| 2% | chr16 | 28838911 | 28839140 | + | chr16 | 28840722 | 28840813 | + | ENST00000395547; ENST00000564304; ENST00000570200; ENST00000568266 ENST00000340394; ENST00000325215; ENST00000336783; ENST00000382686; | TSF |
| 2% | chr16 | 28838911 | 28839140 | + | chr16 | 28840722 | 28840813 | + | ENST00000395547; ENST00000564304; ENST00000570200; ENST00000568266 ENST00000340394; ENST00000325215; ENST00000336783; ENST00000382686; | TSF |
| 2% | chr16 | 28838911 | 28839140 | + | chr16 | 28840722 | 28840813 | + | ENST00000395547; ENST00000564304; ENST00000570200; ENST00000568266 ENST00000340394; ENST00000325215; ENST00000336783; ENST00000382686; | TSF |
| 2% | chr16 | 28838911 | 28839140 | + | chr16 | 28840722 | 28840813 | + | ENST00000395547; ENST00000564304; ENST00000570200; ENST00000568266 ENST00000340394; ENST00000325215; ENST00000336783; ENST00000382686; | TSF |
| 2% | chr16 | 28838911 | 28839140 | + | chr16 | 28840722 | 28840813 | + | ENST00000395547; ENST00000564304; ENST00000570200; ENST00000568266 ENST00000340394; ENST00000325215; ENST00000336783; ENST00000382686; | TSF |
| 2% | chr11 | 67803205 | 67803255 | + | chr11 | 67803929 | 67804060; 67803981 | + | ENST00000313468; ENST00000528492; ENST00000526339 | TSF |
| 2% | chr11 | 67803205 | 67803255 | + | chr11 | 67803929 | 67804060; 67803981 | + | ENST00000313468; ENST00000528492; ENST00000526339 | TSF |
| 2% | chr12 | 123873690 | 123873729 | + | chr12 | 123873984 | 123874101 | + | ENST00000330479; ENST00000402868 | TSF |
| 2% | chr12 | 133142351 | 133142413 | + | chr12 | 133144067 | 133144112 | + | ENST00000434748; ENST00000261673 | TSF |
| 2% | chr12 | 50813695 | 50814670 | + | chr12 | 50821548 | 50821692 | + | ENST00000293618; ENST00000429001; ENST00000548174; ENST00000398473; ENST00000522085; ENST00000518444; ENST00000551886; ENST00000347328; ENST00000550260 | TSF |
| 2% | chr12 | 50813695 | 50814670 | + | chr12 | 50821548 | 50821692 | + | ENST00000293618; ENST00000429001; ENST00000548174; ENST00000398473; ENST00000522085; ENST00000518444; ENST00000551886; ENST00000347328; ENST00000550260 | TSF |
| 2% | chr12 | 50813695 | 50814670 | + | chr12 | 50821548 | 50821692 | + | ENST00000293618; ENST00000429001; ENST00000548174; ENST00000398473; ENST00000522085; ENST00000518444; ENST00000551886; ENST00000347328; ENST00000550260 | TSF |
| 2% | chr12 | 50813695 | 50814670 | + | chr12 | 50821548 | 50821692 | + | ENST00000293618; ENST00000429001; ENST00000548174; ENST00000398473; ENST00000522085; ENST00000518444; ENST00000551886; ENST00000347328; ENST00000550260 | TSF |
| 2% | chr12 | 50813695 | 50814670 | + | chr12 | 50821548 | 50821692 | + | ENST00000293618; ENST00000429001; ENST00000548174; ENST00000398473; ENST00000522085; ENST00000518444; ENST00000551886; ENST00000347328; ENST00000550260 | TSF |
| 2% | chr12 | 50813695 | 50814670 | + | chr12 | 50821548 | 50821692 | + | ENST00000293618; ENST00000429001; ENST00000548174; ENST00000398473; ENST00000522085; ENST00000518444; ENST00000551886; ENST00000347328; ENST00000550260 | TSF |
| 2% | chr12 | 50813695 | 50814670 | + | chr12 | 50821548 | 50821692 | + | ENST00000293618; ENST00000429001; ENST00000548174; ENST00000398473; ENST00000522085; ENST00000518444; ENST00000551886; ENST00000347328; ENST00000550260 | TSF |
| 2% | chr12 | 50813695 | 50814670 | + | chr12 | 50821548 | 50821692 | + | ENST00000293618; ENST00000429001; ENST00000548174; ENST00000398473; ENST00000522085; ENST00000518444; ENST00000551886; ENST00000347328; ENST00000550260 | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr8 | 128749913 | 128749923 | + | chr8 | 128750494 | 128751265 | + | ENST00000377970 | TSF |
| 2% | chr19 | 50391349 | 50391391 | + | chr19 | 50391488 | 50391574 | + | ENST00000221543; ENST00000535102 | TSF |
| 2% | chr7 | 30847611 | 30847863 | + | chr7 | 30868295 | 30868353 | + | ENST00000265299 | TSF |
| 2% | chr20 | 389765 | 390021 | + | chr20 | 390525 | 390669 | + | ENST00000411647; ENST00000382214; ENST00000356286; ENST00000415942; ENST00000475269 | TSF |
| 2% | chr20 | 389765 | 390021 | + | chr20 | 390525 | 390669 | + | ENST00000411647; ENST00000382214; ENST00000356286; ENST00000415942; ENST00000475269 | TSF |
| 2% | chr20 | 389765 | 390021 | + | chr20 | 390525 | 390669 | + | ENST00000411647; ENST00000382214; ENST00000356286; ENST00000415942; ENST00000475269 | TSF |
| 2% | chr20 | 389765 | 390021 | + | chr20 | 390525 | 390669 | + | ENST00000411647; ENST00000382214; ENST00000356286; ENST00000415942; ENST00000475269 | TSF |
| 2% | chr20 | 389765 | 390021 | + | chr20 | 390525 | 390669 | + | ENST00000411647; ENST00000382214; ENST00000356286; ENST00000415942; ENST00000475269 | TSF |
| 2% | chr1 | 222838237 | 222838358 | + | chr1 | 222838651 | 222838961 | + | ENST00000344922; ENST00000344441; ENST00000340535 | TSF |
| 2% | chr19 | 36405278 | 36405224 | − | chr19 | 36398166 | 36398120 | − | ENST00000585901; ENST00000544690; ENST00000262629 | TSF |
| 2% | chr1 | 154581117 | 154581067 | − | chr1 | 154575102 | 154573517 | − | ENST00000292205; ENST00000368474; ENST00000529168 | TSF |
| 2% | chr1 | 154581117 | 154581067 | − | chr1 | 154575102 | 154573517 | − | ENST00000292205; ENST00000368474; ENST00000529168 | TSF |
| 2% | chr6 | 32547977 | 32547972 | − | chr6 | 32546881 | 32546868 | − | ENST00000360004 | TSF |
| 2% | chr2 | 163165782 | 163165417 | − | chr2 | 163163365 | 163163219 | − | ENST00000263642 | TSF |
| 2% | chr3 | 128721625 | 128721589 | − | chr3 | 128706672 | 128706459 | − | ENST00000511438; ENST00000265068; ENST00000515659 | TSF |
| 2% | chr3 | 128721625 | 128721589 | − | chr3 | 128706672 | 128706459 | − | ENST00000511438; ENST00000265068; ENST00000515659 | TSF |
| 2% | chr13 | 45925262 | 45925234 | − | chr13 | 45914303 | 45914129 | − | ENST00000379056; ENST00000530705; ENST00000379060; ENST00000379055; ENST00000309246; ENST00000527226 | TSF |
| 2% | chr13 | 45925262 | 45925234 | − | chr13 | 45914303 | 45914129 | − | ENST00000379056; ENST00000530705; ENST00000379060; ENST00000379055; ENST00000309246; ENST00000527226 | TSF |
| 2% | chr13 | 45925262 | 45925234 | − | chr13 | 45914303 | 45914129 | − | ENST00000379056; ENST00000530705; ENST00000379060; ENST00000379055; ENST00000309246; ENST00000527226 | TSF |
| 2% | chr9 | 130715295 | 130715152 | − | chr9 | 130712818 | 130712702 | − | ENST00000373095 | TSF |
| 2% | chr15 | 40187476 | 40186733 | − | chr15 | 40099459 | 40099207 | − | ENST00000561100; ENST00000543580 | TSF |
| 2% | chr17 | 5014630 | 5014371 | − | chr17 | 5013063 | 5012689; 5012527 | − | ENST00000575898; ENST00000250076; ENST00000416429 | TSF |
| 2% | chr17 | 5014630 | 5014371 | − | chr17 | 5013063 | 5012689; 5012527 | − | ENST00000575898; ENST00000250076; ENST00000416429 | TSF |
| 2% | chr17 | 5014630 | 5014371 | − | chr17 | 5013063 | 5012689; 5012527 | − | ENST00000575898; ENST00000250076; ENST00000416429 | TSF |
| 2% | chrX | 48708290 | 48708228 | − | chrX | 48690751 | 48690279 | − | ENST00000218230 | TSF |
| 2% | chrX | 53579130 | 53578958 | − | chrX | 53578441 | 53578227 | − | ENST00000427052; ENST00000342160; ENST00000262854 | TSF |
| 2% | chr4 | 83752701 | 83752626 | − | chr4 | 83752128 | 83752090 | − | ENST00000503937; ENST00000432794 | TSF |
| 2% | chr2 | 31719227 | 31719225 | − | chr2 | 31628830 | 31628773 | − | ENST00000379416 | TSF |
| 2% | chr18 | 47213717 | 47213643 | − | chr18 | 47017800 | 47017775 | − | ENST00000584895; ENST00000577910; ENST00000579408; ENST00000579248; ENST00000580261; ENST00000418495; ENST00000580210; ENST00000583637; ENST00000578532; ENST00000583036; ENST00000580387; ENST00000578528 | TSF |
| 2% | chr18 | 47213717 | 47213643 | − | chr18 | 47017800 | 47017775 | − | ENST00000584895; ENST00000577910; ENST00000579408; ENST00000579248; ENST00000580261; ENST00000418495; ENST00000580210; ENST00000583637; ENST00000578532; ENST00000583036; ENST00000580387; ENST00000578528 | TSF |
| 2% | chr18 | 47213717 | 47213643 | − | chr18 | 47017800 | 47017775 | − | ENST00000584895; ENST00000577910; ENST00000579408; ENST00000579248; ENST00000580261; ENST00000418495; ENST00000580210; ENST00000583637; ENST00000578532; ENST00000583036; ENST00000580387; ENST00000578528 | TSF |
| 2% | chr18 | 47213717 | 47213643 | − | chr18 | 47017800 | 47017775 | − | ENST00000584895; ENST00000577910; ENST00000579408; ENST00000579248; ENST00000580261; ENST00000418495; ENST00000580210; ENST00000583637; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr18 | 47213717 | 47213643 | − | chr18 | 47017800 | 47017775 | − | ENST00000578532; ENST00000583036; ENST00000580387; ENST00000578528 ENST00000584895; ENST00000577910; ENST00000579408; ENST00000579248; ENST00000580261; ENST00000418495; ENST00000580210; ENST00000583637; | TSF |
| 2% | chr18 | 47213717 | 47213643 | − | chr18 | 47017800 | 47017775 | − | ENST00000578532; ENST00000583036; ENST00000580387; ENST00000578528 ENST00000584895; ENST00000577910; ENST00000579408; ENST00000579248; ENST00000580261; ENST00000418495; ENST00000580210; ENST00000583637; | TSF |
| 2% | chr18 | 47213717 | 47213643 | − | chr18 | 47017800 | 47017775 | − | ENST00000578532; ENST00000583036; ENST00000580387; ENST00000578528 ENST00000584895; ENST00000577910; ENST00000579408; ENST00000579248; ENST00000580261; ENST00000418495; ENST00000580210; ENST00000583637; ENST00000578532; ENST00000583036; ENST00000580387; ENST00000578528 | TSF |
| 2% | chr8 | 63949410 | 63948932 | − | chr8 | 63948329 | 63948215 | − | ENST00000260118 | TSF |
| 2% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr7 | 102212392 | 102212170 | − | chr7 | 102210371 | 102210282 | − | ENST00000489144; ENST00000379340; ENST00000486319; ENST00000508848; ENST00000513506; ENST00000514917; ENST00000507355; ENST00000608621; ENST00000511313; ENST00000513438 | TSF |
| 2% | chr6 | 32552703 | 32552631 | − | chr6 | 32549391 | 32549334 | − | ENST00000360004 | TSF |
| 2% | chr18 | 71747213 | 47213601 | − | chr18 | 47017800 | 47017775 | − | ENST00000584895; ENST00000577910; ENST00000579408; ENST00000579248; ENST00000580261; ENST00000418495; ENST00000580210; ENST00000583637; ENST00000578532; ENST00000583036; ENST00000580387; ENST00000578528 | TSF |
| 2% | chr18 | 71747213 | 47213601 | − | chr18 | 47017800 | 47017775 | − | ENST00000584895; ENST00000577910; ENST00000579408; ENST00000579248; ENST00000580261; ENST00000418495; ENST00000580210; ENST00000583637; ENST00000578532; ENST00000583036; ENST00000580387; ENST00000578528 | TSF |
| 2% | chr18 | 71747213 | 47213601 | − | chr18 | 47017800 | 47017775 | − | ENST00000584895; ENST00000577910; ENST00000579408; ENST00000579248; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr18 | 71747213 | 47213601 | – | chr18 | 47017800 | 47017775 | – | ENST00000580261; ENST00000418495; ENST00000580210; ENST00000583637; ENST00000578532; ENST00000583036; ENST00000580387; ENST00000578528 ENST00000584895; ENST00000577910; ENST00000579408; ENST00000579248; | TSF |
| 2% | chr18 | 71747213 | 47213601 | – | chr18 | 47017800 | 47017775 | – | ENST00000580261; ENST00000418495; ENST00000580210; ENST00000583637; ENST00000578532; ENST00000583036; ENST00000580387; ENST00000578528 ENST00000584895; ENST00000577910; ENST00000579408; ENST00000579248; | TSF |
| 2% | chr18 | 71747213 | 47213601 | – | chr18 | 47017800 | 47017775 | – | ENST00000580261; ENST00000418495; ENST00000580210; ENST00000583637; ENST00000578532; ENST00000583036; ENST00000580387; ENST00000578528 ENST00000584895; ENST00000577910; ENST00000579408; ENST00000579248; | TSF |
| 2% | chr18 | 71747213 | 47213601 | – | chr18 | 47017800 | 47017775 | – | ENST00000580261; ENST00000418495; ENST00000580210; ENST00000583637; ENST00000578532; ENST00000583036; ENST00000580387; ENST00000578528 ENST00000584895; ENST00000577910; ENST00000579408; ENST00000579248; | TSF |
| 2% | chr22 | 38620420 | 38620354 | – | chr22 | 38617717 | 38617476 | – | ENST00000361906; ENST00000361684 | TSF |
| 2% | chr22 | 22141039 | 22140985 | – | chr22 | 22127271 | 22127162 | – | ENST00000215832; ENST00000398822; ENST00000544786 | TSF |
| 2% | chr6 | 161637963 | 161637691 | – | chr6 | 161587449 | 161587280; 161587148 | – | ENST00000320285; ENST00000366908; ENST00000436279; ENST00000366905 | TSF |
| 2% | chr6 | 161637963 | 161637691 | – | chr6 | 161587449 | 161587280; 161587148 | – | ENST00000320285; ENST00000366908; ENST00000436279; ENST00000366905 | TSF |
| 2% | chr6 | 161637963 | 161637691 | – | chr6 | 161587449 | 161587280; 161587148 | – | ENST00000320285; ENST00000366908; ENST00000436279; ENST00000366905 | TSF |
| 2% | chr12 | 50285408 | 50285280 | – | chr12 | 50284897 | 50284847; 50284860 | – | ENST00000320634; ENST00000550890; ENST00000550195; ENST00000552669; ENST00000552863; ENST00000550635; ENST00000547871 | TSF |
| 2% | chr12 | 50285408 | 50285280 | – | chr12 | 50284897 | 50284847; 50284860 | – | ENST00000320634; ENST00000550890; ENST00000550195; ENST00000552669; ENST00000552863; ENST00000550635; ENST00000547871 | TSF |
| 2% | chr12 | 50285408 | 50285280 | – | chr12 | 50284897 | 50284847; 50284860 | – | ENST00000320634; ENST00000550890; ENST00000550195; ENST00000552669; ENST00000552863; ENST00000550635; ENST00000547871 | TSF |
| 2% | chr12 | 50285408 | 50285280 | – | chr12 | 50284897 | 50284847; 50284860 | – | ENST00000320634; ENST00000550890; ENST00000550195; ENST00000552669; ENST00000552863; ENST00000550635; ENST00000547871 | TSF |
| 2% | chr12 | 50285408 | 50285280 | – | chr12 | 50284897 | 50284847; 50284860 | – | ENST00000320634; ENST00000550890; ENST00000550195; ENST00000552669; ENST00000552863; ENST00000550635; ENST00000547871 | TSF |
| 2% | chr12 | 50285408 | 50285280 | – | chr12 | 50284897 | 50284847; 50284860 | – | ENST00000320634; ENST00000550890; ENST00000550195; ENST00000552669; ENST00000552863; ENST00000550635; ENST00000547871 | TSF |
| 2% | chr4 | 83764590 | 83764450 | – | chr4 | 83763634 | 83763293; 83763338 | – | ENST00000503937; ENST00000348405; ENST00000395310; ENST00000443462; ENST00000326950; ENST00000432794; ENST00000448323; ENST00000505472; ENST00000508502; ENST00000355196; ENST00000264405; ENST00000505984 | TSF |
| 2% | chr4 | 83764590 | 83764450 | – | chr4 | 83763634 | 83763293; 83763338 | – | ENST00000503937; ENST00000348405; ENST00000395310; ENST00000443462; ENST00000326950; ENST00000432794; ENST00000448323; ENST00000505472; ENST00000508502; ENST00000355196; ENST00000264405; ENST00000505984 | TSF |
| 2% | chr4 | 83764590 | 83764450 | – | chr4 | 83763634 | 83763293; 83763338 | – | ENST00000503937; ENST00000348405; ENST00000395310; ENST00000443462; ENST00000326950; ENST00000432794; | TSF |

TABLE 58-continued

Transcript fusion for Stomach adenocarcinoma (STAD) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
|   |    |    |    |    |    |    |    |    | ENST00000448323; ENST00000505472; ENST00000508502; ENST00000355196; ENST00000264405; ENST00000505984 | |

TABLE 59

Transcript fusion for Testicular Germ Cell Tumors (TGCT) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 68% | chr5 | 54993786 | 54993674 | − | ENST00000396865; ENST00000539768; ENST00000318672; ENST00000508124; ENST00000511233; ENST00000503891; ENST00000513993; ENST00000505563; ENST00000506624; ENST00000507109 | chr5 | 54993040 | 54992544 | − | TSF |
| 64% | chr10 | 70432652 | 70432802 | + | ENST00000373644 | chr10 | 70433158 | 70433321 | + | TSF |
| 52% | chr15 | 58957396 | 58957296 | − | ENST00000260408 | chr15 | 58947615 | 58947395 | − | TAF |
| 51% | chr12 | 71509738 | 71509630 | − | ENST00000549357 | chr12 | 71504233 | 71503634 | − | TAF |
| 49% | chr12 | 32369181 | 32369393 | + | ENST00000548411; ENST00000281474; ENST00000395758 | chr12 | 32375738 | 32375900 | + | TSF |
| 47% | chr20 | 29632611 | 29632721 | + | ENST00000278882; ENST00000358464 | chr20 | 29652086 | 29652324 | + | TSF |
| 38% | chr19 | 35514331 | 35514451 | + | ENST00000599564; ENST00000317991; ENST00000504615; ENST00000411896 | chr19 | 35514601 | 35514631 | + | TAF |
| 38% | chr19 | 35514331 | 35514451 | + | ENST00000599564; ENST00000317991; ENST00000504615; ENST00000411896 | chr19 | 35514601 | 35514631 | + | TAF |
| 38% | chr19 | 35514331 | 35514451 | + | ENST00000599564; ENST00000317991; ENST00000504615; ENST00000411896 | chr19 | 35514601 | 35514631 | + | TAF |
| 38% | chr19 | 35514331 | 35514451 | + | ENST00000599564; ENST00000317991; ENST00000504615; ENST00000411896 | chr19 | 35514601 | 35514631 | + | TAF |
| 33% | chr2 | 47690170 | 47690293 | + | ENST00000233146; ENST00000543555; ENST00000406134 | chr2 | 47691419 | 47691669 | + | TSF |
| 33% | chr2 | 47690170 | 47690293 | + | ENST00000233146; ENST00000543555; ENST00000406134 | chr2 | 47691419 | 47691669 | + | TSF |
| 32% | chr9 | 125054028 | 125054119 | + | ENST00000297908; ENST00000344641; ENST00000373723; ENST00000373729; ENST00000394315 | chr9 | 125068067 | 125068171 | + | TSF |
| 32% | chr9 | 125054028 | 125054119 | + | ENST00000297908; ENST00000344641; ENST00000373723; ENST00000373729; ENST00000394315 | chr9 | 125068067 | 125068171 | + | TSF |
| 32% | chr9 | 125054028 | 125054119 | + | ENST00000297908; ENST00000344641; ENST00000373723; ENST00000373729; ENST00000394315 | chr9 | 125068067 | 125068171 | + | TSF |
| 30% | chr2 | 175809671 | 175809616 | − | ENST00000409900; ENST00000409156 | chr2 | 175805622 | 175805109 | − | TAF |
| 29% | chr5 | 82554349 | 82554496 | + | ENST00000282268; ENST00000338635; ENST00000396027; ENST00000511817 | chr5 | 82606608 | 82606935 | + | TAF |
| 29% | chr7 | 81964567 | 81964451 | − | ENST00000356860; ENST00000356253; ENST00000423588 | chr7 | 81929467 | 81929190 | − | TSF |
| 28% | chr2 | 42924916 | 42924974 | + | ENST00000405592; ENST00000406652; ENST00000407270; ENST00000454356; ENST00000406911; ENST00000409019; ENST00000405094 | chr2 | 42925555 | 42925601 | + | TAF |
| 28% | chr2 | 42924916 | 42924974 | + | ENST00000405592; ENST00000406652; ENST00000407270; ENST00000454356; ENST00000406911; ENST00000409019; ENST00000405094 | chr2 | 42925555 | 42925601 | + | TAF |
| 27% | chr2 | 128260448 | 128260391 | − | ENST00000295321; ENST00000455721 | chr2 | 128258799 | 128257878 | − | TAF |
| 27% | chr2 | 128260448 | 128260391 | − | ENST00000295321; ENST00000455721 | chr2 | 128258799 | 128257878 | − | TAF |
| 27% | chr7 | 64254947 | 64254949 | + | ENST00000307355; ENST00000494380; ENST00000440155; ENST00000440598 | chr7 | 64257358 | 64257449 | + | TAF |
| 27% | chr1 | 32696528 | 32696620 | + | ENST00000373586 | chr1 | 32696861 | 32697110 | + | TAF |
| 27% | chr7 | 27582719 | 27582586 | − | ENST00000265395; ENST00000425715 | chr7 | 27581374 | 27579272 | − | TAF |
| 27% | chr7 | 27582719 | 27582586 | − | ENST00000265395; ENST00000425715 | chr7 | 27581374 | 27579272 | − | TAF |
| 27% | chr1 | 11115983; 11115877 | 11115838 | − | ENST00000376957; ENST00000490101 | chr1 | 11115464 | 11115178 | − | TSF |
| 27% | chr1 | 11115983; 11115877 | 11115838 | − | ENST00000376957; ENST00000490101 | chr1 | 11115464 | 11115178 | − | TSF |
| 26% | chr20 | 35842163 | 35842268 | + | ENST00000237530; ENST00000373622 | chr20 | 35844460 | 35844765 | + | TAF |
| 26% | chr20 | 35842163 | 35842268 | + | ENST00000237530; ENST00000373622 | chr20 | 35844460 | 35844765 | + | TAF |
| 26% | chr9 | 17143286 | 17143374 | + | ENST00000380647; ENST00000262360; ENST00000425824; ENST00000380641 | chr9 | 17166816 | 17167136 | + | TSF |
| 23% | chrX | 119708472 | 119708406 | − | ENST00000404115 | chrX | 119705855 | 119705820 | − | TSF |
| 21% | chrX | 64743587; 64743497 | 64743440 | − | ENST00000374807; ENST00000374811; ENST00000374804; ENST00000469091 | chrX | 64742373 | 64741630 | − | TAF |

TABLE 59-continued

Transcript fusion for Testicular Germ Cell Tumors (TGCT) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 21% | chrX | 64743587; 64743497 | 64743440 | − | ENST00000374807; ENST00000374811; ENST00000374804; ENST00000469091 | chrX | 64742373 | 64741630 | − | TAF |
| 21% | chrX | 64743587; 64743497 | 64743440 | − | ENST00000374807; ENST00000374811; ENST00000374804; ENST00000469091 | chrX | 64742373 | 64741630 | − | TAF |
| 21% | chrX | 64743587; 64743497 | 64743440 | − | ENST00000374807; ENST00000374811; ENST00000374804; ENST00000469091 | chrX | 64742373 | 64741630 | − | TAF |
| 20% | chr22 | 24323139 | 24323226 | + | ENST00000215780; ENST00000402588 | chr22 | 24324557 | 24324632 | + | TAF |
| 20% | chr5 | 74984990 | 74984837 | − | ENST00000428202; ENST00000514838; ENST00000380475; ENST00000510798; ENST00000446329 | chr5 | 74983153 | 74982863 | − | TAF |
| 20% | chr5 | 74984990 | 74984837 | − | ENST00000428202; ENST00000514838; ENST00000380475; ENST00000510798; ENST00000446329 | chr5 | 74983153 | 74982863 | − | TAF |
| 20% | chr5 | 74984990 | 74984837 | − | ENST00000428202; ENST00000514838; ENST00000380475; ENST00000510798; ENST00000446329 | chr5 | 74983153 | 74982863 | − | TAF |
| 20% | chr5 | 74984990 | 74984837 | − | ENST00000428202; ENST00000514838; ENST00000380475; ENST00000510798; ENST00000446329 | chr5 | 74983153 | 74982863 | − | TAF |
| 19% | chr8 | 73921122 | 73921440 | + | ENST00000276603; ENST00000276602; ENST00000518874 | chr8 | 73925091 | 73925180 | + | TSF |
| 19% | chr1 | 225156461 | 225156576 | + | ENST00000430092; ENST00000400952; ENST00000366849; ENST00000439375 | chr1 | 225157336 | 225158402 | + | TSF |
| 19% | chr1 | 225156461 | 225156576 | + | ENST00000430092; ENST00000400952; ENST00000366849; ENST00000439375 | chr1 | 225157336 | 225158402 | + | TSF |
| 18% | chr19 | 37618030 | 37619808 | + | ENST00000337995 | chr19 | 37621046 | 37621237 | + | TAF |
| 17% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 17% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 17% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 17% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 17% | chr16 | 81142298 | 81142167 | − | ENST00000533478; ENST00000525539 | chr16 | 81141929 | 81141855 | − | TAF |
| 17% | chr16 | 81142298 | 81142167 | − | ENST00000533478; ENST00000525539 | chr16 | 81141929 | 81141855 | − | TAF |
| 17% | chr4 | 57319769 | 57319927 | + | ENST00000514888; ENST00000264221; ENST00000505164; ENST00000399688; ENST00000512576 | chr4 | 57321183 | 57321327 | + | TSF |
| 17% | chr4 | 57319769 | 57319927 | + | ENST00000514888; ENST00000264221; ENST00000505164; ENST00000399688; ENST00000512576 | chr4 | 57321183 | 57321327 | + | TSF |
| 17% | chr4 | 57319769 | 57319927 | + | ENST00000514888; ENST00000264221; ENST00000505164; ENST00000399688; ENST00000512576 | chr4 | 57321183 | 57321327 | + | TSF |
| 17% | chr4 | 99325628 | 99325753 | + | ENST00000514888; ENST00000264221; ENST00000505164; ENST00000399688; ENST00000512576 | chr1 | 99330014 | 99330389 | + | TSF |
| 17% | chr4 | 99325628 | 99325753 | + | ENST00000514888; ENST00000264221; ENST00000505164; ENST00000399688; ENST00000512576 | chr4 | 99330014 | 99330389 | + | TSF |
| 17% | chr4 | 99325628 | 99325753 | + | ENST00000514888; ENST00000264221; ENST00000505164; ENST00000399688; ENST00000512576 | chr4 | 99330014 | 99330389 | + | TSF |
| 17% | chr4 | 99325628 | 99325753 | + | ENST00000514888; ENST00000264221; ENST00000505164; ENST00000399688; ENST00000512576 | chr4 | 99330014 | 99330389 | + | TSF |
| 17% | chr4 | 99325628 | 99325753 | + | ENST00000514888; ENST00000264221; ENST00000505164; ENST00000399688; ENST00000512576 | chr4 | 99330014 | 99330389 | + | TSF |
| 17% | chr4 | 99325628 | 99325753 | + | ENST00000514888; ENST00000264221; ENST00000505164; ENST00000399688; ENST00000512576 | chr4 | 99330014 | 99330389 | + | TSF |
| 17% | chr7 | 140080190 | 140080082 | − | ENST00000514888; ENST00000264221; ENST00000505164; ENST00000399688; ENST00000512576 | chr7 | 140075454 | 140075361 | − | TSF |
| 16% | chr15 | 71144671 | 71144566 | − | ENST00000559140 | chr15 | 71144059 | 71143957 | − | TAF |
| 16% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 16% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |

TABLE 59-continued

Transcript fusion for Testicular Germ Cell Tumors (TGCT) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 16% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 16% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 16% | chr12 | 102547647 | 102547754 | + | ENST00000327680; ENST00000378128; ENST00000541394; ENST00000358383; ENST00000392911; ENST00000412715; ENST00000417507; ENST00000457614 | chr12 | 102548605 | 102548938 | + | TSF |
| 15% | chr2 | 71607643 | 71607695 | + | ENST00000377802; ENST00000355812; ENST00000264447; ENST00000409544 | chr2 | 71620524 | 71622486 | + | TAF |
| 15% | chr12 | 6943089 | 6943213 | + | ENST00000251761; ENST00000396725; ENST00000606935 | chr12 | 6943989 | 6944119 | + | TAF |
| 15% | chr12 | 6943089 | 6943213 | + | ENST00000251761; ENST00000396725; ENST00000606935 | chr12 | 6943989 | 6944119 | + | TAF |
| 15% | chr12 | 6943089 | 6943213 | + | ENST00000251761; ENST00000396725; ENST00000606935 | chr12 | 6943989 | 6944119 | + | TAF |
| 15% | chr17 | 4908150 | 4908295 | + | ENST00000320785 | chr17 | 4908583 | 4909022 | + | TAF |
| 15% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 15% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 15% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 15% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 15% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 15% | chr9 | 15506635 | 15506559 | − | ENST00000380738; ENST00000380733; ENST00000380715; ENST00000380716; ENST00000397519 | chr9 | 15492223 | 15492056 | − | TAF |
| 15% | chr9 | 96030909 | 96031028 | + | ENST00000427277; ENST00000297954; ENST00000349097; ENST00000395477; ENST00000432730; ENST00000411624; ENST00000448251 | chr9 | 96040344 | 96040994 | + | TSF |
| 15% | chr9 | 96030909 | 96031028 | + | ENST00000427277; ENST00000297954; ENST00000349097; ENST00000395477; ENST00000432730; ENST00000411624; ENST00000448251 | chr9 | 96040344 | 96040994 | + | TSF |
| 15% | chr9 | 96030909 | 96031028 | + | ENST00000427277; ENST00000297954; ENST00000349097; ENST00000395477; ENST00000432730; ENST00000411624; ENST00000448251 | chr9 | 96040344 | 96040994 | + | TSF |
| 15% | chr9 | 96030909 | 96031028 | + | ENST00000427277; ENST00000297954; ENST00000349097; ENST00000395477; ENST00000432730; ENST00000411624; ENST00000448251 | chr9 | 96040344 | 96040994 | + | TSF |
| 15% | chr9 | 96030909 | 96031028 | + | ENST00000427277; ENST00000297954; ENST00000349097; ENST00000395477; ENST00000432730; ENST00000411624; ENST00000448251 | chr9 | 96040344 | 96040994 | + | TSF |
| 15% | chr8 | 139890559 | 139889993 | − | ENST00000303045; ENST00000435777 | chr8 | 139875196 | 139875126 | − | TSF |
| 15% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 15% | chr3 | 137906397; 137906427 | 137906441 | + | ENST00000469044; ENST00000461600; ENST00000461822; ENST00000470821; ENST00000471709; ENST00000393058; ENST00000538260; ENST00000463485 | chr3 | 137907243 | 137907252 | + | TSF |
| 15% | chr3 | 48716169 | 48715997 | − | ENST00000341520; ENST00000416649; ENST00000294129; ENST00000413374 | chr3 | 48702393 | 48702198 | − | TSF |
| 15% | chr3 | 48716169 | 48715997 | − | ENST00000341520; ENST00000416649; ENST00000294129; ENST00000413374 | chr3 | 48702393 | 48702198 | − | TSF |
| 15% | chr3 | 48716169 | 48715997 | − | ENST00000341520; ENST00000416649; ENST00000294129; ENST00000413374 | chr3 | 48702393 | 48702198 | − | TSF |
| 15% | chr8 | 139626163 | 139626110 | − | ENST00000303045; ENST00000435777 | chr8 | 139623600 | 139623460 | − | TSF |
| 15% | chr8 | 139626163 | 139626110 | − | ENST00000303045; ENST00000435777 | chr8 | 139623600 | 139623460 | − | TSF |

TABLE 59-continued

Transcript fusion for Testicular Germ Cell Tumors (TGCT) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 14% | chr1 | 147438786 | 147438895 | + | ENST00000314163 | chr1 | 147440564 | 147440653 | + | TAF |
| 14% | chr3 | 196230044 | 196229744 | − | ENST00000318037; ENST00000437070 | chr3 | 196223342 | 196223041 | − | TAF |
| 14% | chr16 | 2825557; 2825626 | 2825452 | − | ENST00000262306; ENST00000409906; ENST00000409477; ENST00000494946 | chr16 | 2823834 | 2823809 | − | TAF |
| 14% | chr16 | 2825557; 2825626 | 2825452 | − | ENST00000262306; ENST00000409906; ENST00000409477; ENST00000494946 | chr16 | 2823834 | 2823809 | − | TAF |
| 14% | chr16 | 2825557; 2825626 | 2825452 | − | ENST00000262306; ENST00000409906; ENST00000409477; ENST00000494946 | chr16 | 2823834 | 2823809 | − | TAF |
| 13% | chr6 | 41606488 | 41606563 | + | ENST00000432027; ENST00000419164; ENST00000373051; ENST00000441667; ENST00000230321; ENST00000373050; ENST00000446650; ENST00000435476 | chr6 | 41607515 | 41607595 | + | TAF |
| 13% | chr10 | 15151838 | 15151701 | − | ENST00000378165; ENST00000378150; ENST00000540259; ENST00000535341 | chr10 | 15148697 | 15148684 | − | TAF |
| 13% | chr10 | 15151838 | 15151701 | − | ENST00000378165; ENST00000378150; ENST00000540259; ENST00000535341 | chr10 | 15148697 | 15148684 | − | TAF |
| 13% | chr10 | 15151838 | 15151701 | − | ENST00000378165; ENST00000378150; ENST00000540259; ENST00000535341 | chr10 | 15148697 | 15148684 | − | TAF |
| 13% | chr10 | 15151838 | 15151701 | − | ENST00000378165; ENST00000378150; ENST00000540259; ENST00000535341 | chr10 | 15148697 | 15148684 | − | TAF |
| 13% | chr1 | 41463066 | 41463198 | + | ENST00000372621; ENST00000541520; ENST00000372616 | chr1 | 41465502 | 41465535 | + | TAF |
| 13% | chr1 | 41463066 | 41463198 | + | ENST00000372621; ENST00000541520; ENST00000372616 | chr1 | 41465502 | 41465535 | + | TAF |
| 13% | chr6 | 35314915 | 35314927 | + | ENST00000448077 | chr6 | 35351354 | 35351915 | + | TAF |
| 13% | chr6 | 151742456 | 151742380 | − | ENST00000336451; ENST00000367303; ENST00000444024 | chr6 | 151739714 | 151739579 | − | TSF |
| 13% | chr6 | 151742456 | 151742380 | − | ENST00000336451; ENST00000367303; ENST00000444024 | chr6 | 151739714 | 151739579 | − | TSF |
| 13% | chr6 | 151742456 | 151742380 | − | ENST00000336451; ENST00000367303; ENST00000444024 | chr6 | 151739714 | 151739579 | − | TSF |
| 13% | chr4 | 146617711 | 146617784 | + | ENST00000438731; ENST00000511965 | chr4 | 146620339 | 146620424 | + | TSF |
| 13% | chr4 | 146617711 | 146617784 | + | ENST00000438731; ENST00000511965 | chr4 | 146620339 | 146620424 | + | TSF |
| 12% | chr15 | 34826374 | 34826255 | − | ENST00000342314; ENST00000267731 | chr15 | 34679464 | 34679458 | − | TAF |
| 12% | chr2 | 172725333; 172725194 | 172725191 | − | ENST00000422440; ENST00000263812; ENST00000392592; ENST00000426896; ENST00000475360 | chr2 | 172723793 | 172722363 | − | TSF |
| 12% | chr2 | 172725333; 172725194 | 172725191 | − | ENST00000422440; ENST00000263812; ENST00000392592; ENST00000426896; ENST00000475360 | chr2 | 172723793 | 172722363 | − | TSF |
| 12% | chr2 | 172725333; 172725194 | 172725191 | − | ENST00000422440; ENST00000263812; ENST00000392592; ENST00000426896; ENST00000475360 | chr2 | 172723793 | 172722363 | − | TSF |
| 11% | chr12 | 64833024 | 64833095 | + | ENST00000332707 | chr12 | 64833417 | 64833459 | + | TAF |
| 11% | chr2 | 211342488 | 211342490 | + | ENST00000523702; ENST00000430249 | chr2 | 211384275 | 211384452 | + | TAF |
| 11% | chr12 | 57060050 | 57059988 | − | ENST00000262033; ENST00000414274; ENST00000436399; ENST00000456859 | chr12 | 57059571 | 57059432 | − | TAF |
| 11% | chr12 | 57060050 | 57059988 | − | ENST00000262033; ENST00000414274; ENST00000436399; ENST00000456859 | chr12 | 57059571 | 57059432 | − | TAF |
| 11% | chr12 | 57060050 | 57059988 | − | ENST00000262033; ENST00000414274; ENST00000436399; ENST00000456859 | chr12 | 57059571 | 57059432 | − | TAF |
| 11% | chr12 | 57060050 | 57059988 | − | ENST00000262033; ENST00000414274; ENST00000436399; ENST00000456859 | chr12 | 57059571 | 57059432 | − | TAF |
| 11% | chr1 | 244855181; 244855186 | 244855322 | + | ENST00000302550; ENST00000263831 | chr1 | 244863163 | 244863387 | + | TAF |
| 11% | chr1 | 244855181; 244855186 | 244855322 | + | ENST00000302550; ENST00000263831 | chr1 | 244863163 | 244863387 | + | TAF |
| 11% | chr14 | 51355542 | 51355621 | + | ENST00000337334; ENST00000353130; ENST00000395752 | chr14 | 51359931 | 51360328 | + | TAF |
| 11% | chr14 | 51355542 | 51355621 | + | ENST00000337334; ENST00000353130; ENST00000395752 | chr14 | 51359931 | 51360328 | + | TAF |
| 11% | chr14 | 51355542 | 51355621 | + | ENST00000337334; ENST00000353130; ENST00000395752 | chr14 | 51359931 | 51360328 | + | TAF |
| 11% | chr2 | 242275390; 242275258 | 242275513 | + | ENST00000391973; ENST00000428282; ENST00000360051; ENST00000407017; ENST00000391971; ENST00000401990; ENST00000407971; ENST00000436795; ENST00000411484; ENST00000402092; ENST00000443492; ENST00000437066; ENST00000449239; ENST00000457874 | chr2 | 242276200 | 242276228 | + | TAF |
| 11% | chr2 | 242275390; 242275258 | 242275513 | + | ENST00000391973; ENST00000428282; ENST00000360051; ENST00000407017; ENST00000391971; ENST00000401990; ENST00000407971; ENST00000436795; ENST00000411484; ENST00000402092; ENST00000443492; ENST00000437066; | chr2 | 242276200 | 242276228 | + | TAF |

TABLE 59-continued

Transcript fusion for Testicular Germ Cell Tumors (TGCT) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 11% | chr2 | 242275390; 242275258 | 242275513 | + | ENST00000449239; ENST00000457874 ENST00000391973; ENST00000428282; ENST00000360051; ENST00000407017; ENST00000391971; ENST00000401990; ENST00000407971; ENST00000436795; ENST00000411484; ENST00000402092; ENST00000443492; ENST00000437066; | chr2 | 242276200 | 242276228 | + | TAF |
| 11% | chr2 | 242275390; 242275258 | 242275513 | + | ENST00000449239; ENST00000457874 ENST00000391973; ENST00000428282; ENST00000360051; ENST00000407017; ENST00000391971; ENST00000401990; ENST00000407971; ENST00000436795; ENST00000411484; ENST00000402092; ENST00000443492; ENST00000437066; | chr2 | 242276200 | 242276228 | + | TAF |
| 11% | chr2 | 242275390; 242275258 | 242275513 | + | ENST00000449239; ENST00000457874 ENST00000391973; ENST00000428282; ENST00000360051; ENST00000407017; ENST00000391971; ENST00000401990; ENST00000407971; ENST00000436795; ENST00000411484; ENST00000402092; ENST00000443492; ENST00000437066; | chr2 | 242276200 | 242276228 | + | TAF |
| 11% | chr22 | 46136249 | 46136418 | + | ENST00000381061; ENST00000252934; ENST00000435026; ENST00000451241 | chr22 | 46194492 | 46194955 | + | TAF |
| 11% | chr22 | 46136249 | 46136418 | + | ENST00000381061; ENST00000252934; ENST00000435026; ENST00000451241 | chr22 | 46194492 | 46194955 | + | TAF |
| 11% | chr22 | 46136249 | 46136418 | + | ENST00000381061; ENST00000252934; ENST00000435026; ENST00000451241 | chr22 | 46194492 | 46194955 | + | TAF |
| 11% | chr22 | 46136249 | 46136418 | + | ENST00000381061; ENST00000252934; ENST00000435026; ENST00000451241 | chr22 | 46194492 | 46194955 | + | TAF |
| 11% | chr15 | 89011139 | 89011255 | + | ENST00000560708; ENST00000325844; ENST00000353598 | chr15 | 89011993 | 89012264 | + | TAF |
| 11% | chr1 | 24463799 | 24463621 | − | ENST00000270800 | chr1 | 24461426 | 24461370 | − | TAF |
| 11% | chr1 | 32560385 | 32560572 | + | ENST00000336294; ENST00000373634; ENST00000427288 | chr1 | 32561261 | 32561358 | + | TSF |
| 11% | chr1 | 32560385 | 32560572 | + | ENST00000336294; ENST00000373634; ENST00000427288 | chr1 | 32561261 | 32561358 | + | TSF |
| 11% | chr1 | 32560385 | 32560572 | + | ENST00000336294; ENST00000373634; ENST00000427288 | chr1 | 32561261 | 32561358 | + | TSF |
| 11% | chr3 | 54157540 | 54157621 | + | ENST00000415676; ENST00000288197; ENST00000474759 | chr3 | 54326852 | 54327228 | + | TSF |
| 11% | chr7 | 77212872; 77212944 | 77212967 | + | ENST00000248594; ENST00000433369; ENST00000415482; ENST00000418110; ENST00000522115; ENST00000440186; ENST00000447995 | chr7 | 77213910 | 77213912 | + | TSF |
| 11% | chr7 | 77212872; 77212944 | 77212967 | + | ENST00000248594; ENST00000433369; ENST00000415482; ENST00000418110; ENST00000522115; ENST00000440186; ENST00000447995 | chr7 | 77213910 | 77213912 | + | TSF |
| 11% | chr7 | 77212872; 77212944 | 77212967 | + | ENST00000248594; ENST00000433369; ENST00000415482; ENST00000418110; ENST00000522115; ENST00000440186; ENST00000447995 | chr7 | 77213910 | 77213912 | + | TSF |
| 11% | chr15 | 65114590 | 65114465 | − | ENST00000268043; ENST00000333425; ENST00000559239 | chr15 | 65114331 | 65114239 | − | TSF |
| 10% | chr7 | 45649978 | 45650096 | + | ENST00000432715; ENST00000297323 | chr7 | 45652520 | 45652533 | + | TSF |
| 10% | chr7 | 45649978 | 45650096 | + | ENST00000432715; ENST00000297323 | chr7 | 45652520 | 45652533 | + | TSF |
| 10% | chr12 | 4874545 | 4874712 | + | ENST00000252318; ENST00000542998; ENST00000535354 | chr12 | 4884414 | 4884790 | + | TSF |
| 10% | chr12 | 4874545 | 4874712 | + | ENST00000252318; ENST00000542998; ENST00000535354 | chr12 | 4884414 | 4884790 | + | TSF |
| 10% | chr12 | 4874545 | 4874712 | + | ENST00000252318; ENST00000542998; ENST00000535354 | chr12 | 4884414 | 4884790 | + | TSF |
| 10% | chr1 | 33272212 | 33272083 | − | ENST00000373477 | chr1 | 33270484 | 33269340 | − | TSF |
| 9% | chr14 | 66096210; 66096217 | 66096324 | + | ENST00000360689; ENST00000394586; ENST00000342677; ENST00000557164; ENST00000394585; ENST00000358307 | chr14 | 66099743 | 66101298 | + | TSF |
| 9% | chr14 | 66096210; 66096217 | 66096324 | + | ENST00000360689; ENST00000394586; ENST00000342677; ENST00000557164; ENST00000394585; ENST00000358307 | chr14 | 66099743 | 66101298 | + | TSF |
| 9% | chr14 | 66096210; 66096217 | 66096324 | + | ENST00000360689; ENST00000394586; ENST00000342677; ENST00000557164; ENST00000394585; ENST00000358307 | chr14 | 66099743 | 66101298 | + | TSF |
| 9% | chr12 | 56742407 | 56742313 | − | ENST00000314128; ENST00000557235 | chr12 | 56740986 | 56740975 | − | TSF |
| 9% | chr12 | 56742407 | 56742313 | − | ENST00000314128; ENST00000557235 | chr12 | 56740986 | 56740975 | − | TSF |
| 9% | chr20 | 30060816 | 30060759 | − | ENST00000317676 | chr20 | 30059856 | 30059283 | − | TSF |

TABLE 59-continued

Transcript fusion for Testicular Germ Cell Tumors (TGCT) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 9% | chr14 | 76662221 | 76662315 | + | ENST00000312858; ENST00000261530; ENST00000554799; ENST00000553588 | chr14 | 76666223 | 76666696 | + | TSF |
| 9% | chr14 | 76662221 | 76662315 | + | ENST00000312858; ENST00000261530; ENST00000554799; ENST00000553588 | chr14 | 76666223 | 76666696 | + | TSF |
| 9% | chr14 | 76662221 | 76662315 | + | ENST00000312858; ENST00000261530; ENST00000554799; ENST00000553588 | chr14 | 76666223 | 76666696 | + | TSF |
| 9% | chrX | 133963256 | 133963312 | + | ENST00000370784; ENST00000370785 | chrX | 133972757 | 133974403 | + | TSF |
| 9% | chr19 | 53357525 | 53357511 | − | ENST00000595646; ENST00000243639; ENST00000597924; ENST00000602144 | chr19 | 53258356 | 53258315 | − | TSF |
| 9% | chr19 | 53321211 | 53321197 | − | ENST00000457749; ENST00000596559; ENST00000594602 | chr19 | 53258356 | 53258315 | − | TSF |
| 8% | chr1 | 72163822 | 72163691 | − | ENST00000357731; ENST00000306821 | chr1 | 72145446 | 72144785 | − | TSF |
| 8% | chr1 | 72163822 | 72163691 | − | ENST00000357731; ENST00000306821 | chr1 | 72145446 | 72144785 | − | TSF |
| 8% | chr20 | 40102157 | 40101962 | − | ENST00000373233 | chr20 | 40101067 | 40101036 | − | TSF |
| 8% | chr6 | 151738534 | 151738414 | − | ENST00000336451; ENST00000367303 | chr6 | 151732046 | 151731858 | − | TSF |
| 8% | chr6 | 151738534 | 151738414 | − | ENST00000336451; ENST00000367303 | chr6 | 151732046 | 151731858 | − | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr7 | 73459552 | 73459623 | + | ENST00000445912; ENST00000252034; ENST00000358929; ENST00000320492; ENST00000438906; ENST00000414324; ENST00000380562; ENST00000380575; ENST00000380584; ENST00000458204; ENST00000357036; ENST00000429192; ENST00000380576; ENST00000320399 | chr7 | 73460337 | 73460377 | + | TSF |
| 7% | chr17 | 15443875 | 15443747 | − | ENST00000519970; ENST00000584811; ENST00000438826; ENST00000428082; ENST00000518321 | chr17 | 15435156 | 15434353 | − | TSF |
| 7% | chr17 | 15443875 | 15443747 | − | ENST00000519970; ENST00000584811; ENST00000438826; ENST00000428082; ENST00000518321 | chr17 | 15435156 | 15434353 | − | TSF |
| 7% | chr17 | 15443875 | 15443747 | − | ENST00000519970; ENST00000584811; ENST00000438826; ENST00000428082; ENST00000518321 | chr17 | 15435156 | 15434353 | − | TSF |
| 7% | chr1 | 63955889 | 63955754 | − | ENST00000371092; ENST00000271002; ENST00000489099; ENST00000283568 | chr1 | 63952444 | 63951983 | − | TSF |
| 7% | chr1 | 63955889 | 63955754 | − | ENST00000371092; ENST00000271002; ENST00000489099; ENST00000283568 | chr1 | 63952444 | 63951983 | − | TSF |
| 7% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 7% | chr19 | 3869015; 3869013 | 3868963 | − | ENST00000262961; ENST00000438164; ENST00000587212; ENST00000586578; ENST00000439086 | chr19 | 3855694 | 3855445 | − | TSF |
| 7% | chr5 | 79498872 | 79498705 | − | ENST00000507668; ENST00000509193; ENST00000512972; ENST00000512721 | chr5 | 79481724 | 79481327 | − | TSF |
| 7% | chr11 | 76944217 | 76944070 | − | ENST00000315938; ENST00000376217 | chr11 | 76940716 | 76940641 | − | TSF |
| 7% | chr1 | 207857217 | 207857302 | + | ENST00000508064; ENST00000294997 | chr1 | 207860136 | 207860394 | + | TSF |
| 7% | chr1 | 207857217 | 207857302 | + | ENST00000508064; ENST00000294997 | chr1 | 207860136 | 207860394 | + | TSF |
| 7% | chr1 | 212209233 | 212209284 | + | ENST00000366991; ENST00000542077 | chr1 | 212211973 | 212212067 | + | TSF |

TABLE 59-continued

Transcript fusion for Testicular Germ Cell Tumors (TGCT) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 7% | chr20 | 29978286 | 29978226 | − | ENST00000339144; ENST00000376321; ENST00000376315 | chr20 | 29976162 | 29976126 | − | TSF |
| 7% | chr16 | 81142298 | 81142167 | − | ENST00000533478; ENST00000525539 | chr16 | 81139177 | 81139155 | − | TSF |
| 7% | chr16 | 81142298 | 81142167 | − | ENST00000533478; ENST00000525539 | chr16 | 81139177 | 81139155 | − | TSF |
| 6% | chr16 | 88873689 | 88873890 | + | ENST00000301019 | chr16 | 88875475 | 88875490 | + | TSF |
| 6% | chr17 | 58329803 | 58329742 | − | ENST00000300896; ENST00000592339; ENST00000590133; ENST00000589335; ENST00000393003 | chr17 | 58323153 | 58323061 | − | TSF |
| 6% | chr17 | 58329803 | 58329742 | − | ENST00000300896; ENST00000592339; ENST00000590133; ENST00000589335; ENST00000393003 | chr17 | 58323153 | 58323061 | − | TSF |
| 6% | chr17 | 58329803 | 58329742 | − | ENST00000300896; ENST00000592339; ENST00000590133; ENST00000589335; ENST00000393003 | chr17 | 58323153 | 58323061 | − | TSF |
| 6% | chr17 | 58329803 | 58329742 | − | ENST00000300896; ENST00000592339; ENST00000590133; ENST00000589335; ENST00000393003 | chr17 | 58323153 | 58323061 | − | TSF |
| 5% | chr7 | 26192119 | 26192688 | + | ENST00000056233 | chr7 | 26210356 | 26210396 | + | TSF |
| 5% | chr22 | 39448079 | 39448358 | + | ENST00000308521 | chr22 | 39449757 | 39450008 | + | TSF |
| 5% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 5% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 5% | chr19 | 55178148; 55178145 | 55178200 | + | ENST00000391736; ENST00000270452; ENST00000430952; ENST00000391734; ENST00000391733; ENST00000434286 | chr19 | 55178294 | 55178458 | + | TSF |
| 5% | chr5 | 140044498 | 140044686 | + | ENST00000358337; ENST00000506393 | chr5 | 140046629 | 140046654 | + | TSF |
| 5% | chr5 | 128864213 | 128864370 | + | ENST00000274487 | chr5 | 128868409 | 128868509 | + | TSF |
| 5% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 5% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 5% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 5% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 5% | chr15 | 43705532; 43705526; 43705484 | 43705317 | − | ENST00000263801; ENST00000382039; ENST00000382044; ENST00000450115; ENST00000434595 | chr15 | 43702724 | 43702621 | − | TSF |
| 5% | chr13 | 53307494; 53307473 | 53307354 | − | ENST00000448904; ENST00000377962; ENST00000431550 | chr13 | 53304269 | 53303967 | − | TSF |
| 5% | chr13 | 53307494; 53307473 | 53307354 | − | ENST00000448904; ENST00000377962; ENST00000431550 | chr13 | 53304269 | 53303967 | − | TSF F |
| 5% | chr3 | 185414451 | 185414400 | − | ENST00000382199; ENST00000421047; ENST00000457616; ENST00000346192 | chr3 | 185411016 | 185410789 | − | TSF |
| 5% | chr3 | 185414451 | 185414400 | − | ENST00000382199; ENST00000421047; ENST00000457616; ENST00000346192 | chr3 | 185411016 | 185410789 | − | TSF |
| 5% | chr20 | 3614958 | 3615036 | + | ENST00000262919 | chr20 | 3615708 | 3616042 | + | TSF |
| 5% | chr22 | 48885405 | 48885516 | + | ENST00000402357; ENST00000336769 | chr22 | 48915770 | 48916108 | + | TSF |
| 5% | chr16 | 29497154 | 29495055 | − | ENST00000354563 | chr16 | 29392982 | 29392973 | − | TSF |
| 5% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 5% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 5% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 5% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 5% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |

TABLE 59-continued

Transcript fusion for Testicular Germ Cell Tumors (TGCT) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 5% | chr16 | 69418613; 69418553; 69418599 | 69418483 | − | ENST00000254942; ENST00000603068; ENST00000566750; ENST00000569542; ENST00000566257; ENST00000567296; ENST00000567841 | chr16 | 69413560 | 69413452 | − | TSF |
| 5% | chr14 | 55615191 | 55615113 | − | ENST00000247191 | chr14 | 55613267 | 55613026 | − | TSF |
| 5% | chr7 | 74867341 | 74867229 | − | ENST00000426327 | chr7 | 74856485 | 74856184 | − | TSF |
| 5% | chr17 | 15449230 | 15449099 | − | ENST00000522212; ENST00000519970; ENST00000225576; ENST00000581273; ENST00000584811; ENST00000438826; ENST00000428082; ENST00000518321; ENST00000419890 | chr17 | 15435156 | 15434353 | − | TSF |
| 5% | chr17 | 15449230 | 15449099 | − | ENST00000522212; ENST00000519970; ENST00000225576; ENST00000581273; ENST00000584811; ENST00000438826; ENST00000428082; ENST00000518321; ENST00000419890 | chr17 | 15435156 | 15434353 | − | TSF |
| 5% | chr17 | 15449230 | 15449099 | − | ENST00000522212; ENST00000519970; ENST00000225576; ENST00000581273; ENST00000584811; ENST00000438826; ENST00000428082; ENST00000518321; ENST00000419890 | chr17 | 15435156 | 15434353 | − | TSF |
| 5% | chr17 | 15449230 | 15449099 | − | ENST00000522212; ENST00000519970; ENST00000225576; ENST00000581273; ENST00000584811; ENST00000438826; ENST00000428082; ENST00000518321; ENST00000419890 | chr17 | 15435156 | 15434353 | − | TSF |
| 5% | chr8 | 55013499 | 55013468 | − | ENST00000316963; ENST00000343231; ENST00000518546; ENST00000522007; ENST00000521898 | chr8 | 54994583 | 54994275 | − | TSF |
| 4% | chr9 | 78547295 | 78547399 | + | ENST00000545128; ENST00000376767; ENST00000376752 | chr9 | 78565414 | 78565806 | + | TSF |
| 4% | chr16 | 88873689 | 88873890 | + | ENST00000301019 | chr16 | 88875489 | 88875490 | + | TSF |
| 4% | chr8 | 71619168 | 71619388 | + | ENST00000408926; ENST00000520030 | chr8 | 71625661 | 71625673 | + | TSF |
| 4% | chr9 | 128510829; 128510854 | 128510902 | + | ENST00000342287; ENST00000373487; ENST00000373489; ENST00000373492; ENST00000373482; ENST00000491787; ENST00000447726 | chr9 | 128572989 | 128573209 | + | TSF |
| 4% | chr9 | 128510829; 128510854 | 128510902 | + | ENST00000342287; ENST00000373487; ENST00000373489; ENST00000373492; ENST00000373482; ENST00000491787; ENST00000447726 | chr9 | 128572989 | 128573209 | + | TSF |
| 4% | chr11 | 60701014 | 60701216 | + | ENST00000453848; ENST00000005286; ENST00000536409 | chr11 | 60701443 | 60701575 | + | TSF |
| 4% | chr11 | 60701014 | 60701216 | + | ENST00000453848; ENST00000005286; ENST00000536409 | chr11 | 60701443 | 60701575 | + | TSF |
| 4% | chr11 | 60701014 | 60701216 | + | ENST00000453848; ENST00000005286; ENST00000536409 | chr11 | 60701443 | 60701575 | + | TSF |
| 4% | chr7 | 74157788 | 74157859 | + | ENST00000324896; ENST00000346152; ENST00000353920; ENST00000416070 | chr7 | 74158483 | 74158600 | + | TSF |
| 4% | chr7 | 74157788 | 74157859 | + | ENST00000324896; ENST00000346152; ENST00000353920; ENST00000416070 | chr7 | 74158483 | 74158600 | + | TSF |
| 4% | chr7 | 74157788 | 74157859 | + | ENST00000324896; ENST00000346152; ENST00000353920; ENST00000416070 | chr7 | 74158483 | 74158600 | + | TSF |
| 4% | chr7 | 74157788 | 74157859 | + | ENST00000324896; ENST00000346152; ENST00000353920; ENST00000416070 | chr7 | 74158483 | 74158600 | + | TSF |
| 4% | chr12 | 71509738 | 71509630 | − | ENST00000549357 | chr12 | 71507025 | 71506982 | − | TSF |
| 4% | chr10 | 99229480 | 99229403 | − | ENST00000438925; ENST00000370782; ENST00000327238; ENST00000355839; ENST00000434392; ENST00000437002 | chr10 | 99229305 | 99229286 | − | TSF |
| 4% | chr10 | 99229480 | 99229403 | − | ENST00000438925; ENST00000370782; ENST00000327238; ENST00000355839; ENST00000434392; ENST00000437002 | chr10 | 99229305 | 99229286 | − | TSF |
| 4% | chr10 | 99229480 | 99229403 | − | ENST00000438925; ENST00000370782; ENST00000327238; ENST00000355839; ENST00000434392; ENST00000437002 | chr10 | 99229305 | 99229286 | − | TSF |
| 4% | chr10 | 99229480 | 99229403 | − | ENST00000438925; ENST00000370782; ENST00000327238; ENST00000355839; ENST00000434392; ENST00000437002 | chr10 | 99229305 | 99229286 | − | TSF |
| 4% | chr1 | 154794660; 154794654 | 154794565 | − | ENST00000271915; ENST00000361147; ENST00000358505 | chr1 | 154761737 | 154761457 | − | TSF |
| 4% | chr1 | 154794660; 154794654 | 154794565 | − | ENST00000271915; ENST00000361147; ENST00000358505 | chr1 | 154761737 | 154761457 | − | TSF |
| 4% | chr1 | 154794660; 154794654 | 154794565 | − | ENST00000271915; ENST00000361147; ENST00000358505 | chr1 | 154761737 | 154761457 | − | TSF |
| 4% | chr13 | 42457627 | 42457523 | − | ENST00000379310; ENST00000281496 | chr13 | 42456370 | 42455523 | − | TSF |
| 4% | chr7 | 619014 | 618893 | − | ENST00000544935; ENST00000537384 | chr7 | 618449 | 618307 | − | TSF |

TABLE 59-continued

Transcript fusion for Testicular Germ Cell Tumors (TGCT) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 4% | chr7 | 619014 | 618893 | − | ENST00000406797; ENST00000403562; ENST00000360274; ENST00000400758; ENST00000430040 ENST00000544935; ENST00000537384;chr7 ENST00000406797; ENST00000403562; ENST00000360274; ENST00000400758; ENST00000430040 | 618449 | 618307 | − | TSF |
| 4% | chr16 | 397025 | 396148 | − | ENST00000262320; ENST00000354866 chr16 | 369976 | 369697 | − | TSF |
| 4% | chr20 | 50803610; 50803604 | 50803371 | − | ENST00000371518; ENST00000361387;chr20 ENST00000346617; ENST00000371515; ENST00000216923 | 50801861 | 50801561 | − | TSF |
| 4% | chr20 | 50803610; 50803604 | 50803371 | − | ENST00000371518; ENST00000361387;chr20 ENST00000346617; ENST00000371515; ENST00000216923 | 50801861 | 50801561 | − | TSF |

TABLE 60

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 77% | chr14 | 51360331 | 51362440 | + | chr14 | 51368547 | 51368629 | + | ENST00000337334; ENST00000353130; ENST00000395752 | TSF |
| 68% | chr10 | 70433076 | 70433244 | + | chr10 | 70441156 | 70441245 | + | ENST00000373644 | TSF |
| 60% | chr18 | 51273 | 49727 | − | chr18 | 49237 | 49129 | − | ENST00000308911 | TSF |
| 59% | chr12 | 6602868 | 6602840 | − | chr12 | 6602138 | 6602028 | − | ENST00000229238 | TAF |
| 56% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 56% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 56% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 56% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 56% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 56% | chr16 | 23606905 | 23606750 | − | chr16 | 23598640 | 23598518 | − | ENST00000007516; ENST00000570319 | TSF |
| 53% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 53% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 53% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 53% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 53% | chrX | 793481 | 48793462 | – | chrX | 48792291 | 48792227 | – | ENST00000396743; ENST00000455452; ENST00000156084; ENST00000376488; ENST00000428668 | TAF |
| 53% | chrX | 793481 | 48793462 | – | chrX | 48792291 | 48792227 | – | ENST00000396743; ENST00000455452; ENST00000156084; ENST00000376488; ENST00000428668 | TAF |
| 52% | chrX | 2291342 | 2291084 | – | chr | 2209644 | 2209543 | – | ENST00000334651; ENST00000412516; ENST00000444280 | TAF |
| 52% | chrX | 2291342 | 2291084 | – | chr | 2209644 | 2209543 | – | ENST00000334651; ENST00000412516; ENST00000444280 | TAF |
| 52% | chrX | 2291342 | 2291084 | – | chr | 2209644 | 2209543 | – | ENST00000334651; ENST00000412516; ENST00000444280 | TAF |
| 52% | chrX | 2291342 | 2291084 | – | chr | 2209644 | 2209543 | – | ENST00000334651; ENST00000412516; ENST00000444280 | TAF |
| 52% | chrX | 2291342 | 2291084 | – | chr | 2209644 | 2209543 | – | ENST00000334651; ENST00000412516; ENST00000444280 | TAF |
| 52% | chrX | 2291342 | 2291084 | – | chr | 2209644 | 2209543 | – | ENST00000334651; ENST00000412516; ENST00000444280 | TAF |
| 52% | chrX | 2291342 | 2291084 | – | chr | 2209644 | 2209543 | – | ENST00000334651; ENST00000412516; ENST00000444280 | TAF |
| 52% | chrX | 2291342 | 2291084 | – | chr | 2209644 | 2209543 | – | ENST00000334651; ENST00000412516; ENST00000444280 | TAF |
| 51% | chr19 | 39110121 | 39110170 | + | chr19 | 39110977 | 39111075 | + | ENST00000248342; ENST00000588934; ENST00000545173; ENST00000586513; ENST00000592558 | TAF |
| 51% | chr19 | 39110121 | 39110170 | + | chr19 | 39110977 | 39111075 | + | ENST00000248342; ENST00000588934; ENST00000545173; ENST00000586513; ENST00000592558 | TAF |
| 51% | chr19 | 39110121 | 39110170 | + | chr19 | 39110977 | 39111075 | + | ENST00000248342; ENST00000588934; ENST00000545173; ENST00000586513; ENST00000592558 | TAF |
| 51% | chr19 | 39110121 | 39110170 | + | chr19 | 39110977 | 39111075 | + | ENST00000248342; ENST00000588934; ENST00000545173; ENST00000586513; ENST00000592558 | TAF |
| 51% | chr19 | 39110121 | 39110170 | + | chr19 | 39110977 | 39111075 | + | ENST00000248342; ENST00000588934; ENST00000545173; ENST00000586513; ENST00000592558 | TAF |
| 45% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 45% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 45% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 45% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 45% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 43% | chr20 | 30060256 | 30059518 | – | chr20 | 30053466 | 30053309 | – | ENST00000317676 | TAF |
| 42% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 42% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 42% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 42% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 41% | chr11 | 93468219 | 93468129 | – | chr11 | 93467826 | 93467791; 93467814 | – | ENST00000393259; ENST00000527169 | TAF |
| 41% | chr11 | 93468219 | 93468129 | – | chr11 | 93467826 | 93467791; 93467814 | – | ENST00000393259; ENST00000527169 | TAF |
| 41% | chr3 | 185411133 | 185410965 | – | chr3 | 185410550 | 185410487 | – | ENST00000382199; ENST00000421047; ENST00000457616; ENST00000346192 | TAF |
| 41% | chr3 | 185411133 | 185410965 | – | chr3 | 185410550 | 185410487 | – | ENST00000382199; ENST00000421047; ENST00000457616; ENST00000346192 | TAF |
| 41% | chr1 | 1422590 | 1422685 | + | chr1 | 1423243 | 1423294 | + | ENST00000308647 | TSF |
| 39% | chr2 | 38983894 | 38983253 | – | chr2 | 38977336 | 38977156 | – | ENST00000313117; ENST00000425778; ENST00000425941; ENST00000446327; | TSF |

TABLE 60-continued

Transcript fusion for Testicular Germ Cell Tumors (TGCT) Coordinates of the fusion sequences for which the donor is the TE.

| 1' | 2' | 3' | 4' | 5' 6' | 7' | 8' | 9' 10' | 11' |
|---|---|---|---|---|---|---|---|---|
| 39% | chr2 | 38983894 | 38983253 | − chr2 | 38977336 | 38977156 | − | ENST00000409276; ENST00000431066; ENST00000443213 ENST00000313117; ENST00000425778;TSF ENST00000425941; ENST00000446327; |
| 39% | chr2 | 38983894 | 38983253 | − chr2 | 38977336 | 38977156 | − | ENST00000409276; ENST00000431066; ENST00000443213 ENST00000313117; ENST00000425778;TSF ENST00000425941; ENST00000446327; |
| 39% | chr2 | 38983894 | 38983253 | − chr2 | 38977336 | 38977156 | − | ENST00000409276; ENST00000431066; ENST00000443213 ENST00000313117; ENST00000425778;TSF ENST00000425941; ENST00000446327; |
| 39% | chr2 | 38983894 | 38983253 | − chr2 | 38977336 | 38977156 | − | ENST00000409276; ENST00000431066; ENST00000443213 ENST00000313117; ENST00000425778;TSF ENST00000425941; ENST00000446327; |
| 37% | chr7 | 150730019 | 150730148 | + chr7 | 150730692 | 150730929; 150731004; 150730700 | + | ENST00000461373; ENST00000358849;TAF ENST00000489192; ENST00000297504; ENST00000356058; ENST00000498578; ENST00000477719; ENST00000477092 |
| 37% | chr7 | 150730019 | 150730148 | + chr7 | 150730692 | 150730929; 150731004; 150730700 | + | ENST00000461373; ENST00000358849;TAF ENST00000489192; ENST00000297504; ENST00000356058; ENST00000498578; ENST00000477719; ENST00000477092 |
| 37% | chr7 | 150730019 | 150730148 | + chr7 | 150730692 | 150730929; 150731004; 150730700 | + | ENST00000461373; ENST00000358849;TAF ENST00000489192; ENST00000297504; ENST00000356058; ENST00000498578; ENST00000477719; ENST00000477092 |
| 37% | chr7 | 150730019 | 150730148 | + chr7 | 150730692 | 150730929; 150731004; 150730700 | + | ENST00000461373; ENST00000358849;TAF ENST00000489192; ENST00000297504; ENST00000356058; ENST00000498578; ENST00000477719; ENST00000477092 |
| 37% | chr7 | 150730019 | 150730148 | + chr7 | 150730692 | 150730929; 150731004; 150730700 | + | ENST00000461373; ENST00000358849;TAF ENST00000489192; ENST00000297504; ENST00000356058; ENST00000498578; ENST00000477719; ENST00000477092 |
| 37% | chr7 | 150730019 | 150730148 | + chr7 | 150730692 | 150730929; 150731004; 150730700 | + | ENST00000461373; ENST00000358849;TAF ENST00000489192; ENST00000297504; ENST00000356058; ENST00000498578; ENST00000477719; ENST00000477092 |
| 36% | chr7 | 74158449 | 74158566 | + chr7 | 74159097 | 74159280 | + | ENST00000324896; ENST00000346152;TAF ENST00000353920; ENST00000416070 |
| 35% | chr7 | 48039730 | 48039725 | − chr7 | 48035743 | 48035628 | − | ENST00000453071; ENST00000297325;TSF ENST00000412371; ENST00000412142; ENST00000395572; ENST00000453192; ENST00000438771 |
| 35% | chr7 | 48039730 | 48039725 | − chr7 | 48035743 | 48035628 | − | ENST00000453071; ENST00000297325;TSF ENST00000412371; ENST00000412142; ENST00000395572; ENST00000453192; ENST00000438771 |
| 35% | chr7 | 48039730 | 48039725 | − chr7 | 48035743 | 48035628 | − | ENST00000453071; ENST00000297325;TSF ENST00000412371; ENST00000412142; ENST00000395572; ENST00000453192; ENST00000438771 |
| 34% | chr7 | 73098299 | 73098330 | + chr7 | 73100966 | 73101061 | + | ENST00000265758; ENST00000432522;TAF ENST00000421744; ENST00000428163; ENST00000423166; ENST00000423497 |
| 34% | chr7 | 73098299 | 73098330 | + chr7 | 73100966 | 73101061 | + | ENST00000265758; ENST00000432522;TAF ENST00000421744; ENST00000428163; ENST00000423166; ENST00000423497 |
| 34% | chr7 | 73098299 | 73098330 | + chr7 | 73100966 | 73101061 | + | ENST00000265758; ENST00000432522;TAF ENST00000421744; ENST00000428163; ENST00000423166; ENST00000423497 |
| 34% | chr7 | 73098299 | 73098330 | + chr7 | 73100966 | 73101061 | + | ENST00000265758; ENST00000432522;TAF ENST00000421744; ENST00000428163; ENST00000423166; ENST00000423497 |
| 34% | chr7 | 73098299 | 73098330 | + chr7 | 73100966 | 73101061 | + | ENST00000265758; ENST00000432522;TAF ENST00000421744; ENST00000428163; ENST00000423166; ENST00000423497 |
| 34% | chr2 | 175806110 | 175805544 | − chr2 | 175783293 | 175783262 | − | ENST00000409900; ENST00000409156 TAF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 34% | chr2 | 175806110 | 175805544 | − | chr2 | 175783293 | 175783262 | − | ENST00000409900; ENST00000409156 | TAF |
| 34% | chr15 | 40187476 | 40186733 | − | chr15 | 40099459 | 40099207 | − | ENST00000561100; ENST00000543580 | TSF |
| 33% | chr12 | 122430912 | 122431615 | + | chr12 | 122437622 | 122437850 | + | ENST00000288912 | TAF |
| 33% | chr7 | 21979898 | 21979880 | − | chr7 | 21956512 | 21956372 | − | ENST00000406877; ENST00000373934 | TAF |
| 33% | chr7 | 21979898 | 21979880 | − | chr7 | 21956512 | 21956372 | − | ENST00000406877; ENST00000373934 | TAF |
| 32% | chr17 | 79214190 | 79214239 | + | chr17 | 79214787 | 79214816; 79214953 | + | ENST00000431388; ENST00000576002 | TAF |
| 32% | chr17 | 79214190 | 79214239 | + | chr17 | 79214787 | 79214816; 79214953 | + | ENST00000431388; ENST00000576002 | TAF |
| 32% | chr5 | 176950016 | 176949956 | − | chr5 | 176949072 | 176948976 | − | ENST00000514747; ENST00000329540; ENST00000443375; ENST00000524677 | TAF |
| 31% | chr19 | 54631006 | 54631115 | + | chr19 | 54631448 | 54631575 | + | ENST00000321030; ENST00000419967 | TAF |
| 31% | chr19 | 54631006 | 54631115 | + | chr19 | 54631448 | 54631575 | + | ENST00000321030; ENST00000419967 | TAF |
| 31% | chr12 | 6602868 | 6602754 | − | chr12 | 6602138 | 6602028 | − | ENST00000229238 | TSF |
| 31% | chr1 | 53346099 | 53346501 | + | chr1 | 53347143 | 53347337 | + | ENST00000371532; ENST00000371528 | TSF |
| 31% | chr3 | 48252382 | 48252880 | + | chr3 | 48265844 | 48265951 | + | ENST00000296435; ENST00000576243 | TSF |
| 29% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 29% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 29% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 29% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 29% | chr2 | 38983894 | 38983132 | − | chr2 | 38977336 | 38977156 | − | ENST00000313117; ENST00000425778; ENST00000425941; ENST00000446327; ENST00000409276; ENST00000431066; ENST00000443213 | TAF |
| 29% | chr1 | 52322378 | 52322114 | − | chr1 | 52306186 | 52305898 | − | ENST00000352171; ENST00000354831 | TSF |
| 29% | chr1 | 52322378 | 52322114 | − | chr1 | 52306186 | 52305898 | − | ENST00000352171; ENST00000354831 | TSF |
| 29% | chr19 | 39347374 | 39346206 | − | chr19 | 39338074 | 39337956 | − | ENST00000221419; ENST00000601449; ENST00000600233; ENST00000601813 | TSF |
| 29% | chr19 | 39347374 | 39346206 | − | chr19 | 39338074 | 39337956 | − | ENST00000221419; ENST00000601449; ENST00000600233; ENST00000601813 | TSF |
| 29% | chr19 | 39347374 | 39346206 | − | chr19 | 39338074 | 39337956 | − | ENST00000221419; ENST00000601449; ENST00000600233; ENST00000601813 | TSF |
| 29% | chr17 | 3367100 | 3366820 | − | chr17 | 3366061 | 3366001; 3366037 | − | ENST00000397168; ENST00000572969; ENST00000355380; ENST00000575375; ENST00000573128; ENST00000541913; ENST00000268981; ENST00000574051; ENST00000572582; ENST00000574457 | TSF |
| 29% | chr17 | 3367100 | 3366820 | − | chr17 | 3366061 | 3366001; 3366037 | − | ENST00000397168; ENST00000572969; ENST00000355380; ENST00000575375; ENST00000573128; ENST00000541913; ENST00000268981; ENST00000574051; ENST00000572582; ENST00000574457 | TSF |
| 29% | chr17 | 3367100 | 3366820 | − | chr17 | 3366061 | 3366001; 3366037 | − | ENST00000397168; ENST00000572969; ENST00000355380; ENST00000575375; ENST00000573128; ENST00000541913; ENST00000268981; ENST00000574051; ENST00000572582; ENST00000574457 | TSF |
| 29% | chr17 | 3367100 | 3366820 | − | chr17 | 3366061 | 3366001; 3366037 | − | ENST00000397168; ENST00000572969; ENST00000355380; ENST00000575375; ENST00000573128; ENST00000541913; ENST00000268981; ENST00000574051; ENST00000572582; ENST00000574457 | TSF |
| 29% | chr17 | 3367100 | 3366820 | − | chr17 | 3366061 | 3366001; 3366037 | − | ENST00000397168; ENST00000572969; ENST00000355380; ENST00000575375; ENST00000573128; ENST00000541913; ENST00000268981; ENST00000574051; ENST00000572582; ENST00000574457 | TSF |
| 28% | chr7 | 23675523 | 23676342 | + | chr7 | 23682550 | 23682734; 23682643 | + | ENST00000307471; ENST00000409765; ENST00000448353; ENST00000410069 | TSF |
| 28% | chr7 | 23675523 | 23676342 | + | chr7 | 23682550 | 23682734; 23682643 | + | ENST00000307471; ENST00000409765; ENST00000448353; ENST00000410069 | TSF |
| 28% | chr19 | 39347374 | 39346430 | − | chr19 | 39338074 | 39337956 | − | ENST00000221419; ENST00000601449; ENST00000600233; ENST00000601813 | TSF |
| 28% | chr19 | 39347374 | 39346430 | − | chr19 | 39338074 | 39337956 | − | ENST00000221419; ENST00000601449; | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 28% | chr19 | 39347374 | 39346430 | − | chr19 | 39338074 | 39337956 | − | ENST00000600233; ENST00000601813 ENST00000221419; ENST00000601449; | TSF |
| 26% | chr20 | 18495298 | 18495446 | + | chr20 | 18496294 | 18496380 | + | ENST00000450074; ENST00000262544; ENST00000336714; ENST00000377475; ENST00000377465 | TSF |
| 26% | chr20 | 18495298 | 18495446 | + | chr20 | 18496294 | 18496380 | + | ENST00000450074; ENST00000262544; ENST00000336714; ENST00000377475; ENST00000377465 | TSF |
| 25% | chr12 | 54862718 | 54862609 | − | chr12 | 54858951 | 54858851 | − | ENST00000546931; ENST00000552397; ENST00000305879 | TSF |
| 25% | chr12 | 54862718 | 54862609 | − | chr12 | 54858951 | 54858851 | − | ENST00000546931; ENST00000552397; ENST00000305879 | TSF |
| 25% | chr3 | 195593372 | 195593261 | − | chr3 | 195591058 | 195591052 | − | ENST00000416152; ENST00000381916; ENST00000333602; ENST00000428187; ENST00000392400 | TSF |
| 24% | chr4 | 39469818 | 39470047 | + | chr4 | 39471639 | 39471784 | + | ENST00000340169; ENST00000261434; ENST00000513731; ENST00000381846 | TAF |
| 24% | chr4 | 39469818 | 39470047 | + | chr4 | 39471639 | 39471784 | + | ENST00000340169; ENST00000261434; ENST00000513731; ENST00000381846 | TAF |
| 24% | chr11 | 64508144 | 64507840 | − | chr11 | 64507635 | 64507485 | − | ENST00000377494; ENST00000394432; ENST00000377497; ENST00000354024; ENST00000431822 | TAF |
| 24% | chr11 | 64508144 | 64507840 | − | chr11 | 64507635 | 64507485 | − | ENST00000377494; ENST00000394432; ENST00000377497; ENST00000354024; ENST00000431822 | TAF |
| 24% | chr11 | 64508144 | 64507840 | − | chr11 | 64507635 | 64507485 | − | ENST00000377494; ENST00000394432; ENST00000377497; ENST00000354024; ENST00000431822 | TAF |
| 24% | chr20 | 42342728 | 42342751 | + | chr20 | 42343774 | 42343923 | + | ENST00000396863; ENST00000217026 | TSF |
| 24% | chr19 | 22699420 | 22699248 | − | chr19 | 22697432 | 22697166 | − | ENST00000593802 | TSF |
| 23% | chr16 | 19723118 | 19723116 | − | chr16 | 19722762 | 19722694 | − | ENST00000219837 | TAF |
| 23% | chr3 | 10112843 | 10113019 | + | chr3 | 10114555 | 10114665 | + | ENST00000287647; ENST00000383806; ENST00000383807; ENST00000419585; ENST00000421731 | TSF |
| 23% | chr3 | 10112843 | 10113019 | + | chr3 | 10114555 | 10114665 | + | ENST00000287647; ENST00000383806; ENST00000383807; ENST00000419585; ENST00000421731 | TSF |
| 23% | chr3 | 10112843 | 10113019 | + | chr3 | 10114555 | 10114665 | + | ENST00000287647; ENST00000383806; ENST00000383807; ENST00000419585; ENST00000421731 | TSF |
| 23% | chr12 | 21426370 | 21426215 | − | chr12 | 21422701 | 21422482 | − | ENST00000307378; ENST00000452078; ENST00000458504; ENST00000537524 | TSF |
| 23% | chr21 | 27478957 | 27478879 | − | chr21 | 27462388 | 27462259 | − | ENST00000346798; ENST00000354192; ENST00000348990; ENST00000357903; ENST00000358918; ENST00000359726; ENST00000448388; ENST00000440126; ENST00000439274 | TSF |
| 23% | chr21 | 27478957 | 27478879 | − | chr21 | 27462388 | 27462259 | − | ENST00000346798; ENST00000354192; ENST00000348990; ENST00000357903; ENST00000358918; ENST00000359726; ENST00000448388; ENST00000440126; ENST00000439274 | TSF |
| 23% | chr21 | 27478957 | 27478879 | − | chr21 | 27462388 | 27462259 | − | ENST00000346798; ENST00000354192; ENST00000348990; ENST00000357903; ENST00000358918; ENST00000359726; ENST00000448388; ENST00000440126; ENST00000439274 | TSF |
| 23% | chr21 | 27478957 | 27478879 | − | chr21 | 27462388 | 27462259 | − | ENST00000346798; ENST00000354192; ENST00000348990; ENST00000357903; ENST00000358918; ENST00000359726; ENST00000448388; ENST00000440126; ENST00000439274 | TSF |
| 23% | chr21 | 27478957 | 27478879 | − | chr21 | 27462388 | 27462259 | − | ENST00000346798; ENST00000354192; ENST00000348990; ENST00000357903; ENST00000358918; ENST00000359726; ENST00000448388; ENST00000440126; ENST00000439274 | TSF |
| 23% | chr20 | 30014070 | 30014925 | + | chr20 | 30037832 | 30037977 | + | ENST00000376309 | TSF |
| 23% | chr14 | 51360331 | 51360476 | + | chr14 | 51368547 | 51368629 | + | ENST00000337334; ENST00000353130; ENST00000395752 | TSF |
| 23% | chr19 | 55501071 | 55501120 | + | chr19 | 55501390 | 55501560; 55501464 | + | ENST00000543010; ENST00000391721; ENST00000339757; ENST00000448584; ENST00000537859; ENST00000427260; ENST00000538819; ENST00000263437; ENST00000543277 | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 23% | chr19 | 55501071 | 55501120 | + | chr19 | 55501390 | 55501560; 55501464 | + | ENST00000543010; ENST00000391721; ENST00000339757; ENST00000448584; ENST00000537859; ENST00000427260; ENST00000538819; ENST00000263437; ENST00000543277 | TSF |
| 23% | chr21 | 27462714 | 27462572 | − | chr21 | 27462388 | 27462259 | − | ENST00000543010; ENST00000391721; ENST00000339757; ENST00000448584; ENST00000537859; ENST00000427260; ENST00000538819; ENST00000263437; ENST00000543277 | TSF |
| 23% | chr21 | 27462714 | 27462572 | − | chr21 | 27462388 | 27462259 | − | ENST00000543010; ENST00000391721; ENST00000339757; ENST00000448584; ENST00000537859; ENST00000427260; ENST00000538819; ENST00000263437; ENST00000543277 | TSF |
| 23% | chr21 | 27462714 | 27462572 | − | chr21 | 27462388 | 27462259 | − | ENST00000543010; ENST00000391721; ENST00000339757; ENST00000448584; ENST00000537859; ENST00000427260; ENST00000538819; ENST00000263437; ENST00000543277 | TSF |
| 23% | chr21 | 27462714 | 27462572 | − | chr21 | 27462388 | 27462259 | − | ENST00000543010; ENST00000391721; ENST00000339757; ENST00000448584; ENST00000537859; ENST00000427260; ENST00000538819; ENST00000263437; ENST00000543277 | TSF |
| 23% | chr21 | 27462714 | 27462572 | − | chr21 | 27462388 | 27462259 | − | ENST00000543010; ENST00000391721; ENST00000339757; ENST00000448584; ENST00000537859; ENST00000427260; ENST00000538819; ENST00000263437; ENST00000543277 | TSF |
| 23% | chr5 | 141373148 | 141373145 | − | chr5 | 141371485 | 141371430 | | ENST00000513454 | TSF |
| 23% | chr14 | 55484360 | 55484310 | − | chr14 | 55480314 | 55480203 | − | ENST00000360586; ENST00000455555 | TSF |
| 23% | chr14 | 55484360 | 55484310 | − | chr14 | 55480314 | 55480203 | − | ENST00000360586; ENST00000455555 | TSF |
| 22% | chr1 | 169819657 | 169819707 | + | chr1 | 169820958 | 169821077 | + | ENST00000359326; ENST00000286031 | TSF |
| 22% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 22% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 22% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 22% | chr8 | 3040579 | 3040513 | − | chr8 | 3038736 | 3038632 | − | ENST00000335551; ENST00000400186; ENST00000602723; ENST00000520002; ENST00000602557; ENST00000537824; ENST00000542608; ENST00000539096 | TSF |
| 22% | chr3 | 122500000 | 122499597 | − | chr3 | 122496753 | 122496568 | − | ENST00000383659; ENST00000306103 | TSF |
| 22% | chr3 | 122500000 | 122499597 | − | chr3 | 122496753 | 122496568 | − | ENST00000383659; ENST00000306103 | TSF |
| 21% | chr19 | 39958795 | 39959001 | + | chr19 | 39959396 | 39959501 | + | ENST00000599117; ENST00000402194; ENST00000432763; ENST00000359191; ENST00000598725 | TAF |
| 21% | chr8 | 104389530 | 104389551 | + | chr8 | 104390255 | 104390471 | + | ENST00000330295; ENST00000520337 | TAF |
| 21% | chr6 | 24710791 | 24710723 | − | chr6 | 24709139 | 24709005 | − | ENST00000378119; ENST00000540769; ENST00000378102 | TAF |
| 21% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 21% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 21% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 21% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 21% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 21% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 21% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 21% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 21% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 21% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 21% | chr1 | 6366296 | 6365480 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 21% | chr12 | 7846135 | 7846037 | − | chr12 | 7843300 | 7842474 | − | ENST00000329913 | TSF |
| 21% | chr6 | 111494644 | 111494728 | + | chr6 | 111498415 | 111498868; 111498889 | + | ENST00000368851; ENST00000439288; ENST00000419619 | TSF |
| 21% | chr6 | 111494644 | 111494728 | + | chr6 | 111498415 | 111498868; 111498889 | + | ENST00000368851; ENST00000439288; ENST00000419619 | TSF |
| 21% | chr6 | 111494644 | 111494728 | + | chr6 | 111498415 | 111498868; 111498889 | + | ENST00000368851; ENST00000439288; ENST00000419619 | TSF |
| 21% | chr1 | 156307574 | 156307468 | − | chr1 | 156305679 | 156305618 | − | ENST00000295688; ENST00000368259; ENST00000413555; ENST00000496684; ENST00000446905; ENST00000478640; ENST00000415548 | TSF |
| 21% | chr1 | 156307574 | 156307468 | − | chr1 | 156305679 | 156305618 | − | ENST00000295688; ENST00000368259; ENST00000413555; ENST00000496684; ENST00000446905; ENST00000478640; ENST00000415548 | TSF |
| 21% | chr1 | 156307574 | 156307468 | − | chr1 | 156305679 | 156305618 | − | ENST00000295688; ENST00000368259; ENST00000413555; ENST00000496684; ENST00000446905; ENST00000478640; ENST00000415548 | TSF |
| 21% | chr1 | 156307574 | 156307468 | − | chr1 | 156305679 | 156305618 | − | ENST00000295688; ENST00000368259; ENST00000413555; ENST00000496684; ENST00000446905; ENST00000478640; ENST00000415548 | TSF |
| 21% | chr1 | 156307574 | 156307468 | − | chr1 | 156305679 | 156305618 | − | ENST00000295688; ENST00000368259; ENST00000413555; ENST00000496684; ENST00000446905; ENST00000478640; ENST00000415548 | TSF |
| 21% | chr1 | 156307574 | 156307468 | − | chr1 | 156305679 | 156305618 | − | ENST00000295688; ENST00000368259; | TSF |

TABLE 60-continued

Transcript fusion for Testicular Germ Cell Tumors (TGCT) Coordinates of the fusion sequences for which the donor is the TE.

| 1' | 2' | 3' | 4' | 5' 6' | 7' | 8' | 9' 10' | 11' |
|---|---|---|---|---|---|---|---|---|
| | | | | | | | | ENST00000413555; ENST00000496684; ENST00000446905; ENST00000478640; ENST00000415548 |
| 20% | chr12 | 57899758 | 57899899 | + chr12 | 157905481 | 57905651 | + | ENST00000537638; ENST00000262027;TAF ENST00000315473 |
| 20% | chr12 | 57899758 | 57899899 | + chr12 | 157905481 | 57905651 | + | ENST00000537638; ENST00000262027;TAF ENST00000315473 |
| 20% | chr12 | 57899758 | 57899899 | + chr12 | 157905481 | 57905651 | + | ENST00000537638; ENST00000262027;TAF ENST00000315473 |
| 20% | chr16 | 89607673 | 89607792 | + chr16 | 89611056 | 89611180 | + | ENST00000268704; ENST00000569820 TAF |
| 20% | chr16 | 89607673 | 89607792 | + chr16 | 89611056 | 89611180 | + | ENST00000268704; ENST00000569820 TAF |
| 20% | chr2 | 234174801 | 234174805 | + chr2 | 234178648 | 234178713 | + | ENST00000347464; ENST00000392017;TAF ENST00000444735; ENST00000373525; ENST00000419681; ENST00000417017; ENST00000392020; ENST00000392018 |
| 20% | chr2 | 234174801 | 234174805 | + chr2 | 234178648 | 234178713 | + | ENST00000347464; ENST00000392017;TAF ENST00000444735; ENST00000373525; ENST00000419681; ENST00000417017; ENST00000392020; ENST00000392018 |
| 20% | chr2 | 234174801 | 234174805 | + chr2 | 234178648 | 234178713 | + | ENST00000347464; ENST00000392017;TAF ENST00000444735; ENST00000373525; ENST00000419681; ENST00000417017; ENST00000392020; ENST00000392018 |
| 20% | chr2 | 234174801 | 234174805 | + chr2 | 234178648 | 234178713 | + | ENST00000347464; ENST00000392017;TAF ENST00000444735; ENST00000373525; ENST00000419681; ENST00000417017; ENST00000392020; ENST00000392018 |
| 20% | chr2 | 234174801 | 234174805 | + chr2 | 234178648 | 234178713 | + | ENST00000347464; ENST00000392017;TAF ENST00000444735; ENST00000373525; ENST00000419681; ENST00000417017; ENST00000392020; ENST00000392018 |
| 20% | chr2 | 234174801 | 234174805 | + chr2 | 234178648 | 234178713 | + | ENST00000347464; ENST00000392017;TAF ENST00000444735; ENST00000373525; ENST00000419681; ENST00000417017; ENST00000392020; ENST00000392018 |
| 20% | chr1 | 113646274 | 113646407 | + chr1 | 113650216 | 113650379 | + | ENST00000361127 TAF |
| 19% | chrX | 2178048 | 2177670 | − chrX | 2161271 | 2161064; 2161103 | − | ENST00000334651; ENST00000412516 TAF |
| 19% | chrX | 2178048 | 2177670 | − chrX | 2161271 | 2161064; 2161103 | − | ENST00000334651; ENST00000412516 TAF |
| 19% | chr9 | 114402184 | 114403068 | + chr9 | 114405137 | 114405208 | + | ENST00000463589; ENST00000447096 TSF |
| 19% | chrX | 71397824 | 71398615 | + chrX | 71406311 | 71406384 | + | ENST00000218432; ENST00000423432;TSF ENST00000373669; ENST00000496835; ENST00000439980; ENST00000446576 |
| 19% | chrX | 71397824 | 71398615 | + chrX | 71406311 | 71406384 | + | ENST00000218432; ENST00000423432;TSF ENST00000373669; ENST00000496835; ENST00000439980; ENST00000446576 |
| 19% | chrX | 71397824 | 71398615 | + chrX | 71406311 | 71406384 | + | ENST00000218432; ENST00000423432;TSF ENST00000373669; ENST00000496835; ENST00000439980; ENST00000446576 |
| 19% | chrX | 71397824 | 71398615 | + chrX | 71406311 | 71406384 | + | ENST00000218432; ENST00000423432;TSF ENST00000373669; ENST00000496835; ENST00000439980; ENST00000446576 |
| 19% | chr12 | 52353922 | 52353971 | + chr12 | 52369049 | 52369288 | + | ENST00000257963; ENST00000541224;TSF ENST00000426655; ENST00000415850 |
| 19% | chr12 | 52353922 | 52353971 | + chr12 | 52369049 | 52369288 | + | ENST00000257963; ENST00000541224;TSF ENST00000426655; ENST00000415850 |
| 19% | chr12 | 52353922 | 52353971 | + chr12 | 52369049 | 52369288 | + | ENST00000257963; ENST00000541224;TSF ENST00000426655; ENST00000415850 |
| 19% | chr12 | 52353922 | 52353971 | + chr12 | 52369049 | 52369288 | + | ENST00000257963; ENST00000541224;TSF ENST00000426655; ENST00000415850 |
| 19% | chr1 | 6366296 | 6365564 | − chr1 | 6355040 | 6354924 | − | ENST00000608083; ENST00000377842;TSF ENST00000377845; ENST00000377855; ENST00000377860; ENST00000418124; ENST00000545482; ENST00000361521; ENST00000473466 |
| 19% | chr1 | 6366296 | 6365564 | − chr1 | 6355040 | 6354924 | − | ENST00000608083; ENST00000377842;TSF ENST00000377845; ENST00000377855; ENST00000377860; ENST00000418124; ENST00000545482; ENST00000361521; ENST00000473466 |
| 19% | chr1 | 6366296 | 6365564 | − chr1 | 6355040 | 6354924 | − | ENST00000608083; ENST00000377842;TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 19% | chr1 | 6366296 | 6365564 | − | chr1 | 6355040 | 6354924 | − | ENST00000377845; ENST00000377855; ENST00000377860; ENST00000418124; ENST00000545482; ENST00000361521; ENST00000473466 ENST00000608083; ENST00000377842; ENST00000377845; ENST00000377855; ENST00000377860; ENST00000418124; ENST00000545482; ENST00000361521; ENST00000473466 | TSF |
| 19% | chr11 | 76935376 | 76935283 | − | chr11 | 76928359 | 76928322; 76928345 | − | ENST00000315938; ENST00000376217 | TSF |
| 19% | chr11 | 76935376 | 76935283 | − | chr11 | 76928359 | 76928322; 76928345 | − | ENST00000315938; ENST00000376217 | TSF |
| 17% | chr9 | 131002678 | 131002811 | + | chr9 | 131004511 | 131004624 | + | ENST00000475805; ENST00000341179; ENST00000372923; ENST00000393594; ENST00000486160 | TAF |
| 17% | chr9 | 131002678 | 131002811 | + | chr9 | 131004511 | 131004624 | + | ENST00000475805; ENST00000341179; ENST00000372923; ENST00000393594; ENST00000486160 | TAF |
| 17% | chr17 | 62480131 | 62480081 | − | chr17 | 62479116 | 62479036 | − | ENST00000539111; ENST00000581355 | TAF |
| 17% | chr17 | 62480131 | 62480081 | − | chr17 | 62479116 | 62479036 | − | ENST00000539111; ENST00000581355 | TAF |
| 17% | chr19 | 15502944 | 15502761 | − | chr19 | 15491423 | 15491328 | − | ENST00000397410; ENST00000595465 | TAF |
| 17% | chr12 | 110610148 | 110610836 | + | chr12 | 110618227 | 110618376 | + | ENST00000552912; ENST00000242591; ENST00000550156 | TAF |
| 17% | chr12 | 110610148 | 110610836 | + | chr12 | 110618227 | 110618376 | + | ENST00000552912; ENST00000242591; ENST00000550156 | TAF |
| 17% | chr 12 | 102411559 | 102411198 | − | chr12 | 102406970 | 102406886 | − | ENST00000240079; ENST00000545679; ENST00000542923 | TAF |
| 17% | chr14 | 51360331 | 51362421 | + | chr14 | 51368547 | 51368629 | + | ENST00000337334; ENST00000353130; ENST00000395752 | TSF |
| 17% | chr20 | 30060256 | 30059441 | − | chr20 | 30053466 | 30053309 | − | ENST00000317676 | TSF |
| 16% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 16% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 16% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 16% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 16% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 16% | chr1 | 52496316 | 52496255 | − | chr1 | 52494302 | 52494250 | − | ENST00000371626 | TAF |
| 16% | chr3 | 48252382 | 48252840 | + | chr3 | 48265844 | 48265951 | + | ENST00000296435; ENST00000576243 | TSF |
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; | TAF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 15% | chr2 | 202003725 | 202004053 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TAF |
| 15% | chrX | 3773692 | 3773630 | − | chrX | 3735819 | 3735816 | − | ENST00000425492 | TAF |
| 15% | chr4 | 107241932 | 107242850 | + | chr4 | 107246142 | 107246275 | + | ENST00000394701 | TAF |
| 15% | chr8 | 144669798 | 144669576 | − | chr8 | 144669019 | 144668899 | − | ENST00000532741; ENST00000442189; ENST00000423316; ENST00000530616; ENST00000533749 | TAF |
| 15% | chr8 | 144669798 | 144669576 | − | chr8 | 144669019 | 144668899 | − | ENST00000532741; ENST00000442189; ENST00000423316; ENST00000530616; ENST00000533749 | TAF |
| 15% | chr8 | 144669798 | 144669576 | − | chr8 | 144669019 | 144668899 | − | ENST00000532741; ENST00000442189; ENST00000423316; ENST00000530616; ENST00000533749 | TAF |
| 15% | chr21 | 147675413 | 47675316 | − | chr21 | 147674758 | 47674690 | − | ENST00000397708; ENST00000291688 | TAF |
| 15% | chr14 | 169863275 | 69863209 | − | chr14 | 169861629 | 69861542 | − | ENST00000557016; ENST00000555373 | TAF |
| 15% | chr14 | 169863275 | 69863209 | − | chr14 | 169861629 | 69861542 | − | ENST00000557016; ENST00000555373 | TAF |
| 15% | chrX | 71397824 | 71398575 | + | chrX | 71406311 | 71406384 | + | ENST00000218432; ENST00000423432; ENST00000373669; ENST00000496835; ENST00000439980; ENST00000446576 | TSF |
| 15% | chrX | 71397824 | 71398575 | + | chrX | 71406311 | 71406384 | + | ENST00000218432; ENST00000423432; ENST00000373669; ENST00000496835; ENST00000439980; ENST00000446576 | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 15% | chrX | 71397824 | 71398575 | + | chrX | 71406311 | 71406384 | + | ENST00000218432; ENST00000423432; ENST00000373669; ENST00000496835; ENST00000439980; ENST00000446576 | TSF |
| 15% | chrX | 71397824 | 71398575 | + | chrX | 71406311 | 71406384 | + | ENST00000218432; ENST00000423432; ENST00000373669; ENST00000496835; ENST00000439980; ENST00000446576 | TSF |
| 15% | chr21 | 43944863 | 43945289 | + | chr21 | 43945886 | 43945967 | + | ENST00000398341; ENST00000352133 | TSF |
| 14% | chr9 | 139611399 | 139611665 | + | chr9 | 139612029 | 139612163 | + | ENST00000371692 | TAF |
| 14% | chr12 | 22637180 | 22637151 | − | chr12 | 22635677 | 22635491 | − | ENST00000333957; ENST00000396028; ENST00000446597; ENST00000536386; ENST00000542676; ENST00000544930; ENST00000545552 | TAF |
| 14% | chr12 | 22637180 | 22637151 | − | chr12 | 22635677 | 22635491 | − | ENST00000333957; ENST00000396028; ENST00000446597; ENST00000536386; ENST00000542676; ENST00000544930; ENST00000545552 | TAF |
| 14% | chr12 | 22637180 | 22637151 | − | chr12 | 22635677 | 22635491 | − | ENST00000333957; ENST00000396028; ENST00000446597; ENST00000536386; ENST00000542676; ENST00000544930; ENST00000545552 | TAF |
| 14% | chr10 | 101952336 | 101952216 | − | chr10 | 101950725 | 101950626 | − | ENST00000370397 | TAF |
| 14% | chr2 | 30474925 | 30475183 | + | chr2 | 30480299 | 30480487; 30480324 | + | ENST00000395323; ENST00000406087; ENST00000401506; ENST00000407930 | TSF |
| 14% | chr2 | 30474925 | 30475183 | + | chr2 | 30480299 | 30480487; 30480324 | + | ENST00000395323; ENST00000406087; ENST00000401506; ENST00000407930 | TSF |
| 14% | chr20 | 30058231 | 05307772 | − | chr20 | 30053466 | 30053309 | − | ENST00000317676 | TSF |
| 13% | chr17 | 426168 | 426165 | − | chr17 | 424978 | 424841 | − | ENST00000437048 | TAF |
| 13% | chr22 | 19971218 | 19971196 | − | chr22 | 19969614 | 19969456 | − | ENST00000263207; ENST00000344269; ENST00000401994; ENST00000406522; ENST00000406259 | TAF |
| 13% | chr22 | 19971218 | 19971196 | − | chr22 | 19969614 | 19969456 | − | ENST00000263207; ENST00000344269; ENST00000401994; ENST00000406522; ENST00000406259 | TAF |
| 13% | chr12 | 64687157 | 64687061 | − | chr12 | 64679840 | 64679734 | − | ENST00000543942; ENST00000333722 | TAF |
| 13% | chr1 | 41465686 | 41465756 | + | chr1 | 41466701 | 41466789 | + | ENST00000372621; ENST00000541520; ENST00000372616 | TSF |
| 13% | chr20 | 30023971 | 30024331 | + | chr20 | 30037832 | 30037977 | + | ENST00000376309 | TSF |
| 13% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 13% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 13% | chr19 | 55449720 | 55449717 | − | chr19 | 55449609 | 55449412 | − | ENST00000340844; ENST00000590030; ENST00000446217; ENST00000588756; ENST00000586379; ENST00000592784 | TSF |
| 13% | chr19 | 1114930 | 1114676 | − | chr19 | 1114421 | 1114230 | − | ENST00000361757; ENST00000587024; ENST00000438103 | TSF |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TSF |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TSF |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TSF |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TSF |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TSF |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TSF |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TSF |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TSF |
| 13% | chr2 | 202003725 | 202004664 | + | chr2 | 202005080 | 202005162; 202005198 | + | ENST00000309955; ENST00000443227; ENST00000341222; ENST00000340870; ENST00000355558; ENST00000341582; ENST00000342795; ENST00000423241; ENST00000439154; ENST00000440180; ENST00000457277; ENST00000494258; ENST00000470178; ENST00000462763; ENST00000479953 | TSF |
| 13% | chr19 | 340691 | 340514 | − | chr19 | 336173 | 336083 | − | ENST00000264819 | TSF |
| 12% | chr12 | 118466627 | 118466694 | + | chr12 | 118467576 | 118467630 | + | ENST00000229043; ENST00000454402; ENST00000392542 | TAF |
| 12% | chr17 | 4908417 | 149081701 | + | chr17 | 4910210 | 4910379 | + | ENST00000320785 | TAF |
| 12% | chr17 | 27054938 | 27054837 | − | chr17 | 27052581 | 27052499 | − | ENST00000292090; ENST00000394933 | TAF |
| 12% | chr12 | 50538043 | 50537986 | − | chr12 | 50537840 | 50537735 | − | ENST00000551697; ENST00000380189; ENST00000317551; ENST00000422340; ENST00000542320; ENST00000547800 | TAF |
| 12% | chr12 | 50538043 | 50537986 | − | chr12 | 50537840 | 50537735 | − | ENST00000551697; ENST00000380189; ENST00000317551; ENST00000422340; ENST00000542320; ENST00000547800 | TAF |
| 12% | chr12 | 50538043 | 50537986 | − | chr12 | 50537840 | 50537735 | − | ENST00000551697; ENST00000380189; ENST00000317551; ENST00000422340; ENST00000542320; ENST00000547800 | TAF |
| 12% | chr12 | 50538043 | 50537986 | − | chr12 | 50537840 | 50537735 | − | ENST00000551697; ENST00000380189; ENST00000317551; ENST00000422340; | TAF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 12% | chr6 | 151739722 | 151739668 | − | chr6 | 151738534 | 151738414; 151738471 | − | ENST00000542320; ENST00000547800 ENST00000336451; ENST00000367303; ENST00000444024 | TAF |
| 12% | chr6 | 151739722 | 151739668 | − | chr6 | 151738534 | 151738414; 151738471 | − | ENST00000336451; ENST00000367303; ENST00000444024 | TAF |
| 12% | chr1 | 156312383 | 156312456 | + | chr1 | 156314371 | 156314499 | + | ENST00000368255; ENST00000368253; ENST00000470342; ENST00000368254; ENST00000481479; ENST00000368252; ENST00000466306; ENST00000368251 | TSF |
| 12% | chr1 | 156312383 | 156312456 | + | chr1 | 156314371 | 156314499 | + | ENST00000368255; ENST00000368253; ENST00000470342; ENST00000368254; ENST00000481479; ENST00000368252; ENST00000466306; ENST00000368251 | TSF |
| 12% | chr7 | 55477082 | 55477474 | + | chr7 | 55479600 | 55479782 | + | ENST00000254770 | TSF |
| 12% | chr14 | 20973494 | 20974255 | + | chr14 | 20978626 | 20979281 | + | ENST00000430083 | TSF |
| 12% | chr16 | 48451457 | 48450727 | − | chr16 | 48396341 | 48395491 | − | ENST00000356721 | TSF |
| 11% | chr2 | 232369617 | 232369808 | + | chr2 | 232576600 | 232576693 | + | ENST00000409321; ENST00000409115; ENST00000341369; ENST00000409683; ENST00000410064; ENST00000412128 | TAF |
| 11% | chr2 | 232369617 | 232369808 | + | chr2 | 232576600 | 232576693 | + | ENST00000409321; ENST00000409115; ENST00000341369; ENST00000409683; ENST00000410064; ENST00000412128 | TAF |
| 11% | chr15 | 78810978 | 78811115 | + | chr15 | 78819722 | 78819905; 78819925 | + | ENST00000388988; ENST00000408962; ENST00000566332; ENST00000569878; ENST00000563233 | TAF |
| 11% | chr15 | 78810978 | 78811115 | + | chr15 | 78819722 | 78819905; 78819925 | + | ENST00000388988; ENST00000408962; ENST00000566332; ENST00000569878; ENST00000563233 | TAF |
| 11% | chr15 | 78810978 | 78811115 | + | chr15 | 78819722 | 78819905; 78819925 | + | ENST00000388988; ENST00000408962; ENST00000566332; ENST00000569878; ENST00000563233 | TAF |
| 11% | chr1 | 224551810 | 224551900 | + | chr1 | 224553581 | 224553693 | + | ENST00000465271; ENST00000366858; ENST00000366857; ENST00000366856 | TAF |
| 11% | chr1 | 224551810 | 224551900 | + | chr1 | 224553581 | 224553693 | + | ENST00000465271; ENST00000366858; ENST00000366857; ENST00000366856 | TAF |
| 11% | chr1 | 224551810 | 224551900 | + | chr1 | 224553581 | 224553693 | + | ENST00000465271; ENST00000366858; ENST00000366857; ENST00000366856 | TAF |
| 11% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr21 | 42597177 | 42597622 | + | chr21 | 42598193 | 42598281 | + | ENST00000328735; ENST00000330333; ENST00000347667 | TAF |
| 11% | chr21 | 42597177 | 42597622 | + | chr21 | 42598193 | 42598281 | + | ENST00000328735; ENST00000330333; ENST00000347667 | TAF |
| 11% | chr21 | 42597177 | 42597622 | + | chr21 | 42598193 | 42598281 | + | ENST00000328735; ENST00000330333; ENST00000347667 | TAF |
| 11% | chr2 | 42871686 | 42872096 | + | chr2 | 42883340 | 42883442 | + | ENST00000405592; ENST00000406652; ENST00000407270; ENST00000454356; ENST00000406911; ENST00000409019; ENST00000405094 | TAF |
| 11% | chr2 | 42871686 | 42872096 | + | chr2 | 42883340 | 42883442 | + | ENST00000405592; ENST00000406652; ENST00000407270; ENST00000454356; ENST00000406911; ENST00000409019; ENST00000405094 | TAF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 11% | chr2 | 42871686 | 42872096 | + | chr2 | 42883340 | 42883442 | + | ENST00000405592; ENST00000406652; ENST00000407270; ENST00000454356; ENST00000406911; ENST00000409019; ENST00000405094 | TAF |
| 11% | chr2 | 42871686 | 42872096 | + | chr2 | 42883340 | 42883442 | + | ENST00000405592; ENST00000406652; ENST00000407270; ENST00000454356; ENST00000406911; ENST00000409019; ENST00000405094 | TAF |
| 11% | chr2 | 42871686 | 42872096 | + | chr2 | 42883340 | 42883442 | + | ENST00000405592; ENST00000406652; ENST00000407270; ENST00000454356; ENST00000406911; ENST00000409019; ENST00000405094 | TAF |
| 11% | chr2 | 42871686 | 42872096 | + | chr2 | 42883340 | 42883442 | + | ENST00000405592; ENST00000406652; ENST00000407270; ENST00000454356; ENST00000406911; ENST00000409019; ENST00000405094 | TAF |
| 11% | chr20 | 2775864 | 2775377 | − | chr20 | 2775285 | 2775183 | − | ENST00000380605 | TAF |
| 11% | chr11 | 322262 | 322206 | − | chr11 | 320772 | 320565 | − | ENST00000399808 | TAF |
| 11% | chr11 | 321450 | 321426 | − | chr11 | 320772 | 320565 | − | ENST00000399808 | TAF |
| 11% | chr7 | 150938296 | 150938250 | − | chr7 | 150937608 | 150937511 | − | ENST00000262188; ENST00000392811; ENST00000356800 | TAF |
| 11% | chr11 | 321638 | 321543 | − | chr11 | 320772 | 320565 | − | ENST00000399808 | TAF |
| 11% | chr11 | 321638 | 321504 | − | chr11 | 320772 | 320565 | − | ENST00000399808 | TAF |
| 11% | chr11 | 321488 | 321465 | − | chr11 | 320772 | 320565 | − | ENST00000399808 | TAF |
| 11% | chr11 | 322580 | 322557 | − | chr11 | 320772 | 320565 | − | ENST00000399808 | TAF |
| 11% | chr21 | 27438394 | 27438253 | − | chr21 | 27425664 | 27425552 | − | ENST00000346798; ENST00000354192; ENST00000348990; ENST00000357903; ENST00000358918; ENST00000359726; ENST00000448388; ENST00000440126; ENST00000439274; ENST00000448850 | TAF |
| 11% | chr21 | 27438394 | 27438253 | − | chr21 | 27425664 | 27425552 | − | ENST00000346798; ENST00000354192; ENST00000348990; ENST00000357903; ENST00000358918; ENST00000359726; ENST00000448388; ENST00000440126; ENST00000439274; ENST00000448850 | TAF |
| 11% | chr21 | 27438394 | 27438253 | − | chr21 | 27425664 | 27425552 | − | ENST00000346798; ENST00000354192; ENST00000348990; ENST00000357903; ENST00000358918; ENST00000359726; ENST00000448388; ENST00000440126; ENST00000439274; ENST00000448850 | TAF |
| 11% | chr21 | 27438394 | 27438253 | − | chr21 | 27425664 | 27425552 | − | ENST00000346798; ENST00000354192; ENST00000348990; ENST00000357903; ENST00000358918; ENST00000359726; ENST00000448388; ENST00000440126; ENST00000439274; ENST00000448850 | TAF |
| 11% | chr21 | 27438394 | 27438253 | − | chr21 | 27425664 | 27425552 | − | ENST00000346798; ENST00000354192; ENST00000348990; ENST00000357903; ENST00000358918; ENST00000359726; ENST00000448388; ENST00000440126; ENST00000439274; ENST00000448850 | TAF |
| 11% | chr21 | 27438394 | 27438253 | − | chr21 | 27425664 | 27425552 | − | ENST00000346798; ENST00000354192; ENST00000348990; ENST00000357903; ENST00000358918; ENST00000359726; ENST00000448388; ENST00000440126; ENST00000439274; ENST00000448850 | TAF |
| 11% | chr11 | 321410 | 321387 | − | chr11 | 320772 | 320565 | − | ENST00000399808 | TAF |
| 11% | chr19 | 39347374 | 39346635 | − | chr19 | 39338074 | 39337956 | − | ENST00000221419; ENST00000601449; ENST00000600233; ENST00000601813 | TAF |
| 11% | chr19 | 39347374 | 39346635 | − | chr19 | 39338074 | 39337956 | − | ENST00000221419; ENST00000601449; ENST00000600233; ENST00000601813 | TAF |
| 11% | chr19 | 39347374 | 39346635 | − | chr19 | 39338074 | 39337956 | − | ENST00000221419; ENST00000601449; ENST00000600233; ENST00000601813 | TAF |
| 11% | chr11 | 321638 | 321582 | − | chr11 | 320772 | 320565 | − | ENST00000399808 | TAF |
| 11% | chr11 | 321716 | 321660 | − | chr11 | 320772 | 320565 | − | ENST00000399808 | TAF |
| 11% | chr11 | 322067 | 322011 | − | chr11 | 320772 | 320565 | − | ENST00000399808 | TAF |
| 11% | chr11 | 322457 | 322401 | − | chr11 | 320772 | 320565 | − | ENST00000399808 | TAF |
| 11% | chr11 | 321911 | 321855 | − | chr11 | 320772 | 320565 | − | ENST00000399808 | TAF |
| 11% | chr8 | 17865642 | 17865919 | + | chr8 | 17867056 | 17867253 | + | ENST00000325083; ENST00000519253; ENST00000524226; ENST00000327578; ENST00000522275 | TSF |
| 11% | chr8 | 17865642 | 17865919 | + | chr8 | 17867056 | 17867253 | + | ENST00000325083; ENST00000519253; ENST00000524226; ENST00000327578; ENST00000522275 | TSF |
| 11% | chr3 | 122500000 | 122499677 | − | chr3 | 122496753 | 122496568 | − | ENST00000383659; ENST00000306103 | TSF |
| 11% | chr3 | 122500000 | 122499677 | − | chr3 | 122496753 | 122496568 | − | ENST00000383659; ENST00000306103 | TSF |
| 11% | chr12 | 48058419 | 48058373 | − | chr12 | 48057373 | 48057288 | − | ENST00000005386; ENST00000432584 | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| | | | | | | | | | ENST00000380650 | |
| 11% | chr 4 | 146620427 | 146622789 | + | chr4 | 146648063 | 146648121 | + | ENST00000438731; ENST00000511965 | TSF |
| 11% | chr1 | 6366296 | 6365322 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 11% | chr1 | 6366296 | 6365322 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 11% | chr1 | 6366296 | 6365322 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 11% | chr1 | 6366296 | 6365322 | − | chr1 | 6355040 | 6354924 | − | ENST00000608083; ENST00000377842; ENST00000377845; ENST00000377855; ENST00000377860; ENST00000418124; ENST00000545482; ENST00000361521; ENST00000473466 | TSF |
| 11% | chr7 | 100418501 | 100418218 | − | chr7 | 100417918 | 100417763 | − | ENST00000360620; ENST00000358173 | TSF |
| 11% | chr7 | 100418501 | 100418218 | − | chr7 | 100417918 | 100417763 | − | ENST00000360620; ENST00000358173 | TSF |
| 10% | chr10 | 199600727 | 99601473 | + | chr10 | 199619215 | 99619340 | + | ENST00000370602 | TSF |
| 10% | chrX | 123618682 | 123617816 | − | chrX | 123615814 | 123615582 | − | ENST00000371130; ENST00000422452 | TSF |
| 10% | chr1 | 49723490 | 49723396 | − | chr1 | 49711536 | 49711442 | − | ENST00000371839; ENST00000371838; ENST00000371836 | TSF |
| 10% | chr1 | 49723490 | 49723396 | − | chr1 | 49711536 | 49711442 | − | ENST00000371839; ENST00000371838; ENST00000371836 | TSF |
| 10% | chr1 | 49723490 | 49723396 | − | chr1 | 49711536 | 49711442 | − | ENST00000371839; ENST00000371838; ENST00000371836 | TSF |
| 9% | chr7 | 26211486 | 26211491 | + | chr7 | 26217563 | 26217742 | + | ENST00000056233 | TSF |
| 9% | chr12 | 12966683 | 12966871 | + | chr12 | 12967065 | 12967158 | + | ENST00000352940; ENST00000358007; ENST00000544400 | TSF |
| 9% | chr12 | 12966683 | 12966871 | + | chr12 | 12967065 | 12967158 | + | ENST00000352940; ENST00000358007; ENST00000544400 | TSF |
| 9% | chr12 | 12966683 | 12966871 | + | chr12 | 12967065 | 12967158 | + | ENST00000352940; ENST00000358007; ENST00000544400 | TSF |
| 9% | chr2 | 88804201 | 88804412 | + | chr2 | 88825923 | 88826015 | + | ENST00000303254 | TSF |
| 9% | chr3 | 48252382 | 48252880 | + | chr3 | 148265095 | 48265202 | + | ENST00000296435; ENST00000576243 | TSF |
| 9% | chr3 | 122500000 | 122499637 | − | chr3 | 122496753 | 122496568 | − | ENST00000383659; ENST00000306103 | TSF |
| 9% | chr3 | 122500000 | 122499637 | − | chr3 | 122496753 | 122496568 | − | ENST00000383659; ENST00000306103 | TSF |
| 9% | chr3 | 146129390 | 146129180 | − | chr3 | 146113708 | 146113692 | − | ENST00000463633 | TSF |
| 9% | chr3 | 31668605 | 31668931 | + | chr3 | 31670790 | 31670903 | + | ENST00000295770 | TSF |
| 9% | chr21 | 37509492 | 37509497 | + | chr21 | 37510123 | 37510230 | + | ENST00000290354 | TSF |
| 9% | chr1 | 27158561 | 27158563 | + | chr1 | 27158938 | 27159098 | + | ENST00000374142 | TSF |
| 9% | chr4 | 146643833 | 146644154 | + | chr4 | 146648063 | 146648121 | + | ENST00000438731; ENST00000511965 | TSF |
| 9% | chr4 | 56766766 | 56766858 | + | chr4 | 56768510 | 56768704 | + | ENST00000381295; ENST00000346134; ENST00000349598 | TSF |
| 9% | chr9 | 114402184 | 114403028 | + | chr9 | 114405137 | 114405208 | + | ENST00000463589; ENST00000447096 | TSF |
| 9% | chr20 | 30060256 | 30059401 | − | chr20 | 30053466 | 30053309 | − | ENST00000317676 | TSF |
| 9% | chr6 | 151732076 | 151731988 | − | chr6 | 151726971 | 151726855 | − | ENST00000336451; ENST00000367303 | TSF |
| 9% | chr3 | 112200904 | 112200031 | − | chr3 | 112198616 | 112198302 | − | ENST00000334529; ENST00000383680 | TSF |
| 9% | chr3 | 112200904 | 112200031 | − | chr3 | 112198616 | 112198302 | − | ENST00000334529; ENST00000383680 | TSF |
| 9% | chr6 | 123908749 | 123908604 | − | chr6 | 123892277 | 123892068 | − | ENST00000398178; ENST00000334268; ENST00000546248; ENST00000542443 | TSF |
| 9% | chr6 | 123908749 | 123908604 | − | chr6 | 123892277 | 123892068 | − | ENST00000398178; ENST00000334268; ENST00000546248; ENST00000542443 | TSF |
| 9% | chr6 | 123908749 | 123908604 | − | chr6 | 123892277 | 123892068 | − | ENST00000398178; ENST00000334268; ENST00000546248; ENST00000542443 | TSF |
| 9% | chr6 | 123908749 | 123908604 | − | chr6 | 123892277 | 123892068 | − | ENST00000398178; ENST00000334268; ENST00000546248; ENST00000542443 | TSF |
| 8% | chr7 | 20707326 | 20708050 | + | chr7 | 20721128 | 20721289 | + | ENST00000404938; ENST00000258738 | TSF |
| 8% | chr3 | 10111144 | 10111811 | + | chr3 | 10114555 | 10114665 | + | ENST00000287647; ENST00000383806; ENST00000383807; ENST00000419585; ENST00000421731 | TSF |
| 8% | chr3 | 10111144 | 10111811 | + | chr3 | 10114555 | 10114665 | + | ENST00000287647; ENST00000383806; ENST00000383807; ENST00000419585; ENST00000421731 | TSF |
| 8% | chr3 | 10111144 | 10111811 | + | chr3 | 10114555 | 10114665 | + | ENST00000287647; ENST00000383806; ENST00000383807; ENST00000419585; ENST00000421731 | TSF |
| 8% | chr12 | 110610148 | 110610701 | + | chr12 | 110618227 | 110618376 | + | ENST00000552912; ENST00000242591; ENST00000550156 | TSF |
| 8% | chr12 | 110610148 | 110610701 | + | chr12 | 110618227 | 110618376 | + | ENST00000552912; ENST00000242591 | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 8% | chr5 | 176950016 | 176949947 | − | chr5 | 176949072 | 176948976 | − | ENST00000550156; ENST00000514747; ENST00000329540; ENST00000443375; ENST00000524677 | TSF |
| 8% | chr16 | 23605688 | 23605658 | − | chr16 | 23598640 | 23598518 | − | ENST00000007516; ENST00000570319 | TSF |
| 8% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 8% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 8% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 8% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 8% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 8% | chr1 | 156305455 | 156305264 | − | chr1 | 156304709 | 156304659 | − | ENST00000295688; ENST00000368258; ENST00000413555; ENST00000496684; ENST00000478640; ENST00000415548 | TSF |
| 7% | chr10 | 94734302 | 94735028 | + | chr10 | 94757231 | 94757372 | + | ENST00000371547; ENST00000371552; ENST00000443748; ENST00000260762; ENST00000495132; ENST00000458552 | TSF |
| 7% | chr10 | 94734302 | 94735028 | + | chr10 | 94757231 | 94757372 | + | ENST00000371547; ENST00000371552; ENST00000443748; ENST00000260762; ENST00000495132; ENST00000458552 | TSF |
| 7% | chr10 | 94734302 | 94735028 | + | chr10 | 94757231 | 94757372 | + | ENST00000371547; ENST00000371552; ENST00000443748; ENST00000260762; ENST00000495132; ENST00000458552 | TSF |
| 7% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 7% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 7% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 7% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 7% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 7% | chrX | 47057962 | 47058027 | + | chrX | 47058202 | 47058318 | + | ENST00000377351; ENST00000412206; ENST00000427561; ENST00000442035; ENST00000457753; ENST00000335972; ENST00000451702 | TSF |
| 7% | chr7 | 56018506 | 56018522 | + | chr7 | 56020872 | 56021011 | + | ENST00000426595 | TSF |
| 7% | chr8 | 30984245 | 30984432 | + | chr8 | 30989881 | 30990022 | + | ENST00000298139 | TSF |
| 7% | chr12 | 4948345 | 4948527 | + | chr12 | 14959904 | 4960077 | + | ENST00000542998 | TSF |
| 7% | chr1 | 17371820 | 17371636 | − | chr1 | 17371383 | 17371256 | − | ENST00000375499 | |
| 7% | chr7 | 95988433 | 95987766 | − | chr7 | 95926263 | 95926210 | − | ENST00000265631; ENST00000416240; ENST00000472162 | TSF |
| 7% | chr7 | 95988433 | 95987766 | − | chr7 | 95926263 | 95926210 | − | ENST00000265631; ENST00000416240; ENST00000472162 | TSF |
| 7% | chr7 | 95988433 | 95987766 | − | chr7 | 95926263 | 95926210 | − | ENST00000265631; ENST00000416240; ENST00000472162 | TSF |
| 7% | chr6 | 13616316 | 13616338 | + | chr6 | 13616695 | 13616753 | + | ENST00000451315; ENST00000420088 | TSF |
| 7% | chr6 | 13616316 | 13616338 | + | chr6 | 13616695 | 13616753 | + | ENST00000451315; ENST00000420088 | TSF |
| 7% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 7% | chr2 | 238935895 | 238935906 | + | chr2 | 238939197 | 238939220; 238939254; | + | ENST00000441728; ENST00000272930; ENST00000448502; ENST00000416292; | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| | | | | | | | 238939236; 238939204 | | ENST00000409633; ENST00000449891; ENST00000455999; ENST00000445676; ENST00000414443; ENST00000409953; ENST00000409332; ENST00000434655; ENST00000434137 | |
| 7% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 7% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 7% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 7% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 7% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 7% | chr2 | 238935895 | 238935906 | + | chr2 | 238939197 | 238939220; 238939254; 238939236; 238939204 | + | ENST00000441728; ENST00000272930; ENST00000448502; ENST00000416292; ENST00000409633; ENST00000449891; ENST00000455999; ENST00000445676; ENST00000414443; ENST00000409953; ENST00000409332; ENST00000434655; ENST00000434137 | TSF |
| 7% | chr8 | 31016146 | 31016403 | + | chr8 | 31024538 | 31024746 | + | ENST00000298139 | TSF |
| 7% | chr6 | 31501566 | 31501436 | − | chr6 | 31500688 | 31500557 | − | ENST00000484566; ENST00000376177; ENST00000396172; ENST00000417556; ENST00000458640; ENST00000415382; ENST00000417023; ENST00000431908; ENST00000427214 | TSF |
| 7% | chr6 | 31501566 | 31501436 | − | chr6 | 31500688 | 31500557 | − | ENST00000484566; ENST00000376177; ENST00000396172; ENST00000417556; ENST00000458640; ENST00000415382; ENST00000417023; ENST00000431908; ENST00000427214 | TSF |
| 7% | chr6 | 31501566 | 31501436 | − | chr6 | 31500688 | 31500557 | − | ENST00000484566; ENST00000376177; ENST00000396172; ENST00000417556; ENST00000458640; ENST00000415382; ENST00000417023; ENST00000431908; ENST00000427214 | TSF |
| 7% | chr6 | 31501566 | 31501436 | − | chr6 | 31500688 | 31500557 | − | ENST00000484566; ENST00000376177; ENST00000396172; ENST00000417556; ENST00000458640; ENST00000415382; ENST00000417023; ENST00000431908; ENST00000427214 | TSF |
| 7% | chr6 | 31501566 | 31501436 | − | chr6 | 31500688 | 31500557 | − | ENST00000484566; ENST00000376177; ENST00000396172; ENST00000417556; ENST00000458640; ENST00000415382; ENST00000417023; ENST00000431908; ENST00000427214 | TSF |
| 7% | chr6 | 31501566 | 31501436 | − | chr6 | 31500688 | 31500557 | − | ENST00000484566; ENST00000376177; ENST00000396172; ENST00000417556; ENST00000458640; ENST00000415382; | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| | | | | | | | | | ENST00000417023; ENST00000431908; ENST00000427214 | |
| 7% | chr6 | 31660537 | 31660355 | – | chr6 | 31659695 | 31659581 | – | ENST00000395952; ENST00000440843 | TSF |
| 7% | chr12 | 14670381 | 14670239 | – | chr12 | 14664645 | 14664445 | – | ENST00000240617 | TSF |
| 7% | chr17 | 5014630 | 5014371 | – | chr17 | 5013063 | 5012689; 5012527 | – | ENST00000575898; ENST00000250076; ENST00000416429 | TSF |
| 7% | chr17 | 5014630 | 5014371 | – | chr17 | 5013063 | 5012689; 5012527 | – | ENST00000575898; ENST00000250076; ENST00000416429 | TSF |
| 7% | chr17 | 5014630 | 5014371 | – | chr17 | 5013063 | 5012689; 5012527 | – | ENST00000575898; ENST00000250076; ENST00000416429 | TSF |
| 7% | chr1 | 6366296 | 6365524 | – | chr1 | 6355040 | 6354924 | – | ENST00000608083; ENST00000377842; ENST00000377845; ENST00000377855; ENST00000377860; ENST00000418124; ENST00000545482; ENST00000361521; ENST00000473466 | TSF |
| 7% | chr1 | 6366296 | 6365524 | – | chr1 | 6355040 | 6354924 | – | ENST00000608083; ENST00000377842; ENST00000377845; ENST00000377855; ENST00000377860; ENST00000418124; ENST00000545482; ENST00000361521; ENST00000473466 | TSF |
| 7% | chr1 | 6366296 | 6365524 | – | chr1 | 6355040 | 6354924 | – | ENST00000608083; ENST00000377842; ENST00000377845; ENST00000377855; ENST00000377860; ENST00000418124; ENST00000545482; ENST00000361521; ENST00000473466 | TSF |
| 7% | chr1 | 6366296 | 6365524 | – | chr1 | 6355040 | 6354924 | – | ENST00000608083; ENST00000377842; ENST00000377845; ENST00000377855; ENST00000377860; ENST00000418124; ENST00000545482; ENST00000361521; ENST00000473466 | TSF |
| 6% | chr1 | 113646274 | 113646357 | + | chr1 | 113650216 | 113650379 | + | ENST00000361127 | TSF |
| 6% | chr6 | 37326936 | 37327118 | + | chr6 | 37328222 | 37328350 | + | ENST00000373479; ENST00000229866; ENST00000394443; ENST00000469316; ENST00000469731 | TSF |
| 6% | chr6 | 37326936 | 37327118 | + | chr6 | 37328222 | 37328350 | + | ENST00000373479; ENST00000229866; ENST00000394443; ENST00000469316; ENST00000469731 | TSF |
| 6% | chr6 | 37326936 | 37327118 | + | chr6 | 37328222 | 37328350 | + | ENST00000373479; ENST00000229866; ENST00000394443; ENST00000469316; ENST00000469731 | TSF |
| 6% | chr6 | 37326936 | 37327118 | + | chr6 | 37328222 | 37328350 | + | ENST00000373479; ENST00000229866; ENST00000394443; ENST00000469316; ENST00000469731 | TSF |
| 6% | chr11 | 57495862 | 57495928 | + | chr11 | 57505080 | 57505140 | + | ENST00000524972; ENST00000378312; ENST00000528395; ENST00000530114; ENST00000278422; ENST00000525035; ENST00000533602; ENST00000528110; ENST00000529403 | TSF |
| 6% | chr11 | 57495862 | 57495928 | + | chr11 | 57505080 | 57505140 | + | ENST00000524972; ENST00000378312; ENST00000528395; ENST00000530114; ENST00000278422; ENST00000525035; ENST00000533602; ENST00000528110; ENST00000529403 | TSF |
| 6% | chr11 | 57495862 | 57495928 | + | chr11 | 57505080 | 57505140 | + | ENST00000524972; ENST00000378312; ENST00000528395; ENST00000530114; ENST00000278422; ENST00000525035; ENST00000533602; ENST00000528110; ENST00000529403 | TSF |
| 6% | chr11 | 57495862 | 57495928 | + | chr11 | 57505080 | 57505140 | + | ENST00000524972; ENST00000378312; ENST00000528395; ENST00000530114; ENST00000278422; ENST00000525035; ENST00000533602; ENST00000528110; ENST00000529403 | TSF |
| 6% | chr11 | 57495862 | 57495928 | + | chr11 | 57505080 | 57505140 | + | ENST00000524972; ENST00000378312; ENST00000528395; ENST00000530114; ENST00000278422; ENST00000525035; ENST00000533602; ENST00000528110; ENST00000529403 | TSF |
| 6% | chr11 | 57495862 | 57495928 | + | chr11 | 57505080 | 57505140 | + | ENST00000524972; ENST00000378312; ENST00000528395; ENST00000530114; ENST00000278422; ENST00000525035; | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 6% | chrX | 71397824 | 71398575 | + | chrX | 71416635 | 71416778; 71416754 | + | ENST00000533602; ENST00000528110; ENST00000529403 ENST00000218432; ENST00000423432; ENST00000373669; ENST00000496835; ENST00000439980; ENST00000446576 | TSF |
| 6% | chrX | 71397824 | 71398575 | + | chrX | 71416635 | 71416778; 71416754 | + | ENST00000218432; ENST00000423432; ENST00000373669; ENST00000496835; ENST00000439980; ENST00000446576 | TSF |
| 6% | chrX | 71397824 | 71398575 | + | chrX | 71416635 | 71416778; 71416754 | + | ENST00000218432; ENST00000423432; ENST00000373669; ENST00000496835; ENST00000439980; ENST00000446576 | TSF |
| 6% | chrX | 71397824 | 71398575 | + | chrX | 71416635 | 71416778; 71416754 | + | ENST00000218432; ENST00000423432; ENST00000373669; ENST00000496835; ENST00000439980; ENST00000446576 | TSF |
| 6% | chr10 | 76984123 | 76984287 | + | chr10 | 76989402 | 76989459 | + | ENST00000298468; ENST00000543351; ENST00000332211; ENST00000535553; ENST00000313132 | TSF |
| 6% | chr10 | 76984123 | 76984287 | + | chr10 | 76989402 | 76989459 | + | ENST00000298468; ENST00000543351; ENST00000332211; ENST00000535553; ENST00000313132 | TSF |
| 6% | chr1 | 27158295 | 27158544 | + | chr1 | 27158938 | 27159098 | + | ENST00000374142 | TSF |
| 6% | chrX | 71397824 | 71398498 | + | chrX | 71416635 | 71416778; 71416754 | + | ENST00000218432; ENST00000423432; ENST00000373669; ENST00000496835; ENST00000439980; ENST00000446576 | TSF |
| 6% | chrX | 71397824 | 71398498 | + | chrX | 71416635 | 71416778; 71416754 | + | ENST00000218432; ENST00000423432; ENST00000373669; ENST00000496835; ENST00000439980; ENST00000446576 | TSF |
| 6% | chrX | 71397824 | 71398498 | + | chrX | 71416635 | 71416778; 71416754 | + | ENST00000218432; ENST00000423432; ENST00000373669; ENST00000496835; ENST00000439980; ENST00000446576 | TSF |
| 6% | chrX | 71397824 | 71398498 | + | chrX | 71416635 | 71416778; 71416754 | + | ENST00000218432; ENST00000423432; ENST00000373669; ENST00000496835; ENST00000439980; ENST00000446576 | TSF |
| 6% | chr1 | 120274523 | 120274561 | + | chr1 | 120277257 | 120277389 | + | ENST00000369409; ENST00000369407 | TSF |
| 6% | chr2 | 32828531 | 32828600 | + | chr2 | 32832522 | 32832710 | + | ENST00000421745 | TSF |
| 6% | chr8 | 139623662 | 139623508 | − | chr8 | 139620232 | 139620179 | − | ENST00000303045; ENST00000435777 | TSF |
| 6% | chr1 | 23762222 | 23762216 | − | chr1 | 23761111 | 23761026 | − | ENST00000495646; ENST00000336689; ENST00000437606 | TSF |
| 6% | chr22 | 51019509 | 51019459 | − | chr22 | 51019089 | 51018994 | − | ENST00000406938 | TSF |
| 6% | chr10 | 97064311 | 97063415 | − | chr10 | 97031541 | 97031390 | − | ENST00000329399 | TSF |
| 6% | chr7 | 148712709 | 148712660 | − | chr7 | 148712134 | 148711996 | − | ENST00000286091 | TSF |
| 6% | chr20 | 29976260 | 29976126 | − | chr20 | 29966194 | 29966155 | − | ENST00000339144 | TSF |
| 5% | chr21 | 19399995 | 19400289 | + | chr21 | 19628826 | 19629135 | + | ENST00000299295; ENST00000543733 | TSF |
| 5% | chr12 | 9072683 | 9072802 | − | chr12 | 9073581 | 9073661 | + | ENST00000538657; ENST00000543824; ENST00000433083; ENST00000544916; ENST00000544539; ENST00000539063; ENST00000540574; ENST00000541181 | TSF |
| 5% | chr12 | 9072683 | 9072802 | − | chr12 | 9073581 | 9073661 | + | ENST00000538657; ENST00000543824; ENST00000433083; ENST00000544916; ENST00000544539; ENST00000539063; ENST00000540574; ENST00000541181 | TSF |
| 5% | chr12 | 9072683 | 9072802 | − | chr12 | 9073581 | 9073661 | + | ENST00000538657; ENST00000543824; ENST00000433083; ENST00000544916; ENST00000544539; ENST00000539063; ENST00000540574; ENST00000541181 | TSF |
| 5% | chr12 | 9072683 | 9072802 | − | chr12 | 9073581 | 9073661 | + | ENST00000538657; ENST00000543824; ENST00000433083; ENST00000544916; ENST00000544539; ENST00000539063; ENST00000540574; ENST00000541181 | TSF |
| 5% | chr12 | 9072683 | 9072802 | − | chr12 | 9073581 | 9073661 | + | ENST00000538657; ENST00000543824; ENST00000433083; ENST00000544916; ENST00000544539; ENST00000539063; ENST00000540574; ENST00000541181 | TSF |
| 5% | chr12 | 9072683 | 9072802 | − | chr12 | 9073581 | 9073661 | + | ENST00000538657; ENST00000543824; ENST00000433083; ENST00000544916; ENST00000544539; ENST00000539063; ENST00000540574; ENST00000541181 | TSF |
| 5% | chr12 | 9072683 | 9072802 | − | chr12 | 9073581 | 9073661 | + | ENST00000538657; ENST00000543824; ENST00000433083; ENST00000544916; ENST00000544539; ENST00000539063; ENST00000540574; ENST00000541181 | TSF |
| 5% | chr11 | 66048968 | 66049045 | + | chr11 | 66049730 | 66049798; 66049824 | + | ENST00000528852; ENST00000311445; ENST00000528063 | TSF |
| 5% | chr11 | 66048968 | 66049045 | + | chr11 | 66049730 | 66049798; 66049824 | + | ENST00000528852; ENST00000311445; ENST00000528063 | TSF |
| 5% | chr11 | 66048968 | 66049045 | + | chr11 | 66049730 | 66049798; | + | ENST00000528852; ENST00000311445; | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| | | | | | | | 66049824 | | ENST00000528063 | |
| 5% | chr17 | 61555745 | 61556008 | + | chr17 | 61556368 | 61556461 | + | ENST00000538928; ENST00000290866; ENST00000428043; ENST00000582627 | TSF |
| 5% | chr17 | 61555745 | 61556008 | + | chr17 | 61556368 | 61556461 | + | ENST00000538928; ENST00000290866; ENST00000428043; ENST00000582627 | TSF |
| 5% | chr17 | 61555745 | 61556008 | + | chr17 | 61556368 | 61556461 | + | ENST00000538928; ENST00000290866; ENST00000428043; ENST00000582627 | TSF |
| 5% | chr17 | 61555745 | 61556008 | + | chr17 | 61556368 | 61556461 | + | ENST00000538928; ENST00000290866; ENST00000428043; ENST00000582627 | TSF |
| 5% | chr14 | 51363110 | 51363531 | + | chr14 | 51368547 | 51368629 | + | ENST00000337334; ENST00000353130; ENST00000395752 | TSF |
| 5% | chr2 | 44903747 | 44903914 | + | chr2 | 44931422 | 44931482 | + | ENST00000378494 | TSF |
| 5% | chrX | 69679853 | 69679903 | + | chrX | 69699000 | 69699114 | + | ENST00000194900; ENST00000374360; ENST00000374355 | TSF |
| 5% | chrX | 69679853 | 69679903 | + | chrX | 69699000 | 69699114 | + | ENST00000194900; ENST00000374360; ENST00000374355 | TSF |
| 5% | chrX | 69679853 | 69679903 | + | chrX | 69699000 | 69699114 | + | ENST00000194900; ENST00000374360; ENST00000374355 | TSF |
| 5% | chr7 | 74480763 | 74480881 | + | chr7 | 74528191 | 74528329 | + | ENST00000356115; ENST00000430511; ENST00000312575; ENST00000423666 | TSF |
| 5% | chr7 | 74480763 | 74480881 | + | chr7 | 74528191 | 74528329 | + | ENST00000356115; ENST00000430511; ENST00000312575; ENST00000423666 | TSF |
| 5% | chr7 | 74480763 | 74480881 | + | chr7 | 74528191 | 74528329 | + | ENST00000356115; ENST00000430511; ENST00000312575; ENST00000423666 | TSF |
| 5% | chr19 | 4412258 | 4412399 | + | chr19 | 4418017 | 4418073 | + | ENST00000301280 | TSF |
| 5% | chr1 | 145666897 | 145667041 | + | chr1 | 145682023 | 145682094 | + | ENST00000369291 | TSF |
| 5% | chr20 | 25146273 | 25146366 | + | chr20 | 25249765 | 25249843 | + | ENST00000216962 | TSF |
| 5% | chr17 | 4700327 | 4700476 | + | chr17 | 4700733 | 4700864 | + | ENST00000270586; ENST00000571309 | TSF |
| 5% | chr17 | 4700327 | 4700476 | + | chr17 | 4700733 | 4700864 | + | ENST00000270586; ENST00000571309 | TSF |
| 5% | chr4 | 146617147 | 146617184 | + | chr4 | 146617711 | 146617784 | + | ENST00000438731; ENST00000511965 | TSF |
| 5% | chr12 | 4653807 | 4654478 | + | chr12 | 4654948 | 4654998 | + | ENST00000321524; ENST00000228843 | TSF |
| 5% | chr12 | 4653807 | 4654478 | + | chr12 | 4654948 | 4654998 | + | ENST00000321524; ENST00000228843 | TSF |
| 5% | chr19 | 5714928 | 5714878 | − | chr19 | 5714282 | 5714194 | − | ENST00000360614; ENST00000590558; ENST00000585374; ENST00000593119; ENST00000590729 | TSF |
| 5% | chr19 | 5714928 | 5714878 | − | chr19 | 5714282 | 5714194 | − | ENST00000360614; ENST00000590558; ENST00000585374; ENST00000593119; ENST00000590729 | TSF |
| 5% | chr19 | 5714928 | 5714878 | − | chr19 | 5714282 | 5714194 | − | ENST00000360614; ENST00000590558; ENST00000585374; ENST00000593119; ENST00000590729 | TSF |
| 5% | chr19 | 40761842 | 40761378 | − | chr19 | 40761176 | 40761065; 40761151 | − | ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; ENST00000416994; ENST00000427375 | TSF |
| 5% | chr19 | 40761842 | 40761378 | − | chr19 | 40761176 | 40761065; 40761151 | − | ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; ENST00000416994; ENST00000427375 | TSF |
| 5% | chr19 | 40761842 | 40761378 | − | chr19 | 40761176 | 40761065; 40761151 | − | ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; ENST00000416994; ENST00000427375 | TSF |
| 5% | chr19 | 40761842 | 40761378 | − | chr19 | 40761176 | 40761065; 40761151 | − | ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 5% | chr19 | 40761842 | 40761378 | − | chr19 | 40761176 | 40761065; 40761151 | − | ENST00000416994; ENST00000427375 ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; | TSF |
| 5% | chr19 | 40761842 | 40761378 | − | chr19 | 40761176 | 40761065; 40761151 | − | ENST00000416994; ENST00000427375 ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; | TSF |
| 5% | chr19 | 40761842 | 40761378 | − | chr19 | 40761176 | 40761065; 40761151 | − | ENST00000416994; ENST00000427375 ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; | TSF |
| 5% | chr19 | 40761842 | 40761378 | − | chr19 | 40761176 | 40761065; 40761151 | − | ENST00000416994; ENST00000427375 ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; | ITSF |
| 5% | chr19 | 40761842 | 40761378 | − | chr19 | 40761176 | 40761065; 40761151 | − | ENST00000416994; ENST00000427375 ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; | TSF |
| 5% | chr19 | 40761842 | 40761378 | − | chr19 | 40761176 | 40761065; 40761151 | − | ENST00000416994; ENST00000427375 ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; | TSF |
| 5% | chr19 | 40761842 | 40761378 | − | chr19 | 40761176 | 40761065; 40761151 | − | ENST00000416994; ENST00000427375 ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; | TSF |
| 5% | chr19 | 40761842 | 40761378 | − | chr19 | 40761176 | 40761065; 40761151 | − | ENST00000416994; ENST00000427375 ENST00000392038; ENST00000424901; ENST00000311278; ENST00000491778; ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; | TSF |
| 5% | chr19 | 40761842 | 40761378 | − | chr19 | 40761176 | 40761065; 40761151 | − | ENST00000416994; ENST00000427375 ENST00000392038; ENST00000424901; ENST00000311278; ENST00000491778; ENST00000441941; ENST00000486368; | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 5% | chr19 | 40761842 | 40761378 | – | chr19 | 40761176 | 40761065; 40761151 | – | | ENST00000596634; ENST00000452077; ENST00000392037; ENST00000416362; ENST00000578123; ENST00000423127; ENST00000358335; ENST00000456441; ENST00000583859; ENST00000580747; ENST00000416994; ENST00000427375 ENST00000392038; ENST00000424901;TSF ENST00000311278; ENST00000491778; ENST00000441941; ENST00000486368; |
| 5% | chr19 | 40761842 | 40761378 | – | chr19 | 40761176 | 40761065; 40761151 | – | | ENST00000596634; ENST00000452077; ENST00000392037; ENST00000416362; ENST00000578123; ENST00000423127; ENST00000358335; ENST00000456441; ENST00000583859; ENST00000580747; ENST00000416994; ENST00000427375 ENST00000392038; ENST00000424901;TSF ENST00000311278; ENST00000491778; ENST00000441941; ENST00000486368; |
| 5% | chr19 | 40761842 | 40761378 | – | chr19 | 40761176 | 40761065; 40761151 | – | | ENST00000596634; ENST00000452077; ENST00000392037; ENST00000416362; ENST00000578123; ENST00000423127; ENST00000358335; ENST00000456441; ENST00000583859; ENST00000580747; ENST00000416994; ENST00000427375 ENST00000392038; ENST00000424901; ENST00000311278; ENST00000491778;TSF ENST00000441941; ENST00000486368; |
| 5% | chr19 | 40761842 | 40761378 | – | chr19 | 40761176 | 40761065; 40761151 | – | | ENST00000596634; ENST00000452077; ENST00000392037; ENST00000416362; ENST00000578123; ENST00000423127; ENST00000358335; ENST00000456441; ENST00000583859; ENST00000580747; ENST00000416994; ENST00000427375 ENST00000392038; ENST00000424901; ENST00000311278; ENST00000491778;TSF ENST00000441941; ENST00000486368; ENST00000596634; ENST00000452077; ENST00000392037; ENST00000416362; ENST00000578123; ENST00000423127; ENST00000358335; ENST00000456441; ENST00000583859; ENST00000580747; ENST00000416994; ENST00000427375 |
| 5% | chr15 | 40186285 | 40186255 | – | chr15 | 40099459 | 40099207 | – | | ENST00000561100; ENST00000543580 TSF |
| 5% | chr15 | 83263939 | 83261988 | – | chr15 | 83240282 | 83240094 | – | | ENST00000563800; ENST00000562019;TSF ENST00000568128; ENST00000261723 |
| 5% | chr15 | 83263939 | 83261988 | – | chr15 | 83240282 | 83240094 | – | | ENST00000563800; ENST00000562019;TSF ENST00000568128; ENST00000261723 |
| 5% | chr11 | 61079810 | 61079683 | – | chr11 | 61079556 | 61079461 | – | | ENST00000301764; ENST00000540166;TSF ENST00000535147 |
| 5% | chr11 | 61079810 | 61079683 | – | chr11 | 61079556 | 61079461 | – | | ENST00000301764; ENST00000540166;TSF ENST00000535147 |
| 5% | chr11 | 61079810 | 61079683 | – | chr11 | 61079556 | 61079461 | – | | ENST00000301764; ENST00000540166;TSF ENST00000535147 |
| 5% | chr21 | 27453972 | 27453597 | – | chr21 | 27425664 | 27425552 | – | | ENST00000346798; ENST00000354192;TSF ENST00000348990; ENST00000357903; ENST00000358918; ENST00000359726; ENST00000448388; ENST00000440126; ENST00000439274; ENST00000448850 |
| 5% | chr21 | 27453972 | 27453597 | – | chr21 | 27425664 | 27425552 | – | | ENST00000346798; ENST00000354192;TSF ENST00000348990; ENST00000357903; ENST00000358918; ENST00000359726; ENST00000448388; ENST00000440126; ENST00000439274; ENST00000448850 |
| 5% | chr21 | 27453972 | 27453597 | – | chr21 | 27425664 | 27425552 | – | | ENST00000346798; ENST00000354192;TSF ENST00000348990; ENST00000357903; ENST00000358918; ENST00000359726; ENST00000448388; ENST00000440126; ENST00000439274; ENST00000448850 |
| 5% | chr21 | 27453972 | 27453597 | – | chr21 | 27425664 | 27425552 | – | | ENST00000346798; ENST00000354192;TSF ENST00000348990; ENST00000357903; ENST00000358918; ENST00000359726; ENST00000448388; ENST00000440126; ENST00000439274; ENST00000448850 |
| 5% | chr21 | 27453972 | 27453597 | – | chr21 | 27425664 | 27425552 | – | | ENST00000346798; ENST00000354192;TSF ENST00000348990; ENST00000357903; ENST00000358918; ENST00000359726; |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 5% | chr21 | 27453972 | 27453597 | − | chr21 | 27425664 | 27425552 | − | ENST00000448388; ENST00000440126; ENST00000439274; ENST00000448850 ENST00000346798; ENST00000354192; ENST00000348990; ENST00000357903; ENST00000358918; ENST00000359726; ENST00000448388; ENST00000440126; ENST00000439274; ENST00000448850 | TSF |
| 5% | chrX | 76851229 | 76851182 | − | chrX | 76849319 | 76849166 | − | ENST00000373344; ENST00000395603 | TSF |
| 5% | chr15 | 40187476 | 40186733 | − | chr15 | 40099398 | 40099207 | − | ENST00000299092; ENST00000561100; ENST00000543580 | TSF |
| 5% | chr12 | 3041463 | 3041468 | + | chr12 | 3042584 | 3042696 | + | ENST00000448120; ENST00000397132 | TSF |
| 5% | chr12 | 3041463 | 3041468 | + | chr12 | 3042584 | 3042696 | + | ENST00000448120; ENST00000397132 | TSF |
| 5% | chr14 | 20973494 | 20974295 | + | chr14 | 20978626 | 20979281 | + | ENST00000430083 | TSF |
| 5% | chr12 | 122599625 | 122599667 | + | chr12 | 122611803 | 122611909 | + | ENST00000319080 | TSF |
| 5% | chr20 | 110606 | 110697 | + | chr20 | 126056 | 126333 | + | ENST00000382398 | TSF |
| 5% | chrX | 71397824 | 71398659 | + | chrX | 71406311 | 71406384 | + | ENST00000218432; ENST00000423432; ENST00000373669; ENST00000496835; ENST00000439980; ENST00000446576 | TSF |
| 5% | chrX | 71397824 | 71398659 | + | chrX | 71406311 | 71406384 | + | ENST00000218432; ENST00000423432; ENST00000373669; ENST00000496835; ENST00000439980; ENST00000446576 | TSF |
| 5% | chrX | 71397824 | 71398659 | + | chrX | 71406311 | 71406384 | + | ENST00000218432; ENST00000423432; ENST00000373669; ENST00000496835; ENST00000439980; ENST00000446576 | TSF |
| 5% | chrX | 71397824 | 71398659 | + | chrX | 71406311 | 71406384 | + | ENST00000218432; ENST00000423432; ENST00000373669; ENST00000496835; ENST00000439980; ENST00000446576 | TSF |
| 5% | chr7 | 77573053 | 77573153 | + | chr7 | 77578995 | 77579150 | + | ENST00000422959; ENST00000307305; ENST00000416283; ENST00000248550 | TSF |
| 5% | chr1 | 13922411 | 13922564 | + | chr1 | 13933668 | 13933801 | + | ENST00000294489; ENST00000376057; ENST00000510906; ENST00000509009 | TSF |
| 5% | chr1 | 13922411 | 13922564 | + | chr1 | 13933668 | 13933801 | + | ENST00000294489; ENST00000376057; ENST00000510906; ENST00000509009 | TSF |
| 5% | chr1 | 13922411 | 13922564 | + | chr1 | 13933668 | 13933801 | + | ENST00000294489; ENST00000376057; ENST00000510906; ENST00000509009 | TSF |
| 5% | chr8 | 620733 | 620243 | − | chr8 | 618782 | 618598; 618491 | − | ENST00000522706; ENST00000523415; ENST00000262109; ENST00000522893 | TSF |
| 5% | chr8 | 620733 | 620243 | − | chr8 | 618782 | 618598; 618491 | − | ENST00000522706; ENST00000523415; ENST00000262109; ENST00000522893 | TSF |
| 5% | chr8 | 620733 | 620243 | − | chr8 | 618782 | 618598; 618491 | − | ENST00000522706; ENST00000523415; ENST00000262109; ENST00000522893 | TSF |
| 5% | chr8 | 620733 | 620243 | − | chr8 | 618782 | 618598; 618491 | − | ENST00000522706; ENST00000523415; ENST00000262109; ENST00000522893 | TSF |
| 5% | chr2 | 17876171 | 17876059 | − | chr2 | 17865030 | 17864905 | − | ENST00000448223; ENST00000351948; ENST00000381272; ENST00000402989 | TSF |
| 5% | chr2 | 163164568 | 163164512 | − | chr2 | 163163365 | 163163219 | − | ENST00000263642 | TSF |
| 5% | chr16 | 74665694 | 74665639 | − | chr16 | 74664855 | 74664679 | − | ENST00000361070; ENST00000571750 | TSF |
| 5% | chr15 | 83667946 | 83667078 | − | chr15 | 83660798 | 83660684 | − | ENST00000451195 | TSF |
| 5% | chr5 | 159516518 | 159516513 | − | chr5 | 159507777 | 159507658 | − | ENST00000456329 | TSF |
| 5% | chr22 | 21355965 | 21355835 | − | chr22 | 21355700 | 21355545 | − | ENST00000215742; ENST00000399133 | TSF |
| 5% | chr15 | 18655840 | 40186430 | − | chr15 | 40099459 | 40099207 | − | ENST00000561100; ENST00000543580 | TSF |
| 5% | chr2 | 172724171 | 172723378 | − | chr2 | 172712459 | 172712344 | − | ENST00000422440; ENST00000426896; ENST00000475360 | TSF |
| 5% | chr2 | 172724171 | 172723378 | − | chr2 | 172712459 | 172712344 | − | ENST00000422440; ENST00000426896; ENST00000475360 | TSF |
| 5% | chr2 | 172724171 | 172723378 | − | chr2 | 172712459 | 172712344 | − | ENST00000422440; ENST00000426896; ENST00000475360 | TSF |
| 5% | chr3 | 171427764 | 171427731 | − | chr3 | 171427499 | 171427350 | − | ENST00000356327; ENST00000351298; ENST00000342215; ENST00000340989 | TSF |
| 5% | chr3 | 171427764 | 171427731 | − | chr3 | 171427499 | 171427350 | − | ENST00000356327; ENST00000351298; ENST00000342215; ENST00000340989 | TSF |
| 5% | chr3 | 171427764 | 171427731 | − | chr3 | 171427499 | 171427350 | − | ENST00000356327; ENST00000351298; ENST00000342215; ENST00000340989 | TSF |
| 5% | chr3 | 171427764 | 171427731 | − | chr3 | 171427499 | 171427350 | − | ENST00000356327; ENST00000351298; ENST00000342215; ENST00000340989 | TSF |
| 5% | chr14 | 28510850 | 50285011 | − | chr14 | 50281575 | 50281472 | − | ENST00000298310; ENST00000545773; ENST00000546046; ENST00000555970 | TSF |
| 5% | chr14 | 28510850 | 50285011 | − | chr14 | 50281575 | 50281472 | − | ENST00000298310; ENST00000545773; ENST00000546046; ENST00000555970 | TSF |
| 5% | chr14 | 28510850 | 50285011 | − | chr14 | 50281575 | 50281472 | − | ENST00000298310; ENST00000545773; ENST00000546046; ENST00000555970 | TSF |
| 5% | chrX | 33097155 | 33096303 | − | chrX | 33038317 | 33038256 | − | ENST00000378677; ENST00000357033; ENST00000420596; ENST00000448370; ENST00000288447 | TSF |
| 5% | chrX | 33097155 | 33096303 | − | chrX | 33038317 | 33038256 | − | ENST00000378677; ENST00000357033; ENST00000420596; ENST00000448370; | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 5% | chrX | 33097155 | 33096303 | − | chrX | 33038317 | 33038256 | − | ENST00000288447 ENST00000378677; ENST00000357033; ENST00000420596; ENST00000448370; | TSF |
| 5% | chrX | 33097155 | 33096303 | − | chrX | 33038317 | 33038256 | − | ENST00000288447 ENST00000378677; ENST00000357033; ENST00000420596; ENST00000448370; | TSF |
| 5% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 5% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 5% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 5% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 5% | chr2 | 38983894 | 38983086 | − | chr2 | 38977336 | 38977156 | − | ENST00000313117; ENST00000425778; ENST00000425941; ENST00000446327; ENST00000409276; ENST00000431066; ENST00000443213 | TSF |
| 5% | chr1 | 33270876 | 33270146 | − | chr1 | 33263444 | 33263364 | − | ENST00000373477 | TSF |
| 5% | chr11 | 57280665 | 57280599 | − | chr11 | 57268802 | 57268625; 57268633 | − | ENST00000278426; ENST00000528450; ENST00000534298; ENST00000530159; ENST00000533066; ENST00000533263 | TSF |
| 5% | chr11 | 57280665 | 57280599 | − | chr11 | 57268802 | 57268625; 57268633 | − | ENST00000278426; ENST00000528450; ENST00000534298; ENST00000530159; ENST00000533066; ENST00000533263 | TSF |
| 5% | chr11 | 57280665 | 57280599 | − | chr11 | 57268802 | 57268625; 57268633 | − | ENST00000278426; ENST00000528450; ENST00000534298; ENST00000530159; ENST00000533066; ENST00000533263 | TSF |
| 5% | chr11 | 57280665 | 57280599 | − | chr11 | 57268802 | 57268625; 57268633 | − | ENST00000278426; ENST00000528450; ENST00000534298; ENST00000530159; ENST00000533066; ENST00000533263 | TSF |
| 5% | chr11 | 57280665 | 57280599 | − | chr11 | 57268802 | 57268625; 57268633 | − | ENST00000278426; ENST00000528450; ENST00000534298;ENST00000530159; ENST00000533066; ENST00000533263 | TSF |
| 5% | chr19 | 1500000 | 1499600 | − | chr19 | 1488279 | 1488187 | − | ENST00000591201; ENST00000300954; ENST00000588195; ENST00000588671 | TSF |
| 5% | chr19 | 1500000 | 1499600 | − | chr19 | 1488279 | 1488187 | − | ENST00000591201; ENST00000300954; ENST00000588195; ENST00000588671 | TSF |
| 5% | chr19 | 1500000 | 1499600 | − | chr19 | 1488279 | 1488187 | − | ENST00000591201; ENST00000300954; ENST00000588195; ENST00000588671 | TSF |
| 5% | chr19 | 1500000 | 1499600 | − | chr19 | 1488279 | 1488187 | − | ENST00000591201; ENST00000300954; ENST00000588195; ENST00000588671 | TSF |
| 5% | chr15 | 40186285 | 40185077 | − | chr15 | 40099459 | 40099207 | − | ENST00000561100; ENST00000543580 | TSF |
| 5% | chr14 | 50113338 | 50113288 | − | chr14 | 50110388 | 50110370 | − | ENST00000216367; ENST00000539565 | TSF |
| 5% | chr12 | 96302230 | 96301454 | − | chr12 | 96300229 | 96300165 | − | ENST00000344280 | TSF |
| 4% | chr12 | 96340433 | 96341255 | + | chr12 | 96346495 | 96346601 | + | ENST00000266736; ENST00000548310 | TSF |
| 4% | chr12 | 96340433 | 96341255 | + | chr12 | 96346495 | 96346601 | + | ENST00000266736; ENST00000548310 | TSF |
| 4% | chr14 | 51365630 | 51365697 | + | chr14 | 51368547 | 51368629 | + | ENST00000337334; ENST00000353130; ENST00000395752 | TSF |
| 4% | chr2 | 11299135 | 11299200 | + | chr2 | 11300592 | 11300674 | + | ENST00000445402; ENST00000295083; ENST00000445921; ENST00000441908; ENST00000402361; ENST00000428481 | TSF |
| 4% | chr2 | 11299135 | 11299200 | + | chr2 | 11300592 | 11300674 | + | ENST00000445402; ENST00000295083; ENST00000445921; ENST00000441908; ENST00000402361; ENST00000428481 | TSF |
| 4% | chr2 | 11299135 | 11299200 | + | chr2 | 11300592 | 11300674 | + | ENST00000445402; ENST00000295083; ENST00000445921; ENST00000441908; ENST00000402361; ENST00000428481 | TSF |
| 4% | chr2 | 11299135 | 11299200 | + | chr2 | 11300592 | 11300674 | + | ENST00000445402; ENST00000295083; ENST00000445921; ENST00000441908; ENST00000402361; ENST00000428481 | TSF |
| 4% | chr2 | 11299135 | 11299200 | + | chr2 | 11300592 | 11300674 | + | ENST00000445402; ENST00000295083; ENST00000445921; ENST00000441908; ENST00000402361; ENST00000428481 | TSF |
| 4% | chr2 | 11299135 | 11299200 | + | chr2 | 11300592 | 11300674 | + | ENST00000445402; ENST00000295083; ENST00000445921; ENST00000441908; ENST00000402361; ENST00000428481 | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 4% | chr6 | 37436378 | 37436635 | + | chr6 | 37438797 | 37438853 | + | ENST00000373451 | TSF |
| 4% | chr9 | 6806927 | 6807744 | + | chr9 | 6814631 | 6814745; 6814766 | + | ENST00000535193; ENST00000438023; ENST00000543771; ENST00000401787; ENST00000381306; ENST00000381309 | TSF |
| 4% | chr9 | 6806927 | 6807744 | + | chr9 | 6814631 | 6814745; 6814766 | + | ENST00000535193; ENST00000438023; ENST00000543771; ENST00000401787; ENST00000381306; ENST00000381309 | TSF |
| 4% | chr9 | 6806927 | 6807744 | + | chr9 | 6814631 | 6814745; 6814766 | + | ENST00000535193; ENST00000438023; ENST00000543771; ENST00000401787; ENST00000381306; ENST00000381309 | TSF |
| 4% | chr9 | 6806927 | 6807744 | + | chr9 | 6814631 | 6814745; 6814766 | + | ENST00000535193; ENST00000438023; ENST00000543771; ENST00000401787; ENST00000381306; ENST00000381309 | TSF |
| 4% | chr9 | 6806927 | 6807744 | + | chr9 | 6814631 | 6814745; 6814766 | + | ENST00000535193; ENST00000438023; ENST00000543771; ENST00000401787; ENST00000381306; ENST00000381309 | TSF |
| 4% | chr1 | 10499523 | 10499583 | + | chr 1 | 10500404 | 10500470 | + | ENST00000400900; ENST00000602787; ENST00000309048; ENST00000477755; ENST00000602446 | TSF |
| 4% | chr1 | 10499523 | 10499583 | + | chr 1 | 10500404 | 10500470 | + | ENST00000400900; ENST00000602787; ENST00000309048; ENST00000477755; ENST00000602446 | TSF |
| 4% | chr1 | 10499523 | 10499583 | + | chr 1 | 10500404 | 10500470 | + | ENST00000400900; ENST00000602787; ENST00000309048; ENST00000477755; ENST00000602446 | TSF |
| 4% | chr8 | 23131391 | 23131513 | + | chr8 | 23146019 | 23146146 | + | ENST00000411463 | TSF |
| 4% | chr10 | 135053342 | 135053345 | + | chr10 | 135053436 | 135053810 | + | ENST00000325980 | TSF |
| 4% | chr4 | 146620427 | 146620571 | + | chr4 | 146648063 | 146648121 | + | ENST00000438731; ENST00000511965 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr2 | 102468305 | 102468327 | + | chr2 | 102472439 | 102472600 | + | ENST00000425019; ENST00000302217; ENST00000324219; ENST00000350198; ENST00000413150; ENST00000347699; ENST00000456652; ENST00000417294; ENST00000350878; ENST00000421882; ENST00000418101 | TSF |
| 4% | chr1 | 207820596 | 207820768 | + | chr1 | 207850734 | 207850913 | + | ENST00000508064 | TSF |
| 4% | chr4 | 6983745 | 6984058 | + | chr4 | 6995911 | 6996029 | + | ENST00000448507; ENST00000409757; ENST00000410031; ENST00000451522 | TSF |
| 4% | chr1 | 213064469 | 213064523 | + | chr1 | 213068328 | 213068395 | + | ENST00000366971; ENST00000419102 | TSF |
| 4% | chr1 | 12002791 | 12002835 | + | chr1 | 12008033 | 12008124 | + | ENST00000449038; ENST00000376369; ENST00000429000; ENST00000196061 | TSF |
| 4% | chr1 | 12002791 | 12002835 | + | chr1 | 12008033 | 12008124 | + | ENST00000449038; ENST00000376369; ENST00000429000; ENST00000196061 | TSF |
| 4% | chr1 | 12002791 | 12002835 | + | chr1 | 12008033 | 12008124 | + | ENST00000449038; ENST00000376369; ENST00000429000; ENST00000196061 | TSF |
| 4% | chr12 | 49659927 | 49660025 | + | chr12 | 49663248 | 49663470; 49663252 | + | ENST00000541364; ENST00000552125; ENST00000301072; ENST00000549183 | TSF |
| 4% | chr12 | 49659927 | 49660025 | + | chr12 | 49663248 | 49663470; 49663252 | + | ENST00000541364; ENST00000552125; ENST00000301072; ENST00000549183 | TSF |
| 4% | chr12 | 49659927 | 49660025 | + | chr12 | 49663248 | 49663470; 49663252 | + | ENST00000541364; ENST00000552125; ENST00000301072; ENST00000549183 | TSF |
| 4% | chr18 | 33553603 | 33553783 | + | chr18 | 33554903 | 33555058 | + | ENST00000592875 | TSF |
| 4% | chr2 | 172724171 | 172723495 | − | chr2 | 172712459 | 172712344 | − | ENST00000422440; ENST00000426896; ENST00000475360 | TSF |
| 4% | chr2 | 172724171 | 172723495 | − | chr2 | 172712459 | 172712344 | − | ENST00000422440; ENST00000426896; ENST00000475360 | TSF |
| 4% | chr2 | 172724171 | 172723495 | − | chr2 | 172712459 | 172712344 | − | ENST00000422440; ENST00000426896; ENST00000475360 | TSF |
| 4% | chr10 | 96908 | 95348 | − | chr10 | 94852 | 94744 | − | ENST00000309812 | TSF |
| 4% | chr5 | 136450001 | 136449976 | − | chr5 | 136448250 | 136448124; 136448181 | − | ENST00000394945; ENST00000282223; ENST00000505690 | TSF |
| 4% | chr5 | 136450001 | 136449976 | − | chr5 | 136448250 | 136448124; 136448181 | − | ENST00000394945; ENST00000282223; ENST00000505690 | TSF |
| 4% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 4% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 4% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 4% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 4% | chr3 | 182833330 | 182833262 | − | chr3 | 182812393 | 182812347 | − | ENST00000265594; ENST00000497830; ENST00000495767; ENST00000476176; ENST00000487634; ENST00000466650; ENST00000486226 | TSF |
| 4% | chr7 | 72720593 | 72720556 | − | chr7 | 72719094 | 72718956; 27719042 | − | ENST00000428206; ENST00000252594; ENST00000438747; ENST00000310326; ENST00000455763 | TSF |
| 4% | chr7 | 72720593 | 72720556 | − | chr7 | 72719094 | 72718956; 72719042 | − | ENST00000428206; ENST00000252594; ENST00000438747; ENST00000310326; ENST00000455763 | TSF |
| 4% | chr7 | 72720593 | 72720556 | − | chr7 | 72719094 | 72718956; 72719042 | − | ENST00000428206; ENST00000252594; ENST00000438747; ENST00000310326; ENST00000455763 | TSF |
| 4% | chr7 | 72720593 | 72720556 | − | chr7 | 72719094 | 72718956; 72719042 | − | ENST00000428206; ENST00000252594; ENST00000438747; ENST00000310326; ENST00000455763 | TSF |

TABLE 60-continued

Transcript fusion for Testicular Germ Cell Tumors (TGCT) Coordinates of the fusion sequences for which the donor is the TE.

| 1' | 2' | 3' | 4' | 5' | 6' | 7' | 8' | 9' | 10' | 11' |
|---|---|---|---|---|---|---|---|---|---|---|
| | | | | | | | 72719042 | | ENST00000438747; ENST00000310326; ENST00000455763 | |
| 4% | chr16 | 81141785 | 81141755 | – | chr16 | 81134889 | 81134728 | – | ENST00000533478; ENST00000525539 | TSF |
| 4% | chr10 | 125779873 | 125779865 | – | chr10 | 125771996 | 125771849 | – | ENST00000346248; ENST00000435907 | TSF |
| 4% | chr19 | 48627094 | 48627044 | – | chr19 | 48626575 | 48626431 | – | ENST00000263274; ENST00000536218; ENST00000594759; ENST00000427526; ENST00000601091 | TSF |
| 4% | chr19 | 48627094 | 48627044 | – | chr19 | 48626575 | 48626431 | – | ENST00000263274; ENST00000536218; ENST00000594759; ENST00000427526; ENST00000601091 | TSF |
| 4% | chr15 | 40187476 | 40186657 | – | chr15 | 40099459 | 40099207 | – | ENST00000561100; ENST00000543580 | TSF |
| 4% | chr3 | 122500000 | 122499557 | – | chr3 | 122496753 | 122496568 | – | ENST00000383659; ENST00000306103 | TSF |
| 4% | chr3 | 122500000 | 122499557 | – | chr3 | 122496753 | 122496568 | – | ENST00000383659; ENST00000306103 | TSF |
| 4% | chr7 | 99061804 | 99061750 | – | chr7 | 99057816 | 99057709 | – | ENST00000413834; ENST00000555673; ENST00000451138; ENST00000414062; ENST00000449683; ENST00000359832; ENST00000292475; ENST00000544611; ENST00000488775; ENST00000394186 | TSF |
| 4% | chr7 | 99061804 | 99061750 | – | chr7 | 99057816 | 99057709 | – | ENST00000413834; ENST00000555673; ENST00000451138; ENST00000414062; ENST00000449683; ENST00000359832; ENST00000292475; ENST00000544611; ENST00000488775; ENST00000394186 | TSF |
| 4% | chr7 | 99061804 | 99061750 | – | chr7 | 99057816 | 99057709 | – | ENST00000413834; ENST00000555673; ENST00000451138; ENST00000414062; ENST00000449683; ENST00000359832; ENST00000292475; ENST00000544611; ENST00000488775; ENST00000394186 | TSF |
| 4% | chr7 | 99061804 | 99061750 | – | chr7 | 99057816 | 99057709 | – | ENST00000413834; ENST00000555673; ENST00000451138; ENST00000414062; ENST00000449683; ENST00000359832; ENST00000292475; ENST00000544611; ENST00000488775; ENST00000394186 | TSF |
| 4% | chrX | 79986798 | 79986587 | – | chrX | 79985519 | 79985415 | – | ENST00000373275 | TSF |
| 4% | chr10 | 13366616 | 13366334 | – | chr10 | 13365047 | 13364835 | – | ENST00000327347; ENST00000545675; ENST00000537130 | TSF |
| 4% | chr10 | 13366616 | 13366334 | – | chr10 | 13365047 | 13364835 | – | ENST00000327347; ENST00000545675; ENST00000537130 | TSF |
| 4% | chr7 | 154755921 | 154755838 | – | chr7 | 154755476 | 154755381 | – | ENST00000404141; ENST00000397192 | TSF |

TABLE 61

Transcript fusion for Thyroid Cancer (THCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 40% | chr9 | 139847344; 139847404; 139847428 | 139847480 | + | ENST00000371633; ENST00000471615; ENST00000371632 | chr9 | 139847940 | 139848024 | + | TAF |
| 40% | chr9 | 139847344; 139847404; 139847428 | 139847480 | + | ENST00000371633; ENST00000471615; ENST00000371632 | chr9 | 139847940 | 139848024 | + | TAF |
| 40% | chr9 | 139847344; 139847404; 139847428 | 139847480 | + | ENST00000371633; ENST00000471615; ENST00000371632 | chr9 | 139847940 | 139848024 | + | TAF |
| 34% | chr19 | 50984141 | 50984234 | + | ENST00000334976; ENST00000376918; ENST00000598585 | chr19 | 51009025 | 51009080 | + | TAF |
| 28% | chr22 | 21576241 | 21576155 | – | ENST00000405188; ENST00000401924; ENST00000424627 | chr22 | 21575420 | 21575160 | – | TAF |
| 27% | chr22 | 25011008 | 25011094 | + | ENST00000248923; ENST00000412658; ENST00000419133; ENST00000400382; ENST00000452551; ENST00000400383; ENST00000400380; ENST00000406383; ENST00000425895 | chr22 | 25011829 | 25012092 | + | TAF |
| 27% | chr15 | 34826374 | 34826255 | – | ENST00000342314; ENST00000267731 | chr15 | 34679464 | 34679458 | – | TAF |

TABLE 61-continued

Transcript fusion for Thyroid Cancer (THCA) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 23% | chr17 | 66538306 | 66538126 | − | ENST00000592554 | chr17 | 66537704 | 66537648 | − | TAF |
| 20% | chr11 | 13402708 | 13402801 | + | ENST00000396441; ENST00000389707; ENST00000401424; ENST00000361003; ENST00000403290; ENST00000403510; ENST00000403482 | chr11 | 13406027 | 13406509 | + | TAF |
| 20% | chr11 | 13402708 | 13402801 | + | ENST00000396441; ENST00000389707; ENST00000401424; ENST00000361003; ENST00000403290; ENST00000403510; ENST00000403482 | chr11 | 13406027 | 13406509 | + | TAF |
| 20% | chr11 | 13402708 | 13402801 | + | ENST00000396441; ENST00000389707; ENST00000401424; ENST00000361003; ENST00000403290; ENST00000403510; ENST00000403482 | chr11 | 13406027 | 13406509 | + | TAF |
| 20% | chr11 | 13402708 | 13402801 | + | ENST00000396441; ENST00000389707; ENST00000401424; ENST00000361003; ENST00000403290; ENST00000403510; ENST00000403482 | chr11 | 13406027 | 13406509 | + | TAF |
| 20% | chr11 | 13402708 | 13402801 | + | ENST00000396441; ENST00000389707; ENST00000401424; ENST0 0000361003; ENST00000403290; ENST00000403510; ENST00000403482 | chr11 | 13406027 | 13406509 | + | TAF |
| 20% | chr11 | 13402708 | 13402801 | + | ENST00000396441; ENST00000389707; ENST00000401424; ENST00000361003; ENST00000403290; ENST00000403510; ENST00000403482 | chr11 | 13406027 | 13406509 | + | TAF |
| 18% | chr15 | 64444837 | 64444941 | + | ENST00000325881; ENST00000558466 | chr15 | 64445122 | 64445138 | + | TSF |
| 16% | chr15 | 64444837 | 64444941 | + | ENST00000325881; ENST00000558466 | chr15 | 64445091 | 64445138 | + | TAF |
| 14% | chr19 | 11526824 | 11526613 | − | ENST00000380456; ENST00000393423; ENST00000567431 | chr19 | 11522106 | 11521984 | − | TAF |
| 14% | chr19 | 11526824 | 11526613 | − | ENST00000380456; ENST00000393423; ENST00000567431 | chr19 | 11522106 | 11521984 | − | TAF |
| 13% | chr10 | 133106654 | 133106474 | − | ENST00000368642 | chr10 | 133064549 | 133063810 | − | TAF |
| 13% | chr11 | 129980433 | 129980556 | + | ENST00000533713; ENST00000528499; ENST00000263574; ENST00000345598; ENST00000338167; ENST00000278756; ENST00000543137 | chr11 | 129987692 | 129987988 | + | TAF |
| 13% | chr11 | 129980433 | 129980556 | + | ENST00000533713; ENST00000528499; ENST00000263574; ENST00000345598; ENST00000338167; ENST00000278756; ENST00000543137 | chr11 | 129987692 | 129987988 | + | TAF |
| 13% | chr11 | 129980433 | 129980556 | + | ENST00000533713; ENST00000528499; ENST00000263574; ENST0 0000345598; ENST00000338167; ENST00000278756; ENST00000543137 | chr11 | 129987692 | 129987988 | + | TAF |

TABLE 61-continued

Transcript fusion for Thyroid Cancer (THCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 13% | chr11 | 129980433 | 129980556 | + | ENST00000533713; ENST00000528499; ENST00000263574; ENST0 0000345598; ENST00000338167; ENST00000278756; ENST00000543137 | chr11 | 129987692 | 129987988 | + | TAF |
| 12% | chr19 | 39077165 | 39077216 | + | ENST00000355481; ENST00000360985; ENST00000359596 | chr19 | 39085644 | 39085967 | + | TAF |
| 12% | chr19 | 39077165 | 39077216 | + | ENST00000355481; ENST00000360985; ENST00000359596 | chr19 | 39085644 | 39085967 | + | TAF |
| 12% | chr19 | 39077165 | 39077216 | + | ENST00000355481; ENST00000360985; ENST00000359596 | chr19 | 39085644 | 39085967 | + | TAF |
| 12% | chr7 | 30469073 | 30468990 | − | ENST00000222823 | chr7 | 30468225 | 30468003 | − | TSF |
| 9% | chrX | 100178050 | 100177782 | − | ENST00000328526; ENST00000372956 | chrX | 100143801 | 100143669 | − | TSF |
| 9% | chrX | 100178050 | 100177782 | − | ENST00000328526; ENST00000372956 | chrX | 100143801 | 1001143669 | − | TSF |
| 5% | chr17 | 45473200 | 45473343 | + | ENST00000331493; ENST00000517484; ENST00000523842 | chr17 | 45474497 | 45476216 | + | TSF |
| 5% | chr17 | 45473200 | 45473343 | + | ENST00000331493; ENST00000517484; ENST00000523842 | chr17 | 45474497 | 45476216 | + | TSF |
| 5% | chr17 | 45473200 | 45473343 | + | ENST00000331493; ENST00000517484; ENST00000523842 | chr17 | 45474497 | 45476216 | + | TSF |
| 5% | chr15 | 64217060 | 64217015 | − | ENST00000261891; ENST00000457488; ENST00000558069 | chr15 | 64216283 | 64216265 | − | TSF |
| 4% | chr9 | 139847344; 139847404; 139847428 | 139847480 | + | ENST00000371633; ENST00000471615; ENST00000371632 | chr9 | 139847768 | 139847869 | + | TSF |
| 4% | chr9 | 139847344; 139847404; 139847428 | 139847480 | + | ENST00000371633; ENST00000471615; ENST00000371632 | chr9 | 139847768 | 139847869 | + | TSF |
| 4% | chr9 | 139847344; 139847404; 139847428 | 139847480 | + | ENST00000371633; ENST00000471615; ENST00000371632 | chr9 | 139847768 | 139847869 | + | TSF |
| 4% | chr17 | 45473200 | 45473343 | + | ENST00000331493; ENST00000517484; ENST00000523842 | chr17 | 45474435 | 45476216 | + | TSF |
| 4% | chr17 | 45473200 | 45473343 | + | ENST00000331493; ENST00000517484; ENST00000523842 | chr17 | 45474435 | 45476216 | + | TSF |
| 4% | chr17 | 45473200 | 45473343 | + | ENST00000331493; ENST00000517484; ENST00000523842 | chr17 | 45474435 | 45476216 | + | TSF |
| 3% | chr10 | 132915197 | 132915062 | − | ENST00000368642 | chr10 | 132903439 | 132903054 | − | TSF |
| 3% | chr19 | 54666021 | 54665838 | − | ENST00000301187; ENST00000416963; ENST00000376591 | chr19 | 54665366 | 54665264 | − | TSF |
| 3% | chr19 | 54666021 | 54665838 | − | ENST00000301187; ENST00000416963; ENST00000376591 | chr19 | 54665366 | 54665264 | − | TSF |
| 3% | chr19 | 54666021 | 54665838 | − | ENST00000301187; ENST00000416963; ENST00000376591 | chr19 | 54665366 | 54665264 | − | TSF |
| 3% | chr19 | 43372507 | 43372253 | − | ENST00000436291; ENST00000595124; ENST00000595356; ENST00000403380; ENST00000312439; ENST00000244296; ENST00000597058 | chr19 | 43257528 | 43257135 | − | TSF |
| 3% | chr19 | 43372507 | 43372253 | − | ENST00000436291; ENST00000595124; ENST00000595356; ENST00000403380; ENST00000312439; ENST00000244296; ENST00000597058 | chr19 | 43257528 | 43257135 | − | TSF |

TABLE 61-continued

Transcript fusion for Thyroid Cancer (THCA) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr19 | 43372507 | 43372253 | – | ENST00000436291; ENST00000595124; ENST00000595356; ENST00000403380; ENST00000312439; ENST00000244296; ENST00000597058 | chr19 | 43257528 | 43257135 | – | TSF |
| 2% | chrX | 100170072 | 100169610 | – | ENST00000328526; ENST00000372956 | chrX | 100143801 | 100143669 | – | TSF |
| 2% | chrX | 100170072 | 100169610 | – | ENST00000328526; ENST00000372956 | chrX | 100143801 | 100143669 | – | TSF |
| 2% | chr7 | 73973957 | 73973985 | + | ENST00000265755; ENST00000455841; ENST00000424337; ENST00000476977; ENST00000470715 | chr7 | 73985447 | 73985582 | + | TSF |
| 2% | chr7 | 73973957 | 73973985 | + | ENST00000265755; ENST00000455841; ENST00000424337; ENST00000476977; ENST00000470715 | chr7 | 73985447 | 73985582 | + | TSF |
| 2% | chr7 | 73973957 | 73973985 | + | ENST00000265755; ENST00000455841; ENST00000424337; ENST00000476977; ENST00000470715 | chr7 | 73985447 | 73985582 | + | TSF |
| 2% | chr7 | 73973957 | 73973985 | + | ENST00000265755; ENST00000455841; ENST00000424337; ENST00000476977; ENST00000470715 | chr7 | 73985447 | 73985582 | + | TSF |
| 2% | chr10 | 50255089 | 50255028 | – | ENST00000332853 | chr10 | 50240450 | 50240427 | – | TSF |
| 2% | chr17 | 11166683 | 11166843 | + | ENST00000432116; ENST00000441885; ENST00000409168; ENST00000343478 | chr17 | 11172072 | 11172130 | + | TSF |
| 2% | chr17 | 11166683 | 11166843 | + | ENST00000432116; ENST00000441885; ENST00000409168; ENST00000343478 | chr17 | 11172072 | 11172130 | + | TSF |
| 2% | chr13 | 53307494; 53307473 | 53307354 | – | ENST00000448904; ENST00000377962; ENST00000431550 | chr13 | 53304269 | 53303967 | – | TSF |
| 2% | chr13 | 53307494; 53307473 | 53307354 | – | ENST00000448904; ENST00000377962; ENST00000431550 | chr13 | 53304269 | 53303967 | – | TSF |
| 2% | chr4 | 25759228 | 25759156 | – | ENST00000399878; ENST00000264868; ENST00000502949; ENST00000510448 | chr4 | 25723603 | 25723555 | – | TSF |
| 2% | chr4 | 25759228 | 25759156 | – | ENST00000399878; ENST00000264868; ENST00000502949; ENST00000510448 | chr4 | 25723603 | 25723555 | – | TSF |
| 2% | chr4 | 25759228 | 25759156 | – | ENST00000399878; ENST00000264868; ENST00000502949; ENST00000510448 | chr4 | 25723603 | 25723555 | – | TSF |
| 2% | chr4 | 25759228 | 25759156 | – | ENST00000399878; ENST00000264868; ENST00000502949; ENST00000510448 | chr4 | 25723603 | 25723555 | – | TSF |
| 2% | chrX | 71401561; 71401615; 71401644 | 71401678 | + | ENST00000373662; ENST00000218432; ENST00000423432; ENST00000373669; ENST00000496835; ENST00000439980; ENST00000446576 | chrX | 71405250 | 71405452 | + | TSF |
| 2% | chrX | 71401561; 71401615; 71401644 | 71401678 | + | ENST00000373662; ENST00000218432; ENST00000423432; ENST00000373669; ENST00000496835; ENST00000439980; | chrX | 71405250 | 71405452 | + | TSF |

TABLE 61-continued

Transcript fusion for Thyroid Cancer (THCA) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 2% | chrX | 71401561; 71401615; 71401644 | 71401678 | + | ENST00000446576 ENST00000373662; ENST00000218432; ENST00000423432; ENST00000373669; ENST00000496835; ENST00000439980; ENST00000446576 | chrX | 71405250 | 71405452 | + | TSF |
| 2% | chr9 | 128510829; 128510854 | 128510902 | + | ENST00000342287; ENST00000373487; ENST00000373489; ENST00000373492; ENST00000373482; ENST00000491787; ENST00000447726 | chr9 | 128572989 | 128573209 | + | TSF |
| 2% | chr9 | 128510829; 128510854 | 128510902 | + | ENST00000342287; ENST00000373487; ENST00000373489; ENST00000373492; ENST00000373482; ENST00000491787; ENST00000447726 | chr9 | 128572989 | 128573209 | + | TSF |
| 2% | chr11 | 58919223 | 58919390 | + | ENST00000528737; ENST00000420244; ENST00000527629; ENST00000361723; ENST00000531408; ENST00000533703; ENST00000531147 | chr11 | 58921988 | 58922183 | + | TSF |
| 2% | chr2 | 135470889 | 135470770 | − | ENST00000281924 | chr2 | 135443800 | 135443742 | − | TSF |
| 1% | chr15 | 64426863 | 64427006 | + | ENST00000560829; ENST00000261889; ENST00000559844; ENST00000561026 | chr15 | 64427210 | 64427230 | + | TSF |
| 1% | chr15 | 64426863 | 64427006 | + | ENST00000560829; ENST00000261889; ENST00000559844; ENST00000561026 | chr15 | 64427210 | 64427230 | + | TSF |
| 1% | chr15 | 64426863 | 64427006 | + | ENST00000560829; ENST00000261889; ENST00000559844; ENST00000561026 | chr15 | 64427210 | 64427230 | + | TSF |
| 1% | chr18 | 56807181 | 56807267 | + | ENST00000587834; ENST00000299714; ENST00000588875 | chr18 | 56814218 | 56814267 | + | TSF |
| 1% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 1% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 1% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 1% | chr8 | 27461912 | 27461808 | − | ENST00000316403; ENST00000546343; ENST00000560366; ENST00000405140; ENST00000523500; ENST00000522098 | chr8 | 27458611 | 27458570 | − | TSF |
| 1% | chrX | 22208561 | 22208619 | + | ENST00000379374; ENST00000537599; ENST00000535894; ENST00000418858 | chrX | 22209939 | 22210210 | + | TSF |
| 1% | chrX | 22208561 | 22208619 | + | ENST00000379374; ENST00000537599; | chrX | 22209939 | 22210210 | + | TSF |

TABLE 61-continued

Transcript fusion for Thyroid Cancer (THCA) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chrX | 22208561 | 22208619 | + | ENST00000535894; ENST00000418858 ENST00000379374; ENST00000537599 | chrX | 22209939 | 22210210 | + | TSF |
| 1% | chr1 | 12476713 | 12476880 | + | ENST00000535894; ENST00000418858 ENST00000356315; ENST00000358136; ENST00000011700; ENST00000543766 | chr1 | 12510638 | 12510871 | + | TSF |
| 1% | chr1 | 12476713 | 12476880 | + | ENST00000356315; ENST00000358136; ENST00000011700; ENST00000543766 | chr1 | 12510638 | 12510871 | + | TSF |
| 1% | chr1 | 12476713 | 12476880 | + | ENST00000356315; ENST00000358136; ENST00000011700; ENST00000543766 | chr1 | 12510638 | 12510871 | + | TSF |
| 1% | chr1 | 12476713 | 12476880 | + | ENST00000356315; ENST00000358136; ENST00000011700; ENST00000543766 | chr1 | 12510638 | 12510871 | + | TSF |
| 1% | chr11 | 810235 | 810357 | + | ENST00000321153; ENST00000530797 | chr11 | 910147 | 910157 | + | TSF |
| 1% | chr15 | 32976758; 32976761 | 32976870 | + | ENST00000300175; ENST00000413748; ENST00000494364; ENST00000497208; ENST00000471027 | chr15 | 32977335 | 32977906 | + | TSF |
| 1% | chr15 | 32976758; 32976761 | 32976870 | + | ENST00000300175; ENST00000413748; ENST00000494364; ENST00000497208; ENST00000471027 | chr15 | 32977335 | 32977906 | + | TSF |
| 1% | chr15 | 32976758; 32976761 | 32976870 | + | ENST00000300175; ENST00000413748; ENST00000494364; ENST00000497208; ENST00000471027 | chr15 | 32977335 | 32977906 | + | TSF |
| 1% | chr7 | 33644477 | 33644587 | + | ENST00000242067; ENST00000350941; ENST00000354265; ENST00000355070; ENST00000396127; ENST00000434373 | chr7 | 33900207 | 33900392 | + | TSF |
| 1% | chr7 | 33644477 | 33644587 | + | ENST00000242067; ENST00000350941; ENST00000354265; ENST00000355070; ENST00000396127; ENST00000434373 | chr7 | 33900207 | 33900392 | + | TSF |
| 1% | chr7 | 33644477 | 33644587 | + | ENST00000242067; ENST00000350941; ENST00000354265; ENST00000355070; ENST00000396127; ENST00000434373 | chr7 | 33900207 | 33900392 | + | TSF |
| 1% | chr7 | 33644477 | 33644587 | + | ENST00000242067; ENST00000350941; ENST00000354265; ENST00000355070; ENST00000396127; ENST00000434373 | chr7 | 33900207 | 33900392 | + | TSF |
| 1% | chr7 | 33644477 | 33644587 | + | ENST00000242067; ENST00000350941; ENST00000354265; ENST00000355070; ENST00000396127; ENST00000434373 | chr7 | 33900207 | 339010392 | + | TSF |
| 1% | chr7 | 33644477 | 33644587 | + | ENST00000242067; ENST00000350941; ENST00000354265; ENST00000355070; ENST00000396127; ENST00000434373 | chr7 | 33900207 | 33900392 | + | TSF |

TABLE 61-continued

Transcript fusion for Thyroid Cancer (THCA) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 1% | chr2 | 89417128 | 89416936 | – | ENST00000490686 | chr2 | 89370042 | 893616766 | – | TSF |
| 1% | chr17 | 60107012 | 60106902 | – | ENST00000397786; ENST00000583958 | chr17 | 60101011 | 60100641 | – | TSF |
| 1% | chr17 | 60107012 | 60106902 | – | ENST00000397786; ENST00000583958 | chr17 | 60101011 | 60100641 | – | TSF |
| 1% | chr19 | 43679621 | 43679367 | – | ENST00000366175; ENST00000407356; ENST00000599812; ENST00000342951; ENST00000404580 | chr19 | 43448254 | 43447862 | – | TSF |
| 1% | chr19 | 43679621 | 43679367 | – | ENST00000366175; ENST00000407356; ENST00000599812; ENST00000342951; ENST00000404580 | chr19 | 43448254 | 43447862 | – | TSF |
| 1% | chr3 | 9825897 | 9825712 | – | ENST00000301964; ENST00000440161; ENST00000343450 | chr3 | 9823380 | 9823336 | – | TSF |
| 1% | chr19 | 43679621 | 43679367 | – | ENST00000366175; ENST00000407356; ENST00000599812; ENST00000342951; ENST00000404580 | chr19 | 43537524 | 43537131 | – | TSF |
| 1% | chr19 | 43679621 | 43679367 | – | ENST00000366175; ENST00000407356; ENST00000599812; ENST00000342951; ENST00000404580 | chr19 | 43537524 | 43537131 | – | TSF |
| 1% | chr19 | 43679621 | 43679367 | – | ENST00000366175; ENST00000407356; ENST00000599812; ENST00000342951; ENST00000404580 | chr19 | 43428976 | 43428578 | – | TSF |
| 1% | chr19 | 43679621 | 43679367 | – | ENST00000366175; ENST00000407356; ENST00000599812; ENST00000342951; ENST00000404580 | chr19 | 43428976 | 434218578 | – | TSF |

TABLE 62

Transcript fusion for Thyroid Cancer (THCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 43% | chr22 | 21575439 | 21575317 | – | chr22 | 21570956 | 21570760 | – | ENST00000405188; ENST00000401924; ENST00000424627 | TAF |
| 43% | chr22 | 21575439 | 21575317 | – | chr22 | 21570956 | 21570760 | – | ENST00000405188; ENST00000401924; ENST00000424627 | TAF |
| 29% | chr9 | 123237538 | 123237484 | – | chr9 | 123234156 | 123234026 | – | ENST00000359309; ENST00000360822; ENST00000349780; ENST00000360190; ENST00000480112; ENST00000416449 | TAF |
| 29% | chr9 | 123237538 | 123237484 | – | chr9 | 123234156 | 123234026 | – | ENST00000359309; ENST00000360822; ENST00000349780; ENST00000360190; ENST00000480112; ENST00000416449 | TAF |
| 29% | chr9 | 123237538 | 123237484 | – | chr9 | 123234156 | 123234026 | – | ENST00000359309; ENST00000360822; ENST00000349780; ENST00000360190; ENST00000480112; ENST00000416449 | TAF |
| 29% | chr9 | 123237538 | 123237484 | – | chr9 | 123234156 | 123234026 | – | ENST00000359309; ENST00000360822; | TAF |

TABLE 62-continued

Transcript fusion for Thyroid Cancer (THCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 29% | chr9 | 123237538 | 123237484 | − | chr9 | 123234156 | 123234026 | − | ENST00000349780; ENST00000360190; ENST00000480112; ENST00000416449 ENST00000359309; ENST00000360822; ENST00000349780; ENST00000360190; ENST00000480112; ENST00000416449 | TAF |
| 28% | chr7 | 30468250 | 30468120 | − | chr7 | 30465326 | 30465254 | − | ENST00000222823 | TSF |
| 23% | chr17 | 48164136 | 48164357 | + | chr17 | 48165108 | 48165233 | + | ENST00000320031; ENST00000007722 | TAF |
| 23% | chr17 | 48164136 | 48164357 | + | chr17 | 48165108 | 48165233 | + | ENST00000320031; ENST00000007722 | TAF |
| 21% | chr11 | 17895953 | 17895767 | − | chr11 | 17809960 | 17809632; 17809702 | − | ENST00000265965; ENST00000529151 | TAF |
| 21% | chr11 | 17895953 | 17895767 | − | chr11 | 17809960 | 17809632; 17809702 | − | ENST00000265965; ENST00000529151 | TAF |
| 21% | chrX | 123618682 | 123617816 | − | chrX | 123615814 | 123615582 | − | ENST00000371130; ENST00000422452 | TSF |
| 20% | chrX | 71529592 | 71529379 | − | chrX | 71522784 | 71522660 | − | ENST00000453707; ENST00000431381; ENST00000427412; ENST00000450875; ENST00000454225 | TSF |
| 20% | chrX | 71529592 | 71529379 | − | chrX | 71522784 | 71522660 | − | ENST00000453707; ENST00000431381; ENST00000427412; ENST00000450875; ENST00000454225 | TSF |
| 20% | chrX | 71529592 | 71529379 | − | chrX | 71522784 | 71522660 | − | ENST00000453707; ENST00000431381; ENST00000427412; ENST00000450875; ENST00000454225 | TSF |
| 20% | chrX | 71529592 | 71529379 | − | chrX | 71522784 | 71522660 | − | ENST00000453707; ENST00000431381; ENST00000427412; ENST00000450875; ENST00000454225 | TSF |
| 14% | chr3 | 124690942 | 124690838 | − | chr3 | 124689645 | 124689496 | − | ENST00000311127; ENST00000487661 | TAF |
| 14% | chr14 | 81544931 | 81545280 | + | chr14 | 81554298 | 81554372 | + | ENST00000541158; ENST00000342443; ENST00000298171; ENST00000554263; ENST00000554435 | TAF |
| 14% | chr14 | 81544931 | 81545280 | + | chr14 | 81554298 | 81554372 | + | ENST00000541158; ENST00000342443; ENST00000298171; ENST00000554263; ENST00000554435 | TAF |
| 14% | chr14 | 81544931 | 81545280 | + | chr14 | 81554298 | 81554372 | + | ENST00000541158; ENST00000342443; ENST00000298171; ENST00000554263; ENST00000554435 | TAF |
| 14% | chr14 | 81544931 | 81545280 | + | chr14 | 81554298 | 81554372 | + | ENST00000541158; ENST00000342443; ENST00000298171; ENST00000554263; ENST00000554435 | TAF |
| 14% | chr15 | 64203056 | 64202899 | − | chr15 | 64200799 | 64200719 | − | ENST00000261891; ENST00000457488 | TAF |
| 14% | chr9 | 128287668 | 287128523 | − | chr9 | 128284044 | 128284031 | − | ENST00000394060 | TAF |
| 12% | chr17 | 7130320 | 7130212 | − | chr17 | 7129958 | 7129740 | − | ENST00000005340; ENST00000575458; ENST00000575086 | TAF |
| 12% | chr17 | 7130320 | 7130212 | − | chr17 | 7129958 | 7129740 | − | ENST00000005340; ENST00000575458; ENST00000575086 | TAF |
| 11% | chr3 | 185411133 | 185410965 | − | chr3 | 185410550 | 185410487 | − | ENST00000382199; ENST00000421047; ENST00000457616; | TAF |

TABLE 62-continued

Transcript fusion for Thyroid Cancer (THCA) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 11% | chr3 | 185411133 | 185410965 | – | chr3 | 185410550 | 185410487 | – | ENST00000346192 ENST00000382199; ENST00000421047; ENST00000457616; ENST00000346192 | TAF |
| 6% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 6% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 6% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 6% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 6% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 6% | chr19 | 11528445 | 11528379 | – | chr19 | 11527733 | 11527510 | – | ENST00000562663; ENST00000563726; ENST00000380456; ENST00000393423; ENST00000567431; ENST00000567080 | TSF |
| 5% | chr9 | 123237538 | 123237538 | – | chr9 | 123234140 | 123234026 | – | ENST00000359309; ENST00000360822; ENST00000349780; ENST00000360190; ENST00000480112; ENST00000416449 | TSF |
| 5% | chr9 | 123237538 | 123237484 | – | chr9 | 123234140 | 123234026 | – | ENST00000359309; ENST00000360822; ENST00000349780; ENST00000360190; ENST00000480112; ENST00000416449 | TSF |
| 5% | chr9 | 123237538 | 123237484 | – | chr9 | 123234140 | 123234026 | – | ENST00000359309; ENST00000360822; ENST00000349780; ENST00000360190; ENST00000480112; ENST00000416449 | TSF |
| 5% | chr9 | 123237538 | 123237538 | – | chr9 | 123234140 | 123234026 | – | ENST00000359309; ENST00000360822; ENST00000349780; ENST00000360190; ENST00000480112; ENST00000416449 | TSF |
| 5% | chr9 | 123237538 | 123237538 | – | chr9 | 123234140 | 123234026 | – | ENST00000359309; ENST00000360822; ENST00000349780; ENST00000360190; ENST00000480112; ENST00000416449 | TSF |
| 5% | chr5 | 86542665 | 86543184 | + | chr5 | 86627165 | 86627317 | + | ENST00000274376; ENST00000515800; ENST00000456692; ENST00000512763; | TSF |

TABLE 62-continued

Transcript fusion for Thyroid Cancer (THCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 5% | chr5 | 86542665 | 86543184 | + | chr5 | 86627165 | 86627317 | + | ENST00000506290 ENST00000274376; ENST00000515800; ENST00000456692; ENST00000512763; ENST00000506290 | TSF |
| 5% | chr3 | 4859338 | 4859117 | − | chr3 | 4856115 | 4856088 | − | ENST00000449914; ENST00000441894 | TSF |
| 5% | chr3 | 4858133 | 4857857 | − | chr3 | 4856115 | 4856088 | − | ENST00000449914; ENST00000441894 | TSF |
| 4% | chr1 | 165468331 | 165468249 | − | chr1 | 165398203 | 165397956 | − | ENST00000359842 | TSF |
| 4% | chr9 | 110017723 | 110017723 | + | chr9 | 110062422 | 110062503 | + | ENST00000419616; ENST00000358015; ENST00000442587 | TSF |
| 4% | chr9 | 110017723 | 110017723 | + | chr9 | 110062422 | 110062503 | + | ENST00000419616; ENST00000358015; ENST00000442587 | TSF |
| 4% | chr9 | 110017723 | 110017723 | + | chr9 | 110062422 | 110062503 | + | ENST00000419616; ENST00000358015; ENST00000442587 | TSF |
| 3% | chr9 | 123237538 | 123237310 | − | chr9 | 123234156 | 123234026 | − | ENST00000359309; ENST00000360822; ENST00000349780; ENST00000360190; ENST00000480112; ENST00000416449 | TSF |
| 3% | chr9 | 123237538 | 123237310 | − | chr9 | 123234156 | 123234026 | − | ENST00000359309; ENST00000360822; ENST00000349780; ENST00000360190; ENST00000480112; ENST00000416449 | TSF |
| 3% | chr9 | 123237538 | 123237310 | − | chr9 | 123234156 | 123234026 | − | ENST00000359309; ENST00000360822; ENST00000349780; ENST00000360190; ENST00000480112; ENST00000416449 | TSF |
| 3% | chr9 | 123237538 | 123237310 | − | chr9 | 123234156 | 123234026 | − | ENST00000359309; ENST00000360822; ENST00000349780; ENST00000360190; ENST00000480112; ENST00000416449 | TSF |
| 3% | chr9 | 123237538 | 123237310 | − | chr9 | 123234156 | 123234026 | − | ENST00000359309; ENST00000360822; ENST00000349780; ENST00000360190; ENST00000416449 | TSF |
| 3% | chr11 | 12515263 | 12515280 | + | chr1 | 12516054 | 12516186 | + | ENST00000356315; ENST00000358136; ENST00000011700; ENST00000543766 | TSF |
| 3% | chr9 | 128286052 | 128286013 | − | chr9 | 128284044 | 128284031 | − | ENST00000394060 | TSF |
| 3% | chr15 | 64445039 | 64445132 | + | chr15 | 64445444 | 64445538; 64445542 | + | ENST00000325881; ENST00000558466 | TSF |
| 3% | chr15 | 64445039 | 64445132 | + | chr15 | 64445444 | 64445542 64445538; | + | ENST00000325881; ENST00000558466 | TSF |
| 3% | chr12 | 130849847 | 130849940 | + | chr12 | 130851678 | 130851803 | + | ENST00000245255 | TSF |
| 3% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; ENST00000590790 | TSF |
| 3% | chr16 | 4708255 | 4708353 | + | chr16 | 4714710 | 4714776 | + | ENST00000262370; ENST00000415496; ENST00000536343; ENST00000587747; ENST00000399577; ENST00000588994; ENST00000586183; | TSF |

TABLE 62-continued

Transcript fusion for Thyroid Cancer (THCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 3% | chr16 | 4708255 | 4708353 | + | chr16 | 4714710 | 4714776 | + | ENST00000590790 ENST00000262370; ENST00000415496; ENST00000536343; ENST00000587747; ENST00000399577; ENST00000588994; ENST00000586183; | TSF |
| 3% | chr16 | 4708255 | 4708353 | + | chr16 | 4714710 | 4714776 | + | ENST00000590790 ENST00000262370; ENST00000415496; ENST00000536343; ENST00000587747; ENST00000399577; ENST00000588994; ENST00000586183; | TSF |
| 3% | chr16 | 4708255 | 4708353 | + | chr16 | 4714710 | 4714776 | + | ENST00000590790 ENST00000262370; ENST00000415496; ENST00000536343; ENST00000587747; ENST00000399577; ENST00000588994; ENST00000586183; | TSF |
| 3% | chr16 | 4708255 | 4708353 | + | chr16 | 4714710 | 4714776 | + | ENST00000590790 ENST00000262370; ENST00000415496; ENST00000536343; ENST00000587747; ENST00000399577; ENST00000588994; ENST00000586183; | TSF |
| 3% | chr16 | 4708255 | 4708353 | + | chr16 | 4714710 | 4714776 | + | ENST00000590790 ENST00000262370; ENST00000415496; ENST00000536343; ENST00000587747; ENST00000399577; ENST00000588994; ENST00000586183; | TSF |
| 3% | chr16 | 4708255 | 4708353 | + | chr16 | 4714710 | 4714776 | + | ENST00000590790 ENST00000262370; ENST00000415496; ENST00000536343; ENST00000587747; ENST00000399577; ENST00000588994; ENST00000586183; | TSF |
| 2% | chr4 | 56493122 | 56492923 | − | chr4 | 56482552 | 56482505 | − | ENST00000264218; ENST00000505262; ENST00000507338 | TSF |
| 2% | chr4 | 56493122 | 56492923 | − | chr4 | 56482552 | 56482505 | − | ENST00000264218; ENST00000505262; ENST00000507338 | TSF |
| 2% | chr4 | 56493122 | 56492923 | − | chr4 | 56482552 | 56482505 | − | ENST00000264218; ENST00000505262; ENST00000507338 | TSF |
| 2% | chr7 | 30737766 | 30737846 | + | chr7 | 30793347 | 30793554 | + | ENST00000013222; ENST00000451002 | TSF |
| 2% | chr7 | 30737766 | 30737846 | + | chr7 | 30793347 | 30793554 | + | ENST00000013222; ENST00000451002 | TSF |
| 2% | chr12 | 117498589 | 117498567 | − | chr12 | 117494691 | 117494611 | − | ENST00000470612; ENST00000335209; ENST00000392545; ENST00000462502 | TSF |
| 2% | chr12 | 117498589 | 117498567 | − | chr12 | 117494691 | 117494611 | − | ENST00000470612; ENST00000335209; ENST00000392545; ENST00000462502 | TSF |
| 2% | chr12 | 117498589 | 117498567 | − | chr12 | 117494691 | 117494611 | − | ENST00000470612; ENST00000335209; ENST00000392545; ENST00000462502 | TSF |
| 2% | chr8 | 11706946 | 11706904 | − | chr8 | 11706673 | 11706555; | ENST00000434271; | TSF |

TABLE 62-continued

Transcript fusion for Thyroid Cancer (THCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 11706570; 11706571; 11706593 | | ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | |
| 2% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 2% | chr8 | 11706946 | 11706904 | – | chr8 | 11706673 | 11706555; 11706570; 71106571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 2% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 2% | chr8 | 11706946 | 11706904 | – | chr8 | 11706673 | 11706555; 11706570; 11706571; 11706593 | – | ENST00000434271; ENST00000353047; ENST00000530640; ENST00000531089; ENST00000453527; ENST00000345125; ENST00000533455; ENST00000534510; ENST00000534636; ENST00000533572; ENST00000530296; ENST00000526195; ENST00000527243; ENST00000534149; ENST00000526645 | TSF |
| 2% | chr8 | 11706946 | 11706904 | – | chr8 | 11706673 | 11706555; | | ENST00000434271; | TSF |

TABLE 62-continued

Transcript fusion for Thyroid Cancer (THCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 11706570;<br>11706571;<br>11706593 | | ENST00000353047;<br>ENST00000530640;<br>ENST00000531089;<br>ENST00000453527;<br>ENST00000345125;<br>ENST00000533455;<br>ENST00000534510;<br>ENST00000534636;<br>ENST00000533572;<br>ENST00000530296;<br>ENST00000526195;<br>ENST00000527243;<br>ENST00000534149;<br>ENST00000526645 | |
| 2% | chr8 | 11706946 | 11706904 | − | chr8 | 11706673 | 11706555;<br>11706570;<br>11706571;<br>11706593 | − | ENST00000434271;<br>ENST00000353047;<br>ENST00000530640;<br>ENST00000531089;<br>ENST00000453527;<br>ENST00000345125;<br>ENST00000533455;<br>ENST00000534510;<br>ENST00000534636;<br>ENST00000533572;<br>ENST00000530296;<br>ENST00000526195;<br>ENST00000527243;<br>ENST00000534149;<br>ENST00000526645 | TSF |
| 2% | chr8 | 11706946 | 11706904 | − | chr8 | 11706673 | 11706555;<br>11706570;<br>11706571;<br>11706593 | − | ENST00000434271;<br>ENST00000353047;<br>ENST00000530640;<br>ENST00000531089;<br>ENST00000453527;<br>ENST00000345125;<br>ENST00000533455;<br>ENST00000534510;<br>ENST00000534636;<br>ENST00000533572;<br>ENST00000530296;<br>ENST00000526195;<br>ENST00000527243;<br>ENST00000534149;<br>ENST00000526645 | TSF |
| 2% | chr14 | 104020098 | 104020199 | + | chr14 | 104053611 | 104053701;<br>104053628;<br>104053671 | + | ENST00000409074;<br>ENST00000472726;<br>ENST00000440963;<br>ENST00000458117;<br>ENST00000556253;<br>ENST00000247618 | TSF |
| 2% | chr14 | 104020098 | 104020199 | + | chr14 | 104053611 | 104053701:<br>104053628;<br>104053671 | + | ENST00000409074;<br>ENST00000472726;<br>ENST00000440963;<br>ENST00000458117;<br>ENST00000556253;<br>ENST00000247618 | TSF |
| 2% | chr14 | 104020098 | 104020199 | + | chr14 | 104053611 | 104053701;<br>104053628;<br>104053671 | + | ENST00000409074;<br>ENST00000472726;<br>ENST00000440963;<br>ENST00000458117;<br>ENST00000556253;<br>ENST00000247618 | TSF |
| 2% | chr14 | 104020098 | 104020199 | + | chr14 | 104053611 | 104053701;<br>104053628;<br>104053671 | + | ENST00000409074;<br>ENST00000472726;<br>ENST00000440963;<br>ENST00000458117;<br>ENST00000556253;<br>ENST00000247618 | TSF |
| 2% | chr10 | 132904406 | 132903251 | − | chr10 | 132902617 | 132902528 | − | ENST00000368642 | TSF |
| 2% | chr3 | 9823188 | 9823088 | − | chr3 | 9822233 | 9822041 | − | ENST00000301964;<br>ENST00000440161 | TSF |
| 2% | chr10 | 97605877 | 97605893 | + | chr10 | 97607203 | 97607463 | + | ENST00000453258;<br>ENST00000371207;<br>ENST00000543964;<br>ENST00000371203; | TSF |

TABLE 62-continued

Transcript fusion for Thyroid Cancer (THCA) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 2% | chr2 | 85823332 | 85823377 | + | chr2 | 85823642 | 85823772 | + | ENST00000539125; ENST00000371205 ENST00000441634; ENST00000306368; ENST00000414390; ENST00000443647; ENST00000456023 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr2 | 85823332 | 85823377 | + | chr2 | 85823642 | 85823772 | + | ENST00000441634; ENST00000306368; ENST00000414390; ENST00000443647; ENST00000456023 | TSF |
| 2% | chr2 | 114188389 | 114188536 | + | chr2 | 114196597 | 114196619 | + | ENST00000358604 | TSF |
| 2% | chr19 | 3014217 | 3014149 | − | chr19 | 3013816 | 3013667; 3013789 | − | ENST00000262953; ENST00000455444; ENST00000591529; ENST00000443826; ENST00000590536; ENST00000426948; ENST00000591457 | TSF |
| 2% | chr19 | 3014217 | 3014149 | − | chr19 | 3013816 | 3013667; 3013789 | − | ENST00000262953; ENST00000455444; ENST00000591529; ENST00000443826; ENST00000590536; ENST00000426948; ENST00000591457 | TSF |
| 2% | chr19 | 3014217 | 3014149 | − | chr19 | 3013816 | 3013667; 3013789 | − | ENST00000262953; ENST00000455444; ENST00000591529; ENST00000443826; ENST00000590536; ENST00000426948; ENST00000591457 | TSF |
| 2% | chr2 | 86095051 | 86094968 | − | chr2 | 86090608 | 86090485 | − | ENST00000393808; ENST00000377332; ENST00000306262; ENST00000525834 | TSF |
| 2% | chr2 | 86095051 | 86094968 | − | chr2 | 86090608 | 86090485 | − | ENST00000393808; ENST00000377332; ENST00000306262; ENST00000525834 | TSF |
| 2% | chr2 | 86095051 | 86094968 | − | chr2 | 86090608 | 86090485 | − | ENST00000393808; ENST00000377332; ENST00000306262; ENST00000525834 | TSF |
| 2% | chr6 | 32547977 | 32547945 | − | chr6 | 32546881 | 32546868 | − | ENST00000360004 | TSF |
| 2% | chr9 | 128286052 | 128286013 | − | chr9 | 128268696 | 128268589 | − | ENST00000373511; ENST00000373498; ENST00000373503; ENST00000265960; ENST00000394063 | TSF |
| 2% | chr9 | 128286052 | 128286013 | − | chr9 | 128268696 | 128268589 | − | ENST00000373511; ENST00000373498; ENST00000373503; ENST00000265960; ENST00000394063 | TSF |
| 1% | chr20 | 9289042 | 9289105 | + | chr20 | 9317773 | 9317853 | + | ENST00000407043; ENST00000441846; ENST00000334005; | TSF |

TABLE 62-continued

Transcript fusion for Thyroid Cancer (THCA) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | ENST00000378473; ENST00000437503; ENST00000416836; ENST00000278655; ENST00000414679; ENST00000378493; ENST00000378501 | |
| 1% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 1% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 1% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 1% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 1% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 1% | chr20 | 9289042 | 9289105 | + | chr20 | 9317773 | 9317853 | + | ENST00000407043; ENST00000441846; ENST00000334005; ENST00000378473; ENST00000437503; ENST00000416836; ENST00000278655; ENST00000414679; ENST00000378493; ENST00000378501 | TSF |
| 1% | chr20 | 57466178 | 57466186 | + | chr20 | 57485409 | 57485456 | + | ENST00000371100; ENST00000371102; ENST00000371095; ENST00000354359; ENST00000371085; ENST00000265620; ENST00000306090 | TSF |
| 1% | chrX | 69366031 | 69366077 | + | chrX | 69366595 | 69366678 | + | ENST00000342206; | TSF |

TABLE 62-continued

Transcript fusion for Thyroid Cancer (THCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr10 | 134034537 | 134034429 | – | chr10 | 134022605 | 134022598; 134022538 | – | ENST00000356413 ENST00000462160; ENST00000368622; ENST00000298630; ENST00000368625 | TSF |
| 1% | chr10 | 134034537 | 134034429 | – | chr10 | 134022605 | 134022598; 134022538 | – | ENST00000356413 ENST00000462160; ENST00000368622; ENST00000298630; ENST00000368625 | TSF |
| 1% | chr9 | 128287668 | 128287523 | – | chr9 | 128268696 | 128268589 | – | ENST00000373511; ENST00000373498; ENST00000373503; ENST00000265960; ENST00000394063 | TSF |
| 1% | chr9 | 128287668 | 128287523 | – | chr9 | 128268696 | 128268589 | – | ENST00000373511; ENST00000373498; ENST00000373503; ENST00000265960; ENST00000394063 | TSF |
| 1% | chr2 | 216248580 | 216248492 | – | chr2 | 216248206 | 216248051 | – | ENST00000421182; ENST00000323926; ENST00000336916; ENST00000357867; ENST00000354785; ENST00000345488; ENST00000346544; ENST00000357009; ENST00000359671; ENST00000446046; ENST00000443816; ENST00000432072; ENST00000356005; ENST00000456923 | TSF |
| 1% | chr2 | 216248580 | 216248492 | – | chr2 | 216248206 | 216248051 | – | ENST00000421182; ENST00000323926; ENST00000336916; ENST00000357867; ENST00000354785; ENST00000345488; ENST00000346544; ENST00000357009; ENST00000359671; ENST00000446046; ENST00000443816; ENST00000432072; ENST00000356005; ENST00000456923 | TSF |
| 1% | chr2 | 216248580 | 216248492 | – | chr2 | 216248206 | 216248051 | – | ENST00000421182; ENST00000323926; ENST00000336916; ENST00000357867; ENST00000354785; ENST00000345488; ENST00000346544; ENST00000357009; ENST00000359671; ENST00000446046; ENST00000443816; ENST00000432072; ENST00000356005; ENST00000456923 | TSF |
| 1% | chr2 | 216248580 | 216248492 | – | chr2 | 216248206 | 216248051 | – | ENST00000421182; ENST00000323926; ENST00000336916; ENST00000357867; ENST00000354785; ENST00000345488; ENST00000346544; ENST00000357009; ENST00000359671; ENST00000446046; ENST00000443816; ENST00000432072; ENST00000356005; ENST00000456923 | TSF |

TABLE 62-continued

Transcript fusion for Thyroid Cancer (THCA) Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr2 | 216248580 | 216248492 | – | chr2 | 216248206 | 216248051 | – | ENST00000421182; ENST00000323926; ENST00000336916; ENST00000357867; ENST00000354785; ENST00000345488; ENST00000346544; ENST00000357009; ENST00000359671; ENST00000446046; ENST00000443816; ENST00000432072; ENST00000356005; ENST00000456923 | TSF |
| 1% | chr2 | 216248580 | 216248492 | – | chr2 | 216248206 | 216248051 | – | ENST00000421182; ENST00000323926; ENST00000336916; ENST00000357867; ENST00000354785; ENST00000345488; ENST00000346544; ENST00000357009; ENST00000359671; ENST00000446046; ENST00000443816; ENST00000432072; ENST00000356005; ENST00000456923 | TSF |
| 1% | chr2 | 216248580 | 216248492 | – | chr2 | 216248206 | 216248051 | – | ENST00000421182; ENST00000323926; ENST00000336916; ENST00000357867; ENST00000354785; ENST00000345488; ENST00000346544; ENST00000357009; ENST00000359671; ENST00000446046; ENST00000443816; ENST00000432072; ENST00000356005; ENST00000456923 | TSF |
| 1% | chr2 | 216248580 | 216248492 | – | chr2 | 216248206 | 216248051 | – | ENST00000421182; ENST00000323926; ENST00000336916; ENST00000357867; ENST00000354785; ENST00000345488; ENST00000346544; ENST00000357009; ENST00000359671; ENST00000446046; ENST00000443816; ENST00000432072; ENST00000356005; ENST00000456923 | TSF |
| 1% | chr2 | 216248580 | 216248492 | – | chr2 | 216248206 | 216248051 | – | ENST00000421182; ENST00000323926; ENST00000336916; ENST00000357867; ENST00000354785; ENST00000345488; ENST00000346544; ENST00000357009; ENST00000359671; ENST00000446046; ENST00000443816; ENST00000432072; ENST00000356005; ENST00000456923 | TSF |
| 1% | chr2 | 216248580 | 216248492 | – | chr2 | 216248206 | 216248051 | – | ENST00000421182; ENST00000323926; ENST00000336916; ENST00000357867; ENST00000354785; | TSF |

TABLE 62-continued

Transcript fusion for Thyroid Cancer (THCA) Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
|   |   |   |   |   |   |   |   |   | ENST00000345488; ENST00000346544; ENST00000357009; ENST00000359671; ENST00000446046; ENST00000443816; ENST00000432072; ENST00000356005; ENST00000456923 | |
| 1% | chr15 | 80424477 | 80425177 | + | chr15 | 80429822 | 80429970; 80429902 | + | ENST00000261749; ENST00000561060; ENST00000559157; ENST00000564367; ENST00000558494; ENST00000559835; ENST00000559775; ENST00000558087 | TSF |
| 1% | chr15 | 80424477 | 80425177 | + | chr15 | 80429822 | 80429970; 80429902 | + | ENST00000261749; ENST00000561060; ENST00000559157; ENST00000564367; ENST00000558494; ENST00000559835; ENST00000559775; ENST00000558087 | TSF |
| 1% | chrX | 130206450 | 130206550 | + | chrX | 130215734 | 130215892 | + | ENST00000276211; ENST00000370922; ENST00000412432 | TSF |
| 1% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 1% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 1% | chr1 | 1562829 | 1562926 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; ENST00000378708; ENST00000514234 | TSF |
| 1% | chr1 | 58943264 | 58943356 | + | chr11 | 58949212 | 58949935 | + | ENST00000227451 | TSF |
| 1% | chr1 | 1562829 | 1562875 | + | chr1 | 1563053 | 1563209 | + | ENST00000520777; ENST00000357210; ENST00000360522; ENST00000378710; ENST00000355826; ENST00000518681; ENST00000505820; ENST00000487053; ENST00000378712; ENST00000504599; | TSF |

TABLE 62-continued

Transcript fusion for Thyroid Cancer (THCA) Coordinates
of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 1% | chr1 | 1562829 | 1562875 | + | chr1 | 1563053 | 1563209 | + | ENST00000378708; ENST00000514234 ENST00000520777; ENST00000357210; ENST00000360522; ENST00000378710; ENST00000355826; ENST00000518681; ENST00000505820; ENST00000487053; ENST00000378712; ENST00000504599; | TSF |
| 1% | chr1 | 1562829 | 1562875 | + | chr1 | 1563053 | 1563209 | + | ENST00000378708; ENST00000514234 ENST00000520777; ENST00000357210; ENST00000360522; ENST00000378710; ENST00000355826; ENST00000518681; ENST00000505820; ENST00000487053; ENST00000378712; ENST00000504599; ENST00000514234 | TSF |
| 1% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 1% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 1% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 1% | chr7 | 29523499 | 29523591 | + | chr7 | 29535568 | 29535652 | + | ENST00000539406; ENST00000222792; ENST00000495789; ENST00000539389; ENST00000546235; ENST00000446446; ENST00000409041; ENST00000424025; ENST00000421775; ENST00000439711 | TSF |
| 1% | chr7 | 151133708 | 151133690 | − | chr7 | 151133411 | 151133266 | − | ENST00000337323 | TSF |
| 1% | chr20 | 32029125 | 32028924 | − | chr20 | 32026832 | 32026647 | − | ENST00000217381 | TSF |
| 1% | chr6 | 39268199 | 39268149 | − | chr6 | 39267513 | 39267203 | − | ENST00000373231 | TSF |

TABLE 63

Transcript fusion for Thymoma (THYM) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 81% | chr10 | 72538392; 72538389 | 72538313 | − | ENST00000299290; ENST00000456372; ENST00000545575 | chr10 | 72537613 | 72537588 | − | TAF |
| 81% | chr10 | 72538392; 72538389 | 72538313 | − | ENST00000299290; ENST00000456372; ENST00000545575 | chr10 | 72537613 | 72537588 | − | TAF |
| 75% | chr1 | 158326518; 158326554 | 158326682 | + | ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 75% | chr1 | 158326518; 158326554 | 158326682 | + | ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 75% | chr1 | 158326518; 158326554 | 158326682 | + | ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 75% | chr1 | 158326518; 158326554 | 158326682 | + | ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 75% | chr1 | 158326518; 158326554 | 158326682 | + | ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 75% | chr1 | 158326518; 158326554 | 158326682 | + | ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 75% | chr1 | 158326518; 158326554 | 158326682 | + | ENST00000444681; ENST00000368167; ENST00000452291; | chr1 | 158327113 | 158327284 | + | TAF |

TABLE 63-continued

Transcript fusion for Thymoma (THYM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 75% | chr1 | 158326518; 158326554 | 158326682 | + | ENST00000368165; ENST00000368166; ENST00000368163; ENST00000368154; ENST00000368155; ENST00000368156; ENST00000368157; ENST00000368160 ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 75% | chr1 | 158326518; 158326554 | 158326682 | + | ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 75% | chr1 | 158326518; 158326554 | 158326682 | + | ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 75% | chr1 | 158326518; 158326554 | 158326682 | + | ENST00000444681; ENST00000368167; ENST00000452291; ENST00000368165; ENST00000368166; ENST00000368163; ENST00000368154; ENST00000368155; ENST00000368156; ENST00000368157; ENST00000368160 | chr1 | 158327113 | 158327284 | + | TAF |
| 68% | chr2 | 87072081 | 87072045 | − | ENST00000393759; ENST00000349455; ENST00000331469; ENST00000390655; ENST00000431506 | chr2 | 87069500 | 87069472 | − | TAF |
| 68% | chr2 | 87072081 | 87072045 | − | ENST00000393759; ENST00000349455; ENST00000331469; ENST00000390655; ENST00000431506 | chr2 | 87069500 | 87069472 | − | TAF |
| 68% | chr2 | 87072081 | 87072045 | − | ENST00000393759; ENST00000349455; ENST00000331469; ENST00000390655; ENST00000431506 | chr2 | 87069500 | 87069472 | − | TAF |
| 68% | chr4 | 108999538 | 108999376 | − | ENST00000265165; ENST00000379951; ENST00000438313; ENST00000510624 | chr4 | 108994190 | 1089941089 | − | TAF |
| 68% | chr4 | 108999538 | 108999376 | − | ENST00000265165; ENST00000379951; ENST00000438313; ENST00000510624 | chr4 | 108994190 | 108994089 | − | TAF |

TABLE 63-continued

Transcript fusion for Thymoma (THYM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 68% | chr4 | 108999538 | 108999376 | – | ENST00000265165; ENST00000379951; ENST00000438313; ENST00000510624 | chr4 | 108994190 | 108994089 | – | TAF |
| 62% | chr1 | 209946293 | 209946364 | + | ENST00000400959; ENST00000367025; ENST00000478359; ENST00000367026; ENST00000367024; ENST00000010338 | chr1 | 209948635 | 209948677 | + | TAF |
| 62% | chr1 | 209946293 | 209946364 | + | ENST00000400959; ENST00000367025; ENST00000478359; ENST00000367026; ENST00000367024; ENST00000010338 | chr1 | 209948635 | 209948677 | + | TAF |
| 61% | chr6 | 42890765; 42890883 | 42891085 | + | ENST00000304672; ENST00000441198 | chr6 | 42891625 | 42891704 | + | TAF |
| 61% | chr6 | 42890765; 42890883 | 42891085 | + | ENST00000304672; ENST00000441198 | chr6 | 42891625 | 42891704 | + | TAF |
| 48% | chr22 | 40365415 | 40365537 | + | ENST00000543252; ENST00000344138; ENST00000540310; ENST00000544756; ENST00000399090; ENST00000407075 | chr22 | 40380179 | 40380375 | + | TAF |
| 48% | chr22 | 40365415 | 40365537 | + | ENST00000543252; ENST00000344138; ENST00000540310; ENST00000544756; ENST00000399090; ENST00000407075 | chr22 | 40380179 | 40380375 | + | TAF |
| 48% | chr22 | 40365415 | 40365537 | + | ENST00000543252; ENST00000344138; ENST00000540310; ENST00000544756; ENST00000399090; ENST00000407075 | chr22 | 40380179 | 40380375 | + | TAF |
| 48% | chr22 | 40365415 | 40365537 | + | ENST00000543252; ENST00000344138; ENST00000540310; ENST00000544756; ENST00000399090; ENST00000407075 | chr22 | 40380179 | 40380375 | + | TAF |
| 48% | chr22 | 40365415 | 40365537 | + | ENST00000543252; ENST00000344138; ENST00000540310; ENST00000544756; ENST00000399090; ENST00000407075 | chr22 | 40380179 | 40380375 | + | TAF |
| 42% | chr12 | 71509738 | 71509630 | – | ENST00000549357 | chr12 | 71504233 | 71503634 | – | TAF |
| 35% | chr4 | 1742553 | 1742713 | + | ENST00000313288 | chr4 | 1745122 | 1745307 | + | TAF |
| 35% | chr11 | 118213322 | 118213268 | – | ENST00000300692; ENST00000529594; ENST00000392884 | chr11 | 118212457 | 118212389 | – | TAF |
| 31% | chr17 | 37321392 | 37321332 | – | ENST00000269586; ENST00000444555 | chr17 | 37320542 | 37320482 | – | TAF |
| 31% | chr9 | 15506635 | 15506559 | – | ENST00000380738; ENST00000380733; ENST00000380715; ENST00000380716; ENST00000397519 | chr9 | 15492223 | 15492056 | – | TAF |
| 31% | chr14 | 107083557 | 107083240 | – | ENST00000455737 | chr14 | 107082668 | 107082471 | – | TSF |
| 30% | chr6 | 42883808 | 42883865 | + | ENST00000304672; ENST00000441198; ENST00000446507 | chr6 | 42890333 | 42890502 | + | TSF |
| 29% | chr10 | 15151838 | 15151701 | – | ENST00000378165; ENST00000378150; ENST00000540259; ENST00000535341 | chr10 | 15148697 | 15148684 | – | TAF |
| 29% | chr10 | 15151838 | 15151701 | – | ENST00000378165; ENST00000378150; ENST00000540259; ENST00000535341 | chr10 | 15148697 | 15148684 | – | TAF |
| 29% | chr10 | 15151838 | 15151701 | – | ENST00000378165; | chr10 | 15148697 | 15148684 | – | TAF |

TABLE 63-continued

Transcript fusion for Thymoma (THYM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 29% | chr10 | 15151838 | 15151701 | – | ENST00000378150; ENST00000540259; ENST00000535341 ENST00000378165; ENST00000378150; ENST00000540259; ENST00000535341 | chr10 | 15148697 | 15148684 | – | TAF |
| 28% | chr22 | 37868566 | 37868481 | – | ENST00000416983; ENST00000356998 | chr22 | 37865350 | 37865175 | – | TAF |
| 28% | chr22 | 37868566 | 37868481 | – | ENST00000416983; ENST00000356998 | chr22 | 37865350 | 37865175 | – | TAF |
| 28% | chr10 | 120905865 | 120905748 | – | ENST00000355697; ENST00000330036 | chr10 | 120901885 | 120901741 | – | TAF |
| 28% | chr10 | 120905865 | 120905748 | – | ENST00000355697; ENST00000330036 | chr10 | 120901885 | 120901741 | – | TAF |
| 27% | chr19 | 37618030 | 37619808 | + | ENST00000337995 | chr19 | 37621046 | 37621237 | + | TAF |
| 26% | chr5 | 82554349 | 82554496 | + | ENST00000282268; ENST00000338635; ENST00000396027; ENST00000511817 | chr5 | 82606608 | 82606935 | + | TAF |
| 24% | chr15 | 101845560 | 101845467 | – | ENST00000398185; ENST00000348070; ENST00000358417 | chr15 | 101841074 | 101840901 | – | TAF |
| 24% | chr15 | 101845560 | 101845467 | – | ENST00000398185; ENST00000348070; ENST00000358417 | chr15 | 101841074 | 101840901 | – | TAF |
| 24% | chr15 | 101845560 | 101845467 | – | ENST00000398185; ENST00000348070; ENST00000358417 | chr15 | 101841074 | 101840901 | – | TAF |
| 23% | chr19 | 8122688; 8122685 | 8122765 | + | ENST00000253451; ENST00000390669 | chr19 | 8301345 | 8301593 | + | TSF |
| 23% | chr19 | 8122688; 8122685 | 8122765 | + | ENST00000253451; ENST00000390669 | chr19 | 8301345 | 8301593 | + | TSF |
| 22% | chr11 | 428199 | 428088 | | ENST00000332826 | chr11 | 424187 | 423924 | – | TAF |
| 22% | chr6 | 27216879 | 27217008 | + | ENST00000230582; ENST00000470870; ENST00000475106; ENST00000485993 | chr6 | 27217348 | 27217694 | + | TSF |
| 22% | chr6 | 27216879 | 27217008 | + | ENST00000230582; ENST00000470870; ENST00000475106; ENST00000485993 | chr6 | 27217348 | 27217694 | + | TSF |
| 21% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 21% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 21% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 21% | chr19 | 13869914; 13869931; 13869925 | 13870086 | + | ENST00000586600; ENST00000221554; ENST00000586666; ENST00000588809; ENST00000585844 | chr19 | 13872305 | 13872412 | + | TAF |
| 21% | chr9 | 130540906 | 130540870 | – | ENST00000314830 | chr9 | 130540563 | 130540257 | – | TAF |
| 21% | chr5 | 74984990 | 74984837 | – | ENST00000428202; ENST00000514838; ENST00000380475; ENST00000510798; ENST00000446329 | chr5 | 74983153 | 74982863 | – | TAF |
| 21% | chr5 | 74984990 | 74984837 | – | ENST00000428202; ENST00000514838; ENST00000380475; ENST00000510798; ENST00000446329 | chr5 | 74983153 | 74982863 | – | TAF |
| 21% | chr5 | 74984990 | 74984837 | – | ENST00000428202; ENST00000514838; | chr5 | 74983153 | 74982863 | – | TAF |

TABLE 63-continued

Transcript fusion for Thymoma (THYM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 21% | chr5 | 74984990 | 74984837 | − | ENST00000380475; ENST00000510798; ENST00000446329 ENST00000428202; ENST00000514838; ENST00000380475; ENST00000510798; ENST00000446329 | chr5 | 74983153 | 74982863 | − | TAF |
| 20% | chr10 | 72538392; 72538389 | 72538313 | − | ENST00000299290; ENST00000456372; ENST00000545575 | chr10 | 72537732 | 72537588 | − | TSF |
| 20% | chr10 | 72538392; 72538389 | 72538313 | − | ENST00000299290; ENST00000456372; ENST00000545575 | chr10 | 72537732 | 72537588 | − | TSF |
| 18% | chr9 | 101984828 | 101984925 | + | ENST00000223641 | chr9 | 101986374 | 101986588 | + | TAF |
| 18% | chr6 | 139363856 | 139363999 | + | ENST00000367660 | chr6 | 139372258 | 139372516 | + | TAF |
| 18% | chr2 | 99786073 | 99786013 | − | ENST00000422537; ENST00000289359; ENST00000409107 | chr2 | 99784175 | 99783867 | − | TAF |
| 18% | chr2 | 99786073 | 99786013 | − | ENST00000422537; ENST00000289359; ENST00000409107 | chr2 | 99784175 | 99783867 | − | TAF |
| 18% | chr2 | 99786073 | 99786013 |  | ENST00000422537; ENST00000289359; ENST00000409107 | chr2 | 199784175 | 199783867 | − | TAF |
| 18% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 18% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 18% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 18% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 18% | chr16 | 4409386 | 4409297 | − | ENST00000572467; ENST00000251166; ENST00000539968; ENST00000537233; ENST00000574025; ENST00000576637 | chr16 | 4409070 | 4408945 | − | TAF |
| 18% | chr17 | 40821639; 40821538 | 40821448 | − | ENST00000591022; ENST00000412503; ENST00000293349 | chr17 | 40820920 | 40820864 | − | TAF |
| 18% | chr17 | 40821639; 40821538 | 40821448 | − | ENST00000591022; ENST00000412503; ENST00000293349 | chr17 | 40820920 | 40820864 | − | TAF |
| 18% | chr17 | 40821639; 40821538 | 40821448 | − | ENST00000591022; ENST00000412503; ENST00000293349 | chr17 | 40820920 | 40820864 | − | TAF |
| 18% | chr2 | 87135092 | 87135139 | + | ENST00000409776 | chr2 | 87137322 | 87137378 | + | TSF |
| 16% | chr19 | 50984141 | 50984234 | + | ENST00000334976; ENST00000376918; ENST00000598585 | chr19 | 51009025 | 51009080 | + | TAF |
| 16% | chr14 | 45590157 | 45590090 | − | ENST00000396062; ENST00000216330 | chr14 | 45588212 | 455188057 | − | TAF |
| 16% | chr4 | 103522052 | 103522166 | + | ENST00000226574; ENST00000394820; ENST00000505458; ENST00000600343 | chr4 | 103522776 | 103522846 | + | TSF |
| 16% | chr4 | 103522052 | 103522166 | + | ENST00000226574; | chr4 | 103522776 | 103522846 | + | TSF |

TABLE 63-continued

Transcript fusion for Thymoma (THYM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|----|----|
| 16% | chr4 | 103522052 | 103522166 | + | ENST00000394820; ENST00000505458; ENST00000600343 ENST00000226574; ENST00000394820; ENST00000505458; ENST00000600343 | chr4 | 103522776 | 103522846 | + | TSF |
| 15% | chr17 | 7130588 | 7130409 | − | ENST00000005340; ENST00000575458; ENST00000575086 | chr17 | 7130277 | 7130132 | − | TAF |
| 15% | chr17 | 7130588 | 7130409 | − | ENST00000005340; ENST00000575458; ENST00000575086 | chr17 | 7130277 | 7130132 | − | TAF |
| 15% | chr17 | 7130588 | 7130409 | − | ENST00000005340; ENST00000575458; ENST00000575086 | chr17 | 7130277 | 7130132 | − | TAF |
| 15% | chr2 | 87135092 | 87135139 | + | ENST00000409776 | chr2 | 87147014 | 87147070 | + | TSF |
| 15% | chr2 | 87144754 | 87144801 | + | ENST00000559485 | chr2 | 87147014 | 87147070 | + | TSF |
| 15% | chr10 | 72541792 | 72541557 | − | ENST00000299290; ENST00000456372; ENST00000545575 | chr10 | 72537613 | 72537588 | − | TSF |
| 15% | chr10 | 72541792 | 72541557 | − | ENST00000299290; ENST00000456372; ENST00000545575 | chr10 | 72537613 | 72537588 | − | TSF |
| 13% | chr19 | 3544937 | 3544807 | − | ENST00000389395; ENST00000398558; ENST00000588918; ENST00000355415; ENST00000589063 | chr19 | 3538708 | 3538306 | − | TAF |
| 13% | chr19 | 3544937 | 3544807 | − | ENST00000389395; ENST00000398558; ENST00000588918; ENST00000355415; ENST00000589063 | chr19 | 3538708 | 3538306 | − | TAF |
| 13% | chr19 | 3544937 | 3544807 | − | ENST00000389395; ENST00000398558; ENST00000588918; ENST00000355415; ENST00000589063 | chr19 | 3538708 | 3538306 | − | TAF |
| 12% | chr2 | 42924916 | 42924974 | + | ENST00000405592; ENST00000406652; ENST00000407270; ENST00000454356; ENST00000406911; ENST00000409019; ENST00000405094 | chr2 | 42925555 | 42925601 | + | TAF |
| 12% | chr2 | 42924916 | 42924974 | + | ENST00000405592; ENST00000406652; ENST00000407270; ENST00000454356; ENST00000406911; ENST00000409019; ENST00000405094 | chr2 | 42925555 | 42925601 | + | TAF |
| 12% | chr8 | 27516013 | 27517056 | + | ENST00000337221; ENST00000301904 | chr8 | 27555709 | 27555926 | + | TAF |
| 12% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 12% | chr6 | 10749855; 10749898 | 10749931 | + | ENST00000379542; ENST00000473166; ENST00000463448; ENST00000460341; ENST00000480294; ENST00000473807; ENST00000461342; | chr6 | 10829240 | 10829256 | + | TAF |

TABLE 63-continued

Transcript fusion for Thymoma (THYM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 12% | chr4 | 108999538 | 108999376 | – | ENST00000475942; ENST00000379530; ENST00000463100; ENST00000481240; ENST00000467317; ENST00000478732 ENST00000265165; ENST00000379951; ENST00000438313; ENST00000510624 | chr4 | 108994185 | 108994089 | – | TSF |
| 12% | chr4 | 108999538 | 108999376 | – | ENST00000265165; ENST00000379951; ENST00000438313; ENST00000510624 | chr4 | 108994185 | 108994089 | – | TSF |
| 12% | chr4 | 108999538 | 108999376 | – | ENST00000265165; ENST00000379951; ENST00000438313; ENST00000510624 | chr4 | 108994185 | 108994089 | – | TSF |
| 12% | chr2 | 88285293 | 88285246 | – | ENST00000420840 | chr2 | 88283035 | 88282979 | – | TSF |
| 11% | chr18 | 12831040; 12831004 | 12830942 | – | ENST00000327283; ENST00000591115; ENST00000353319; ENST00000587703; ENST00000309660; ENST00000591497; ENST00000592776; ENST00000592059 | chr18 | 12827677 | 12827395 | – | TAF |
| 11% | chr18 | 12831040; 12831004 | 12830942 | – | ENST00000327283; ENST00000591115; ENST00000353319; ENST00000587703; ENST00000309660; ENST00000591497; ENST00000592776; ENST00000592059 | chr18 | 12827677 | 12827395 | – | TAF |
| 11% | chr18 | 12831040; 12831004 | 12830942 | – | ENST00000327283; ENST00000591115; ENST00000353319; ENST00000587703; ENST00000309660; ENST00000591497; ENST00000592776; ENST00000592059 | chr18 | 12827677 | 12827395 | – | TAF |
| 11% | chr18 | 12831040; 12831004 | 12830942 | – | ENST00000327283; ENST00000591115; ENST00000353319; ENST00000587703; ENST00000309660; ENST00000591497; ENST00000592776; ENST00000592059 | chr18 | 12827677 | 12827395 | – | TAF |
| 11% | chr1 | 32560385 | 32560572 | + | ENST00000336294; ENST00000373634; ENST00000427288 | chr1 | 32561261 | 32561358 | + | TSF |
| 11% | chr1 | 32560385 | 32560572 | + | ENST00000336294; ENST00000373634; ENST00000427288 | chr1 | 32561261 | 32561358 | + | TSF |
| 11% | chr1 | 32560385 | 32560572 | + | ENST00000336294; ENST00000373634; ENST00000427288 | chr1 | 32561261 | 32561358 | + | TSF |
| 10% | chr20 | 49458303 | 49458437 | + | ENST00000358791; ENST00000371608; ENST00000609336 | chr20 | 49468479 | 49468517 | + | TSF |
| 10% | chr20 | 49458303 | 49458437 | + | ENST00000358791; ENST00000371608; ENST00000609336 | chr20 | 49468479 | 49468517 | + | TSF |
| 10% | chr10 | 72539498 | 72539349 | – | ENST00000299290; ENST00000456372; ENST00000545575 | chr10 | 72537613 | 72537588 | – | TSF |
| 10% | chr10 | 72539498 | 72539349 | – | ENST00000299290; ENST00000456372; ENST00000545575 | chr10 | 72537613 | 72537588 | – | TSF |
| 8% | chr10 | 98095651; 98095648 | 98095731 | + | ENST00000419175; ENST00000371174 | chr10 | 98115406 | 98115502 | + | TSF |
| 8% | chr10 | 98095651; | 98095731 | + | ENST00000419175; | chr10 | 98115406 | 98115502 | + | TSF |

TABLE 63-continued

Transcript fusion for Thymoma (THYM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 8% | chr10 | 98095648 72538392; 72538389 | 72538313 | − | ENST00000371174 ENST00000299290; ENST00000456372; ENST00000545575 | chr10 | 72537677 | 72537588 | − | TSF |
| 8% | chr10 | 72538392; 72538389 | 72538313 | − | ENST00000299290; ENST00000456372; ENST00000545575 | chr10 | 72537677 | 72537588 | − | TSF |
| 7% | chr6 | 42883808 | 42883865 | + | ENST00000304672; ENST00000441198; ENST00000446507 | chr6 | 42891625 | 428191704 | + | TSF |
| 7% | chr2 | 112601176 | 112600989 | − | ENST00000427997; ENST00000341068 | chr2 | 112598811 | 112598755 | − | TSF |
| 7% | chr2 | 112601176 | 112600989 | − | ENST00000427997; ENST00000341068 | chr2 | 112598811 | 1125981755 | − | TSF |
| 6% | chr2 | 112636548 | 112636387 | − | ENST00000341068; ENST00000451367 | chr2 | 112635895 | 112635435 | − | TSF |
| 6% | chr10 | 72541792 | 72541557 | − | ENST00000299290; ENST00000456372; ENST00000545575 | chr10 | 72539689 | 72539621 | − | TSF |
| 6% | chr10 | 72541792 | 72541557 | − | ENST00000299290; ENST00000456372; ENST00000545575 | chr10 | 72539689 | 72539621 | − | TSF |
| 6% | chr16 | 2825557; 2825626 | 2825452 | − | ENST00000262306; ENST00000409906; ENST00000409477; ENST00000494946 | chr16 | 2823822 | 2823809 | − | TSF |
| 6% | chr16 | 2825557; 2825626 | 2825452 | − | ENST00000262306; ENST00000409906; ENST00000409477; ENST00000494946 | chr16 | 2823822 | 2823809 | − | TSF |
| 6% | chr16 | 2825557; 2825626 | 2825452 | − | ENST00000262306; ENST00000409906; ENST00000409477; ENST00000494946 | chr16 | 2823822 | 2823809 | − | TSF |
| 6% | chr3 | 138289340 | 138289160 | − | ENST00000264982; ENST00000542237; ENST00000484888; ENST00000474781; ENST00000481834; ENST00000468900; ENST00000462419; ENST00000464035 | chr3 | 138261631 | 138260784 | − | TSF |
| 6% | chr3 | 138289340 | 138289160 | − | ENST00000264982; ENST00000542237; ENST00000484888; ENST00000474781; ENST00000481834; ENST00000468900; ENST00000462419; ENST00000464035 | chr3 | 138261631 | 138260784 | − | TSF |
| 6% | chr3 | 138289340 | 138289601 | − | ENST00000264982; ENST00000542237; ENST00000484888; ENST00000474781; ENST00000481834; ENST00000468900; ENST00000462419; ENST00000464035 | chr3 | 138261631 | 138260784 | − | TSF |
| 6% | chr3 | 138289340 | 138289160 | − | ENST00000264982; ENST00000542237; ENST00000484888; ENST00000474781; ENST00000481834; ENST00000468900; ENST00000462419; ENST00000464035 | chr3 | 138261631 | 138260784 | − | TSF |
| 5% | chr22 | 35819207 | 35819334 | + | ENST00000216122; ENST00000382011 | chr22 | 35822985 | 35823438 | + | TSF |
| 5% | chr22 | 35819207 | 35819334 | + | ENST00000216122; ENST00000382011 | chr22 | 35822985 | 35823438 | + | TSF |
| 5% | chr6 | 27220587 | 27220728 | + | ENST00000421826; ENST00000230582; ENST00000475106; ENST00000485993 | chr6 | 27221559 | 27221657 | + | TSF |
| 5% | chr6 | 27220587 | 27220728 | + | ENST00000421826; | chr6 | 27221559 | 27221657 | + | TSF |

TABLE 63-continued

Transcript fusion for Thymoma (THYM) Coordinates
of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 5% | chr6 | 27220587 | 2722028 | + | ENST00000230582; ENST00000475106; ENST00000485993 ENST00000421826; ENST00000230582; ENST00000475106; ENST00000485993 | chr6 | 27221559 | 27221657 | + | TSF |
| 5% | chr6 | 27220587 | 2722028 | + | ENST00000421826; ENST00000230582; ENST00000475106; ENST00000485993 | chr6 | 27221559 | 27221657 | + | TSF |
| 5% | chr8 | 624047; 623326; 623657 | 623289 | – | ENST00000522706; ENST00000523415; ENST00000262109; ENST00000522893 | chr8 | 622204 | 621954 | – | TSF |
| 5% | chr8 | 624047; 623326; 623657 | 623289 | – | ENST00000522706; ENST00000523415; ENST00000262109; ENST00000522893 | chr8 | 622204 | 621954 | – | TSF |
| 5% | chr8 | 624047; 623326; 623657 | 623289 | – | ENST00000522706; ENST00000523415; ENST00000262109; ENST00000522893 | chr8 | 622204 | 621954 | – | TSF |
| 5% | chr8 | 624047; 623326; 623657 | 623289 | – | ENST00000522706; ENST00000523415; ENST00000262109; ENST00000522893 | chr8 | 622204 | 621954 | – | TSF |

TABLE 64

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 71% | chr6 | 42890506 | 42890547 | + | chr6 | 42890765 | 42891085 | + | ENST00000304672 | TAF |
| 71% | chr12 | 55350849 | 55350538 | – | chr12 | 55344174 | 55343992; 55344114 | – | ENST00000528240; ENST00000532757 | TAF |
| 71% | chr12 | 55350849 | 55350538 | – | chr12 | 55344174 | 55343992; 55344114 | – | ENST00000528240; ENST00000532757 | TAF |
| 62% | chr17 | 54888692 | 54888652 | – | chr17 | 54872541 | 54872425 | – | ENST00000397861; ENST00000397862; | TAF |
| 61% | chr11 | 17888603 | 17888338 | – | chr11 | 17809960 | 17809632; 17809702 | – | ENST00000575658 ENST00000265965; ENST00000529151 | TAF |
| 61% | chr11 | 17888603 | 17888338 | – | chr11 | 17809960 | 17809632; 17809702 | – | ENST00000265965; ENST00000529151 | TAF |
| 54% | chr15 | 99816054 | 99816395 | + | chr15 | 99881167 | 99816821 | + | ENST00000301981; ENST00000561253; ENST00000422500; ENST00000442993; ENST00000447360; ENST00000561276; ENST00000331450; ENST00000558861 | TAF |
| 54% | chr15 | 99816054 | 99816395 | + | chr15 | 99816781 | 99816821 | + | ENST00000301981; ENST00000561253; ENST00000422500; ENST00000442993; ENST00000447360; ENST00000561276; ENST00000331450; ENST00000558861 | TAF |
| 54% | chr15 | 99816054 | 99816395 | + | chr15 | 99816781 | 99816821 | + | ENST00000301981; ENST00000561253; ENST00000422500; ENST00000442993; ENST00000447360; ENST00000561276; ENST00000331450; ENST00000558861 | TAF |
| 54% | chr15 | 99816054 | 99816395 | + | chr15 | 99816781 | 99816821 | + | ENST00000301981; ENST00000561253; ENST00000422500; ENST00000442993; ENST00000447360; ENST00000561276; ENST00000331450; ENST00000558861 | TAF |
| 54% | chr15 | 99816054 | 99816395 | + | chr15 | 99816781 | 99816821 | + | ENST00000301981; ENST00000561253; ENST00000422500; ENST00000442993; ENST00000447360; ENST00000561276; ENST00000331450; ENST00000558861 | TAF |
| 54% | chr15 | 99816054 | 99816395 | + | chr15 | 99816781 | 99816821 | + | ENST00000301981; ENST00000561253; ENST00000422500; ENST00000442993; ENST00000447360; ENST00000561276; ENST00000331450; ENST00000558861 | TAF |
| 54% | chr15 | 99816054 | 99816395 | + | chr15 | 99816781 | 99816821 | + | ENST00000301981; ENST00000561253; ENST00000422500; ENST00000442993; ENST00000447360; ENST00000561276; | TAF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 54% | chr15 | 99816054 | 99816395 | + | chr15 | 99816781 | 99816821 | + | ENST00000331450; ENST00000558861 ENST00000301981; ENST00000561253; ENST00000422500; ENST00000442993; ENST00000447360; ENST00000561276; ENST00000331450; ENST00000558861 | TAF |
| 53% | chr17 | 37319504 | 37319411 | – | chr17 | 37319111 | 37318964 | – | ENST00000269586; ENST00000444555 | TAF |
| 52% | chr4 | 8231126 | 8231139 | + | chr4 | 8233703 | 8233883 | + | ENST00000245105; ENST00000539824; ENST00000511002 | TAF |
| 52% | chr4 | 8231126 | 8231139 | + | chr4 | 8233703 | 8233883 | + | ENST00000245105; ENST00000539824; ENST00000511002 | TAF |
| 52% | chr9 | 100740768 | 100740868 | + | chr9 | 100756913 | 100757062 | + | ENST00000339399 | TAF |
| 45% | chr11 | 118220011 | 118220037 | + | chr11 | 118220458 | 118220685 | + | ENST00000532917 | TAF |
| 45% | chr1 | 49197473 | 49197246 | – | chr1 | 49193715 | 49193558 | – | ENST00000371833 | TAF |
| 42% | chr6 | 26474324 | 26474624 | + | chr6 | 26475389 | 26476396 | + | ENST00000480218 | TAF |
| 42% | chr6 | 27221686 | 27221989 | + | chr6 | 27222472 | 27222651; 27222534; 27222478 | + | ENST00000421826; ENST00000230582; ENST00000466364; ENST00000475106; ENST00000485993 | TSF |
| 42% | chr6 | 27221686 | 27221989 | + | chr6 | 27222472 | 27222651; 27222534; 27222478 | + | ENST00000421826; ENST00000230582; ENST00000466364; ENST00000475106; ENST00000485993 | TSF |
| 42% | chr6 | 27221686 | 27221989 | + | chr6 | 27222472 | 27222651; 27222534; 27222478 | + | ENST00000421826; ENST00000230582; ENST00000466364; ENST00000475106; ENST00000485993 | TSF |
| 40% | chr16 | 68401373 | 68401247 | – | chr16 | 68398995 | 68398920 | – | ENST00000219334; ENST00000574662; ENST00000568373; ENST00000563226 | TAF |
| 40% | chr16 | 68401373 | 68401247 | – | chr16 | 68398995 | 68398920 | – | ENST00000219334; ENST00000574662; ENST00000568373; ENST00000563226 | TAF |
| 40% | chr16 | 68401373 | 68401247 | – | chr16 | 68398995 | 68398920 | – | ENST00000219334; ENST00000574662; ENST00000568373; ENST00000563226 | TAF |
| 40% | chr16 | 68401373 | 68401247 | – | chr16 | 68398995 | 68398920 | – | ENST00000219334; ENST00000574662; ENST00000568373; ENST00000563226 | TAF |
| 38% | chr17 | 79214190 | 79214239 | + | chr17 | 79214787 | 79214816; 79214953 | + | ENST00000431388; ENST00000576002 | TAF |
| 38% | chr17 | 79214190 | 79214239 | + | chr17 | 179214787 | 79214816; 79214953 | + | ENST00000431388; ENST00000576002 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; | TAF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 38% | chr17 | 80866189 | 80866313 | + | chr17 | 80867161 | 80867183 | + | ENST00000574975; ENST00000572953; ENST00000574422 ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr17 | 80866189 | 80866313 | + | chr17 | 80867161 | 80867183 | + | ENST00000355528; ENST00000539345; ENST00000576160; ENST00000571712; ENST00000576996; ENST00000571316; ENST00000576760; ENST00000572984; ENST00000574975; ENST00000572953; ENST00000574422 | TAF |
| 38% | chr12 | 6602868 | 6602840 | − | chr12 | 6602138 | 6602028 | − | ENST00000229238 | TAF |
| 38% | chr10 | 102260069 | 221059867 | − | chr10 | 102259355 | 102259281 | − | ENST00000370345 | TAF |
| 34% | chr11 | 424193 | 423942 | − | chr11 | 421198 | 421141 | − | ENST00000332826 | TAF |
| 31% | chr19 | 54631006 | 54631115 | + | chr19 | 54631448 | 54631575 | + | ENST00000321030; ENST00000419967 | TAF |
| 31% | chr19 | 54631006 | 54631115 | + | chr19 | 54631448 | 54631575 | + | ENST00000321030; ENST00000419967 | TAF |
| 30% | chr19 | 11555143 | 11555219 | + | chr19 | 11556204 | 11556288 | + | ENST00000591462; ENST00000252455; ENST00000412601; ENST00000592741; ENST00000587327; ENST00000589838 | TAF |
| 30% | chr19 | 11555143 | 11555219 | + | chr19 | 11556204 | 11556288 | + | ENST00000591462; ENST00000252455; ENST00000412601; ENST00000592741; ENST00000587327; ENST00000589838 | TAF |
| 30% | chr19 | 11555143 | 11555219 | + | chr19 | 11556204 | 11556288 | + | ENST00000591462; ENST00000252455; ENST00000412601; ENST00000592741; ENST00000587327; ENST00000589838 | TAF |
| 30% | chr12 | 51681734 | 51681668 | − | chr12 | 51678571 | 51678500 | − | ENST00000452142; ENST00000267012; ENST00000544402 | TAF |
| 30% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 30% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 30% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 30% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 30% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 29% | chr6 | 42890506 | 42890547 | + | chr 6 | 42890883 | 42891085 | + | ENST00000304672; ENST00000441198 | TSF |
| 28% | chr10 | 26814247 | 268114408 | + | chr10 | 26822368 | 26822454 | + | ENST00000376236 | TAF |
| 28% | chr17 | 40820773 | 40820708 | − | chr17 | 40820321 | 40820145 | − | ENST00000591022; ENST00000412503; ENST00000293349 | TAF |
| 28% | chr1 | 169819657 | 169819707 | + | chr1 | 169820958 | 169821077 | + | ENST00000359326; ENST00000286031 | TSF |
| 28% | chr | 161637963 | 161637691 | − | chr6 | 161587449 | 161587280; 161587148 | − | ENST00000320285; ENST00000366908; ENST00000436279; ENST00000366905 | TSF |
| 28% | chr6 | 161637963 | 161637691 | − | chr6 | 161587449 | 161587280; 161587148 | | ENST00000320285; ENST00000366908; ENST00000436279; ENST00000366905 | TSF |
| 28% | chr6 | 161637963 | 161637691 | − | chr6 | 161587449 | 161587280; 161587148 | − | ENST00000320285; ENST00000366908; ENST00000436279; ENST00000366905 | TSF |
| 27% | chr16 | 718049 | 718154 | + | chr16 | 718352 | 718411 | + | ENST00000315082; ENST00000561983; ENST00000563134; ENST00000563637; ENST00000570280; ENST00000562333; ENST00000561929 | TAF |
| 27% | chr16 | 718049 | 718154 | + | chr16 | 718353 | 718411 | + | ENST00000315082; ENST00000561983; ENST00000563134; ENST00000563637; ENST00000570280; ENST00000562333; | TAF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 27% | chr16 | 718049 | 718154 | + | chr16 | 718353 | 718411 | + | ENST00000561929 ENST00000315082; ENST00000561983; ENST00000563134; ENST00000563637; ENST00000570280; ENST00000562333; ENST00000561929 | TAF |
| 27% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 27% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 27% | chr16 | 718049 | 718154 | + | chr16 | 718353 | 718411 | + | ENST00000315082; ENST00000561983; ENST00000563134; ENST00000563637; ENST00000570280; ENST00000562333; ENST00000561929 | TAF |
| 27% | chr10 | 120902016 | 12001765 | − | chr10 | 120900831 | 120900754 | − | ENST00000355697; ENST00000330036 | TAF |
| 25% | chr19 | 4294350 | 4294283 | − | chr19 | 4292882 | 4292596 | − | ENST00000595645; ENST00000301272; ENST00000600114; ENST00000600349 | TAF |
| 25% | chr10 | 72537735 | 72537648 | − | chr10 | 72537091 | 72536909 | − | ENST00000299290; ENST00000456372 | TAF |
| 25% | chr10 | 72537735 | 72537648 | − | chr10 | 72537091 | 72536909 | − | ENST00000299290; ENST00000456372 | TAF |
| 23% | chr5 | 176950016 | 176949956 | − | chr5 | 176949072 | 176948976 | − | ENST00000514747; ENST00000329540; ENST00000443375; ENST00000524677 | TAF |
| 22% | chr19 | 41816860 | 41816920 | + | chr19 | 41822289 | 41822744 | + | ENST00000269967 | TAF |
| 22% | chr4 | 107241932 | 107242850 | + | chr4 | 107246142 | 107246275 | + | ENST00000394701 | TAF |
| 22% | chr8 | 17873227 | 17873340 | + | chr8 | 17882870 | 17882962 | + | ENST00000325083; ENST00000519253; ENST00000524226; ENST00000327578; ENST00000522275 | TAF |
| 22% | chr4 | 154533967 | 154534548 | + | chr4 | 154541908 | 154542032 | + | ENST00000440693; ENST00000409663; ENST00000409959; ENST00000240487 | TAF |
| 21% | chr11 | 64508144 | 64507840 | − | chr11 | 64507635 | 64507485 | − | ENST00000377494; ENST00000394432; ENST00000377497; ENST00000354024; ENST00000431822 | TAF |
| 21% | chr11 | 64508144 | 64507840 | − | chr11 | 64507635 | 64507485 | − | ENST00000377494; ENST00000394432; ENST00000377497; ENST00000354024; ENST00000431822 | TAF |
| 21% | chr11 | 64508144 | 64507840 | − | chr11 | 64507635 | 64507485 | − | ENST00000377494; ENST00000394432; ENST00000377497; ENST00000354024; ENST00000431822 | TAF |
| 21% | chr2 | 87076138 | 87075916 | − | chr2 | 87073896 | 87073807 | − | ENST00000393759; ENST00000331469; ENST00000390655 | TAF |
| 21% | chr2 | 87076138 | 87075916 | − | chr2 | 87073896 | 87073807 | − | ENST00000393759; ENST00000331469; ENST00000390655 | TAF |
| 21% | chr2 | 87076138 | 87075916 | − | chr2 | 87073896 | 87073807 | − | ENST00000393759; ENST00000331469; ENST00000390655 | TAF |
| 20% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 20% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 20% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 20% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 20% | chr17 | 79649571 | 79649473 | − | chr17 | 179649179 | 79649064 | − | ENST00000397498; ENST00000570561; ENST00000576135 | TAF |
| 20% | chr5 | 176950300 | 176950160 | − | chr5 | 176949072 | 176948976 | − | ENST00000514747; ENST00000329540; ENST00000443375; ENST00000524677 | TAF |
| 20% | chr19 | 4294350 | 4294301 | − | chr19 | 4292882 | 4292596 | − | ENST00000595645; ENST00000301272; ENST00000600114; ENST00000600349 | TSF |
| 19% | chr6 | 42890125 | 42890148 | + | chr6 | 42890765 | 42891085 | + | ENST00000304672 | TAF |
| 19% | chr1 | 167417583 | 167417580 | − | chr1 | 167410004 | 167409901 | − | ENST00000362089; ENST00000392122 | TAF |
| 19% | chr1 | 167417583 | 167417580 | − | chr1 | 167410004 | 167409901 | − | ENST00000362089; ENST00000392122 | TAF |
| 19% | chr10 | 121275965 | 121275814 | − | chr10 | 121275164 | 121275021 | − | ENST00000392865; ENST00000369101; ENST00000369103 | TAF |
| 18% | chrX | 48793481 | 48793462 | − | chrX | 48792291 | 48792227 | − | ENST00000396743; ENST00000455452; ENST00000156084; ENST00000376488; | TAF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 18% | chrX | 48793481 | 48793462 | − | chrX | 48792291 | 48792227 | − | ENST00000428668 ENST00000396743; ENST00000455452; ENST00000156084; ENST00000376488; ENST00000428668 | TAF |
| 18% | chr21 | 47741082 | 47741060 | − | chr21 | 47738134 | 47737926 | − | ENST00000291691 | TAF |
| 18% | chr20 | 32882711 | 32882165 | − | chr20 | 321881962 | 32881887 | | ENST00000217426; ENST00000538132 | TAF |
| 18% | chr19 | 18653186 | 18653179 | − | chr19 | 18652805 | 18652489 | | ENST00000453489 | TAF |
| 18% | chr6 | 42890125 | 42890148 | + | chr6 | 42890883 | 42891085 | + | ENST00000304672; ENST00000441198 | TSF |
| 18% | chr7 | 2213442 | 2212885 | − | chr7 | 2188873 | 2188787 | − | ENST00000402746; ENST00000399654; ENST00000406869; ENST00000265854 | TSF |
| 17% | chr4 | 154546282 | 154546350 | + | chr4 | 154547299 | 154547377 | + | ENST00000440693; ENST00000409663; ENST00000409959; ENST00000240487 | TSF |
| 16% | chr2 | 3477590 | 3477886 | + | chr2 | 3481466 | 3481566 | + | ENST00000382110; ENST00000324266; ENST00000415624 | TAF |
| 16% | chrX | 3779692 | 3773630 | − | chrX | 3735819 | 3735816 | − | ENST00000425492 | TAF |
| 15% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 15% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 15% | chr17 | 8044091280 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 15% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 15% | chr7 | 116364854 | 116364901 | + | chr7 | 116371722 | 116371913 | + | ENST00000397752; ENST00000318493; ENST00000436117 | TAF |
| 15% | chr7 | 116364854 | 116364901 | + | chr7 | 116371722 | 116371913 | + | ENST00000397752; ENST00000318493; ENST00000436117 | TAF |
| 15% | chr7 | 116364854 | 116364901 | + | chr7 | 116371722 | 116371913 | + | ENST00000397752; ENST00000318493; ENST00000436117 | TAF |
| 14% | chr19 | 7583497 | 7583591 | + | chr19 | 7584091 | 7584174 | + | ENST00000599312 | TAF |
| 14% | chr19 | 9924904 | 9924814 | − | chr19 | 9922393 | 9921572; 9922383; 9922130; 9922270 | − | ENST00000247977; ENST00000588922; ENST00000585379; ENST00000591009; ENST00000590277; ENST00000586469 | TAF |
| 14% | chr19 | 9924904 | 9924814 | − | chr19 | 9922393 | 9921572; 9922383; 99 22130; 9922270 | − | ENST00000247977; ENST00000588922; ENST00000585379; ENST00000591009; ENST00000590277; ENST00000586469 | TAF |
| 14% | chr19 | 9924904 | 9924814 | − | chr19 | 9922393 | 9921572; 9922383; 9922130; 9922270 | − | ENST00000247977; ENST00000588922; ENST00000585379; ENST00000591009; ENST00000590277; ENST00000586469 | TAF |
| 14% | chr19 | 9924904 | 9924814 | − | chr19 | 9922393 | 9921572; 9922383; 9922130; 9922270 | − | ENST00000247977; ENST00000588922; ENST00000585379; ENST00000591009; ENST00000590277; ENST00000586469 | TAF |
| 14% | chr13 | 51440177 | 51440362 | + | chr13 | 51501543 | 51501614 | + | ENST00000336617; ENST00000422660 | TSF |
| 14% | chr13 | 51440177 | 51440362 | + | chr13 | 51501543 | 51501614 | + | ENST00000336617; ENST00000422660 | TSF |
| 13% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 13% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 13% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 13% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; ENST00000293288 | TAF |
| 13% | chr19 | 49458157 | 49458182 | + | chr19 | 49458944 | 49459090; 49459035 | + | ENST00000539787; ENST00000345358; ENST00000391871; ENST00000515540; ENST00000356483; ENST00000415969; | TAF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 13% | chr16 | 79160209 | 79160459 | + | chr16 | 79245505 | 79245693; 79246031; 79245661 | + | ENST00000293288 ENST00000566780; ENST00000402655; ENST00000406884; ENST00000539474 | TSF |
| 13% | chr16 | 79160209 | 79160459 | + | chr16 | 79245505 | 79245693; 79246031; 79245661 | + | ENST00000566780; ENST00000402655; ENST00000406884; ENST00000539474 | TSF |
| 13% | chr16 | 79160209 | 79160459 | + | chr16 | 79245505 | 79245693; 79246031; 79245661 | + | ENST00000566780; ENST00000402655; ENST00000406884; ENST00000539474 | TSF |
| 13% | chr16 | 75118199 | 75118535 | + | chr16 | 75127470 | 75127565 | + | ENST00000335325; ENST00000320619; ENST00000566250; ENST00000567962 | TSF |
| 13% | chr16 | 75118199 | 75118535 | + | chr16 | 75127470 | 75127565 | + | ENST00000335325; ENST00000320619; ENST00000566250; ENST00000567962 | TSF |
| 13% | chr16 | 75118199 | 75118535 | + | chr4 | 75127470 | 75127565 | + | ENST00000335325; ENST00000320619; ENST00000566250; ENST00000567962 | TSF |
| 12% | chr4 | 185615383 | 1856154 | + | chr4 | 18005615676 | 185615933; 185615746 | + | ENST00000314970; ENST00000515774; ENST00000503752; ENST00000512834; ENST00000508001 | TAF |
| 12% | chr4 | 185615383 | 185615524 | + | chr4 | 185615676 | 185615933; 185615746 | + | ENST00000314970; ENST00000515774; ENST00000503752; ENST00000512834; ENST00000508001 | TAF |
| 12% | chr2 | 99797199 | 99797170 | − | chr2 | 99790479 | 99790378 | − | ENST00000422537; ENST00000289359; ENST00000409107 | TAF |
| 12% | chr2 | 99797199 | 99797170 | − | chr2 | 99790479 | 99790378 | − | ENST00000422537; ENST00000289359; ENST00000409107 | TAF |
| 12% | chr9 | 100872455 | 100872351 | − | chr9 | 100872266 | 100872171 | − | ENST00000375098; ENST00000341469; ENST00000342043 | TAF |
| 12% | chr14 | 45596308 | 45596304 | − | chr14 | 45590823 | 45590688 | − | ENST00000396062; ENST00000216330 | TAF |
| 12% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr1 | 6380703 | 6380649 | − | chr1 | 16378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr1 | 6380703 | 6380649 | − | chr1 | 6378638 | 6378552 | − | ENST00000608083; ENST00000377842; ENST00000377845; ENST00000377855; ENST00000377860; ENST00000418124; ENST00000545482; ENST00000361521; ENST00000473466; ENST00000541130 | TAF |
| 12% | chr19 | 42335927 | 423359140 | + | chr19 | 42364892 | 42364915 | + | ENST00000598742; ENST00000601492; ENST00000600467; ENST00000593863; ENST00000598261; ENST00000598399 | TAF |
| 12% | chr19 | 42335927 | 423359140 | + | chr19 | 42364892 | 42364915 | + | ENST00000598742; ENST00000601492; ENST00000600467; ENST00000593863; ENST00000598261; ENST00000598399 | TAF |
| 12% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 12% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 12% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 12% | chr1 | 26442407 | 26442478 | + | chr1 | 26646662 | 26646793 | + | ENST00000374213 | TAF |
| 12% | chr6 | 43026913 | 43026822 | − | chr6 | 43025971 | 43025803; 43025889; 43025777 | − | ENST00000388752; ENST00000230413; ENST00000489623; ENST00000487429; ENST00000468957 | TAF |
| 12% | chr6 | 43026913 | 43026822 | − | chr6 | 43025971 | 43025803; 43025889; | − | ENST00000388752; ENST00000230413; ENST00000489623; ENST00000487429; | TAF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| 12% | chr6 | 43026913 | 43026822 | − | chr6 | 43025971 | 43025777 43025803; 43025889; 43025777 | − | ENST00000468957 ENST00000388752; ENST00000230413; ENST00000489623; ENST00000487429; ENST00000468957 | TAF |
| 12% | chr6 | 43026913 | 43026822 | − | chr6 | 43025971 | 43025803; 43025889; 43025777 | − | ENST00000388752; ENST00000230413; ENST00000489623; ENST00000487429; ENST00000468957 | TAF |
| 12% | chr6 | 43026913 | 43026822 | − | chr6 | 43025971 | 43025803; 43025889; 43025777 | − | ENST00000388752; ENST00000230413; ENST00000489623; ENST00000487429; ENST00000468957 | TAF |
| 12% | chr17 | 7130320 | 7130212 | − | chr17 | 7129958 | 7129740 | − | ENST00000005340; ENST00000575458; ENST00000575086 | TAF |
| 12% | chr17 | 7130320 | 7130212 | − | chr17 | 7129958 | 7129740 | − | ENST00000005340; ENST00000575458; ENST00000575086 | TAF |
| 11% | chr2 | 62362210 | 62362285 | + | chr2 | 62362966 | 62363076 | + | ENST00000311832; ENST00000458337; ENST00000427417 | TAF |
| 11% | chr20 | 30269169 | 26309014 | − | chr20 | 30253889 | 30253752; 30253838 | − | ENST00000376062; ENST00000376055; ENST00000307677; ENST00000420653; ENST00000450273 | TAF |
| 11% | chr20 | 30269169 | 30269014 | − | chr20 | 30253889 | 30253752; 30253838 | − | ENST00000376062; ENST00000376055; ENST00000307677; ENST00000420653; ENST00000450273 | TAF |
| 11% | chr12 | 102411559 | 102411498 | − | chr12 | 102406970 | 102406886 | − | ENST00000240079; ENST00000545679; ENST00000542923 | TAF |
| 11% | chr19 | 15502944 | 15502761 | − | chr19 | 15491423 | 15491328 | − | ENST00000397410; ENST00000595465 | TAF |
| 11% | chr3 | 47554781 | 47554981 | − | chr3 | 47552716 | 47552638 | − | ENST00000296149; ENST00000442215 | TAF |
| 11% | chr3 | 47554781 | 47554981 | − | chr3 | 147552716 | 47552638 | | ENST00000296149; ENST00000442215 | TAF |
| 11% | chr16 | 79160209 | 79160495 | + | chr16 | 179245505 | 79245693; 79246031; 79245661 | + | ENST00000566780; ENST00000402655; ENST00000406884; ENST00000539474 | TSF |
| 11% | chr16 | 79160209 | 79160495 | + | chr16 | 79245505 | 79245693; 79246031; 79245661 | + | ENST00000566780; ENST00000402655; ENST00000406884; ENST00000539474 | TSF |
| 11% | chr16 | 79160209 | 79160495 | + | chr16 | 79245505 | 79245693; 79246031; 79245661 | + | ENST00000566780; ENST00000402655; ENST00000406884; ENST00000539474 | TSF |
| 10% | chr4 | 1745002 | 1745264 | + | chr4 | 17146245 | 1746351 | + | ENST00000313288 | TSF |
| 10% | chr17 | 54891362 | 54891289 | − | chr17 | 54872541 | 54872425 | | ENST00000397861; ENST00000397862; ENST00000575658 | TSF |
| 10% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 10% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 10% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 10% | chr22 | 89229971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 10% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 10% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 10% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 10% | chr16 | 30391227 | 30391159 | − | chr16 | 30390855 | 30390756 | − | ENST00000321367; ENST00000571393; ENST00000605106; ENST00000566517 | TSF |
| 10% | chr16 | 30391227 | 30391159 | − | chr16 | 30390855 | 30390756 | − | ENST00000321367; ENST00000571393; ENST00000605106; ENST00000566517 | TSF |
| 10% | chr18 | 51573 | 49727 | − | chr18 | 49237 | 49129 | − | ENST00000308911 | TSF |
| 9% | chr8 | 136546987 | 136547139 | + | chr8 | 136554897 | 136555013 | + | ENST00000355849; ENST00000524199; ENST00000517394 | TSF |
| 9% | chr8 | 654698713 | 136547139 | + | chr8 | 136554897 | 136555013 | + | ENST00000355849; ENST00000524199; ENST00000517394 | TSF |
| 9% | chr8 | 136546987 | 136547139 | + | chr8 | 136554897 | 136555013 | + | ENST00000355849; ENST00000524199; ENST00000517394 | TSF |
| 9% | chr19 | 54868492 | 54868321 | − | chr19 | 54868228 | 54868100; 54868205 | − | ENST00000391743; ENST00000348231; ENST00000391742; ENST00000434277; ENST00000313038; ENST00000391741; ENST00000474878 | TSF |
| 9% | chr19 | 86849254 | 54868321 | − | chr19 | 54868228 | 54868100; 54868205 | − | ENST00000391743; ENST00000348231; ENST00000391742; ENST00000434277; ENST00000313038; ENST00000391741; ENST00000474878 | TSF |
| 8% | chr17 | 73357826 | 26733475 | − | chr17 | 26733015 | 26732905 | − | ENST00000321666; ENST00000440501 | TSF |
| 8% | chr17 | 26733578 | 26733475 | − | chr17 | 26733015 | 26732905 | − | ENST00000321666; ENST00000440501 | TSF |
| 8% | chr20 | 44752658 | 44752755 | + | chr20 | 44755279 | 44755340 | + | ENST00000372285; ENST00000466205 | TSF |
| 8% | chr20 | 44752656 | 44752755 | + | chr20 | 44755279 | 44755340 | + | ENST00000372285; ENST00000466205 | TSF |
| 8% | chr14 | 24682204 | 24682139 | − | chr14 | 24681035 | 24680886 | − | ENST00000530611; ENST00000556387; ENST00000347519; ENST00000533523; ENST00000609024; ENST00000533011; ENST00000534106 | TSF |
| 8% | chr14 | 24682204 | 24682139 | − | chr14 | 24681035 | 24680886 | − | ENST00000530611; ENST00000556387; ENST00000347519; ENST00000533523; ENST00000609024; ENST00000533011; ENST00000534106 | TSF |
| 8% | chr14 | 24682204 | 24682139 | − | chr14 | 24681035 | 24680886 | − | ENST00000530611; ENST00000556387; ENST00000347519; ENST00000533523; ENST00000609024; ENST00000533011; ENST00000534106 | TSF |
| 8% | chr14 | 68242204 | 24682139 | − | chr14 | 24681035 | 24680886 | − | ENST00000530611; ENST00000556387; ENST00000347519; ENST00000533523; ENST00000609024; ENST00000533011; ENST00000534106 | TSF |
| 8% | chr14 | 68242204 | 24682139 | − | chr14 | 24681035 | 24680886 | | ENST00000530611; ENST00000556387; ENST00000347519; ENST00000533523; ENST00000609024; ENST00000533011; ENST00000534106 | TSF |
| 7% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 7% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 7% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 7% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 7% | chr12 | 42821122 | 42822199 | + | chr12 | 42835117 | 42835311; 42835231 | + | ENST00000549190; ENST00000395580; ENST00000337898; ENST00000358314; ENST00000395568; ENST00000256678; ENST00000449194; ENST00000552761; ENST00000317560; ENST00000432191 | TSF |
| 7% | chr12 | 42821122 | 42822199 | + | chr12 | 42835117 | 42835311; | + | ENST00000549190; ENST00000395580; | TSF |

TABLE 64-continued

Transcript fusion for Thymoma (THYM)
Coordinates of the fusion sequences for which the donor is the TE.

| 1 | 2' | 3' | 4' | 5' 6' | 7' | 8' | 9' 10' | 11' |
|---|---|---|---|---|---|---|---|---|
| | | | | | | 42835231 | ENST00000337898; ENST00000358314; ENST00000395568; ENST00000256678; ENST00000449194; ENST00000552761; ENST00000317560; ENST00000432191 | |
| 7% | chr2 | 3462278 | 3462286 | + chr2 | 3464034 | 3464107; 3464074 | + ENST00000382110; ENST00000324266; ENST00000441983; ENST00000417243; ENST00000415624 | TSF |
| 7% | chr2 | 3462278 | 3462286 | + chr2 | 3464034 | 3464107; 3464074 | + ENST00000382110; ENST00000324266; ENST00000441983; ENST00000417243; ENST00000415624 | TSF |
| 7% | chr2 | 3462278 | 3462286 | + chr2 | 3464034 | 3464107; 3464074 | + ENST00000382110; ENST00000324266; ENST00000441983; ENST00000417243; ENST00000415624 | TSF |
| 7% | chr2 | 3462278 | 3462286 | + chr2 | 3464034 | 3464107; 3464074 | + ENST00000382110; ENST00000324266; ENST00000441983; ENST00000417243; ENST00000415624 | TSF |
| 7% | chr14 | 68507686 | 68507934 | + chr14 | 68758601 | 68758697 | + ENST00000487861; ENST00000471583; ENST00000487270; ENST00000488612; ENST00000390683 | TSF |
| 7% | chr14 | 68507686 | 68507934 | + chr14 | 68758601 | 68758697 | + ENST00000487861; ENST00000471583; ENST00000487270; ENST00000488612; ENST00000390683 | TSF |
| 7% | chr14 | 68507686 | 68507934 | + chr14 | 68758601 | 68758697 | + ENST00000487861; ENST00000471583; ENST00000487270; ENST00000488612; ENST00000390683 | TSF |
| 7% | chr14 | 68507686 | 68507934 | + chr14 | 68758601 | 68758697 | + ENST00000487861; ENST00000471583; ENST00000487270; ENST00000488612; ENST00000390683 | TSF |
| 7% | chr20 | 43253349 | 43253289 | − chr20 | 43252970 | 43252843 | − ENST00000372874; ENST00000536532; ENST00000537820 | TSF |
| 7% | chr20 | 43253349 | 43253289 | − chr20 | 43252970 | 43252843 | − ENST00000372874; ENST00000536532; ENST00000537820 | TSF |
| 7% | chr20 | 43253349 | 43253289 | − chr20 | 43252970 | 43252843 | − ENST00000372874; ENST00000536532; ENST00000537820 | TSF |
| 6% | chr2 | 198593687 | 198593827 | + chr2 | 198636581 | 198636638 | + ENST00000409845 | TSF |
| 6% | chr6 | 42890506 | 42890547 | + chr6 | 42891967 | 42892011 | + ENST00000304672; ENST00000441198; ENST00000446507 | TSF |
| 6% | chr10 | 26792284 | 26792333 | + chr10 | 26800676 | 26800835 | + ENST00000376236 | TSF |
| 6% | chr1 | 59980221 | 59980497 | + chr1 | 60019796 | 60019899 | + ENST00000371218; ENST00000303721; ENST00000430447; ENST00000371212 | TSF |
| 6% | chr1 | 59980221 | 59980497 | + chr1 | 60019796 | 60019899 | + ENST00000371218; ENST00000303721; ENST00000430447; ENST00000371212 | TSF |
| 6% | chr1 | 59980221 | 59980497 | + chr1 | 60019796 | 60019899 | + ENST00000371218; ENST00000303721; ENST00000430447; ENST00000371212 | TSF |
| 6% | chr2 | 135250933 | 135250213 | − chr2 | 135223796 | 135223685 | − ENST00000281924 | TSF |
| 6% | chr7 | 1014593 | 1014543 | − chr7 | 1012928 | 1012817 | − ENST00000457254; ENST00000344111 | TSF |
| 6% | chr7 | 1014593 | 1014543 | − chr7 | 1012928 | 1012817 | − ENST00000457254; ENST00000344111 | TSF |
| 6% | chr5 | 138724860 | 138724589 | − chr5 | 138724274 | 138724150 | − ENST00000503481; ENST00000302125 | TSF |
| 6% | chr5 | 138724860 | 138724589 | − chr5 | 138724274 | 138724150 | − ENST00000503481; ENST00000302125 | TSF |
| 6% | chr4 | 108981708 | 10898165 | − chr4 | 108969907 | 108969828 | − ENST00000379951 | TSF |
| 6% | chr14 | 105642036 | 105641815 | − chr14 | 561039598 | 105639358 | − ENST00000392568 | TSF |
| 6% | chr4 | 108994237 | 108994141 | − chr4 | 108991926 | 108991819 | − ENST00000265165; ENST00000379951; ENST00000438313; ENST00000510624 | TSF |
| 6% | chr4 | 108994237 | 108994141 | − chr4 | 108991926 | 108991819 | − ENST00000265165; ENST00000379951; ENST00000438313; ENST00000510624 | TSF |
| 5% | chr17 | 7788014 | 7788052 | + chr17 | 7788257 | 7788401 | + ENST00000380358 | TSF |
| 5% | chr22 | 32013425 | 32013525 | + chr22 | 32014101 | 32014147; | + ENST00000414585; ENST00000443326; ENST00000540643; ENST00000432498; ENST00000443011; ENST00000400289; ENST00000400288 | TSF |
| 5% | chr22 | 32013425 | 32013525 | + chr22 | 32014101 | 32014147; 32014212 | + ENST00000414585; ENST00000443326; ENST00000540643; ENST00000432498; ENST00000443011; ENST00000400289; ENST00000400288 | TSF |
| 5% | chr5 | 133458649 | 133458682 | + chr5 | 133473750 | 133473855; 133473887 | + ENST00000378564; ENST00000321584; ENST00000321603; ENST00000342854; ENST00000395029; ENST00000518887; ENST00000517851; ENST00000521639; ENST00000522375; ENST00000432532; ENST00000378560; ENST00000520958; ENST00000518915; ENST00000395023; ENST00000519447; ENST00000517741; ENST00000520652; ENST00000519037 | TSF |
| 5% | chr5 | 133458649 | 133458682 | + chr5 | 133473750 | 133473855; 133473887 | + ENST00000378564; ENST00000321584; ENST00000321603; ENST00000342854; | TSF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | | | ENST00000395029; ENST00000518887; ENST00000517851; ENST00000521639; ENST00000522375; ENST00000432532; ENST00000378560; ENST00000520958; ENST00000518915; ENST00000395023; ENST00000519447; ENST00000517741; ENST00000520652; ENST00000519037 | |
| 5% | chr5 | 133458649 | 133458682 | + | chr5 | 33473750 | 133473855; 133473887 | + | ENST00000378564; ENST00000321584; ENST00000321603; ENST00000342854; ENST00000395029; ENST00000518887; ENST00000517851; ENST00000521639; ENST00000522375; ENST00000432532; ENST00000378560; ENST00000520958; ENST00000518915; ENST00000395023; ENST00000519447; ENST00000517741; ENST00000520652; ENST00000519037 | TSF |
| 5% | chr5 | 133458649 | 133458582 | + | chr5 | 133473750 | 1334738515; 133473887 | + | ENST00000378564; ENST00000321584; ENST00000321603; ENST00000342854; ENST00000395029; ENST00000518887; ENST00000517851; ENST00000521639; ENST00000522375; ENST00000432532; ENST00000378560; ENST00000520958; ENST00000518915; ENST00000395023; ENST00000519447; ENST00000517741; ENST00000520652; ENST00000519037 | TSF |
| 5% | chr5 | 133458649 | 133458682 | + | chr5 | 133473750 | 133473855; 133473887 | + | ENST00000378564; ENST00000321584; ENST00000321603; ENST00000342854; ENST00000395029; ENST00000518887; ENST00000517851; ENST00000521639; ENST00000522375; ENST00000432532; ENST00000378560; ENST00000520958; ENST00000518915; ENST00000395023; ENST00000519447; ENST00000517741; ENST00000520652; ENST00000519037 | TSF |
| 5% | chr5 | 133458649 | 133458682 | + | chr5 | 133473750 | 133473855; 133473887 | + | ENST00000378564; ENST00000321584; ENST00000321603; ENST00000342854; ENST00000395029; ENST00000518887; ENST00000517851; ENST00000521639; ENST00000522375; ENST00000432532; ENST00000378560; ENST00000520958; ENST00000518915; ENST00000395023; ENST00000519447; ENST00000517741; ENST00000520652; ENST00000519037 | TSF |
| 5% | chr5 | 133458649 | 133458682 | + | chr5 | 133473750 | 133473855; 133473887 | + | ENST00000378564; ENST00000321584; ENST00000321603; ENST00000342854; ENST00000395029; ENST00000518887; ENST00000517851; ENST00000521639; ENST00000522375; ENST00000432532; ENST00000378560; ENST00000520958; ENST00000518915; ENST00000395023; ENST00000519447; ENST00000517741; ENST00000520652; ENST00000519037 | TSF |
| 5% | chr5 | 133458649 | 133458682 | + | chr5 | 133473750 | 133473855; 133473887 | + | ENST00000378564; ENST00000321584; ENST00000321603; ENST00000342854; ENST00000395029; ENST00000518887; ENST00000517851; ENST00000521639; ENST00000522375; ENST00000432532; ENST00000378560; ENST00000520958; ENST00000518915; ENST00000395023; ENST00000519447; ENST00000517741; ENST00000520652; ENST00000519037 | TSF |
| 5% | chr5 | 133458649 | 133458682 | + | chr5 | 133473750 | 133473855; 133473887 | + | ENST00000378564; ENST00000321584; ENST00000321603; ENST00000342854; ENST00000395029; ENST00000518887; ENST00000517851; ENST00000521639; ENST00000522375; ENST00000432532; ENST00000378560; ENST00000520958; ENST00000518915; ENST00000395023; ENST00000519447; ENST00000517741; ENST00000520652; ENST00000519037 | TSF |
| 5% | chr5 | 133458649 | 133458682 | + | chr5 | 133473750 | 133473855; 133473887 | + | ENST00000378564; ENST00000321584; ENST00000321603; ENST00000342854; ENST00000395029; ENST00000518887; ENST00000517851; ENST00000521639; ENST00000522375; ENST00000432532; | TSF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|----|----|----|----|----|----|----|----|-----|-----|
| 5% | chr5 | 133458679 | 133458682 | + | chr5 | 133473750 | 133473855; 133473887 | + | ENST00000378560; ENST00000520958; ENST00000518915; ENST00000395023; ENST00000519447; ENST00000517741; ENST00000520652; ENST00000519037 ENST00000378564; ENST00000321584; ENST00000321603; ENST00000342854; ENST00000395029; ENST00000518887; ENST00000517851; ENST00000521639; ENST00000522375; ENST00000432532; | ITSF |
| 5% | chr5 | 133458649 | 133458682 | + | chr5 | 133476750 | 133473855; 1334738 87 | + | ENST00000378560; ENST00000520958; ENST00000518915; ENST00000395023; ENST00000519447; ENST00000517741; ENST00000520652; ENST00000519037 ENST00000378564; ENST00000321584; ENST00000321603; ENST00000342854; ENST00000395029; ENST00000518887; ENST00000517851; ENST00000521639; ENST00000522375; ENST00000432532; | TSF |
| 5% | chr5 | 133458649 | 133458682 | + | chr5 | 133479750 | 133473855; 133473887 | + | ENST00000378560; ENST00000520958; ENST00000518915; ENST00000395023; ENST00000519447; ENST00000517741; ENST00000520652; ENST00000519037 ENST00000378564; ENST00000321584; ENST00000321603; ENST00000342854; ENST00000395029; ENST00000518887; ENST00000517851; ENST00000521639; ENST00000522375; ENST00000432532; | TSF |
| 5% | chr12 | 123464400 | 123464485 | + | chr12 | 123465676 | 123465846; | + | ENST00000315580; ENST00000543566; ENST00000539770; ENST00000542099; ENST00000392435; ENST00000453766 | TSF |
| 5% | chr12 | 123464400 | 123464485 | + | chr12 | 123465676 | 123465846; 123465813 | + | ENST00000315580; ENST00000543566; ENST00000539770; ENST00000542099; ENST00000392435; ENST00000453766 | TSF |
| 5% | chr12 | 123464400 | 123464485 | + | chr12 | 123465676 | 123465846; 123465813 | + | ENST00000315580; ENST00000543566; ENST00000539770; ENST00000542099; ENST00000392435; ENST00000453766 | TSF |
| 5% | chr12 | 123464400 | 123464485 | + | chr12 | 123465676 | 123465846; 123465813 | + | ENST00000315580; ENST00000543566; ENST00000539770; ENST00000542099; ENST00000392435; ENST00000453766 | TSF |
| 5% | chr12 | 123464400 | 123464485 | + | chr12 | 123465676 | 123465846; 123465813 | + | ENST00000315580; ENST00000543566; ENST00000539770; ENST00000542099; ENST00000392435; ENST00000453766 | TSF |
| 5% | chr12 | 123464400 | 123464485 | + | chr12 | 123465676 | 123465846; 123465813 | + | ENST00000315580; ENST00000543566; ENST00000539770; ENST00000542099; ENST00000392435; ENST00000453766 | TSF |
| 5% | chr22 | 37624777 | 376246148 | − | chr22 | 37622843 | 37622713; 37622793 | − | ENST00000249071; ENST00000406508; ENST00000405484; ENST00000441619 | TSF |
| 5% | chr22 | 37624777 | 37624648 | − | chr22 | 37622843 | 37622713; 37622793 | − | ENST00000249071; ENST00000406508; ENST00000405484; ENST00000441619 | TSF |
| 5% | chr3 | 141719378 | 141719074 | − | chr3 | 141713983 | 141713862; 141713905; 141713913 | − | ENST00000499676; ENST00000489671; ENST00000486111; ENST00000467072; ENST00000317104; ENST00000310282; ENST00000479040; ENST00000397991; ENST00000467667; ENST00000497579; ENST00000488107; ENST00000475734; ENST00000494358; ENST00000467634 | TSF |
| 5% | chr3 | 141719378 | 141719074 | − | chr3 | 141713983 | 141713862; 141713905; 141713913 | − | ENST00000499676; ENST00000489671; ENST00000486111; ENST00000467072; ENST00000317104; ENST00000310282; ENST00000479040; ENST00000397991; ENST00000467667; ENST00000497579; ENST00000488107; ENST00000475734; ENST00000494358; ENST00000467634 | TSF |
| 5% | chr3 | 141719378 | 141719074 | − | chr3 | 141713983 | 141713862; 141713905; 141713913 | − | ENST00000499676; ENST00000489671; ENST00000486111; ENST00000467072; ENST00000317104; ENST00000310282; ENST00000479040; ENST00000397991; ENST00000467667; ENST00000497579; ENST00000488107; ENST00000475734; ENST00000494358; ENST00000467634 | TSF |
| 5% | chr3 | 141719378 | 141719074 | − | chr3 | 141713983 | 141713862; | − | ENST00000499676; ENST00000489671; | TSF |

TABLE 64-continued

Transcript fusion for Thymoma (THYM)
Coordinates of the fusion sequences for which the donor is the TE.

| 1 | 2' | 3' | 4' | 5' | 6' | 7' | 8' | 9' | 10' | 11' |
|---|---|---|---|---|---|---|---|---|---|---|
| | | | | | | | 141713905; 141713913 | | ENST00000486111; ENST00000467072; ENST00000317104; ENST00000310282; ENST00000479040; ENST00000397991; ENST00000467667; ENST00000497579; ENST00000488107; ENST00000475734; ENST00000494358; ENST00000467634 | |
| 5% | chr3 | 141719378 | 141719074 | – | chr3 | 141713983 | 141713862; 141713905; 141713913 | – | ENST00000499676; ENST00000489671; ENST00000486111; ENST00000467072; ENST00000317104; ENST00000310282; ENST00000479040; ENST00000397991; ENST00000467667; ENST00000497579; ENST00000488107; ENST00000475734; ENST00000494358; ENST00000467634 | TSF |
| 5% | chr3 | 141719378 | 141719074 | – | chr3 | 141713983 | 141713862; 141713905; 141713913 | – | ENST00000499676; ENST00000489671; ENST00000486111; ENST00000467072; ENST00000317104; ENST00000310282; ENST00000479040; ENST00000397991; ENST00000467667; ENST00000497579; ENST00000488107; ENST00000475734; ENST00000494358; ENST00000467634 | TSF |
| 5% | chr3 | 141719378 | 141719074 | – | chr3 | 141713983 | 141713862; 141713905; 141713913 | – | ENST00000499676; ENST00000489671; ENST00000486111; ENST00000467072; ENST00000317104; ENST00000310282; ENST00000479040; ENST00000397991; ENST00000467667; ENST00000497579; ENST00000488107; ENST00000475734; ENST00000494358; ENST00000467634 | TSF |
| 5% | chr3 | 141719378 | 141719074 | – | chr3 | 141713983 | 141713862; 141713905; 141713913 | – | ENST00000499676; ENST00000489671; ENST00000486111; ENST00000467072; ENST00000317104; ENST00000310282; ENST00000479040; ENST00000397991; ENST00000467667; ENST00000497579; ENST00000488107; ENST00000475734; ENST00000494358; ENST00000467634 | TSF |
| 5% | chr3 | 171419378 | 141719074 | – | chr3 | 141713983 | 141713862; 141713905; 141713913 | – | ENST00000499676; ENST00000489671; ENST00000486111; ENST00000467072; ENST00000317104; ENST00000310282; ENST00000479040; ENST00000397991; ENST00000467667; ENST00000497579; ENST00000488107; ENST00000475734; ENST00000494358; ENST00000467634 | TSF |
| 5% | chrX | 70328788 | 70328686 | – | chrX | 70328545 | 70328449; 70328512 | – | ENST00000374202; ENST00000456850; ENST00000464642 | TSF |
| 5% | chrX | 32878870 | 70328686 | – | chrX | 70328545 | 70328449; 70328512 | – | ENST00000374202; ENST00000456850; ENST00000464642 | TSF |
| 5% | chrX | 152970153 | 152969992 | – | chrX | 152969549 | 152969414; 152969476 | – | ENST00000441714; ENST00000345046; ENST00000458587; ENST00000442093; ENST00000429550; ENST00000416815; ENST00000423827; ENST00000430088 | TSF |
| 5% | chrX | 152970153 | 152969992 | – | chrX | 152969549 | 152969414; 152969476 | – | ENST00000441714; ENST00000345046; ENST00000458587; ENST00000442093; ENST00000429550; ENST00000416815; ENST00000423827; ENST00000430088 | TSF |
| 5% | chrX | 152970153 | 152969992 | – | chrX | 152969549 | 152969414; 152969476 | – | ENST00000441714; ENST00000345046; ENST00000458587; ENST00000442093; ENST00000429550; ENST00000416815; ENST00000423827; ENST00000430088 | TSF |
| 5% | chrX | 152970153 | 152969992 | – | chrX | 152969549 | 152969414; 152969476 | – | ENST00000441714; ENST00000345046; ENST00000458587; ENST00000442093; ENST00000429550; ENST00000416815; ENST00000423827; ENST00000430088 | TSF |
| 5% | chrX | 152970153 | 152969992 | – | chrX | 152969549 | 152969414; 152969476 | – | ENST00000441714; ENST00000345046; ENST00000458587; ENST00000442093; ENST00000429550; ENST00000416815; ENST00000423827; ENST00000430088 | TSF |
| 5% | chrX | 152970153 | 152969992 | – | chrX | 152969549 | 152969414; 152969476 | – | ENST00000441714; ENST00000345046; ENST00000458587; ENST00000442093; ENST00000429550; ENST00000416815; ENST00000423827; ENST00000430088 | TSF |
| 5% | chr10 | 95433302 | 95433070 | – | chr10 | 95430605 | 95430527 | – | ENST00000359204 | TSF |

TABLE 65

Transcript fusion for Uterine Corpus Endometrial Carcinoma (UCEC)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 24% | chr12 | 71928895 | 71928966 | + | ENST00000266674; ENST00000536515; ENST00000540815 | chr12 | 71938771 | 71938901 | + | TSF |
| 20% | chr20 | 35842163 | 35842268 | + | ENST00000237530; ENST00000373622 | chr20 | 35844460 | 35844765 | + | TAF |
| 20% | chr20 | 35842163 | 35842268 | + | ENST00000237530; ENST00000373622 | chr20 | 35844460 | 35844765 | + | TAF |
| 20% | chr10 | 120905865 | 120905748 | − | ENST00000355697; ENST00000330036 | chr10 | 120901885 | 120901741 | − | TAF |
| 20% | chr10 | 120905865 | 120905748 | − | ENST00000355697; ENST00000330036 | chr10 | 120901885 | 120901741 | − | TAF |
| 18% | chr4 | 1742553 | 1742713 | + | ENST00000313288 | chr4 | 1745122 | 1745307 | + | TAF |
| 18% | chr1 | 225156461 | 225156576 | + | ENST00000430092; ENST00000400952; ENST00000366849; ENST00000439375 | chr1 | 225157336 | 225158402 | + | TSF |
| 18% | chr1 | 225156461 | 225156576 | + | ENST00000430092; ENST00000400952; ENST00000366849; ENST00000439375 | chr1 | 225157336 | 225158402 | + | TSF |
| 17% | chr5 | 82554349 | 82554496 | + | ENST00000282268; ENST00000338635; ENST00000396027; ENST00000511817 | chr5 | 82606608 | 82606935 | + | TAF |
| 17% | chr19 | 3544937 | 3544807 | − | ENST00000389395; ENST00000398558; ENST00000588918; ENST00000355415; ENST00000589063 | chr19 | 3538708 | 3538306 | − | TAF |
| 17% | chr19 | 3544937 | 3544807 | − | ENST00000389395; ENST00000398558; ENST00000588918; ENST00000355415; ENST00000589063 | chr19 | 3538708 | 3538306 | − | TAF |
| 17% | chr19 | 3544937 | 3544807 | − | ENST00000389395; ENST00000398558; ENST00000588918; ENST00000355415; ENST00000589063 | chr19 | 3538708 | 3538306 | − | TAF |
| 17% | chr19 | 44129402 | 44129230 | − | ENST00000222374 | chr19 | 44129055 | 44128921 | − | TAF |
| 17% | chr13 | 43659904 | 43659974 | + | ENST00000379221 | chr13 | 43670953 | 43671210 | + | TAF |
| 16% | chr1 | 32696528 | 32696620 | + | ENST00000373586 | chr1 | 32696861 | 32697110 | + | TAF |
| 16% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 16% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 16% | chr2 | 220239744 | 220239577 | − | ENST00000273075; ENST00000373972; ENST00000523282 | chr2 | 220227530 | 220227195 | − | TAF |
| 16% | chr2 | 220239744 | 220239577 | − | ENST00000273075; ENST00000373972; ENST00000523282 | chr2 | 220227530 | 220227195 | − | TAF |
| 16% | chr2 | 220239744 | 220239577 | − | ENST00000273075; ENST00000373972; ENST00000523282 | chr2 | 220227530 | 220227195 | − | TAF |
| 12% | chr19 | 35514331 | 35514451 | + | ENST00000599564; ENST00000317991; ENST00000504615; ENST00000411896 | chr19 | 35514601 | 35514631 | + | TAF |
| 12% | chr19 | 35514331 | 35514451 | + | ENST00000599564; ENST00000317991; ENST00000504615; ENST00000411896 | chr19 | 35514601 | 35514631 | + | TAF |
| 12% | chr19 | 35514331 | 35514451 | + | ENST00000599564; ENST00000317991; ENST00000504615; ENST00000411896 | chr19 | 35514601 | 35514631 | + | TAF |
| 12% | chr19 | 35514331 | 35514451 | + | ENST00000599564; ENST00000317991; ENST00000504615; ENST00000411896 | chr19 | 35514601 | 35514631 | + | TAF |
| 12% | chr9 | 15506635 | 15506559 | − | ENST00000380738; ENST00000380733; ENST00000380715; ENST00000380716; ENST00000397519 | chr9 | 15492223 | 15492056 | − | TAF |
| 11% | chr2 | 26624858 | 26625012 | + | ENST00000288710; ENST00000421869 | chr2 | 26630464 | 26631004 | + | TAF |
| 11% | chr20 | 43560983 | 43561073 | + | ENST00000255136; ENST00000217073 | chr20 | 43561176 | 43561224 | + | TAF |
| 9% | chr1 | 11115983; 11115877 | 11115838 | − | ENST00000376957; ENST00000490101 | chr1 | 11115464 | 11115178 | − | TSF |
| 9% | chr1 | 11115983; 11115877 | 11115838 | − | ENST00000376957; ENST00000490101 | chr1 | 11115464 | 11115178 | − | TSF |
| 9% | chr3 | 48716169 | 48715997 | − | ENST00000341520; ENST00000416649; ENST00000294129; ENST00000413374 | chr3 | 48702393 | 48702198 | − | TSF |
| 9% | chr3 | 48716169 | 48715997 | − | ENST00000341520; ENST00000416649; ENST00000294129; ENST00000413374 | chr3 | 48702393 | 48702198 | − | TSF |
| 9% | chr3 | 48716169 | 48715997 | − | ENST00000341520; ENST00000416649; ENST00000294129; ENST00000413374 | chr3 | 48702393 | 48702198 | − | TSF |
| 8% | chr11 | 101937216; 101937273 | 101382937 | + | ENST00000434758; ENST00000526781; ENST00000529204 | chr11 | 101937956 | 101938097 | + | TSF |
| 8% | chr11 | 101937216; 101937273 | 101382937 | + | ENST00000434758; ENST00000526781; ENST00000529204 | chr11 | 101937956 | 101938097 | + | TSF |
| 7% | chr4 | 57319769 | 57319927 | + | ENST00000514888; ENST00000264221; ENST00000505164; ENST00000399688; ENST00000512576 | chr4 | 57321183 | 57321327 | + | TSF |

TABLE 65-continued

Transcript fusion for Uterine Corpus Endometrial Carcinoma (UCEC)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 7% | chr4 | 57319769 | 57319927 | + | ENST00000514888; ENST00000264221; ENST00000505164; ENST00000399688; ENST00000512576 | chr4 | 57321183 | 57321327 | + | TSF |
| 7% | chr4 | 57319769 | 57319927 | + | ENST00000514888; ENST00000264221; ENST00000505164; ENST00000399688; ENST00000512576 | chr4 | 57321183 | 57321327 | + | TSF |
| 7% | chr9 | 3856184 | 3856009 | − | ENST00000324333; ENST00000381971 | chr9 | 3855631 | 3855480 | − | TSF |
| 7% | chr9 | 3856184 | 3856009 | − | ENST00000324333; ENST00000381971 | chr9 | 3855631 | 3855480 | − | TSF |
| 7% | chr16 | 30783410 | 30783511 | + | ENST00000324685; ENST00000402121; ENST00000563683; ENST00000357890 | chr16 | 30785136 | 30785155 | + | TSF |
| 7% | chr16 | 30783410 | 30783511 | + | ENST00000324685; ENST00000402121; ENST00000563683; ENST00000357890 | chr16 | 30785136 | 30785155 | + | TSF |
| 7% | chr16 | 30783410 | 30783511 | + | ENST00000324685; ENST00000402121; ENST00000563683; ENST00000357890 | chr16 | 30785136 | 30785155 | + | TSF |
| 7% | chr16 | 30783410 | 30783511 | + | ENST00000324685; ENST00000402121; ENST00000563683; ENST00000357890 | chr16 | 30785136 | 30785155 | + | TSF |
| 6% | chr15 | 81436003 | 81436161 | + | ENST00000286732 | chr15 | 81439636 | 81439809 | + | TSF |
| 6% | chr7 | 91771800 | 91771777 | − | ENST00000435873 | chr7 | 91767155 | 91766808 | − | TSF |
| 5% | chr10 | 79796952 | 79797062 | + | ENST00000435275; ENST00000440692; ENST00000372360; ENST00000360830 | chr4 | 176584518 | 176584519 | + | TSF |
| 5% | chr10 | 126205749 | 126205840 | + | ENST00000368842 | chr10 | 126251911 | 126252288 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 142925245 | 42925476 | + | TSF |
| 5% | chr8 | 42924698; 42924750 | 42924802 | + | ENST00000534420; ENST00000302279; ENST00000533998; ENST00000342116; ENST00000531266; ENST00000525699; ENST00000529687; ENST00000533336 | chr8 | 42925245 | 42925476 | + | TSF |
| 4% | chr4 | 4421856 | 4421774 | − | ENST00000306200 | chr4 | 4417890 | 4417824 | − | TSF |
| 4% | chr1 | 155036300 | 155036412 | + | ENST00000368409; ENST00000359751; ENST00000556931; ENST00000505139; ENST00000427683 | chr1 | 155036918 | 155037085 | + | TSF |
| 4% | chr12 | 113623819 | 113623826 | + | ENST00000552495 | chr12 | 113623998 | 113624117 | + | TSF |
| 4% | chr2 | 28352138 | 28352247 | + | ENST00000344773; ENST00000379624; ENST00000342045; ENST00000361704; ENST00000379632; ENST00000379629 | chr2 | 28362015 | 28362218 | + | TSF |
| 4% | chr16 | 50583333 | 50583466 | + | ENST00000268459 | chr16 | 50614862 | 50614981 | + | TSF |
| 4% | chr19 | 53352466; 53352373 | 53352340 | − | ENST00000595646; ENST00000243639; ENST00000597924; ENST00000601847 | chr19 | 53339322 | 53339166 | − | TSF |
| 4% | chr19 | 53352466; 53352373 | 53352340 | − | ENST00000595646; ENST00000243639; ENST00000597924; ENST00000601847 | chr19 | 53339322 | 53339166 | − | TSF |
| 3% | chr22 | 25202408 | 25202451 | + | ENST00000400358; ENST00000400359 | chr22 | 25209976 | 25210040 | + | TSF |
| 3% | chr9 | 125054028 | 125054119 | + | ENST00000297908; ENST00000344641; ENST00000373723; ENST00000373729; ENST00000394315 | chr9 | 125068067 | 125068171 | + | TSF |
| 3% | chr9 | 125054028 | 125054119 | + | ENST00000297908; ENST00000344641; ENST00000373723; ENST00000373729; ENST00000394315 | chr9 | 125068067 | 125068171 | + | TSF |
| 3% | chr9 | 125054028 | 125054119 | + | ENST00000297908; ENST00000344641; ENST00000373723; ENST00000373729; ENST00000394315 | chr9 | 125068067 | 125068171 | + | TSF |
| 3% | chr16 | 50666192 | 50666319 | + | ENST00000268459 | chr16 | 50682755 | 50682972 | + | TSF |
| 3% | chr17 | 79912179 | 179912132 | − | ENST00000409678 | chr17 | 79911834 | 79911647 | − | TSF |
| 3% | chr4 | 25759228 | 25759156 | − | ENST00000399878; ENST00000264868; ENST00000502949; ENST00000510448 | chr4 | 25723603 | 25723555 | − | TSF |
| 3% | chr4 | 25759228 | 25759156 | | ENST00000399878; ENST00000264868; ENST00000502949; ENST00000510448 | chr4 | 25723603 | 25723555 | − | TSF |
| 3% | chr4 | 25759228 | 25759156 | − | ENST00000399878; ENST00000264868 | chr4 | 25723603 | 25723555 | − | TSF |

TABLE 65-continued

Transcript fusion for Uterine Corpus Endometrial Carcinoma (UCEC)
Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 3% | chr4 | 25759228 | 25759156 | − | ENST00000502949; ENST00000510448 ENST00000399878; ENST00000264868; ENST00000502949; ENST00000510448 | chr4 | 25723603 | 25723555 | − | TSF |
| 3% | chr6 | 110567463 | 110567335 | − | ENST00000338882 | chr6 | 110565813 | 110565664 | − | TSF |

TABLE 66

Transcript fusion for Uterine Corpus Endometrial Carcinoma (UCEC) Coordinates of the fusion sequences for which the donor is the TE.

| 1 | 2' | 3' | 4' | 5' | 6' | 7 | 8' | 9' | 10' | 11' |
|---|---|---|---|---|---|---|---|---|---|---|
| 39% | chr8 | 27947459 | 27947920 | + | chr8 | 27954736 | 27954835 | + | ENST00000256398; ENST00000523687; ENST00000518112 | TAF |
| 39% | chr8 | 27947459 | 27947920 | + | chr8 | 27954736 | 27954835 | + | ENST00000256398; ENST00000523687; ENST00000518112 | TAF |
| 36% | chr5 | 54528691 | 54528595 | − | chr5 | 54528374 | 54528189 | − | ENST00000282572 | TAF |
| 35% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 35% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 35% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 35% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 35% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 35% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 32% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 32% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 32% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 32% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 32% | chr19 | 49121994 | 49121817 | − | chr19 | 49121134 | 49121048 | − | ENST00000549920; ENST00000547897; ENST00000084795; ENST00000550645; ENST00000549370; ENST00000549273 | TAF |
| 28% | chr8 | 27947459 | 27947849 | + | chr8 | 27954736 | 27954835 | + | ENST00000256398; ENST00000523687; ENST00000518112 | TAF |
| 28% | chr8 | 27947459 | 27947849 | + | chr8 | 27954736 | 27954835 | + | ENST00000256398; ENST00000523687; ENST00000518112 | TAF |
| 26% | chr11 | 93468219 | 93468129 | − | chr11 | 93467826 | 93467791; 93467814 | − | ENST00000393259; ENST00000527169 | TAF |
| 26% | chr11 | 93468219 | 93468129 | − | chr11 | 93467826 | 93467791; 93467814 | − | ENST00000393259; ENST00000527169 | TAF |
| 23% | chr10 | 120902016 | 120901765 | − | chr10 | 120900831 | 120900754 | − | ENST00000355697; ENST00000330036 | TAF |
| 22% | chr1 | 46797740 | 46797497 | − | chr1 | 46764042 | 46763956 | − | ENST00000343304 | TAF |
| 22% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 22% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 22% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 22% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |

TABLE 66-continued

Transcript fusion for Uterine Corpus Endometrial Carcinoma (UCEC) Coordinates of the fusion sequences for which the donor is the TE.

| 1 | 2' | 3' | 4' | 5' | 6' | 7 | 8' | 9' | 10' | 11' |
|---|---|---|---|---|---|---|---|---|---|---|
| 21% | chr17 | 79214190 | 79214239 | + | chr17 | 79214787 | 79214816; 79214953 | + | ENST00000431388; ENST00000576002 | TAF |
| 21% | chr17 | 79214190 | 79214239 | + | chr17 | 79214787 | 79214816; 79214953 | + | ENST00000431388; ENST00000576002 | TAF |
| 21% | chr12 | 6602868 | 6602840 | − | chr12 | 6602138 | 6602028 | − | ENST00000229238 | TAF |
| 20% | chr8 | 104389530 | 104389551 | + | chr8 | 104390255 | 104390471 | + | ENST00000330295; ENST00000520337 | TAF |
| 19% | chrX | 3773692 | 3773630 | − | chrX | 3735819 | 3735819 | − | ENST00000425492 | TAF |
| 18% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 18% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 18% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 18% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 17% | chr6 | 31154067 | 31153803 | − | chr6 | 31133824 | 31133704 | − | ENST00000259915 | TAF |
| 17% | chr7 | 56018506 | 56018522 | + | chr7 | 56020872 | 56021011 | + | ENST00000426595 | TSF |
| 16% | chr4 | 107241932 | 107242850 | + | chr4 | 107246142 | 107246275 | + | ENST00000394701 | TAF |
| 16% | chr19 | 54631006 | 54631115 | + | chr19 | 54631448 | 54631575 | + | ENST00000321030; ENST00000419967 | TAF |
| 16% | chr19 | 54631006 | 54631115 | + | chr19 | 54631448 | 54631575 | + | ENST00000321030; ENST00000419967 | TAF |
| 16% | chr7 | 150938296 | 150938250 | − | chr7 | 150937608 | 150937511 | − | ENST00000262188; ENST00000392811; ENST00000356800 | TAF |
| 15% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 15% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 15% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 15% | chrX | 71397824 | 71398498 | + | chrX | 71406311 | 71406384 | + | ENST00000218432; ENST00000423432; ENST00000373669; ENST00000496835; ENST00000439980; ENST00000446576 | TAF |
| 14% | chr14 | 105944002 | 105944268 | + | chr14 | 105944603 | 105944697 | + | ENST00000483017; ENST00000329146 | TAF |
| 14% | chr14 | 105944002 | 105944232 | + | chr14 | 105944603 | 105944697 | + | ENST00000483017; ENST00000329146 | TAF |
| 14% | chr14 | 105944002 | 105944250 | + | chr14 | 105944603 | 105944697 | + | ENST00000483017; ENST00000329146 | TAF |
| 14% | chr1 | 40781678 | 40781517 | − | chr1 | 40781336 | 40781262 | − | ENST00000372748; ENST00000417105; ENST00000372736 | TAF |
| 14% | chr1 | 40781678 | 40781517 | − | chr1 | 40781336 | 40781262 | − | ENST00000372748; ENST00000417105; ENST00000372736 | TAF |
| 14% | chr1 | 40781678 | 40781517 | − | chr1 | 40781336 | 40781262 | − | ENST00000372748; ENST00000417105; ENST00000372736 | TAF |
| 14% | chr1 | 86821476 | 86821330 | − | chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 14% | chr1 | 86821476 | 86821330 | − | chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 14% | chr1 | 86821476 | 86821330 | − | chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 14% | chr1 | 86821476 | 86821330 | − | chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 14% | chr1 | 156025381 | 156025466 | + | chr1 | 156028106 | 156028162; 156028200 | + | ENST00000368305; ENST00000368304; ENST00000368302 | TAF |
| 14% | chr1 | 156025381 | 156025466 | + | chr1 | 156028106 | 156028162; 156028200 | + | ENST00000368305; ENST00000368304; ENST00000368302 | TAF |
| 14% | chr3 | 197680391 | 197680531 | + | chr3 | 197680874 | 197681018; 197680991 | + | ENST00000464167; ENST00000448864; ENST00000442341 | TAF |
| 14% | chr3 | 197680391 | 197680531 | + | chr3 | 197680874 | 197681018; 197680991 | + | ENST00000464167; ENST00000448864; ENST00000442341 | TAF |
| 14% | chr4 | 4864193 | 4864335 | + | chr4 | 4864428 | 4864870 | + | ENST00000382723 | TAF |
| 14% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 14% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 14% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 14% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 14% | chr8 | 39759879 | 39759967 | + | chr8 | 39775394 | 39775489; 39775448 | + | ENST00000518804; ENST00000519154; ENST00000522495; ENST00000522840; ENST00000518237; ENST00000253513 | TSF |
| 13% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 13% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; ENST00000423577 | TAF |
| 13% | chr9 | 130569975 | 130570054 | + | chr9 | 130570513 | 130570590; 130570580 | + | ENST00000373247; ENST00000373245; ENST00000393706; ENST00000373228; ENST00000373225; ENST00000431857; | TAF |

TABLE 66-continued

Transcript fusion for Uterine Corpus Endometrial Carcinoma (UCEC) Coordinates of the fusion sequences for which the donor is the TE.

| 1 | 2' | 3' | 4' | 5' | 6' | 7 | 8' | 9' | 10' | 11' |
|---|---|---|---|---|---|---|---|---|---|---|
| 13% | chr9 | 130569975 | 130570054 | + | chr9 | 130570513 | 130570590; 130570580 | + | ENST00000423577 ENST00000373247; ENST00000373245; ENST00000393706; ENST00000373228; ENST00000373225; ENST00000431857; ENST00000423577 | TAF |
| 13% | chrX | 129264697 | 129264593 | − | chrX | 129264141 | 129263945 | − | ENST00000440263; ENST00000460436; ENST00000346424; ENST00000319908; ENST00000287295 | TAF |
| 12% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 12% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 12% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 12% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 12% | chr19 | 42335927 | 42335940 | + | chr19 | 42364892 | 42364915 | + | ENST00000598742; ENST00000601492; ENST00000600467; ENST00000593863; ENST00000598261; ENST00000598399 | TAF |
| 12% | chr4 | 4437494 | 4437287 | − | chr4 | 4436585 | 4436497 | − | ENST00000505286; ENST00000306200; ENST00000503861; ENST00000512195; ENST00000507908 | TAF |
| 12% | chr4 | 4437494 | 4437287 | − | chr4 | 4436585 | 4436497 | − | ENST00000505286; ENST00000306200; ENST00000503861; ENST00000512195; ENST00000507908 | TAF |
| 12% | chr4 | 4437494 | 4437287 | − | chr4 | 4436585 | 4436497 | − | ENST00000505286; ENST00000306200; ENST00000503861; ENST00000512195; ENST00000507908 | TAF |
| 12% | chr4 | 4437494 | 4437287 | − | chr4 | 4436585 | 4436497 | − | ENST00000505286; ENST00000306200; ENST00000503861; ENST00000512195; ENST00000507908 | TAF |
| 12% | chr4 | 4437494 | 4437287 | − | chr4 | 4436585 | 4436497 | − | ENST00000505286; ENST00000306200; ENST00000503861; ENST00000512195; ENST00000507908 | TAF |
| 12% | chr7 | 74158449 | 74158566 | + | chr7 | 74159097 | 74159280 | + | ENST00000324896; ENST00000346152; ENST00000353920; ENST00000416070 | TAF |
| 12% | chr14 | 105944002 | 105944214 | + | chr14 | 105944603 | 105944697 | + | ENST00000483017; ENST00000329146 | TAF |
| 12% | chr17 | 79911953 | 79911734 | − | chr17 | 79911143 | 79910837 | − | ENST00000409678 | TAF |
| 12% | chr1 | 206288369 | 206288105 | − | chr1 | 206243250 | 206243150 | − | ENST00000331555 | TSF |
| 11% | chr1 | 21901654 | 21901670 | + | chr1 | 21902226 | 21902417 | + | ENST00000539907; ENST00000540617; ENST00000374840; ENST00000374832; ENST00000425315 | TAF |
| 11% | chr2 | 133363747 | 133363763 | + | chr2 | 133402674 | 133403179 | + | ENST00000329321 | TAF |
| 11% | chr12 | 64687157 | 64687061 | − | chr12 | 64679840 | 64679734 | − | ENST00000543942; ENST00000333722 | TAF |
| 10% | chr1 | 165863702 | 165863816 | + | chr1 | 165865427 | 165865569 | + | ENST00000367879 | TAF |
| 10% | chr14 | 102691697 | 102691432 | − | chr14 | 102691131 | 102691116 | − | ENST00000559838 | TAF |
| 10% | chr20 | 43919547 | 43919514 | − | chr20 | 43882476 | 43882216 | − | ENST00000338380 | TAF |
| 10% | chr19 | 39347374 | 39346430 | − | chr19 | 39338074 | 39337956 | − | ENST00000221419; ENST00000601449; ENST00000600233; ENST00000601813 | TSF |
| 10% | chr19 | 39347374 | 39346430 | − | chr19 | 39338074 | 39337956 | − | ENST00000221419; ENST00000601449; ENST00000600233; ENST00000601813 | TSF |
| 10% | chr19 | 39347374 | 39346430 | − | chr19 | 39338074 | 39337956 | − | ENST00000221419; ENST00000601449; ENST00000600233; ENST00000601813 | TSF |
| 10% | chr19 | 39347374 | 39346206 | − | chr19 | 39338074 | 39337956 | − | ENST00000221419; ENST00000601449; ENST00000600233; ENST00000601813 | TSF |
| 10% | chr19 | 39347374 | 39346206 | − | chr19 | 39338074 | 39337956 | − | ENST00000221419; ENST00000601449; ENST00000600233; ENST00000601813 | TSF |
| 10% | chr19 | 39347374 | 39346206 | − | chr19 | 39338074 | 39337956 | − | ENST00000221419; ENST00000601449; ENST00000600233; ENST00000601813 | TSF |
| 8% | chr1 | 169819657 | 169819707 | + | chr1 | 169820958 | 169821077 | + | ENST00000359326; ENST00000286031 | TSF |
| 8% | chr19 | 50174724 | 50174836 | + | chr19 | 50176955 | 50177005; 50177034 | + | ENST00000441864; ENST00000246785; ENST00000600947; ENST00000598306 | TSF |
| 8% | chr19 | 50174724 | 50174836 | + | chr19 | 50176955 | 50177005; 50177034 | + | ENST00000441864; ENST00000246785; ENST00000600947; ENST00000598306 | TSF |
| 8% | chr19 | 50391349 | 50391391 | + | chr19 | 50391488 | 50391574 | + | ENST00000221543; ENST00000535102 | TSF |
| 8% | chr4 | 4475319 | 4475221 | − | chr4 | 4473433 | 4473366 | − | ENST00000505286; ENST00000306200 | TSF |
| 8% | chr4 | 4475319 | 4475221 | − | chr4 | 4473433 | 4473366 | − | ENST00000505286; ENST00000306200 | TSF |
| 7% | chr6 | 80022917 | 80022085 | − | chr6 | 79924739 | 79924689 | − | ENST00000275036; ENST00000344726 | TSF |
| 7% | chr6 | 80022917 | 80022085 | − | chr6 | 79924739 | 79924689 | − | ENST00000275036; ENST00000344726 | TSF |
| 7% | chrX | 3812116 | 3812054 | − | chrX | 3735819 | 3735816 | − | ENST00000425492 | TSF |
| 6% | chr12 | 105386081 | 105386186 | + | chr12 | 105388256 | 105388474; 105388257 | + | ENST00000552951; ENST00000280749 | TSF |
| 6% | chr12 | 105386081 | 105386186 | + | chr12 | 105388256 | 105388474; 105388257 | + | ENST00000552951; ENST00000280749 | TSF |
| 6% | chr8 | 74036014 | 74035742 | − | chr8 | 73993448 | 73993254 | − | ENST00000297354 | TSF |
| 6% | chr22 | 42511426 | 42511212 | − | chr22 | 42483179 | 42483064 | − | ENST00000602404; ENST00000498737 | TSF |
| 5% | chr11 | 60694460 | 60694542 | + | chr11 | 60694676 | 60694890 | + | ENST00000453848; ENST00000005286 | TSF |
| 5% | chr11 | 60694460 | 60694542 | + | chr11 | 60694676 | 60694890 | + | ENST00000453848; ENST00000005286 | TSF |
| 5% | chr17 | 39976225 | 39976301 | + | chr17 | 39976521 | 39976713 | + | ENST00000321562; ENST00000455106; ENST00000544340 | TSF |
| 5% | chr19 | 1114930 | 1114676 | − | chr19 | 1114421 | 1114230 | − | ENST00000361757; ENST00000587024; ENST00000438103 | TSF |
| 5% | chr8 | 39766308 | 39766549 | + | chr8 | 39775394 | 39775489; 39775448 | + | ENST00000518804; ENST00000519154; ENST00000522495; ENST00000522840; ENST00000518237; ENST00000253513 | TSF |
| 5% | chr8 | 39766308 | 39766549 | + | chr8 | 39775394 | 39775489; 39775448 | + | ENST00000518804; ENST00000519154; ENST00000522495; ENST00000522840; ENST00000518237; ENST00000253513 | TSF |
| 5% | chr8 | 39766308 | 39766549 | + | chr8 | 39775394 | 39775489; | + | ENST00000518804; ENST00000519154; ENST00000522495; | TSF |

TABLE 66-continued

Transcript fusion for Uterine Corpus Endometrial Carcinoma (UCEC) Coordinates of the fusion sequences for which the donor is the TE.

| 1 | 2' | 3' | 4' | 5' | 6' | 7 | 8' | 9' | 10' | 11' |
|---|---|---|---|---|---|---|---|---|---|---|
| 5% | chr8 | 39766308 | 39766549 | + | chr8 | 39775394 | 39775448 39775489; 39775448 | + | ENST00000522840; ENST00000518237; ENST00000253513 ENST00000518804; ENST00000519154; ENST00000522495; ENST00000522840; ENST00000518237; ENST00000253513 | TSF |
| 5% | chr8 | 39766308 | 39766549 | + | chr8 | 39775394 | 39775489; 39775448 | + | ENST00000518804; ENST00000519154; ENST00000522495; ENST00000522840; ENST00000518237; ENST00000253513 | TSF |
| 5% | chr17 | 39974832 | 39974893 | + | chr17 | 39975462 | 39975651 | + | ENST00000321562 | TSF |
| 4% | chr19 | 49847402 | 49847303 | − | chr19 | 49846655 | 49846488 | − | ENST00000598810; ENST00000593945; ENST00000601519; ENST00000311227; ENST00000377214; ENST00000539846 | TSF |
| 4% | chr17 | 13442614 | 13442384 | − | chr17 | 13400135 | 13399514 | − | ENST00000284110 | TSF |
| 4% | chr12 | 6602868 | 6602754 | − | chr12 | 6602138 | 6602028 | − | ENST00000229238 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr22 | 29117574 | 29117506 | − | chr22 | 29115473 | 29115383; 29115458 | − | ENST00000348295; ENST00000382566; ENST00000382578; ENST00000404276; ENST00000328354; ENST00000405598; ENST00000382580; ENST00000433728; ENST00000448511; ENST00000402731; ENST00000403642; ENST00000439200 | TSF |
| 4% | chr20 | 110606 | 110697 | + | chr20 | 126056 | 126333 | + | ENST00000382398 | TSF |
| 4% | chr8 | 39766308 | 39766867 | + | chr8 | 39775394 | 39775489; 39775448 | + | ENST00000518804; ENST00000519154; ENST00000522495; ENST00000522840; ENST00000518237; ENST00000253513 | TSF |
| 4% | chr8 | 39766308 | 39766867 | + | chr8 | 39775394 | 39775489; 39775448 | + | ENST00000518804; ENST00000519154; ENST00000522495; ENST00000522840; ENST00000518237; ENST00000253513 | TSF |
| 4% | chr8 | 39766308 | 39766867 | + | chr8 | 39775394 | 39775489; 39775448 | + | ENST00000518804; ENST00000519154; ENST00000522495; ENST00000522840; ENST00000518237; ENST00000253513 | TSF |
| 4% | chr8 | 39766308 | 39766867 | + | chr8 | 39775394 | 39775489; 39775448 | + | ENST00000518804; ENST00000519154; ENST00000522495; ENST00000522840; ENST00000518237; ENST00000253513 | TSF |
| 4% | chr8 | 39766308 | 39766867 | + | chr8 | 39775394 | 39775489; 39775448 | + | ENST00000518804; ENST00000519154; ENST00000522495; ENST00000522840; ENST00000518237; ENST00000253513 | TSF |
| 4% | chr1 | 1422590 | 1422685 | + | chr1 | 1423243 | 1423294 | + | ENST00000308647 | TSF |
| 4% | chr18 | 51273 | 49727 | − | chr18 | 49237 | 49129 | − | ENST00000308911 | TSF |
| 4% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chr2 | 38983894 | 38983253 | − | chr2 | 38977336 | 38977156 | − | ENST00000313117; ENST00000425778; ENST00000425941; ENST00000446327; ENST00000409276; ENST00000431066; ENST00000443213 | TSF |
| 4% | chr15 | 74475607 | 74475594 | − | chr15 | 74474801 | 74474684 | − | ENST00000395105; ENST00000423167; ENST00000323940; ENST00000449139; ENST00000416286; ENST00000535552; ENST00000563965; ENST00000574278; ENST00000572785 | TSF |
| 4% | chr15 | 74475607 | 74475594 | − | chr15 | 74474801 | 74474684 | − | ENST00000395105; ENST00000423167; ENST00000323940; ENST00000449139; ENST00000416286; ENST00000535552; ENST00000563965; ENST00000574278; ENST00000572785 | TSF |
| 3% | chr7 | 56018506 | 56018522 | + | chr7 | 56022602 | 56022871; 56022865 | + | ENST00000426595; ENST00000285298; ENST00000443449 | TSF |
| 3% | chr7 | 56018506 | 56018522 | + | chr7 | 56022602 | 56022871; 56022865 | + | ENST00000426595; ENST00000285298; ENST00000443449 | TSF |
| 3% | chr1 | 156716197 | 156716133 | − | chr1 | 156715165 | 156715089 | − | ENST00000357325; ENST00000537739; ENST00000368209; ENST00000368206 | TSF |
| 3% | chr4 | 4508675 | 4508569 | − | chr4 | 14473433 | 4473366 | − | ENST00000505286; ENST00000306200 | TSF |
| 3% | chr4 | 4508675 | 4508569 | − | chr4 | 14473433 | 4473366 | − | ENST00000505286; ENST00000306200 | TSF |
| 3% | chr15 | 93253529 | 93253499 | − | chr15 | 93173575 | 93173444 | − | ENST00000327355 | TSF |
| 3% | chr11 | 60663653 | 60661987 | − | chr11 | 60658735 | 60658638 | − | ENST00000227524; ENST00000535326 | TSF |
| 3% | chr3 | 13918009 | 13917401 | − | chr3 | 13916670 | 13916444 | − | ENST00000285018 | TSF |

TABLE 67

Transcript fusion for Uterine Carcinosarcoma (UCS) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 33% | chr15 | 79054907 | 79054745 | − | ENST00000388820 | chr15 | 79054428 | 79054400 | − | TAF |
| 32% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 32% | chr6 | 10749855; 10749898 | 10749931 | + | ENST00000379542; ENST00000473166; ENST00000463448; ENST00000460341; ENST00000480294; ENST00000473807; ENST00000461342; ENST00000475942; ENST00000379530; ENST00000463100; ENST00000481240; ENST00000467317; ENST00000478732 | chr6 | 10829240 | 10829256 | + | TAF |
| 30% | chr4 | 5317425 | 1742713 | + | ENST00000313288 | chr4 | 1745122 | 1745307 | + | TAF |
| 26% | chr12 | 6943089 | 6943213 | + | ENST00000251761; ENST00000396725; ENST00000606935 | chr12 | 6943989 | 6944119 | + | TAF |
| 26% | chr12 | 6943089 | 6943213 | + | ENST00000251761; ENST00000396725; ENST00000606935 | chr12 | 6943989 | 6944119 | + | TAF |
| 26% | chr12 | 6943089 | 6943213 | + | ENST00000251761; ENST00000396725; ENST00000606935 | chr12 | 6943989 | 6944119 | + | TAF |
| 25% | chr19 | 35514331 | 35514451 | + | ENST00000599564; ENST00000317991; ENST00000504615; ENST00000411896 | chr19 | 35514601 | 35514631 | + | TAF |
| 25% | chr19 | 35514331 | 35514451 | + | ENST00000599564; ENST00000317991; ENST00000504615; ENST00000411896 | chr19 | 35514601 | 35514631 | + | TAF |
| 25% | chr19 | 35514331 | 35514451 | + | ENST00000599564; ENST00000317991; ENST00000504615; ENST00000411896 | chr19 | 35514601 | 35514631 | + | TAF |
| 25% | chr19 | 35514331 | 35514451 | + | ENST00000599564; ENST00000317991; ENST00000504615; ENST00000411896 | chr19 | 35514601 | 35514631 | + | TAF |
| 23% | chr16 | 30783410 | 30783511 | + | ENST00000324685; ENST00000402121; ENST00000563683; ENST00000357890 | chr16 | 30785136 | 30785155 | + | TSF |
| 23% | chr16 | 30783410 | 30783511 | + | ENST00000324685; ENST00000402121; ENST00000563683; ENST00000357890 | chr16 | 30785136 | 30785155 | + | TSF |
| 23% | chr16 | 30783410 | 30783511 | + | ENST00000324685; ENST00000402121; ENST00000563683; ENST00000357890 | chr16 | 30785136 | 30785155 | + | TSF |
| 23% | chr16 | 30783410 | 30783511 | + | ENST00000324685; ENST00000402121; ENST00000563683; ENST00000357890 | chr16 | 30785136 | 30785155 | + | TSF |
| 19% | chr19 | 39077165 | 39077216 | + | ENST00000355481; ENST00000360985; ENST00000359596 | chr19 | 39085644 | 39085967 | + | TAF |
| 19% | chr19 | 39077165 | 39077216 | + | ENST00000355481; ENST00000360985; ENST00000359596 | chr19 | 39085644 | 39085967 | + | TAF |
| 19% | chr19 | 39077165 | 39077216 | + | ENST00000355481; ENST00000360985; ENST00000359596 | chr19 | 39085644 | 39085967 | + | TAF |
| 19% | chr2 | 220239744 | 220239577 | − | ENST00000355481; ENST00000360985; ENST00000359596 | chr2 | 220227530 | 220227195 | − | TAF |
| 19% | chr2 | 220239744 | 220239577 | − | ENST00000355481; ENST00000360985; ENST00000359596 | chr2 | 220227530 | 220227195 | − | TAF |
| 19% | chr2 | 220239744 | 220239577 | − | ENST00000355481; ENST00000360985; ENST00000359596 | chr2 | 220227530 | 220227195 | − | TAF |
| 18% | chr1 | 11115983; 11115877 | 11115838 | − | ENST00000376957; ENST00000490101 | chr1 | 11115464 | 11115178 | − | TSF |
| 18% | chr1 | 11115983; 11115877 | 11115838 | − | ENST00000376957; ENST00000490101 | chr1 | 11115464 | 11115178 | − | TSF |
| 16% | chr1 | 32696528 | 32696620 | + | ENST00000373586 | chr1 | 32696861 | 32697110 | + | TAF |
| 16% | chr7 | 27582719 | 27582586 | − | ENST00000265395; ENST00000425715 | chr7 | 27581374 | 27579272 | − | TAF |
| 16% | chr7 | 27582719 | 27582586 | − | ENST00000265395; ENST00000425715 | chr7 | 27581374 | 27579272 | − | TAF |
| 16% | chr12 | 71928895 | 71928966 | + | ENST00000266674; ENST00000536515; ENST00000540815 | chr12 | 71938771 | 719 38901 | + | TSF |
| 12% | chr12 | 64833024 | 64833095 | + | ENST00000332707 | chr12 | 64833417 | 64833459 | + | TAF |
| 12% | chr6 | 41606488 | 41606563 | + | ENST00000432027; ENST00000419164; ENST00000373051; ENST00000441667; ENST00000230321; ENST00000373050; ENST00000446650; ENST00000435476 | chr6 | 41607515 | 41607595 | + | TAF |
| 12% | chr14 | 101200486 | 101200513 | + | ENST00000341267; ENST00000331224 | chr14 | 101473144 | 101473392 | + | TAF |
| 12% | chr5 | 131593428 | 131593520 | + | ENST00000253754; ENST00000379018 | chr5 | 131596019 | 131596316 | + | TAF |
| 12% | chr4 | 536612008 | 120085549 | + | ENST00000307128 | chr4 | 120089717 | 120089827 | + | TAF |
| 12% | chr20 | 53092486 | 53092551 | + | ENST00000262593 | chr20 | 53111339 | 53111426 | + | TAF |
| 12% | chr20 | 33439171 | 33439034 | − | ENST00000336431 | chr20 | 33438000 | 33437979 | − | TAF |
| 12% | chr10 | 120905865 | 120905748 | − | ENST00000355697; ENST00000330036 | chr10 | 120901885 | 120901741 | − | TAF |
| 12% | chr10 | 120905865 | 120905748 | − | ENST00000355697; ENST00000330036 | chr10 | 120901885 | 120901741 | − | TAF |
| 12% | chr19 | 39390161 | 39390146 | − | ENST00000249396; ENST00000358931; ENST00000443898 | chr19 | 39389554 | 39389434 | − | TAF |
| 12% | chr1 | 38532560 | 32560572 | + | ENST00000336294; ENST00000373634; ENST00000427288 | chr1 | 32561261 | 32561358 | + | TAF |
| 12% | chr1 | 38532560 | 32560572 | + | ENST00000336294; ENST00000373634 | chr1 | 32561261 | 32561358 | + | TAF |

TABLE 67-continued

Transcript fusion for Uterine Carcinosarcoma (UCS) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 12% | chr1 | 32560385 | 32560572 | + | ENST00000427288 ENST00000336294; ENST00000373634; ENST00000427288 | chr1 | 32561261 | 32561358 | + | TSF |
| 11% | chr13 | 115030625 | 115030715 | + | ENST00000360383; ENST00000375312; ENST00000356221; ENST00000375310; ENST00000252457; ENST00000375308; ENST00000252458 | chr13 | 115035038 | 115035171 | + | TAF |
| 11% | chr13 | 115030625 | 115030715 | + | ENST00000360383; ENST00000375312; ENST00000356221; ENST00000375310; ENST00000252457; ENST00000375308; ENST00000252458 | chr13 | 115035038 | 115035171 | + | TAF |
| 11% | chr13 | 115030625 | 115030715 | + | ENST00000360383; ENST00000375312; ENST00000356221; ENST00000375310; ENST00000252457; ENST00000375308; ENST00000252458 | chr13 | 115035038 | 115035171 | + | TAF |
| 11% | chr13 | 115030625 | 115030715 | + | ENST00000360383; ENST00000375312; ENST00000356221; ENST00000375310; ENST00000252457; ENST00000375308; ENST00000252458 | chr13 | 115035038 | 1151035171 | + | TAF |
| 11% | chr20 | 43560983 | 43561073 | + | ENST00000255136; ENST00000217073 | chr20 | 43561176 | 43561224 | + | TAF |
| 11% | chr19 | 44129402 | 44129230 | – | ENST00000222374 | chr19 | 44129055 | 44128921 | – | TAF |
| 11% | chrX | 152730513 | 152730446 | – | ENST00000370211; ENST00000370212; ENST00000370210 | chrX | 152728559 | 152728505 | – | TAF |
| 11% | chrX | 152730513 | 152730446 | – | ENST00000370211; ENST00000370212; ENST00000370210 | chrX | 152728559 | 152728505 | – | TAF |
| 11% | chr13 | 96505911 | 96505797 | – | ENST00000376747 | chr13 | 96498149 | 96497437 | – | TAF |
| 11% | chr2 | 217366064 | 217366082 | + | ENST00000491306; ENST00000456586 | chr2 | 217393993 | 217394327 | + | TSF |
| 11% | chr2 | 217366064 | 217366082 | + | ENST00000491306; ENST00000456586 | chr2 | 217393993 | 217394327 | + | TSF |
| 11% | chr3 | 8775563 | 8775676 | + | ENST00000343849; ENST00000397368 | chr3 | 8819163 | 8819386 | + | TSF |
| 11% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 11% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 11% | chr19 | 50213980 | 50214114 | + | ENST00000323446; ENST00000392518; ENST00000354199; ENST00000598293; ENST00000405931; ENST00000595031 | chr19 | 50214968 | 50214999 | + | TSF |
| 11% | chr6 | 43005749 | 43005597 | – | ENST00000265348; ENST00000535468 | chr6 | 43005086 | 43004995 | – | TSF |
| 11% | chr6 | 43005749 | 43005597 | – | ENST00000265348; ENST00000535468 | chr6 | 43005086 | 43004995 | – | TSF |

TABLE 68

Transcript fusion for Uterine Carcinosarcoma (UCS) Coordinates of the fusion sequences for which the donor is the TE.

| 1+B2: L152 | 2' | 3' | 4' | 5' | 6' | 7' | 8' | 9' | 10' | 11' |
|---|---|---|---|---|---|---|---|---|---|---|
| 70% | chr8 | 104389530 | 104389551 | + | chr8 | 104390255 | 104390471 | + | ENST00000330295; ENST00000520337 | TAF |
| 51% | chr3 | 197680391 | 197680531 | + | chr3 | 197680874 | 197681018; 197680991 | + | ENST00000464167; ENST00000448864; ENST00000442341 | TAF |
| 51% | chr3 | 197680391 | 197680531 | + | chr3 | 197680874 | 197681018; 197680991 | + | ENST00000464167; ENST00000448864; ENST00000442341 | TAF |
| 46% | chr7 | 150938296 | 150938250 | – | chr7 | 150937608 | 150937511 | – | ENST00000262188; ENST00000392811; ENST00000356800 | TAF |
| 44% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 44% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 44% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 44% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 44% | chr19 | 49121994 | 49121817 | – | chr19 | 49121134 | 49121048 | – | ENST00000549920; ENST00000547897; ENST00000084795; ENST00000550645; ENST00000549370; ENST00000549273 | TAF |
| 44% | chr22 | 22899971 | 22899965 | – | chr22 | 22893511 | 22893189; 22893185; 22893481; 22893274 | – | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 44% | chr22 | 22899971 | 22899965 | – | chr22 | 22893511 | 22893189; 22893185; 22893481; 22893274 | – | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |

TABLE 68-continued

Transcript fusion for Uterine Carcinosarcoma (UCS) Coordinates of the fusion sequences for which the donor is the TE.

| 1+B2: L152 | 2' | 3' | 4' | 5' | 6' | 7' | 8' | 9 | 10' | 11' |
|---|---|---|---|---|---|---|---|---|---|---|
| 44% | chr22 | 22899971 | 22899965 | – | chr22 | 22893511 | 22893189; 22893185; 22893481; 22893274 | – | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 44% | chr22 | 22899971 | 22899965 | – | chr22 | 22893511 | 22893189; 22893185; 22893481; 22893274 | – | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 44% | chr22 | 22899971 | 22899965 | – | chr22 | 22893511 | 22893189; 22893185; 22893481; 22893274 | – | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 44% | chr22 | 22899971 | 22899965 | – | chr22 | 22893511 | 22893189; 22893185; 22893481; 22893274 | – | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 44% | chr22 | 22899971 | 22899965 | – | chr22 | 22893511 | 22893189; 22893185; 22893481; 22893274 | – | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 40% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 40% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 40% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 40% | chr7 | 73098299 | 73098330 | + | chr7 | 73100966 | 73101061 | + | ENST00000265758; ENST00000432522; ENST00000421744; ENST00000428163; ENST00000423166; ENST00000423497 | TAF |
| 39% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 39% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 39% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 39% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 39% | chr11 | 93468219 | 93468129 | – | chr11 | 93467826 | 93467791; 93467814 | – | ENST00000393259; ENST00000527169 | TAF |
| 39% | chr11 | 93468219 | 93468129 | – | chr11 | 93467826 | 93467791; 93467814 | – | ENST00000393259; ENST00000527169 | TAF |
| 39% | chr12 | 6602868 | 6602840 | – | chr12 | 6602138 | 6602028 | – | ENST00000229238 | TAF |
| 32% | chr7 | 130127044 | 130127065 | + | chr7 | 130135209 | 130135363 | + | ENST00000223215; ENST00000437945 | TAF |
| 32% | chr7 | 130127044 | 130127065 | + | chr7 | 130135209 | 130135363 | + | ENST00000223215; ENST00000437945 | TAF |
| 30% | chr17 | 79214190 | 79214239 | + | chr17 | 79214787 | 79214816; 79214953 | + | ENST00000431388; ENST00000576002 | TAF |
| 30% | chr17 | 79214190 | 79214239 | + | chr17 | 79214787 | 79214816; 79214953 | + | ENST00000431388; ENST00000576002 | TAF |
| 30% | chr17 | 39976225 | 39976301 | + | chr17 | 39976521 | 39976713 | + | ENST00000321562; ENST00000455106; ENST00000544340 | TSF |
| 28% | chr9 | 131002678 | 131002811 | + | chr9 | 131004511 | 131004624 | + | ENST00000475805; ENST00000341179; ENST00000372923; ENST00000393594; ENST00000486160 | TAF |
| 28% | chr9 | 131002678 | 131002811 | + | chr9 | 131004511 | 131004624 | + | ENST00000475805; ENST00000341179; ENST00000372923; ENST00000393594; ENST00000486160 | TAF |
| 25% | chr1 | 240569724 | 240569786 | + | chr1 | 240601361 | 240601510 | + | ENST00000319653; ENST00000545751 | TAF |
| 25% | chr1 | 156025381 | 156025466 | + | chr1 | 156028106 | 156028162; 156028200 | + | ENST00000368305; ENST00000368304; ENST00000368302 | TAF |
| 25% | chr1 | 156025381 | 156025466 | + | chr1 | 156028106 | 156028162; 156028200 | + | ENST00000368305; ENST00000368304; ENST00000368302 | TAF |
| 25% | chr7 | 73466655 | 73466891 | + | chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 25% | chr7 | 73466655 | 73466891 | + | chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 25% | chr7 | 73466655 | 73466891 | + | chr7 | 73467493 | 73467639 | + | ENST00000445912; ENST00000252034; ENST00000358929; | TAF |

TABLE 68-continued

Transcript fusion for Uterine Carcinosarcoma (UCS) Coordinates of the fusion sequences for which the donor is the TE.

| 1+B2: L152 | 2' | 3' | 4' | 5' 6' | 7' | 8' | 9 | 10' | 11' |
|---|---|---|---|---|---|---|---|---|---|
| 25% | chr7 | 73466655 | 73466891 | + chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 25% | chr7 | 73466655 | 73466891 | + chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 25% | chr7 | 73466655 | 73466891 | + chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 25% | chr7 | 73466655 | 73466891 | + chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 25% | chr7 | 73466655 | 73466891 | + chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 25% | chr7 | 73466655 | 73466891 | + chr7 | 73467493 | 73467639 | + | ENST00000445912; ENST00000252034; ENST00000358929; ENST00000320492; ENST00000414324; ENST00000380562; ENST00000380575; ENST00000380584; ENST00000458204; ENST00000357036; ENST00000429192; ENST00000380553; ENST00000380576; ENST00000320399 | TAF |
| 25% | chr1 | 40781678 | 40781517 | − chr1 | 40781336 | 40781262 | − | ENST00000372748; ENST00000417105; ENST00000372736 | TAF |
| 25% | chr1 | 40781678 | 40781517 | − chr1 | 40781336 | 40781262 | − | ENST00000372748; ENST00000417105; ENST00000372736 | TAF |
| 25% | chr1 | 40781678 | 40781517 | − chr1 | 40781336 | 40781262 | − | ENST00000372748; ENST00000417105; ENST00000372736 | TAF |
| 23% | chr19 | 54631006 | 54631115 | + chr19 | 54631448 | 54631575 | + | ENST00000321030; ENST00000419967 | TAF |
| 23% | chr19 | 54631006 | 54631115 | + chr19 | 54631448 | 54631575 | + | ENST00000321030; ENST00000419967 | TAF |
| 23% | chr20 | 44453914 | 44453823 | − chr20 | 44453473 | 44453422 | − | ENST00000372555 | TAF |
| 21% | chrX | 48793481 | 48793462 | − chrX | 48792291 | 48792227 | − | ENST00000396743; ENST00000455452; ENST00000156084; ENST00000376488; ENST00000428668 | TAF |
| 21% | chrX | 48793481 | 48793462 | − chrX | 48792291 | 48792227 | − | ENST00000396743; ENST00000455452; ENST00000156084; ENST00000376488; ENST00000428668 | TAF |
| 19% | chr4 | 107241932 | 107242850 | + chr4 | 107246142 | 107246275 | + | ENST00000394701 | TAF |
| 19% | chr20 | 35857318 | 35857337 | + chr20 | 35858376 | 35858462 | + | ENST00000237530; ENST00000373622; ENST00000437329; ENST00000456400 | TAF |
| 19% | chr20 | 35857318 | 35857337 | + chr20 | 35858376 | 35858462 | + | ENST00000237530; ENST00000373622; ENST00000437329; ENST00000456400 | TAF |
| 19% | chr20 | 35857318 | 35857337 | + chr20 | 35858376 | 35858462 | + | ENST00000237530; ENST00000373622; ENST00000437329; ENST00000456400 | TAF |
| 19% | chr20 | 35857318 | 35857337 | + chr20 | 35858376 | 35858462 | + | ENST00000237530; ENST00000373622; ENST00000437329; ENST00000456400 | TAF |
| 19% | chr20 | 61475759 | 61475132 | − chr20 | 61473449 | 61473327 | − | ENST00000335351 | TAF |
| 19% | chr12 | 6602868 | 6602754 | − chr12 | 6602138 | 6602028 | − | ENST00000229238 | TSF |
| 18% | chr1 | 86821476 | 86821330 | − chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 18% | chr1 | 86821476 | 86821330 | − chr1 | 86820542 | 86820457; 816820538 | − | ENST00000359242; ENST00000460698; ENST00000317336; ENST00000370567; ENST00000394731; ENST00000370566; ENST00000462648; ENST00000294678; ENST00000531412 | TAF |
| 18% | chr1 | 86821476 | 86821330 | − chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 18% | chr1 | 86821476 | 86821330 | − chr1 | 86820542 | 86820457; 86820538 | − | ENST00000359242; ENST00000460698; ENST00000317336; ENST00000370567; ENST00000394731; ENST00000370566; ENST00000462648; ENST00000294678; ENST00000531412 | TAF |
| 18% | chr19 | 55649945 | 55649877 | − chr19 | 55649442 | 55649344; 55649329; 55649386 | − | ENST00000587758; ENST00000291901; ENST00000356783; ENST00000588426; ENST00000536926; ENST00000588981; ENST00000593194; ENST00000589745; ENST00000587465; ENST00000585321; ENST00000593046; ENST00000589226; ENST00000588147 | TAF |
| 18% | chr19 | 55649945 | 55649877 | − chr19 | 55649442 | 55649329; 55649344; | − | ENST00000587758; ENST00000291901; ENST00000356783; ENST00000588426; ENST00000536926; ENST00000588981; | TAF |

TABLE 68-continued

Transcript fusion for Uterine Carcinosarcoma (UCS) Coordinates of the fusion sequences for which the donor is the TE.

| 1+B2:L152 | 2' | 3' | 4' | 5' | 6' | 7' | 8' | 9 | 10' | 11' |
|---|---|---|---|---|---|---|---|---|---|---|
| | | | | | | | 55649386 | | ENST00000593194; ENST00000589745; ENST00000587465; ENST00000585321; ENST00000593046; ENST00000589226; ENST00000588147 | |
| 18% | chr19 | 55649945 | 55649877 | – | chr19 | 55649442 | 55649329; 55649344; 55649386 | – | ENST00000587758; ENST00000291901; ENST00000356783; ENST00000588426; ENST00000536926; ENST00000588981; ENST00000593194; ENST00000589745; ENST00000587465; ENST00000585321; ENST00000593046; ENST00000589226; ENST00000588147 | TAF |
| 18% | chr19 | 55649945 | 55649877 | – | chr19 | 55649442 | 55649329; 55649344; 55649386 | – | ENST00000587758; ENST00000291901; ENST00000356783; ENST00000588426; ENST00000536926; ENST00000588981; ENST00000593194; ENST00000589745; ENST00000587465; ENST00000585321; ENST00000593046; ENST00000589226; ENST00000588147 | TAF |
| 18% | chr19 | 55649945 | 55649877 | – | chr19 | 55649442 | 55649329; 55649344; 55649386 | – | ENST00000587758; ENST00000291901; ENST00000356783; ENST00000588426; ENST00000536926; ENST00000588981; ENST00000593194; ENST00000589745; ENST00000587465; ENST00000585321; ENST00000593046; ENST00000589226; ENST00000588147 | TAF |
| 18% | chr9 | 136393635 | 136393545 | – | chr9 | 136385410 | 136385296 | – | ENST00000339996 | TAF |
| 18% | chr1 | 169819657 | 169819707 | + | chr1 | 169820958 | 169821077 | + | ENST00000359326; ENST00000286031 | TSF |
| 16% | chr18 | 43686699 | 43686799 | + | chr18 | 43698147 | 43698282 | + | ENST00000282058; ENST00000592471 | TAF |
| 16% | chr18 | 43686699 | 43686799 | + | chr18 | 43698147 | 43698282 | + | ENST00000282058; ENST00000592471 | TAF |
| 16% | chr17 | 39974832 | 39974854 | + | chr17 | 39975462 | 39975651 | + | ENST00000321562 | TAF |
| 16% | chr17 | 79649571 | 79649473 | – | chr17 | 79649179 | 79649064 | – | ENST00000397498; ENST00000570561; ENST00000576135 | TAF |
| 16% | chr3 | 185411133 | 185410965 | – | chr3 | 185410550 | 185410487 | – | ENST00000382199; ENST00000421047; ENST00000457616; ENST00000346192 | TAF |
| 16% | chr3 | 185411133 | 185410965 | – | chr3 | 185410550 | 185410487 | – | ENST00000382199; ENST00000421047; ENST00000457616; ENST00000346192 | TAF |
| 16% | chr21 | 47675413 | 47675316 | – | chr21 | 47674758 | 47674690 | – | ENST00000397708; ENST00000291688 | TAF |
| 16% | chr17 | 39974832 | 39974893 | + | chr17 | 39975462 | 39975651 | + | ENST00000321562 | TSF |
| 14% | chr7 | 2289080 | 2289115 | + | chr7 | 2289492 | 2289637 | + | ENST00000356714; ENST00000397049; ENST00000397046; ENST00000397048; ENST00000339737; ENST00000343985 | TAF |
| 14% | chr19 | 42335927 | 42335940 | + | chr19 | 42365240 | 42365281; 42365294 | + | ENST00000598742; ENST00000601492; ENST00000600467; ENST00000593863; ENST00000598261; ENST00000598399 | TAF |
| 14% | chr19 | 42335927 | 42335940 | + | chr19 | 42365240 | 42365281; 42365294 | + | ENST00000598742; ENST00000601492; ENST00000600467; ENST00000593863; ENST00000598261; ENST00000598399 | TAF |
| 14% | chr19 | 42335927 | 42335940 | + | chr19 | 42365240 | 42365281; 42365294 | + | ENST00000598742; ENST00000601492; ENST00000600467; ENST00000593863; ENST00000598261; ENST00000598399 | TAF |
| 14% | chr19 | 42335927 | 42335940 | + | chr19 | 42365240 | 42365281; 42365294 | + | ENST00000598742; ENST00000601492; ENST00000600467; ENST00000593863; ENST00000598261; ENST00000598399 | TAF |
| 14% | chr19 | 42335927 | 42335940 | + | chr19 | 42365240 | 42365281; 42365294 | + | ENST00000598742; ENST00000601492; ENST00000600467; ENST00000593863; ENST00000598261; ENST00000598399 | TAF |
| 14% | chr3 | 180632728 | 180632783 | + | chr3 | 180651122 | 180651174 | + | ENST00000357559; ENST00000445140; ENST00000480918; ENST00000484042 | TAF |
| 14% | chr3 | 180632728 | 180632783 | + | chr3 | 180651122 | 180651174 | + | ENST00000357559; ENST00000445140; ENST00000480918; ENST00000484042 | TAF |
| 14% | chr3 | 180632728 | 180632783 | + | chr3 | 180651122 | 180651174 | + | ENST00000357559; ENST00000445140; ENST00000480918; ENST00000484042 | TAF |
| 14% | chr13 | 43628887 | 29643679 | + | chr13 | 43643066 | 43643139 | + | ENST00000379221 | TAF |
| 14% | chr10 | 120902016 | 120901765 | – | chr10 | 120900831 | 120900754 | – | ENST00000355697; ENST00000330036 | TAF |
| 14% | chrX | 3773692 | 3773630 | – | chrX | 3735819 | 3735816 | – | ENST00000425492 | TAF |
| 12% | chr1 | 120274523 | 120274578 | + | chr1 | 120277257 | 120277389 | + | ENST00000369450; ENST00000369407 | TAF |
| 12% | chr1 | 155036912 | 155037036 | + | chr1 | 155039206 | 155039492 | + | ENST00000368409; ENST00000359751; ENST00000427683 | TAF |
| 12% | chr1 | 155036912 | 155037036 | + | chr1 | 155039206 | 155039492 | + | ENST00000368409; ENST00000359751; ENST00000427683 | TAF |
| 12% | chr1 | 155036912 | 155037036 | + | chr1 | 155039206 | 155039492 | + | ENST00000368409; ENST00000359751; ENST00000427683 | TAF |
| 12% | chr1 | 165863702 | 165863816 | + | chr1 | 165865427 | 165865569 | + | ENST00000367879 | TAF |
| 12% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 12% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 12% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 12% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 12% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |
| 12% | chr2 | 28190037 | 28190310 | + | chr2 | 28210860 | 28210954 | + | ENST00000436924; ENST00000344773; ENST00000379624; ENST00000342045; ENST00000361704; ENST00000379632; ENST00000379629; ENST00000604932 | TAF |

TABLE 68-continued

Transcript fusion for Uterine Carcinosarcoma (UCS) Coordinates of the fusion sequences for which the donor is the TE.

| 1+B2: L152 2' | 3' | 4' | 5' 6' | 7' | 8' | 9 10' | 11' |
|---|---|---|---|---|---|---|---|
| 12% chr20 | 2775864 | 2775374 | − chr20 | 2775285 | 2775183 | − ENST00000380605 | TAF |
| 12% chr10 | 101952336 | 216101952 | − chr10 | 101950725 | 101950626 | − ENST00000370397 | TAF |
| 12% chr5 | 173041966 | 173041919 | − chr5 | 173040258 | 173040134 | − ENST00000311086; ENST00000285908 | TAF |
| 12% chr5 | 173041966 | 173041919 | − chr5 | 173040258 | 173040134 | − ENST00000311086; ENST00000285908 | TAF |
| 12% chr13 | 37599378 | 37599328 | − chr13 | 37598330 | 37598172 | − ENST00000490716; ENST00000495071; ENST00000360252; ENST00000475892; ENST00000469488; ENST00000356185; ENST00000350612; ENST00000464744; ENST00000542180 | TAF |
| 12% chr13 | 37599378 | 37599328 | − chr13 | 37598330 | 37598172 | − ENST00000490716; ENST00000495071; ENST00000360252; ENST00000475892; ENST00000469488; ENST00000356185; ENST00000350612; ENST00000464744; ENST00000542180 | TAF |
| 12% chr13 | 37599378 | 37599328 | − chr13 | 37598330 | 37598172 | − ENST00000490716; ENST00000495071; ENST00000360252; ENST00000475892; ENST00000469488; ENST00000356185; ENST00000350612; ENST00000464744; ENST00000542180 | TAF |
| 12% chr13 | 37599378 | 37599328 | − chr13 | 37598330 | 37598172 | − ENST00000490716; ENST00000495071; ENST00000360252; ENST00000475892; ENST00000469488; ENST00000356185; ENST00000350612; ENST00000464744; ENST00000542180 | TAF |
| 12% chr13 | 37599378 | 37599328 | − chr13 | 37598330 | 37598172 | − ENST00000490716; ENST00000495071; ENST00000360252; ENST00000475892; ENST00000469488; ENST00000356185; ENST00000350612; ENST00000464744; ENST00000542180 | TAF |
| 12% chr5 | 54528691 | 28554595 | − chr5 | 54528374 | 54528189 | − ENST00000282572 | |
| 12% chr1 | 53070435 | 53070501 | + chr1 | 53072356 | 53072617 | + ENST00000361314 | TSF |
| 12% chr1 | 59980221 | 59980497 | + chr1 | 60019796 | 60019899 | + ENST00000371218; ENST00000303721; ENST00000430447; ENST00000371212 | TSF |
| 12% chr1 | 59980221 | 59980497 | + chr1 | 60019796 | 60019899 | + ENST00000371218; ENST00000303721; ENST00000430447; ENST00000371212 | TSF |
| 12% chr1 | 59980221 | 59980497 | + chr1 | 60019796 | 60019899 | + ENST00000371218; ENST00000303721; ENST00000430447; ENST00000371212 | TSF |
| 11% chr19 | 48283383 | 48283451 | + chr19 | 48283982 | 48284006 | + ENST00000601048; ENST00000593892; ENST00000599874; ENST00000595615 | TAF |
| 11% chr19 | 48283383 | 48283451 | + chr19 | 48283982 | 48284006 | + ENST00000601048; ENST00000593892; ENST00000599874; ENST00000595615 | TAF |
| 11% chr19 | 58515808 | 58516068 | + chr19 | 58517275 | 58517367; 58517363 | + ENST00000550135; ENST00000553254 | TAF |
| 11% chr19 | 58515808 | 58516068 | + chr19 | 58517275 | 58517367; 58517363 | + ENST00000550135; ENST00000553254 | TAF |
| 11% chr6 | 26474324 | 26474624 | + chr6 | 26476389 | 26476396 | + ENST00000480218 | TAF |
| 11% chr5 | 135398466 | 135398602 | + chr5 | 135398875 | 135398915; 135398898 | + ENST00000442011; ENST00000305126; ENST00000514554; ENST00000508076; ENST00000503087 | TAF |
| 11% chr5 | 135398466 | 135398602 | + chr5 | 135398875 | 135398915; 135398898 | + ENST00000442011; ENST00000305126; ENST00000514554; ENST00000508076; ENST00000503087 | TAF |
| 11% chr19 | 42335927 | 42335940 | + chr19 | 42364892 | 42364915 | + ENST00000598742; ENST00000601492; ENST00000600467; ENST00000593863; ENST00000598261; ENST00000598399 | TAF |
| 11% chr19 | 42335927 | 42335940 | + chr19 | 42364892 | 42364915 | + ENST00000598742; ENST00000601492; ENST00000600467; ENST00000593863; ENST00000598261; ENST00000598399 | TAF |
| 11% chr19 | 42335927 | 42335940 | + chr19 | 42364892 | 42364915 | + ENST00000598742; ENST00000601492; ENST00000600467; ENST00000593863; ENST00000598261; ENST00000598399 | TAF |
| 11% chr19 | 42335927 | 42335940 | + chr19 | 42364892 | 42364915 | + ENST00000598742; ENST00000601492; ENST00000600467; ENST00000593863; ENST00000598261; ENST00000598399 | TAF |
| 11% chrX | 71397824 | 71398498 | + chrX | 71406311 | 71406384 | + ENST00000218432; ENST00000423432; ENST00000373669; ENST00000496835; ENST00000439980; ENST00000446576 | TAF |
| 11% chrX | 71397824 | 71398498 | + chrX | 71406311 | 71406384 | + ENST00000218432; ENST00000423432; ENST00000373669; ENST00000496835; ENST00000439980; ENST00000446576 | TAF |
| 11% chrX | 71397824 | 71398498 | + chrX | 71406311 | 71406384 | + ENST00000218432; ENST00000423432; ENST00000373669; ENST00000496835; ENST00000439980; ENST00000446576 | TAF |
| 11% chrX | 71397824 | 71398498 | + chrX | 71406311 | 71406384 | + ENST00000218432; ENST00000423432; ENST00000373669; ENST00000496835; ENST00000439980; ENST00000446576 | TAF |
| 11% chr19 | 39958795 | 39959001 | + chr19 | 39959396 | 39959501 | + ENST00000599117; ENST00000402194; ENST00000432763; ENST00000359191; ENST00000598725 | TAF |
| 11% chr2 | 133363747 | 133363763 | + chr2 | 133402674 | 133403179 | + ENST00000329321 | |
| 11% chr19 | 39110121 | 39110170 | + chr19 | 39110977 | 39111075 | + ENST00000248342; ENST00000588934; ENST00000545173; ENST00000586513; ENST00000592558 | TAF |
| 11% chr19 | 39110121 | 39110170 | + chr19 | 39110977 | 39111075 | + ENST00000248342; ENST00000588934; ENST00000545173; ENST00000586513; ENST00000592558 | TAF |
| 11% chr19 | 39110121 | 39110170 | + chr19 | 39110977 | 39111075 | + ENST00000248342; ENST00000588934; ENST00000545173; ENST00000586513; ENST00000592558 | TAF |
| 11% chr19 | 39110121 | 39110170 | + chr19 | 39110977 | 39111075 | + ENST00000248342; ENST00000588934; ENST00000545173; ENST00000586513; ENST00000592558 | TAF |
| 11% chr19 | 39110121 | 39110170 | + chr19 | 39110977 | 39111075 | + ENST00000248342; ENST00000588934; ENST00000545173; ENST00000586513; ENST00000592558 | TAF |
| 11% chr7 | 2289080 | 2289194 | + chr7 | 2289492 | 2289637 | + ENST00000356714; ENST00000397049; ENST00000397046; ENST00000397048; ENST00000339737; ENST00000343985 | TAF |
| 11% chr13 | 76173531 | 76175706 | + chr13 | 76178905 | 76178963 | + ENST00000377595; ENST00000419068 | TAF |

TABLE 68-continued

Transcript fusion for Uterine Carcinosarcoma (UCS) Coordinates of the fusion sequences for which the donor is the TE.

| 1+B2:L152 | 2' | 3' | 4' | 5' | 6' | 7' | 8' | 9 | 10' | 11' |
|---|---|---|---|---|---|---|---|---|---|---|
| 11% | chr2 | 10945150 | 10944882 | – | chr2 | 10942766 | 10942625 | – | ENST00000272227; ENST00000404371; ENST00000404824; ENST00000540494; ENST00000381611 | TAF |
| 11% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr1 | 6380703 | 6380649 | – | chr1 | 6378638 | 6378552 | – | ENST00000608083; ENST00000377842; ENST00000377845; ENST00000377855; ENST00000377860; ENST00000418124; ENST00000545482; ENST00000361521; ENST00000473466; ENST00000541130 | TAF |
| 11% | chr20 | 43919547 | 43919514 | – | chr20 | 43882374 | 43882216 | – | ENST00000338380 | |
| 11% | chr5 | 823586 | 823504 | – | chr5 | 822010 | 821976 | – | ENST00000424784; ENST00000283441 | TAF |
| 11% | chr8 | 48617118 | 48617136 | + | chr8 | 48625224 | 48625434 | + | ENST00000297423; ENST00000518074; ENST00000541342; ENST00000519401; ENST00000517693 | TSF |
| 11% | chr8 | 48617118 | 48617136 | + | chr8 | 48625224 | 48625434 | + | ENST00000297423; ENST00000518074; ENST00000541342; ENST00000519401; ENST00000517693 | TSF |
| 11% | chr8 | 48617118 | 48617136 | + | chr8 | 48625224 | 48625434 | + | ENST00000297423; ENST00000518074; ENST00000541342; ENST00000519401; ENST00000517693 | TSF |
| 11% | chr6 | 41610978 | 41611118 | + | chr6 | 41613864 | 41614046 | + | ENST00000432027; ENST00000419164; ENST00000373051; ENST00000441667; ENST00000230321; ENST00000446650 | TSF |
| 11% | chr6 | 41610978 | 41611118 | + | chr6 | 41613864 | 41614046 | + | ENST00000432027; ENST00000419164; ENST00000373051; ENST00000441667; ENST00000230321; ENST00000446650 | TSF |
| 11% | chr6 | 41610978 | 41611118 | + | chr6 | 41613864 | 41614046 | + | ENST00000432027; ENST00000419164; ENST00000373051; ENST00000441667; ENST00000230321; ENST00000446650 | TSF |
| 11% | chr6 | 41610978 | 41611118 | + | chr6 | 41613864 | 41614046 | + | ENST00000432027; ENST00000419164; ENST00000373051; ENST00000441667; ENST00000230321; ENST00000446650 | TSF |
| 11% | chr6 | 41610978 | 41611118 | + | chr6 | 41613864 | 41614046 | + | ENST00000432027; ENST00000419164; ENST00000373051; ENST00000441667; ENST00000230321; ENST00000446650 | TSF |
| 11% | chr7 | 56018506 | 56018522 | + | chr7 | 56020872 | 56021011 | + | ENST00000426595 | TSF |

TABLE 69

Transcript fusion for Uveal Melanoma (UVM) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 99% | chr12 | 110511233 | 110511227 | – | ENST00000548191 | chr12 | 110496968 | 110496909 | – | TAF |
| 98% | chr12 | 110495101 | 110494994 | – | ENST00000309050 | chr12 | 110493610 | 110493335 | – | TAF |
| 95% | chr11 | 88960991 | 88961138 | + | ENST00000263321 | chr11 | 88974422 | 88974649 | + | TAF |
| 81% | chr8 | 54793576 | 54793644 | + | ENST00000276500 | chr8 | 54826057 | 54826421 | + | TAF |
| 60% | chr19 | 3544937 | 3544807 | – | ENST00000389395; ENST00000398558; ENST00000588918; ENST00000355415; ENST00000589063 | chr19 | 3538708 | 3538306 | – | TAF |
| 60% | chr19 | 3544937 | 3544807 | – | ENST00000389395; ENST00000398558; ENST00000588918; ENST00000355415; ENST00000589063 | chr19 | 3538708 | 3538306 | – | TAF |
| 60% | chr19 | 3544937 | 3544807 | – | ENST00000389395; ENST00000398558; ENST00000588918; ENST00000355415; ENST00000589063 | chr19 | 3538708 | 3538306 | – | TAF |
| 57% | chr8 | 54791818 | 54792162 | + | ENST00000297313 | chr8 | 54826057 | 54826421 | + | TSF |
| 57% | chr15 | 28090198 | 28090105 | – | ENST00000353809; ENST00000354638 | chr15 | 27964474 | 27964338 | – | TSF |
| 57% | chr15 | 28090198 | 28090105 | – | ENST00000353809; ENST00000354638 | chr15 | 27964474 | 27964338 | – | TSF |
| 52% | chr14 | 51355542 | 51355621 | + | ENST00000337334; ENST00000353130; ENST00000395752 | chr14 | 51359931 | 51360328 | + | TAF |
| 52% | chr14 | 51355542 | 51355621 | + | ENST00000337334; ENST00000353130; ENST00000395752 | chr14 | 51359931 | 51360328 | + | TAF |
| 52% | chr14 | 51355542 | 51355621 | + | ENST00000337334; ENST00000353130; ENST00000395752 | chr14 | 51359931 | 51360328 | + | TAF |
| 32% | chr17 | 1028702; 1028625 | 1028518 | – | ENST00000302538; ENST00000544583; ENST00000574437; ENST00000575934; ENST00000574139; ENST00000570525; ENST00000574266 | chr17 | 1005267 | 1004964 | – | TSF |
| 32% | chr17 | 1028702; 1028625 | 1028518 | – | ENST00000302538; ENST00000544583; ENST00000574437; ENST00000575934; ENST00000574139; ENST00000570525; ENST00000574266 | chr17 | 1005267 | 1004964 | – | TSF |
| 31% | chr12 | 110511233 | 110511227 | – | ENST00000548191 | chr12 | 110496919 | 110496909 | – | TSF |

TABLE 69-continued

Transcript fusion for Uveal Melanoma (UVM) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 26% | chr11 | 117186511 | 117186251 | − | ENST00000313005; ENST00000528053; ENST00000428381; ENST00000445823; ENST00000513780 | chr11 | 117167925 | 117167869 | − | TSF |
| 25% | chr19 | 39077165 | 39077216 | + | ENST00000355481; ENST00000360985; ENST00000359596 | chr19 | 39085644 | 39085967 | + | TAF |
| 25% | chr19 | 39077165 | 39077216 | + | ENST00000355481; ENST00000360985; ENST00000359596 | chr19 | 39085644 | 39085967 | + | TAF |
| 25% | chr19 | 39077165 | 39077216 | + | ENST00000355481; ENST00000360985; ENST00000359596 | chr19 | 39085644 | 39085967 | + | TAF |
| 24% | chr20 | 53092486 | 53092551 | + | ENST00000262593 | chr20 | 53111339 | 53111426 | + | TAF |
| 22% | chr12 | 110495101 | 110494994 | − | ENST00000309050 | chr12 | 110493672 | 110493335 | − | TSF |
| 20% | chr8 | 74939024 | 74939076 | + | ENST00000284818; ENST00000518893 | chr8 | 74944554 | 74944936 | + | TAF |
| 20% | chr8 | 74939024 | 74939076 | + | ENST00000284818; ENST00000518893 | chr8 | 74944554 | 74944936 | + | TAF |
| 18% | chrX | 64743587; 64743497 | 64743440 | − | ENST00000374807; ENST00000374811; ENST00000374804; ENST00000469091 | chrX | 64742373 | 64741630 | − | TAF |
| 18% | chrX | 64743587; 64743497 | 64743440 | − | ENST00000374807; ENST00000374811; ENST00000374804; ENST00000469091 | chrX | 64742373 | 64741630 | − | TAF |
| 18% | chrX | 64743587; 64743497 | 64743440 | − | ENST00000374807; ENST00000374811; ENST00000374804; ENST00000469091 | chrX | 64742373 | 64741630 | − | TAF |
| 18% | chrX | 64743587; 64743497 | 64743440 | − | ENST00000374807; ENST00000374811; ENST00000374804; ENST00000469091 | chrX | 64742373 | 64741630 | − | TAF |
| 16% | chr19 | 34986608 | 34986676 | + | ENST00000270288; ENST00000590071; ENST00000585928 | chr19 | 34986786 | 34987070 | + | TAF |
| 16% | chr19 | 34986608 | 34986676 | + | ENST00000270288; ENST00000590071; ENST00000585928 | chr19 | 34986786 | 34987070 | + | TAF |
| 16% | chr19 | 34986608 | 34986676 | + | ENST00000270288; ENST00000590071; ENST00000585928 | chr19 | 34986786 | 34987070 | + | TAF |
| 16% | chr15 | 58957396 | 58957296 | − | ENST00000260408 | chr15 | 58947615 | 58947395 | − | TAF |
| 15% | chr5 | 43382154 | 43382066 | − | ENST00000489442; ENST00000361115; ENST00000513525 | chr5 | 43376990 | 43376680 | − | TAF |
| 15% | chr5 | 43382154 | 43382066 | − | ENST00000489442; ENST00000361115; ENST00000513525 | chr5 | 43376990 | 43376680 | − | TAF |
| 15% | chr1 | 74563634 | 74563535 | − | ENST00000225276; ENST00000588920 | chr17 | 74560019 | 74559800 | − | TSF |
| 15% | chr17 | 74563634 | 74563535 | − | ENST00000225276; ENST00000588920 | chr17 | 74560019 | 74559800 | − | TSF |
| 14% | chr1 | 212606286 | 212606462 | + | ENST00000366988 | chr1 | 212608047 | 212608089 | + | TAF |
| 14% | chr10 | 84718705 | 84718831 | + | ENST00000372141; ENST00000404547; ENST00000372142; ENST00000404576; ENST00000556918; ENST00000537893; ENST00000545131 | chr10 | 84720295 | 84720298 | + | TSF |
| 14% | chr10 | 84718705 | 84718831 | + | ENST00000372141; ENST00000404547; ENST00000372142; ENST00000404576; ENST00000556918; ENST00000537893; ENST00000545131 | chr10 | 84720295 | 84720298 | + | TSF |
| 14% | chr10 | 84718705 | 84718831 | + | ENST00000372141; ENST00000404547; ENST00000372142; ENST00000404576; ENST00000556918; ENST00000537893; ENST00000545131 | chr10 | 84720295 | 84720298 | + | TSF |
| 14% | chr10 | 84718705 | 84718831 | + | ENST00000372141; ENST00000404547; ENST00000372142; ENST00000404576; ENST00000556918; ENST00000537893; ENST00000545131 | chr10 | 84720295 | 84720298 | + | TSF |
| 14% | chr10 | 84718705 | 84718831 | + | ENST00000372141; ENST00000404547; ENST00000372142; ENST00000404576; ENST00000556918; ENST00000537893; ENST00000545131 | chr10 | 84720295 | 84720298 | + | TSF |
| 14% | chr11 | 6624732 | 6624634 | − | ENST00000254605; ENST00000534343; ENST00000533907; ENST00000530762 | chr11 | 6614053 | 6614046 | − | TSF |
| 12% | chr1 | 245246924 | 245246990 | + | ENST00000366523; ENST00000366522; ENST00000447569; ENST00000366521; ENST00000551317; ENST00000425550; ENST00000427529 | chr1 | 245288007 | 245288330 | + | TAF |
| 12% | chr1 | 245246924 | 245246990 | + | ENST00000366523; ENST00000366522; ENST00000447569; ENST00000366521; ENST00000551317; ENST00000425550; ENST00000427529 | chr1 | 245288007 | 245288330 | + | TAF |
| 12% | chr1 | 245246924 | 245246990 | + | ENST00000366523; ENST00000366522; ENST00000447569; ENST00000366521; ENST00000551317; ENST00000425550; ENST00000427529 | chr1 | 245288007 | 245288330 | + | TAF |
| 12% | chr1 | 245246924 | 245246990 | + | ENST00000366523; ENST00000366522; ENST00000447569; ENST00000366521; ENST00000551317; ENST00000425550; ENST00000427529 | chr1 | 245288007 | 245288330 | + | TAF |
| 12% | chr1 | 245246924 | 245246990 | + | ENST00000366523; ENST00000366522; ENST00000447569; ENST00000366521; ENST00000551317; ENST00000425550; ENST00000427529 | chr1 | 245288007 | 245288330 | + | TAF |
| 12% | chr10 | 120905865 | 120905748 | − | ENST00000355697; ENST00000330036 | chr10 | 120901885 | 120901741 | − | TAF |
| 12% | chr10 | 120905865 | 120905748 | − | ENST00000355697; ENST00000330036 | chr10 | 120901885 | 120901741 | − | TAF |
| 12% | chr17 | 7130588 | 7130409 | − | ENST00000005340; ENST00000575458; ENST00000575086 | chr17 | 7130277 | 7130132 | − | TAF |
| 12% | chr17 | 7130588 | 7130409 | − | ENST00000005340; ENST00000575458; ENST00000575086 | chr17 | 7130277 | 7130132 | − | TAF |
| 12% | chr17 | 7130588 | 7130409 | − | ENST00000005340; ENST00000575458; ENST00000575086 | chr17 | 7130277 | 7130132 | − | TAF |
| 11% | chr1 | 25891664 | 25891698 | + | ENST00000374338 | chr1 | 25916660 | 25916675 | + | TSF |
| 10% | chr8 | 109468102 | 109468159 | + | ENST00000220853; ENST00000519642 | chr8 | 109468381 | 109468590 | + | TSF |
| 10% | chr8 | 109468102 | 109468159 | + | ENST00000220853; ENST00000519642 | chr8 | 109468381 | 109468590 | + | TSF |
| 10% | chr9 | 130213596 | 130213560 | − | ENST00000361436; ENST00000536368 | chr9 | 130213398 | 130213359 | − | TSF |
| 9% | chr2 | 33783739 | 33784097 | + | ENST00000402538; ENST00000403687; ENST00000407811 | chr2 | 33793051 | 33793065 | + | TSF |
| 9% | chr2 | 33783739 | 33784097 | + | ENST00000402538; ENST00000403687; ENST00000407811 | chr2 | 33793051 | 33793065 | + | TSF |
| 9% | chr15 | 69347674 | 59347840 | + | ENST00000448182; ENST00000260364; ENST00000455873; ENST00000388866; ENST00000530406 | chr15 | 69354923 | 69354995 | + | TSF |
| 9% | chr15 | 69347674 | 59347840 | + | ENST00000448182; ENST00000260364; ENST00000455873; ENST00000388866; ENST00000530406 | chr15 | 69354923 | 69354995 | + | TSF |
| 9% | chr15 | 69347674 | 59347840 | + | ENST00000448182; ENST00000260364; ENST00000455873; ENST00000388866; ENST00000530406 | chr15 | 69354923 | 69354995 | + | TSF |
| 9% | chr15 | 69347674 | 59347840 | + | ENST00000448182; ENST00000260364; ENST00000455873; ENST00000388866; ENST00000530406 | chr15 | 69354923 | 69354995 | + | TSF |

TABLE 69-continued

Transcript fusion for Uveal Melanoma (UVM) Coordinates of the fusion sequences for which the donor is the exon.

| 1 | 2 | 3 | 4 | 5 | 6 | 7 | 8 | 9 | 10 | 11 |
|---|---|---|---|---|---|---|---|---|---|---|
| 9% | chr15 | 69347674 | 59347840 | + | ENST00000388866; ENST00000530406 ENST00000448182; ENST00000260364; ENST00000455873; ENST00000388866; ENST00000530406 | chr15 | 69354923 | 69354995 | + | TSF |
| 8% | chr4 | 91321187 | 91321280 | + | ENST00000505073; ENST00000509176; ENST00000432775; ENST00000333691 | chr4 | 91325075 | 91325176 | + | TSF |
| 8% | chr11 | 88960991 | 88961082 | + | ENST00000263321 | chr11 | 88974422 | 88974649 | + | TSF |
| 8% | chr13 | 48651447 | 48651289 | − | ENST00000258648; ENST00000378586 | chr13 | 48616414 | 48616057 | − | TSF |
| 8% | chr13 | 48651447 | 48651289 | − | ENST00000258648; ENST00000378586 | chr13 | 48616414 | 48616057 |  | TSF |

TABLE 70

Transcript fusion for Uveal Melanoma (UVM) Coordinates of the fusion sequences for which the donor is the TE.

| 1 | 2' | 3' | 4' | 5' | 6' | 7 | 8' | 9 | 10' | 11' |
|---|---|---|---|---|---|---|---|---|---|---|
| 99% | chr16 | 1521687 | 1521625 | − | chr16 | 1515339 | 1515268 | − | ENST00000382745; ENST00000564568 | TAF |
| 99% | chr16 | 1521687 | 1521625 | − | chr16 | 1515339 | 1515268 | − | ENST00000382745; ENST00000564568 | TAF |
| 98% | chr15 | 93221696 | 93221360 | − | chr15 | 93173575 | 93173444 | − | ENST00000327355 | TAF |
| 92% | chr17 | 30850448 | 30850415 | − | chr17 | 30821933 | 30821777 | − | ENST00000318217; ENST0000394649 | TAF |
| 86% | chr11 | 87906665 | 87906580 | − | chr11 | 87883123 | 87882843 | − | ENST00000243662; ENST00000526372 | TAF |
| 75% | chr11 | 126273341 | 126273381 | + | chr11 | 126275991 | 126276045 | + | ENST00000534733 | TAF |
| 64% | chr8 | 145134058 | 145134309 | + | chr8 | 145134846 | 145135052; 145134924 | + | ENST00000316052; ENST00000525936; ENST00000527954 | TAF |
| 64% | chr8 | 145134058 | 145134309 | + | chr8 | 145134846 | 145135052; 145134924 | + | ENST00000316052; ENST00000525936; ENST00000527954 | TAF |
| 64% | chr8 | 145134058 | 145134309 | + | chr8 | 145134846 | 145135052; 145134924 | + | ENST00000316052; ENST00000525936; ENST00000527954 | TAF |
| 64% | chr9 | 5907671 | 5907721 | + | chr9 | 5908640 | 5908708 | + | ENST00000381477; ENST00000381476; ENST00000381471 | TSF |
| 62% | chrX | 71529592 | 71529379 | − | chrX | 71522784 | 71522660 | − | ENST00000453707; ENST00000431381; ENST00000427412; ENST00000450875; ENST00000454225 | TSF |
| 62% | chrX | 71529592 | 71529379 | − | chrX | 71522784 | 71522660 | − | ENST00000453707; ENST00000431381; ENST00000427412; ENST00000450875; ENST00000454225 | TSF |
| 62% | chrX | 71529592 | 71529379 | − | chrX | 71522784 | 71522660 | − | ENST00000453707; ENST00000431381; ENST00000427412; ENST00000450875; ENST00000454225 | TSF |
| 62% | chrX | 71529592 | 71529379 | − | chrX | 71522784 | 71522660 | − | ENST00000453707; ENST00000431381; ENST00000427412; ENST00000450875; ENST00000454225 | TSF |
| 62% | chr21 | 33707090 | 33707025 | − | chr21 | 33706643 | 33706472 | − | ENST00000382751 | TSF |
| 59% | chr3 | 98482258 | 98482283 | + | chr3 | 98487274 | 98487373 | + | ENST00000492254 | TAF |
| 59% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 59% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 59% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 59% | chr17 | 80440912 | 80441180 | + | chr17 | 80441592 | 80441655; 80441659 | + | ENST00000390006; ENST00000309794; ENST00000345415; ENST00000457415; ENST00000412079; ENST00000577432; ENST00000584513 | TAF |
| 57% | chr1 | 54879137 | 54879029 | − | chr1 | 54870603 | 54870531 | − | ENST00000371320; ENST00000371319; ENST00000357475 | TAF |
| 57% | chr1 | 54879137 | 54879029 | − | chr1 | 54870603 | 54870531 | − | ENST00000371320; ENST00000371319; ENST00000357475 | TAF |
| 57% | chr1 | 54879137 | 54879029 | − | chr1 | 54870603 | 54870531 | − | ENST00000371320; ENST00000371319; ENST00000357475 | TAF |
| 46% | chr1 | 594935212 | 212595005 | + | chr1 | 212615911 | 212615967 | + | ENST00000366988 | TAF |
| 46% | chr15 | 28127352 | 28127177 | − | chr15 | 281170 68 | 28117009 | − | ENST00000353809; ENST00000354638 | TAF |
| 45% | chr8 | 638103144 | 144638200 | + | chr8 | 144640548 | 144640621 | + | ENST00000533063 | TAF |
| 44% | chr17 | 74583012 | 74582951 | − | chr17 | 74574898 | 74574838; 74574881 | − | ENST00000225276; ENST00000585736 | TAF |
| 44% | chr17 | 74583012 | 74582951 | − | chr17 | 74574898 | 74574838; 74574881 |  | ENST00000225276; ENST00000585736 | TAF |
| 42% | chr1 | 45139523 | 45139439 | − | chr1 | 45125967 | 45125846 | − | ENST00000372242; ENST00000372243; ENST00000372237; ENST00000372235; ENST00000420706 | TAF |
| 42% | chr1 | 45139523 | 45139439 | − | chr1 | 45125967 | 45125846 | − | ENST00000372242; ENST00000372243; ENST00000372237; ENST00000372235; ENST00000420706 | TAF |
| 42% | chr1 | 45139523 | 45139439 | − | chr1 | 45125967 | 45125846 | − | ENST00000372242; ENST00000372243; ENST00000372237; ENST00000372235; ENST00000420706 | TAF |
| 42% | chr1 | 45139523 | 45139439 | − | chr1 | 45125967 | 45125846 | − | ENST00000372242; ENST00000372243; ENST00000372237; ENST00000372235; ENST00000420706 | TAF |
| 39% | chr12 | 56363784 | 56363834 | + | chr12 | 56364828 | 56365031 | + | ENST00000266970; ENST00000553376; ENST00000440311; ENST00000354056 | TAF |
| 38% | chr11 | 1620310 | 1620075 | − | chr11 | 1619101 | 1618947 | − | ENST00000412090 | TAF |

TABLE 70-continued

Transcript fusion for Uveal Melanoma (UVM) Coordinates of the fusion sequences for which the donor is the TE.

| 1 | 2' | 3' | 4' | 5' | 6' | 7 | 8' | 9 | 10' | 11' |
|---|---|---|---|---|---|---|---|---|---|---|
| 36% | chr17 | 426168 | 426165 | − | chr17 | 424978 | 424841 | − | ENST00000437048 | TAF |
| 36% | chr10 | 99667221 | 99666955 | − | chr10 | 99664571 | 99664426 | − | ENST00000413387; ENST00000370597; ENST00000298819; ENST00000309155; ENST00000370591 | TAF |
| 36% | chr10 | 99667221 | 99666955 | − | chr10 | 99664571 | 99664426 | − | ENST00000413387; ENST00000370597; ENST00000298819; ENST00000309155; ENST00000370591 | TAF |
| 36% | chr10 | 99667221 | 99666955 | − | chr10 | 996645 71 | 99664426 | − | ENST00000413387; ENST00000370597; ENST00000298819; ENST00000309155; ENST00000370591 | TAF |
| 35% | chr1 | 240569724 | 240569786 | + | chr1 | 240601361 | 240601510 | + | ENST00000319653; ENST00000545751 | TAF |
| 35% | chr17 | 80418062 | 80418199 | + | chr17 | 80422163 | 80422306 | + | ENST00000309794; ENST00000581202; ENST00000374611; ENST00000457415; ENST00000581795; ENST00000577432; ENST00000582907 | TAF |
| 35% | chr17 | 80418062 | 80418199 | + | chr17 | 80422163 | 80422306 | + | ENST00000309794; ENST00000581202; ENST00000374611; ENST00000457415; ENST00000581795; ENST00000577432; ENST00000582907 | TAF |
| 35% | chr17 | 80418062 | 80418199 | + | chr17 | 80422163 | 80422306 | + | ENST00000309794; ENST00000581202; ENST00000374611; ENST00000457415; ENST00000581795; ENST00000577432; ENST00000582907 | TAF |
| 35% | chr17 | 80418062 | 80418199 | + | chr17 | 80422163 | 80422306 | + | ENST00000309794; ENST00000581202; ENST00000374611; ENST00000457415; ENST00000581795; ENST00000577432; ENST00000582907 | TAF |
| 35% | chr17 | 80418062 | 80418199 | + | chr17 | 80422163 | 80422306 | + | ENST00000309794; ENST00000581202; ENST00000374611; ENST00000457415; ENST00000581795; ENST00000577432; ENST00000582907 | TAF |
| 35% | chr17 | 80418062 | 80418199 | + | chr17 | 80422163 | 80422306 | + | ENST00000309794; ENST00000581202; ENST00000374611; ENST00000457415; ENST00000581795; ENST00000577432; ENST00000582907 | TAF |
| 35% | chr17 | 80418062 | 80418199 | + | chr17 | 80422163 | 80422306 | + | ENST00000309794; ENST00000581202; ENST00000374611; ENST00000457415; ENST00000581795; ENST00000577432; ENST00000582907 | TAF |
| 34% | chr1 | 236326774 | 236327054 | + | chr1 | 236332006 | 236332055 | + | ENST00000366592; ENST00000454895 | TSF |
| 34% | chr1 | 236326774 | 236327054 | + | chr1 | 236332006 | 236332055 | + | ENST00000366592; ENST00000454895 | TSF |
| 34% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 34% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 34% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 34% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 34% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 34% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 34% | chr22 | 22899971 | 22899965 | − | chr22 | 22893511 | 22893189; 22893185; 22893481; 22893274 | − | ENST00000398743; ENST00000398741; ENST00000543184; ENST00000405655; ENST00000402697; ENST00000439106; ENST00000438888; ENST00000420709; ENST00000406503; ENST00000442481; ENST00000403441 | TSF |
| 31% | chr16 | 19886067 | 19886054 | − | chr16 | 19884168 | 19883138 | − | ENST00000537135 | TAF |
| 30% | chr8 | 109321615 | 109321565 | − | chr8 | 109254142 | 109254028 | − | ENST00000220849; ENST00000522445; ENST00000521440; ENST00000521297 | TAF |
| 30% | chr8 | 109321615 | 109321565 | − | chr8 | 109254142 | 109254028 | − | ENST00000220849; ENST00000522445; ENST00000521440; ENST00000521297 | TAF |
| 30% | chr8 | 109321615 | 109321565 | − | chr8 | 109254142 | 109254028 | − | ENST00000220849; ENST00000522445; ENST00000521440; ENST00000521297 | TAF |
| 30% | chr8 | 109321615 | 109321565 | − | chr8 | 109254142 | 109254028 | − | ENST00000220849; ENST00000522445; ENST00000521440; ENST00000521297 | TAF |
| 30% | chr1 | 212596286 | 212598077 | + | chr1 | 212617681 | 212617784 | + | ENST00000366988 | TSF |
| 30% | chr12 | 56353740 | 56353706 | − | chr12 | 56352391 | 56352257; 56352273; 56352331 | − | ENST00000449260; ENST00000552882; ENST00000550464; ENST00000548747; ENST00000539511; ENST00000548493; ENST00000550447; ENST00000548803; ENST00000547137; ENST00000546543; ENST00000549418; ENST00000549233 | TSF |
| 30% | chr12 | 56353740 | 56353706 | − | chr12 | 56352391 | 56352257; 56352273; 56352331 | − | ENST00000449260; ENST00000552882; ENST00000550464; ENST00000548747; ENST00000539511; ENST00000548493; ENST00000550447; ENST00000548803; ENST00000547137; | TSF |

TABLE 70-continued

Transcript fusion for Uveal Melanoma (UVM) Coordinates of the fusion sequences for which the donor is the TE.

| 1 | 2' | 3' | 4' | 5' 6' | 7 | 8' | 9 | 10' | 11' |
|---|---|---|---|---|---|---|---|---|---|
| 30% | chr12 | 56353740 | 56353706 | − chr12 | 56352391 | 56352257; 56352273; 56352331 | − | ENST00000546543; ENST00000549418; ENST00000549233 ENST00000449260; ENST00000552882; ENST00000550464; ENST00000548747; ENST00000539511; ENST00000548493; ENST00000550447; ENST00000548803; ENST00000547137; | TSF |
| 30% | chr12 | 56353740 | 56353706 | − chr12 | 56352391 | 56352257; 56352273; 56352331 | − | ENST00000546543; ENST00000549418; ENST00000549233 ENST00000449260; ENST00000552882; ENST00000550464; ENST00000548747; ENST00000539511; ENST00000548493; ENST00000550447; ENST00000548803; ENST00000547137; | TSF |
| 30% | chr12 | 56353740 | 56353706 | − chr12 | 56352391 | 56352257; 56352273; 56352331 | − | ENST00000546543; ENST00000549418; ENST00000549233 ENST00000449260; ENST00000552882; ENST00000550464; ENST00000548747; ENST00000539511; ENST00000548493; ENST00000550447; ENST00000548803; ENST00000547137; | TSF |
| 30% | chr12 | 56353740 | 56353706 | − chr12 | 56352391 | 56352257; 56352273; 56352331 | − | ENST00000546543; ENST00000549418; ENST00000549233 ENST00000449260; ENST00000552882; ENST00000550464; ENST00000548747; ENST00000539511; ENST00000548493; ENST00000550447; ENST00000548803; ENST00000547137; | TSF |
| 30% | chr12 | 56353740 | 56353706 | − chr12 | 56352391 | 56352257; 56352273; 56352331 | − | ENST00000546543; ENST00000549418; ENST00000549233 ENST00000449260; ENST00000552882; ENST00000550464; ENST00000548747; ENST00000539511; ENST00000548493; ENST00000550447; ENST00000548803; ENST00000547137; | TSF |
| 30% | chr12 | 56353740 | 56353706 | − chr12 | 56352391 | 56352257; 56352273; 56352331 | − | ENST00000546543; ENST00000549418; ENST00000549233 ENST00000449260; ENST00000552882; ENST00000550464; ENST00000548747; ENST00000539511; ENST00000548493; ENST00000550447; ENST00000548803; ENST00000547137; ENST00000546543; ENST00000549418; ENST00000549233 | TSF |
| 29% | chr7 | 20686966 | 20686997 | + chr7 | 20687158 | 20687271 | + | ENST00000404938 | TSF |
| 28% | chr13 | 60978922 | 60979204 | + chr13 | 61013822 | 61013906 | + | ENST00000535286 | TAF |
| 28% | chr15 | 41968651 | 41968463 | − chr15 | 41815513 | 41815443 | − | ENST00000561603; ENST00000304330; ENST00000562303 | TAF |
| 28% | chr15 | 41968651 | 41968463 | − chr15 | 41815513 | 41815443 | − | ENST00000561603; ENST00000304330; ENST00000562303 | TAF |
| 28% | chr15 | 41968651 | 41968463 | − chr15 | 41815513 | 41815443 | − | ENST00000561603; ENST00000304330; ENST00000562303 | TAF |
| 26% | chr19 | 42335927 | 42335940 | + chr19 | 42364892 | 42364915 | + | ENST00000598742; ENST00000601492; ENST00000600467; ENST00000593863; ENST00000598261; ENST00000598399 | TAF |
| 26% | chr19 | 42335927 | 42335940 | + chr19 | 42364892 | 42364915 | + | ENST00000598742; ENST00000601492; ENST00000600467; ENST00000593863; ENST00000598261; ENST00000598399 | TAF |
| 26% | chr19 | 42335927 | 42335940 | + chr19 | 42364892 | 42364915 | + | ENST00000598742; ENST00000601492; ENST00000600467; ENST00000593863; ENST00000598261; ENST00000598399 | TAF |
| 26% | chr19 | 42335927 | 42335940 | + chr19 | 42364892 | 42364915 | + | ENST00000598742; ENST00000601492; ENST00000600467; ENST00000593863; ENST00000598261; ENST00000598399 | TAF |
| 26% | chr19 | 42335927 | 42335940 | + chr19 | 42364892 | 42364915 | + | ENST00000598742; ENST00000601492; ENST00000600467; ENST00000593863; ENST00000598261; ENST00000598399 | TAF |
| 26% | chr13 | 78549747 | 78549482 | − chr13 | 78492759 | 78492226 | − | ENST00000377211 | TAF |
| 26% | chr4 | 89198618 | 89198541 | − chr4 | 89198395 | 89198295; 89198287 | − | ENST00000608933; ENST00000295908; ENST00000315194; ENST00000514204 | TSF |
| 26% | chr4 | 89198618 | 89198541 | − chr4 | 89198395 | 89198295; 89198287 | − | ENST00000608933; ENST00000295908; ENST00000315194; ENST00000514204 | TSF |
| 26% | chr4 | 89198618 | 89198541 | − chr4 | 89198395 | 89198295; 89198287 | − | ENST00000608933; ENST00000295908; ENST00000315194; ENST00000514204 | TSF |
| 26% | chr4 | 89198618 | 89198541 | − chr4 | 89198395 | 89198295; 89198287 | − | ENST00000608933; ENST00000295908; ENST00000315194; ENST00000514204 | TSF |
| 25% | chr21 | 44307009 | 44307069 | + chr21 | 44317037 | 44317157 | + | ENST00000354250; ENST00000340344 | TAF |
| 25% | chr21 | 44307009 | 44307069 | + chr21 | 44317037 | 44317157 | + | ENST00000354250; ENST00000340344 | TAF |
| 25% | chr15 | 28123956 | 28123431 | − chr15 | 28117068 | 28117009 | − | ENST00000353809; ENST00000354638 | TSF |
| 24% | chr7 | 2289080 | 2289115 | + chr7 | 2289492 | 2289637 | + | ENST00000356714; ENST00000397049; ENST00000397046; ENST00000397048;ENST00000339737; ENST00000343985 | TAF |
| 24% | chr17 | 80812047 | 80812141 | + chr17 | 80828100 | 80828256 | + | ENST00000355528; ENST00000397466; ENST00000539345 | TSF |
| 24% | chr17 | 80812047 | 80812141 | + chr17 | 80828100 | 80828256 | + | ENST00000355528; ENST00000397466; ENST00000539345 | TSF |
| 24% | chr17 | 80812047 | 80812141 | + chr17 | 80828100 | 80828256 | + | ENST00000355528; ENST00000397466; ENST00000539345 | TSF |
| 24% | chr9 | 131400020 | 131399953 | − chr9 | 131399306 | 131399197 | − | ENST00000372715; ENST00000451652 | TSF |
| 24% | chr9 | 131400020 | 131399953 | − chr9 | 131399306 | 131399197 | − | ENST00000372715; ENST00000451652 | TSF |
| 22% | chr1 | 1496761 | 1496712 | − chr1 | 1480382 | 1480243 | − | ENST00000291386 | TSF |
| 21% | chr14 | 102691697 | 102691432 | − chr14 | 102691131 | 102691116 | − | ENST00000559838 | TAF |
| 20% | chr9 | 74533392 | 74533471 | + chr9 | 74561922 | 74562028 | + | ENST00000334731; ENST00000377031; ENST00000486911 | TAF |
| 20% | chr9 | 74533392 | 74533471 | + chr9 | 74561922 | 74562028 | + | ENST00000334731; ENST00000377031; ENST00000486911 | TAF |
| 20% | chr9 | 74533392 | 74533471 | + chr9 | 74561922 | 74562028 | + | ENST00000334731; ENST00000377031; ENST00000486911 | TAF |
| 20% | chr19 | 41816850 | 41816920 | + chr19 | 41822289 | 41822744 | + | ENST00000269967 | TAF |
| 20% | chr10 | 111986999 | 111987095 | + chr10 | 111987947 | 111988079 | + | ENST00000332674; ENST00000453116; ENST00000239007; ENST00000393134 | TAF |
| 20% | chr10 | 111986999 | 111987095 | + chr10 | 111987947 | 111988079 | + | ENST00000332674; ENST00000453116; ENST00000239007; ENST00000393134 | TAF |
| 20% | chr10 | 111986999 | 111987095 | + chr10 | 111987947 | 111988079 | + | ENST00000332674; ENST00000453116; ENST00000239007; ENST00000393134 | TAF |
| 20% | chr8 | 54841106 | 54841324 | + chr8 | 54852136 | 54852284 | + | ENST00000297313; ENST00000344277; ENST00000276500 | TAF |
| 19% | chr11 | 46670360 | 46670417 | + chr11 | 46670687 | 46670733 | + | ENST00000312040; ENST00000434074; ENST00000451945; ENST00000529655; ENST00000533325; ENST00000530500; ENST00000526508; ENST00000524625; ENST00000359513; ENST00000528494; ENST00000395549 | TAF |

TABLE 70-continued

Transcript fusion for Uveal Melanoma (UVM) Coordinates of the fusion sequences for which the donor is the TE.

| 1 | 2' | 3' | 4' | 5' 6' | 7 | 8' | 9 | 10' | 11' |
|---|---|---|---|---|---|---|---|---|---|
| 19% | chr11 | 46670360 | 46670417 | + chr11 | 46670687 | 46670733 | + | ENST00000312040; ENST00000434074; ENST00000451945; ENST00000529655; ENST00000533325; ENST00000530500; ENST00000526508; ENST00000524625; ENST00000359513; ENST00000528494; ENST00000395549 | TAF |
| 19% | chr11 | 46670360 | 46670417 | + chr11 | 46670687 | 46670733 | + | ENST00000312040; ENST00000434074; ENST00000451945; ENST00000529655; ENST00000533325; ENST00000530500; ENST00000526508; ENST00000524625; ENST00000359513; ENST00000528494; ENST00000395549 | TAF |
| 19% | chr11 | 46670360 | 46670417 | + chr11 | 46670687 | 46670733 | + | ENST00000312040; ENST00000434074; ENST00000451945; ENST00000529655; ENST00000533325; ENST00000530500; ENST00000526508; ENST00000524625; ENST00000359513; ENST00000528494; ENST00000395549 | TAF |
| 19% | chr11 | 46670360 | 46670417 | + chr11 | 46670687 | 46670733 | + | ENST00000312040; ENST00000434074; ENST00000451945; ENST00000529655; ENST00000533325; ENST00000530500; ENST00000526508; ENST00000524625; ENST00000359513; ENST00000528494; ENST00000395549 | TAF |
| 19% | chr19 | 54631006 | 54631115 | + chr19 | 54631448 | 54631575 | + | ENST00000321030; ENST00000419967 | TAF |
| 19% | chr19 | 54631006 | 54631115 | + chr19 | 54631448 | 54631575 | + | ENST00000321030; ENST00000419967 | TAF |
| 18% | chr11 | 126266642 | 126266739 | + chr11 | 126275991 | 126276045 | + | ENST00000534733 | TSF |
| 16% | chr12 | 110610148 | 110610836 | + chr12 | 110618227 | 110618376 | + | ENST00000552912; ENST00000242591; ENST00000550156 | TAF |
| 16% | chr12 | 110610148 | 110610836 | + chr12 | 110618227 | 110618376 | + | ENST00000552912; ENST00000242591; ENST00000550156 | TAF |
| 16% | chr7 | 150730019 | 150730148 | + chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 16% | chr7 | 150730019 | 150730148 | + chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 16% | chr7 | 150730019 | 150730148 | + chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 16% | chr7 | 150730019 | 150730148 | + chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 16% | chr7 | 150730019 | 150730148 | + chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 16% | chr7 | 150730019 | 150730148 | + chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 16% | chr7 | 150730019 | 150730148 | + chr7 | 150730692 | 150730929; 150731004; 150730700 | + | ENST00000461373; ENST00000358849; ENST00000489192; ENST00000297504; ENST00000356058; ENST00000498578; ENST00000477719; ENST00000477092 | TAF |
| 16% | chr11 | 126245394 | 126245491 | + chr11 | 126275991 | 126276045 | + | ENST00000534733 | TSF |
| 16% | chr12 | 104229950 | 104229670 | − chr12 | 104208899 | 104208715 | − | ENST00000392876 | TSF |
| 16% | chr12 | 56357933 | 56357814 | − chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 16% | chr12 | 56357933 | 56357814 | − chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 16% | chr12 | 56357933 | 56357814 | − chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 16% | chr12 | 56357933 | 56357814 | − chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 16% | chr12 | 56357933 | 56357814 | − chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 16% | chr12 | 56357933 | 56357814 | − chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 16% | chr12 | 56357933 | 56357814 | − chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 16% | chr12 | 56357933 | 56357814 | − chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |

TABLE 70-continued

Transcript fusion for Uveal Melanoma (UVM) Coordinates of the fusion sequences for which the donor is the TE.

| 1 | 2' | 3' | 4' | 5' | 6' | 7 | 8' | 9 | 10' | 11' |
|---|---|---|---|---|---|---|---|---|---|---|
| 16% | chr12 | 56357933 | 56357814 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 15% | chr10 | 111986999 | 111987135 | + | chr10 | 111987947 | 111988079 | + | ENST00000332674; ENST00000453116; ENST00000239007; ENST00000393134 | TAF |
| 15% | chr10 | 111986999 | 111987135 | + | chr10 | 111987947 | 111988079 | + | ENST00000332674; ENST00000453116; ENST00000239007; ENST00000393134 | TAF |
| 15% | chr10 | 111986999 | 111987135 | + | chr10 | 111987947 | 111988079 | + | ENST00000332674; ENST00000453116; ENST00000239007; ENST00000393134 | TAF |
| 15% | chr7 | 2289080 | 2289194 | + | chr7 | 2289492 | 2289637 | + | ENST00000356714; ENST00000397049; ENST00000397046; ENST00000397048; ENST00000339737; ENST00000343985 | TAF |
| 15% | chr10 | 82214092 | 82214127 | + | chr10 | 82264484 | 82264534 | + | ENST00000429989; ENST00000372158; ENST00000341863; ENST00000372156 | TAF |
| 15% | chr10 | 82214092 | 82214127 | + | chr10 | 82264484 | 82264534 | + | ENST00000429989; ENST00000372158; ENST00000341863; ENST00000372156 | TAF |
| 15% | chr2 | 238451313 | 238451319 | + | chr2 | 238455249 | 238455326 | + | ENST00000410032; ENST00000264605; ENST00000338530; ENST00000409373; ENST00000437893; ENST00000415753; ENST00000432475; ENST00000434770 | TAF |
| 15% | chr2 | 238451313 | 238451319 | + | chr2 | 238455249 | 238455326 | + | ENST00000410032; ENST00000264605; ENST00000338530; ENST00000409373; ENST00000437893; ENST00000415753; ENST00000432475; ENST00000434770 | TAF |
| 15% | chr2 | 238451313 | 238451319 | + | chr2 | 238455249 | 238455326 | + | ENST00000410032; ENST00000264605; ENST00000338530; ENST00000409373; ENST00000437893; ENST00000415753; ENST00000432475; ENST00000434770 | TAF |
| 15% | chrX | 3773692 | 3773630 | − | chrX | 3735819 | 3735816 | − | ENST00000425492 | TAF |
| 15% | chr19 | 48627094 | 48627044 | − | chr19 | 48626575 | 48626431 | − | ENST00000263274; ENST00000536218; ENST00000594759; ENST00000427526; ENST00000601091 | TSF |
| 15% | chr19 | 48627094 | 48627044 | − | chr19 | 48626575 | 48626431 | − | ENST00000263274; ENST00000536218; ENST00000594759; ENST00000427526; ENST00000601091 | TSF |
| 15% | chr8 | 144691011 | 144690934 | − | chr8 | 144690296 | 144690232 | − | ENST00000220966; ENST00000433751 | TSF |
| 15% | chr8 | 144691011 | 144690934 | − | chr8 | 144690296 | 144690232 | − | ENST00000220966; ENST00000433751 | TSF |
| 15% | chr16 | 70714570 | 70714506 | − | chr16 | 70713958 | 70713874 | − | ENST00000338779 | TSF |
| 15% | chr7 | 100850556 | 100850506 | − | chr7 | 100850185 | 100850060 | − | ENST00000454310; ENST00000223127 | TSF |
| 14% | chr6 | 26474324 | 26474624 | + | chr6 | 26476389 | 26476396 | + | ENST00000480218 | TAF |
| 14% | chr1 | 93299408 | 93299506 | + | chr1 | 93300336 | 93300470 | + | ENST00000370321; ENST00000315741 | TAF |
| 14% | chr1 | 93299408 | 93299506 | + | chr1 | 93300336 | 93300470 | + | ENST00000370321; ENST00000315741 | TAF |
| 14% | chr5 | 54528691 | 54528595 | − | chr5 | 54528374 | 54528189 | − | ENST00000282572 | TAF |
| 14% | chr1 | 183600359 | 183599874 | − | chr1 | 183599772 | 183599596 | − | ENST00000367534; ENST00000359856; ENST00000294742 | TAF |
| 14% | chr1 | 183600359 | 183599874 | − | chr1 | 183599772 | 183599596 | − | ENST00000367534; ENST00000359856; ENST00000294742 | TAF |
| 14% | chr19 | 36028515 | 36028550 | + | chr19 | 36029209 | 36029305; 36029276 | + | ENST00000222286; ENST00000586334; ENST00000585510 | TSF |
| 14% | chr19 | 36028515 | 36028550 | + | chr19 | 36029209 | 36029305; 36029276 | + | ENST00000222286; ENST00000586334; ENST00000585510 | TSF |
| 14% | chr19 | 36028515 | 36028550 | + | chr19 | 36029209 | 36029305; 36029276 | + | ENST00000222286; ENST00000586334; ENST00000585510 | TSF |
| 14% | chr12 | 110610148 | 110610701 | + | chr12 | 110618227 | 110618376 | + | ENST00000552912; ENST00000242591; ENST00000550156 | TSF |
| 14% | chr12 | 110610148 | 110610701 | + | chr12 | 110618227 | 110618376 | + | ENST00000552912; ENST00000242591; ENST00000550156 | TSF |
| 14% | chr15 | 31367719 | 31365913 | − | chr15 | 31362429 | 31362234; 31362036 | − | ENST00000397795; ENST00000256552; ENST00000542188; ENST00000558445; ENST00000559177; ENST00000560658; ENST00000559179 | TSF |
| 14% | chr15 | 31367719 | 31365913 | − | chr15 | 31362429 | 31362234; 31362036 | − | ENST00000397795; ENST00000256552; ENST00000542188; ENST00000558445; ENST00000559177; ENST00000560658; ENST00000559179 | TSF |
| 14% | chr15 | 31367719 | 31365913 | − | chr15 | 31362429 | 31362234; 31362036 | − | ENST00000397795; ENST00000256552; ENST00000542188; ENST00000558445; ENST00000559177; ENST00000560658; ENST00000559179 | TSF |
| 14% | chr15 | 31367719 | 31365913 | − | chr15 | 31362429 | 31362234; 31362036 | − | ENST00000397795; ENST00000256552; ENST00000542188; ENST00000558445; ENST00000559177; ENST00000560658; ENST00000559179 | TSF |
| 14% | chr15 | 31367719 | 31365913 | − | chr15 | 31362429 | 31362234; 31362036 | − | ENST00000397795; ENST00000256552; ENST00000542188; ENST00000558445; ENST00000559177; ENST00000560658; ENST00000559179 | TSF |
| 12% | chr21 | 42597177 | 42597622 | + | chr21 | 42598193 | 42598281 | + | ENST00000328735; ENST00000330333; ENST00000347667 | TAF |
| 12% | chr21 | 42597177 | 42597622 | + | chr21 | 42598193 | 42598281 | + | ENST00000328735; ENST00000330333; ENST00000347667 | TAF |
| 12% | chr21 | 42597177 | 42597622 | + | chr21 | 42598193 | 42598281 | + | ENST00000328735; ENST00000330333; ENST00000347667 | TAF |
| 12% | chr1 | 212594935 | 212594948 | + | chr1 | 212615907 | 212615967 | + | ENST00000366988 | TAF |
| 12% | chr8 | 104389530 | 104389551 | + | chr8 | 104390255 | 104390471 | + | ENST00000330295; ENST00000520337 | TAF |
| 12% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 12% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 12% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 12% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |

TABLE 70-continued

Transcript fusion for Uveal Melanoma (UVM) Coordinates of the fusion sequences for which the donor is the TE.

| 1 | 2' | 3' | 4' | 5' | 6' | 7 | 8' | 9 | 10' | 11' |
|---|---|---|---|---|---|---|---|---|---|---|
| 12% | chr9 | 128362212 | 128362114 | − | chr9 | 128348006 | 128347834 | − | ENST00000373511; ENST00000373498; ENST00000350766; ENST00000265960; ENST00000394060; ENST00000468896 | TAF |
| 12% | chr10 | 120902016 | 120901765 | − | chr10 | 120900831 | 120900754 | − | ENST00000355697; ENST00000330036 | |
| 12% | chr6 | 108394895 | 108394846 | − | chr6 | 108385503 | 108385389 | − | ENST00000193322 | TSF |
| 12% | chrX | 153207989 | 153207921 | − | chrX | 153207484 | 153207403 | − | ENST00000393700; ENST00000369997 | TSF |
| 12% | chr15 | 28127352 | 28127177 | − | chr15 | 28096621 | 28096528 | − | ENST00000353809; ENST00000354638 | TSF |
| 11% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 11% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 11% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 11% | chr17 | 75318693 | 75318752 | + | chr17 | 75398141 | 75398484; 75398785; 75398497; 75398565 | + | ENST00000589070; ENST00000427177; ENST00000591198; ENST00000329047; ENST00000590294; ENST00000591934; ENST00000423034; ENST00000589140 | TAF |
| 11% | chr1 | 156095197 | 156095265 | + | chr1 | 156100408 | 156100564 | + | ENST00000368301; ENST00000361308; ENST00000347559; ENST00000368300; ENST00000368299; ENST00000448611; ENST00000368297; ENST00000504687; ENST00000473598; ENST00000392353 | TAF |
| 11% | chr1 | 156095197 | 156095265 | + | chr1 | 156100408 | 156100564 | + | ENST00000368301; ENST00000361308; ENST00000347559; ENST00000368300; ENST00000368299; ENST00000448611; ENST00000368297; ENST00000504687; ENST00000473598; ENST00000392353 | TAF |
| 11% | chr1 | 156095197 | 156095265 | + | chr1 | 156100408 | 156100564 | + | ENST00000368301; ENST00000361308; ENST00000347559; ENST00000368300; ENST00000368299; ENST00000448611; ENST00000368297; ENST00000504687; ENST00000473598; ENST00000392353 | TAF |
| 11% | chr1 | 156095197 | 156095265 | + | chr1 | 156100408 | 156100564 | + | ENST00000368301; ENST00000361308; ENST00000347559; ENST00000368300; ENST00000368299; ENST00000448611; ENST00000368297; ENST00000504687; ENST00000473598; ENST00000392353 | TAF |
| 11% | chr1 | 156095197 | 156095265 | + | chr1 | 156100408 | 156100564 | + | ENST00000368301; ENST00000361308; ENST00000347559; ENST00000368300; ENST00000368299; ENST00000448611; ENST00000368297; ENST00000504687; ENST00000473598; ENST00000392353 | TAF |
| 11% | chr1 | 156095197 | 156095265 | + | chr1 | 156100408 | 156100564 | + | ENST00000368301; ENST00000361308; ENST00000347559; ENST00000368300; ENST00000368299; ENST00000448611; ENST00000368297; ENST00000504687; ENST00000473598; ENST00000392353 | TAF |
| 11% | chr11 | 321638 | 321582 | − | chr11 | 320772 | 320565 | − | ENST00000399808 | TAF |
| 11% | chr11 | 322262 | 322206 | − | chr11 | 320772 | 320565 | − | ENST00000399808 | TAF |
| 11% | chr11 | 321716 | 321660 | − | chr11 | 320772 | 320565 | − | ENST00000399808 | TAF |
| 11% | chr11 | 321450 | 321426 | − | chr11 | 320772 | 320565 | − | ENST00000399808 | TAF |
| 11% | chr11 | 322067 | 322011 | − | chr11 | 320772 | 320565 | − | ENST00000399808 | TAF |
| 11% | chr11 | 321638 | 321543 | − | chr11 | 320772 | 320565 | − | ENST00000399808 | TAF |
| 11% | chr11 | 321638 | 321504 | − | chr11 | 320772 | 320565 | − | ENST00000399808 | TAF |
| 11% | chr2 | 39225691 | 39225641 | − | chr2 | 39224566 | 39224394 | − | ENST00000426016; ENST00000402219; ENST00000395038 | TAF |
| 11% | chr2 | 39225691 | 39225641 | − | chr2 | 39224566 | 39224394 | − | ENST00000426016; ENST00000402219; ENST00000395038 | TAF |
| 11% | chr11 | 321488 | 321465 | | chr11 | 320772 | 320565 | − | ENST00000399808 | TAF |
| 11% | chr11 | 322457 | 322401 | − | chr11 | 320772 | 320565 | − | ENST00000399808 | TAF |
| 11% | chr11 | 322580 | 322557 | − | chr11 | 320772 | 320565 | − | ENST00000399808 | TAF |
| 11% | chr11 | 321911 | 321855 | − | chr11 | 320772 | 320565 | − | ENST00000399808 | TAF |
| 11% | chr11 | 321410 | 321387 | − | chr11 | 320772 | 320565 | − | ENST00000399808 | TAF |
| 10% | chr1 | 212601578 | 212602888 | + | chr1 | 212615907 | 212615967 | + | ENST00000366988 | TSF |
| 10% | chr17 | 39976225 | 39976301 | + | chr17 | 39976521 | 39976713 | + | ENST00000321562; ENST00000455106; ENST00000544340 | TSF |
| 10% | chr1 | 212596286 | 212598195 | + | chr1 | 212615907 | 212615967 | + | ENST00000366988 | TSF |
| 10% | chr9 | 5907671 | 5907771 | + | chr9 | 5908640 | 5908708 | + | ENST00000381477; ENST00000381476; ENST00000381471 | TSF |
| 10% | chr4 | 142977397 | 142977072 | − | chr4 | 142950067 | 142949935 | − | ENST00000513000; ENST00000262992; ENST00000308502; ENST00000508116 | TSF |
| 9% | chr7 | 20707326 | 20708050 | + | chr7 | 20721128 | 20721289 | + | ENST00000404938; ENST00000258738 | TSF |
| 9% | chr1 | 212596286 | 212598077 | + | chr1 | 212615911 | 212615967 | + | ENST00000366988 | TSF |
| 9% | chr14 | 61868140 | 61868698 | + | chr14 | 61909829 | 61909979 | + | ENST00000332981; ENST00000553830 | TSF |
| 9% | chr14 | 61868140 | 61868698 | + | chr14 | 61909829 | 61909979 | + | ENST00000332981; ENST00000553830 | TSF |
| 9% | chr4 | 91324981 | 91325170 | + | chr4 | 91389385 | 91389505 | + | ENST00000505073; ENST00000509176; ENST00000432775; ENST00000333691 | TSF |
| 9% | chr4 | 91324981 | 91325170 | + | chr4 | 91389385 | 91389505 | + | ENST00000505073; ENST00000509176; ENST00000432775; ENST00000333691 | TSF |
| 9% | chr4 | 91324981 | 91325170 | + | chr4 | 91389385 | 91389505 | + | ENST00000505073; ENST00000509176; ENST00000432775; ENST00000333691 | TSF |

TABLE 70-continued

Transcript fusion for Uveal Melanoma (UVM) Coordinates of the fusion sequences for which the donor is the TE.

| 1 | 2' | 3' | 4' | 5' | 6' | 7 | 8' | 9 | 10' | 11' |
|---|---|---|---|---|---|---|---|---|---|---|
| 9% | chr1 | 168067171 | 168067120 | − | chr1 | 168066470 | 168065746 | − | ENST00000367838; ENST00000271357; ENST00000539777; ENST00000361697; ENST00000537209; ENST00000546300; ENST00000367835 | TSF |
| 9% | chr2 | 17876171 | 17876059 | − | chr2 | 17865030 | 17864905 | − | ENST00000448223; ENST00000351948; ENST00000381272; ENST00000402989 | TSF |
| 8% | chr17 | 74943634 | 74943777 | + | chr17 | 74943912 | 74944168 | + | ENST00000301618; ENST00000569840; ENST00000428789 | TSF |
| 8% | chr1 | 212601578 | 212602718 | + | chr1 | 212615907 | 212615967 | + | ENST00000366988 | TSF |
| 8% | chr12 | 56359010 | 56358944 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 8% | chr12 | 56359010 | 56358944 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 8% | chr12 | 56359010 | 56358944 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 8% | chr12 | 56359010 | 56358944 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 8% | chr12 | 56359010 | 56358944 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 8% | chr12 | 56359010 | 56358944 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 8% | chr12 | 56359010 | 56358944 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 8% | chr12 | 56359010 | 56358944 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 8% | chr12 | 56359010 | 56358944 | − | chr12 | 56355516 | 56355406 | − | ENST00000449260; ENST00000552882; ENST00000548747; ENST00000360714; ENST00000536427; ENST00000548493; ENST00000548803; ENST00000547137; ENST00000546543; ENST00000549418; ENST00000549233 | TSF |
| 8% | chr10 | 22995124 | 22994872 | − | chr10 | 22898646 | 22898549 | − | ENST00000376573 | TSF |
| 8% | chr13 | 78549747 | 78549606 | − | chr13 | 78492759 | 78492226 | − | ENST00000377211 | TSF |
| 8% | chr17 | 28255620 | 28255510 | − | chr17 | 28252573 | 28252490 | − | ENST00000582084; ENST00000590153 | TSF |
| 8% | chr1 | 1496761 | 1496712 | − | chr1 | 1479367 | 1479249 | − | ENST00000291386 | TSF |

Description of the sequences

| SEQ ID NO | Description |
|---|---|
| 1-117 | LUAD peptide sequences from P1 application |
| 118-431 | Table 3 from P1 application Fusion sequences with exon donor |
| 432-910 | Table 4 from P1 application Fusion sequence with TE donor |
| 911-972 | New sequences - TCGA-ACC Fusion sequences with exon donor |
| 973-1237 | New sequences - TCGA-BLCA Fusion sequences with exon donor |
| 1238-1466 | New sequences - TCGA-BRCA Fusion sequences with exon donor |
| 1467-1632 | New sequences - TCGA-CESC Fusion sequences with exon donor |
| 1633-1696 | New sequences - TCGA-CHOL Fusion sequences with exon donor |
| 1697-1801 | New sequences - TCGA-COAD Fusion sequences with exon donor |
| 1802-1925 | New sequences - TCGA-DLBC Fusion sequences with exon donor |

-continued

| Description of the sequences | |
|---|---|
| SEQ ID NO | Description |
| 1926-2205 | New sequences - TCGA-ESCA Fusion sequences with exon donor |
| 2206-2393 | New sequences - TCGA-GBM Fusion sequences with exon donor |
| 2394-2608 | New sequences - TCGA-HNSC Fusion sequences with exon donor |
| 2609-2721 | New sequences - TCGA-KICH Fusion sequences with exon donor |
| 2722-2890 | New sequences - TCGA-KIRC Fusion sequences with exon donor |
| 2891-2986 | New sequences - TCGA-KIRP Fusion sequences with exon donor |
| 2987-3277 | New sequences - TCGA-LGG Fusion sequences with exon donor |
| 3278-3435 | New sequences - TCGA-LIHC Fusion sequences with exon donor |
| 3436-3624 | New sequences - TCGA-LUAD Fusion sequences with exon donor |
| 3625-3946 | New sequences - TCGA-LUSC Fusion sequences with exon donor |
| 3947-4001 | New sequences - TCGA-MESO Fusion sequences with exon donor |
| 4002-4597 | New sequences - TCGA-OV Fusion sequences with exon donor |
| 4598-4660 | New sequences - TCGA-PAAD Fusion sequences with exon donor |
| 4661-4811 | New sequences - TCGA-PCPG Fusion sequences with exon donor |
| 4812-4970 | New sequences - TCGA-PRAD Fusion sequences with exon donor |
| 4971-5030 | New sequences - TCGA-READ Fusion sequences with exon donor |
| 5031-5150 | New sequences - TCGA-SARC Fusion sequences with exon donor |
| 5151-5266 | New sequences - TCGA-SKCM Fusion sequences with exon donor |
| 5267-5628 | New sequences - TCGA-STAD Fusion sequences with exon donor |
| 5629-5876 | New sequences - TCGA-TGCT Fusion sequences with exon donor |
| 5877-5979 | New sequences - TCGA-THCA Fusion sequences with exon donor |
| 5980-6119 | New sequences - TCGA-THYM Fusion sequences with exon donor |
| 6120-6190 | New sequences - TCGA-UCEC Fusion sequences with exon donor |
| 6191-6247 | New sequences - TCGA-UCS Fusion sequences with exon donor |
| 6248-6315 | New sequences - TCGA-UVM Fusion sequences with exon donor |
| 6316-6441 | New sequences - TCGA-ACC Fusion sequences with TE donor |
| 6442-6810 | New sequences - TCGA-BLCA Fusion sequences with TE donor |
| 6811-7275 | New sequences - TCGA-BRCA Fusion sequences with TE donor |
| 7276-7515 | New sequences - TCGA-CESC Fusion sequences with TE donor |
| 7516-7638 | New sequences - TCGA-CHOL Fusion sequences with TE donor |
| 7639-7817 | New sequences - TCGA-COAD Fusion sequences with TE donor |
| 7818-8055 | New sequences - TCGA-DLBC Fusion sequences with TE donor |
| 8056-8703 | New sequences - TCGA-ESCA Fusion sequences with TE donor |
| 8704-9163 | New sequences - TCGA-GBM Fusion sequences with TE donor |
| 9164-9653 | New sequences - TCGA-HNSC Fusion sequences with TE donor |
| 9654-9883 | New sequences - TCGA-KICH Fusion sequences with TE donor |
| 9884-10277 | New sequences - TCGA-KIRC Fusion sequences with TE donor |

```
                      Description of the sequences
SEQ ID NO   Description 10278-10454 New sequences - TCGA-KIRP Fusion sequences with TE donor 10455-11125 New sequences - TCGA-LGG Fusion sequences with TE donor 11126-11547 New sequences - TCGA-LIHC Fusion sequences with TE donor 11548-11890 New sequences - TCGA-LUAD Fusion sequences with TE donor 11891-12574 New sequences - TCGA-LUSC Fusion sequences with TE donor 12575-12698 New sequences - TCGA-MESO Fusion sequences with TE donor 12699-13750 New sequences - TCGA-OV Fusion sequences with TE donor 13751-13828 New sequences - TCGA-PAAD Fusion sequences with TE donor 13829-14029 New sequences - TCGA-PCPG Fusion sequences with TE donor 14030-14419 New sequences - TCGA-PRAD Fusion sequences with TE donor 14420-14524 New sequences - TCGA-READ Fusion sequences with TE donor 14525-14776 New sequences - TCGA-SARC Fusion sequences with TE donor 14777-15051 New sequences - TCGA-SKCM Fusion sequences with TE donor 15052-15902 New sequences - TCGA-STAD Fusion sequences with TE donor 15903-16545 New sequences - TCGA-TGCT Fusion sequences with TE donor 16546-16688 New sequences - TCGA-THCA Fusion sequences with TE donor 16689-16951 New sequences - TCGA-THYM Fusion sequences with TE donor 16952-17101 New sequences - TCGA-UCEC Fusion sequences with TE donor 17102-17261 New sequences - TCGA-UCS Fusion sequences with TE donor 17262-17492 New sequences - TCGA-UVM Fusion sequences with TE donor
```

SEQUENCE LISTING

The patent contains a lengthy sequence listing. A copy of the sequence listing is available in electronic form from the USPTO web site (https://seqdata.uspto.gov/?pageRequest=docDetail&DocID=US12152077B1). An electronic copy of the sequence listing will also be available from the USPTO upon request and payment of the fee set forth in 37 CFR 1.19(b)(3).

The invention claimed is:

1. A method of antibody production comprising a step of contacting multiple antibodies or antigen-binding fragments thereof with a tumor neoantigen peptide and selecting an antibody, or antigen-binding fragment thereof, that binds to the tumor neoantigen peptide, the improvement comprising:
   using a tumor neoantigen peptide identified by a method comprising
      selecting, among mRNA sequences from cancer cells, a fusion transcript comprising a junction between a transposable element (TE) sequence and an exonic sequence, and including an Open Reading Frame (ORF), and
      selecting a tumor neoantigen peptide of at least 8 amino acids in length, encoded by part of the ORF of the fusion transcript.

2. The method of claim 1 wherein the antibody, or antigen-binding fragment thereof, is selected from a library of human antibody sequences.

3. The method of claim 1 wherein the antibody, or antigen-binding fragment thereof, is generated by immunizing an animal with a polypeptide comprising the tumor neoantigen peptide, followed by the selection step.

4. The method of claim 1 wherein the antibody or antigen-binding fragment thereof is part of a T-Cell Receptor (TCR).

5. The method of claim 4 wherein the TCR comprises a TCRa and/or TCRb chain or TCRg and/or TCRd chain.

6. The method of claim 1, wherein the tumor neoantigen peptide is encoded by a canonical open reading frame of an exon.

7. The method of claim 1, wherein the tumor neoantigen peptide is encoded by a non-canonical open reading frame of an exon.

8. The method of claim 1, wherein the tumor neoantigen peptide is in association with an MHC or HLA molecule.

9. The method of claim 1, wherein the antibody is a multispecific antibody that further targets an immune cell antigen.

\* \* \* \* \*